US010526311B2

(12) United States Patent
Chessari et al.

(10) Patent No.: US 10,526,311 B2
(45) Date of Patent: Jan. 7, 2020

(54) ISOINDOLINONE INHIBITORS OF THE MDM2-P53 INTERACTION HAVING ANTICANCER ACTIVITY

(71) Applicants: ASTEX THERAPEUTICS LIMITED, Cambridge (GB); CANCER RESEARCH TECHNOLOGY LIMITED, London (GB)

(72) Inventors: Gianni Chessari, Cambridge (GB); Steven Howard, Cambridge (GB); Ildiko Maria Buck, London (GB); Benjamin David Cons, Cambridge (GB); Christopher Norbert Johnson, Saffron Walden (GB); Rhian Sara Holvey, Cambridge (GB); David Charles Rees, Cambridge (GB); Jeffrey David St. Denis, Cambridge (GB); Emiliano Tamanini, Cambridge (GB); Bernard Thomas Golding, Newcastle upon Tyne (GB); Ian Robert Hardcastle, Hexham (GB); Celine Florence Cano, Newcastle upon Tyne (GB); Duncan Charles Miller, Newcastle upon Tyne (GB); Martin Edward Mäntylä Noble, Newcastle upon Tyne (GB); Roger John Griffin, London (GB); James Daniel Osborne, Cambridge (GB); Joanne Peach, Cambridge (GB); Arwel Lewis, Royston (GB); Kim Louise Hirst, Saffron Walden (GB); Benjamin Paul Whittaker, Potton (GB); David Wyn Watson, Duxford (GB); Dale Robert Mitchell, Saffron Walden (GB)

(73) Assignees: ASTEX THERAPEUTICS LIMITED, Cambridge (GB); CANCER RESEARCH TECHNOLOGY LIMITED, London (GB)

( * ) Notice: Subject to any disclaimer, the term of this patent is extended or adjusted under 35 U.S.C. 154(b) by 0 days.

(21) Appl. No.: 15/763,724

(22) PCT Filed: Sep. 29, 2016

(86) PCT No.: PCT/GB2016/053041
§ 371 (c)(1),
(2) Date: Mar. 27, 2018

(87) PCT Pub. No.: WO2017/055859
PCT Pub. Date: Apr. 6, 2017

(65) Prior Publication Data
US 2019/0055215 A1  Feb. 21, 2019

(30) Foreign Application Priority Data

Sep. 29, 2015 (GB) .................. 1517216.6

(51) Int. Cl.
*C07D 401/06* (2006.01)
*A61K 31/4439* (2006.01)
(Continued)

(52) U.S. Cl.
CPC .......... *C07D 401/06* (2013.01); *A61K 31/444* (2013.01); *A61K 31/4439* (2013.01);
(Continued)

(58) Field of Classification Search
CPC ............................. C07D 401/06; A61P 35/00
See application file for complete search history.

(56) References Cited

U.S. PATENT DOCUMENTS 3,466,298 A    9/1969  Sulkowski et al.
3,763,178 A   10/1973  Sulkowski et al.
(Continued)

FOREIGN PATENT DOCUMENTS

CH    374071    12/1963
DE   2313227     9/1973
(Continued)

OTHER PUBLICATIONS

Esfandiari, Armen et al., "Chemical Inhibition of Wild-Type p53-Induced Phosphatase 1 (WIP1/PPM1D) by GSK2830371 Potentiates the Sensitivity to MDM2 Inhibitors in a p53-Dependent Manner," Molecular Cancer Therapeutics, Feb. 1, 2016, pp. 379-391.
(Continued)

*Primary Examiner* — Golam M Shameem
(74) *Attorney, Agent, or Firm* — Heslin Rothenberg Farley & Mesiti P.C.

(57) ABSTRACT

The invention provides a compound of formula (I):

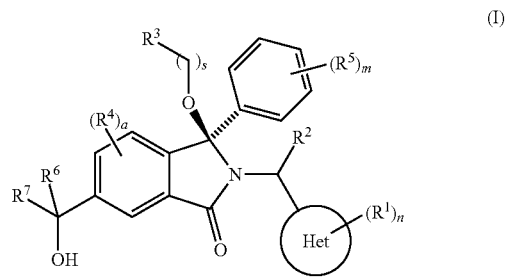

or tautomer or a solvate or a pharmaceutically acceptable salt thereof, wherein the various substituents are as defined in the claims.
Also provided are pharmaceutical compositions containing the compounds of formula (I), processes for making the compounds and the medical uses of the compounds.

25 Claims, No Drawings

(51) Int. Cl.

| | | |
|---|---|---|
| C07D 401/14 | (2006.01) | |
| C07D 403/06 | (2006.01) | |
| C07D 407/14 | (2006.01) | |
| C07D 409/14 | (2006.01) | |
| C07D 417/14 | (2006.01) | |
| A61P 35/00 | (2006.01) | |
| A61K 31/444 | (2006.01) | |
| A61K 31/4545 | (2006.01) | |
| A61K 31/496 | (2006.01) | |
| A61K 31/501 | (2006.01) | |
| A61K 31/506 | (2006.01) | |
| A61K 31/5377 | (2006.01) | |
| A61K 45/06 | (2006.01) | |

(52) U.S. Cl.
CPC ........ *A61K 31/4545* (2013.01); *A61K 31/496* (2013.01); *A61K 31/501* (2013.01); *A61K 31/506* (2013.01); *A61K 31/5377* (2013.01); *A61K 45/06* (2013.01); *A61P 35/00* (2018.01); *C07D 401/14* (2013.01); *C07D 403/06* (2013.01); *C07D 407/14* (2013.01); *C07D 409/14* (2013.01); *C07D 417/14* (2013.01); *C07B 2200/05* (2013.01)

(56) References Cited

U.S. PATENT DOCUMENTS

| | | | |
|---|---|---|---|
| 3,898,232 | A | 8/1975 | Cotrel et al. |
| 4,001,271 | A | 1/1977 | Cotrel et al. |
| 4,200,759 | A | 4/1980 | Dickinson |
| 4,244,966 | A | 1/1981 | Lippman et al. |
| 4,312,809 | A | 1/1982 | Haugwitz |
| 4,331,600 | A | 5/1982 | Golec, Jr. et al. |
| 4,505,921 | A | 3/1985 | Beregi et al. |
| 6,344,468 | B1 | 2/2002 | Schindler et al. |
| 8,258,175 | B2 | 9/2012 | Willems et al. |
| 8,618,158 | B2 | 12/2013 | Golding et al. |
| 9,358,222 | B2 | 6/2016 | Golding et al. |
| 2005/0004207 | A1 | 1/2005 | Straub et al. |
| 2006/0264473 | A1 | 11/2006 | Khazak et al. |
| 2012/0264738 | A1 | 10/2012 | Sugimoto et al. |
| 2014/0194486 | A1 | 7/2014 | Golding et al. |
| 2016/0355478 | A1 | 12/2016 | Golding et al. |
| 2018/0118684 | A1 | 5/2018 | Golding et al. |
| 2019/0016708 | A1 | 1/2019 | Chessari et al. |

FOREIGN PATENT DOCUMENTS

| | | | |
|---|---|---|---|
| EP | 0461079 | A2 | 12/1991 |
| EP | 1199306 | A1 | 4/2002 |
| EP | 1566378 | A1 | 8/2005 |
| EP | 2108642 | A1 | 10/2009 |
| GB | 1325065 | | 8/1973 |
| GB | 1601701 | | 11/1981 |
| JP | 2000506163 | A | 5/2000 |
| JP | 2004217591 | | 8/2004 |
| JP | 2005255660 | A | 9/2005 |
| KR | 20130088577 | A | 8/2013 |
| WO | 9732846 | A1 | 9/1997 |
| WO | 9942444 | A1 | 8/1999 |
| WO | 0132928 | A2 | 5/2001 |
| WO | 03051359 | A1 | 6/2003 |
| WO | 03101450 | A1 | 12/2003 |
| WO | 2005021532 | A1 | 3/2005 |
| WO | 2005095341 | A1 | 10/2005 |
| WO | 2006020879 | A1 | 2/2006 |
| WO | 2006024837 | A1 | 3/2006 |
| WO | 2007/021309 | A1 | 2/2007 |
| WO | 2008/024892 | A2 | 2/2008 |
| WO | 2008/117061 | A2 | 10/2008 |
| WO | 2008151184 | A1 | 12/2008 |
| WO | 2009156735 | A2 | 12/2009 |
| WO | 2010031713 | A1 | 3/2010 |
| WO | 2011076786 | A1 | 6/2011 |
| WO | 2011098398 | A1 | 8/2011 |
| WO | 2011153509 | A1 | 12/2011 |
| WO | 2012175487 | A1 | 12/2012 |
| WO | 2012175520 | A1 | 12/2012 |
| WO | 2013/120835 | A1 | 8/2013 |
| WO | 2013111105 | A1 | 8/2013 |
| WO | 2014/070948 | A1 | 5/2014 |
| WO | 2015161032 | A1 | 10/2015 |
| WO | 2017/055859 | A1 | 4/2017 |
| WO | 2017/055860 | A1 | 4/2017 |
| WO | 2017/068412 | A1 | 4/2017 |
| WO | 2017/087607 | A1 | 5/2017 |

OTHER PUBLICATIONS

Zhang, Xiaoling et al., "Degradation of MDM2 by the Interaction Between Berberine and DAXX Leads to Potent Apoptosis in MDM2-Overexpressing Cancer Cells," Cancer Research, Therapeutics, Targets and Chemical Biology, Oct. 8, 2010, pp. 9895-9904.
Great Britain Search Report for GB1517216.6, dated Jun. 27, 2016, 2 pp.
International Search Report for PCT/GB2016/053041, dated Nov. 28, 2016, 6 pp.
Prodrug [online, wikipedia], [retrieved on Mar. 11, 2007], Retrieved from the internet, URL http://en.wikipedia.org/wiki/Prodrugs.
Lala, P.K., et al., Role of nitric oxide in tumor progression: Lessons from experimental tumors, Cancer and Metastasis Reviews, vol. 17, No. 1, pp. 91-106 (1998).
Golub, T.R., et al., Molecular Classification of Cancer: Class Discovery and Class Prediction by Gene Expression Monitoring, Science, vol. 286, pp. 531-537 (1999).
Cancer [online, medline], [retrieved on Jul. 6, 2007], Retrieved from the internet, URL http://www.nlm.nih.gov/medlineplus/cancer.html.
Cancer [online, wikipedia], [retrieved on Jul. 6, 2007], Retrieved from the internet, URL http://en.wikipedia.org/wiki/Cancer.
Bartfeld, H.D., et al., 3-Oxo-Isoindole, Tetrahedron Letters, No. 10, pp. 757-760 (1970).
Caplus 95:150329 record for Lencbergs, I., et al., 3-Hydroxy-3-(α-aminobenzyl)-2-substituted 1-isoindolinones, Latvijas PSR Zinatnu Akademijas Vestis, Kimijas Serija (1981), (3), 335-40.
Rebek, Jr., J., et al., Olefin Epoxidation with a-Substituted Hydroperoxides, J. Am. Chem. Soc., vol. 102, pgs. 5602-5605 (1980).
Griffiths, J., et al., Model Studies for Damage to Nucleic Acids Mediated by Thiyl Radicals, Tetrahedron, vol. 48, No. 26, pp. 5543-5556 (1992).
Park, J.S., et al., Noble 2-[3(Cyclopentyloxy)-4-Methoxyphenyl]-1-Isoindolinone Derivatives. Part I; Synthesis and SAR Studies for the Inhibition of TNF-α Production, Arch. Pharma. Res., vol. 24, No. 5, pp. 367-370 (2001).
Ito, Y., et al., Solid-State and Solution Photolyses of Tetracyanobenzene with Benzyl Cyanlides or Benzyl Alcohols, Tetrahedron, vol. 56, pp. 7139-7152 (2000).
Vivekananda Bhatt, M., et al., Aspects of Tautomerism. Part V. † Solvent, Substituent, and Steric Effects on the Ring-Chain Tautomerism of o-Benzoylbenzamides, Journal of the Chemical Society, Perkin Transactions II, pp. 1160-1166 (1973).
Topliss, J.G., Chemistry, et al., Antihypertensive Agents. III. 3-Hydroxy-3-phenylphthalimidines, Journal of Medicinal Chemistry, vol. 7, pp. 453-456 (1964).
Charlesworth, E.H., et al., Fluoranthene studies. III. A synthesis of 3-bromo-6-nitrofluorenone, Canadian Journal of Chemistry, vol. 46, No. 3, pp. 463-465 (1968).
STN 1972:419475 (Caplus) record for Valters, R., et al., Ring-chain transformations involving the carbonyl group. XI. Acid chlorides and amides of 2-benzoyl-3-,4-, 5-, and 6-nitrobenzoic acids, Rizh. Politekh. Inst., Riga, USSR, Latvijas PSR Zinatnu Akademijas Vestis, Kimijas Serija, vol. 1, pp. 61-65 (1972).
Yang et al., "Practical Proline-Catalyzed Asymmetric Mannich Reaction of Aldehydes with N-Boc-Imines," Nature Protocols, vol. 2, No. 8, 2007, pp. 1937-1942.

(56) References Cited

OTHER PUBLICATIONS

Körmendy, Academiae K., Über Reaktionen in Polyaminsynthesen Mit Phthaliminoakjylhaloiden, I., Acta Chimica Academic Scientiarum Hungaricae, pp. 255-264 (1958).
Inaba, M., et al., Reversal of Resistance to Vincristine in P388 Leukemia by Various Polycyclic Clinical Drugs, with a Special Emphasis on Quinacrine, Cancer Research, vol. 48, No. 8, pp. 2064-2067 (1988).
Croisy-Delcey, M., et al., Dipheyl Quinolines and Isoquinolines: Synthesis and Primary Biological Evaluation, Bioorganic and Medicinal Chemistry, vol. 8, pp. 2629-2641 (2000).
Kitching, M.S., et al., Synthesis of 3-Alkoxy- and 3-Alkylamino-2-alkyl-3-arylisoindolinones, Synlett, vol. 81, pp. 997-999 (1999).
Nikitin, K.V., et al., Synthesis of 5-alkyl- and 5-aryl-1,5-dihydro-2H-pyrrol-2-ones via coupling of 5-chloro-1,5-dihydro-2H-pyrrol-2-ones with organometallic compounds, Can. J. Chem., vol. 78, pp. 1285-1288 (2000).
Truitt, P., et al., 3-Phenylphthalimidines, New Compounds, J. Med. Chem., vol. 8, pp. 731-732 (1965).
Liebl, R., et al., Notiz zur Synthese von 3-[Aklyl(aryl)thio]isoindolinonen aus 2-Formylbenzoesäure-methylester, Liebigs Ann. Chem., pp. 1093-1094 (1985).
Usov, V.A., et al., Formation of Isoquinolones and Isoindolones in the Oxidation of 2-Aryl-1-phenylamino-3-phenyliminoindenes, Chemistry of Heterocyclic Compounds (Khimiya Geterotsiklicheskikh Soedinenil), vol. 5, No. 4, pp. 474-477 (1969).
Ahmed, M., et al., Preparation of Some Isoindolo[2,1-f]phenanthridine Derivatives, J. Chem. Soc., Perkins Trans. 1, pp. 601-605 (1977).
Beanlands, D.S., et al., Therapeutic Trial of a New Oral Diuretic, Canadian Medical Association Journal, vol. 84, pp. 91-95 (1961).
Chene, P., et al. A Small Synthetic Peptide, which Inhibits the p53-hdm2 Interaction, Stimulates the p53 Pathway in Tumour Cell Lines, J. Molecular Biology, vol. 299, pp. 245-253 (2000).
Donehower, L.A., et al., Mice deficient for p53 are developmentally normal but susceptible to spontaneous tumours, Nature, vol. 356, pp. 215-221 (1992).
Epsztajn, J., et al., Application of Organolithium and Related Reagents in Synthesis. Part 23: Synthetic Strategies Based on ortho-Aromatic Metallation. Synthesis of 4b-Arylisoindolo[2,1-α]quinolone derivatives, Tetrahedron, vol. 56 pp. 4837-4844 (2000).
Ghosh, M., et al., Overexpression of Mdm2 and MdmX Fusion Proteins Alters p53 Mediated Transactivation, Ubiquitination, and Degradation, American Chemical Society, Biochemistry, vol. 42, pp. 2291-2299 (2003).
Lane, D.P., p53, guardian of the genome, Nature, vol. 358, pp. 15-16 (1992).
Levine, A.J., p53, the Cellular Gatekeeper for Growth and Division, Cell, vol. 88, pp. 323-331 (1997).
Oliner, J.D., et al., Amplification of a gene encoding a p53-associated protein in human sarcomas, Nature, vol. 358, pp. 80-83 (1992).
Schon, O., et al., Molecular Mechanism of the Interaction between MDM2 and p53, Journal of Molecular Biology, vol. 323, pp. 491-501 (2002).
Toledo, F., et al., Regulating the p53 pathway: in vitro hypotheses, in vivo veritas, Nature Reviews Cancer, vol. 6, pp. 909-923 (2006).
Vassilev, L.T., et al., In Vivo Activation of the p53 Pathway by Small-Molecule Antagonists of MDM2, Science, vol. 303, pp. 844-848 (2004).
Golik, U., The Synthesis of some 2,4-Benzodiazepin-1-ones, Potent C.N.S. Agents (I), Journal of Heterocyclic Chemistry, vol. 12, No. 5, pp. 903-908 (1975).
Hardcastle, I.R., et al., Small-Molecule Inhibitors of the MDM2-p53 Protein-Protein Interaction Based on an Isoindolinone Scaffold, Journal of Medicinal Chemistry (2006), 49(21), 6209-6221.
Suzuki, T., et al., Novel Chemoselective Desulfurization of γ-Phenylthio-Substituted Aromatic Lactams: Application to the Synthesis of Isoindolobenzazepine Alkaloid, Lennoxamine, *Synlett*, No. 20, pp. 3407-3410 (2006).
Ying, H., et Binding, The Docking Based 3D-QSAR Studies on Isoindolinone Derived Inhibitors of p53-MDM2 Binding, Letters in Drug Design & Discovery, vol. 11, pp. 50-58 (2014).
Mondal, C., et al., Comparative validated molecular modeling of p53-HDM2 inhibitors as antiproliferative agents, European Journal of Medicinal Chemistry, vol. 90, pp. 860-875 (2015).
Dong, X., et al., QSAR Models for isoindolinone-based p53-MDM2 Interaction Inhibitors Using Linear and Non-linear Statistical Methods, Chem Biol Drug Des, vol. 79, pp. 691-702 (2012).
Watson, A.F., et al., MDM2-p53 protein-protein interactions inhibitors: A-ring substituted isoindolinones, Bioorganic & Medicinal Chemistry Letters, vol. 21, pp. 5916-5919 (2011).
Riedinger, Isoindolinone C., et al., Understanding Small-Molecule Binding to MDM2: Insights into Structural Effects of Inhibitors from NMR Spectroscopy, Chem Biol Drug Des, vol. 77, pp. 301-308 (2011).
Hardcastle, I.R., et al., "Isoindolinone Inhibitors of the Murine Double Minute 2 (MDM2)-p53 Protein—Protein Interaction: Structure—Activity Studies Leading to Improved Potency", Journal of Medicinal Chemistry, vol. 54, pp. 1233-1243 (2011).
Grigoreva, T.A., et al., "Proapoptotic modification of substituted isoindolinones as MDM2-p53 inhibitors", *Bioorganic & Medicinal Chemistry Letters*, vol. 27, pp. 5197-5202 (2017).
Riedinger, C., et al., "Analysis of Chemical Shift Changes Reveals the Binding Modes of Isoindolinone Inhibitors of the MDM2-p53 Interaction", *Journal of the American Chemical Society*, vol. 130, No. 47, pp. 16038-16044 (2008).
Esfandiari et al., "Chemical Inhibition of Wild-Type p-53-Induced Phosphatase 1 (WIP1/PPM1D) by GSK2830371 Potentiates the Sensitivity to MDM2 Inhibitors in a p53-Dependent Manner," Molecular Cancer Therapeutics, Feb. 1, 2016, 379-391.
Zhang et al., "Degradation of MDM2 by the Interaction Between Berberine and DAXX Leads to Potent Apoptosis in MDM2-Overexpressing Cancer Cells," Cancer Research, Dec. 1, 2010, 9895-9904.
Howard et al., "Isoindolinone Inhibitors of the MDM2-P53 Interaction and Process for Making Them," U.S. Appl. No. 16/498,207, filed Sep. 26, 2019.
Chessari et al., "Combination of Isoindolinone Derivatives with SGI-110," U.S. Appl. No. 16/497,135, filed Sep. 24, 2019.

ISOINDOLINONE INHIBITORS OF THE MDM2-P53 INTERACTION HAVING ANTICANCER ACTIVITY

CROSS REFERENCE TO RELATED APPLICATIONS

This application is a national stage filing under section 371 of International Application No. PCT/GB2016/053041, filed on Sep. 29, 2016, and published on Apr. 6, 2017 as WO 2017/055859, which claims priority to Great Britain Application No. 1517216.6, filed on Sep. 29, 2015. The entire contents of WO 2017/055859 are hereby incorporated herein by reference.

FIELD OF THE INVENTION

The invention relates to new isoindolin-1-one derivatives, to pharmaceutical compositions comprising said compounds and to the use of said compounds in the treatment of diseases, e.g. cancer.

RELATED APPLICATIONS

This application is related to United Kingdom patent application number 1517216.6 filed 29 Sep. 2015, the contents of which are incorporated herein by reference in their entirety.

BACKGROUND OF THE INVENTION

The transformation-related protein 53 (TP53) gene encodes a 53 KDa protein—p53. The tumour suppressor protein p53 reacts to cellular stresses, such as hypoxia, DNA damage and oncogenic activation, via a number of post-translational modifications including phosphorylation, acetylation and methylation, and acts as a signalling node in the diverse pathways that become activated. p53 has additional roles in other physiological processes, including autophagy, cell adhesion, cell metabolism, fertility, and stem cell aging and development. Phosphorylation of p53, resulting from activation of kinases including ATM, CHK1 and 2, and DNA-PK, results in a stabilised and transcriptionally active form of the protein, thus producing a range of gene products. The responses to p53 activation include apoptosis, survival, cell-cycle arrest, DNA-repair, angiogenesis, invasion and autoregulation. The specific combination of which, in concert with the cell's genetic background, gives rise to the observed cellular effect i.e. apoptosis, cell-cycle arrest or senescence. For tumour cells, the apoptotic pathway may be favoured due to the loss of tumour suppressor proteins and associated cell cycle checkpoint controls, coupled with oncogenic stress.

Under conditions of stress such as hypoxia and DNA damage it is known that the cellular level of the protein p53 increases. p53 is known to initiate transcription of a number of genes which govern progression through the cell cycle, the initiation of DNA repair and programmed cell death. This provides a mechanism for the tumour suppressor role of p53 evidenced through genetic studies.

The activity of p53 is negatively and tightly regulated by a binding interaction with the MDM2 protein, the transcription of which is itself directly regulated by p53. p53 is inactivated when its transactivation domain is bound by the MDM2 protein. Once inactivated the functions of p53 are repressed and the p53-MDM2 complex becomes a target for ubiquitinylation.

In normal cells the balance between active p53 and inactive MDM2-bound p53 is maintained in an autoregulatory negative feedback loop. That is to say that p53 can activate MDM2 expression, which in turn leads to the repression of p53.

It has been found that inactivation of p53 by mutation is common in around half of all common adult sporadic cancers. Furthermore, in around 10% of tumours, gene amplification and over-expression of MDM2 results in the loss of functional p53, thereby allowing malignant transformation and uncontrolled tumour growth.

Inactivation of p53 by a range of mechanisms is a frequent causal event in the development and progression of cancer. These include inactivation by mutation, targeting by oncogenic viruses and, in a significant proportion of cases, amplification and/or an elevated rate of transcription of the MDM2 gene resulting in overexpression or increased activation of the MDM2 protein. Gene amplification of MDM2 giving rise to overexpression of MDM2 protein has been observed in tumour samples taken from common sporadic cancers. Overall, around 10% of tumours had MDM2 amplification, with the highest incidence found in hepatocellular carcinoma (44%), lung (15%), sarcomas and osteosarcomas (28%), and Hodgkin disease (67%) (Danovi et al., Mol. Cell. Biol. 2004, 24, 5835-5843, Toledo et al., Nat Rev Cancer 2006, 6, 909-923, Gembarska et al., Nat Med 2012, 18, 1239-1247). Normally, transcriptional activation of MDM2 by activated p53 results in increased MDM2 protein levels, forming a negative feedback loop. The essential nature of p53 regulation by MDM2 and MDMX is demonstrated by gene knockout mouse models. MDM2−/− knockout mice are embryonically lethal around the time of implantation. Lethality is rescued in the double knockout for Mdm2 and Trp53. MDM2 inhibits the activity of p53 directly, by binding to and occluding the p53 transactivation domain, and by promoting the proteosomal destruction of the complex, through its E3-ubiquitin ligase activity. In addition, MDM2 is a transcriptional target of p53, and so the two proteins are linked in an autoregulatory feedback loop, ensuring that p53 activation is transient.

The induction of the p14ARF protein, the alternate reading frame (ARF) product of the p16INK4a locus, is also a mechanism of negatively regulating the p53-MDM2 interaction. p14ARF directly interacts with MDM2 and leads to up-regulation of p53 transcriptional response. Loss of p14ARF by a homozygous mutation in the CDKN2A (INK4A) gene will lead to elevated levels in MDM2 and, therefore, loss of p53 function and cell cycle control.

Although MDMX shows strong amino acid sequence and structural homology to MDM2, neither protein can substitute for loss of the other; MDMX null mice die in utero, whereas MDM2 knockout is lethal during early embryogenesis, however both can be rescued by p53 knockout, demonstrating p53-dependence of the lethality. MDMX also binds p53 and inhibits p53-dependent transcription, but unlike MDM2 it is not transcriptionally activated by p53 and so does not form the same autoregulatory loop. Furthermore, MDMX has neither E3 ubiquitin ligase activity nor a nuclear localisation signal, however it is believed to contribute to p53 degradation by forming heterodimers with MDM2 and contributing to MDM2 stabilisation.

The therapeutic rationale for MDM2-p53 inhibition is that a potent inhibitor of the protein-protein interaction will liberate p53 from the repressive control of MDM2, and activate p53 mediated cell death in the tumour. In tumours, selectivity is envisioned to result from p53 sensing preexisting DNA-damage or oncogenic activation signals that had previously been blocked by the action of MDM2 at normal or overexpressed levels. In normal cells, p53 activation is anticipated to result in activation of non-apoptotic pathways and if anything a protective growth inhibition response. In addition due to the non-genotoxic mechanism of action for MDM2-p53 inhibitors they are suitable for the treatment of cancer in particular in the pediatric population.

About 50% of cancers harbour cells in which TP53, the gene that encodes for p53, is mutated resulting in a loss of the protein's tumour suppressor function and sometimes even in p53 protein versions that gain novel oncogenic functions.

Cancers where there is a high level of MDM2 amplification include liposarcoma (88%), soft tissue sarcoma (20%), osteosarcoma (16%) oesophageal cancer (13%), and certain paediatric malignancies including B-cell malignancies.

The present invention describes a novel series of compounds which selectively inhibit the MDM2-p53 interaction and which have anticancer activity.

SUMMARY OF THE INVENTION

In one aspect, the invention provides a compound of formula (I):

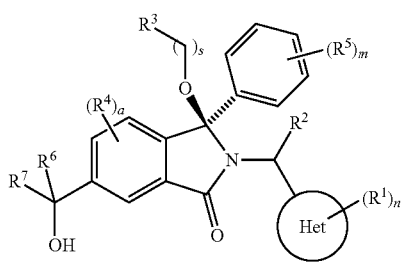

or a tautomer or a solvate or a pharmaceutically acceptable salt thereof, wherein:

Het is pyridinyl, pyrimidinyl, pyrazinyl or pyridazinyl, or an N-oxide thereof $R^1$ is attached to a carbon atom and is independently selected from hydroxy, halogen, nitro, nitrile, $C_{1-4}$alkyl, halo$C_{1-4}$alkyl, hydroxy$C_{1-4}$alkyl, $C_{2-6}$alkenyl, $C_{1-4}$alkoxy, halo$C_{1-4}$alkoxy, $C_{2-4}$alkynyl, $-O_{0,1}-(CR^xR^y)_v-CO_2H$, $-(CR^xR^y)_v-CO_2C_{1-4}$alkyl, $-(CR^xR^y)_v-CON(C_{1-4}$alkyl$)_2$, $-P(=O)(R^x)_2$, $-S(O)_d-R^x$, $-S(O)_d$-heterocyclic group with 3 to 6 ring members and $-S(O)_d-N(R^8)_2$;

$R^2$ is selected from hydrogen, $C_{1-4}$ alkyl, $C_{2-6}$alkenyl, hydroxy$C_{1-4}$alkyl, $-(CR^xR^y)_u-CO_2H$, $-(CR^xR^y)_u-CO_2C_{1-4}$alkyl, and $-(CR^xR^y)_u-CONR^xR^y$;

s is selected from 0 and 1;

$R^3$ is hydrogen or $-(A)_t-(CR^xR^y)_q-X$;

t is selected from 0 and 1;

q is selected from 0, 1 and 2;

wherein when $R^3$ is $-(A)_t-(CR^xR^y)_q-X$ then (i) at least one of s, t and q is other than 0 and (ii) when t is 0 then s is 1 and q is other than 0;

A is a $C_{3-6}$cycloalkyl group or a heterocyclic group with 3 to 6 ring members, wherein the heterocyclic group comprises one or more (e.g. 1, 2, or 3) heteroatoms selected from N, O, S and oxidised forms thereof;

X is selected from hydrogen, halogen, $-CN$, $-OR^9$, $-(CH_2)_v-CO_2H$, $-(CH_2)_v-CO_2C_{1-4}$alkyl, $-S(O)_d-R^x$, $-C(=O)-C_{1-4}$alkyl, $-S(O)_d-N(H)_e(C_{1-4}$alkyl$)_{2-e}$, $-NR^xR^y$, $-NHSO_2R^x$, $-NR^xCOR^y$, and $-C(=O)NR^xR^y$;

$R^4$ and $R^5$ are independently selected from halogen, nitrile, $C_{1-4}$ alkyl, halo$C_{1-4}$alkyl, $C_{1-4}$alkoxy and halo$C_{1-4}$alkoxy;

$R^6$ and $R^7$ are independently selected from hydrogen, $C_{1-6}$alkyl, halo$C_{1-6}$alkyl, $C_{2-6}$alkenyl, $C_{2-6}$alkynyl, hydroxy, hydroxy$C_{1-6}$alkyl, $-COOC_{1-6}$alkyl, $-(CH_2)_j-O-C_{1-6}$alkyl, $-(CH_2)_j-O$-(hydroxy$C_{1-6}$alkyl), $-C_{1-6}$alkyl-$NR^xR^y$, $-(CR^xR^y)_p-CONR^xR^y$, $-(CR^xR^y)_p-NR^xCOR^y$, $-(CR^xR^y)_p-O-CH_2-CONR^xR^y$, heterocyclic group with 3 to 7 ring members, $-CH_2$-heterocyclic group with 3 to 7 ring members, $-CH_2-O$-heterocyclic group with 3 to 7 ring members, $-CH_2-NH$-heterocyclic group with 3 to 7 ring members, $-CH_2-N(C_{1-6}$alkyl$)$-heterocyclic group with 3 to 7 ring members, $-C(=O)NH$-heterocyclic group with 3 to 7 ring members, $C_{3-8}$cycloalkyl, $-CH_2-C_{3-8}$cycloalkyl, $-CH_2-O-C_{3-8}$cycloalkyl, and $C_{3-8}$cycloalkenyl, wherein said cycloalkyl, cycloalkenyl or heterocyclic groups may be optionally substituted by one or more $R^z$ groups, and wherein in each instance the heterocyclic group comprises one or more (e.g. 1, 2, or 3) heteroatoms selected from N, O, S and oxidised forms thereof;

or the $R^6$ and $R^7$ groups, together with the carbon atom to which they are attached, can join to form a $C_{3-6}$cycloalkyl or heterocyclyl group with 3 to 6 ring members, wherein the heterocyclic group comprises one or more (e.g. 1, 2, or 3) heteroatoms selected from N, O, S and oxidised forms thereof, and wherein said $C_{3-6}$cycloalkyl and heterocyclyl groups may be optionally substituted by one or more $R^z$ groups;

$R^8$ and $R^9$ are independently selected from hydrogen, $C_{1-6}$alkyl, halo$C_{1-6}$alkyl, hydroxy$C_{1-6}$alkyl, $-(CH_2)_k-O-C_{1-6}$alkyl, $-(CH_2)_k-O$-(hydroxy$C_{1-6}$alkyl), hydroxy$C_{1-6}$alkoxy, $-(CH_2)_k-CO_2C_{1-6}$alkyl, $-(CH_2)_k-CO_2H$, $-C_{1-6}$ alkyl-$N(H)_e(C_{1-4}$alkyl$)_{2-e}$, $-(CH_2)_j-C_{3-8}$cycloalkyl and $-(CH_2)_j-C_{3-8}$cycloalkenyl;

$R^x$ and $R^y$ are independently selected from hydrogen, halogen, nitro, nitrile, $C_{1-6}$alkyl, halo$C_{1-6}$alkyl, $C_{2-6}$alkenyl, $C_{2-6}$alkynyl, hydroxy, hydroxy$C_{1-6}$alkyl, $C_{1-6}$alkoxy, $-(CH_2)_k-O-C_{1-6}$alkyl, hydroxy$C_{1-6}$alkoxy, $-COOC_{1-6}$alkyl, $-N(H)_e(C_{1-4}$alkyl$)_{2-e}$, $-C_{1-6}$alkyl-$N(H)_e(C_{1-4}$alkyl$)_{2-e}$, $-(CH_2)_k-C(=O)N(H)_e(C_{1-4}$alkyl$)_{2-e}$, $C_{3-8}$cycloalkyl and $C_{3-8}$cycloalkenyl;

or the $R^x$ and $R^y$ groups, together with the carbon or nitrogen atom to which they are attached, can join to form a $C_{3-6}$cycloalkyl or saturated heterocyclyl group with 3 to 6 ring members which may be optionally fused to an aromatic heterocyclyl group of 3 to 5 ring members;

or when on a carbon atom the $R^x$ and $R^y$ groups can join together to form a $=CH_2$ group;

$R^z$ is independently selected from halogen, nitro, nitrile, $C_{1-6}$alkyl, halo$C_{1-6}$alkyl, $C_{2-6}$alkenyl, $C_{2-6}$alkynyl, $=O$, hydroxy, hydroxy$C_{1-6}$alkyl, $C_{1-6}$alkoxy, $-(CH_2)_k-O-C_{1-6}$alkyl, hydroxy$C_{1-6}$alkoxy, $-C(=O)C_{1-6}$alkyl, $-C(=O)C_{1-6}$alkyl-OH, $-C(=O)C_{1-6}$alkyl-$N(H)_e(C_{1-4}$alkyl$)_{2-e}$, $-C(=O)N(H)_e(C_{1-4}$alkyl$)_{2-e}$, $-(CH_2)_r-CO_2C_{1-6}$alkyl, $-(CH_2)_r-CO_2H$, $-N(H)_e(C_{1-4}$alkyl$)_{2-e}$, $-C_{1-6}$alkyl-$N(H)_e(C_{1-4}$alkyl$)_{2-e}$, heterocyclyl group with 3 to 6 ring members, heterocyclyl group with 3 to 6 ring members substituted by —C(=O)C$_{1-4}$alkyl, heterocyclyl group with 3 to 6 ring members substituted by —C(=O)OC$_{1-4}$alkyl, heterocyclyl group with 3 to 6 ring members substituted by —C(=O)N(H)$_e$(C$_{1-4}$alkyl)$_{2-e}$, —C(=O)heterocyclyl group with 3 to 6 ring members, C$_{3-8}$cycloalkyl and C$_{3-8}$cycloalkenyl, wherein if R$^7$ is pyridine then R$^z$ is other then —NH$_2$;

a, j, d, e, n, r and p are independently selected from 0, 1 and 2;

k and m are independently selected from 1 and 2;

u is selected from 0, 1, 2 and 3; and v and w are independently selected from 0 and 1.

In a further aspect aspect, the invention provides a compound of formula (I):

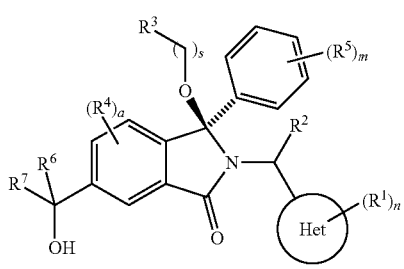

(I)

or a tautomer or a solvate or a pharmaceutically acceptable salt thereof, wherein:

Het is pyridinyl, pyrimidinyl, pyrazinyl or pyridazinyl, or an N-oxide thereof

R$^1$ is attached to a carbon atom and is independently selected from hydroxy, halogen, nitro, nitrile, C$_{1-4}$alkyl, haloC$_{1-4}$alkyl, hydroxyC$_{1-4}$alkyl, C$_{2-6}$alkenyl, C$_{1-4}$alkoxy, haloC$_{1-4}$alkoxy, C$_{2-4}$alkynyl, —(CR$^x$R$^y$)$_v$—CO$_2$H, —(CR$^x$R$^y$)$_v$—CO$_2$C$_{1-4}$alkyl, —(CR$^x$R$^y$)$_v$—CON(C$_{1-4}$alkyl)$_2$, —P(=O)(R$^x$)$_2$, —S(O)$_d$—R$^x$, —S(O)$_d$-heterocyclic group with 3 to 6 ring members and —S(O)$_d$—N(R$^8$)$_2$;

R$^2$ is selected from hydrogen, C$_{1-4}$ alkyl, C$_{2-6}$alkenyl, hydroxyC$_{1-4}$alkyl, —(CR$^x$R$^y$)$_u$—CO$_2$H, —(CR$^x$R$^y$)$_u$—CO$_2$C$_{1-4}$alkyl, and —(CR$^x$R$^y$)$_u$—CONR$^x$R$^y$;

s is selected from 0 and 1;

R$^3$ is hydrogen or -(A)$_t$-(CR$^x$R$^y$)$_q$—X;

t is selected from 0 and 1;

q is selected from 0, 1 and 2;

wherein when R$^3$ is -(A)$_t$-(CR$^x$R$^y$)$_q$—X then (i) at least one of s, t and q is other than 0 and (ii) when t is 0 then s is 1 and q is other than 0;

A is a C$_{3-6}$cycloalkyl group or a heterocyclic group with 3 to 6 ring members, wherein the heterocyclic group comprises one or more (e.g. 1, 2, or 3) heteroatoms selected from N, O, S and oxidised forms thereof;

X is selected from hydrogen, halogen, —CN, —OR$^9$, —(CH$_2$)$_v$—CO$_2$H, —(CH$_2$)$_v$—CO$_2$C$_{1-4}$alkyl, —S(O)$_d$—R$^x$, —C(=O)—C$_{1-4}$alkyl, —S(O)$_d$—N(H)$_e$(C$_{1-4}$alkyl)$_{2-e}$, —NR$^x$R$^y$, —NHSO$_2$R$^x$, —NR$^x$COR$^y$, and —C(=O)NR$^x$R$^y$;

R$^4$ and R$^5$ are independently selected from halogen, nitrile, C$_{1-4}$ alkyl, haloC$_{1-4}$alkyl, C$_{1-4}$alkoxy and haloC$_{1-4}$alkoxy;

R$^6$ and R$^7$ are independently selected from hydrogen, C$_{1-6}$alkyl, haloC$_{1-6}$alkyl, C$_{2-6}$alkenyl, C$_{2-6}$alkynyl, hydroxy, hydroxyC$_{1-6}$alkyl, —COOC$_{1-6}$alkyl, —(CH$_2$)$_j$—O—C$_{1-6}$alkyl, —(CH$_2$)$_j$—O—(hydroxy C$_{1-6}$alkyl), —C$_{1-6}$alkyl-NR$^x$R$^y$, —(CR$^x$R$^y$)$_p$—CON-R$^x$R$^y$, —(CR$^x$R$^y$)$_p$—NR$^x$COR$^y$, —(CR$^x$R$^y$)$_p$—O—CH$_2$—CONR$^x$R$^y$, heterocyclic group with 3 to 7 ring members, —CH$_2$-heterocyclic group with 3 to 7 ring members, —CH$_2$—O-heterocyclic group with 3 to 7 ring members, —CH$_2$—NH-heterocyclic group with 3 to 7 ring members, —CH$_2$—N(C$_{1-6}$alkyl)-heterocyclic group with 3 to 7 ring members, —C(=O)NH-heterocyclic group with 3 to 7 ring members, C$_{3-8}$cycloalkyl, —CH$_2$—C$_{3-8}$cycloalkyl, —CH$_2$—O—C$_{3-8}$cycloalkyl, and C$_{3-8}$cycloalkenyl, wherein said cycloalkyl, cycloalkenyl or heterocyclic groups may be optionally substituted by one or more R$^z$ groups, and wherein in each instance the heterocyclic group comprises one or more (e.g. 1, 2, or 3) heteroatoms selected from N, O, S and oxidised forms thereof;

or the R$^6$ and R$^7$ groups, together with the carbon atom to which they are attached, can join to form a C$_{3-6}$cycloalkyl or heterocyclyl group with 3 to 6 ring members, wherein the heterocyclic group comprises one or more (e.g. 1, 2, or 3) heteroatoms selected from N, O, S and oxidised forms thereof, and wherein said C$_{3-6}$cycloalkyl and heterocyclyl groups may be optionally substituted by one or more R$^z$ groups;

R$^8$ and R$^9$ are independently selected from hydrogen, C$_{1-6}$alkyl, haloC$_{1-6}$alkyl, hydroxyC$_{1-6}$alkyl, —(CH$_2$)$_k$—O—C$_{1-6}$alkyl, —(CH$_2$)$_k$—O-(hydroxy C$_{1-6}$alkyl), hydroxyC$_{1-6}$alkoxy, —(CH$_2$)$_k$—CO$_2$C$_{1-6}$alkyl, —(CH$_2$)$_k$—CO$_2$H, —C$_{1-6}$ alkyl-N(H)$_e$(C$_{1-4}$alkyl)$_{2-e}$, —(CH$_2$)$_j$—C$_{3-8}$cycloalkyl and —(CH$_2$)$_j$—C$_{3-8}$cycloalkenyl;

R$^x$ and R$^y$ are independently selected from hydrogen, halogen, nitro, nitrile, C$_{1-6}$alkyl, haloC$_{1-6}$alkyl, C$_{2-6}$alkenyl, C$_{2-6}$alkynyl, hydroxy, hydroxyC$_{1-6}$alkyl, C$_{1-6}$alkoxy, —(CH$_2$)$_k$—O—C$_{1-6}$alkyl, hydroxy C$_{1-6}$alkoxy, —COOC$_{1-6}$alkyl, —N(H)$_e$(C$_{1-4}$alkyl)$_{2-e}$, —C$_{1-6}$alkyl-N(H)$_e$(C$_{1-4}$alkyl)$_{2-e}$, —(CH$_2$)$_k$—C(=O)N(H)$_e$(C$_{1-4}$alkyl)$_{2-e}$, C$_{3-8}$cycloalkyl and C$_{3-8}$cycloalkenyl;

or the R$^x$ and R$^y$ groups, together with the carbon or nitrogen atom to which they are attached, can join to form a C$_{3-6}$cycloalkyl or saturated heterocyclyl group with 3 to 6 ring members which may be optionally fused to an aromatic heterocyclyl group of 3 to 5 ring members;

or when on a carbon atom the R$^x$ and R$^y$ groups can join together to form a =CH$_2$ group;

R$^z$ is independently selected from halogen, nitro, nitrile, C$_{1-6}$alkyl, haloC$_{1-6}$alkyl, C$_{2-6}$alkenyl, C$_{2-6}$alkynyl, =O, hydroxy, hydroxyC$_{1-6}$alkyl, C$_{1-6}$alkoxy, —(CH$_2$)$_k$—O—C$_{1-6}$alkyl, hydroxyC$_{1-6}$alkoxy, —C(=O)C$_{1-6}$alkyl, —C(=O)C$_{1-6}$alkyl-OH, —C(=O)C$_{1-6}$alkyl-N(H)$_e$(C$_{1-4}$alkyl)$_{2-e}$, —C(=O)N(H)$_e$(C$_{1-4}$alkyl)$_{2-e}$, —(CH$_2$)$_r$—CO$_2$C$_{1-6}$alkyl, —(CH$_2$)$_r$—CO$_2$H, —N(H)$_e$(C$_{1-4}$alkyl)$_{2-e}$, —C$_{1-6}$alkyl-N(H)$_e$(C$_{1-4}$alkyl)$_{2-e}$, heterocyclyl group with 3 to 6 ring members, heterocyclyl group with 3 to 6 ring members substituted by —C(=O)C$_{1-4}$alkyl, heterocyclyl group with 3 to 6 ring members substituted by —C(=O)OC$_{1-4}$alkyl, heterocyclyl group with 3 to 6 ring members substituted by —C(=O)N(H)$_e$(C$_{1-4}$alkyl)$_{2-e}$, —C(=O)heterocyclyl group with 3 to 6 ring members, C$_{3-8}$cycloalkyl and C$_{3-8}$cycloalkenyl, wherein if R$^7$ is pyridine then R$^z$ is other then —NH$_2$;

a, j, d, e, n, r and p are independently selected from 0, 1 and 2;

k and m are independently selected from 1 and 2;

u is selected from 0, 1, 2 and 3; and v and w are independently selected from 0 and 1.

In further aspects of the invention there is provided a compound of formula (I) for use in the prophylaxis or treatment of a disease or condition as described herein, methods for the prophylaxis or treatment of a disease or condition as described herein comprising administering to a patient a compound of formula (I), pharmaceutical compositions comprising a compound of formula (I) and processes for the synthesis of a compound of formula (I).

Definitions

Unless the context indicates otherwise, references to formula (I) in all sections of this document (including the uses, methods and other aspects of the invention) include references to all other sub-formula, sub-groups, embodiments and examples as defined herein.

"Potency" is a measure of drug activity expressed in terms of the amount required to produce an effect of given intensity. A highly potent drug evokes a larger response at low concentrations. Potency is proportional to affinity and efficacy. Affinity is the ability of the drug to bind to a receptor. Efficacy is the relationship between receptor occupancy and the ability to initiate a response at the molecular, cellular, tissue or system level.

The term "antagonist" refers to a type of receptor ligand or drug that blocks or dampens agonist-mediated biological responses. Antagonists have affinity but no agonistic efficacy for their cognate receptors, and binding will disrupt the interaction and inhibit the function of any ligand (e.g. endogenous ligands or substrates, an agonist or inverse agonist) at receptors. The antagonism may arise directly or indirectly, and may be mediated by any mechanism and at any physiological level. As a result, antagonism of ligands may under different circumstances manifest itself in functionally different ways. Antagonists mediate their effects by binding to the active site or to allosteric sites on receptors, or they may interact at unique binding sites not normally involved in the biological regulation of the receptor's activity. Antagonist activity may be reversible or irreversible depending on the longevity of the antagonist-receptor complex, which, in turn, depends on the nature of antagonist receptor binding.

As used herein, the term "mediated", as used e.g. in conjunction with MDM2/p53 as described herein (and applied for example to various physiological processes, diseases, states, conditions, therapies, treatments or interventions) is intended to operate limitatively so that the various processes, diseases, states, conditions, treatments and interventions to which the term is applied are those in which the protein plays a biological role. In cases where the term is applied to a disease, state or condition, the biological role played by the protein may be direct or indirect and may be necessary and/or sufficient for the manifestation of the symptoms of the disease, state or condition (or its aetiology or progression). Thus, the protein function (and in particular aberrant levels of function, e.g. over- or under-expression) need not necessarily be the proximal cause of the disease, state or condition: rather, it is contemplated that the mediated diseases, states or conditions include those having multifactorial aetiologies and complex progressions in which the protein in question is only partially involved. In cases where the term is applied to treatment, prophylaxis or intervention, the role played by the protein may be direct or indirect and may be necessary and/or sufficient for the operation of the treatment, prophylaxis or outcome of the intervention. Thus, a disease state or condition mediated by a protein includes the development of resistance to any particular cancer drug or treatment.

The term "treatment" as used herein in the context of treating a condition i.e. state, disorder or disease, pertains generally to treatment and therapy, whether for a human or an animal (e.g. in veterinary applications), in which some desired therapeutic effect is achieved, for example, the inhibition of the progress of the condition, and includes a reduction in the rate of progress, a halt in the rate of progress, amelioration of the condition, diminishment or alleviation of at least one symptom associated or caused by the condition being treated and cure of the condition. For example, treatment can be diminishment of one or several symptoms of a disorder or complete eradication of a disorder.

The term "prophylaxis" (i.e. use of a compound as prophylactic measure) as used herein in the context of treating a condition i.e. state, disorder or disease, pertains generally to the prophylaxis or prevention, whether for a human or an animal (e.g. in veterinary applications), in which some desired preventative effect is achieved, for example, in preventing occurrence of a disease or guarding from a disease. Prophylaxis includes complete and total blocking of all symptoms of a disorder for an indefinite period of time, the mere slowing of the onset of one or several symptoms of the disease, or making the disease less likely to occur.

References to the prophylaxis or treatment of a disease state or condition such as cancer include within their scope alleviating or reducing the incidence e.g. of cancer.

The combinations of the invention may produce a therapeutically efficacious effect relative to the therapeutic effect of the individual compounds/agents when administered separately.

The term 'efficacious' includes advantageous effects such as additivity, synergism, reduced side effects, reduced toxicity, increased time to disease progression, increased time of survival, sensitization or resensitization of one agent to another, or improved response rate. Advantageously, an efficacious effect may allow for lower doses of each or either component to be administered to a patient, thereby decreasing the toxicity of chemotherapy, whilst producing and/or maintaining the same therapeutic effect. A "synergistic" effect in the present context refers to a therapeutic effect produced by the combination which is larger than the sum of the therapeutic effects of the agents of the combination when presented individually. An "additive" effect in the present context refers to a therapeutic effect produced by the combination which is larger than the therapeutic effect of any of the agents of the combination when presented individually. The term "response rate" as used herein refers, in the case of a solid tumour, to the extent of reduction in the size of the tumour at a given time point, for example 12 weeks. Thus, for example, a 50% response rate means a reduction in tumour size of 50%. References herein to a "clinical response" refer to response rates of 50% or greater. A "partial response" is defined herein as being a response rate of less than 50%.

As used herein, the term "combination", as applied to two or more compounds and/or agents, is intended to define material in which the two or more agents are associated. The terms "combined" and "combining" in this context are to be interpreted accordingly.

The association of the two or more compounds/agents in a combination may be physical or non-physical. Examples of physically associated combined compounds/agents include:

compositions (e.g. unitary formulations) comprising the two or more compounds/agents in admixture (for example within the same unit dose);

compositions comprising material in which the two or more compounds/agents are chemically/physicochemically linked (for example by crosslinking, molecular agglomeration or binding to a common vehicle moiety);

compositions comprising material in which the two or more compounds/agents are chemically/physicochemically co-packaged (for example, disposed on or within lipid vesicles, particles (e.g. micro- or nanoparticles) or emulsion droplets);

pharmaceutical kits, pharmaceutical packs or patient packs in which the two or more compounds/agents are co-packaged or co-presented (e.g. as part of an array of unit doses);

Examples of non-physically associated combined compounds/agents include:

material (e.g. a non-unitary formulation) comprising at least one of the two or more compounds/agents together with instructions for the extemporaneous association of the at least one compound to form a physical association of the two or more compounds/agents;

material (e.g. a non-unitary formulation) comprising at least one of the two or more compounds/agents together with instructions for combination therapy with the two or more compounds/agents;

material comprising at least one of the two or more compounds/agents together with instructions for administration to a patient population in which the other(s) of the two or more compounds/agents have been (or are being) administered;

material comprising at least one of the two or more compounds/agents in an amount or in a form which is specifically adapted for use in combination with the other(s) of the two or more compounds/agents.

As used herein, the term "combination therapy" is intended to define therapies which comprise the use of a combination of two or more compounds/agents (as defined above). Thus, references to "combination therapy", "combinations" and the use of compounds/agents "in combination" in this application may refer to compounds/agents that are administered as part of the same overall treatment regimen. As such, the posology of each of the two or more compounds/agents may differ: each may be administered at the same time or at different times. It will therefore be appreciated that the compounds/agents of the combination may be administered sequentially (e.g. before or after) or simultaneously, either in the same pharmaceutical formulation (i.e. together), or in different pharmaceutical formulations (i.e. separately). Simultaneously in the same formulation is as a unitary formulation whereas simultaneously in different pharmaceutical formulations is non-unitary. The posologies of each of the two or more compounds/agents in a combination therapy may also differ with respect to the route of administration.

As used herein, the term "pharmaceutical kit" defines an array of one or more unit doses of a pharmaceutical composition together with dosing means (e.g. measuring device) and/or delivery means (e.g. inhaler or syringe), optionally all contained within common outer packaging. In pharmaceutical kits comprising a combination of two or more compounds/agents, the individual compounds/agents may unitary or non-unitary formulations. The unit dose(s) may be contained within a blister pack. The pharmaceutical kit may optionally further comprise instructions for use.

As used herein, the term "pharmaceutical pack" defines an array of one or more unit doses of a pharmaceutical composition, optionally contained within common outer packaging. In pharmaceutical packs comprising a combination of two or more compounds/agents, the individual compounds/agents may unitary or non-unitary formulations. The unit dose(s) may be contained within a blister pack. The pharmaceutical pack may optionally further comprise instructions for use.

The term 'optionally substituted' as used herein refers to a group which may be unsubstituted or substituted by a substituent as herein defined.

The prefix "$C_{x-y}$" (where x and y are integers) as used herein refers to the number of carbon atoms in a given group. Thus, a $C_{1-6}$ alkyl group contains from 1 to 6 carbon atoms, a $C_{3-6}$ cycloalkyl group contains from 3 to 6 carbon atoms, a $C_{1-4}$ alkoxy group contains from 1 to 4 carbon atoms, and so on.

The term 'halo' or 'halogen' as used herein refers to fluorine, chlorine, bromine or iodine, in particular fluorine or chlorine.

Each and every hydrogen in the compound (such as in an alkyl group or where referred to as hydrogen) includes all isotopes of hydrogen, in particular $^1$H and $^2$H (deuterium).

The term 'oxo' as used herein refers to the group =O.

The term '$C_{1-4}$alkyl' as used herein as a group or part of a group refers to a linear or branched saturated hydrocarbon group containing from 1 to 4 carbon atoms respectively. Examples of such groups include methyl, ethyl, n-propyl, isopropyl, n-butyl, isobutyl, sec-butyl, tert butyl and the like.

The term '$C_{2-4}$alkenyl' or '$C_{2-6}$alkenyl' as used herein as a group or part of a group refers to a linear or branched hydrocarbon group containing from 2 to 4, or 2 to 6 carbon atoms, respectively, and containing a carbon carbon double bond. Examples of such groups include $C_{3-4}$alkenyl or $C_{3-6}$alkenyl groups, such as ethenyl (vinyl), 1-propenyl, 2-propenyl (allyl), isopropenyl, butenyl, buta-1,4-dienyl, pentenyl, and hexenyl.

The term '$C_{2-4}$alkynyl' or '$C_{2-6}$alkynyl' as used herein as a group or part of a group refers to a linear or branched hydrocarbon group having from 2 to 4 or 2 to 6 carbon atoms, respectively, and containing a carbon carbon triple bond. Examples of such groups include $C_{3-4}$alkynyl or $C_{3-6}$alkynyl groups such as ethynyl and 2 propynyl (propargyl) groups.

The term '$C_{1-4}$alkoxy' as used herein as a group or part of a group refers to an —O—$C_{1-4}$alkyl group wherein $C_{1-4}$alkyl is as defined herein. Examples of such groups include methoxy, ethoxy, propoxy, butoxy, and the like.

The term '$C_{3-6}$cycloalkyl' as used herein refers to a saturated monocyclic hydrocarbon ring of 3 to 6 carbon atoms. Examples of such groups include cyclopropyl, cyclobutyl, cyclopentyl or cyclohexyl and the like.

The term '$C_{3-6}$cycloalkenyl' as used herein refers to a partially saturated monocyclic hydrocarbon ring of 3 to 6 carbon atoms having one or more (usually one) carbon carbon double bond(s). Examples of such groups include cyclopentenyl, cyclohexenyl, and cyclohexadienyl.

The term 'hydroxy$C_{1-4}$alkyl' as used herein as a group or part of a group refers to a $C_{1-4}$alkyl group as defined herein wherein one or more (e.g. 1, 2 or 3) than one hydrogen atom is replaced with a hydroxyl group. The term 'hydroxy $C_{1-4}$alkyl' therefore includes monohydroxy$C_{1-4}$ alkyl, and also polyhydroxy$C_{1-4}$ alkyl. There may be one, two, three or more hydrogen atoms replaced with a hydroxyl group, so the hydroxy$C_{1-4}$alkyl may have one, two, three or more hydroxyl groups. Examples of such groups include hydroxymethyl, hydroxyethyl, hydroxypropyl and the like.

The term 'haloC$_{1-4}$alkyl' as used herein as a group or part of a group refers to a C$_{1-4}$alkyl group as defined herein wherein one or more (e.g. 1, 2 or 3) than one hydrogen atom is replaced with a halogen. The term 'haloC$_{1-4}$alkyl' therefore includes monohaloC$_{1-4}$alkyl and also polyhalo C$_{1-4}$alkyl.

There may be one, two, three or more hydrogen atoms replaced with a halogen, so the haloC$_{1-4}$alkyl may have one, two, three or more halogens. Examples of such groups include fluoroethyl, fluoromethyl, difluoromethyl, trifluoromethyl or trifluoroethyl and the like.

The term 'haloC$_{1-4}$alkoxy' as used herein as a group or part of a group refers to a —O—C$_{1-4}$alkyl group as defined herein wherein one or more (e.g. 1, 2 or 3) than one hydrogen atom is replaced with a halogen. The terms 'haloC$_{1-4}$alkoxy' therefore include monohaloC$_{1-4}$alkoxy, and also polyhaloC$_{1-4}$alkoxy. There may be one, two, three or more hydrogen atoms replaced with a halogen, so the haloC$_{1-4}$alkoxy may have one, two, three or more halogens. Examples of such groups include fluoroethyloxy, difluoromethoxy or trifluoromethoxy and the like.

The term "heterocyclyl group" as used herein shall, unless the context indicates otherwise, include both aromatic and non-aromatic ring systems. Thus, for example, the term "heterocyclyl group" include within their scope aromatic, non-aromatic, unsaturated, partially saturated and saturated heterocyclyl ring systems. In general, unless the context indicates otherwise, such groups may be monocyclic or bicyclic (including fused, spiro and bridged bicyclic groups) and may contain, for example, 3 to 12 ring members, more usually 5 to 10 ring members. Reference to 4 to 7 ring members includes 4, 5, 6 or 7 atoms in the ring and reference to 4 to 6 ring members include 4, 5, or 6 atoms in the ring. Examples of monocyclic groups are groups containing 3, 4, 5, 6, 7 and 8 ring members, more usually 3 to 7, or 4 to 7 and preferably 5, 6 or 7 ring members, more preferably 5 or 6 ring members. Examples of bicyclic groups are those containing 8, 9, 10, 11 and 12 ring members, and more usually 9 or 10 ring members. The heterocyclyl groups can be heteroaryl groups having from 5 to 12 ring members, more usually from 5 to 10 ring members. Where reference is made herein to a heterocyclyl group, the heterocyclyl ring can, unless the context indicates otherwise, be optionally substituted i.e. unsubstituted or substituted, by one or more (e.g. 1, 2, 3, or 4 in particular one or two) substituents as defined herein.

The heterocyclyl group can be, for example, a five membered or six membered monocyclic ring or a bicyclic structure formed from fused five and six membered rings or two fused six membered rings, or two fused five membered rings. Each ring may contain up to five heteroatoms particularly selected from nitrogen, sulfur and oxygen and oxidised forms of nitrogen or sulfur. Particularly the heterocyclyl ring will contain up to 4 heteroatoms, more particularly up to 3 heteroatoms, more usually up to 2, for example a single heteroatom. In one embodiment, the heterocyclyl ring will contain one or two heteroatoms selected from N, O, S and oxidised forms of N or S. In one embodiment, the heterocyclyl ring contains at least one ring nitrogen atom. The nitrogen atoms in the heterocyclyl rings can be basic, as in the case of an imidazole or pyridine, or essentially non-basic as in the case of an indole or pyrrole nitrogen. In general the number of basic nitrogen atoms present in the heterocyclyl group, including any amino group substituents of the ring, will be less than five.

The heterocyclyl groups can be attached via a carbon atom or a heteroatom (e.g. nitrogen). Equally the heterocyclyl groups can be substituted on a carbon atom or on a heteroatom (e.g. nitrogen).

Examples of five membered aromatic heterocyclyl groups include but are not limited to pyrrolyl, furanyl, thienyl, imidazolyl, furazanyl, oxazolyl, oxadiazolyl, oxatriazolyl, isoxazolyl, thiazolyl, thiadiazolyl, isothiazolyl, pyrazolyl, triazolyl and tetrazolyl groups.

Examples of six membered aromatic heterocyclic groups include but are not limited to pyridinyl, pyrazinyl, pyridazinyl, pyrimidinyl and triazinyl.

The term "heteroaryl" is used herein to denote a heterocyclyl group having aromatic character. The term "heteroaryl" embraces polycyclic (e.g. bicyclic) ring systems wherein one or more rings are non-aromatic, provided that at least one ring is aromatic. In such polycyclic systems, the group may be attached by the aromatic ring, or by a non-aromatic ring.

Examples of heteroaryl groups are monocyclic and bicyclic groups containing from five to twelve ring members, and more usually from five to ten ring members.

Examples of five membered heteroaryl groups include but are not limited to pyrrole, furan, thiophene, imidazole, furazan, oxazole, oxadiazole, oxatriazole, isoxazole, thiazole, thiadiazole, isothiazole, pyrazole, triazole and tetrazole groups.

Examples of six membered heteroaryl groups include but are not limited to pyridine, pyrazine, pyridazine, pyrimidine and triazine.

A bicyclic heteroaryl group may be, for example, a group selected from:
  a) a benzene ring fused to a 5- or 6-membered ring containing 1, 2 or 3 ring heteroatoms;
  b) a pyridine ring fused to a 5- or 6-membered ring containing 0, 1, 2 or 3 ring heteroatoms;
  c) a pyrimidine ring fused to a 5- or 6-membered ring containing 0, 1 or 2 ring heteroatoms;
  d) a pyrrole ring fused to a 5- or 6-membered ring containing 0, 1, 2 or 3 ring heteroatoms;
  e) a pyrazole ring fused to a 5- or 6-membered ring containing 0, 1 or 2 ring heteroatoms;
  f) an imidazole ring fused to a 5- or 6-membered ring containing 0, 1 or 2 ring heteroatoms;
  g) an oxazole ring fused to a 5- or 6-membered ring containing 0, 1 or 2 ring heteroatoms;
  h) an isoxazole ring fused to a 5- or 6-membered ring containing 0, 1 or 2 ring heteroatoms;
  i) a thiazole ring fused to a 5- or 6-membered ring containing 0, 1 or 2 ring heteroatoms;
  j) an isothiazole ring fused to a 5- or 6-membered ring containing 0, 1 or 2 ring heteroatoms;
  k) a thiophene ring fused to a 5- or 6-membered ring containing 0, 1, 2 or 3 ring heteroatoms;
  l) a furan ring fused to a 5- or 6-membered ring containing 0, 1, 2 or 3 ring heteroatoms;
  m) a cyclohexyl ring fused to a 5- or 6-membered ring containing 1, 2 or 3 ring heteroatoms; and
  n) a cyclopentyl ring fused to a 5- or 6-membered ring containing 1, 2 or 3 ring heteroatoms.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo[1,2-a]imidazole).

Particular examples of bicyclic heteroaryl groups containing a six membered ring fused to a five membered ring include but are not limited to benzofuran, benzothiophene, benzimidazole, benzoxazole, isobenzoxazole, benzisoxazole, benzothiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), triazolopyrimidine (e.g. [1,2,4]triazolo[1,5-a]pyrimidine), benzodioxole, imidazopyridine and pyrazolopyridine (e.g. pyrazolo[1,5-a]pyridine) groups.

Particular examples of bicyclic heteroaryl groups containing two fused six membered rings include but are not limited to quinoline, isoquinoline, chroman, thiochroman, isochroman, chromene, isochromene, benzodioxan, quinolizine, benzoxazine, pyridopyridine, quinoxaline, quinazoline, cinnoline, phthalazine, naphthyridine and pteridine groups.

Examples of polycyclic heteroaryl groups containing an aromatic ring and a non-aromatic ring include, tetrahydroisoquinoline, tetrahydroquinoline, dihydrobenzthiophene, dihydrobenzofuran, 2,3-dihydro-benzo[1,4]dioxine, benzo[1,3]dioxole, 4,5,6,7-tetrahydrobenzofuran, tetrahydrotriazolopyrazine (e.g. 5,6,7,8-tetrahydro-[1,2,4]triazolo[4,3-a]pyrazine), chroman, thiochroman, isochroman, chromene, isochromene, benzodioxan, benzoxazine, benzodiazepine, and indoline groups.

A nitrogen-containing heteroaryl ring must contain at least one ring nitrogen atom. The nitrogen-containing heteroaryl ring can be N-linked or C-linked. Each ring may, in addition, contain up to about four other heteroatoms particularly selected from nitrogen, sulfur and oxygen. Particularly the heteroaryl ring will contain up to 3 heteroatoms, for example 1, 2 or 3, more usually up to 2 nitrogens, for example a single nitrogen. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of nitrogen-containing heteroaryl groups include, but are not limited to, monocyclic groups such as pyridinyl, pyrrolyl, imidazolyl, oxazolyl, oxadiazolyl, thiadiazolyl, oxatriazolyl, isoxazolyl, thiazolyl, isothiazolyl, furazanyl, pyrazolyl, pyrazinyl, pyrimidinyl, pyridazinyl, triazinyl, triazolyl (e.g., 1,2,3-triazolyl, 1,2,4-triazolyl), tetrazolyl, and bicyclic groups such as quinolinyl, isoquinolinyl, benzimidazolyl, benzoxazolyl, benzisoxazole, benzothiazolyl and benzisothiazole, indolyl, 3H-indolyl, isoindolyl, indolizinyl, isoindolinyl, purinyl (e.g., adenine [6-aminopurine], guanine [2-amino-6-hydroxypurine]), indazolyl, quinolizinyl, benzoxazinyl, benzodiazepinyl, pyridopyridinyl, quinoxalinyl, quinazolinyl, cinnolinyl, phthalazinyl, naphthyridinyl and pteridinyl.

Examples of nitrogen-containing polycyclic heteroaryl groups containing an aromatic ring and a non-aromatic ring include tetrahydroisoquinolinyl, tetrahydroquinolinyl, and indolinyl.

The term "non-aromatic" embraces, unless the context indicates otherwise, unsaturated ring systems without aromatic character, partially saturated and saturated heterocyclyl ring systems. The terms "unsaturated" and "partially saturated" refer to rings wherein the ring structure(s) contains atoms sharing more than one valence bond i.e. the ring contains at least one multiple bond e.g. a C=C, C≡C or N=C bond. The term "saturated" refers to rings where there are no multiple bonds between ring atoms. Saturated heterocyclyl groups include piperidinyl, morpholinyl, and thiomorpholinyl. Partially saturated heterocyclyl groups include pyrazolinyl, for example pyrazolin-2-yl and pyrazolin-3-yl.

Examples of non-aromatic heterocyclyl groups are groups having from 3 to 12 ring members, more usually 5 to 10 ring members. Such groups can be monocyclic or bicyclic, for example, have 3 to 7 ring members in particular 4 to 6 ring members. Such groups particularly have from 1 to 5 or 1 to 4 heteroatom ring members (more usually 1, 2, or 3 heteroatom ring members), usually selected from nitrogen, oxygen and sulfur and oxidised forms thereof. The heterocyclyl groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic amide moieties (e.g. as in pyrrolidone), cyclic thioamides, cyclic thioesters, cyclic ureas (e.g. as in imidazolidin-2-one) cyclic ester moieties (e.g. as in butyrolactone), cyclic sulfones (e.g. as in sulfolane and sulfolene), cyclic sulfoxides, cyclic sulfonamides and combinations thereof (e.g. thiomorpholine).

Particular examples include morpholinyl, piperidinyl (e.g. piperidin-1-yl, piperidin-2-yl, piperidin-3-yl and piperidin-4-yl), piperidinonyl, pyrrolidinyl (e.g. pyrrolidin-1-yl, pyrrolidin-2-yl and pyrrolidin-3-yl), pyrrolidonyl, azetidinyl, pyranyl (2H-pyran or 4H-pyran), dihydrothienyl, dihydropyranyl, dihydrofuranyl, dihydrothiazolyl, tetrahydrofuranyl, tetrahydrothienyl, dioxanyl, oxanyl (also known as tetrahydropyranyl) (e.g. oxan-4-yl), imidazolinyl, imidazolidinonyl, oxazolinyl, thiazolinyl, pyrazolin-2-yl, pyrazolidinyl, piperazinonyl, piperazinyl, and N-alkyl piperazines such as N-methyl piperazinyl. In general, typical non-aromatic heterocyclyl groups include saturated groups such as piperidinyl, pyrrolidinyl, azetidinyl, morpholinyl, piperazinyl and N-alkyl piperazines such as N-methyl piperazinyl.

The terms "oxan" and "oxanyl" as used herein refer to the group:

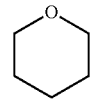

which may also be referred to as "tetrahydropyran" or "tetrahydropyranyl".

In a nitrogen-containing non-aromatic heterocyclyl ring the ring must contain at least one ring nitrogen atom. The nitrogen-containing heterocyclyl ring can be N-linked or C-linked. The heterocylic groups can contain, for example, cyclic amine moieties (e.g. as in pyrrolidinyl), cyclic amides (such as a pyrrolidinonyl, piperidinonyl or caprolactamyl), cyclic sulfonamides (such as an isothiazolidinyl 1,1-dioxide, [1,2]thiazinanyl 1,1-dioxide or [1,2]thiazepanyl 1,1-dioxide) and combinations thereof.

Particular examples of nitrogen-containing non-aromatic heterocyclyl groups include aziridinyl, morpholinyl, thiomorpholinyl, piperidinyl (e.g. piperidin-1-yl, piperidin-2yl, piperidin-3-yl and piperidin-4-yl), pyrrolidinyl; (e.g. pyrrolidin-1-yl, pyrrolidin-2-yl and pyrrolidin-3-yl), pyrrolidonyl, dihydrothiazolyl, imidazolinyl, imidazolidinonyl, oxazolinyl, thiazolinyl, 6H-1,2,5-thiadiazinyl, pyrazolin-2-yl, pyrazolin-3-yl, pyrazolidinyl, piperazinyl, and N-alkyl piperazines such as N-methyl piperazinyl.

The heterocyclyl groups can be polycyclic fused ring systems or bridged ring systems such as the oxa- and aza analogues of bicycloalkanes, tricycloalkanes (e.g. adamantane and oxa-adamantane). For an explanation of the distinction between fused and bridged ring systems, see Advanced Organic Chemistry, by Jerry March, 4th Edition, Wiley Interscience, pages 131-133, 1992.

Where, in a definition of a cyclic group or ring, it is stated that the cyclic group contains a certain number of heteroatom ring members, e.g. as in the phrase "a 5 or 6 membered ring containing 0, 1 or 2 nitrogen ring members", this is to be taken as meaning that apart from the certain number of heteroatom ring members specified, the remaining ring members are carbon atoms.

The compound of formula (I) may contain saturated cyclic groups that can be joined to the rest of the molecule by one or more bonds. When the cyclic group is joined to the rest of the molecule by two or more bonds, these bonds (or two of these bonds) can be made to the same atom (usually a carbon atom) of the ring or different atoms of the ring. Where the bonds are made to the same atom of the ring, this results in a cyclic group with a single atom (usually a quaternary carbon) bound to two groups. In other words, when the compound of formula (I) includes a cyclic group that group may either be linked to the rest of the molecule by a bond or the cyclic group and the rest of the molecule can have an atom in common e.g. a spiro compound.

The heterocyclyl group can each be unsubstituted or substituted by one or more (e.g. 1, 2 or 3) substituent groups. For example, heterocyclyl or carbocyclyl groups can be unsubstituted or substituted by 1, 2, 3 or 4 substituents and particularly it is unsubstituted or has 1, 2 or 3 substituents as defined herein. Where the cyclic group is saturated there may be 2 substituents joined to the same carbon (where the substituents are the same so called geminal or 'gem' disubstitution).

A combination of substituents is permissible only if such as combination results in a stable or chemically feasible compound (i.e. one that is not substantially altered when kept at 40° C. or less for at least a week).

The various functional groups and substituents making up the compounds of the invention are particularly chosen such that the molecular weight of the compound of the invention does not exceed 1000. More usually, the molecular weight of the compound will be less than 750, for example less than 700, or less than 650, or less than 600, or less than 550. More particularly, the molecular weight is less than 525 and, for example, is 500 or less.

DETAILED DESCRIPTION OF THE INVENTION

The invention provides a compound of formula (I):

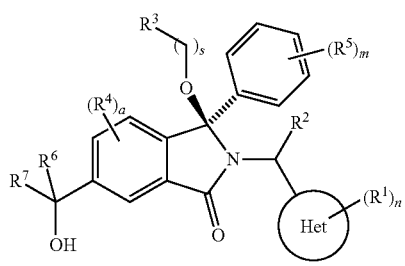

(I)

or a tautomer or a solvate or a pharmaceutically acceptable salt thereof, wherein Het, $R^1$, $R^2$, $R^3$, $R^4$, $R^5$, $R^6$, $R^7$, a, m, n and s are as defined herein.

The compounds of the formula (I) have a chiral centre, marked below with a "*":

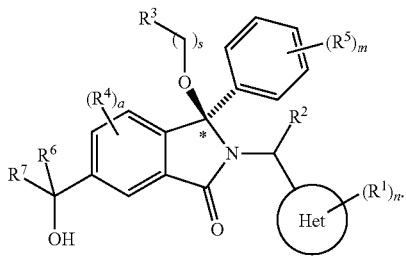

The compounds of formula (I) include a stereocentre at the position indicated (referred to herein as (3)) and are chiral non-racemic. Compounds of formula (I) have the stereochemistry shown by the hashed and solid wedged bonds and this stereoisomer predominates.

Typically, at least 55% (e.g. at least 60%, 65%, 70%, 75%, 80%, 85%, 90% or 95%) of the compound of the formula (I) is present as the shown stereoisomer. In one general embodiment, 97% (e.g. 99%) or more (e.g. substantially all) of the total amount of the compound of the formula (I) may be present as a single stereoisomer.

The compounds may also include one or more further chiral centres (e.g. in the —$CR^6R^7OH$ group and/or in the $R^3$ group and/or in the —$CHR^2$ group).

Typically, the compound of formula (I) has an enantiomeric excess of at least 10% (e.g. at least 20%, 40%, 60%, 80%, 85%, 90% or 95%). In one general embodiment, the compound of formula (I) has an enantiomeric excess of 97% (e.g. 99%) or more.

For the purposes of this section the isoindolin-1-one ring is numbered as followed:

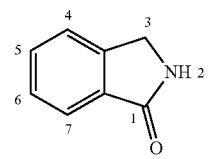

Compounds are named in accordance with protocols utilized by chemical naming software packages.

Het

Het is pyridinyl, pyrimidinyl, pyrazinyl or pyridazinyl, or an N-oxide thereof.

In one embodiment Het is pyridinyl, pyrimidinyl or pyridazinyl, or an N-oxide thereof.

In one embodiment Het is pyridinyl or pyrimidinyl, or an N-oxide thereof. In one embodiment Het is pyridinyl or pyrimidinyl. In one embodiment, Het is optionally substituted pyrimidin-2-yl.

In one embodiment, the point of attachment of the Het group is at the 2-position of the Het group and the Het is pyridin-2-yl, pyrimidin-2-yl, or pyridazin-2yl. In other words, the Het ring is attached to the rest of the molecule by a carbon atom adjacent to a nitrogen atom in the Het ring.

In one embodiment, Het is pyridinyl. In particular, Het may be pyridin-2-yl and the compound of formula (I) is a compound of formula (Ia) or a tautomer or a solvate or a pharmaceutically acceptable salt thereof, or pyridin-3-yl and the compound of formula (I) is a compound of formula (Ib) or a tautomer or a solvate or a pharmaceutically acceptable salt thereof:

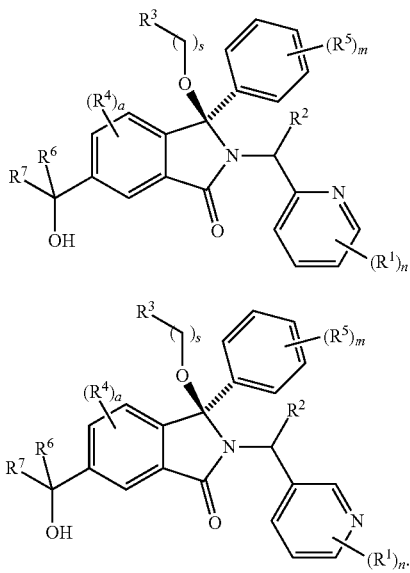

In one embodiment, Het is N-oxide pyridinyl. In particular, Het may be N-oxide pyridin-2-yl and the compound of formula (I) is a compound of formula (Ia') or a tautomer or a solvate or a pharmaceutically acceptable salt thereof:

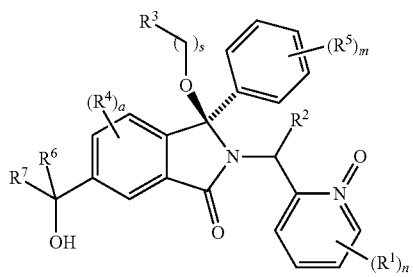

In one embodiment, Het is pyrimidinyl. In particular, Het may be pyrimidin-2-yl and the compound of formula (I) is a compound of formula (Ic) or a tautomer or a solvate or a pharmaceutically acceptable salt thereof:

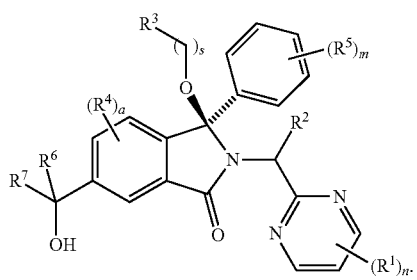

In one embodiment the compound of formula (I) can be pyridin-2-yl or pyrimidin-2-yl and the compound of formula (I) is a compound of formula (Id) or a tautomer or a solvate or a pharmaceutically acceptable salt thereof:

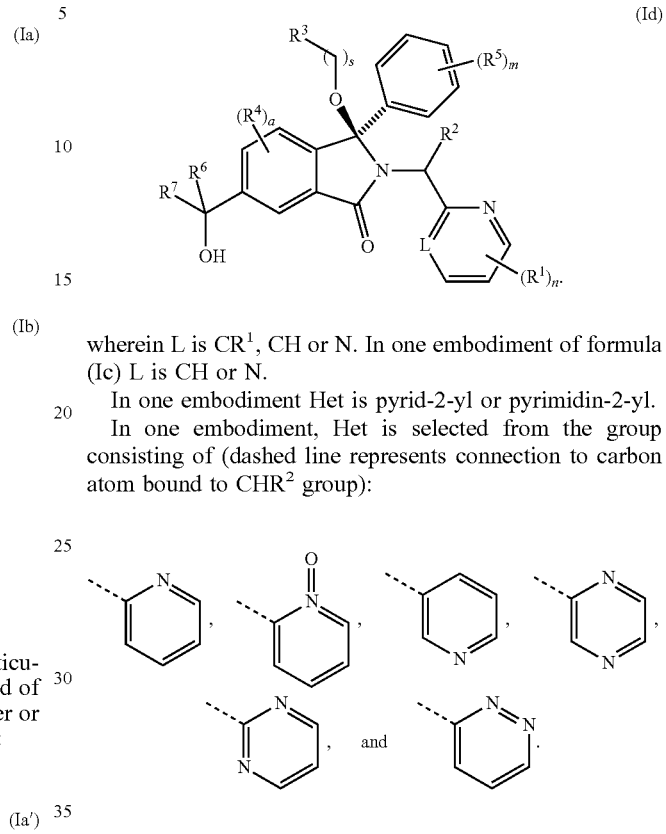

wherein L is $CR^1$, CH or N. In one embodiment of formula (Ic) L is CH or N.

In one embodiment Het is pyrid-2-yl or pyrimidin-2-yl.

In one embodiment, Het is selected from the group consisting of (dashed line represents connection to carbon atom bound to $CHR^2$ group):

In one embodiment, Het is selected from the group consisting of (dashed line represents connection to carbon atom bound to $CHR^2$ group):

$R^1$ and n $R^1$ is the substituent(s) on the Het group. $R^1$ is attached to a carbon atom (not a nitrogen atom) of the Het group.

n is 0, 1, 2 or 3. In other words, the Het group may have 0, 1, 2 or 3 substituents $R^1$.

In one embodiment n is 1, 2 or 3. In one embodiment n is 1 or 2. In another embodiment n is 1.

When n is 2 or 3 (i.e. the Het group is substituted with more than one $R^1$) the substituents $R^1$ may be the same or different (i.e. are independently selected from the definitions of $R^1$).

$R^1$ may be attached to a carbon atom at the ortho (or o-), meta (or m-) or para (or p-) position of the 6-membered Het group, wherein the position is defined relative to the point of attachment of the 6-membered Het group to the group —$CHR^2$—.

$R^1$ is independently selected from hydroxy, halogen, nitro, nitrile, $C_{1-4}$alkyl, halo$C_{1-4}$alkyl, hydroxy$C_{1-4}$alkyl, $C_{2-6}$alkenyl, $C_{1-4}$alkoxy, halo$C_{1-4}$alkoxy, $C_{2-4}$alkynyl, $—O_{0,1}—(CR^xR^y)_v—CO_2H$, $—(CR^xR^y)_v—CO_2C_{1-4}$alkyl, $—(CR^xR^y)_v—CON(C_{1-4}$alkyl$)_2$, $—P(=O)(R^x)_2$, $—S(O)_d—R^x$, $—S(O)_d$-heterocyclic group with 3 to 6 ring members and $—S(O)_d—N(R^8)_2$.

In one embodiment, $R^1$ is independently selected from hydroxy, halogen, nitro, nitrile, $C_{1-4}$alkyl, halo$C_{1-4}$alkyl, hydroxy$C_{1-4}$alkyl, $C_{2-6}$alkenyl, $C_{1-4}$alkoxy, halo$C_{1-4}$alkoxy, $C_{2-4}$alkynyl, $—(CR^xR^y)_v—CO_2H$, $—(CR^xR^y)_v—CO_2C_{1-4}$alkyl, $—(CR^xR^y)_v—CON(C_{1-4}$alkyl$)_2$, $—P(=O)(R^x)_2$, $—S(O)_d—R^x$, $—S(O)_d$-heterocyclic group with 3 to 6 ring members and $—S(O)_d—N(R^8)_2$.

In one embodiment, $R^1$ is attached to a carbon atom and is independently selected from hydroxy, halogen, nitro, nitrile, $C_{1-4}$alkyl, halo$C_{1-4}$alkyl, hydroxy$C_{1-4}$alkyl, $C_{2-6}$alkenyl, $C_{1-4}$alkoxy, halo$C_{1-4}$alkoxy, $C_{2-4}$alkynyl, $—(CR^xR^y)_v—CO_2C_{1-4}$alkyl, $—(CR^xR^y)_v—CON(C_{1-4}$alkyl$)_2$, $—P(=O)(R^x)_2$, $—S(O)_d—R^x$, $—S(O)_d$-heterocyclic group with 3 to 6 ring members and $—S(O)_d—N(R^8)_2$;

In one embodiment, $R^1$ is independently selected from halogen, hydroxy, nitrile, $C_{1-4}$alkyl, $C_{2-4}$alkynyl, or $C_{1-4}$alkoxy, for example $R^1$ is independently selected from fluoro, chloro, hydroxy, nitrile, methyl or methoxy.

In one embodiment $R^1$ is independently selected from halogen (e.g. chloro), $C_{1-4}$alkyl (e.g. methyl), $C_{1-4}$alkoxy (e.g. methoxy), $—O_{0,1}—(CR^xR^y)_v—CO_2H$ (e.g. $—CO_2H$, $—(CH_2)—CO_2H$, $—(C(CH_3)_2)—CO_2H$, or $—O(CH_2)—CO_2H$) or $—S(O)_d—R^x$ (e.g. $SO_2CH_3$).

In one embodiment $R^1$ is $O_{0,1}—(CR^xR^y)_v—CO_2H$ in particular $—CO_2H$, $—(CH_2)—CO_2H$, $—(C(CH_3)_2)—CO_2H$, or $—O(CH_2)—CO_2H$, such as $—(C(CH_3)_2)—CO_2H$.

In one embodiment, $R^1$ is chloro or nitrile, in particular chloro.

In one embodiment, $R^1$ is nitro (i.e. p-$NO_2$).

In one embodiment, $R^1$ is nitro at the ortho or meta position.

In another embodiment, n is 1 and $R^1$ is chloro or nitrile.

In another embodiment, n is 1 and $R^1$ is chloro.

In another embodiment, n is 1 and $R^1$ is nitrile.

In one embodiment, one of the $R^1$ groups or the $R^1$ group (where n=1) is at the para-position (i.e. para to the point of attachment of the six-membered ring). In one embodiment n is 1 and $R^1$ is p-chloro or p-nitrile.

In one embodiment, n is 1 and $R^1$ is halogen (e.g. Cl or F), nitrile, $C_{1-4}$alkoxy (e.g. $—OCH_3$) or $C_{1-4}$alkyl (e.g. $CH_3$).

In one embodiment, n is 2. In one embodiment when n is 2, the Het group is substituted with (i) o-($—S(O)_d—C_{1-4}$alkyl) or o-($—S(O)_d$-heterocyclic group with 3 to 6 ring members) and (ii) halogen (e.g. Cl or F), nitrile, or $C_{1-4}$ alkyl, in particular chloro, nitrile or methyl.

In another embodiment, one or more $R^1$ is $—SO_2CH_3$, or $—SO_2$-heterocyclic group with 6 ring members e.g. $—SO_2$-(morpholinyl), in particular $—SO_2$-(1-morpholinyl).

In one embodiment, $R^1$ is o-($—S(O)_d—C_{1-4}$alkyl) or o-($—S(O)_d$-heterocyclic group with 3 to 6 ring members).

In one embodiment, n is 2 and $R^1$ is (i) $—SO_2CH_3$ and (ii) chloro.

In one embodiment n is 2 and $R^1$ is (i) $—SO_2CH_3$ and (ii) chloro, nitrile or methyl.

In one embodiment, Het and $R^1$ form a group:

wherein in particular, $R^1$ is halogen (for example chloro), nitrile or $C_{1-4}$alkyl (for example $—CH_3$) and $R^x$ is $C_{1-4}$alkyl (for example $—CH_3$).

In one embodiment, Het and $R^1$ form a group:

wherein in particular, $R^1$ is $C_{1-4}$alkyl (for example $—CH_3$) and $R^x$ is $C_{1-4}$alkyl (for example $—CH_3$).

In one embodiment when n is 2, the Het group is substituted with (i) o-OH or o-$CH_2OH$ and (ii) halogen (e.g. Cl or F), nitrile, or $C_{1-4}$ alkyl, in particular chloro, or nitrile. In one embodiment, when n is 2, the Het group is substituted with (i) hydroxy and (ii) halogen (e.g. Cl or F) or nitrile, in particular chloro or nitrile. In one embodiment, when n is 2, the Het group is substituted with (i) o-hydroxy and (ii) p-Cl or p-CN (e.g. p-Cl).

In one embodiment, n is 2 and $R^1$ is fluorine (e.g. at the ortho and para positions of the Het group).

In one embodiment, $R^1$ is halogen (e.g. Cl or F), $C_{1-4}$alkynyl (e.g. $—C≡CH$), nitrile, $—(CH_2)_xCOOH$ (e.g. $—COOH$) or $—SO_2C_{1-4}$alkyl (e.g. $SO_2CH_3$) and n is 1 or 2.

In one embodiment, n is 1 and $R^1$ is Cl (e.g. p-Cl), CN (e.g. p-CN), F e.g. (p-F), $CH_3$ (e.g. p-$CH_3$), or $OCH_3$ (p-$OCH_3$), or n is 2 and (i) $R^1$ is p-F; o-F, or (ii) p-$CH_3$; o-$OCH_3$; or (iii) p-Cl, o-$SO_2CH_3$ or (iv) p-Cl, o-OH.

In one embodiment, n is 1 and $R^1$ is Cl (e.g. p-Cl), CN (e.g. p-CN), F e.g. (p-F), $CH_3$ (e.g. p-$CH_3$), or $OCH_3$ (p-$OCH_3$).

In one embodiment, n is 2 and (i) $R^1$ is p-F; o-F, or (ii) p-$CH_3$; o-$OCH_3$; or (iii) p-Cl, o-$SO_2CH_3$ or (iv) p-Cl, o-OH.

In one embodiment, n is 2 and $R^1$ is p-Cl and o-OH.

In one embodiment, $R^1$ is $—O_{0,1}(CR^xR^y)_v COOH$ (e.g. $—COOH$, $—CH_2COOH$, $—OCH_2COOH$ or $—C(CH_3)_2 COOH$).

In one embodiment, n is 2 and $R^1$ is p-Cl and o-$O_{0,1}(CR^xR^y)_v COOH$ (e.g. $—COOH$, $—CH_2COOH$, $—OCH_2COOH$ or $—O—C(CH_3)_2COOH$).

In one embodiment n is 1 and $R^1$ is $—Cl$, $—CN$, $—OMe$, $—O_{0,1}(CR^xR^y)_v COOH$ (e.g. $—COOH$) or $C_{1-4}$ alkyl (e.g. $—CH_3$) (e.g. p-Cl, p-CN or p-OMe). In one embodiment n is 1 and $R^1$ is $—Cl$ or $—CN$ (e.g. p-Cl or p-CN).

In one embodiment n is 1 and $R^1$ is $—Cl$, $—CN$ or $—OMe$ (e.g. p-Cl, p-CN or p-OMe). In one embodiment n is 1 and $R^1$ is $—Cl$ or $—CN$ (e.g. p-Cl or p-CN).

In one embodiment, $R^1$ is independently selected from hydroxy, halogen (e.g. chlorine), nitrile, $C_{1-4}$alkyl (e.g. methyl), $C_{1-4}$alkoxy (e.g. methoxy), and $—O_{0,1}—(CR^xR^y)_v—CO_2H$ (e.g. $—CO_2H$).

In one embodiment $R^1$ is $O_{0,1}—(CR^xR^y)_v—CO_2H$ in particular $—CO_2H$, $—(CH_2)—CO_2H$, $—(C(CH_3)_2)—CO_2H$, or $—O(CH_2)—CO_2H$, such as $—CO_2H$.

$R^2$ $R^2$ is selected from hydrogen, $C_{1-4}$ alkyl, $C_{2-6}$alkenyl, hydroxy$C_{1-4}$alkyl, $-(CR^xR^y)_u-CO_2H$, $-(CR^xR^y)_u-CO_2C_{1-4}$alkyl, and $-(CR^xR^y)_u-CONR^xR^y$.

In one embodiment u is selected from 0, 1, or 2. In one embodiment u is selected from 0 or 1.

In one embodiment, $R^2$ is selected from hydrogen, $C_{1-4}$ alkyl, $C_{2-6}$alkenyl, hydroxy$C_{1-4}$alkyl and $-(CR^xR^y)_u-CO_2H$. In one embodiment, $R^2$ is selected from hydrogen, $C_{1-4}$ alkyl, hydroxy$C_{1-4}$alkyl and $-(CR^xR^y)_u-CO_2H$. In one embodiment, $R^2$ is selected from hydrogen, $C_{1-4}$ alkyl, $C_{2-6}$alkenyl, and hydroxy$C_{1-4}$alkyl. In another embodiment $R^2$ is selected from hydrogen and $-(CH_2)_u-CO_2H$ (e.g. $-CH_2-CO_2H$).

In one embodiment, $R^2$ is hydrogen, $C_{1-4}$ alkyl (e.g. $-CH_3$), hydroxy$C_{1-4}$alkyl (e.g. $CH_2OH$) or $-(CH_2)_u$COOH (e.g. $-COOH$, $-CH_2COOH$, $-CH_2CH_2-CO_2H$, $-(CH(CH_3))-CO_2H$ or $-(C(CH_3)_2-CO_2H$, such as $-COOH$, $-CH_2COOH$, $-CH_2CH_2-CO_2H$, or $-(CH(CH_3))-CO_2H$).

In one embodiment, $R^2$ is selected from hydrogen, $C_{1-4}$ alkyl, $C_{2-6}$alkenyl, and hydroxy$C_{1-4}$alkyl.

In one embodiment, $R^2$ is hydrogen, $C_{1-4}$ alkyl (e.g. $-CH_3$), hydroxy$C_{1-4}$alkyl (e.g. $CH_2OH$) or $-(CH_2)_u$COOH (e.g. $-CH_2COOH$).

In one embodiment, $R^2$ is selected from hydrogen, $-CH_3$, $-CH_2OH$, and $-CH(OH)CH_2OH$.

In one embodiment, $R^2$ is selected from hydrogen, $-CH_3$, $-CH_2OH$, $-CH=CH_2$ and $-CH(OH)CH_2OH$.

In one embodiment, $R^2$ is selected from hydrogen, $-CH_3$, $-CH_2OH$, and $-CH_2CO_2H$.

In one embodiment, $R^2$ is hydrogen or $C_{1-4}$ alkyl (e.g. $-CH_3$ or $-CH_2CH_3$).

In one embodiment, $R^2$ is selected from hydrogen, $-CH_3$ and $-CH_2CH_3$. In one embodiment, $R^2$ is selected from hydrogen and methyl.

In one embodiment, $R^2$ is selected from hydrogen and $-(R^xR^y)_u-CO_2H$ (e.g. $-COOH$, $-CH_2COOH$, $-CH_2CH_2-CO_2H$, $-(CH(CH_3))-CO_2H$ and $-(C(CH_3)_2-CO_2H)$.

In one embodiment, $R^2$ is $-(R^xR^y)_u$COOH (e.g. $-CH_2COOH$, $-CH_2CH_2-CO_2H$, $-(CH(CH_3))-CO_2H$

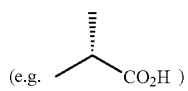

or $-(C(CH_3)_2-CO_2H)$.

In one embodiment, $R^2$ is hydrogen, $C_{1-4}$ alkyl (e.g. $-CH_3$) or $-(CH_2)_u$COOH (e.g. $-CH_2COOH$, $-CH_2CH_2-CO_2H$ or $-(CH(CH_3))-CO_2H$).

In one embodiment, $R^2$ is hydrogen, $C_{1-4}$ alkyl (e.g. $-CH_3$) or $-(CH_2)_u$COOH (e.g. $-CH_2COOH$).

In one embodiment, $R^2$ is $-(CR^xR^y)_u-CO_2H$ (e.g. $-CH_2-CO_2H$).

In another embodiment, $R^2$ is selected from $-(CH(CH_3))-CO_2H$ and $-(C(CH_3)_2-CO_2H)$

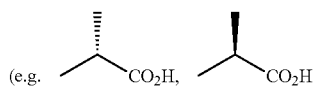

or $-(C(CH_3)_2-CO_2H)$.

In another embodiment, $R^2$ is hydrogen and the compound of formula (I) is a compound of formula (Ie) or a tautomer or a solvate or a pharmaceutically acceptable salt thereof:

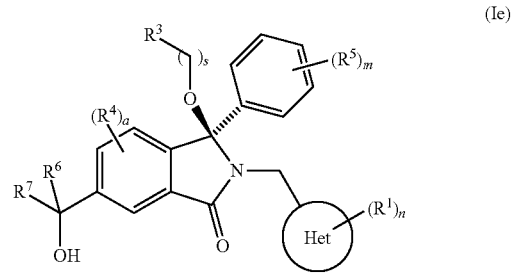

(Ie)

When $R^2$ is other than hydrogen, the compound of formula (I) can exist as at least two diastereoisomers:

Diastereoisomer 1A

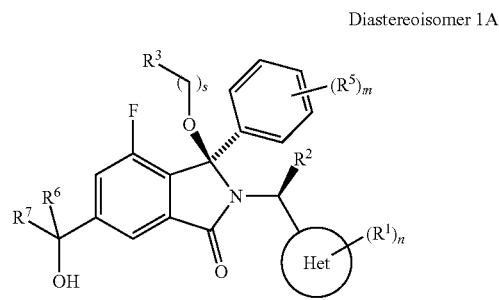

Diastereoisomer 1B

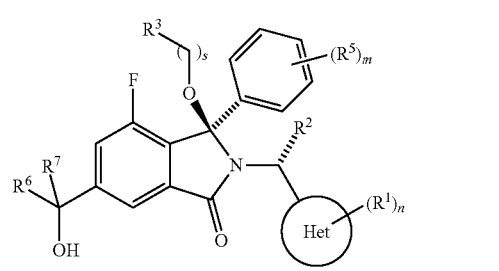

For the avoidance of doubt, the general formula (I) and all subformulae cover both individual diastereoisomers and mixtures of the diastereoisomers which are related as epimers at the $-CHR^2-$ group. In one embodiment the compound of formula I is diastereoisomer 1A or a tautomer or a solvate or a pharmaceutically acceptable salt thereof. In one embodiment the compound of formula I is diastereoisomer 1B or a tautomer or a solvate or a pharmaceutically acceptable salt thereof.

In one embodiment, the compound is diastereoisomer 1A and $R^2$ is selected from:
  i. $C_{1-4}$ alkyl, $C_{2-6}$alkenyl, hydroxy$C_{1-4}$alkyl, $-(R^xR^y)_u-CO_2H$ (e.g. $-COOH$, $-CH_2COOH$, $-CH_2CH_2-CO_2H$, $-(CH(CH_3))-CO_2H$ and $-(C(CH_3)_2-CO_2H)$, $-(CH_2)_u-CO_2C_{1-4}$alkyl, and $-(CH_2)_u-CONR^xR^y$; or
  ii. $C_{1-4}$ alkyl, $C_{2-6}$alkenyl, and hydroxy$C_{1-4}$alkyl.

In one embodiment, the compound is diastereoisomer 1A and $R^2$ is selected from:
  i. $C_{1-4}$ alkyl, $C_{2-6}$alkenyl, hydroxy$C_{1-4}$alkyl, $-(CH_2)_u-CO_2H$, $-(CH_2)_u-CO_2C_{1-4}$alkyl, and $-(CH_2)_u-CONR^xR^y$; or
  ii. $C_{1-4}$ alkyl, $C_{2-6}$alkenyl, and hydroxy$C_{1-4}$alkyl.

In another embodiment $R^2$ is selected from hydrogen and —$(R^xR^y)_u$—$CO_2H$ (e.g. —COOH, —$CH_2COOH$, —$CH_2CH_2$—$CO_2H$, —$(CH(CH_3))$—$CO_2H$ and —$(C(CH_3)_2$—$CO_2H)$.

In another embodiment $R^2$ is selected from hydrogen and —$(CH_2)_u$—$CO_2H$ (e.g. —$CH_2$—$CO_2H$).

In one embodiment, the compound is diastereoisomer 1A and $R^2$ is selected from:
 i. —$CH_3$, —$CH_2OH$, —CH=$CH_2$ and —CH(OH)$CH_2OH$; or
 ii. $C_{1-4}$ alkyl (e.g. —$CH_3$ or —$CH_2CH_3$); or
 iii. —$CH_3$ and —$CH_2CH_3$.

In one embodiment, the compound is diastereoisomer 1B and $R^2$ is selected from:
 i. $C_{1-4}$ alkyl, $C_{2-6}$alkenyl, hydroxy$C_{1-4}$alkyl, —$(R^xR^y)_u$—$CO_2H$ (e.g. —COOH, —$CH_2COOH$, —$CH_2CH_2$—$CO_2H$, —$(CH(CH_3))$—$CO_2H$ and —$(C(CH_3)_2$—$CO_2H)$, —$(CH_2)_u$—$CO_2C_{1-4}$alkyl, and —$(CH_2)_u$—$CONR^xR^y$; or
 ii. $C_{1-4}$ alkyl, $C_{2-6}$alkenyl, and hydroxy$C_{1-4}$alkyl.

In one embodiment, the compound is diastereoisomer 1B and $R^2$ is selected from:
 i. $C_{1-4}$ alkyl, $C_{2-6}$alkenyl, hydroxy$C_{1-4}$alkyl, —$(CH_2)_u$—$CO_2H$, —$(CH_2)_u$—$CO_2C_{1-4}$alkyl, and —$(CH_2)_u$—$CONR^xR^y$; or
 ii. $C_{1-4}$ alkyl, $C_{2-6}$alkenyl, and hydroxy$C_{1-4}$alkyl.

In another embodiment $R^2$ is selected from hydrogen and —$(CH_2)_u$—$CO_2H$ (e.g. —$CH_2$—$CO_2H$).

In one embodiment, the compound is diastereoisomer 1B and $R^2$ is selected from:
 i. —$CH_3$, —$CH_2OH$, —CH=$CH_2$ and —CH(OH)$CH_2OH$; or
 ii. $C_{1-4}$ alkyl (e.g. —$CH_3$ or —$CH_2CH_3$); or
 iii. —$CH_3$ and —$CH_2CH_3$.

In another embodiment $R^2$ is selected from hydrogen and —$(R^xR^y)_u$—$CO_2H$ (e.g. —COOH, —$CH_2COOH$, —$CH_2CH_2$—$CO_2H$, —$(CH(CH_3))$—$CO_2H$ and —$(C(CH_3)_2$—$CO_2H)$, In one embodiment $R^2$ is selected from $C_{1-4}$ alkyl, hydroxy$C_{1-4}$alkyl, —$(CH_2)_u$—$CO_2H$, —$(CH_2)_u$—$CO_2C_{1-4}$alkyl, and —$(CH_2)_w$—$CONR^xR^y$ (in particular —$CH_2$—$CO_2H$) and the compound is diastereoisomer 1A.

In one embodiment $R^2$ is selected from $C_{1-4}$ alkyl, hydroxy$C_{1-4}$alkyl, —$(CH_2)_u$—$CO_2H$, —$(CH_2)_u$—$CO_2C_{1-4}$alkyl, and —$(CH_2)_u$—$CONR^xR^y$ (in particular —$CH_2$—$CO_2H$) and the compound is diastereoisomer 1B.

In one embodiment $R^2$ is hydroxy$C_{1-4}$alkyl (e.g. —$CH_2OH$) and the compound is diastereoisomer 1A.

In one embodiment $R^2$ is —$(CH_2)_u$—$CO_2H$ (e.g. —$CH_2$—$CO_2H$) and the compound is diastereoisomer 1A.

In one embodiment $R^2$ and the hydrogen on the carbon to which it is attached are $^2H$ (i.e. deuterium).

$R^3$ and s $R^3$ is hydrogen or -$(A)_t$-$(CR^xR^y)_q$—X;
 s is selected from 0 and 1;
 t is selected from 0 and 1;
 q is selected from 0, 1 and 2;
 wherein when $R^3$ is -$(A)_t$-$(CR^xR^y)_q$—X then (i) at least one of s, t and q is other than 0 and (ii) when t is 0 then s is 1 and q is other than 0;
 A is a $C_{3-6}$cycloalkyl group or a heterocyclic group with 3 to 6 ring members, wherein the heterocyclic group comprises one or more (e.g. 1, 2, or 3) heteroatoms selected from N, O, S and oxidised forms thereof;
 X is selected from hydrogen, halogen, —CN, —$OR^9$, —$(CH_2)_v$—$CO_2H$, —$(CH_2)_v$—$CO_2C_{1-4}$alkyl, —$S(O)_d$—$R^x$, —C(=O)—$C_{1-4}$alkyl, —$S(O)_d$—$N(H)_e(C_{1-4}$alkyl$)_{2-e}$, —$NR^xR^y$, —$NHSO_2R^x$, —$NR^xCOR^y$, and —C(=O)$NR^xR^y$;

$R^9$ is independently selected from hydrogen, $C_{1-6}$alkyl, halo$C_{1-6}$alkyl, hydroxy$C_{1-6}$alkyl, —$(CH_2)_k$—O—$C_{1-6}$alkyl, —$(CH_2)_k$-O-(hydroxy$C_{1-6}$alkyl), hydroxy$C_{1-6}$alkoxy, —$(CH_2)_k$—$CO_2C_{1-6}$alkyl, —$(CH_2)_k$—$CO_2H$, —$C_{1-6}$ alkyl-$N(H)_e(C_{1-4}$alkyl$)_{2-e}$, —$(CH_2)_j$—$C_{3-8}$cycloalkyl and —$(CH_2)_j$—$C_{3-8}$cycloalkenyl;

$R^x$ and $R^y$ are independently selected from hydrogen, halogen, nitro, nitrile, $C_{1-6}$alkyl, halo$C_{1-6}$alkyl, $C_{2-6}$alkenyl, $C_{2-6}$alkynyl, hydroxy, hydroxy$C_{1-6}$alkyl, $C_{1-6}$alkoxy, —$(CH_2)_k$—O—$C_{1-6}$alkyl, hydroxy$C_{1-6}$alkoxy, —COO$C_{1-6}$alkyl, —$N(H)_e(C_{1-4}$alkyl$)_{2-e}$, —$C_{1-6}$alkyl-$N(H)_e(C_{1-4}$alkyl$)_{2-e}$, —$(CH_2)_k$—C(=O)$N(H)_e(C_{1-4}$alkyl$)_{2-e}$, $C_{3-8}$cycloalkyl and $C_{3-8}$cycloalkenyl;

or the $R^x$ and $R^y$ groups, together with the carbon or nitrogen atom to which they are attached, can join to form a $C_{3-6}$cycloalkyl or saturated heterocyclyl group with 3 to 6 ring members which may be optionally fused to an aromatic heterocyclyl group of 3 to 5 ring members or can join to form a =CH group;

j, d, and e are independently selected from 0, 1 and 2;
k is selected from 1 and 2; and
v is independently selected from 0 and 1.

In one embodiment when t is 1 the group —$(CR^xR^y)_q$—X and the rest of the molecule are attached to the same carbon atom in the group A. In one embodiment when t is 1 the group $(CR^xR^y)_q$—X and the rest of the molecule are attached to different carbon atoms in the group A.

In one embodiment, $R^3$ is hydrogen or -$(A)_t$-$(CR^xR^y)_q$—X;
 s is selected from 0 and 1;
 t is selected from 0 and 1;
 q is selected from 0, 1 and 2;
 wherein when $R^3$ is -$(A)_t$-$(CR^xR^y)_q$—X then (i) at least one of s, t and q is other than 0 and (ii) when t is 0 then s is 1 and q is other than 0;
 A is a $C_{3-6}$cycloalkyl group or a heterocyclic group with 3 to 6 ring members, wherein the heterocyclic group comprises one or more (e.g. 1, 2, or 3) heteroatoms selected from N, O, S and oxidised forms thereof;
 X is selected from hydrogen, halogen, —CN, —$OR^9$, —$(CH_2)_v$—$CO_2H$, —$(CH_2)_v$—$CO_2C_{1-4}$alkyl, —$S(O)_d$—$R^x$, —C(=O)—$C_{1-4}$alkyl, —$S(O)_d$—$N(H)_e(C_{1-4}$alkyl$)_{2-e}$, —$NR^xR^y$, —$NHSO_2R^x$, —$NR^xCOR^y$, and —C(=O)$NR^xR^y$;

$R^9$ is independently selected from hydrogen and $C_{1-6}$alkyl;

$R^x$ and $R^y$ are independently selected from hydrogen and $C_{1-6}$alkyl;

d and e are independently selected from 0, 1 and 2;
v is independently selected from 0 and 1.

In one embodiment, $R^3$ is hydrogen or -$(A)_t$-$(CR^xR^y)_q$—X;
 s is selected from 0 and 1;
 t is selected from 0 and 1;
 q is selected from 0, 1 and 2;
 wherein when $R^3$ is -$(A)_t$-$(CR^xR^y)_q$—X then (i) at least one of s, t and q is other than 0 and (ii) when t is 0 then s is 1 and q is other than 0;
 A is a $C_{3-6}$cycloalkyl group or a heterocyclic group with 3 to 6 ring members, wherein the heterocyclic group comprises one or more (e.g. 1, 2, or 3) heteroatoms selected from N, O, S and oxidised forms thereof;

X is selected from hydrogen, halogen, —CN, —$OR^9$, —$(CH_2)_v$—$CO_2H$, —$(CH_2)_v$—$CO_2C_{1-4}$alkyl, —C(=O)—$C_{1-4}$alkyl, —$NR^xR^y$, —$NR^xCOR^y$, and —C(=O)$NR^xR^y$;

$R^9$ is independently selected from hydrogen and $C_{1-6}$alkyl;

$R^x$ and $R^y$ are independently selected from hydrogen and $C_{1-6}$alkyl;

v is independently selected from 0 and 1.

In one embodiment, $R^3$ is hydrogen or -(A)$_t$-(CR$^x$R$^y$)$_q$—X;

s is selected from 0 and 1;

t is selected from 0 and 1;

q is selected from 0, 1 and 2;

wherein when $R^3$ is -(A)$_t$-(CR$^x$R$^y$)$_q$—X then (i) at least one of s, t and q is other than 0 and (ii) when t is 0 then s is 1 and q is other than 0;

A is a $C_{3-6}$cycloalkyl group or a heterocyclic group with 3 to 6 ring members, wherein the heterocyclic group comprises one or more (e.g. 1, 2, or 3) heteroatoms selected from N, O, S and oxidised forms thereof;

X is selected from hydrogen, halogen, —CN, —$OR^9$, —$NR^xCOR^y$, and —C(=O)$NR^xR^y$;

$R^9$ is independently selected from hydrogen and $C_{1-6}$alkyl;

$R^x$ and $R^y$ are independently selected from hydrogen and $C_{1-6}$alkyl;

v is independently selected from 0 and 1.

In one embodiment, $R^3$ is hydrogen or -(A)$_t$-(CR$^x$R$^y$)$_q$—X;

s is selected from 0 and 1;

t is selected from 0 and 1;

q is selected from 0, 1 and 2;

wherein when $R^3$ is -(A)$_t$-(CR$^x$R$^y$)$_q$—X then (i) at least one of s, t and q is other than 0 and (ii) when t is 0 then s is 1 and q is other than 0;

A is a $C_{3-6}$cycloalkyl group or a heterocyclic group with 3 to 6 ring members, wherein the heterocyclic group comprises one or more (e.g. 1, 2, or 3) heteroatoms selected from N, O, S and oxidised forms thereof;

X is selected from hydrogen, halogen (e.g. fluoro), —$OR^9$, —$NR^xCOR^y$; and —C(=O)$NR^xR^y$;

$R^9$ is independently selected from hydrogen and $C_{1-6}$alkyl;

$R^x$ and $R^y$ are independently selected from hydrogen and $C_{1-6}$alkyl;

v is independently selected from 0 and 1.

In one embodiment, $R^3$ is hydrogen and s is 1 i.e. the moiety —(CH$_2$)$_s$R$^3$ is —CH$_3$.

In one embodiment, $R^3$ is hydrogen and s is 0 i.e. the moiety —(CH$_2$)$_s$R$^3$ is —H.

In one embodiment, t is 1 and A is a $C_{3-6}$cycloalkyl group or a heterocyclic group with 3 to 6 ring members, wherein the heterocyclic group comprises one or more (e.g. 1 or 2) heteroatoms selected from N, O, S and oxidised forms thereof.

In one embodiment, t is 1 and A is a $C_{3-6}$cycloalkyl group. In one embodiment, A is a $C_{3-5}$cycloalkyl group. For example, A is selected from a cyclopropyl group, a cyclobutyl group and a cyclopentyl group. In one embodiment, A is a cyclopropyl group. In one embodiment, A is a cyclobutyl group.

In particular, t is 1 and A is cyclopropyl.

In one embodiment, t is 1 and A is a heterocyclic group with 3 to 6 ring members, wherein the heterocyclic group comprises one or more (e.g. 1, 2, or 3) heteroatoms selected from N, O, S and oxidised forms thereof.

In one embodiment, t is 1 and A is a heterocyclic group with 3 to 5 ring members, wherein the heterocyclic group comprises one or more (e.g. 1, 2, or 3) heteroatoms selected from N, O, S and oxidised forms thereof.

In one embodiment, t is 1 and A is an unsaturated heterocyclic group with 3 to 5 ring members, wherein the heterocyclic group comprises one or more (e.g. 1, 2, or 3) heteroatoms selected from N, O, S and oxidised forms thereof, in particular O.

In one embodiment, t is 1 and A is a saturated heterocyclic group with 3 to 5 ring members, wherein the heterocyclic group comprises one or more (e.g. 1, 2, or 3) heteroatoms selected from N, O, S and oxidised forms thereof, in particular O.

In one embodiment, t is 1 and A is a heterocyclic group which is selected from morpholinyl, piperidinyl (e.g. piperidin-1-yl, piperidin-2-yl, piperidin-3-yl and piperidin-4-yl), piperidinonyl, pyrrolidinyl (e.g. pyrrolidin-1-yl, pyrrolidin-2-yl and pyrrolidin-3-yl), pyrrolidonyl, azetidinyl, oxetanyl, pyranyl (2H-pyran or 4H-pyran), dihydrothienyl, dihydropyranyl, dihydrofuranyl, dihydrothiazolyl, tetrahydrofuranyl (e.g. tetrahydrofuran-3-yl), tetrahydrothienyl, dioxanyl, oxanyl (e.g. oxan-4-yl), imidazolinyl, imidazolidinonyl, oxazolinyl, thiazolinyl, pyrazolin-2-yl, pyrazolidinyl, piperazinonyl, piperazinyl, and N-alkyl piperazines such as N-methyl piperazinyl.

In one embodiment, t is 1 and A is a heterocyclic group which is selected from morpholinyl, piperidinyl (e.g. piperidin-1-yl, piperidin-2-yl, piperidin-3-yl and piperidin-4-yl), piperidinonyl, pyrrolidinyl (e.g. pyrrolidin-1-yl, pyrrolidin-2-yl and pyrrolidin-3-yl), pyrrolidonyl, azetidinyl, oxetanyl, pyranyl (2H-pyran or 4H-pyran), dihydropyranyl, dihydrofuranyl, dihydrothiazolyl, tetrahydrofuranyl (e.g. tetrahydrofuran-3-yl), dioxanyl, oxanyl (e.g. oxan-4-yl), imidazolinyl, imidazolidinonyl, oxazolinyl, pyrazolin-2-yl, pyrazolidinyl, piperazinonyl, piperazinyl, and N-alkyl piperazines such as N-methyl piperazinyl.

In particular, t is 1 and A is a heterocyclic group which is oxetanyl (e.g. oxetan-3-yl).

In particular, t is 1 and A is a heterocyclic group which is tetrahydrofuranyl (e.g. tetrahydrofuran-3-yl).

In one embodiment, X is hydrogen, s is 0 and q is 0, and $R^3$ is a heterocyclic group with 3 to 6 ring members, wherein the heterocyclic group comprises one or more (e.g. 1, 2, or 3) heteroatoms selected from N, O, S and oxidised forms thereof. In particular, $R^3$ is tetrahydrofuranyl (e.g. tetrahydrofuran-3-yl).

In one embodiment, s is 0 and t is 1 and A is attached directly to the oxygen atom bound to the isoindolinone. In one embodiment s is 1 and the cycloalkyl group is attached via a methylene group (i.e. —CH$_2$—) to the oxygen atom bound to the isoindolinone.

In one embodiment, A is tetrahydrofuranyl and X is hydrogen.

In one embodiment A is selected from cyclopropyl, oxetanyl and tetrahydrofuranyl.

In one embodiment, A is oxetanyl and X is fluorine.

In one embodiment, q is 0. In one embodiment, q is 1. In one embodiment, q is 2.

When q is not 0, $R^x$ and $R^y$ are selected from hydrogen, halogen (e.g. fluorine), hydroxy and methyl e.g. hydrogen and methyl, in particular hydrogen.

In one embodiment, q is 1 and at least one $R^x$ and $R^y$ is hydrogen. In one embodiment, q is 2 and at least two $R^x$ and $R^y$ are hydrogen e.g. three $R^x$ and $R^y$ are hydrogen.

In one embodiment, —(CR$^x$R$^y$)$_q$— is selected from —CH$_2$— and —CH$_2$CH$_2$—.

In one embodiment, $R^x$ and $R^y$ together form a saturated heterocyclyl group with 3 to 6 ring members.

In one embodiment t is 0 and $-(CR^xR^y)_q-$ is $-CH_2-$.
In one embodiment t is 0, s is 0, $-(CR^xR^y)_q-$ is $-CH_2-$ and X is hydroxy.

In one embodiment, X is selected from $-CN$, $-OH$, $-O-C_{1-4}$alkyl, $-O$-hydroxy$C_{1-4}$alkyl, $-S(O)_d-C_{1-4}$alkyl, $-C(=O)-C_{1-4}$alkyl, $-NR^xR^y$, $-NR^xCOR^y$ and $-C(=O)NR^xR^y$.

In one embodiment, X is selected from $-CN$, $-OH$, $-O-CH_2CH_2OH$, $-S(O)_d-C_{1-4}$alkyl and $-C(=O)NR^xR^y$ (e.g. $-C(=O)NH_2$ or $-C(=O)NH(CH_3)$). In one embodiment X is selected from $-CN$, $-OH$, $-C(=O)NH_2$ or $-C(=O)NH(CH_3)$.

In one embodiment, X is selected from hydrogen, halogen, $-CN$, $-OR^9$, and $-C(=O)NR^xR^y$. In another embodiment, X is selected from hydrogen, halogen, $-CN$, $-OH$, $-OCH_3$, and $-C(=O)NH_2$. In another embodiment, X is selected from hydrogen, fluorine, $-CN$, $-OH$, and $-C(=O)NH_2$.

In one embodiment, X is selected from hydrogen, fluorine, $-CN$, $-OH$ and $-C(=O)NH_2$. In one embodiment, X is selected from hydrogen, $-CN$, $-OH$ and $-C(=O)NH_2$. In one embodiment, X is selected from $-CN$, $-OH$ and $-C(=O)NH_2$.

In one embodiment X is selected from $-OH$ and $-C(=O)NH_2$ e.g. $-OH$.

In one embodiment, X is $-C(=O)NR^xR^y$ (e.g. $-C(=O)NH_2$ or $-C(=O)NH(CH_3)$).

In one embodiment, $R^x$ and $R^y$ are hydrogen, halogen (e.g. fluorine), hydroxy and methyl. In one embodiment, $R^x$ and $R^y$ are hydrogen and methyl. In one embodiment, $R^x$ and $R^y$ together form a saturated heterocyclyl group with 3 to 6 ring members.

In one embodiment, A is a $C_{3-6}$cycloalkyl group (i.e. g is 1, 2 or 3) and t is 1 and s is 0 or 1, and the compound of formula (I) is a compound of formula (If) or a tautomer or a solvate or a pharmaceutically acceptable salt thereof:

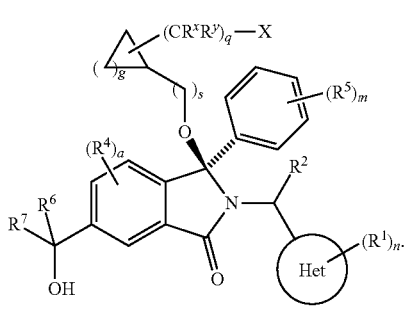

(If)

In one embodiment, A is a $C_{3-6}$cycloalkyl group (i.e. g is 1, 2 or 3) and t is 1 and s is 1, and the compound of formula (I) is a compound of formula (Ig) or a tautomer or a solvate or a pharmaceutically acceptable salt thereof:

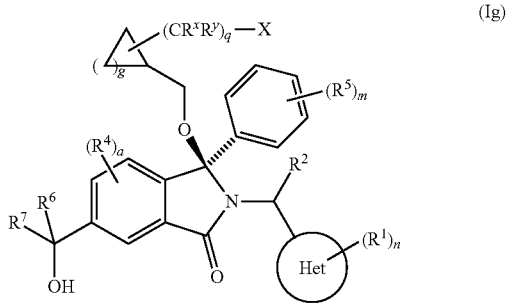

(Ig)

In one embodiment, A is a $C_{3-6}$cycloalkyl group (i.e. g is 1, 2 or 3) and t is 1 and s is 0, and the compound of formula (I) is a compound of formula (Ig') or a tautomer or a solvate or a pharmaceutically acceptable salt thereof:

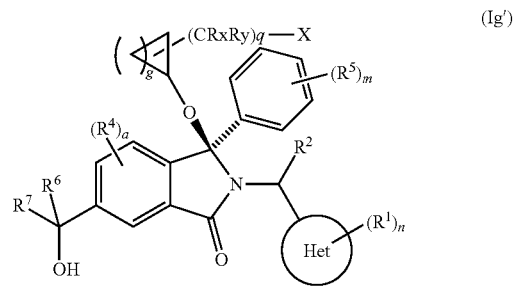

(Ig')

In one embodiment, the compound of formula (I) is a compound of formula (Ig) and g is 2.

In one embodiment, A is a $C_{3-6}$cycloalkyl group (i.e. g is 1, 2 or 3) and t is 1 and s is 1, and the cycloalkyl group is geminally disubstituted (i.e. the group $-(CR^xR^y)_q-X$ and the $-CH_2-O$-isoindolinone group are both attached to the same atom of the cycloalkyl group), and the compound of formula (I) is a compound of formula (Ih) or a tautomer or a solvate or a pharmaceutically acceptable salt thereof:

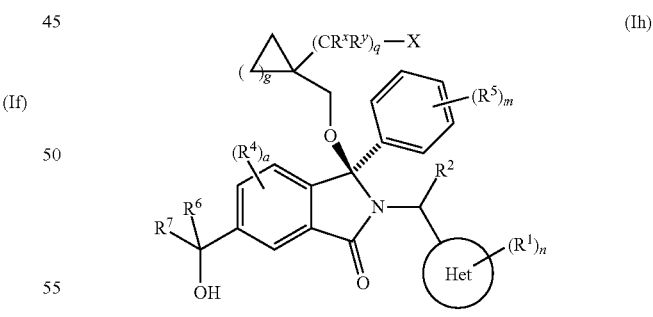

(Ih)

In one embodiment, A is a cyclopropyl group (i.e. g is 1), t is 1 and s is 1. Therefore the cycloalkyl group is a cyclopropyl group and the compound of formula (I) is a compound of formula (Ii) or a tautomer or a solvate or a pharmaceutically acceptable salt thereof:

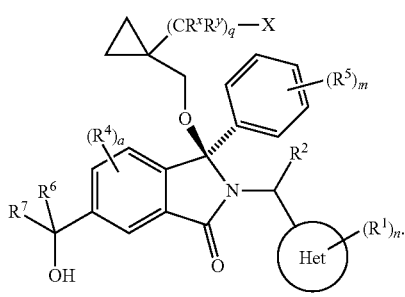

(Ii)

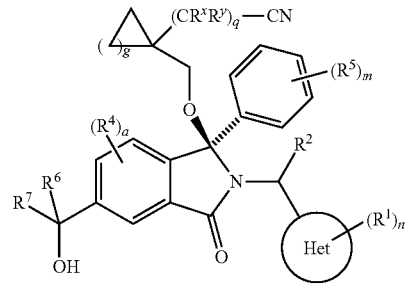

(Ik')

In one embodiment, A is a $C_{3-6}$cycloalkyl group (i.e. g is 1, 2 or 3), t is 1, s is 1 and X is hydroxy, and the compound of formula (I) is a compound of the formula (Ij) or a tautomer or a solvate or a pharmaceutically acceptable salt thereof:

In another embodiment, A is a $C_{3-6}$cycloalkyl group (i.e. g is 1, 2 or 3), t is 1, s is 1 and $R^x$ and $R^y$ are hydrogen (including $^1H$ and $^2H$) and the compound of formula (I) is a compound of formula (IL) or a tautomer or a solvate or a pharmaceutically acceptable salt thereof:

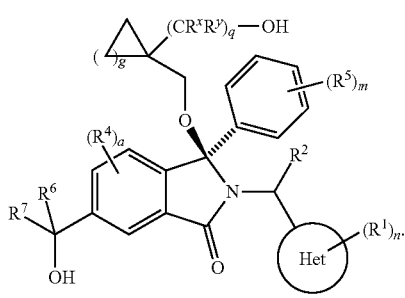

(Ij)

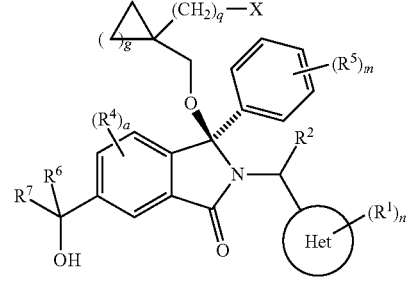

(IL)

In one embodiment, A is a $C_{3-6}$cycloalkyl group (i.e. g is 1, 2 or 3), t is 1, s is 1 and X is —C(═O)NH$_2$ and the compound of formula (I) is a compound of the formula (Ik) or a tautomer or a solvate or a pharmaceutically acceptable salt thereof:

In one embodiment, A is a cyclopropyl or cyclobutyl group (i.e. g is 1 or 2), t is 1, s is 1 and X is hydroxy and the compound of formula (IL) is a compound of formula (Im) or a tautomer or a solvate or a pharmaceutically acceptable salt thereof:

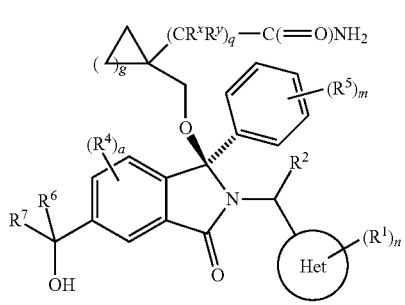

(Ik)

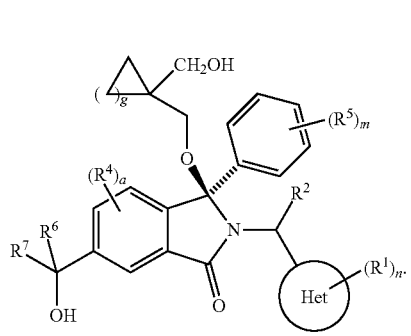

(Im)

In one embodiment, A is a $C_{3-6}$cycloalkyl group (i.e. g is 1, 2 or 3), t is 1, s is 1 and X is —CN and the compound of formula (I) is a compound of the formula (Ik') or a tautomer or a solvate or a pharmaceutically acceptable salt thereof:

In one embodiment, g is 1 and the compound of formula (Im) is a compound of the formula (Im') or a tautomer or a solvate or a pharmaceutically acceptable salt thereof:

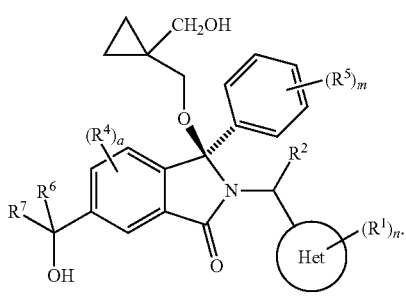

(Im')

In one embodiment, A is a $C_3$-cycloalkyl group (i.e. g is 1), t is 1, s is 1 and X is —C(=O)NH$_2$ and the compound of formula (I) is a compound of formula (In) or a tautomer or a solvate or a pharmaceutically acceptable salt thereof:

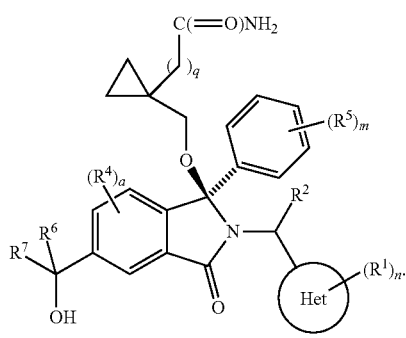

(In)

wherein q is 0 or 1. In one embodiment of the compound (In), q is 0.

In one embodiment, A is a $C_3$-cycloalkyl group (i.e. g is 1), t is 1, s is 1 and X is —CN and the compound of formula (I) is a compound of formula (In') or a tautomer or a solvate or a pharmaceutically acceptable salt thereof:

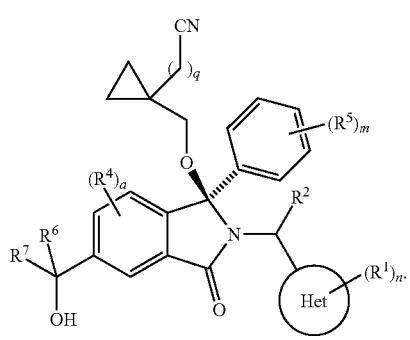

(In')

wherein q is 0 or 1. In one embodiment of the compound (In), q is 0.

In one embodiment of formula (I) and subformulae thereof, the hydrogens in the —(CR$^x$R$^y$)— group of R$^3$ are $^2$H (i.e. deuterium, D). In one embodiment, the hydrogens in the group —CH$_2$—O group are $^2$H (i.e. deuterium, D). In one embodiment, the hydrogens in the —(CR$^x$R$^y$)— and —CH$_2$—O groups are $^2$H (i.e. deuterium, D).

In one embodiment q is 0 or 1 and R$^x$ and R$^y$ are hydrogen or deuterium.

In one embodiment, A is cyclopropyl (i.e. g is 1), t is 1, s is 1, X is hydroxy and the hydrogens in the —(CR$^x$R$^y$)— and —CH$_2$—O groups are $^2$H (or D), and the compound of formula (I) is a compound of formula (Io) or a tautomer or a solvate or a pharmaceutically acceptable salt thereof:

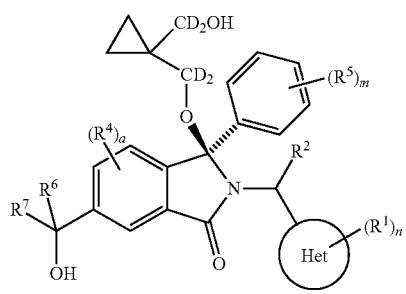

(Io)

In one embodiment the compound of formula (I) is a compound of formula (Io') or (Io") or a tautomer or a solvate or a pharmaceutically acceptable salt thereof:

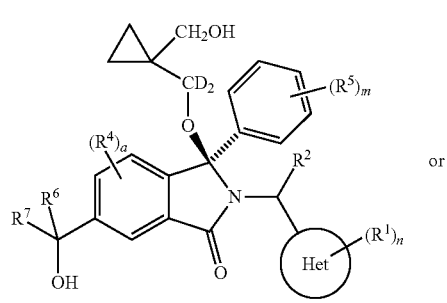

(Io')

or

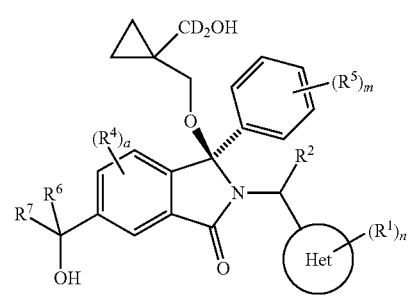

(Io")

In one embodiment, R$^3$ is —(CR$^x$R$^y$)$_q$—X and s is 1, t is 0 and q is 1 or 2, and the compound of formula (I) is a compound of the formula (Ip):

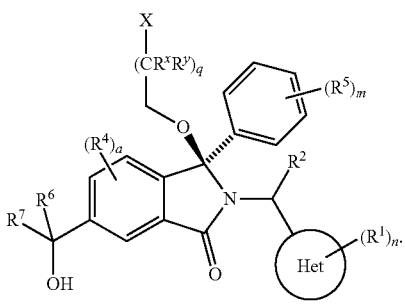
(Ip)

In one embodiment, $R^x$ and $R^y$ are H, and the compound of formula (Ip) is a compound of the formula (Ip') or a tautomer or a solvate or a pharmaceutically acceptable salt thereof:

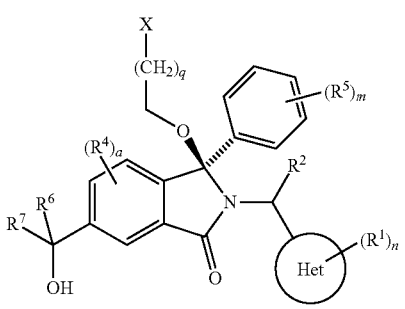
(Ip')

In one embodiment, A is a $C_{3-6}$cycloalkyl group or saturated heterocyclic group with 3 to 6 ring members, wherein t is 1, and s is 1, Y is independently selected from —CH$_2$—, O, or SO$_2$, i is 0 or 1, g is 1, 2, 3 or 4 and i+g is 1, 2, 3 or 4 and the compound of formula (I) is a compound of the formula (Iq) or a tautomer or a solvate or a pharmaceutically acceptable salt thereof:

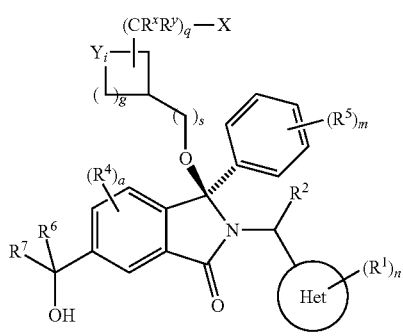
(Iq)

In one embodiment the compound of formula (I) is a compound of the formula (Iq') or a tautomer or a solvate or a pharmaceutically acceptable salt thereof:

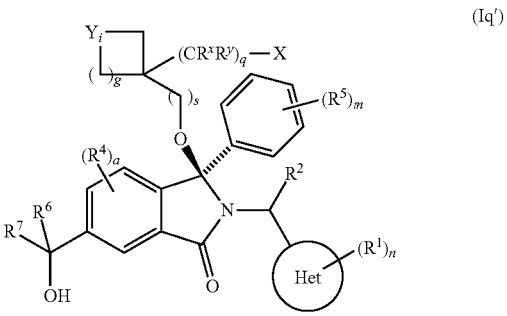
(Iq')

In one embodiment the compound of (Iq') is where q is 1 and $R^x$, $R^y$ and X are hydrogen.

In one embodiment of the compound of formula (Iq'), q is 1, $R^x$ and $R^y$ are hydrogen, and X is hydroxy.

In one embodiment of the compound of formula (Iq'), q is 1, $R^x$ and $R^y$ are hydrogen, and X is fluorine.

In one embodiment of the compound of formula (Iq'), q is 0. In one embodiment of the compound of formula (Iq'), q is 0 and X is fluorine.

In one embodiment q is 0 and X is F and the compound of formula (Iq') is a compound of the formula (Iq") or a tautomer or a solvate or a pharmaceutically acceptable salt thereof:

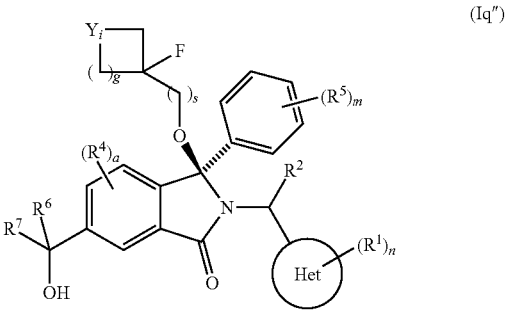
(Iq")

In one embodiment of the compound of (Iq') or the compound of (Iq"), g is 1, i is 1 and Y is O.

In one embodiment g is 1, i is 1, Y is O, q is 0 and X is F and the compound of formula (Iq') is a compound of the formula (Iq'") or a tautomer or a solvate or a pharmaceutically acceptable salt thereof:

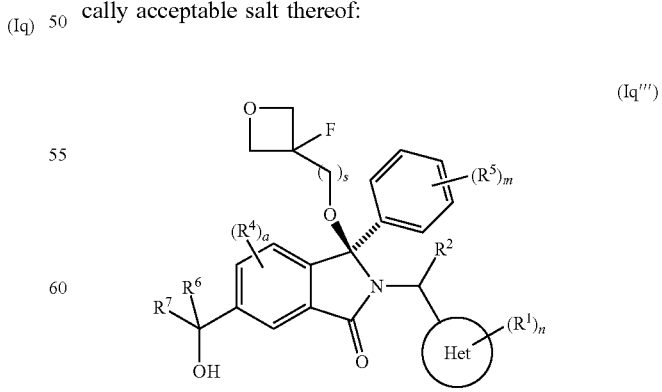
(Iq'")

In one embodiment, i is 1 and Y is O or SO$_2$, in particular O. In one embodiment, the compound of formula (Iq) is a compound of formula (Iq'''') or a tautomer or a solvate or a pharmaceutically acceptable salt thereof:

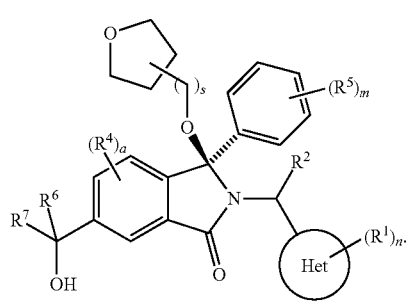

In one embodiment, s is 0, t is 1, A is tetrahydofuranyl, q is 0 and X is hydrogen. In one embodiment, $R^3$ is tetrahydrofuranyl and s is 0.

In one embodiment, —(CH$_2$)$_s$R$^3$ is selected from the following table (point of attachment to the oxygen represented by dashed bond or bond terminus marked "*"):

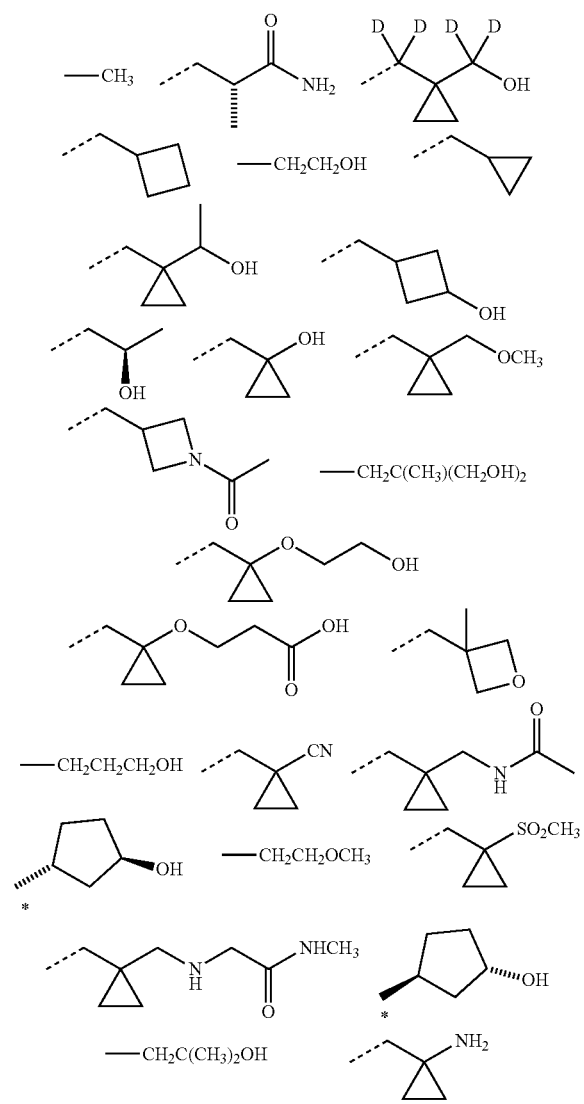

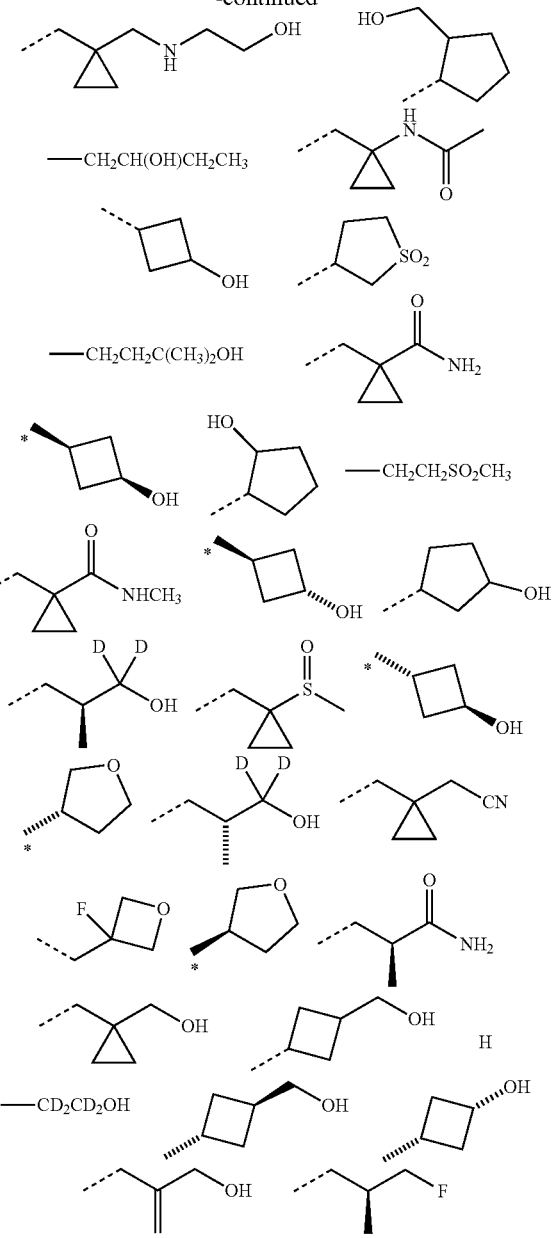

In one embodiment, —(CH$_2$)$_s$R$^3$ is selected from the following table (point of attachment to the oxygen represented by dashed bond or bond terminus marked "*"):

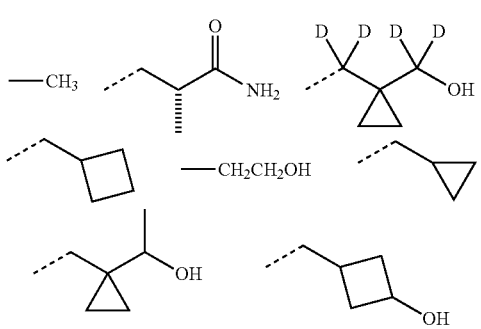

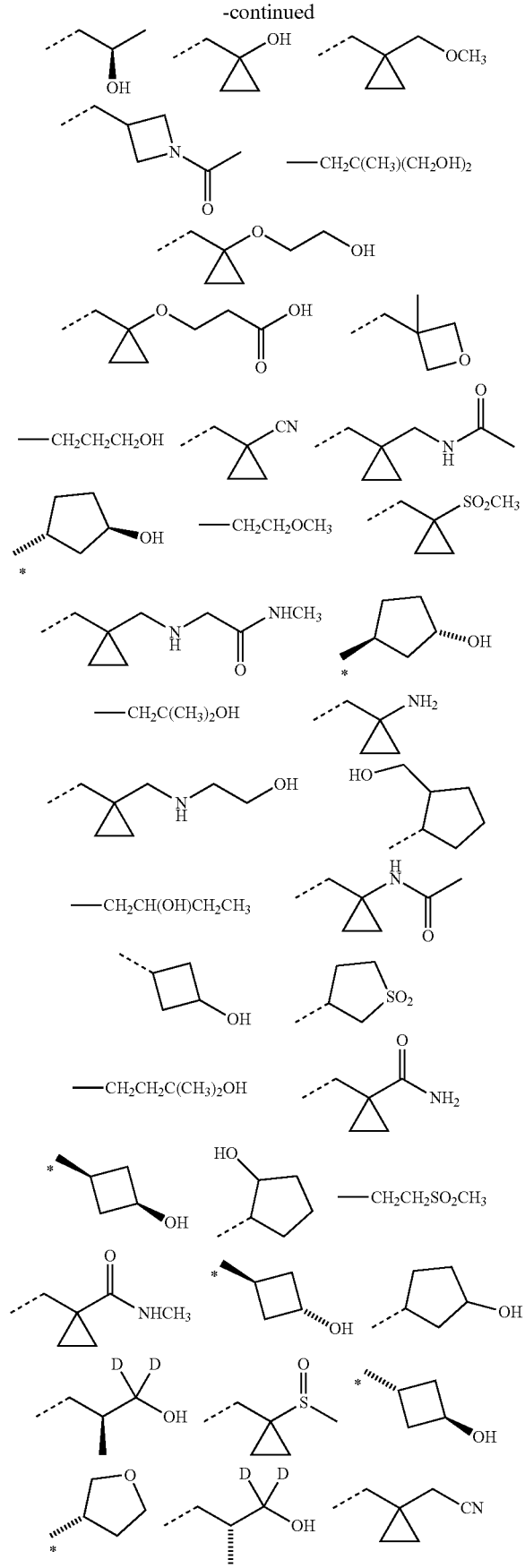

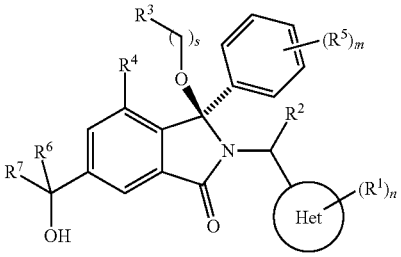

In one embodiment A is cyclopropyl, t is 1, s is 1, $R^x$ and $R^y$ are hydrogen and X is —OH.

In one embodiment A is cyclopropyl, t is 1, s is 1, $R^x$ and $R^y$ are hydrogen and X is —CN.

In one embodiment $R^3$ is hydrogen and s is 1. In one embodiment, X is hydrogen and s, t, and q are 0.
$R^4$ and a a is 0, 1, 2 or 3. In other words, the phenyl group of the isoindolin-1-one may have 0, 1, 2 or 3 substituents $R^4$.

In one embodiment a is 0 or 1. In another embodiment a is 0. In another embodiment a is 1.

When a is 2 or 3 (i.e. the phenyl group of the isoindolin-1-one is substituted with more than one $R^4$) the substituents $R^4$ may be the same or different (i.e. are independently selected from the definitions of $R^4$).

In one embodiment, a is 1 and the substituent $R^4$ is at the 4-position of the isoindolin-1-one, and the compound of formula (I) is a compound of formula (Ir) or a tautomer or a solvate or a pharmaceutically acceptable salt thereof:

(Ir)

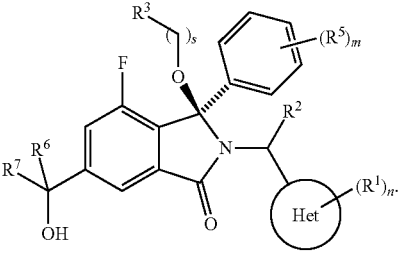

$R^4$ is independently selected from halogen, nitrile, $C_{1-4}$ alkyl, halo$C_{1-4}$alkyl, $C_{1-4}$alkoxy and halo$C_{1-4}$alkoxy.

In one embodiment, $R^4$ is halogen. In one embodiment, $R^4$ is fluoro or chloro. In another embodiment, $R^4$ is fluoro.

In one embodiment, a is 1, the substituent $R^4$ is at the 4-position of the isoindolin-1-one, and $R^4$ is F and the compound of formula (I) is a compound of formula (Is) or a tautomer or a solvate or a pharmaceutically acceptable salt thereof:

(Is)

In one embodiment, a is 0, and the compound of formula (I) is a compound of formula (It) or a tautomer or a solvate or a pharmaceutically acceptable salt thereof:

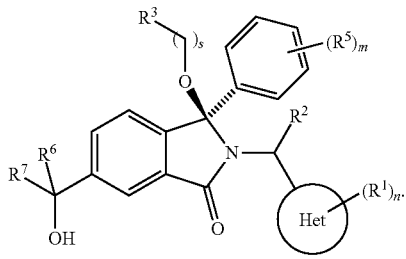

(It)

In one embodiment, $R^4$ is $C_{1-4}$ alkyl (e.g. —$CH_3$), or halogen (e.g. F or Cl) and a is 1.

In one embodiment, a is 0 and $R^4$ is absent (i.e. hydrogen).

In one embodiment a is 0 or 1 and $R^4$ is halogen (e.g. fluorine).

$R^5$ and m m is 1 or 2. In other words, the phenyl group may have 1 or 2 substituents $R^5$.

In one embodiment, m is 1 and the phenyl group has one substituent.

$R^5$ may be attached at the ortho (or o-), meta (or m-) or para (or p-) position of the phenyl group, wherein the position is defined relative to the point of attachment of the phenyl group to the 3-position of the isoindolin-1-one ring.

When m is 2 (i.e. the phenyl group is substituted with more than one $R^5$) the substituents $R^5$ may be the same or different (i.e. are independently selected from the definitions of $R^5$).

In one embodiment, m is 1 and the substituent $R^4$ is at the p-position of the phenyl group, and the compound of formula (I) is a compound of formula (Iu) or a tautomer or a solvate or a pharmaceutically acceptable salt thereof:

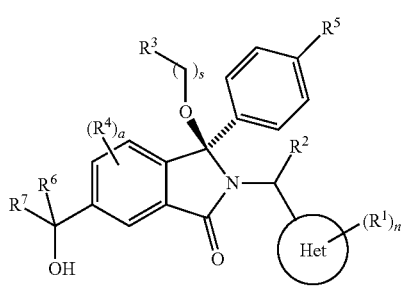

(Iu)

$R^5$ is independently selected from halogen, nitrile, $C_{1-4}$ alkyl, halo$C_{1-4}$alkyl, $C_{1-4}$alkoxy and halo$C_{1-4}$alkoxy.

In one embodiment, $R^5$ is halogen, $C_{1-4}$ alkyl, halo $C_{1-4}$alkyl or $C_{1-4}$alkoxy. In another embodiment $R^5$ is halogen (e.g. chloro).

In one embodiment, $R^5$ is halogen (e.g. Cl or F), $C_{1-4}$ alkyl (e.g. —$CH_2CH_3$), nitrile, halo$C_{1-4}$alkyl (e.g. —$CF_3$, or —$CF_2CH_3$), or halo$C_{1-4}$alkoxy (e.g. —$OCF_3$), and m is 1 or 2.

In one embodiment, m is 1 and $R^5$ is selected from halogen, nitrile, $C_{1-4}$ alkyl, halo$C_{1-4}$alkyl, $C_{1-4}$alkoxy and halo$C_{1-4}$alkoxy.

In one embodiment, m=1 and $R^5$ is —Cl (e.g. p-Cl), —F (e.g. p-F), —CN (e.g. p-CN), —$CF_3$ (e.g. p-$CF_3$), —$OCF_3$ (e.g. p-$OCF_3$), $CF_2CH_3$ (e.g. p-$CF_2CH_3$) or —$CH_2CH_3$ (e.g. p-$CH_2CH_3$), or m=2 and $R^5$ is p-F or m-F.

$R^6$ and $R^7$ $R^6$ and $R^7$ are independently selected from hydrogen, $C_{1-6}$alkyl, halo$C_{1-6}$alkyl, $C_{2-6}$alkenyl, $C_{2-6}$alkynyl, hydroxy, hydroxy$C_{1-6}$alkyl, —COO$C_{1-6}$alkyl, —$(CH_2)_j$—O—$C_{1-6}$alkyl, —$(CH_2)_j$—O-(hydroxy$C_{1-6}$alkyl), —$C_{1-6}$alkyl-$NR^xR^y$, —$(CR^xR^y)_p$—CON$R^xR^y$, —$(CR^xR^y)_p$—$NR^xCOR^y$, —$(CR^xR^y)_p$—O—$CH_2$—CON$R^xR^y$, heterocyclic group with 3 to 7 ring members, —$CH_2$-heterocyclic group with 3 to 7 ring members, —$CH_2$—O-heterocyclic group with 3 to 7 ring members, —$CH_2$—NH-heterocyclic group with 3 to 7 ring members, —$CH_2$—N($C_{1-6}$alkyl)-heterocyclic group with 3 to 7 ring members, —C(=O)NH-heterocyclic group with 3 to 7 ring members, $C_{3-8}$cycloalkyl, —$CH_2$—$C_{3-8}$cycloalkyl, —$CH_2$—O—$C_{3-8}$cycloalkyl, and $C_{3-8}$cycloalkenyl, wherein said cycloalkyl, cycloalkenyl or heterocyclic groups may be optionally substituted by one or more $R^z$ groups, and wherein in each instance the heterocyclic group comprises one or more (e.g. 1, 2, or 3) heteroatoms selected from N, O, S and oxidised forms thereof;

or the $R^6$ and $R^7$ groups, together with the carbon atom to which they are attached, can join to form a $C_{3-6}$cycloalkyl or heterocyclyl group with 3 to 6 ring members, wherein the heterocyclic group comprises one or more (e.g. 1, 2, or 3) heteroatoms selected from N, O, S and oxidised forms thereof, and wherein said $C_{3-6}$cycloalkyl and heterocyclyl groups may be optionally substituted by one or more $R^z$ groups;

$R^x$ and $R^y$ are independently selected from hydrogen, halogen, nitro, nitrile, $C_{1-6}$alkyl, halo$C_{1-6}$alkyl, $C_{2-6}$alkenyl, $C_{2-6}$alkynyl, hydroxy, hydroxy$C_{1-6}$alkyl, $C_{1-6}$alkoxy, —$(CH_2)_k$—O—$C_{1-6}$alkyl, hydroxy$C_{1-6}$alkoxy, —COO$C_{1-6}$ alkyl, —N(H)$_e$($C_{1-4}$alkyl)$_{2-e}$, —$C_{1-6}$alkyl-N(H)$_e$($C_{1-4}$ alkyl)$_{2-e}$, —$(CH_2)_k$—C(=O)N(H)$_e$($C_{1-4}$alkyl)$_{2-e}$, $C_{3-8}$cycloalkyl and $C_{3-8}$cycloalkenyl;

or the $R^x$ and $R^y$ groups, together with the carbon or nitrogen atom to which they are attached, can join to form a $C_{3-6}$cycloalkyl or saturated heterocyclyl group with 3 to 6 ring members which may be optionally fused to an aromatic heterocyclyl group of 3 to 5 ring members;

or when on a carbon atom the $R^x$ and $R^y$ groups can join together to form a =$CH_2$ group;

$R^z$ is independently selected from halogen, nitro, nitrile, $C_{1-6}$alkyl, halo$C_{1-6}$alkyl, $C_{2-6}$alkenyl, $C_{2-6}$alkynyl, =O, hydroxy, hydroxy$C_{1-6}$alkyl, $C_{1-6}$alkoxy, —$(CH_2)_k$—O—$C_{1-6}$alkyl, hydroxy$C_{1-6}$alkoxy, —C(=O)$C_{1-6}$alkyl, —C(=O)$C_{1-6}$alkyl-OH, —C(=O)$C_{1-6}$alkyl-N(H)$_e$ ($C_{1-4}$alkyl)$_{2-e}$, —C(=O)N(H)$_e$($C_{1-4}$alkyl)$_{2-e}$, —$(CH_2)_r$—CO$_2C_{1-6}$alkyl, —$(CH_2)_r$—CO$_2$H, —N(H)$_e$($C_{1-4}$alkyl)$_{2-e}$, —$C_{1-6}$alkyl-N(H)$_e$($C_{1-4}$alkyl)$_{2-e}$, heterocyclyl group with 3 to 6 ring members, heterocyclyl group with 3 to 6 ring members substituted by —C(=O)$C_{1-4}$alkyl, heterocyclyl group with 3 to 6 ring members substituted by —C(=O) O$C_{1-4}$alkyl, heterocyclyl group with 3 to 6 ring members substituted by —C(=O)N(H)$_e$($C_{1-4}$alkyl)$_{2-e}$, —C(=O)heterocyclyl group with 3 to 6 ring members, $C_{3-8}$cycloalkyl and $C_{3-8}$cycloalkenyl, wherein if $R^7$ is pyridine then $R^z$ is other then —$NH_2$;

j, e, r and p are independently selected from 0, 1 and 2; and k is selected from 1 and 2.

In one embodiment, $R^6$ and $R^7$ are independently selected from hydrogen, $C_{1-6}$alkyl, halo$C_{1-6}$alkyl, $C_{2-6}$alkenyl, $C_{2-6}$alkynyl, hydroxy, hydroxy$C_{1-6}$alkyl, —COO$C_{1-6}$alkyl, —$(CH_2)_j$—O—$C_{1-6}$alkyl, —$(CH_2)_j$—O-(hydroxy $C_{1-6}$alkyl), —$C_{1-6}$alkyl-$NR^xR^y$, —$(CR^xR^y)_p$—CON$R^xR^y$, —(CR$^x$R$^y$)$_p$—NR$^x$COR$^y$, —(CR$^x$R$^y$)$_p$—O—CH$_2$—CONR$^x$R$^y$, heterocyclic group with 3 to 7 ring members, —CH$_2$-heterocyclic group with 3 to 7 ring members, —CH$_2$—O-heterocyclic group with 3 to 7 ring members, —CH$_2$—NH-heterocyclic group with 3 to 7 ring members, —CH$_2$—N(C$_{1-6}$alkyl)-heterocyclic group with 3 to 7 ring members, —C(=O)NH-heterocyclic group with 3 to 7 ring members, C$_{3-8}$cycloalkyl, —CH$_2$—C$_{3-8}$cycloalkyl, —CH$_2$—O—C$_{3-8}$cycloalkyl, and C$_{3-8}$cycloalkenyl, wherein said cycloalkyl, cycloalkenyl or heterocyclic groups may be optionally substituted by one or more R$^z$ groups, and wherein in each instance the heterocyclic group comprises one or more (e.g. 1, 2, or 3) heteroatoms selected from N, O, S and oxidised forms thereof;

In one embodiment R$^7$ is a cycloalkyl, cycloalkenyl or heterocyclic group optionally substituted by one or more R$^z$ selected from C$_{1-6}$alkyl (e.g. methyl), C$_{1-6}$alkoxy (e.g. methoxy) and —C(=O)C$_{1-6}$alkyl (e.g. —C(=O)CH$_3$).

In one embodiment R$^7$ is a cycloalkyl or cycloalkenyl group optionally substituted by one or more R$^z$ groups wherein R$^z$ is hydroxy.

R$^6$ and R$^7$ may be the same or different.

When R$^6$ and R$^7$ are different, the compound of formula (I) can exist as at least two diastereoisomers:

Diastereoisomer 2A

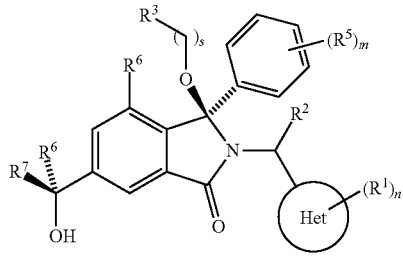

Diastereoisomer 2B

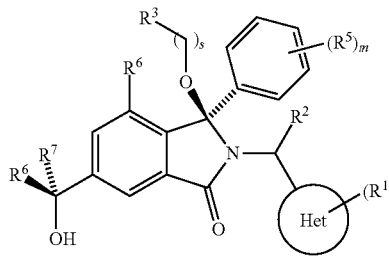

For the avoidance of doubt, the general formula (I) and all subformulae cover both individual diastereoisomers and mixtures of the diastereoisomers which are related as epimers at the —CR$^6$R$^7$OH group.

In one embodiment of the compound of formula (I) R$^6$ and R$^7$ are different and the compound is diastereoisomer 2A or a tautomer or a solvate or a pharmaceutically acceptable salt thereof.

In one embodiment of the compound of formula (I) R$^6$ and R$^7$ are different and the compound is diastereoisomer 2B or a tautomer or a solvate or a pharmaceutically acceptable salt thereof.

In one embodiment, R$^6$ is methyl and the compound of formula (I) is a compound of formula (Iv) or a tautomer or a solvate or a pharmaceutically acceptable salt thereof:

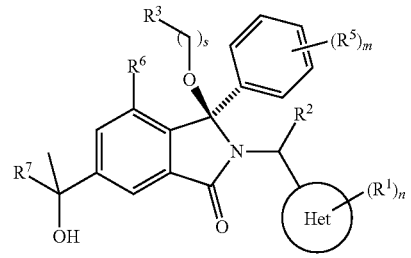

(Iv)

In one embodiment, R$^6$ is ethyl and the compound of formula (I) is a compound of formula (Iv') or a tautomer or a solvate or a pharmaceutically acceptable salt thereof:

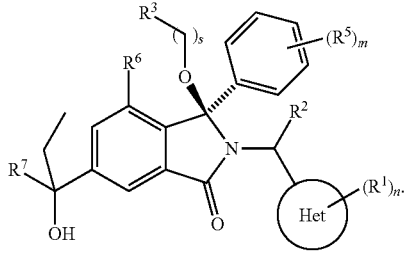

(Iv')

In one embodiment, R$^7$ is selected from C$_{1-6}$alkyl or haloC$_{1-6}$alkyl. In one embodiment R$^7$ is a C$_{3-6}$cycloalkyl (e.g. cyclopropyl, cyclobutyl or cyclohexyl) optionally substituted by one or more R$^z$ groups (e.g. —OH).

In one embodiment, R$^7$ is selected from C$_{1-6}$alkyl, hydroxyC$_{1-6}$alkyl, —(CH$_2$)$_j$—O—C$_{1-6}$alkyl, —(CH$_2$)$_j$—O-(hydroxyC$_{1-6}$alkyl), —C$_{1-6}$alkyl-NR$^x$R$^y$ (e.g. —C$_{1-6}$alkyl-N(H)$_e$(C$_{1-4}$alkyl)$_{2-e}$), —(CR$^x$R$^y$)$_p$—NR$^x$COR$^y$, heterocyclic group with 3 to 7 ring members, —CH$_2$-heterocyclic group with 3 to 7 ring members, —CH$_2$—NH-heterocyclic group with 3 to 7 ring members, —CH$_2$—N(C$_{1-6}$alkyl)-heterocyclic group with 3 to 7 ring members, —C(=O)NH-heterocyclic group with 3 to 7 ring members, C$_{3-8}$cycloalkyl, and —CH$_2$—C$_{3-8}$cycloalkyl, wherein said cycloalkyl or heterocyclic groups may be optionally substituted by one or more R$^z$ groups, and wherein in each instance the heterocyclic group comprises one or more (e.g. 1, 2, or 3) heteroatoms selected from N, O, S and oxidised forms thereof.

In one embodiment, R$^7$ is selected from C$_{1-6}$alkyl, hydroxyC$_{1-6}$alkyl, —(CH$_2$)$_j$—O—C$_{1-6}$alkyl, —(CH$_2$)$_j$—O-(hydroxyC$_{1-6}$alkyl), —C$_{1-6}$alkyl-N(H)$_e$(C$_{1-4}$alkyl)$_{2-e}$, heterocyclic group with 3 to 7 ring members, —CH$_2$-heterocyclic group with 3 to 7 ring members, —CH$_2$—NH-heterocyclic group with 3 to 7 ring members, —CH$_2$—N(C$_{1-6}$alkyl)-heterocyclic group with 3 to 7 ring members, —C(=O)NH-heterocyclic group with 3 to 7 ring members, C$_{3-8}$cycloalkyl, and —CH$_2$—C$_{3-8}$cycloalkyl, wherein said cycloalkyl or heterocyclic groups may be optionally substituted by one or more R$^z$ groups, and wherein in each instance the heterocyclic group comprises one or more (e.g. 1, 2, or 3) heteroatoms selected from N, O, S and oxidised forms thereof.

In one embodiment, R$^7$ is selected from heterocyclic group with 3 to 7 ring members, —CH$_2$-heterocyclic group with 3 to 7 ring members, —CH$_2$—NH-heterocyclic group with 3 to 7 ring members, —CH$_2$—N(CH$_3$)-heterocyclic group with 3 to 7 ring members, —C(=O)NH-heterocyclic group with 3 to 7 ring members, $C_{3-6}$cycloalkyl, and —$CH_2$—$C_{3-6}$cycloalkyl, wherein said cycloalkyl or heterocyclic groups may be optionally substituted by one or more $R^z$ groups, and wherein in each instance the heterocyclic group comprises one or more (e.g. 1, 2, or 3) heteroatoms selected from N, O, S and oxidised forms thereof.

In one embodiment, $R^7$ is selected from heterocyclic group with 3 to 7 ring members and —$CH_2$-heterocyclic group with 3 to 7 ring members, wherein said heterocyclic groups may be optionally substituted by one or more $R^z$ groups, and wherein in each instance the heterocyclic group comprises one or more (e.g. 1, or 2) heteroatoms selected from N, O, S and oxidised forms thereof.

In embodiment, the heterocyclic group is saturated. In one embodiment, $R^7$ is saturated heterocyclic group with 3 to 6 ring members or —$CH_2$-(saturated heterocyclic group with 3 to 6 ring members) such as wherein the heterocyclic group is selected from oxetanyl, oxanyl, piperidinyl, piperazinyl, morpholinyl, pyrrolidinyl, imidazolinyl, azetidinyl, thiomorpolinyl, such as oxanyl, piperdinyl or piperazinyl.

In one embodiment, $R^7$ is selected from saturated heterocyclic group with 3 to 6 ring members and —$CH_2$-saturated heterocyclic group with 3 to 6 ring members, wherein said heterocyclic groups may be optionally substituted by one or more $R^z$ groups, and wherein in each instance the heterocyclic group comprises one or more (e.g. 1, 2, or 3) heteroatoms selected from N, O, S. In one embodiment, $R^7$ is selected from a nitrogen containing saturated heterocyclic group with 3 to 6 ring member and —$CH_2$-(nitrogen containing saturated heterocyclic group with 3 to 6 ring members), wherein said heterocyclic groups may be optionally substituted by one or more $R^z$ groups, and wherein the heterocyclic group may optionally contain one or more (e.g. 1, 2, or 3) additional heteroatoms selected from N, O, S.

In one embodiment, $R^7$ is nitrogen containing saturated heterocyclic group with 3 to 7 ring members or —$CH_2$-(nitrogen containing saturated heterocyclic group with 3 to 7 ring members), wherein said nitrogen containing saturated heterocyclic groups may be optionally substituted by one or more $R^z$ groups and wherein the nitrogen containing saturated heterocyclic group may optionally contain one or more (e.g. 1, 2, or 3) additional heteroatoms selected from N, O, S. In one embodiment the nitrogen containing saturated heterocyclic group with 3 to 7 ring members (such as 3 to 6 ring members) is selected from piperidinyl, piperazinyl, morpholinyl, pyrrolidinyl, imidazolinyl, azetidinyl, thiomorpolinyl, such as piperdinyl or piperazinyl.

In one embodiment, $R^7$ is nitrogen containing aromatic heterocyclic group with 3 to 6 ring members or —$CH_2$-(nitrogen containing aromatic heterocyclic group with 3 to 6 ring members), wherein said heterocyclic groups may be optionally substituted by one or more $R^z$ groups and wherein the heterocyclic group may optionally contain one or more (e.g. 1, 2, or 3) additional heteroatoms selected from N, O, S.

In another embodiment, $R^7$ is nitrogen containing aromatic heterocyclic group with 3 to 6 ring members, wherein said heterocyclic group may be unsubsituted or substituted by one or more $R^z$ groups, for example selected from halogen (e.g. fluorine), $C_{1-6}$alkyl (e.g. methyl), $C_{1-6}$alkoxy (e.g. methoxy), and —C(=O)$C_{1-6}$alkyl (e.g. —C(=O)$CH_3$).

In one embodiment, $R^7$ is oxygen containing aromatic heterocyclic group with 3 to 6 ring members or —$CH_2$-(oxygen containing aromatic heterocyclic group with 3 to 6 ring members), wherein said heterocyclic groups may be optionally substituted by one or more $R^z$ groups and wherein the heterocyclic group may optionally contain one or more (e.g. 1, 2, or 3) additional heteroatoms selected from N, O, S.

In another embodiment, $R^7$ is oxygen containing aromatic heterocyclic group with 3 to 6 ring members, wherein said heterocyclic group may be unsubsituted or substituted by one or more $R^z$ groups, for example $R^z$ groups selected from halogen (e.g. fluorine), $C_{1-6}$alkyl (e.g. methyl), $C_{1-6}$alkoxy (e.g. methoxy), and —C(=O)$C_{1-6}$alkyl (e.g. —C(=O)$CH_3$).

In one embodiment $R^7$ is selected from heterocyclyl groups containing 5 or 6 ring members optionally substituted by one or more $R^z$.

In one embodiment $R^7$ is selected from aromatic heterocyclyl groups containing 5 ring members optionally substituted by one or more $R^z$. In one embodiment $R^7$ is selected from an aromatic nitrogen containing (e.g. diaza) hetetero-cyclyl group containing 5 ring members optionally substituted by one or more $R^z$. In one embodiment $R^7$ is pyrazolyl (e.g. pyrazol-4-yl or pyrazol-3-yl).

In one embodiment $R^7$ is selected from a saturated heteterocyclyl group containing 6 ring members optionally substituted by one or more $R^z$. In one embodiment $R^7$ is selected from a saturated oxygen or nitrogen containing heteterocyclyl group containing 6 ring members optionally substituted by one or more $R^z$.

In one embodiment $R^7$ is selected from oxanyl, piperidinyl, pyrazolyl or imidazolyl optionally substituted by one or more $R^z$. In one embodiment $R^7$ is selected from oxanyl, piperidinyl, pyrazolyl or imidazolyl optionally substituted by one or more $R^z$, where $R^z$ is selected from halo (e.g. —F) or $C_{1-4}$alkyl (e.g. methyl).

In one embodiment $R^7$ is selected from oxanyl (also known as tetrahydropyranyl) or piperidinyl optionally substituted by one or more $R^z$. In one embodiment $R^7$ is selected from oxanyl or piperidinyl unsubstituted or substituted by one or more $R^z$, where $R^z$ is selected from halo (e.g. —F) or $C_{1-4}$alkyl (e.g. methyl), in particular halo (e.g. —F).

In one embodiment, $R^7$ is $C_{3-8}$cycloalkyl such as $C_{3-6}$cycloalkyl (e.g. cyclobutyl or cyclohexyl) optionally substituted by one or more $R^z$, for example where $R^z$ is hydroxy. In one embodiment, $R^7$ is cyclohexyl optionally substituted by one or more hydroxy. In one embodiment $R^7$ is cyclohexyl optionally substituted by one or more hydroxyl, in the trans stereochemistry (e.g. trans-4-hydroxycyclohexane).

In one embodiment $R^7$ is selected from —$CH_2$—NH-heterocyclic group with 3 to 7 ring members (e.g. —$CH_2$—NH-oxanyl and —$CH_2$—N($C_{1-6}$alkyl)-heterocyclic group with 3 to 7 ring members (e.g. —$CH_2NCH_3$-(piperidinyl) optionally substituted by one or more $R^z$ groups (e.g. methyl, —$COCH_3$).

In one embodiment, $R^7$ is —$(CR^xR^y)_p$—$CONR^xR^y$ or —C(=O)NH-heterocyclic group with 3 to 7 ring members. In one embodiment, $R^7$ is —C(=O)NH-heterocyclic group with 4 to 6 ring members (e.g. piperidinyl, pyrazolyl, or azetidinyl).

In one embodiment, $R^7$ is —$(CR^xR^y)_p$—$CONR^xR^y$. In one embodiment $R^7$ is —$(CR^xR^y)_p$—$CONH(C_{1-4}$alkyl), in particular —(CO)$NHCH_3$, —(CO)$NHCH_2CH_3$ or —(CO)NH(CH($CH_3$)$_2$).

In one embodiment $R^7$ is —C(=O)NH-heterocyclic group with 3 to 7 ring members (e.g. —C(=O)NH-piperidinyl, —C(=O)NH-azetidinyl or —C(=O)NH-pyrazolyl) optionally substituted by one or more $R^z$ groups (e.g. methyl, —$COCH_3$).

In one embodiment, $R^7$ is —$C_{1-6}$alkyl-$NR^xR^y$ (e.g. —$C_{1-6}$alkyl-N(H)$_e$($C_{1-4}$alkyl)$_{2-e}$). In one embodiment $R^7$ is —CH$_2$NH$_2$, —CH$_2$NHCH$_3$, or —CH$_2$N(CH$_3$)$_2$. In one embodiment R$^7$ is —C$_{1-6}$alkyl-NR$^x$R$^y$ wherein R$^x$ is C$_{3-8}$cycloalkyl. In one embodiment R$^7$ is —C$_{1-2}$alkyl-NH—C$_{3-6}$cycloalkyl (e.g. —CH$_2$—NH-cyclopropyl).

In one embodiment, R$^7$ is —C$_{1-6}$alkyl-NR$^x$R$^y$ wherein the R$^x$ and R$^y$ groups, together with the nitrogen atom to which they are attached, can join to form a C$_{3-6}$cycloalkyl or heterocyclyl group with 3 to 6 ring members. In one embodiment, R$^x$ and R$^y$ together form a saturated heterocyclyl group with 3 to 6 ring members e.g. piperazinyl.

In one embodiment R$^7$ is —C$_{1-6}$alkyl-NR$^x$R$^y$, wherein the R$^x$ and R$^y$ groups, together with the nitrogen atom to which they are attached, join to form a C$_{3-6}$cycloalkyl or saturated heterocyclyl group with 3 to 6 ring members which may be optionally fused to an aromatic heterocyclyl group of 3 to 5 ring members. In one embodiment R$^7$ is —C$_{1-6}$alkyl-NR$^x$R$^y$, wherein the R$^x$ and R$^y$ groups, together with the nitrogen atom to which they are attached, join to form a saturated heterocyclyl group with 3 to 6 ring members which is fused to an aromatic heterocyclyl group of 3 to 5 ring members. R$^z$ is independently selected from halogen, nitro, nitrile, C$_{1-6}$alkyl, haloC$_{1-6}$alkyl, C$_{2-6}$alkenyl, C$_{2-6}$alkynyl, =O, hydroxy, hydroxyC$_{1-6}$alkyl, C$_{1-6}$alkoxy, —(CH$_2$)$_k$—O—C$_{1-6}$alkyl, hydroxyC$_{1-6}$alkoxy, —C(=O)C$_{1-6}$alkyl, —C(=O)C$_{1-6}$alkyl-OH, —C(=O)C$_{1-6}$alkyl-N(H)$_e$(C$_{1-4}$alkyl)$_{2-e}$, —C(=O)N(H)$_e$(C$_{1-4}$alkyl)$_{2-e}$, —(CH$_2$)$_r$CO$_2$C$_{1-6}$alkyl, —(CH$_2$)$_r$CO$_2$H, —N(H)$_e$(C$_{1-4}$alkyl)$_{2-e}$, —C$_{1-6}$alkyl-N(H)$_e$(C$_{1-4}$alkyl)$_{2-e}$, heterocyclyl group with 3 to 6 ring members, heterocyclyl group with 3 to 6 ring members substituted by —C(=O)C$_{1-4}$alkyl, heterocyclyl group with 3 to 6 ring members substituted by —C(=O)OC$_{1-4}$alkyl, heterocyclyl group with 3 to 6 ring members substituted by —C(=O)N(H)$_e$(C$_{1-4}$alkyl)$_{2-e}$, —C(=O)heterocyclyl group with 3 to 6 ring members, C$_{3-8}$cycloalkyl and C$_{3-8}$cycloalkenyl.

In one embodiment R$^z$ is independently selected from halogen (e.g. fluorine), C$_{1-6}$alkyl (e.g. methyl), C$_{1-6}$alkoxy (e.g. methoxy), and —C(=O)C$_{1-6}$alkyl (e.g. —C(=O)CH$_3$).

In one embodiment R$^z$ is independently selected from C$_{1-6}$alkyl (e.g. methyl), C$_{1-6}$alkoxy (e.g. methoxy), and —C(=O)C$_{1-6}$alkyl (e.g. —C(=O)CH$_3$).

In one embodiment, R$^7$ is C$_{1-6}$alkyl (e.g. methyl or ethyl), haloC$_{1-6}$alkyl (e.g. trifluoromethyl), C$_{2-6}$alkenyl (e.g. C$_2$alkenyl), hydroxyC$_{1-6}$alkyl (e.g. —CH$_2$OH, —CH$_2$CH$_2$OH), —C$_{1-6}$alkyl-NR$^x$R$^y$ (e.g. —CH$_2$NH$_2$, —CH$_2$NHCH$_3$, —CH$_2$N(CH$_3$)$_2$, or —CH$_2$—NH-cyclopropyl), —(CR$^x$R$^y$)$_p$—CONR$^x$R$^y$ (e.g. —(CO)NHCH$_3$, —(CO)NHCH$_2$CH$_3$, —(CO)NHCH$_2$CH$_2$NH$_2$ or —(CO)NH(CH(CH$_3$)$_2$), —(CH$_2$)$_j$—O—C$_{1-6}$alkyl (e.g. —CH$_2$OCH$_3$, —CH$_2$OCH$_2$CH$_3$ or —CH$_2$OCD$_3$), —(CR$^x$R$^y$)$_p$—NR$^x$COR$^y$ (e.g. —CH$_2$NHCOCH$_3$), —(CR$^x$R$^y$)$_p$—O—CH$_2$—CONR$^x$R$^y$ (e.g. —CH$_2$—O—CH$_2$CON(CH$_3$)$_2$), —(CH$_2$)$_j$—O-(hydroxyC$_{1-6}$alkyl) (e.g. —CH$_2$—O—CH$_2$CH$_2$OH), —C(=O)NH-heterocyclic group with 3 to 7 ring members, C$_{3-6}$cycloalkyl, heterocyclic group with 3 to 7 ring members (e.g. oxanyl), or —CH$_2$-heterocyclic group with 3 to 7 ring members wherein the cycloalkyl or heterocyclic group comprises one or more (e.g. 1, 2, or 3) heteroatoms selected from N, O, S and oxidised forms and may be optionally substituted by one or more R$^z$ groups (for example selected from C$_{1-6}$alkyl (e.g. methyl), C$_{1-6}$alkoxy (e.g. methoxy) and —C(=O)C$_{1-6}$alkyl (e.g. —C(=O)CH$_3$)). In one embodiment, R$^6$ is methyl or ethyl and R$^7$ is C$_{1-6}$alkyl (e.g. methyl), hydroxyC$_{1-6}$alkyl, —C$_{1-6}$alkyl-NR$^x$R$^y$, —(CR$^x$R$^y$)$_p$—CONR$^x$R$^y$, —(CH$_2$)$_j$—O—C$_{1-6}$alkyl, —(CR$^x$R$^y$)$_p$—NR$^x$COR$^y$, —(CR$^x$R$^y$)$_p$—O—CH$_2$—CONR$^x$R$^y$, —(CH$_2$)$_j$—O-(hydroxyC$_{1-6}$alkyl), heterocyclic group with 3 to 7 ring members (e.g. oxanyl), or —CH$_2$-heterocyclic group with 3 to 7 ring members wherein the heterocyclic group comprises one or more (e.g. 1, 2, or 3) heteroatoms selected from N, O, S and oxidised forms and may be optionally substituted by one or more R$^z$ groups selected from C$_{1-6}$alkyl (e.g. methyl), C$_{1-6}$alkoxy (e.g. methoxy) and —C(=O)C$_{1-6}$alkyl (e.g. —C(=O)CH$_3$).

In one embodiment, R$^6$ is selected from hydrogen, C$_{1-6}$alkyl (e.g. —CH$_3$, —CH$_2$CH$_3$ or —CH$_2$CH$_2$CH$_3$), C$_{2-6}$alkenyl (e.g. —CH=CH$_2$) and haloC$_{1-6}$alkyl (e.g. —CF$_3$).

In one embodiment, R$^6$ is selected from hydrogen, C$_{1-6}$alkyl (e.g. —CH$_3$ or —CH$_2$CH$_3$), C$_{2-6}$alkenyl (e.g. —CH=CH$_2$) and haloC$_{1-6}$alkyl (e.g. —CF$_3$).

In one embodiment, R$^7$ is C$_{1-6}$alkyl (e.g. —CH$_3$ or —CH$_2$CH$_3$), C$_{3-8}$cycloalkyl (e.g. cyclopropyl, cyclobutyl or cyclohexyl), C$_{2-6}$alkenyl (e.g. —CH=CH$_2$), haloC$_{1-6}$alkyl (e.g. —CF$_3$), hydroxyC$_{1-6}$alkyl (e.g. —CH$_2$OH or —CH$_2$CH$_2$OH), —C$_{1-6}$alkyl-NR$^x$R$^y$ (e.g. —CH$_2$NH$_2$, —CH$_2$N(CH$_3$)$_2$, —CH$_2$NHCH$_3$, or —CH$_2$NH(cyclopropyl)), —(CR$^x$R$^y$)$_p$—CONR$^x$R$^y$ (e.g. —C(=O)NHCH$_3$, —(CO)NHCH$_2$CH$_3$, —(CO)NHCH$_2$CH$_2$NH$_2$, —C(=O)NH(CH(CH$_3$)$_2$)), or —(CH$_2$)$_j$—O—C$_{1-6}$alkyl (e.g. —CH$_2$OCH$_3$, —CH$_2$OCH$_2$CH$_3$ or —CH$_2$OCD$_3$), —(CR$^x$R$^y$)$_p$—NR$^x$COR$^y$ (e.g. —CH$_2$NHC(=O)CH$_3$), —(CR$^x$R$^y$)$_p$—O—CH$_2$—CONR$^x$R$^y$ (e.g. —CH$_2$OCH$_2$C(=O)N(CH$_3$)$_2$), —(CH$_2$)$_j$—O-(hydroxyC$_{1-6}$alkyl) (e.g. —CH$_2$OCH$_2$CH$_2$OH), heterocyclic group with 3 to 7 ring members e.g.
(point of attachment represented by dashed bond):

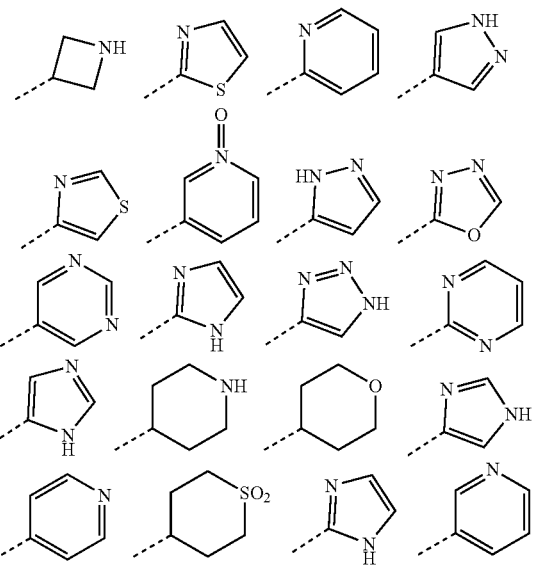

or —CH$_2$-heterocyclic group with 3 to 7 ring members e.g. (point of attachment represented by dashed bond)

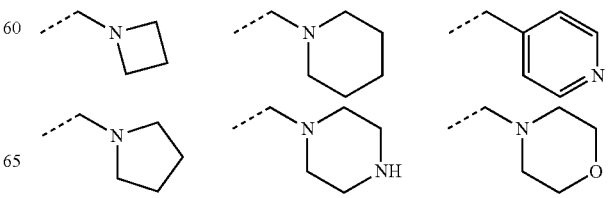

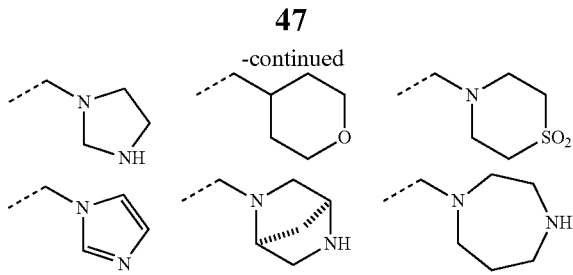

wherein when the moiety R[7] comprises a heterocyclic group, the heterocyclic group may be optionally substituted by one or more R[z] groups selected from $C_{1-6}$alkyl (e.g. methyl), hydroxyalkyl (e.g. —CH$_2$CH$_2$OH), halogen (e.g. fluoro), =O, $C_{1-6}$ alkoxy (e.g. methoxy), —C(=O)C$_{1-6}$ alkyl (e.g. —C(=O)CH$_3$), —C(=O)hydroxyC$_{1-6}$alkyl (e.g. —C(=O)CH$_2$—H), heterocyclyl group with 3 to 6 ring members (e.g. oxetanyl or pyrimidinyl), and —S(O)$_d$—C$_{1-4}$alkyl wherein d is selected from 0, 1 and 2 (e.g. —SO$_2$—CH$_3$).

In one embodiment, R[7] is $C_{1-6}$alkyl (e.g. —CH$_3$ or —CH$_2$CH$_3$), $C_{3-8}$cycloalkyl (e.g. cyclopropyl, cyclobutyl or cyclohexyl), $C_{2-6}$alkenyl (e.g. —CH=CH$_2$), haloC$_{1-6}$alkyl (e.g. —CF$_3$), hydroxyC$_{1-6}$alkyl (e.g. —CH$_2$OH or —CH$_2$CH$_2$OH), —C$_{1-6}$alkyl-NR$^x$R$^y$ (e.g. —CH$_2$NH$_2$, —CH$_2$N(CH$_3$)$_2$, —CH$_2$NHCH$_3$, or —CH$_2$NH(cyclopropyl)), —(CR$^x$R$^y$)$_p$—CONR$^x$R$^y$ (e.g. —C(=O)NHCH$_3$, —(CO)NHCH$_2$CH$_3$, —(CO)NHCH$_2$CH$_2$NH$_2$, —C(=O)NH(CH(CH$_3$)$_2$)), or —(CH$_2$)$_j$—O—C$_{1-6}$alkyl (e.g. —CH$_2$OCH$_3$, —CH$_2$OCH$_2$CH$_3$ or —CH$_2$OCD$_3$), —(CR$^x$R$^y$)$_p$—NR$^x$COR$^y$ (e.g. —CH$_2$NHC(=O)CH$_3$), —(CR$^x$R$^y$)$_p$—O—CH$_2$—CONR$^x$R$^y$ (e.g. —CH$_2$OCH$_2$C(=O)N(CH$_3$)$_2$), —(CH$_2$)$_j$—O-(hydroxyC$_{1-6}$alkyl) (e.g. —CH$_2$OCH$_2$CH$_2$OH), heterocyclic group with 3 to 7 ring members e.g.

(point of attachment represented by dashed bond):

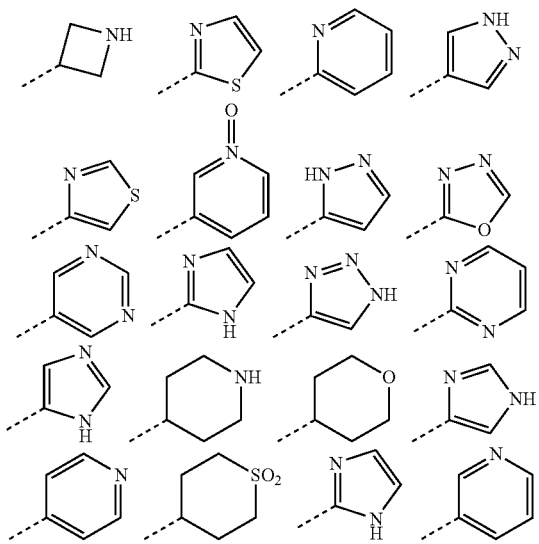

or —CH$_2$—heterocyclic group with 3 to 7 ring members e.g. (point of attachment represented by dashed bond)

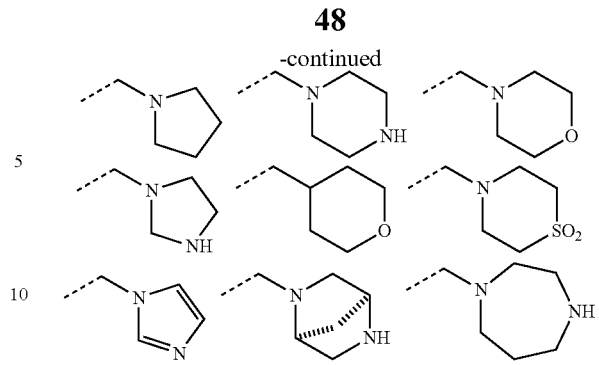

wherein when the moiety R[7] comprises a heterocyclic group, the heterocyclic group may be optionally substituted by one or more R[z] groups selected from $C_{1-6}$alkyl (e.g. methyl), halogen (e.g. fluoro), =O, $C_{1-6}$alkoxy (e.g. methoxy), —C(=O)C$_{1-6}$alkyl (e.g. —C(=O)CH$_3$), —C(=O)hydroxyC$_{1-6}$alkyl (e.g. —C(=O)CH$_2$OH), heterocyclyl group with 3 to 6 ring members (e.g. pyrimidinyl), and —S(O)$_d$—C$_{1-4}$alkyl wherein d is selected from 0, 1 and 2 (e.g. —SO$_2$—CH$_3$).

In one embodiment of formula (I) R[7] is a heterocyclic group with 3 to 7 ring members optionally substituted by one or more R[z] groups e.g.

(point of attachment represented by dashed bond)

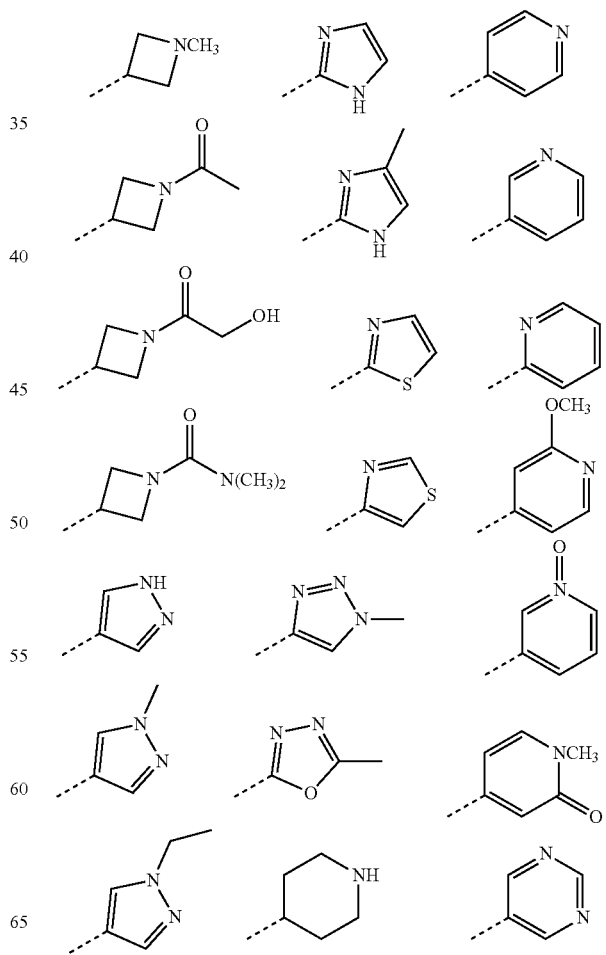

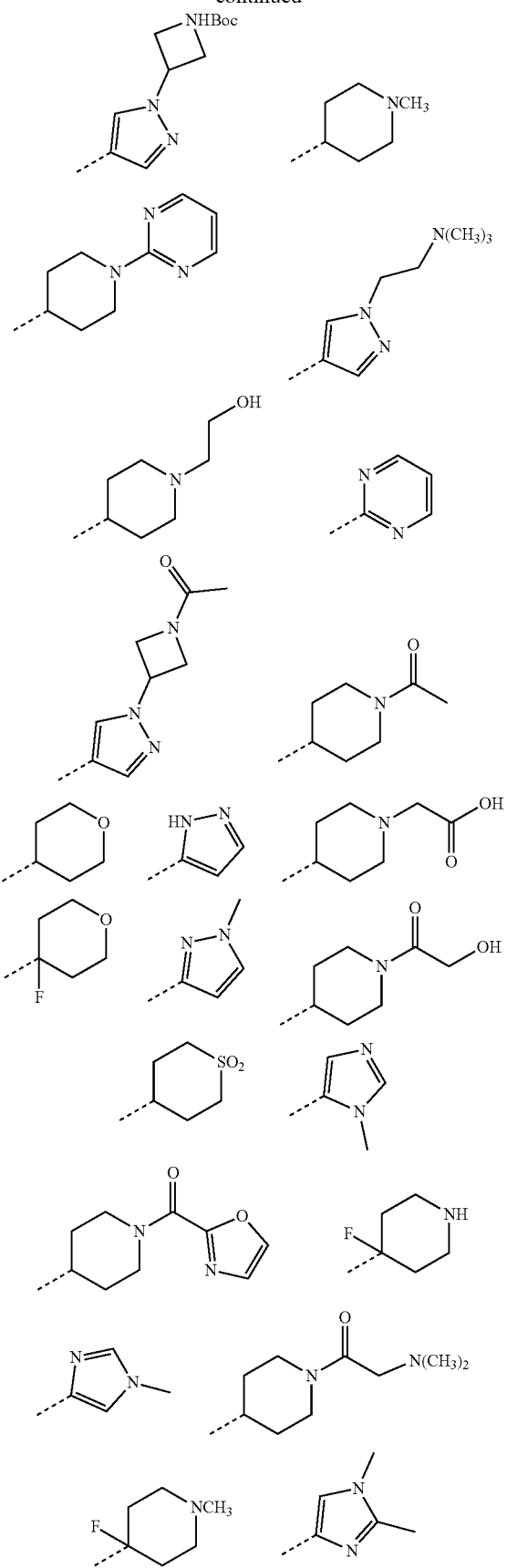
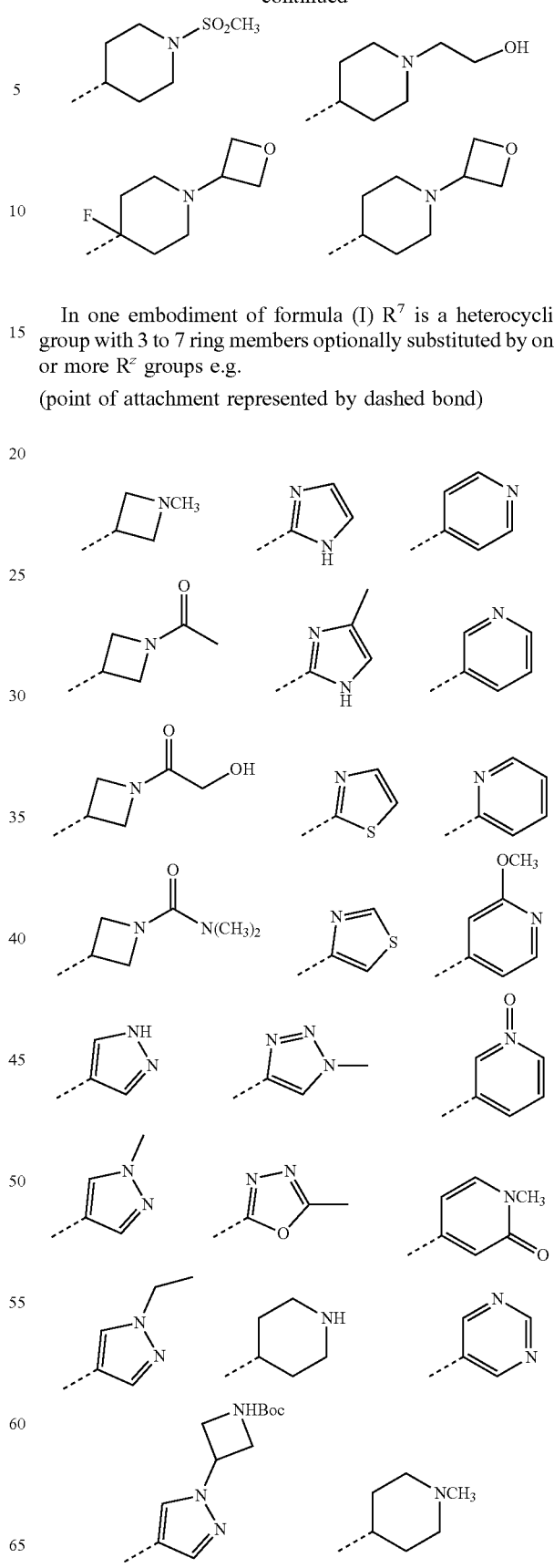
In one embodiment of formula (I) $R^7$ is a heterocyclic group with 3 to 7 ring members optionally substituted by one or more $R^z$ groups e.g.
(point of attachment represented by dashed bond)

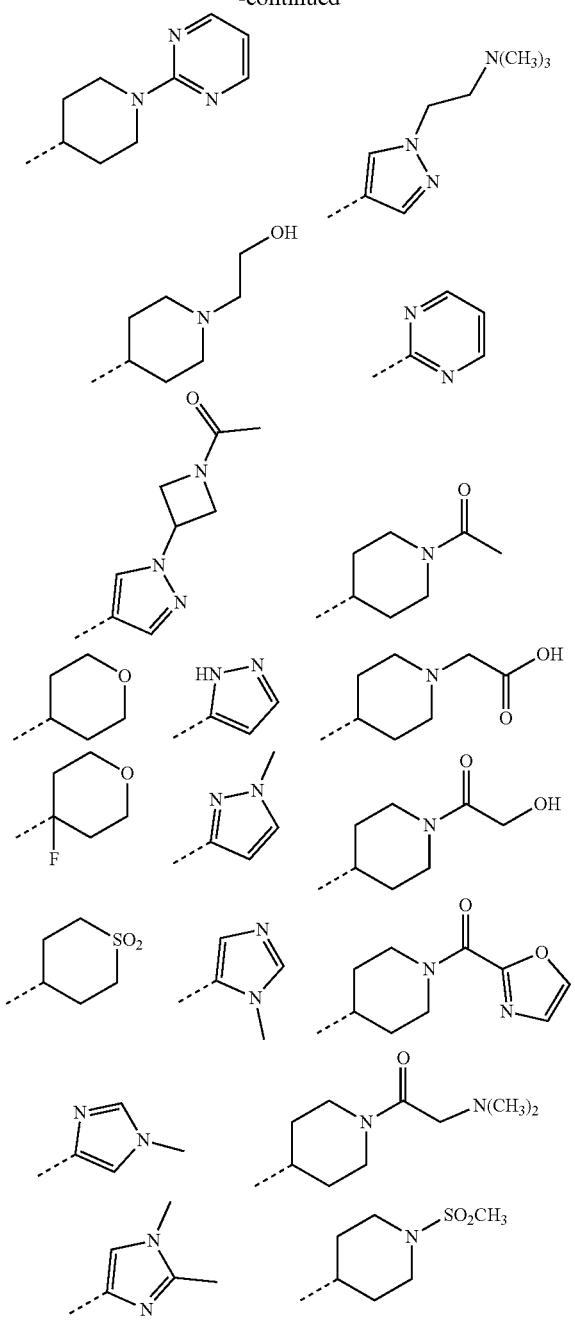
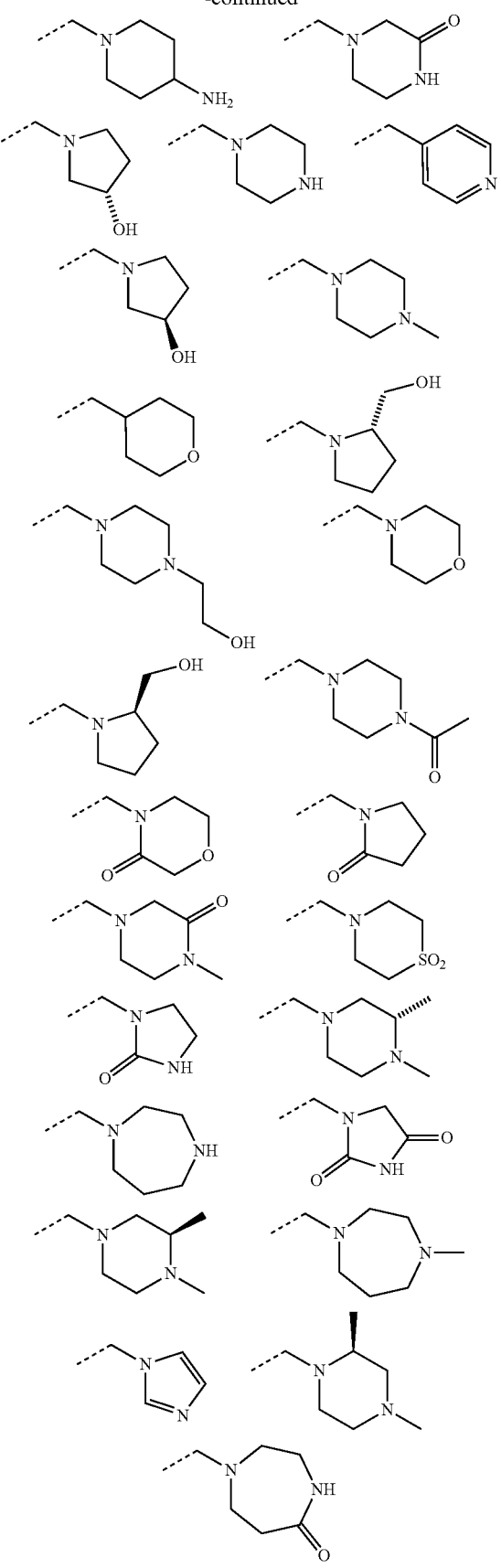
In one embodiment, $R^7$ is a —$CH_2$-heterocyclic group with 3 to 7 ring members optionally substituted by by one or more $R^z$ groups e.g.
(point of attachment represented by dashed bond)
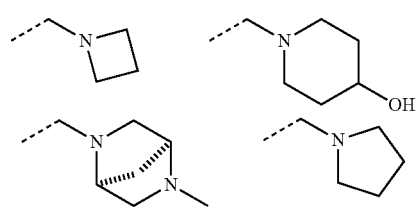

In one embodiment R[7] is selected from:
(point of attachment represented by dashed bond):

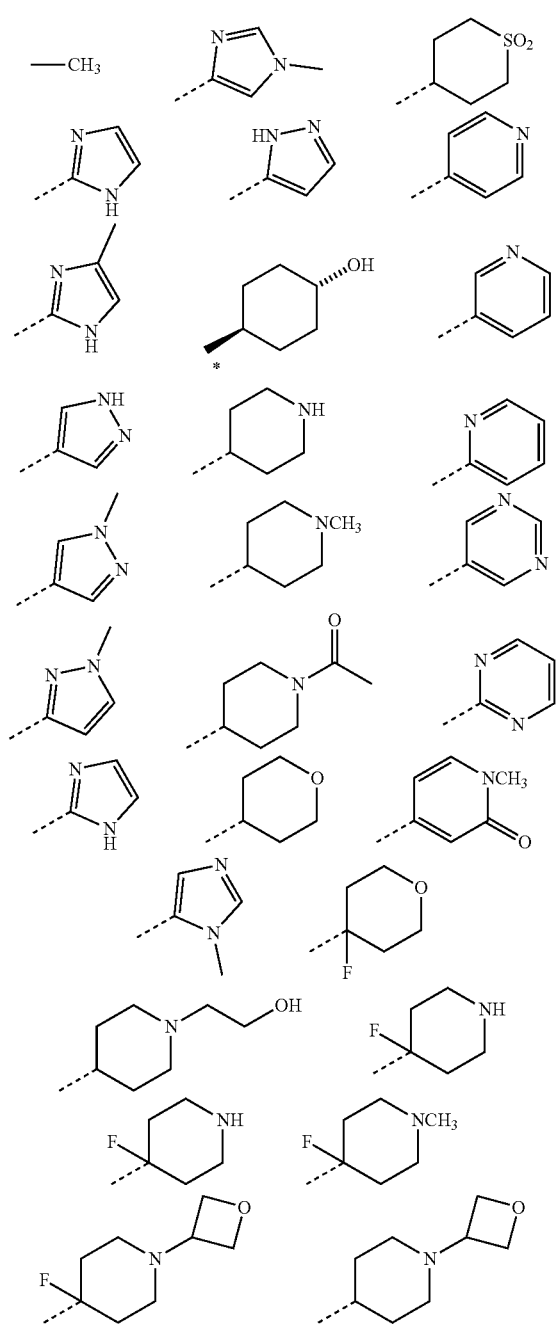

In one embodiment R[7] is selected from:
(point of attachment represented by dashed bond):

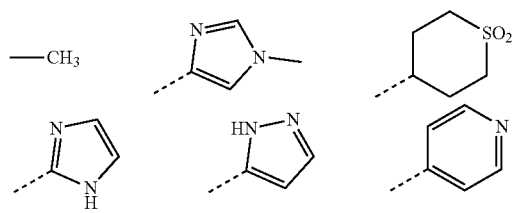

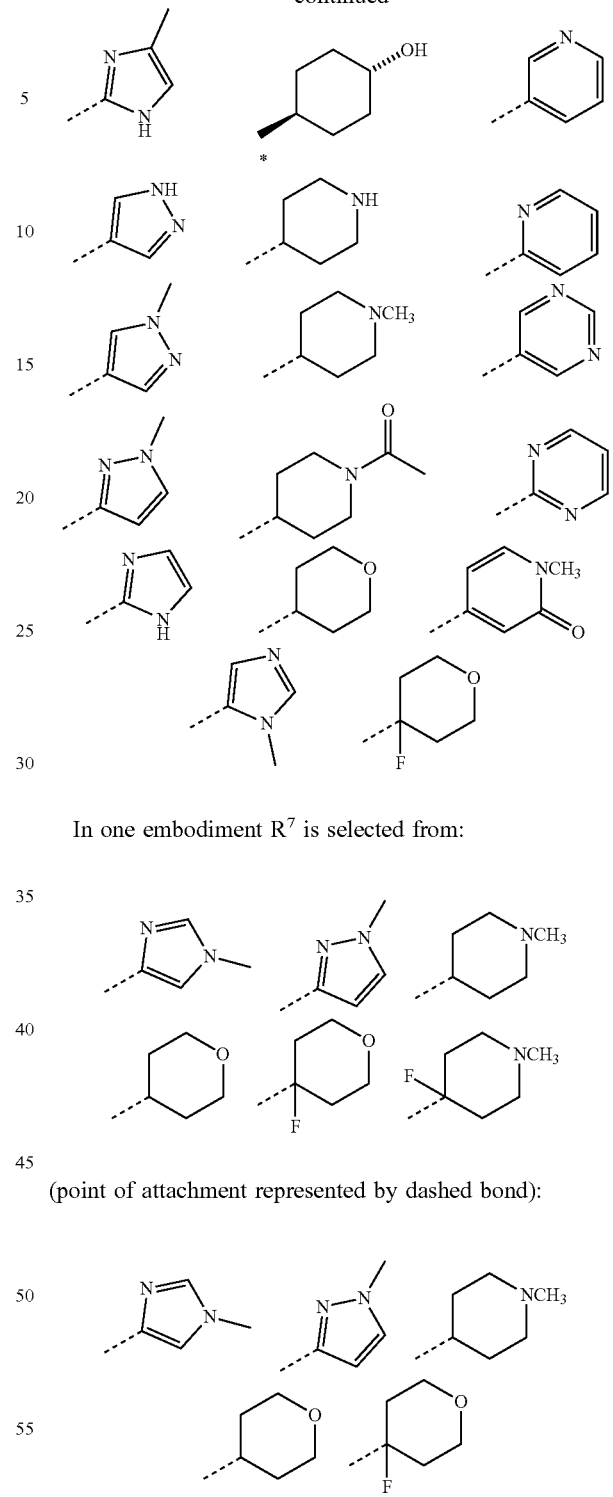

In one embodiment R[7] is selected from:

(point of attachment represented by dashed bond):

In one embodiment, R[6] is hydrogen or $C_{1-6}$alkyl (such as —CH$_3$, —CH$_2$CH$_3$ or —CH$_2$CH$_2$CH$_3$, e.g. —CH$_3$ or —CH$_2$CH$_3$). In one embodiment, R[6] is $C_{1-6}$alkyl. In one embodiment, R[6] is methyl or ethyl. In one embodiment, R[6] is ethyl.

In one embodiment, R[6] is $C_{1-6}$alkyl (such as methyl or ethyl e.g. methyl) and R[7] is selected from hydroxy$C_{1-6}$alkyl and —(CH$_2$)—O—$C_{1-6}$alkyl. In one embodiment, R[6] is methyl and $R^7$ is selected from methyl, —CH$_2$—OH and —CH$_2$—OCH$_3$. In one embodiment $R^6$ is methyl and $R^7$ is methyl, ethyl, or propyl.

In one embodiment $R^6$ is methyl and $R^7$ is methyl.

In one embodiment, $R^6$ is $C_{1-6}$alkyl or halo$C_{1-6}$alkyl (e.g. methyl, monofluoromethyl, trifluoromethyl or ethyl).

In one embodiment, $R^6$ is $C_{3-8}$cycloalkyl such as $C_{3-6}$cycloalkyl (e.g. cyclopropyl).

In one embodiment $R^6$ is $C_{1-6}$alkyl (e.g. —CH$_3$, —CH$_2$CH$_3$ or —CH$_2$CH$_2$CH$_3$ such as methyl or ethyl e.g. ethyl) and $R^7$ is selected from:
(point of attachment represented by dashed bond or bond terminus marked "*"):

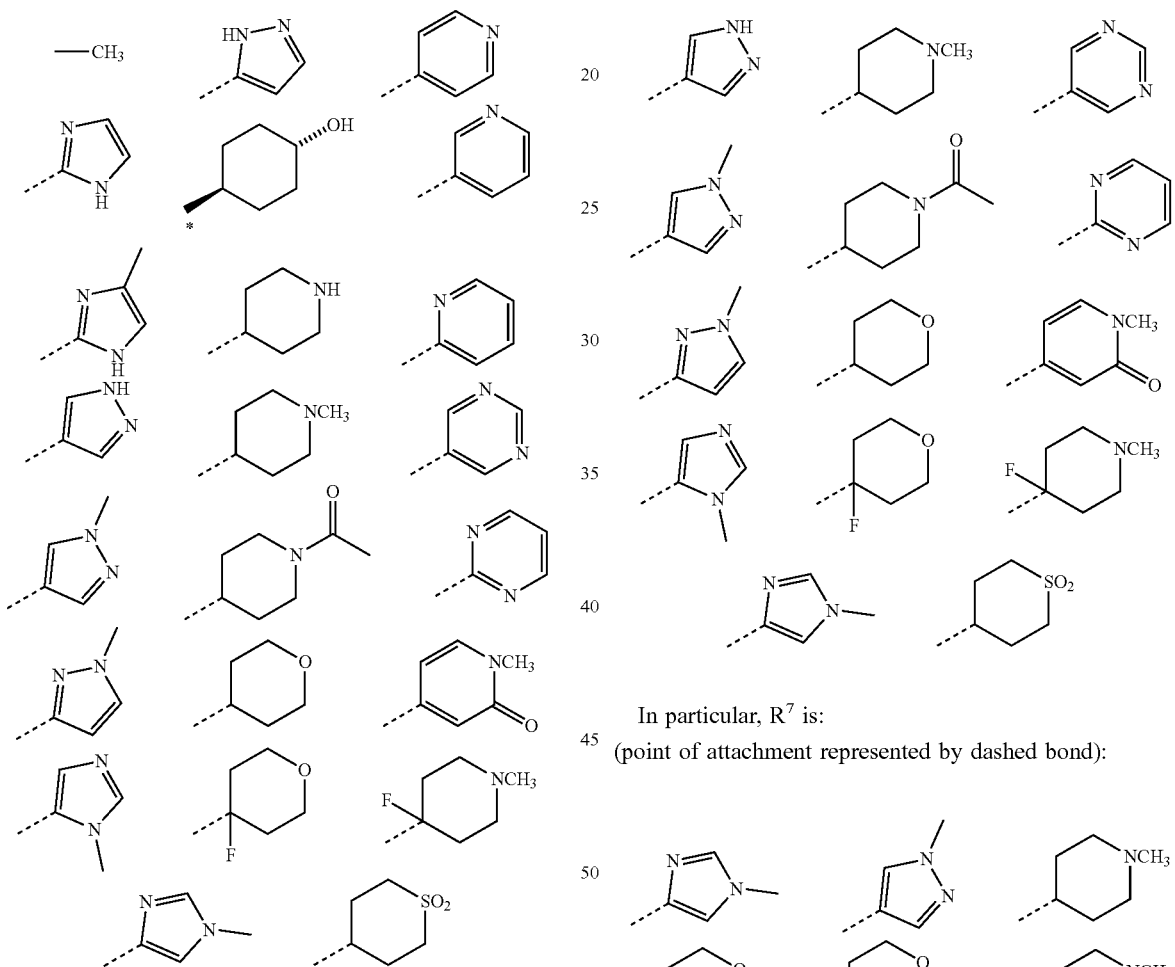

In one embodiment $R^6$ is $C_{1-6}$alkyl (e.g. —CH$_3$, —CH$_2$CH$_3$ or —CH$_2$CH$_2$CH$_3$ such as methyl or ethyl e.g. ethyl) and $R^7$ is selected from:
(point of attachment represented by dashed bond or bond terminus marked "*"):

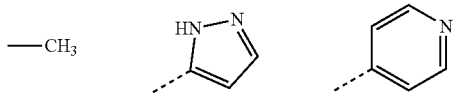

In particular, $R^7$ is:
(point of attachment represented by dashed bond):

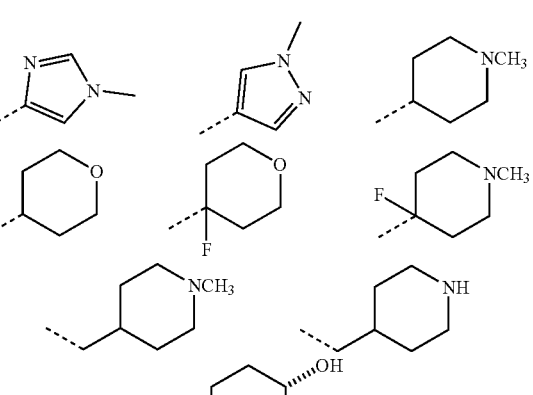

In particular, R⁷ is:
(point of attachment represented by dashed bond):

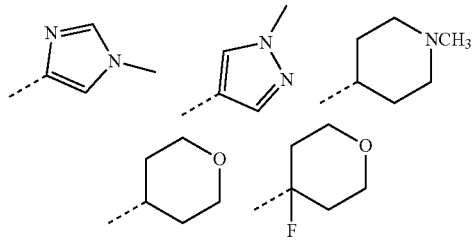

In one embodiment, R⁶ is $C_{1-6}$alkyl (e.g. —CH₃, —CH₂CH₃ or —CH₂CH₂CH₃) such as methyl or ethyl e.g. methyl) and R⁷ is oxanyl, and the compound of formula (I) is a compound of formula (Iw):

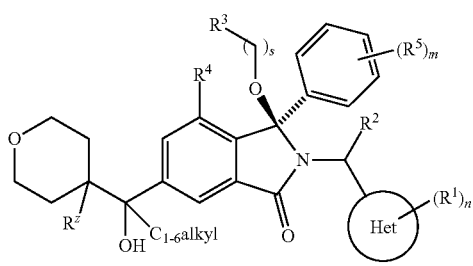

(Iw)

In one embodiment of formula (Iw) $R_z$ is hydrogen or fluorine.

In one embodiment, R⁷ is imidazolyl and the compound of formula (I) is a compound of formula (Ix) or a tautomer or a solvate or a pharmaceutically acceptable salt thereof:

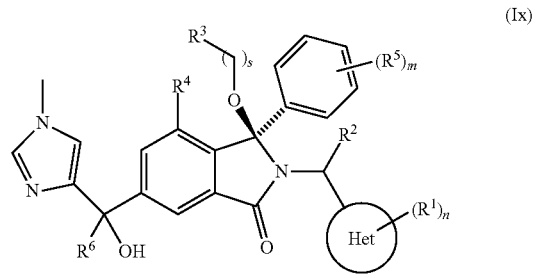

(Ix)

In one embodiment, R⁷ is N-methyl piperidinyl and the compound of formula (I) is a compound of formula (Ix') or a tautomer or a solvate or a pharmaceutically acceptable salt thereof:

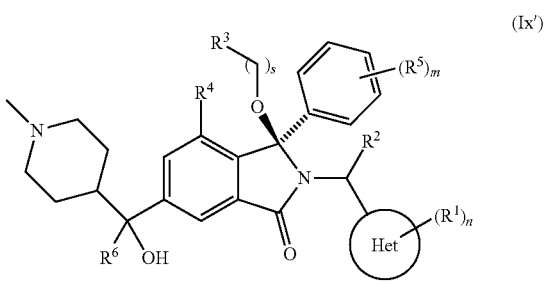

(Ix')

In one embodiment, R⁷ is 4-fluoro-1-methylpiperidin-4-yl and the compound of formula (I) is a compound of formula (Ix") or a tautomer or a solvate or a pharmaceutically acceptable salt thereof:

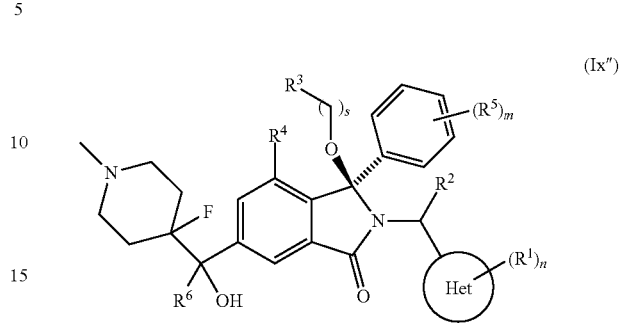

(Ix")

In one embodiment, R⁷ is pyrazolyl optionally substituted by one or more $R^z$ groups (e.g. methyl). In one embodiment, R⁷ is N-methylpyrazol-3-yl or N-methylpyrazol-4-yl.

In one embodiment, R⁷ is selected from methyl, oxanyl, pyrazolyl, imidazolyl, piperidinyl, and cyclohexyl wherein said cycloalkyl and heterocyclic groups are optionally substituted by one or more $R^z$ groups (e.g. methyl, fluorine, or hydroxyl).

In one embodiment, R⁷ is selected from piperidinyl optionally substituted by one or more $R^z$ groups (e.g. methyl, fluorine, or hydroxyl, in particular methyl and fluorine).

In one embodiment, the compound of formula (I) is a compound of formula (Ix) and R⁶ is $C_{1-4}$alkyl.

In one embodiment, R⁶ is $C_{1-6}$alkyl (e.g. —CH₃, —CH₂CH₃ or —CH₂CH₂CH₃ such as methyl or ethyl e.g. ethyl) and R⁷ is a heterocyclic group with 3 to 7 ring members optionally substituted by one or more $R^z$ groups.

In one embodiment, R⁶ is $C_{1-6}$alkyl (e.g. —CH₃, —CH₂CH₃ or —CH₂CH₂CH₃ such as methyl or ethyl e.g. ethyl) and R⁷ is imidazolyl optionally substituted by one or more $R^z$ groups (e.g. methyl imidazolyl).

In one embodiment, R⁶ is $C_{1-6}$alkyl (e.g. —CH₃, —CH₂CH₃ or —CH₂CH₂CH₃ such as methyl or ethyl e.g. ethyl) and R⁷ is piperidinyl optionally substituted by one or more $R^z$ groups (e.g. methyl piperidinyl).

In one embodiment R⁶ is $C_{1-6}$alkyl (e.g. —CH₃, —CH₂CH₃ or —CH₂CH₂CH₃ such as methyl or ethyl e.g. ethyl) and R⁷ is $C_{1-4}$alkyl, hydroxyl$C_{1-4}$alkyl, methoxy$C_{1-4}$alkyl, a heterocyclic group with 5 or 6 ring members or $C_{3-6}$cycloalkyl, wherein the heterocyclic group or $C_{3-6}$cycloalkyl group is optionally substituted by one or more $R^z$ (e.g. methyl, halogen (such as fluorine), C(═O)Me, or —OH).

In one embodiment R⁶ is $C_{1-6}$alkyl (e.g. —CH₃, —CH₂CH₃ or —CH₂CH₂CH₃ such as methyl or ethyl e.g. ethyl) and R⁷ is methyl, ethyl, hydroxylmethyl, hydroxyethyl, methoxymethyl, piperidinyl, oxanyl, imidazolyl, pyrazolyl, cyclobutyl, cyclohexyl, optionally substituted by one or more $R^z$ (e.g. methyl, halogen (such as fluorine), C(═O)Me, or —OH).

In one embodiment, R⁶ and R⁷ are both the same. In one embodiment, R⁶ and R⁷ are both methyl, and the compound of formula (I) is a compound of formula (Iy) or a tautomer or a solvate or a pharmaceutically acceptable salt thereof:

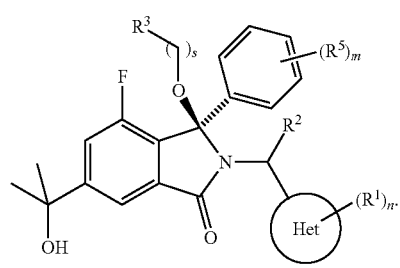
(Iy)
In one embodiment the group —CR⁶R⁷OH is other than —C(CH₃)₂OH.
In one embodiment, R⁷ is selected from the group consisting of:
(point of attachment represented by dashed bond or bond terminus indicated by "*"):
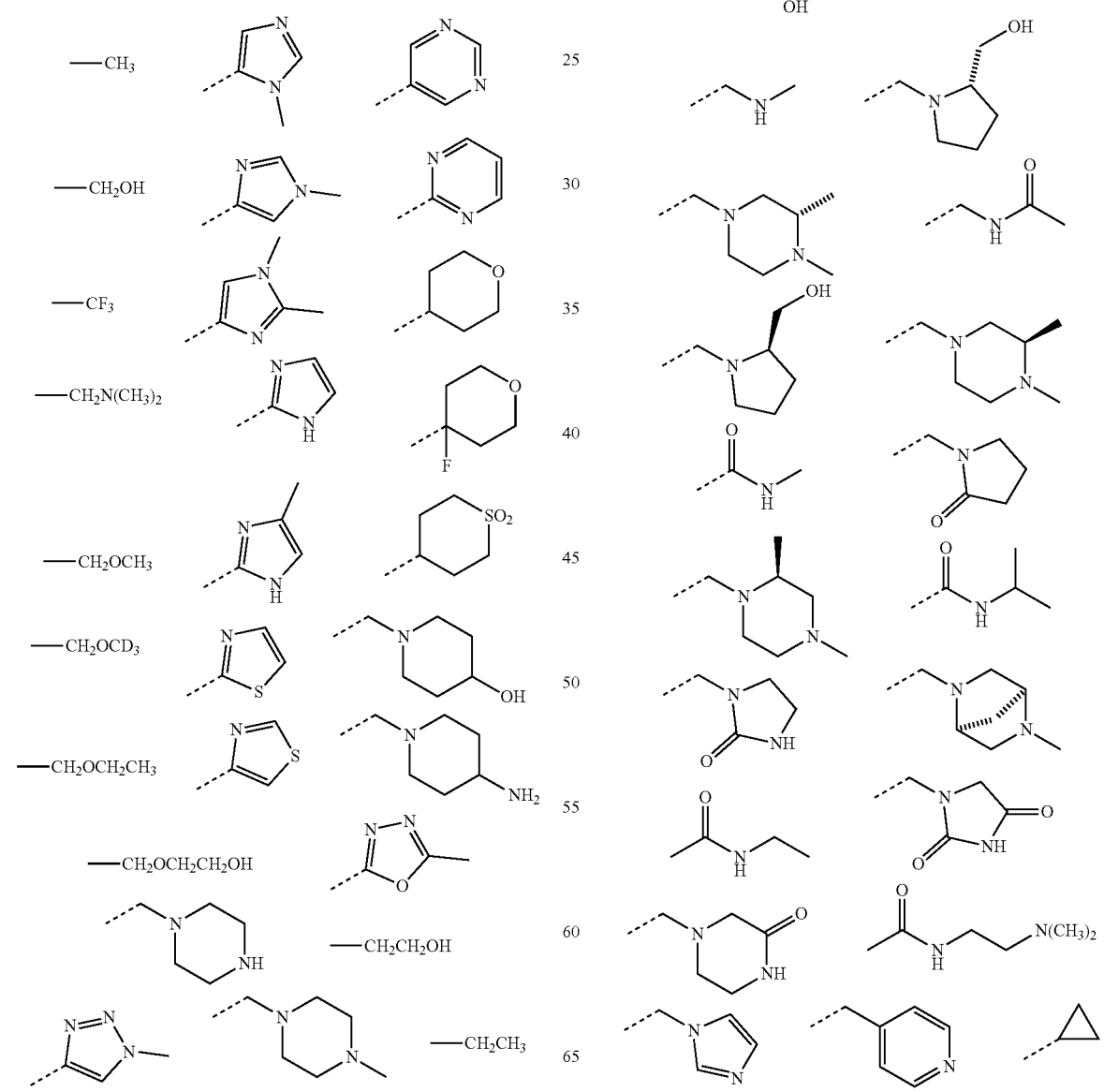

61
-continued
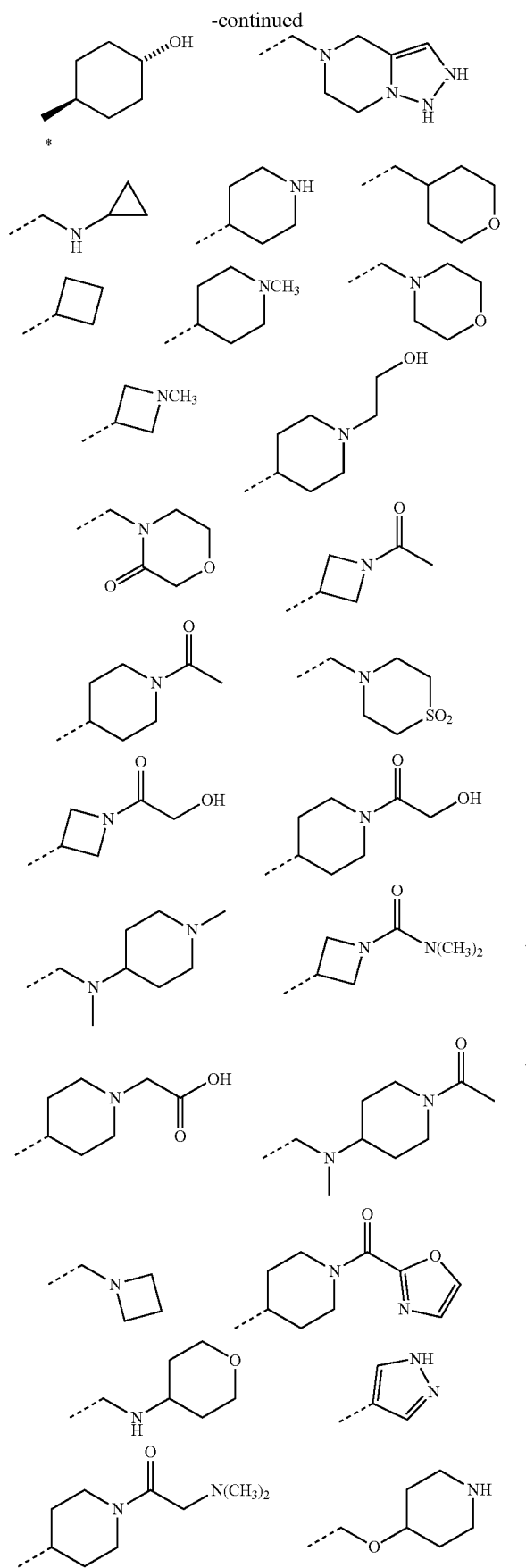
62
-continued
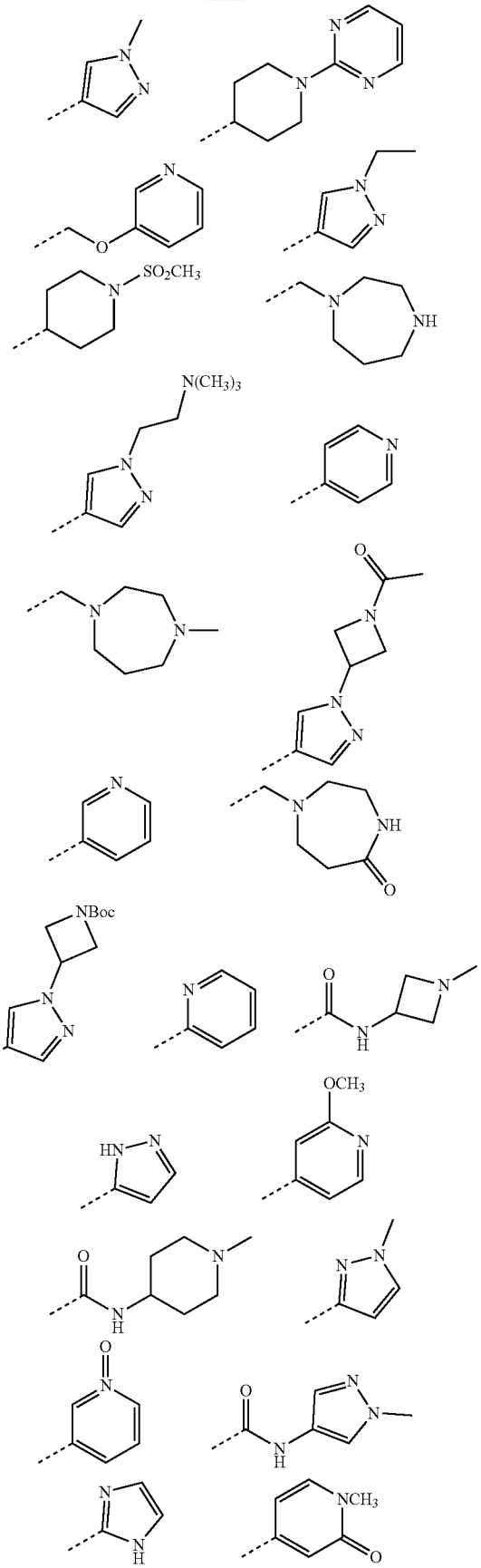

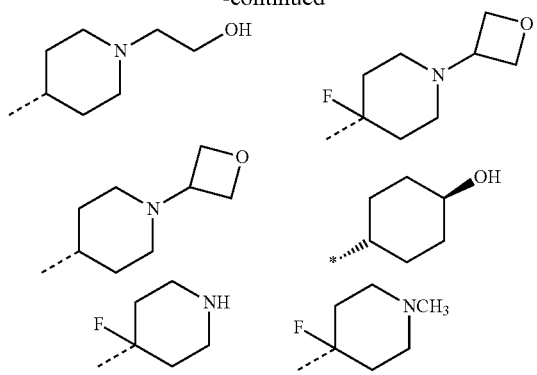

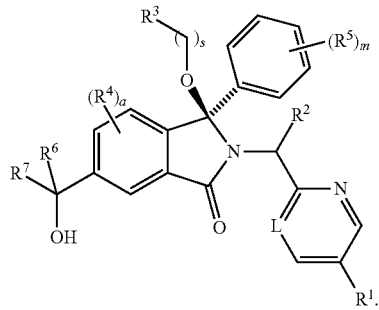

In one embodiment $R^z$ is independently selected from halogen, nitro, nitrile, $C_{1-6}$alkyl, halo$C_{1-6}$alkyl, $C_{2-6}$alkenyl, $C_{2-6}$alkynyl, =O, hydroxy, hydroxy$C_{1-6}$alkyl, $C_{1-6}$alkoxy, —$(CH_2)_k$—O—$C_{1-6}$alkyl, hydroxy$C_{1-6}$alkoxy, —C(=O)$C_{1-6}$alkyl, —C(=O)$C_{1-6}$alkyl-OH, —C(=O)$C_{1-6}$alkyl-N(H)$_e$($C_{1-4}$alkyl)$_{2-e}$, —C(=O)N(H)$_e$($C_{1-4}$alkyl)$_{2-e}$, —$(CH_2)_k$—$CO_2C_{1-6}$alkyl, —$(CH_2)_r$—$CO_2H$, —NH($C_{1-4}$alkyl), —N($C_{1-4}$alkyl)$_2$, —$C_{1-6}$alkyl-N(H)$_e$($C_{1-4}$alkyl)$_{2-e}$, heterocyclyl group with 3 to 6 ring members, heterocyclyl group with 3 to 6 ring members substituted by —C(=O)$C_{1-4}$alkyl, heterocyclyl group with 3 to 6 ring members substituted by —C(=O)O$C_{1-4}$alkyl, heterocyclyl group with 3 to 6 ring members substituted by —C(=O)N(H)$_e$($C_{1-4}$alkyl)$_{2-e}$, —C(=O)heterocyclyl group with 3 to 6 ring members, $C_{3-8}$cycloalkyl and $C_{3-8}$cycloalkenyl.

In another embodiment $R^z$ is independently selected from halogen, nitro, nitrile, $C_{1-6}$alkyl, halo$C_{1-6}$alkyl, $C_{2-6}$alkenyl, $C_{2-6}$alkynyl, =O, hydroxy, hydroxy$C_{1-6}$alkyl, $C_{1-6}$alkoxy, —$(CH_2)_k$—O—$C_{1-6}$alkyl, hydroxy$C_{1-6}$alkoxy, —C(=O)$C_{1-6}$alkyl, —C(=O)$C_{1-6}$alkyl-OH, —C(=O)$C_{1-6}$alkyl-N(H)$_e$($C_{1-4}$alkyl)$_{2-e}$, —C(=O)N(H)$_e$($C_{1-4}$alkyl)$_{2-e}$, —$(CH_2)_r$$CO_2C_{1-6}$alkyl, —$(CH_2)_r$$CO_2H$, —$C_{1-6}$alkyl-N(H)$_e$($C_{1-4}$alkyl)$_{2-e}$, heterocyclyl group with 3 to 6 ring members, heterocyclyl group with 3 to 6 ring members substituted by —C(=O)$C_{1-4}$alkyl, heterocyclyl group with 3 to 6 ring members substituted by —C(=O)O$C_{1-4}$alkyl, heterocyclyl group with 3 to 6 ring members substituted by —C(=O)N(H)$_e$($C_{1-4}$alkyl)$_{2-e}$, —C(=O)heterocyclyl group with 3 to 6 ring members, $C_{3-8}$cycloalkyl and $C_{3-8}$cycloalkenyl.

In another embodiment when $R^7$ contains a saturated heterocyclic group then $R^z$ is independently selected from halogen, nitro, nitrile, $C_{1-6}$alkyl, halo$C_{1-6}$alkyl, $C_{2-6}$alkenyl, $C_{2-6}$alkynyl, =O, hydroxy, hydroxy$C_{1-6}$alkyl, $C_{1-6}$alkoxy, —$(CH_2)_k$—O—$C_{1-6}$alkyl, hydroxy$C_{1-6}$alkoxy, —C(=O)$C_{1-6}$alkyl, —C(=O)$C_{1-6}$alkyl-OH, —C(=O)$C_{1-6}$alkyl-N(H)$_e$($C_{1-4}$alkyl)$_{2-e}$, —C(=O)N(H)$_e$($C_{1-4}$alkyl)$_{2-e}$, —$(CH_2)_r$$CO_2C_{1-6}$alkyl, —$(CH_2)_r$$CO_2H$, —N(H)$_e$($C_{1-4}$alkyl)$_{2-e}$, —$C_{1-6}$alkyl-N(H)$_e$($C_{1-4}$alkyl)$_{2-e}$, heterocyclyl group with 3 to 6 ring members, heterocyclyl group with 3 to 6 ring members substituted by —C(=O)$C_{1-4}$alkyl, heterocyclyl group with 3 to 6 ring members substituted by —C(=O)O$C_{1-4}$alkyl, heterocyclyl group with 3 to 6 ring members substituted by —C(=O)N(H)$_e$($C_{1-4}$alkyl)$_{2-e}$, —C(=O)heterocyclyl group with 3 to 6 ring members, $C_{3-8}$cycloalkyl and $C_{3-8}$cycloalkenyl.

Subformulae

In one embodiment, the compound of formulae (I) is a compound of formulae (II) or a tautomer or a solvate or a pharmaceutically acceptable salt thereof:

(II)

wherein L is $CR^1$, CH or N and $R^1$, $R^2$, $R^3$, $R^4$, $R^5$, $R^6$, $R^7$, a, m and s are as defined herein. In one embodiment L is CH. In one embodiment L is N. In one embodiment L is $CR^1$ such as C—OH or C-hydroxy$C_{1-4}$alkyl (e.g. C—OH or C—$CH_2OH$).

In one embodiment, $R^1$ is chloro, nitrile, methyl or methoxy. In one embodiment, $R^1$ is hydroxy or hydroxy $C_{1-4}$alkyl (e.g. hydroxyl).

In one embodiment, $R^1$ is $O_{0,1}(CR^xR^y)_v COOH$ (e.g. —COOH, —$CH_2COOH$, —$OCH_2COOH$ or —C($CH_3$)$_2$COOH.

In another embodiment, $R^1$ is chloro or nitrile and the compound of formula (II) is a compound of formula (IIa) or (IIb) or a tautomer or a solvate or a pharmaceutically acceptable salt thereof:

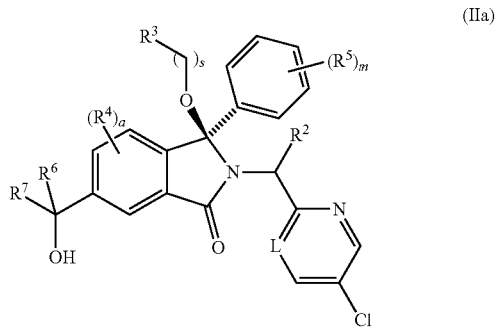

(IIa)

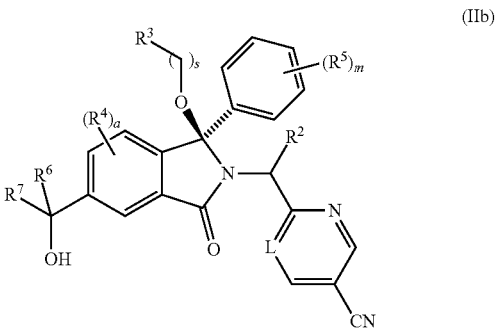

(IIb)

wherein $R^1$, $R^2$, $R^3$, $R^4$, $R^5$, $R^7$, m and s are as defined herein.

In one embodiment, $R^6$ is methyl or ethyl, and the compound of formula (II) is a compound of formula (IIIa) or (IIIb) or a tautomer or a solvate or a pharmaceutically acceptable salt thereof:

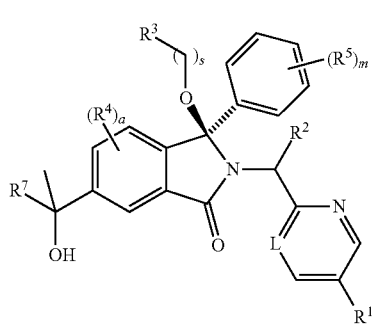

(IIIa)

wherein $R^1$, $R^2$, $R^3$, $R^4$, $R^5$, $R^7$, m and s are as defined herein.

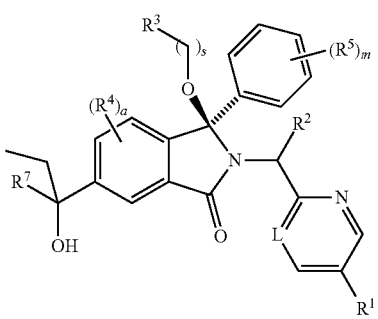

(IIIb)

wherein $R^1$, $R^2$, $R^3$, $R^4$, $R^5$, $R^7$, a, m and s are as defined herein.

In one embodiment, a is 1 and the compound of formula (II) is a compound of formula (IVa) or a tautomer or a solvate or a pharmaceutically acceptable salt thereof:

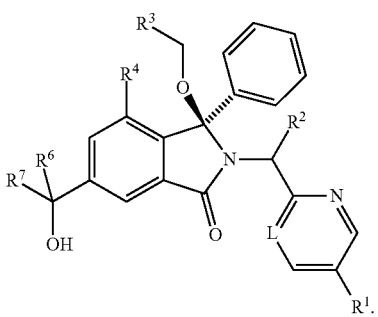

(IVa)

wherein $R^1$, $R^2$, $R^3$, $R^4$, $R^5$, $R^7$, m and s are as defined herein.

In one embodiment, s is 0 and the compound of formula (II) is a compound of formula (IVb) or a tautomer or a solvate or a pharmaceutically acceptable salt thereof:

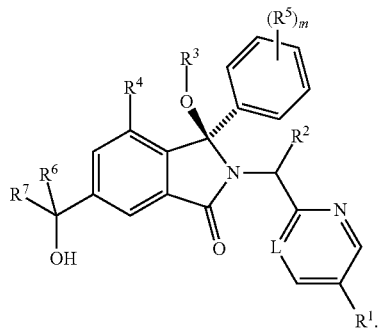

(IVb)

wherein $R^1$, $R^2$, $R^3$, $R^4$, $R^5$, $R^7$, m and s are as defined herein.

In one embodiment, $R^4$ is F and the compound of formula (I) is a compound of formula (V) or a tautomer or a solvate or a pharmaceutically acceptable salt thereof:

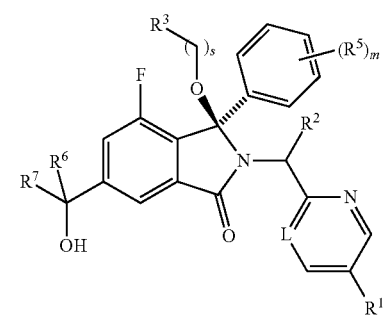

(V)

wherein $R^1$, $R^2$, $R^3$, $R^5$, $R^7$, m and s are as defined herein.

In one embodiment, m is 1 and the substituent $R^4$ is at the 4-position of the phenyl group, and the compound of formula (II) is a compound of formula (VI) or a tautomer or a solvate or a pharmaceutically acceptable salt thereof:

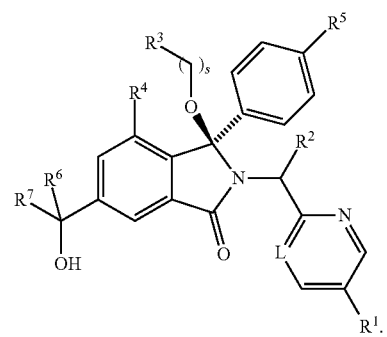

(VI)

In one embodiment, $R^5$ is chloro and the compound of formula (VI) is a compound of formula (VIa) or a tautomer or a solvate or a pharmaceutically acceptable salt thereof:

(VIa)

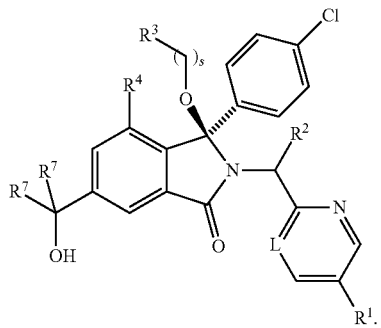

In one embodiment, A is a $C_{3-6}$cycloalkyl group (g is 1, 2 or 3) and t is 1, and the compound of formula (VI) is a compound of formula (VII) or a tautomer or a solvate or a pharmaceutically acceptable salt thereof:

(VII)

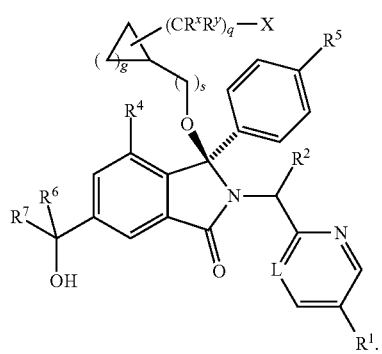

In one embodiment, A is a $C_{3-6}$cycloalkyl group (g is 1, 2 or 3) and t is 1, and the cycloalkyl group is geminally disubstituted (i.e. the group —$(CR^xR^y)$—X and the $CH_2$ group (where s is 1) or the oxygen atom (where s is 0) are both attached to the same atom of the cycloalkyl group, and the compound of formula (VII) is a compound of formula (VIIa) or a tautomer or a solvate or a pharmaceutically acceptable salt thereof:

(VIIa)

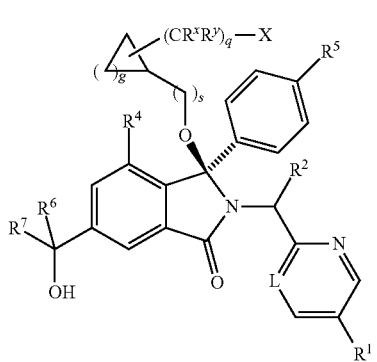

In one embodiment, g is 1, and so the cycloalkyl group is a cyclopropyl group and the compound of formula (VIIa) is a compound of formula (VIIb) or a tautomer or a solvate or a pharmaceutically acceptable salt thereof:

(VIIb)

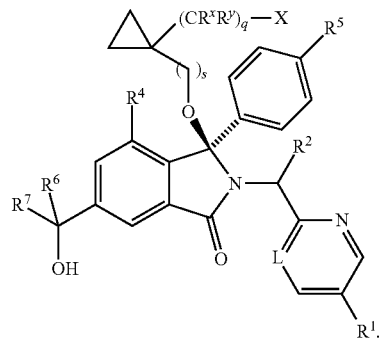

In one embodiment, s is 1, and the compound of formula (VIIb) is a compound of formula (VIIc) or a tautomer or a solvate or a pharmaceutically acceptable salt thereof:

(VIIc)

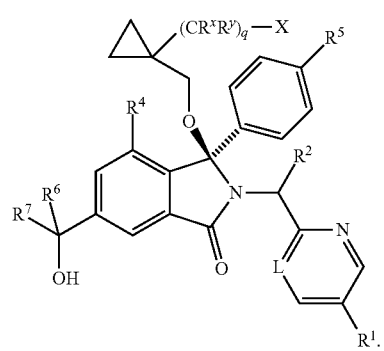

In one embodiment, $R^x$ and $R^y$ are hydrogen (including $^1H$ and $^2H$) and q is 1 and the compound of formula (VIIc) is a compound of (VIIId) or a tautomer or a solvate or a pharmaceutically acceptable salt thereof:

(VIId)

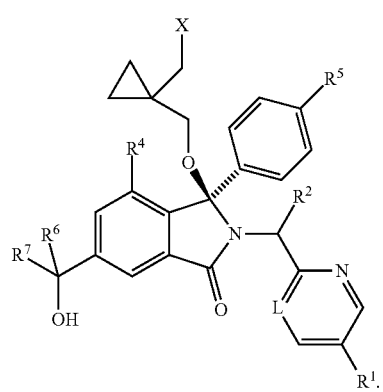

In one embodiment, the compound of formula (VIId) is a compound of (VIId') or a tautomer or a solvate or a pharmaceutically acceptable salt thereof:

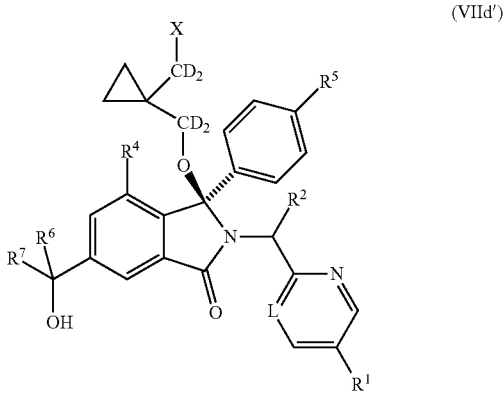

(VIId')

In one embodiment, the compound of formula (VIId) is a compound of (VIId') and X is hydroxy.

In one embodiment, X is hydroxy, and the compound of formula (VIId) is a compound of the formula (VIIe) or a tautomer or a solvate or a pharmaceutically acceptable salt thereof:

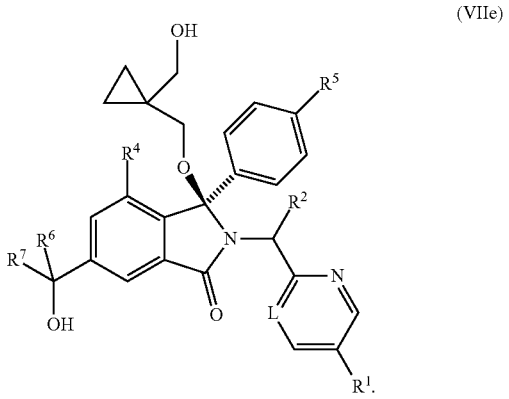

(VIIe)

In one embodiment, X is —C(=O)NH$_2$ and the compound of formula (VIIe) is a compound of the formula (VIIe') or a tautomer or a solvate or a pharmaceutically acceptable salt thereof:

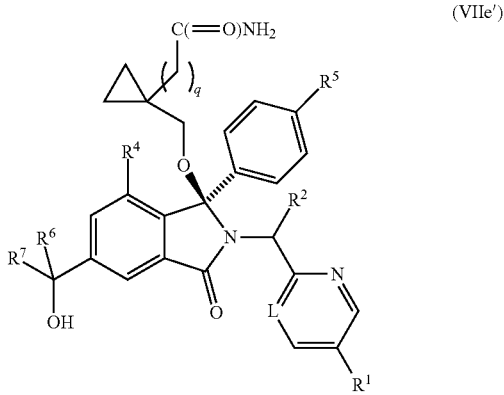

(VIIe')

wherein q is 0 or 1, and in particular q is 0.

In one embodiment, X is —CN and the compound of formula (VIId) is a compound of the formula (VIIe") or a tautomer or a solvate or a pharmaceutically acceptable salt thereof:

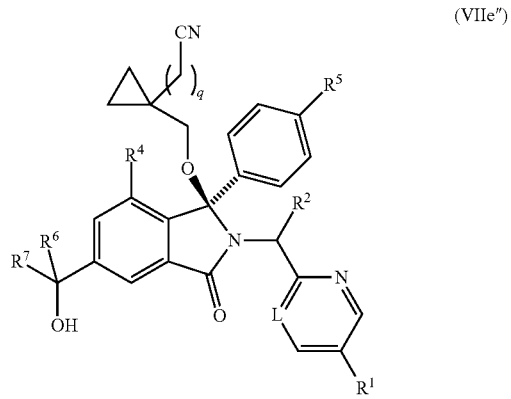

(VIIe")

wherein q is 0 or 1, and in particular q is 0.

In one embodiment, R$^3$ is methyl, and the compound of formula (VI) is a compound of formula (VIIf) or a tautomer or a solvate or a pharmaceutically acceptable salt thereof:

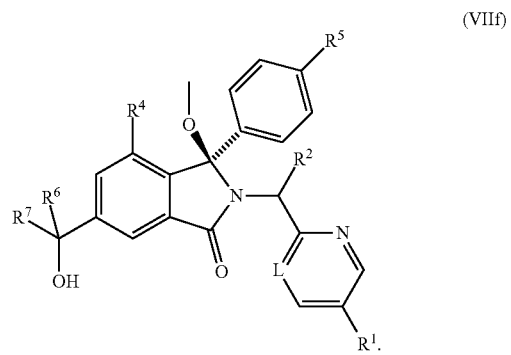

(VIIf)

In one embodiment of Formula (VIIa-e') R$^6$ is methyl. In one embodiment of Formula (VIIa-e') R$^6$ is ethyl.

In one embodiment of Formula (VIIe") or (VIIf) R$^6$ is methyl. In one embodiment of Formula (VIIe") or (VIIf)R$^6$ is ethyl.

In one embodiment of Formula (VIIe") or (VIIf)R$^6$ is methyl. In one embodiment of Formula (VIIe") or (VIIf) R$^6$ is ethyl.

In one embodiment of the compound of formula (VIIa-e'), R$^7$ is selected from methyl, oxanyl, pyrazolyl, imidazolyl, piperidinyl, and cyclohexyl wherein said cycloalkyl and heterocyclic groups are optionally substituted by one or more R$^z$ groups (e.g. methyl, fluorine, or hydroxy).

In one embodiment of the compound of formula (VIIa-e'), R$^7$ is selected from oxanyl and methyl.

In one embodiment of the compound of formula (VIIe") or (VIIf), R$^7$ is selected from methyl, oxanyl, pyrazolyl, imidazolyl, piperidinyl, and cyclohexyl wherein said cycloalkyl and heterocyclic groups are optionally substituted by one or more R$^z$ groups (e.g. methyl, fluorine, or hydroxy).

In one embodiment of the compound of formula (VIIe") or (VIIf), R$^7$ is selected from oxanyl and methyl.

In one embodiment of the compound of formula (VIIa-f), $R^7$ is selected from piperidinyl optionally substituted by one or more $R^z$ groups (e.g. methyl, fluorine, or hydroxy).

In another embodiment, the compound of formula (I) is a compound of formula (a) or a tautomer or a solvate or a pharmaceutically acceptable salt thereof:

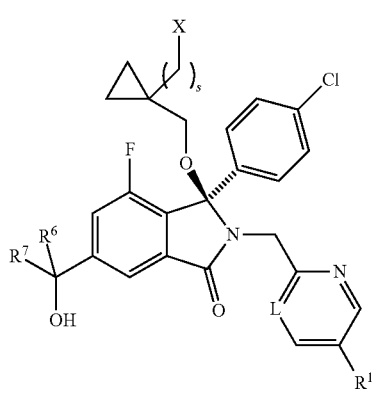

(a)

wherein $R^1$ is chloro or nitrile, X is hydroxyl when s is 1 or X is —C(=O)NH$_2$ when s is 0.

In another embodiment, the compound of formula (I) is a compound of formula (a') or a tautomer or a solvate or a pharmaceutically acceptable salt thereof:

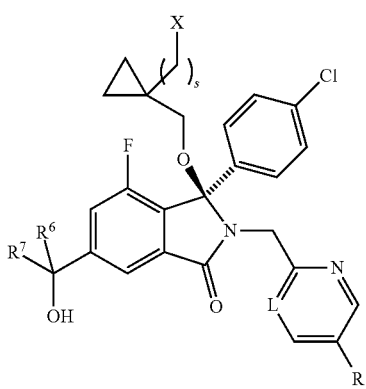

(a')

wherein $R^1$ is chloro or nitrile, X is hydroxyl when s is 1 or X is —CN when s is 0.

In one embodiment of the compound of formula (a), $R^7$ is selected from methyl, oxanyl, pyrazolyl, imidazolyl, piperidinyl, and cyclohexyl wherein said cycloalkyl and heterocyclic groups are optionally substituted by one or more $R^z$ groups (e.g. methyl, fluorine, or hydroxy).

In one embodiment of the compound of formula (a), $R^7$ is oxanyl or methyl.

In one embodiment of the compound of formula (a), $R^7$ is piperidinyl, optionally substituted with $C_{1-6}$ alkyl (e.g. methyl) and/or halo (e.g. flouro).

In one embodiment of the compound of formula (a'), $R^7$ is selected from methyl, oxanyl, pyrazolyl, imidazolyl, piperidinyl, and cyclohexyl wherein said cycloalkyl and heterocyclic groups are optionally substituted by one or more $R^z$ groups (e.g. methyl, fluorine, or hydroxy).

In one embodiment of the compound of formula (a'), $R^7$ is oxanyl or methyl.

In one embodiment of the compound of formula (a'), $R^7$ is piperidinyl, optionally substituted with $C_{1-6}$alkyl (e.g. methyl) and/or halo (e.g. flouro).

In one embodiment, A is a heterocyclyl group with 3 to 6 ring members, wherein the heterocyclic group comprises one or more (e.g. 1, 2, or 3) heteroatoms selected from N, O, S and oxidised forms thereof (t is 1; g is 1, 2, 3 or 4; Z represents N, O, S and oxidised forms thereof; i is 1, 2, or 3; and i+g=2, 3, 4 or 5), and the compound of formula (VI) is a compound of formula (b) or a tautomer or a solvate or a pharmaceutically acceptable salt thereof:

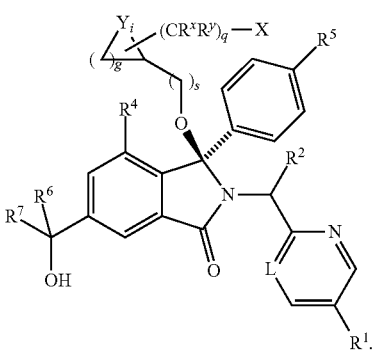

(b)

In one embodiment, Y is O and i is 1 and the compound of formula (b) is a compound of formula (ba) or a tautomer or a solvate or a pharmaceutically acceptable salt thereof:

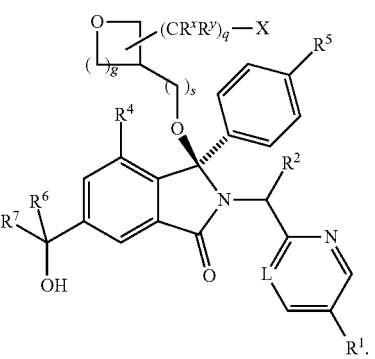

(ba)

In one embodiment, s is 0, g is 2, q is 0 and X is hydrogen, and the compound of formula (b) is a compound of formula (bb) or a tautomer or a solvate or a pharmaceutically acceptable salt thereof:

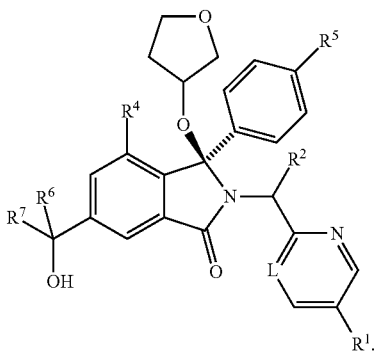

(bb)

In one embodiment, s is 0, g is 1, Y is O and i is 1 and the compound of formula (b) is a compound of formula (bc) or a tautomer or a solvate or a pharmaceutically acceptable salt thereof:

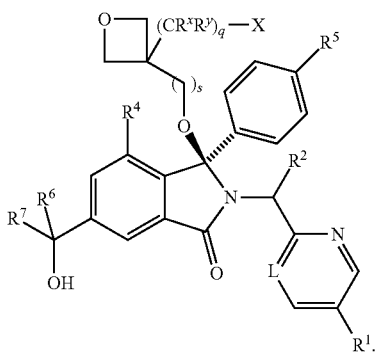

(bc)

In one embodiment, the compound of formula (bc) is where q is 0 and X is fluorine.

In another embodiment, the compound of formula (I) is a compound of formula (c) or a tautomer or a solvate or a pharmaceutically acceptable salt thereof:

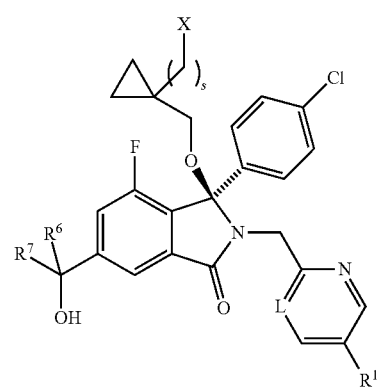

(c)

wherein $R^1$ is chloro or nitrile, s is 1 and X is hydroxyl or s is 0 and X is —C(=O)NH$_2$.

In another embodiment, the compound of formula (I) is a compound of formula (c') or a tautomer or a solvate or a pharmaceutically acceptable salt thereof:

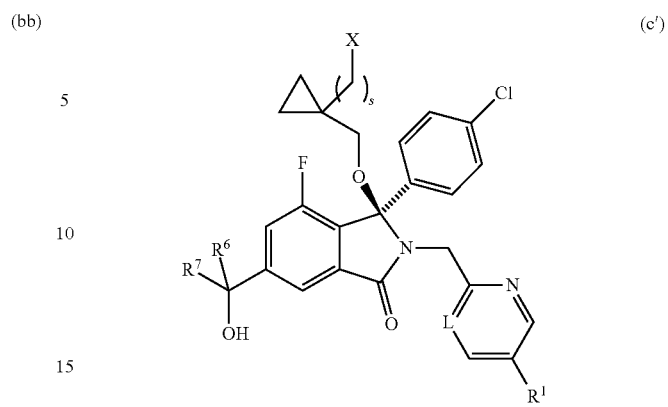

(c')

wherein $R^1$ is chloro or nitrile, s is 1 and X is hydroxyl or s is 0 and X is —CN.

In one embodiment of the compound of formula (c), $R^7$ is selected from methyl, oxanyl, pyrazolyl, imidazolyl, piperidinyl, and cyclohexyl wherein said cycloalkyl and heterocyclic groups are optionally substituted by one or more $R^z$ groups (e.g. methyl, fluorine, or hydroxy).

In one embodiment of the compound of formula (c), $R^7$ is oxanyl or methyl.

In one embodiment of the compound of formula (c), $R^7$ is piperidinyl, optionally substituted with $C_{1-6}$ alkyl (e.g. methyl) and/or halo (e.g. flouro).

In one embodiment of the compound of formula (c'), $R^7$ is selected from methyl, oxanyl, pyrazolyl, imidazolyl, piperidinyl, and cyclohexyl wherein said cycloalkyl and heterocyclic groups are optionally substituted by one or more $R^z$ groups (e.g. methyl, fluorine, or hydroxy).

In one embodiment of the compound of formula (c'), $R^7$ is oxanyl or methyl.

In one embodiment of the compound of formula (c'), $R^7$ is piperidinyl, optionally substituted with $C_{1-6}$ alkyl (e.g. methyl) and/or halo (e.g. flouro).

In one embodiment the compound of formula (I) is a compound of formula (II), (IIa), (IIIb), (IIIa), (IIIb), (IVa), (IVb), (V), (VI), (VIa), (VII), (VIIa), (VIIb), (VIIc), (VIId), (VIId'), (VIIe), (VIIe'), (a), (b), (ba), (bb), (bc) or (c) and L is CH. In one embodiment the compound of formula (I) is a compound of formula (II), (IIa), (IIb), (IIIa), (IIIb), (IVa), (IVb), (V), (VI), (VIa), (VII), (VIIa), (VIIb), (VIIc), (VIId), (VIId'), (VIIe), (VIIe'), (a), (b), (ba), (bb), (bc) or (c) and L is N.

In one embodiment the compound of formula (I) is a compound of formula (II), (IIa), (IIb), (IIIa), (IIIb), (IVa), (IVb), (V), (VI), (VIa), (VII), (VIIa), (VIIb), (VIIc), (VIId), (VIId'), (VIIe), (VIIe'), (VIIe''), (VIIf), (a), (a'), (b), (ba), (bb), (bc), (c) or (c') and L is CH. In one embodiment the compound of formula (I) is a compound of formula (II), (IIa), (IIb), (IIIa), (IIIb), (IVa), (IVb), (V), (VI), (VIa), (VII), (VIIa), (VIIb), (VIIc), (VIId), (VIId'), (VIIe), (VIIe'), (a), (b), (ba), (bb), (bc) or (c) and L is N.

In one embodiment, the invention provides a compound of formula (I) or a tautomer or a solvate or a pharmaceutically acceptable salt thereof wherein:

Het is pyridinyl, pyrimidinyl, or pyridazinyl, or an N-oxide thereof $R^1$ is attached to a carbon atom and is independently selected from hydroxy, halogen, nitro, nitrile, $C_{1-4}$alkyl, halo$C_{1-4}$alkyl, hydroxy$C_{1-4}$alkyl, $C_{2-6}$alkenyl, $C_{1-4}$alkoxy, halo$C_{1-4}$alkoxy, and $C_{2-4}$alkynyl;

$R^2$ is selected from hydrogen, $C_{1-4}$ alkyl, $C_{2-6}$alkenyl, hydroxyC$_{1-4}$alkyl and —CH$_2$CO$_2$H;

$R^3$ is hydrogen or -(A)$_t$-(CR$^x$R$^y$)$_q$—X;

s and t are independently selected from 0 and 1;

q is selected from 0, 1 and 2;

wherein when $R^3$ is -(A)$_t$-(CR$^x$R$^y$)$_q$—X then (i) at least one of s, t and q is other than 0 and (ii) when t is 0 then s is 1 and q is other than 0;

A is a $C_{3-6}$cycloalkyl group or a heterocyclic group with 3 to 6 ring members, wherein the heterocyclic group comprises one or more (e.g. 1, 2, or 3) heteroatoms selected from N, O, S and oxidised forms thereof;

X is selected from hydrogen, halogen, —CN, —OR$^9$, —(CH$_2$)$_v$—CO$_2$H, —(CH$_2$)$_v$—CO$_2$C$_{1-4}$alkyl, —C(=O)—C$_{1-4}$alkyl, —NR$^x$R$^y$, —NHSO$_2$R$^x$, —NR$^x$COR$^y$; and —C(=O)NR$^x$R$^y$;

$R^4$ and $R^5$ are independently selected from halogen, nitrile, $C_{1-4}$ alkyl, haloC$_{1-4}$alkyl, $C_{1-4}$alkoxy and haloC$_{1-4}$ alkoxy;

$R^6$ and $R^7$ are independently selected from hydrogen, $C_{1-6}$alkyl, haloC$_{1-6}$alkyl, $C_{2-6}$alkenyl, $C_{2-6}$alkynyl, hydroxy, hydroxyC$_{1-6}$alkyl, —COOC$_{1-6}$alkyl, heterocyclic group with 3 to 7 ring members, —CH$_2$-heterocyclic group with 3 to 7 ring members, —CH$_2$—O-heterocyclic group with 3 to 7 ring members, —CH$_2$—NH-heterocyclic group with 3 to 7 ring members, —CH$_2$—N(C$_{1-6}$alkyl)-heterocyclic group with 3 to 7 ring members, —C(=O)NH-heterocyclic group with 3 to 7 ring members, $C_{3-8}$cycloalkyl, —CH$_2$—C$_{3-8}$cycloalkyl, —CH$_2$—O—C$_{3-8}$cycloalkyl, and C$_{3-8}$cycloalkenyl, wherein said cycloalkyl, cycloalkenyl or heterocyclic groups may be optionally substituted by one or more R$^z$ groups, and wherein in each instance the heterocyclic group comprises one or more (e.g. 1, 2, or 3) heteroatoms selected from N, O, S and oxidised forms thereof;

$R^9$ is selected from hydrogen, $C_{1-6}$alkyl, haloC$_{1-6}$alkyl, hydroxyC$_{1-6}$alkyl, —(CH$_2$)$_k$—O—C$_{1-6}$alkyl, —(CH$_2$)$_k$—O-(hydroxyC$_{1-6}$alkyl), hydroxyC$_{1-6}$alkoxy, —(CH$_2$)$_k$—CO$_2$C$_{1-6}$alkyl, —(CH$_2$)$_k$—CO$_2$H, —C$_{1-6}$alkyl-N(H)$_e$(C$_{1-4}$ alkyl)$_{2-e}$, —(CH$_2$)$_j$—C$_{3-8}$cycloalkyl and —(CH$_2$)$_j$—C$_{3-8}$cycloalkenyl;

$R^x$ and $R^y$ are independently selected from hydrogen, halogen, nitro, nitrile, C$_{1-6}$alkyl, haloC$_{1-6}$alkyl, C$_{2-6}$alkenyl, C$_{2-6}$alkynyl, hydroxy, hydroxyC$_{1-6}$alkyl, C$_{1-6}$alkoxy, —(CH$_2$)$_k$—O—C$_{1-6}$alkyl, hydroxyC$_{1-6}$alkoxy, —COOC$_{1-6}$ alkyl, —N(H)$_e$(C$_{1-4}$alkyl)$_{2-e}$, —C$_{1-6}$alkyl-N(H)$_e$(C$_{1-4}$ alkyl)$_{2-e}$, —(CH$_2$)$_k$—C(=O)N(H)$_e$(C$_{1-4}$alkyl)$_{2-e}$, C$_{3-8}$cycloalkyl and C$_{3-8}$cycloalkenyl;

$R^z$ is independently selected from halogen, nitro, nitrile, C$_{1-6}$alkyl, haloC$_{1-6}$alkyl, C$_{2-6}$alkenyl, C$_{2-6}$alkynyl, =O, hydroxy, hydroxyC$_{1-6}$alkyl, C$_{1-6}$alkoxy, —(CH$_2$)$_k$—O—C$_{1-6}$alkyl, hydroxyC$_{1-6}$alkoxy, —C(=O)C$_{1-6}$alkyl, —C(=O)C$_{1-6}$alkyl-OH, —C(=O)C$_{1-6}$alkyl-N(H)$_e$(C$_{1-4}$alkyl)$_{2-e}$, —C(=O)N(H)$_e$(C$_{1-4}$alkyl)$_{2-e}$, —(CH$_2$)$_r$—CO$_2$C$_{1-6}$alkyl, —(CH$_2$)$_r$—CO$_2$H, —N(H)$_e$(C$_{1-4}$alkyl)$_{2-e}$, —C$_{1-6}$alkyl-N(H)$_e$(C$_{1-4}$alkyl)$_{2-e}$, heterocyclyl group with 3 to 6 ring members, heterocyclyl group with 3 to 6 ring members substituted by —C(=O)C$_{1-4}$alkyl, heterocyclyl group with 3 to 6 ring members substituted by —C(=O)OC$_{1-4}$alkyl, heterocyclyl group with 3 to 6 ring members substituted by —C(=O)N(H)$_e$(C$_{1-4}$alkyl)$_{2-e}$, —C(=O)heterocyclyl group with 3 to 6 ring members, C$_{3-8}$cycloalkyl and C$_{3-8}$cycloalkenyl;

n, e, r and j are independently selected from 0, 1 and 2;

k and m are independently selected from 1 and 2; and v and a are independently selected from 0 and 1.

In one embodiment, the invention provides a compound of formula (I) or a tautomer or a solvate or a pharmaceutically acceptable salt thereof, wherein:

Het is pyridinyl or pyrimidinyl;

$R^1$ is attached to a carbon atom and is independently selected from hydroxy, halogen, nitro, nitrile and C$_{1-4}$alkyl;

$R^2$ is selected from hydrogen, $C_{1-4}$ alkyl, $C_{2-6}$alkenyl, hydroxyC$_{1-4}$alkyl and —CH$_2$CO$_2$H;

$R^3$ is hydrogen or -(A)$_t$-(CR$^x$R$^y$)$_q$—X;

s and t are independently selected from 0 and 1;

q is selected from 0, 1 and 2;

wherein when $R^3$ is -(A)$_t$-(CR$^x$R$^y$)$_q$—X then (i) at least one of s, t and q is other than 0 and (ii) when t is 0 then s is 1 and q is other than 0;

A is a $C_{3-6}$cycloalkyl group or a heterocyclic group with 3 to 6 ring members, wherein the heterocyclic group comprises one or more (e.g. 1, 2, or 3) heteroatoms selected from N, O, S and oxidised forms thereof;

X is selected from hydrogen, halogen, —CN, —OR$^9$, —(CH$_2$)$_v$—CO$_2$H, —(CH$_2$)$_v$—CO$_2$C$_{1-4}$alkyl, —C(=O)—C$_{1-4}$alkyl, —NR$^x$R$^y$, —NHSO$_2$R$^x$, —NR$^x$COR$^y$; and —C(=O)NR$^x$R$^y$;

$R^4$ and $R^5$ are independently selected from halogen, nitrile and C$_{1-4}$ alkyl;

$R^6$ is selected from hydrogen, C$_{1-6}$alkyl, haloC$_{1-6}$alkyl, C$_{2-6}$alkenyl, and C$_{2-6}$alkynyl;

$R^7$ is selected from hydrogen, C$_{1-6}$alkyl, haloC$_{1-6}$alkyl, C$_{2-6}$alkenyl, C$_{2-6}$alkynyl, hydroxy, hydroxyC$_{1-6}$alkyl, —COOC$_{1-6}$alkyl, heterocyclic group with 3 to 7 ring members, —CH$_2$-heterocyclic group with 3 to 7 ring members, —CH$_2$—O-heterocyclic group with 3 to 7 ring members, —CH$_2$—NH-heterocyclic group with 3 to 7 ring members, —CH$_2$—N(C$_{1-6}$alkyl)-heterocyclic group with 3 to 7 ring members, —C(=O)NH-heterocyclic group with 3 to 7 ring members, C$_{3-8}$cycloalkyl, —CH$_2$—C$_{3-8}$cycloalkyl, —CH$_2$—O—C$_{3-8}$cycloalkyl, and C$_{3-8}$cycloalkenyl, wherein said cycloalkyl, cycloalkenyl or heterocyclic groups may be optionally substituted by one or more R$^z$ groups, and wherein in each instance the heterocyclic group comprises one or more (e.g. 1, 2, or 3) heteroatoms selected from N, O, S and oxidised forms thereof;

$R^9$ is selected from hydrogen, C$_{1-6}$alkyl, haloC$_{1-6}$alkyl, hydroxyC$_{1-6}$alkyl, —(CH$_2$)$_k$—O—C$_{1-6}$alkyl, —(CH$_2$)$_k$—O-(hydroxyC$_{1-6}$alkyl), hydroxyC$_{1-6}$alkoxy, —(CH$_2$)$_k$—CO$_2$C$_{1-6}$alkyl, —(CH$_2$)$_k$—CO$_2$H, —C$_{1-6}$ alkyl-N(H)$_e$(C$_{1-4}$ alkyl)$_{2-e}$, —(CH$_2$)$_j$—C$_{3-8}$cycloalkyl and —(CH$_2$)$_j$—C$_{3-8}$cycloalkenyl;

$R^x$ and $R^y$ are independently selected from hydrogen, halogen, nitro, nitrile, C$_{1-6}$alkyl, haloC$_{1-6}$alkyl, C$_{2-6}$alkenyl, C$_{2-6}$alkynyl, hydroxy, hydroxyC$_{1-6}$alkyl, C$_{1-6}$alkoxy, —(CH$_2$)$_k$—O—C$_{1-6}$alkyl, hydroxyC$_{1-6}$alkoxy, —COOC$_{1-6}$ alkyl, —N(H)$_e$(C$_{1-4}$alkyl)$_{2-e}$, —C$_{1-6}$alkyl-N(H)$_e$(C$_{1-4}$ alkyl)$_{2-e}$, —(CH$_2$)$_k$—C(=O)N(H)$_e$(C$_{1-4}$alkyl)$_{2-e}$, C$_{3-8}$cycloalkyl and C$_{3-8}$cycloalkenyl;

$R^z$ is independently selected from halogen, nitro, nitrile, C$_{1-6}$alkyl, haloC$_{1-6}$alkyl, C$_{2-6}$alkenyl, C$_{2-6}$alkynyl, =O, hydroxy, hydroxyC$_{1-6}$alkyl, C$_{1-6}$alkoxy, —(CH$_2$)$_k$—O—C$_{1-6}$alkyl, hydroxyC$_{1-6}$alkoxy, —C(=O)C$_{1-6}$alkyl, —C(=O)C$_{1-6}$alkyl-OH, —C(=O)C$_{1-6}$alkyl-N(H)$_e$(C$_{1-4}$alkyl)$_{2-e}$, —C(=O)N(H)$_e$(C$_{1-4}$alkyl)$_{2-e}$, —(CH$_2$)$_r$—CO$_2$C$_{1-6}$alkyl, —(CH$_2$)$_r$—CO$_2$H, —N(H)$_e$(C$_{1-4}$alkyl)$_{2-e}$, —C$_{1-6}$alkyl-N(H)$_e$(C$_{1-4}$alkyl)$_{2-e}$, heterocyclyl group with 3 to 6 ring members, heterocyclyl group with 3 to 6 ring members substituted by —C(=O)C$_{1-4}$alkyl, heterocyclyl group with 3 to 6 ring members substituted by —C(=O)OC$_{1-4}$alkyl, heterocyclyl group with 3 to 6 ring members substituted by —C(=O)N(H)$_e$(C$_{1-4}$alkyl)$_{2-e}$, —C(=O)heterocyclyl group with 3 to 6 ring members, C$_{3-8}$cycloalkyl and C$_{3-8}$cycloalkenyl;
n, e, r and j are independently selected from 0, 1 and 2;
k and m are independently selected from 1 and 2; and
v and a are independently selected from 0 and 1.

In one embodiment, the invention provides a compound of formula (I) or a tautomer or a solvate or a pharmaceutically acceptable salt thereof, wherein:
Het is pyridinyl or pyrimidinyl
R$^1$ is attached to a carbon atom and is independently selected from hydroxy, halogen, nitro, nitrile and C$_{1-4}$alkyl;
R$^2$ is selected from hydrogen, C$_{1-4}$ alkyl, C$_{2-6}$alkenyl, hydroxyC$_{1-4}$alkyl and —CH$_2$CO$_2$H;
R$^3$ is hydrogen or -(A)$_t$-(CR$^x$R$^y$)$_q$—X;
s and t are independently selected from 0 and 1;
q is selected from 0, 1 and 2;
wherein when R$^3$ is -(A)$_t$-(CR$^x$R$^y$)$_q$—X then (i) at least one of s, t and q is other than 0 and (ii) when t is 0 then s is 1 and q is other than 0;
A is a heterocyclic group with 3 to 6 ring members, wherein the heterocyclic group comprises one or more (e.g. 1, 2, or 3) heteroatoms selected from N, O, S and oxidised forms thereof;
X is selected from hydrogen, halogen, —CN and —OR$^9$;
R$^4$ and R$^5$ are independently selected from halogen, nitrile and C$_{1-4}$ alkyl;
R$^6$ is selected from hydrogen and C$_{1-6}$alkyl;
R$^7$ is selected from heterocyclic group with 3 to 7 ring members, —CH$_2$-heterocyclic group with 3 to 7 ring members, C$_{3-8}$cycloalkyl, and —CH$_2$—C$_{3-8}$cycloalkyl, wherein said cycloalkyl or heterocyclic groups may be optionally substituted by one or more R$^z$ groups, and wherein in each instance the heterocyclic group comprises one or more (e.g. 1, 2, or 3) heteroatoms selected from N, O, S and oxidised forms thereof;
R$^9$ is selected from hydrogen and C$_{1-6}$alkyl;
R$^x$ and R$^y$ are independently selected from hydrogen and C$_{1-6}$alkyl;
R$^z$ is independently selected from halogen, nitro, nitrile, C$_{1-6}$alkyl, haloC$_{1-6}$alkyl, C$_{2-6}$alkenyl, hydroxy, hydroxyC$_{1-6}$alkyl, C$_{1-6}$alkoxy, —C(=O)C$_{1-6}$alkyl, and —N(H)$_e$(C$_{1-4}$alkyl)$_{2-e}$;
n and e are independently selected from 0, 1 and 2;
m is selected from 1 and 2; and
a is selected from 0 and 1.

In one embodiment, the invention provides a compound of formula (I) or a tautomer or a solvate or a pharmaceutically acceptable salt thereof, wherein:
Het is pyridinyl or pyrimidinyl
R$^1$ is attached to a carbon atom and is independently selected from halogen, hydroxy and nitrile;
R$^2$ is selected from hydrogen, C$_{1-4}$ alkyl and —CH$_2$CO$_2$H;
R$^3$ is hydrogen or -(A)$_t$-(CR$^x$R$^y$)$_q$—X;
A is a heterocyclic group with 3 to 6 ring members, wherein the heterocyclic group comprises one or more (e.g. 1, 2, or 3) heteroatoms selected from N, O, S and oxidised forms thereof;
s and t are independently selected from 0 and 1;
q is selected from 0, 1 and 2;
wherein when R$^3$ is -(A)$_t$-(CR$^x$R$^y$)$_q$—X then (i) at least one of s, t and q is other than 0 and (ii) when t is 0 then s is 1 and q is other than 0;
X is selected from hydrogen, halogen or —OR$^9$;
R$^4$ and R$^5$ are independently selected from halogen;
R$^6$ is selected from hydrogen and C$_{1-6}$alkyl;
R$^7$ is selected from heterocyclic group with 3 to 7 ring members, —CH$_2$-heterocyclic group with 3 to 7 ring members, C$_{3-8}$cycloalkyl, and —CH$_2$—C$_{3-8}$cycloalkyl, wherein said cycloalkyl, cycloalkenyl or heterocyclic groups may be optionally substituted by one or more R$^z$ groups, and wherein in each instance the heterocyclic group comprises one or more (e.g. 1, 2, or 3) heteroatoms selected from N, O, S and oxidised forms thereof;
R$^9$ is selected from hydrogen and C$_{1-6}$alkyl;
R$^x$ and R$^y$ are independently selected from hydrogen and C$_{1-6}$alkyl;
R$^z$ is independently selected from halogen, nitro, nitrile, and C$_{1-6}$alkyl;
n is 1 and m is 1; and
a is selected from 0 and 1.

In one embodiment, the invention provides a compound of formula (I) or a tautomer or a solvate or a pharmaceutically acceptable salt thereof, wherein:
Het is pyridinyl or pyrimidinyl
R$^1$ is attached to a carbon atom and is independently selected from halogen, hydroxy and nitrile;
R$^2$ is selected from hydrogen, C$_{1-4}$ alkyl and —CH$_2$CO$_2$H;
R$^3$ is -(A)$_t$-(CR$^x$R$^y$)$_q$—X;
A is a heterocyclic group with 3 to 6 ring members, wherein the heterocyclic group comprises one or more (e.g. 1, 2, or 3) heteroatoms selected from N, O, S and oxidised forms thereof;
s and t are independently selected from 0 and 1;
q is selected from 0, 1 and 2;
wherein (i) at least one of s, t and q is other than 0 and (ii) when t is 0 then s is 1 and q is other than 0;
X is selected from hydrogen, halogen and —OR$^9$;
R$^4$ and R$^5$ are independently selected from halogen;
R$^6$ is selected from hydrogen and C$_{1-6}$alkyl;
R$^7$ is a heterocyclic group with 3 to 7 ring members optionally substituted by one or more R$^z$ groups;
R$^9$ is selected from hydrogen and C$_{1-6}$alkyl;
R$^x$ and R$^y$ are independently selected from hydrogen and C$_{1-6}$alkyl;
R$^z$ is independently selected from halogen and C$_{1-6}$alkyl;
n is, 1 and m is 1 and
a is 1.

In one embodiment, the invention provides a compound of formula (I) or a tautomer or a solvate or a pharmaceutically acceptable salt thereof, wherein:
Het is pyridinyl or pyrimidinyl
R$^1$ is attached to a carbon atom and is independently selected from halogen, hydroxy and nitrile;
R$^2$ is selected from hydrogen, C$_{1-4}$ alkyl and —CH$_2$CO$_2$H;
R$^3$ is hydrogen and s is 1;
wherein (i) at least one of s, t and q is other than 0 and (ii) when t is 0 then s is 1 and q is other than 0;
R$^4$ and R$^5$ are independently selected from halogen;
R$^6$ is selected from hydrogen and C$_{1-6}$alkyl;
R$^7$ is a heterocyclic group with 3 to 7 ring members optionally substituted by one or more R$^z$ groups;
R$^9$ is selected from hydrogen and C$_{1-6}$alkyl;
R$^z$ is independently selected from halogen and C$_{1-6}$alkyl;
n is, 1 and m is 1 and
a is 1.

In one embodiment, the invention provides a compound of formula (I) or a tautomer or a solvate or a pharmaceutically acceptable salt thereof, wherein:
Het is pyridinyl, pyrimidinyl, or pyridazinyl, or an N-oxide thereof;

$R^1$ is halogen (e.g. Cl), nitrile, hydroxy, $C_{1-4}$alkoxy (e.g. —OCH$_3$), $C_{1-4}$alkyl (e.g. CH$_3$) or —S(O)$_d$—$C_{1-4}$alkyl;

n is 1 or 2;

$R^2$ is selected from hydrogen, $C_{1-4}$ alkyl (e.g. —CH$_3$), hydroxyC$_{1-4}$alkyl (e.g. —CH$_2$OH or —CH(OH)CH$_2$OH), —CH$_2$CO$_2$H and $C_{2-6}$alkenyl (e.g. —CH=CH$_2$);

the moiety —(CH$_2$)$_s$R$^3$ is selected from:

(point of attachment to the oxygen represented by dashed bond or bond terminus indicated by *):

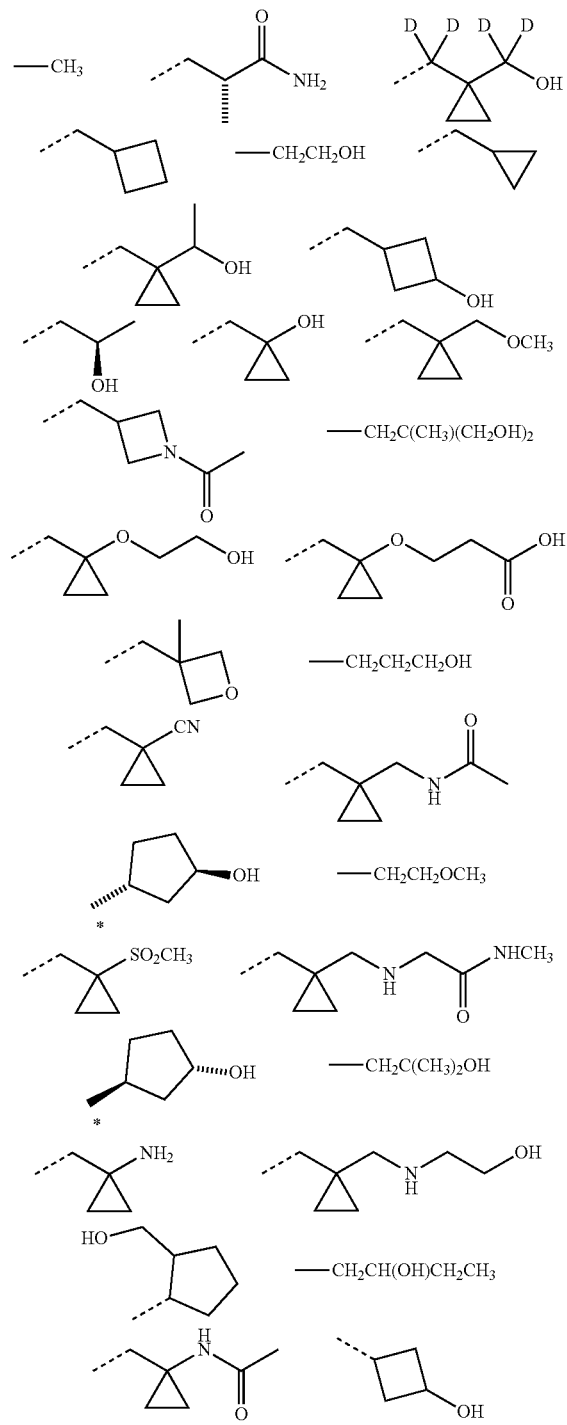

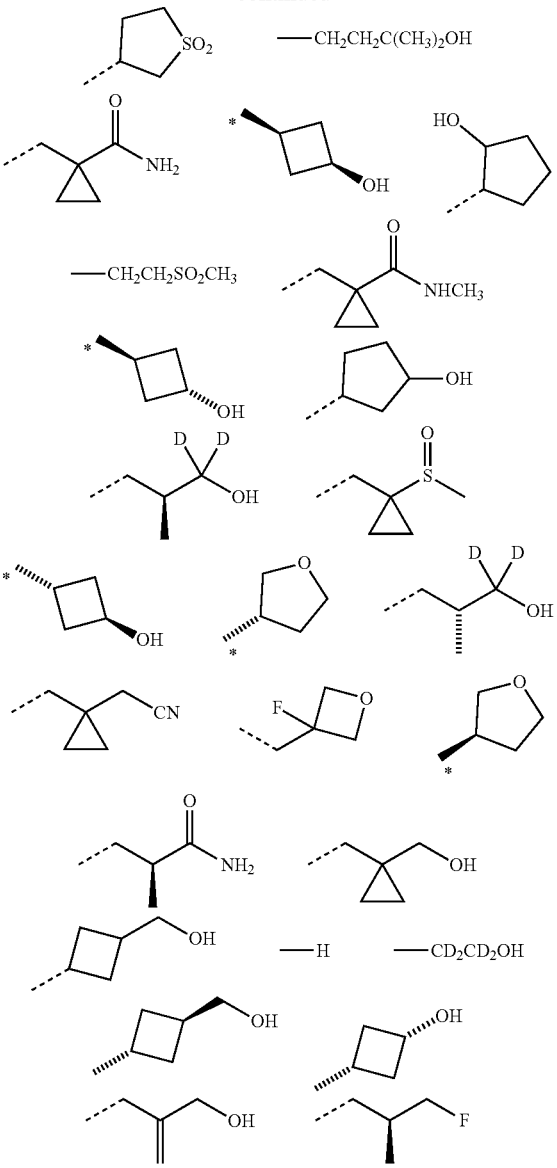

$R^4$ is $C_{1-4}$ alkyl (e.g. —CH$_3$), or halogen (e.g. F or Cl);

a is 0 or 1;

$R^5$ is halogen (e.g. Cl or F), $C_{1-4}$ alkyl (e.g. —CH$_2$CH$_3$), nitrile, haloC$_{1-4}$alkyl (e.g. —CF$_3$, or —CF$_2$CH$_3$), or halo C$_{1-4}$alkoxy (e.g. —OCF$_3$);

m is 1 or 2;

$R^6$ is hydrogen, $C_{1-6}$alkyl (e.g. —CH$_3$ or —CH$_2$CH$_3$), $C_{2-6}$alkenyl (e.g. —CH=CH$_2$) and haloC$_{1-6}$alkyl (e.g. —CF$_3$ or —CH$_2$F);

$R^7$ is $C_{1-6}$alkyl (e.g. —CH$_3$ or —CH$_2$CH$_3$), $C_{3-8}$cycloalkyl (e.g. cyclopropyl, cyclobutyl or cyclohexyl), $C_{2-6}$alkenyl (e.g. —CH=CH$_2$), haloC$_{1-6}$alkyl (e.g. —CF$_3$), hydroxyC$_{1-6}$alkyl (e.g. —CH$_2$OH or —CH$_2$CH$_2$OH), —C$_{1-6}$alkyl-NR$^x$R$^y$ (e.g. —CH$_2$NH$_2$, —CH$_2$N(CH$_3$)$_2$, —CH$_2$NHCH$_3$, or —CH$_2$NH(cyclopropyl)), —(CR$^x$R$^y$)$_p$—CONR$^x$R$^y$ (e.g. —C(=O)NHCH$_3$, —(CO)NHCH$_2$CH$_3$, —(CO)NHCH$_2$CH$_2$NH$_2$, —C(=O)NH(CH(CH$_3$)$_2$)), or —(CH$_2$)$_j$—O—C$_{1-6}$alkyl (e.g. —CH$_2$OCH$_3$, —CH$_2$OCH$_2$CH$_3$ or —CH$_2$OCD$_3$), —(CR$^x$R$^y$)$_p$—NR$^x$-COR$^y$ (e.g. —CH$_2$NHC(=O)CH$_3$), —(CR$^x$R$^y$)$_p$—O—

CH$_2$—CONR$^x$R$^y$ (e.g. —CH$_2$OCH$_2$C(=O)N(CH$_3$)$_2$), —(CH$_2$)$_j$—O-(hydroxyC$_{1-6}$alkyl) (e.g. —CH$_2$OCH$_2$CH$_2$OH), heterocyclic group with 3 to 7 ring members e.g.
(point of attachment represented by dashed bond):

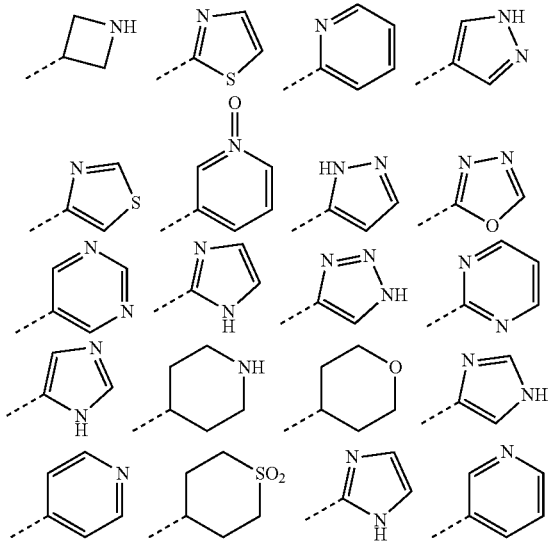

or —CH$_2$-heterocyclic group with 3 to 7 ring members e.g. (point of attachment represented by dashed bond)

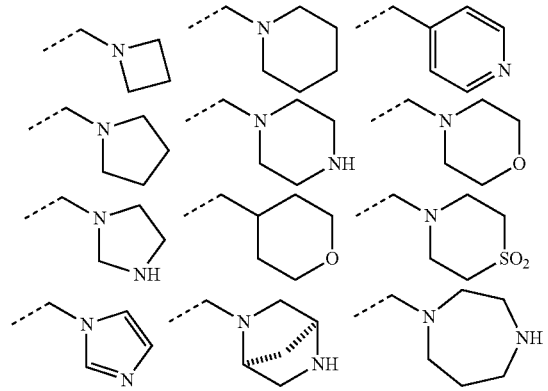

wherein when the moiety R$^7$ comprises a heterocyclic group, the heterocyclic group may be optionally substituted by one or more R$^z$ groups selected from C$_{1-6}$alkyl (e.g. methyl), hydroxyalkyl (e.g. —CH$_2$CH$_2$OH), halogen (e.g. fluoro), =O, C$_{1-6}$alkoxy (e.g. methoxy), —C(=O)C$_{1-6}$alkyl (e.g. —C(=O)CH$_3$), —C(=O)hydroxyC$_{1-6}$alkyl (e.g. —C(=O) CH$_2$OH), heterocyclyl group with 3 to 6 ring members (e.g. oxetanyl or pyrimidinyl), and —S(O)$_d$—C$_{1-4}$alkyl wherein d is selected from 0, 1 and 2 (e.g. —SO$_2$—CH$_3$).

In one embodiment of formula (I) R$^7$ is a heterocyclic group with 3 to 7 ring members e.g.
(point of attachment represented by dashed bond)

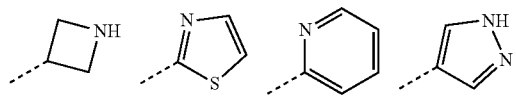

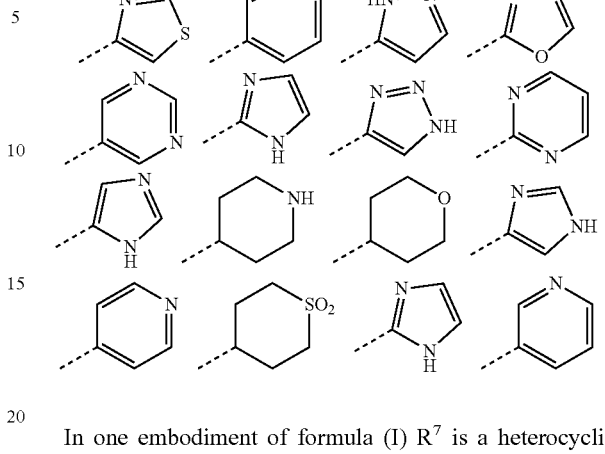

In one embodiment of formula (I) R$^7$ is a heterocyclic group with 3 to 7 ring members optionally substituted by one or more R$^z$ groups e.g.
(point of attachment represented by dashed bond)

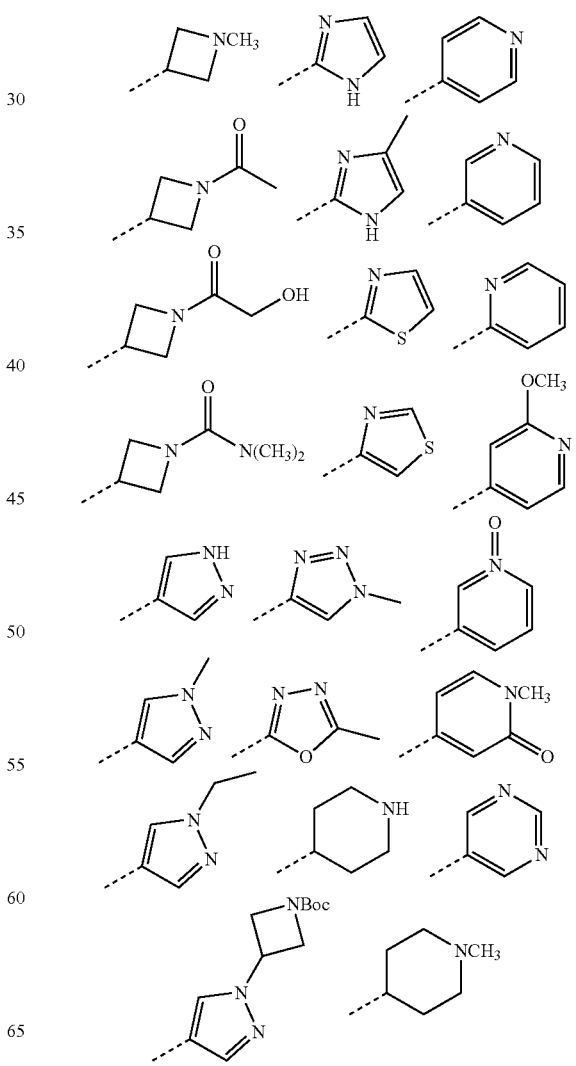

-continued

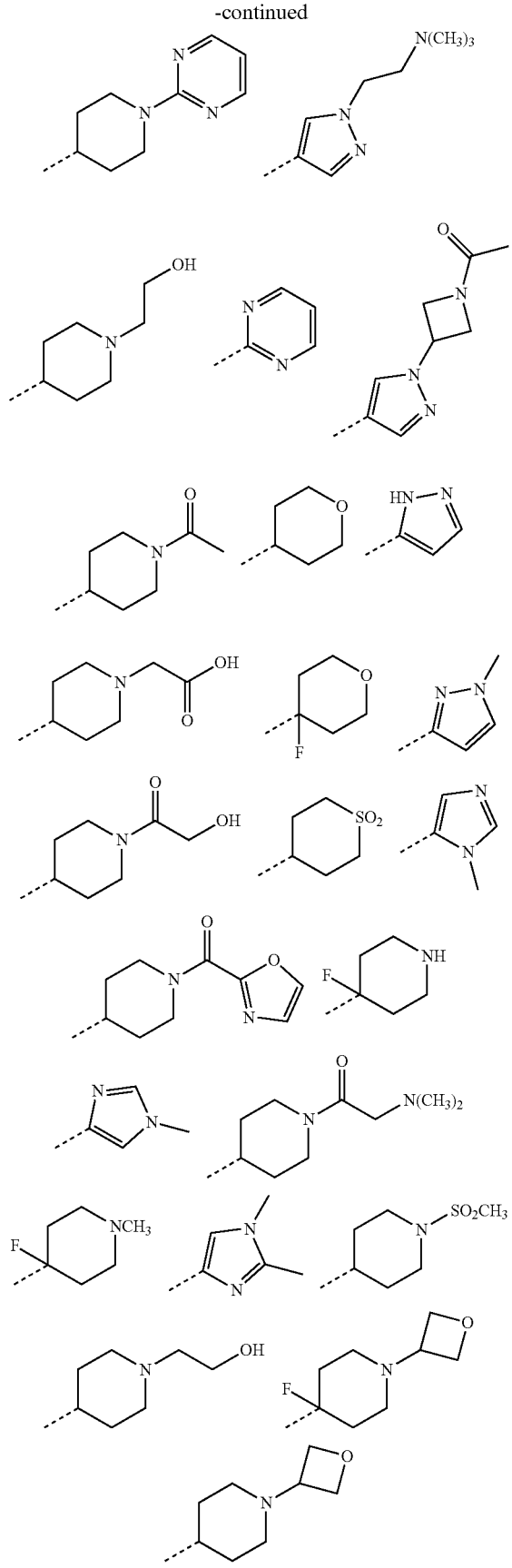

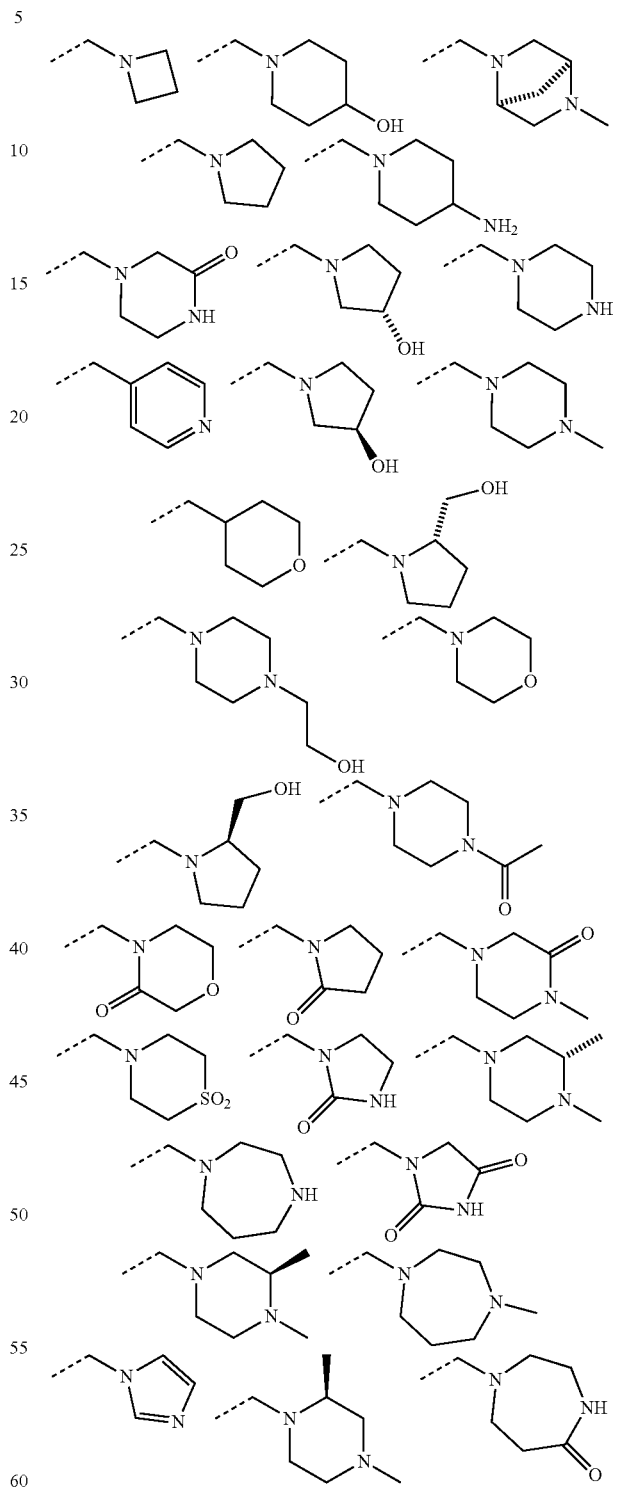

or a —CH$_2$-heterocyclic group with 3 to 7 ring members optionally substituted by one or more R$^z$ groups e.g. (point of attachment represented by dashed bond)

In one embodiment, the invention provides a compound of formula (I) or a tautomer or a solvate or a pharmaceutically acceptable salt thereof, wherein:

Het is pyridinyl, pyrimidinyl, or pyridazinyl, or an N-oxide thereof;

R[1] is halogen (e.g. Cl), nitrile, hydroxy, $C_{1-4}$alkoxy (e.g. —$OCH_3$), $C_{1-4}$alkyl (e.g. $CH_3$) or —$S(O)_d$—$C_{1-4}$alkyl;

n is 1 or 2;

R[2] is selected from hydrogen, $C_{1-4}$ alkyl (e.g. —$CH_3$), hydroxy$C_{1-4}$alkyl (e.g. —$CH_2OH$ or —$CH(OH)CH_2OH$), —$CH_2CO_2H$ and $C_{2-6}$alkenyl (e.g. —$CH=CH_2$);

the moiety —$(CH_2)_sR^3$ is selected from:

(point of attachment to the oxygen represented by dashed bond or bond terminus indicated by *):

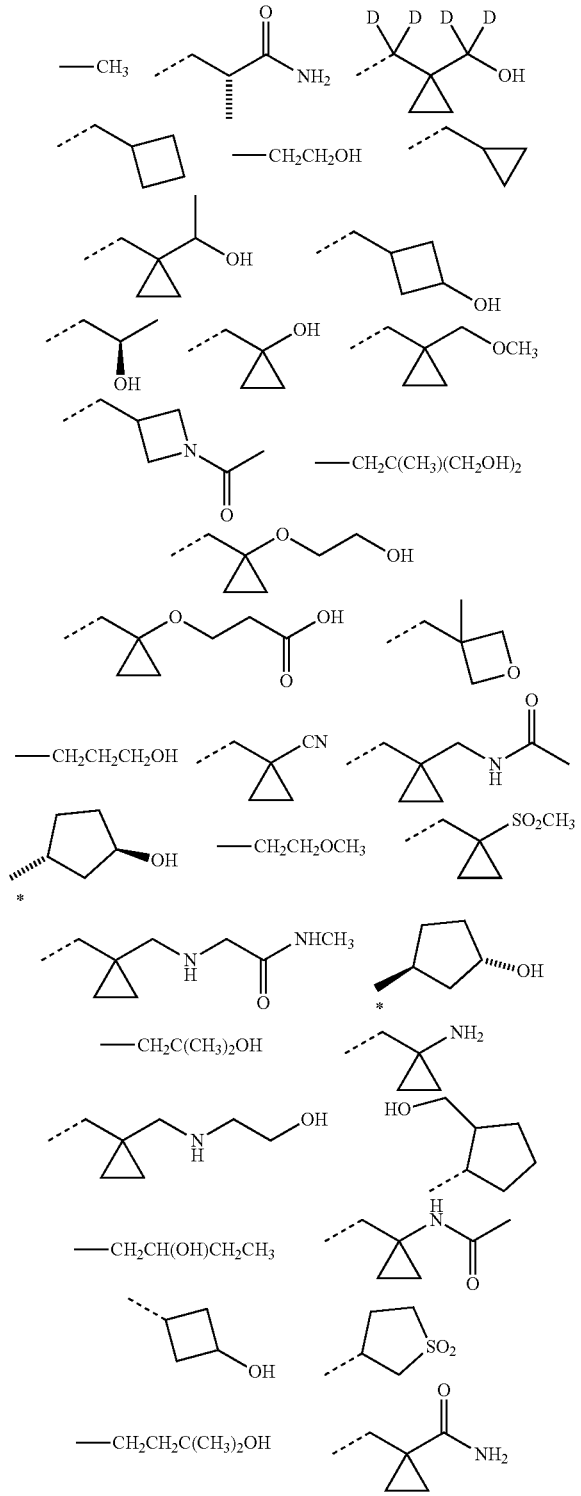

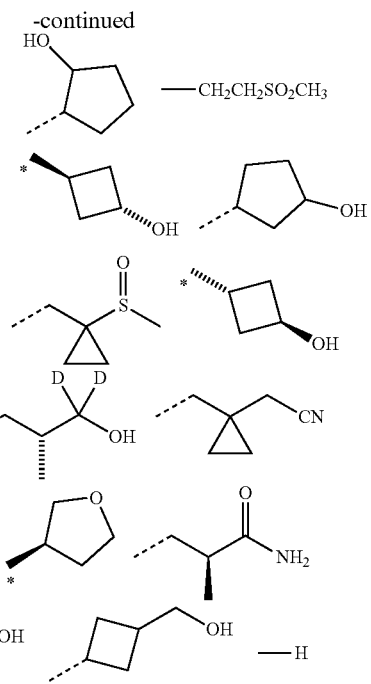

R[4] is $C_{1-4}$ alkyl (e.g. —$CH_3$), or halogen (e.g. F or Cl);

a is 0 or 1;

R[5] is halogen (e.g. Cl or F), $C_{1-4}$ alkyl (e.g. —$CH_2CH_3$), nitrile, halo$C_{1-4}$alkyl (e.g. —$CF_3$, or —$CF_2CH_3$), or halo $C_{1-4}$alkoxy (e.g. —$OCF_3$);

m is 1 or 2;

R[6] is hydrogen, $C_{1-6}$alkyl (e.g. —$CH_3$ or —$CH_2CH_3$), $C_{2-6}$alkenyl (e.g. —$CH=CH_2$) and halo$C_{1-6}$alkyl (e.g. —$CF_3$ or —$CH_2F$);

R[7] is $C_{1-6}$alkyl (e.g. —$CH_3$ or —$CH_2CH_3$), $C_{3-8}$cycloalkyl (e.g. cyclopropyl, cyclobutyl or cyclohexyl), $C_{2-6}$alkenyl (e.g. —$CH=CH_2$), halo$C_{1-6}$alkyl (e.g. —$CF_3$), hydroxy$C_{1-6}$alkyl (e.g. —$CH_2OH$ or —$CH_2CH_2OH$), —$C_{1-6}$alkyl-$NR^xR^y$ (e.g. —$CH_2NH_2$, —$CH_2N(CH_3)_2$, —$CH_2NHCH_3$, or —$CH_2NH(cyclopropyl)$), —$(CR^xR^y)_p$—$CONR^xR^y$ (e.g. —$C(=O)NHCH_3$, —$(CO)NHCH_2CH_3$, —$(CO)NHCH_2CH_2NH_2$, —$C(=O)NH(CH(CH_3)_2)$), or —$(CH_2)_j$—$O$—$C_{1-6}$alkyl (e.g. —$CH_2OCH_3$, —$CH_2OCH_2CH_3$ or —$CH_2OCD_3$), —$(CR^xR^y)_p$—$NR^x$-$COR^y$ (e.g. —$CH_2NHC(=O)CH_3$), —$(CR^xR^y)_p$—$O$—$CH_2$—$CONR^xR^y$ (e.g. —$CH_2OCH_2C(=O)N(CH_3)_2$), —$(CH_2)_j$—$O$-(hydroxy$C_{1-6}$alkyl) (e.g. —$CH_2OCH_2CH_2OH$), heterocyclic group with 3 to 7 ring members e.g.

(point of attachment represented by dashed bond):

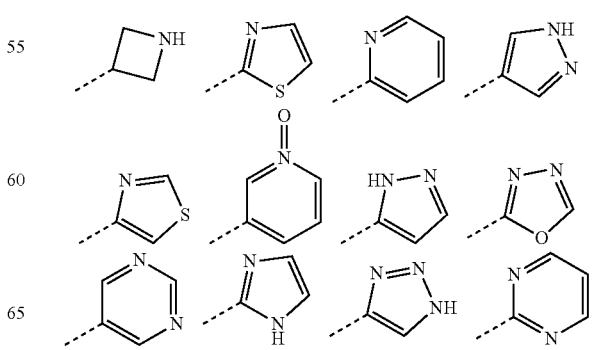

-continued

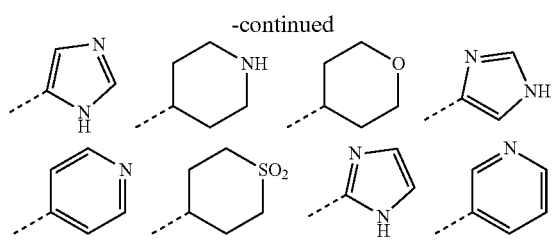

or —CH$_2$-heterocyclic group with 3 to 7 ring members e.g.
(point of attachment represented by dashed bond)

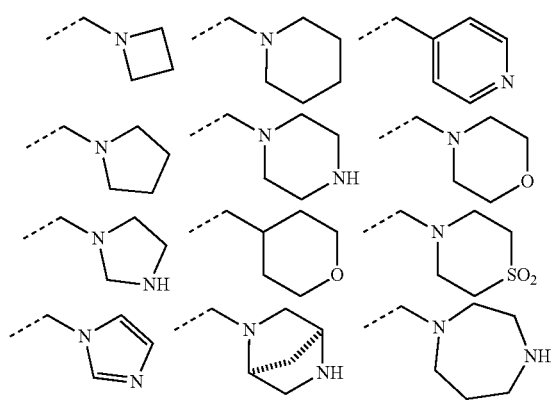

wherein when R$^7$ comprises a heterocyclic group, the heterocyclic group may be optionally substituted by one or more R$^z$ groups selected from C$_{1-6}$alkyl (e.g. methyl), halogen (e.g. fluoro), =O, C$_{1-6}$alkoxy (e.g. methoxy), —C(=O) C$_{1-6}$alkyl (e.g. —C(=O)CH$_3$), —C(=O)hydroxyC$_{1-6}$alkyl (e.g. —C(=O)CH$_2$OH), heterocyclyl group with 3 to 6 ring members (e.g. pyrimidinyl), and —S(O)$_d$—C$_{1-4}$alkyl wherein d is selected from 0, 1 and 2 (e.g. —SO$_2$—CH$_3$).

In one embodiment of formula (I) R$^7$ is a heterocyclic group with 3 to 7 ring members e.g.
(point of attachment represented by dashed bond)

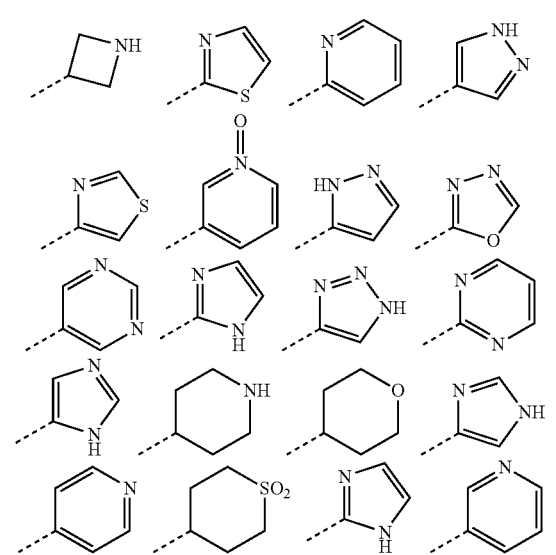

In one embodiment of formula (I) R$^7$ is a heterocyclic group with 3 to 7 ring members optionally substituted by one or more R$^z$ groups e.g.
(point of attachment represented by dashed bond)

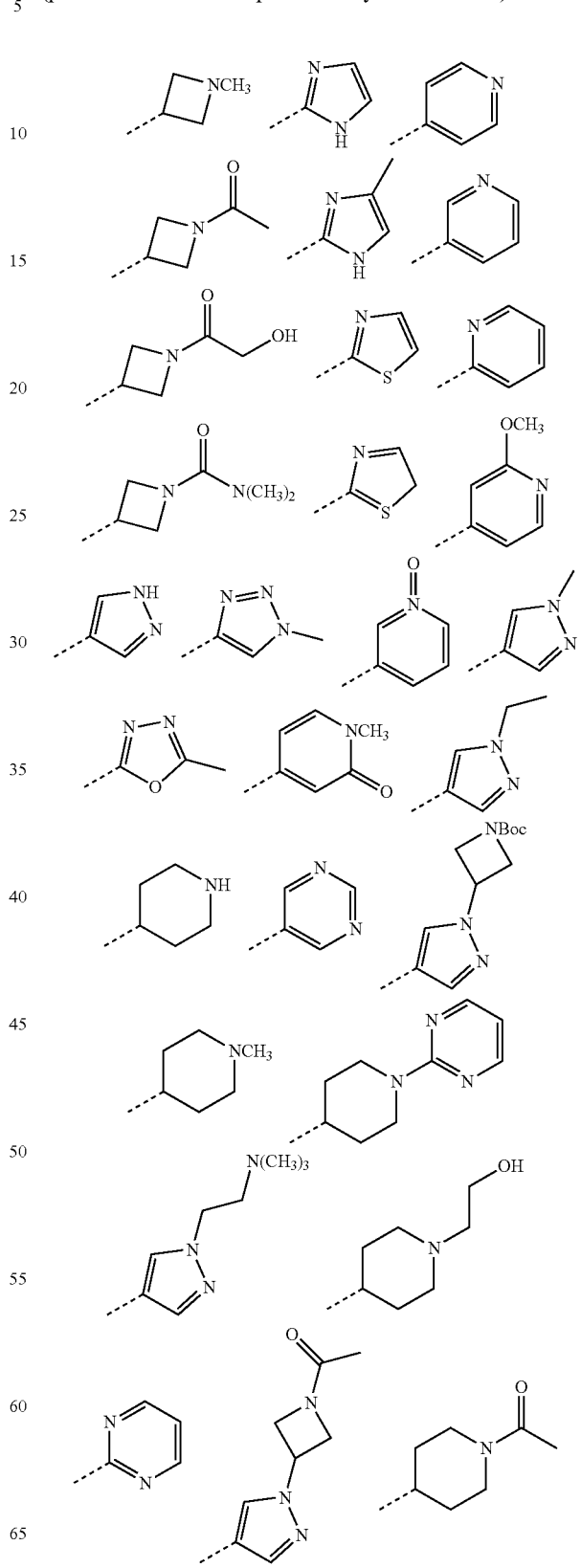

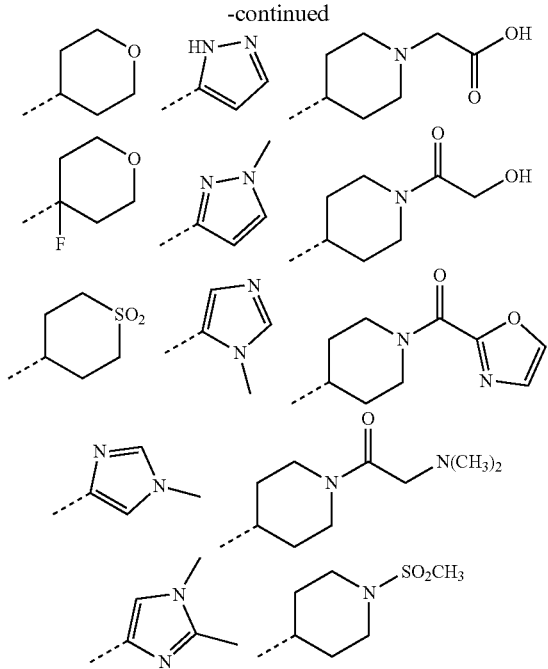

or a —CH$_2$-heterocyclic group with 3 to 7 ring members optionally substituted by one or more R$^z$ groups e.g.
(point of attachment represented by dashed bond)

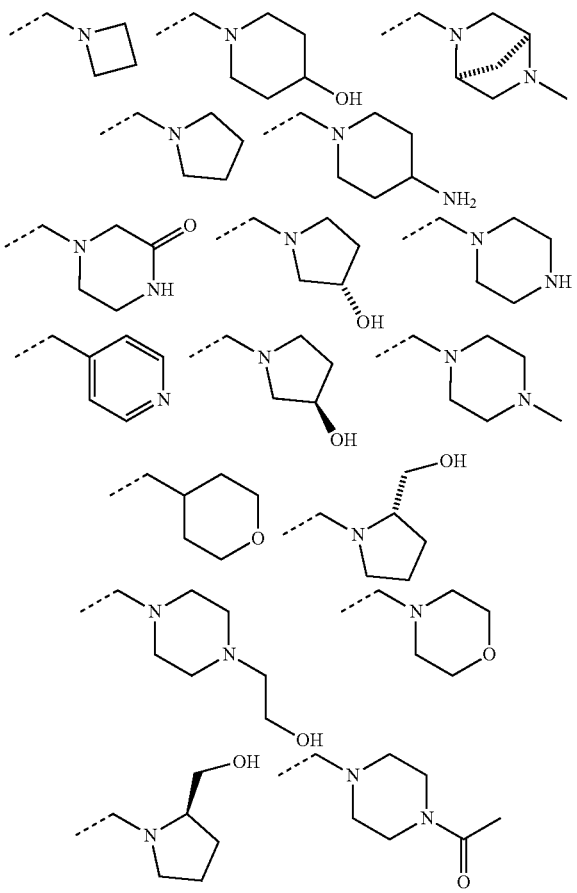

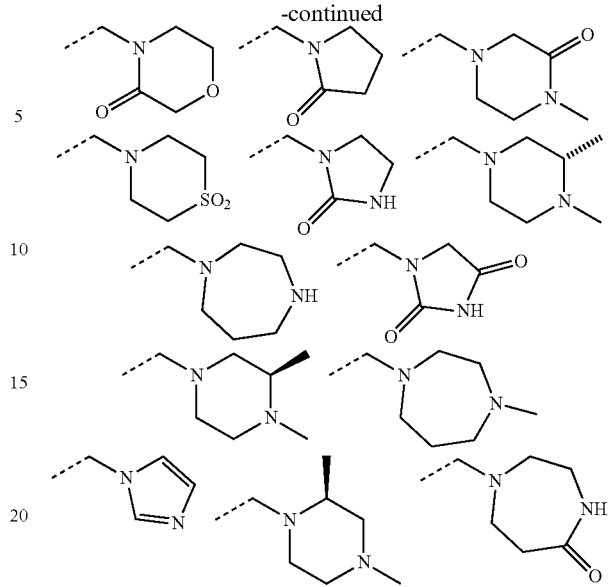

In one embodiment, the invention provides a compound of formula (I) or a tautomer or a solvate or a pharmaceutically acceptable salt thereof, wherein:
Het is pyridin-2-yl or pyrimidin-2-yl;
R$^1$ is —Cl, —CN, —OH or —OMe;
n is 1;
R$^2$ is hydrogen;
R$^3$ is -(A)$_t$-(CR$^x$R$^y$)$_q$—X;
s is 0 or 1;
t is 1;
A is selected from cyclopropyl, oxetanyl and tetrahydrofuranyl;
X is selected from hydrogen, fluorine, —CN, —OH and —C(═O)NH$_2$,
q is 0 or 1 and R$^x$ and R$^y$ are hydrogen or deuterium;
a is 0 or 1 and R$^4$ is halogen (e.g. fluorine);
R$^5$ is halogen (e.g. Cl);
m is 1;
R$^6$ is C$_{1-4}$alkyl (e.g. methyl or ethyl);
R$^7$ is C$_{1-4}$alkyl (e.g. methyl or ethyl), hydroxylC$_{1-4}$alkyl (e.g. hydroxylmethyl or hydroxyethyl), methoxyC$_{1-4}$alkyl (e.g. methoxymethyl), a heterocyclic group with 5 or 6 ring members (e.g. piperidinyl, oxanyl, imidazolyl or pyrazolyl) or C$_{3-6}$cycloalkyl (e.g. cyclobutyl or cyclohexyl) wherein said heterocyclic group with 5 or 6 ring members and C$_{3-6}$cycloalkyl groups may be optionally substituted with one or two R$^z$ groups independently selected from methyl, halogen (such as fluorine), —C(═O)Me, and —OH.

In one embodiment, the invention provides a compound of formula (I) or a tautomer or a solvate or a pharmaceutically acceptable salt thereof, wherein:
Het is pyridin-2-yl or pyrimidin-2-yl;
R$^1$ is —Cl, —CN, —OH or —OMe;
n is 1;
R$^2$ is hydrogen;
R$^3$ is hydrogen and s is 1;
a is 0 or 1 and R$^4$ is halogen (e.g. fluorine);
R$^5$ is halogen (e.g. Cl);
m is 1;
R$^6$ is C$_{1-4}$alkyl (e.g. methyl or ethyl);
R$^7$ is C$_{1-4}$alkyl (e.g. methyl or ethyl), hydroxylC$_{1-4}$alkyl (e.g. hydroxylmethyl or hydroxyethyl), methoxyC$_{1-4}$alkyl (e.g. methoxymethyl), a heterocyclic group with 5 or 6 ring members (e.g. piperidinyl, oxanyl, imidazolyl or pyrazolyl) or $C_{3-6}$cycloalkyl (e.g. cyclobutyl or cyclohexyl) wherein said heterocyclic group with 5 or 6 ring members and $C_{3-6}$cycloalkyl groups may be optionally substituted with one or two $R^z$ groups independently selected from methyl, halogen (such as fluorine), —C(=O)Me, and —OH.

In one embodiment, the invention provides a compound of formula (I) which is one of the Examples 1-580 or is selected from the Examples 1-580 or a tautomer, N-oxide, pharmaceutically acceptable salt or solvate thereof.

In one embodiment, the invention provides a compound of formula (I) which is one of the Examples 1-460 or is selected from the Examples 1-460 or a tautomer, N-oxide, pharmaceutically acceptable salt or solvate thereof.

In one embodiment, the invention provides a compound of formula (I) which is one of the Examples 1-459 or is selected from the Examples 1-459 or a tautomer, N-oxide, pharmaceutically acceptable salt or solvate thereof.

In one embodiment, the invention provides a compound of formula (I) which is selected from the following compounds, or a tautomer, N-oxide, pharmaceutically acceptable salt or solvate thereof:
(3R)-3-(4-chlorophenyl)-2-[(5-chloropyrimidin-2-yl) methyl]-4-fluoro-6-{1-hydroxy-1-[trans-4-hydroxycyclohexyl]ethyl}-3-{[1-(hydroxymethyl)cyclopropyl] methoxy}-2,3-dihydro-1H-isoindol-1-one;
2-{[(1R)-1-(4-chlorophenyl)-7-fluoro-5-[1-hydroxy-1-(1-methyl-1H-imidazol-4-yl)propyl]-3-oxo-1-[(3S)-oxolan-3-yloxy]-2,3-dihydro-1H-isoindol-2-yl] methyl}pyrimidine-5-carbonitrile;
(3R)-2-[(5-chloro-3-hydroxypyridin-2-yl)methyl]-3-(4-chlorophenyl)-4-fluoro-6-[1-hydroxy-1-(1-methyl-1H-imidazol-4-yl)propyl]-3-(2-hydroxyethoxy)-2,3-dihydro-1H-isoindol-1-one;
6-{[(1R)-1-(4-chlorophenyl)-7-fluoro-5-[1-(4-fluorooxan-4-yl)-1-hydroxypropyl]-3-oxo-1-[(3S)-oxolan-3-yloxy]-2,3-dihydro-1H-isoindol-2-yl]methyl}pyridine-3-carbonitrile;
6-{[(1R)-1-(4-chlorophenyl)-7-fluoro-1-[(3-fluorooxetan-3-yl)methoxy]-5-[1-hydroxy-1-(1-methyl-1H-imidazol-4-yl) propyl]-3-oxo-2,3-dihydro-1H-isoindol-2-yl] methyl}pyridine-3-carbonitrile;
6-{[(1R)-1-(4-chlorophenyl)-7-fluoro-1-({1-[hydroxy($^2$H$_2$) methyl]cyclopropyl}($^2$H$_2$)methoxy)-5-[1-hydroxy-1-(1-methyl-1H-imidazol-4-yl)propyl]-3-oxo-2,3-dihydro-1H-isoindol-2-yl]methyl}pyridine-3-carbonitrile; and
(3R)-3-(4-chlorophenyl)-2-[(5-chloropyrimidin-2-yl) methyl]-4-fluoro-6-[1-hydroxy-1-(1-methylpiperidin-4-yl)propyl]-3-[(3S)-oxolan-3-yloxy]-2,3-dihydro-1H-isoindol-1-one.

In one embodiment, the invention provides a compound of formula (I) which is diastereoisomer 2A and is selected from the following compounds, or a tautomer, N-oxide, pharmaceutically acceptable salt or solvate thereof:
(3R)-3-(4-chlorophenyl)-2-[(5-chloropyrimidin-2-yl) methyl]-4-fluoro-6-{1-hydroxy-1-[trans-4-hydroxycyclohexyl]ethyl}-3-{[1-(hydroxymethyl)cyclopropyl] methoxy}-2,3-dihydro-1H-isoindol-1-one;
2-{[(1R)-1-(4-chlorophenyl)-7-fluoro-5-[1-hydroxy-1-(1-methyl-1H-imidazol-4-yl)propyl]-3-oxo-1-[(3S)-oxolan-3-yloxy]-2,3-dihydro-1H-isoindol-2-yl] methyl}pyrimidine-5-carbonitrile;
(3R)-2-[(5-chloro-3-hydroxypyridin-2-yl)methyl]-3-(4-chlorophenyl)-4-fluoro-6-[1-hydroxy-1-(1-methyl-1H-imidazol-4-yl)propyl]-3-(2-hydroxyethoxy)-2,3-dihydro-1H-isoindol-1-one;
6-{[(1R)-1-(4-chlorophenyl)-7-fluoro-5-[1-(4-fluorooxan-4-yl)-1-hydroxypropyl]-3-oxo-1-[(3S)-oxolan-3-yloxy]-2,3-dihydro-1H-isoindol-2-yl]methyl}pyridine-3-carbonitrile;
6-{[(1R)-1-(4-chlorophenyl)-7-fluoro-1-[(3-fluorooxetan-3-yl)methoxy]-5-[1-hydroxy-1-(1-methyl-1H-imidazol-4-yl) propyl]-3-oxo-2,3-dihydro-1H-isoindol-2-yl] methyl}pyridine-3-carbonitrile;
6-{[(1R)-1-(4-chlorophenyl)-7-fluoro-1-({1-[hydroxy($^2$H$_2$) methyl]cyclopropyl}($^2$H$_2$)methoxy)-5-[1-hydroxy-1-(1-methyl-1H-imidazol-4-yl)propyl]-3-oxo-2,3-dihydro-1H-isoindol-2-yl]methyl}pyridine-3-carbonitrile; and
(3R)-3-(4-chlorophenyl)-2-[(5-chloropyrimidin-2-yl) methyl]-4-fluoro-6-[1-hydroxy-1-(1-methylpiperidin-4-yl)propyl]-3-[(3S)-oxolan-3-yloxy]-2,3-dihydro-1H-isoindol-1-one.

In one embodiment, the invention provides a compound of formula (I) which is diastereoisomer 2B and is selected from the following compounds, or a tautomer, N-oxide, pharmaceutically acceptable salt or solvate thereof:
(3R)-3-(4-chlorophenyl)-2-[(5-chloropyrimidin-2-yl) methyl]-4-fluoro-6-{1-hydroxy-1-[trans-4-hydroxycyclohexyl]ethyl}-3-{[1-(hydroxymethyl)cyclopropyl] methoxy}-2,3-dihydro-1H-isoindol-1-one;
2-{[(1R)-1-(4-chlorophenyl)-7-fluoro-5-[1-hydroxy-1-(1-methyl-1H-imidazol-4-yl)propyl]-3-oxo-1-[(3S)-oxolan-3-yloxy]-2,3-dihydro-1H-isoindol-2-yl] methyl}pyrimidine-5-carbonitrile;
(3R)-2-[(5-chloro-3-hydroxypyridin-2-yl)methyl]-3-(4-chlorophenyl)-4-fluoro-6-[1-hydroxy-1-(1-methyl-1H-imidazol-4-yl)propyl]-3-(2-hydroxyethoxy)-2,3-dihydro-1H-isoindol-1-one;
6-{[(1R)-1-(4-chlorophenyl)-7-fluoro-5-[1-(4-fluorooxan-4-yl)-1-hydroxypropyl]-3-oxo-1-[(3S)-oxolan-3-yloxy]-2,3-dihydro-1H-isoindol-2-yl]methyl}pyridine-3-carbonitrile;
6-{[(1R)-1-(4-chlorophenyl)-7-fluoro-1-[(3-fluorooxetan-3-yl)methoxy]-5-[1-hydroxy-1-(1-methyl-1H-imidazol-4-yl) propyl]-3-oxo-2,3-dihydro-1H-isoindol-2-yl] methyl}pyridine-3-carbonitrile;
6-{[(1R)-1-(4-chlorophenyl)-7-fluoro-1-({1-[hydroxy($^2$H$_2$) methyl]cyclopropyl}($^2$H$_2$)methoxy)-5-[1-hydroxy-1-(1-methyl-1H-imidazol-4-yl)propyl]-3-oxo-2,3-dihydro-1H-isoindol-2-yl]methyl}pyridine-3-carbonitrile; and
(3R)-3-(4-chlorophenyl)-2-[(5-chloropyrimidin-2-yl) methyl]-4-fluoro-6-[1-hydroxy-1-(1-methylpiperidin-4-yl)propyl]-3-[(3S)-oxolan-3-yloxy]-2,3-dihydro-1H-isoindol-1-one.

In one embodiment, the invention provides a compound of formula (I) which is selected from the following compounds, or a tautomer, N-oxide, pharmaceutically acceptable salt or solvate thereof:
(3R)-3-(4-chlorophenyl)-2-[(5-chloropyrimidin-2-yl) methyl]-4-fluoro-6-[2-hydroxy-1-(4-methylpiperazin-1-yl)butan-2-yl]-3-[(3S)-oxolan-3-yloxy]-2,3-dihydro-1H-isoindol-1-one;
(3R)-3-(4-chlorophenyl)-2-[(5-chloropyrimidin-2-yl) methyl]-4-fluoro-6-[1-(4-fluoro-1-methylpiperidin-4-yl)-1-hydroxypropyl]-3-methoxy-2,3-dihydro-1H-isoindol-1-one;
1-({[(1R)-1-(4-chlorophenyl)-2-[(5-chloropyrimidin-2-yl) methyl]-7-fluoro-5-[1-(4-fluoro-1-methylpiperidin-4-yl)-1-hydroxypropyl]-3-oxo-2,3-dihydro-1H-isoindol-1-yl] oxy}methyl)cyclopropane-1-carbonitrile;
(3R)-3-(4-chlorophenyl)-2-[(5-chloropyrimidin-2-yl) methyl]-4-fluoro-6-[1-(4-fluoro-1-methylpiperidin-4-yl)-

1-hydroxypropyl]-3-[cis-3-hydroxycyclobutoxy]-2,3-dihydro-1H-isoindol-1-one; and
(3R)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-[(2R)-2-hydroxypropoxy]-2,3-dihydro-1H-isoindol-1-one.

In one embodiment, the invention provides a compound of formula (I) which is 1-({[(1R)-1-(4-chlorophenyl)-2-[(5-chloropyrimidin-2-yl)methyl]-7-fluoro-5-[1-(4-fluoro-1-methylpiperidin-4-yl)-1-hydroxypropyl]-3-oxo-2,3-dihydro-1H-isoindol-1-yl]oxy}methyl)cyclopropane-1-carbonitrile, or a tautomer, N-oxide, pharmaceutically acceptable salt or solvate thereof.

In one embodiment, the invention provides a compound of formula (I) which is (3R)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-methoxy-2,3-dihydro-1H-isoindol-1-one, or a tautomer, N-oxide, pharmaceutically acceptable salt or solvate thereof.

In one embodiment, the invention provides a compound of formula (I) which is diastereoisomer 2A and is 1-({[(1R)-1-(4-chlorophenyl)-2-[(5-chloropyrimidin-2-yl)methyl]-7-fluoro-5-[1-(4-fluoro-1-methylpiperidin-4-yl)-1-hydroxypropyl]-3-oxo-2,3-dihydro-1H-isoindol-1-yl]oxy}methyl)cyclopropane-1-carbonitrile, or a tautomer, N-oxide, pharmaceutically acceptable salt or solvate thereof.

In one embodiment, the invention provides a compound of formula (I) which is diastereoisomer 2A and is (3R)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-methoxy-2,3-dihydro-1H-isoindol-1-one, or a tautomer, N-oxide, pharmaceutically acceptable salt or solvate thereof.

In one embodiment, the invention provides a compound of formula (I) which is diastereoisomer 2B and is 1-({[(1R)-1-(4-chlorophenyl)-2-[(5-chloropyrimidin-2-yl)methyl]-7-fluoro-5-[1-(4-fluoro-1-methylpiperidin-4-yl)-1-hydroxypropyl]-3-oxo-2,3-dihydro-1H-isoindol-1-yl]oxy}methyl)cyclopropane-1-carbonitrile, or a tautomer, N-oxide, pharmaceutically acceptable salt or solvate thereof.

In one embodiment, the invention provides a compound of formula (I) which is diastereoisomer 2B and is (3R)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-methoxy-2,3-dihydro-1H-isoindol-1-one, or a tautomer, N-oxide, pharmaceutically acceptable salt or solvate thereof.

In one embodiment the compound of formula (I) is (3R)-3-(4-chlorophenyl)-2-[(5-chloropyrimidin-2-yl)methyl]-4-fluoro-6-[(1S)-1-(4-fluoro-1-methylpiperidin-4-yl)-1-hydroxypropyl]-3-methoxy-2,3-dihydro-1H-isoindol-1-one, or a tautomer, N-oxide, pharmaceutically acceptable salt or solvate thereof.

In one embodiment the compound of formula (I) is (3R)-3-(4-chlorophenyl)-2-[(5-chloropyrimidin-2-yl)methyl]-4-fluoro-6-[(1R)-1-(4-fluoro-1-methylpiperidin-4-yl)-1-hydroxypropyl]-3-methoxy-2,3-dihydro-1H-isoindol-1-one, or a tautomer, N-oxide, pharmaceutically acceptable salt or solvate thereof.

In one embodiment the compound of formula (I) is 1-({[(1R)-1-(4-chlorophenyl)-2-[(5-chloropyrimidin-2-yl)methyl]-7-fluoro-5-[(1S)-1-(4-fluoro-1-methylpiperidin-4-yl)-1-hydroxypropyl]-3-oxo-2,3-dihydro-1H-isoindol-1-yl]oxy}methyl)cyclopropane-1-carbonitrile, or a tautomer, N-oxide, pharmaceutically acceptable salt or solvate thereof.

In one embodiment the compound of formula (I) is 1-({[(1R)-1-(4-chlorophenyl)-2-[(5-chloropyrimidin-2-yl)methyl]-7-fluoro-5-[(1R)-1-(4-fluoro-1-methylpiperidin-4-yl)-1-hydroxypropyl]-3-oxo-2,3-dihydro-1H-isoindol-1-yl]oxy}methyl)cyclopropane-1-carbonitrile, or a tautomer, N-oxide, pharmaceutically acceptable salt or solvate thereof.

For the avoidance of doubt, it is to be understood that each general and specific embodiment and example for one substituent may be combined with each general and specific embodiment and example for one or more, in particular all, other substituents as defined herein and that all such embodiments are embraced by this application.

Salts, Solvates, Tautomers, Isomers, N-Oxides, Esters, Prodrugs and Isotopes

A reference to a compound of the formula (I), sub-groups thereof (e.g. formulae I(a), I(a'), I(b), I(c), I(d), I(e), I(f), I(g), I(g'), I(h), I(i), I(j), I(k), I(L), I(m), I(m'), I(n), I(o), I(o'), I(o"), I(p), I(p'), I(q), I(q'), I(q"), I(q'''), I(r), I(s), I(t), I(u), I(v), I(v'), I(w), I(x), I(x'), I(y), (II), (IIa), (IIb), (IIIa), (IIIb), (IVa), (IVb), (V), (VI), (VIa), (VII), (VIIa), (VIIb), (VIIc), (VIId), (VIId'), (VIIe), (VIIe'), (a), (b), (ba), (bb), (bc), or (c)) and any example also includes ionic forms, salts, solvates, isomers (including geometric and stereochemical isomers unless specified), tautomers, N-oxides, esters, prodrugs, isotopes and protected forms thereof, for example, as discussed below; in particular, the salts or tautomers or isomers or N-oxides or solvates thereof; and more particularly the salts or tautomers or N-oxides or solvates thereof. In one embodiment reference to a compound of the formula (I), sub-groups thereof (e.g. formulae I(a), I(a'), I(b), I(c), I(d), I(e), I(f), I(g), I(g'), I(h), I(i), I(j), I(k), I(L), I(m), I(m'), I(n), I(o), I(o'), I(o"), I(p), I(p'), I(q), I(q'), I(q"), I(q'''), I(q''''), I(q), I(r), I(s), I(t), I(u), I(v), I(v'), I(w), I(x), I(x'), I(y), (II), (IIa), (IIb), (IIIa), (IIIb), (IVa), (IVb), (V), (VI), (VIa), (VII), (VIIa), (VIIb), (VIIc), (VIId), (VIId'), (VIIe), (VIIe'), (a), (b), (ba), (bb), (bc), or (c)) and any example also includes the salts or tautomers or solvates thereof.

Salts

Many compounds of the formula (I) can exist in the form of salts, for example acid addition salts or, in certain cases salts of organic and inorganic bases such as carboxylate, sulfonate and phosphate salts. All such salts are within the scope of this invention, and references to compounds of the formula (I) include the salt forms of the compounds.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts (mono- or di-salts) may be formed with a wide variety of acids, both inorganic and organic. Examples of acid addition salts include mono- or di-salts formed with an acid selected from acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, methanesulfonic (mesylate), ethanesulfonic, naphthalenesulfonic, valeric, acetic, propanoic, butanoic, malonic, glucuronic and lactobionic acids. One particular salt is the hydrochloride salt.

In one embodiment the compound is the lactate salt (e.g. L-(+)-lactic acid salt) or hydrochloride salt.

If the compound is anionic, or has a functional group which may be anionic (e.g., —COOH may be —COO—), then a salt may be formed with an organic or inorganic base, generating a suitable cation. Examples of suitable inorganic cations include, but are not limited to, alkali metal ions such as Li$^+$, Na$^+$ and K$^+$, alkaline earth metal cations such as Ca$^{2+}$ and Mg$^{2+}$, and other cations such as Al$^{3+}$ or Zn$^+$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

Where the compounds of the formula (I) contain an amine function, these may form quaternary ammonium salts, for example by reaction with an alkylating agent according to methods well known to the skilled person. Such quaternary ammonium compounds are within the scope of formula (I).

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salt forms, which may be useful, for example, in the purification or separation of the compounds of the invention, also form part of the invention.

In one embodiment of the invention, there is provided a pharmaceutical composition comprising a solution (e.g. an aqueous solution) containing a compound of the formula (I) and sub-groups and examples thereof as described herein in the form of a salt in a concentration of greater than 10 mg/ml, typically greater than 15 mg/ml and typically greater than 20 mg/ml.

N-Oxides

Compounds of the formula (I) containing an amine function may also form N-oxides. A reference herein to a compound of the formula (I) that contains an amine function also includes the N-oxide.

Where a compound contains several amine functions one, or more than one, nitrogen atom may be oxidised to form an N-oxide. Particular examples of N-oxides are the N-oxides of a tertiary amine or a nitrogen atom of a nitrogen-containing heterocyclic group.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

In one embodiment of the invention, the compound is an N-oxide, for example from a nitrogen atom on the Het group, for example a pyridine N-oxide.

Geometric Isomers and Tautomers

Compounds of the formula (I) may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I).

For example, certain heteroaryl rings can exist in the two tautomeric forms such as A and B shown below. For simplicity, a formula may illustrate one form but the formula is to be taken as embracing both tautomeric forms.

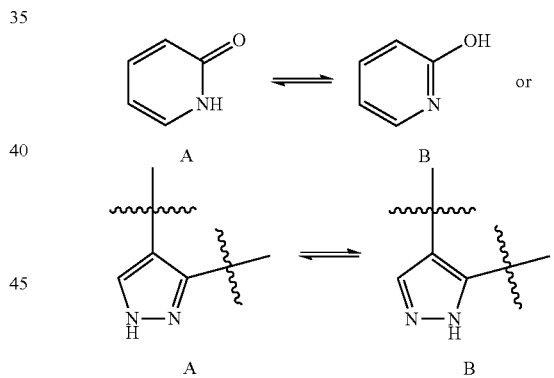

Other examples of tautomeric forms include, for example, keto-, enol-, and enolate-forms, as in, for example, the following tautomeric pairs: keto/enol (illustrated below), imine/enamine, amide/imino alcohol, amidine/enediamines, nitroso/oxime, thioketone/enethiol, and nitro/aci-nitro.

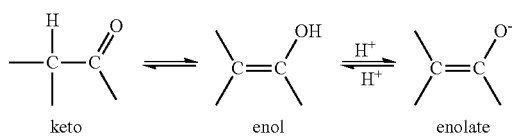

Stereoisomers

Unless otherwise mentioned or indicated, the chemical designation of compounds denotes the mixture of all possible stereochemically isomeric forms.

Stereocentres are illustrated in the usual fashion, using 'hashed' or 'solid' wedged lines. e.g.

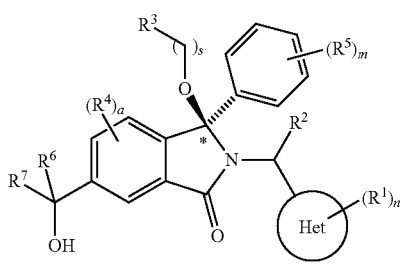

Where a compound is described as a mixture of two diastereoisomers/epimers, the configuration of the stereocentre is not specified and is represented by straight lines.

Where compounds of the formula (I) contain one or more chiral centres, and can exist in the form of two or more optical isomers, references to compounds of the formula (I) include all optical isomeric forms thereof (e.g. enantiomers, epimers and diastereoisomers), either as individual optical isomers, or mixtures (e.g. racemic or scalemic mixtures) or two or more optical isomers, unless the context requires otherwise.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog, *Angew. Chem. Int. Ed. Engl.*, 1966, 5, 385-415.

Optical isomers can be separated by a number of techniques including chiral chromatography (chromatography on a chiral support) and such techniques are well known to the person skilled in the art.

As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulfonic acid, separating the diastereoisomers by preferential crystallisation, and then dissociating the salts to give the individual enantiomer of the free base.

Additionally enantiomeric separation can be achieved by covalently linking a enantiomerically pure chiral auxiliary onto the compound and then performing diastereisomer separation using conventional methods such as chromatography. This is then followed by cleavage of the aforementioned covalent linkage to generate the appropriate enantiomerically pure product.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers.

Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer).

Compounds encompassing double bonds can have an E (entgegen) or Z (zusammen) stereochemistry at said double bond. Substituents on bivalent cyclic or (partially) saturated radicals may have either the cis- or trans-configuration. The terms cis and trans when used herein are in accordance with Chemical Abstracts nomenclature (J. Org. Chem. 1970, 35 (9), 2849-2867), and refer to the position of the substituents on a ring moiety.

Of special interest are those compounds of formula (I) which are stereochemically pure. When a compound of formula (I) is for instance specified as R, this means that the compound is substantially free of the S isomer. If a compound of formula (I) is for instance specified as E, this means that the compound is substantially free of the Z isomer. The terms cis, trans, R, S, E and Z are well known to a person skilled in the art.

Isotopic Variations

The present invention includes all pharmaceutically acceptable isotopically-labeled compounds of the invention, i.e. compounds of formula (I), wherein one or more atoms are replaced by atoms having the same atomic number, but an atomic mass or mass number different from the atomic mass or mass number usually found in nature.

Examples of isotopes suitable for inclusion in the compounds of the invention comprise isotopes of hydrogen, such as $^{2}$H (D) and $^{3}$H (T), carbon, such as $^{11}$C, $^{13}$C and $^{14}$C, chlorine, such as $^{36}$Cl, fluorine, such as $^{18}$F, iodine, such as $^{123}$I, $^{125}$I and $^{131}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

Certain isotopically-labelled compounds of formula (I), for example, those incorporating a radioactive isotope, are useful in drug and/or substrate tissue distribution studies. The compounds of formula (I) can also have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^{3}$H (T), and carbon-14, i.e. $^{14}$C, are particularly useful for this purpose in view of their ease of incorporation and ready means of detection.

Substitution with heavier isotopes such as deuterium, i.e. $^{2}$H (D), may afford certain therapeutic advantages resulting from greater metabolic stability, for example, increased in vivo half-life or reduced dosage requirements, and hence may be used in some circumstances.

In particular, every reference to hydrogen in the application should be constructed to cover $^{1}$H and $^{2}$H, whether hydrogen is defined explicitly, or hydrogen is present implicitly to satisfy the relevant atom's (in particular carbon's) valency.

Substitution with positron emitting isotopes, such as $^{11}$C, $^{18}$F, $^{15}$O and $^{13}$N, can be useful in Positron Emission Topography (PET) studies for examining target occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Esters

Esters such as carboxylic acid esters, acyloxy esters and phosphate esters of the compounds of formula (I) bearing a carboxylic acid group or a hydroxyl group are also embraced by Formula (I). Examples of esters are compounds containing the group —C(=O)OR, wherein R is an ester substituent, for example, a $C_{1-7}$ alkyl group, a $C_{3-12}$ heterocyclyl group, or a $C_{5-12}$ aryl group, typically a $C_{1-6}$ alkyl group. Particular examples of ester groups include, but are not limited to, —C(=O)OCH$_3$, —C(=O)OCH$_2$CH$_3$, —C(=O)OC(CH$_3$)$_3$, and —C(=O)OPh. Examples of acyloxy (reverse ester) groups are represented by —OC(=O)R, wherein R is an acyloxy substituent, for example, a $C_{1-6}$ alkyl group, a $C_{3-12}$ heterocyclyl group, or a $C_{5-12}$ aryl group, typically a $C_{1-6}$ alkyl group. Particular examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph. Examples of phosphate esters are those derived from phosphoric acid.

In one embodiment of the invention, formula (I) includes within its scope esters of compounds of the formula (I) bearing a carboxylic acid group or a hydroxyl group. In another embodiment of the invention, formula (I) does not include within its scope esters of compounds of the formula (I) bearing a carboxylic acid group or a hydroxyl group.

Solvates and Crystalline Forms

Also encompassed by formula (I) are any polymorphic forms of the compounds, and solvates such as hydrates, alcoholates and the like.

The compounds of the invention may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include compounds of the invention in combination with water, isopropanol, ethanol, methanol, DMSO, ethyl acetate, acetic acid or ethanolamine and the like. The compounds of the invention may exert their biological effects whilst they are in solution.

Solvates are well known in pharmaceutical chemistry. They can be important to the processes for the preparation of a substance (e.g. in relation to their purification, the storage of the substance (e.g. its stability) and the ease of handling of the substance and are often formed as part of the isolation or purification stages of a chemical synthesis. A person skilled in the art can determine by means of standard and long used techniques whether a hydrate or other solvate has formed by the isolation conditions or purification conditions used to prepare a given compound. Examples of such techniques include thermogravimetric analysis (TGA), differential scanning calorimetry (DSC), X-ray crystallography (e.g. single crystal X-ray crystallography or X-ray powder diffraction) and Solid State NMR (SS-NMR, also known as Magic Angle Spinning NMR or MAS-NMR). Such techniques are as much a part of the standard analytical toolkit of the skilled chemist as NMR, IR, HPLC and MS.

Alternatively the skilled person can deliberately form a solvate using crystallisation conditions that include an amount of the solvent required for the particular solvate. Thereafter the standard methods described herein, can be used to establish whether solvates had formed.

Furthermore, the compounds of the present invention may have one or more polymorph or amorphous crystalline forms and as such are intended to be included in the scope of the invention.

Complexes

Formula (I) also includes within its scope complexes (e.g. inclusion complexes or clathrates with compounds such as cyclodextrins, or complexes with metals) of the compounds. Inclusion complexes, clathrates and metal complexes can be formed by means of methods well known to the skilled person.

Prodrugs

Also encompassed by formula (I) are any pro-drugs of the compounds of the formula (I). By "prodrugs" is meant for example any compound that is converted in vivo into a biologically active compound of the formula (I).

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is:

$C_{1-7}$alkyl (e.g., -Me, -Et, -nPr, -iPr, -nBu, -sBu, -iBu, -tBu);

$C_{1-7}$aminoalkyl (e.g., aminoethyl; 2-(N,N-diethylamino) ethyl; 2-(4-morpholino)ethyl); and acyloxy-$C_{1-7}$alkyl (e.g., acyloxymethyl; acyloxyethyl; pivaloyloxymethyl; acetoxymethyl; 1-acetoxyethyl; 1-(1-methoxy-1-methyl) ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-oxanyloxy) carbonyloxymethyl; 1-(4-oxanyloxy)carbonyloxyethyl; (4-oxanyl)carbonyloxymethyl; and 1-(4-tetrahydropyranyl)carbonyloxyethyl).

Also, some prodrugs are activated enzymatically to yield the active compound, or a compound which, upon further chemical reaction, yields the active compound (for example, as in antigen-directed enzyme pro-drug therapy (ADEPT), gene-directed enzyme pro-drug therapy (GDEPT), and ligand-directed enzyme pro-drug therapy (LIDEPT), etc.). For example, the prodrug may be a sugar derivative or other glycoside conjugate, or may be an amino acid ester derivative. In one embodiment formula (I) does not include pro-drugs of the compounds of the formula (I) within its scope.

Methods for the Preparation of Compounds of Formula (I)

In this section, as in all other sections of this application unless the context indicates otherwise, references to formula (I) also include all other subformula (e.g. formulae I(a), I(a'), I(b), I(c), I(d), I(e), I(t), I(g), I(g'), I(h), I(i), I(j), I(k), I(L), I(m), I(m'), I(n), I(o), I(o'), I(o"), I(p), I(p'), I(q), I(q'), I(q"), I(q'''), I(q''''), I(r), I(s), I(t), I(u), I(v), I(v'), I(w), I(x), I(x'), I(y), (II), (IIa), (IIb), (IIIa), (IIIb), (Iva), (IVb), (V), (VI), (VIa), (VII), (VIIa), (VIIb), (VIIc), (VIId), (VIIId'), (VIIe), (VIIe'), (a), (b), (ba), (bb), (bc), or (c)) and examples thereof as defined herein, unless the context indicates otherwise.

Compounds of the formula (I) can be prepared in accordance with synthetic methods well known to the skilled person.

According to a further aspect of the invention there is provided a process for preparing a compound of formula (I), or a tautomer, N-oxide, pharmaceutically acceptable salt, or solvate thereof which comprises:

(a) reacting a compound of formula (XXXIII) with an organometallic reagent of the formula $R^7M$ (where M is a metal), for example a Grignard reagent of the formula $R^7MgBr$:

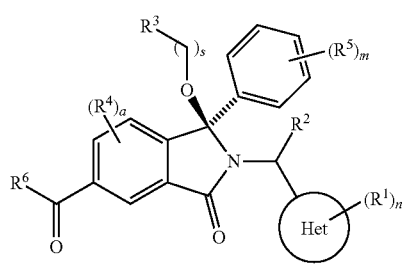

(XXXIII)

wherein Het, $R^1$, $R^2$, $R^3$, $R^4$, $R^5$, $R^6$, a, s m and n are as defined herein;

(b) interconversion of a compound of formula (I) or protected derivative thereof to a further compound of formula (I) or protected derivative thereof; and/or (c) deprotection of a protected derivative of a compound of formula (I); and/or (d) providing a compound of formula (I) and forming a pharmaceutically acceptable salt of the compound.

The required intermediates are either commercially available, known in the literature, prepared by methods analogous to those in the literature or prepared by methods analogous to those described in the example experimental procedures below. Other compounds may be prepared by functional group interconversion of the groups using methods well known in the art.

The general synthetic route for the preparation of compounds of formula XV, a key intermediate is set out in the Schemes below.

Scheme 1

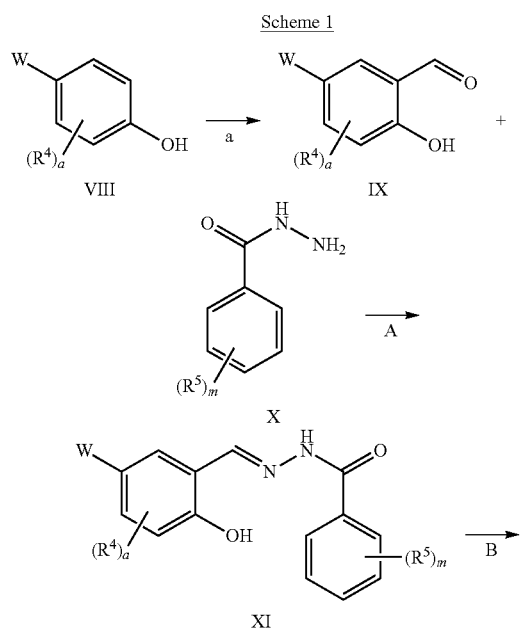

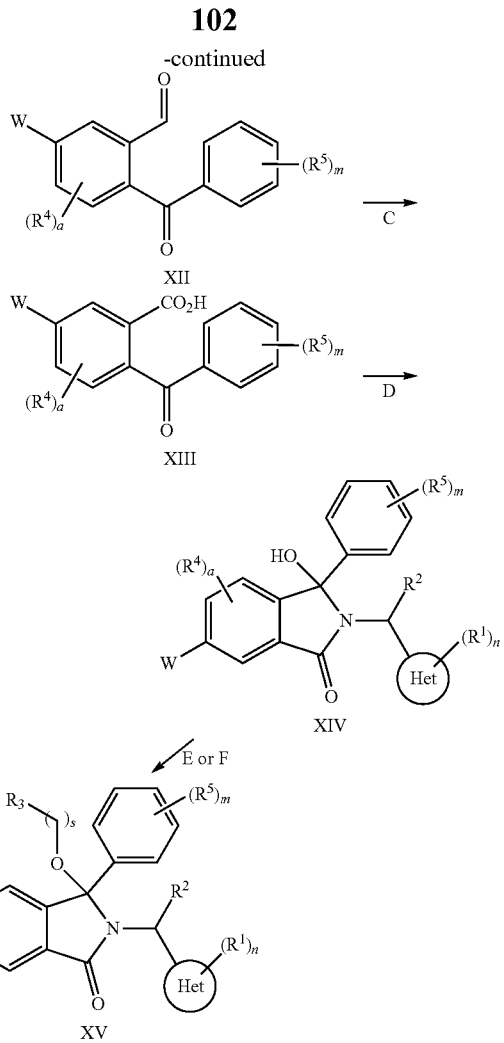

Example reagents and conditions for Scheme 1: a) NaOH, H$_2$O, CHCl$_3$, 85° C.; A) AcOH, rt; B) Pb(OAc)$_4$, THF, 0° C.; C) NaClO$_2$, H$_2$NSO$_3$H, CH$_3$CN, H$_2$O, rt; D) i) SOCl$_2$, DMF, THF, ii) amine, i-Pr$_2$EtN, THF; E) i) SOCl$_2$, DMF, THF, ii) $R^3(CH_2)_S$—OH, K$_2$CO$_3$, THF; F) InBr$_3$, $R^3(CH_2)_S$—OH, DCE, 85° C.; separation and isolation of the 3(R) enantiomer can be achieved at this stage by chiral HPLC.

In Scheme 1, $R^1$, $R^2$, $R^3$, $R^4$ and $R^5$ are as described herein and W represents a leaving group, such as for example halo, e.g. bromo, or a carbonyl group, such as for example acetyl.

N-aroylhydrazone (XI) can be prepared by condensing benzaldehyde (IX) with benzhydrazide (X). Reaction with Pb(OAc)$_4$ yields aldehyde (XII), from which a Pinnick oxidation provides acid (XIII). The appropriate benzylamine can then be used to provide 3-hydroxyisoindolinone (XIV), and the $R^3$-containing side chain added using thionyl chloride or InBr$_3$ and the appropriate alcohol.

Intermediates of formula (XV) can be used as a starting point for the synthesis of compounds of the present invention having varying functionality in the $R^3$, $R^6$ and $R^7$ positions of Formula I.

Scheme 2 below sets out example procedures for introducing various $R^6$ moieties starting from intermediates of formula (XVI) (which is the compound of formula (XV) wherein W is Br).

Scheme 2

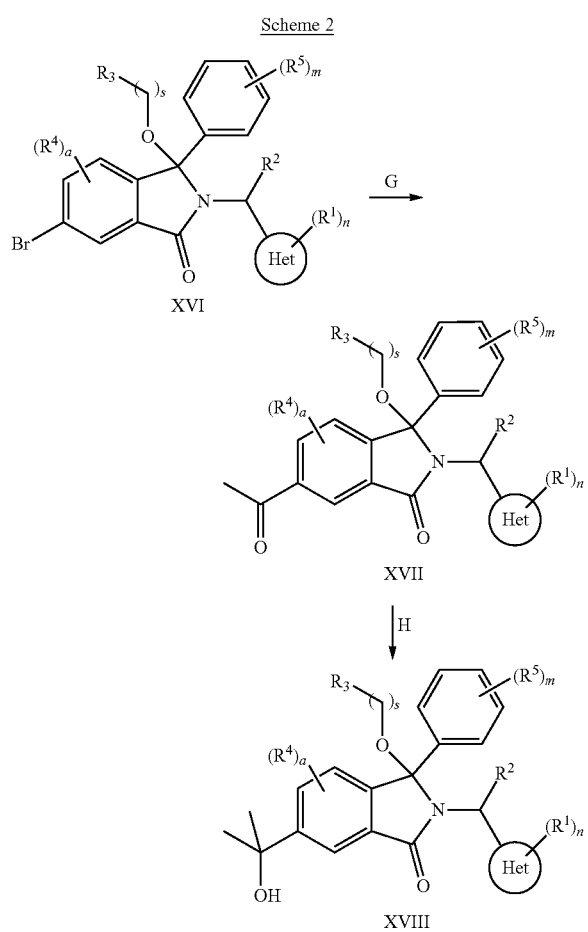

Example reagents and conditions for Scheme 2: G) (i) toluene, 1,4-dioxane, LiCl, tributyl(1-ethoxyvinyl)tin, Pd(PPh$_3$)$_4$, (ii) HCl, H$_2$O/THF. H) MeMgCl, in the presence of ZnCl$_2$ and/or LaCl$_3$-2LiCl, THF. Separation and isolation of the 3(R) enantiomer can be achieved at any stage by chiral HPLC.

Bromide (XVI) can be converted to methyl ketone (XVII) for example using 1,4-dioxane, LiCl, tributyl(1-ethoxyvinyl)tin, Pd(PPh$_3$)$_4$, and further converted to the alcohol XVIII by reaction with a methyl Grignard reagent.

Compounds wherein R$^6$ and R$^7$ are hydrogen, can also be prepared according to the general synthetic Scheme 3. Where R$^3$ contains a hydroxyl group, this can be protected during the synthesis by using standard protecting groups (e.g. TBDMS, TBDPS). Deprotection can be performed using standard conditions (e.g. TBAF)

Scheme 3

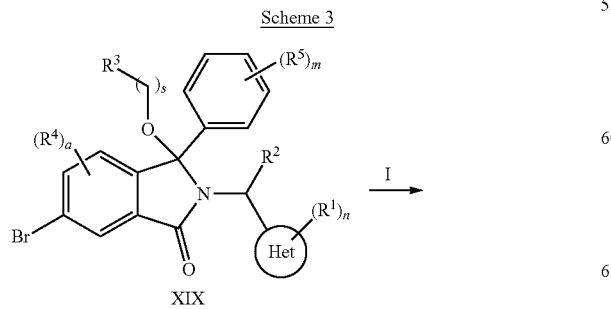

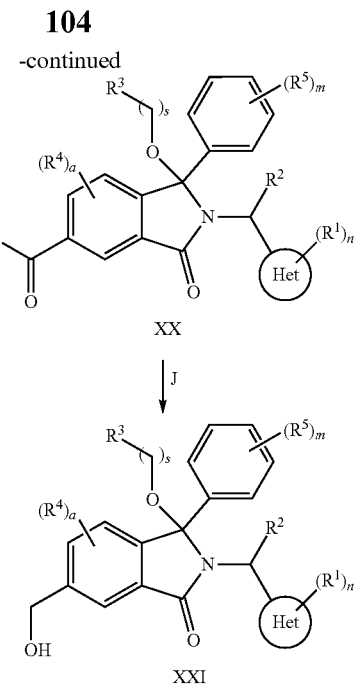

Example reagents and conditions for Scheme 3: I) HCOOLi.H$_2$O, Ac$_2$O, Et$_3$N, 4,5-Bis(diphenylphosphino)-9,9-dimethylxanthene, Pd(OAc)$_2$, DMF; J) LiBH$_4$, THF. Separation and isolation of the 3(R) enantiomer can be achieved at any stage by chiral HPLC.

Compounds of formula (XVIII), first shown in Scheme 2, wherein R$^6$ and R$^7$ are methyl, can also be prepared according to the general synthetic Scheme 4.

In Scheme 4, an intermediate of formula (XXIV) is prepared from an intermediate of formula (XXIII) according to procedure F (InBr$_3$ with R$^3$(CH$_2$)$_s$—OH). The intermediate of formula (XXIV) is then converted to the compound of formula (XVIII) by a Grignard reaction.

Scheme 4

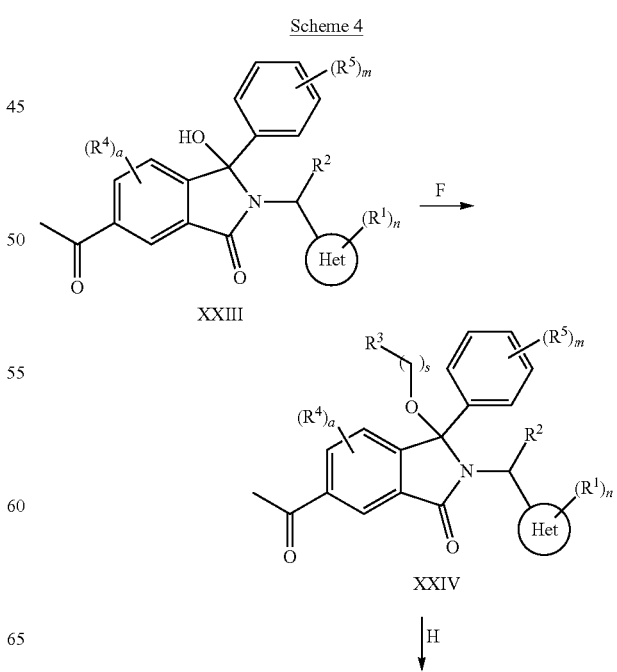

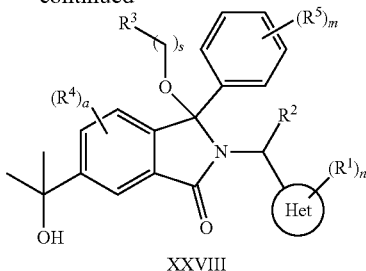

XXVIII

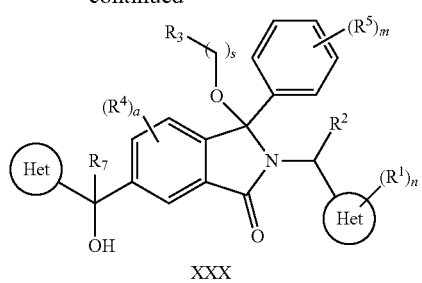

XXX

Example reagents and conditions: F) InBr$_3$, R$^3$(CH$_2$)$_s$—OH, DCE, 85° C.; H) MeMgCl, ZnCl$_2$, THF, 0° C. Separation and isolation of the 3(R) enantiomer can be achieved at stage F or H by chiral HPLC Compounds of general formula XXX can also be prepared according to Schemes 5 and 6.

Example reagents and conditions: L) nBuLi, Het-CHO, THF, −78° C.; M) MnO$_2$, MeCN, or I$_2$, KI, K$_2$CO$_3$; D) i) SOCl$_2$, DMF, THF, ii) amine, i-Pr$_2$EtN, THF or HATU, amine, DIPEA, DMF; E) i) SOCl$_2$, DMF, THF, ii) R$^3$(CH$_2$)$_s$—OH, K$_2$CO$_3$, THF; F) InBr$_3$, R$^3$(CH$_2$)$_s$—OH, DCE, 85° C.; N) R$_7$MgX in the presence of ZnCl$_2$ and/or LaCl$_3$-2LiCl, THF or Al(R$_7$)$_3$, THF or EtLi, ZnEt$_2$, THF. Separation of enantiomers and/or diastereoisomers at Stages E, F and N can be achieved by either chiral and/or achiral HPLC.

Intermediate XIII (where W is Br) is reacted with nBuLi and an appropriate aldehyde to provide alcohol XXVI which is oxidised to the corresponding ketone (XXVII) either using MnO$_2$ or I$_2$/KI. Intermediate XXVII is then converted into the 3-hydroxyisoindolinone XXIX following procedures D and E (of F) described above.

Intermediates of formula XXIX can be used as a starting point for the synthesis of compounds of the present invention having varying functionality in the R$^7$ position of Formula I.

Alternatively the R$^7$ substituents are introduced earlier in the synthesis as shown in Scheme 6. Intermediates of formula XXVII can react with organometallic reagents to provide tertiary alcohol (XXXI) which is then converted to final compounds of Formula I following procedures D and E (or F) (Scheme 6).

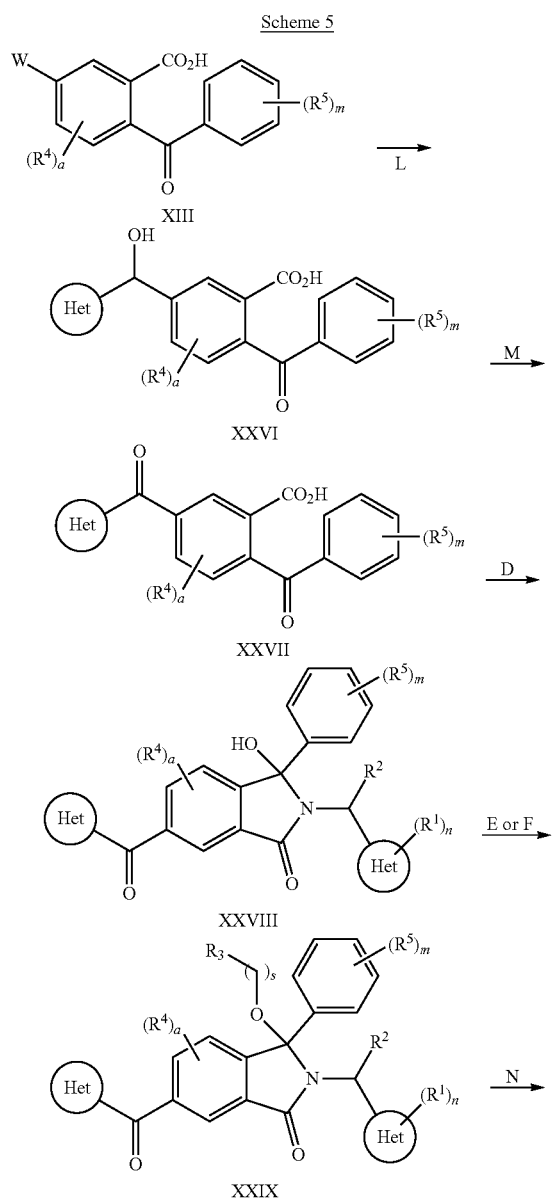

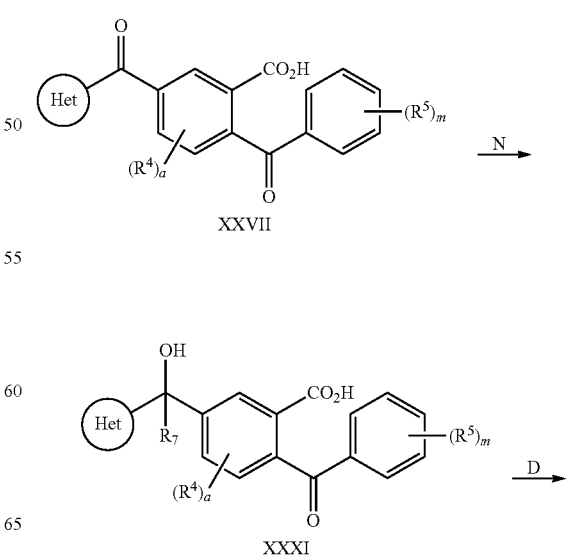

-continued

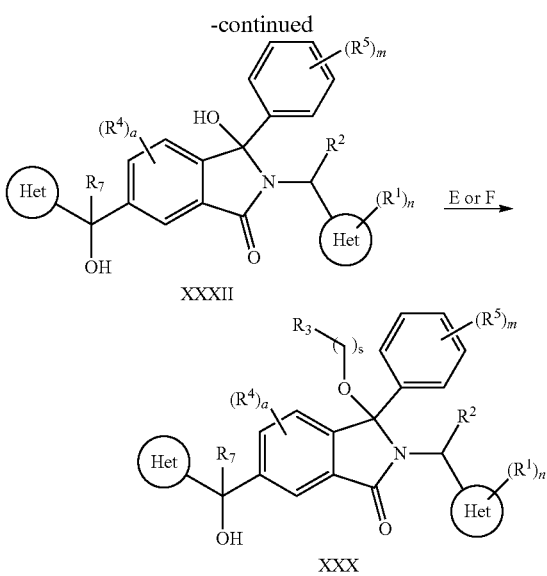

Example reagents and conditions: N) R₇MgX in the presence of ZnCl₂ and/or LaCl₃·2LiCl, THF or Al(R₇)₃, THF or EtLi, ZnEt₂, THF; D) i) SOCl₂, DMF, THF, ii) amine, i-Pr₂EtN, THF or HATU, amine, DIPEA, DMF; E) i) SOCl₂, DMF, THF, ii) R³(CH₂)$_S$—OH, K₂CO₃, THF; F) InBr₃, R³(CH₂)$_S$—OH, DCE, 85° C. Separation of enantiomers and/or diastereoisomers at Stages N and E/F can be achieved by either chiral and/or achiral HPLC.

Compounds of formula XVI (first shown in Scheme 2) can also be used to make compounds of formula XXIX using methods outlined in Scheme 7. In this case, XVI can be converted into a suitable boronate using, for example, Miyaura conditions. The boronate is then treated with an appropriate heterocyclic iodide (or heterocyclic bromide) in the presence of carbon monoxide, a suitable catalyst (such as Pd(dppf)Cl₂.) and a solvent (such as toluene or ansole).

Alternatively, compounds of formula XVI can be treated with an appropriate heterocyclic stannane in the presence of carbon monoxide, a suitable catalyst [such as Pd(dppf)Cl₂] and a solvent (such as DMF) to give compounds of formula XXIX (Scheme 7). Separation and isolation of the 3(R) intermediate can be achieved at any stage using chiral HPLC. Compounds of formula XXIX can then be progressed to compounds of formula XXX (as shown in Scheme 5).

Scheme 7

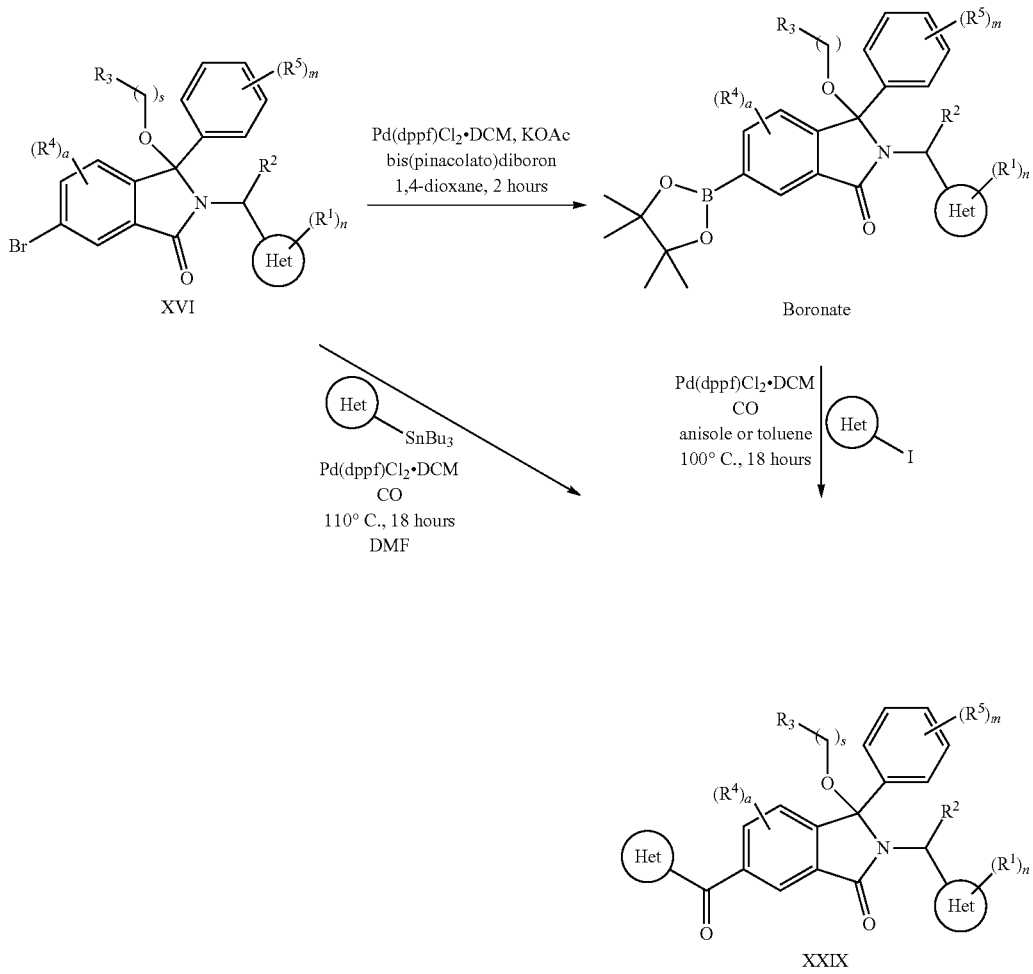

Compounds of formula XVI can also be used to make compounds of formula XXIX using methods outlined in Scheme 8. In this case, compounds of formula XVI can be used to make a Weinreb amide derivative using N,O-dimethylhydroxylamine hydrochloride in the presence of carbon monoxide and a suitable palladium catalyst (e.g. Xantphos G3 catalyst). The Weinreb amide can then be reacted with an appropriate metallated heterocycle (e.g. the product of 4-bromo-1-methyl-1H-pyrazole and nBuLi in THF) to give compounds of formula XXIX (Scheme 8). Separation and isolation of the 3(R) intermediate can be achieved at any stage using chiral HPLC. Compounds of formula XXIX can then be progressed to compounds of formula XXX (as shown in Scheme 5).

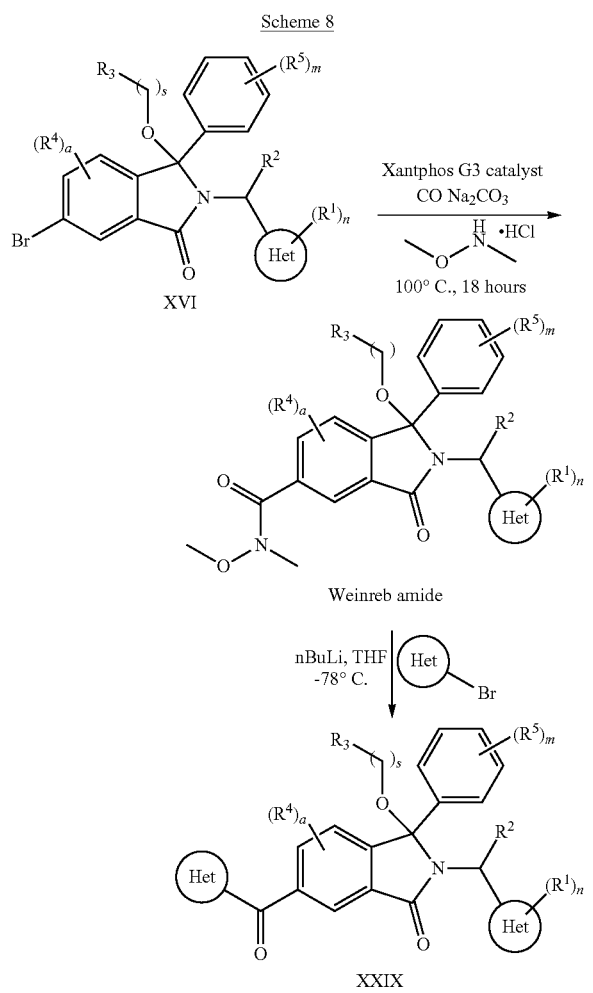

Scheme 8

It will be appreciated that certain compounds can exist in different diastereomeric and/or enantiomeric forms and that processes for their preparation may make use of enantiomerically pure synthetic precursors.

Alternatively racemic precursors may be used and the mixtures of diastereoisomers generated in these process may be separated by methods well known to the person skilled in the art, for example using non-chiral or chiral preparative chromatography or resolution using diastereomeric derivatives: for example crystallisation of a salt formed with an enantiomerically pure acid such as L-tartaric acid (or enantiomerically pure base such as (1R)-1-phenylethan-1-amine); or enantiomer separation of a diastereomeric derivative formed by covalently linking a enantiomerically pure chiral auxiliary onto the compound, followed by separation using conventional methods such as chiral or non-chiral chromatography. The aforementioned covalent linkage is then cleaved to generate the appropriate enantiomerically pure product.

A wide range of well known functional group interconversions are known by a person skilled in the art for converting a precursor compound to a compound of formula I and are described in *Advanced Organic Chemistry* by Jerry March, $4^{th}$ Edition, John Wiley & Sons, 1992. For example possible metal catalysed functionalisations such as using organo-tin reagents (the Stille reaction), Grignard reagents and reactions with nitrogen nucleophiles are described in 'Palladium Reagents and Catalysts' [Jiro Tsuji, Wiley, ISBN 0-470-85032-9] and Handbook of OrganoPalladium Chemistry for Organic Synthesis [Volume 1, Edited by Ei-ichi Negishi, Wiley, ISBN 0-471-31506-0].

If appropriate, the reactions previously described below are followed or preceded by one or more reactions known to the skilled of the art and are performed in an appropriate order to achieve the requisite substitutions defined above to afford other compounds of formula (I). Non-limiting examples of such reactions whose conditions can be found in the literature include:
 protection of reactive functions,
 deprotection of reactive functions,
 halogenation,
 dehalogenation,
 dealkylation,
 alkylation or arylation of amine, aniline, alcohol and phenol,
 Mitsunobu reaction on hydroxyl groups,
 cycloaddition reactions on appropriate groups,
 reduction of nitro, esters, cyano, aldehydes,
 transition metal-catalyzed coupling reactions,
 acylation,
 sulfonylation/introduction of sulfonyl groups,
 saponification/hydrolysis of ester groups,
 amidification or transesterification of ester groups,
 esterification or amidification of carboxylic groups,
 halogen exchange,
 nucleophilic substitution with amine, thiol or alcohol,
 reductive amination,
 oxime formation on carbonyl and hydroxylamine groups,
 S-oxidation,
 N-oxidation,
 salification.

It will be appreciated that certain compounds e.g. compounds of formulae (I), I(a), I(a'), I(b), I(c), I(d), I(e), I(f), I(g), I(g'), I(h), I(i), I(j), I(k), I(L), I(m), I(m'), I(n), I(o), I(o'), I(o"), I(p), I(p'), I(q), I(q'), I(q"), I(q'''), I(q''''), I(r), I(s), I(t), I(u), I(v), I(v'), I(w), I(x), I(x'), I(y), (II), (IIa), (IIb), (IIIa), (IIIb), (Iva), (IVb), (V), (VI), (VIa), (VII), (VIIa), (VIIb), (VIIc), (VIId), (VIIId'), (VIIe), (VIIe'), (a), (b), (ba), (bb), (bc), or (c) can exist in different diastereomeric and/or enantiomeric forms and that processes for their preparation may make use of enantiomerically pure synthetic precursors.

Alternatively racemic precursors may be used and the mixtures of diastereoisomers generated in these process may be separated by methods well known to the person skilled in the art, for example using non-chiral or chiral preparative chromatography or resolution using diastereomeric derivatives: for example crystallisation of a salt formed with an enantiomerically pure acid such as L-tartaric acid; or enantiomer separation of a diastereomeric derivative formed by covalently linking a enantiomerically pure chiral auxiliary onto the compound, followed by separation using conventional methods such as chiral chromatography. The aforementioned covalent linkage is then cleaved to generate the appropriate enantiomerically pure product.

Certain of the required intermediates, are either commercially available, known in the literature, prepared by methods analogous to those in the literature or prepared by methods analogous to those described in the example experimental procedures below. Other compounds may be prepared by functional group interconversion using methods well known in the art.

In a further embodiment the invention provides a novel intermediate. In one embodiment the invention provides a novel intermediate of (VII), (VIII), (IX), (X), (XI), (XII), (XIII), (XIV), (XV), (XVI), (XVII), (XIX), (XX), (XXI), (XXIII) and (XXIV).

Protecting Groups

In many of the reactions described herein, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Green and P. Wuts; 3rd Edition; John Wiley and Sons, 1999).

In particular the compound may be synthesised in protected forms and the protecting groups removed to generate a compound of formula (I).

A hydroxy group may be protected, for example, as an ether (—OR) or an ester (—OC(=O)R), for example, as: a t-butyl ether; a tetrahydropyranyl (THP) ether; a benzyl, benzhydryl (diphenylmethyl), or trityl (triphenylmethyl) ether; a trimethylsilyl or t-butyldimethylsilyl ether; or an acetyl ester (—OC(=O)CH$_3$).

An aldehyde or ketone group may be protected, for example, as an acetal (R—CH(OR)$_2$) or ketal (R$_2$C(OR)$_2$), respectively, in which the carbonyl group (>C=O) is treated with, for example, a primary alcohol. The aldehyde or ketone group is readily regenerated by hydrolysis using a large excess of water in the presence of acid.

An amine group may be protected, for example, as an amide (—NRCO—R) or a carbamate (—NRCO—OR), for example, as: a methyl amide (—NHCO—CH$_3$); a benzyl carbamate (—NHCO—OCH$_2$C$_6$H$_5$, —NH-Cbz or NH—Z); as a t-butyl carbamate (—NHCO—OC(CH$_3$)$_3$, —NH-Boc); a 2-biphenyl-2-propyl carbamate (—NHCO—OC(CH$_3$)$_2$C$_6$H$_4$C$_6$H$_5$, —NH-Bpoc), as a 9-fluorenylmethyl carbamate (—NH-Fmoc), as a 6-nitroveratryl carbamate (—NH-Nvoc), as a 2-trimethylsilylethyl carbamate (—NH-Teoc), as a 2,2,2-trichloroethyl carbamate (—NH-Troc), as an allyl carbamate (—NH-Alloc), or as a 2(-phenylsulfonyl)ethyl carbamate (—NH-Psec).

Other protecting groups for amines, such as cyclic amines and heterocyclic N—H groups, include toluenesulfonyl (tosyl) and methanesulfonyl (mesyl) groups, benzyl groups such as a para-methoxybenzyl (PMB) group and tetrahydropyranyl (THP) groups.

A carboxylic acid group may be protected as an ester for example, as: an C$_{1-7}$ alkyl ester (e.g., a methyl ester; a t-butyl ester); a C$_{1-7}$ haloalkyl ester (e.g., a C$_{1-7}$ trihaloalkyl ester); a triC$_{1-7}$ alkylsilyl-C$_{1-7}$alkyl ester; or a C$_{5-20}$ aryl-C$_{1-7}$ alkyl ester (e.g., a benzyl ester; a nitrobenzyl ester; para-methoxybenzyl ester. A thiol group may be protected, for example, as a thioether (—SR), for example, as: a benzyl thioether; an acetamidomethyl ether (—S—CH$_2$NHC(=O)CH$_3$).

Isolation and Purification of the Compounds of the Invention

The compounds of the invention can be isolated and purified according to standard techniques well known to the person skilled in the art and examples of such methods include chromatographic techniques such as column chromatography (e.g. flash chromatography) and HPLC. One technique of particular usefulness in purifying the compounds is preparative liquid chromatography using mass spectrometry as a means of detecting the purified compounds emerging from the chromatography column.

Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.;* 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.;* 2003; 5(3); 322-9. An example of such a system for purifying compounds via preparative LC-MS is described below in the Examples section of this application (under the heading "Mass Directed Purification LC-MS System").

Methods of recrystallisation of compounds of formula (I) and salt thereof can be carried out by methods well known to the skilled person—see for example (P. Heinrich Stahl (Editor), Camille G. Wermuth (Editor), ISBN: 3-90639-026-8, Handbook of Pharmaceutical Salts: Properties, Selection, and Use, Chapter 8, Publisher Wiley-VCH). Products obtained from an organic reaction are seldom pure when isolated directly from the reaction mixture. If the compound (or a salt thereof) is solid, it may be purified and/or crystallized by recrystallisation from a suitable solvent. A good recrystallisation solvent should dissolve a moderate quantity of the substance to be purified at elevated temperatures but only a small quantity of the substance at lower temperature. It should dissolve impurities readily at low temperatures or not at all. Finally, the solvent should be readily removed from the purified product. This usually means that it has a relatively low boiling point and a person skilled in the art will know recrystallising solvents for a particular substance, or if that information is not available, test several solvents. To get a good yield of purified material, the minimum amount of hot solvent to dissolve all the impure material is used. In practice, 3-5% more solvent than necessary is used so the solution is not saturated. If the impure compound contains an impurity which is insoluble in the solvent it may then be removed by filtration and then allowing the solution to crystallize. In addition, if the impure compound contains traces of coloured material that are not native to the compound, it may be removed by adding a small amount of decolorizing agent e.g. activating charcoal to the hot solution, filtering it and then allowing it to crystallize. Usually crystallization spontaneously occurs upon cooling the solution. If it is not, crystallization may be induced by cooling the solution below room temperature or by adding a single crystal of pure material (a seed crystal). Recrystallisation can also be carried out and/or the yield optimized by the use of an anti-solvent or co-solvent. In this case, the compound is dissolved in a suitable solvent at elevated temperature, filtered and then an additional solvent in which the required compound has low solubility is added to aid crystallization. The crystals are then typically isolated using vacuum filtration, washed and then dried, for example, in an oven or via desiccation.

Other examples of methods for purification include sublimation, which includes an heating step under vacuum for example using a cold finger, and crystallization from melt (Crystallization Technology Handbook 2nd Edition, edited by A. Mersmann, 2001).

Biological Effects

It is envisaged that the compound of the invention will be useful in medicine or therapy. The compounds of the invention, subgroups and examples thereof, have been shown to inhibit the interaction of p53 with MDM2. Such inhibition leads to cell proliferative arrest and apoptosis, which may be useful in preventing or treating disease states or conditions described herein, for example the diseases and conditions discussed below and the diseases and conditions described in the "Background of the Invention" section above in which p53 and MDM2 play a role. Thus, for example, it is envisaged that the compounds of the invention may be useful in alleviating or reducing the incidence of cancer.

The compounds of the present invention may be useful for the treatment of the adult population. The compounds of the present invention may be useful for the treatment of the pediatric population.

The compounds of the present invention have been shown to be good inhibitors of the formation of MDM2-p53 complex. The antagonist compounds of formula (I) are capable of binding to MDM2 and exhibiting potency for MDM2. The efficacies of the compounds of the present invention have been determined against MDM2/p53 using the assay protocol described herein and other methods known in the art. More particularly, the compounds of the formula (I) and sub-groups thereof have affinity for MDM2/p53.

Certain compounds of the invention are those having $IC_{50}$ values of less than 0.1 µM in particular less than 0.01 or 0.001 µM.

MDM2/p53 function has been implicated in many diseases due to its role in a variety of process for example vascular remodelling and antiangiogenic processes and regulation of metabolic pathways, as well as in oncogenesis. As a consequence of their affinity for MDM2 it is anticipated that the compounds may prove useful in treating or preventing a range of diseases or conditions including autoimmune conditions; diabetes mellitus; chronic inflammatory diseases, for example lupus nephritis, systemic lupus erythematosus (SLE), autoimmune mediated glomerulonephritis, rheumatoid arthritis, psoriasis, inflammatory bowel disease, autoimmune diabetes mellitus, Eczema hypersensitivity reactions, asthma, COPD, rhinitis, and upper respiratory tract disease; hyperkeratotic diseases such as autosomal recessive congenital ichthyosis (ARCI); kidney diseases including glomerular disorders, chronic kidney disease (CKD) renal inflammation, podocyte loss, glomerulosclerosis, proteinuria, and progressive kidney disease; cardiovascular diseases for example cardiac hypertrophy, restenosis, arrhythmia, atherosclerosis; ischemic injury associated myocardial infarctions, vascular injury, stroke and reperfusion injury; vascular proliferative diseases; ocular diseases such as age-related macular degeneration in particular wet form of age-related macular degeneration, ischemic proliferative retinopathies such as retinopathy of prematurity (ROP) and diabetic retinopathy, and hemangioma.

As a consequence of their affinity for MDM2 it is anticipated that the compounds may prove useful in treating or preventing proliferative disorders such as cancers.

Examples of cancers (and their benign counterparts) which may be treated (or inhibited) include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, bowel, colorectal, rectum and anus), liver (hepatocellular carcinoma), gall bladder and biliary system, exocrine pancreas, kidney (for example renal cell carcinoma), lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, testes, cervix, myometrium, endometrium, thyroid (for example thyroid follicular carcinoma), brain, adrenal, prostate, skin and adnexae (for example melanoma, basal cell carcinoma, squamous cell carcinoma, keratoacanthoma, dysplastic naevus); haematological malignancies (i.e. leukemias, lymphomas) and premalignant haematological disorders and disorders of borderline malignancy including haematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenous leukemia [AML], chronic myelogenous leukemia [CML], chronic myelomonocytic leukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocytic leukemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcoma protuberans; tumours of the central or peripheral nervous system (for example astrocytomas (e.g. gliomas), neuromas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example Xeroderma Pigmentosum).

Growth of cells is a closely controlled function. Cancer, a condition of abnormal cell growth, results when cells replicate in an uncontrolled manner (increasing in number), uncontrollably grow (getting larger) and/or experience reduced cell death by apoptosis (programmed cell death), necrosis, or annoikis. In one embodiment abnormal cell growth is selected from uncontrolled cell proliferation, excessive cell growth or reduced programmed cell death. In particular, the condition or disease of abnormal cell growth is a cancer.

Thus, in the pharmaceutical compositions, uses or methods of this invention for treating a disease or condition comprising abnormal cell growth (i.e. uncontrolled and/or rapid cell growth), the disease or condition comprising abnormal cell growth in one embodiment is a cancer.

Many diseases are characterized by persistent and unregulated angiogenesis. Chronic proliferative diseases are often accompanied by profound angiogenesis, which can contribute to or maintain an inflammatory and/or proliferative state, or which leads to tissue destruction through the invasive proliferation of blood vessels. Tumour growth and metastasis have been found to be angiogenesis-dependent. Compounds of the invention may therefore be useful in preventing and disrupting initiation of tumour angiogenesis.

Angiogenesis is generally used to describe the development of new or replacement blood vessels, or neovascularisation. It is a necessary and physiological normal process by which vasculature is established in the embryo. Angiogenesis does not occur, in general, in most normal adult tissues, exceptions being sites of ovulation, menses and wound healing. Many diseases, however, are characterized by persistent and unregulated angiogenesis. For instance, in arthritis, new capillary blood vessels invade the joint and destroy cartilage. In diabetes (and in many different eye diseases), new vessels invade the macula or retina or other ocular structures, and may cause blindness. The process of atherosclerosis has been linked to angiogenesis. Tumor growth and metastasis have been found to be angiogenesis-dependent. The compounds may be beneficial in the treatment of diseases such as cancer and metastasis, ocular diseases, arthritis and hemangioma.

Therefore, the compounds of the invention may be useful in the treatment of metastasis and metastatic cancers. Metastasis or metastatic disease is the spread of a disease from one organ or part to another non-adjacent organ or part. The cancers which can be treated by the compounds of the invention include primary tumours (i.e. cancer cells at the originating site), local invasion (cancer cells which penetrate and infiltrate surrounding normal tissues in the local area), and metastatic (or secondary) tumours ie. tumours that have formed from malignant cells which have circulated through the bloodstream (haematogenous spread) or via lymphatics or across body cavities (trans-coelomic) to other sites and tissues in the body. In particular, the compounds of the invention may be useful in the treatment of metastasis and metastatic cancers.

In one embodiment the haematological malignancies is a leukaemia. In another embodiment the haematological malignancies is a lymphoma. In one embodiment the cancer is AML. In another embodiment the cancer is CLL.

In one embodiment the compound of the invention is for use in the prophylaxis or treatment of leukemia, such as acute or chronic leukaemia, in particular acute myeloid leukaemia (AML), acute lymphocytic leukaemia (ALL), chronic lymphocytic leukaemia (CLL), or chronic myeloid leukemia (CML). In one embodiment the compound of the invention is for use in the prophylaxis or treatment of lymphoma, such as acute or chronic lymphoma, in particular Burkitt lymphoma, Hodgkin lymphoma, non-Hodgkin lymphoma or diffuse large B-cell lymphoma.

In one embodiment the compound of the invention is for use in the prophylaxis or treatment of acute myeloid leukaemia (AML) or acute lymphocytic leukaemia (ALL).

One embodiment includes a compound of the invention for use in the prophylaxis or treatment of cancer in a patient selected from a sub-population possessing cancers which are p53 wild-type or have an MDM2 amplification The cancers may be cancers which are sensitive to treatment with MDM2 inhibitors. The cancers may be cancers which overexpress MDM2. The cancer may be cancers which are p53 wild-type.

Particular cancers include those with an MDM2 amplification and/or MDM2 overexpression, for example, hepatocellular carcinoma, lung, sarcomas, osteosarcomas, and Hodgkin disease.

Particular cancers include those with wild-type p53. Particulars cancers include those cancer cells with wild-type p53, particularly but not exclusively, if MDM2 is highly expressed.

In one embodiment the cancer is a p53 functional tumours. In one embodiment this disease to be treated is p53 functional solid and haematological malignancies. In another embodiment the patient to be treated has p53 mutant tumour for example AML patients with p53 mutant tumour.

In one embodiment the cancer is a tumour of the brain, for example glioma, or neuroblastoma.

In one embodiment the cancer is a cancer of the skin, for example melanoma.

In one embodiment the cancer is a cancer of the lung, for example mesothelioma. In one embodiment the mesothelioma is malignant peritoneal mesothelioma or malignant pleural mesothelioma.

In one embodiment the cancer is a cancer of the gastrointestinal tract, for example GIST, gastric, colorectal or bowel.

In one embodiment the cancer is osteosarcoma.

In one embodiment the cancer is liposarcoma.

In one embodiment the cancer is Ewing's sarcoma.

In one embodiment, the cancer is liposarcoma, soft tissue sarcoma, osteosarcoma, oesophageal cancer, and certain paediatric malignancies including B-cell malignancies.

In one embodiment, the cancer is colorectal, breast, lung and brain

In one embodiment, the cancer is a paediatric cancer.

Whether a particular cancer is one which is sensitive to MDM2 inhibitors, may be determined by a method as set out in the section headed "Methods of Diagnosis".

A further aspect provides the use of a compound for the manufacture of a medicament for the treatment of a disease or condition as described herein, in particular cancer.

Certain cancers are resistant to treatment with particular drugs. This can be due to the type of the tumour (most common epithelial malignancies are inherently chemoresistant and prostate is relatively resistant to currently available regimens of chemotherapy or radiation therapy) or resistance can arise spontaneously as the disease progresses or as a result of treatment. In this regard, references to prostate includes prostate with resistance towards anti-androgen therapy, in particular abiraterone or enzalutamide, or castrate-resistant prostate. Similarly references to multiple myeloma includes bortezomib-insensitive multiple myeloma or refractory multiple myeloma and references to chronic myelogenous leukemia includes imitanib-insensitive chronic myelogenous leukemia and refractory chronic myelogenous leukemia. In this regard, references to mesothelioma includes mesothelioma with resistance towards topoisomerase poisons, alkylating agents, antitubulines, antifolates, platinum compounds and radiation therapy, in particular cisplatin-resistant mesothelioma.

The compounds may also be useful in the treatment of tumour growth, pathogenesis, resistance to chemo- and radio-therapy by sensitising cells to chemotherapy and as an anti-metastatic agent.

Therapeutic anticancer interventions of all types necessarily increase the stresses imposed on the target tumour cells. Inhibitors of MDM2/p53 represent a class of chemotherapeutics with the potential for: (i) sensitizing malignant cells to anticancer drugs and/or treatments; (ii) alleviating or reducing the incidence of resistance to anticancer drugs and/or treatments; (iii) reversing resistance to anticancer drugs and/or treatments; (iv) potentiating the activity of anticancer drugs and/or treatments; (v) delaying or preventing the onset of resistance to anticancer drugs and/or treatments.

In one embodiment the invention provides a compound for use in the treatment of a disease or condition which is mediated by MDM2. In a further embodiment the disease or condition which is mediated by MDM2 is a cancer which is characterised by overexpression and/or increased activity of MDM2, or high copy number MDM2 and/or wildtype p53.

A further aspect provides the use of a compound for the manufacture of a medicament for the treatment of a disease or condition as described herein, in particular cancer.

In one embodiment there is provided a compound for use in the prophylaxis or treatment of a disease or condition mediated by MDM2/p53. In one embodiment there is provided a compound for inhibiting the interaction between of MDM2 protein with p53.

In one embodiment there is provided a pharmaceutical composition comprising an effective amount of at least one compound as defined. In a further aspect of the present invention, there is provided a compound as defined in the present In one embodiment there is provided a method for the prophylaxis or treatment of cancer comprising the steps of administering to a mammal a medicament comprising at least one compound as defined.

Methods of Diagnosis

Prior to administration of a compound of the formula (I), a patient may be screened to determine whether a disease or condition from which the patient is or may be suffering is one which would be susceptible to treatment with a compound which inhibits Mdm2/p53. The term 'patient' includes human and veterinary subjects such as primates, in particular human patients.

For example, a biological sample taken from a patient may be analysed to determine whether a condition or disease, such as cancer, that the patient is or may be suffering from is one which is characterised by a genetic abnormality or abnormal protein expression which leads to up-regulation of the levels of MDM2 or to upregulation of a biochemical pathway downstream of MDM2/p53.

Examples of such abnormalities that result in activation or sensitisation of MDM2, loss of, or inhibition of regulatory pathways impacting on MDM2 expression, up-regulation of receptors or their ligands, cytogenetic aberrations or presence of mutant variants of the receptors or ligands. Tumours with up-regulation of MDM2/p53, in particular over-expression of MDM2 or exhibit wild-type p53, may be particularly sensitive to inhibitors of MDM2/p53. For example, amplification of MDM2 and/or deletion of its negative regulator such as p14ARF has been identified in a range of cancers as discussion in the Introduction section.

The term up-regulation includes elevated expression or over-expression, including gene amplification (i.e. multiple gene copies), cytogenetic aberration and increased expression by a transcriptional or post-translational effect. Thus, the patient may be subjected to a diagnostic test to detect a marker characteristic of up-regulation of MDM2. The term diagnosis includes screening. By marker we include genetic markers including, for example, the measurement of DNA composition to identify presence of mutations in p53 or amplification MDM2 or deletion (loss) of p14ARF. The term marker also includes markers which are characteristic of up regulation of MDM2/p53, including protein levels, protein state and mRNA levels of the aforementioned proteins. Gene amplification includes greater than 7 copies, as well as gains of between 2 and 7 copies.

The diagnostic tests and screens are typically conducted on a biological sample (i.e. body tissue or body fluids) selected from tumour biopsy samples, blood samples (isolation and enrichment of shed tumour cells), cerebrospinal fluid, plasma, serum, saliva, stool biopsies, sputum, chromosome analysis, pleural fluid, peritoneal fluid, buccal smears, skin biopsy or urine.

Methods of identification and analysis of cytogenetic aberration, genetic amplification, mutations and up-regulation of proteins are known to a person skilled in the art. Screening methods could include, but are not limited to, standard methods such as DNA sequence analysis by conventional Sanger or next-generation sequencing methods, reverse-transcriptase polymerase chain reaction (RT-PCR), RNA sequencing (RNAseq), nanostring hybridisation proximity RNA nCounter assays, or in-situ hybridization such as fluorescence in situ hybridization (FISH) or allele-specific polymerase chain reaction (PCR).

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. (2004) Current Protocols in Molecular Biology, John Wiley & Sons Inc., or Innis, M. A. et al., eds. (1990) PCR Protocols: a guide to methods and applications, Academic Press, San Diego. Reactions and manipulations involving nucleic acid techniques are also described in Sambrook et al., (2001), $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference. An example of an in-situ hybridisation technique for assessing mRNA expression would be fluorescence in-situ hybridisation (FISH) (see Angerer (1987) Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radioisotopes or fluorescent reporters. Certain probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. (2004) Current Protocols in Molecular Biology, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Methods for gene expression profiling are described by (DePrimo et al. (2003), *BMC Cancer*, 3:3). Briefly, the protocol is as follows: double-stranded cDNA is synthesized from total RNA using a (dT)24 oligomer for priming first-strand cDNA synthesis from polyadenylated mRNA, followed by second strand cDNA synthesis with random hexamer primers. The double-stranded cDNA is used as a template for in vitro transcription of cRNA using biotinylated ribonucleotides. cRNA is chemically fragmented according to protocols described by Affymetrix (Santa Clara, Calif., USA), and then hybridized overnight to gene-specific oligonucleotide probes on Human Genome Arrays. Alternatively, single nucleotide polymorphism (SNP) arrays, a type of DNA microarray, can be used to detect polymorphisms within a population.

Alternatively, the protein products expressed from the mRNAs may be assayed by immunohistochemistry of tumour samples, solid phase immunoassay with microtitre plates, Western blotting, 2-dimensional SDS-polyacrylamide gel electrophoresis, ELISA, flow cytometry and other methods known in the art for detection of specific proteins e.g. capillary electrophoresis. Detection methods would include the use of site specific antibodies. The skilled person will recognize that all such well-known techniques can be used for detection of upregulation of MDM2 and p53, detection of MDM2 or p53 variants or mutants, or loss of negative regulators of MDM2 in the present case.

Abnormal levels of proteins such as MDM2 or p53 can be measured using standard protein assays, for example, those assays described herein. Elevated levels or overexpression could also be detected in a tissue sample, for example, a tumour tissue by measuring the protein levels with an assay such as that from Chemicon International. The protein of interest would be immunoprecipitated from the sample lysate and its levels measured. Assay methods also include the use of markers.

In other words, p53 and MDM2 overexpression can be measured by tumour biopsy.

Methods for assessing gene copy changes include techniques commonly used in cytogenetic laboratories such as MLPA (Multiplex Ligation-dependent Probe Amplification) a multiplex PCR method detecting abnormal copy numbers, or other PCR techniques which can detect gene amplification, gain and deletion.

Ex-functional assays could also be utilised where appropriate, for example measurement of circulating leukemia cells in a cancer patient, to assess the response to challenge with an MDM2/p53 inhibitor.

Therefore all of these techniques could also be used to identify tumours particularly suitable for treatment with the compounds of the invention.

Therefore in a further aspect of the invention includes use of a compound according to the invention for the manufacture of a medicament for the treatment or prophylaxis of a disease state or condition in a patient who has been screened and has been determined as suffering from, or being at risk of suffering from, a disease or condition which would be susceptible to treatment with an MDM2/p53 inhibitor.

Another aspect of the invention includes a compound of the invention for use in the prophylaxis or treatment of cancer in a patient selected from a sub-population possessing amplification of MDM2.

Another aspect of the invention includes a compound of the invention for use in the prophylaxis or treatment of cancer in a patient selected from a sub-population possessing p53 wild-type.

Another aspect of the invention includes a compound of the invention for use in the prophylaxis or treatment of cancer in a patient possessing loss of a MDM2 negative regulator such as p14ARF.

MRI determination of vessel normalization (e.g. using MRI gradient echo, spin echo, and contrast enhancement to measure blood volume, relative vessel size, and vascular permeability) in combination with circulating biomarkers may also be used to identify patients suitable for treatment with a compound of the invention.

Thus a further aspect of the invention is a method for the diagnosis and treatment of a disease state or condition mediated by MDM2/p53, which method comprises (i) screening a patient to determine whether a disease or condition from which the patient is or may be suffering is one which would be susceptible to treatment with MDM2/p53 inhibitor; and (ii) where it is indicated that the disease or condition from which the patient is thus susceptible, thereafter administering to the patient a compound of formula (I) and sub-groups or examples thereof as defined herein.

Advantages of Compounds of the Invention

The compounds of the formula (I) have a number of advantages over prior art compounds. Compounds of the invention may have particular advantage in one or more of the following aspects:

(i) Superior potency;
(ii) Superior in vivo efficacy
(iii) Superior PK;
(iv) Superior metabolic stability;
(v) Superior oral bioavailabilty; and
(vi) Superior physiochemical properties.

Superior Potency and In Vivo Efficacy

The compounds of the formula (I) have increased affinity for MDM2 and in particular increased cell potency against cell lines known to be sensitive to MDM2 antagonists.

Enhanced target engagement is a highly desirable property in a pharmaceutical compound as it allows for a reduced dosage of drug and a good separation ('therapeutic window') between MDM2 activity and toxic effects.

The compounds of the formula (I) have improved cell potency and/or improved selectivity for p53 WT vs mutant p53 cell lines. As a result of increased potency against MDM2 compounds of the invention may have increased in vivo efficacy in cancer cell lines and in vivo models. In addition the compounds show selectivity for MDM2 over MDMX, despite the close sequence, structural and functional similarity between these genetic paralogues.

Superior PK and Metabolic Stability

The compounds of the formula (I) may have advantageous ADMET properties for example better metabolic stability (for example as determined with mouse liver microsomes), a better P450 profile, short half-life and/or beneficial clearance (e.g. low or high clearance). It has also been found that many compounds of the formula (I) have an improved PK profile.

These features could confer the advantage of having more drug available in the systemic circulation to reach the appropriate site of action to exert its therapeutic effect. Increased drug concentrations to exert pharmacological action in tumours potentially leads to improved efficacy which thereby allows reduced dosages to be administered. Thus, the compounds of formula (I) should exhibit reduced dosage requirements and should be more readily formulated and administered.

This results in a good separation ('therapeutic window') between MDM2 activity and toxic effects. Many compounds of the formula (I) have a reduction in Cmax required for efficacy (due to better MDM2 potency and/or PK).

Superior Oral Bioavailability

Potentially the compounds of the invention have physiochemical properties suitable for oral exposure (oral exposure or AUC). In particular, compounds of the formula (I) may exhibit improved oral bioavailability or improved reproducibility of oral absorption. Oral bioavailability can be defined as the ratio (F) of the plasma exposure of a compound when dosed by the oral route to the plasma exposure of the compound when dosed by the intravenous (i.v.) route, expressed as a percentage.

Compounds having an oral bioavailability (F value) of greater than 10%, 20% or 30%, more particularly greater than 40%, are particularly advantageous in that they may be administered orally rather than, or as well as, by parenteral administration.

Superior Physiochemical Properties

The compounds of the formula (I) may have advantageous physiochemical properties in particular chemical stability in acidic conditions and reduced lipophilicity.

Lipophilicity can be measured using a partition-coefficient (log P) or a distribution-coefficient (log D). The partition coefficient is a ratio of concentrations of un-ionized compound between two immiscible phases (n-octanol and water) at equilibrium whereas the distribution coefficient is the ratio of the sum of the concentrations of all forms of the compound (ionized plus un-ionized) in each of the two phases. High lipophilicity is associated with poor drug like properties such us low aqueous solubility, poor pharmacokinetics properties (low oral bioavailability), undesired drug metabolism and high promiscuity. Compounds with optimal lipophilicity might have greater chances of success in drug development. However reduced log P (or calculated log P, c log P) can be challenging to achieve whilst retaining an acceptable level of potency for inhibition of protein-protein interactions (PPIs) due to the lipophilic nature of the targets involved.

Pharmaceutical Formulations

While it is possible for the active compound to be administered alone, it is generally presented as a pharmaceutical composition (e.g. formulation).

Thus, the present invention further provides pharmaceutical compositions, as defined above, and methods of making a pharmaceutical composition comprising (e.g admixing) at least one compound of formula (I) (and sub-groups thereof as defined herein), together with one or more pharmaceutically acceptable excipients and optionally other therapeutic or prophylactic agents as described herein.

The pharmaceutically acceptable excipient(s) can be selected from, for example, carriers (e.g. a solid, liquid or semi-solid carrier), adjuvants, diluents, fillers or bulking agents, granulating agents, coating agents, release-controlling agents, binding agents, disintegrants, lubricating agents, preservatives, antioxidants, buffering agents, suspending agents, thickening agents, flavouring agents, sweeteners, taste masking agents, stabilisers or any other excipients conventionally used in pharmaceutical compositions. Examples of excipients for various types of pharmaceutical compositions are set out in more detail below.

The term "pharmaceutically acceptable" as used herein pertains to compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compounds of the formula (I) can be formulated in accordance with known techniques, see for example, Remington's Pharmaceutical Sciences, Mack Publishing Company, Easton, Pa., USA.

The pharmaceutical compositions can be in any form suitable for oral, parenteral, topical, intranasal, intrabronchial, sublingual, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short-term infusion or longer term infusion and can be via passive delivery or through the utilisation of a suitable infusion pump or syringe driver.

Pharmaceutical formulations adapted for parenteral administration include aqueous and non-aqueous sterile injection solutions which may contain anti-oxidants, buffers, bacteriostats, co-solvents, surface active agents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

The formulations may be presented in unit-dose or multi-dose containers, for example sealed ampoules, vials and prefilled syringes, and may be stored in a freeze-dried (lyophilised) condition requiring only the addition of the sterile liquid carrier, for example water for injections, immediately prior to use. In one embodiment, the formulation is provided as an active pharmaceutical ingredient in a bottle for subsequent reconstitution using an appropriate diluent.

The pharmaceutical formulation can be prepared by lyophilising a compound of formula (I), or sub-groups thereof. Lyophilisation refers to the procedure of freeze-drying a composition. Freeze-drying and lyophilisation are therefore used herein as synonyms.

Extemporaneous injection solutions and suspensions may be prepared from sterile powders, granules and tablets.

Pharmaceutical compositions of the present invention for parenteral injection can also comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as sunflower oil, safflower oil, corn oil or olive oil), and injectable organic esters such as ethyl oleate. Proper fluidity can be maintained, for example, by the use of thickening materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol, sorbic acid, and the like. It may also be desirable to include agents to adjust tonicity such as sugars, sodium chloride, and the like. Prolonged absorption of the injectable pharmaceutical form may be brought about by the inclusion of agents which delay absorption such as aluminum monostearate and gelatin.

In one typical embodiment of the invention, the pharmaceutical composition is in a form suitable for i.v. administration, for example by injection or infusion. For intravenous administration, the solution can be dosed as is, or can be injected into an infusion bag (containing a pharmaceutically acceptable excipient, such as 0.9% saline or 5% dextrose), before administration.

In another typical embodiment, the pharmaceutical composition is in a form suitable for sub-cutaneous (s.c.) administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated. Coatings may act either as a protective film (e.g. a polymer, wax or varnish) or as a mechanism for controlling drug release or for aesthetic or identification purposes. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum, duodenum, jejenum or colon.

Instead of, or in addition to, a coating, the drug can be presented in a solid matrix comprising a release controlling agent, for example a release delaying agent which may be adapted to release the compound in a controlled manner in the gastrointestinal tract. Alternatively the drug can be presented in a polymer coating e.g. a polymethacrylate polymer coating, which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. In another alternative, the coating can be designed to disintegrate under microbial action in the gut. As a further alternative, the active compound can be formulated in a delivery system that provides osmotic control of the release of the compound. Osmotic release and other delayed release or sustained release formulations (for example formulations based on ion exchange resins) may be prepared in accordance with methods well known to those skilled in the art.

The compound of formula (I) may be formulated with a carrier and administered in the form of nanoparticles, the increased surface area of the nanoparticles assisting their absorption. In addition, nanoparticles offer the possibility of direct penetration into the cell. Nanoparticle drug delivery systems are described in "Nanoparticle Technology for Drug Delivery", edited by Ram B Gupta and Uday B. Kompella, Informa Healthcare, ISBN 9781574448573, published 13$^{th}$ March 2006. Nanoparticles for drug delivery are also described in J. Control. Release, 2003, 91 (1-2), 167-172, and in Sinha et al., Mol. Cancer Ther. August 1, (2006) 5, 1909.

The pharmaceutical compositions typically comprise from approximately 1% (w/w) to approximately 95% active ingredient and from 99% (w/w) to 5% (w/w) of a pharmaceutically acceptable excipient or combination of excipients. Typically, the compositions comprise from approximately 20% (w/w) to approximately 90%,% (w/w) active ingredient and from 80% (w/w) to 10% of a pharmaceutically acceptable excipient or combination of excipients. The pharmaceutical compositions comprise from approximately 1% to approximately 95%, typically from approximately 20% to approximately 90%, active ingredient. Pharmaceutical compositions according to the invention may be, for example, in unit dose form, such as in the form of ampoules, vials, suppositories, pre-filled syringes, dragées, tablets or capsules.

The pharmaceutically acceptable excipient(s) can be selected according to the desired physical form of the formulation and can, for example, be selected from diluents (e.g solid diluents such as fillers or bulking agents; and liquid diluents such as solvents and co-solvents), disintegrants, buffering agents, lubricants, flow aids, release controlling (e.g. release retarding or delaying polymers or waxes) agents, binders, granulating agents, pigments, plasticizers, antioxidants, preservatives, flavouring agents, taste masking agents, tonicity adjusting agents and coating agents.

The skilled person will have the expertise to select the appropriate amounts of ingredients for use in the formulations. For example tablets and capsules typically contain 0-20% disintegrants, 0-5% lubricants, 0-5% flow aids and/or 0-99% (w/w) fillers/or bulking agents (depending on drug dose).

They may also contain 0-10% (w/w) polymer binders, 0-5% (w/w) antioxidants, 0-5% (w/w) pigments. Slow release tablets would in addition contain 0-99% (w/w) polymers (depending on dose). The film coats of the tablet or capsule typically contain 0-10% (w/w) release-controlling (e.g. delaying) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

Pharmaceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into a polymer or waxy matrix that allow the active ingredients to diffuse or be released in measured amounts.

The compounds of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman, J. Pharm. Sci., 60, 1281-1300 (1971)) and are useful in increasing dissolution rates and increasing the bioavailability of poorly water-soluble drugs.

This invention also provides solid dosage forms comprising the solid solution described herein. Solid dosage forms include tablets, capsules, chewable tablets and dispersible or effervescent tablets. Known excipients can be blended with the solid solution to provide the desired dosage form. For example, a capsule can contain the solid solution blended with (a) a disintegrant and a lubricant, or (b) a disintegrant, a lubricant and a surfactant. In addition a capsule can contain a bulking agent, such as lactose or microcrystalline cellulose. A tablet can contain the solid solution blended with at least one disintegrant, a lubricant, a surfactant, a bulking agent and a glidant. A chewable tablet can contain the solid solution blended with a bulking agent, a lubricant, and if desired an additional sweetening agent (such as an artificial sweetener), and suitable flavours. Solid solutions may also be formed by spraying solutions of drug and a suitable polymer onto the surface of inert carriers such as sugar beads ('non-pareils'). These beads can subsequently be filled into capsules or compressed into tablets.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use and nasal delivery include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped moldable or waxy material containing the active compound. Solutions of the active compound may also be used for rectal administration.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the formula (I) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 miligrams to 1 gram, of active compound.

The active compound will be administered to a patient in need thereof (for example a human or animal patient) in an amount sufficient to achieve the desired therapeutic effect.

Methods of Treatment

The compounds of the formula (I) and sub-groups as defined herein may be useful in the prophylaxis or treatment of a range of disease states or conditions mediated by MDM2/p53. Examples of such disease states and conditions are set out above.

The compounds are generally administered to a subject in need of such administration, for example a human or animal patient, typically a human.

The compounds will typically be administered in amounts that are therapeutically or prophylactically useful and which generally are non-toxic. However, in certain situations (for example in the case of life threatening diseases), the benefits of administering a compound of the formula (I) may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively they may be administered in a continuous manner or in a manner that provides intermittent dosing (e.g. a pulsatile manner).

A typical daily dose of the compound of formula (I) can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound of the formula (I) can be administered on a daily basis or on a repeat basis every 2, or 3, or 4, or 5, or 6, or 7, or 10 or 14, or 21, or 28 days for example.

Dosages may also be expressed as the amount of drug administered relative to the body surface area of the patient (mg/m$^2$). IA typical daily dose of the compound of formula (I) can be in the range from 3700 pg/m$^2$ to 3700 mg/m$^2$, more typically 185 ng/m$^2$ to 925 mg/m$^2$, and more usually 370 ng/m$^2$ to 555 mg/m$^2$ (e.g. 370 ng/m$^2$ to 370 mg/m$^2$, and more typically 37 mg/m$^2$ to 740 mg/m$^2$, for example 37 mg/m$^2$ to 370 mg/m$^2$) although higher or lower doses may be administered where required. The compound of the formula (I) can be administered on a daily basis or on a repeat basis every 2, or 3, or 4, or 5, or 6, or 7, or 10 or 14, or 21, or 28 days for example.

The compounds of the invention may be administered orally in a range of doses, for example 0.1 to 5000 mg or 1 to 1500 mg, 2 to 800 mg, or 5 to 500 mg, e.g. 2 to 200 mg or 10 to 1000 mg, particular examples of doses including 10, 20, 50 and 80 mg. The compound may be administered once or more than once each day. The compound can be administered continuously (i.e. taken every day without a break for the duration of the treatment regimen). Alternatively, the compound can be administered intermittently (i.e. taken continuously for a given period such as a week, then discontinued for a period such as a week and then taken continuously for another period such as a week and so on throughout the duration of the treatment regimen). Examples of treatment regimens involving intermittent administration include regimens wherein administration is in cycles of one week on, one week off; or two weeks on, one week off; or three weeks on, one week off; or two weeks on, two weeks off; or four weeks on two weeks off; or one week on three weeks off—for one or more cycles, e.g. 2, 3, 4, 5, 6, 7, 8, 9 or 10 or more cycles. This discontinuous treatment can also be based upon numbers of days rather than a full week. For example, the treatment can comprise daily dosing for 1 to 6 days, no dosing for 1 to 6 days with this pattern repeating during the treatment protocol. The number of days (or weeks) wherein the compounds of the invention are not dosed do not necessarily have to equal the number of days (or weeks) wherein the compounds of the invention are dosed.

In one embodiment, the compounds of the invention can be administered in amounts from 3 mg/m$^2$ to 125 mg/m$^2$ daily. Treatment can be by continuous daily dosing or more usually consist of multiple cycles of treatment separated by treatment breaks. One example of a single treatment cycle is 5 consecutive daily doses followed by 3 weeks without treatment.

One particular dosing regimen is once a day (e.g. orally) for a week (e.g. 5 days of treatment), followed by a treatment break of 1, 2, or 3 weeks. An alternative dosing regimen is once a week (e.g. orally), for 1, 2, 3 or 4 weeks.

In one particular dosing schedule, a patient will be given an infusion of a compound of the formula (I) for periods of one hour daily for up to ten days in particular up to five days for one week, and the treatment repeated at a desired interval such as two to four weeks, in particular every three weeks.

More particularly, a patient may be given an infusion of a compound of the formula (I) for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

The compounds of the invention can also be administered by bolus or continuous infusion. The compound of the invention can be given daily to once every week, or once every two weeks, or once every three weeks, or once every four weeks during the treatment cycle. If administered daily during a treatment cycle, this daily dosing can be discontinuous over the number of weeks of the treatment cycle: for example, dosed for a week (or a number of days), no dosing for a week (or a number of days, with the pattern repeating during the treatment cycle.

In a further particular dosing schedule, a patient is given a continuous infusion for a period of 12 hours to 5 days, and in particular a continuous infusion of 24 hours to 72 hours.

Ultimately, however, the quantity of compound administered and the type of composition used will be commensurate with the nature of the disease or physiological condition being treated and will be at the discretion of the physician.

It may be beneficial to use a compound of the invention as a single agent or to combine the compound of the invention with another agent which acts via a different mechanism to regulate cell growth thus treating two of the characteristic features of cancer development. Combination experiments can be performed, for example, as described in Chou T C, Talalay P. Quantitative analysis of dose-effect relationships: the combined effects of multiple drugs or enzyme inhibitors. Adv Enzyme Regulat 1984; 22: 27-55.

The compounds as defined herein can be administered as the sole therapeutic agent or they can be administered in combination therapy with one of more other compounds (or therapies) for treatment of a particular disease state, for example a neoplastic disease such as a cancer as hereinbefore defined. For the treatment of the above conditions, the compounds of the invention may be advantageously employed in combination with one or more other medicinal agents, more particularly, with other anti-cancer agents or adjuvants (supporting agents in the therapy) in cancer therapy. Examples of other therapeutic agents or treatments that may be administered together (whether concurrently or at different time intervals) with the compounds of the formula (I) include but are not limited to:

Topoisomerase I inhibitors
Antimetabolites
Tubulin targeting agents
DNA binder and topoisomerase II inhibitors
Alkylating Agents
Monoclonal Antibodies.
Anti-Hormones
Signal Transduction Inhibitors
Proteasome Inhibitors
DNA methyl transferase inhibitors
Cytokines and retinoids
Chromatin targeted therapies
Radiotherapy, and,
Other therapeutic or prophylactic agents.

Particular examples of anti-cancer agents or adjuvants (or salts thereof), include but are not limited to any of the agents selected from groups (i)-(xlviii), and optionally group (xlix), below:

(i) Platinum compounds, for example cisplatin (optionally combined with amifostine), carboplatin or oxaliplatin;

(ii) Taxane compounds, for example paclitaxel, paclitaxel protein bound particles (Abraxane™), docetaxel, cabazitaxel or larotaxel;

(iii) Topoisomerase I inhibitors, for example camptothecin compounds, for example camptothecin, irinotecan (CPT11), SN-38, or topotecan;

(iv) Topoisomerase II inhibitors, for example anti-tumour epipodophyllotoxins or podophyllotoxin derivatives for example etoposide, or teniposide;

(v) Vinca alkaloids, for example vinblastine, vincristine, liposomal vincristine (Onco-TCS), vinorelbine, vindesine, vinflunine or vinvesir;

(vi) Nucleoside derivatives, for example 5-fluorouracil (5-FU, optionally in combination with leucovorin), gemcitabine, capecitabine, tegafur, UFT, S1, cladribine, cytarabine (Ara-C, cytosine arabinoside), fludarabine, clofarabine, or nelarabine;

(vii) Antimetabolites, for example clofarabine, aminopterin, or methotrexate, azacitidine, cytarabine, floxuridine, pentostatin, thioguanine, thiopurine, 6-mercaptopurine, or hydroxyurea (hydroxycarbamide);

(viii) Alkylating agents, such as nitrogen mustards or nitrosourea, for example cyclophosphamide, chlorambucil, carmustine (BCNU), bendamustine, thiotepa, melphalan, treosulfan, lomustine (CCNU), altretamine, busulfan, dacarbazine, estramustine, fotemustine, ifosfamide (optionally in combination with mesna), pipobroman, procarbazine, streptozocin, temozolomide, uracil, mechlorethamine, methylcyclohexylchloroethylnitrosurea, or nimustine (ACNU);

(ix) Anthracyclines, anthracenediones and related drugs, for example daunorubicin, doxorubicin (optionally in combination with dexrazoxane), liposomal formulations of doxorubicin (eg. Caelyx™, Myocet™, Doxil™), idarubicin, mitoxantrone, epirubicin, amsacrine, or valrubicin;

(x) Epothilones, for example ixabepilone, patupilone, BMS-310705, KOS-862 and ZK-EPO, epothilone A, epothilone B, desoxyepothilone B (also known as epothilone D or KOS-862), aza-epothilone B (also known as BMS-247550), aulimalide, isolaulimalide, or luetherobin;

(xi) DNA methyl transferase inhibitors, for example temozolomide, azacytidine, or decitabine;

(xii) Antifolates, for example methotrexate, pemetrexed disodium, or raltitrexed;

(xiii) Cytotoxic antibiotics, for example antinomycin D, bleomycin, mitomycin C, dactinomycin, carminomycin, daunomycin, levamisole, plicamycin, or mithramycin;

(xiv) Tubulin-binding agents, for example combrestatin, colchicines or nocodazole;

(xv) Signal Transduction inhibitors such as Kinase inhibitors for example receptor tyrosine kinase inhibitors (e.g. EGFR (epithelial growth factor receptor) inhibitors, VEGFR (vascular endothelial growth factor receptor) inhibitors, PDGFR (platelet-derived growth factor receptor) inhibitors, Axl inhibitors, MTKI (multi target kinase inhibitors), Raf inhibitors, ROCK inhibitors, mTOR inhibitors, MEK inhibitors or PI3K Inhibitors) for example imatinib mesylate, erlotinib, gefitinib, dasatinib, lapatinib, dovotinib, axitinib, nilotinib, vandetanib, vatalinib, pazopanib, sorafenib, sunitinib, temsirolimus, everolimus (RAD 001), vemurafenib (PLX4032 or RG7204), dabrafenib, encorafenib, selumetinib (AZD6244), trametinib (GSK121120212), dactolisib (BEZ235), buparlisib (BKM-120; NVP-BKM-120), BYL719, copanlisib (BAY-80-6946), ZSTK-474, CUDC-907, apitolisib (GDC-0980; RG-7422), pictilisib (pictrelisib, GDC-0941, RG-7321), GDC-0032, GDC-0068, GSK-2636771, idelalisib (formerly CAL-101, GS 1101, GS-1101), MLN1117 (INK1117), MLN0128 (INK128), IPI-145 (INK1197), LY-3023414, ipatasertib, afuresertib, MK-2206, MK-8156, LY-3023414, LY294002, SF1126 or PI-103, sonolisib (PX-866), or AT13148.

(xvi) Aurora kinase inhibitors for example AT9283, barasertib (AZD1152), TAK-901, MK0457 (VX680), cenisertib (R-763), danusertib (PHA-739358), alisertib (MLN-8237), or MP-470;

(xvii) CDK inhibitors for example AT7519, roscovitine, seliciclib, alvocidib (flavopiridol), dinaciclib (SCH-727965), 7-hydroxy-staurosporine (UCN-01), JNJ-7706621, BMS-387032 (a.k.a. SNS-032), PHA533533, ZK-304709, or AZD-5438 and including CDK4 inhibitors such as palbociclib (PD332991) and ribociclib (LEE-011);

(xviii) PKA/B inhibitors and PKB (akt) pathway inhibitors for example AT13148, AZ-5363, Semaphore, SF1126 and MTOR inhibitors such as rapamycin analogues, AP23841 and AP23573, calmodulin inhibitors (forkhead translocation inhibitors), API-2/TCN (triciribine), RX-0201, enzastaurin HCl (LY317615), NL-71-101, SR-13668, PX-316, or KRX-0401 (perifosine/NSC 639966);

(xix) Hsp90 inhibitors for example onalespib (AT13387), herbimycin, geldanamycin (GA), 17-allylamino-17-desmethoxygeldanamycin (17-AAG) e.g. NSC-330507, Kos-953 and CNF-1010, 17-dimethylaminoethylamino-17-demethoxygeldanamycin hydrochloride (17-DMAG) e.g. NSC-707545 and Kos-1022, NVP-AUY922 (VER-52296), NVP-BEP800, CNF-2024 (BIIB-021 an oral purine), ganetespib (STA-9090), SNX-5422 (SC-102112) or IPI-504;

(xx) Monoclonal Antibodies (unconjugated or conjugated to radioisotopes, toxins or other agents), antibody derivatives and related agents, such as anti-CD, anti-VEGFR, anti-HER2 or anti-EGFR antibodies, for example rituximab (CD20), ofatumumab (CD20), ibritumomab tiuxetan (CD20), GA101 (CD20), tositumomab (CD20), epratuzumab (CD22), lintuzumab (CD33), gemtuzumab ozogamicin (CD33), alemtuzumab (CD52), galiximab (CD80), trastuzumab (HER2 antibody), pertuzumab (HER2), trastuzumab-DM1 (HER2), ertumaxomab (HER2 and CD3), cetuximab (EGFR), panitumumab (EGFR), necitumumab (EGFR), nimotuzumab (EGFR), bevacizumab (VEGF), catumaxumab (EpCAM and CD3), abagovomab (CA125), farletuzumab (folate receptor), elotuzumab (CS1), denosumab (RANK ligand), figitumumab (IGF1R), CP751,871 (IGF1R), mapatumumab (TRAIL receptor), metMAB (met), mitumomab (GD3 ganglioside), naptumomab estafenatox (5T4), or siltuximab (IL6) or immunomodulating agents such as CTLA-4 blocking antibodies and/or antibodies against PD-1 and PD-L1 and/or PD-L2 for example ipilimumab (CTLA4), MK-3475 (pembrolizumab, formerly lambrolizumab, anti-PD-1), nivolumab (a anti-PD-1), BMS-936559 (anti-PD-L1), MPDL320A, AMP-514 or MED14736 (anti-PD-L1), or tremelimumab (formerly ticilimumab, CP-675, 206, anti-CTLA-4);

(xxi) Estrogen receptor antagonists or selective estrogen receptor modulators (SERMs) or inhibitors of estrogen synthesis, for example tamoxifen, fulvestrant, toremifene, droloxifene, faslodex, or raloxifene;

(xxii) Aromatase inhibitors and related drugs, such as exemestane, anastrozole, letrazole, testolactone aminoglutethimide, mitotane or vorozole;

(xxiii) Antiandrogens (i.e. androgen receptor antagonists) and related agents for example bicalutamide, nilutamide, flutamide, cyproterone, or ketoconazole;

(xxiv) Hormones and analogues thereof such as medroxyprogesterone, diethylstilbestrol (a.k.a. diethylstilboestrol) or octreotide;

(xxv) Steroids for example dromostanolone propionate, megestrol acetate, nandrolone (decanoate, phenpropionate), fluoxymestrone or gossypol, (xxvi) Steroidal cytochrome P450 17alpha-hydroxylase-17, 20-lyase inhibitor (CYP17), e.g. abiraterone;

(xxvii) Gonadotropin releasing hormone agonists or antagonists (GnRAs) for example abarelix, goserelin acetate, histrelin acetate, leuprolide acetate, triptorelin, buserelin, or deslorelin;

(xxviii) Glucocorticoids, for example prednisone, prednisolone, dexamethasone;

(xxix) Differentiating agents, such as retinoids, rexinoids, vitamin D or retinoic acid and retinoic acid metabolism blocking agents (RAMBA) for example accutane, alitretinoin, bexarotene, or tretinoin;

(xxx) Farnesyltransferase inhibitors for example tipifarnib;

(xxxi) Chromatin targeted therapies such as histone deacetylase (HDAC) inhibitors for example sodium butyrate, suberoylanilide hydroxamide acid (SAHA), depsipeptide (FR 901228), dacinostat (NVP-LAQ824), R306465/JNJ-16241199, JNJ-26481585, trichostatin A, vorinostat, chlamydocin, A-173, JNJ-MGCD-0103, PXD-101, or apicidin;

(xxxii) Drugs targeting the ubiquitin-proteasome pathway including proteasome Inhibitors for example bortezomib, carfilzomib, CEP-18770, MLN-9708, or ONX-0912; NEDD8 inhibitors; HDM2 antagonist and deubiquitinases (DUBs);

(xxxiii) Photodynamic drugs for example porfimer sodium or temoporfin;

(xxxiv) Marine organism-derived anticancer agents such as trabectidin;

(xxxv) Radiolabelled drugs for radioimmunotherapy for example with a beta particle-emitting isotope (e.g., Iodine-131, Yittrium-90) or an alpha particle-emitting isotope (e.g., Bismuth-213 or Actinium-225) for example ibritumomab or Iodine tositumomab or alpha radium 223;

(xxxvi) Telomerase inhibitors for example telomestatin;

(xxxvii) Matrix metalloproteinase inhibitors for example batimastat, marimastat, prinostat or metastat;

(xxxviii) Recombinant interferons (such as interferon-γ and interferon α) and interleukins (e.g. interleukin 2), for example aldesleukin, denileukin diftitox, interferon alfa 2a, interferon alfa 2b, or peginterferon alfa 2b;

(xxxix) Selective immunoresponse modulators for example thalidomide, or lenalidomide;

(xl) Therapeutic Vaccines such as sipuleucel-T (Provenge) or OncoVex;

(xli) Cytokine-activating agents include Picibanil, Romurtide, Sizofiran, Virulizin, or Thymosin;

(xlii) Arsenic trioxide;

(xliii) Inhibitors of G-protein coupled receptors (GPCR) for example atrasentan;

(xliv) Enzymes such as L-asparaginase, pegaspargase, rasburicase, or pegademase;

(xlv) DNA repair inhibitors such as PARP inhibitors for example, olaparib, velaparib, iniparib, INO-1001, AG-014699, or ONO-2231;

(xlvi) Agonists of Death receptor (e.g. TNF-related apoptosis inducing ligand (TRAIL) receptor), such as mapatumumab (formerly HGS-ETR1), conatumumab (formerly AMG 655), PR095780, lexatumumab, dulanermin, CS-1008, apomab or recombinant TRAIL ligands such as recombinant Human TRAIL/Apo2 Ligand;

(xlvii) Immunotherapies such as immune checkpoint inhibitors; cancer vaccines and CAR-T cell therapy;

(xlviii) Regulators of Cell death (apoptosis) including Bcl-2 (B-cell lymphoma 2) antagonists such as venetoclax (ABT-199 or GDC-0199), ABT-737, ABT-263, TW-37, sabutoclax, obatoclax, and MIM1 and IAP antagonists including LCL-161 (Novartis), Debio-1143 (Debiopharma/Ascenta), AZD5582, Birinapant/TL-32711 (TetraLogic), CUDC-427/GDC-0917/RG-7459 (Genentech), JP1201 (Joyant), T-3256336 (Takeda), GDC-0152 (Genentech) or HGS-1029/AEG-40826 (HGS/Aegera);

(xlix) Prophylactic agents (adjuncts); i.e. agents that reduce or alleviate some of the side effects associated with chemotherapy agents, for example anti-emetic agents, agents that prevent or decrease the duration of chemotherapy-associated neutropenia and prevent complications that arise from reduced levels of platelets, red blood cells or white blood cells, for example interleukin-11 (e.g. oprelvekin), erythropoietin (EPO) and analogues thereof (e.g. darbepoetin alfa), colony-stimulating factor analogs such as granulocyte macrophage-colony stimulating factor (GM-CSF) (e.g. sargramostim), and granulocyte-colony stimulating factor (G-CSF) and analogues thereof (e.g. filgrastim, pegfilgrastim), agents that inhibit bone resorption such as denosumab or bisphosphonates e.g. zoledronate, zoledronic acid, pamidronate and ibandronate, agents that suppress inflammatory responses such as dexamethasone, prednisone, and prednisolone, agents used to reduce blood levels of growth hormone and IGF-I (and other hormones) in patients with acromegaly or other rare hormone-producing tumours, such as synthetic forms of the hormone somatostatin e.g. octreotide acetate, antidote to drugs that decrease levels of folic acid such as leucovorin, or folinic acid, agents for pain e.g. opiates such as morphine, diamorphine and fentanyl, non-steroidal anti-inflammatory drugs (NSAID) such as COX-2 inhibitors for example celecoxib, etoricoxib and lumiracoxib, agents for mucositis e.g. palifermin, agents for the treatment of side-effects including anorexia, cachexia, oedema or thromoembolic episodes, such as megestrol acetate.

Each of the compounds present in the combinations of the invention may be given in individually varying dose schedules and via different routes. As such, the posology of each of the two or more agents may differ: each may be administered at the same time or at different times. A person skilled in the art would know through his or her common general knowledge the dosing regimes and combination therapies to use. For example, the compound of the invention may be using in combination with one or more other agents which are administered according to their existing combination regimen. Examples of standard combination regimens are provided below.

The taxane compound is advantageously administered in a dosage of 50 to 400 mg per square meter ($mg/m^2$) of body surface area, for example 75 to 250 $mg/m^2$, particularly for paclitaxel in a dosage of about 175 to 250 $mg/m^2$ and for docetaxel in about 75 to 150 $mg/m^2$ per course of treatment.

The camptothecin compound is advantageously administered in a dosage of 0.1 to 400 mg per square meter ($mg/m^2$) of body surface area, for example 1 to 300 $mg/m^2$, particularly for irinotecan in a dosage of about 100 to 350 mg/m$^2$ and for topotecan in about 1 to 2 mg/m$^2$ per course of treatment.

The anti-tumour podophyllotoxin derivative is advantageously administered in a dosage of 30 to 300 mg per square meter (mg/m$^2$) of body surface area, for example 50 to 250 mg/m$^2$, particularly for etoposide in a dosage of about 35 to 100 mg/m$^2$ and for teniposide in about 50 to 250 mg/m$^2$ per course of treatment.

The anti-tumour vinca alkaloid is advantageously administered in a dosage of 2 to 30 mg per square meter (mg/m$^2$) of body surface area, particularly for vinblastine in a dosage of about 3 to 12 mg/m$^2$ for vincristine in a dosage of about 1 to 2 mg/m$^2$, and for vinorelbine in dosage of about 10 to 30 mg/m$^2$ per course of treatment.

The anti-tumour nucleoside derivative is advantageously administered in a dosage of 200 to 2500 mg per square meter (mg/m$^2$) of body surface area, for example 700 to 1500 mg/m$^2$, particularly for 5-FU in a dosage of 200 to 500 mg/m$^2$, for gemcitabine in a dosage of about 800 to 1200 mg/m$^2$ and for capecitabine in about 1000 to 2500 mg/m$^2$ per course of treatment.

The alkylating agents such as nitrogen mustard or nitrosourea is advantageously administered in a dosage of 100 to 500 mg per square meter (mg/m$^2$) of body surface area, for example 120 to 200 mg/m$^2$, particularly for cyclophosphamide in a dosage of about 100 to 500 mg/m$^2$, for chlorambucil in a dosage of about 0.1 to 0.2 mg/kg, for carmustine in a dosage of about 150 to 200 mg/m$^2$, and for lomustine in a dosage of about 100 to 150 mg/m$^2$ per course of treatment.

The anti-tumour anthracycline derivative is advantageously administered in a dosage of 10 to 75 mg per square meter (mg/m$^2$) of body surface area, for example 15 to 60 mg/m$^2$, particularly for doxorubicin in a dosage of about 40 to 75 mg/m$^2$, for daunorubicin in a dosage of about 25 to 45 mg/m$^2$, and for idarubicin in a dosage of about 10 to 15 mg/m$^2$ per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, typically 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m$^2$) of body surface area, or as known in the art, if different. Trastuzumab is advantageously administered in a dosage of 1 to 5 mg per square meter (mg/m$^2$) of body surface area, particularly 2 to 4 mg/m$^2$ per course of treatment.

Where the compound of the formula (I) is administered in combination therapy with one, two, three, four or more other therapeutic agents (typically one or two, more typically one), the compounds can be administered simultaneously or sequentially. In the latter case, the two or more compounds will be administered within a period and in an amount and manner that is sufficient to ensure that an advantageous or synergistic effect is achieved. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s). These dosages may be administered for example once, twice or more per course of treatment, which may be repeated for example every 7, 14, 21 or 28 days.

It will be appreciated that the typical method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of formula (I) and another anticancer agent may range from 1/10 to 10/1, more in particular from 1/5 to 5/1, even more in particular from 1/3 to 3/1.

The compounds of the invention may also be administered in conjunction with non-chemotherapeutic treatments such as radiotherapy, photodynamic therapy, gene therapy; surgery and controlled diets. Radiotherapy may be for radical, palliative, adjuvant, neoadjuvant or prophylactic purposes.

The compounds of the present invention also have therapeutic applications in sensitising tumour cells for radiotherapy and chemotherapy. Hence the compounds of the present invention can be used as "radiosensitizer" and/or "chemosensitizer" or can be given in combination with another "radiosensitizer" and/or "chemosensitizer". In one embodiment the compound of the invention is for use as chemosensitiser.

The term "radiosensitizer" is defined as a molecule administered to patients in therapeutically effective amounts to increase the sensitivity of the cells to ionizing radiation and/or to promote the treatment of diseases which are treatable with ionizing radiation.

The term "chemosensitizer" is defined as a molecule administered to patients in therapeutically effective amounts to increase the sensitivity of cells to chemotherapy and/or promote the treatment of diseases which are treatable with chemotherapeutics.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

For use in combination therapy with another chemotherapeutic agent, the compound of the formula (I) and one, two, three, four or more other therapeutic agents can be, for example, formulated together in a dosage form containing two, three, four or more therapeutic agents i.e. in a unitary pharmaceutical composition containing all components. In an alternative, the individual therapeutic agents may be formulated separately and presented together in the form of a kit, optionally with instructions for their use.

In one embodiment the pharmaceutical composition comprises a compound of formula I together with a pharmaceutically acceptable carrier and optionally one or more therapeutic agent(s)

In another embodiment the invention relates to the use of a combination according to the invention in the manufacture of a pharmaceutical composition for inhibiting the growth of tumour cells.

In a further embodiment the invention relates to a product containing a compound of formula I and one or more anticancer agent, as a combined preparation for simultaneous, separate or sequential use in the treatment of patients suffering from cancer.

EXAMPLES

The invention will now be illustrated, but not limited, by reference to the specific embodiments described in the following examples. Compounds are named using an automated naming package such as AutoNom (MDL) or Che-mAxon Structure to Name or are as named by the chemical supplier. In the examples, the following abbreviations are used:

AcOH acetic acid
Boc tert-butyloxycarbonyl
Boc-Abu-OH (S)-2-(Boc-amino)butyric acid
BuLi butyllithium
CDI 1,1-carbonyldiimidazole
DAST Diethylaminosulfur trifluoride
DCM dichloromethane
DCMA Dicyclohexyylmethylamine
DIPEA N-ethyl-N-(1-methylethyl)-2-propylamine
DMC dimethyl carbonate
DMF N,N-dimethylformamide
DMSO dimethyl sulfoxide
EDC 1-ethyl-3-(3'-dimethylaminopropyl)-carbodiimide hydrochloride
$Et_3N$ triethylamine
EtOAc ethyl acetate
EtOH ethanol
$Et_2O$ diethyl ether
HATU 2-(7-aza-1H-benzotriazole-1-yl)-1,1,3,3-tetramethyluronium hexafluorophosphate)
HBTU O-benzotriazole-N,N,N',N'-tetramethyl-uronium-hexafluoro-phosphate
HCl hydrochloric acid
HOAc acetic acid
HOAt 1-hydroxyazabenzotriazole
HOBt 1-hydroxybenzotriazole
HPLC high pressure liquid chromatography
IPA isopropyl alcohol
KHMDS potassium hexamethyldisilazide
LiHMDS lithium bis(trimethylsilyl)amide
MeCN acetonitrile
MeOH methanol
mins. minutes
MS mass spectrometry
MW microwave
$NaBH(OAc)_3$ sodium triacetoxyborohydride
NaOtBu potassium tert-butoxide
NMP N-methyl-2-pyrrolidinone
NMR nuclear magnetic resonance spectroscopy
$Pd_2(dba)_3$ tris(dibenzylideneacetone)dipalladium (o)
$Pd(OAc)_2$ palladium (2) acetate
$Pd(PPh_3)_4$ tetrakis(triphenylphosphine)palladium (0)
petrol petroleum ether fraction with boiling point range 40-60° C.
PyBrop bromo-tris-pyrrolidino-phosphonium hexafluorophosphate
RT room temperature
$SiO_2$ silica
TBTU N,N,N',N'-tetramethyl-O-(benzotriazol-1-yl)uronium tetrafluoroborate
TEA triethylamine
TFA trifluoroacetic acid
THF tetrahydrofuran
UV Ultraviolet Column Chromatography Purification using column chromatography can be achieved, for example using a Biotage automated flash purification system with UV monitoring at 298 nm and collection at 254 nm. Biotage automated chromatography pre-packed silica cartridges were used in most cases. Where stated, the purification of some compounds was performed using Biotage C18 reversed phase silica columns, which have octadecyl (end-capped) functionalised silica or Biotage KP-NH cartridges were used for the separation of highly polar compounds, which uses primary amine bonded silica.

Where necessary, semi-preparative HPLC can be carried out, for example using one of the following machines: (i) Varian Prostar Modular HPLC system with a binary pumping system, UV detector and fraction collector and controlled by Varian Star software. (ii) Agilent 1200 HPLC system with a binary pump, autosampler, fraction collector and diode array detector and controlled by Agilent ChemStation software.

Analytical LC-MS System Description

In the following examples, many of the compounds prepared were characterised by mass spectroscopy using the systems and suitable operating conditions set out below. Where atoms with different isotopes are present and a single mass quoted, the mass quoted for the compound is the monoisotopic mass (i.e. $^{35}Cl$; $^{79}Br$ etc.). Several systems can be used, as described below, and these can be equipped with, and can be set up to run under, closely similar operating conditions. Possible operating conditions are also described below.

Aqilent 1200SL-6140 LC-MS system—RAPID:
HPLC System: Agilent 1200 series SL
Mass Spec Detector: Agilent 6140 single quadrupole
Second Detector: Agilent 1200 MWD SL
Agilent MS Running Conditions:
Capillary voltage: 3000V on ES pos (2700V on ES Neg)
Fragmentor/Gain: 190 on ES pos (160 on ES neg)
Gain: 1
Drying gas flow: 12.0 L/min
Gas Temperature: 345° C.
Nebuliser Pressure: 60 psig
Scan Range: 125-800 amu
Ionisation Mode: ElectroSpray Positive-Negative switching
Shimadzu Nexera LC-MS System
HPLC System: Shimadzu SIL-30AC autosampler/2× Shimadzu LC-30AD pumps
Mass Spec Detector: Shimadzu LCMS-2020 single quadrupole MS
Second Detector: Shimadzu SPD-M20A diode array detector
Shimadzu MS Running Conditions:
Qarray DC voltage: 20V on ES Pos (−20V on ES Neg)
Drying gas flow: 20.0 L/min
DL Temperature: 300° C.
Heat Block Temperature: 350° C.
Nebulising Gas Flow: 1.5 L/min
Scan Range: 100-750 amu
Ionisation Mode: ElectroSpray Positive-Negative switching
Mass Directed Purification LC-MS System Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.;* 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; J Comb Chem.; 2003; 5(3); 322-9.

Several systems for purifying compounds via preparative LC-MS are described below although a person skilled in the art will appreciate that alternative systems and methods to those described could be used. In particular, normal phase preparative LC based methods might be used in place of the reverse phase methods described here. Most preparative LC-MS systems utilise reverse phase LC and volatile acidic modifiers, since the approach is very effective for the purification of small molecules and because the eluents are compatible with positive ion electrospray mass spectrometry. Employing other chromatographic solutions e.g. normal phase LC, alternatively buffered mobile phase, basic modifiers etc as outlined in the analytical methods described above could alternatively be used to purify the compounds.

Preparative LC-MS System Description:
Waters Fractionlynx System:
Hardware:
2767 Dual Loop Autosampler/Fraction Collector
2525 preparative pump
CFO (column fluidic organiser) for column selection
RMA (Waters reagent manager) as make up pump
Waters ZQ Mass Spectrometer
Waters 2996 Photo Diode Array detector
Waters ZQ Mass Spectrometer
Software:
Masslynx 4.1
Waters MS running conditions:
Capillary voltage: 3.5 kV (3.2 kV on ES Negative)
Cone voltage: 25 V
Source Temperature: 120° C.
Multiplier: 500 V
Scan Range: 125-800 amu
Ionisation Mode: ElectroSpray Positive or
ElectroSpray Negative
Aqilent 1100 LC-MS Preparative System:
Hardware:
Autosampler: 1100 series "prepALS"
Pump: 1100 series "PrepPump" for preparative flow gradient and 1100 series "QuatPump" for
pumping modifier in prep flow
UV detector: 1100 series "MWD" Multi Wavelength Detector
MS detector: 1100 series "LC-MSD VL"
Fraction Collector: 2×"Prep-FC"
Make Up pump: "Waters RMA"
Agilent Active Splitter
Software:
Chemstation: Chem32
Agilent MS running conditions:
Capillary voltage: 4000 V (3500 V on ES Negative)
Fragmentor/Gain: 150/1
Drying gas flow: 13.0 L/min
Gas Temperature: 350° C.
Nebuliser Pressure: 50 psig
Scan Range: 125-800 amu
Ionisation Mode: ElectroSpray Positive or
ElectroSpray Negative
Columns:

A range of commercially available columns—both achiral and chiral—may be used such that, in conjunction with the changes in mobile phase, organic modifier and pH, they enabled the greatest cover in terms of a broad range of selectivity. All columns were used in accordance with the manufacturers recommended operating conditions. Typically 5 micron particle sized columns were used where available. For example, columns from Waters (including but not limited to XBridge Prep Phenyl 5μ OBD 100×19 mm, XBridge Prep C18 5μ OBD 100×19 mm, Waters Atlantis Prep T3 OBD 5μ 100×19 mm and SunFire Prep C18 OBD 5μ 100×19 mm), Phenomenex (including but not limited to Synergy MAX-RP and LUX™ Cellulose-2), Astec (Chirobiotic™ columns including but not limited to V, V2 and T2) and Diacel® (including but not limited to Chiralpak® AD-H) were available for screening.

Eluents:

Mobile phase eluent was chosen in conjunction with column manufacturers recommended stationary phase limitations in order to optimise a columns separation performance.

Methods:

According to the analytical trace the most appropriate preparative chromatography type was chosen. A typical routine was to run an analytical LC-MS using the type of chromatography (low or high pH) most suited for compound structure. Once the analytical trace showed good chromatography a suitable preparative method of the same type was chosen.

Solvent:

All compounds were usually dissolved in 100% MeOH or 100% DMSO or 90:10 Methanol:Water+0.2% Formic Acid.

Supercritical Fluid Chromatography (SFC)

In some cases, final compounds were purified by Supercritcal Fluid Chromatography (SFC) using a Waters Thar Prep100 preparative SFC system (P200 CO2 pump, 2545 modifier pump, 2998 UV/VIS detector, 2767 liquid handler with Stacked Injection Module). The Waters 2767 liquid handler acted as both auto-sampler and fraction collector.

The column used for the preparative purification of the compounds was a Diacel Chiralpak IA/IB/IC, YMC Amylose/Cellulose C or Phenomenex Lux Cellulose-4 at 5 um 20-21.2×250 mm unless otherwise stated.

Appropriate isocratic methods were selected based on methanol, ethanol or isopropanol solvent systems under un-modified or basic conditions. The standard method used was typically 5-55% modifier/CO2, 100 ml/min, 120 Bar backpressure, 40° C. column temperature.

All compounds were screened analytically prior to the purification step. Each sample was run under both un-modified and basic conditions (5.0 ul injection, 5/95 gradient for 5 minutes) across ethanol, methanol and isopropanol. If necessary, secondary screen across extended solvents such as acetonitrile, ethyl acetate and THF may also be considered. A decision was then made by the analyst as to what pH and which isocratic condition to use depending on where the desired product elutes and the separation achieved.

The modifier used under basic conditions was diethyl amine (0.1% V/V). Occasionally formic acid (0.1% V/V) may be used as an acidic modifier.

The purification was controlled by Waters Fractionlynx software through monitoring at 210-400 nm and triggered a threshold collection value at 260 nm unless otherwise started. Collected fractions were analysed by SFC (Waters/Thar SFC systems with Waters SQD). The fractions that contained the desired product were concentrated by vacuum centrifugation.

From the information provided someone skilled in the art could purify the compounds described herein by preparative LC-MS.

Synthetic Methods

By following methods similar and/or analogous to general procedures below, the compounds set out below were prepared.

The following synthetic procedures are provided for illustration of the methods used; for a given preparation or step the precursor used may not necessarily derive from the individual batch synthesised according to the step in the description given.

Where a compound is described as a mixture of two diastereoisomers/epimers, the configuration of the stereocentre is not specified and is represented by straight lines.

As understood by a person skilled in the art, compounds synthesised using the protocols as indicated may exist as a solvate e.g. hydrate, and/or contain residual solvent or minor impurities. Compounds isolated as a salt form, may be integer stoichiometric i.e. mono- or di-salts, or of intermediate stoichiometry.

Some of the compounds below are isolated as the salt, for example depending on the acid used in the purification method. Some compounds are isolated as the free base.

Compounds containing a single stereocentre (R-configuration) at the 3-position are typically isolated as a single isomer using preparative chiral HPLC (as described in general methods); at (or towards) the final stage of the synthetic sequence. In these cases the stereochemistry at the 3-position is designated in accordance with IUPAC, using 'hashed' or 'solid' wedged lines. Unless stated otherwise, a straight like at a stereocentre indicates the compound exists as a mixture of both isomers.

An example [(3R)-3-(4-Chlorophenyl)-2-[(5-chloropyridin-2-yl)methyl]-4-fluoro-3-[(1-hydroxycyclopropyl)methoxy]-6-(2-hydroxypropan-2-yl)-2,3-dihydro-1H-isoindol-1-one] is shown in Figure A.

FIG. A: Example showing purification of 3R-isomer by chiral HPLC; (3R)-3-(4-Chlorophenyl)-2-[(5-chloropyridin-2-yl)methyl]-4-fluoro-3-[(1-hydroxycyclopropyl)methoxy]-6-(2-hydroxypropan-2-yl)-2,3-dihydro-1H-isoindol-1-one.

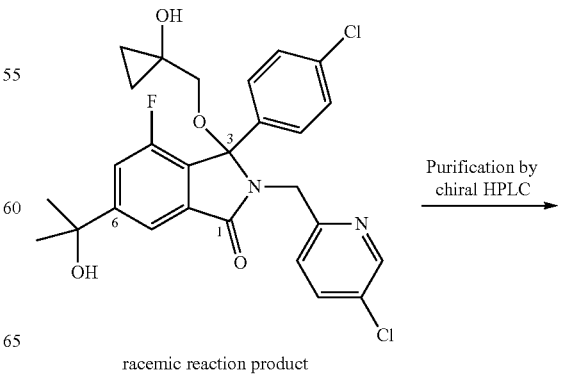

racemic reaction product

-continued

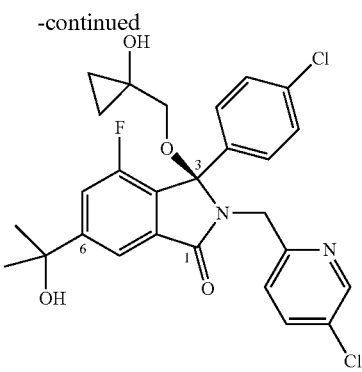

Example (single enantiomer with R-configuration)

Compounds containing a second stereocentre (e.g. adjacent to the 6-position) are typically isolated as a single isomer by preparative achiral and/or chiral HPLC. In these cases, the stereochemistry at the 3 position is designated in the usual fashion, using 'hashed' or 'solid' wedged lines. An asterisk (*) at the second stereocentre indicates one (or both) of the diasteroisomers associated with this position was/were isolated separately. For example, the 2 isomers of (3R)-3-(4-chlorophenyl)-2-[(5-chloropyridin-2-yl)methyl]-4-fluoro-6-[1-hydroxy-1-(1-methyl-1H-pyrazol-4-yl)ethyl]-3-[(1-hydroxycyclopropyl)methoxy]-2,3-dihydro-1H-isoindol-1-one were separated by preparative achiral and/or chiral HPLC to give two separate Examples (Figure B).

Note: Depending on the specific substitution pattern, the numbering system in some analogues may differ, according to the formal convention of nomenclature.

FIG. B: Asterisk (*) means the two isomers were separated and isolated to give the two diasteroisomeric examples

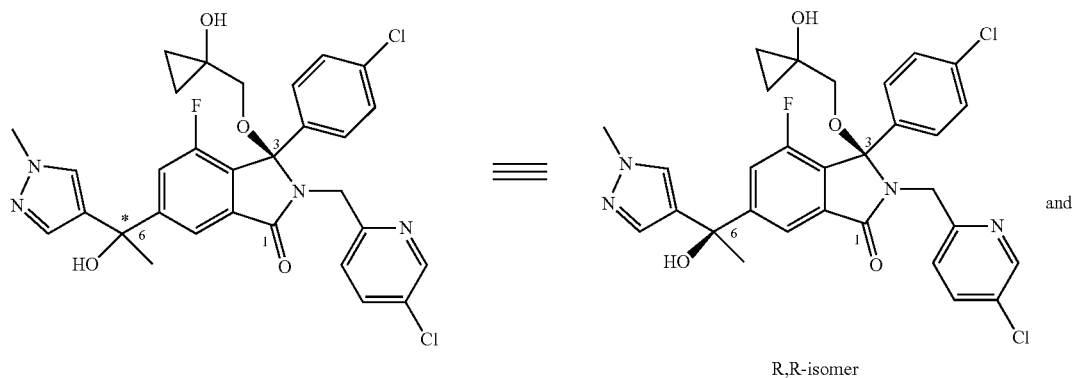

R,R-isomer and

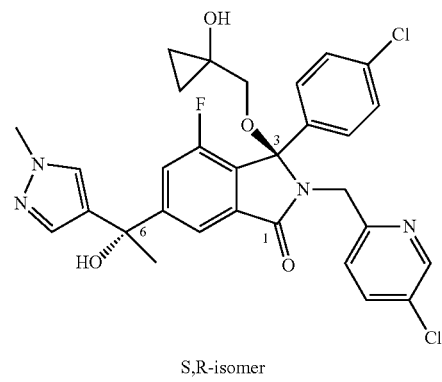

S,R-isomer

In other cases, isomers were separated at an intermediate stage in the synthesis and only one isomer progressed to the final Example. The relevant isomers can be characterised by either optical rotation of linearly polarized light and/or or relative retention time on a chiral HPLC column. In these cases, an asterisk (*) indicates that the compound was isolated as a single isomer. This is illustrated by Example 280 (Figure C)

FIG. C: Synthesis of Example 280, (1-({[(1R)-1-(4-chlorophenyl)-2-[(5-cyanopyridin-2-yl)methyl]-7-fluoro-5-[1-hydroxy-1-(oxan-4-yl)ethyl]-3-oxo-2,3-dihydro-1H-isoindol-1-yl]oxy}methyl)cyclopropane-1-carboxamide). Example is derived from the levorotary enantiomer of compound (3), followed by a preparative chiral HPLC at the final stage.

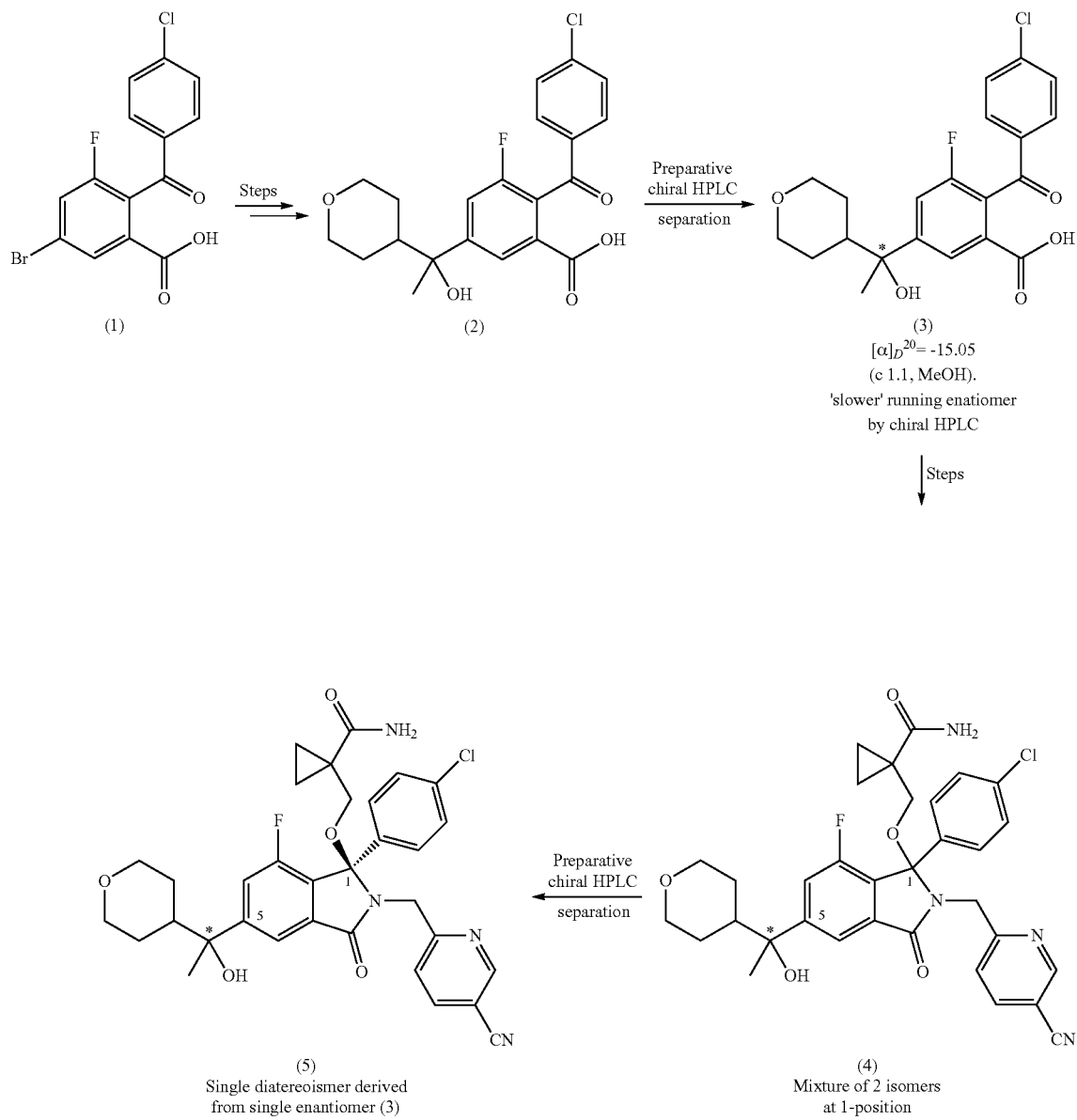

Examples containing further additional chiral substituents (e.g. 3-cyclopentanediol) are also typically isolated as a single isomer by preparative chiral HPLC. The stereochemistry at all 3 positions is designated in the usual fashion, using 'hashed' or 'solid' wedged lines. An example is shown in Figure D Figure D: Showing synthetic routes towards the two Examples which were isolated as single isomers by preparative chiral HPLC.

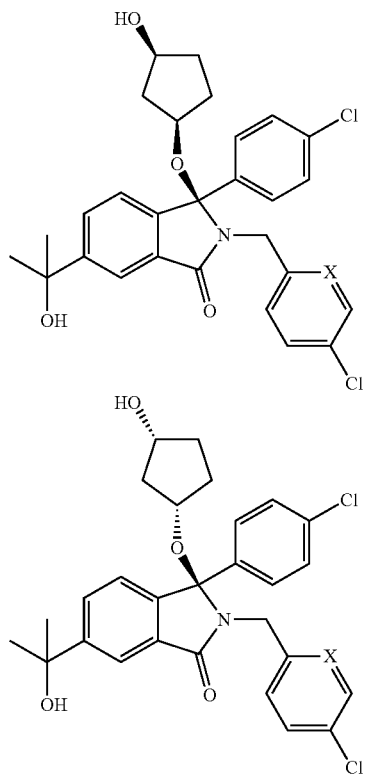

The optical isomers may be characterised by their optical activity (i.e. as + and − isomers, or d and l isomers). The stereocentre can also assigned as "R or S" according to the nomenclature developed by Cahn, Ingold and Prelog, see *Advanced Organic Chemistry* by Jerry March, 4th Edition, John Wiley & Sons, New York, 1992, pages 109-114, and see also Cahn, Ingold & Prelog, *Angew. Chem. Int. Ed. Engl.*, 1966, 5, 385-415.

Optical isomers can be separated by a number of techniques including chiral chromatography (chromatography on a chiral support) and such techniques are well known to the person skilled in the art.

As an alternative to chiral chromatography, optical isomers of basic compounds can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulfonic acid, separating the diastereoisomeric salts by preferential crystallisation, and then dissociating the salts to give the individual enantiomer of the free base. Likewise, optical iomers of acidic compounds can be separated by forming diastereoisomeric salts with chiral amines such as Brucine, Cinchonidine, quinine etc.

Additionally enantiomeric separation can be achieved by covalently linking a enantiomerically pure chiral auxiliary onto the compound and then performing diastereisomer separation using conventional methods such as chromatography. This is then followed by cleavage of the aforementioned covalent linkage to generate the appropriate enantiomerically pure product. Examples could include making menthol esters of an acidic compound.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers.

Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer).

Compounds encompassing double bonds can have an E (entgegen) or Z (zusammen) stereochemistry at said double bond. Substituents on bivalent cyclic or (partially) saturated radicals may have either the cis- or trans-configuration. The terms cis and trans when used herein are in accordance with Chemical Abstracts nomenclature (J. Org. Chem. 1970, 35 (9), 2849-2867), and refer to the position of the substituents on a ring moiety.

Of special interest are those compounds of formula (I) which are stereochemically pure. When a compound of formula (I) is for instance specified as R, this means that the compound is substantially free of the S isomer. If a compound of formula (I) is for instance specified as E, this means that the compound is substantially free of the Z isomer. The terms cis, trans, R, S, E and Z are well known to a person skilled in the art.

Preparation 1: {1-[Hydroxy($^2$H$_2$)methyl]cyclopropyl}($^2$H$_2$)methanol

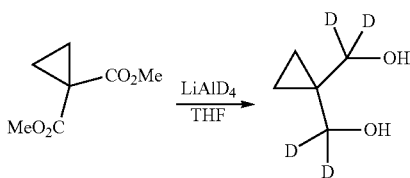

To a suspension of LiAID$_4$ (3.15 g, 75 mmol) in THF (75 mL) was added a solution of the ester (4.74 g, 30 mmol) in THF (25 mL) at 0° C. The reaction mixture was left to warm to room temperature and stirred for 16 h. The mixture was cooled (ice bath) and 2N aqueous NaOH (15 mL) was added slowly. The reaction mixture was stirred at room temperature for 1 h, filtered through a plug of MgSO$_4$ and then concentrated in vacuo. The residue was dissolved in DCM and the water layer removed. The organic layer was dried (MgSO$_4$) and then the solvent evaporated to afford colourless oil (3.0 g, 94%).

1H NMR (400 MHz, DMSO-d6): 4.30 (2H, s), 0.30 (4H, s).

Preparation 2: 1-Hydroxymethyl-cyclopropanol

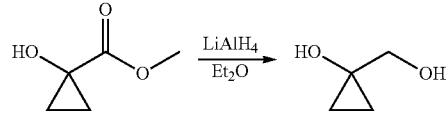

An Et$_2$O solution (10 mL) of ester (3.17 g, 27.35 mmol) was added dropwise to a stirring solution of LiAlH$_4$ (2.08 g, 54.71 mmol) in Et$_2$O (60 mL) at 0° C. under N$_2$. After stirring for 20 minutes the reaction was quenched by sequential addition of H$_2$O (2 mL), 2M NaOH (2 mL) and H$_2$O (6 mL). MgSO$_4$ and celite were added, additional Et$_2$O was added to aid stirring and the mixture was stirred for 5 minutes before being filtered, washed with Et$_2$O (50 ml) and concentrated in vacuo to give the title compound (1.44 g, 16.35 mmol, 60% yield) as a light yellow oil. $^1$H NMR (CDCl$_3$) 3.65 (2H, s), 0.97-0.68 (2H, m), 0.68-0.49 (2H, m).

Preparation 3: (1-Methoxy-cyclopropyl)-methanol

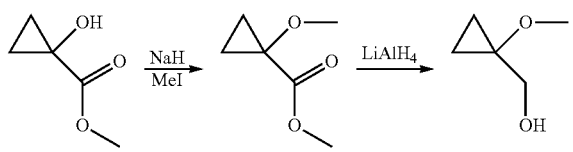

Step 1: 1-Methoxy-cyclopropanecarboxylic Acid methyl ester

To a solution of 1-hydroxy-cyclopropanecarboxylic acid methyl ester (2.0 g, 17.24 mmol) in THF (20 mL) was added NaH (60%, 1.04 g, 26.0 mmol) in small portions at 00° C. The reaction mixture was stirred for 15 mins, iodomethane (2.0 mL, 32.12 mmol) was added and the mixture was stirred at room temperature overnight. Saturated NH$_4$Cl was added and the product was extracted with EtOAc. The organic phase was dried, filtered and the solvent evaporated to afford yellow oil (1.64 g, 74%).

1H NMR (400 MHz, CDCl3): 3.77 (3H, s), 3.44 (3H, s), 1.33-1.24 (4H, m).

Step 2: (1-Methoxy-cyclopropyl)-methanol

LiAlH$_4$ (0.98 g, 25.7 mmol) was added to ice-cooled THF (30 mL). A solution of 1-methoxy-cyclopropanecarboxylic acid methyl ester (1.67 g, 12.85 mmol) in THF (10 mL) was slowly added. The reaction mixture was stirred at 00° C. for 1 h, then at room temperature for 1 h, cooled with ice and 2N NaOH (5 mL) was slowly added. The reaction mixture was stirred at room temperature for 1 h, MgSO$_4$ was added, the precipitate was filtered, the filtrate evaporated to afford pale yellow oil (1.3 g, 99%).

1H NMR (400 MHz, CDCl3): 3.68 (2H, s), 3.36 (3H, s), 1.82 (1H, s), 1.28 (4H, t).

Preparation 4: 1-Hydroxymethyl-cyclopropanecarbonitrile

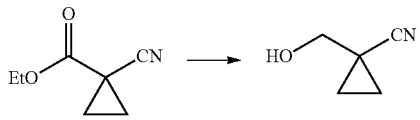 [SMILES: CCOC(=O)C1(C#N)CC1 ; N#CC1(CO)CC1]

Ethyl 1-cyano-cyclopropanecarboxylate (5.08 g, 36.51 mmol) was dissolved in 1,2-dimethyoxyethane (100 mL) and methanol (10 mL) and cooled to 0° C. NaBH$_4$ (2.77 g, 73.02 mmol) was added in portions over 1 h and the reaction was left to warm to room temperature over 18 h. The reaction was quenched with saturated aqueous NH$_4$Cl (20 mL) and extracted with EtOAc (300 mL then 100 mL). The combined organic extracts were dried over MgSO$_4$ and concentrated in vacuo to give the title compound as a colourless oil (3.58 g). $^1$H NMR (400 MHz, DMSO-d$_6$): 5.29 (1H, t), 3.40 (2H, d), 1.22-1.12 (2H, m), 0.97-0.89 (2H, m).

Preparation 5: (1-Methanesulfonyl-cyclopropyl)-methanol

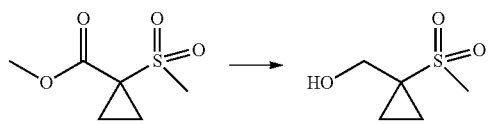

The title compound was prepared from 1-methanesulfonyl-cyclopropanecarboxylic acid methyl ester (2.0 g, 10.4 mmol) in a similar manner to that described in Preparation 2. $^1$H NMR (400 MHz, CDCl3): 3.93 (2H, s), 3.06 (3H, s), 2.43 (1H, s), 1.56-1.47 (2H, m), 1.09-1.02 (2H, m).

Preparation 6: N-(1-Hydroxymethyl-cyclopropyl)-acetamide

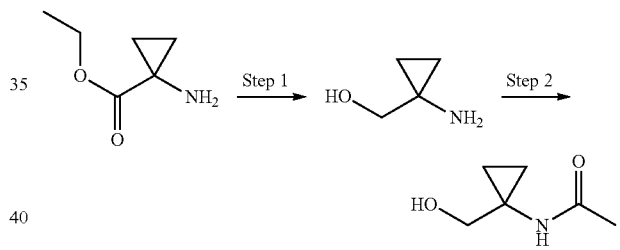

Step 1: (1-Amino-cyclopropyl)-methanol

1-Amino-cyclopropanecarboxylic acid ethyl ester dihydrochloride (3.0 g, 18.1) was partitioned between NaHCO$_3$ and EtOAc and the aqueous phase was extracted with EtOAc (3×). The organic phases were collected, dried over Na$_2$SO$_4$, filtered and concentrated in vacuo to give 1-amino-cyclopropanecarboxylic acid ethyl ester as a free base (1.2 g).

The title compound was then prepared from 1-amino-cyclopropanecarboxylic acid ethyl ester in a similar manner to that described in Preparation 2. $^1$H NMR (400 MHz, DMSO-d6): 5.31-4.10 (1H, m), 3.26 (2H, s), 1.77 (2H, s), 0.42-0.21 (4H, m).

Step 2: N-(1-Hydroxymethyl-cyclopropyl)-acetamide

Acetic anhydride (860 µL, 9 mmol) was added to a solution of (1-amino-cyclopropyl)-methanol (667 mg, 7.57 mmol) in EtOAc (20 mL) and the reaction was stirred at room temperature for 16 hours. Solid NaHCO$_3$ (200 mg) was added to reaction mixture which was then filtered through Celite. The solvent was removed in vacuo and the Preparation 7: (1R,3S)-3-(tert-Butyl-dimethyl-silanyloxy)-cyclopentanol

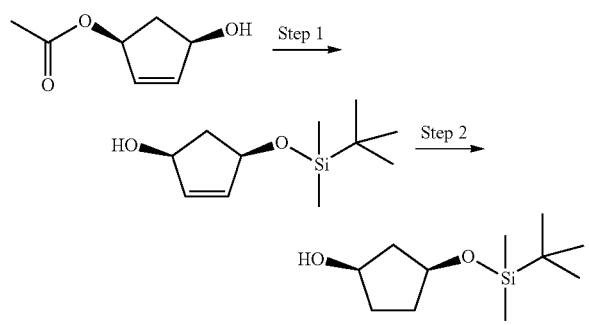

Step 1: (1S,4R)-4-(tert-Butyl-dimethyl-silanyloxy)-cyclopent-2-enol

To a solution of acetic acid (1S,4R)-4-hydroxy-cyclopent-2-enyl ester (Aldrich) (2.0 g, 14.1 mmol) in THF (70 mL) at 0° C. were added imidazole (1.9 g, 28.2 mmol) and tert-butyldimethyl chlorosilane (2.5 g, 17.0 mmol) and then the reaction mixture was stirred at room temperature for 16 hours. The reaction was quenched with water and the product was extracted with EtOAc. The organic phase was dried over $Na_2SO_4$, filtered and concentrated in vacuo to give 4.0 g of a colourless oil (quantitative yield). The crude material was dissolved in MeOH (90 mL), $K_2CO_3$ (2.4 g, 17 mmoL) was added and the resulting suspension was stirred for 2 hours at room temperature. The mixture was concentrated in vacuo to ~1/2 of the volume and the residue was partitione between water and EtOAc. The organic phase was collected, dried over $Na_2SO_4$, filtered and concentrated in vacuo to give 3.15 g of a colourless oil (quant. yield).

$^1$H NMR (400 MHz, CDCl3): 5.97 (1H, d), 5.93-5.84 (1H, m), 4.68 (1H, t), 4.61 (1H, t), 3.56 (1H, s), 2.77-2.65 (1H, m), 1.66-1.48 (1H, m), 0.92 (9H, s), 0.21-0.10 (6H, m).

Step 2: (1R,3S)-3-(tert-Butyl-dimethyl-silanyloxy)-cyclopentanol

A suspension of (1S,4R)-4-(tert-butyl-dimethyl-silanyloxy)-cyclopent-2-enol (3.0 g, 14.0 mmol) and Pt on Alumina (5 wt %, 2.7 g) in EtOAc (50 mL) and EtOH (10 mL) was stirred under $H_2$ (1 atm) for 16 hours. The reaction mixture was filtered through Celite and the solvent was removed in vacuo to give 2.3 g of the desired product as a colourless oil. 1H NMR (400 MHz, CDCl3): 4.41 (1H, t), 4.33-4.06 (1H, m), 2.73 (1H, s), 2.00-1.83 (4H, m), 1.83-1.72 (1H, m), 1.72-1.47 (1H, m), 0.95-0.66 (9H, m), 0.29--0.08 (6H, m).

Preparation 8: (1S,3R)-Cyclopentane-1,3-diol

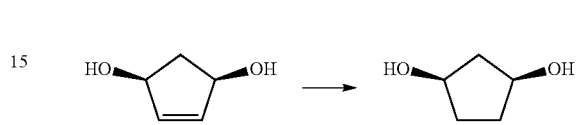

A suspension of (1R,3S)-cyclopent-4-ene-1,3-diol (1.54 g, 15.4 mmol) and Pt on Alumina (5 w %, 3 g) in a mixture of EtOAc (50 mL) and EtOH (10 mL) was stirred under $H_2$ (1 atm) for 16 hours. The reaction mixture was filtered through Celite and the solvent was removed in vacuo to give the desired product as a colourless oil (1.6 g, quant. yield). $^1$H NMR (400 MHz, DMSO-d6): 4.46 (2H, d), 4.23-3.58 (2H, m), 2.08-1.96 (1H, m), 1.60 (4H, dd), 1.39-1.27 (1H, m).

Preparation 9: (+1-) 3-(tert-Butyl-dimethyl-silanyloxy)-cyclopentanol

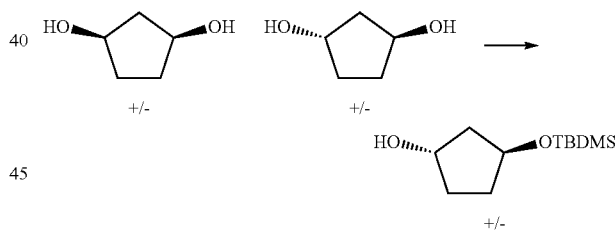

A solution of TBDMSCl (20.7 g, 137.2 mmol) in THF (200 mL) was added to a solution of cyclopentane-1,3-diol (Cis+Trans mixture) (20.0 g, 196 mmol) and imidazole (13.3 g, 196 mmol) in THF (600 mL) and the resulting suspension was stirred at room temperature for 16 hours. The mixture was diluted with EtOAc and washed with water and brine. The organic phase was dried over $Na_2SO_4$, filtered and concentrated in vacuo. The residue was purified by Biotage (gradient 0-50% EtOAc in petrol) to give the desired product as a colourless oil (20.5 g, Y=48%). $^1$H NMR (400 MHz, CDCl3): 4.54-4.35 (2H, m), 2.69-1.92 (2H, m), 1.92-1.69 (2H, m), 1.69-1.43 (3H, m), 1.08-0.63 (9H, m), 0.40--0.12 (6H, m).

Preparation 10A: 6-Bromo-3-(4-Chloro-2-Fluorophenyl)-2-((5-Chloropyridin-2-Yl)Methyl)-3-Hydroxyisoindolin-1-One

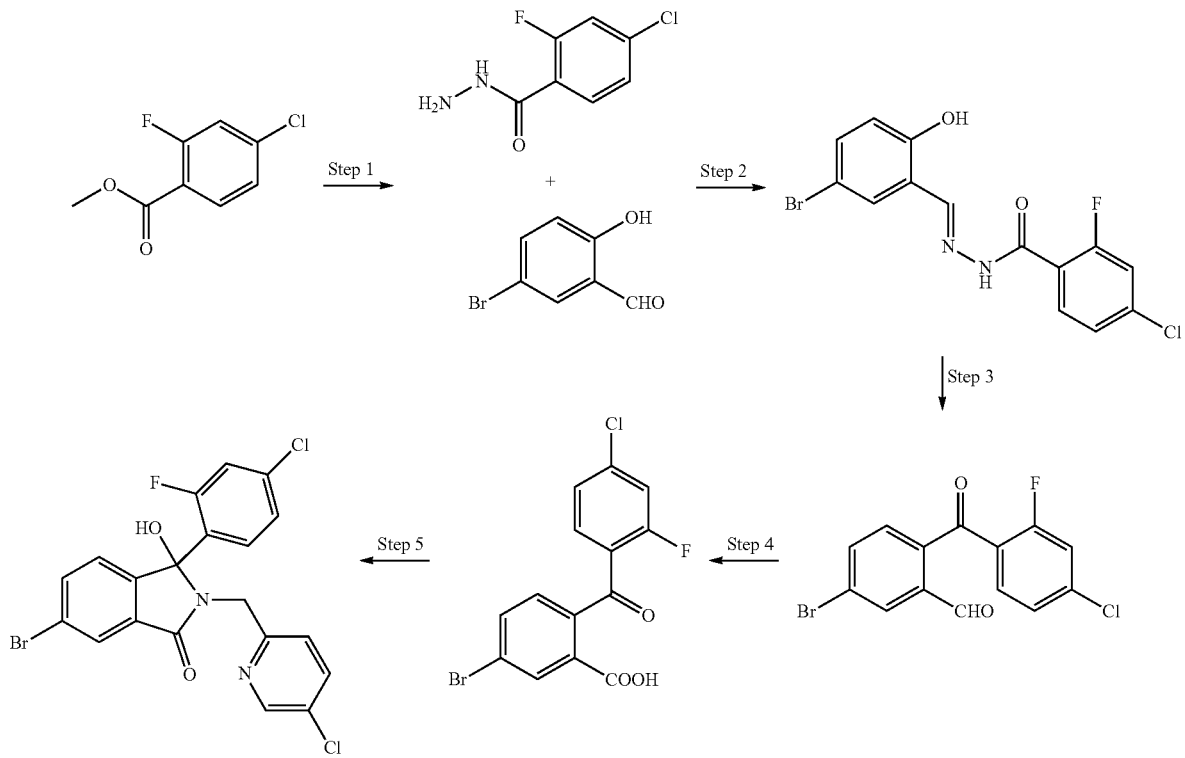

Preparation 10A, Step 1: 4-Chloro-2-fluorobenzohydrazide

Methyl 4-chloro-2-fluorobenzoate (10.0 g, 53.19 mmol) was dissolved in EtOH (150 mL) at RT under $N_2$. Hydrazine monohydrate (12.95 mL, 265.96 mmol) was added and the resultant solution heated at 80° C. for 30 minutes. Solution allowed to cool and stand overnight, solvent was removed in vacuo. to afford crude title compound as fine yellow needles (10.83 g). $^1$H NMR (400 MHz, MeOD) 7.71 (1H, m) 7.37-7.32 (2H, m).

Preparation 10A, Step 2: (E/Z)—N'-(5-Bromo-2-hydroxybenzylidene)-4-chloro-2-fluorobenzohydrazide 5-Bromo-2-hydroxybenzaldehyde (4.28 g, 21.28 mmol) was dissolved in acetic acid (100 mL). Crude 4-chloro-2-fluorobenzohydrazide (4.00 g) was added at RT and the resultant solution stirred for 15 min. A yellow solid had precipitated and the reaction mixture was poured into ice cold water (100 mL). The yellow solid was filtered off under vacuum, washing once with ether. The solid was dried overnight to afford crude title compound as a yellow solid (6.35 g). $^1$H NMR (400 MHz, DMSO) 8.53 (1H, s), 7.81 (1H, d), 7.75 (1H, dd), 7.65 (1H, dd), 7.48-7.38 (2H, m), 6.91 (1H, d).

Preparation 10A, Step 3: 5-Bromo-2-(4-chloro-2-fluorobenzoyl)benzaldehyde

THF (170 mL) was added to crude (E/Z)—N'-(5-bromo-2-hydroxybenzylidene)-4-chloro-2-fluorobenzohydrazide (6.35 g) to form a suspension. Pb(OAc)$_4$ (7.58 g, 17.12 mmol) was then added portion wise and the resultant solution stirred at RT under $N_2$ overnight. The reaction mixture was filtered through Celite, washing with EtOAc. The organic filtrate was washed with sat. NaHCO$_3$ $_{(aq)}$ and brine, dried over MgSO$_4$, filtered and solvent removed in vacuo to give crude material. Purified by column chromatography, Biotage Isolera, 100 g KP-sil cartridge 0-50% EtOAc/isohexane to afford the title compound as an orange oil (1.48 g). $^1$H NMR (400 MHz, DMSO) 10.01 (1H, s), 8.29 (1H, d), 8.06 (1H, dd), 7.78 (1H, dd), 7.64 (1H, dd), 7.58 (1H, d), 7.50 (1H, dd).

Preparation 10A, Step 4: 5-Bromo-2-(4-chloro-2-fluorobenzoyl)benzoic Acid

To a solution of 5-bromo-2-(4-chloro-2-fluorobenzoyl) benzaldehyde (1.48 g, 4.34 mmol) in acetonitrile (55 mL) was added a solution of sodium chlorite (0.508 g, 5.64 mmol) in water (6.0 mL), followed by a solution of sulfamic acid (0.547 g, 5.64 mmol) in water (6.0 mL). The resultant mixture was stirred at RT for 30 min before solvent was removed in vacuo. The crude oil was diluted with EtOAc and the organics washed with water and brine and dried over MgSO$_4$. The suspension was filtered and solvent removed in vacuo to afford the title compound as a dark yellow solid (1.34 g, 87%). $^1$H NMR (400 MHz, DMSO) 13.69 (1H, s), 8.06 (1H, d), 7.95 (1H, dd), 7.70 (1H, dd), 7.57 (1H, dd), 7.48-7.42 (2H, m).

Preparation 10A, Step 5: 6-Bromo-3-(4-chloro-2-fluorophenyl)-2-((5-chloropyridin-2-yl)methyl)-3-hydroxyisoindolin-1-one To a solution of 5-bromo-2-(4-chloro-2-fluorobenzoyl) benzoic acid (1.34 g, 3.75 mmol) in dry THF (20.0 mL) was added SOCl$_2$ (0.55 mL, 7.50 mmol) and a catalytic amount of DMF, the resultant solution was stirred at RT under $N_2$ for 4 h. Solvent was removed in vacuo after this time and the residue dissolved in dry THF (20.0 mL) before (5-chloropyridine-2-yl)methaneamine dihydrochloride (0.905 mg, 4.13 mmol) and DIPEA (2.02 mL, 11.63 mmol) were added and the resultant solution stirred at RT overnight. Reaction mixture diluted with EtOAc, washed with water (×2) and brine, organic layer dried over $MgSO_4$, filtered and solvent removed in vacuo to give crude material as a light brown solid. Crude solid was triturated from ether to afford the title compound as a beige solid (1.32 g, 73%). $^1$H NMR (400 MHz, DMSO) 8.30 (1H, d), 7.94 (2H, d), 7.91 (2H, dd), 7.79 (2H, dd), 7.76 (2H, dd), 7.56 (1H, s), 7.32 (1H, dd), 7.26 (2H, dd), 7.04 (1H, dd), 4.54 (1H, d), 4.44 (1H, d).

The following compounds were prepared in a similar manner:

Preparation 10B: 6-Bromo-2-((5-chloropyridin-2-yl)methyl)-3-(4-ethylphenyl)-3-hydroxyisoindolin-1-one

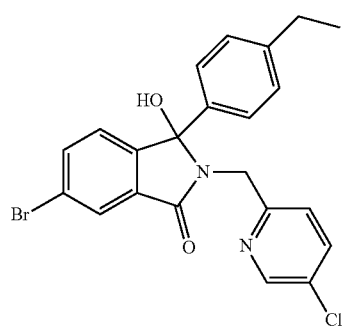 [SMILES: CCc1ccc(C2(O)c3ccc(Br)cc3C(=O)N2Cc2ccc(Cl)cn2)cc1]

The title compound was prepared from 5-bromo-2-hydroxybenzaldehyde and 4-ethylbenzohydrazide in a similar manner to that described in Preparation 10A, steps 2-5. $^1$H NMR (400 MHz, $CDCl_3$): 8.39 (d, 1H), 7.90 (d, 1H), 7.69 (dd, 1H), 7.63 (dd, 1H), 7.37 (d, 3H), 7.20 (dd, 3H), 4.98 (d, 1H), 4.13 (d, 1H), 2.65 (q, 2H), 1.22 (t, 3H).

Preparation 10C: 6-Bromo-2-((5-chloropyridin-2-yl)methyl)-3-(4-(1,1-difluoroethyl)phenyl)-3-hydroxyisoindolin-1-one

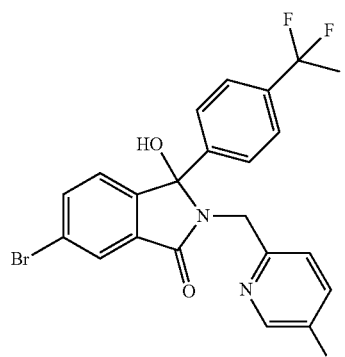

6-Bromo-2-((5-chloropyridin-2-yl)methyl)-3-(4-(1,1-difluoroethyl)phenyl)-3-hydroxyisoindolin-1-one was prepared from ethyl 4-(1,1-difluoroethyl)benzoate in a similar manner to that described in Preparation 10A, steps 1-5.

Preparation 10D: 4-(5-Bromo-2-((5-chloropyridin-2-yl)methyl)-1-hydroxy-3-oxoisoindolin-1-yl)benzonitrile

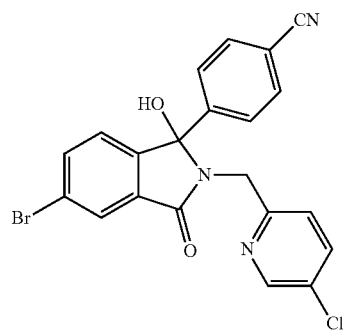 [SMILES: N#Cc1ccc(C2(O)c3ccc(Br)cc3C(=O)N2Cc2ccc(Cl)cn2)cc1]

The title compound was prepared from methyl 4-cyanobenzoate in a similar manner to that described in Preparation 10A, steps 1-5. $^1$H NMR (400 MHz, DMSO) 8.36 (1H, d), 7.96 (1H, d), 7.81 (1H, dd), 7.73 (1H, dd), 7.69 (2H, d), 7.57 (1H, s), 7.44 (2H, d), 7.27-7.23 (2H, m), 4.56 (1H, d), 4.43 (1H, d).

Preparation 10E: 6-Bromo-2-((5-chloropyridin-2-yl)methyl)-3-(4-fluorophenyl)-3-hydroxyisoindolin-1-one

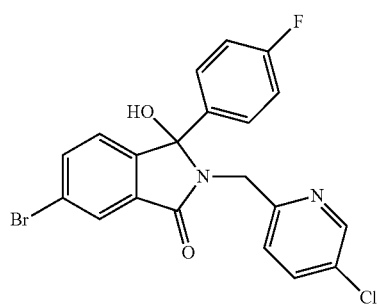 [SMILES: O=C1c2cc(Br)ccc2C(O)(c2ccc(F)cc2)N1Cc1ccc(Cl)cn1]

The title compound was prepared from methyl 4-fluorobenzohydrazide in a similar manner to that described in Preparation 10A, steps 2-5. MS: [M−H]$^-$=447.1

Preparation 10F: 6-Bromo-2-((5-chloropyridin-2-yl)methyl)-3-hydroxy-3-(4-(trifluoromethyl)phenyl)isoindolin-1-one

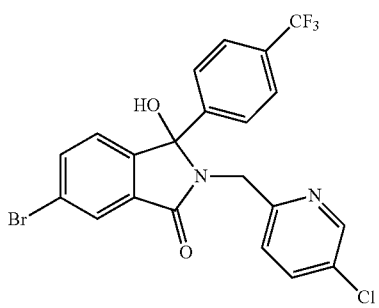 [SMILES: O=C1c2cc(Br)ccc2C(O)(c2ccc(C(F)(F)F)cc2)N1Cc1ccc(Cl)cn1]

The title compound was prepared from methyl 4-(trifluoromethyl)benzohydrazide in a similar manner to that described in Preparation 10A, steps 2-5. MS: [M−H]⁻=497.2

Preparation 10G: 6-Bromo-2-((5-chloropyridin-2-yl)methyl)-3-(3,4-difluorophenyl)-3-hydroxyisoindolin-1-one

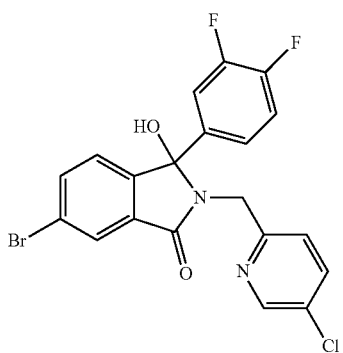 [SMILES: O=C1c2cc(Br)ccc2C(O)(c2ccc(F)c(F)c2)N1Cc1ccc(Cl)cn1]

The title compound was prepared from methyl 3,4-difluorobenzoate in a similar manner to that described in Preparation 10A, steps 1-5. $^1$H NMR (400 MHz, DMSO-d6): 8.39 (1H, d), 7.94 (1H, d), 7.80 (1H, dd), 7.75 (1H, dd), 7.49 (1H, s), 7.35-7.22 (4H, m), 7.04-7.01 (1H, m), 4.56 (1H, d, 4.46 (1H, d).

Preparation 10H: 2-[(5-Chloropyridin-2-yl)methyl]-3-hydroxy-6-(2-hydroxypropan-2-yl)-3-[4-(trifluoromethoxy)phenyl]-2,3-dihydro-1H-isoindol-1-one

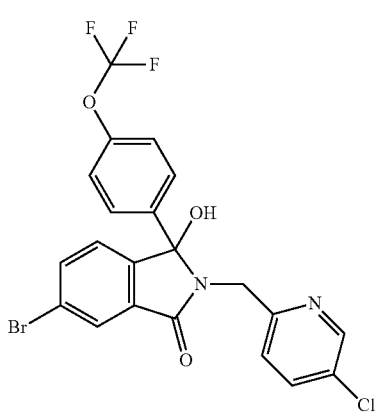 [SMILES: O=C1c2cc(Br)ccc2C(O)(c2ccc(OC(F)(F)F)cc2)N1Cc1ccc(Cl)cn1]

The title compound was prepared from methyl 4-trifluoromethoxybenzoate in a similar manner to that described in Preparation 10A, steps 1-5. $^1$H NMR (400 MHz, DMSO-d$_6$): 8.36 (1H, d), 7.95 (1H, s) 7.80 (1H, dd) 7.67 (1H, dd), 7.49 (1H, s), 7.36 (1H, dd), 7.27 (1H, d), 7.26-7.16 (3H, m), 4.52 (2H, dd).

Preparation 10I: 6-Bromo-4-chloro-3-(4-chlorophenyl)-2-[(5-chloropyridin-2-yl)methyl]-3-hydroxy-2,3-dihydro-1H-isoindol-1-one

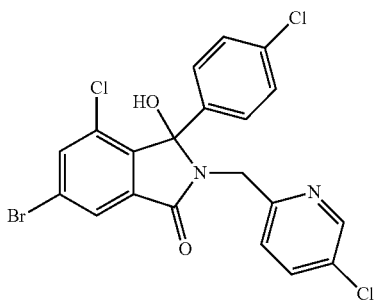 [SMILES: O=C1c2cc(Br)cc(Cl)c2C(O)(c2ccc(Cl)cc2)N1Cc1ccc(Cl)cn1]

The title compound was prepared from 5-bromo-3-chloro-2-hydroxybenzaldehyde and 4-chlorobenzhydrazide in a similar manner to that described in Preparation 10A, steps 2-5. MS: [M−H]⁻=497.2

Preparation 11:
(1-Hydroxymethyl-cyclopropyl)-carbamic acid 2-trimethylsilanyl-ethyl ester

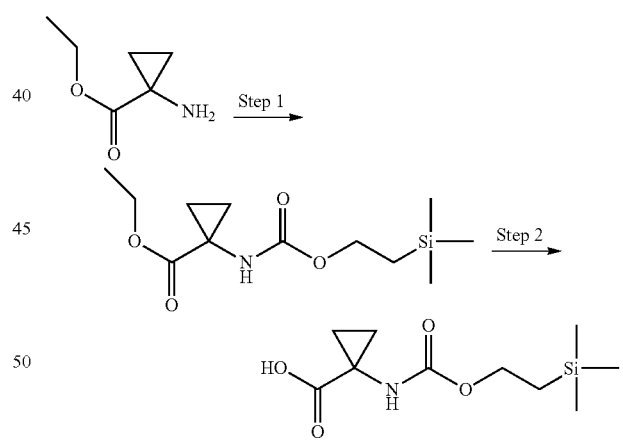

Step 1: 1-(2-Trimethylsilanyl-ethoxycarbonylamino)-cyclopropanecarboxylic Acid methyl ester To a solution of 1-amino-cyclopropanecarboxylic acid ethyl ester hydrochloride (2.0 g, 12.0 mmol) in dioxane (60 mL) were added triethylamine (4.2 mL, 30.0 mmol) and 1-[2-(trimethylsilyl)ethoxycarbonyloxy]pyrrolidin-2,5-dione (4.7 g, 18.0 mmol) and the reaction mixture was stirred for 16 h. Water (50 mL) was added, the product was extracted with EtOAc. The organic phase was washed with 1N HCl, dried, filtered and the solvent evaporated. The crude product was purified on Biotage using 0-30% EtOAc in petrol to afford the product (3.26 g, 99%).

Step 2: (1-Hydroxymethyl-cyclopropyl)-carbamic Acid 2-trimethylsilanyl-ethyl ester LiAlH$_4$ (0.77 g, 20.4 mmol) was added to ice-cooled THF (30 mL). A solution of 1-(2-trimethylsilanyl-ethoxycarbonylamino)-cyclopropanecarboxylic acid methyl ester (2.79 g, 10.2 mmol) in THF (20 mL) was slowly added. The reaction mixture was stirred at 0° C. for 1 h, then at room temperature for 1 h, cooled with ice and 2N NaOH (4 mL) was slowly added. The reaction mixture was stirred at room temperature for 1 h, MgSO$_4$ was added, the precipitate was filtered, the filtrate evaporated to afford colourless oil (2.3 g, 99%). 1H NMR (400 MHz, DMSO-d6): 7.23 (1H, s), 4.58 (1H, t), 3.99 (2H, t), 3.39 (2H, d), 0.90 (2H, t), 0.77-0.41 (4H, m), 0.02 (9H, s).

Preparation 12: 1-Hydroxymethyl-cyclopropanecarboxylic Acid methylamide

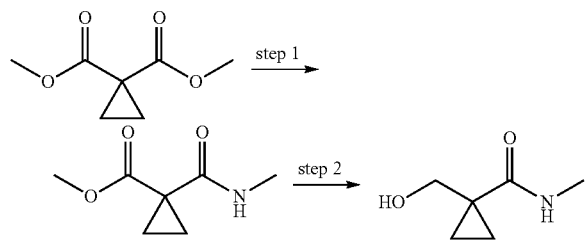

Step 1: 1-Methylcarbamoyl-cyclopropanecarboxylic Acid methyl ester

Methylamine (2M solution in THF, 35 mL, 69.9 mmol) was added to a solution of cyclopropane-1,1-dicarboxylic acid dimethyl ester (10.0 g, 63.3 mmol) in MeOH (50 mL) and the reaction mixture was stirred at room temperature for 3 days. The solvent was removed in vacuo and the residue was purified by column chromatography (gradient 0-100% EtOAc in Petrol) to give the desired product as a clear oil (4.74 g). $^1$H NMR (400 MHz, DMSO-d6): 8.24 (1H, s), 3.63 (3H, s), 2.65 (3H, d), 1.33 (4H, s).

Step 2: 1-Hydroxymethyl-cyclopropanecarboxylic Acid methylamide

A solution of 1-methylcarbamoyl-cyclopropanecarboxylic acid methyl ester (4.7 g, 29.9 mmol) in THF (100 mL) was slowly added to a suspension of lithium aluminium hydride (2.3 g, 59.8 mmol) in THF (100 mL) at 0° C. under N$_2$. The reaction was stirred at the same temperature for 20 minutes and then quenched by careful addition of 2N NaOH until gas development ceased. The reaction mixture was filtered through Celite and the filter cake was washed with EtOAc (300 mL). The organic phase was dried over Na$_2$SO$_4$, filtered and concentrated in vacuo to give 3.4 g of the desired product a s white solid. $^1$H NMR (400 MHz, DMSO-d6): 7.44 (1H, s), 5.00 (1H, t), 3.49 (2H, d), 2.62 (3H, d), 1.13-0.73 (2H, m), 0.73-0.27 (2H, m).

Preparation 13: (S)-1-(5-Chloro-pyridin-2-yl)-ethylamine

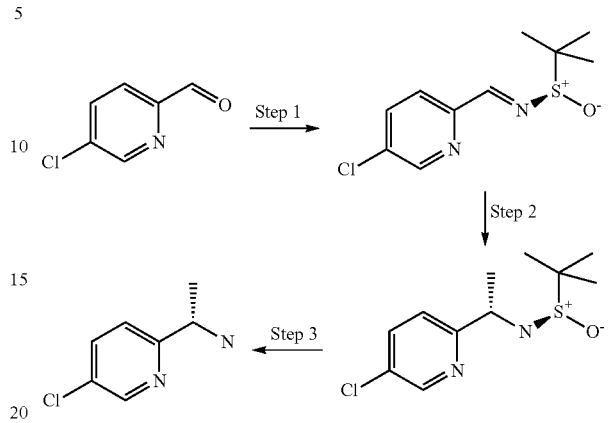

Step 1: (S)-2-Methyl-propane-2-sulfinic Acid 1-(5-chloro-pyridin-2-yl)-methylideneamide 5-Chloro-pyridine-2-carbaldehyde (5.70 g, 40.43 mmol), (S)-(−)-2-methyl-2-propanesulfinamide (5.14 g, 42.45 mmol) and cesium carbonate (14.50 g, 44.47 mmol) were suspended in CH$_2$Cl$_2$ (40 mL) and stirred for 3 days. The reaction mixture was passed through celite, diluted with CH$_2$Cl$_2$ (30 mL), washed with brine (30 mL), dried over MgSO$_4$ and concentrated in vacuo to give the title compound as a white solid (10.33 g). MS: [M+H] 245

Step 2: (S,S)—N-[(5-Chloropyridin-2-yl)methylidene]-2-methylpropane-2-sulfinamide Methylmagnesium chloride (22.5 mL, 3M in THF, 67.46 mmol) was added dropwise to a stirring solution of (S)-2-methyl-propane-2-sulfinic acid 1-(5-chloro-pyridin-2-yl)-methylideneamide (10.33 g, 42.16 mmol) in THF (120 mL) at −78° C. under N$_2$. The reaction was stirred for 90 minutes then quenched with saturated aqueous NH$_4$Cl solution (50 mL) and brine (50 mL) and extracted with ethyl acetate (3×100 mL). The combined organic layers were dried over MgSO$_4$ and concentrated in vacuo. The residual solid was suspended in 6 mL 1:1 IPA/ethanol and heated to 70° C. until all solids had dissolved. The solution was left to cool to room temperature over 16 hours and the formed crystals were filtered and washed with ice cold 1:1 IPA/ethanol (5 ml) and dried in a vacuum oven for 24 hours to give the title compound as colourless crystals (5.59 g). MS: [M+H] 261.

Step 3: (S)-1-(5-Chloro-pyridin-2-yl)-ethylamine (S,S)—N-[(5-Chloropyridin-2-yl)methylidene]-2-methylpropane-2-sulfinamide (5.59 g, 21.50 mmol) was dissolved in 2M HCl in Et$_2$O (35 mL). The reaction was stirred for 18 hours and the resulting precipitate was filtered and dried in a vacuum oven for 24 hours to give the title compound as an off-white powder (4.85 g 2×HCl salt). MS: [M+H] 157.
(The opposite isomer can be prepared in an analogous way using (R)-(−)-2-methyl-2-propanesulfinamide)

Preparation 14: (1S,2S)-2-(tert-Butyl-diphenyl-silyloxymethyl)-cyclopentanol

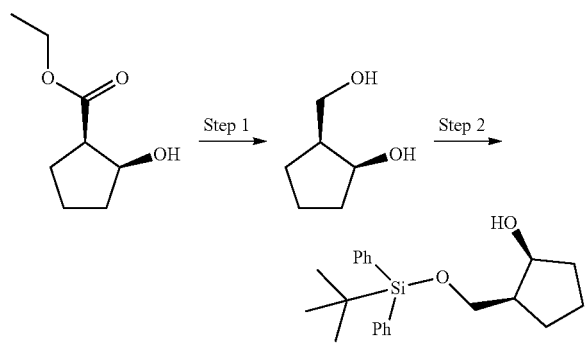

Step 1: (1S,2S)-2-Hydroxymethyl-cyclopentanol

A solution of ethyl (1R,2S)-2-hydroxy-cyclopentanecarboxylate (1 g, 6.33 mmol) in THF (10 mL) was added dropwise to a stirring suspension of LiAlH₄ (0.36 g, 9.49 mmol) in THF (10 mL) under N₂ at 0° C. The reaction was stirred for 30 mins and quenched with water (0.3 mL), 2M NaOH (0.3 mL) and water (1 mL). MgSO₄ and celite were added and stirred for 5 mins. The mixture was filtered through celite and washed with diethyl ether (2×50 mL). The filtrate was concentrated in vacuo to give the title compound as a colourless oil (0.81 g). ¹H NMR (400 MHz, CDCl₃): 4.51-4.29 (1H, m), 3.98-3.74 (2H, m), 2.20-2.03 (3H, m), 1.96-1.80 (2H, m), 1.75-1.63 (2H, m), 1.63-1.53 (2H, m).

Step 2: (1S,2S)-2-(tert-Butyl-diphenyl-silyloxymethyl)-cyclopentanol (1S,2S)-2-Hydroxymethyl-cyclopentanol (0.73 g, 6.33 mmol) was dissolved in CH₂Cl₂ (20 mL) and tert-butyldiphenylsilylchloride (1.74 g, 6.33 mmol), imidazole (0.86 g, 12.66 mmol) and N,N-dimethylpyridine (0.08 g, 0.63 mmol) were added and the reaction was stirred overnight. The reaction was quenched with saturated aqueous ammonium chloride (20 mL) and water (5 ml) and was extracted with CH₂Cl₂ (2×30 mL). The combined organic extracts were dried over MgSO₄, concentrated in vacuo and purified by Biotage (0-30% EtOAc/Petrol) to give the title compound as a colourless oil (1.87 g). ¹H NMR (400 MHz, DMSO-d6): 7.73-7.57 (6H, m), 7.50-7.40 (6H, m), 4.23 (1H, d), 4.14-4.06 (1H, m), 3.88 (1H, dd), 3.59 (1H, dd), 1.98-1.89 (1H, m), 1.76-1.61 (3H, m), 1.61-1.46 (2H, m), 1.46-1.33 (1H, m), 1.00 (9H, s).

Preparation 15: rac-1-(1-(Hydroxymethyl)cyclopropyl)ethan-1-ol

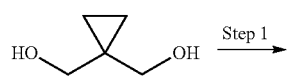

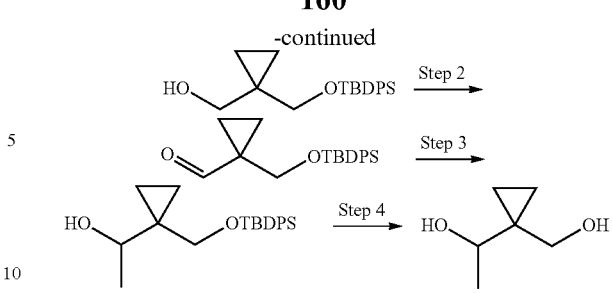

Step 1: (1-(((tert-Butyldiphenylsilyl)oxy)methyl)cyclopropyl)methanol

Under a N₂ atmosphere, an oven-dried flask was charged with 1,1-bis(hydroxymethyl)cyclopropane (700 mg, 6.85 mmol), anhydrous CH₂Cl₂ (30 mL) and Et₃N (0.57 mL, 4.11 mmol) to give a colourless solution. After cooling to 0° C. using an ice-bath, TBDPSCl (0.89 mL, 3.42 mmol) was added and the resulting mixture stirred for 20 h. The solvent was evaporated, EtOAc (20 mL) added and the mixture washed with H₂O (20 mL) then brine (20 mL). The organic phase was dried (Na₂SO₄), filtered and concentrated in vacuo. FCC [petrol-ethyl acetate (100:0)→(80:20)] of the crude residue afforded (1-(((tert-butyldiphenylsilyl)oxy)methyl)cyclopropyl)methanol (967 mg, 83%) as a colourless oil which solidified on standing; $R_f$=0.53 (30% EtOAc: Petrol); ¹H NMR (500 MHz, CDCl₃) δ 7.67-7.69 (4H, m, 4×ArH), 7.38-7.44 (6H, m, 6×ArH), 3.62-3.63 (4H, s, ×s, 2×CH₂), 1.07 (9H, s, 3×CH₃), 0.48-0.50 (2H, m, Cy-Py-H₂), 0.35-0.37 (2H, m, Cy-Py-H).

Step 2: 1-(((tert-Butyldiphenylsilyl)oxy)methyl)cyclopropane-1-carbaldehyde

Oxalyl chloride (0.52 mL, 6.01 mmol) and anhydrous CH₂Cl₂ (30 mL) were cooled to −78° C. under N₂ and treated with DMSO (0.85 mL, 12.0 mmol) in CH₂Cl₂ (12 mL). The colourless solution was stirred for 10 min and then treated dropwise with a solution of (1-(((tert-butyldiphenylsilyl)oxy)methyl)cyclopropyl)methanol (1.78 g, 5.23 mmol) in CH₂Cl₂ (26 mL). The white suspension was left for 0.5 h and then treated dropwise with Et₃N (2.80 mL, 19.9 mmol). The reaction mixture was left at −78° C. for 0.5 h and then the cooling bath was removed. The mixture allowed to reach ambient temperature and stirred for a further h. The mixture was diluted with H₂O (40 mL) and extracted with CH₂Cl₂ (2×50 mL). The combined organics were dried over Na₂SO₄, filtered and the solvent removed in vacuo. FCC [petrol-ethyl acetate (100:0)→(80:20)] of the crude residue afforded 1-(((tert-butyldiphenylsilyl)oxy)methyl)cyclopropane-1-carbaldehyde (1.61 g, 91%) as a colourless oil; $R_f$=0.76 (30% EtOAc:Petrol); ¹H NMR (500 MHz, CDCl₃) δ 9.09 (1H, s, CHO), 7.63 (4H, dd, J=1.5 and 8.0 Hz, 4×ArH), 7.36-7.42 (6H, m, 6×ArH), 3.93 (2H, s, CH₂), 1.12-1.15 (2H, m, Cy-Py-H₂), 1.07-1.10 (2H, m, Cy-Py-H), 1.03 (9H, s, 3×CH₃).

Step 3: 1-(1-(((tert-Butyldiphenylsilyl)oxy)methyl)cyclopropyl)ethan-1-ol 1-(((tert-Butyldiphenylsilyl)oxy)methyl)cyclopropane-1-carbaldehyde (820 mg, 2.42 mmol) was dissolved in anhydrous THF (12 mL) under N₂ and cooled to 0° C. for the addition of MeMgCl (3M in THF, 2.0 mL, 6.05 mmol). The cooling was removed after 0.5 h and the reaction mixture allowed to reach ambient temperature. After 2.75 h, TLC showed the reaction to be at completion and so it was quenched via the gentle addition of saturated aqueous NH$_4$Cl (10 mL) and then extracted with EtOAc (2×20 mL). The combined organics were dried (Na$_2$SO$_4$), filtered and the solvent removed in vacuo. FCC [petrol-ethyl acetate (100:0)→(70:30)] of the crude residue afforded 1-(1-(((tert-butyldiphenylsilyl)oxy)methyl)cyclopropyl)ethan-1-ol (782 mg, 91%) as a colourless gum/oil; R$_f$=0.69 (30% EtOAc: Petrol); $^1$H NMR (500 MHz, CDCl$_3$) δ 7.67-7.69 (4H, m, 4×ArH), 7.38-7.45 (6H, m, 6×ArH), 3.90 (1H, d, J=10.5 Hz, CH$_2$), 3.46-3.52 (1H, m, CH), 3.32 (1H, d, J=10.5 Hz, CH$_2$), 1.24 (3H, d, 6.5 Hz, CH$_3$), 1.07 (9H, s, 3×CH$_3$), 0.60-0.63 (1H, m, Cy-Py-H), 0.37-0.43 (2H, m, Cy-Py-H$_2$), 0.25-0.26 (1H, m, Cy-Py-H).

Step 4:
1-(1-(Hydroxymethyl)cyclopropyl)ethan-1-ol 1-(1-(((tert-Butyldiphenylsilyl)oxy)methyl)cyclopropyl)ethan-1-ol (882 mg, 2.49 mmol) was dissolved in anhydrous THF (12.5 mL) under N$_2$ and then cooled to 0° C. TBAF (1M in THF, 4.98 mL, 4.98 mmol) was added and the cooling removed after 10 min. The reaction mixture was allowed to reach room temperature and stirred for 2.75 h, after which time TLC showed the reaction to be at completion.

Diluted with EtOAc (10 mL) and washed with H$_2$O (20 mL). The aqueous layer was further extracted with EtOAc (10 mL) and then the combined organics dried over Na$_2$SO$_4$, filtered and the solvent removed in vacuo. FCC [dichloromethane-methanol (100:0)→(90:10)] of the crude residue afforded 1-(1-(hydroxymethyl)cyclopropyl)ethan-1-ol (119 mg, 41%) as an off white gum; R$_f$=0.61 (10% MeOH: CH$_2$Cl$_2$); $^1$H NMR (500 MHz, CDCl$_3$) δ 4.05 (1H, d, J=11.5 Hz, CH$_2$), 3.43-3.47 (1H, m, CH), 3.19 (1H, d, J=11.5 Hz, CH$_2$), 1.29 (3H, d, J=6.5 Hz, CH$_3$), 0.58-0.64 (2H, m, Cy-Py-H$_2$), 0.39-0.45 (2H, m, Cy-Py-H).

Preparation 16:
2-((tert-Butyldimethylsilyl)oxy)ethan-1-amine

A solution of tert-butyldimethylsilyl chloride (3.15 g, 21 mmol) in dichloromethane (10 mL) was added dropwise over 3 min to a stirred solution of ethanolamine (1.22 g, 20.0 mmol) and imidazole (2.72 g, 40.0 mmol) in dichloromethane (20 mL) at room temperature, and the resulting mixture stirred for 2 h.

Water (20 mL) was added and the phases separated. The aqueous was extracted with DCM (2×20 mL) and the combined organic phases dried (MgSO$_4$), filtered and the solvent removed in vacuo. $^1$H NMR (500 MHz, CDCl$_3$) δ 3.60 (2H, t, J=5.3 Hz, CH$_2$OTBDMS), 2.75 (2H, t, J=5.3 Hz, CH$_2$NH$_2$), 1.47 (2H, br s, NH$_2$), 0.88 (9H, s, (CH$_3$)$_3$), 0.04 (6H, s, (CH$_3$)$_2$).

Preparation 17: (5-Chloro-3-(methylsulfonyl)pyridin-2-yl)methanamine dihydrochloride Salt

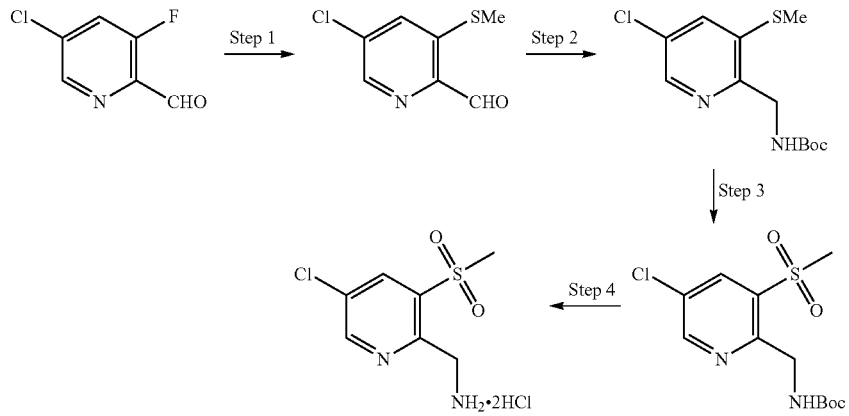

Step 1: 5-Chloro-3-(methylthio)picolinaldehyde

Sodium thiomethoxide (2.20 g, 31.4 mmol) was added to 5-chloro-3-fluoropicolinaldehyde (5 g, 31.4 mmol) in DMF (40 mL) and the mixture stirred for 18 h at RT. The reaction was diluted with water (20 mL) and EtOAc (25 mL). The aqueous phase was extracted with EtOAc (2×25 mL) and organic layers were combined and further washed with brine (25 mL) and 4% LiCl (2×25 mL). Organics were dried over MgSO$_4$, filtered and solvent removed under reduced pressure. The crude material was purified by column chromatography on silica, eluting with a gradient of 0-50% EtOAc in isohexane to afford the title compound (3.43 g, 58%). MS: [M+H]$^+$=188.

Step 2: tert-Butyl ((5-chloro-3-(methylthio)pyridin-2-yl)methyl)carbamate tert-Butyl carbamate (6.44 g, 55.02 mmol) was added to 5-chloro-3-(methylthio)picolinaldehyde (3.43 g, 18.34 mmol) in acetonitrile (100 mL) and dichloromethane (100 mL) and the mixture was stirred for 15 min at RT. Triethylsilane (8.78 mL, 55.02 mmol) and TFA (2.82 mL, 36.68 mmol) were added and the reaction was stirred for 3 days.

The mixture was diluted with sat. NaHCO₃ (aq) (50 mL) and extracted into dichloromethane (2×50 mL). The organic extracts were combined, passed through a phase separator cartridge and concentrated under reduced pressure. The crude material was purified by column chromatography on silica, eluting with a gradient of 0-30% EtOAc in isohexane to afford the title compound (3.74 g, 71%). MS: [M-CO₂ᵗBu+H]+=189.

Step 3: tert-Butyl ((5-chloro-3-(methylsulfonyl)pyridin-2-yl)methyl)carbamate

Na₂WO₄ (17 mg) and hydrogen peroxide (0.79 mL, 30% solution in water, 6.94 mmol) were added to tert-butyl ((5-chloro-3-(methylthio)pyridin-2-yl)methyl)carbamate (1.00 g, 3.47 mmol) in acetic acid (5 mL) and the mixture stirred at RT for 24 h. Further portions of hydrogen peroxide (0.39 mL, 6.94 mmol) and Na₂WO₄ (8.5 mg, 0.025 mmol) were added and the mixture was stirred an additional 24 h. Further portions of hydrogen peroxide (0.2 mL, 1.73 mmol) and Na₂WO₄ (4.2 mg) were added and the mixture was stirred for 5 h. The reaction was concentrated under reduced pressure, the crude residue neutralised with sat. NaHCO₃ (aq) (10 mL) and extracted into DCM (2×10 mL). The organic extracts were combined, passed through a phase separator cartridge and concentrated under reduced pressure. The crude material was purified by silica column chromatography, eluting with a gradient of 0-50% EtOAc in isohexane to afford the title compound (0.99 g, 89%). MS: [M CO₂ᵗBu+H]⁺=221.

Step 4: (5-Chloro-3-(methylsulfonyl)pyridin-2-yl)methanamine tert-Butyl ((5-chloro-3-(methylsulfonyl)pyridin-2-yl)methyl)carbamate (0.99 g, 3.09 mmol) was stirred in 4M HCl in dioxane (10 mL) for 18 h. The mixture was concentrated under reduced pressure to afford the title compound as the hydrochloride salt (0.99 g, quantitative). ¹H NMR (400 MHz, DMSO) 9.11 (1H, d), 8.59 (3H, s), 8.50 (1H, d), 4.66 (2H, s), 2.57 (3H). MS: [M+H]⁺=221.

Preparation 18:
(3,5-Difluoropyridin-2-yl)methanamine

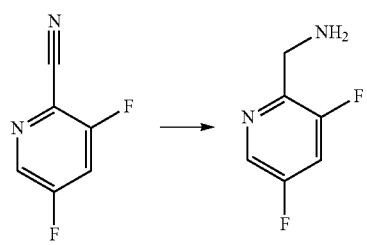 [SMILES: N#Cc1ncc(F)cc1F ; NCc1ncc(F)cc1F]

3,5-difluoropicolinonitrile (23.19 mmol) was dissolved in ethanol with stirring then concentrated aqueous hydrochloric acid (2.6 mL) was added. Palladium (10% on carbon) was added under nitrogen then the mixture was hydrogenated at 30 psi for 2 h using Parr apparatus. The catalyst was removed by filtration and the filtrate was concentrated under reduced pressure. The residue was partitioned between EtOAc (40 mL) and water (40 mL). The aqueous layer was separated then the pH was adjusted to 9 with 50% aqueous sodium hydroxide solution (3~4 mL) and extracted with dichloromethane (3×40 mL). The combined extracts were dried (MgSO₄) and concentrated under reduced pressure to afford a pale green/brown oil (2.5 g, 75%). ¹H NMR (400 MHz, DMSO) 8.45 (1H, d), 7.89-7.84 (1H, m), 3.82 (2H, s), 3.33 (1H, bs), 1.87 (1H, bs).

Preparation 19:
2-(Aminomethyl)pyrimidine-5-carbonitrile hydrochloride

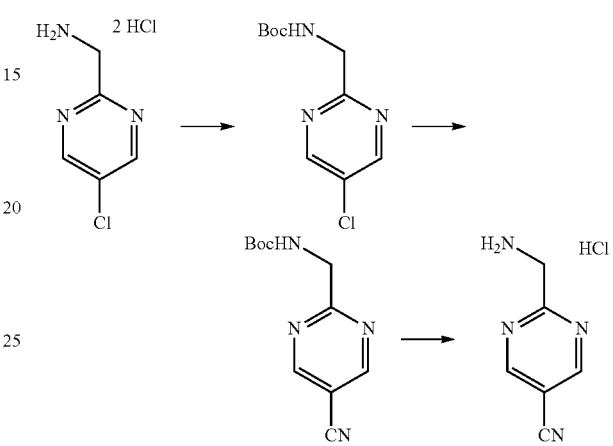

Step 1: tert-Butyl ((5-chloropyrimidin-2-yl)methyl)carbamate (5-Chloropyrimidin-2-yl)methanamine dihydrochloride (10 g, 46.2 mmol) was suspended in DCM (100 mL) with stirring at RT under an atmosphere of nitrogen. A solution of di-tert-butyl dicarbonate (12.0 g, 46.2 mmol) and triethylamine (15.2 g, 21 mL, 148.0 mmol) in DCM (100 mL) was added to the suspension of (5-chloropyrimidin-2-yl)methanamine dihydrochloride drop-wise. The reaction was stirred at 40° C. for 18 h then cooled to RT and filtered. The filtrate was washed with H₂O (100 mL), dried (MgSO₄), filtered and concentrated under reduced pressure to afford the title compound (11.3 g, 100%). ¹H NMR (400 MHz, DMSO) 8.94 (2H, s), 7.37 (1H, dd), 4.37 (2H, d), 1.45-1.42 (9H, m).

Step 2: tert-Butyl ((5-cyanopyrimidin-2-yl)methyl)carbamate

A two-necked 1 L round bottomed flask equipped with a magnetic stirrer was charged with tert-butyl ((5-chloropyrimidin-2-yl)methyl)carbamate (11.3 g, 46.6 mmol), Xphos (4.44 g, 9.32 mmol), zinc cyanide (5.5 g, 46.6 mmol) and tris(dibenzylideneacetone)dipalladium(0) (2.14 g, 2.33 mmol). DMF degassed with nitrogen (225 mL) was added and the reaction was degassed for a further 1 min. The reaction was then stirred and heated at 120° C. using a pre-heated stirrer hot plate for 2 hours. The reaction was allowed to cool then DMF was removed under reduced pressure. The resulting residue was partitioned between EtOAc (500 mL) and H₂O (500 mL). The solids were filtered and the filter cake washed with EtOAc (250 mL). The filtrates were combined and the layers were separated. The aqueous portion was extracted with EtOAc (250 mL). The combined organic portions were dried (MgSO₄) and concentrated under reduced pressure The crude material was purified by silica column chromatography using a 300 gram interchim cartridge, eluting with a gradient of 0-25% EtOAc in isohexane to afford the title compound (7.44 g, 68%). $^1$H NMR (400 MHz, CDCl$_3$) 8.97 (2H, s), 5.57-5.48 (1H, m), 4.67 (2H, d), 1.61 (2H, s), 1.41-1.23 (9H, m).

Step 3: 2-(Aminomethyl)pyrimidine-5-carbonitrile hydrochloride

A stirred solution of tert-butyl ((5-cyanopyrimidin-2-yl)methyl)carbamate (7.34 g, 31.4 mmol) in anhydrous dichloromethane (235 mL) was added 4N hydrochloric acid in dioxane (80 mL) at room temperature. The reaction was allowed to stir for 1.5 hours. The volatiles were removed under reduced pressure to afford the titled compound (5.5 g, 100%) as a free flowing yellow solid. $^1$H NMR (400 MHz, DMSO) 9.46 (2H, s), 8.68 (3H, s), 4.52-4.45 (2H, m);

Preparation 20: 2-(4-Chlorobenzoyl)-3-fluoro-5-(1-methyl-1H-imidazole-4-carbonyl)benzoic Acid

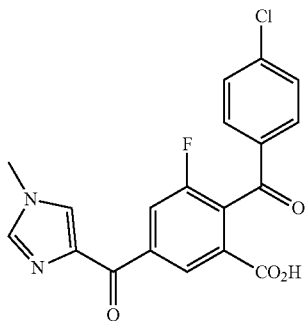

The title compound was prepared in using procedures similar to those described in Example 200 Step 1 and Step 2, but using 1-methyl-1H-imidazole-4-carbaldehyde instead of 1-methyl-1H-pyrazole-4-carboxylate in Step 1; and using manganese dioxide in 1,4-dioxane at 100° C. instead of TEMPO/sodium hypochlorite in Step 2. MS [M+H]$^+$=387

Preparation 21

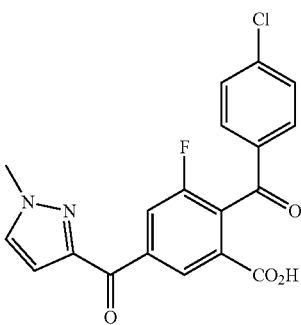 [SMILES: Cn1ccc(C(=O)c2cc(F)c(C(=O)c3ccc(Cl)cc3)c(C(=O)O)c2)n1]

The title compound was prepared in a similar manner to Preparation 20, but using 1-methyl-1H-pyrazole-3-carbaldehyde instead of 1-methyl-1H-imidazole-4-carbaldehyde. MS [M+H]$^+$=387

Preparation 22: (+)-2-(4-Chlorobenzoyl)-3-fluoro-5-(1-hydroxy-1-(tetrahydro-2H-pyran-4-yl)ethyl)benzoic and (−)-2-(4-Chlorobenzoyl)-3-fluoro-5-(1-hydroxy-1-(tetrahydro-2H-pyran-4-yl)ethyl)benzoic Acid (*Both Isomers Separated and Isolated)

(*both isomers separated and isolated)

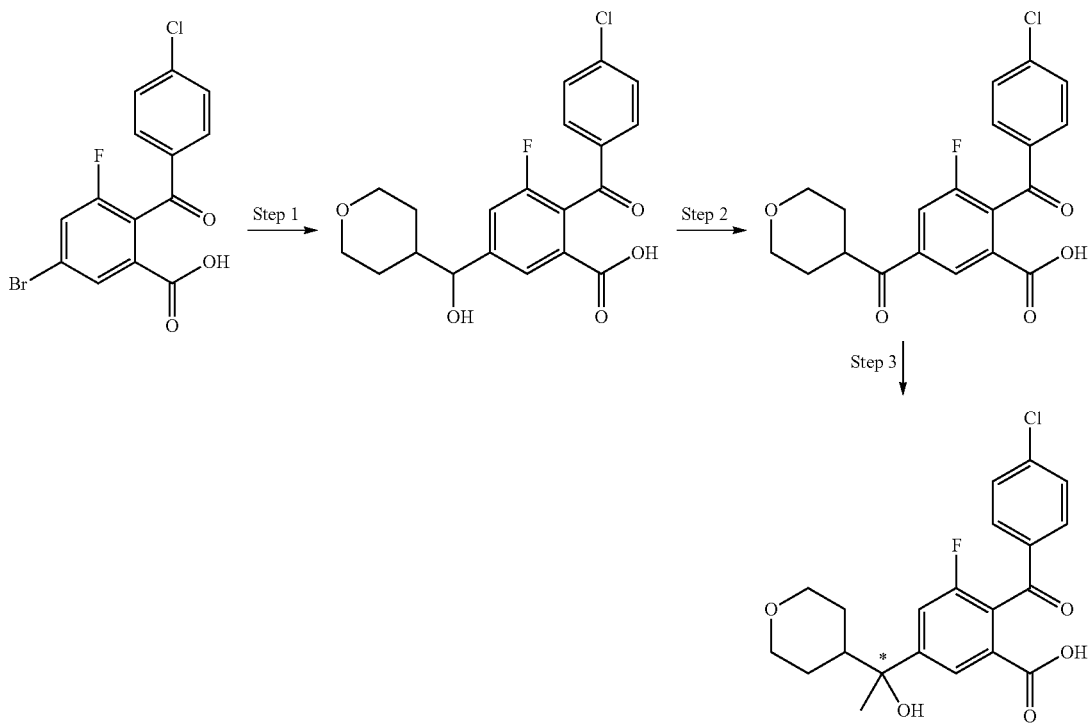

Step 1: 2-(4-Chlorobenzoyl)-3-fluoro-5-(hydroxy (tetrahydro-2H-pyran-4-yl)methyl)benzoic Acid To a round bottomed flask was added 5-bromo-2-(4-chlorobenzoyl)-3-fluorobenzoic acid (60 g, 168 mmol), the flask was then flushed with nitrogen and THF was added (800 mL). The reaction was cooled to −78° C. and di-n-butylmagnesium solution (84 mL, 84 mmol, 1M in heptane) was added, keeping the internal temperature below −65° C. The reaction was stirred at −78° C. for 30 min. To this solution was then added n-BuLi (114.5 mL, 201.6 mmol, 1.76M in hexanes) over 15 minutes (ensuring the internal temperature does not rise above −65° C.) and the reaction was stirred for a further 30 minutes at −78° C. After this time a solution of tetrahydro-2H-pyran-4-carbaldehyde (27 g, 235 mmol) was added as a THF (30 mL) solution over 10 minutes (the addition exhibited an exotherm, internal temperature rose to −65° C.). The reaction was warmed to RT over 1 h. To the reaction was added 1M HCl aqueous solution (800 mL). The organics were extracted with EtOAc (2×500 mL), dried (MgSO$_4$), filtered and concentrated under reduced pressure. The crude residue was purified by Biotage using 340 g SNAP silica cartridge (all solvents doped with 0.1% formic acid), eluting with EtOAc in isohexane (0 to 100% gradient elution). Fractions containing pure product were concentrated under reduced pressure to afford the title compound (17.4 g, 26% yield). MS: [M+H]$^+$=393.

Step 2: 2-(4-Chlorobenzoyl)-3-fluoro-5-(tetrahydro-2H-pyran-4-carbonyl)benzoic Acid 2-(4-Chlorobenzoyl)-3-fluoro-5-(hydroxy(tetrahydro-2H-pyran-4-yl)methyl)benzoic acid (17.4 g, 44.4 mmol) was stirred in DCM (400 mL) at RT then TEMPO (0.69 g, 4.44 mmol) and tetra-n-butylammonium chloride (5.72 g, 17.8 mmol) were added followed by OXONE®, monopersulfate compound (30 g, 97.7 mmol). The reaction was allowed to stir at RT for 18 h. TEMPO (0.69 g, 4.44 mmol) was added and the reaction was allowed to stir at RT for an additional 48 h. The solids were removed by filtration and the filter cake was washed with DCM (2×100 mL). The combined filtrates were concentrated under reduced pressure and the resulting residue dissolved in EtOAc (500 mL). The combined organic portions were washed with 2M HCl aqueous solution (2×500 mL) and brine (200 mL), dried (MgSO$_4$), filtered and concentrated to afford the title compound as a pale yellow foam (16 g, 92% yield). MS: [M−H]$^−$=389

Step 3: 2-(4-Chlorobenzoyl)-3-fluoro-5-(1-hydroxy-1-(tetrahydro-2H-pyran-4-yl)ethyl)benzoic Acid 2-(4-Chlorobenzoyl)-3-fluoro-5-(tetrahydro-2H-pyran-4-carbonyl)benzoic acid (15.8 g, 40.5 mmol) was dissolved in THF (650 mL) with stirring under nitrogen and cooled to −20° C. MeMgCl (50.8 mL, 150 mmol, 2.95M in THF) was added over a period of 15 min. LCMS analysis after 5 min indicated complete reaction. The reaction was quenched with saturated aqueous ammonium chloride solution (100 mL) then the pH was adjusted to ~3 by the addition of 2M HCl aqueous solution (150 mL). The reaction was diluted with water (200 mL) and EtOAc (200 mL). The layers were separated and the aqueous portion extracted with EtOAc (300 mL). The combined organic portions were dried (MgSO$_4$) and concentrated to afford a pale yellow foam (16.6 g) which was separated using chiral SFC to give the two enatiomers:

(+)-2-(4-chlorobenzoyl)-3-fluoro-5-(1-hydroxy-1-(tetrahydro-2H-pyran-4-yl)ethyl)benzoic acid (faster eluting isomer) (5.5 g, 66% yield). $^1$H NMR (400 MHz, CDCl$_3$) 7.92 (1H, s), 7.71 (2H, d), 7.51 (1H, dd), 7.43 (2H, d), 4.15-4.09 (2H, m), 3.41-3.27 (2H, m), 1.89-1.78 (1H, m), 1.65-1.52 (4H, m), 1.51-1.43 (2H, s), 1.26 (2H, dd); Carboxylic acid proton not observed. MS: [M+H]$^+$=407; $[\alpha]_D^{20}$=+14.22 (c 1.1, MeOH).

(−)-2-(4-chlorobenzoyl)-3-fluoro-5-(1-hydroxy-1-(tetrahydro-2H-pyran-4-yl)ethyl)benzoic acid (slower eluting isomer): MS: [M+H]$^+$=407; $[\alpha]_D^{20}$=−15.05 (c 1.1, MeOH).

Preparation 23: (Fluorotetrahydropyran) 2-(4-Chlorobenzoyl)-3-fluoro-5-(4-fluorotetrahydro-2H-pyran-4-carbonyl)benzoic Acid

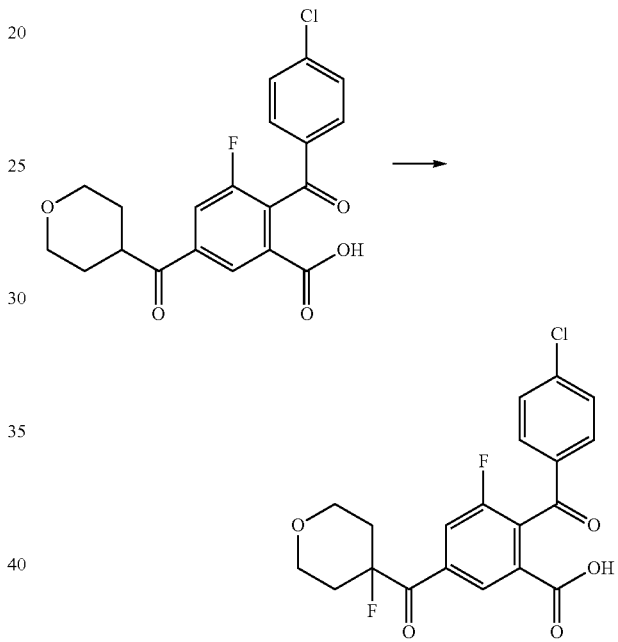

A solution of 2-(4-chlorobenzoyl)-3-fluoro-5-(tetrahydro-2H-pyran-4-carbonyl)benzoic acid (Preparation 22, step 2) (4.5 g, 11.5 mmol) in THF (100 mL) was cooled to −78° C. and sodium(trimethylsilyl)amide (1.0M in THF, 28.8 mL, 28.8 mmol) was added dropwise. The reaction was stirred at −78° C. for 10 min. To the solution was then added N-fluorobenzenesulfonimide (4.7 g, 15.0 mmol) in a single portion as a solid, and the reaction was stirred for a further 10 min at −78° C. before warming to room temperature over 1 h. At this stage the reaction mixture was re-cooled to −78° C. and a second portion of sodium(trimethylsilyl)amide (1.0M in THF, 28.8 mL, 28.8 mmol) was added dropwise. The reaction was stirred at −78° C. for 10 min. To the solution was then added a second portion of N-fluorobenzenesulfonimide (4.7 g, 15.0 mmol) in a single portion as a solid, and the reaction was stirred for a further 10 min at −78° C. before warming to room temperature over 1 h. The reaction was then re-cooled to −78° C. and a third portion of sodium (trimethylsilyl)amide (1.0M in THF, 28.8 mL, 28.8 mmol) was added dropwise. The reaction was stirred at −78° C. for 10 min. To the solution was then added a third portion of N-fluorobenzenesulfonimide (4.7 g, 15.0 mmol) in a single portion as a solid, and the reaction was stirred for a further 10 min at −78° C. before warming to room temperature over 1 h. The reaction was quenched with water (200 mL) acidified to pH2 with 2M aqueous HCl. The mixture was extracted with ethyl acetate (2×100 mL), dried over MgSO$_4$, filtered and concentrated under reduced pressure. The crude material was purified by column chromatography on silica, eluting with a gradient of 0-100% ethyl acetate in isohexane, then a second column on silica eluting with 0-5% MeOH in CH$_2$Cl$_2$ to afford the title compound (3.06 g, 65%). MS: [M−H]$^−$=407.

Preparation 24: (+)-5-[1-(1-tert-Butoxycarbonyl-4-piperidyl)-1-hydroxy-ethyl]-2-(4-chlorobenzoyl)-3-fluoro-benzoic Acid and (−) 5-[1-(1-tert-Butoxycarbonyl-4-piperidyl)-1-hydroxy-ethyl]-2-(4-chlorobenzoyl)-3-fluoro-benzoic Acid (*both isomers separated and isolated)

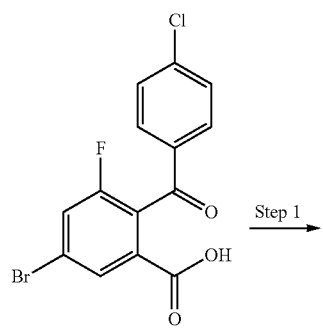

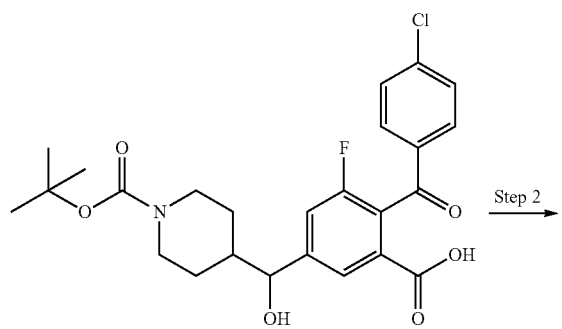

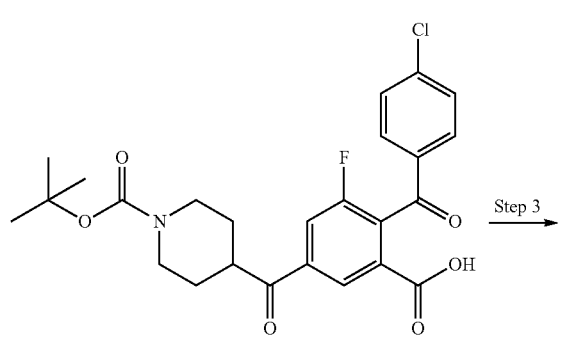

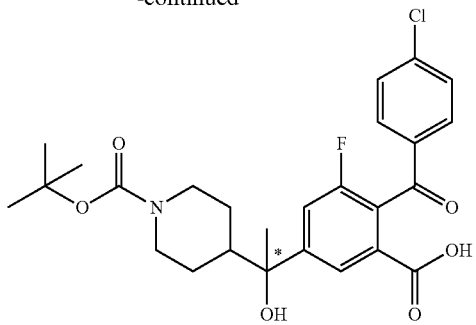

Step 1: 5-[(1-tert-Butoxycarbonyl-4-piperidyl)-hydroxy-methyl]-2-(4-chlorobenzoyl)-3-fluoro-benzoic Acid Using 2-(4-chlorobenzoyl)-3-fluoro-5-bromobenzoic acid 40.0 g, 112.0 mmol) (Manchester Organics, MOL1216), the title compound was prepared using a similar procedure to that described in Preparation 22, but using 1-Boc-4-piperidinecarboxaldehyde instead of tetrahydro-2H-pyran-4-carbaldehyde. The crude product was purified by column chromatography on silica, eluting with a gradient of EtOAc in hexanes (solvents doped with 0.1% formic acid) to afford the title compound as an off white solid (22.5 g, 42% yield). MS: [M−H]$^−$=490.

Step 2: 5-(1-tert-Butoxycarbonylpiperidine-4-carbonyl)-2-(4-chlorobenzoyl)-3-fluoro-benzoic Acid A solution of bleach (8%, 105 mL) and sodium hydrogen carbonate (5.08 g, 60.4 mmol) in water (50 mL) was added portion-wise to a stirred mixture of 5-[(1-tert-butoxycarbonyl-4-piperidyl)-hydroxy-methyl]-2-(4-chlorobenzoyl)-3-fluoro-benzoic acid (23.7 g, 48.3 mmol), TEMPO (755 mg, 4.84 mmol) and aqueous potassium bromide (10%, 40 mL) in EtOAc (100 mL), maintaining the internal temperature below 5° C. After 30 min, aqueous saturated sodium sulphite solution was added drop-wise until the orange colour disappeared. The layers were separated and the aqueous layer was extracted with EtOAc. The combined organic portions were dried (MgSO$_4$), filtered and concentrated under reduced pressure. The crude material was purified by column chromatography on silica, eluting with a gradient of 0-40% EtOAc in isohexane to afford the title compound as an off white solid (21.7 g, 53% yield). MS: [M−H]$^−$=488.

Step 3: 5-[1-(1-tert-Butoxycarbonyl-4-piperidyl)-1-hydroxy-ethyl]-2-(4-chlorobenzoyl)-3-fluoro-benzoic Acid A solution of 5-(1-tert-butoxycarbonylpiperidine-4-carbonyl)-2-(4-chlorobenzoyl)-3-fluoro-benzoic acid (15.5 g, 31.7 mmol) in THF (300 mL) under nitrogen was cooled to −10° C. and methylmagnesium chloride (2.3M in THF, 34.5 mL, 79.4 mmol) was added over 5 min. Immediately after the completion of the addition, LCMS analysis indicated complete consumption of the starting material. The reaction was quenched by addition of aqueous HCl (1M, 200 mL). The layers were separated and the aqueous layer was extracted with EtOAc. The combined organic portions were dried (MgSO$_4$), filtered and concentrated under reduced pressure. The crude material was purified by column chromatography on silica, eluting with a gradient of 0-40% EtOAc in DCM (containing 0.1% formic acid) to afford the title compound as an off white foam (15.1 g, 93% yield). Enantiomer separation was achieved by chiral preparative HPLC to give.

Faster running isomer: (+)-5-[1-(1-tert-butoxycarbonyl-4-piperidyl)-1-hydroxy-ethyl]-2-(4-chlorobenzoyl)-3-fluoro-benzoic acid; MS: [M−H]⁻=504.

Slower running isomer: (−)-5-[1-(1-tert-butoxycarbonyl-4-piperidyl)-1-hydroxy-ethyl]-2-(4-chlorobenzoyl)-3-fluoro-benzoic acid; MS: [M−H]⁻=504.

Preparation 25: (2-(4-Chlorobenzoyl)-3-fluoro-5-(1-hydroxy-1-(1-methylpiperidin-4-yl)ethyl)benzoic Acid (Example prepared and isolated as a single isomer at the position shown*)

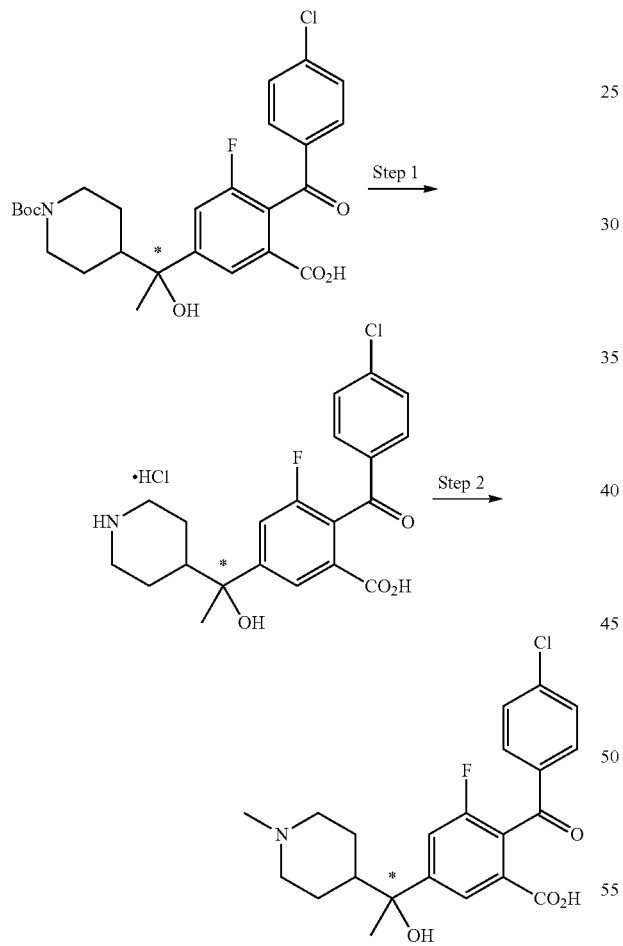

Step 1: 2-(4-Chlorobenzoyl)-3-fluoro-5-(1-hydroxy-1-(piperidin-4-yl)ethyl)benzoic Acid hydrochloride (−)-5-(1-(1-(tert-Butoxycarbonyl)piperidin-4-yl)-1-hydroxyethyl)-2-(4-chlorobenzoyl)-3-fluorobenzoic acid (Preparation 24, step 3) (6.09 g, 12.0 mmol) was stirred in 4N HCl in dioxane (70 mL) at RT for 10 min and concentrated under reduced pressure. The residue was used in the next step without further purification (6.88 g). MS: [M+H]⁺= 406.

Step 2: 2-(4-Chlorobenzoyl)-3-fluoro-5-(1-hydroxy-1-(1-methylpiperidin-4-yl)ethyl)benzoic Acid (2-(4-Chlorobenzoyl)-3-fluoro-5-(1-hydroxy-1-(piperidin-4-yl)ethyl)benzoic acid hydrochloride (6.88 g, assume 12.0 mmol) was stirred in MeOH (100 mL) at RT under nitrogen. Formaldehyde (37% wt in water, 1.95 mL, 24 mmol) was added and the reaction mixture stirred at RT for 5 min, then NaBH₃CN (905 mg, 14.4 mmol) was added. The reaction mixture was stirred at RT for 1 d, concentrated under reduced pressure and used in the next step without further purification. MS: [M+H]⁺=420.

Preparation 26; 2-(4-Chlorobenzoyl)-3-fluoro-5-(1-hydroxy-1-(1-methylpiperidin-4-yl)ethyl)benzoic Acid (Example prepared and isolated as a single isomer at the position shown*)

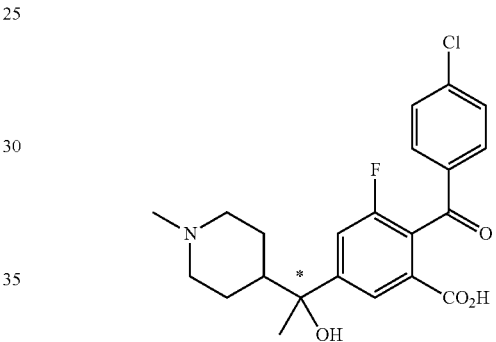

The title compound was prepared in an analogous fashion to Preparation 25, using (+)-5-(1-(1-(tert-butoxycarbonyl)piperidin-4-yl)-1-hydroxyethyl)-2-(4-chlorobenzoyl)-3-fluorobenzoic acid (Preparation 24, step 3) instead of (−)-5-(1-(1-(tert-butoxycarbonyl)piperidin-4-yl)-1-hydroxyethyl)-2-(4-chlorobenzoyl)-3-fluorobenzoic acid. MS: [M+H]⁺=406.

Preparation 27: 5-(1-(1-(tert-Butoxycarbonyl)azetidin-3-yl)-1-hydroxyethyl)-2-(4-chlorobenzoyl)-3-fluorobenzoic Acid (*both isomers separated and isolated)

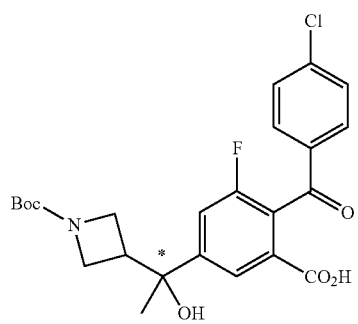 [SMILES: CC(C)(C)OC(=O)N1CC(C(C)(O)c2cc(F)c(C(=O)c3ccc(Cl)cc3)c(C(=O)O)c2)C1]

The title compound was prepared in a similar fashion to Preparation 22, but using and tert-butyl 3-formylazetidine-1-carboxylate instead of tetrahydro-2H-pyran-4-carbaldehyde. Purification by chiral SCF chromatography gave the two enetiomers.

Fast running isomer (Isomer A) (1.56 g) MS: [M+Na]$^+$= 500

Slow running isomer (Isomer B) (1.92 g) MS: [M+Na]$^+$= 500

Preparation 28: 4-((tert-Butyldiphenylsilyl)oxy)cyclohexanecarbaldehyde (trans stereochemistry)

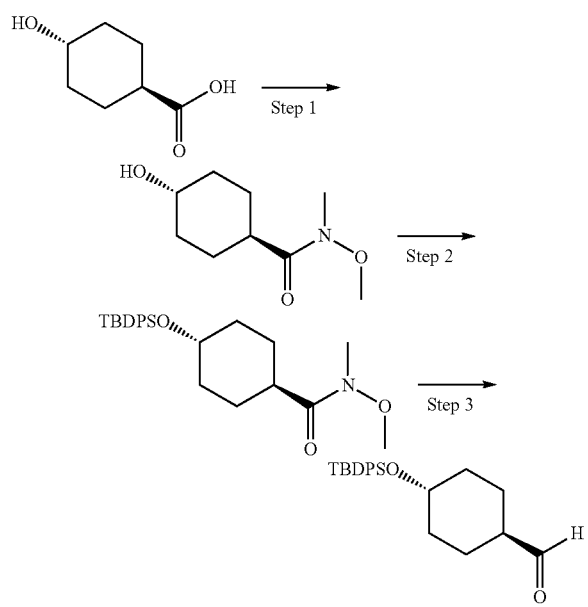

Step 1:
4-Hydroxy-N-methoxy-N-methylcyclohexanecarboxamide (trans stereochemistry)

To a solution of 4-hydroxycyclohexanecarboxylic acid (25 g, 173 mmol), EDCl (32 g, 208 mmol) and N,O-dimethylhydroxylamine hydrochloride (19 g, 191 mmol) in DCM (500 mL) under nitrogen at room temperature was added EtN$^i$Pr$_2$ (91 mL, 520 mmol) and the resultant mixture stirred for 20 hours. The reaction was quenched with 2N aqueous HCl (50 mL), partitioned with water (400 mL), layers shaken and separated, the aqueous re-extracted with DCM (2×150 mL). The combined organic extracts were dried (MgSO$_4$), filtered, and concentrated under reduced pressure to yield the desired product (21 g—containing some EtN$^i$Pr$_2$) as a thick pale yellow oil. $^1$H NMR (400 MHz, CDCl$_3$) 3.70 (3H, s), 3.68-3.59 (1H, m), 3.18 (3H, s), 2.70-2.55 (1H, m), 2.10-2.02 (2H, m), 1.88-1.80 (2H, m), 1.63-1.53 (2H, m), 1.38-1.26 (2H, m), OH missing.

Step 2

4-hydroxy-N-methoxy-N-methylcyclohexanecarboxamide (12.2 g, 65 mmol), was dissolved in DMF (200 mL) and stirred at room temperature under a nitrogen atmosphere. tert-butyl(chloro) diphenylsilane (19.7 g, 71 mmol) was added, followed by imidazole (4.88 g, 71 mmol). The reaction was stirred overnight. The DMF was evaporated under reduced pressure, and the resulting residue was re-dissolved in EtOAc (250 mL). The organic layer was washed with 4% aqueous LiCl solution (2×150 mL), and then dried (MgSO4), filtered, and evaporated under reduced pressure. The crude residue was purified by silica column chromatography (gradient elution 0 to 60% EtOAc in iso-Hex), to give the pure product as a colour less oil which crystallises upon standing (19.0 g, 69% yield). MS: (M+H)+=426.

Step 3: 4-((tert-Butyldiphenylsilyl)oxy)cyclohexanecarbaldehyde (trans stereochemistry)

(1R,4r)-4-((tert-butyldiphenylsilyl)oxy)-N-methoxy-N-methylcyclohexanecarboxamide (0.5 g, 1.17 mmol) was dissolved in dry THF (7.5 mL) under a nitrogen atmosphere. The solution was cooled to −78° C., and then DIBAL (1M in hexane, 2.11 mL, 2.11 mmol) was added dropwise. The mixture was stirred at −78° C. for 1.5 h and then quenched with 10% aqueous Rochelle salt solution (10 mL). The mixture was allowed to warm to room temperature and was then diluted further with EtOAc (40 mL) and more Rochelle salt solution (15 mL). The mixture was stirred for 20 mins before being transferred to a separating funnel. The organic phase was collected, and the aqueous phase was extracted with EtOAc (2×30 mL). The combined organic extracts were dried (MgSO$_4$), filtered, and evaporated under reduced pressure to give a crude residue which was used in next step without further purification (purity assessed by $^1$H NMR). $^1$H NMR (400 MHz, CDCl$_3$) 9.56 (1H, s), 7.67-7.65 (4H, m), 7.43-7.34 (6H, m), 3.64-3.55 (1H, m), 2.20-2.13 (1H, m), 1.95-1.80 (4H, m), 1.48-1.37 (2H, m), 1.28-1.20 (2H, m), 1.05 (9H, s).

Preparation 29: 2-(4-Chlorobenzoyl)-5-(cyclobutanecarbonyl)-3-fluorobenzoic Acid

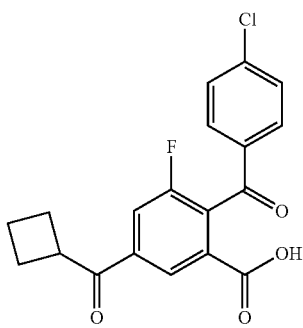 [SMILES: O=C(O)c1cc(C(=O)C2CCC2)cc(F)c1C(=O)c1ccc(Cl)cc1]

Starting from cyclobutylaldehyde, the title compound was prepared by using procedures similar to those described in Example 200, steps 1-2. MS: [M−H]$^−$=359

Preparation 30: 5-(1-{1-[(tert-Butoxy)carbonyl]piperidin-4-yl}-1-hydroxypropyl)-2-(4-chlorobenzoyl)-3-fluorobenzoic Acid

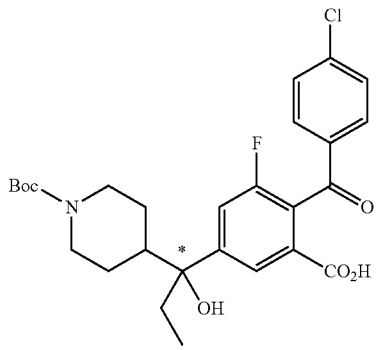 [SMILES: CCC(O)(c1cc(F)c(C(=O)c2ccc(Cl)cc2)c(C(=O)O)c1)C1CCN(C(=O)OC(C)(C)C)CC1]

To 10 mL of THF at −50° C. under nitrogen atmosphere were added liethylzinc (7.5 mL, 1M solution in hexanes, 3 equivs) and ethyl lithium (15 mL, 0.5M solution in benzene/isohexane, 3 equivs). The white suspension was stirred at −50° C. for 1 h then 5-(1-tert-butoxycarbonylpiperidine-4-carbonyl)-2-(4-chlorobenzoyl)-3-fluoro-benzoic acid (Preparation 24, step 2, 1.22 g, 2.5 mmol) was added (all at once) in solution in 10 mL of THF. The mixture turned dark orange immediately. The mixture was stirred at −50° C. for 10 min, then quenched with a saturated aqueous solution of ammonium chloride, and let warm to RT. The aqueous phase was extracted 3× with ethyl acetate, then the combined organic phases were washed with brine, dried on magnesium sulfate, filtered and concentrated. Purified by silica gel chromatography, eluted with isohexane (+0.1% formic acid) and ethyl acetate (+0.1% formic acid), 5 to 100% ethyl acetate, to give the desired product as a white solid (0.69 g, 53%).

Purification by chiral SCF chromatography gave the two enatiomers.

Fast running isomer (Isomer A) MS: $[M+H]^+=518$

Slow running isomer (Isomer B) MS: $[M+H]^+=518$

Preparation 30B: 5-[(1S)-1-{1-[(tert-butoxy)carbonyl]piperidin-4-yl}-1-hydroxypropyl]-2-(4-chlorobenzoyl)-3-fluorobenzoic Acid

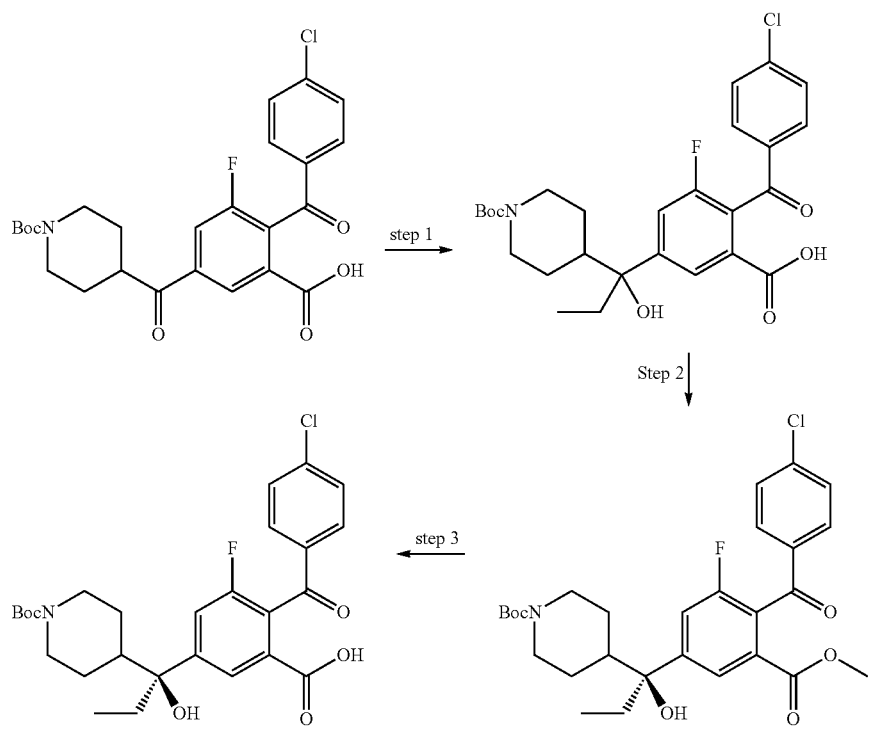

Step 1

To 100 mL of THF at −50° C. under nitrogen atmosphere were added diethylzinc (45 mL, 1M solution in hexanes, 2 equivs) and ethyl lithium (26 mL, 1.72M solution in dibutylether, 2 equivs). The white suspension was stirred at −50° C. for 1 h then the piperidine ketone (Preparation 24 step 2) (11.0 g, 23 mmol) was added (all at once) in solution in 100 mL of THF. The mixture was stirred at −50° C. for 15 min. The reaction was quenched with a 1N hydrochloric acid aqueous solution, and the mixture was let warm to RT. The aqueous phase was extracted with ethyl acetate (3×150 mL) and then the combined organic phases were washed with brine, dried on magnesium sulfate, filtered and concentrated. The crude mix was purified by silica gel chromatography using a 300 g column and elution with isohexane (+0.1% formic acid) and ethyl acetate (+0.1% formic acid), 10 to 100% ethyl acetate, to give the desired product as a white solid (11.2 g, 96%).

Step 2: tert-butyl 4-[(1S)-1-[4-(4-chlorobenzoyl)-3-fluoro-5-(methoxycarbonyl)phenyl]-1-hydroxypropyl]piperidine-1-carboxylate To a mixture of 2 (11.0 g, 21 mmol) in DMF (90 mL) were added potassium carbonate (3.45 g, 1.2 equiv.), and iodomethane (1.43 mL, 1.1 equiv.). The reaction was stirred at RT for 1 h. The mixture was diluted with water and extracted with ethyl acetate 3×, the combined organic phases were dried on magnesium sulfate filtered concentrated. 10.5 g of methyl ester were obtained.

The mixture of enantiomers was separated by chiral SFC. 3.0 g of fast running isomer and 3.6 g of slow running isomer obtained. (LUX CELLULOSE-4 15/85 MeOH (0.5% DEA)/CO2, 100 ml/min, 120 bar, 40 C, GLS 40 PSI, SYSTEM 3400 PSI, DROP 131 Bar, STACKER, DAD 255 nm)

(−)-tert-butyl 4-[(1S)-1-[4-(4-chlorobenzoyl)-3-fluoro-5-(methoxycarbonyl)phenyl]-1-hydroxypropyl]piperidine-1-carboxylate MS: [M+H]$^+$=534, [α]$_D^{20}$=−34.15 (c=1.18 g/100 mL, MeOH).

(+)-tert-butyl 4-[(1R)-1-[4-(4-chlorobenzoyl)-3-fluoro-5-(methoxycarbonyl)phenyl]-1-hydroxypropyl]piperidine-1-carboxylate MS: [M+H]$^+$=534, [α]$_D^{20}$=+24.46 (c=1.024 g/100 mL, MeOH).

Step 3: (−)-5-[(1S)-1-{1-[(tert-butoxy)carbonyl]piperidin-4-yl}-1-hydroxypropyl]-2-(4-chlorobenzoyl)-3-fluorobenzoic Acid (−)-isomer (3.0 g, 5.6 mmol) was dissolved in methanol (15 mL) and THF (25 mL). Lithium hydroxide (24 mg, 5 equiv.) in water (15 mL) was then added, and the mixture stirred at RT for 1 h. The mixture was concentrated under vacuum to remove methanol and tetrahydrofuran. The aqueous phase was then acidified with HCl 1N and extracted with ethyl acetate. The combined organic phases were dried on magnesium sulfate filtered concentrated to yield 3.1 g of the title compound. [α]$_D^{20}$=−37.51 (c=0.97 g/100 mL, MeOH). MS: [M−H$^+$]$^-$ 518.

Preparation 31: 6-[(1S)-1-Aminoethyl]pyridine-3-carbonitrile

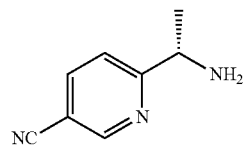

Title compound was prepared in a similar manner to Preparation 13 using 6-formylnicotinitrile instead of 5-chloropyridine-2-carbaldehyde. $^1$H NMR (400 MHz, DMSO-d6): 9.11 (1H, dd), 8.66 (3H, s), 8.43 (1H, dd), 7.80 (1H, d), 4.70-4.57 (1H, m), 1.52 (4H, d).

Preparation 32: [1-(Methylsulfanyl)cyclopropyl]methanol

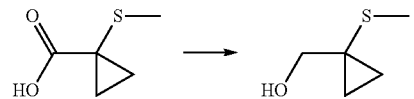

A solution of 1-(methylsulfanyl)cyclopropane-1-carboxylic acid (6 g, 45.45 mmol) in THF (50 ml) was added slowly to a suspension of LiAlH$_4$ (2.59 g, 68.18 mmol) in THF (100 ml) at 0° C. under N$_2$. After 2 hours the reaction was quenched with saturated aqueous Na$_2$SO$_3$ (5 ml) and stirred for 10 minutes. MgSO$_4$ and celite were added and the mixture was filtered. The solids were washed with ethyl acetate (350 ml) and the combined filtrates were concentrated in vacuo to give the title compound. (5.9 g, 94%). $^1$H NMR (400 MHz, DMSO-d6): 4.74 (1H, t), 3.45 (2H, d), 2.13-2.08 (3H, m), 0.83-0.78 (2H, m), 0.68-0.62 (2H, m).

Preparation 33: (1S)-1-(5-Chloropyridin-2-yl)prop-2-en-1-amine

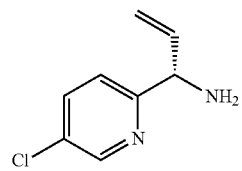

The title compound was prepared in a similar manner to Preparation 13 using vinylmagnesium bromide instead of methylmagnesium chloride in step 2.
MS: [M+H]$^+$=169.

Preparation 34: 2-(4-Chlorobenzoyl)-3-fluoro-5-(1-hydroxy-1-methyl-ethyl)benzoic Acid

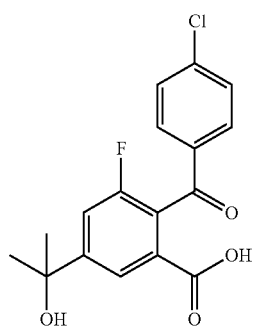 [SMILES: CC(C)(O)c1cc(F)c(C(=O)c2ccc(Cl)cc2)c(C(=O)O)c1]

The title compound was prepared in a similar manner to Example 200, step 1, but with the addition of LaCl3.2LiCl and using acetone instead of 1-methyl-1H-pyrazole-4-carboxaldehyde. MS: [M+H]$^+$=337.

Preparation 35: (+)-(R)-2-(4-chlorobenzoyl)-3-fluoro-5-(1-(4-fluorotetrahydro-2H-pyran-4-yl)-1-hydroxypropyl)benzoic Acid

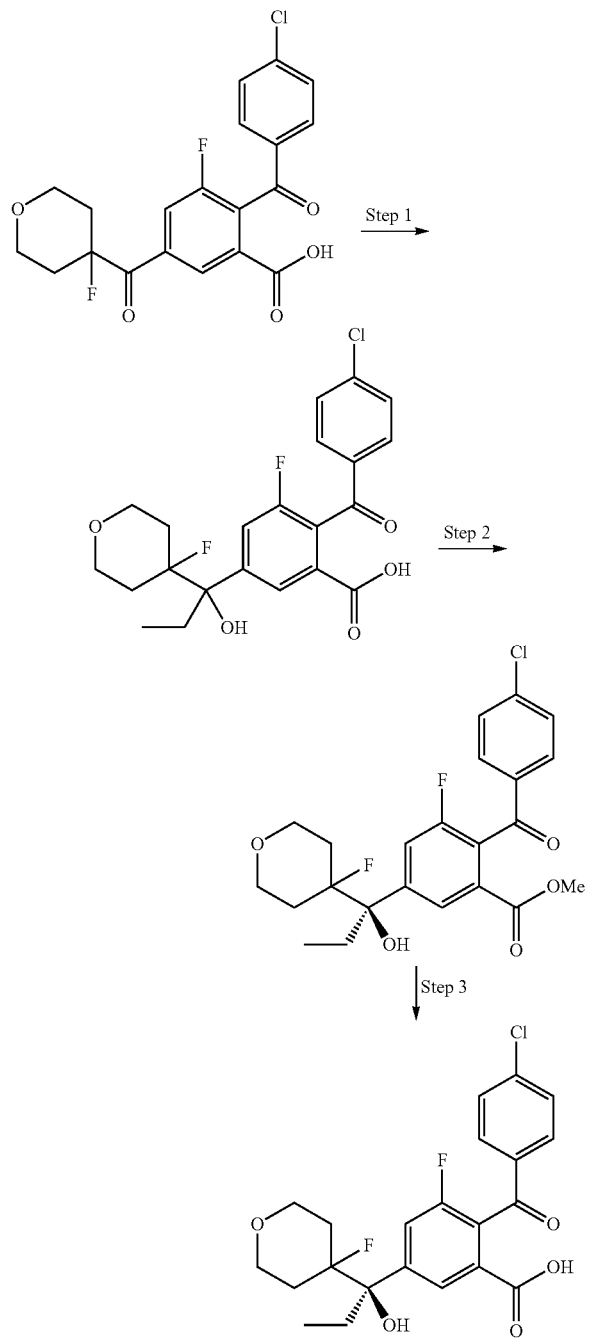

Step 1: 2-(4-Chlorobenzoyl)-3-fluoro-5-(1-(4-fluorotetrahydro-2H-pyran-4-yl)-1-hydroxypropyl)benzoic Acid A three neck flask was fitted with a nitrogen inlet, a pressure equalising dropping funnel, and a suba seal. The flask was charged with dry THF (210 mL) and cooled to −50° C. Diethyl zinc (228 mL, 228 mmol, 1M in hexanes) was added to the flask followed by drop-wise addition of ethyl lithium (154.5 mL, 228 mmol, 1.48M in dibutyl ether). The mixture was stirred at −50° C. for 45 minutes. The dropping funnel was charged with a solution of 2-(4-chlorobenzoyl)-3-fluoro-5-(4-fluorotetrahydro-2H-pyran-4-carbonyl)benzoic acid (Preparation 23, 37.4 g, 91 mmol) in dry THF (210 mL), and this was added drop-wise to the reaction mixture. Once addition was complete, the reaction was stirred at −50° C. for 10 minutes before quenching cautiously with water (300 mL) and allowed to warm to room temperature. The mixture was acidified to ~pH 2 with 1M HCl solution and extracted into EtOAc (2×500 mL). The combined organic extracts were dried (MgSO$_4$), filtered and evaporated under reduced pressure to give the title compound (35.29 g, 88%) as a colourless foam. The product was deemed sufficiently pure to be used in the subsequent step. MS: [M+H]$^+$=439

Step 2: Methyl (R)-2-(4-chlorobenzoyl)-3-fluoro-5-(1-(4-fluorotetrahydro-2H-pyran-4-yl)-1-hydroxypropyl)benzoate To a stirred solution of (+/−)-2-(4-chlorobenzoyl)-3-fluoro-5-(1-(4-fluorotetrahydro-2H-pyran-4-yl)-1-hydroxypropyl)benzoic acid (35.29 g, 80 mmol) in DMF (250 mL) was added potassium carbonate (16.6 g, 120 mmol) followed by iodomethane (6.50 mL, 103 mmol). The mixture was stirred overnight at room temperature and then filtered and evaporated to dryness under reduced pressure. The residue was re-dissolved in EtOAc (300 mL) and washed with 4% aqueous LiCl solution (2×150 mL). The organic extract was dried (MgSO$_4$), filtered and evaporated under reduced pressure to give a crude product (34.6 g). The enantiomers were separated using chiral SFC (+)-Methyl-(R)-2-(4-chlorobenzoyl)-3-fluoro-5-(1-(4-fluorotetrahydro-2H-pyran-4-yl)-1-hydroxypropyl)benzoate. Fast Eluting Isomer*

$^1$H NMR (400 MHz, CDCl$_3$) 7.97 (1H, s), 7.71 (2H, d), 7.57 (1H, d), 7.43 (2H, d), 3.86 (2H, ddd), 3.71-3.59 (3H, m), 2.28-2.18 (1H, m), 2.03-1.60 (5H, m), 0.76 (3H, t). MS: [M+H]$^+$=453. [α]$_D^{20}$=+18.35 (c 1.0, MeOH).

(−)-Methyl-(S)-2-(4-chlorobenzoyl)-3-fluoro-5-(1-(4-fluorotetrahydro-2H-pyran-4-yl)-1-hydroxypropyl)benzoate. Slow Eluting Isomer*

$^1$H NMR (400 MHz, CDCl$_3$) 7.95 (1H, s), 7.74 (2H, d), 7.54 (1H, d), 7.45 (2H, d), 3.86 (2H, td), 3.72 (3H, s), 3.71-3.60 (2H, m), 2.28-2.20 (2H, m), 2.05-1.90 (3H, m), 0.95-0.86 (1H, m), 0.77 (3H, t). MS: [M+H]$^+$=453. [α]$_D^{20}$=−13.40 (c 1.0, MeOH).

Step 3: (+)-(R)-2-(4-Chlorobenzoyl)-3-fluoro-5-(1-(4-fluorotetrahydro-2H-pyran-4-yl)-1-hydroxypropyl)benzoic Acid Methyl (R)-2-(4-chlorobenzoyl)-3-fluoro-5-(1-(4-fluorotetrahydro-2H-pyran-4-yl)-1-hydroxypropyl)benzoate (5.4 g, 11 mmol) was dissolved in THF (100 mL) and methanol (50 mL). A solution of lithium hydroxide (0.31 g, 13 mmol) in water (50 mL) was added and the mixture was stirred for 45 minutes. More lithium hydroxide (0.1 g) in water (5 mL) was added and stirring was continued for 1 hour. The reaction was reduced in volume under vacuum to remove the volatiles and the remaining solution was adjusted to pH 5 with 2M HCl. The mixture was extracted with ethyl acetate (2×50 mL) and the combined organic extracts were dried (MgSO$_4$), filtered and evaporated under reduced pressure to give the title compound (5.37 g, quant) as a colourless solid. $^1$H NMR (400 MHz, CDCl$_3$): 7.97 (1H, s), 7.71 (2H, d), 7.57 (1H, d), 7.43 (2H, d), 3.86 (2H, ddd), 3.71-3.59 (3H, m), 2.28-2.18 (1H, m), 2.03-1.60 (5H, m), 0.76 (3H, t). $[\alpha]_D^{20}$=+16.06 (c 1.04, MeOH).

Preparation 36: 2-(4-chlorobenzoyl)-3-fluoro-5-(1-hydroxy-1-trans-4-hydroxycyclohexyl)propyl)benzoic Acid (*isolated as a single isomer)

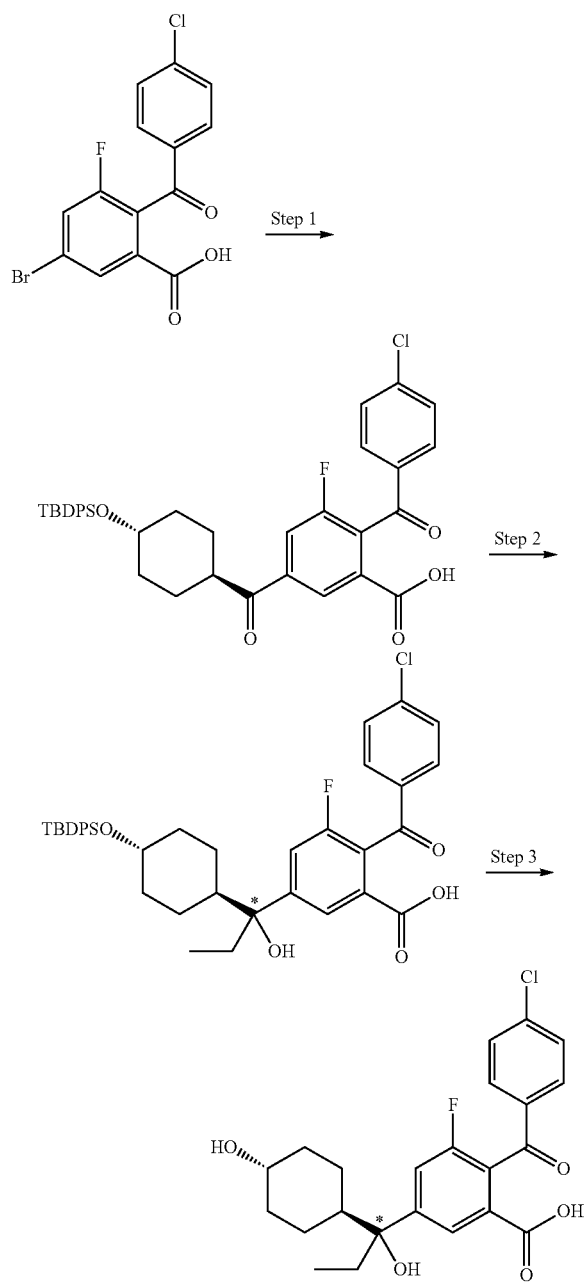

Step 1: 5-(trans-4-((tert-Butyldiphenylsilyl)oxy)cyclohexane-1-carbonyl)-2-(4-chlorobenzoyl)-3-fluorobenzoic Acid Starting from trans-4-((tert-butyldiphenylsilyl)oxy)cyclohexanecarbaldehyde (Preparation 28), the title compound was prepared using procedures similar to those described in Preparation 24, steps 1 and 2. MS: [M−H]$^-$=641.

Step 2: 5-(1-(trans-4-((tert-butyldiphenylsilyl)oxy)cyclohexyl)-1-hydroxypropyl)-2-(4-chlorobenzoyl)-3-fluorobenzoic Acid The title compound was prepared using the procedure described in Preparation 35, and the enantiomers were separated by chiral SFC.

(+)-5-(1-(trans-4-((tert-butyldiphenylsilyl)oxy)cyclohexyl)-1-hydroxypropyl)-2-(4-chlorobenzoyl)-3-fluorobenzoic acid: *Fast Eluting Isomer $^1$H NMR (400 MHz, CDCl$_3$) 7.8 (1H, s), 7.70-7.63 (6H, m), 7.43-7.34 (9H, m), 3.55-3.46 (1H, m), 1.94-1.78 (5H, m), 1.43-1.24 (3H, m), 1.03 (9H, s), 0.96-0.83 (3H, m), 0.69 (3H, t) exchangeable protons not observed. MS: [M−H]$^-$=671. $[\alpha]_D^{20}$=+27.65 (c 1.0 MeOH).

(−)-5-(1-(trans-4-((tert-butyldiphenylsilyl)oxy)cyclohexyl)-1-hydroxypropyl)-2-(4-chlorobenzoyl)-3-fluorobenzoic Acid: *Slow Eluting Isomer $^1$H NMR (400 MHz, CDCl$_3$) 7.79 (1H, s), 7.70-7.63 (6H, m), 7.44-7.33 (9H, m), 3.54-3.48 (1H, m), 1.96-1.75 (5H, m), 1.46-1.16 (3H, m), 1.03 (9H, s), 0.96-0.85 (3H, m), 0.69 (3H, t), exchangeable protons not observed. MS: [M−H]$^-$=671 $[\alpha]_D^{20}$=−24.62 (c 1.0, MeOH).

Step 3: 2-(4-chlorobenzoyl)-3-fluoro-5-(1-hydroxy-1-trans-4-hydroxycyclohexyl)propyl)benzoic Acid (−)-5-1-(trans-4-((tert-Butyldiphenylsilyl)oxy)cyclohexyl)-1-hydroxypropyl)-2-(4-chlorobenzoyl)-3-fluorobenzoic acid (3.5 g, 5.2 mmol) was dissolved in THF (70 mL) and the mixture was treated with TBAF (1M in THF, 20.7 mL, 20.7 mmol) and heated overnight at 60° C. The reaction was quenched with saturated aqueous NaHCO$_3$ solution and extracted with ethyl acetate (2×75 mL). The combined organic layers were dried (MgSO$_4$), filtered and evaporated to dryness under reduced pressure to give a crude product. The residue was purified by column chromatography (gradient elution, 20% to 100% ethyl acetate in iso-hexane (with 0.1% formic acid)) to give the title compound (1.92 g, 85%) as a colourless oil. MS: [M−H]$^-$=433.

Preparation 37: 2-(but-1-en-2-yl)-4,4,5,5-tetramethyl-1,3,2-dioxaborolane

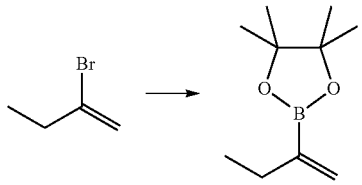

To a flask containing 2-bromobut-1-ene (2.5 g, 19.0 mmol) under $N_2$ was added $Et_2O$ (50 mL). The reaction was cooled to −78° C. and t-BuLi (1.6M in hexanes, 23 ml, 37 mmol) was added dropwise. The reaction was stirred for 30 minutes at −78° C. To the reaction was added 2-isopropoxy-4,4,5,5-tetramethyl-1,3,2-dioxaborolane (10.6 g, 57 mmol) dropwise and the reaction was then stirred for a further 1 hour at −78° C. After this time the reaction was warmed to room temperature, water (50 mL) was added and the pH adjusted to <7 with 1M HCl. The mixture was extracted with $Et_2O$ (3×50 mL), and the combined organic phases were dried with $MgSO_4$, filtered and concentrated under reduced pressure to yield the title compound (3.49 g) as a colourless oil which was used without further purification. $^1H$ NMR (400 MHz, $CDCl_3$) 5.75 (d, 1H), 5.61 (s, 1H), 2.16 (q, 2H), 1.28 (s, 12H), 1.02 (t, 3H).

Preparation 38: (−)-5-(1-(1-(tert-butoxycarbonyl)-4-fluoropiperidin-4-yl)-1-hydroxypropyl)-2-(4-chlorobenzoyl)-3-fluorobenzoic Acid (*both isomers separated and isolated)

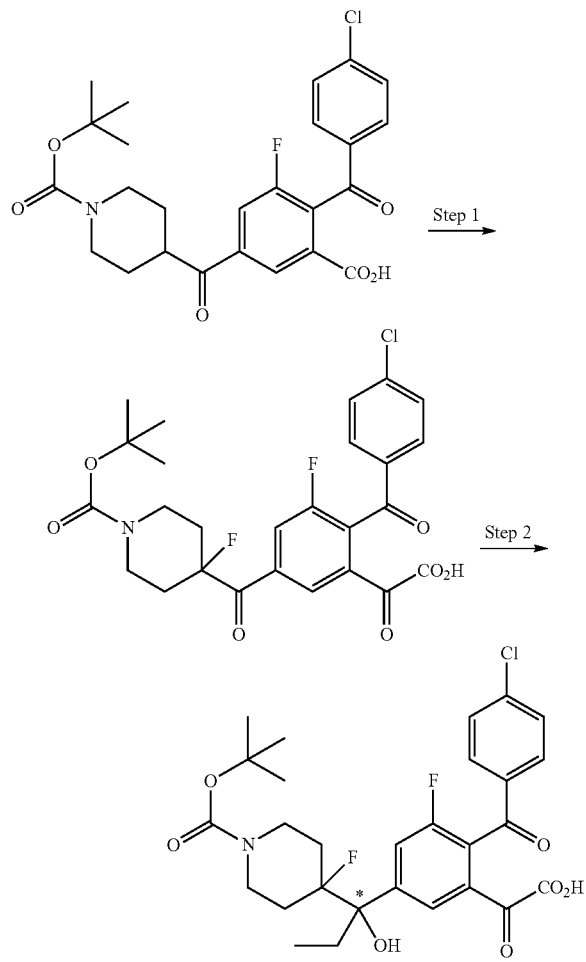

Step 1: 5-(1-(tert-Butoxycarbonyl)-4-fluoropiperidine-4-carbonyl)-2-(4-chlorobenzoyl)-3-fluorobenzoic Acid A mixture of 5-(1-(tert-butoxycarbonyl)piperidine-4-carbonyl)-2-(4-chlorobenzoyl)-3-fluorobenzoic acid (Preparation 24 step 2, 50 g, 0.102 mol) and NaOH (4.32 g, 0.108 mol) was stirred in anhydrous THF (250 mL) and anhydrous MeOH (90 mL) until all the NaOH dissolved. The solution was evaporated under reduced pressure and the residue dissolved in anhydrous THF (400 mL) and added over 1 minute to a stirred solution of 1M LHMDS in hexanes (125 mL) in anhydrous THF (100 mL) at −40° C. under nitrogen. The mixture was stirred for 20 minutes at −40° C. prior to the addition of a solution of N-fluorobenzenesulfonimide (48.6 g, 0.154 mol) in anhydrous THF (400 mL) in a steady stream over 1 minute. On complete addition the mixture was stirred with cooling in a bath at −40° C. for 20 minutes. The mixture was quenched with water (500 mL), stirred at room temperature for 30 minutes, the pH adjusted to pH2 with 2N HCl and then the aqueous was extracted with EtOAc (2×750 mL). The combined organics were dried ($MgSO_4$) and the solvent evaporated. The residue was triturated with DCM (500 mL) and the solid filtered, washed with DCM and dried to afford the title compound as a colourless solid (31.3 g, 60%). MS $[M-H]^-=506$.

Step 2: (−)-5-(1-(1-(tert-butoxycarbonyl)-4-fluoropiperidin-4-yl)-1-hydroxypropyl)-2-(4-chlorobenzoyl)-3-fluorobenzoic Acid To anhydrous THF (130 mL) at −50° C. under nitrogen was added a 1.72M solution of EtLi in dibutyl ether (38.4 mL, 65.96 mmol) followed by 1M diethylzinc in hexanes (66.4 mL). This was stirred at −50° C. for 70 minutes prior to addition of a solution of 5-(1-(tert-butoxycarbonyl)-4-fluoropiperidine-4-carbonyl)-2-(4-chlorobenzoyl)-3-fluorobenzoic acid (13.4 g, 26.38 mmol) in anhydrous THF (130 mL) in a gentle stream over 1 minute. On complete addition the mixture was stirred at −50° C. for 20 minutes, quenched by careful addition of water (200 mL), warmed to room temperature, acidified with 1M HCl and extracted into EtOAc (2×500 mL). Combined extracts were dried ($MgSO_4$) and the solvent evaporated under reduced pressure. The residue was triturated with isohexane (500 mL), the solvent decanted and the colourless solid dried to afford the title compound as the racemate. (13.9 g, 99%). MS $[M-H]^-=536$. The racemate (11.2 g) was separated by SFC to afford the title compound as the slow eluting isomer (5.11 g, 45% yield).

(+)-5-(1-(1-(tert-butoxycarbonyl)-4-fluoropiperidin-4-yl)-1-hydroxypropyl)-2-(4-chlorobenzoyl)-3-fluorobenzoic Acid: Fast Eluting Isomer*

$^1H$ NMR (400 MHz, $CDCl_3$) 7.97 (1H, s), 7.72 (2H, d), 7.54 (1H, d), 7.43 (2H, d), 4.01-4.01 (2H, m), 3.00-2.89 (2H, m), 2.28-2.19 (1H, m), 2.08-1.98 (2H, m), 1.81-1.50 (3H, m), 1.43 (9H, s), 0.75 (3H, dd), exchangeable protons not observed. $[\alpha]_D^{20}=+31.41°$ (c 1, MeOH).

(−)-5-(1-(1-(tert-butoxycarbonyl)-4-fluoropiperidin-4-yl)-1-hydroxypropyl)-2-(4-chlorobenzoyl)-3-fluorobenzoic Acid: Slow Eluting Isomer*

$^1H$ NMR (400 MHz, $CDCl_3$) 7.97 (1H, s), 7.72 (2H, d), 7.54 (1H, d), 7.43 (2H, d), 4.01-4.01 (2H, m), 3.00-2.89 (2H, m), 2.28-2.19 (1H, m), 2.08-1.98 (2H, m), 1.81-1.50 (3H, m), 1.43 (9H, s), 0.75 (3H, dd), exchangeable protons not observed. $[\alpha]_D^{20}=-31.33°$ (c 1, MeOH).

Preparation 39: 2-(4-chlorobenzoyl)-3-fluoro-5-(2-hydroxybutan-2-yl)benzoic Acid (*both isomers separated and isolated)

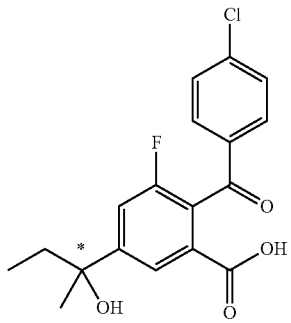 [SMILES: CCC(C)(O)c1cc(F)c(C(=O)c2ccc(Cl)cc2)c(C(=O)O)c1]

The title compound was prepared in a similar manner to that described in Preparation 24, step 1 except using ethyl methyl ketone. The resulting enantiomeric mixture was purified via chiral preparatory chromatography to provide the separated enantiomeric pairs.

(+)-2-(4-chlorobenzoyl)-3-fluoro-5-(2-hydroxybutan-2-yl)benzoic Acid

1H NMR (400 MHz, DMSO-d6): 13.48 (1H, s), 7.95 (1H, s), 7.70 (2H, d), 7.65-7.56 (3H, m), 5.21 (1H, s), 1.87-1.71 (2H, m), 1.48 (3H, s), 0.74 (3H, t).

(−)-2-(4-chlorobenzoyl)-3-fluoro-5-(2-hydroxybutan-2-yl)benzoic Acid

1H NMR (400 MHz, DMSO-d6): 13.48 (1H, s), 7.95 (1H, s), 7.70 (2H, d), 7.65-7.59 (3H, m), 5.21 (1H, s), 1.86-1.68 (2H, m), 1.48 (3H, s), 0.75 (3H, t).

Preparation 40: (5-chloro-3-((4-methoxybenzyl)oxy)pyridin-2-yl)methanamine

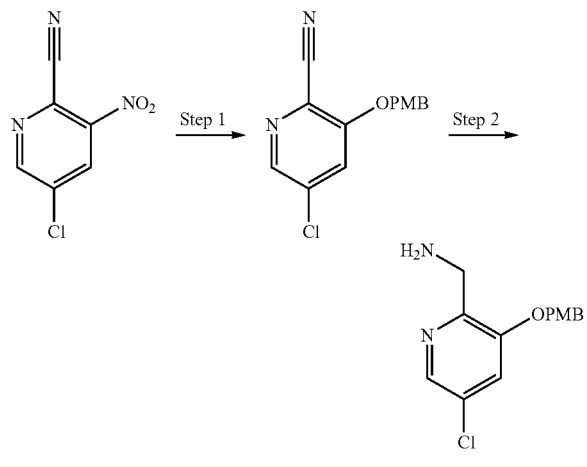

Step 1: 5-chloro-3-((4-methoxybenzyl)oxy)picolinonitrile

To an ice-cooled solution of 4-methoxybenzyl alcohol (8.67 g, 62.8 mmol) in dry THF (180 mL) under nitrogen atmosphere was added sodium hydride (2.92 g, 73.2 mmol) portion-wise. The mixture was allowed to warm to room temperature over 1 hour before being added drop-wise to an ice-cooled solution of 5-chloro-3-nitropicolinonitrile (9.6 g, 52.3 mmol) in THF (120 mL). The mixture was stirred for 10 minutes and was then quenched by slow addition of saturated aqueous NaHCO₃ solution (50 mL). The mixture was diluted with ethyl acetate (200 mL) and the organic layer was collected. The organic layer was washed with water (250 mL) and brine (250 mL), dried (MgSO₄), filtered and evaporated under reduced pressure to give a brown oil. The residue was triturated with iso-hexane:diethyl ether (1:1, 400 mL) and the resulting solid was collected by filtration to give the title compound (11.5 g, 80%) as an off white solid. ¹H NMR (400 MHz, CDCl₃) 8.23 (1H, d), 7.39-7.34 (3H, m), 6.94 (2H, d), 5.17 (2H, s), 3.83 (3H, s).

Step 2: (5-chloro-3-((4-methoxybenzyl)oxy)pyridin-2-yl)methanamine

A 5 L flask, fitted with an overhead stirrer, was charged with 5-chloro-3-((4-methoxybenzyl)oxy)picolinonitrile (25 g, 91.2 mmol) and dry methanol (1200 mL). Nickel (II) chloride hexahydrate (2.17 g, 9.12 mmol) was added and the suspension was stirred under a nitrogen atmosphere. The mixture was cooled in an ice bath and then sodium borohydride (24.1 g, 638 mmol) was added portion-wise (with caution) over a 10 minute period. The reaction was stirred for 30 minutes at 0° C. Analysis by LCMS indicated incomplete reaction so more nickel (II) chloride hexahydrate (2.17 g, 9.12 mmol) and sodium borohydride (24.1 g, 638 mmol) were added (portion-wise with caution). The reaction was stirred overnight, allowing to warm slowly to room temperature.

Diethylenetriamine (22 mL, 182 mmol). was added and the mixture was stirred at room temperature for 1 hour. The volatiles were removed under reduced pressure and the resulting residue was dissolved in ethyl acetate (1200 mL) and washed with saturated aqueous NaHCO₃ solution (2×600 mL). The organic layer was dried (MgSO₄), filtered and evaporated under reduced pressure to give a crude product which was purified by column chromatography (gradient elution 0 to 5% 7N methanolic ammonia in DCM) to give the title compound (9.4 g, 37%) as a pale brown solid. ¹H NMR (400 MHz, CDCl₃) 8.12 (1H, d, J=1.9 Hz), 7.33 (2H, d, J=8.7 Hz), 7.18 (1H, d, J=1.9 Hz), 6.93 (2H, d, J=8.7 Hz), 5.01 (2H, s), 3.97 (2H, s), 3.83 (3H, s); NH₂ not observed.

Preparation 41: (2-Bromo-6-methylpyridin-3-yl)methanamine dihydrochloride

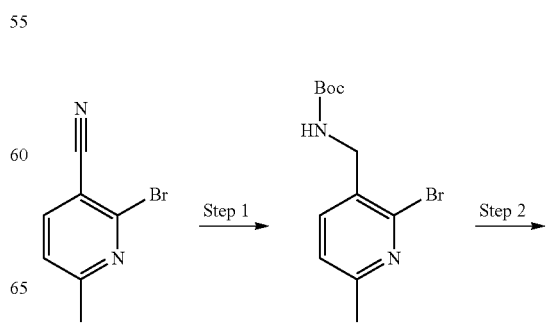

-continued

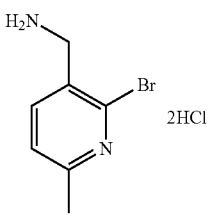

Step 1: tert-Butyl N-[(2-bromo-6-methylpyridin-3-yl)methyl]carbamate

To a stirred solution of 2-bromo-6-methylpyridine-3-carbonitrile (2.0 g, 10.0 mmol) in dry methanol (70 mL), cooled to 0° C., were added Boc$_2$O (4.36 g, 20.0 mmol) and NiCl$_{2\text{-}6}$H$_2$O (0.24 g, 1.0 mmol). NaBH$_4$ (2.65 g, 70.0 mmol) was then added in small portions over 30 min. The reaction was exothermic and effervescent. The resulting reaction mixture containing a finely divided black precipitate was allowed to warm to room temperature and left to stir for a further 1 h, at which point diethylenetriamine (1.1 mL, 20.0 mmol) was added. The solvent was evaporated, saturated NaHCO$_3$ was added and the product was extracted with EtOAc, the organic phase was dried, the solvent evaporated. The crude product was purified by column chromatography to afford the title compound (1.2 g, 40%). MS: [M+H]$^+$=301.

Step 2: (2-Bromo-6-methylpyridin-3-yl)methanamine dihydrochloride

A solution of tert-butyl N-[(2-bromo-6-methylpyridin-3-yl)methyl]carbamate (1.2 g, 4.0 mmol) in 4M dioxane—HCl (20 mL) was stirred for 16 hr. The solvent was evaporated to afford white solid (1.02 g, 99%). MS: [M+H]$^+$= 203.

Examples 1-580

Example 1: (3R)-3-(4-chlorophenyl)-2-[(5-chloropyridin-2-yl)methyl]-4-fluoro-3-({1-[hydroxy($^2$H$_2$)methyl]cyclopropyl}($^2$H$_2$)methoxy)-6-(2-hydroxypropan-2-yl)-2,3-dihydro-1H-isoindol-1-one

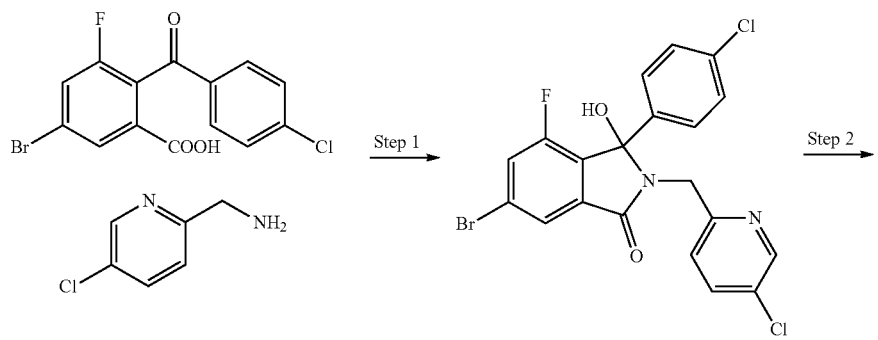

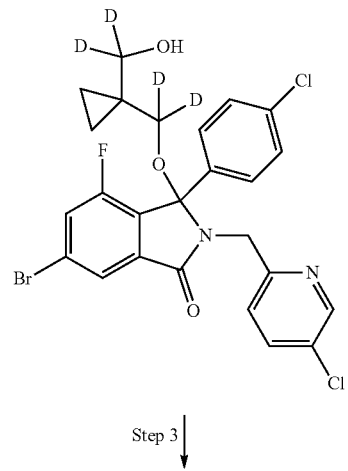

Step 3 ↓

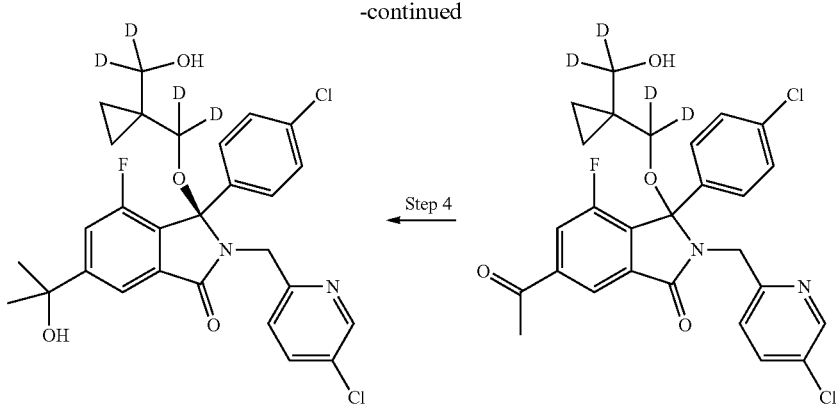

Step 4

Example 1, Step 1: 6-Bromo-3-(4-chloro-phenyl)-2-(5-chloro-pyridin-2-ylmethyl)-4-fluoro-3-hydroxy-2,3-dihydro-isoindol-1-one To a solution of 5-bromo-2-(4-chloro-benzoyl)-3-fluoro-benzoic acid (Manchester Organics, MOL1216) (10.7 g, 30.0 mmol) in THF (100 mL) was added DMF (0.1 mL) and SOCl$_2$ (4.4 mL, 60.0 mmol). The resulting solution was stirred for 16 h under N$_2$. The volatiles were removed in vacuo. The residue was dissolved in THF (100 mL), cooled to 0° C. under N$_2$, (5-chloropyridine-2-yl)methaneamine dihydrochloride (Anichem, H12670) (6.9 g, 32.0 mmol) and DIPEA (16.7 mL, 96.0 mmol) were added the reaction mixture was stirred at room temperature for 4 hours. Water (150 mL) was added and the product was extracted with EtOAc (2×150 mL). The combined organic layers were washed with brine (200 mL) and dried over MgSO$_4$. The solvent was removed in vacuo and the residue was triturated with EtOAc—petrol (1:1, 100 mL) to afford off-white solid (9.56 g, 66%). MS: [M+H]$^+$=483

Example 1, step 2 6-Bromo-3-(4-chlorophenyl)-2-[(5-chloropyridin-2-yl)methyl]-4-fluoro-3-({1-[hydroxy($^2$H$_2$)methyl]cyclopropyl}($^2$H$_2$)methoxy)-2,3-dihydro-1H-isoindol-1-one To a solution of 6-bromo-3-(4-chloro-phenyl)-2-(5-chloro-pyridin-2-ylmethyl)-4-fluoro-3-hydroxy-2,3-dihydro-isoindol-1-one (9.64 g, 20.0 mmol) in DCE (200 mL) were added {1-[hydroxy($^2$H$_2$)methyl]cyclopropyl}($^2$H$_2$)methanol (8.5 g, 80.0 mmol) (preparation 1) and InBr$_3$ (10.6 g, 30.0 mmol) and the reaction mixture was stirred for 3 hours under nitrogen at 90° C. The reaction mixture was cooled, washed with water (2×150 mL). The organic phase was dried over MgSO$_4$, concentrated in vacuo and purified by Biotage using 0-50% EtOAc/in petrol as the eluent to give the title compound as a white solid (8.9 g, 78%). MS: [M+H]$^+$=569

Example 1 step 3 6-Acetyl-3-(4-chlorophenyl)-2-[(5-chloropyridin-2-yl)methyl]-4-fluoro-3-({1-[hydroxy($^2$H$_2$)methyl]cyclopropyl}($^2$H$_2$)methoxy)-2,3-dihydro-1H-isoindol-1-one To a solution of 6-bromo-3-(4-chlorophenyl)-2-[(5-chloropyridin-2-yl)methyl]-4-fluoro-3-({1-[hydroxy($^2$H$_2$)methyl]cyclopropyl}($^2$H$_2$)methoxy)-2,3-dihydro-1H-isoindol-1-one (3.73 g, 6.54 mmol) in toluene (30 mL) and 1,4-dioxane (30 mL) were added LiCl (0.8 g, 19.62 mmol) and tributyl(1-ethoxyvinyl)tin (2.2 mL, 6.54 mmol) and the solution was degassed for 15 minutes. Pd(PPh$_3$)$_4$ (0.38 g, 0.32 mmol) was added and the reaction mixture was heated to 100° C. for 2 h. After cooling to room temperature, the reaction mixture was diluted with EtOAc (60 mL) and washed with saturated aqueous NaHCO$_3$ (60 mL). The organic phase was dried over MgSO$_4$, concentrated in vacuo and purified by Biotage using 0-50% EtOAc in petrol as the eluent. The isolated product was dissolved in 1,4-dioxane (20 mL) and 1M HCl (5 mL) was added and the reaction was stirred for 0.5 h. The reaction was quenched with saturated aqueous NaHCO$_3$ (30 mL) and extracted with EtOAc (3×30 mL). The combined organic extracts were dried over MgSO$_4$ and concentrated in vacuo to give the title compound as a yellow oil (2.65 g, 76%). MS: [M+H]$^+$=533

Example 1, Step 4: (3R)-3-(4-Chlorophenyl)-2-[(5-chloropyridin-2-yl)methyl]-4-fluoro-3-({1-[hydroxy($^2$H$_2$)methyl]cyclopropyl}($^2$H$_2$)methoxy)-6-(2-hydroxypropan-2-yl)-2,3-dihydro-1H-isoindol-1-one MeMgCl (1.45 mL, 3M in THF, 4.32 mmol) and ZnCl$_2$ (0.6 mL, 0.5M in THF, 1.2 mmol) were added to THF (10 mL) and the mixture was stirred at room temperature for 1 h under nitrogen. Cooled with ice and an ice cooled solution of (3R)-6-acetyl-3-(4-chlorophenyl)-2-[(5-chloropyridin-2-yl)methyl]-4-fluoro-3-({1-[hydroxy($^2$H$_2$)methyl]cyclopropyl}($^2$H$_2$)methoxy)-2,3-dihydro-1H-isoindol-1-one (0.72 g, 1.35 mmol) in THF (10 mL) was added and the reaction mixture was stirred at room temperature for 3 h. The reaction was quenched with saturated NH$_4$Cl (10 mL) and extracted with EtOAc (3×20 mL). The combined organic extracts were dried over MgSO$_4$, concentrated in vacuo and purified by Biotage using 0-100% EtOAc in petrol as the eluent to afford the racemic mixture (0.38 g, 51%). Separation by chiral preparative LCMS gave the title compound as a colourless solid (0.127 g).

1H NMR (400 MHz, DMSO-d6): 8.35 (1H, d), 7.80 (1H, d), 7.72 (1H, dd), 7.51 (1H, dd), 7.33-7.17 (5H, m), 5.37 (1H, s), 4.46 (2H, s), 4.38 (1H, s), 1.48 (6H, s), 0.39-0.30 (2H, m), 0.23-0.07 (2H, m). MS: [M+H]$^+$=547

Example 2: (3R)-3-(4-Chlorophenyl)-2-[(5-chloro-pyridin-2-yl)methyl]-4-fluoro-6-(2-hydroxypropan-2-yl)-3-methoxy-2,3-dihydro-1H-isoindol-1-one

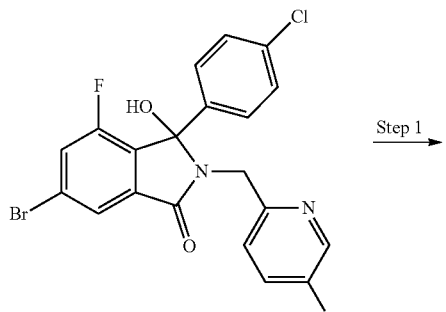

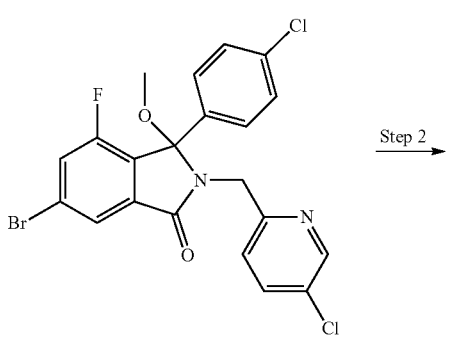

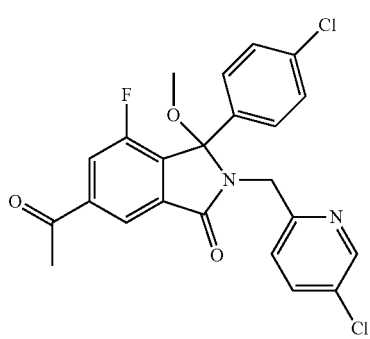

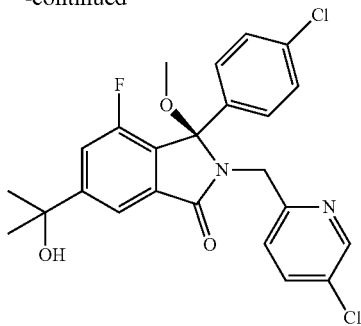

Example 2, Step 1: 6-Bromo-3-(4-chlorophenyl)-2-[(5-chloropyridin-2-yl)methyl]-4-fluoro-3-methoxy-2,3-dihydro-1H-isoindol-1-one To a solution of 6-bromo-3-(4-chloro-phenyl)-2-(5-chloro-pyridin-2-ylmethyl)-4-fluoro-3-hydroxy-2,3-dihydro-isoindol-1-one (0.77 g, 1.6 mmol) (Example 1, step 1) in THF were added $SOCl_2$ (0.23 mL, 3.2 mmol) and DMF (0.05 mL) and the reaction mixture was stirred at room temperature for 2 h. The solvent was evaporated in vacuo, the residue was dissolved in MeOH (15 mL), stirred for 0.5 h. The solvent was evaporated, the residue was dissolved in EtOAc (20 mL), washed with saturated $NaHCO_3$. The organic phase was dried ($MgSO_4$), filtered and the solvent evaporated. The crude product was purified by Biotage using 0-30% EtOAc/in petrol as the eluent to give the title compound as a yellow oil (0.55 g, 69%). MS: $[M+H]^+=495$

Example 2, Step 2: 6-Acetyl-3-(4-chlorophenyl)-2-[(5-chloropyridin-2-yl)methyl]-4-fluoro-3-methoxy-2,3-dihydro-1H-isoindol-1-one 6-Acetyl-3-(4-chlorophenyl)-2-[(5-chloropyridin-2-yl)methyl]-4-fluoro-3-methoxy-2,3-dihydro-1H-isoindol-1-one was prepared from 6-bromo-3-(4-chlorophenyl)-2-[(5-chloropyridin-2-yl)methyl]-4-fluoro-3-methoxy-2,3-dihydro-1H-isoindol-1-one in a similar manner to that described in Example 1, step 3. MS: $[M+H]^+=459$.

Example 2, Step 3: (3R)-3-(4-Chlorophenyl)-2-[(5-chloropyridin-2-yl)methyl]-4-fluoro-6-(2-hydroxy-propan-2-yl)-3-methoxy-2,3-dihydro-1H-isoindol-1-one (3R)-3-(4-chlorophenyl)-2-[(5-chloropyridin-2-yl)methyl]-4-fluoro-6-(2-hydroxypropan-2-yl)-3-methoxy-2,3-dihydro-1H-isoindol-1-one was prepared from 6-acetyl-3-(4-chlorophenyl)-2-[(5-chloropyridin-2-yl)methyl]-4-fluoro-3-methoxy-2,3-dihydro-1H-isoindol-1-one in a similar manner to that described in Example 1, step 4. Purification by chiral preparative LCMS gave the title compound as a colourless solid.

1H NMR (400 MHz, DMSO-d6): 8.39 (1H, d), 7.82 (1H, d), 7.75 (1H, dd), 7.53 (1H, dd), 7.34-7.23 (5H, m), 5.38 (1H, s), 4.51 (1H, d), 4.36 (1H, d), 2.89 (3H, s), 1.48 (6H, s). MS: $[M+H]^+=473$

Example 3: 6-{[(1R)-1-(4-chlorophenyl)-7-fluoro-1-[(1-hydroxycyclopropyl)methoxy]-5-(2-hydroxypropan-2-yl)-3-oxo-2,3-dihydro-1H-isoindol-2-yl]methyl}pyridine-3-carbonitrile

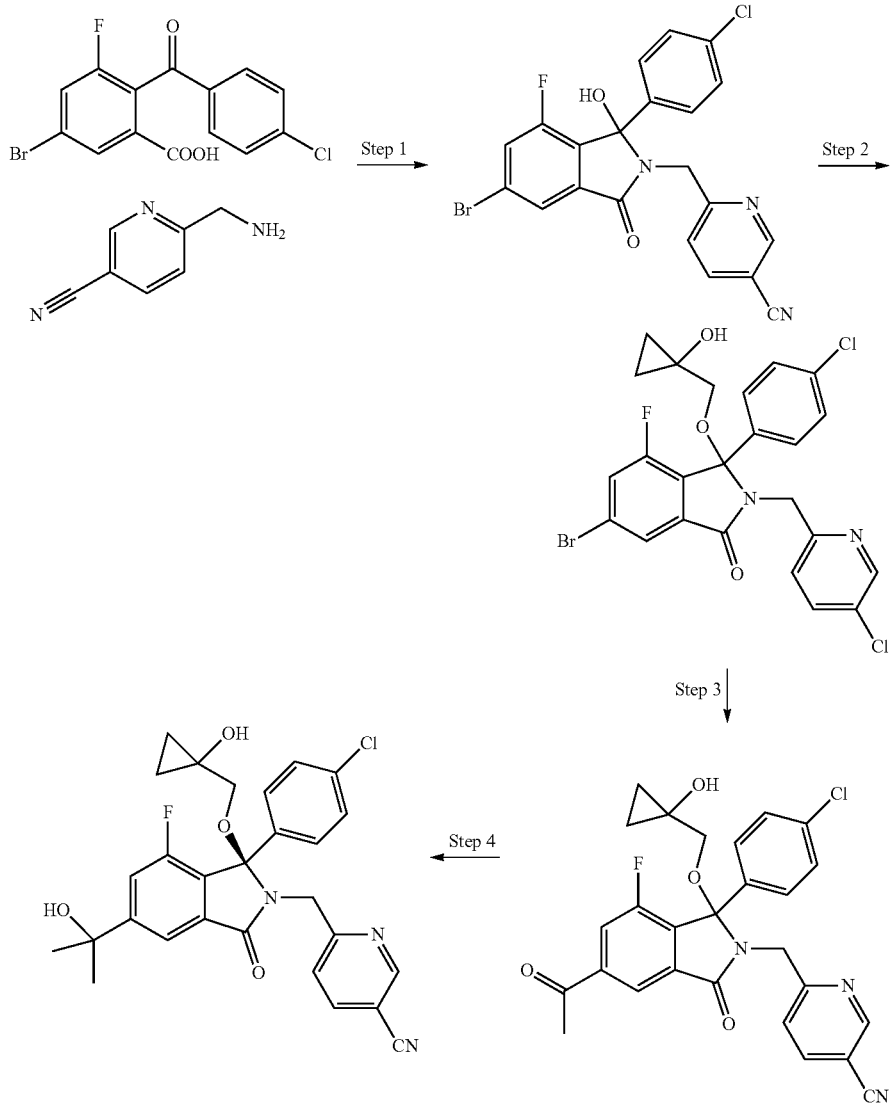

Example 3, Step 1: 6-[5-Bromo-1-(4-chloro-phenyl)-7-fluoro-1-hydroxy-3-oxo-1,3-dihydro-isoindol-2-ylmethyl]-nicotinonitrile 5-Bromo-2-(4-chloro-benzoyl)-3-fluoro-benzoic acid (Manchester Organics, MOL1216) (20 g, 56.02 mmol) was dissolved in THF (200 mL), to which was added DMF (1 mL) and $SOCl_2$ (8.17 mL, 112.04 mmol). The resulting solution was stirred for 16 h under $N_2$. The volatiles were removed in vacuo and the residue was dissolved in THF (200 mL), cooled to 0° C. under $N_2$, and 6-aminomethyl-nicotinonitrile (Anichem, NP2051) (16.7 g, 61.62 mmol, 76% w/w) and DIPEA (32.1 mL, 184.87 mmol) were added to the reaction. The resulting solution was stirred at 0° C. for 4 hours. Solvent was removed in vacuo and the residue was partitioned between EtOAc (350 mL) and water (350 mL). The aqueous layer was extracted with EtOAc (2×200 mL). The combined organic layers were sequentially washed with aqueous 10% $KH_2PO_4$ (100 mL) and brine (200 mL) and dried over $MgSO_4$. Solvent was removed in vacuo until ~100 mL remained, heptane (100 mL) was added and a further ~50 mL solvent was removed in vacuo. The remaining solution was left for 0.5 h during which time a precipitate formed. Solid was isolated by vacuum filtration and washed with EtOAc (2×100 mL) and heptane (2×200 mL) to give the title compound (13.02 g) as a pale solid. MS: [M–H] 471.

Filtrate was concentrated to ~1/2 volume and left to stand for 20 h during which time a precipitate formed. Solid was isolated by vacuum filtration and washed with EtOAc (100 mL) and heptane (100 mL) to give the title compound (3.54 g) as a pale solid. MS: [M–H] 471.

Filtrate was concentrated to dryness and the residual solid was triturated with heptane/EtOAc (3:1, 2×50 mL) to give the title compound (2.38 g) as a pale solid. MS: [M–H] 471. Batches were combined to give 18.94 g of the title compound.

Example 3, Step 2: 6-[5-Bromo-1-(4-chloro-phenyl)-7-fluoro-1-(1-hydroxy-cyclopropylmethoxy)-3-oxo-1,3-dihydro-isoindol-2-ylmethyl]-nicotinonitrile 6-[5-Bromo-1-(4-chloro-phenyl)-7-fluoro-1-hydroxy-3-oxo-1,3-dihydro-isoindol-2-ylmethyl]-nicotinonitrile (1.42 g, 3 mmol) was dissolved in THF (30 mL) and DMF (2 drops) and $SOCl_2$ (0.44 mL, 6 mmol) were added and the reaction was stirred for 2 hours. The volatiles were removed in vacuo and the resulting solid was dissolved in THF (30 mL) and 1-hydroxymethyl-cyclopropanol (Preparation 2) (0.53 g, 6 mmol) and $K_2CO_3$ (0.83 g, 6 mmol) were added and the reaction was stirred for 16 h. The reaction was quenched with water (30 mL) and brine (5 mL) and extracted with EtOAc (3×50 mL). The combined organic extracts were dried over $MgSO_4$, concentrated in vacuo and purified by Biotage using 0-80% EtOAc/in petrol as the eluent to give the title compound as a pale yellow solid (0.89 g). MS: [M−H] 540.

Example 3, Step 3: 6-[5-Acetyl-1-(4-chloro-phenyl)-7-fluoro-1-(1-hydroxy-cyclopropylmethoxy)-3-oxo-1,3-dihydro-isoindol-2-ylmethyl]-nicotinonitrile 6-[5-Bromo-1-(4-chloro-phenyl)-7-fluoro-1-(1-hydroxy-cyclopropylmethoxy)-3-oxo-1,3-dihydro-isoindol-2-ylmethyl]-nicotinonitrile (0.89 g, 1.63 mmol) was dissolved in toluene (10 mL) and 1,4-dioxane (10 mL). LiCl (0.2 g, 4.9 mmol) and tributyl(1-ethoxyvinyl)tin (0.55 mL, 1.63 mmol) were added and the solution was degassed for 15 minutes. $Pd(PPh_3)_4$ (0.09 g, 0.08 mmol) was added and the reaction mixture was heated to 100° C. for 1 h. After cooling to room temperature, the reaction mixture was diluted with EtOAc (20 mL) and washed with saturated aqueous $NaHCO_3$ (20 mL). The organic phase was dried over $MgSO_4$, concentrated in vacuo and purified by Biotage using 0-100% EtOAc in petrol as the eluent. The isolated product was dissolved in 1,4-dioxane (10 mL) and 2M HCl (4 mL) was added and the reaction was stirred for 1 h. The reaction was quenched with saturated aqueous $NaHCO_3$ (30 mL) and extracted with DCM (3×20 mL). The combined organic extracts were dried over $MgSO_4$ and concentrated in vacuo to give the title compound as a dark oil (0.4 g) MS: [M−H] 504.

Example 3, Step 4: 6-{[(1R)-1-(4-chlorophenyl)-7-fluoro-1-[(1-hydroxycyclopropyl)methoxy]-5-(2-hydroxypropan-2-yl)-3-oxo-2,3-dihydro-1H-isoindol-2-yl]methyl}pyridine-3-carbonitrile 6-[5-Acetyl-1-(4-chloro-phenyl)-7-fluoro-1-(1-hydroxy-cyclopropylmethoxy)-3-oxo-1,3-dihydro-isoindol-2-ylmethyl]-nicotinonitrile (0.42 g, 0.84 mmol) was dissolved in THF (20 mL) under $N_2$ at 0° C. $ZnCl_2$ (0.36 mL, 0.5M in THF) and MeMgCl (0.84 mL, 3M in THF) were added and the reaction was stirred for 1 h. The reaction was quenched with saturated $NH_4Cl$ (10 mL) and extracted with DCM (3×30 mL). The combined organic extracts were dried over $MgSO_4$, concentrated in vacuo and purified by Biotage using 20-100% EtOAc in petrol as the eluent. Purification by chiral preparative LCMS gave the title compound as a colourless solid (0.07 g).

1H NMR (400 MHz, DMSO-d6): 8.78-8.74 (1H, m), 8.08 (1H, dd), 7.82 (1H, d), 7.56-7.51 (1H, m), 7.32 (3H, d), 7.28 (2H, d), 5.52 (1H, s), 5.39 (1H, s), 4.59 (2H, d), 3.22 (1H, d), 2.96 (1H, d), 1.49 (6H, d), 0.54 (2H, s), 0.40-0.35 (1H, m), 0.31-0.26 (1H, m). MS: [M−H] 520

Example 4: 1-({[(1R)-1-(4-chlorophenyl)-2-[(5-chloropyridin-2-yl)methyl]-7-fluoro-5-(2-hydroxypropan-2-yl)-3-oxo-2,3-dihydro-1H-isoindol-1-yl]oxy}methyl)cyclopropane-1-carboxamide

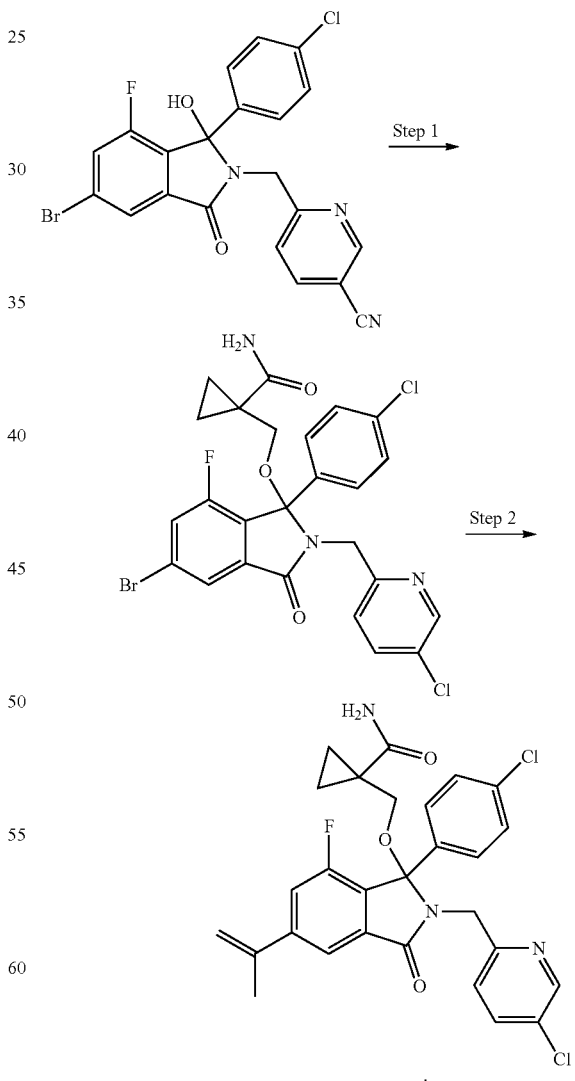

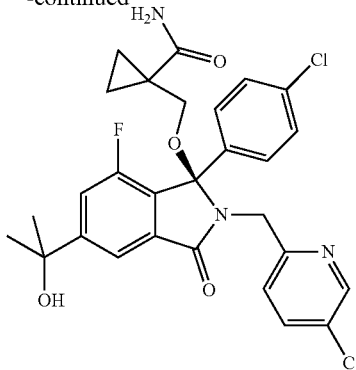

Example 4, Step 1: 1-[5-Bromo-1-(4-chloro-phenyl)-2-(5-chloro-pyridin-2-ylmethyl)-7-fluoro-3-oxo-2,3-dihydro-1H-isoindol-1-yloxymethyl]-cyclopropanecarboxylic Acid Amide The title compound (0.8 g) was prepared from 6-bromo-3-(4-chloro-phenyl)-2-(5-chloro-pyridin-2-ylmethyl)-4-fluoro-3-hydroxy-2,3-dihydro-isoindol-1-one (Example 1, step 1) (0.96 g, 2 mmol) and 1-hydroxymethyl-cyclopropanecarboxylic acid amide (0.46 g, 4 mmol) in a similar manner to that described in Example 3, step 2.

Example 4, Step 2: 1-[5-Acetyl-1-(4-chloro-phenyl)-2-(5-chloro-pyridin-2-ylmethyl)-7-fluoro-3-oxo-2,3-dihydro-1H-isoindol-1-yloxymethyl]-cyclopropanecarboxylic Acid Amide 1-[5-Bromo-1-(4-chloro-phenyl)-2-(5-chloro-pyridin-2-ylmethyl)-7-fluoro-3-oxo-2,3-dihydro-1H-isoindol-1-yloxymethyl]-cyclopropanecarboxylic acid amide (0.8 g, 1.40 mmol) was dissolved in THF (15 mL) and isopropenylboronic acid pinacol ester (0.4 mL, 2.1 mmol), NaOH (0.06 g, 1.40 mmol) and N,N-dicyclohexylmethylamine (0.3 mL, 1.40 mmol) were added and the solution was degassed for 15 minutes. Pd(dppf)Cl$_2$ (0.05 mg, 0.14 mmol) was added and the reaction was heated to reflux for 2 h, cooled to room temperature, filtered through celite, diluted with EtOAc (50 mL) and washed with 2M HCl (30 mL) and brine (30 mL). The organic phase was dried over MgSO$_4$, concentrated in vacuo and purified by Biotage using 0-80% EtOAc in petrol as the eluent to give the title compound as an orange solid (0.64 g). MS: [M+H] 540.

Example 4, Step 3: 1-({[(1R)-1-(4-chlorophenyl)-2-[(5-chloropyridin-2-yl)methyl]-7-fluoro-5-(2-hydroxypropan-2-yl)-3-oxo-2,3-dihydro-1H-isoindol-1-yl]oxy}methyl)cyclopropane-1-carboxamide A solution of 1-[5-acetyl-1-(4-chloro-phenyl)-2-(5-chloro-pyridin-2-ylmethyl)-7-fluoro-3-oxo-2,3-dihydro-1H-isoindol-1-yloxymethyl]-cyclopropanecarboxylic acid amide (0.64 g, 1.19 mmol) in THF (3 mL) was added to a stirring suspension of Hg(OAc)$_2$ (0.6 g, 1.90 mmol) in water (1.4 mL). The reaction was stirred for 2 h, HClO$_4$ (32 μl) was added and the reaction was stirred for a further 4 h. 2M NaOH (1.67 mL) and NaBH$_4$ (0.09 g, 2.38 mmol) were added and the reaction was stirred for a further 2 h. The reaction mixture was diluted with EtOAc (10 mL), filtered through celite, washed with water (10 mL), dried over MgSO$_4$, concentrated in vacuo and purified by Biotage using 30-100% EtOAc in petrol as the eluent. Purification by preparative chiral LCMS gave the title compound as a colourless solid (0.1 g).

1H NMR (400 MHz, DMSO-d6): 8.35 (1H, d), 7.80 (1H, s), 7.73 (1H, dd), 7.53 (1H, d), 7.31 (2H, d), 7.23 (3H, dd), 7.03 (1H, d), 6.85 (1H, s), 5.38 (1H, s), 4.47 (2H, s), 3.47 (1H, d), 3.08 (1H, d), 1.48 (6H, s), 0.99-0.87 (2H, m), 0.59-0.44 (2H, m). MS: [M+H] 558.

Example 5: 6-{[(1R)-1-(4-Chlorophenyl)-7-fluoro-1-({1-[hydroxy($^2$H$_2$)methyl]cyclopropyl}($^2$H$_2$)methoxy)-5-(2-hydroxypropan-2-yl)-3-oxo-2,3-dihydro-1H-isoindol-2-yl]methyl}pyridine-3-carbonitrile

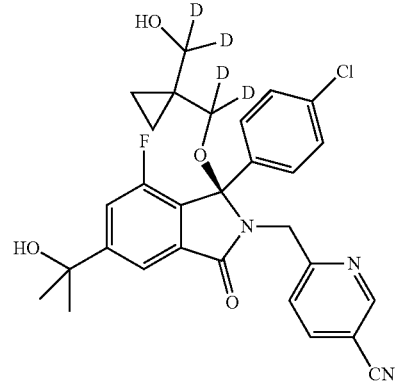 [SMILES: [2H]C([2H])(O)C1(C([2H])([2H])O[C@]2(c3ccc(Cl)cc3)c3c(F)cc(C(C)(C)O)cc3C(=O)N2Cc2ccc(C#N)cn2)CC1]

The title compound was prepared from 6-[5-bromo-1-(4-chloro-phenyl)-7-fluoro-1-hydroxy-3-oxo-1,3-dihydro-isoindol-2-ylmethyl]-nicotinonitrile (Example 3, step 1) in a similar manner to that described in Example 1, steps 2-4.

1H NMR (400 MHz, DMSO-d6): 8.77 (1H, d), 8.10 (1H, dd), 7.81 (1H, d), 7.53 (1H, d), 7.39-7.21 (5H, m), 5.38 (1H, s), 4.55 (2H, q), 4.39 (1H, s), 1.49 (6H, s), 0.40-0.30 (2H, m), 0.26-0.09 (2H, m). MS: [M−H] 520

Example 6: (3R)-3-(4-chlorophenyl)-2-[(5-chloropyridin-2-yl)methyl]-3-(2-hydroxyethoxy)-6-(2-hydroxypropan-2-yl)-2,3-dihydro-1H-isoindol-1-one ¹H NMR (400 MHz, DMSO-d6): 8.39-8.31 (2H, m), 8.21 (1H, dd), 7.73 (1H, dd), 7.41 (1H, d), 7.35-7.26 (4H, m), 7.23 (1H, d), 4.70 (1H, t), 4.58 (1H, d), 4.48 (1H, d),

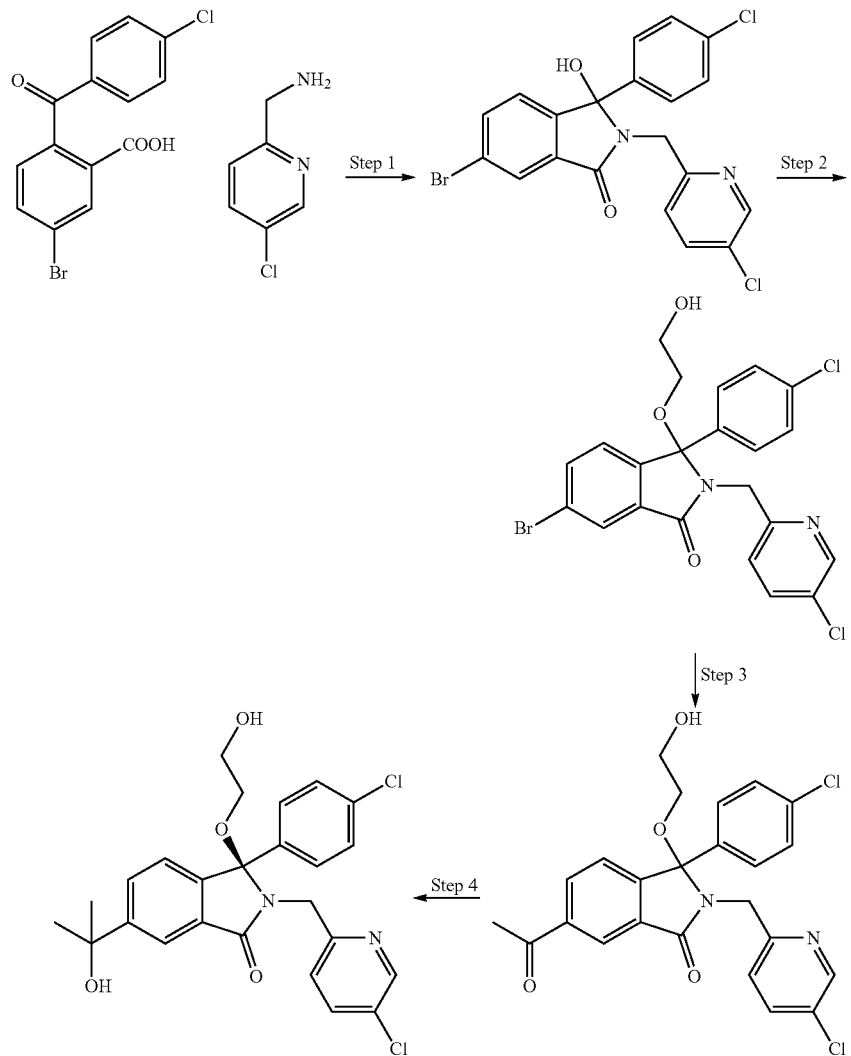

3.43-3.28 (2H, m), 3.07-2.97 (1H, m), 2.89-2.80 (1H, m), 2.69 (3H, s).

Example 6, Step 2: 6-Bromo-3-(4-chloro-phenyl)-2-(5-chloro-pyridin-2-ylmethyl)-3-(2-hydroxy-ethoxy)-2,3-dihydro-isoindol-1-one The title compound was prepared from 6-bromo-3-(4-chloro-phenyl)-2-(5-chloro-pyridin-2-ylmethyl)-3hydroxy-2,3-dihydro-isoindol-1-one (1.0 g, 2.1 mmol) and ethylene glycol (600 µL, 10.7 mmol) in a similar manner to that described in Example 1, step 2. MS: [M−H]⁻=507.

¹H NMR (400 MHz, DMSO-d6): 8.36 (1H, d), 8.02 (1H, d), 7.85 (1H, dd), 7.72 (1H, dd), 7.29 (4H, d), 7.21 (2H, t), 4.69 (1H, t), 4.54 (1H, d), 4.45 (1H, d), 3.39-3.25 (2H, m), 3.05-2.97 (1H, m), 2.90-2.81 (1H, m).

Example 6, Step 3: 6-Acetyl-3-(4-chloro-phenyl)-2-(5-chloro-pyridin-2-ylmethyl)-3-(2-hydroxy-ethoxy)-2,3-dihydro-isoindol-1-one The title compound was prepared from 6-bromo-3-(4-chloro-phenyl)-2-(5-chloro-pyridin-2-ylmethyl)-3-(2-hydroxy-ethoxy)-2,3-dihydro-isoindol-1-one (1.0 g, 1.9 mmol) in a similar manner to that described in Example 1, step 3.

Example 6, Step 4: (3R)-3-(4-chlorophenyl)-2-[(5-chloropyridin-2-yl)methyl]-3-(2-hydroxyethoxy)-6-(2-hydroxypropan-2-yl)-2,3-dihydro-1H-isoindol-1-one The title compound was prepared from 6-acetyl-3-(4-chloro-phenyl)-2-(5-chloro-pyridin-2-ylmethyl)-3-(2-hydroxy-ethoxy)-2,3-dihydro-isoindol-1-one (700 mg, 1.5 mmol) in a similar manner to that described in Example 1, step 4. MS: [M−C₂H₅O₂]⁺=425.

1H NMR (400 MHz, DMSO-d6): 8.36 (1H, d), 7.94 (1H, d), 7.75 (1H, dd), 7.71 (1H, dd), 7.28 (4H, s), 7.24-7.14 (2H, m), 5.25 (1H, s), 4.66 (1H, t), 4.56 (1H, d), 4.43 (1H, d), 3.31-3.23 (2H, m), 3.00-2.92 (1H, m), 2.88-2.79 (1H, m), 1.48 (6H, d).

Example 7: (3R)-3-(4-Chlorophenyl)-2-[(5-chloro-pyridin-2-yl)methyl]-3-{[1-(hydroxymethyl)cyclopropyl]methoxy}-6-(2-hydroxypropan-2-yl)-2,3-dihydro-1H-isoindol-1-one

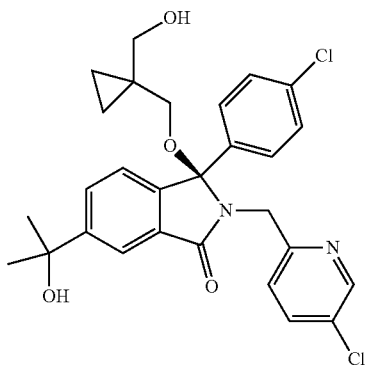 [SMILES: CC(C)(O)c1ccc2c(c1)C(=O)N(Cc1ccc(Cl)cn1)[C@@]2(OCC1(CO)CC1)c1ccc(Cl)cc1]

The title compound was prepared from 6-bromo-3-(4-chloro-phenyl)-2-(5-chloro-pyridin-2-ylmethyl)-3hydroxy-2,3-dihydro-isoindol-1-one (Example 6, step 1) in a similar manner to that described in Example 1, steps 2-4 using (1-hydroxymethyl-cyclopropyl)-methanol instead of {1-[hydroxy($^2H_2$)methyl]cyclopropyl}($^2H_2$)methanol in step 2.

H NMR (400 MHz, DMSO-d6): 8.36 (1H, d), 7.92 (1H, d), 7.77-7.69 (2H, m), 7.29 (2H, d), 7.23 (3H, d), 7.18 (1H, d), 5.24 (1H, s), 4.53-4.41 (3H, m), 3.49-3.41 (1H, m), 3.24 (1H, dd), 2.95-2.77 (2H, m), 1.48 (6H, s), 0.31 (2H, s), 0.20-0.11 (1H, m), 0.05 (1H, d). MS: [M-$C_2H_5O_2$]$^+$=425

Example 8: (3R)-3-(4-Chlorophenyl)-2-[(5-chloro-pyridin-2-yl)methyl]-6-(2-hydroxypropan-2-yl)-3-methoxy-2,3-dihydro-1H-isoindol-1-one

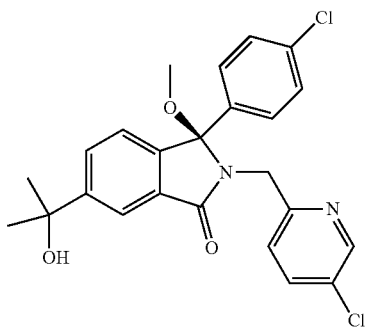 [SMILES: CO[C@]1(c2ccc(Cl)cc2)c2ccc(C(C)(C)O)cc2C(=O)N1Cc1ccc(Cl)cn1]

The title compound was prepared from 6-bromo-3-(4-chloro-phenyl)-2-(5-chloro-pyridin-2-ylmethyl)-3hydroxy-2,3-dihydro-isoindol-1-one (Example 6, step 1) in a similar manner to that described in Example 2, steps 1-3.

1H NMR (400 MHz, DMSO-d6): 8.39 (1H, d), 7.94 (1H, d), 7.80-7.70 (2H, m), 7.35-7.12 (6H, m), 5.25 (1H, s), 4.52 (1H, d), 4.38 (1H, d), 2.77 (3H, s), 1.48 (6H, s). m/z: 426

Example 9: (3R)-3-(4-Chlorophenyl)-2-[(5-chloro-pyridin-2-yl)methyl]-6-(2-hydroxypropan-2-yl)-3-(3-hydroxypropoxy)-2,3-dihydro-1H-isoindol-1-one

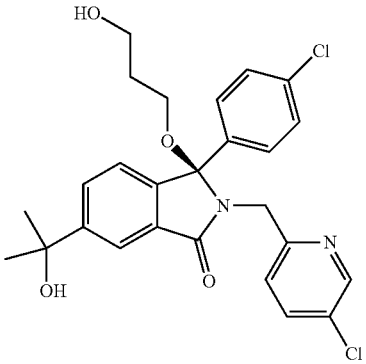 [SMILES: CC(C)(O)c1ccc2c(c1)C(=O)N(Cc1ccc(Cl)cn1)[C@@]2(OCCCO)c1ccc(Cl)cc1]

The title compound was prepared from 6-bromo-3-(4-chloro-phenyl)-2-(5-chloro-pyridin-2-ylmethyl)-3hydroxy-2,3-dihydro-isoindol-1-one (Example 6, step 1) in a similar manner to that described in Example 1, steps 2-4 using propane-1,3-diol instead of {1-[hydroxy($^2H_2$)methyl]cyclopropyl}($^2H_2$)methanol in step 2.

1H NMR (400 MHz, DMSO-d6): 8.38 (1H, d), 7.93 (1H, d), 7.77-7.69 (2H, m), 7.30 (2H, d), 7.28-7.19 (3H, m), 7.17 (1H, d), 5.24 (1H, s), 4.55 (1H, d), 4.40-4.31 (2H, m), 3.45-3.33 (2H, m), 3.05-2.95 (1H, m), 2.93-2.83 (1H, m), 1.50-1.42 (7H, m), 1.41-1.30 (1H, m). m/z: 409

Example 10: (3R)-2-[(5-Chloro-1-oxo-1λ$^5$-pyridin-2-yl)methyl]-3-(4-chlorophenyl)-3-{[1-(hydroxymethyl)cyclopropyl]methoxy}-6-(2-hydroxypropan-2-yl)-2,3-dihydro-1H-isoindol-1-one

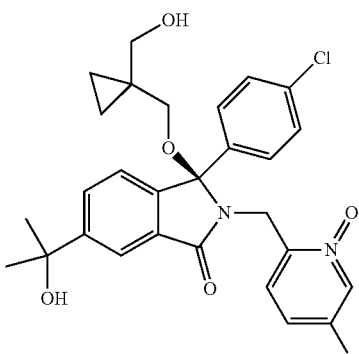

To a solution of (3R)-3-(4-chlorophenyl)-2-[(5-chloro-pyridin-2-yl)methyl]-3-{[1-(hydroxymethyl)cyclopropyl]methoxy}-6-(2-hydroxypropan-2-yl)-2,3-dihydro-1H-isoindol-1-one (Example 7)(27.3 mg, 0.052 mmol) in dichloromethane (1.5 mL) was added m-chloro-perbenzoic acid (77%, 14.0 mg, 0.062 mmol) and the reaction mixture was stirred at room temperature overnight. It was diluted with dichloromethane, washed with 10% sodium thiosulfate, 1M NaOH and water. The organic phase was dried, filtered and the solvent evaporated to afford white solid (25 mg, 90%).

1H NMR (400 MHz, DMSO-d6): 8.42 (1H, d), 7.95 (1H, d), 7.78 (1H, dd), 7.33-7.12 (7H, m), 5.27 (1H, s), 4.61-4.43 (3H, m), 3.45-3.35 (2H, m), 2.97 (1H, d), 2.91 (1H, d), 1.49 (6H, s), 0.42-0.32 (2H, m), 0.32-0.15 (2H, m). MS: [M–H]⁻= 541

Example 11: (3R)-3-(4-Chlorophenyl)-2-[(5-chloro-pyridin-2-yl)methyl]-4-fluoro-3-[(1-hydroxycyclo-propyl)methoxy]-6-(2-hydroxypropan-2-yl)-2,3-dihydro-1H-isoindol-1-one

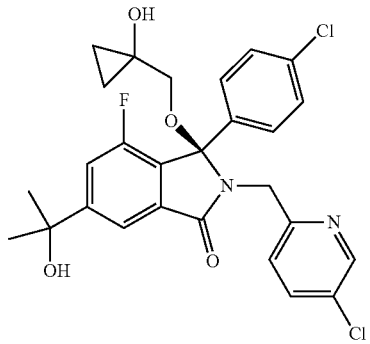 [SMILES: CC(C)(O)c1cc(F)c2c(c1)C(=O)N(Cc1ccc(Cl)cn1)[C@@]2(OCC1(O)CC1)c1ccc(Cl)cc1]

The title compound was prepared 6-bromo-3-(4-chloro-phenyl)-2-(5-chloro-pyridin-2-ylmethyl)-4-fluoro-3-hydroxy-2,3-dihydro-isoindol-1-one (Example 1, step 1) in a similar manner to that described in Example 3, steps 2-4.

1H NMR (400 MHz, DMSO-d6): 8.34 (1H, d), 7.81 (1H, d), 7.70 (1H, dd), 7.55-7.47 (1H, m), 7.31 (2H, d), 7.28 (2H, d), 7.17 (1H, d), 5.50 (1H, s), 5.37 (1H, s), 4.50 (2H, s), 3.16 (1H, d), 2.97 (1H, d), 1.48 (6H, d), 0.58-0.48 (2H, m), 0.42-0.21 (2H, m). m/z: 529

Example 12: (3R)-3-(4-Chlorophenyl)-4-fluoro-3-({1-[hydroxy(²H₂)methyl]cyclopropyl}(²H₂)methoxy)-6-(2-hydroxypropan-2-yl)-2-[(6-methyl-pyridazin-3-yl)methyl]-2,3-dihydro-1H-isoindol-1-one

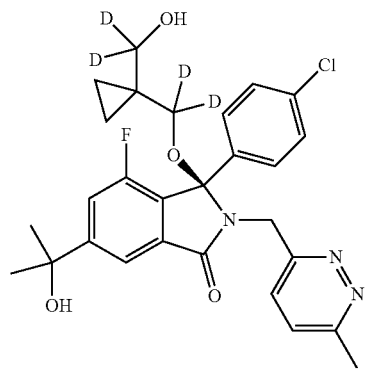 [SMILES: [2H]C([2H])(O)C1(C([2H])([2H])O[C@]2(c3ccc(Cl)cc3)c3c(F)cc(C(C)(C)O)cc3C(=O)N2Cc2ccc(C)nn2)CC1]

The title compound was prepared in a similar manner to that described in Example 1, steps 1-4 using C-(6-methyl-pyridazin-3-yl)-methylamine instead of (5-chloropyridine-2-yl)methaneamine dihydrochloride in step 1.

1H NMR (400 MHz, DMSO-d6): 7.81 (1H, s), 7.52 (1H, d), 7.39-7.19 (6H, m), 4.63 (2H, s), 1.48 (6H, s), 0.40-0.29 (2H, m), 0.22-0.09 (2H, m). m/z: 530

Example 13: (3R)-3-(4-Chlorophenyl)-2-[(5-chloro-pyridin-2-yl)methyl]-4-fluoro-6-(2-hydroxypropan-2-yl)-3-[(1-methoxycyclopropyl)methoxy]-2,3-dihydro-1H-isoindol-1-one

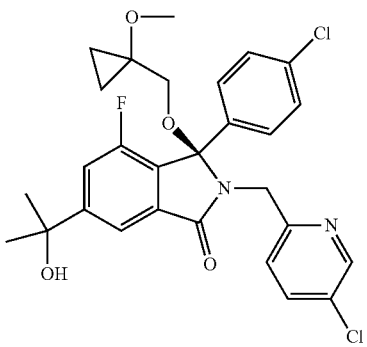 [SMILES: COC1(CO[C@]2(c3ccc(Cl)cc3)c3c(F)cc(C(C)(C)O)cc3C(=O)N2Cc2ccc(Cl)cn2)CC1]

The title compound was prepared from 6-bromo-3-(4-chloro-phenyl)-2-(5-chloro-pyridin-2-ylmethyl)-4-fluoro-3-hydroxy-2,3-dihydro-isoindol-1-one (Example 1, step 1) in a similar manner to that described in Example 3, steps 2-4 using (1-methoxy-cyclopropyl)-methanol (Preparation 3) instead of 1-hydroxymethyl-cyclopropanol in step 2.

1H NMR (400 MHz, DMSO-d6): 8.38 (1H, d), 7.81 (1H, d), 7.75 (1H, dd), 7.54 (1H, dd), 7.38-7.22 (5H, m), 5.38 (1H, s), 4.50 (1H, d), 4.39 (1H, d), 3.27-3.14 (5H, m), 1.48 (6H, s), 0.73-0.61 (2H, m), 0.42-0.34 (1H, m), 0.28-0.20 (1H, m). [M-C₅H₁₀O₂]⁺+ +443

Example 14 and Example 15: (3R)-3-(4-Chlorophenyl)-2-[(5-chloropyridin-2-yl)methyl]-6-(1,2-dihydroxypropan-2-yl)-3-{[1-(hydroxymethyl)cyclopropyl]methoxy}-2,3-dihydro-1H-isoindol-1-one (*both isomers separated and isolated)

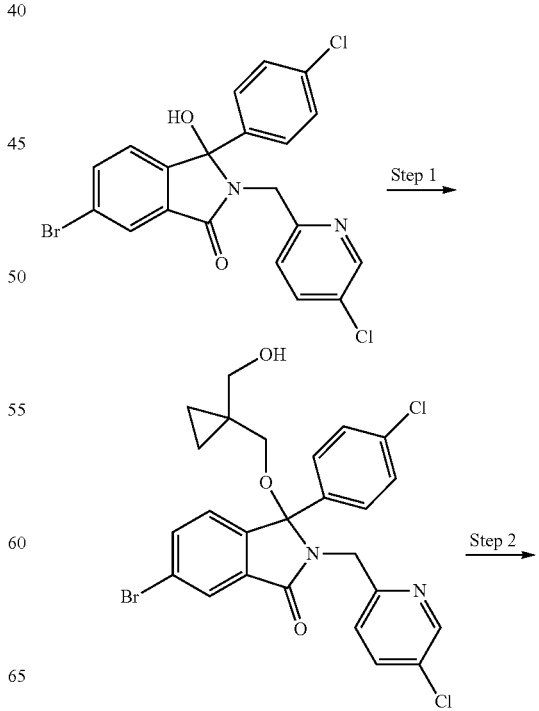

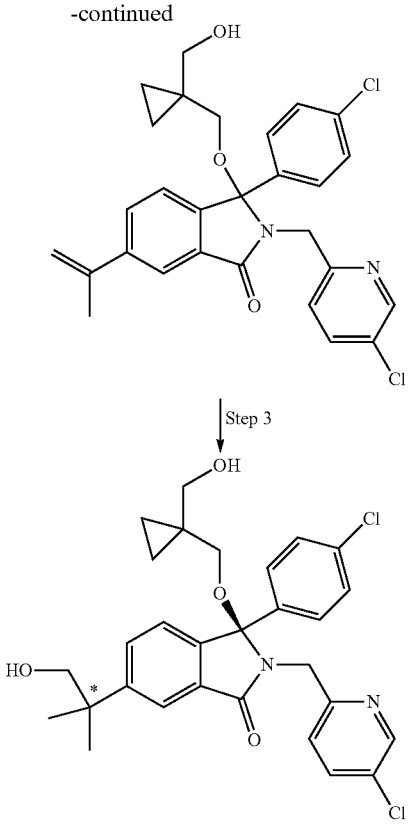

Example 14 and Example 15, Step 1: 6-Bromo-3-(4-chlorophenyl)-2-[(5-chloropyridin-2-yl)methyl]-3-{[1-(hydroxymethyl)cyclopropyl]methoxy}-2,3-dihydro-1H-isoindol-1-one The title compound was prepared from 6-bromo-3-(4-chloro-phenyl)-2-(5-chloro-pyridin-2-ylmethyl)-3hydroxy-2,3-dihydro-isoindol-1-one (Example 6, step 1) in a similar manner to that described in Example 1, step 2 using (1-hydroxymethyl-cyclopropyl)-methanol instead of {1-[hydroxy($^2H_2$)methyl]cyclopropyl}($^2H_2$)methanol.

Example 14 and Example 15, Step 2: 3-(4-Chlorophenyl)-2-[(5-chloropyridin-2-yl)methyl]-3-{[1-(hydroxymethyl)cyclopropyl]methoxy}-6-(prop-1-en-2-yl)-2,3-dihydro-1H-isoindol-1-one 6-Bromo-3-(4-chlorophenyl)-2-[(5-chloropyridin-2-yl)methyl]-3-{[1-(hydroxymethyl)cyclopropyl]methoxy}-2,3-dihydro-1H-isoindol-1-one (2.6 g, 4.74 mmol) was reacted with isopropenylboronic acid pinacol ester in a similar manner to that described in Example 4, step 2 to afford the product (2.03 g, 85%). MS: [M−H]⁻=507.

Example 14 and Example 15, Step 3: (3R)-3-(4-Chlorophenyl)-2-[(5-chloropyridin-2-yl)methyl]-6-(1,2-dihydroxypropan-2-yl)-3-{[1-(hydroxymethyl)cyclopropyl]methoxy}-2,3-dihydro-1H-isoindol-1-one To a solution of 3-(4-chlorophenyl)-2-[(5-chloropyridin-2-yl)methyl]-3-{[1-(hydroxymethyl)cyclopropyl]methoxy}-6-(prop-1-en-2-yl)-2,3-dihydro-1H-isoindol-1-one (1.16 g, 2.28 mmol) in t-butanol (10 mL) and water (10 mL) was added AD-mix β at 00° C. and the mixture was stirred for 48 h. 10% $Na_2S_2O_4$ (20 mL) was added and stirred for 30 mins. The product was extracted with EtOAc (2×20 mL), The organic phase was dried, filtered and the solvent evaporated. The crude product was purified by Biotage using 0-100% EtOAc in petrol as eluent. Product (0.45 g) and starting material I(0.3 g) were isolated. The starting material was reacted again in a similar way to afford further product (0.185 g). The single compounds were separated with chiral HPLC. The products were separated by chiral HPLC.

Example 14 Isomer 1

1H NMR (400 MHz, DMSO-d6): 8.36 (1H, d), 7.92 (1H, d), 7.76-7.68 (2H, m), 7.32-7.14 (6H, m), 5.16 (1H, s), 4.79 (1H, t), 4.53-4.41 (3H, m), 3.60-3.42 (3H, m), 3.24 (1H, dd), 2.95-2.82 (2H, m), 1.44 (3H, s), 0.32 (2H, s), 0.16 (1H, d), 0.04 (1H, d). m/z: 541

Example 15 Isomer 2

1H NMR (400 MHz, DMSO-d6): 8.36 (1H, d), 7.90 (1H, d), 7.77-7.68 (2H, m), 7.33-7.13 (6H, m), 5.16 (1H, s), 4.79 (1H, t), 4.54-4.40 (3H, m), 3.53-3.41 (3H, m), 3.24 (1H, dd), 2.96-2.81 (2H, m), 1.44 (3H, s), 0.36-0.26 (2H, m), 0.15 (1H, d), 0.03 (1H, d). m/z: 541

Example 16 and Example 17: (3R)-3-(4-Chlorophenyl)-2-[(5-chloropyridin-2-yl)methyl]-6-(1,2-dihydroxypropan-2-yl)-4-fluoro-3-({1-[hydroxy($^2H_2$)methyl]cyclopropyl}($^2H_2$)methoxy)-2,3-dihydro-1H-isoindol-1-one (*both isomers separated and isolated)

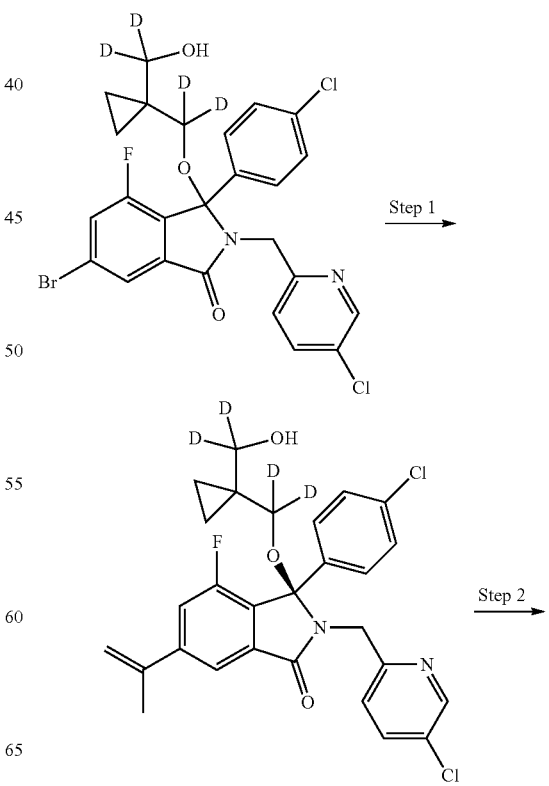

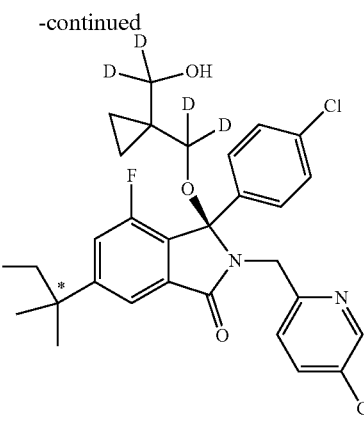

Example 16 and Example 17, Step 1: (3R)-3-(4-Chlorophenyl)-2-[(5-chloropyridin-2-yl)methyl]-4-fluoro-3-({1-[hydroxy($^2H_2$)methyl]cyclopropyl}($^2H_2$)methoxy)-6-(prop-1-en-2-yl)-2,3-dihydro-1H-isoindol-1-one 6-Bromo-3-(4-chlorophenyl)-2-[(5-chloropyridin-2-yl)methyl]-4-fluoro-3-({1-[hydroxy($^2H_2$)methyl]cyclopropyl}($^2H_2$)methoxy)-2,3-dihydro-1H-isoindol-1-one (Example 1, step 2) (8.9 g, 15.6 mmol) was reacted with isopropenylboronic acid pinacol ester in a similar manner to that described in Example 4, step 2 to afford the product (9.0 g). The enantiomers were separated by chiral HPLC and the (3R)-enantiomer was used for the dihydroxylation. 1H NMR (400 MHz, DMSO-d6): 8.35 (1H, d), 7.79 (1H, d), 7.72 (1H, dd), 7.61 (1H, dd), 7.33-7.14 (5H, m), 5.69 (1H, s), 5.30 (1H, s), 4.55-4.40 (2H, m), 4.38 (1H, s), 3.92 (1H, s), 2.18 (3H, s), 1.08 (6H, s), 0.39-0.30 (2H, m), 0.25-0.09 (2H, m).

Example 16 and Example 17, Step 2: (3R)-3-(4-Chlorophenyl)-2-[(5-chloropyridin-2-yl)methyl]-6-(1,2-dihydroxypropan-2-yl)-4-fluoro-3-({1-[hydroxy($^2H_2$)methyl]cyclopropyl}($^2H_2$)methoxy)-2,3-dihydro-1H-isoindol-1-one (3R)-3-(4-Chlorophenyl)-2-[(5-chloropyridin-2-yl)methyl]-4-fluoro-3-({1-[hydroxy($^2H_2$)methyl]cyclopropyl}($^2H_2$)methoxy)-6-(prop-1-en-2-yl)-2,3-dihydro-1H-isoindol-1-one was reacted with AD-mix β in a similar manner to that described in Example 14 and Example 15 step 3.

The isomers were separated by chiral HPLC.

Example 16 Isomer 1

1H NMR (400 MHz, DMSO-d6): 8.36 (1H, d), 7.79 (1H, d), 7.72 (1H, dd), 7.47 (1H, d), 7.33-7.17 (5H, m), 5.29 (1H, s), 4.98-4.68 (1H, m), 4.44 (3H, s), 3.54-3.41 (2H, m), 1.44 (3H, s), 0.35 (2H, s), 0.23-0.15 (1H, m), 0.15-0.06 (1H, m). m/z 563

Example 17 Isomer 2

1H NMR (400 MHz, DMSO-d6): 8.36 (1H, d), 7.78 (1H, d), 7.72 (1H, dd), 7.52-7.44 (1H, m), 7.34-7.17 (5H, m), 5.29 (1H, s), 5.01-4.62 (1H, m), 4.43 (3H, s), 3.53-3.41 (2H, m), 1.44 (3H, s), 0.34 (2H, s), 0.23-0.15 (1H, m), 0.15-0.05 (1H, m) m/z: 563

Example 18 and Example 19: (3R)-3-(4-Chlorophenyl)-2-[(5-chloropyridin-2-yl)methyl]-6-(2,4-dihydroxybutan-2-yl)-3-{[1-(hydroxymethyl)cyclopropyl]methoxy}-2,3-dihydro-1H-isoindol-1-one (*both isomers separated and isolated)

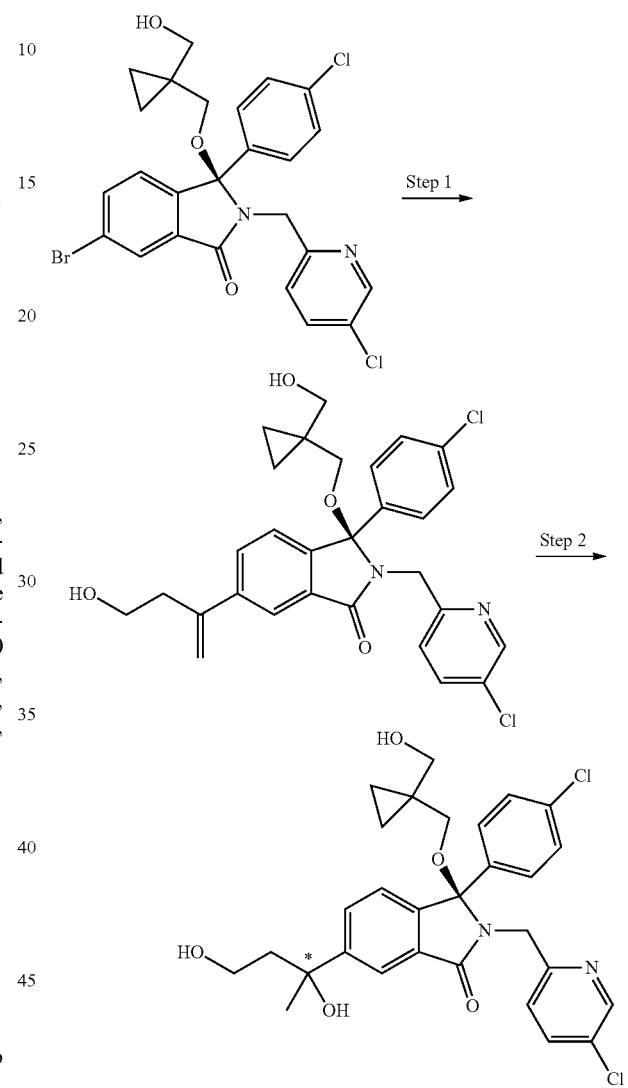

Example 18 and Example 19, Step 1: (3R)-3-(4-Chlorophenyl)-2-[(5-chloropyridin-2-yl)methyl]-6-(4-hydroxybut-1-en-2-yl)-3-{[1-(hydroxymethyl)cyclopropyl]methoxy}-2,3-dihydro-1H-isoindol-1-one (3R)-6-Bromo-3-(4-chlorophenyl)-2-[(5-chloropyridin-2-yl)methyl]-3-{[1-(hydroxymethyl)cyclopropyl]methoxy}-2,3-dihydro-1H-isoindol-1-one (obtained by chiral separation of racemic material Example 14 and Example 15, Step 1 (645 mg, 1.18 mmol) was dissolved in anhydrous THF (13 mL) and powdered NaOH (47 mg, 1.18 mmol), DCMA (0.25 mL, 1.18 mmol) and 3-butane-1-ol-3-boronic acid pinacol ester (0.36 mL, 1.76 mmol) were added sequentially at room temperature under a $N_2$ atmosphere. The yellow solution was degassed with $N_2$ for 20 min, then Pd(dppf)

Cl₂—CH₂Cl₂ (47 mg, 0.18 mmol) was added and the dark brown solution heated at reflux for 1 h. After cooling to room temperature, the reaction mixture was absorbed directly onto silica for purification. FCC [dichloromethane-methanol (100:0)→(95:5)] of the crude residue afforded the title compound (610 mg, 96%) as a beige foam. MS: [M-C₅H₉O₂]⁺ 438.

Example 18 and Example 19, Step 2: (3R)-3-(4-Chlorophenyl)-2-[(5-chloropyridin-2-yl)methyl]-6-(2,4-dihydroxybutan-2-yl)-3-{[1-(hydroxymethyl)cyclopropyl]methoxy}-2,3-dihydro-1H-isoindol-1-one (3R)-3-(4-Chlorophenyl)-2-[(5-chloropyridin-2-yl)methyl]-6-(4-hydroxybut-1-en-2-yl)-3-{[1-(hydroxymethyl)cyclopropyl]methoxy}-2,3-dihydro-1H-isoindol-1-one was converted to the title compounds in a similar manner to that described in Example 4, step 3. The two diastereoisomers were separated by chiral HPLC.

Example 18 Isomer 1

¹H NMR (500 MHz, CDCl₃) 8.34 (1H, d, 7-H), 7.92 (1H, d, ArH), 7.73 (1H, dd, ArH), 7.52 (1H, dd, ArH), 7.32 (1H, d, ArH), 7.25-7.16 (4H, m, 4×ArH), 7.14 (1H, d, ArH), 4.49 (2H, s, NCH₂), 3.86-3.78 (1H, m, CH₂OH), 3.68 (2H, d, 4'-H'), 3.59-3.52 (1H, m, CH₂OH), 3.39 (2H, d, 4'-H), 3.26 (2H, d, 2'-H'), 2.72 (2H, d, 2'-H), 2.20-2.03 (2H, 2×m, CH₂CH₂OH), 1.61 (3H, s, CH₃), 0.53-0.45 (2H, m, Cy-Pr—H₂) and 0.36-0.24 (2H, m, Cy-Pr—H). MS: [M-C₅H₉O₂]⁺ 455.

Example 19 Isomer 2

¹H NMR (500 MHz, CDCl₃) 8.35 (1H, d, 7-H), 7.92 (1H, d, ArH) 7.73 (1H, dd, ArH), 7.55 (1H, dd, ArH), 7.34 (1H, d, ArH), 7.27-7.17 (4H, m, 4×ArH), 7.14 (1H, d, ArH), 4.49 (2H, s, NCH₂), 3.86-3.80 (1H, m, CH₂OH), 3.73 (2H, d, 4'-H'), 3.58-3.52 (1H, m, CH₂OH), 3.36 (2H, d, 4'-H), 3.31 (2H, d, 2'-H'), 2.67 (2H, d, 2'-H), 2.19-2.03 (2H, 2×m, CH₂CH₂OH), 1.61 (3H, s, CH₃), 0.52-0.46 (2H, m, Cy-Pr—H₂) and 0.35-0.24 (2H, m, Cy-Pr—H). MS: [M-C₅H₉O₂]⁺ 455.

Example 20 and Example 21: 6-{[(1R)-1-(4-Chlorophenyl)-5-(2,4-dihydroxybutan-2-yl)-7-fluoro-1-({1-[hydroxy(²H₂)methyl]cyclopropyl}(²H₂)methoxy)-3-oxo-2,3-dihydro-1H-isoindol-2-yl]methyl}pyridine-3-carbonitrile (*both isomers separated and isolated)

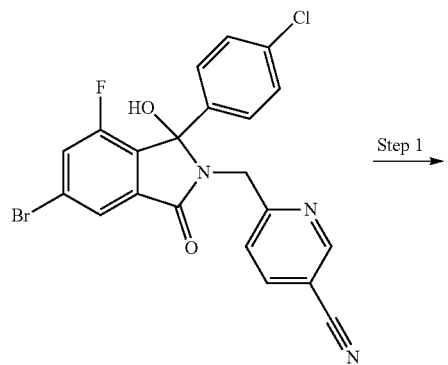

Example 20 and Example 21, Step 1: 6-{[(1R)-5-Bromo-1-(4-chlorophenyl)-7-fluoro-1-({1-[hydroxy(²H₂)methyl]cyclopropyl}(²H₂)methoxy)-3-oxo-2,3-dihydro-1H-isoindol-2-yl]methyl}pyridine-3-carbonitrile 6-[5-Bromo-1-(4-chloro-phenyl)-7-fluoro-1-hydroxy-3-oxo-1,3-dihydro-isoindol-2-ylmethyl]-nicotinonitrile (Example 3, step 1) (12.0 g, 25.5 mmol) was reacted with {1-[hydroxy(²H₂)methyl]cyclopropyl}(²H₂)methanol (10.8 g, 102 mmol) (preparation 1) in a similar manner to that described in Example 3, step 2. The enantiomers were separated with chiral HPLC and the R-enantiomer was used in the next step. MS: [M−H]⁻=559.

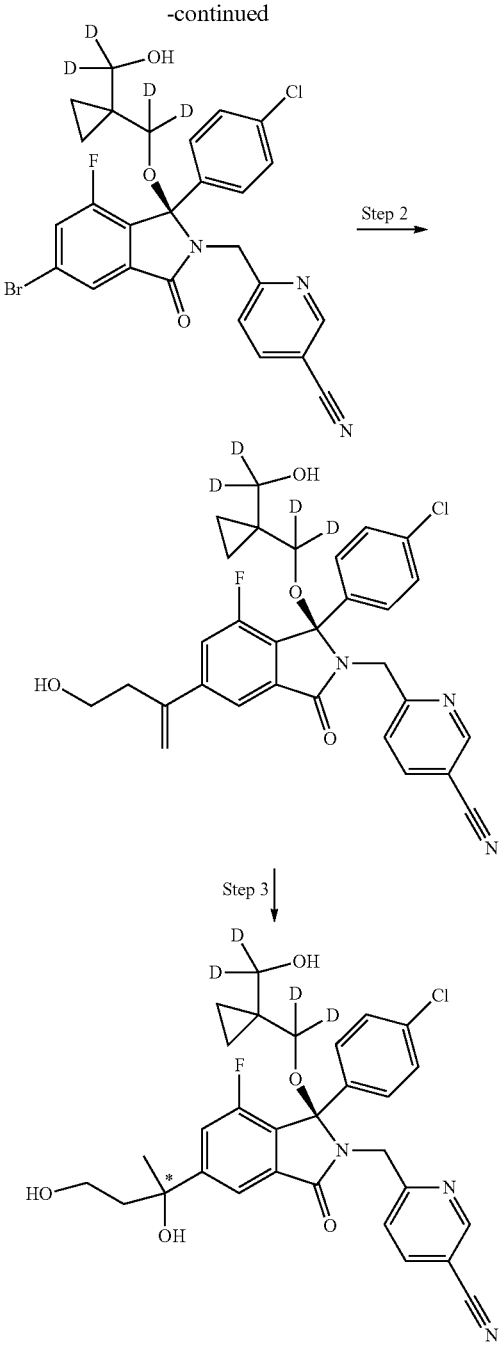

Example 20 and Example 21, Step 2: 6-{[(1R)-1-(4-Chlorophenyl)-7-fluoro-1-({1-[hydroxy($^2H_2$)methyl]cyclopropyl}($^2H_2$)methoxy)-5-(4-hydroxy-but-1-en-2-yl)-3-oxo-2,3-dihydro-1H-isoindol-2-yl]methyl}pyridine-3-carbonitrile 6-{[(1R)-5-Bromo-1-(4-chlorophenyl)-7-fluoro-1-({1-[hydroxy($^2H_2$)methyl]cyclopropyl}($^2H_2$)methoxy)-3-oxo-2,3-dihydro-1H-isoindol-2-yl]methyl}pyridine-3-carbonitrile (0.84 g, 1.5 mmol) was reacted with 3-butene-1-ol-3-boronic acid pinacol ester (0.46 mL, 2.25 mmol) in a similar manner to that described in Example 18 and Example 19 to afford the title compound (0.41 g, 50%). MS: [M−H]⁻=550

Example 20 and Example 21, Step 3: 6-{[(1R)-1-(4-Chlorophenyl)-5-(2,4-dihydroxybutan-2-yl)-7-fluoro-1-({1-[hydroxy($^2H_2$)methyl]cyclopropyl}($^2H_2$)methoxy)-3-oxo-2,3-dihydro-1H-isoindol-2-yl]methyl}pyridine-3-carbonitrile 6-{[(1R)-1-(4-Chlorophenyl)-7-fluoro-1-({1-[hydroxy($^2H_2$)methyl]cyclopropyl}($^2H_2$)methoxy)-5-(4-hydroxybut-1-en-2-yl)-3-oxo-2,3-dihydro-1H-isoindol-2-yl]methyl}pyridine-3-carbonitrile was converted to the title compounds in a similar manner to that described in Example 4, step 3. The two diastereoisomers were separated by chiral HPLC.

Example 20 Isomer 1

1H NMR (400 MHz, DMSO-d6): 8.77 (1H, d), 8.10 (1H, dd), 7.77 (1H, d), 7.49 (1H, d), 7.35 (1H, d), 7.32-7.22 (4H, m), 5.38 (1H, s), 4.71-4.46 (2H, m), 4.43-4.37 (2H, m), 3.49-3.38 (1H, m), 3.27-3.17 (1H, m), 1.96 (2H, t), 1.50 (3H, s), 0.40-0.30 (2H, m), 0.24-0.08 (2H, m). m/z: 568

Example 21 Isomer 2

1H NMR (400 MHz, DMSO-d6): 8.78 (1H, d), 8.10 (1H, dd), 7.76 (1H, d), 7.49 (1H, d), 7.39-7.20 (5H, m), 5.38 (1H, s), 4.67-4.45 (2H, m), 4.44-4.36 (2H, m), 3.48-3.38 (1H, m), 3.27-3.18 (1H, m), 2.06-1.88 (2H, m), 1.49 (3H, s), 0.40-0.30 (2H, m), 0.24-0.07 (2H, m). m/z: 568

Example 22 and Example 23: (3R)-3-(4-Chlorophenyl)-2-[(5-chloropyridin-2-yl)methyl]-6-[1-(dimethylamino)-2-hydroxypropan-2-yl]-4-fluoro-3-({1-[hydroxy($^2H_2$)methyl]cyclopropyl}($^2H_2$)methoxy)-2,3-dihydro-1H-isoindol-1-one (*both isomers separated and isolated)

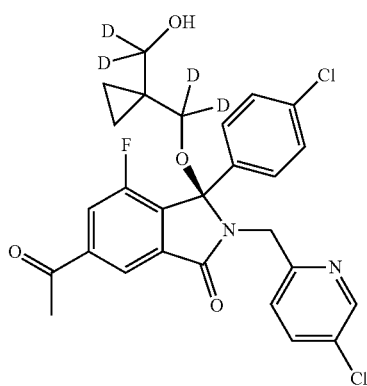

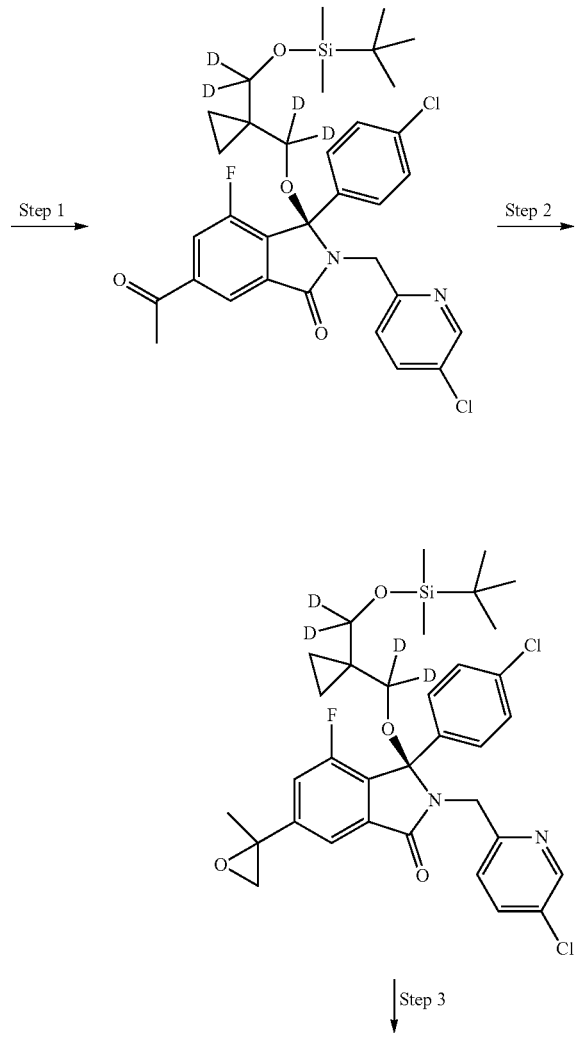

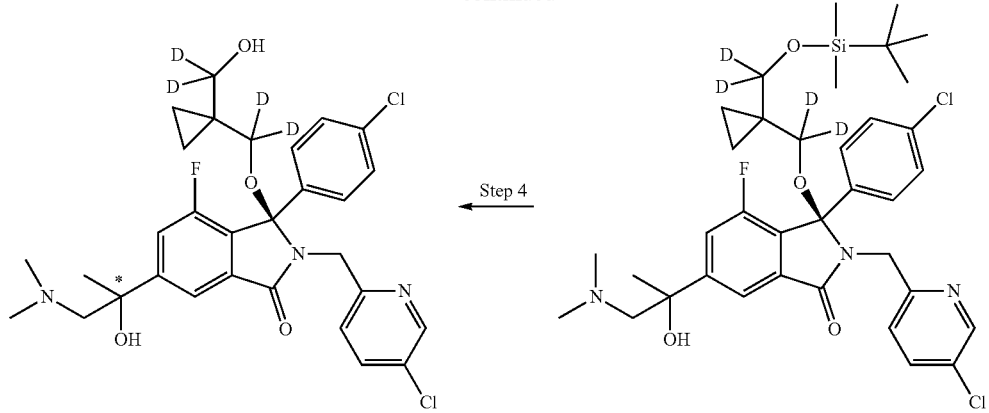

Example 22 and Example 23, Step 1: (3R)-6-Acetyl-3-[(1-{[(tert-butyldimethylsilyl)oxy]($^2H_2$)methyl}cyclopropyl)($^2H_2$)methoxy]-3-(4-chlorophenyl)-2-[(5-chloropyridin-2-yl)methyl]-4-fluoro-2,3-dihydro-1H-isoindol-1-one To a solution of (3R)-6-acetyl-3-(4-chlorophenyl)-2-[(5-chloropyridin-2-yl)methyl]-4-fluoro-3-({1-[hydroxy($^2H_2$)methyl]cyclopropyl}($^2H_2$)methoxy)-2,3-dihydro-1H-isoindol-1-one (obtained from chiral separation of Example 1, step 3) (0.9 g, 1.86 mmol) in THF (15 mL) were added TBDMS-Cl (0.63 g, 4.2 mmol) and imidazole (0.47 g, 6.9 mmol) and the reaction mixture was stirred at room temperature overnight. Water (20 mL) was added and the product was extracted with EtOAc (2×20 mL). The organic phase was dried, filtered and the solvent evaporated. The crude product was purified by Biotage using 0-30% EtOAc in petrol as the eluent to give the title compound (0.94 g, 78%). MS: [M−H]⁻=645.

Example 22 and Example 23, Step 2: (3R)-3-[(1-{[(Tert-butyldimethylsilyl)oxy]($^2H_2$)methyl}cyclopropyl)($^2H_2$)methoxy]-3-(4-chlorophenyl)-2-[(5-chloropyridin-2-yl)methyl]-4-fluoro-6-(2-methyloxiran-2-yl)-2,3-dihydro-1H-isoindol-1-one To a solution of (3R)-6-acetyl-3-[(1-{[(tert-butyldimethylsilyl)oxy]($^2H_2$)methyl}cyclopropyl)($^2H_2$)methoxy]-3-(4-chlorophenyl)-2-[(5-chloropyridin-2-yl)methyl]-4-fluoro-2,3-dihydro-1H-isoindol-1-one (0.936 g, 1.44 mmol) in THF (10 mL) were added DMSO (10 mL), trimethylsulfoxonium iodide (0.35 g, 1.59 mmol) and sodium hydride (60%, 0.064 g, 1.59 mmol) in small portions. The reaction mixture was stirred at room temperature overnight. Water (30 mL) was added, the product was extracted with EtOAc (3×20 mL). the combined organic phase was washed with brine (3×20 mL), dried and the solvent evaporated to afford the epoxide (0.807 g, 85%). 1H NMR (400 MHz, DMSO-d6): 8.36 (1H, dd), 7.76-7.65 (2H, m), 7.43-7.17 (6H, m), 4.47-4.40 (2H, m), 3.08 (1H, t), 2.87 (1H, dd), 1.72 (3H, s), 0.79 (9H, d), 0.39-0.29 (2H, m), 0.25-0.14 (2H, m), −0.01--0.05 (6H, m).

Example 22 and Example 23, Step 3: (3R)-3-[(1-{[(Tert-butyldimethylsilyl)oxy]($^2H_2$)methyl}cyclopropyl)($^2H_2$)methoxy]-3-(4-chlorophenyl)-2-[(5-chloropyridin-2-yl)methyl]-6-[1-(dimethylamino)-2-hydroxypropan-2-yl]-4-fluoro-2,3-dihydro-1H-isoindol-1-one To a solution of (3R)-3-[(1-{[(tert-butyldimethylsilyl)oxy]($^2H_2$)methyl}cyclopropyl)($^2H_2$)methoxy]-3-(4-chlorophenyl)-2-[(5-chloropyridin-2-yl)methyl]-4-fluoro-6-(2-methyloxiran-2-yl)-2,3-dihydro-1H-isoindol-1-one (0.44 g, 0.67 mmol) in MeOH (6 mL) was added a solution of dimethylamine in MeOH (2M, 3.0 mL, 6.0 mmol) and the reaction mixture was heated in a reactive vial at 65° C. for 2 h. The solvent was evaporated, the residue was dissolved in EtOAc, washed with water, dried and the solvent evaporated to afford the title compound (0.27 g, 57%). MS: [M−H]⁻=704.

Example 22 and Example 23, Step 4: (3R)-3-(4-chlorophenyl)-2-[(5-chloropyridin-2-yl)methyl]-6-[1-(dimethylamino)-2-hydroxypropan-2-yl]-4-fluoro-3-({1[hydroxy($^2H_2$)methyl]cyclopropyl}($^2H_2$)methoxy)-2,3-dihydro-1H-isoindol-1-one To an ice cooled solution of (3R)-3-[(1-{[(tert-butyldimethylsilyl)oxy]($^2H_2$)methyl}cyclopropyl)($^2H_2$)methoxy]-3-(4-chlorophenyl)-2-[(5-chloropyridin-2-yl)methyl]-6-[1-(dimethylamino)-2-hydroxypropan-2-yl]-4-fluoro-2,3-dihydro-1H-isoindol-1-one (0.27 g, 0.38 mmol) in THF (10 mL) was added a solution of TBAF in THF (1M, 0.6 mL, 0.6 mmol) and the reaction mixture was stirred at room temperature overnight. The solvent was evaporated and the residue was purified by Biotage using 0-10% MeOH in DCM. The isomers were separated by chiral HPLC.

Example 22 Isomer 1

1H NMR (400 MHz, DMSO-d6): 8.36 (1H, d), 7.78 (1H, s), 7.72 (1H, dd), 7.50 (1H, d), 7.33-7.16 (5H, m), 5.21 (1H, s), 4.52-4.43 (2H, m), 4.43-4.36 (1H, m), 2.12 (6H, s), 1.47 (3H, s), 0.39-0.30 (2H, m), 0.21-0.05 (2H, m). m/z: 590

Example 23 Isomer 2

1H NMR (400 MHz, DMSO-d6): 8.36 (1H, d), 7.79 (1H, s), 7.72 (1H, dd), 7.49 (1H, d), 7.33-7.19 (5H, m), 5.22 (1H, s), 4.46 (2H, s), 4.38 (1H, s), 2.13 (6H, s), 1.47 (3H, s), 0.34 (2H, d), 0.21-0.02 (2H, m). m/z: 590

Example 24 and Example 25: (3R)-3-(4-Chlorophenyl)-2-[(5-chloropyridin-2-yl)methyl]-4-fluoro-3-({1-[hydroxy($^2$H$_2$)methyl]cyclopropyl}($^2$H$_2$)methoxy)-6-(2-hydroxy-1-methoxypropan-2-yl)-2,3-dihydro-1H-isoindol-1-one (*both isomers separated and isolated)

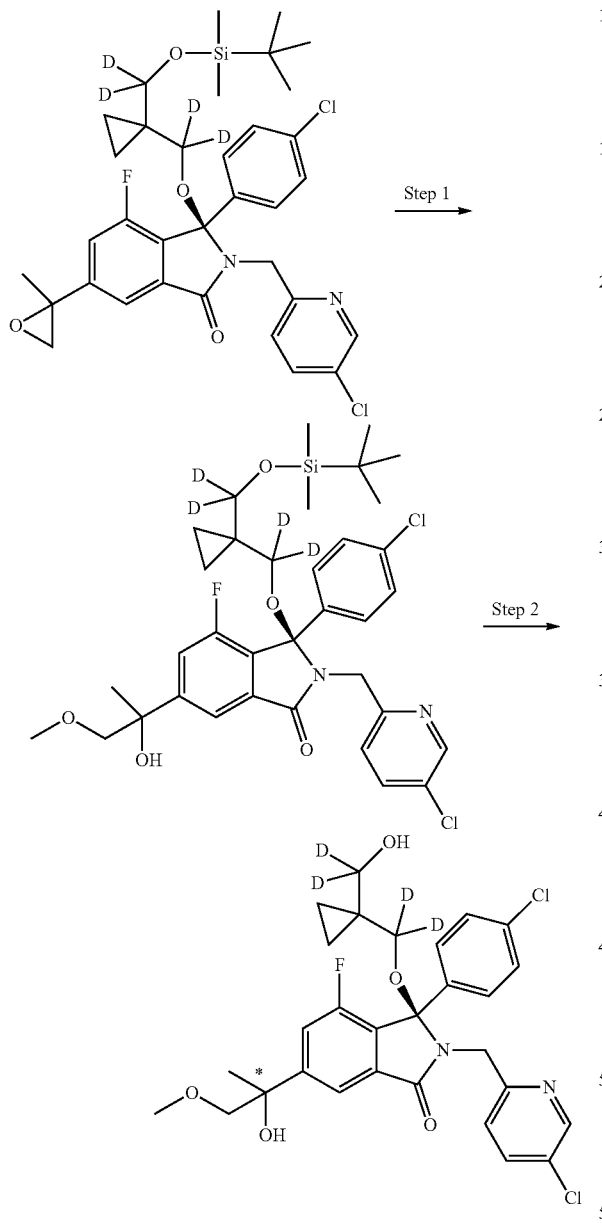

Example 24 and Example 25, Step 1: (3R)-3-[(1-{[(Tert-butyldimethylsilyl)oxy]($^2$H$_2$)methyl}cyclopropyl)($^2$H$_2$)methoxy]-3-(4-chlorophenyl)-2-[(5-chloropyridin-2-yl)methyl]-4-fluoro-6-(2-hydroxy-1-methoxypropan-2-yl)-2,3-dihydro-1H-isoindol-1-one Sodium (0.125 g, 5.44 mmol) was dissolved in anhydrous MeOH (5 mL). A solution of (3R)-3-[(1-{[(tert-butyldimethylsilyl)oxy]($^2$H$_2$)methyl}cyclopropyl)($^2$H$_2$)methoxy]-3-(4-chlorophenyl)-2-[(5-chloropyridin-2-yl)methyl]-4-fluoro-6-(2-methyloxiran-2-yl)-2,3-dihydro-1H-isoindol-1-one (Example 22, Example 23, step 2) (0.36 g, 0.544 mmol) in MeOH (4 mL) was added and the reaction mixture was heated at 65° C. for 3 h. The solvent was evaporated, the residue was dissolved in EtOAc, washed with water, dried filtered and the solvent evaporated to afford the title compound (0.31 g, 83%). MS: [M–H]$^-$=691.

Example 24 and Example 25, Step 2: (3R)-3-(4-Chlorophenyl)-2-[(5-chloropyridin-2-yl)methyl]-4-fluoro-3-({1-[hydroxy($^2$H$_2$)methyl]cyclopropyl}($^2$H$_2$)methoxy)-6-(2-hydroxy-1-methoxypropan-2-yl)-2,3-dihydro-1H-isoindol-1-one (3R)-3-[(1-{[(Tert-butyldimethylsilyl)oxy]($^2$H$_2$)methyl}cyclopropyl)($^2$H$_2$)methoxy]-3-(4-chlorophenyl)-2-[(5-chloropyridin-2-yl)methyl]-4-fluoro-6-(2-hydroxy-1-methoxypropan-2-yl)-2,3-dihydro-1H-isoindol-1-one (0.31 g, 0.45 mmol) was treated with TBAF in a similar way described in Example 22, and Example 23, step 4 to afford the title compound (0.2 g, 75%). The two isomers were separated by chiral HPLC.

Example 24 Isomer 1

1H NMR (400 MHz, DMSO-d6): 8.36 (1H, d), 7.79 (1H, d), 7.72 (1H, dd), 7.49 (1H, dd), 7.34-7.18 (5H, m), 5.49 (1H, s), 4.46 (2H, s), 4.38 (1H, s), 3.52-3.41 (2H, m), 3.26 (3H, s), 1.45 (3H, s), 0.39-0.29 (2H, m), 0.22-0.05 (2H, m). m/z 577

Example 25 Isomer 2

1H NMR (400 MHz, DMSO-d6): 8.36 (1H, d), 7.78 (1H, d), 7.72 (1H, dd), 7.49 (1H, dd), 7.34-7.18 (5H, m), 5.49 (1H, s), 4.46 (2H, s), 4.39 (1H, s), 3.52-3.37 (2H, m), 3.26 (3H, s), 1.45 (3H, s), 0.39-0.29 (2H, m), 0.22-0.05 (2H, m). m/z: 577

Example 26: (3R)-3-(4-Chlorophenyl)-2-[(5-chloropyridin-2-yl)methyl]-4-fluoro-3-[3-hydroxy-2-(hydroxymethyl)-2-methylpropoxy]-6-(2-hydroxypropan-2-yl)-2,3-dihydro-1H-isoindol-1-one

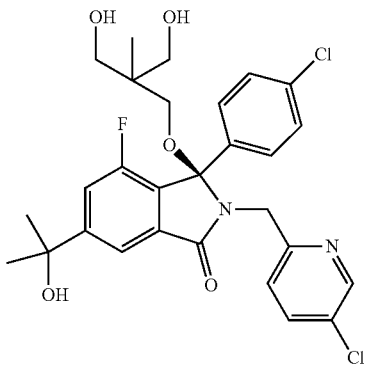 [SMILES: CC(CO)(CO)CO[C@]1(c2ccc(Cl)cc2)c2c(F)cc(C(C)(C)O)cc2C(=O)N1Cc1ccc(Cl)cn1]

The title compound was prepared from 6-bromo-3-(4-chloro-phenyl)-2-(5-chloro-pyridin-2-ylmethyl)-4-fluoro-3-hydroxy-2,3-dihydro-isoindol-1-one (Example 1, step 1) in a similar manner to that described in Example 3, steps 2-4 using (2-hydroxymethyl-2-methyl-propane-1,3-diol instead of 1-hydroxymethyl-cyclopropanol in step 2.

1H NMR (400 MHz, DMSO-d6): 8.31 (1H, d), 7.81 (1H, d), 7.67 (1H, dd), 7.52 (1H, d), 7.28-7.09 (5H, m), 5.38 (1H, s), 4.62 (1H, d), 4.43-4.29 (3H, m), 3.29-3.20 (3H, m), 3.10 (1H, d), 2.76 (1H, d), 1.49 (6H, s), 0.79 (3H, s) m/z: 563.

Example 27: 1-({[(1R)-1-(4-chlorophenyl)-2-[(5-chloropyridin-2-yl)methyl]-7-fluoro-5-(2-hydroxy-propan-2-yl)-3-oxo-2,3-dihydro-1H-isoindol-1-yl]oxy}methyl)cyclopropane-1-carbonitrile

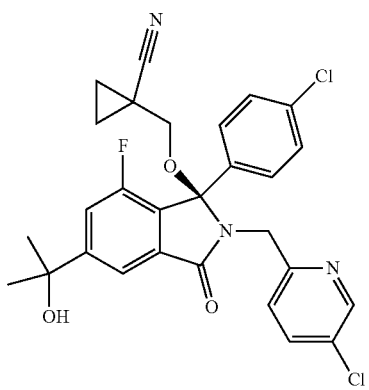 [SMILES: CC(C)(O)c1cc(F)c2c(c1)C(=O)N(Cc1ccc(Cl)cn1)[C@@]2(OCC1(C#N)CC1)c1ccc(Cl)cc1]

The title compound was prepared from 6-bromo-3-(4-chloro-phenyl)-2-(5-chloro-pyridin-2-ylmethyl)-4-fluoro-3-hydroxy-2,3-dihydro-isoindol-1-one (Example 1, step 1) in a similar manner to that described in Example 3, steps 2-4 using 1-hydroxymethyl-cyclopropanecarbonitrile (Preparation 4) instead of 1-hydroxymethyl-cyclopropanol in step 2.

1H NMR (400 MHz, DMSO-d6): 8.38 (1H, d), 7.80 (1H, d), 7.75 (1H, dd), 7.54 (1H, dd), 7.40-7.20 (5H, m), 5.39 (1H, s), 4.62-4.32 (2H, m), 3.30 (1H, d), 3.06 (1H, d), 1.48 (6H, s), 1.28-1.16 (2H, m), 0.93-0.81 (1H, m), 0.79-0.67 (1H, m). m/z: 540

Example 28: (3R)-3-(4-Chlorophenyl)-4-fluoro-3-{[1-(hydroxymethyl)cyclopropyl]methoxy}-6-(2-hydroxypropan-2-yl)-2-[(5-methylpyridin-2-yl)methyl]-2,3-dihydro-1H-isoindol-1-one

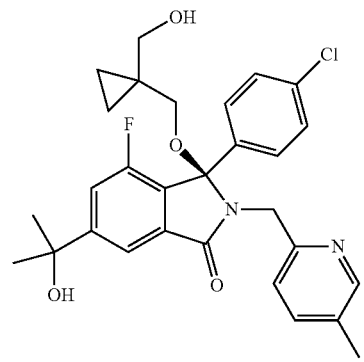 [SMILES: Cc1ccc(CN2C(=O)c3cc(C(C)(C)O)cc(F)c3[C@]2(OCC2(CO)CC2)c2ccc(Cl)cc2)nc1]

The title compound was prepared in a similar manner to that described in Example 3, steps 1-4 using C-(5-methyl-pyridin-2-yl)-methylamine dihydrochloride (Anichem, NP1770) instead of 6-aminomethyl-nicotinonitrile in step 1 and (1-hydroxymethyl-cyclopropyl)-methanol instead of 1-hydroxymethyl-cyclopropanol in step 2.

1H NMR (400 MHz, DMSO-d6): 8.19 (1H, s), 7.79 (1H, d), 7.54-7.42 (2H, m), 7.30 (2H, d), 7.26 (2H, d), 7.09 (1H, d), 5.50-5.20 (1H, m), 4.51-4.35 (2H, m), 3.04-2.89 (2H, m), 2.22 (3H, s), 1.48 (6H, s), 0.39-0.25 (2H, m), 0.21-0.06 (2H, m). m/z: 525

Example 29: (3R)-3-(4-Chlorophenyl)-4-fluoro-3-{[1-(hydroxymethyl)cyclopropyl]methoxy}-6-(2-hydroxypropan-2-yl)-2-[(5-methoxypyridin-2-yl)methyl]-2,3-dihydro-1H-isoindol-1-one

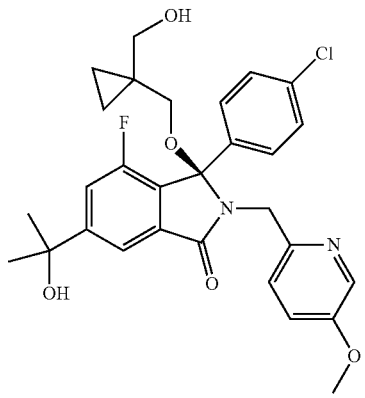 [SMILES: COc1ccc(CN2C(=O)c3cc(C(C)(C)O)cc(F)c3[C@]2(OCC2(CO)CC2)c2ccc(Cl)cc2)nc1]

The title compound was prepared in a similar manner to that described in Example 3, steps 1-4 using C-(5-methoxy-pyridin-2-yl)-methylamine hydrochloride instead of 6-aminomethyl-nicotinonitrile in step 1 and (1-hydroxymethyl-cyclopropyl)-methanol instead of 1-hydroxymethyl-cyclopropanol in step 2.

1H NMR (400 MHz, DMSO-d6): 8.01 (1H, d), 7.78 (1H, d), 7.49 (1H, dd), 7.33-7.15 (5H, m), 7.10 (1H, d), 5.37 (1H, s), 4.47-4.31 (3H, m), 3.76 (3H, s), 3.43-3.36 (1H, m), 3.29 (1H, dd), 2.96 (1H, d), 2.92 (1H, d), 1.48 (6H, s), 0.38-0.29 (2H, m), 0.19-0.06 (2H, m). m/z: 541-

Example 30: 3-(4-Chlorophenyl)-2-[(5-chloropyrimidin-2-yl)methyl]-4-fluoro-3-{[1-(hydroxymethyl)cyclopropyl]methoxy}-6-(2-hydroxypropan-2-yl)-2,3-dihydro-1H-isoindol-1-one

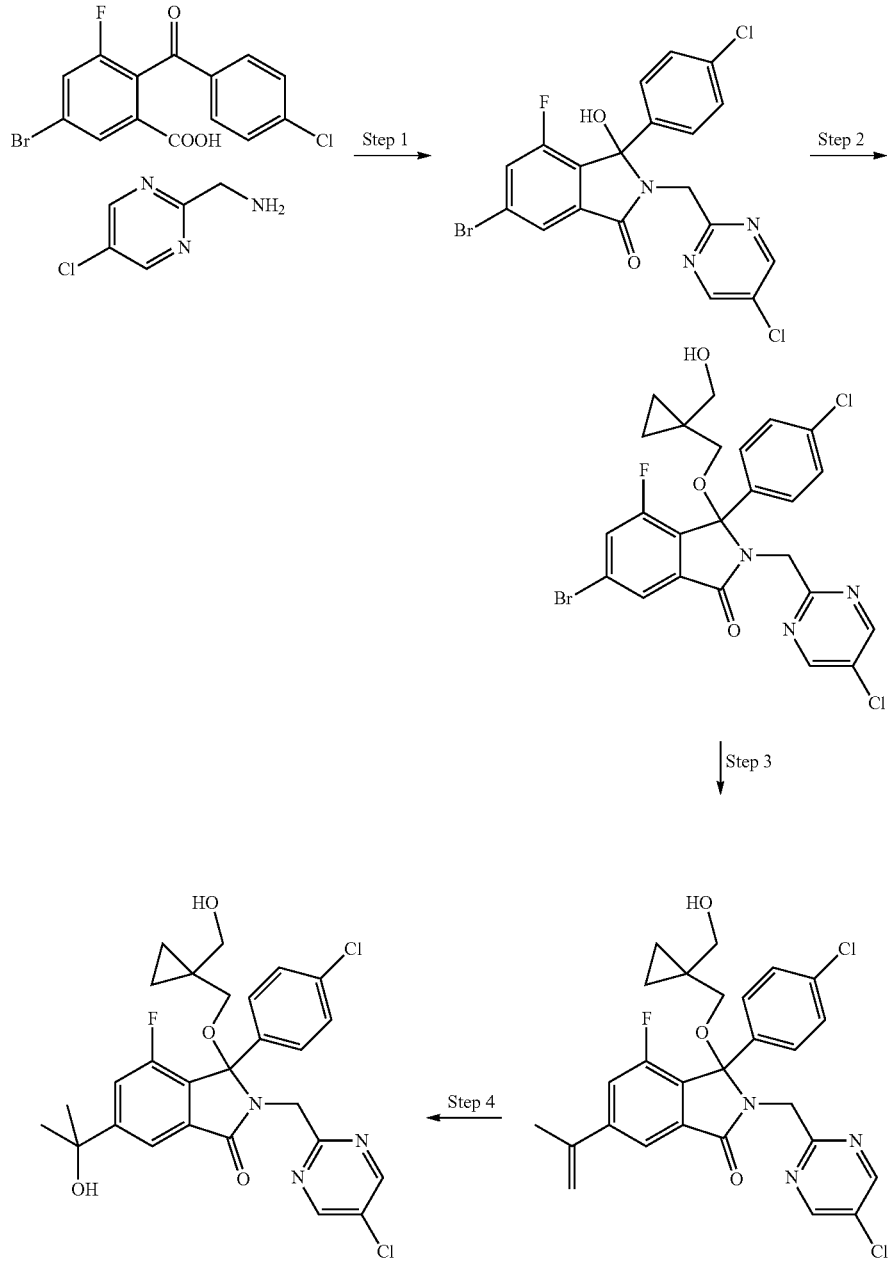

Example 30, Step 1: 6-Bromo-3-(4-chlorophenyl)-2-[(5-chloropyrimidin-2-yl)methyl]-4-fluoro-3-hydroxy-2,3-dihydro-1H-isoindol-1-one The title compound was prepared in a similar manner to that described in Example 1, step 1 using 1-(5-chloro-2-pyrimidyl)methaneamine hydrochloride (ChemBridge) instead of (5-chloropyridine-2-yl)methaneamine dihydrochloride.

1H NMR (400 MHz, DMSO-d6): 8.70 (2H, s), 7.84 (1H, d), 7.80 (1H, dd), 7.54 (1H, s), 7.32-7.23 (4H, m), 4.61 (2H, s).

Example 30, Step 2: 6-Bromo-3-(4-chlorophenyl)-2-[(5-chloropyrimidin-2-yl)methyl]-4-fluoro-3-{[1-(hydroxymethyl)cyclopropyl]methoxy}-2,3-dihydro-1H-isoindol-1-one The title compound was prepared in a similar manner to that described in Example 3, step 2 using (1-hydroxymethyl-cyclopropyl)-methanol instead of 1-hydroxymethyl-cyclopropanol. MS: [M−H]⁻=566.

Example 30, Step 3: 3-(4-chlorophenyl)-2-[(5-chloropyrimidin-2-yl)methyl]-4-fluoro-3-{[1-(hydroxymethyl)cyclopropyl]methoxy}-6-(prop-1-en-2-yl)-2,3-dihydro-1H-isoindol-1-one 6-Bromo-3-(4-chlorophenyl)-2-[(5-chloropyrimidin-2-yl)methyl]-4-fluoro-3-{[1-(hydroxymethyl)cyclopropyl]methoxy}-2,3-dihydro-1H-isoindol-1-one) was reacted with isopropenylboronic acid pinacol ester in a similar manner to that described in Example 4, step 2 to afford the product. MS: [M−H]⁻=526.

Example 30, Step 4: 3-(4-Chlorophenyl)-2-[(5-chloropyrimidin-2-yl)methyl]-4-fluoro-3-{[1-(hydroxymethyl)cyclopropyl]methoxy}-6-(2-hydroxypropan-2-yl)-2,3-dihydro-1H-isoindol-1-one 3-(4-Chlorophenyl)-2-[(5-chloropyrimidin-2-yl)methyl]-4-fluoro-3-{[1-(hydroxymethyl)cyclopropyl]methoxy}-6-(prop-1-en-2-yl)-2,3-dihydro-1H-isoindol-1-one was converted to the title compound in a similar manner as described in Example 4, step 3.

1H NMR (400 MHz, DMSO-d6): 8.73 (2H, s), 7.78 (1H, d), 7.52 (1H, dd), 7.33-7.25 (4H, m), 5.37 (1H, s), 4.67-4.47 (2H, m), 4.47-4.36 (1H, m), 2.93 (1H, d), 2.36-2.31 (1H, m), 1.48 (6H, s), 0.36 (2H, t), 0.26-0.14 (2H, m). m/z: 544

Example 31: (3R)-3-(4-chlorophenyl)-2-[(5-chloropyridin-2-yl)methyl]-3-[(1-hydroxycyclopropyl)methoxy]-6-(2-hydroxypropan-2-yl)-2,3-dihydro-1H-isoindol-1-one

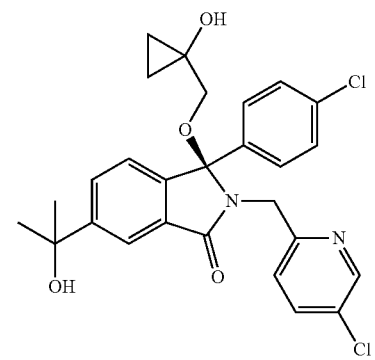 [SMILES: CC(C)(O)c1ccc2c(c1)C(=O)N(Cc1ccc(Cl)cn1)[C@@]2(OCC1(O)CC1)c1ccc(Cl)cc1]

The title compound was prepared from 6-bromo-3-(4-chloro-phenyl)-2-(5-chloro-pyridin-2-ylmethyl)-3-hydroxy-2,3-dihydro-isoindol-1-one (Example 6, step 1) in a similar manner to that described in Example 3, steps 2-4.

1H NMR (400 MHz, DMSO-d6): 8.35 (1H, d), 7.93 (1H, d), 7.79-7.67 (2H, m), 7.33-7.22 (4H, m), 7.22-7.14 (2H, m), 5.47 (1H, s), 5.25 (1H, s), 4.60-4.42 (2H, m), 2.97 (1H, d), 2.91 (1H, d), 1.48 (6H, d), 0.57-0.45 (2H, m), 0.36-0.18 (2H, m). m/z: 511

Example 32: (3R)-3-(4-Chlorophenyl)-2-[(5-chloropyridin-2-yl)methyl]-3-({1-[hydroxy(²H₂)methyl]cyclopropyl}(²H₂)methoxy)-6-(2-hydroxypropan-2-yl)-2,3-dihydro-1H-isoindol-1-one

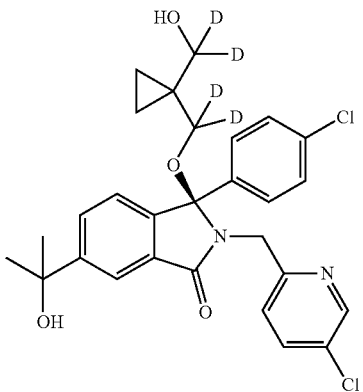 [SMILES: [2H]C([2H])(O)C1(C([2H])([2H])O[C@]2(c3ccc(Cl)cc3)c3ccc(C(C)(C)O)cc3C(=O)N2Cc2ccc(Cl)cn2)CC1]

The title compound was prepared from 6-bromo-3-(4-chloro-phenyl)-2-(5-chloro-pyridin-2-ylmethyl)-3-hydroxy-2,3-dihydro-isoindol-1-one (Example 6, step 1) in a similar manner to that described in Example 1, steps 2-4.

1H NMR (400 MHz, DMSO-d6): 8.36 (1H, d), 7.92 (1H, d), 7.77-7.69 (2H, m), 7.32-7.15 (6H, m), 5.24 (1H, s), 4.53-4.43 (2H, m), 4.43-4.39 (1H, m), 1.48 (6H, s), 0.35-0.26 (2H, m), 0.19-0.11 (1H, m), 0.08-0.00 (1H, m). m/z: 529

Example 33: (3R)-3-(4-chlorophenyl)-2-[(5-chloropyridin-2-yl)methyl]-4-fluoro-6-(2-hydroxypropan-2-yl)-3-[(1-methanesulfonylcyclopropyl)methoxy]-2,3-dihydro-1H-isoindol-1-one

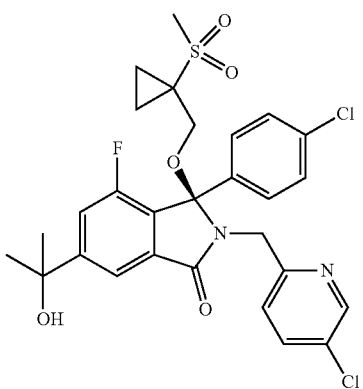 [SMILES: CC(C)(O)c1cc(F)c2c(c1)C(=O)N(Cc1ccc(Cl)cn1)[C@@]2(OCC1(S(C)(=O)=O)CC1)c1ccc(Cl)cc1]

The title compound was prepared from 6-bromo-3-(4-chloro-phenyl)-2-(5-chloro-pyri in-2-ylmethyl)-4-fluoro-3-hydroxy-2,3-dihydro-isoindol-1-one (Example 1, step 1) in a similar manner to that described in Example 3, steps 2-4, using (1-methanesulfonyl-cyclopropyl)-methanol (Preparation 5) instead of 1-hydroxymethyl-cyclopropanol in step 2.

1H NMR (400 MHz, DMSO-d6): 8.38 (1H, d), 7.82 (1H, d), 7.74 (1H, dd), 7.57 (1H, dd), 7.37-7.18 (5H, m), 5.40 (1H, s), 4.43 (2H, s), 3.50 (2H, s), 3.12 (3H, s), 1.49 (6H, s), 1.40-1.21 (2H, m), 0.99-0.79 (2H, m). m/z: 593

Example 34: N-[1-({[(1R)-1-(4-chlorophenyl)-2-[(5-chloropyridin-2-yl)methyl]-7-fluoro-5-(2-hydroxypropan-2-yl)-3-oxo-2,3-dihydro-1H-isoindol-1-yl]oxy}methyl)cyclopropyl]acetamide

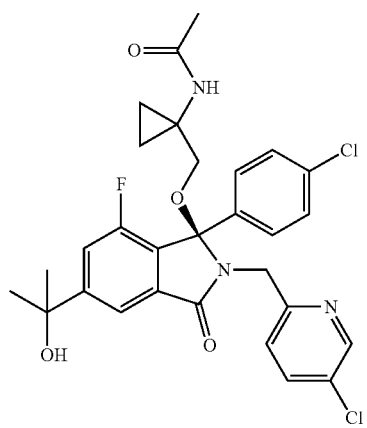 [SMILES: CC(=O)NC1(CO[C@]2(c3ccc(Cl)cc3)c3c(F)cc(C(C)(C)O)cc3C(=O)N2Cc2ccc(Cl)cn2)CC1]

The title compound was prepared from 6-bromo-3-(4-chloro-phenyl)-2-(5-chloro-pyridin-2-ylmethyl)-4-fluoro-3-hydroxy-2,3-dihydro-isoindol-1-one (Example 1, step 1) in a similar manner to that described in Example 3, steps 2-4, using N-(1-hydroxymethyl-cyclopropyl)-acetamide (Preparation 6) instead of 1-hydroxymethyl-cyclopropanol in step 2.

1H NMR (400 MHz, DMSO-d6): 8.35 (1H, d), 8.28 (1H, s), 7.79 (1H, d), 7.71 (1H, dd), 7.53-7.46 (1H, m), 7.36-7.21 (4H, m), 7.17 (1H, d), 5.38 (1H, s), 4.43 (2H, s), 3.09 (1H, d), 3.04 (1H, d), 1.74 (3H, s), 1.48 (6H, s), 0.63-0.49 (3H, m), 0.46-0.33 (1H, m).

Example 35: 6-{[(1R)-1-(4-Chlorophenyl)-1-({1-[hydroxy($^2H_2$)methyl]cyclopropyl}($^2H_2$)methoxy)-5-(2-hydroxypropan-2-yl)-3-oxo-2,3-dihydro-1H-isoindol-2-yl]methyl}pyridine-3-carbonitrile

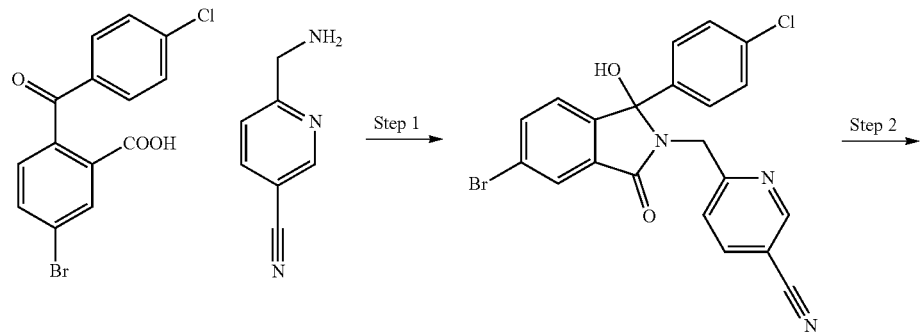

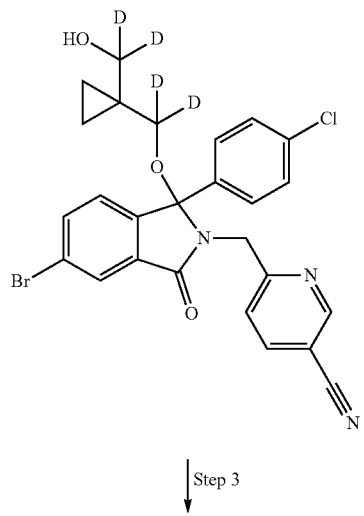

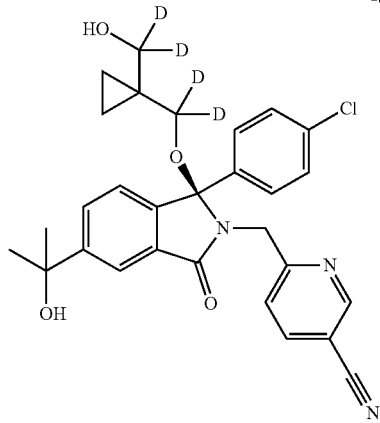

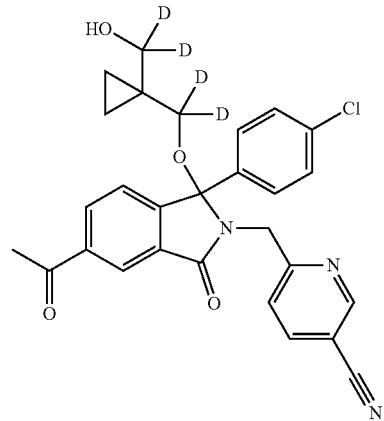

Example 35, Step 1: 6-[5-Bromo-1-(4-chloro-phenyl)-1-hydroxy-3-oxo-1,3-dihydro-isoindol-2-ylmethyl]-nicotinonitrile The title compound was prepared from 5-bromo-2-(4-chloro-benzoyl)-benzoic acid (Manchester Organics) (1.5 g, 4.4 mmol) and 6-aminomethyl-nicotinonitrile dihydrochloride (1.0 g, 4.85 mmol) in a similar manner to that described in Example 1, step 1. MS: [M−H]⁻=454.

Example 35, Step 2: 6-{[(1R)-5-Bromo-1-(4-chlorophenyl)-1-({1-[hydroxy(²H₂)methyl]cyclopropyl}(²H₂)methoxy)-3-oxo-2,3-dihydro-1H-isoindol-2-yl]methyl}pyridine-3-carbonitrile The title compound was prepared from 6-[5-bromo-1-(4-chloro-phenyl)-1-hydroxy-3-oxo-1,3-dihydro-isoindol-2-ylmethyl]-nicotinonitrile (1.1 g, 2.43 mmol) in a similar manner to that described in Example 3, step 2. MS: [M−H]⁻= 541.

Example 35, Step 3: 6-{[(1R)-5-Acetyl-1-(4-chlorophenyl)-1-({1-[hydroxy(²H₂)methyl]cyclopropyl}(²H₂)methoxy)-3-oxo-2,3-dihydro-1H-isoindol-2-yl]methyl}pyridine-3-carbonitrile The title compound was prepared from 6-{[5-bromo-1-(4-chlorophenyl)-1-({1-[hydroxy(2H₂)methyl]cyclopropyl}(2H₂)methoxy)-3-oxo-2,3-dihydro-1H-isoindol-2-yl]methyl}pyridine-3-carbonitrile (650 mg, 1.2 mmol) in a similar manner to that described in Example 3, step 3. MS: [M−H]⁻=504.

Example 35, Step 4: 6-{[(1R)-1-(4-Chlorophenyl)-1-({1-[hydroxy(²H₂)methyl]cyclopropyl}(²H₂)methoxy)-5-(2-hydroxypropan-2-yl)-3-oxo-2,3-dihydro-1H-isoindol-2-yl]methyl}pyridine-3-carbonitrile The title compound was prepared from 6-{[5-acetyl-1-(4-chlorophenyl)-1-({1-[hydroxy(2H₂)methyl]cyclopropyl}(2H₂)methoxy)-3-oxo-2,3-dihydro-1H-isoindol-2-yl]methyl}pyridine-3-carbonitrile (530 mg, 1.0 mmol) in a similar manner to that described in Example 1, step 4. MS: [M−H]⁻=520.

1H NMR (400 MHz, DMSO-d6): 8.80-8.75 (1H, m), 8.10 (1H, dd), 7.93 (1H, d), 7.76 (1H, dd), 7.37 (1H, d), 7.32-7.16 (5H, m), 5.26 (1H, s), 4.64-4.47 (2H, m), 4.43 (1H, s), 1.48 (6H, s), 0.31 (2H, t), 0.23-0.01 (2H, m).

Example 36: 6-{[(1R)-1-(4-chlorophenyl)-7-fluoro-1-{[1-(hydroxymethyl)cyclopropyl]methoxy}-5-(2-hydroxypropan-2-yl)-3-oxo-2,3-dihydro-1H-isoindol-2-yl]methyl}pyridine-3-carbonitrile

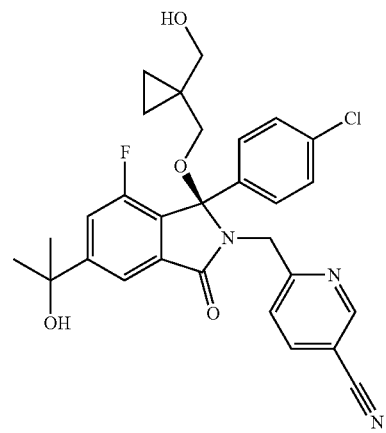 [SMILES: CC(C)(O)c1cc(F)c2c(c1)C(=O)N(Cc1ccc(C#N)cn1)[C@@]2(OCC1(CO)CC1)c1ccc(Cl)cc1]

The title compound was prepared from 6-[5-bromo-1-(4-chloro-phenyl)-7-fluoro-1-hydroxy-3-oxo-1,3-dihydro-isoindol-2-ylmethyl]-nicotinonitrile (Example 3, step 1) in a similar manner to that described in Example 3, step 2-4, using (1-hydroxymethyl-cyclopropyl)-methanol instead of 1-hydroxymethyl-cyclopropanol in step 2.

1H NMR (400 MHz, DMSO-d6): 8.80-8.75 (1H, m), 8.10 (1H, dd), 7.81 (1H, d), 7.53 (1H, dd), 7.39-7.14 (5H, m), 5.38 (1H, s), 4.63-4.48 (2H, m), 4.45 (1H, t), 3.40-3.33 (2H, m), 3.14 (1H, d), 2.92 (1H, d), 1.48 (6H, s), 0.36 (2H, s), 0.26-0.08 (2H, m). m/z534

Example 37: (3R)-3-(4-Chlorophenyl)-4-fluoro-3-({1-[hydroxy($^2$H$_2$)methyl]cyclopropyl}($^2$H$_2$)methoxy)-6-(2-hydroxypropan-2-yl)-2-[(6-methoxy-pyridin-3-yl)methyl]-2,3-dihydro-1H-isoindol-1-one

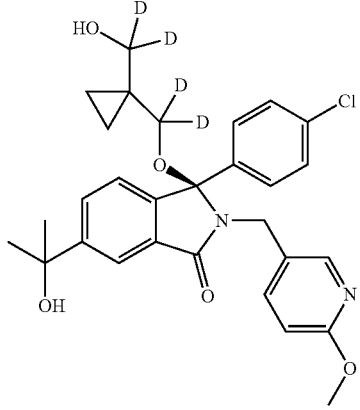 [SMILES: [2H]C([2H])(O)C1(C([2H])([2H])O[C@]2(c3ccc(Cl)cc3)c3ccc(C(C)(C)O)cc3C(=O)N2Cc2ccc(OC)nc2)CC1]

The title compound was prepared in a similar manner to that described in Example 1, step 1-4 using C-(6-methoxy-pyridin-3-yl)-methylamine instead of (5-chloropyridine-2-yl)methaneamine dihydrochloride in step 1.

1H NMR (400 MHz, DMSO-d6): 7.78 (1H, d), 7.72 (1H, d), 7.52-7.39 (2H, m), 7.31 (2H, d), 7.21 (2H, d), 6.60 (1H, d), 5.37 (1H, s), 4.41-4.24 (3H, m), 3.77 (3H, s), 1.47 (6H, s), 0.36 (2H, d), 0.22-0.12 (2H, m). m/z: 545

Example 38 and Example 39: (3R)-3-(4-chlorophenyl)-2-[(5-chloropyridin-2-yl)methyl]-3-[(3-hydroxycyclopentyl)oxy]-6-(2-hydroxypropan-2-yl)-2,3-dihydro-1H-isoindol-1-one (Both isomers as shown)

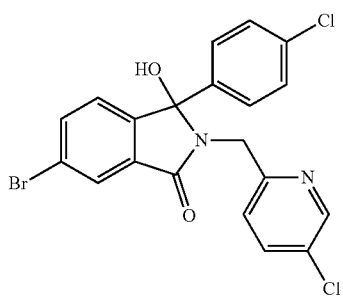

Step 1

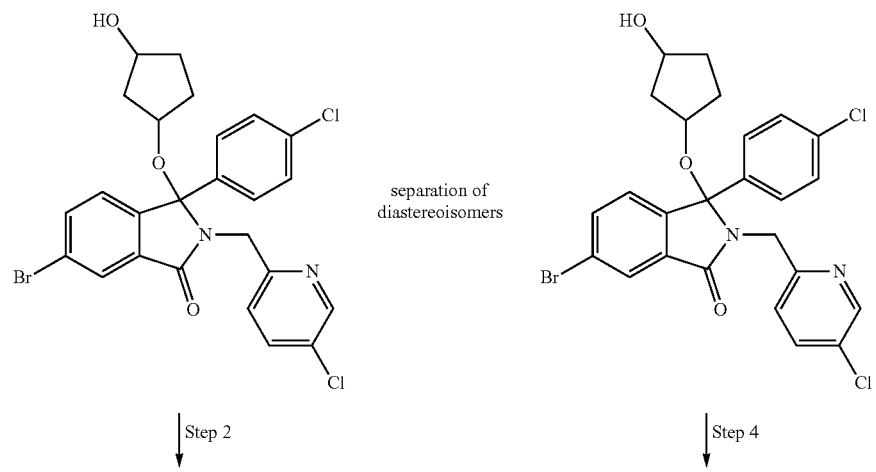

separation of diastereoisomers

Step 2　　　　　　　　　　　　Step 4

229

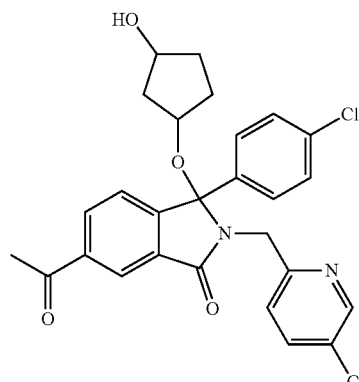

↓ Step 3

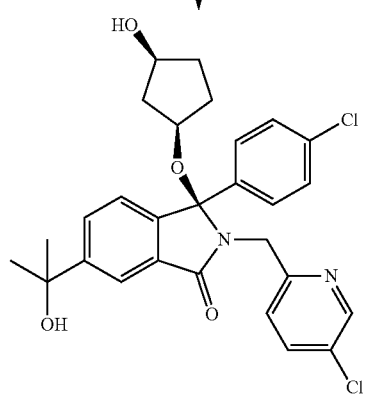

230

-continued

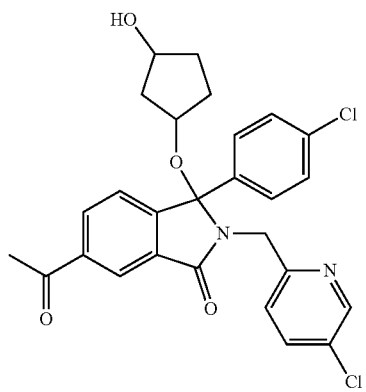

↓ Step 5

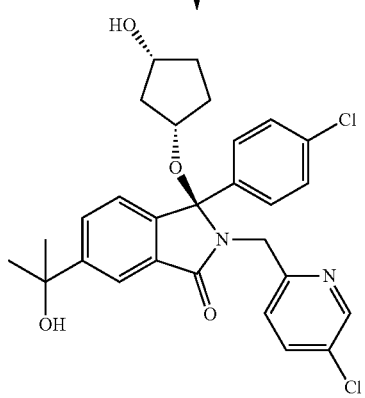

Example 38 and Example 39, Step 1: 6-Bromo-3-(4-chloro-phenyl)-2-(5-chloro-pyridin-2-ylmethyl)-3-(3-hydroxy-cyclopentyloxy)-2,3-dihydro-isoindol-1-one To a solution of 6-bromo-3-(4-chloro-phenyl)-2-(5-chloro-pyridin-2-ylmethyl)-3-hydroxy-2,3-dihydro-isoindol-1-one (Example 6, step 1) (1.23 g, 2.66 mmol) in DCE (20 mL) were added (1R,3S)-3-(tert-butyl-dimethyl-silanyloxy)-cyclopentanol (Preparation 7) (2.3 g, 10.6 mmol) and InBr$_3$ (660 mg, 1.86 mmol) and the reaction mixture was stirred at 85° C. for 16 hours. The mixture was cooled to room temperature, diluted with DCM and washed with water. The organic phase was dried over Na$_2$SO$_4$, filtered and concentrated in vacuo. The residue was purified by Biotage (0-100% gradient EtOAc in petrol) to give 300 mg of the first diastereoisomer (isomer 1) as a orange semi-solid and 350 mg of the second diastereoisomer (isomer 2) as an orange semi-solid. MS: [M–H]$^-$=547

Isomer 1: $^1$H NMR (400 MHz, DMSO-d6): 8.35 (1H, d), 8.01 (1H, d), 7.83 (1H, dd), 7.71 (1H, dd), 7.29-7.22 (6H, m), 4.57-4.47 (2H, m), 4.43 (1H, d), 3.86-3.74 (1H, m), 3.66-3.55 (1H, m), 1.54-1.39 (4H, m), 1.39-1.29 (2H, m)

Isomer 2: $^1$H NMR (400 MHz, DMSO-d6): 8.34 (1H, d), 8.01 (1H, d), 7.82 (1H, dd), 7.71 (1H, dd), 7.30-7.13 (6H, m), 4.58-4.47 (2H, m), 4.42 (1H, d), 3.88-3.78 (1H, m), 3.67-3.57 (1H, m), 1.74-1.54 (2H, m), 1.54-1.37 (2H, m), 1.37-1.27 (1H, m), 1.15-1.01 (1H, m).

Example 38, Step 2: 6-Acetyl-3-(4-chloro-phenyl)-2-(5-chloro-pyridin-2-ylmethyl)-3-(3-hydroxy-cyclopentyloxy)-2,3-dihydro-isoindol-1-one The title compound was prepared from 6-bromo-3-(4-chloro-phenyl)-2-(5-chloro-pyridin-2-ylmethyl)-3-(3-hydroxy-cyclopentyloxy)-2,3-dihydro-isoindol-1-one (isomer 1) (300 mg, 0.55 mmol) in a similar manner to that described in Example 1, step 3.
MS: [M–H]$^-$=509

Example 38, step 3: (3R)-3-(4-Chloro-phenyl)-2-(5-chloro-pyridin-2-ylmethyl)-3-(3-hydroxy-cyclopentyloxy)-6-(1-hydroxy-1-methyl-ethyl)-2,3-dihydro-isoindol-1-one The title compound was prepared from 6-acetyl-3-(4-chloro-phenyl)-2-(5-chloro-pyridin-2-ylmethyl)-3-(3-hydroxy-cyclopentyloxy)-2,3-dihydro-isoindol-1-one (isomer 1) (230 mg, 0.50 mmol) in a similar manner to that described in Example 1, step 4. MS: [M–H]$^-$=525
1H NMR (400 MHz, DMSO-d6): 8.34 (1H, d), 7.92 (1H, d), 7.76-7.67 (2H, m), 7.29-7.16 (6H, m), 5.25 (1H, s), 4.56-4.40 (3H, m), 3.81-3.72 (1H, m), 3.62-3.52 (1H, m), 1.57-1.24 (12H, m)

Example 39, Step 4: 6-Acetyl-3-(4-chloro-phenyl)-2-(5-chloro-pyridin-2-ylmethyl)-3-(3-hydroxy-cyclopentyloxy)-2,3-dihydro-isoindol-1-one The title compound was prepared from 6-bromo-3-(4-chloro-phenyl)-2-(5-chloro-pyridin-2-ylmethyl)-3-(3-hydroxy-cyclopentyloxy)-2,3-dihydro-isoindol-1-one (isomer 2) (350 mg, 0.64 mmol) in a similar manner to that described in Example 1, step 3. MS: [M−H]⁻=509

Example 39, step 5: (3R)-3-(4-Chloro-phenyl)-2-(5-chloro-pyridin-2-ylmethyl)-3-(3-hydroxy-cyclopentyloxy)-6-(1-hydroxy-1-methyl-ethyl)-2,3-dihydro-isoindol-1-one The title compound was prepared from 6-acetyl-3-(4-chloro-phenyl)-2-(5-chloro-pyridin-2-ylmethyl)-3-(3-hydroxy-cyclopentyloxy)-2,3-dihydro-isoindol-1-one (isomer 2) (210 mg, 0.41 mmol) in a similar manner to that described in Example 1, step 4. MS: [M−H]⁻=525

1H NMR (400 MHz, DMSO-d6): 8.34 (1H, d), 7.92 (1H, d), 7.76-7.66 (2H, m), 7.28-7.12 (6H, m), 5.25 (1H, s), 4.62-4.33 (3H, m), 3.86-3.77 (1H, m), 3.64-3.54 (1H, m), 1.71-1.54 (2H, m), 1.54-1.36 (8H, m), 1.32-1.22 (1H, m), 1.18-0.97 (1H, m).

Example 40 and Example 41: 6-{[(1R)-1-(4-chloro-phenyl)-7-fluoro-1-[(3-hydroxycyclopentyl)oxy]-5-(2-hydroxypropan-2-yl)-3-oxo-2,3-dihydro-1H-isoindol-2-yl]methyl}pyridine-3-carbonitrile (Both isomers as shown)

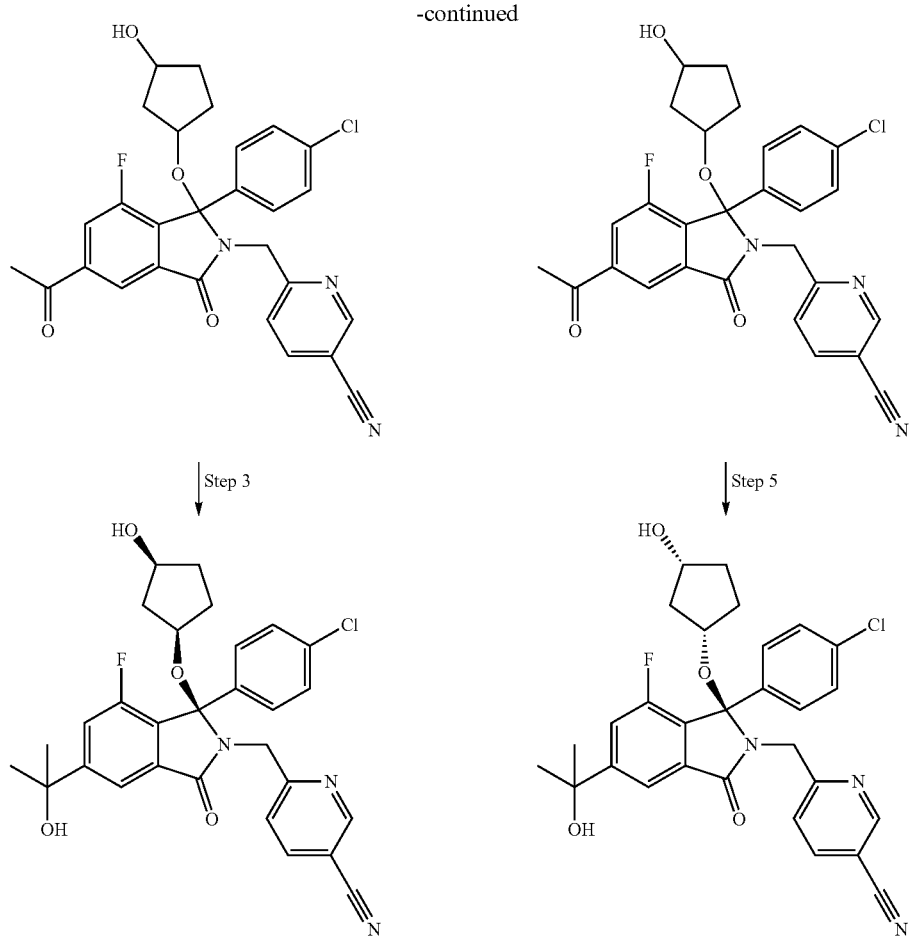

Example 40 and Example 41, Step 1: 6-[5-Bromo-1-(4-chloro-phenyl)-7-fluoro-1-(3-hydroxy-cyclopentyloxy)-3-oxo-1,3-dihydro-isoindol-2-ylmethyl]-nicotinonitrile The title compounds were prepared form 6-[5-bromo-1-(4-chloro-phenyl)-7-fluoro-1-hydroxy-3-oxo-1,3-dihydro-isoindol-2-ylmethyl]-nicotinonitrile (Example 3, step 1) (1.2 g, 2.5 mmol) and (1S,3R)-cyclopentane-1,3-diol (Preparation 8) (1.04 g, 10.2 mmol) in a similar manner to that described in Example 38/Example 39, step 1. isomer 1 MS: [M−H]⁻=555; isomer 2 MS: [M−H]⁻=555.

Example 40, Step 2: 6-[5-Acetyl-1-(4-chloro-phenyl)-7-fluoro-1-(3-hydroxy-cyclopentyloxy)-3-oxo-1,3-dihydro-isoindol-2-ylmethyl]-nicotinonitrile The title compound was prepared from 6-[5-bromo-1-(4-chloro-phenyl)-7-fluoro-1-(3-hydroxy-cyclopentyloxy)-3-oxo-1,3-dihydro-isoindol-2-ylmethyl]-nicotinonitrile (isomer 1) (450 mg, 0.81 mmol) in a similar manner to that described in Example 1, step 3. MS: [M−H]⁻=518.

Example 40, Step 3: 6-[(R)-1-(4-Chloro-phenyl)-7-fluoro-1-(3-hydroxy-cyclopentyloxy)-5-(1-hydroxy-1-methyl-ethyl)-3-oxo-1,3-dihydro-isoindol-2-ylmethyl]-nicotinonitrile The title compound was prepared from 6-[5-acetyl-1-(4-chloro-phenyl)-7-fluoro-1-(3-hydroxy-cyclopentyloxy)-3-oxo-1,3-dihydro-isoindol-2-ylmethyl]-nicotinonitrile (350 mg, 0.67 mmol) in a similar manner to that described in Example 1, step 4. MS: [M−H]⁻=534.

1H NMR (400 MHz, DMSO-d6): 8.76 (1H, d), 8.09 (1H, dd), 7.81 (1H, d), 7.52 (1H, dd), 7.36 (1H, d), 7.26 (4H, s), 5.40 (1H, s), 4.65-4.55 (2H, m), 4.49 (1H, d), 3.84-3.74 (1H, m), 3.74-3.65 (1H, m), 1.66-1.52 (1H, m), 1.52-1.34 (11H, m).

Example 41, Step 4: 6-[5-Acetyl-1-(4-chloro-phenyl)-7-fluoro-1-(3-hydroxy-cyclopentyloxy)-3-oxo-1,3-dihydro-isoindol-2-ylmethyl]-nicotinonitrile The title compound was prepared from 6-[5-bromo-1-(4-chloro-phenyl)-7-fluoro-1-(3-hydroxy-cyclopentyloxy)-3-oxo-1,3-dihydro-isoindol-2-ylmethyl]-nicotinonitrile (isomer 2) (453 mg, 0.81 mmol) in a similar manner to that described in Example 1, step 3. MS: [M−H]⁻=518.

Example 41, Step 5: 6-{[(1R)-1-(4-chlorophenyl)-7-fluoro-1-[(3-hydroxycyclopentyl)oxy]-5-(2-hydroxy-propan-2-yl)-3-oxo-2,3-dihydro-1H-isoindol-2-yl]methyl}pyridine-3-carbonitrile The title compound was prepared from 6-[5-acetyl-1-(4-chloro-phenyl)-7-fluoro-1-(3-hydroxy-cyclopentyloxy)-3-oxo-1,3-dihydro-isoindol-2-ylmethyl]-nicotinonitrile (300 mg, 0.58 mmol) in a similar manner to that described in Example 1, step 4. MS: [M−H]⁻=534.

235
1H NMR (400 MHz, DMSO-d6): 8.77 (1H, d), 8.09 (1H, dd), 7.82 (1H, d), 7.52 (1H, dd), 7.36 (1H, d), 7.25 (4H, s), 5.39 (1H, s), 4.65-4.53 (2H, m), 4.49 (1H, d), 3.90-3.81 (1H, m), 3.77-3.68 (1H, m), 1.75-1.60 (2H, m), 1.53-1.39 (8H, m), 1.39-1.22 (1H, m), 1.19-1.03 (1H, m).
236
Example 42 and Example 43: 6-{[(1R)-1-(4-chlorophenyl)-7-fluoro-1-[(3-hydroxycyclopentyl)oxy]-5-(2-hydroxypropan-2-yl)-3-oxo-2,3-dihydro-1H-isoindol-2-yl]methyl}pyridine-3-carbonitrile
(Both isomers as shown)
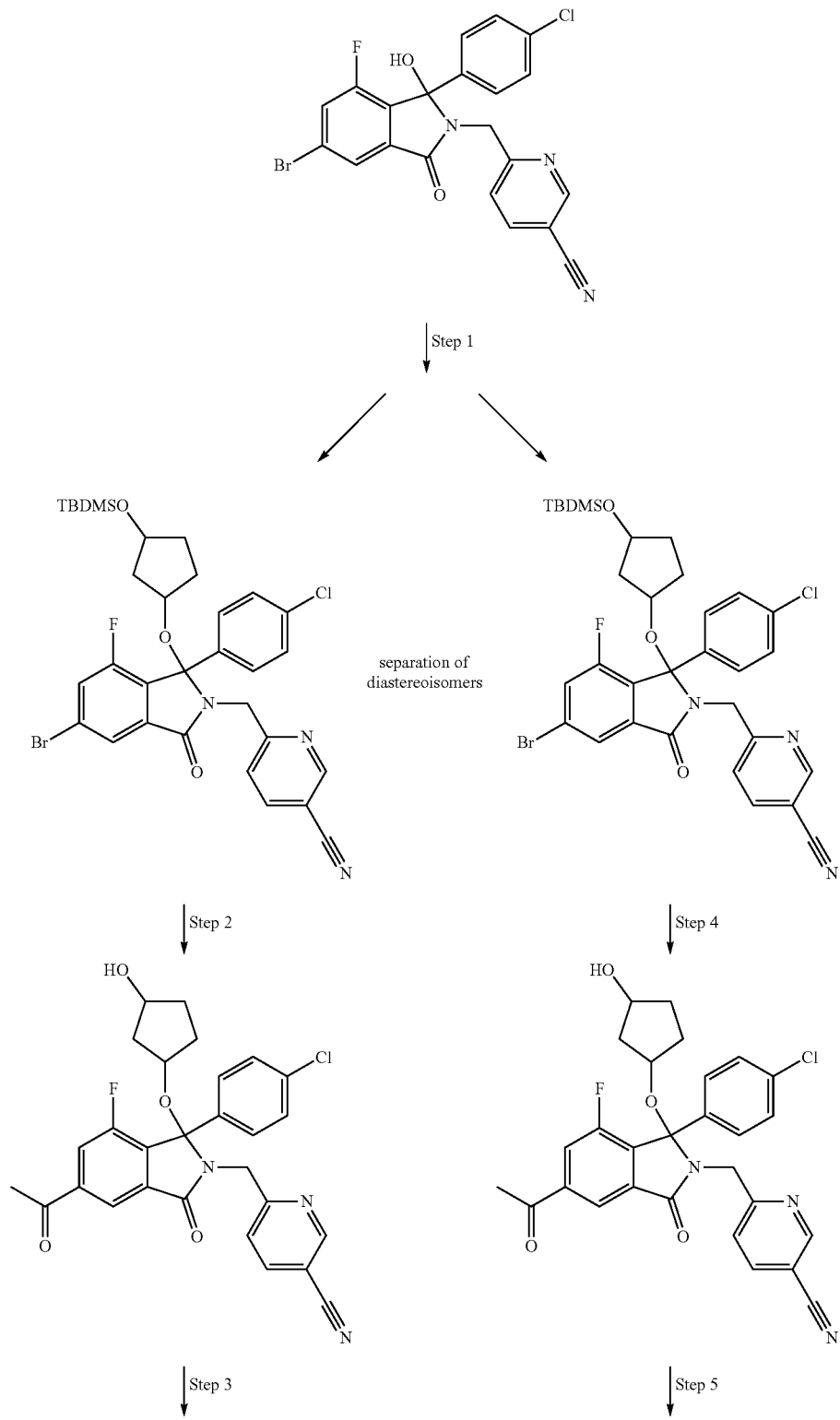

237

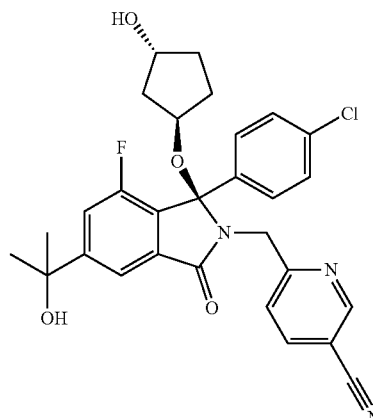

238

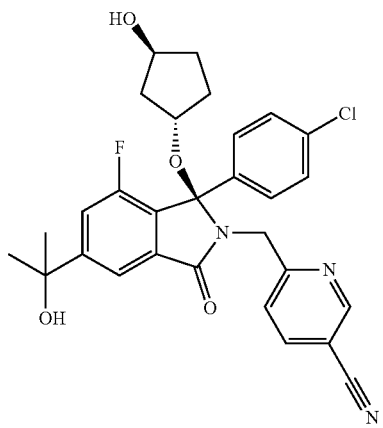

Example 42 and Example 43, Step 1: 6-[5-Bromo-1-[3-(tert-butyl-dimethyl-silanyloxy)-cyclopentyloxy]-1-(4-chloro-phenyl)-7-fluoro-3-oxo-1,3-dihydro-isoindol-2-ylmethyl]-nicotinonitrile The title compounds were prepared form 6-[5-bromo-1-(4-chloro-phenyl)-7-fluoro-1-hydroxy-3-oxo-1,3-dihydro-isoindol-2-ylmethyl]-nicotinonitrile (Example 3, step 1) (1.2 g, 2.5 mmol) and (+/−) 3-(tert-butyl-dimethyl-silanyloxy)-cyclopentanol (Preparation 9) (1.1 g, 5.1 mmol) in a similar manner to that described in Example 38/Example 39, step 1. Isomer 1 MS: [M−H]⁻=669; Isomer 2 MS: [M−H]⁻=669.

Example 42, Step 2: 6-[5-Acetyl-1-(4-chloro-phenyl)-7-fluoro-1-(3-hydroxy-cyclopentyloxy)-3-oxo-1,3-dihydro-isoindol-2-ylmethyl]-nicotinonitrile The title compound was prepared from 6-[5-bromo-1-[3-(tert-butyl-dimethyl-silanyloxy)-cyclopentyloxy]-1-(4-chloro-phenyl)-7-fluoro-3-oxo-1,3-dihydro-isoindol-2-ylmethyl]-nicotinonitrile (isomer 1) (1.0 g, 1.5 mmol) in a similar manner to that described in Example 1, step 3. MS: [M−H]⁻=518.

Example 42, Step 3: 6-{[(1R)-1-(4-chlorophenyl)-7-fluoro-1-[(3-hydroxycyclopentyl)oxy]-5-(2-hydroxypropan-2-yl)-3-oxo-2,3-dihydro-1H-isoindol-2-yl]methyl}pyridine-3-carbonitrile The title compound was prepared from 6-[5-acetyl-1-(4-chloro-phenyl)-7-fluoro-1-(3-hydroxy-cyclopentyloxy)-3-oxo-1,3-dihydro-isoindol-2-ylmethyl]-nicotinonitrile (TRANS 1) (266 mg, 0.51 mmol) in a similar manner to that described in Example 1, step 4. MS: [M−H]⁻=534.

1H NMR (400 MHz, DMSO-d6): 8.75 (1H, d), 8.08 (1H, dd), 7.83 (1H, d), 7.56-7.49 (1H, m), 7.35 (1H, d), 7.28-7.20 (4H, m), 5.40 (1H, s), 4.63 (1H, d), 4.51-4.40 (2H, m), 4.11 (1H, d), 3.97-3.87 (1H, m), 1.90-1.78 (1H, m), 1.62-1.53 (1H, m), 1.49 (6H, s), 1.45-1.24 (4H, m).

Example 43, Step 4: 6-[5-Acetyl-1-(4-chloro-phenyl)-7-fluoro-1-(3-hydroxy-cyclopentyloxy)-3-oxo-1,3-dihydro-isoindol-2-ylmethyl]-nicotinonitrile The title compound was prepared from 6-[5-bromo-1-[3-(tert-butyl-dimethyl-silanyloxy)-cyclopentyloxy]-1-(4-chloro-phenyl)-7-fluoro-3-oxo-1,3-dihydro-isoindol-2-ylmethyl]-nicotinonitrile (580 mg, 0.86 mmol) in a similar manner to that described in Example 1, step 3. MS: [M−H]⁻= 518.

Example 43, Step 5: 6-{[(1R)-1-(4-chlorophenyl)-7-fluoro-1-[(3-hydroxycyclopentyl)oxy]-5-(2-hydroxypropan-2-yl)-3-oxo-2,3-dihydro-1H-isoindol-2-yl]methyl}pyridine-3-carbonitrile The title compound was prepared from 6-[5-acetyl-1-(4-chloro-phenyl)-7-fluoro-1-(3-hydroxy-cyclopentyloxy)-3-oxo-1,3-dihydro-isoindol-2-ylmethyl]-nicotinonitrile (415 mg, 0.80 mmol) in a similar manner to that described in Example 1, step 4. MS: [M−H]⁻=534.

1H NMR (400 MHz, DMSO-d6): 8.77 (1H, d), 8.10 (1H, dd), 7.83 (1H, d), 7.53 (1H, dd), 7.37 (1H, d), 7.29-7.14 (4H, m), 5.41 (1H, s), 4.61 (1H, d), 4.49 (1H, d), 4.40 (1H, d), 4.12 (1H, s), 3.95-3.85 (1H, m), 1.91-1.75 (1H, m), 1.69-1.55 (2H, m), 1.50 (6H, s), 1.36-1.25 (2H, m), 1.21-1.10 (1H, m).

Example 44 and Example 45: (3R)-3-(4-chlorophenyl)-2-[(5-chloropyridin-2-yl)methyl]-3-{[(1R,3R)-3-hydroxycyclopentyl]oxy}-6-(2-hydroxypropan-2-yl)-2,3-dihydro-1H-isoindol-1-one and (3R)-3-(4-chlorophenyl)-2-[(5-chloropyridin-2-yl)methyl]-3-{[(1S,3S)-3-hydroxycyclopentyl]oxy}-6-(2-hydroxypropan-2-yl)-2,3-dihydro-1H-isoindol-1-one
And (Both isomers as shown)
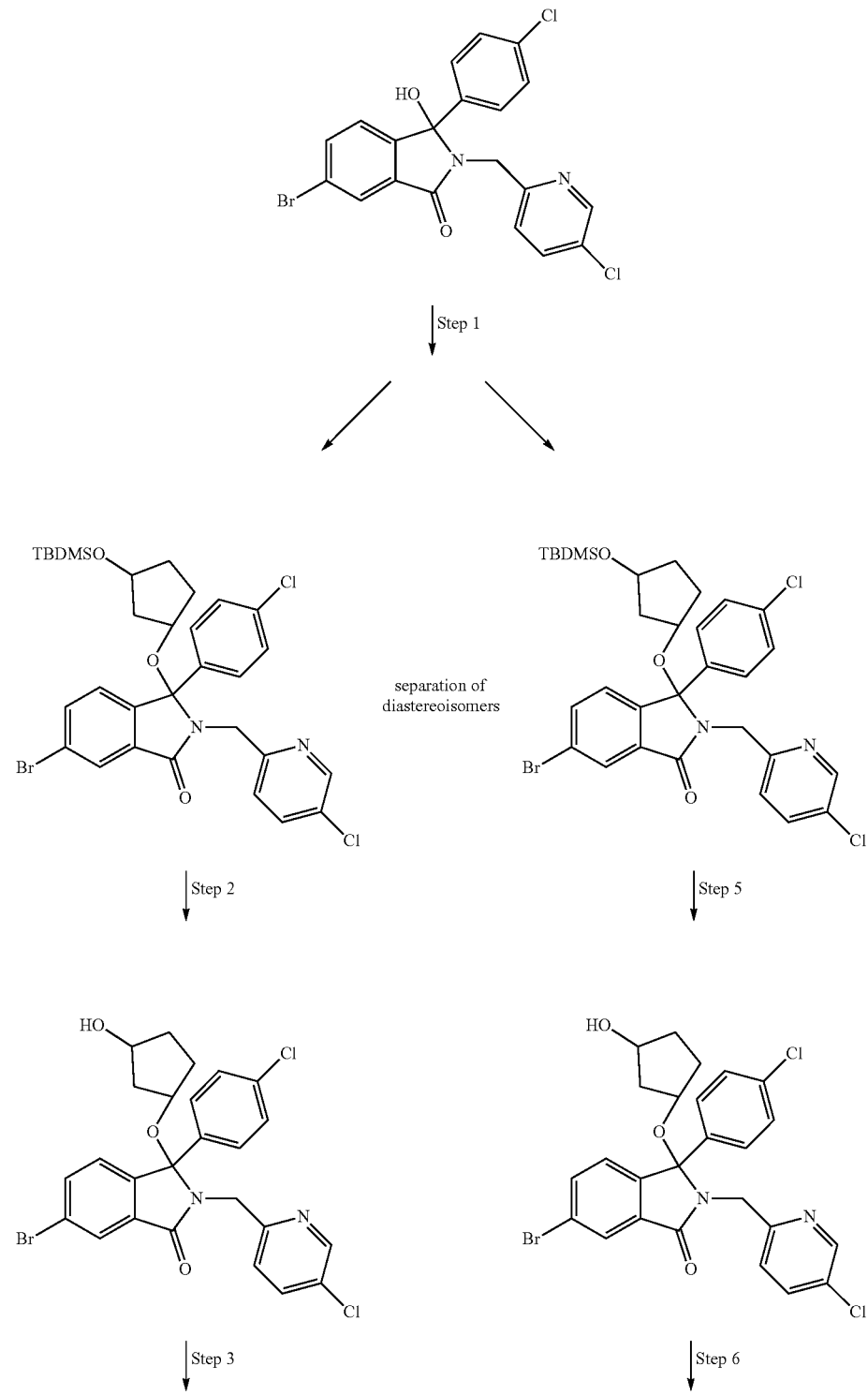 [SMILES: O=C1c2cc(Br)ccc2C(O)(c2ccc(Cl)cc2)N1Cc1ccc(Cl)cn1 ; CC(C)(C)[Si](C)(C)OC1CCC(OC2(c3ccc(Cl)cc3)c3ccc(Br)cc3C(=O)N2Cc2ccc(Cl)cn2)C1 ; CC(C)(C)[Si](C)(C)OC1CCC(OC2(c3ccc(Cl)cc3)c3ccc(Br)cc3C(=O)N2Cc2ccc(Cl)cn2)C1 ; O=C1c2cc(Br)ccc2C(OC2CCC(O)C2)(c2ccc(Cl)cc2)N1Cc1ccc(Cl)cn1 ; O=C1c2cc(Br)ccc2C(OC2CCC(O)C2)(c2ccc(Cl)cc2)N1Cc1ccc(Cl)cn1]

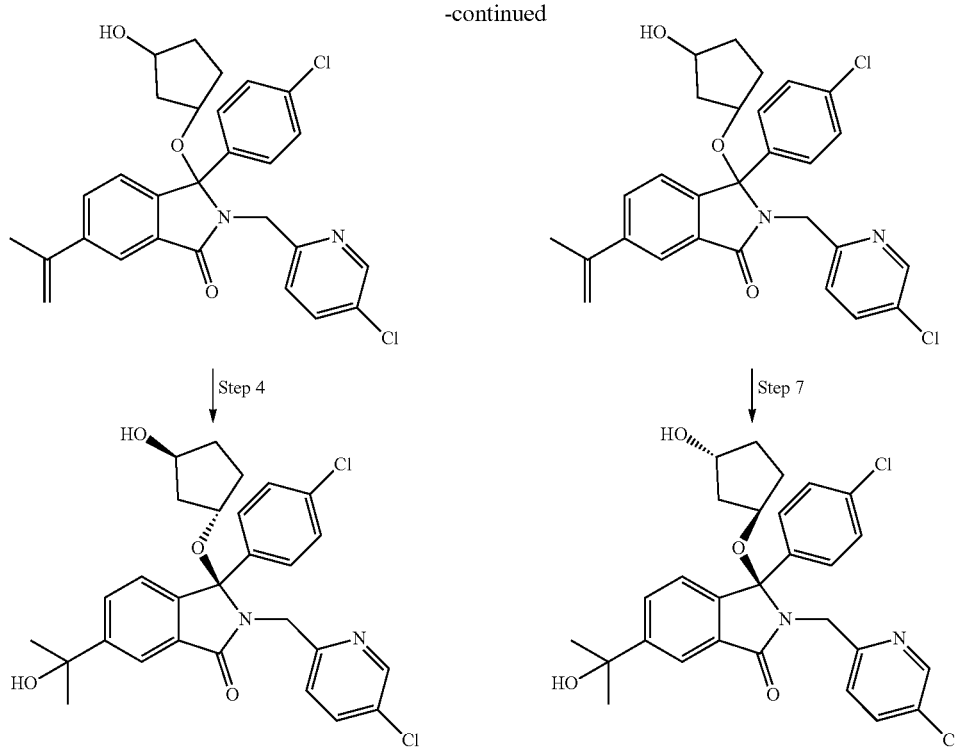

Example 44 and Example 45, Step 1: 6-Bromo-3-((trans-3-((tert-butyldimethylsilyl)oxy)cyclopentyl) oxy)-3-(4-chlorophenyl)-2-((5-chloropyridin-2-yl)methyl)isoindolin-1-one The title compounds were prepared form 6-bromo-3-(4-chloro-phenyl)-2-(5-chloro-pyridin-2-ylmethyl)-3-hydroxy-2,3-dihydro-isoindol-1-one (Example 6, step 1) (0.2 g, 0.43 mmol) and (+/−) 3-(tert-butyl-dimethyl-silanyloxy)-cyclopentanol (Preparation 9) (186 μL, 0.86 mmol, 2 eq.) in a similar manner to that described in Example 38/Example 39, step 1. The two set of diastereoisomers were separated on Silica.

Isomer 1 ¹H NMR (500 MHz; CDCl₃): −0.02 (3H, s), −0.01 (3H), 0.81 (9H, s), 1.28-1.52 (4H, m), 1.57-1.65 (1H, m), 1.81-1.91 (1H, m), 3.79-3.87 (1H, m), 4.22-4.29 (1H, m), 4.42 (1H, d), 4.64 (1H, d), 7.04 (1H, d), 7.06-7.14 (4H, m), 7.19 (1H, d), 7.44 (1H, dd), 7.63 (1H, dd), 8.06 (1H, d), 8.26 (1H);

Isomer 2 ¹H NMR (500 MHz; CDCl₃): 0.09 (3H, s), −0.05 (3H, s), 0.78 (9H, s), 1.20-1.29 (1H, m), 1.32-1.40 (1H, m), 1.40-1.51 (1H, m), 1.55-1.64 (1H, m), 1.65-1.75 (1H, m), 1.85-1.95 (1H, m), 3.79-3.83 (1H, m), 4.20-4.26 (1H, m), 4.39 (1H, d), 4.74 (1H, d), 7.02 (1H, d), 7.05-7.13 (4H, m), 7.14 (1H, d), 7.42 (1H, dd), 7.65 (1H, dd), 8.06 (1H, d), 8.24 (1H, d).

Example 44, Step 2: 6-Bromo-3-(4-chlorophenyl)-2-((5-chloropyridin-2-yl)methyl)-3-((trans-3-hydroxycyclopentyl) oxy)isoindolin-1-one TBAF (2.21 mL, 1M in THF, 2.21 mmol, 1.1 eq.) was added to 6-bromo-3-((trans-3-((tert-butyldimethylsilyl)oxy) cyclopentyl)oxy)-3-(4-chlorophenyl)-2-((5-chloropyridin-2-yl)methyl)isoindolin-1-one (isomer 1) (1.332 g, 2.01 mmol, 1 eq) in THF (30 mL) and the reaction was stirred at r.t. for 48 h, partitioned between EtOAc (2×40 mL) and water (30 mL). The organic extracts were combined, washed with brine, dried over MgSO₄ and the solvent removed in vacuo. Purification by MPLC with a gradient from 40-60% EtOAc/petrol gave the title compound as a white foam (955 mg, 87%). ¹H NMR (500 MHz; CDCl₃) 1.13 (1H, d), 1.30-1.36 (1H, m), 1.38-1.53 (2H, m), 1.67-1.79 (2H, m), 1.96-2.03 (1H, m), 3.86-3.93 (1H, m), 4.32-4.39 (1H, m), 4.41 (1H, d), 4.69 (1H, d), 7.04 (1H, d), 7.06-7.14 (4H, m, 7.17 (1H, d), 7.44 (1H, dd), 7.64 (1H, dd), 8.06 (1H, d), 8.24 (1H, d).

Example 44, Step 3: 3-(4-Chlorophenyl)-2-((5-chloropyridin-2-yl)methyl)-3-((trans-3-hydroxycyclopentyl)oxy)-6-(prop-1-en-2-yl)isoindolin-1-one The title compound was prepared from 6-bromo-3-(4-chlorophenyl)-2-((5-chloropyridin-2-yl)methyl)-3-((trans-3-hydroxycyclopentyl) oxy)isoindolin-1-one (935 mg, 1.70 mmol, 1 eq.), in a similar manner to that described in the Example 4 step 2. ¹H NMR (500 MHz; CDCl₃) 1.30-1.38 (1H, m), 1.38-1.46 (1H, m), 1.46-1.54 (1H, m), 1.68-1.80 (2H, m), 1.96-2.03 (1H, m), 2.21 (3H, s), 3.87-3.95 (1H, m), 4.33-4.39 (1H, m), 4.45 (1H, d), 4.73 (1H, d), 5.22 (1H, br s), 5.50 (1H, br s), 7.01-7.23 (6H, m), 7.42-7.47 (1H, m), 7.61-7.67 (1H, m), 8.01 (1H, d), 8.25 (1H, d).

Example 44, Step 4: (3R)-3-(4-chlorophenyl)-2-[(5-chloropyridin-2-yl)methyl]-3-{[(1R,3R)-3-hydroxycyclopentyl]oxy}-6-(2-hydroxypropan-2-yl)-2,3-dihydro-1H-isoindol-1-one The title compound was prepared from 3-(4-chlorophenyl)-2-((5-chloropyridin-2-yl)methyl)-3-((trans-3-hydroxycyclopentyl)oxy)-6-(prop-1-en-2-yl)isoindolin-1-one (720 mg, 1.41 mmol, 1 eq.), in a similar manner to that described in the Example 4, step 3. The enantiomers were separated by chiral HPLC to give enantiomer 2 (18 mg), ¹H NMR (500 MHz; CDCl₃) 1.30-1.37 (1H, m), 1.37-1.45 (1H, m), 1.45-1.54 (1H, m), 1.64 (3H, s), 1.65 (3H, s), 1.69-1.80 (2H, m), 1.97-2.06 (1H, m), 3.86-3.93 (1H, m), 4.33-4.39 (1H, m), 4.46 (1H, d), 4.73 (1H, d), 7.04-7.16 (5H, m), 7.20 (1H, d), 7.44 (1H, dd), 7.23 (1H, dd), 8.02 (1H, d), 8.25 (1H, d); MS (ES+) 425.3, 427.3

Example 45, Step 5: 6-Bromo-3-(4-chlorophenyl)-2-((5-chloropyridin-2-yl)methyl)-3-((3-hydroxycyclopentyl)oxy)isoindolin-1-one The title compound was prepared from 6-bromo-3-((3-((tert-butyldimethylsilyl)oxy)cyclopentyl)oxy)-3-(4-chlorophenyl)-2-((5-chloropyridin-2-yl)methyl)isoindolin-1-one (Example 44, step 1, isomer 2) (630 mg, 0.95 mmol) in a similar manner that described in Example 44, step 2. ¹H NMR (500 MHz, CDCl₃) 8.25-8.24 (1H, m), 8.06-8.05 (1H, m), 7.65-7.63 (1H, m), 7.45-7.43 (1H, m), 7.18-7.16 (1H, m), 7.12-7.07 (4H, m), 7.06-7.04 (1H, m), 4.70 (1H, d), 4.39 (1H, d), 4.39-4.35 (1H, m), 3.94-3.89 (1H, m), 2.03-1.95 (1H, m), 1.79-1.74 (1H, m), 1.58-1.36 (4H, m).

Example 45, Step 6: 3-(4-Chlorophenyl)-2-((5-chloropyridin-2-yl)methyl)-3-((3-hydroxycyclopentyl)oxy)-6-(prop-1-en-2-yl)isoindolin-1-one The title compound was prepared from 6-bromo-3-(4-chlorophenyl)-2-((5-chloropyridin-2-yl)methyl)-3-((trans-3-hydroxycyclopentyl) oxy)isoindolin-1-one (935 mg, 1.70 mmol, 1 eq.), in a similar manner to that described in the Example 4, step 2.

¹H NMR (500 MHz, CDCl₃) 8.25-8.24 (1H, m). 8.00 (1H, m), 7.63-7.62 (1H, m), 7.44-7.42 (1H, m), 7.20-7.18 (1H, m), 7.13-7.04 (5H, m), 5.49 (1H, s), 5.21 (1H, s), 4.74-4.68 (1H, m), 4.43-4.37 (2H, m), 3.95-3.89 (1H, m), 2.21 (3H, s), 2.02-1.97 (1H, m), 1.79-1.74 (1H, m), 1.57-1.34 (4H, m).

Example 45, Step 7: (3R)-3-(4-chlorophenyl)-2-[(5-chloropyridin-2-yl)methyl]-3-{[(1S,3S)-3-hydroxycyclopentyl]oxy}-6-(2-hydroxypropan-2-yl)-2,3-dihydro-1H-isoindol-1-one The title compound was prepared from 3-(4-chlorophenyl)-2-((5-chloropyridin-2-yl)methyl)-3-((trans-3-hydroxycyclopentyl)oxy)-6-(prop-1-en-2-yl)isoindolin-1-one (720 mg, 1.41 mmol, 1 eq.), in a similar manner to that described in the Example 4, step 3. Purification by chiral HPLC gave the title compound as a white solid (45.1 mg, 6.5%). MS: [M-OH(c-pentyl)O]⁺=425. ¹H NMR (500 MHz, CDCl₃) 8.23 (1H, d), 8.02 (1H, d), 7.72 (1H, dd), 7.43 (1H, dd), 7.20 (1H, d), 7.15-7.11 (3H, m), 7.08-7.07 (2H, m), 4.73 (1H, d), 4.42 (1H, d), 4.39-4.35 (1H, m), 3.94-3.89 (1H, m), 2.02-1.95 (1H, m), 1.79-1.74 (1H, m), 1.65 (3H, s), 1.64 (3H, s), 1.56-1.46 (3H, m), 1.41-1.35 (1H, m).

Example 46: (3S)-3-(4-Chloro-2-fluorophenyl)-2-[(5-chloropyridin-2-yl)methyl]-3-{[1-(hydroxymethyl)cyclopropyl]methoxy}-6-(2-hydroxypropan-2-yl)-2,3-dihydro-1H-isoindol-1-one

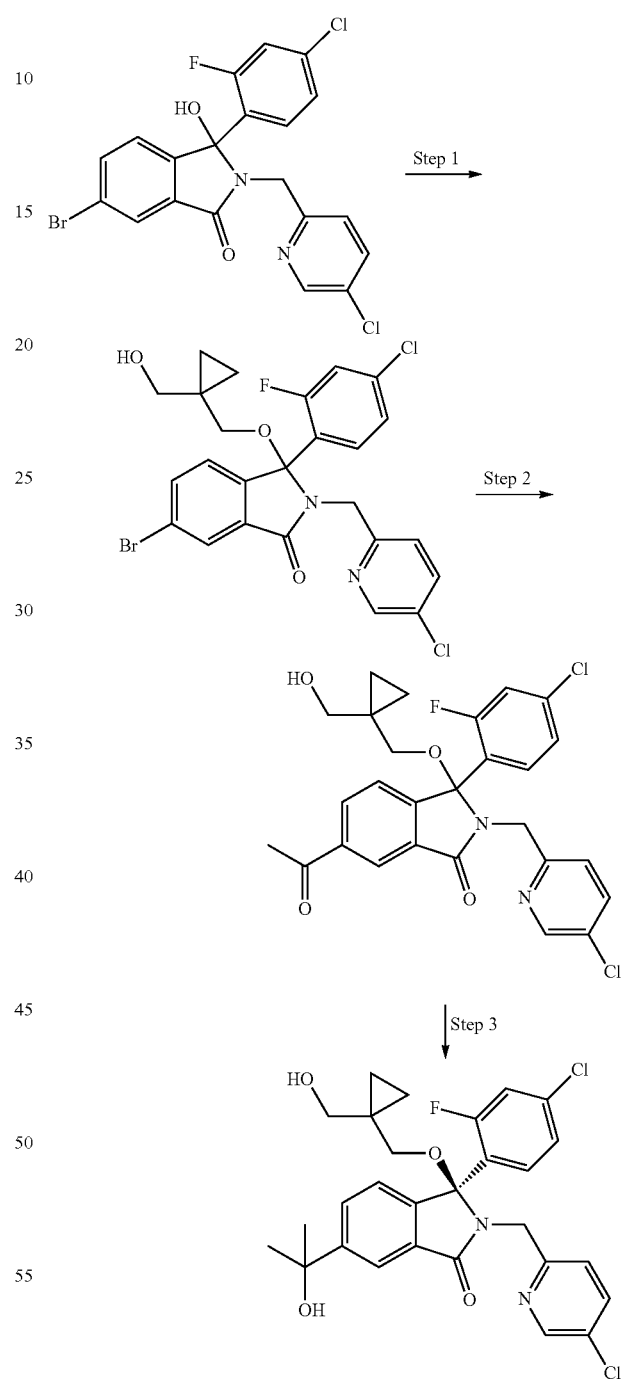

Example 46, Step 1: 6-Bromo-3-(4-chloro-2-fluorophenyl)-2-((5-chloropyridin-2-yl)methyl)-3-((1-(hydroxymethyl)cyclopropyl)methoxy)isoindolin-1-one 6-Bromo-3-(4-chloro-2-fluorophenyl)-2-((5-chloropyridin-2-yl)methyl)-3-hydroxyisoindolin-1-one (Preparation 10A) (1.0 g, 2.08 mmol), was converted to the title compound in a similar manner to that described in Example 1, step 2, using (1-hydroxymethyl-cyclopropyl)-methanol instead of {1-[hydroxy($^2$H$_2$)methyl]cyclopropyl}($^2$H$_2$)methanol. $^1$H NMR (400 MHz, CDCl$_3$) 8.28 (1H, d), 8.01-7.96 (2H, m), 7.65 (1H, dd), 7.54 (1H, dd), 7.41 (1H, d), 7.20 (1H, dd), 7.04 (1H, d), 6.72 (1H, dd), 4.58 (1H, d), 4.36 (1H, d), 3.68 (1H, dd), 3.43 (1H, dd), 3.30 (1H, d), 2.66 (1H, d), 2.62-2.57 (1H, m), 0.54-0.50 (2H, m), 0.34-0.31 (2H, m).

Example 46, Step 2: 6-Acetyl-3-(4-chloro-2-fluorophenyl)-2-((5-chloropyridin-2-yl)methyl)-3-((1-(hydroxymethyl)cyclopropyl)methoxy)isoindolin-1-one The title compound was prepared from 6-bromo-3-(4-chloro-2-fluorophenyl)-2-((5-chloropyridin-2-yl)methyl)-3-((1-(hydroxymethyl)cyclopropyl)methoxy)isoindolin-1-one in a similar manner to that described in Example 1, step 3.
$^1$H NMR (400 MHz, CDCl$_3$) 8.41 (1H, d), 8.29 (1H, d), 8.17 (1H, dd), 8.01 (1H, dd), 7.55 (1H, dd), 7.43 (1H, d), 7.28-7.27 (1H, m), 7.21 (1H, dd), 6.72 (1H, d), 4.62 (1H, d), 4.40 (1H, d), 3.67 (1H, m), 3.43 (1H, dd), 3.33 (1H, d), 2.67 (3H, s), 2.63-2.56 (2H, m), 0.52-0.51 (2H, m), 0.36-0.27 (2H, m).

Example 46, Step 3: (3S)-3-(4-Chloro-2-fluorophenyl)-2-[(5-chloropyridin-2-yl)methyl]-3-{[1-(hydroxymethyl)cyclopropyl]methoxy}-6-(2-hydroxypropan-2-yl)-2,3-dihydro-1H-isoindol-1-one The title compound was prepared from 6-acetyl-3-(4-chloro-2-fluorophenyl)-2-((5-chloropyridin-2-yl)methyl)-3-((1-(hydroxymethyl)cyclopropyl)methoxy) isoindolin-1-one in a similar manner to that described in Example 1, step 4.
$^1$H NMR (400 MHz, CDCl$_3$) 8.28 (1H, d), 8.01-7.95 (2H, m), 7.73 (1H, dd), 7.55-7.52 (1H, m), 7.44 (1H, d), 7.19 (1H, dd), 7.12 (1H, d), 6.71 (1H, dd), 4.60 (1H, d), 4.40 (1H, d), 3.68 (1H, dd), 3.42 (1H, d), 3.26 (1H, d), 2.69-2.61 (2H, m), 1.77 (1H, s), 1.62 (6H, d), 0.51-0.46 (2H, dd), 0.36-0.28 (2H, m). MS: [M+H]$^+$=545.

The following compound was prepared in a similar manner:

Example 47: ((3R)-2-[(5-chloropyridin-2-yl)methyl]-3-(4-ethylphenyl)-3-{[1-(hydroxymethyl)cyclopropyl]methoxy}-6-(2-hydroxypropan-2-yl)-2,3-dihydro-1H-isoindol-1-one The title compound was prepared from 6-bromo-2-((5-chloropyridin-2-yl)methyl)-3-(4-ethylphenyl)-3-hydroxyisoindolin-1-one (Preparation 10B) in a similar manner to that described in Example 46, steps 1-3.

$^1$H NMR (400 MHz, CDCl$_3$): 8.33 (1H, d), 7.96 (1H, d), 7.72 (1H, dd), 7.46 (1H, dd), 7.18 (3H, dd), 7.02 (2H, d), 4.49 (2H, d), 3.71 (1H, d), 3.40-3.34 (1H, m), 3.26 (1H, d), 2.79-2.86 (1H, m), 2.74 (1H, d), 2.57 (2H, q), 1.83 (1H, s), 1.61-1.64 (6H, m) 1.17 (3H, dd), 0.53-0.45 (2H, m), 0.35-0.25 (2H, m).

Example 48: 4-[(1R)-2-[(5-Chloropyridin-2-yl)methyl]-1-({1-[hydroxy($^2$H$_2$)methyl]cyclopropyl}($^2$H$_2$)methoxy)-5-(2-hydroxypropan-2-yl)-3-oxo-2,3-dihydro-1H-isoindol-1-yl]benzonitrile

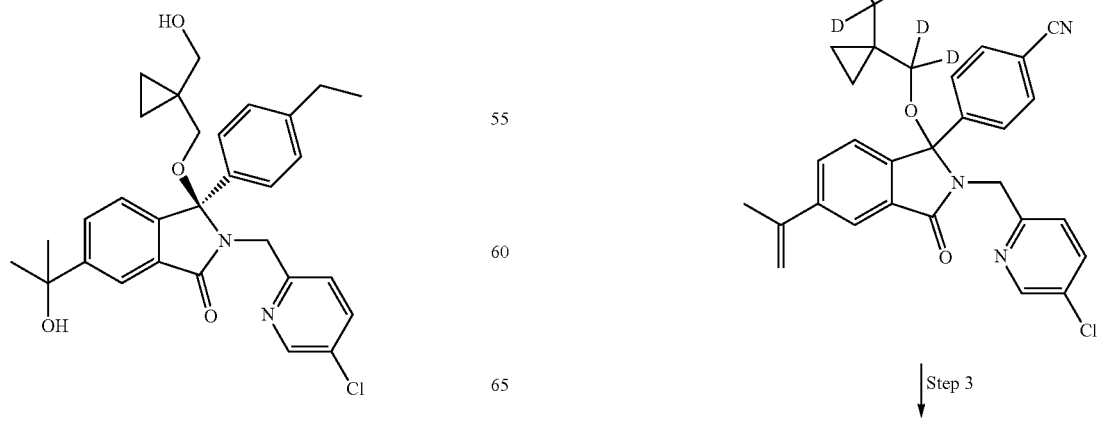

-continued

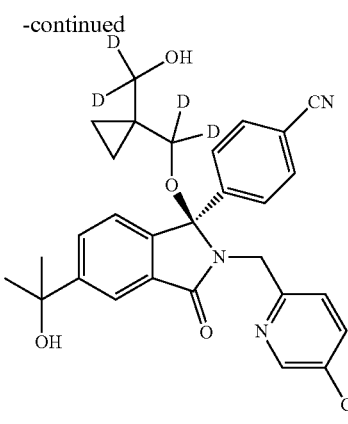

Example 48, Step 1: 4-(5-Bromo-2-((5-chloropyridin-2-yl)methyl)-1-((1-(hydroxy($^2$H$_2$)methyl)cyclopropyl)($^2$H$_2$)methoxy)-3-oxoisoindolin-1-yl)benzonitrile The title compound was prepared from 4-(5-bromo-2-((5-chloropyridin-2-yl)methyl)-1-hydroxy-3-oxoisoindolin-1-yl)benzonitrile (Preparation 10D) in a similar manner to that described in Example 1, step 2.

$^1$H NMR (400 MHz, CDCl$_3$) 8.33 (1H, d), 8.03 (1H, d), 7.67 (1H, dd), 7.55-7.51 (3H, m), 7.42 (2H, d), 7.34 (1H, d), 7.01 (1H, d), 4.49-4.40 (2H, m), 2.58 (1H, s), 0.55-0.49 (2H, m), 0.36-0.27 (2H, m).

Example 48, Step 2: 4-(2-((5-Chloropyridin-2-yl)methyl)-1-((1-(hydroxy($^2$H$_2$)methyl)cyclopropyl)($^2$H$_2$)methoxy)-3-oxo-5-(prop-1-en-2-yl)isoindolin-1-yl)benzonitrile The title compound was prepared from 4-(5-bromo-2-((5-chloropyridin-2-yl)methyl)-1-((1-(hydroxy($^2$H$_2$)methyl)cyclopropyl)($^2$H$_2$)methoxy)-3-oxoisoindolin-1-yl)benzonitrile in a similar manner to that described in Example 4, step 2.

$^1$H NMR (400 MHz, CDCl$_3$) 8.33 (1H, d), 7.97 (1H, d), 7.65 (1H, dd), 7.55-7.50 (3H, m), 7.44 (2H, d), 7.36 (1H, d), 7.08 (1H, d), 5.47 (1H, s), 5.21 (1H, s), 4.52-4.42 (2H, m), 2.59 (1H, s), 2.18 (3H, s), 0.55-0.48 (2H, m), 0.37-0.26 (2H, m).

Example 48, Step 3: 4-[(1R)-2-[(5-Chloropyridin-2-yl)methyl]-1-({1-[hydroxy($^2$H$_2$)methyl]cyclopropyl}($^2$H$_2$)methoxy)-5-(2-hydroxypropan-2-yl)-3-oxo-2,3-dihydro-1H-isoindol-1-yl]benzonitrile The title compound was prepared from 4-(2-((5-chloropyridin-2-yl)methyl)-1-((1-(hydroxy($^2$H$_2$)methyl)cyclopropyl)($^2$H$_2$)methoxy)-3-oxo-5-(prop-1-en-2-yl)isoindolin-1-yl) in a similar manner to that described in Example 4, step 3.

$^1$H NMR (400 MHz, DMSO-d6) 8.36 (1H, d), 7.97 (1H, d), 7.80-7.70 (4H, m), 7.42 (2H, d), 7.26 (1H, d), 7.22 (1H, d), 5.29 (1H, s), 4.54-4.48 (3H, m), 1.51 (6H, d), 0.36 (2H, dd), 0.22-0.19 (1H, m), 0.12-0.09 (1H, m).

Example 49: (3R)-2-[(5-Chloropyridin-2-yl)methyl]-3-(4-fluorophenyl)-3-({1-[hydroxy($^2$H$_2$)methyl]cyclopropyl}($^2$H$_2$)methoxy)-6-(2-hydroxypropan-2-yl)-2,3-dihydro-1H-isoindol-1-one

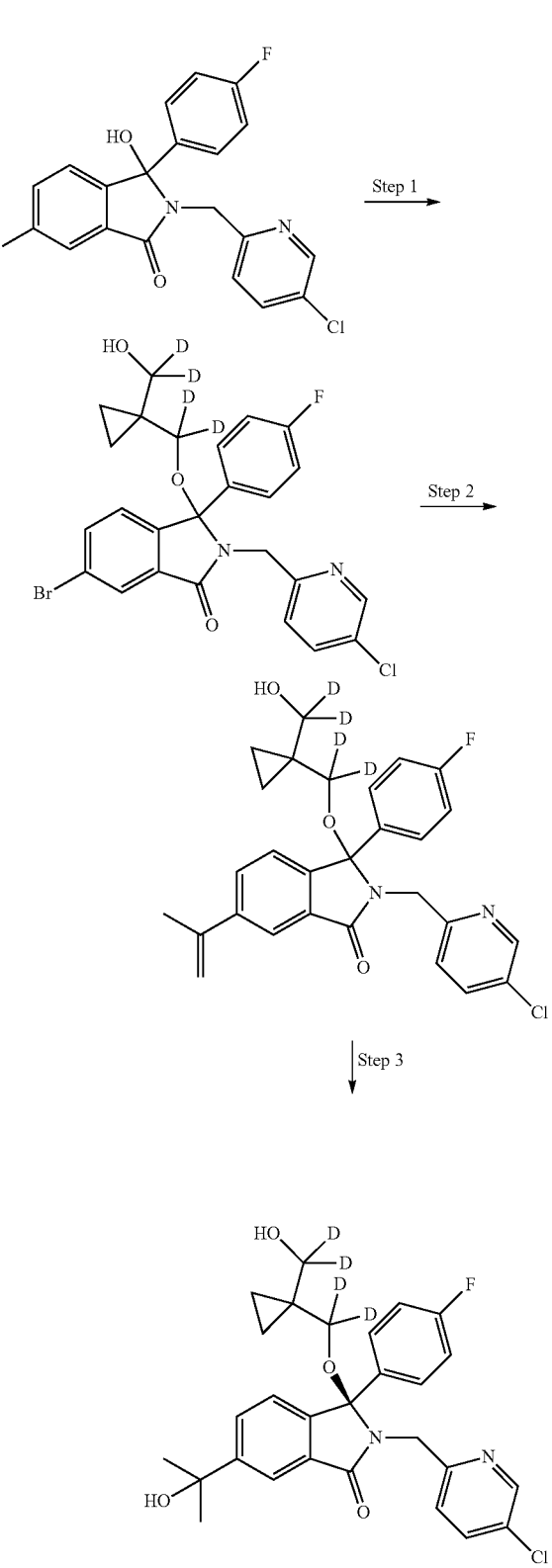

Example 49, Step 1: 6-Bromo-2-[(5-chloropyridin-2-yl)methyl]-3-(4-fluorophenyl)-3-({1-[hydroxy($^2$H$_2$)methyl]cyclopropyl}($^2$H$_2$)methoxy)-2,3-dihydro-1H-isoindol-1-one The title compound was prepared from 6-bromo-2-((5-chloropyridin-2-yl)methyl)-3-(4-fluorophenyl)-3-hydroxy-isoindolin-1-one (10E) in a similar manner to that described in Example 1, step 2.

1H NMR (500 MHz, CDCl$_3$) 8.36 (1H, d), 8.01 (1H, d), 7.66 (1H, dd), 7.54 (1H, dd), 7.32 (1H, d), 7.29-7.26 (2H, m), 7.05 (1H, d), 6.93-6.90 (2H, m), 4.46 (2H, s), 0.52-0.47 (2H, m), 0.36-0.24 (2H, m).

Example 49, Step 2: 2-[(5-Chloropyridin-2-yl)methyl]-3-(4-fluorophenyl)-3-({1-[hydroxy($^2$H$_2$)methyl]cyclopropyl}($^2$H$_2$)methoxy)-6-(prop-1-en-2-yl)-2,3-dihydro-1H-isoindol-1-one The title compound was prepared from 6-bromo-2-[(5-chloropyridin-2-yl)methyl]-3-(4-fluorophenyl)-3-({1-[hydroxy($^2$H$_2$)methyl]cyclopropyl}($^2$H$_2$)methoxy)-2,3-dihydro-1H-isoindol-1-one in a similar manner to that described in Example 4, step 2.

1H NMR (500 MHz, CDCl$_3$) 8.35 (1H, d), 7.95 (1H, d), 7.65-7.63 (1H, m), 7.52-7.50 (1H, m), 7.33-7.26 (3H, m), 7.12-7.10 (1H, m), 6.92-6.88 (2H, m), 5.46 (1H, s), 5.19 (1H, s), 4.47 (2H, s), 0.51-0.46 (2H, m), 0.35-0.23 (2H, m).

Example 49, Step 3: (3R)-2-[(5-Chloropyridin-2-yl)methyl]-3-(4-fluorophenyl)-3-({1-[hydroxy($^2$H$_2$)methyl]cyclopropyl}($^2$H$_2$)methoxy)-6-(2-hydroxypropan-2-yl)-2,3-dihydro-1H-isoindol-1-one The title compound was prepared from 2-[(5-chloropyridin-2-yl)methyl]-3-(4-fluorophenyl)-3-({1-[hydroxy($^2$H$_2$)methyl]cyclopropyl}($^2$H$_2$)methoxy)-6-(prop-1-en-2-yl)-2,3-dihydro-1H-isoindol-1-one in a similar manner to that described in Example 4, step 3.

MS: [M+H]$^+$=515.4. 1H NMR (500 MHz, CDCl$_3$) 8.35 (1H, d), 7.97 (1H, d), 7.38 (1H, dd), 7.51 (1H, dd), 7.34-7.32 (1H, m), 7.30-7.26 (2H, m), 7.13 (1H, d), 6.92-6.89 (2H, m), 4.47 (2H, s), 1.62 (3H, s), 1.61 (3H, s), 0.51-0.46 (2H, m), 0.35-0.23 (2H, m).

Example 50: (3R)-2-[(5-Chloropyridin-2-yl)methyl]-3-({1-[hydroxy($^2$H$_2$)methyl]cyclopropyl}($^2$H$_2$)methoxy)-6-(2-hydroxypropan-2-yl)-3-[4-(trifluoromethyl)phenyl]-2,3-dihydro-1H-isoindol-1-one

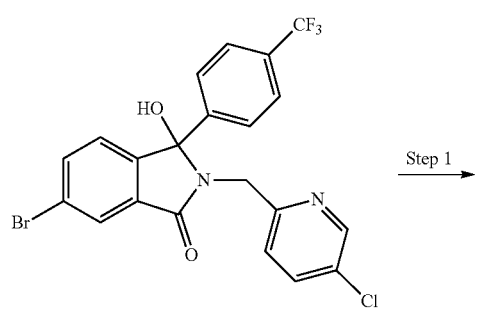

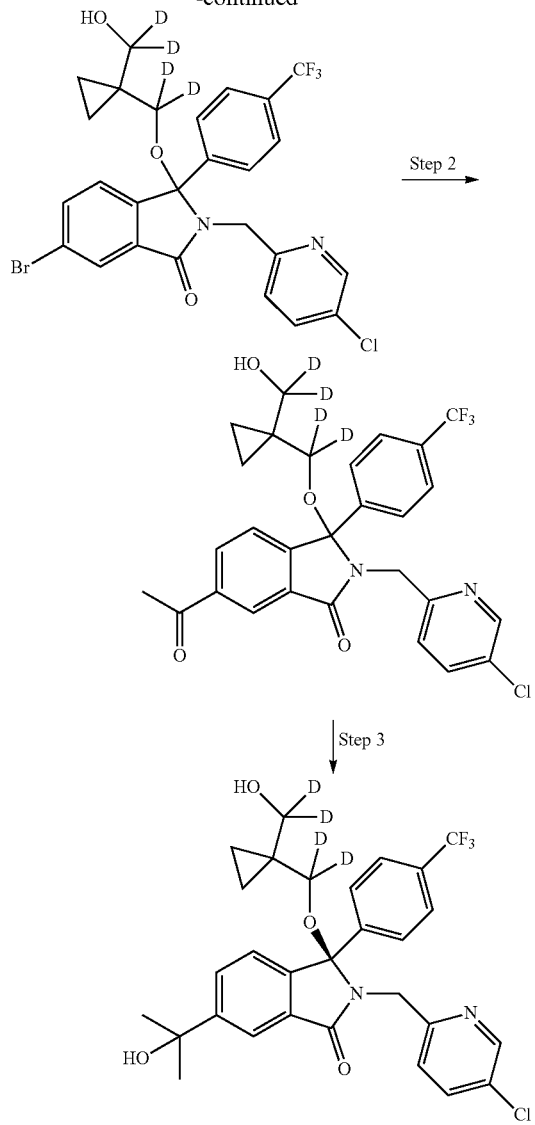

Example 50, Step 1: 6-Bromo-2-[(5-chloropyridin-2-yl)methyl]-3-{2-[1-(2-hydroxypropan-2-yl)cyclopropyl]propan-2-yl}-3-[4-(trifluoromethyl)phenyl]-2,3-dihydro-1H-isoindol-1-one The title compound was prepared from 6-bromo-2-[(5-chloropyridin-2-yl)methyl]-3-hydroxy-3-[4-(trifluoromethyl)phenyl]-2,3-dihydro-1H-isoindol-1-one (Preparation 10F) in a similar manner to that described in Example 1, step 2.

1H NMR (500 MHz, CDCl$_3$) 0.27-0.37 (2H, m), 0.49-0.54 (2H, m), 4.43 (1H, d), 4.53 (1H, d), 7.04 (1H, d), 7.29 (1H, d), 7.38-7.40 (2H, m), 7.45-7.47 (2H, m), 7.50 (1H, dd), 7.66 (1H, dd), 8.03 (1H, d), 8.29 (1H, d).

Example 50, Step 2: 6-Acetyl-2-[(5-chloropyridin-2-yl)methyl]-3-({1-HO 0 [hydroxy(2H$_2$)methyl]cyclopropyl}(2H$_2$)methoxy)-3-[4-(trifluoromethyl)phenyl]-2,3-dihydro-1H-isoindol-1-one To a microwave vial were added 6-bromo-2-[(5-chloropyridin-2-yl)methyl]-3-{2-[1-(2-hydroxypropan-2-yl)cyclopropyl]propan-2-yl)}-3-[4-(trifluoromethyl)phenyl]-2,3-dihydro-1H-isoindol-1-one (500 mg, 0.85 mmol), CsF (516.5 mg, 3.40 mmol) and Pd(PPh₃)₄ (98.6 mg, 0.085 mmol). DCE (0.85 mL) was added and the mixture degassed with N₂ for 10 min, then acetyl trimethylsilane (197 mg, 0.24 mL, 1.70 mmol) was added. The resulting mixture was heated at 75° C. for 5 h, cooled to RT and diluted with EtOAc (25 mL). The mixture was filtered through Celite and washed with EtOAc (50 mL). The solution was concentrated onto silica and purified by Biotage using 0-20% EtOAc in petrol as the eluent followed by reverse phase chromatography (C18) using 0-100% MeCN (0.1% HCOOH) in water (0.1% HCOOH) gave the title compound as a white solid (130.4 mg). 1H NMR (500 MHz, CDCl₃) 8.44 (1H, d), 8.31 (1H, d), 8.17 (1H, dd), 7.51 (1H, dd), 7.48-7.47 (2H, m), 7.42-7.40 (2H, m), 7.33 (1H, d), 7.28-7.26 (1H, m), 4.55 (1H, d), 4.47 (1H, d), 2.67 (3H, s), 0.54-0.50 (2H, m), 0.38-0.25 (2H, m).

Example 50, Step 3: (3R)-2-[(5-Chloropyridin-2-yl)methyl]-3-({1-[hydroxy(²H₂)methyl]cyclopropyl}(²H₂)methoxy)-6-(2-hydroxypropan-2-yl)-3-[4-(trifluoromethyl)phenyl]-2,3-dihydro-1H-isoindol-1-one The title compound was prepared from 6-acetyl-2-[(5-chloropyridin-2-yl)methyl]-3-({1-[hydroxy(²H₂)methyl]cyclopropyl}(²H₂)methoxy)-3-[4-(trifluoromethyl)phenyl]-2,3-dihydro-1H-isoindol-1-one in a similar manner to that described for Example 1, step 4.

1H NMR (500 MHz, CDCl₃) 8.29 (1H, d), 8.00 (1H, d), 7.74 (1H, dd), 7.50 (1H, dd), 7.45-7.40 (4H, m), 7.33 (1H, d), 7.13 (1H, d), 4.58 (1H, d), 4.49 (1H, d), 1.63-1.62 (6H, m), 0.54-0.49 (2H, m), 0.38-0.26 (2H, m). MS: [M-(OHCD₂(cPr)CD₂O)]⁺=459.3.

Example 51: (3R)-2-[(5-chloropyridin-2-yl)methyl]-3-[4-(1,1-difluoroethyl)phenyl]-3-{[1-(hydroxymethyl)cyclopropyl]methoxy}-6-(2-hydroxypropan-2-yl)-2,3-dihydro-1H-isoindol-1-one

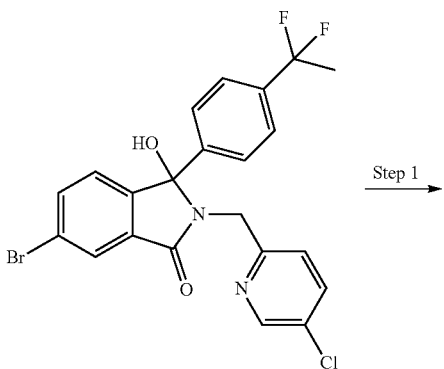

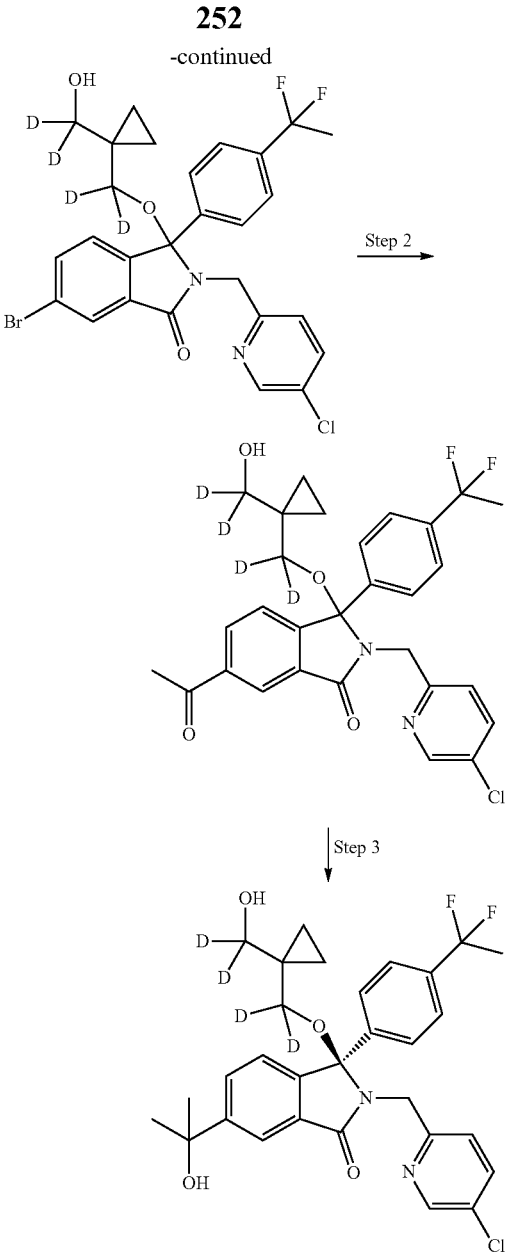

Example 51, Step 1: 6-Bromo-2-((5-chloropyridin-2-yl)methyl)-3-(4-(1,1-difluoroethyl)phenyl)-3-((1-(hydroxy(²H₂)methyl)cyclopropyl) (²H₂)methoxy) isoindolin-1-one Crude 6-bromo-2-((5-chloropyridin-2-yl)methyl)-3-(4-(1,1-difluoroethyl)phenyl)-3-((1-(hydroxy(²H₂)methyl)cyclopropyl) (²H₂)methoxy)isoindolin-1-one (0.820 g) was prepared from crude 6-bromo-2-((5-chloropyridin-2-yl)methyl)-3-(4-(1,1-difluoroethyl)phenyl)-3-hydroxyisoindolin-1-one (Preparation 10C) (1.77 g) and {1-[hydroxy(²H₂)methyl]cyclopropyl}(²H₂)methanol (1.90 g, 17.92 mmol) in a similar manner to that described in Example 1, step 2. ¹H NMR (400 MHz, CDCl₃): 8.30 (1H, dd), 8.03 (1H, dd), 7.66 (1H, dd), 7.48 (1H, dd), 7.34-7.24 (5H, m), 7.05 (1H, dd), 4.53 (1H, d), 4.42 (1H, d), 1.86 (3H, m), 0.53-0.49 (2H, m), 0.36-0.30 (2H, m).

Example 51, Step 2: 6-Acetyl-2-((5-chloropyridin-2-yl)methyl)-3-(4-(1,1-difluoroethyl)phenyl)-3-((1-(hydroxy($^2H_2$)methyl)cyclopropyl) ($^2Ha$)methoxy)isoindolin-1-one Crude 6-acetyl-2-((5-chloropyridin-2-yl)methyl)-3-(4-(1,1-difluoroethyl)phenyl)-3-((1-(hydroxy($^2H_2$)methyl)cyclopropyl) ($^2H_2$)methoxy)isoindolin-1-one (0.40 g) was prepared from crude 6-bromo-2-((5-chloropyridin-2-yl)methyl)-3-(4-(1,1-difluoroethyl)phenyl)-3-((1-(hydroxy($^2H_2$)methyl)cyclopropyl) ($^2H_2$)methoxy)isoindolin-1-one (0.82 g) in a similar manner to that described in Example 1, step 3. $^1$H NMR (400 MHz, CDCl$_3$): 8.43 (1H, dd), 8.32 (1H, dd), 8.16 (1H, dd), 7.49 (1H, dd), 7.36-7.26 (6H, m), 4.55 (1H, d), 4.47 (1H, d), 2.67 (3H, s), 1.86 (3H, dd), 0.53-0.49 (2H, m), 0.33-0.26 (2H, m).

Example 51, Step 3: (3R)-2-[(5-chloropyridin-2-yl)methyl]-3-[4-(1,1-difluoroethyl)phenyl]-3-{[1-(hydroxymethyl)cyclopropyl]methoxy}-6-(2-hydroxypropan-2-yl)-2,3-dihydro-1H-isoindol-1-one (R)-2-((5-Chloropyridin-2-yl)methyl)-3-(4-(1,1-difluoroethyl)phenyl)-3-((1-(hydroxy($^2H_2$)methyl)cyclopropyl) ($^2H_2$)methoxy)-6-(2-hydroxypropan-2-yl)isoindolin-1-one (0.013 g) was prepared from crude 6-acetyl-2-((5-chloropyridin-2-yl)methyl)-3-(4-(1,1-difluoroethyl)phenyl)-3-((1-(hydroxy($^2H_2$)methyl)cyclopropyl) ($^2H_2$)methoxy)isoindolin-1-one (0.16 g, 0.29 mmol) in a similar manner to that described in Example 1, step 4. Purification by chiral preparative LCMS gave the title compound as the slow running enantiomer. $^1$H NMR (400 MHz, CDCl$_3$): 8.30 (1H, d), 7.99 (1H, d), 7.74 (1H, dd), 7.47 (1H, dd), 7.33 (4H, s), 7.30 (1H, d), 7.14 (1H, d), 4.55 (1H, d), 4.45 (1H, d), 2.66 (1H, s), 1.86 (3H, dd), 1.78 (1H, s), 1.62 (6H, d), 0.52-0.49 (2H, m), 0.36-0.27 (2H, m). MS: [M-OC$^2$H$_2$(cPr)C$^2$H$_2$OH]+=455.

Example 52: (3R)-2-[(5-chloropyridin-2-yl)methyl]-3-(3,4-difluorophenyl)-3-({1-[hydroxy($^2H_2$)methyl]cyclopropyl}($^2H_2$)methoxy)-6-(2-hydroxypropan-2-yl)-2,3-dihydro-1H-isoindol-1-one

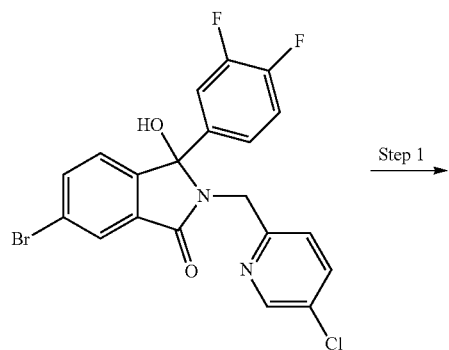

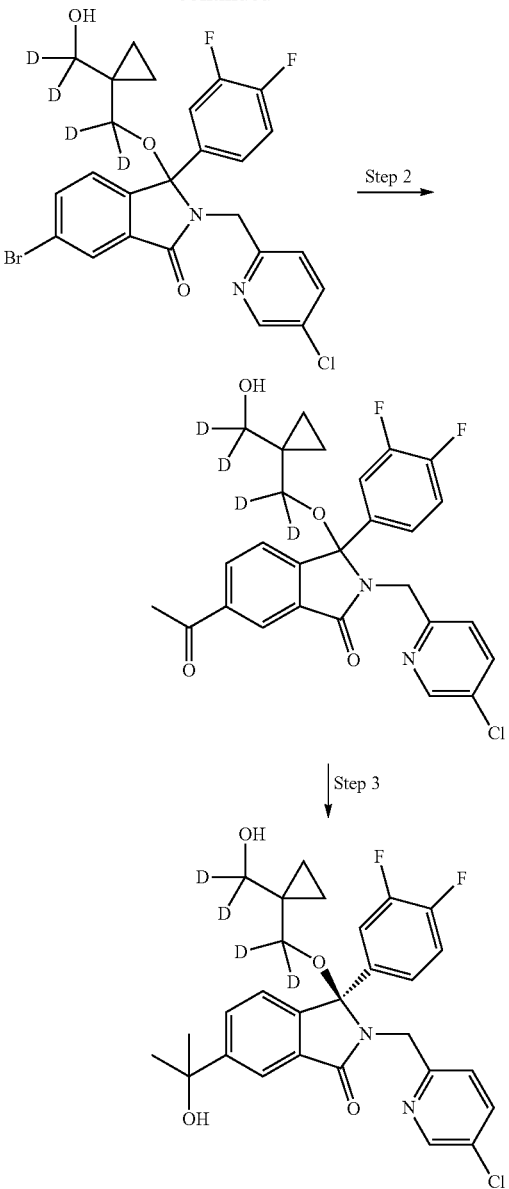

Example 52, Step 1: 6-Bromo-2-((5-chloropyridin-2-yl)methyl)-3-(3,4-difluorophenyl)-3-((1-(hydroxy($^2H_2$)methyl)cyclopropyl) ($^2H_2$) methoxy)isoindolin-1-one 6-Bromo-2-((5-chloropyridin-2-yl)methyl)-3-(3,4-difluorophenyl)-3-((1-(hydroxy($^2H_2$) methyl)cyclopropyl) ($^2H_2$) methoxy)isoindolin-1-one (1.55 g, 65%) was prepared from 6-bromo-2-((5-chloropyridin-2-yl)methyl)-3-(3,4-difluorophenyl)-3-hydroxyisoindolin-1-one (Preparation 10G) (2.0 g, 4.30 mmol) and {1-[hydroxy($^2H_2$)methyl]cyclopropyl}($^2H_2$)methanol (2.28 g, 21.47 mmol) in a similar manner to that described in Example 1, step 2. $^1$H NMR (400 MHz, CDCl$_3$): 8.37 (1H, d), 8.02 (1H, s), 7.67 (1H, dd), 7.55 (1H, dd), 7.34 (1H, d), 7.24-7.17 (1H, m), 7.06-6.95 (3H, m), 4.50-4.40 (2H, m), 2.61-2.57 (1H, m), 0.53-0.48 (2H, m), 0.35-0.25 (2H, m).

Example 52, Step 2: 6-Acetyl-2-((5-chloropyridin-2-yl)methyl)-3-(3,4-difluorophenyl)-3-((1-(hydroxy($^2$H$_2$)methyl)cyclopropyl) ($^2$H$_2$) methoxy)isoindolin-1-one 6-Acetyl-2-((5-chloropyridin-2-yl)methyl)-3-(3,4-difluorophenyl)-3-((1-(hydroxy($^2$H$_2$)methyl)cyclopropyl) ($^2$H$_2$) methoxy)isoindolin-1-one (0.973 g, 67%) was prepared from 6-bromo-2-((5-chloropyridin-2-yl)methyl)-3-(3,4-difluorophenyl)-3-((1-(hydroxy($^2$H$_2$)methyl)cyclopropyl) ($^2$H$_2$) methoxy)isoindolin-1-one (1.55 g, 2.80 mmol) in a similar manner to that described in Example 1, step 3. $^1$H NMR (400 MHz, CDCl$_3$): 8.42 (1H, dd), 8.38 (1H, dd), 8.17 (1H, dd), 7.57 (1H, dd), 7.37 (1H, d), 7.29-7.26 (1H, m), 7.25-7.18 (1H, m), 7.06-6.96 (2H, m), 4.53-4.45 (2H, m), 2.67 (3H, s), 0.53-0.48 (2H, m), 0.35-0.23 (2H, m).

Example 52, Step 3: (3R)-2-[(5-chloropyridin-2-yl)methyl]-3-(3,4-difluorophenyl)-3-({1-[hydroxy($^2$H$_2$)methyl]cyclopropyl}($^2$H$_2$)methoxy)-6-(2-hydroxypropan-2-yl)-2,3-dihydro-1H-isoindol-1-one (R)-2-((5-chloropyridin-2-yl)methyl)-3-(3,4-difluorophenyl)-3-((1-(hydroxy($^2$H$_2$)methyl)cyclopropyl) ($^2$H$_2$) methoxy)-6-(2-hydroxypropan-2-yl)isoindolin-1-one (0.078 g, 15%) was prepared from 6-acetyl-2-((5-chloropyridin-2-yl)methyl)-3-(3,4-difluorophenyl)-3-((1-(hydroxy($^2$H$_2$)methyl)cyclopropyl) ($^2$H$_2$) methoxy)isoindolin-1-one (0.50 g, 0.97 mmol) in a similar manner to that described in Example 1, step 4. Purification by chiral preparative LCMS gave the title compound as the fast running enantiomer. $^1$H NMR (400 MHz, CDCl$_3$): 8.36 (1H, dd), 7.97 (1H, dd), 7.75 (1H, dd), 7.54 (1H, dd), 7.36 (1H, dd), 7.22-7.16 (1H, m), 7.13 (1H, dd), 7.02-6.97 (2H, m), 4.52-4.43 (2H, m), 2.63 (1H, s), 1.80 (1H, s), 1.62 (6H, d), 0.53-0.46 (2H, m), 0.34-0.25 (2H, m). MS: [M-OC$^2$H$_2$(cPr)C$^2$H$_2$OH]+=427.

The following compound was prepared in an analoguous manner:

Example 53: (3R)-2-[(5-chloropyridin-2-yl)methyl]-3-({1-[hydroxy($^2$H$_2$)methyl]cyclopropyl}($^2$H$_2$)methoxy)-6-(2-hydroxypropan-2-yl)-3-[4-(trifluoromethoxy)phenyl]-2,3-dihydro-1H-isoindol-1-one

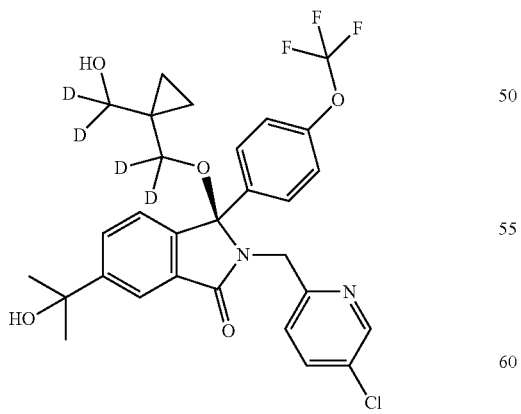

The title compound was prepared from 2-[(5-chloropyridin-2-yl)methyl]-3-hydroxy-6-(2-hydroxypropan-2-yl)-3-[4-(trifluoromethoxy)phenyl]-2,3-dihydro-1H-isoindol-1-one (Preparation 10H) in a similar manner to that described in Example 52, steps 1-3. $^1$H NMR (400 MHz, CDCl$_3$): 8.31 (1H, s), 7.98 (1H, s), 7.75 (1H, d), 7.48 (1H, d), 7.33-7.28 (3H, m), 7.14 (1H, d), 7.03 (2H, d), 4.57 (1H, d), 4.44 (1H, d), 1.80 (1H, br s), 1.60 (6H, s), 1.20 (1h, d), 0.51-0.47 (2H, m), 0.33-0.27 (2H, m).

Example 54: (3R)-4-Chloro-3-(4-chlorophenyl)-2-[(5-chloropyridin-2-yl)methyl]-6-(2-hydroxypropan-2-yl)-3-methoxy-2,3-dihydro-1H-isoindol-1-one

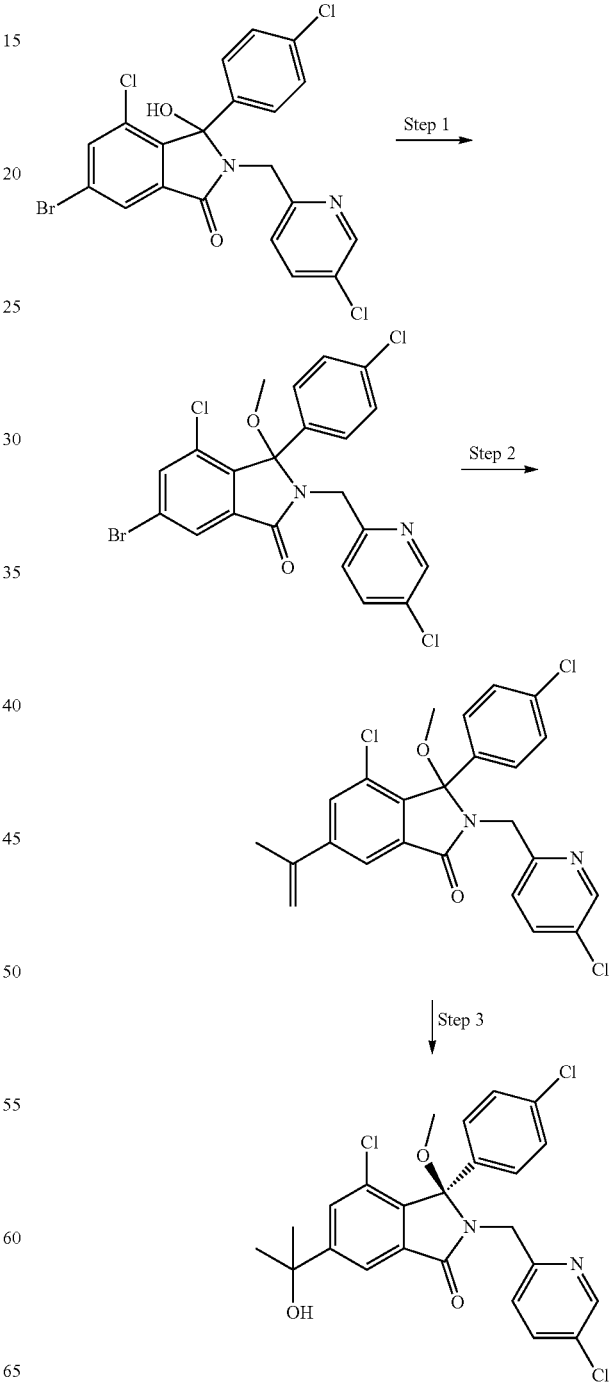

Example 54, Step 1: 6-Bromo-4-chloro-3-(4-chlorophenyl)-2-[(5-chloropyridin-2-yl)methyl]-3-methoxy-2,3-dihydro-1H-isoindol-1-one The title compound was prepared from 6-bromo-4-chloro-3-(4-chlorophenyl)-2-[(5-chloropyridin-2-yl)methyl]-3-hydroxy-2,3-dihydro-1H-isoindol-1-one (10 I) in a similar manner to that described in Example 2, step 1. MS: [M-OCH$_3$]$^+$ 481.

Example 54, Step 2: 4-Chloro-3-(4-chlorophenyl)-2-[(5-chloropyridin-2-yl)methyl]-3-methoxy-6-(prop-1-en-2-yl)-2,3-dihydro-1H-isoindol-1-one The title compound was prepared from 6-bromo-4-chloro-3-(4-chlorophenyl)-2-[(5-chloropyridin-2-yl)methyl]-3-methoxy-2,3-dihydro-1H-isoindol-1-one in a similar manner to that described in Example 4, step 2. [M-OCH$_3$]$^+$ 443.

Example 54, Step 3: (3R)-4-Chloro-3-(4-chlorophenyl)-2-[(5-chloropyridin-2-yl)methyl]-6-(2-hydroxypropan-2-yl)-3-methoxy-2,3-dihydro-1H-isoindol-1-one The title compound was prepared from 4-chloro-3-(4-chlorophenyl)-2-[(5-chloropyridin-2-yl)methyl]-3-methoxy-6-(prop-1-en-2-yl)-2,3-dihydro-1H-isoindol-1-one in a similar manner to that described in Example 4, step 3.
$^1$H NMR (500 MHz, CDCl$_3$): 8.34 (1H, d, N=HC), 7.93 (1H, d, ArH), 7.68 (1H, d, ArH), 7.48 (1H, dd, ArH), 7.21-7.16 (5H, m, 5×ArH), 4.59 (1H, d, NC—H'), 4.40 (1H, d, NC—H), 2.90 (3H, s, CH$_3$) and 1.62 (6H, s, 2×CH$_3$). MS: [M-OCH$_3$]$^+$ 459.

Example 55 and Example 56: (3R)-3-(4-Chlorophenyl)-2-[(5-chloropyridin-2-yl)methyl]-6-[1-hydroxy-1-(1H-pyrazol-4-yl)ethyl]-3-methoxy-2,3-dihydro-1H-isoindol-1-one (*both isomers separated and isolated)

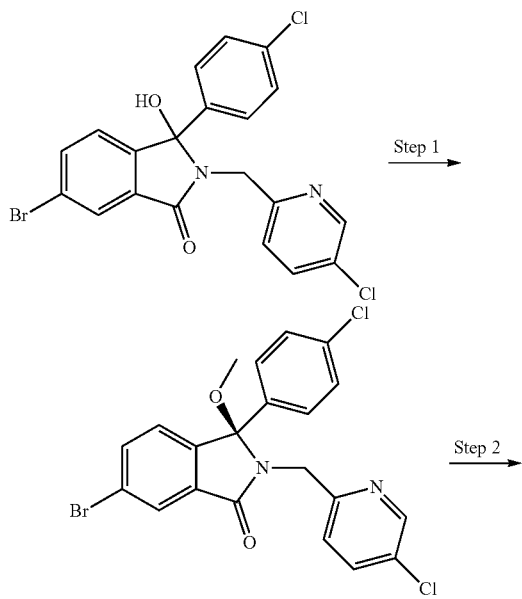

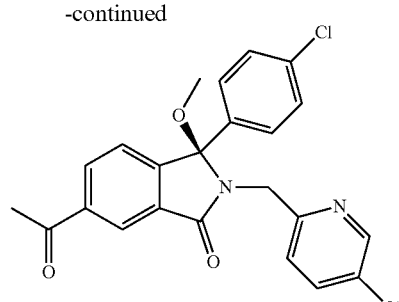

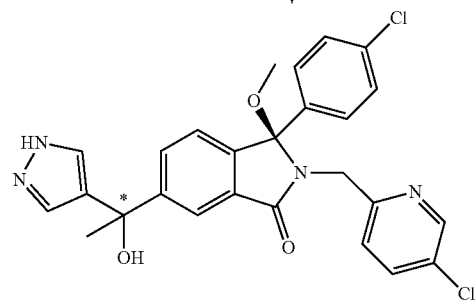

Example 55 and Example 56, Step 1: (3R)-6-Bromo-3-(4-chlorophenyl)-2-[(5-chloropyridin-2-yl)methyl]-3-methoxy-2,3-dihydro-1H-isoindol-1-one Prepared in a similar manner to that described for Example 2, step 1. The R enantiomer was separated by chiral HPLC to give the title compound. 1H NMR (500 MHz, CDCl$_3$) 8.34 (1H, d), 8.06 (1H, d), 7.65 (1H, dd), 7.49 (1H, dd), 7.26-7.16 (5H, m), 7.03 (1H, d), 4.58 (1H, d), 4.45 (1H, d), 2.83 (3H, s).

Example 55 and Example 56, Step 2: (3R)-6-Acetyl-3-(4-chlorophenyl)-2-[(5-chloropyridin-2-yl)methyl]-3-methoxy-2,3-dihydro-1H-isoindol-1-one Prepared from (3R)-6-bromo-3-(4-chlorophenyl)-2-[(5-chloropyridin-2-yl)methyl]-3-methoxy-2,3-dihydro-1H-isoindol-1-one in a similar manner to that described in Example 50, step 2. Purification by Biotage using 0-40% EtOAc in petrol as the eluent gave the title compound as an off white solid (149.7 mg, 32%). 1H NMR (500 MHz, CDCl$_3$) 8.46 (1H, d), 8.35 (1H, d), 8.16 (1H, dd), 7.50 (1H, dd), 7.26-7.23 (2H, m), 7.21-7.17 (4H, m), 4.63 (1H, d), 4.47 (1H, d), 2.82 (3H, s), 2.67 (3H, s).

Example 55 and Example 56, Step 3: (3R)-3-(4-Chlorophenyl)-2-[(5-chloropyridin-2-yl)methyl]-6-[1-hydroxy-1-(1H-pyrazol-4-yl)ethyl]-3-methoxy-2,3-dihydro-1H-isoindol-1-one At −78° C., to a solution of 4-bromopyrazole (74.8 mg, 0.509 mmol) in THF (2.0 mL) was added n-BuLi (2.35M in hexanes, 0.43 mL, 1.017 mmol) and the resulting solution stirred at −78° C. for 45 min then at RT for 1.5 h. The solution was cooled back to −78° C. and a cooled solution of (3R)-6-acetyl-3-(4-chlorophenyl)-2-[(5-chloropyridin-2-yl)methyl]-3-methoxy-2,3-dihydro-1H-isoindol-1-one (149.7 mg, 0.339 mmol) in THF (1.4 mL) was added dropwise. The reaction was warmed to RT and stirred for 2 h then quenched by careful addition of saturated aqueous NH$_4$Cl solution (10 mL). The mixture was extracted into EtOAc (2×50 mL), washed with brine and dried over MgSO$_4$. Purified by Biotage using reverse phase conditions (C18) using 50-100% MeCN (0.1% HCOOH) in water (0.1% HCOOH) as the eluent gave the diastereoisomeric mixture as a white solid (45.5 mg). The reaction was repeated from (3R)-6-acetyl-3-(4-chlorophenyl)-2-[(5-chloropyridin-2-yl)methyl]-3-methoxy-2,3-dihydro-1H-isoindol-1-one (86 mg, 0.195 mmol) and the combined products purified by semi-preparative HPLC and Chiral HPLC gave Example 55 (*isomer 1) as a white solid (18.7 mg). 1H NMR (500 MHz, CDCl$_3$) 8.33 (1H, d), 7.98 (1H, s), 7.72-7.70 (1H, m), 7.57 (2H, s br), 7.47 (1H, dd), 7.22-7.15 (5H, m), 7.11 (1H, d), 4.60 (1H, d), 4.45 (1H, d), 2.81 (3H, s), 1.96 (3H, s). MS: [M–H]$^-$=507.2 and Example 56 *(isomer 2) as a white solid (19.7 mg). MS: [M–H]$^-$=507.2. 1H NMR (500 MHz, CDCl$_3$) 8.33 (1H, d), 7.99 (1H, s), 7.70 (1H, d), 7.63 (2H, s br), 7.48 (1H, dd), 7.23-7.15 (5H, m), 7.12 (1H, d), 4.59 (1H, d), 4.48 (1H, d), 2.82 (3H, s), 1.97 (3H, s).

Example 57 and Example 58: (3R)-3-(4-chlorophenyl)-2-[(5-chloropyridin-2-yl)methyl]-6-[1-hydroxy-1-(1-methyl-1H-pyrazol-4-yl)ethyl]-3-methoxy-2,3-dihydro-1H-isoindol-1-one (*both isomers separated and isolated)

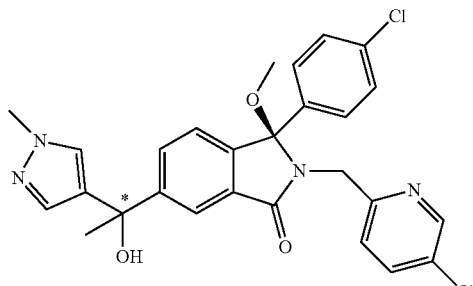

(3R)-6-Acetyl-3-(4-chlorophenyl)-2-[(5-chloropyridin-2-yl)methyl]-3-methoxy-2,3-dihydro-1H-isoindol-1-one (Example 55 and Example 56, step 2) was converted to the title compound in a similar manner that described in Example 55 and Example 56, step 3, using 4-bromo-1-methyl-pyrazole instead of 4-bromopyrazole. The mixture of diastereoisomers were separated by chiral HPLC.

Example 57: *(Fast Running)

1H NMR (500 MHz, CDCl$_3$) 1.92 (3H, s), 2.82 (3H, s), 3.88 (3H, s), 4.50 (1H, d), 4.63 (1H, d), 7.11-7.12 (1H, m), 7.15-7.17 (2H, m), 7.20-7.22 (2H, m), 7.25-7.27 (2H, m), 7.39 (1H, s), 7.51 (1H, dd), 7.72 (1H, dd), 7.98 (1H, d), 8.34 (1H, d). m/z 523.3 [M+H]$^+$

Example 58: *(Slow Running)

1H NMR (500 MHz, CDCl$_3$) 1.92 (3H, s, CH$_3$), 2.82 (3H, s, CH$_3$), 3.88 (3H, s, CH$_3$), 4.50 (1H, d, J=15.5 Hz, NCHH'), 4.63 (1H, d, J=15.5 Hz, NCHH'), 7.10-7.12 (1H, m, ArH), 7.15-7.17 (2H, m, 2×ArH), 7.20-7.22 (2H, m, 2×ArH), 7.23-7.28 (2H, m, 2×ArH), 7.38 (1H, s, ArH), 7.50 (1H, dd, J=2.5 and 8.4 Hz, ArH), 7.72 (1H, dd, J=1.7 and 8.0 Hz, ArH), 7.99 (1H, d, J=1.7 Hz, ArH), 8.34 (1H, d, J=2.5 Hz, ArH). m/z 523.3 [M+H]$^+$ Example 59: (3R)-3-(4-Chlorophenyl)-2-[(5-chloropyridin-2-yl)methyl]-3-[(2S)-3-hydroxy-2-methyl(3,3-$^2$H$_2$)propoxy]-6-(2-hydroxypropan-2-yl)-2,3-dihydro-1H-isoindol-1-one

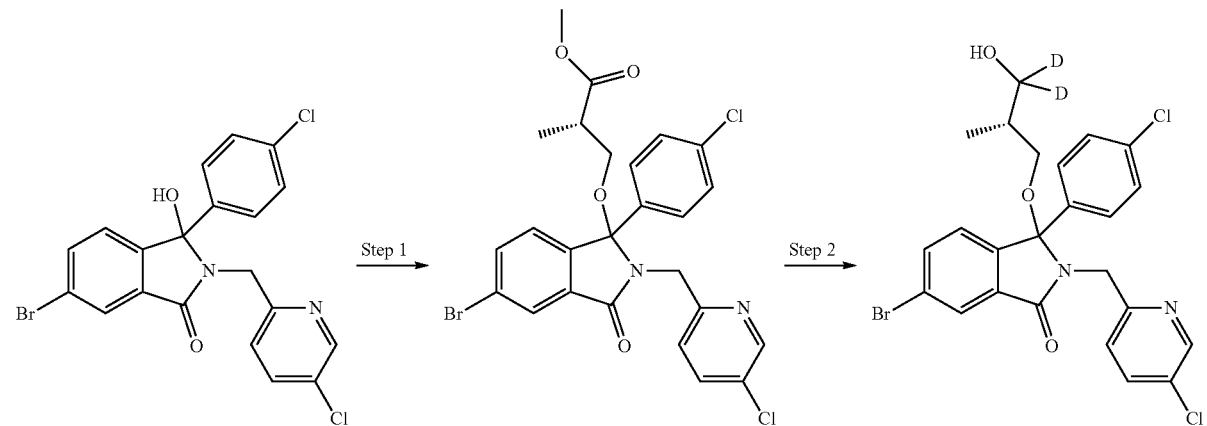

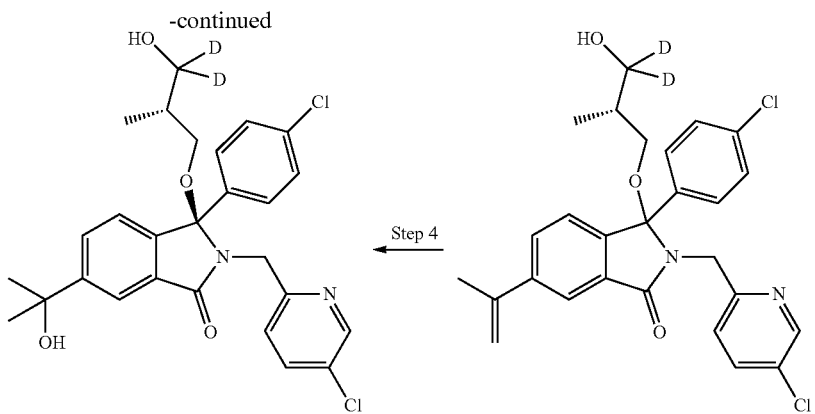

Example 59, Step 1: Methyl (2S)-3-{[5-bromo-1-(4-chlorophenyl)-2-[(5-chloropyridin-2-yl)methyl]-3-oxo-2,3-dihydro-1H-isoindol-1-yl]oxy}-2-methylpropanoate The title compound was prepared from 6-bromo-3-(4-chloro-phenyl)-2-((5-chloro-pyridin-2-ylmethyl)-3-hydroxy-2,3-dihydro-isoindol-1-one (Example 6, step 1) and methyl (S)-(+)3-hydroxy-2-methyl-propionate in a similar manner to that described in Example 1, step 2. MS: [M-$C_5H_9O_3$]$^+$ 447.

Example 59, Step 2: 6-Bromo-3-(4-chlorophenyl)-2-[(5-chloropyridin-2-yl)methyl]-3-[(2S)-3-hydroxy-2-methyl(3,3-$^2$H$_2$)propoxy]-2,3-dihydro-1H-isoindol-1-one Methyl (2S)-3-{[5-bromo-1-(4-chlorophenyl)-2-[(5-chloropyridin-2-yl)methyl]-3-oxo-2,3-dihydro-1H-isoindol-1-yl]oxy}-2-methylpropanoate (832 mg, 1.48 mmol) was dissolved in anhydrous THF (15 mL) under nitrogen and LiBD$_4$ (42 mg, 1.62 mmol) was added in one portion at room temperature. The reaction mixture was stirred at 60° C. for 18 h, cooled to 0° C. and quenched with water (2.5 mL). 1M HCl was added dropwise until effervescence ceased, extracted with EtOAc (3×10 mL), dried over anhydrous Na$_2$SO$_4$, filtered and the solvent removed in vacuo. FCC [petrol-ethyl acetate (100:0)→(40:60)] of the crude residue afforded the title compound (359 mg, 45%) as a white foam. MS: [M-$C_4H_7D_2O_2$]$^+$ 447.

Example 59, Step 3: 3-(4-Chlorophenyl)-2-[(5-chloropyridin-2-yl)methyl]-3-[(2S)-3-hydroxy-2-methyl(3,3-$^2$H$_2$)propoxy]-6-(prop-1-en-2-yl)-2,3-dihydro-1H-isoindol-1-one The title compound was prepared from 6-bromo-3-(4-chlorophenyl)-2-[(5-chloropyridin-2-yl)methyl]-3-[(2S)-3-hydroxy-2-methyl(3,3-$^2$H$_2$)propoxy]-2,3-dihydro-1H-isoindol-1-one in a similar manner to that described in Example 4, step 2. MS: [M-$C_4H_7D_2O_2$]$^+$ 409.

Example 59, step 4 (3R)-3-(4-Chlorophenyl)-2-[(5-chloropyridin-2-yl)methyl]-3-[(2S)-3-hydroxy-2-methyl(3,3-$^2$H$_2$)propoxy]-6-(2-hydroxypropan-2-yl)-2,3-dihydro-1H-isoindol-1-one The title compound was prepared from 3-(4-chlorophenyl)-2-[(5-chloropyridin-2-yl)methyl]-3-[(2S)-3-hydroxy-2-methyl(3,3-$^2$H$_2$)propoxy]-6-(prop-1-en-2-yl)-2,3-dihydro-1H-isoindol-1-one in a similar manner to that described in Example 4, step 3. $^1$H NMR (500 MHz, DMSO-d$_6$) 8.37 (1H, d, N=CH), 7.93 (1H, d, ArH), 7.76-7.71 (2H, m, 2×ArH), 7.31-7.27 (2H, m, 2×ArH), 7.26-7.20 (3H, m, 3×ArH), 7.15 (1H, d, ArH), 5.25 (1H, s, (CH$_3$)$_2$OH), 4.53 (1H, d, NC—H'), 4.41-4.35 (2H, m, N C—H, OH), 2.73-2.72 (2H, m, CH$_2$), 1.50-1.44 (7H, m, C(CH$_3$)$_2$, CH$_3$CH) and 0.71-0.67 (3H, m, CH$_3$). MS: [M-$C_4H_7D_2O_2$]$^+$ 425.

Example 60: (3R)-3-(4-Chlorophenyl)-2-[(5-chloropyridin-2-yl)methyl]-3-[(2R)-3-hydroxy-2-methyl(3,3-$^2$H$_2$)propoxy]-6-(2-hydroxypropan-2-yl)-2,3-dihydro-1H-isoindol-1-one

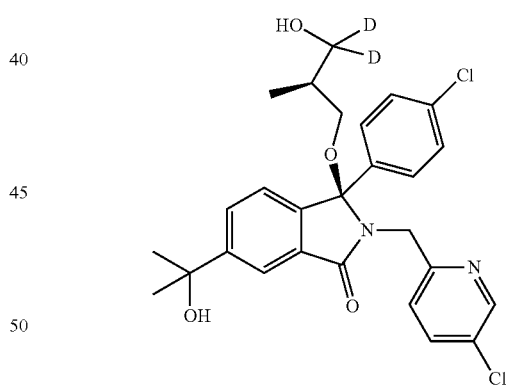

The title compound was prepared from 6-bromo-3-(4-chloro-phenyl)-2-((5-chloro-pyridin-2-ylmethyl)-3-hydroxy-2,3-dihydro-isoindol-1-one (Example 6, step 1) in a similar manner to that described in Example 59, steps 1-4 using (R)-(−)3-hydroxy-2-methyl-propionate instead of (S)-(+)3-hydroxy-2-methyl-propionate in step 1.

$^1$H NMR (500 MHz, CDCl$_3$) 8.37 (1H, d, N=CH), 7.99 (1H, d, ArH) 7.74 (1H, dd, ArH), 7.63 (1H, dd, ArH), 7.39 (1H, d, ArH), 7.22-7.11 (5H, m, 5×ArH), 4.63-4.52 (2H, m, NC—H, NC—H'), 3.15-3.09 (1H, m, CH$_2$), 2.84-2.79 (1H, m, CH$_2$), 1.93-1.87 (1H, m, CH$_3$CH), 1.64-1.60 (6H, m, 2×C(CH$_3$)$_2$) and 0.86-0.82 (3H, m, CH$_3$). MS: [M-$C_4H_7D_2O_2$]$^+$ 425.

Example 61: 3-{[(1R)-1-(4-Chlorophenyl)-2-[(5-chloropyridin-2-yl)methyl]-5-(2-hydroxypropan-2-yl)-3-oxo-2,3-dihydro-1H-isoindol-1-yl]oxy}-1λ⁶-thiolane-1,1-dione Isomer 1

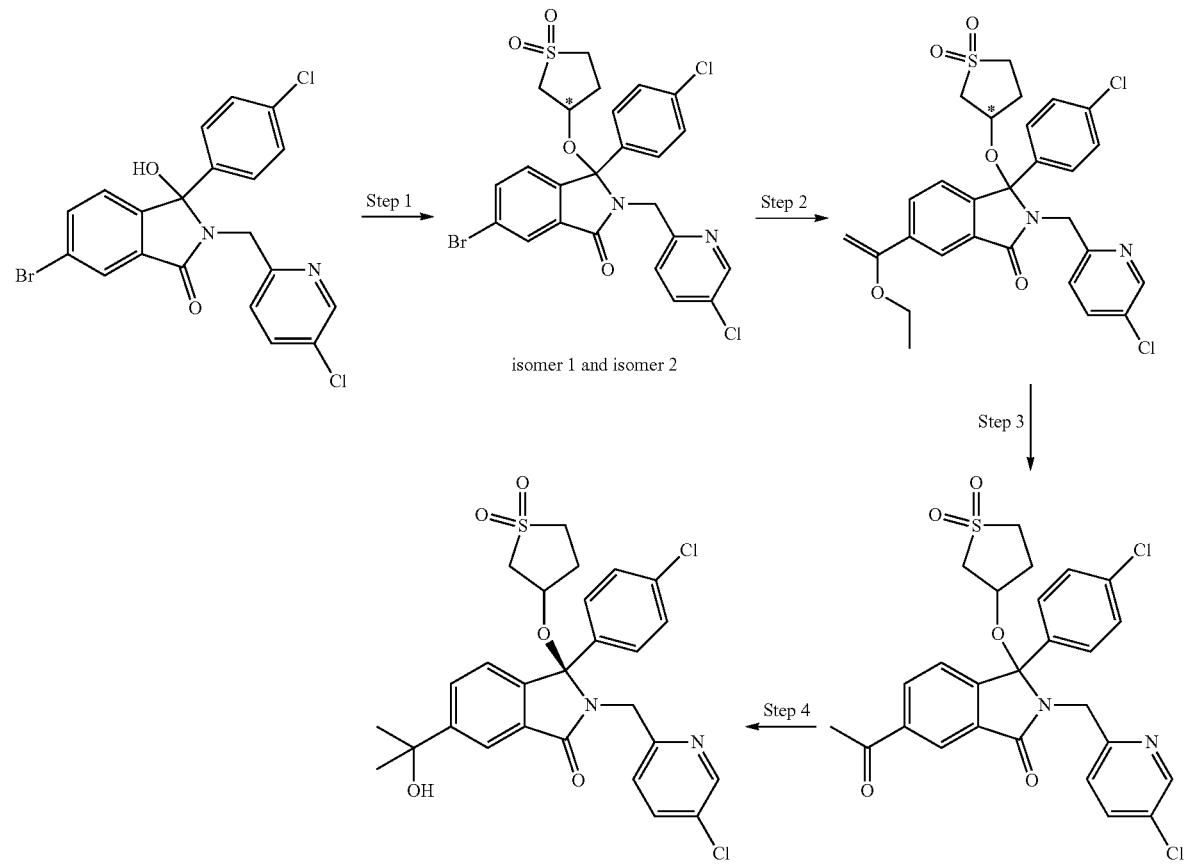

isomer 1 and isomer 2

Example 61, Step 1: 6-Bromo-3-(4-chlorophenyl)-2-((5-chloropyridin-2-yl)methyl)-3-((1,1-dioxidotetrahydrothiophen-3-yl)oxy)isoindolin-1-one The title compound was prepared from 6-bromo-3-(4-chlorophenyl)-2-((5-chloropyridin-2-yl)methyl)-3-hydroxyisoindolin-1-one (Example 6, step 1) (1.00 g, 2.15 mmol) and 3-hydroxytetrahydrothiophene 1,1-dioxide (587 mg, 4.31 mmol) in a similar manner to that described in Example 1, step 2.

¹H NMR (400 MHz, DMSO) 8.38 (0.5H, d), 8.36 (0.5H, d), 8.05-8.03 (1H, m), 7.86 (0.5H, dd), 7.84 (0.5H, dd), 7.77-7.72 (1H, m), 7.42 (0.5H, d), 7.36 (0.5H, d), 7.29-7.21 (5H, m), 4.59-4.39 (2H, m), 4.32-4.25 (1H, m), 3.30-3.21 (1H, m), 3.14-2.91 (2.5H, m), 2.71 (0.5H, dd), 2.11-1.86 (2H, m) as a mix of diastereoisomers.

Example 61, Step 2: 3-(4-Chlorophenyl)-2-((5-chloropyridin-2-yl)methyl)-3-((1,1-dioxidotetrahydrothiophen-3-yl)oxy)-6-(1-ethoxyvinyl)isoindolin-1-one To a degassed solution of 6-bromo-3-(4-chlorophenyl)-2-((5-chloropyridin-2-yl)methyl)-3-((1,1-dioxidotetrahydrothiophen-3-yl)oxy)isoindolin-1-one (504 mg, 0.87 mmol), tributyl(1-ethoxyvinyl)tin (0.29 mL, 0.87 mmol) and LiCl (110 mg, 2.60 mmol) in toluene (4 mL) and 1,4-dioxane (4 mL) was added Pd(PPh₃)₄ (100 mg, 0.09 mmol) and the reaction mixture was heated to 100° C. for 3 h. After cooling to room temperature, the reaction mixture was diluted with saturated aqueous NaHCO₃ (30 mL) and extracted with EtOAc (2×30 mL). The combined organic extracts were filtered through a hydrophobic frit, concentrated in vacuo and purified by Biotage using 0-100% EtOAc in iso-hexane as eluent. The two diastereoisomers were separated to yield 122 and 180 mg, 61%, each as a yellow oil. *Earlier eluting product (isomer 1): ¹H NMR (400 MHz, CDCl₃) 8.34 (1H, d), 8.20 (1H, s), 7.84 (1H, dd), 7.52 (1H, dd), 7.23-7.15 (6H, m), 4.78 (1H, d), 4.49-4.32 (3H, m), 3.96 (2H, q), 3.31-3.22 (1H, m), 2.94 (2H, m), 2.05-2.04 (2H, m), 1.44 (3H, dd), 1.38-1.16 (2H, m). *Later eluting product (isomer 2): ¹H NMR (400 MHz, CDCl₃) 8.33 (1H, d), 8.20 (1H, d), 7.84 (1H, dd), 7.55 (1H, dd), 7.29 (1H, d), 7.25-7.22-7.14 (5H, m), 4.78 (1H, d), 4.56 (1H, d), 4.44 (1H, d), 4.36-4.27 (2H, m), 3.96 (2H, q), 3.31-3.22 (1H, m), 2.96-2.82 (2H, m), 2.57 (1H, dd), 1.44 (3H, dd), 1.41-1.20 (2H, m).

Example 61, Step 3: 6-Acetyl-3-(4-chlorophenyl)-2-((5-chloropyridin-2-yl)methyl)-3-((1,1-dioxidotetrahydrothiophen-3-yl)oxy)isoindolin-1-one The earlier eluting product (isomer 1) (122 mg, 0.21 mmol) was dissolved in 1,4-dioxane (5 mL) and 1M HCl (5 mL) was added and the reaction was stirred for 1 h. The reaction was quenched with saturated aqueous NaHCO₃ (20 mL) and extracted with CH$_2$Cl$_2$ (20 mL). The organic extracts were filtered through a hydrophobic frit and concentrated in vacuo to give the title compound as a yellow oil (116 mg, 100%). $^1$H NMR (400 MHz, CDCl$_3$) 8.47-8.47 (1H, m), 8.36 (1H, d), 8.19 (1H, dd), 7.55 (1H, dd), 7.33 (1H, d), 7.25-7.16 (5H, m), 4.51-4.38 (3H, m), 3.33-3.24 (1H, m), 2.99-2.93 (2H, m), 2.69 (3H, s), 2.05-1.84 (2H, m), 1.45-1.08 (1H, m).

Example 61, Step 4: 3-{[(1R)-1-(4-Chlorophenyl)-2-[(5-chloropyridin-2-yl)methyl]-5-(2-hydroxypropan-2-yl)-3-oxo-2,3-dihydro-1H-isoindol-1-yl]oxy}-1λ$^6$-thiolane-1,1-dione 6-Acetyl-3-(4-chlorophenyl)-2-((5-chloropyridin-2-yl)methyl)-3-((1,1-dioxidotetrahydrothiophen-3-yl)oxy)isoindolin-1-one was converted to the title compound in a similar manner to that in Example 1, step 4. Purification by chiral preparative LCMS gave the title compound as a colourless solid.

1H NMR (400 MHz, CDCl$_3$) 8.35 (1H, d), 8.03 (1H, d), 7.78 (1H, dd), 7.53 (1H, dd), 7.22-7.17 (6H, m), 4.47 (1H, d), 4.41 (1H, d), 4.36-4.31 (2H, m), 3.32-3.20 (1H, m), 2.99-2.91 (2H, m), 2.08-1.89 (2H, m), 1.80 (1H, s), 1.65 (3H, s), 1.64 (3H, s). MS: [M+H]$^+$=561.

Example 62: 3-{[(1R)-1-(4-Chlorophenyl)-2-[(5-chloropyridin-2-yl)methyl]-5-(2-hydroxypropan-2-yl)-3-oxo-2,3-dihydro-1H-isoindol-1-yl]oxy}-1λ$^6$-thiolane-1,1-dione Isomer 2

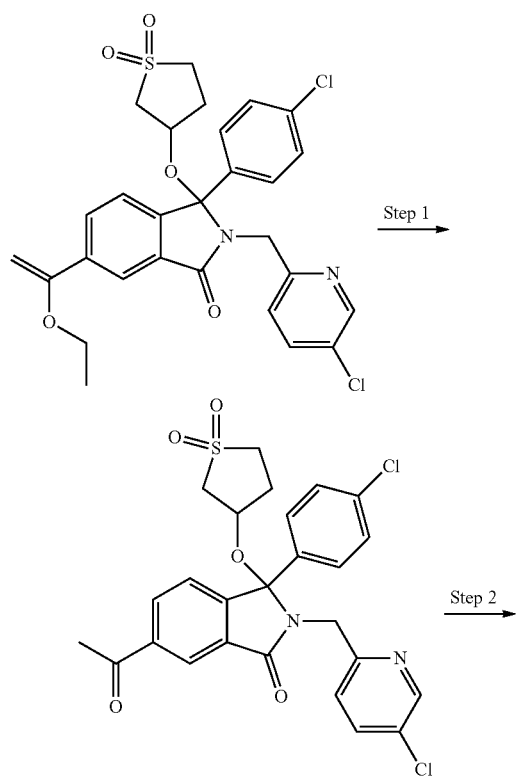

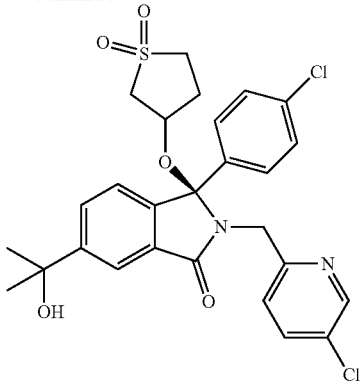

Example 62, Step 1: 6-Acetyl-3-(4-chlorophenyl)-2-((5-chloropyridin-2-yl)methyl)-3-((1,1-dioxidotetrahydrothiophen-3-yl)oxy)isoindolin-1-one The later eluting product (isomer 2) (Example 61, step 2), 3-(4-chlorophenyl)-2-((5-chloropyridin-2-yl)methyl)-3-((1,1-dioxidotetrahydrothiophen-3-yl)oxy)-6-(1-ethoxyvinyl)isoindolin-1-one, 180 mg, 0.31 mmol) was dissolved in 1,4-dioxane (5 mL) and 1M HCl (5 mL) was added and the reaction was stirred for 1 h. The reaction was quenched with saturated aqueous NaHCO$_3$ (20 mL) and extracted with CH$_2$Cl$_2$ (20 mL). The organic extracts were filtered through a hydrophobic frit and concentrated in vacuo to give the title compound as a yellow oil (171 mg, 100%). $^1$H NMR (400 MHz, CDCl$_3$) 8.47 (1H, s), 8.35 (1H, d), 8.18 (1H, dd), 7.60-7.56 (1H, m), 7.31 (2H, dd), 7.22 (4H, m), 4.59 (1H, d), 4.45-4.34 (2H, m), 3.33-3.24 (1H, m), 2.98-2.80 (2H, m), 2.69 (3H, s), 2.55 (1H, dd), 2.09-2.02 (1H, m), 1.45-1.24 (1H, m).

Example 62, Step 2: 3-{[(1R)-1-(4-Chlorophenyl)-2-[(5-chloropyridin-2-yl)methyl]-5-(2-hydroxypropan-2-yl)-3-oxo-2,3-dihydro-1H-isoindol-1-yl]oxy}-1λ$^6$-thiolane-1,1-dione 6-Acetyl-3-(4-chlorophenyl)-2-((5-chloropyridin-2-yl)methyl)-3-((1,1-dioxidotetrahydrothiophen-3-yl)oxy)isoindolin-1-one was converted to the title compound in a similar manner to that in Example 1, step 4. Purification by chiral preparative LCMS gave the title compound as a colourless solid (33 mg).

1H NMR (400 MHz, CDCl$_3$) 8.33 (1H, d), 8.04 (1H, d), 7.76 (1H, dd), 7.55 (1H, dd), 7.29 (1H, d), 7.24-7.16 (5H, m), 4.57 (1H, d), 4.44 (1H, d), 4.32-4.26 (1H, m), 3.31-3.23 (1H, m), 2.96-2.83 (2H, m), 2.56 (1H, dd), 2.07-2.00 (2H, m), 1.80 (1H, s), 1.64 (3H, s), 1.63 (3H, s).

Example 63: 2-[1-({[(1R)-1-(4-chlorophenyl)-2-[(5-chloropyridin-2-yl)methyl]-5-(2-hydroxypropan-2-yl)-3-oxo-2,3-dihydro-1H-isoindol-1-yl]oxy}methyl)cyclopropyl]acetonitrile

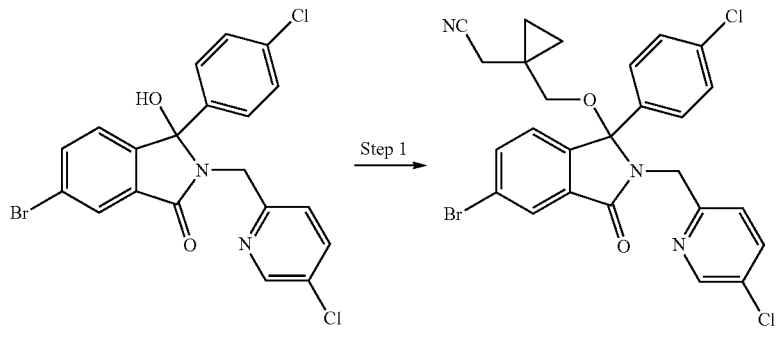

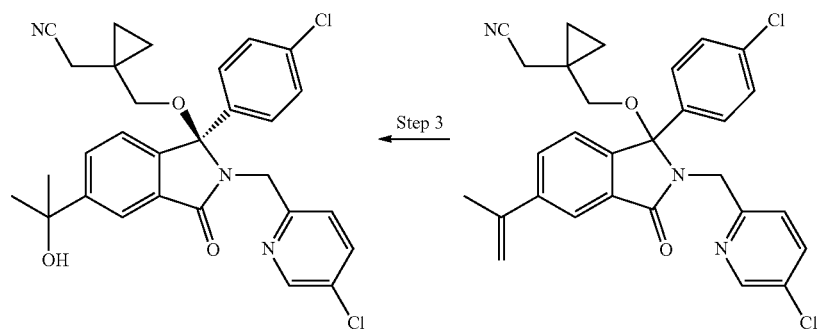

Example 63, Step 1: 2-(1-(((5-Bromo-1-(4-chlorophenyl)-2-((5-chloropyridin-2-yl)methyl)-3-oxoisoindolin-1-yl)oxy)methyl)cyclopropyl)acetonitrile The title compound (0.693 g) was prepared from 6-bromo-3-(4-chlorophenyl)-2-((5-chloropyridin-2-yl)methyl)-3-hydroxyisoindolin-1-one (Example 6, step 1) (1.00 g, 2.15 mmol) and 2-(1-(hydroxymethyl)cyclopropyl)acetonitrile (0.436 mL, 4.30 mmol) in a similar manner to that described in Example 1, step 2. $^1$H NMR (400 MHz, CDCl$_3$) 8.32 (1H, d), 8.04 (1H, d), 7.69 (1H, dd), 7.50 (1H, dd), 7.25-7.19 (5H, m), 7.09 (1H, d), 4.47 (2H, s), 2.99-2.90 (2H, m), 2.65 (1H, d), 2.31 (1H, d), 0.60-0.57 (2H, m), 0.41-0.33 (2H, m).

Example 63, Step 2: 2-(1-(((1-(4-Chlorophenyl)-2-((5-chloropyridin-2-yl)methyl)-3-oxo-5-(prop-1-en-2-yl)isoindolin-1-yl)oxy)methyl)cyclopropyl)acetonitrile The title compound was prepared from 2-(1-(((5-bromo-1-(4-chlorophenyl)-2-((5-chloropyridin-2-yl)methyl)-3-oxoisoindolin-1-yl)oxy)methyl)cyclopropyl)acetonitrile in a similar manner to that described in Example 4, step 2.

$^1$H NMR (400 MHz, CDCl$_3$) 8.32 (1H, d), 7.98 (1H, d), 7.67 (1H, dd), 7.49 (1H, dd), 7.26-7.14 (6H, m), 5.48 (1H, s), 5.21 (1H, s), 4.51 (2H, s), 2.97-2.90 (2H, m), 2.66 (1H, d), 2.33 (1H, d), 2.19 (3H, s), 0.58 (2H, s), 0.40-0.32 (2H, m).

Example 63, Step 3: 2-[1-({[(1R)-1-(4-chlorophenyl)-2-[(5-chloropyridin-2-yl)methyl]-5-(2-hydroxypropan-2-yl)-3-oxo-2,3-dihydro-1H-isoindol-1-yl]oxy}methyl)cyclopropyl]acetonitrile The title compound was prepared from 2-(1-(((1-(4-chlorophenyl)-2-((5-chloropyridin-2-yl)methyl)-3-oxo-5-(prop-1-en-2-yl)isoindolin-1-yl)oxy)methyl)cyclopropyl)acetonitrile in a similar manner to that described in Example 4, step 3. Purification by chiral preparative LCMS gave the title compound.

$^1$H NMR (400 MHz, CDCl$_3$) 8.32 (1H, d), 8.01 (1H, d), 7.76 (1H, dd), 7.49 (1H, dd), 7.25-7.22 (3H, m), 7.20-7.16 (3H, m), 4.51 (2H, s), 2.96-2.88 (2H, m), 2.65 (1H, d), 2.32 (1H, d), 1.78 (1H, s), 1.63 (6H, d), 0.58 (2H, s), 0.37 (2H, dd). MS: [M+H]$^+$=536

269

Example 64: (3R)-3-[(1-acetylazetidin-3-yl)methoxy]-3-(4-chlorophenyl)-2-[(5-chloropyridin-2-yl)methyl]-6-(2-hydroxypropan-2-yl)-2,3-dihydro-1H-isoindol-1-one

270

CDCl$_3$): 8.47 (s, 1H), 8.32 (d, 1H), 8.20-8.15 (m, 1H), 7.51 (dd, 1H), 7.35-7.30 (m, 5H), 7.25 (dd, 2H), 7.19 (s, 4H), 5.08 (s, 2H), 4.62 (d, 1H), 4.42 (d, 1H), 4.04-3.97 (m, 2H), 3.70-3.60 (m, 2H), 3.29 (dd, 1H), 2.95 (dd, 1H), 2.67 (s, 4H).

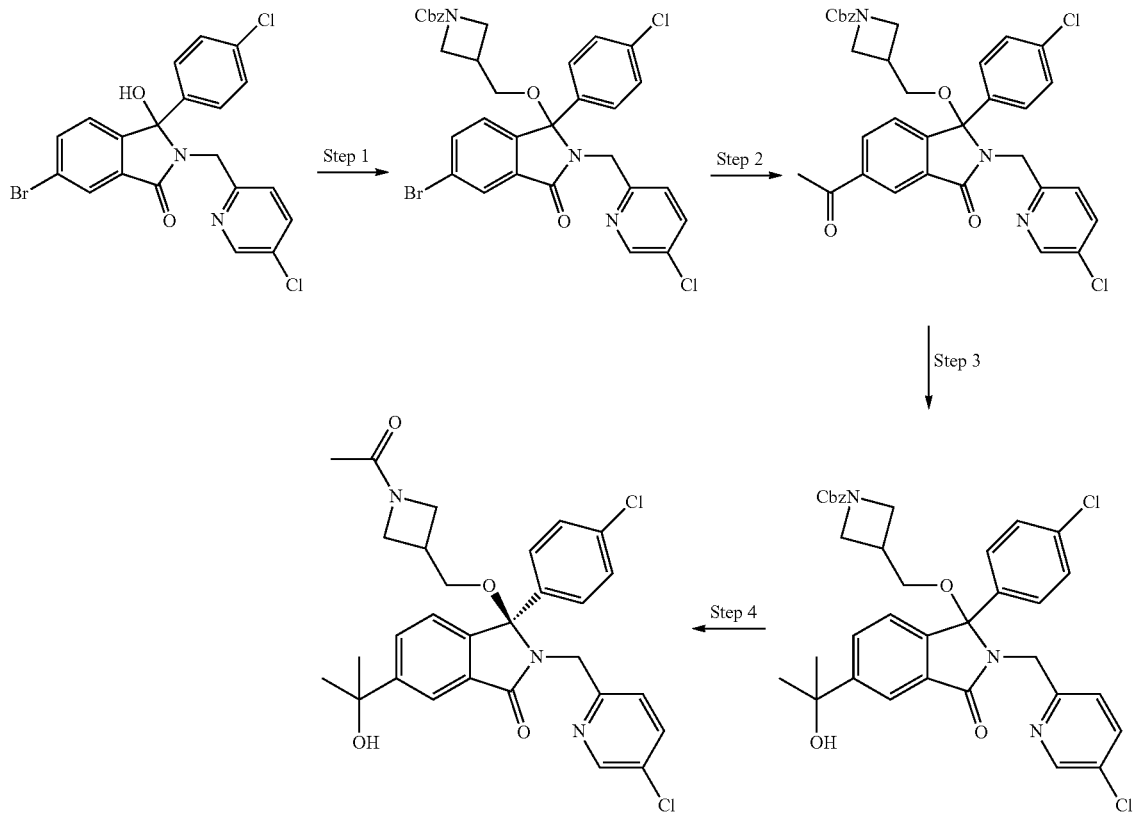

Example 64, Step 1: Benzyl 3-(((5-bromo-1-(4-chlorophenyl)-2-((5-chloropyridin-2-yl)methyl)-3-oxoisoindolin-1-yl)oxy)methyl)azetidine-1-carboxylate Benzyl 3-(((5-bromo-1-(4-chlorophenyl)-2-((5-chloropyridin-2-yl)methyl)-3-oxoisoindolin-1-yl)oxy)methyl)azetidine-1-carboxylate (1.46 g, 75%) was prepared from 6-bromo-3-(4-chlorophenyl)-2-((5-chloropyridin-2-yl)methyl)-3-hydroxyisoindolin-1-one Example 6, step 1) (1.38 g, 3.02 mmol) in a similar manner to that described in Example 1, step 2. $^1$H NMR (400 MHz, CDCl$_3$): 8.31 (1H, d), 8.06 (1H, d), 7.67 (1H, dd), 7.49 (1H, dd), 7.37-7.33 (5H, m), 7.21 (1H, d), 7.19-7.14 (4H, m), 7.01 (1H, d), 5.09 (2H, s), 4.55 (1H, d), 4.39 (1H, d), 4.03-3.97 (2H, m), 3.68-3.61 (2H, m), 3.24 (1H, dd), 2.96 (1H, dd), 2.60-2.51 (1H, m).

Example 64, Step 2: Benzyl 3-(((5-acetyl-1-(4-chlorophenyl)-2-((5-chloropyridin-2-yl)methyl)-3-oxoisoindolin-1-yl)oxy)methyl)azetidine-1-carboxylate Benzyl 3-(((5-acetyl-1-(4-chlorophenyl)-2-((5-chloropyridin-2-yl)methyl)-3-oxoisoindolin-1-yl)oxy)methyl)azetidine-1-carboxylate (690 mg, 49%) was prepared from benzyl 3-(((5-bromo-1-(4-chlorophenyl)-2-((5-chloropyridin-2-yl)methyl)-3-oxoisoindolin-1-yl)oxy)methyl)azetidine-1-carboxylate (1.46 g, 2.25 mmol) in a similar manner to that described in Example 1, step 3. $^1$H NMR (400 MHz, Example 64, Step 3: Benzyl 3-(((1-(4-chlorophenyl)-2-((5-chloropyridin-2-yl)methyl)-5-(2-hydroxypropan-2-yl)-3-oxoisoindolin-1-yl)oxy)methyl)azetidine-1-carboxylate Benzyl 3-(((1-(4-chlorophenyl)-2-((5-chloropyridin-2-yl)methyl)-5-(2-hydroxypropan-2-yl)-3-oxoisoindolin-1-yl)oxy)methyl)azetidine-1-carboxylate (475 mg, 67%) was prepared from benzyl 3-(((5-acetyl-1-(4-chlorophenyl)-2-((5-chloropyridin-2-yl)methyl)-3-oxoisoindolin-1-yl)oxy)methyl)azetidine-1-carboxylate (690 mg, 1.09 mmol) in a similar manner to that described in Example 1, step 4. $^1$H NMR (400 MHz, CDCl$_3$): 8.31 (1H, d), 8.03 (1H, d), 7.75 (1H, dd), 7.48 (1H, dd), 7.36-7.33 (5H, m), 7.24 (1H, d), 7.17-7.15 (4H, m), 7.10 (1H, d), 5.08 (2H, s), 4.58 (1H, d), 4.42 (1H, d), 4.03-3.95 (2H, m), 3.69-3.62 (2H, m), 3.19 (1H, dd), 2.99-2.93 (1H, m), 2.59-2.50 (1H, m), 2.07 (1H, s), 1.64-1.62 (6H, m).

Example 64, Step 4: (3R)-3-[(1-acetylazetidin-3-yl)methoxy]-3-(4-chlorophenyl)-2-[(5-chloropyridin-2-yl)methyl]-6-(2-hydroxypropan-2-yl)-2,3-dihydro-1H-isoindol-1-one To a round bottomed flask was added benzyl 3-(((1-(4-chlorophenyl)-2-((5-chloropyridin-2-yl)methyl)-5-(2-hydroxypropan-2-yl)-3-oxoisoindolin-1-yl)oxy)methyl)azetidine-1-carboxylate (265 mg, 0.41 mmol), 8M KOH solution (3 mL) and MeOH (4 mL). The reaction was stirred at 70° C. for 4 h. The reaction was cooled and water (20 mL) was added. The mixture was extracted with EtOAc (2×20 mL), dried over MgSO$_4$ and concentrated in vacuo. The crude oil was purified with a Biotage, 0-10% MeOH/DCM, to give the title compound as a racemate (129 mg, 57%). Purification by chiral preparative SFC gave the title compound as a white solid. $^1$H NMR (400 MHz, CDCl$_3$): 8.32 (1H, dd), 8.03 (1H, dd), 7.76 (1H, dd), 7.53-7.48 (1H, m), 7.30-7.24 (1H, m), 7.22-7.15 (4H, m), 7.11 (1H, dd), 4.60 (1H, dd), 4.43 (1H, dd), 4.12-3.94 (2H, m), 3.78 (0.5H, dd) 3.69-3.60 (1.5H, m), 3.27-3.17 (1H, m), 3.01-2.94 (1H, m), 2.63-2.52 (1H, m), 1.89-1.81 (4H, m), 1.65-1.64 (6H, m).

Example 65: (3R)-3-(4-chlorophenyl)-2-[(5-chloropyridin-2-yl)methyl]-3-[3-(hydroxymethyl)cyclobutoxy]-6-(2-hydroxypropan-2-yl)-2,3-dihydro-1H-isoindol-1-one

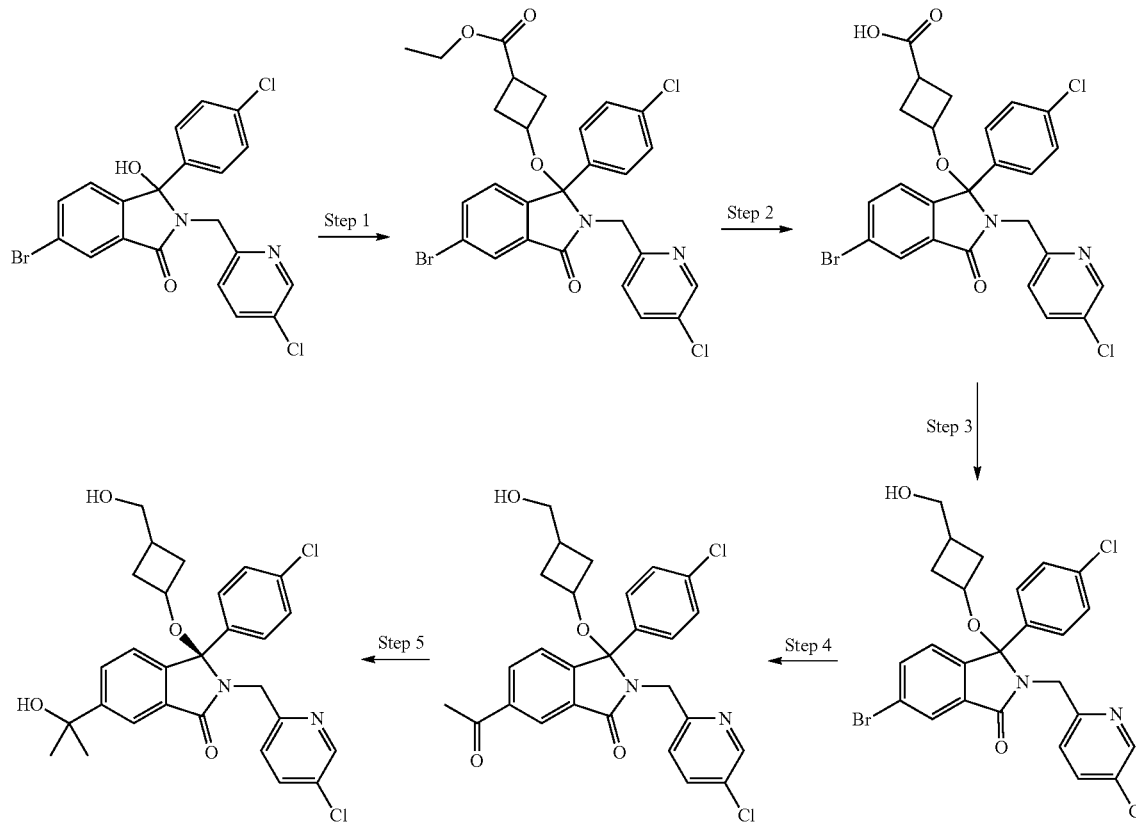

Example 65, Step 1: Ethyl 3-((5-bromo-1-(4-chlorophenyl)-2-((5-chloropyridin-2-yl)methyl)-3-oxoisoindolin-1-yl)oxy)cyclobutanecarboxylate To a solution of 6-bromo-3-(4-chlorophenyl)-2-((5-chloropyridin-2-yl)methyl)-3-hydroxyisoindolin-1-one (Example 6, step 1) (3.22 g, 6.94 mmol) in toluene (70 mL) was added ethyl 3-hydroxycyclobutanecarboxylate (2.0 g, 13.87 mmol) and InBr$_3$ (3.69 g, 10.40 mmol) and the reaction mixture was stirred for 2.5 hours under nitrogen at 90° C. The reaction mixture was cooled, diluted with CH$_2$Cl2 (200 mL), washed with water (150 mL) and brine (150 mL). The organic phase was filtered through a hydrophobic frit, concentrated in vacuo and purified by Biotage using 0-100% EtOAc in iso-hexane as eluent to give the title compound as a viscous yellow oil (3.16 g, 77%). $^1$H NMR (400 MHz, CDCl$_3$): 8.33 (1H, d), 8.05 (1H, d), 7.61 (1H, dd), 7.48 (1H, dd), 7.24-7.15 (5H, m), 7.03 (1H, d), 4.58 (1H, d), 4.40 (1H, d), 4.09 (2H, q), 3.62-3.54 (1H, m), 2.34-2.17 (2H, m), 2.09-2.01 (1H, m), 1.96-1.87 (1H, m), 1.66-1.59 (1H, m), 1.22 (3H, dd).

Example 65, Step 2: 3-((5-Bromo-1-(4-chlorophenyl)-2-((5-chloropyridin-2-yl)methyl)-3-oxoisoindolin-1-yl)oxy)cyclobutanecarboxylic Acid To a stirred mixture of ethyl 3-((5-bromo-1-(4-chlorophenyl)-2-((5-chloropyridin-2-yl)methyl)-3-oxoisoindolin-1-yl)oxy)cyclobutanecarboxylate (1.62 g, 2.74 mmol) in a mixture of THF (106 mL) and H$_2$O (35 mL) at room temperature was added lithium hydroxide (577 mg) and methanol (10 mL) and the reaction stirred for 2 h then neutralised by addition of 2M aqueous hydrochloric acid and the volatiles removed in vacuo. The residue was diluted with H$_2$O (30 mL) and acidified to pH 1-2 by addition of 2M aqueous hydrochloric acid. The aqueous portion was extracted with CH$_2$Cl2 (2×50 mL), the combined organic extracts filtered through a hydrophobic frit and concentrated in vacuo to afford the title compound as a pale yellow solid (1.53 g, 99%). $^1$H NMR (400 MHz, CDCl$_3$): 8.32 (1H, d), 8.06 (1H, d), 7.63 (1H, dd), 7.49 (1H, dd), 7.19-7.16 (5H, m), 7.04 (1H, d), 4.59 (1H, d), 4.47 (1H, d), 3.75 (2H, dd), 3.64-3.55 (1H, m), 2.42-2.24 (2H, m), 2.18-1.97 (2H, m).

Example 65, Step 3: 6-Bromo-3-(4-chlorophenyl)-2-((5-chloropyridin-2-yl)methyl)-3-(3-(hydroxymethyl)cyclobutoxy)isoindolin-1-one To a stirred solution of 3-((5-bromo-1-(4-chlorophenyl)-2-((5-chloropyridin-2-yl)methyl)-3-oxoisoindolin-1-yl)oxy)cyclobutanecarboxylic acid (1.53 g, 2.72 mmol) in THF (14 mL) under nitrogen was added 1,1'-carbonyldiimidazole (883 mg, 5.44 mmol). The reaction was allowed to stir at room temperature for 2 h, cooled to 0° C. then added portion-wise to a pre-cooled 0° C. stirred solution of sodium borohydride (515 mg, 13.61 mmol) in H$_2$O (16.6 mL). After the addition was complete the reaction was allowed to warm to room temperature and stirred for 2 hours, cooled again to 0° C. and quenched by the addition of 2M aqueous hydrochloric acid until pH 1 was attained. The mixture was extracted with ethyl acetate (2×20 mL). The combined organic extracts were dried over MgSO$_4$ and concentrated in vacuo to yield the title compound as a yellow oil (863 mg, 58%). $^1$H NMR (400 MHz, CDCl$_3$): 8.30 (1H, d), 8.05 (1H, d), 7.61 (1H, dd), 7.47 (1H, dd), 7.21-7.13 (6H, m), 7.03 (1H, d), 4.62-4.46 (2H, m), 3.65-3.46 (3H, m), 2.00-1.48 (5H, m).

Example 65, Step 4: 6-Acetyl-3-(4-chlorophenyl)-2-((5-chloropyridin-2-yl)methyl)-3-(3-(hydroxymethyl)cyclobutoxy)isoindolin-1-one The title compound was prepared from 6-bromo-3-(4-chlorophenyl)-2-((5-chloropyridin-2-yl)methyl)-3-(3-(hydroxymethyl)cyclobutoxy)isoindolin-1-one in a similar manner to that described in Example 1, step 3.

$^1$H NMR (400 MHz, CDCl$_3$) 8.46 (1H, s), 8.31 (1H, d), 8.11 (1H, dd), 7.51-7.46 (1H, m), 7.27 (1H, d), 7.23-7.14 (6H, m), 4.63-4.48 (2H, m), 3.60-3.43 (3H, m), 2.68 (3H, s), 1.81-1.55 (4H, m), 1.47-1.14 (1H, m).

Example 65, Step 5: (3R)-3-(4-chlorophenyl)-2-[(5-chloropyridin-2-yl)methyl]-3-[3-(hydroxymethyl)cyclobutoxy]-6-(2-hydroxypropan-2-yl)-2,3-dihydro-1H-isoindol-1-one 6-Acetyl-3-(4-chlorophenyl)-2-((5-chloropyridin-2-yl)methyl)-3-(3-(hydroxymethyl)cyclobutoxy)isoindolin-1-one (351 mg, 0.69 mmol) was converted to the title compound in a similar manner to that described in Example 1, step 4 to afford the racemic mixture (194 mg, 53%). Purification by chiral preparative LCMS gave the title compound as a colourless solid (66 mg). 1H NMR (400 MHz, CDCl$_3$): 8.31 (1H, d), 8.01 (1H, d), 7.69 (1H, dd), 7.46 (1H, dd), 7.22-7.18 (3H, m), 7.16-7.10 (3H, m), 4.58 (1H, d), 4.50 (1H, d), 3.56-3.47 (3H, m), 1.79 (1H, s), 1.78-1.67 (3H, m), 1.63 (3H, s), 1.63 (3H, s), 1.61-1.57 (1H, m), 1.49-1.41 (1H, m), 1.22 (1H, t).

Example 66: (3R)-3-[(1-Aminocyclopropyl)methoxy]-3-(4-chlorophenyl)-2-[(5-chloropyridin-2-yl)methyl]-4-fluoro-6-(2-hydroxypropan-2-yl)-2,3-dihydro-1H-isoindol-1-one

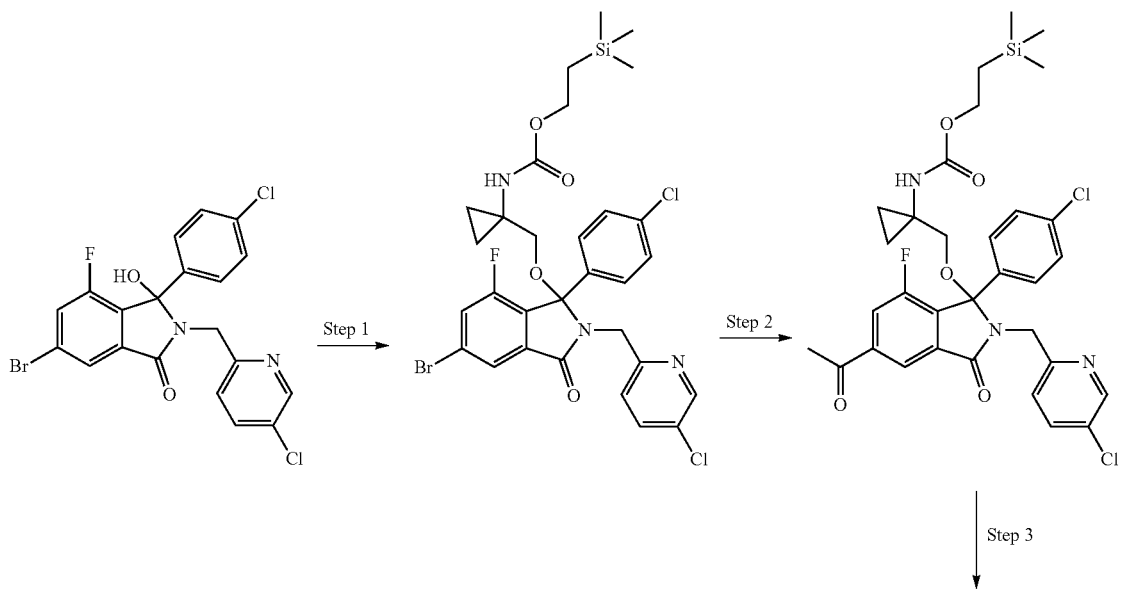

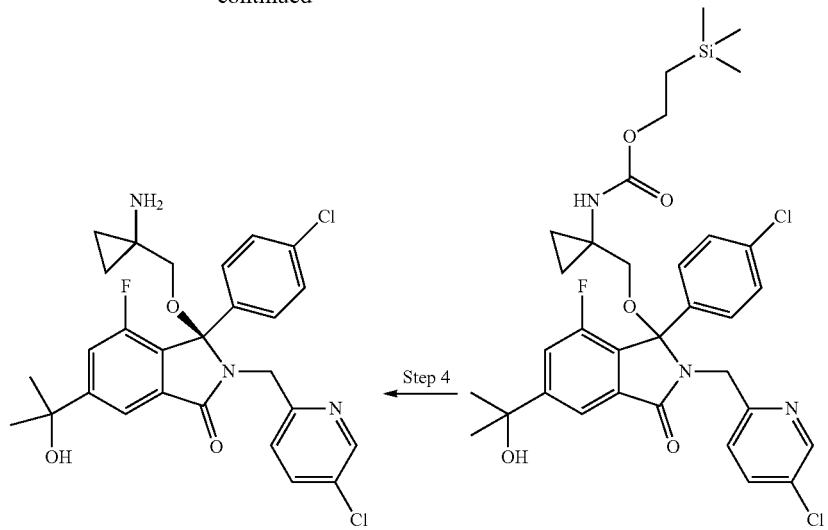

Example 66, Step 1: 2-(Trimethylsilyl)ethyl N-[1-({[5-bromo-1-(4-chlorophenyl)-2-[(5-chloropyridin-2-yl)methyl]-7-fluoro-3-oxo-2,3-dihydro-1H-isoindol-1-yl]oxy}methyl)cyclopropyl]carbamate 6-Bromo-3-(4-chloro-phenyl)-2-(5-chloro-pyridin-2-yl-methyl)-4-fluoro-3-hydroxy-2,3-dihydro-isoindol-1-one (Example 1, step 1) (0.964 g, 2 mmol) was reacted with (1-hydroxymethyl-cyclopropyl)-carbamic acid 2-trimethylsilanyl-ethyl ester (Preparation 11) (0.924 g, 4.0 mmol) in a similar manner to that described in Example 3, step 2 to afford the title compound (0.89 g, 64%). MS: [M+H]⁺=696

Example 66, Step 2: 2-(Trimethylsilyl)ethyl N-[1-({[5-acetyl-1-(4-chlorophenyl)-2-[(5-chloropyridin-2-yl)methyl]-7-fluoro-3-oxo-2,3-dihydro-1H-isoindol-1-yl]oxy}methyl)cyclopropyl]carbamate 2-(Trimethylsilyl)ethyl N-[1-({[5-bromo-1-(4-chlorophenyl)-2-[(5-chloropyridin-2-yl)methyl]-7-fluoro-3-oxo-2,3-dihydro-1H-isoindol-1-yl]oxy}methyl)cyclopropyl]carbamate was converted to the title compound in a similar manner to that described in Example 1, step 3. [M+H]⁺=696.

Example 66, Step 3: 2-(Trimethylsilyl)ethyl N-[1-({[L-(4-chlorophenyl)-2-[(5-chloropyridin-2-yl)methyl]-7-fluoro-5-(2-hydroxypropan-2-yl)-3-oxo-2,3-dihydro-1H-isoindol-1-yl]oxy}methyl)cyclopropyl]carbamate To a solution of 2-(trimethylsilyl)ethyl N-[1-({[5-acetyl-1-(4-chlorophenyl)-2-[(5-chloropyridin-2-yl)methyl]-7-fluoro-3-oxo-2,3-dihydro-1H-isoindol-1-yl]oxy}methyl)cyclopropyl]carbamate (0.36 g, 0.54 mmol) in THF was added a THF solution of LaCl₃·2LiCl (1.1 mL, 0.5M in THF) and the reaction mixture was stirred for 1 h. The reaction mixture was cooled with ice and the solution MeMgCl (0.9 mL, 3M, 2.7 mmol) was added, the ice bath removed and the reaction mixture was stirred for 1 h. Saturated NH₄Cl was added, the product extracted with EtOAc. The organic phase was dried, the solvent evaporated and the residue was purified on Biotage, eluted with EtOAc in petrol (0-100%) to afford the product (0.23 g, 64%). [M+H]⁺=674.

Example 66, Step 4: (3R)-3-[(1-Aminocyclopropyl)methoxy]-3-(4-chlorophenyl)-2-[(5-chloropyridin-2-yl)methyl]-4-fluoro-6-(2-hydroxypropan-2-yl)-2,3-dihydro-1H-isoindol-1-one To a solution of 2-(trimethylsilyl)ethyl N-[1-({[1-(4-chlorophenyl)-2-[(5-chloropyridin-2-yl)methyl]-7-fluoro-5-(2-hydroxypropan-2-yl)-3-oxo-2,3-dihydro-1H-isoindol-1-yl]oxy}methyl)cyclopropyl]carbamate (0.23 g, 0.34 mmol) in THF (5 mL) was added TBAF (1M solution in THF, 1.0 mL, 1.0 mmol) and the reaction mixture was stirred overnight, then heated at 50° C. for 1 h. The solvent was evaporated, the crude product was purified on Biotage, eluted with MeOH in EtOAc (0-10%), followed by chiral chromatography to afford the title compound (46 mg).

1H NMR (400 MHz, DMSO-d6): 8.37 (1H, d), 7.80 (1H, d), 7.72 (1H, dd), 7.51 (1H, dd), 7.30 (4H, s), 7.20 (1H, d), 5.38 (1H, s), 4.62-4.32 (2H, m), 3.08 (1H, d), 2.85 (1H, d), 2.00 (2H, s), 1.48 (6H, d), 0.42-0.30 (2H, m), 0.30-0.17 (2H, m). m/z: 528

Example 67: 1-({[(1R)-1-(4-Chlorophenyl)-2-[(5-chloropyridin-2-yl)methyl]-7-fluoro-5-(2-hydroxypropan-2-yl)-3-oxo-2,3-dihydro-1H-isoindol-1-yl]oxy}methyl)-N-methylcyclopropane-1-carboxamide

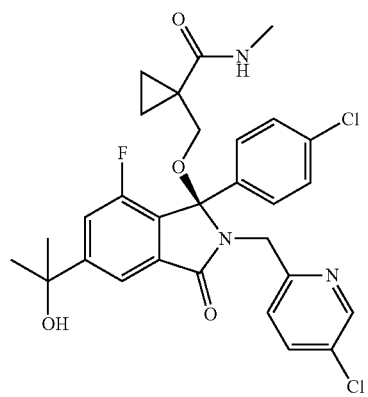 [SMILES: CNC(=O)C1(CO[C@]2(c3ccc(Cl)cc3)c3c(F)cc(C(C)(C)O)cc3C(=O)N2Cc2ccc(Cl)cn2)CC1]

The title compound was prepared from 6-bromo-3-(4-chloro-phenyl)-2-(5-chloro-pyridin-2-ylmethyl)-4-fluoro-3-hydroxy-2,3-dihydro-isoindol-1-one (Example 1, step 1) in a similar manner to that described in Example 3, steps 2-4, using 1-hydroxymethyl-cyclopropanecarboxylic acid methylamide (Preparation 12) instead of 1-hydroxymethyl-cyclopropanol in step 2.

1H NMR (400 MHz, DMSO-d6): 8.35 (1H, d), 7.80 (1H, d), 7.73 (1H, dd), 7.53 (1H, d), 7.30 (3H, d), 7.21 (3H, dd), 5.39 (1H, s), 4.47 (2H, d), 3.50 (1H, d), 3.07 (1H, d), 2.60 (3H, d), 1.48 (6H, s), 1.00-0.85 (2H, m), 0.61-0.46 (2H, m). m/z: 572

Example 68 and Example 69: 1-({[(1R)-1-(4-Chlorophenyl)-2-[(5-chloropyridin-2-yl)methyl]-7-fluoro-5-[2-hydroxy-1-(piperazin-1-yl)propan-2-yl]-3-oxo-2,3-dihydro-1H-isoindol-1-yl]oxy}methyl)cyclopropane-1-carboxamide (*both isomers separated and isolated)

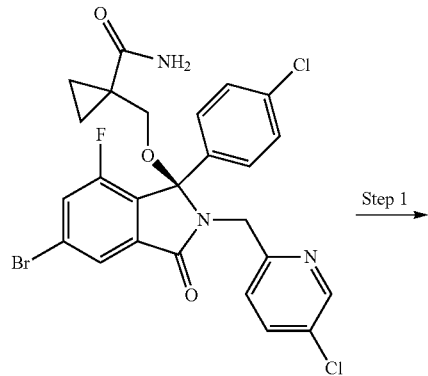

Step 1

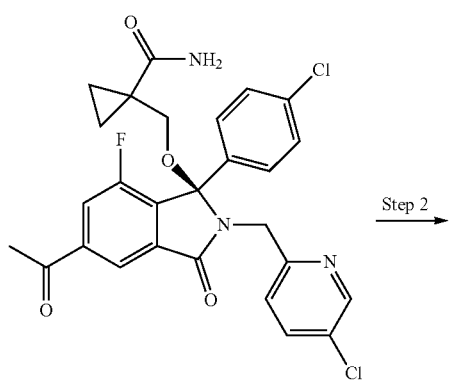

Step 2

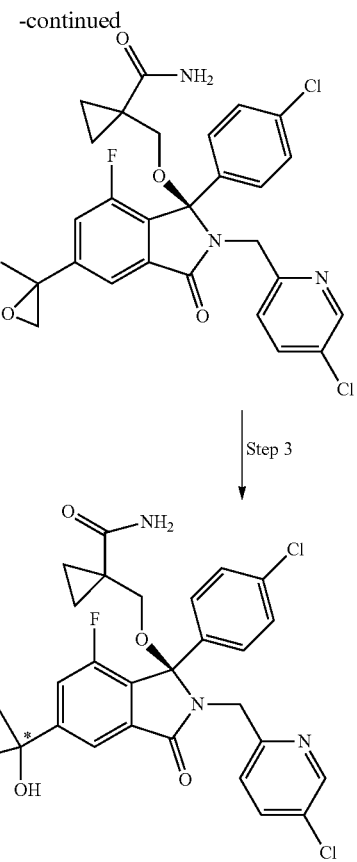

1-({[(1R)-5-Bromo-1-(4-chlorophenyl)-2-[(5-chloropyridin-2-yl)methyl]-7-fluoro-3-oxo-2,3-dihydro-1H-isoindol-1-yl]oxy}methyl)cyclopropane-1-carboxamide (Example 4, step 1, the R-enantiomer was separated by chiral HPLC) (1.75 g, 3.0 mmol) was converted to the title compound (1.23 g, 75%) in a similar manner to that described in Example 1, step 3. $[M+H]^+=542$.

Example 68 and Example 69 Step 2: 1-({[(1R)-1-(4-Chlorophenyl)-2-[(5-chloropyridin-2-yl)methyl]-7-fluoro-5-(2-methyloxiran-2-yl)-3-oxo-2,3-dihydro-1H-isoindol-1-yl]oxy}methyl)cyclopropane-1-carboxamide 1-({[(1R)-5-Acetyl-1-(4-chlorophenyl)-2-[(5-chloropyridin-2-yl)methyl]-7-fluoro-3-oxo-2,3-dihydro-1H-isoindol-1-yl]oxy}methyl)cyclopropane-1-carboxamide (0.5 g, 0.92 mmol) was converted to the title compound (0.38 g, 75%) in a similar manner to that described in Example 22, Example 23, step 2. $[M+H]^+=556$ Example 68 and Example 69 Step 3: 1-({[(1R)-1-(4-Chlorophenyl)-2-[(5-chloropyridin-2-yl)methyl]-7-fluoro-5-[2-hydroxy-1-(piperazin-1-yl)propan-2-yl]-3-oxo-2,3-dihydro-1H-isoindol-1-yl]oxy}methyl)cyclopropane-1-carboxamide A solution of 1-({[(1R)-1-(4-chlorophenyl)-2-[(5-chloropyridin-2-yl)methyl]-7-fluoro-5-(2-methyloxiran-2-yl)-3-oxo-2,3-dihydro-1H-isoindol-1-yl]oxy}methyl)cyclopropane-1-carboxamide (0.2 g, 0.36 mmol) and piperazine (0.31 g, 3.6 mmol) in MeOH (5 mL) was heated at 65° C. for 3 h. The solvent was evaporated, water was added and the product was extracted with DCM. The organic phase was washed with water, dried and the solvent evaporated (0.179 g). The two diastereoisomers were separated by chiral HPLC.

Example 68 (isomer 1)

1H NMR (400 MHz, DMSO-d6): 8.36 (1H, d), 7.82 (1H, s), 7.74 (1H, dd), 7.51 (1H, d), 7.31 (2H, d), 7.21 (3H, t), 7.05 (1H, s), 6.87 (1H, s), 5.21 (1H, s), 4.59-4.27 (2H, m), 3.55 (1H, d), 2.92 (1H, d), 2.30-2.13 (4H, m), 1.97-1.76 (1H, m), 1.49 (3H, s), 1.03-0.85 (2H, m), 0.54-0.40 (2H, m). [M+H]$^+$=642

Example 69 (isomer 2)

1H NMR (400 MHz, DMSO-d6): 8.34 (1H, dd), 7.83-7.77 (1H, m), 7.72 (1H, dd), 7.53 (1H, d), 7.34-7.25 (2H, m), 7.20 (3H, d), 7.04 (1H, s), 6.87 (1H, s), 5.23-5.16 (1H, m), 4.56-4.33 (2H, m), 3.53 (1H, d), 2.97-2.90 (1H, m), 2.28-2.14 (4H, m), 1.93-1.76 (1H, m), 1.50 (3H, s), 1.05-0.82 (2H, m), 0.55-0.42 (2H, m). [M+H]$^+$=642

Example 70: 1-({[(1R)-1-(4-chlorophenyl)-2-[(1S)-1-(5-chloropyridin-2-yl)ethyl]-7-fluoro-5-(2-hydroxypropan-2-yl)-3-oxo-2,3-dihydro-1H-isoindol-1-yl]oxy}methyl)cyclopropane-1-carboxamide and Example 71: 1-({[(1R)-1-(4-chlorophenyl)-2-[(1R)-1-(5-chloropyridin-2-yl)ethyl]-7-fluoro-5-(2-hydroxypropan-2-yl)-3-oxo-2,3-dihydro-1H-isoindol-1-yl]oxy}methyl)cyclopropane-1-carboxamide

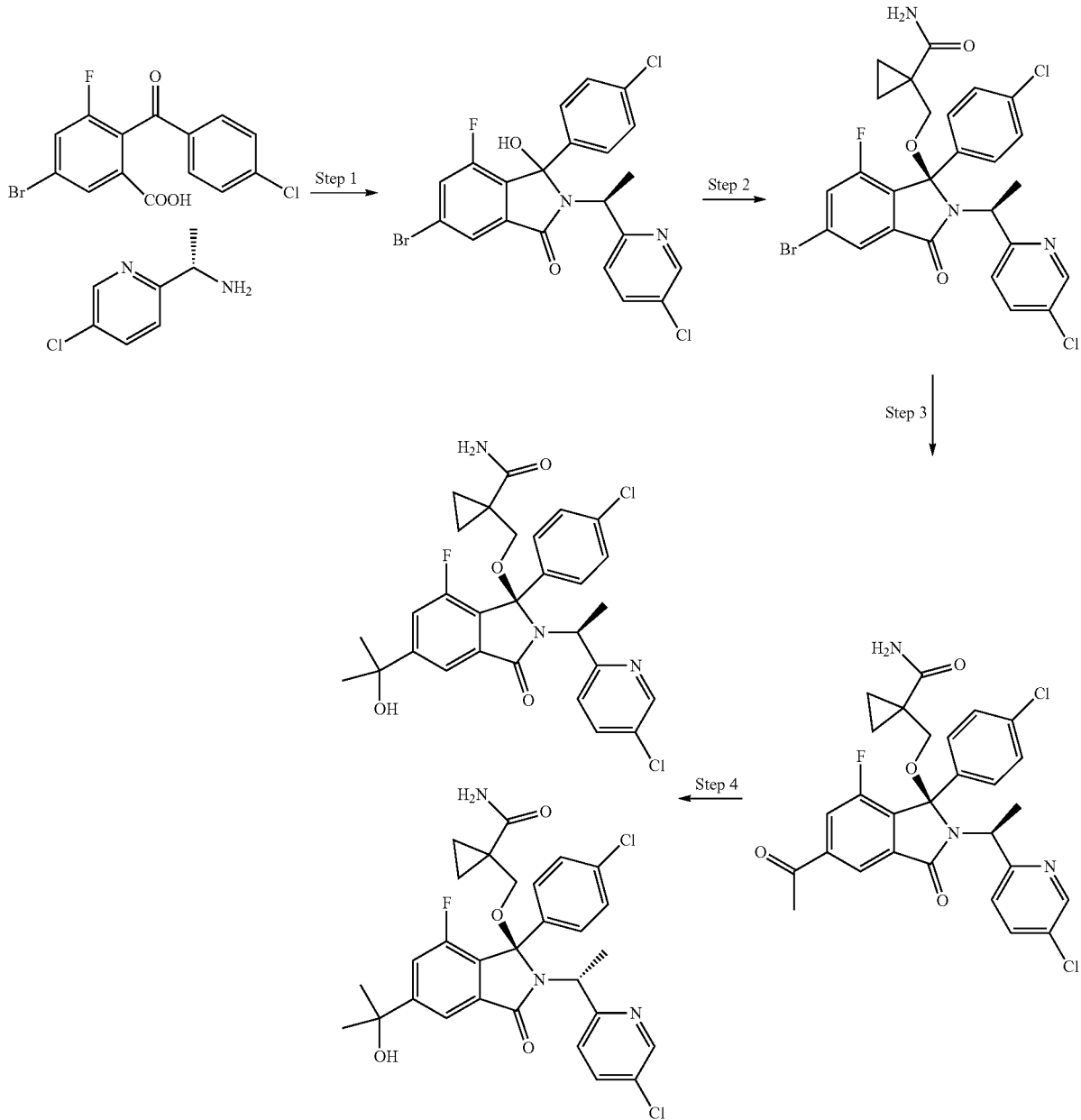

Example 70 and Example 71, Step 1. 6-Bromo-3-(4-chloro-phenyl)-2-((S)-5-chloro-pyridin-2-yl-ethyl)-4-fluoro-3-hydroxy-2,3-dihydro-isoindol-1-one The title compound was prepared from 5-bromo-2-(4-chloro-benzoyl)-3-fluoro-benzoic acid (6.50 g, 18.21 mmol) and (S)-1-(5-chloro-pyridin-2-yl)-ethylamine dihydrochloride (Preparation 13) (4.57 g, 20.03 mmol) in a similar manner to that described in Example 1, step 1. MS: [M+H] 495.

Example 70 and Example 71, Step 2: 1-({[5-Bromo-(R)-1-(4-chlorophenyl)-2-[(S)-1-(5-chloro-pyridin-2-yl)ethyl]-7-fluoro-3-oxo-2,3-dihydro-1H-isoindol-1-yl]oxy}methyl)cyclopropane-1-carboxamide The title compound was prepared from 6-bromo-3-(4-chloro-phenyl)-2-((S)-5-chloro-pyridin-2-ylethyl)-4-fluoro-3-hydroxy-2,3-dihydro-isoindol-1-one (0.99 g, 2 mmol) and 1-hydroxymethyl-cyclopropanecarboxamide (0.69 g, 6 mmol) in a similar manner to that described in Example 3, step 2. The major diastereoisomer was separated by chromatography. MS: [M+H] 592

Example 70 and Example 71, Step 3. 1-({[(R)-5-Acetyl-1-(4-chlorophenyl)-2-[(S)-1-(5-chloropyridin-2-yl)ethyl]-7-fluoro-3-oxo-2,3-dihydro-1H-isoindol-1-yl]oxy}methyl)cyclopropane-1-carboxamide The title compound was prepared from 1-({[5-bromo-(R)-1-(4-chlorophenyl)-2-[(S)-1-(5-chloropyridin-2-yl)ethyl]-7-fluoro-3-oxo-2,3-dihydro-1H-isoindol-1-yl]oxy}methyl)cyclopropane-1-carboxamide (0.48 g, 0.8 mmol) in a similar manner to that described in Example 1, step 3. MS: [M+H] 556.

Example 70 and Example 71, Step 4. 1-({[(1R)-1-(4-chlorophenyl)-2-[(1S)-1-(5-chloropyridin-2-yl)ethyl]-7-fluoro-5-(2-hydroxypropan-2-yl)-3-oxo-2,3-dihydro-1H-isoindol-1-yl]oxy}methyl)cyclopropane-1-carboxamide (Example 70) and 1-({[(1R)-1-(4-chlorophenyl)-2-[(1R)-1-(5-chloropyridin-2-yl)ethyl]-7-fluoro-5-(2-hydroxypropan-2-yl)-3-oxo-2,3-dihydro-1H-isoindol-1-yl]oxy}methyl)cyclopropane-1-carboxamide (Example 71)

The title compounds were prepared from 1-({[(R)-5-acetyl-1-(4-chlorophenyl)-2-[(S)-1-(5-chloropyridin-2-yl)ethyl]-7-fluoro-3-oxo-2,3-dihydro-1H-isoindol-1-yl]oxy}methyl)cyclopropane-1-carboxamide (0.38 g, 0.68 mmol) in a similar manner to that described in Example 1, step 4. Separation by chiral preparative LCMS gave Example 70 as a colourless solid (83 mg) and Example 71 as a colourless solid (3 mg).

Example 70

1H NMR (400 MHz, DMSO-d6): 8.21 (1H, d), 7.76 (1H, d), 7.67 (1H, dd), 7.52 (1H, d), 7.32 (1H, d), 7.19-6.99 (5H, m), 6.92 (1H, s), 5.38 (1H, s), 4.64-4.54 (1H, m), 3.67 (1H, d), 3.12 (1H, d), 1.81 (3H, d), 1.49 (6H, s), 1.12-0.97 (2H, m), 0.88-0.70 (2H, m). m/z: 572

Example 71

1H NMR (400 MHz, DMSO-d6): 8.21 (1H, d), 7.80-7.73 (1H, m), 7.72-7.48 (2H, m), 7.32 (1H, d), 7.21-6.98 (5H, m), 6.92 (1H, s), 5.37 (1H, s), 4.65-4.51 (1H, m), 3.67 (1H, d), 3.12 (1H, d), 1.81 (3H, d), 1.49 (6H, s), 1.12-0.96 (2H, m), 0.82-0.69 (2H, m). m/z: 572

Example 72: (3R)-3-(4-Chlorophenyl)-2-[(1S)-1-(5-chloropyridin-2-yl)ethyl]-3-[(1-hydroxycyclopropyl)methoxy]-6-(2-hydroxypropan-2-yl)-2,3-dihydro-1H-isoindol-1-one

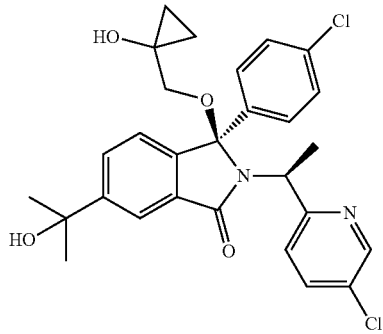 [SMILES: C[C@@H](c1ccc(Cl)cn1)N1C(=O)c2cc(C(C)(C)O)ccc2[C@]1(OCC1(O)CC1)c1ccc(Cl)cc1]

The title compound was prepared in a similar manner to that described in Example 70 and Example 71, steps 1-4, except that 1-hydroxymethyl-cyclopropanol was used in step 2 instead of 1-hydroxymethyl-cyclopropanecarboxamide. LCMS (ESI+) m/z=527.4 [M+H]+. 1H-NMR Spectrum: (500 MHz, CDCl3) 0.53-0.58 (2H, m, cyclopropane CH2CH2), 0.84-0.92 (2H, m, cyclopropane CH2CH2), 1.61 (6H, s, 2×CH3), 1.71 (1H, s, OH), 1.87 (3H, d, CH3), 2.99 (1H, d, C—O—CHH), 3.25 (1H, s, OH), 3.50 (1H, d, C—O—CHH), 4.71 (1H, q, N—CH—CH3), 7.04 (2H, d, H—Ar), 7.08 (1H, d, H-4), 7.15 (2H, d, H—Ar), 7.47 (1H, d, H—Ar), 7.53 (1H, d, H—Ar), 7.71 (1H, d, H-5), 8.00 (1H, s, H-7), 8.12 (1H, s, H—Ar).

Example 73: 6-{[(1R)-1-(4-chlorophenyl)-7-fluoro-1-{[2-(hydroxymethyl)cyclopentyl]oxy}-5-(2-hydroxypropan-2-yl)-3-oxo-2,3-dihydro-1H-isoindol-2-yl]methyl}pyridine-3-carbonitrile

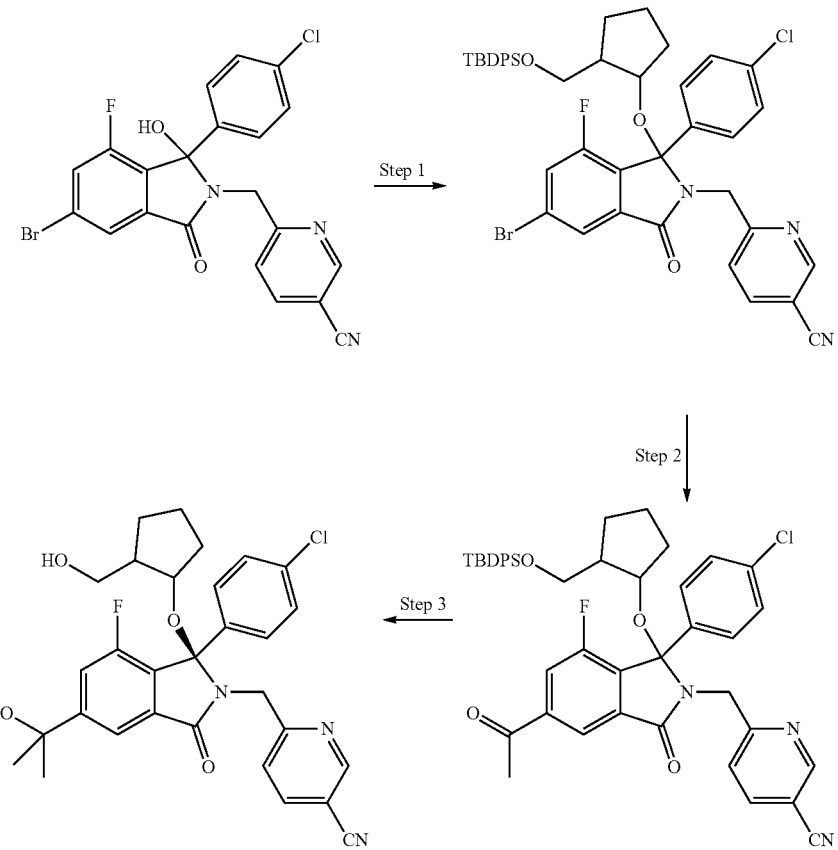

Example 73, Step 1: 6-{[(1R)-5-Bromo-1-{[(1S,2S)-2-{[(tert-butyldiphenylsilyl)oxy]methyl}cyclopentyl]oxy}-1-(4-chlorophenyl)-7-fluoro-3-oxo-2,3-dihydro-1H-isoindol-2-yl]methyl}pyridine-3-carbonitrile The title compound was prepared from 6-[5-bromo-1-(4-chloro-phenyl)-7-fluoro-1-hydroxy-3-oxo-1,3-dihydro-isoindol-2-ylmethyl]-nicotinonitrile (Example 3, step 1) (1.18 g, 2.5 mmol) and (1S,2S)-2-(tert-butyl-diphenyl-silyloxymethyl)-cyclopentanol (Preparation 14) (1.87 g, 5.28 mmol) in a similar manner to that described in Example 1, step 2. MS: [M-$C_{22}H_{29}O_2Si$] 456.

Example 73, Step 2: 6-{[(1R)-5-Acetyl-1-{[(1S,2S)-2-{[(tert-butyldiphenylsilyl)oxy]methyl}cyclopentyl]oxy}-1-(4-chlorophenyl)-7-fluoro-3-oxo-2,3-dihydro-1H-isoindol-2-yl]methyl}pyridine-3-carbonitrile The title compound was prepared from 6-{[(1R)-5-bromo-1-{[(1S,2S)-2-{[(tert-butyldiphenylsilyl)oxy]methyl}cyclopentyl]oxy}-1-(4-chlorophenyl)-7-fluoro-3-oxo-2,3-dihydro-1H-isoindol-2-yl]methyl}pyridine-3-carbonitrile in a similar manner to that described in Example 1, step 3. MS: [M−H] 770.

Example 73 Step 3: 6-{[(1R)-1-(4-chlorophenyl)-7-fluoro-1-{[2-(hydroxymethyl)cyclopentyl]oxy}-5-(2-hydroxypropan-2-yl)-3-oxo-2,3-dihydro-1H-isoindol-2-yl]methyl}pyridine-3-carbonitrile Methylmagnesium chloride (0.5 mL, 1.56 mmol, 3M in THF) and zinc(II) chloride (0.2 mL, 0.1 mmol, 0.5M in THF) were combined in THF (5 ml) under $N_2$ and stirred for 30 mins. The reaction mixture was cooled to 0° C. and a solution of 6-{[(1R)-5-acetyl-1-{[(1S,2S)-2-{[(tert-butyldiphenylsilyl)oxy]methyl}cyclopentyl]oxy}-1-(4-chlorophenyl)-7-fluoro-3-oxo-2,3-dihydro-1H-isoindol-2-yl]methyl}pyridine-3-carbonitrile (0.4 g, 0.52 mmol) in THF (10 ml) was added slowly. The ice bath was removed and the reaction was stirred at room temperature for 1 hr before methylmagnesium chloride (0.5 mL, 1.56 mmol, 3M in THF) was added and the reaction stirred for a further 20 min. The reaction was quenched with saturated aqueous ammonium chloride (20 mL) and extracted with $CH_2Cl2$ (3×50 mL). The combined extracts were dried over $MgSO_4$ and concentrated in vacuo.

The residual solid was dissolved in THF (15 ml) and placed under $N_2$. TBAF (0.78 mL, 0.78 mmol, 1M in THF) was added and the reaction was stirred overnight. The reaction was quenched with saturated aqueous ammonium chloride (20 mL) and extracted with $CH_2Cl2$ (3×30 mL).

The combined extracts were dried over MgSO₄, concentrated in vacuo and purified by preparative HPLC to give the title compound (0.05 g).

1H NMR (400 MHz, DMSO-d6): 8.66 (1H, d), 8.01 (1H, dd), 7.83 (1H, d), 7.55 (1H, d), 7.25 (1H, d), 7.16 (4H, s), 5.40 (1H, s), 4.92 (1H, d), 4.33-4.24 (2H, m), 3.75-3.63 (2H, m), 3.51-3.42 (1H, m), 1.82-1.72 (2H, m), 1.61 (3H, dd), 1.57-1.46 (9H, m). m/z: 548

Example 74: (3R)-3-(4-Chlorophenyl)-2-[(5-chloropyridin-2-yl)methyl]-6-(2-hydroxypropan-2-yl)-3-[(3-methyloxetan-3-yl)methoxy]-2,3-dihydro-1H-isoindol-1-one

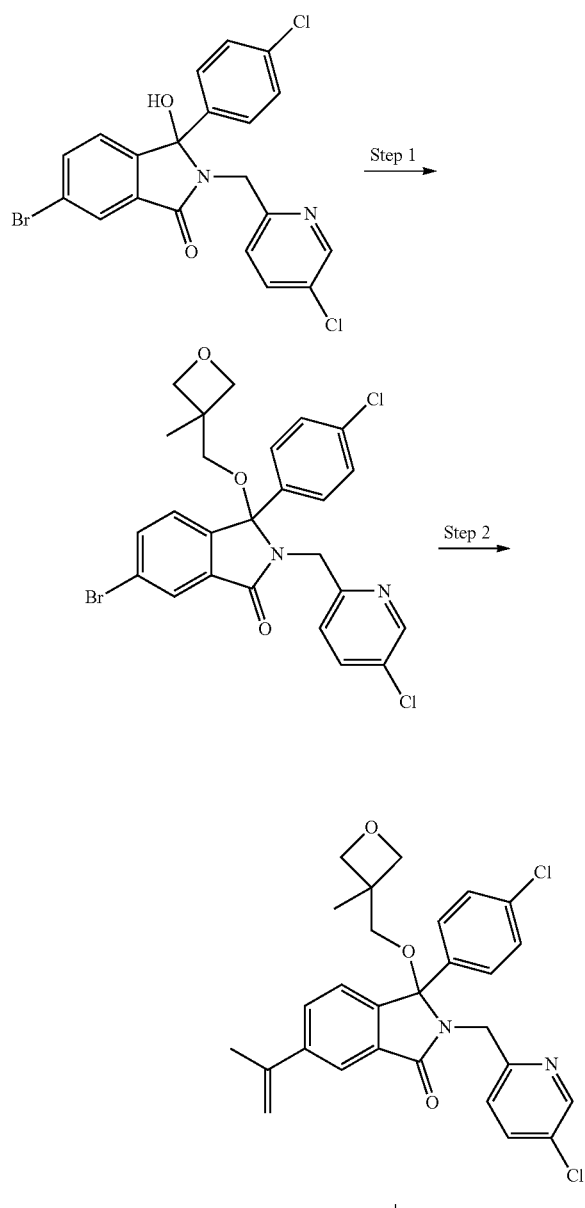

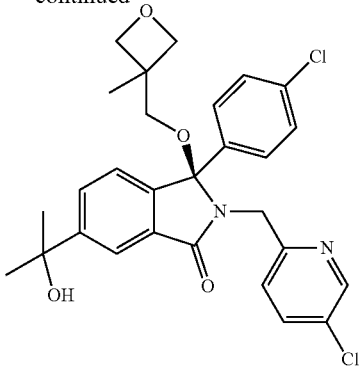

Example 74, Step 1: 6-Bromo-3-(4-chlorophenyl)-2-[(5-chloropyridin-2-yl)methyl]-3-[(3-methyloxetan-3-yl)methoxy]-2,3-dihydro-1H-isoindol-1-one The title compound (210 mg, 62%) was prepared from 6-bromo-3-(4-chloro-phenyl)-2-(5-chloro-pyridin-2-ylmethyl)-3hydroxy-2,3-dihydro-isoindol-1-one (Example 6, step 1) (285 mg, 0.62 mmol) and 3-methyl-3-oxetanemethanol (0.123 mL, 1.23 mmol) in a similar manner to that described in Example 1, steps 2. m/z (ES⁺) 447.2 [M-sidechain]⁺.

Example 74, Step 2: 3-(4-Chlorophenyl)-2-[(5-chloropyridin-2-yl)methyl]-3-[(3-methyloxetan-3-yl)methoxy]-6-(prop-1-en-2-yl)-2,3-dihydro-1H-isoindol-1-one 6-Bromo-3-(4-chlorophenyl)-2-[(5-chloropyridin-2-yl)methyl]-3-[(3-methyloxetan-3-yl)methoxy]-2,3-dihydro-1H-isoindol-1-one (210 mg, 0.38 mmol) was reacted with isopropenylboronic acid ester (0.108 mL, 0.58 mmol) in a similar manner to that described in Example 4, step 2 to afford the title compound (121 mg, 62%). m/z (ES*) 408.3 [M-C₅H₁₀O₂]⁺

Example 74, Step 3: (3R)-3-(4-Chlorophenyl)-2-[(5-chloropyridin-2-yl)methyl]-6-(2-hydroxypropan-2-yl)-3-[(3-methyloxetan-3-yl)methoxy]-2,3-dihydro-1H-isoindol-1-one The title compound was prepared from 3-(4-chlorophenyl)-2-[(5-chloropyridin-2-yl)methyl]-3-[(3-methyloxetan-3-yl)methoxy]-6-(prop-1-en-2-yl)-2,3-dihydro-1H-isoindol-1-one in a similar manner to that described in Example 4, step 3, followed by separation by chiral HPLC.

1H NMR (500 MHz, CDCl₃) 8.18 (1H, d), 7.98 (1H, d), 7.71 (1H, dd), 7.54 (1H, dd), 7.18-7.09 (6H, m), 4.52 (1H, d), 4.44 (1H, d), 4.33 (2H, dd), 4.19 (2H, dd), 3.13 (1H, d), 2.82 (1H, d), 1.49 (6H, s), 1.14 (3H, s).

Example 75: (3R)-3-(4-chlorophenyl)-2-[(5-chloropyridin-2-yl)methyl]-4-fluoro-6-(2-hydroxypropan-2-yl)-3-[(3S)-oxolan-3-yloxy]-2,3-dihydro-1H-isoindol-1-one

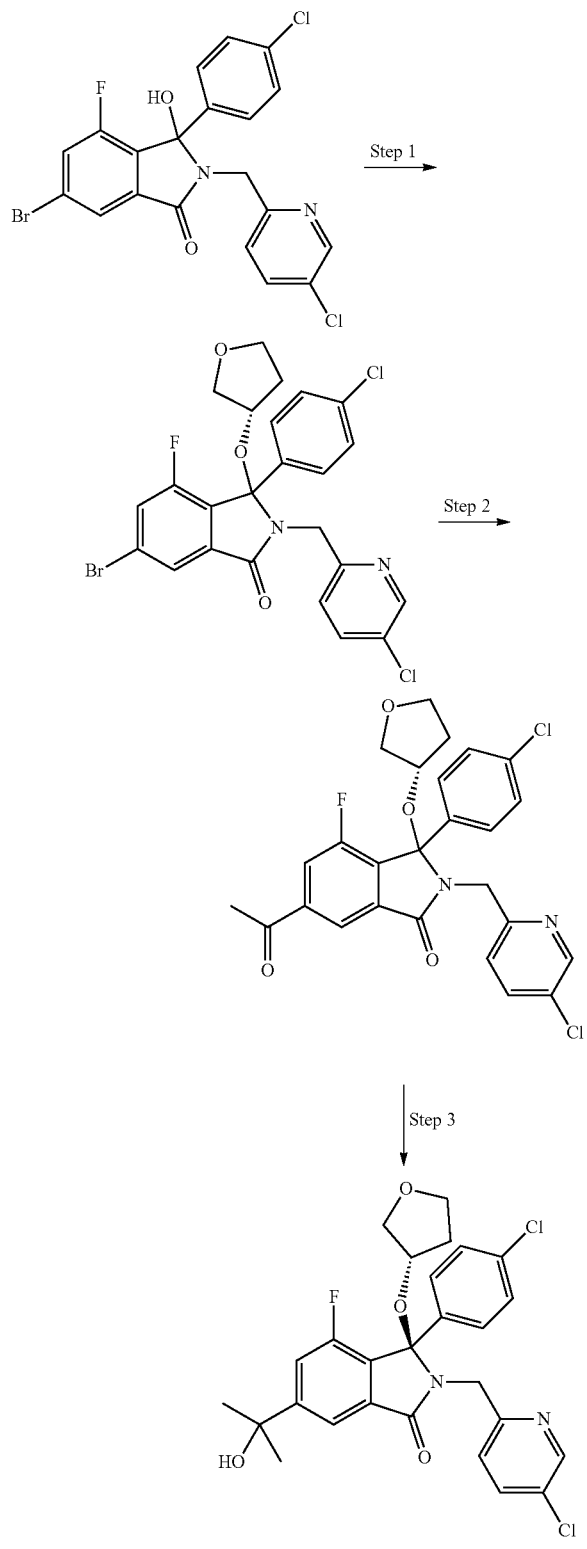

Example 75, Step 1: 6-Bromo-3-(4-chlorophenyl)-2-((5-chloropyridin-2-yl)methyl)-4-fluoro-3-(((S)-tetrahydrofuran-3-yl)oxy)isoindolin-1-one Prepared in a similar manner to that described for Example 1, step 2, from: 6-bromo-3-(4-chlorophenyl)-2-((5-chloropyridin-2-yl)methyl)-4-fluoro-3-hydroxyisoindolin-1-one (300 mg, 0.62 mmol), (S)-tetrahydrofuran-3-ol (175 mg, 0.16 mL, 1.99 mmol) MS: [M-(S)-tetrahydrofuran-3-ol)]$^+$=465.2.

Example 75, Step 2: 6-Acetyl-3-(4-chlorophenyl)-2-((5-chloropyridin-2-yl)methyl)-4-fluoro-3-(((S)-tetrahydrofuran-3-yl)oxy)isoindolin-1-one In a microwave vial, a solution of 6-bromo-3-(4-chlorophenyl)-2-((5-chloropyridin-2-yl)methyl)-4-fluoro-3-(((S)-tetrahydrofuran-3-yl)oxy)isoindolin-1-one (244 mg, 0.44 mmol) in DMF (2.9 mL) was degassed with nitrogen for 20 min then tributyl(1-ethoxyvinyl)tin (327 mg, 0.31 mL, 0.91 mmol) added followed by Pd(PPh$_3$)$_2$Cl$_2$ (15.5 mg, 0.022 mmol) and the resulting mixture heated at 70° C. for 1 h then cooled to RT. The reaction was diluted with aqueous KF solution (0.5 g in 5 mL water) and stirred vigorously for 1 h then filtered through Celite, washed through with EtOAc. The organic layer was separated, washed with brine, dried over MgSO$_4$ and concentrated under vacuum. Purified by Biotage using 0-30% EtOAc in petrol as the eluent gave 3-(4-chlorophenyl)-2-((5-chloropyridin-2-yl)methyl)-6-(1-ethoxyvinyl)-4-fluoro-3-(((S)-tetrahydrofuran-3-yl)oxy)isoindolin-1-one (214 mg). 3-(4-Chlorophenyl)-2-((5-chloropyridin-2-yl)methyl)-6-(1-ethoxyvinyl)-4-fluoro-3-(((S)-tetrahydrofuran-3-yl)oxy)isoindolin-1-one (200 mg, 0.368 mmol) was dissolved in dioxane (2.0 mL) and 1.0M aqueous HCl (2.0 mL) added and the mixture stirred at RT for 1 h. The reaction was quenched by addition of saturated aqueous NaHCO$_3$, extracted into DCM (2×50 mL), washed with brine, dried over MgSO$_4$ and concentrated under vacuum to give the title compound (176 mg, 93%). MS: [M-(S)-tetrahydrofuran-3-ol)]$^+$=429.2.

Example 75, Step 3: (3R)-3-(4-chlorophenyl)-2-[(5-chloropyridin-2-yl)methyl]-4-fluoro-6-(2-hydroxypropan-2-yl)-3-[(3S)-oxolan-3-yloxy]-2,3-dihydro-1H-isoindol-1-one Prepared in a similar manner to that described for Example 1, step 4 from 6-acetyl-3-(4-chlorophenyl)-2-((5-chloropyridin-2-yl)methyl)-4-fluoro-3-(((S)-tetrahydrofuran-3-yl)oxy) isoindolin-1-one. Chiral HPLC gave (R)-3-(4-chlorophenyl)-2-((5-chloropyridin-2-yl)methyl)-4-fluoro-6-(2-hydroxypropan-2-yl)-3-(((S)-tetrahydrofuran-3-yl)oxy)isoindolin-1-one.

1H NMR (500 MHz, CDCl$_3$) 8.32 (1H, d), 7.83 (1H, d), 7.50 (1H, dd), 7.41 (1H, dd), 7.23-7.20 (3H, m), 7.17-7.15 (2H, m), 4.57 (2H, s), 4.01-3.97 (1H, m), 3.88-3.83 (1H, m), 3.69-3.62 (2H, m), 3.33-3.30 (1H, m), 1.68-1.64 (2H, m), 1.62 (3H, s), 1.61 (3H, s). MS: [M-(S)-tetrahydrofuran-3-ol)]$^+$=443.3.

Example 76: (3R)-3-(4-chlorophenyl)-2-[(5-chloro-pyridin-2-yl)methyl]-4-fluoro-6-(2-hydroxypropan-2-yl)-3-[(3R)-oxolan-3-yloxy]-2,3-dihydro-1H-isoindol-1-one

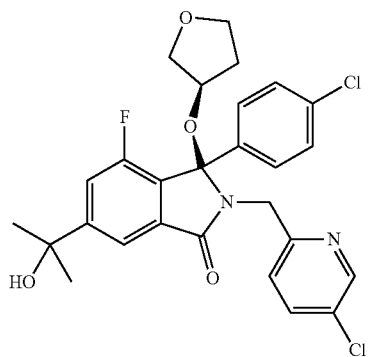

The title compound was prepared in a similar manner to that described for Example 75, steps 1-3, except that (R)-tetrahydrofuran-3-ol was used in step 1 instead of (S)-tetrahydrofuran-3-ol.

1H NMR (500 MHz, CDCl$_3$) 8.35 (1H, d), 7.83 (1H, d), 7.52 (1H, dd), 7.42 (1H, dd), 7.24-7.18 (5H, m), 4.58 (1H, d), 4.41 (1H, d), 4.04-4.00 (1H, m), 3.94-3.90 (1H, m), 3.67-3.62 (1H, m), 3.36-3.35 (2H, m), 1.92-1.86 (1H, m), 1.63 (3H, s), 1.62 (3H, s), 1.57-1.50 (1H, m). MS: [M-(S)-tetrahydrofuran-3-ol)]$^+$=443.2.

Example 77 and Example 78: (3R)-3-(4-chlorophenyl)-2-[(5-chloropyridin-2-yl)methyl]-6-[1-hydroxy-1-(pyridin-3-yl)ethyl]-3-methoxy-2,3-dihydro-1H-isoindol-1-one (*both isomers separated and isolated)

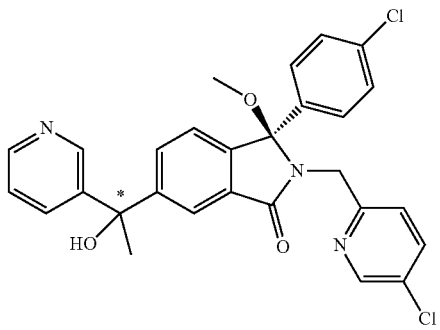 [SMILES: CO[C@]1(c2ccc(Cl)cc2)c2ccc(C(C)(O)c3cccnc3)cc2C(=O)N1Cc1ccc(Cl)cn1]

In a dry flask at RT under N$_2$ was added (R)-6-acetyl-3-(4-chlorophenyl)-2-((5-chloropyridin-2-yl)methyl)-3-methoxyisoindolin-1-one (Example 55 and Example 56, step 2) (0.80 g, 1.81 mmol) and LaCl$_3$.2LiCl (3.0 mL, 0.6M THF) and solution stirred at RT for 90 minutes. THF (2.0 mL) was added and solution cooled to 0° C. In a second dry flask at RT under N$_2$ in parallel was added 3-bromopyridine (0.196 mL, 1.99 mmol) and $^i$PrMgCl.LiCl (1.60 mL, 2.08 mmol, 1.3M THF) and solution stirred at RT for 2 h. This solution was then added to the solution containing the ketone at 0° C. and resultant solution stirred at this temperature for 1 h. Reaction mixture quenched using sat. NH$_4$Cl $_{(aq)}$, diluted with EtOAc and brine. Layers separated, aqueous extracted with EtOAc (×2), organics combined, dried over MgSO$_4$, filtered and solvent removed in vacuo to give a yellow oil. Crude material purified by column chromatography, Biotage Isolera, 25 g KP-sil cartridge 0-100% EtOAc/isohexane 10CV, 100% EtOAc 5CV, to afford crude mixture of diastereoisomers (0.34 g). Purification by achiral preparative LCMS, followed by chiral preparative LCMS gave the title compounds. *Fast running diastereoisomer: Example 77 (128 mg, 14%) $^1$H NMR (400 MHz, CDCl$_3$) 8.65 (1H, d), 8.51 (1H, dd), 8.33 (1H, dd), 7.99 (1H, dd), 7.81-7.78 (1H, m), 7.64 (1H, dd), 7.47 (1H, dd), 7.30-7.27 (1H, m), 7.24-7.10 (6H, m), 4.60 (1H, d), 4.45 (1H, d), 2.80 (3H, s), 2.42 (1H, s), 2.05 (3H, s). MS: [M-OMe]+=488.
*Slow running diastereoisomer: Example 78 (0.119 g, 14%) $^1$H NMR (400 MHz, CDCl$_3$): 8.65 (1H, d), 8.52-8.49 (1H, m), 8.33 (1H, d), 7.99 (1H, d), 7.81-7.77 (1H, m), 7.64 (1H, dd), 7.47 (1H, dd), 7.29-7.27 (1H, m), 7.23-7.10 (6H, m), 4.59 (1H, d), 4.46 (1H, d), 2.81 (3H, s), 2.42 (1H, s), 2.05 (3H, s). MS: [M-OMe]+=488.

Example 79 and Example 80: (3R)-3-(4-chlorophenyl)-2-[(5-chloropyridin-2-yl)methyl]-6-[1-hydroxy-1-(oxan-4-yl)ethyl]-3-methoxy-2,3-dihydro-1H-isoindol-1-one (*both isomers separated and isolated)

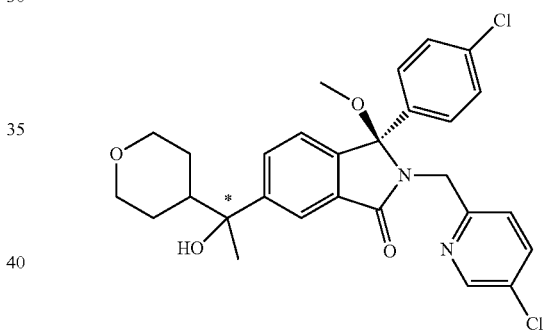

Mg turnings (0.055 g, 2.28 mmol) and dry THF (1.0 mL) were added to an oven dried flask followed by a few crystals of iodine and 4-bromotetrahydropyran (0.256 mL, 2.28 mmol) at RT under N$_2$. Solution heated slowly to 65° C. and stirred for 1 h at this temperature. Cooled to 0° C. after this time. In a second dry flask at RT under N$_2$ in parallel was added (R)-6-acetyl-3-(4-chlorophenyl)-2-((5-chloropyridin-2-yl)methyl)-3-methoxyisoindolin-1-one (Example 55 and Example 56, step 2) (0.25 g, 0.57 mmol), followed by LaCl$_3$.2LiCl (0.95 mL, 0.6M THF) and solution stirred at RT for 90 minutes. Cooled to 0° C. after this time and added, via syringe, to the solution of Grignard reagent. Reaction mixture stirred at 0° C. for 1 h before being quenched with sat. NH$_4$Cl $_{(aq)}$, diluted with EtOAc and brine. The layers were separated, aqueous was extracted with EtOAc (×2), organics combined, dried over MgSO$_4$, filtered and solvent removed in vacuo to afford crude mixture of diastereoisomers (0.32 g). Purification by achiral preparative LCMS, followed by chiral preparative LCMS gave the title compounds. *Fast running diastereoisomer Example 79 (13 mg, 5%) 1H NMR, $^1$H NMR (400 MHz, CDCl$_3$): 8.34 (1H, dd), 7.94 (1H, d), 7.66 (1H, dd), 7.48 (1H, dd), 7.25-7.11 (6H, m), 4.61 (1H, d), 4.47 (1H, d), 4.03-3.91 (2H, m), 3.37-3.25 (2H, m), 2.81

(3H, s), 1.91-1.81 (1H, m), 1.76 (1H, s), 1.61 (3H, s), 1.58-1.54 (1H, m), 1.49-1.37 (2H, m), 1.31-1.25 (1H, m). MS: [M-OMe]+=495.

Slow running diastereoisomer Example 80 (15 mg, 5%)
$^1$H NMR (400 MHz, CDCl$_3$): 8.34 (1H, dd), 7.94 (1H, d), 7.66 (1H, dd), 7.48 (1H, dd), 7.25-7.11 (6H, m), 4.61 (1H, d), 4.47 (1H, d), 4.03-3.91 (2H, m), 3.37-3.25 (2H, m), 2.81 (3H, s), 1.91-1.81 (1H, m), 1.76 (1H, s), 1.61 (3H, s), 1.58-1.54 (1H, m), 1.49-1.37 (2H, m), 1.31-1.25 (1H, m). MS: [M-OMe]+=495.

Example 81: 6-{[(1R)-1-(4-chlorophenyl)-7-fluoro-1-[(cis-3-hydroxycyclobutyl)methoxy]-5-(2-hydroxypropan-2-yl)-3-oxo-2,3-dihydro-1H-isoindol-2-yl]methyl}pyridine-3-carbonitrile 8.61 (1H, d), 7.85 (1H), 7.73 (1H, dd), 7.33 (1H, dd), 7.27 (1H, d,), 7.19 (2H, d), 7.14 (2H, d), 4.15-4.05 (2H, m), 3.57-3.53 (1H, m), 3.09 (1H, dd), 2.88 (1H, dd), 2.34-2.21 (2H, m), 1.80-1.69 (1H, m), 1.65-1.54 (2H, m) 0.83-0.80 (9H, m), 0.01 (6H, s).

Example 81, Step 2

6-(((R)-5-Bromo-1-(((cis)-3-((tert-butyldimethylsilyl)oxy)cyclobutyl)methoxy)-1-(4-chlorophenyl)-7-fluoro-3-oxoisoindolin-2-yl)methyl)nicotinonitrile (1.36 g, 2.02 mmol) was reacted with tetrabutylammonium fluoride (1M solution in tetrahydrofuran, 4.04 mL, 4.04 mmol) in a similar manner as described in Example 22 and Example 23, step 4 to give the title compound as a orange oil (500 mg,

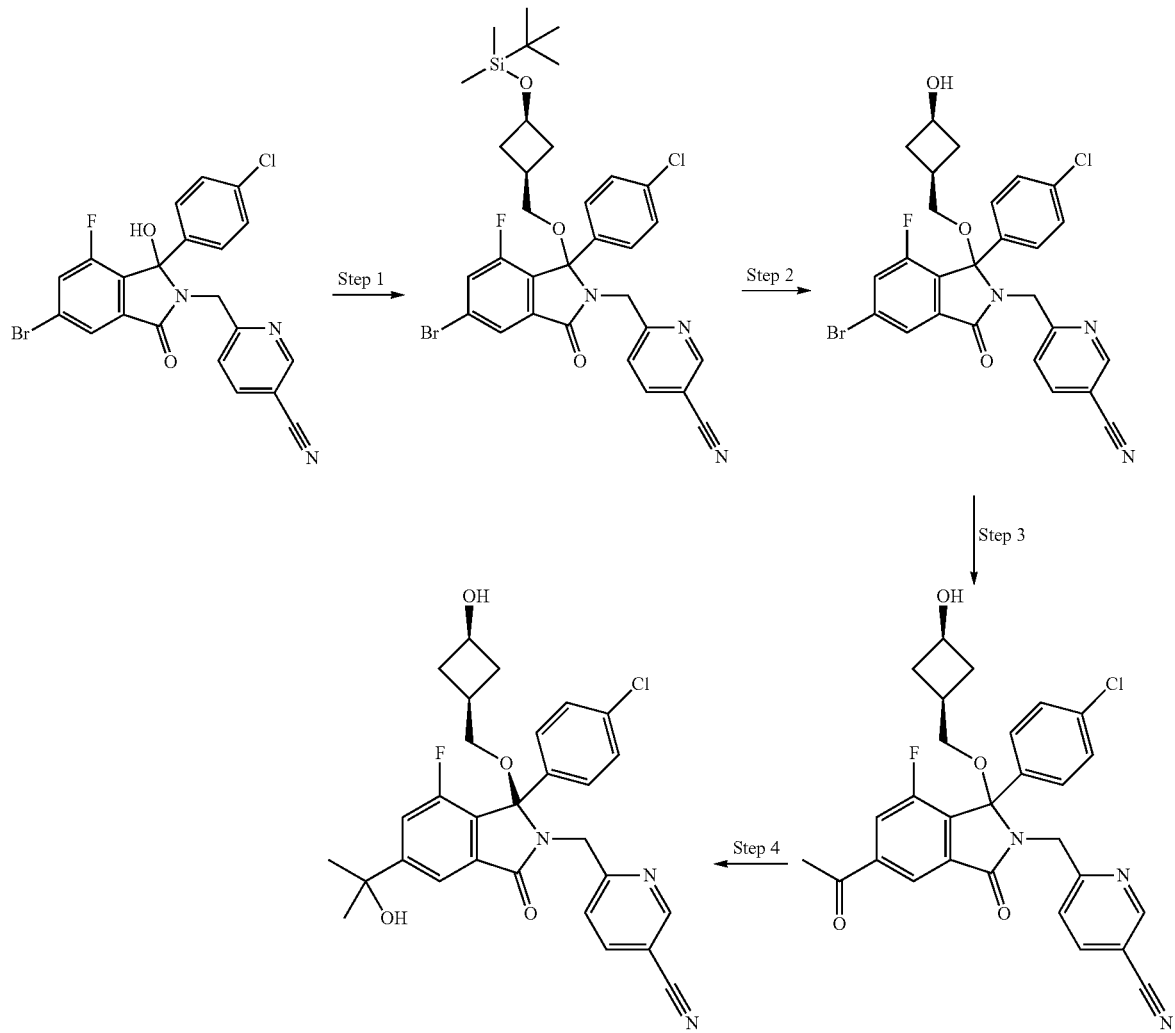

Example 81, Step 1

6-[5-Bromo-1-(4-chloro-phenyl)-7-fluoro-1-hydroxy-3-oxo-1,3-dihydro-isoindol-2-ylmethyl]-nicotinonitrile (Example 3, step 1) (1.63 g, 3.46 mmol) was reacted with ((cis)-3-((tert-butyldimethylsilyl)oxy)cyclobutyl)methanol (1.5 g, 6.93 mmol) in a similar manner to that described in Example 3, step 2 to give the title compound as a orange oil (1.36 g, 2.02 mmol, 58%). $^1$H NMR (400 MHz, CDCl$_3$):

0.99 mmol, 49%). $^1$H NMR (400 MHz, CDCl$_3$): 8.65 (1H, d), 7.90 (1H, s), 7.78 (1H, dd), 7.37 (1H, d), 7.31 (1H, d), 7.21 (4H, q), 4.56 (2H, d), 4.20-4.08 (1H, m), 3.16 (1H, dd), 2.93 (1H, dd), 2.39-2.30 (2H, m), 1.91-1.80 (1H, m), 1.64-1.54 (2H, m).

Example 81, Step 3

6-(((R)-5-Bromo-1-(4-chlorophenyl)-7-fluoro-1-(((cis)-3-hydroxycyclobutyl)methoxy)-3-oxoisoindolin-2-yl)

methyl)nicotinonitrile (500 mg, 0.99 mmol) was converted to the title compound (300 mg, 0.56 mmol, 56%) in a similar manner as described in Example 1, step 3. $^1$H NMR (400 MHz, CDCl$_3$): 8.67 (1H, d), 8.28 (1H, d), 7.82-7.78 (2H, m), 7.70-7.64 (1H, m), 7.49-7.44 (1H, m), 7.35 (1H, d), 7.22 (2H, dd), 4.60 (2H, dd), 4.20-4.11 (1H, m), 3.20 (1H, dd), 2.93 (1H, dd), 2.68 (3H, s), 2.39-2.29 (2H, m), 1.90-1.77 (2H, m), 1.62-1.50 (1H, m).

Example 81, Step 4: 6-{[(1R)-1-(4-chlorophenyl)-7-fluoro-1-[(cis-3-hydroxycyclobutyl)methoxy]-5-(2-hydroxypropan-2-yl)-3-oxo-2,3-dihydro-1H-isoindol-2-yl]methyl}pyridine-3-carbonitrile 6-(((R)-5-Acetyl-1-(4-chlorophenyl)-7-fluoro-1-(((cis)-3-hydroxycyclobutyl)methoxy)-3-oxoisoindolin-2-yl)methyl)nicotinonitrile (300 mg, 0.56 mmol) was converted to the title compound (80 mg, 0.15 mmol, 26%) in a similar manner to that described in Example 66, step 3. Purification by chiral preparative LCMS gave the title compound as a colourless solid (15 mg) as the second eluting enantiomer. $^1$H NMR (400 MHz, CDCl$_3$): 8.65 (1H, d), 7.82 (1H, d), 7.77 (1H, dd), 7.43 (1H, dd), 7.33 (1H, d), 7.25-7.22 (2H, m), 7.19-7.17 (2H, d), 4.59 (2H, d), 4.20-4.11 (1H, m), 3.13 (1H, dd), 2.95 (1H, dd), 2.38-2.30 (2H, m), 1.85 (2H, s), 1.74 (1H, d), 1.63 (6H, s).

Example 82 and Example 83: 1-({[(1R)-1-(4-chlorophenyl)-2-[(5-chloropyridin-2-yl)methyl]-7-fluoro-5-[1-hydroxy-1-(oxan-4-yl)ethyl]-3-oxo-2,3-dihydro-1H-isoindol-1-yl]oxy}methyl)cyclopropane-1-carboxamide (*both isomers separated and isolated)

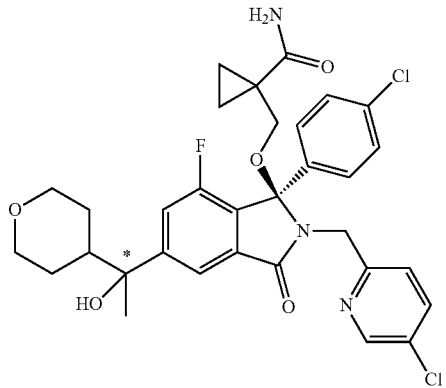 [SMILES: CC(O)(c1cc(F)c2c(c1)C(=O)N(Cc1ccc(Cl)cn1)[C@@]2(OCC1(C(N)=O)CC1)c1ccc(Cl)cc1)C1CCOCC1]

(R)-1-(((5-Acetyl-1-(4-chlorophenyl)-2-((5-chloropyridin-2-yl)methyl)-7-fluoro-3-oxoisoindolin-1-yl)oxy)methyl)cyclopropanecarboxamide (Example 69, step 1) (0.50 g, 0.92 mmol) was dissolved in dry THF (3.0 mL) before LaCl$_3$.2LiCl (1.54 mL, 0.6M THF) was added and solution stirred at RT under N$_2$ for 1 h. Tetrahydropyran magnesium chloride (9.22 mL, 4.61 mmol, 0.5M Me-THF) was then added and the resultant solution stirred at RT for 15 minutes. The reaction was quenched with sat. NH$_4$Cl$_{(aq)}$ (40 mL), diluted with EtOAc (25 mL). Layers separated, aqueous extracted with EtOAc (2×25 mL), organics combined, dried over MgSO$_4$, filtered and solvent removed in vacuo to afford a yellow oil. Purified by column chromatography, Biotage Isolera, 10 g KP-sil cartridge 50-100% EtOAc/isohexane 10CV, 100% EtOAc 10CV to afford crude racemic mixture (150 mg). Purification by chiral preparative LCMS gave the title compounds.

Example 82: *Fast Running Isomer $^1$H NMR (400 MHz, CDCl$_3$) 8.38 (1H, dd), 7.70 (1H, d), 7.60 (1H, dd), 7.40-7.35 (2H, m), 7.28-7.33 (4H, m), 4.48 (1H, m), 4.24 (1H, d), 4.04-3.92 (2H, m), 3.62 (1H, d), 3.38-3.24 (2H, m), 3.07 (1H, d), 1.87-1.80 (1H, m), 1.69 (1H, s), 1.58 (3H, s), 1.48-1.38 (3H, m), 1.26-1.17 (3H, m), 0.64-0.58 (1H, m), 0.52-0.46 (1H, m). MS: [M+H]$^+$=628.

Example 83:* Slow Running Isomer $^1$H NMR (400 MHz, CDCl$_3$) 8.38 (1H, dd), 7.67 (1H, d), 7.61 (1H, dd), 7.41-7.37 (2H, m), 7.31 (4H, d), 4.48 (1H, d), 4.24 (1H, d), 4.04-3.92 (2H, m), 3.63 (1H, d), 3.38-3.25 (2H, m), 3.03 (1H, d), 1.86-1.78 (1H, m), 1.72 (1H, s), 1.58 (3H, s), 1.47-1.37 (3H, m), 1.27-1.19 (3H, m), 0.64-0.58 (1H, m), 0.52-0.46 (1H, m); MS: [M+H]$^+$=628.

Example 84: 6-{[(1R)-1-(4-chlorophenyl)-7-fluoro-1-(3-hydroxycyclobutoxy)-5-(2-hydroxypropan-2-yl)-3-oxo-2,3-dihydro-1H-isoindol-2-yl]methyl}pyridine-3-carbonitrile

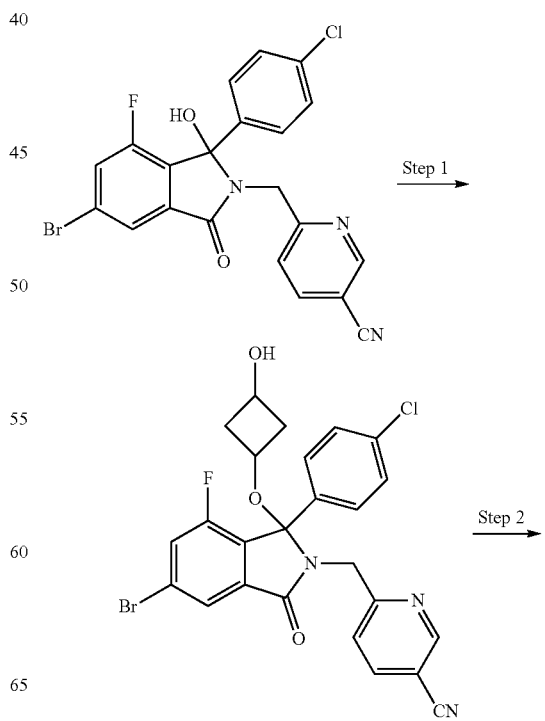

-continued

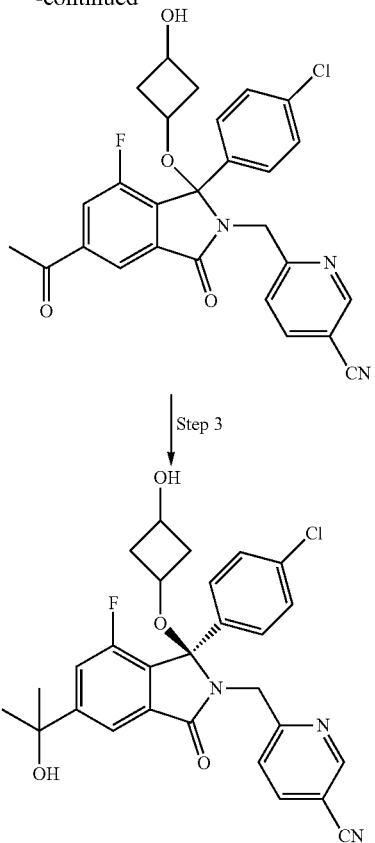

Example 84, Step 1: 6-[5-Bromo-1-(4-chloro-phenyl)-7-fluoro-1-(3-hydroxycyclobutoxy)-3-oxo-1,3-dihydro-isoindol-2-ylmethyl]-nicotinonitrile 6-((5-Bromo-1-(4-chlorophenyl)-7-fluoro-1-(3-hydroxycyclobutoxy)-3-oxoisoindolin-2-yl)methyl)nicotinonitrile (0.061 g, 54%) was prepared from 6-((5-bromo-1-(4-chlorophenyl)-7-fluoro-1-hydroxy-3-oxoisoindolin-2-yl)methyl)nicotinonitrile (Example 3, step 1) (100 mg) in a similar manner to that described in Example 3, step 2. $^1$H NMR (400 MHz, CDCl$_3$): 8.66 (1H, dd), 7.89 (1H, d), 7.78 (1H, dd), 7.35 (1H, dd), 7.29 (1H, dd), 7.26-7.18 (4H, m), 4.62 (1H, d), 4.47 (1H, d), 3.74-3.65 (1H, m), 3.38-3.29 (1H, m), 2.21-2.12 (1H, m), 2.01-1.93 (3H, m), 1.81 (1H, s).

Example 84, Step 2: 6-[5-Acetyl-1-(4-chloro-phenyl)-7-fluoro-1-(3-hydroxycyclobutoxy)-3-oxo-1,3-dihydro-isoindol-2-ylmethyl]-nicotinonitrile The title compound (120 mg, 26%) was prepared from 6-[5-bromo-1-(4-chloro-phenyl)-7-fluoro-1-(3-hydroxycyclobutoxy)-3-oxo-1,3-dihydro-isoindol-2-ylmethyl]-nicotinonitrile (501 mg) in a manner similar to that described in Example 1, step 3. $^1$H NMR (400 MHz, CDCl$_3$): 8.68 (1H, d), 8.27 (1H, d), 7.78 (2H, m), 7.66 (2H, m), 7.55 (1H, m), 7.46 (2H, m), 4.66 (1H, d), 4.48 (1H, d), 3.67 (1H, m), 3.37 (1H, m), 2.67 (3H, s), 2.18 (1H, m), 1.94-1.87 (3H, m), 1.73 (1H, d).

Example 84, Step 3: 6-{[(1R)-1-(4-chlorophenyl)-7-fluoro-1-(3-hydroxycyclobutoxy)-5-(2-hydroxypropan-2-yl)-3-oxo-2,3-dihydro-1H-isoindol-2-yl]methyl}pyridine-3-carbonitrile The title compound (6 mg, 5.2%) was prepared from 6-[5-acetyl-1-(4-chloro-phenyl)-7-fluoro-1-(3-hydroxycyclobutoxy)-3-oxo-1,3-dihydro-isoindol-2-ylmethyl]-nicotinonitrile (120 mg) in a manner similar to that described in Example 1, step 4. $^1$H NMR (400 MHz, CDCl$_3$): 8.66 (1H, d), 7.81 (1H, d), 7.77 (1H, dd), 7.39 (1H, dd), 7.31 (1H, d), 7.28-7.24 (2H, m under CDCl$_3$), 7.19 (2H, d), 4.64 (1H, d), 4.50 (1H, d), 3.67 (1H, dd), 3.36-3.28 (1H, m), 2.21-2.12 (1H, m), 2.00-1.87 (3H, m), 1.84 (1H, s), 1.66 (1H, d), 1.62 (6H, s).

Example 85 and Example 86: (3R)-6-[1-(1-acetylpiperidin-4-yl)-1-hydroxyethyl]-3-(4-chlorophenyl)-2-[(5-chloropyridin-2-yl)methyl]-3-methoxy-2,3-dihydro-1H-isoindol-1-one (*both isomers separated and isolated)

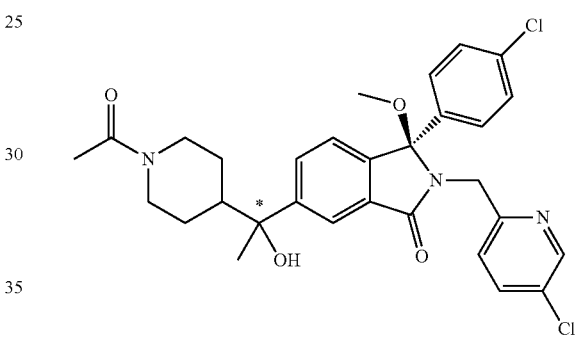

Magnesium turnings (280 mg, 11.5 mmol) were sonicated in anhydrous THF (15 mL) for 5 minutes and the solvent decanted off. They were then added to a stirred solution of 1-(4-bromopiperidin-1-yl)ethanone (600 mg, 2.91 mmol) in anhydrous THF (5 mL) under nitrogen. Iodine (3 crystals) was added and the mixture heated at 90° C. for 4 h then cooled to 00° C. To the reaction was added a pre-mixed solution of (R)-6-acetyl-3-(4-chlorophenyl)-2-((5-chloropyridin-2-yl)methyl)-3-methoxyisoindolin-1-one (Example 55 and Example 56, step 2) (330 mg, 0.75 mmol), 0.6M LaCl$_3$.2LiCl in THF (1.25 mL, 0.75 mmol) and anhydrous THF (5 mL) (pre-stirred at room temperature under nitrogen for 30 min). The mixture was stirred at 00° C. for 30 min then allowed to warm to room temperature and stand overnight and finally refluxed for 3 h. The reaction mixture was cooled, quenched with saturated NH$_4$Cl (20 mL), diluted with water (20 mL) and extracted with EtOAc (2×100 mL). Combined extracts were dried (MgSO$_4$) and evaporated and the residue chromatographed on silica gel eluting with 0-100% EtOAc in DCM gradient then 10% MeOH in DCM to afford a pale brown solid. Purification by chiral preparative chromatography afforded Example 85 (*Faster running isomer) (5 mg, 0.28%). 1H NMR (400 MHz, CDCl$_3$) 8-36-8-34 (1H, m), 7.92 (1H, s), 7.67-7.62 (1H, m), 7.50-7.47 (1H, m), 7.30-7.10 (6H, m), 4.73-4.40 (3H, m), 3.90-3.70 (1H, m), 3.05-2.85 (1H, m), 2.80 (3H, s), 2.50-2.35 (1H, m), 2.04 (3H, s), 1.90-1.65 (3H, m), 1.61 (3H, s), 1.58-1.35 (1H, m), 1.13-1.10 (2H, m). MS(ES+) m/z 568\570 [M+H]$^+$. Further elution gave Example 86

(*Slower running isomer) (4 mg, 0.26%). 1H NMR (400 MHz, CDCl$_3$) 8.36-8.34 (1H, m), 7.92 (1H, m), 7.67-7.62 (1H, m), 7.50-7.47 (1H, m), 7.30-7.10 (6H, m), 4.73-4.40 (3H, m), 3.90-3.70 (1H, m), 3.05-2.85 (1H, m), 2.80 (3H, s), 2.50-2.35 (1H, m), 2.04 (3H, s), 1.90-1.65 (3H, m), 1.61 (3H, s), 1.58-1.35 (1H, m), 1.13-1.10 (2H, m). MS(ES+) m/z 568\570 [M+H]$^+$.

Example 87: 6-{[(1R)-1-(4-chlorophenyl)-1-(cyclopropylmethoxy)-5-(2-hydroxypropan-2-yl)-3-oxo-2,3-dihydro-1H-isoindol-2-yl]methyl}pyridine-3-carbonitrile

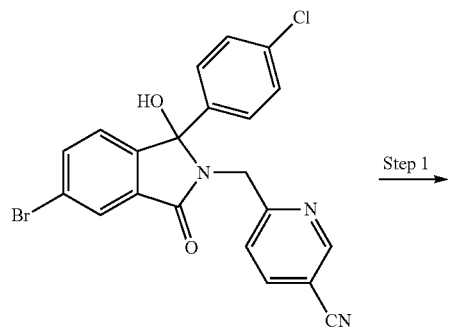

Step 1

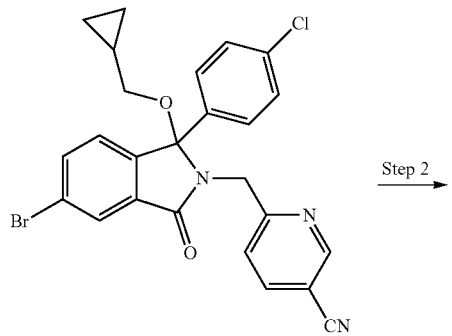

Step 2

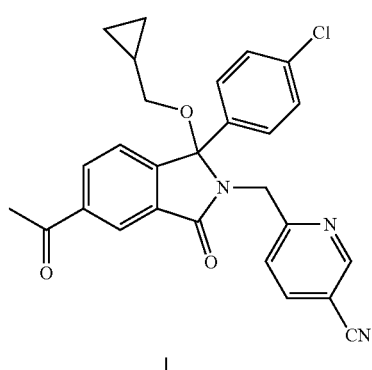

Step 3

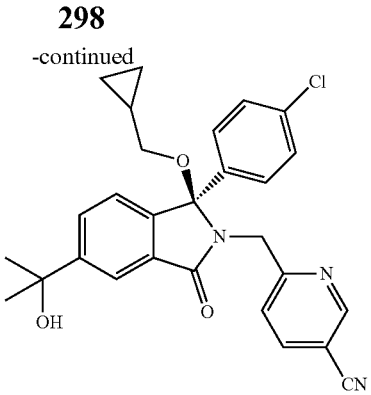

Example 87, Step 1: 6-((5-Bromo-1-(4-chlorophenyl)-1-(cyclopropylmethoxy)-3-oxoisoindolin-2-yl)methyl)nicotinonitrile The title compound was prepared from 6-((5-bromo-1-(4-chlorophenyl)-1-hydroxy-3-oxoisoindolin-2-yl)methyl)nicotinonitrile (Example 35, step 1) (1.00 g, 2.22 mmol) and cyclopropylmethanol in a similar manner to that described in Example 3, step 2 to give a pale orange solid (0.75 g, 66%). NMR (400 MHz, CDCl$_3$): 8.64-8.62 (1H, m), 8.06-8.05 (1H, m), 7.75-7.60 (2H, m), 7.30-7.10 (5H, m), 7.04 (1H, d), 4.70-4.50 (2H, m), 2.95-2.85 (1H, m), 2.75-2.65 (1H, m), 0.85-0.70 (1H, m), 0.60-0.45 (2H, m), 0.15-0.00 (2H, m).

Example 87, Step 2: 6-((5-Acetyl-1-(4-chlorophenyl)-1-(cyclopropylmethoxy)-3-oxoisoindolin-2-yl)methyl)nicotinonitrile The title compound was prepared from 6-((5-bromo-1-(4-chlorophenyl)-1-(cyclopropylmethoxy)-3-oxoisoindolin-2-yl)methyl)nicotinonitrile (920 mg, 1.8 mmol) in a similar manner to that described in Example 1, step 3 (620 mg, 70%). NMR (400 MHz, CDCl$_3$) 8.65 (1H, dd), 8.45 (1H, dd), 8.17 (1H, dd), 7.77 (1H, dd), 7.35-7.10 (6H, m), 4.70-4.55 (2H, m), 2.95-2.85 (1H, m), 2.75-2.65 (1H, m), 2.69 (3H, s), 0.85-0.70 (1H, m), 0.55-0.45 (2H, m), 0.10-0.00 (2H, m).

Example 87, Step 3: 6-{[(1R)-1-(4-chlorophenyl)-1-(cyclopropylmethoxy)-5-(2-hydroxypropan-2-yl)-3-oxo-2,3-dihydro-1H-isoindol-2-yl]methyl}pyridine-3-carbonitrile The title compound was prepared from 6-((5-acetyl-1-(4-chlorophenyl)-1-(cyclopropylmethoxy)-3-oxoisoindolin-2-yl)methyl)nicotinonitrile (620 mg, 1.27 mmol) in a similar manner to that described in Example 1, step 4 (125 mg, 20%). Isomer separation by chiral preparative LCMS afforded Example 87 (Faster running isomer) (52.8 mg). NMR (400 MHz, CDCl$_3$): 8.64-8.62 (1H, m), 8.02 (1H, d), 7.80-7.70 (2H, m), 7.33 (1H, d), 7.30-7.16 (3H, m), 7.15-7.10 (3H, m), 4.70-4.55 (2H, m), 2.95-2.85 (1H, m), 2.75-2.65 (1H, m), 1.63 (6H, s), 0.85-0.70 (1H, m), 0.50-0.44 (2H, m), 0.07-0.00 (2H, m). MS(ES+) m/z 416 [MH-OCH$_2$(cPr)]$^+$.

299

Example 88: (3R)-3-(4-Chlorophenyl)-2-[(5-chloropyridin-2-yl)methyl]-6-[1-hydroxy-1-(1-oxo-1λ⁵-pyridin-3-yl)ethyl]-3-methoxy-2,3-dihydro-1H-isoindol-1-one

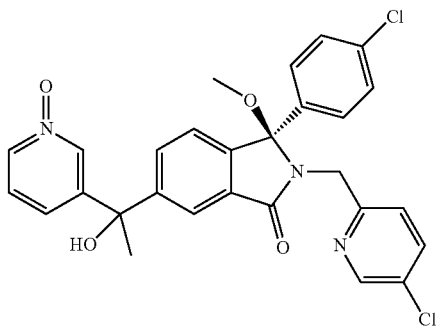 [SMILES: CO[C@]1(c2ccc(Cl)cc2)c2ccc(C(C)(O)c3ccc[n+]([O-])c3)cc2C(=O)N1Cc1ccc(Cl)cn1]

The title compound (35 mg) was prepared from (3R)-3-(4-chlorophenyl)-2-[(5-chloropyridin-2-yl)methyl]-6-[1-hydroxy-1-(pyridin-3-yl)ethyl]-3-methoxy-2,3-dihydro-1H-isoindol-1-one (45 mg) (Example 78) in a similar manner as described in Example 10.

1H NMR (400 MHz, DMSO-d6): 8.38 (1H, d), 8.31 (1H, s), 8.09 (1H, dd), 7.94 (1H, d), 7.80-7.70 (2H, m), 7.44-7.33 (2H, m), 7.32-7.18 (6H, m), 6.36 (1H, s), 4.52 (1H, d), 4.37 (1H, d), 2.76 (3H, s), 1.92 (3H, s). MS: [M-OCH$_3$]+=504.

Example 89 and Example 90: 6-{[(1R)-1-(4-chlorophenyl)-7-fluoro-5-[1-hydroxy-1-(oxan-4-yl)ethyl]-1-{[1-(hydroxymethyl)cyclopropyl]methoxy}-3-oxo-2,3-dihydro-1H-isoindol-2-yl]methyl}pyridine-3-carbonitrile (*both isomers separated and isolated)

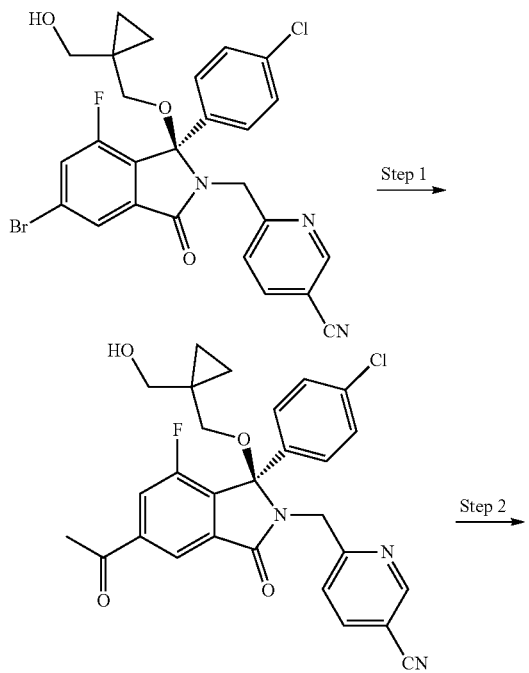

300

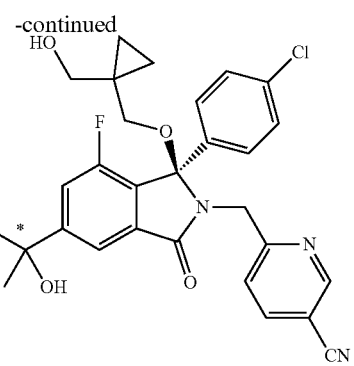

Example 89 and Example 90, Step 1: (R)-6-((5-Acetyl-1-(4-chlorophenyl)-7-fluoro-1-((1-(hydroxymethyl)cyclopropyl)methoxy)-3-oxoisoindolin-2-yl)methyl)nicotinonitrile The title compound was prepared from (R)-6-((5-bromo-1-(4-chlorophenyl)-7-fluoro-1-((1-(hydroxymethyl)cyclopropyl)methoxy)-3-oxoisoindolin-2-yl)methyl)nicotinonitrile (2.00 g, 3.6 mmol) in a similar manner to that described in Example 1, step 3 (1.60 g). 1H NMR (400 MHz, CDCl$_3$) 8.68 (1H, dd), 8.24 (1H, dd), 7.90-7.75 (2H, m), 7.65-7.50 (2H, m), 7.30-7.15 (3H, m), 4.55 (2H, s), 3.70-3.60 (1H, m), 3.50-3.40 (2H, m), 2.84 (1H, d), 2.66 (3H, s), 2.30 (1H, t), 0.55-0.25 (4H, m).

Example 89 and Example 90, Step 2: 6-{[(1R)-1-(4-chlorophenyl)-7-fluoro-5-[1-hydroxy-1-(oxan-4-yl)ethyl]-1-{[1-(hydroxymethyl)cyclopropyl]methoxy}-3-oxo-2,3-dihydro-1H-isoindol-2-yl]methyl}pyridine-3-carbonitrile The title compound was prepared from (R)-6-((5-acetyl-1-(4-chlorophenyl)-7-fluoro-1-((1-(hydroxymethyl)cyclopropyl)methoxy)-3-oxoisoindolin-2-yl)methyl)nicotinonitrile (496 mg, 1.0 mmol) in a similar manner to that described in Example 82 and Example 83 (71.4 mg). Isomer separation by chiral preparative LCMS afforded Example 89 (*Faster running isomer) (35 mg). 1H NMR (400 MHz, CDCl$_3$) 8.68 (1H, dd), 7.81 (1H, dd), 7.72 (1H, d), 7.45-7.30 (2H, m), 7.28-7.15 (4H, m), 4.54 (2H, s), 4.10-3.85 (2H, m), 3.70-3.45 (2H, m), 3.40-3.20 (3H, m), 2.95-2.85 (1H, m), 2.30 (1H, t), 1.85-1.70 (1H, m), 1.58 (3H, s), 1.50-1.35 (4H, m), 1.30-1.15 (1H. m), 0.55-0.25 (4H, m). MS(ES+) m/z 506 [MH-OCH$_2$(cPr)CH$_2$OH]$^+$.

Further elution gave Example 90 (*Slower running isomer) (23 mg). NMR (400 MHz, CDCl$_3$) 8.69 (1H, dd), 7.82 (1H, dd), 7.69 (1H, d), 7.44-7.30 (2H, m), 7.28-7.15 (4H, m), 4.54 (2H, s), 4.05-3.85 (2H, m), 3.65-3.45 (2H, m), 3.40-3.20 (3H, m), 2.95-2.85 (1H, m), 2.30 (1H, t), 1.85-1.70 (1H, m), 1.58 (3H, s), 1.50-1.35 (4H, m), 1.30-1.15 (1H. m), 0.55-0.25 (4H, m). MS(ES+) m/z 506 [MH-OCH$_2$(cPr)CH$_2$OH]$^+$.

Example 91 and Example 92: (3R)-3-(4-chlorophenyl)-2-[(5-chloropyridin-2-yl)methyl]-6-[2-hydroxy-1-(oxan-4-yl)propan-2-yl]-3-methoxy-2,3-dihydro-1H-isoindol-1-one (*both isomers separated and isolated)

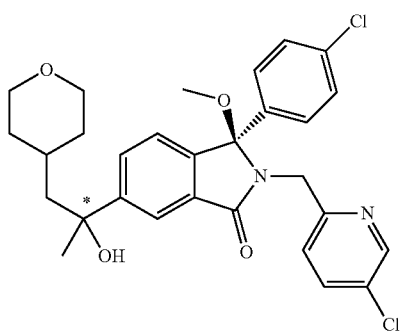 [SMILES: CO[C@]1(c2ccc(Cl)cc2)c2ccc(C(C)(O)CC3CCOCC3)cc2C(=O)N1Cc1ccc(Cl)cn1]

The title compounds were prepared from (R)-6-acetyl-3-(4-chlorophenyl)-2-((5-chloropyridin-2-yl)methyl)-3-methoxyisoindolin-1-one (Example 55 and Example 56, step 2) (150 mg, 0.34 mmol) in a similar manner to that described in Example 79 and Example 80, using 4-bromomethyltetrahydropyran. Isomer separation by chiral preparative LCMS afforded:

Example 91 (*Faster Running) (2 mg)

MS(ES+) m/z 563 [MNa]+.
1H NMR (400 MHz, DMSO_cap): 8.39 (1H, d), 7.91 (1H, s), 7.74 (2H, dd), 7.34-7.12 (6H, m), 5.13 (1H, s), 4.50 (1H, d), 4.39 (1H, d), 3.78-3.54 (2H, m), 3.22-3.00 (2H, m), 2.76 (3H, s), 1.79-1.60 (2H, m), 1.60-1.42 (5H, m), 1.39-1.01 (3H, m).

Example 92 (*Slower Running Isomer) (2 mg)

MS(ES+) m/z 563 [MNa]+.
1H NMR (400 MHz, DMSO_cap): 8.39 (1H, d), 7.94 (1H, s), 7.79-7.66 (2H, m), 7.35-7.11 (6H, m), 5.14 (1H, s), 4.51 (1H, d), 4.37 (1H, d), 3.77-3.66 (1H, m), 3.66-3.54 (1H, m), 3.21-2.99 (2H, m), 2.76 (3H, s), 1.79-1.60 (2H, m), 1.58-1.44 (5H, m), 1.28-1.03 (3H, m).

Example 93: (3R)-3-(4-Chlorophenyl)-2-[(5-chloropyridin-2-yl)methyl]-3-(3-hydroxy-3-methylbutoxy)-6-(2-hydroxypropan-2-yl)-2,3-dihydro-1H-isoindol-1-one

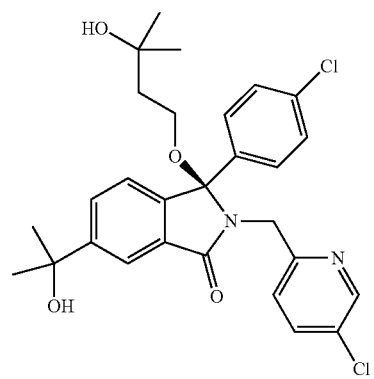 [SMILES: CC(C)(O)CCO[C@]1(c2ccc(Cl)cc2)c2ccc(C(C)(C)O)cc2C(=O)N1Cc1ccc(Cl)cn1]

The title compound was prepared from 6-bromo-3-(4-chloro-phenyl)-2-(5-chloro-pyridin-2-ylmethyl)-3hydroxy-2,3-dihydro-isoindol-1-one (Example 6, step 1) in a similar manner to that described in Example 1, steps 2-4 using 3-methyl-butane-1,3-diol instead of {1-[hydroxy(²H₂)methyl]cyclopropyl}(²H₂)methanol in step 2. 1H NMR (400 MHz, DMSO-d6): 8.66 (1H, d), 8.01 (1H, dd), 7.83 (1H, d), 7.55 (1H, d), 7.25 (1H, d), 7.16 (4H, s), 5.40 (1H, s), 4.92 (1H, d), 4.33-4.24 (2H, m), 3.75-3.63 (2H, m), 3.51-3.42 (1H, m), 1.82-1.72 (2H, m), 1.61 (3H, dd), 1.57-1.46 (9H, m). m/z: 425

Example 94: (3R)-3-(4-Chlorophenyl)-2-[(5-chloropyridin-2-yl)methyl]-6-(2-hydroxypropan-2-yl)-3-(2-methanesulfonylethoxy)-2,3-dihydro-1H-isoindol-1-one

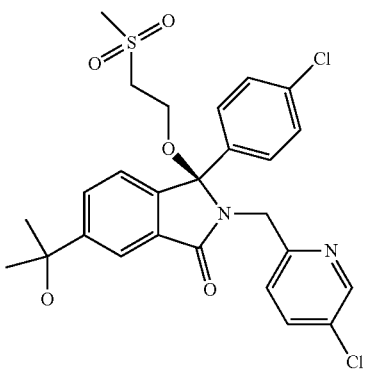 [SMILES: CC(C)(O)c1ccc2c(c1)C(=O)N(Cc1ccc(Cl)cn1)[C@@]2(OCCS(C)(=O)=O)c1ccc(Cl)cc1]

The title compound was prepared from 6-bromo-3-(4-chloro-phenyl)-2-(5-chloro-pyridin-2-ylmethyl)-3hydroxy-2,3-dihydro-isoindol-1-one (Example 6, step 1) in a similar manner to that described in Example 1, steps 2-4 using 2-methanesulfonyl-ethanol instead of {1-[hydroxy(²H₂)methyl]cyclopropyl}(²H₂)methanol in step 2. 1H NMR (400 MHz, DMSO-d6): 8.38 (1H, d), 7.95 (1H, d), 7.82-7.71 (2H, m), 7.34-7.17 (6H, m), 5.27 (1H, s), 4.56 (1H, d), 4.43 (1H, d), 3.50-3.40 (1H, m), 3.28-3.15 (3H, m), 3.04 (3H, s), 1.48 (6H, s). m/z: 549

Example 95: (3R)-3-(4-chlorophenyl)-2-[(5-chloropyridin-2-yl)methyl]-3-(cyclobutylmethoxy)-6-(2-hydroxypropan-2-yl)-2,3-dihydro-1H-isoindol-1-one

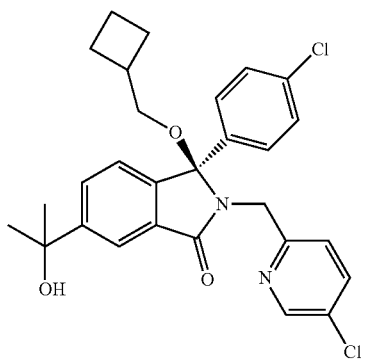 [SMILES: CC(C)(O)c1ccc2c(c1)C(=O)N(Cc1ccc(Cl)cn1)[C@@]2(OCC1CCC1)c1ccc(Cl)cc1]

303

The title compound was prepared from 6-bromo-3-(4-chlorophenyl)-2-((5-chloropyridin-2-yl)methyl)-3-hydroxy-isoindolin-1-one (Example 6, step 1) in a similar manner to that described in Example 1, steps 2-4, using cyclobutanol instead of {1-[hydroxy($^2$H$_2$)methyl]cyclopropyl}($^2$H$_2$) methanol in step 2.

$^1$H NMR (400 MHz, CDCl$_3$): 8.30 (1H, d), 8.01 (1H, d), 7.69 (1H, dd), 7.44 (1H, dd), 7.22-7.17 (3H, m), 7.15-7.10 (3H, m), 4.55-4.54 (2H, m), 3.62-3.53 (1H, m), 2.00-1.90 (1H, m), 1.88-1.76 (2H, m), 1.70-1.61 (7H, m), 1.49 (1H, q), 1.37-1.30 (1H, m), 1.22-1.11 (1H, m). MS: [M+H]+=497.

Example 96: (3R)-3-(4-chlorophenyl)-2-[(5-chloro-pyridin-2-yl)methyl]-3-(2-hydroxy-2-methyl-propoxy)-6-(2-hydroxypropan-2-yl)-2,3-dihydro-1H-isoindol-1-one

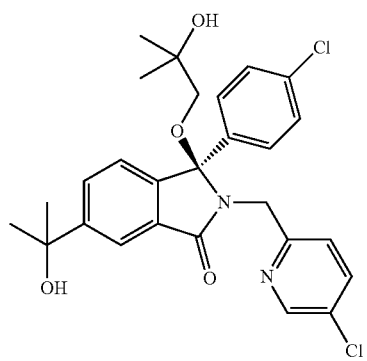 [SMILES: CC(C)(O)CO[C@]1(c2ccc(Cl)cc2)c2ccc(C(C)(C)O)cc2C(=O)N1Cc1ccc(Cl)cn1]

The title compound was prepared from 6-bromo-3-(4-chlorophenyl)-2-((5-chloropyridin-2-yl)methyl)-3-hydroxy-isoindolin-1-one (Example 6, step 1) in a similar manner to that described in Example 1, steps 2-4, using 2-methyl-1,2-propanediol instead of {1-[hydroxy($^2$H$_2$)methyl]cyclopropyl}($^2$H$_2$)methanol in step 2.

$^1$H NMR (400 MHz, CDCl$_3$): 8.33 (1H, d), 7.98 (1H, s), 7.76-7.72 (1H, m), 7.52 (1H, dd), 7.34 (1H, d), 7.24-7.18 (4H, m), 7.12 (1H, d), 4.48-4.47 (2H, m), 3.22 (1H, s), 3.06 (1H, d), 2.78 (1H, d), 1.78 (1H, s), 1.63 (6H, s), 1.26 (3H, s), 1.12 (3H, s). MS: [M+H]+=515.

Example 97 and Example 98: (3R)-3-(4-chlorophenyl)-2-[(5-chloropyridin-2-yl)methyl]-4-fluoro-3-(2-hydroxybutoxy)-6-(2-hydroxypropan-2-yl)-2,3-dihydro-1H-isoindol-1-one (*both isomers separated and isolated)

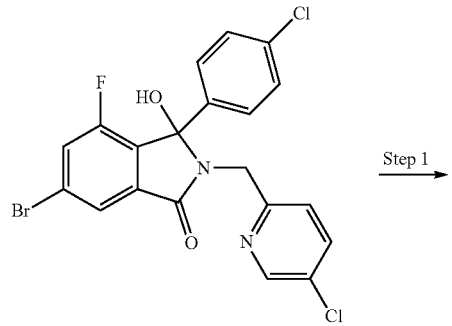

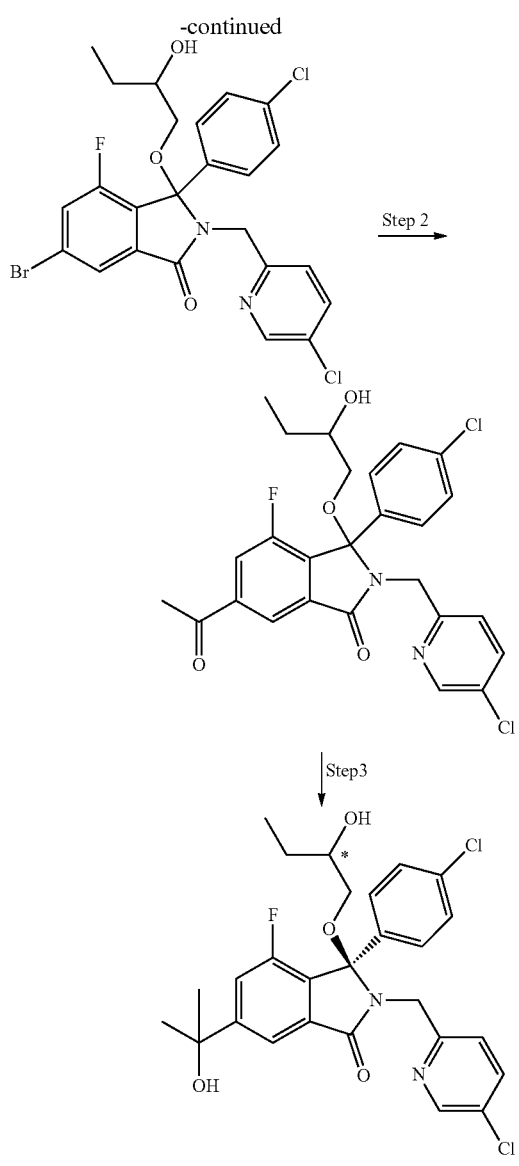

Example 97 and Example 98, Step 1: 6-Bromo-3-(4-chlorophenyl)-2-((5-chloropyridin-2-yl)methyl)-4-fluoro-3-(2-hydroxybutoxy)isoindolin-1-one The title compound (1.82 g, 3.28 mmol, 79%) was prepared from 6-bromo-3-(4-chloro-phenyl)-2-(5-chloro-pyridin-2-ylmethyl)-4-fluoro-3-hydroxy-2,3-dihydro-isoindol-1-one (Example 1, step 1) (2.00 g, 4.15 mmol) and 1,2-butanediol (0.74 mL, 8.30 mmol) in a similar manner to that described in Example 2, step 1. $^1$H NMR (400 MHz, CDCl$_3$): 8.38 (1H, dd), 7.84 (1H, dd), 7.59-7.54 (1H, m), 7.37-7.32 (2H, m), 7.31-7.23 (4H, m), 4.55 (0.5H, d), 4.48-4.37 (1H, m), 4.28 (0.5H, d), 3.85-3.77 (0.5H, m), 3.56 (0.5H, d), 3.51-3.44 (0.5H, m), 3.30 (0.5H, dd), 3.24-3.17 (1H, m), 3.08 (0.5H, dd), 2.96 (0.5H, dd), 1.57-1.36 (2H, m), 0.95-0.89 (3H, m) as a mix of diastereoisomers.

Example 97 and Example 98, Step 2: 6-Acetyl-3-(4-chlorophenyl)-2-((5-chloropyridin-2-yl)methyl)-3-(2-hydroxy-2-methylpropoxy)isoindolin-1-one The title compound (1.45 g, 2.80 mmol, 85%) was prepared from 6-bromo-3-(4-chlorophenyl)-2-((5-chloropyridin-2-yl)methyl)-4-fluoro-3-(2-hydroxybutoxy)isoindolin-1-one (1.82 g, 3.28 mmol) in a similar manner to that described in Example 1, step 3. ¹H NMR (400 MHz, CDCl₃): 8.38 (1H, dd), 8.24 (1H, dd), 7.81-7.78 (1H, m), 7.60-7.55 (1H, m), 7.35 (1H, d), 7.33-7.23 (4H, m), 4.62 (0.5H, d), 4.54-4.43 (1H, m), 4.34 (0.5H, d), 3.85-3.77 (0.5H, m), 3.73 (0.5H, d), 3.51-3.43 (0.5H, m), 3.40 (0.5H, d), 3.32 (0.5H, dd), 3.22 (0.5H, dd), 3.08 (0.5H, dd), 2.96 (0.5H, dd), 2.66 (3H, s), 1.58-1.30 (2H, m), 0.91 (3H, t) as a mix of diastereoisomers.

Example 97 and Example 98, Step 3: (3R)-3-(4-chlorophenyl)-2-[(5-chloropyridin-2-yl)methyl]-4-fluoro-3-(2-hydroxybutoxy)-6-(2-hydroxypropan-2-yl)-2,3-dihydro-1H-isoindol-1-one The title compounds were prepared from 6-acetyl-3-(4-chlorophenyl)-2-((5-chloropyridin-2-yl)methyl)-3-(2-hydroxy-2-methylpropoxy)isoindolin-1-one in a similar manner to that described in Example 1, step 4. The diastereoisomers were separated by chiral HPLC.

Example 97 (*Isomer 1)

¹H NMR (400 MHz, CDCl3:) 8.39 (1H, d), 7.77 (1H, d), 7.56 (1H, dd), 7.42-7.34 (2H, m), 7.30 (2H, d), 7.26 (2H, d), 4.58 (1H, d), 4.30 (1H, d), 3.51-3.44 (1H, m), 3.27 (1H, dd), 3.21 (1H, d), 2.97 (1H, dd), 1.80 (1H, s), 1.61-1.60 (6H, m), 1.54-1.41 (2H, m), 0.91 (3H, dd). MS: [M+H]+=533.

Example 98 (*Isomer 2)

¹H NMR (400 MHz, CDCl₃): 8.37 (1H, d), 7.76 (1H, d), 7.55 (1H, dd), 7.42-7.34 (2H, m), 7.29 (2H, d), 7.23 (2H, d), 4.49 (1H, d), 4.41 (1H, d), 3.82-3.76 (1H, m), 3.47 (1H, d), 3.20-3.07 (2H, m), 1.82 (1H, s), 1.61 (3H, s), 1.60 (3H, s), 1.43-1.36 (2H, m), 0.91 (3H, dd). MS: [M+H]+=533.

Example 99 and Example 100: 2-{2-[(1R)-1-(4-chlorophenyl)-2-[(5-chloropyridin-2-yl)methyl]-1-methoxy-3-oxo-2,3-dihydro-1H-isoindol-5-yl]-2-hydroxypropoxy}-N,N-dimethylacetamide (*both isomers separated and isolated)

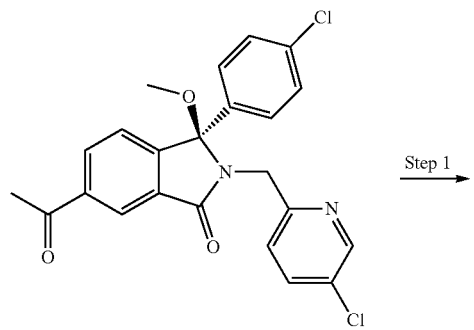

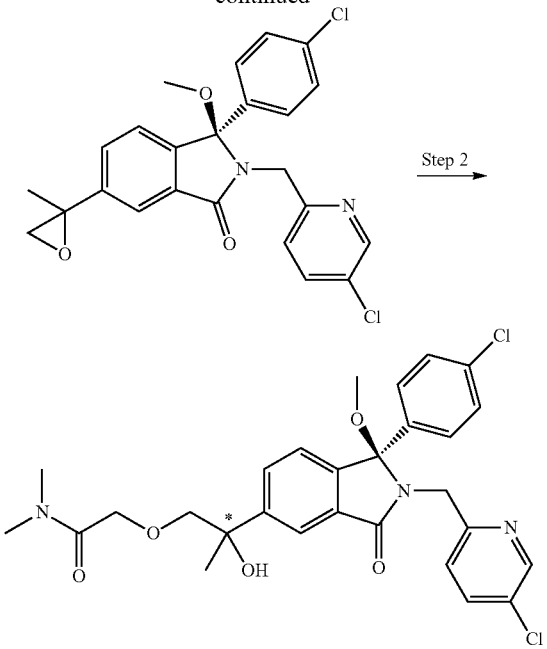

Example 99 and Example 100, Step 1: (3R)-3-(4-Chlorophenyl)-2-((5-chloropyridin-2-yl)methyl)-3-methoxy-6-(2-methyloxiran-2-yl)isoindolin-1-one The title compound (1.7 g, 3.73 mmol, 92%) was prepared from (R)-6-acetyl-3-(4-chlorophenyl)-2-((5-chloropyridin-2-yl)methyl)-3-methoxyisoindolin-1-one (Example 55 and Example 56, step 2) (1.79 g, 4.06 mmol) in a similar manner to that described in Example 22 and Example 23, step 2. ¹H NMR (400 MHz, CDCl₃): 8.34 (1H, dd), 7.96-7.96 (1H, m), 7.56-7.47 (2H, m), 7.18-7.12 (6H, m), 4.61 (1H, dd), 4.48 (1H, dd), 3.05-3.02 (1H, m), 2.83-2.82 (4H, m), 1.78 (3H, s).

Example 99 and Example 100, Step 2: 2-{2-[(1R)-1-(4-chlorophenyl)-2-[(5-chloropyridin-2-yl)methyl]-1-methoxy-3-oxo-2,3-dihydro-1H-isoindol-5-yl]-2-hydroxypropoxy}-N,N-dimethylacetamide To a solution of 2-hydroxy-N,N-dimethylacetamide (226 mg, 2.20 mmol) in DMSO (3 mL) was added KOH (12 mg, 0.22 mmol) and the reaction warmed to 60° C. for 1 hour before addition of (3R)-3-(4-chlorophenyl)-2-((5-chloropyridin-2-yl)methyl)-3-methoxy-6-(2-methyloxiran-2-yl)isoindolin-1-one (100 mg, 0.22 mmol). The reaction mixture was stirred for 88 hours under at 60° C. The reaction mixture was cooled, diluted with EtOAc (20 mL), washed with water (20 mL). The organic phase was dried (MgSO₄), filtered, concentrated in vacuo and purified by Biotage using 0-100% EtOAc in iso-hexane as eluent. Separation by chiral preparative LCMS gave the title compounds:

Example 99 *Faster Running Diastereoisomer (12 mg, 0.021 mmol, 10%)

¹H NMR (400 MHz, CDCl₃) 8.33 (1H, d), 8.00 (1H, d), 7.84 (1H, dd), 7.47 (1H, dd), 7.23-7.19 (3H, m), 7.16-7.10 (3H, m), 5.66 (1H, s), 4.59 (1H, d), 4.48 (1H, d), 4.21 (2H, d), 3.84 (1H, d), 3.69 (1H, d), 2.97 (3H, s), 2.87 (3H, s), 2.80 (3H, s), 1.55 (3H, s). MS: [M+H]+=558.

Example 100*Slower Running Diastereoisomer (12 mg, 0.021 mmol, 10%)

¹H NMR (400 MHz, CDCl₃): 8.34 (1H, d), 7.97 (1H, d), 7.87 (1H, dd), 7.47 (1H, dd), 7.25-7.19 (3H, m), 7.17-7.11 (3H, m), 5.72 (1H, s), 4.60 (1H, d), 4.46 (1H, d), 4.22-4.20 (2H, m), 3.82 (1H, d), 3.68 (1H, d), 2.97 (3H, s), 2.87 (3H, s), 2.80 (3H, s), 1.55 (3H, s). MS: [M+H]+=558.

Example 101: (3R)-3-(4-chlorophenyl)-2-[(5-chloro-pyridin-2-yl)methyl]-4-fluoro-3-{[1-(2-hydroxy-ethoxy)cyclopropyl]methoxy}-6-(2-hydroxypropan-2-yl)-2,3-dihydro-1H-isoindol-1-one added ethylbromoacetate (0.42 mL, 3.80 mmol) followed by sodiumbis(trimethylsilyl)amide (0.6M in toluene, 6.34 mL, 3.80 mmol). The reaction mixture was allowed to warm slowly to room temperature and stirred for a total of 4 hours. A saturated aqueous solution of NH₄CL (150 mL) was added and the mixture extracted with EtOAc (2×100 mL), dried (MgSO4), filtered concentrated in vacuo and purified by Biotage using 0-100% EtOAc in iso-hexane as eluent to furnish a white solid (1.44 g, 89%). ¹H NMR (400 MHz, CDCl₃): 8.32 (1H, d), 7.88 (1H, d), 7.50 (1H, dd), 7.36 (1H, dd), 7.23 (3H, d), 7.21-7.15 (2H, m), 4.50 (1H, d), 4.42 (1H, d), 4.29-4.11 (4H, m), 3.36 (1H, d), 3.22 (1H, d), 1.27 (3H, t), 0.98-0.93 (2H, m), 0.47-0.43 (2H, m).

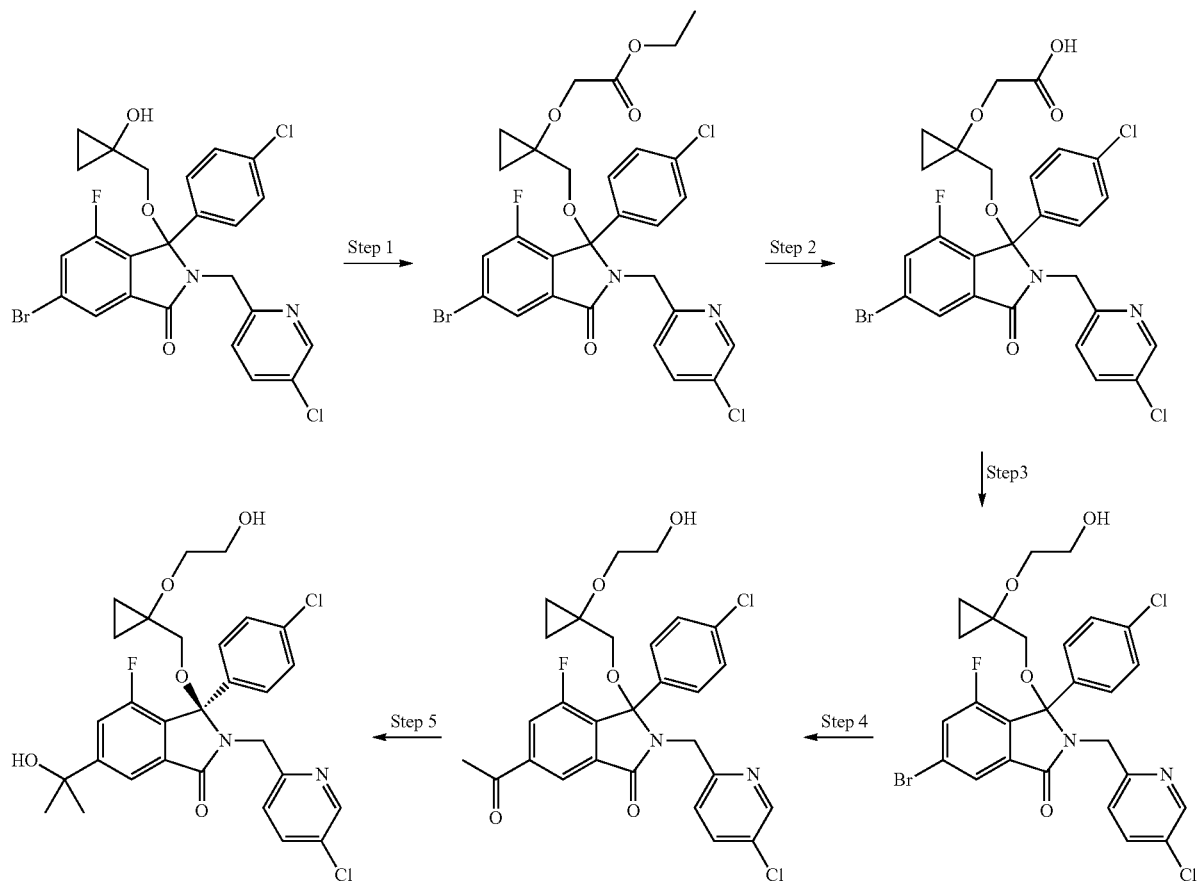

Example 101, Step 1: Ethyl 2-(1-(((5-bromo-1-(4-chlorophenyl)-2-((5-chloropyridin-2-yl)methyl)-7-fluoro-3-oxoisoindolin-1-yl)oxy)methyl)cyclopropoxy)acetate To a pre-cooled −78° C. solution of 6-bromo-3-(4-chlorophenyl)-2-((5-chloropyridin-2-yl)methyl)-4-fluoro-3-((1-hydroxycyclopropyl)methoxy)isoindolin-1-one (prepared from 6-bromo-3-(4-chloro-phenyl)-2-(5-chloro-pyridin-2-ylmethyl)-4-fluoro-3-hydroxy-2,3-dihydro-isoindol-1-one (Example 1, step 1) and 1-hydroxymethyl-cyclopropanol in a similar manner to that described in Example 3, step 2) (1.40 g, 2.54 mmol) in anh. THF (30 mL) under N₂ was Example 101, Step 2: 2-(1-(((5-Bromo-1-(4-chloro-phenyl)-2-((5-chloropyridin-2-yl)methyl)-7-fluoro-3-oxoisoindolin-1-yl)oxy)methyl)cyclopropoxy)acetic acid The title compound (1.18 g, 1.93 mmol, 85%) was prepared from ethyl 2-(1-(((5-bromo-1-(4-chlorophenyl)-2-((5-chloropyridin-2-yl)methyl)-7-fluoro-3-oxoisoindolin-1-yl)oxy)methyl)cyclopropoxy)acetate (1.44 g, 2.26 mmol) in a similar manner to that described in Example 65, step 2. ¹H NMR (400 MHz, CDCl₃): 8.33 (1H, d), 7.86 (1H, d), 7.57

(1H, dd), 7.35 (2H, dd), 7.21 (4H, s), 3.77-3.73 (2H, m), 3.64 (1H, d), 2.89 (1H, d), 1.88-1.83 (2H, m), 1.02-0.95 (2H, m), 0.59-0.42 (2H, m).

Example 101, Step 3: 6-Bromo-3-(4-chlorophenyl)-2-((5-chloropyridin-2-yl)methyl)-4-fluoro-3-((1-(2-hydroxyethoxy)cyclopropyl)methoxy)isoindolin-1-one The title compound (1.05 g, 1.76 mmol, 91%) was prepared from 2-(1-(((5-bromo-1-(4-chlorophenyl)-2-((5-chloropyridin-2-yl)methyl)-7-fluoro-3-oxoisoindolin-1-yl)oxy)methyl)cyclopropoxy)acetic acid (1.18 g, 1.93 mmol) in a similar manner to that described in Example 65, step 3. $^1$H NMR (400 MHz, CDCl$_3$): 8.32 (1H, d), 7.89 (1H, d), 7.50 (1H, dd), 7.36 (1H, dd), 7.26-7.19 (5H, m), 4.53 (1H, d), 4.47 (1H, d), 3.68-3.63 (4H, m), 3.36 (1H, d), 3.15 (1H, d), 2.09 (1H, s), 0.87-0.85 (2H, m), 0.45 (2H, m).

Example 101, Step 4: 6-Acetyl-3-(4-chlorophenyl)-2-((5-chloropyridin-2-yl)methyl)-4-fluoro-3-((1-(2-hydroxyethoxy)cyclopropyl)methoxy)isoindolin-1-one The title compound (250 mg, 0.45 mmol, 25%) was prepared from 6-bromo-3-(4-chlorophenyl)-2-((5-chloropyridin-2-yl)methyl)-4-fluoro-3-((1-(2-hydroxyethoxy)cyclopropyl)methoxy)isoindolin-1-one (1.05 g, 1.76 mmol) in a similar manner to that described in Example 1, step 3. $^1$H NMR (400 MHz, CDCl$_3$): 8.33 (1H, d), 8.27 (1H, d), 7.80 (1H, dd), 7.53-7.46 (1H, m), 7.26-7.13 (5H, m), 4.57 (1H, d), 4.51 (1H, d), 3.67-3.65 (4H, m), 3.40 (1H, d), 3.13 (1H, d), 2.67 (3H, s), 2.04 (1H, s), 0.88-0.84 (2H, m), 0.49-0.39 (2H, m).

Example 101, Step 5: (3R)-3-(4-chlorophenyl)-2-[(5-chloropyridin-2-yl)methyl]-4-fluoro-3-{[1-(2-hydroxyethoxy)cyclopropyl]methoxy}-6-(2-hydroxypropan-2-yl)-2,3-dihydro-1H-isoindol-1-one The title compound was isolated as the slowest running enantiomer (29 mg, 0.050 mmol, 11%) and prepared from 6-acetyl-3-(4-chlorophenyl)-2-((5-chloropyridin-2-yl)methyl)-4-fluoro-3-((1-(2-hydroxyethoxy)cyclopropyl)methoxy)isoindolin-1-one in a similar manner to that described in Example 1, step 4. $^1$H NMR (400 MHz, CDCl$_3$): 8.32 (1H, d), 7.80 (1H, d), 7.49 (1H, dd), 7.41 (1H, dd), 7.28-7.18 (5H, m), 4.56 (1H, d), 4.49 (1H, d), 3.67-3.65 (4H, m), 3.30 (1H, d), 3.20 (1H, d), 2.16 (1H, dd), 1.83 (1H, s), 1.62 (3H, s), 1.61 (3H, s), 0.84 (2H, s), 0.46-0.41 (2H, m). MS: [M+H]+=575.

Example 102 and Example 103: (3R)-3-(4-chlorophenyl)-2-[(5-chloropyridin-2-yl)methyl]-6-[2-hydroxy-1-(2-hydroxyethoxy)propan-2-yl]-3-methoxy-2,3-dihydro-1H-isoindol-1-one (*both isomers separated and isolated)

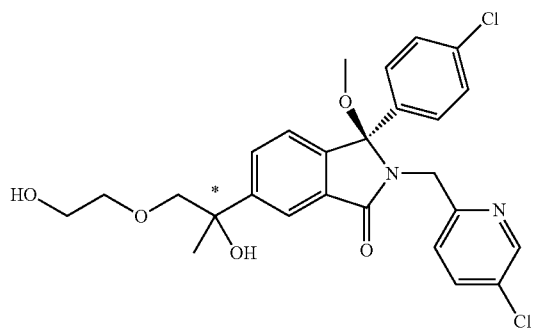 [SMILES: CO[C@]1(c2ccc(Cl)cc2)c2ccc(C(C)(O)COCCO)cc2C(=O)N1Cc1ccc(Cl)cn1]

The title compounds were prepared from (3R)-3-(4-chlorophenyl)-2-((5-chloropyridin-2-yl)methyl)-3-methoxy-6-(2-methyloxiran-2-yl)isoindolin-1-one (Example 99 and Example 100, step 1) (75 mg, 0.16 mmol) in a similar manner to that described in Example 99 and Example 100, step 2 using ethylene glycol instead of 2-hydroxy-N,N-dimethylacetamide.

Example 102, *Fast Eluting Diastereoisomer (10 mg)

$^1$H NMR (400 MHz, CDCl$_3$) 8.33 (1H, d), 8.02 (1H, d), 7.72 (1H, dd), 7.47 (1H, dd), 7.24-7.11 (6H, m), 4.60 (1H, d), 4.47 (1H, d), 3.75-3.60 (6H, m), 3.41 (1H, s), 2.81 (3H, s), 2.28-2.19 (1H, m), 1.57 (3H, s). MS: [M+H]+=517

Example 103, *Slow Eluting Diastereoisomer (9 mg)

$^1$H NMR (400 MHz, CDCl$_3$) 8.34 (1H, d), 8.01 (1H, d), 7.72 (1H, dd), 7.47 (1H, dd), 7.24-7.11 (6H, m), 4.60 (1H, d), 4.47 (1H, d), 3.75-3.60 (6H, m), 3.38 (1H, s), 2.81 (3H, s), 2.18 (1H, s), 1.57 (3H, s). MS: [M+H]+=517.

Example 104 and Example 105: (3R)-3-(4-chlorophenyl)-2-[(5-chloropyridin-2-yl)methyl]-6-[2-hydroxy-1-(piperazin-1-yl)propan-2-yl]-3-methoxy-2,3-dihydro-1H-isoindol-1-one (*both isomers separated and isolated)

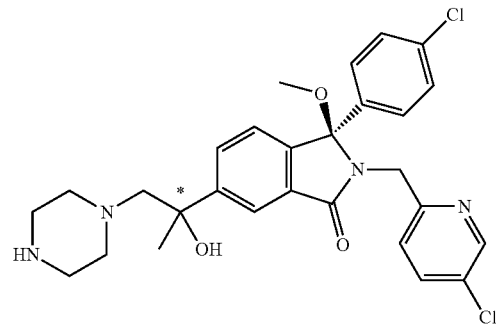 [SMILES: CO[C@]1(c2ccc(Cl)cc2)c2ccc(C(C)(O)CN3CCNCC3)cc2C(=O)N1Cc1ccc(Cl)cn1]

(3R)-3-(4-Chlorophenyl)-2-((5-chloropyridin-2-yl)methyl)-3-methoxy-6-(2-methyloxiran-2-yl)isoindolin-1-one (Example 99 and Example 100, step 1) (100 mg, 0.22 mmol), piperazine (473 mg, 5.50 mmol) were stirred in anhydrous methanol (2.5 mL) in a microwave vial. The tube was purged with nitrogen, sealed then the reaction was stirred at 60° C. (thermal heating) for 18 hours. The reaction was allowed to cool then the volatiles were removed under reduced pressure. The resulting residue was was dissolved in ethyl acetate (10 mL), washed with water (5 mL), passed through a phase separation cartridge then concentrated under reduced pressure. The residue was purified by Biotage Flashmaster Personal (2 gram silica cartridge) eluting with 5% 7N methanolic ammonia in dichloromethane to afford the diastereomeric mixture as colourless oil (60 mg, 0.11 mmol, 50%). Purification by chiral preparative LCMS gave Example 104 as a colourless solid (5 mg) as the *first eluting diastereoisomer and Example 105 as a colourless solid (5 mg) as the *second eluting diastereoisomer. $^1$H NMR identical for both diastereoisomers. $^1$H NMR (400 MHz, CDCl$_3$): 8.34 (1H, d), 7.96 (1H, d), 7.72 (1H, dd), 7.47 (1H, dd), 7.24-7.14 (5H, m), 7.10 (1H, d), 4.60 (1H, d), 4.46 (1H, d), 2.85-2.70 (8H, m), 2.65 (1H, d), 2.49-2.39 (2H, m), 2.30-2.23 (2H, m), 1.50 (3H, s). MS: [M+H]+=541

The following compounds were prepared in a similar manner:

Example 106 and Example 107: (3R)-3-(4-chlorophenyl)-2-[(5-chloropyridin-2-yl)methyl]-6-[2-hydroxy-1-(morpholin-4-yl) propan-2-yl]-3-methoxy-2,3-dihydro-1H-isoindol-1-one (*both isomers separated and isolated)

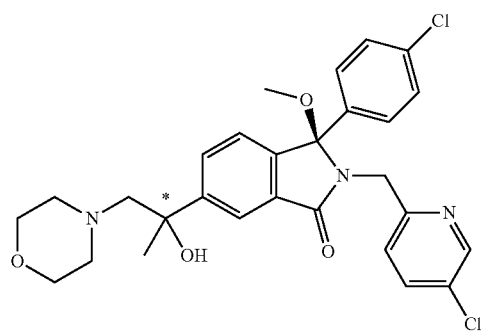 [SMILES: CO[C@]1(c2ccc(Cl)cc2)c2ccc(C(C)(O)CN3CCOCC3)cc2C(=O)N1Cc1ccc(Cl)cn1]

The title compounds were prepared in a similar manner that described in Example 104 and Example 105 using morpholine instead of piperazine. Purification by chiral preparative LCMS gave Example 106 as a colourless solid as the *first eluting diastereoisomer and Example 107 as a colourless solid as the *second eluting diastereoisomer. $^1$H NMR identical for both diastereoisomers. $^1$H NMR (400 MHz, CDCl$_3$): 8.34 (1H, d), 7.99 (1H, d), 7.70 (1H, dd), 7.48 (1H, dd), 7.25-7.14 (5H, m), 7.11 (1H, d), 4.60 (1H, d), 4.46 (1H, d), 4.32 (1H, s), 3.61-3.55 (4H, m), 2.84 (1H, d), 2.79 (3H, s), 2.67 (1H, d), 2.47-2.39 (2H, m), 2.32-2.27 (2H, m), 1.50 (3H, s). MS: [M+H]+=542

Example 108 and Example 109: (3R)-3-(4-chlorophenyl)-2-[(5-chloropyridin-2-yl)methyl]-6-[2-hydroxy-1-(methylamino)propan-2-yl]-3-methoxy-2,3-dihydro-1H-isoindol-1-one (*both isomers separated and isolated)

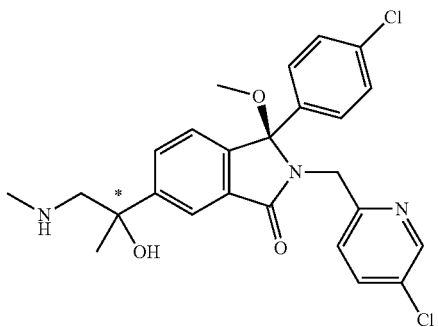 [SMILES: CNCC(C)(O)c1ccc2c(c1)C(=O)N(Cc1ccc(Cl)cn1)[C@@]2(OC)c1ccc(Cl)cc1]

The title compounds were prepared in a similar manner that described in Example 104 and Example 105 using methylamine instead of piperazine. Purification by chiral preparative LCMS gave Example 108 as a colourless solid as the *first eluting diastereoisomer and Example 109 as a colourless solid as the* second eluting diastereoisomer. $^1$H NMR identical for both diastereoisomers.

$^1$H NMR (400 MHz, CDCl$_3$) 8.34 (1H, d), 7.94 (1H, d), 7.74 (1H, dd), 7.47 (1H, dd), 7.25-7.10 (6H, m), 4.61 (1H, d), 4.47 (1H, d), 3.06 (1H, d), 2.81 (3H, s), 2.72 (1H, d), 2.39 (3H, s), 1.49 (3H, s).

Example 110 and Example 111: (3R)-3-(4-chlorophenyl)-2-[(5-chloropyridin-2-yl)methyl]-6-[1-(cyclopropylamino)-2-hydroxypropan-2-yl]-3-methoxy-2,3-dihydro-1H-isoindol-1-one (*both isomers separated and isolated)

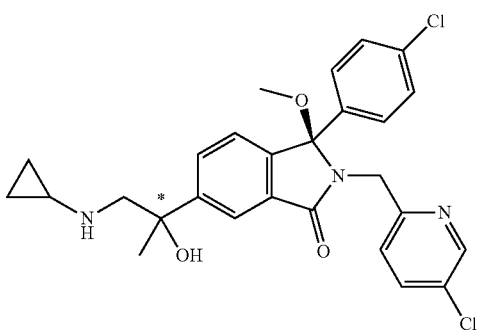 [SMILES: CO[C@]1(c2ccc(Cl)cc2)c2ccc(C(C)(O)CNC3CC3)cc2C(=O)N1Cc1ccc(Cl)cn1]

The title compounds were prepared in a similar manner that described in Example 104 and Example 105 using cyclopropylamine instead of piperazine. Purification by chiral preparative LCMS gave Example 110 as the *first eluting diastereoisomer and Example 111 as a as the *second eluting diastereoisomer. $^1$H NMR identical for both diastereoisomers.

$^1$H NMR (400 MHz, CDCl$_3$): 8.34 (1H, d), 7.95 (1H, d), 7.70 (1H, dd), 7.47 (1H, dd), 7.19-7.08 (6H, 6), 4.60 (1H, d), 4.47 (1H, d), 3.90 (1H, bs), 3.22 (1H, d), 2.88 (1H, d), 2.81 (3H, s), 2.16-2.09 (1H, m), 1.48 (3H, s), 0.45-0.25 (4H, m). MS: [M+H]+=512

Example 112 and Example 113: (3R)-3-(4-chlorophenyl)-2-[(5-chloropyridin-2-yl)methyl]-6-[2-hydroxy-1-(4-methyl-3-oxopiperazin-1-yl)propan-2-yl]-3-methoxy-2,3-dihydro-1H-isoindol-1-one (*both isomers separated and isolated)

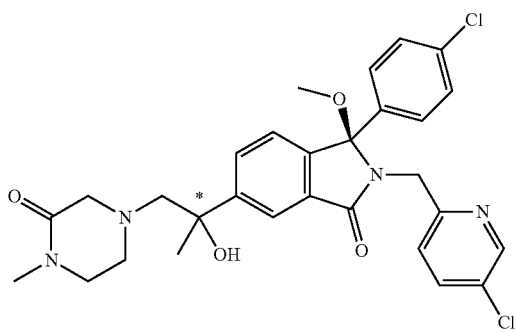 [SMILES: CO[C@]1(c2ccc(Cl)cc2)c2ccc(C(C)(O)CN3CCN(C)C(=O)C3)cc2C(=O)N1Cc1ccc(Cl)cn1]

The title compounds were prepared in a similar manner that described in Example 104 and Example 105 using 1-methylpiperazine-2-one instead of piperazine. Purification by chiral preparative LCMS gave Example 112 as the *first eluting diastereoisomer and Example 113 as a as the *second eluting diastereoisomer. ¹H NMR identical for both diastereoisomers. ¹H NMR (400 MHz, CDCl₃): 8.34 (1H, d), 7.99 (1H, d), 7.68 (1H, dd), 7.47 (1H, dd), 7.24-7.11 (6H, m), 4.59 (1H, d), 4.48 (1H, d), 3.79 (1H, s), 3.23-3.04 (3H, m), 2.90-2.70 (6H, m), 2.81 (3H, s), 2.77-2.60 (3H, m), 1.53 (3H, s). MS: [M+H]+=569

Example 114 and Example 115: N-{2-[(1R)-1-(4-chlorophenyl)-2-[(5-chloropyridin-2-yl)methyl]-1-methoxy-3-oxo-2,3-dihydro-1H-isoindol-5-yl]-2-hydroxypropyl}acetamide (*both isomers separated and isolated)

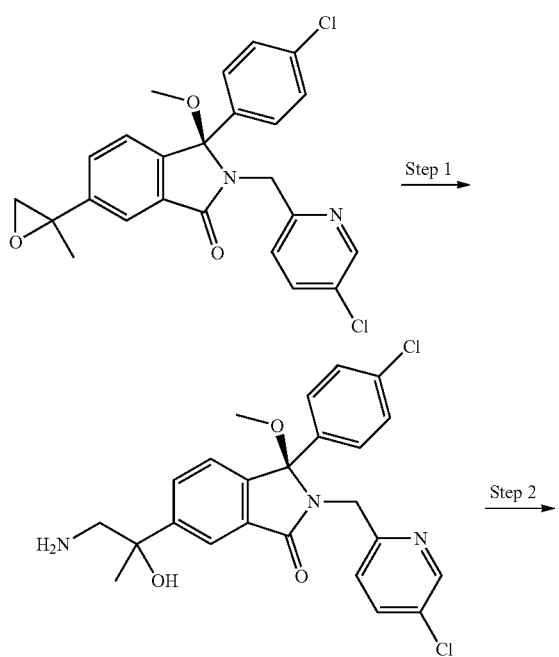

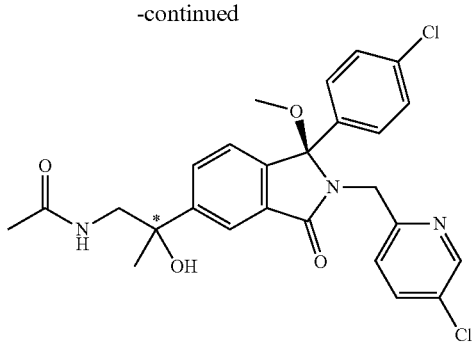

Example 114 and Example 115: step 1: (3R)-6-(1-Amino-2-hydroxypropan-2-yl)-3-(4-chlorophenyl)-2-((5-chloropyridin-2-yl)methyl)-3-methoxyisoindolin-1-one (3R)-3-(4-Chlorophenyl)-2-((5-chloropyridin-2-yl)methyl)-3-methoxy-6-(2-methyloxiran-2-yl)isoindolin-1-one (Example 99 and Example 100, step 1) (100 mg, 0.22 mmol) and 7N methanolic ammonia (5 mL, 35 mmol) were placed in a microwave vial. The tube was purged with nitrogen, sealed then stirred at 60° C. (thermal heating) for 18 hours. The reaction was allowed to cool then the volatiles were removed under to afford the title compound as a colourless oil (104 mg, 0.22 mmol, 100%). ¹H NMR (400 MHz, CDCl₃): 8.34-8.34 (1H, m), 7.96-7.94 (1H, m), 7.76-7.66 (1H, m), 7.52 (1H, s), 7.25-7.11 (6H, m), 4.61 (1H, dd), 4.47 (1H, dd), 3.99 (1H, d), 3.12 (1H, dd,), 2.88-2.83 (m, 1H), 2.81 (3H, s), 1.51 (3H, d). Material contained minor impurities but used directly in the next step.

Example 114 and Example 115, Step 2: N-{2-[(1R)-1-(4-chlorophenyl)-2-[(5-chloropyridin-2-yl)methyl]-1-methoxy-3-oxo-2,3-dihydro-1H-isoindol-5-yl]-2-hydroxypropyl}acetamide HATU (100 mg, 0.26 mmol), was stirred in dimethyl formamide (2 mL) under an atmosphere of nitrogen at room temperature then glacial acetic acid (14 mg, 14 uL, 0.24 mmol) was added followed by Hunig's base (114 mg, 156 uL, 0.88 mmol) and stirred for 30 min. A solution of (3R)-6-(1-amino-2-hydroxypropan-2-yl)-3-(4-chlorophenyl)-2-((5-chloropyridin-2-yl)methyl)-3-methoxyisoindolin-1-one (104 mg, 0.22 mmol) in dimethyl formamide (2 mL) was added at room temperature. The reaction was allowed to stir for 18 h then evaporated under reduced pressure. The residue was dissolved in ethyl (20 mL) acetate, washed with 1M aqueous hydrochloric acid (10 mL), saturated aqueous sodium hydrogen carbonate solution (10 mL), dried (MgSO₄) and concentrated under reduced pressure. The residue was purified by Biotage Flashmaster Personal (5 gram silica cartridge) eluting with 0-5% methanol in ethyl acetate to afford the diastereomeric mixture as a colourless oil (90 mg, 0.17 mmol, 80%). Purification by chiral preparative gave Example 112 as a colourless solid (7 mg) as the *first eluting diastereoisomer and Example 113 as a colourless solid (8 mg) as the *second eluting diastereoisomer. ¹H NMR identical for both diastereoisomers. ¹H NMR (400 MHz, CDCl₃): 8.35 (1H, d), 7.97 (1H, d), 7.75 (1H, dd), 7.48 (1H, dd), 7.23-7.13 (6H, m), 5.87 (1H, dd), 4.61

(1H, d), 4.46 (1H, d), 4.12-4.12 (1H, m), 3.70 (1H, dd,), 3.49 (1H, dd), 2.81 (3H, s), 1.95 (3H, s), 1.58 (3H, s). MS: [M+H]+=514

Example 116 and Example 117: (3R)-6-[1-(4-acetylpiperazin-1-yl)-2-hydroxypropan-2-yl]-3-(4-chlorophenyl)-2-[(5-chloropyridin-2-yl)methyl]-3-methoxy-2,3-dihydro-1H-isoindol-1-one (*both isomers separated and isolated)

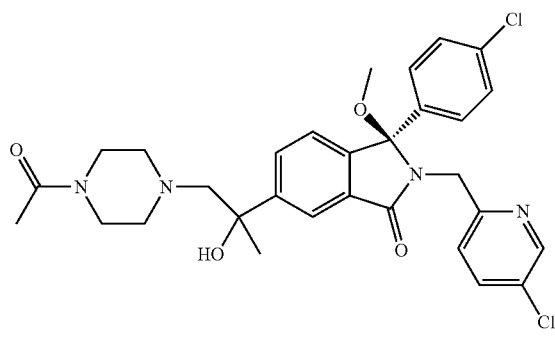 [SMILES: CO[C@]1(c2ccc(Cl)cc2)c2ccc(C(C)(O)CN3CCN(C(C)=O)CC3)cc2C(=O)N1Cc1ccc(Cl)cn1]

The title compounds were prepared in a similar manner that described in Example 104 and Example 105 using N-acetyl-piperazine instead of piperazine. Purification by chiral preparative LCMS gave Example 116 (59.0 mg, 33%) as the *first eluting diastereoisomer and Example 117 (54.0 mg, 30%) as a as the *second eluting diastereoisomer.

Example 116

$^1$H NMR (400 MHz, CDCl$_3$) 8.35 (1H, dd), 7.96 (1H, dd), 7.72 (1H, dd), 7.48 (1H, dd), 7.24-7.18 (5H, m), 7.11 (1H, dd), 4.60 (1H, d), 4.46 (1H, d), 4.11 (1H, s), 3.56-3.29 (4H, m), 2.86 (1H, d), 2.78 (3H, s), 2.71 (1H, d), 2.52-2.44 (1H, m), 2.38-2.33 (2H, m), 2.27-2.19 (1H, m), 2.04 (3H, s), 1.53 (3H, s). MS: [M+H]+=583.

Example 117

$^1$H NMR (400 MHz, CDCl$_3$) 8.35 (1H, dd), 7.99 (1H, dd), 7.69 (1H, dd), 7.49 (1H, dd), 7.25-7.15 (5H, m), 7.11 (1H, dd), 4.60 (1H, d), 4.47 (1H, d), 4.11 (1H, s), 3.54-3.44 (2H, m), 3.38-3.33 (2H, m), 2.84 (1H, d), 2.79 (3H, s), 2.71 (1H, d), 2.51-2.44 (1H, m), 2.42-2.31 (2H, m), 2.29-2.22 (1H, m), 2.04 (3H, s), 1.52 (3H, s). MS: [M+H]+=583.

Example 118 and Example 119: 6-{[(1R)-1-(4-chlorophenyl)-7-fluoro-1-[(2-hydroxycyclopentyl)oxy]-5-(2-hydroxypropan-2-yl)-3-oxo-2,3-dihydro-1H-isoindol-2-yl]methyl}pyridine-3-carbonitrile

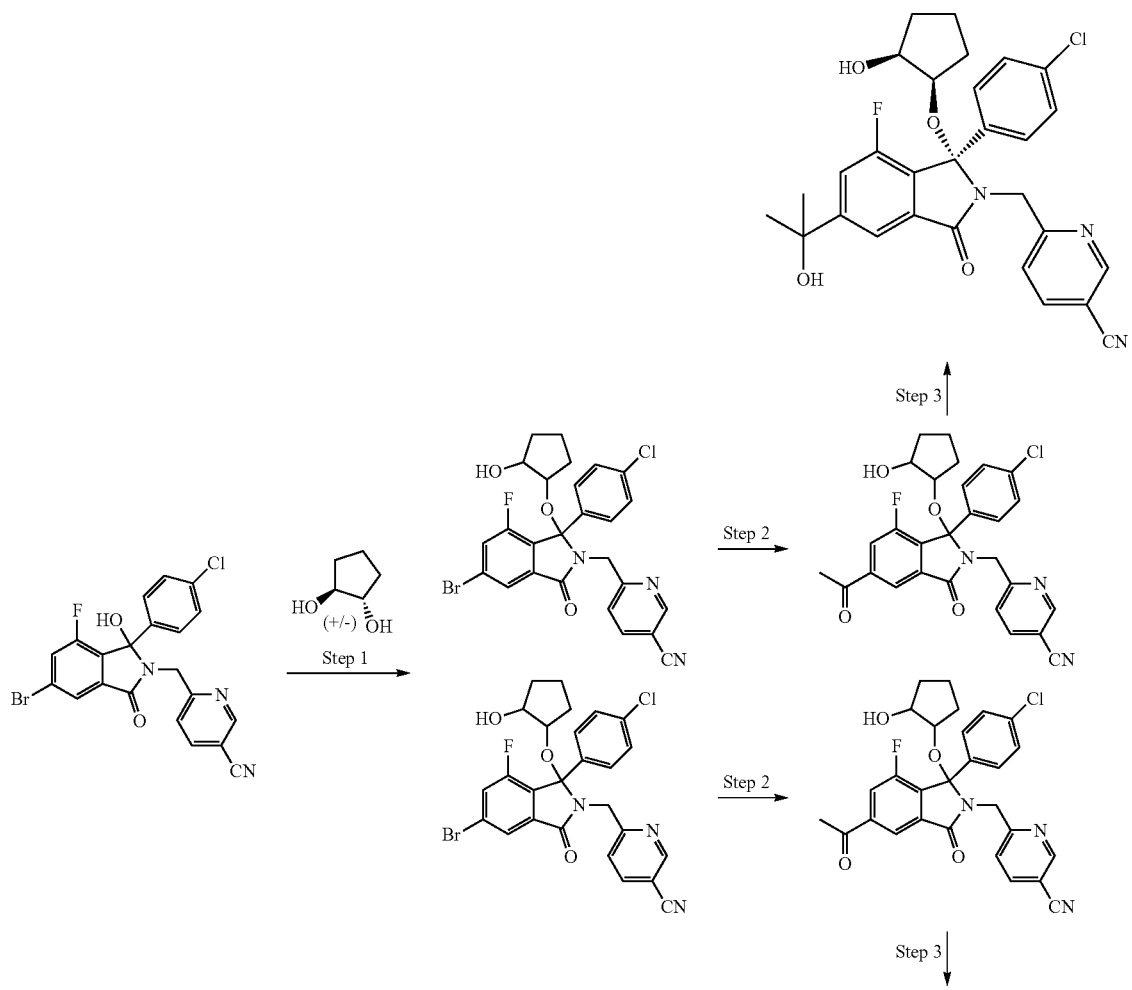

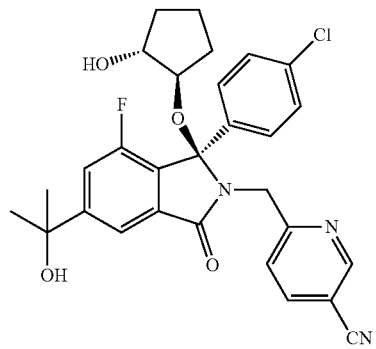

Example 118, Step 1: 6-((5-Bromo-1-(4-chlorophenyl)-7-fluoro-1-((2-hydroxycyclopentyl)oxy)-3-oxoisoindolin-2-yl)methyl)nicotinonitrile 6-((5-Bromo-1-(4-chlorophenyl)-7-fluoro-1-((2-hydroxycyclopentyl)oxy)-3-oxoisoindolin-2-yl)methyl)nicotinonitrile (268 mg, 15%) was prepared from 6-((5-bromo-1-(4-chlorophenyl)-7-fluoro-1-hydroxy-3-oxoisoindolin-2-yl)methyl)nicotinonitrile (Example 3, step 1) (1.50 g, 3.17 mmol) in a similar manner to that described in Example 1, step 2 using (+/−)-trans cyclopentane-1,2-diol instead of {1-[hydroxy($^2$H$_2$)methyl]cyclopropyl}($^2$H$_2$)methanol. The two diastereomers were separated via chromatography using a Biotage, 0-60% EtOAc/DCM, to give the title compound as the fastest eluting diastereomer. $^1$H NMR (400 MHz, CDCl$_3$): 8.67 (1H, d), 7.85-7.81 (2H, m), 7.39-7.34 (2H, m), 7.23-7.17 (4H, m), 4.71 (1H, d), 4.37 (1H, d), 4.26-4.19 (1H, m), 3.79-3.70 (1H, m) 1.80-1.30 (6H, m).

Example 118, Step 2: 6-((5-Acetyl-1-(4-chlorophenyl)-7-fluoro-1-((2-hydroxycyclopentyl)oxy)-3-oxoisoindolin-2-yl)methyl)nicotinonitrile The title compound (130 mg, 54%) was prepared from 6-((5-bromo-1-(4-chlorophenyl)-7-fluoro-1-((2-hydroxycyclopentyl)oxy)-3-oxoisoindolin-2-yl)methyl)nicotinonitrile (268 mg, 0.47 mmol) in a similar manner to that described in Example 1, step 3. $^1$H NMR (400 MHz, CDCl$_3$): 8.57 (1H, dd), 8.30 (1H, d), 7.82 (1H, dd), 7.73 (1H, dd), 7.57-7.53 (1H, m), 7.16 (2H, d), 7.10 (2H, d), 4.87 (1H, d), 4.43 (1H, d), 4.15-4.09 (1H, m), 3.55-3.49 (1H, m), 2.68 (3H, s), 2.03-1.95 (1H, m), 1.79-1.69 (2H, m), 1.65-1.59 (1H, m), 1.48-1.24 (2H, m).

Example 118, Step 3: 6-{[(1R)-1-(4-chlorophenyl)-7-fluoro-1-[(2-hydroxycyclopentyl)oxy]-5-(2-hydroxypropan-2-yl)-3-oxo-2,3-dihydro-1H-isoindol-2-yl]methyl}pyridine-3-carbonitrile The title compound (30 mg, 22%) was prepared from 6-((5-acetyl-1-(4-chlorophenyl)-7-fluoro-1-((2-hydroxycyclopentyl)oxy)-3-oxoisoindolin-2 yl)methyl)nicotinonitrile (130 mg, 0.25 mmol) in a similar manner to that described in Example 1, step 4. $^1$H NMR (400 MHz, CDCl$_3$): 8.56 (1H, dd), 7.85 (1H, d), 7.70 (1H, dd), 7.47 (1H, dd), 7.26-7.24 (1H, m), 7.16 (2H, d), 7.08 (2H, d), 4.86 (1H, d), 4.42 (1H, d), 4.17-4.09 (1H, m), 3.51 (1H, dd), 2.07-1.95 (1H, m), 1.88 (1H, s), 1.80-1.68 (2H, m), 1.65-1.63 (6H, m,), 1.51-1.41 (2H, m), 1.25 (1H, d). MS: [M+H]$^+$=536.

Example 119, Step 1: 6-((5-Bromo-1-(4-chlorophenyl)-7-fluoro-1-((2-hydroxycyclopentyl)oxy)-3-oxoisoindolin-2-yl)methyl)nicotinonitrile 6-((5-Bromo-1-(4-chlorophenyl)-7-fluoro-1-((2-hydroxycyclopentyl)oxy)-3-oxoisoindolin-2-yl)methyl)nicotinonitrile (1.32 g, 74%) was prepared from 6-((5-bromo-1-(4-chlorophenyl)-7-fluoro-1-hydroxy-3-oxoisoindolin-2-yl)methyl)nicotinonitrile (Example 3, step 1) (1.50 g, 3.17 mmol) in a similar manner to that described in Example 1, step 2, using (+/−)-trans cyclopentane-1,2-diol instead of {1-[hydroxy($^2$H$_2$)methyl]cyclopropyl}($^2$H$_2$)methanol. The two diastereomers were separated with a Biotage, 0-60% EtOAc/DCM, to give the title compound as the slowest eluting diastereomer. $^1$H NMR (400 MHz, CDCl$_3$): 8.56 (1H, d), 7.92 (1H, d), 7.72 (1H, dd), 7.46-7.38 (1H, m), 7.23 (1H, d), 7.15 (2H, d), 7.09 (2H, d), 4.85 (1H, d), 4.40 (1H, d), 4.15-4.08 (1H, m), 3.51 (1H, dd), 2.03-1.94 (1H, m), 1.81-1.58 (3H, m), 1.53-1.42 (3H, m).

Example 119, Step 2: 6-((5-Acetyl-1-(4-chlorophenyl)-7-fluoro-1-((2-hydroxycyclopentyl)oxy)-3-oxoisoindolin-2-yl)methyl)nicotinonitrile The title compound was (323 mg, 27%) was prepared from 6-((5-bromo-1-(4-chlorophenyl)-7-fluoro-1-((2-hydroxycyclopentyl)oxy)-3-oxoisoindolin-2-yl)methyl)nicotinonitrile (1.32 g, 2.33 mmol) in a similar manner to that described in Example 1, step 3. $^1$H NMR (400 MHz, CDCl$_3$): 8.65 (1H, d), 8.22 (1H, d), 7.84-7.77 (2H, m), 7.40 (1H, d), 7.23 (2H, d), 7.19 (2H, d), 4.74 (1H, d), 4.42 (1H, d), 4.22-4.16 (1H, m), 3.78-3.71 (1H, m), 3.57 (1H, d), 2.67 (3H, s), 2.04-1.95 (1H, m), 1.73-1.32 (5H, m).

Example 119, Step 3: 6-{[(1R)-1-(4-chlorophenyl)-7-fluoro-1-[(2-hydroxycyclopentyl)oxy]-5-(2-hydroxypropan-2-yl)-3-oxo-2,3-dihydro-1H-isoindol-2-yl]methyl}pyridine-3-carbonitrile The title compound (48 mg, 14%) was prepared from 6-((5-acetyl-1-(4-chlorophenyl)-7-fluoro-1-((2-hydroxycyclopentyl)oxy)-3-oxoisoindolin-2-yl)methyl)nicotinonitrile (323 mg, 0.62 mmol) in a similar manner to that described in Example 1, step 4. $^1$H NMR (400 MHz, CDCl$_3$): 8.64 (1H, d), 7.81 (1H, dd), 7.75 (1H, d), 7.42-7.38 (2H, m), 7.24 (2H, d), 7.18 (2H, d), 4.70 (1H, d), 4.39 (1H, d), 4.21-4.14 (1H, m), 3.77-3.71 (1H, m), 3.49 (1H, s), 2.05-1.91 (2H, m), 1.78-1.32 (m, 11H). MS: [M+H]$^+$=536.

Example 120 and Example 121: (3R)-3-(4-chlorophenyl)-2-[(5-chloropyridin-2-yl)methyl]-6-[1-hydroxy-1-(pyrimidin-5-yl)ethyl]-3-methoxy-2,3-dihydro-1H-isoindol-1-one (*both isomers separated and isolated)

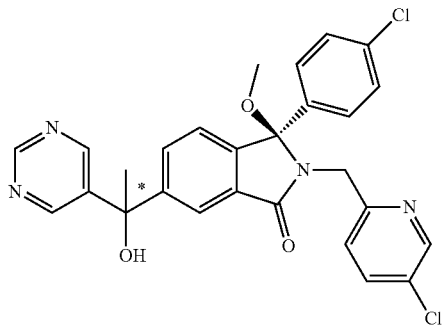 [SMILES: CO[C@]1(c2ccc(Cl)cc2)c2ccc(C(C)(O)c3cncnc3)cc2C(=O)N1Cc1ccc(Cl)cn1]

To a round bottomed flask was added (R)-6-acetyl-3-(4-chlorophenyl)-2-((5-chloropyridin-2-yl)methyl)-3-methoxyisoindolin-1-one (Example 55 and Example 56, step 2) (150 mg, 0.34 mmol). The flask was flushed with $N_2$ and THF (1 mL) was added followed by $LaCl_3.2LiCl$ (204 □L, 0.34 mmol, 0.6M, THF solution), the solution was stirred for 1 h 30 mins. During this time a THF 1:1 $Et_2O$ (3 mL) solution of 5-bromopyrimidine (270 mg, 1.70 mmol) was cooled to −110° C. and n-BuLi (1.06 mL, 1.70 mmol, 2.5M in hexanes) was added dropwise. The reaction was stirred at −110° C. for 1 h. The solution of ketone was added to the lithiated pyrimidine and stirred for 30 mins at −110° C. The reaction was warmed to RT and quenched via the addition of ammonium chloride solution (10 mL). The crude mixture was extracted with EtOAc (2×10 mL) and the organics were dried with $MgSO_4$, filtered and concentrated in vacuo. The two diastereomers were purified using a Biotage, 40-100% EtOAc/DCM, to give the title compound as a colourless oil, which was separated via chiral preparative SFC:

Example 120 (*Fastest Eluting Isomer) (13 mg, 7%)

$^1$H NMR (400 MHz, $CDCl_3$): 9.13 (1H, s), 8.80 (2H, s), 8.34 (1H, d), 8.01 (1H, d), 7.64 (1H, dd), 7.48 (1H, dd), 7.24-7.14 (6H, m), 4.60 (1H, d), 4.46 (1H, d), 2.81 (3H, s), 2.46 (1H, s), 2.08 (3H, s). MS: $[M+H]^+$=521.

Example 121 (*Slowest Eluting Isomer) (15 mg, 8%)

$^1$H NMR (400 MHz, $CDCl_3$): 9.13 (1H, s), 8.80 (2H, s), 8.34 (1H, d), 8.02 (1H, d), 7.64 (1H, dd), 7.48 (1H, dd), 7.23-7.14 (6H, m), 4.60 (1H, d), 4.46 (1H, d), 2.81 (3H, s), 2.49 (1H, s), 2.08 (3H, s). MS: $[M+H]^+$=521.

Example 122 and Example 123: (3R)-3-(4-chlorophenyl)-2-[(5-chloropyridin-2-yl)methyl]-6-[1-hydroxy-1-(pyridin-4-yl)ethyl]-3-methoxy-2,3-dihydro-1H-isoindol-1-one (*both isomers separated and isolated)

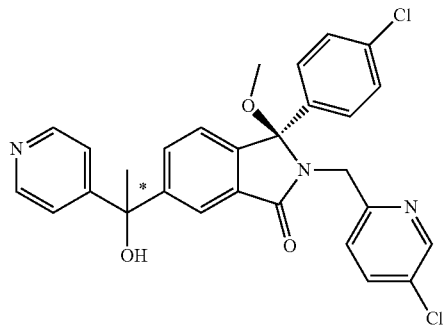 [SMILES: CO[C@]1(c2ccc(Cl)cc2)c2ccc(C(C)(O)c3ccncc3)cc2C(=O)N1Cc1ccc(Cl)cn1]

The title compounds were prepared from (R)-6-acetyl-3-(4-chlorophenyl)-2-((5-chloropyridin-2-yl)methyl)-3-methoxyisoindolin-1-one (Example 55 and Example 56, step 2) (150 mg, 0.34 mmol) in a similar manner to that described in Example 77 and Example 78. Chiral separation afforded:

Example 122 (*Fastest Eluting Isomer) (25 mg, 11%)

$^1$H_NMR (400 MHz, $CDCl_3$): 8.57-8.55 (2H, m), 8.34 (1H, d), 8.00 (1H, d), 7.62 (1H, dd), 7.48 (1H, dd), 7.36-7.34 (2H, m), 7.24-7.20 (2H, m), 7.18 (3H, d), 7.11 (1H, d), 4.60 (1H, d), 4.45 (1H, d), 2.80 (3H, s), 2.43 (1H, s), 2.01 (3H, s). MS: $[M+H]^+$=520.

Example 123 (*Slowest Eluting Isomer) (25 mg, 14%)

$^1$H NMR (400 MHz, $CDCl_3$): 8.58-8.55 (2H, m), 8.34 (1H, d), 8.00 (1H, d), 7.62 (1H, dd), 7.47 (1H, dd), 7.36-7.34 (2H, m), 7.24-7.14 (5H, m), 7.11 (1H, d), 4.60 (1H, d), 4.46 (1H, d), 2.80 (3H, s), 2.36 (1H, s), 2.01 (3H, s). MS: $[M+H]^+$=520.

Example 124: 6-{[(1R)-1-(4-chlorophenyl)-7-fluoro-1-[(2-hydroxycyclopentyl)oxy]-5-(2-hydroxypropan-2-yl)-3-oxo-2,3-dihydro-1H-isoindol-2-yl]methyl}pyridine-3-carbonitrile

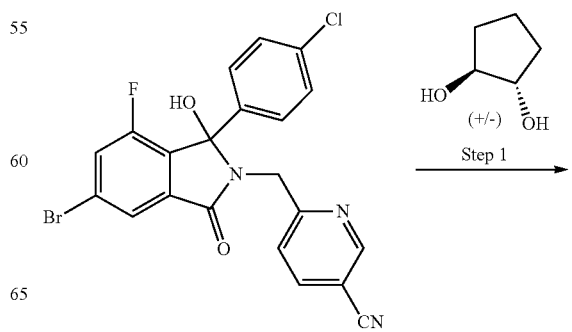

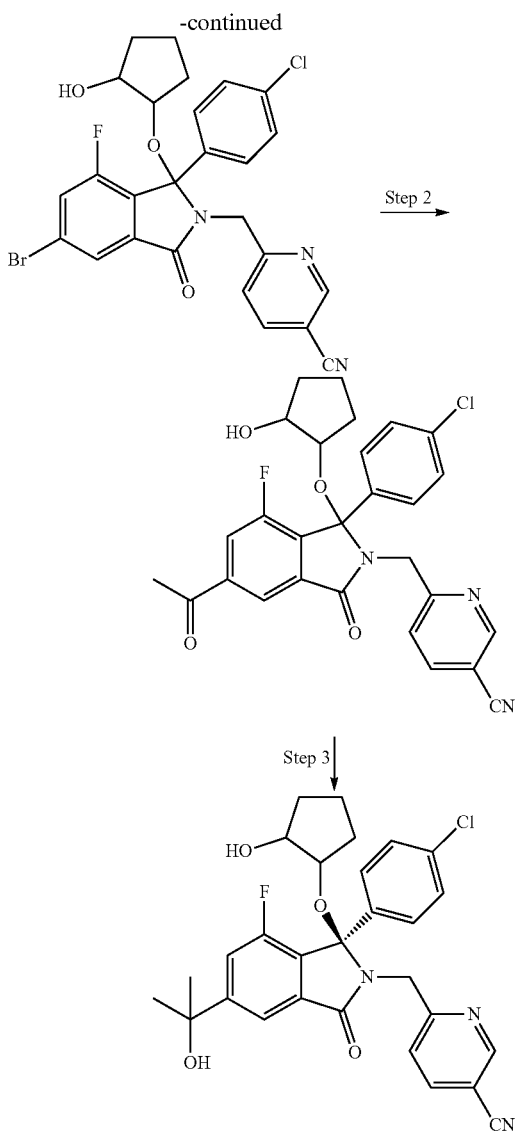

Example 124, Step 1: 6-((5-Bromo-1-(4-chlorophenyl)-7-fluoro-1-((2-hydroxycyclopentyl)oxy)-3-oxoisoindolin-2-yl)methyl)nicotinonitrile 6-((5-Bromo-1-(4-chlorophenyl)-7-fluoro-1-((2-hydroxycyclopentyl)oxy)-3-oxoisoindolin-2-yl)methyl)nicotinonitrile (288 mg, 25%) was prepared from 6-((5-bromo-1-(4-chlorophenyl)-7-fluoro-1-hydroxy-3-oxoisoindolin-2-yl)methyl)nicotinonitrile (Example 3, step 1) (1.0 g, 2.11 mmol) in a similar manner to that described in Example 1, step 2. The two diastereomers were separated with a Biotage, 0-60% EtOAc/DCM, to give the title compound as the fastest eluting diastereomer was progressed to the final compound. $^1$H NMR (400 MHz, CDCl$_3$): 8.58 (1H, d), 7.93 (1H, d), 7.72 (1H, dd), 7.44 (1H, dd), 7.22-7.18 (3H, m), 7.13 (2H, d), 4.86 (1H, d), 4.43 (1H, d), 3.64-3.58 (1H, m), 3.55-3.50 (1H, m), 2.34-2.25 (1H, m), 2.04 (1H, s), 1.88-1.80 (3H, m) 1.74-1.64 (1H, m), 1.46-1.32 (1H, m).

Example 124, Step 2: 6-((5-Acetyl-1-(4-chlorophenyl)-7-fluoro-1-((2-hydroxycyclopentyl)oxy)-3-oxoisoindolin-2-yl)methyl)nicotinonitrile 6-((5-Acetyl-1-(4-chlorophenyl)-7-fluoro-1-((2-hydroxycyclopentyl)oxy)-3-oxoisoindolin-2-yl)methyl)nicotinonitrile (180 mg, 68%) was prepared from 6-((5-bromo-1-(4-chlorophenyl)-7-fluoro-1-((2-hydroxycyclopentyl)oxy)-3-oxoisoindolin-2-yl)methyl)nicotinonitrile (288 mg, 0.51 mmol) in a similar manner to that described in Example 1, step 3. $^1$H NMR (400 MHz, CDCl$_3$): 8.59 (1H, dd), 8.31 (1H, d), 7.86 (1H, dd), 7.74 (1H, dd), 7.25-7.18 (3H, m), 7.14 (2H, d), 4.88 (1H, d), 4.46 (1H, d), 3.65-3.59 (1H, m), 3.50-3.48 (1H, m), 2.70 (3H, s), 2.29 (1H, d), 1.88-1.79 (2H, m), 1.68-1.52 (2H, m), 1.28-1.24 (2H, m).

Example 124, Step 3: 6-{[(1R)-1-(4-chlorophenyl)-7-fluoro-1-[(2-hydroxycyclopentyl)oxy]-5-(2-hydroxypropan-2-yl)-3-oxo-2,3-dihydro-1H-isoindol-2-yl]methyl}pyridine-3-carbonitrile 6-(((1R)-1-(4-Chlorophenyl)-7-fluoro-1-((2-hydroxycyclopentyl)oxy)-5-(2-hydroxypropan-2-yl)-3-oxoisoindolin-2-yl)methyl)nicotinonitrile (31 mg, 17%) was prepared from 6-((5-acetyl-1-(4-chlorophenyl)-7-fluoro-1-((2-hydroxycyclopentyl)oxy)-3-oxoisoindolin-2-yl)methyl)nicotinonitrile (180 mg, 0.34 mmol) in a similar manner to that described in Example 1, step 4. $^1$H NMR (400 MHz, CDCl$_3$): 8.58 (1H, dd), 7.86 (1H, d), 7.70 (1H, dd), 7.48 (1H, dd), 7.22-7.18 (3H, m), 7.12 (2H, d), 4.87 (1H, d), 4.45 (1H, d), 3.64-3.58 (1H, m), 3.49-3.45 (1H, m), 2.32 (1H, d), 1.88 (1H, s), 1.88-1.77 (2H, m), 1.73-1.63 (7H, m), 1.55-1.49 (2H, m), 1.40-1.32 (1H, m). MS: [M+H]+=536.

Example 125 and Example 126: (3R)-3-(4-chlorophenyl)-2-[(5-chloropyridin-2-yl)methyl]-6-[1-hydroxy-1-(2-methoxypyridin-4-yl)ethyl]-3-methoxy-2,3-dihydro-1H-isoindol-1-one (*both isomers separated and isolated)

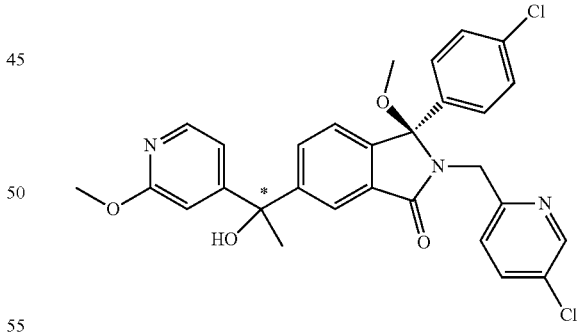

(3R)-3-(4-Chlorophenyl)-2-((5-chloropyridin-2-yl)methyl)-6-(1-hydroxy-1-(2-methoxypyridin-4-yl)ethyl)-3-methoxyisoindolin-1-one, Example 125, fast running diastereoisomer, (16.6 mg, 9%) and Example 126, slow running diastereoisomer (15.0 mg, 8%) were prepared from (R)-6-acetyl-3-(4-chlorophenyl)-2-((5-chloropyridin-2-yl)methyl)-3-methoxyisoindolin-1-one (Example 55 and Example 56, step 2) (150 mg, 0.34 mmol) in a similar manner to that described in Example 120 and Example 121. Purification by chiral preparative LCMS gave the title compounds.

Example 125 Isomer 1

¹H NMR (400 MHz, CDCl₃) 8.33 (1H, dd), 8.10 (1H, dd), 7.97 (1H, dd), 7.63 (1H, dd), 7.47 (1H, dd), 7.24-7.14 (5H, m), 7.10 (1H, dd), 6.88 (1H, dd), 6.84 (1H, dd), 4.60 (1H, d), 4.45 (1H, d), 3.93 (3H, s), 2.80 (3H, s), 2.22 (1H, s), 1.97 (3H, s). MS: [M+H]+=550.

Example 126 Isomer 2

¹H NMR (400 MHz, CDCl₃) 8.33 (1H, dd), 8.10 (1H, dd), 7.97 (1H, dd), 7.63 (1H, dd), 7.47 (1H, dd), 7.24-7.14 (5H, m), 7.10 (1H, dd), 6.88 (1H, dd), 6.83 (1H, dd), 4.59 (1H, d), 4.46 (1H, d), 3.93 (3H, s), 2.80 (3H, s), 2.23 (1H, s), 1.97 (3H, s). MS: [M+H]+=550.

Example 127: 1-({[(1R)-5-[1-(4-Acetylpiperazin-1-yl)-2-hydroxypropan-2-yl]-1-(4-chlorophenyl)-2-[(5-chloropyridin-2-yl)methyl]-7-fluoro-3-oxo-2,3-dihydro-1H-isoindol-1-yl]oxy}methyl)cyclopropane-1-carboxamide

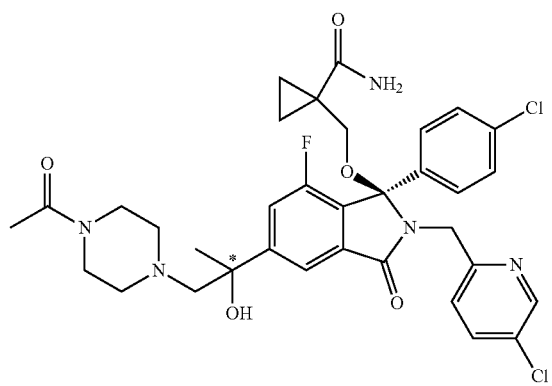

(Example isolated as a single isomer at the position shown*)

To a solution of 1-({[(1R)-1-(4-chlorophenyl)-2-[(5-chloropyridin-2-yl)methyl]-7-fluoro-5-[2-hydroxy-1-(piperazin-1-yl)propan-2-yl]-3-oxo-2,3-dihydro-1H-isoindol-1-yl]oxy}methyl)cyclopropane-1-carboxamide (Example 68) (10 mg, 0.017 mmol) in DCM (2 mL) was added acetic anhydride (2 □L, 0.02 mmol) and the mixture was stirred overnight. It was diluted with DCM, washed with saturated NaHCO₃, dried and the solvent evaporated to afford the title compound (7 mg, 60%).

1H NMR (400 MHz, DMSO_cap): 8.35 (1H, d), 7.83 (1H, s), 7.73 (1H, dd), 7.53 (1H, d), 7.31 (2H, d), 7.22 (3H, dd), 7.03 (1H, s), 6.92-6.81 (1H, m), 5.30 (1H, s), 4.47 (2H, d), 3.52 (1H, d), 2.97 (1H, d), 2.43-2.24 (4H, m), 1.94 (3H, s), 1.51 (3H, s), 0.99 (1H, dd), 0.95-0.88 (1H, m), 0.55-0.43 (2H, m);
MS: [M+H]⁺=684

Examples 128 and 129: 1-({[(1R)-1-(4-Chlorophenyl)-2-[(5-chloropyridin-2-yl)methyl]-7-fluoro-5-[2-hydroxy-1-(4-methylpiperazin-1-yl)propan-2-yl]-3-oxo-2,3-dihydro-1H-isoindol-1-yl]oxy}methyl)cyclopropane-1-carboxamide (*both isomers separated and isolated)

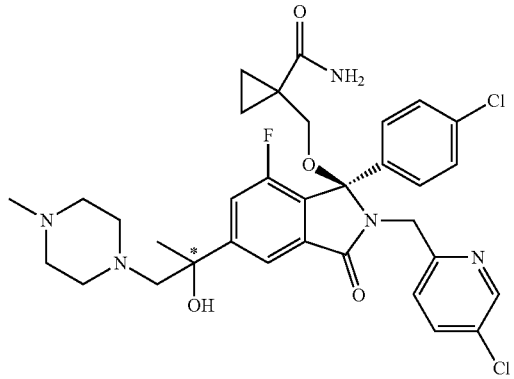

The title compounds were prepared using procedures similar to those described in Example 68 and Example 69.

Example 128 (Fast Running Isomer)

1H NMR (400 MHz, DMSO-d6): 8.34 (1H, d), 7.78 (1H, s), 7.72 (1H, dd), 7.53 (1H, d), 7.29 (2H, d), 7.25-7.17 (3H, m), 7.05 (1H, s), 6.87 (1H, s), 5.76 (1H, s), 5.21 (1H, s), 4.72-4.27 (2H, m), 2.95 (1H, d), 2.34 (5H, s), 2.17 (4H, s), 2.08 (3H, s), 1.53-1.48 (3H, m), 1.05-0.97 (1H, m), 0.95-0.87 (1H, m), 0.56-0.43 (2H, m).
MS: [M+H]⁺=656

Example 129 (Slow Running Isomer)

1H NMR (400 MHz, DMSO-d6): 8.36 (1H, d), 7.81 (1H, s), 7.74 (1H, dd), 7.51 (1H, d), 7.32 (2H, d), 7.22 (3H, dd), 7.05 (1H, s), 6.86 (1H, s), 5.76 (1H, s), 5.25 (1H, s), 4.60-4.27 (2H, m), 3.53 (1H, d), 2.94 (1H, d), 2.46-1.96 (12H, m), 1.51-1.46 (3H, m), 1.02-0.86 (2H, m), 0.54-0.41 (2H, m) MS: [M+H]⁺=656

Examples 130 and 131: 1-({[(1R)-1-(4-Chlorophenyl)-2-[(5-chloropyridin-2-yl)methyl]-7-fluoro-5-(2-hydroxy-1-methoxypropan-2-yl)-3-oxo-2,3-dihydro-1H-isoindol-1-yl]oxy}methyl)cyclopropane-1-carboxamide (*both isomers separated and isolated)

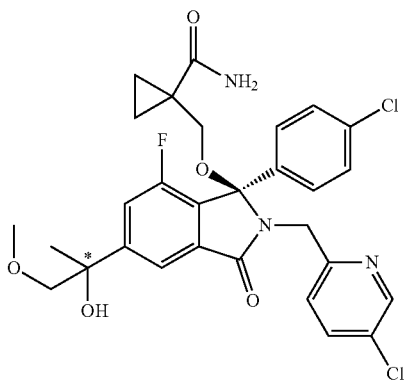

1-({[(1R)-1-(4-Chlorophenyl)-2-[(5-chloropyridin-2-yl)methyl]-7-fluoro-5-(2-methyloxiran-2-yl)-3-oxo-2,3-dihydro-1H-isoindol-1-yl]oxy}methyl)cyclopropane-1-carboxamide (Example 68 and Example 69, step 2) (615 mg, 1.1 mmol) was treated with sodium methoxide (11 mmol) in methanol (5 mL). The reaction mixture was heated at 65° C. for 2 h, cooled, concentrated, water was added and the pH was adjusted to pH=8. The product was extracted with DCM, the organic phase was dried, the solvent evaporated. The crude product was purified on Silica, eluted with EtOAc-MeOH 0-10% to afford the mixture of diastereoisomers (325 mg, 50%). The two diastereoisomers were separated by chiral HPLC.

Example 130 (Fast Running Isomer, 54 mg, 8%)

1H NMR (400 MHz, DMSO-d6): 8.35 (1H, d), 7.79 (1H, d), 7.73 (1H, dd), 7.55-7.48 (1H, m), 7.31 (2H, d), 7.23 (3H, dd), 7.00 (1H, s), 6.84 (1H, s), 5.47 (1H, s), 4.47 (2H, s), 3.52-3.42 (3H, m), 3.27 (3H, s), 3.07 (1H, d), 1.45 (3H, s), 1.01-0.87 (2H, m), 0.59-0.43 (2H, m); MS: [M+H]$^+$=588

Example 131 (Slow Running Isomer, 100 mg, 16%)

1H NMR (400 MHz, DMSO-d6): 8.35 (1H, d), 7.80 (1H, d), 7.73 (1H, dd), 7.54-7.47 (1H, m), 7.31 (2H, d), 7.23 (3H, dd), 7.00 (1H, s), 6.84 (1H, s), 5.47 (1H, s), 4.47 (2H, s), 3.54-3.42 (3H, m), 3.26 (3H, s), 3.08 (1H, d), 1.46 (3H, s), 1.02-0.88 (2H, m), 0.59-0.43 (2H, m); MS: [M+H]$^+$=588

Examples 132 and 133: (3R)-3-(4-Chlorophenyl)-2-[(5-chloropyridin-2-yl)methyl]-6-[1-hydroxy-1-(1-methyl-1H-imidazol-5-yl)ethyl]-3-methoxy-2,3-dihydro-1H-isoindol-1-one (*both isomers separated and isolated)

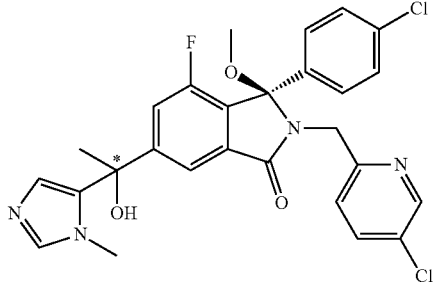

To a solution of 1-methyl-5-bromo-imidazole (800 mg, 5.0 mmol) in DCM (5 mL) was added ethyl-magnesium bromide (3M in diethyl ether, 1.7 mL, 5.0 mmol) and the reaction mixture was stirred for 2 h. To a solution of (R)-6-acetyl-3-(4-chlorophenyl)-2-((5-chloropyridin-2-yl)methyl)-3-methoxyisoindolin-1-one (Example 55 and Example 56, step 2) (530 mg, 1.2 mmol) in THF (10 mL) was added LaCl$_2$×2LiCl (0.6M in THF, 2.0 mL, 1.2 mmol) and stirred for 1 h. The reaction mixture was cooled to 00° C. and half of the prepared imidazole Grignard reagent was added and stirred for 1 h. The reaction was quenched with saturated NH$_4$Cl solution, the product extracted with DCM. The crude product purified on Silica, eluted with EtOAc-MeOH 0-10% to afford the mixture of diastereoisomers (337 mg, 50%). The two diastereoisomers were separated by chiral HPLC.

Example 132 (Fast Running Isomer, 67 mg, 11%)

1H NMR (400 MHz, DMSO-d6): 8.38 (1H, d), 7.80 (1H, d), 7.73 (1H, dd), 7.54-7.47 (2H, m), 7.32-7.15 (6H, m), 7.03 (1H, d), 6.13 (1H, s), 4.50 (1H, d), 4.38 (1H, d), 3.20 (3H, s), 2.77 (3H, s), 1.82 (3H, s) MS: [M+H]$^+$=523

Example 133 (Slow Running Isomer, 74 mg, 12%)

1H NMR (400 MHz, DMSO-d6): 8.38 (1H, d), 7.76-7.67 (2H, m), 7.61 (1H, dd), 7.53 (1H, s), 7.32-7.17 (6H, m), 7.06 (1H, d), 6.14 (1H, s), 4.50 (1H, d), 4.37 (1H, d), 3.21 (3H, s), 2.77 (3H, s), 1.82 (3H, s).
MS: [M+H]$^+$=523

Examples 134 and 135: (3R)-3-(4-Chlorophenyl)-2-[(5-chloropyridin-2-yl)methyl]-6-[1-hydroxy-1-(1H-pyrazol-5-yl)ethyl]-3-methoxy-2,3-dihydro-1H-isoindol-1-one (*both isomers separated and isolated)

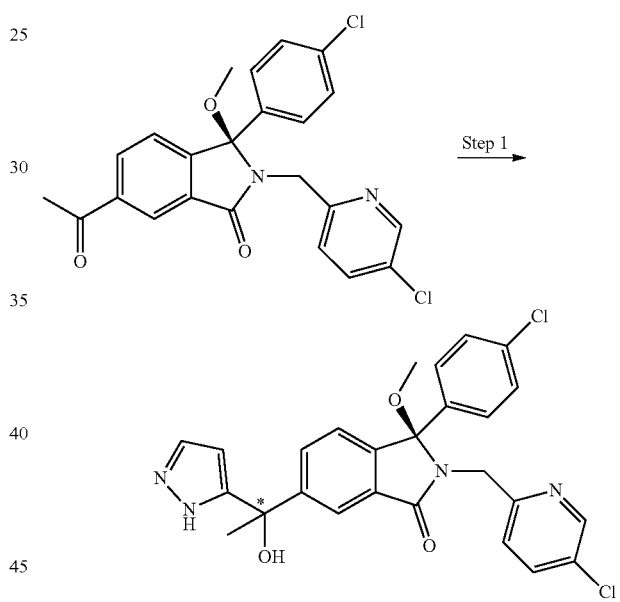

To a solution of 1-tosyl-1H-pyrazole (360 mg, 0.82 mmol) in THF (2.0 mL) at −78° C. was added tBuLi (1.6M in pentane, 0.76 mL, 1.22 mmol) and stirred at −78° C. for 10 minutes. A −78° C. solution of (R)-6-acetyl-3-(4-chlorophenyl)-2-((5-chloropyridin-2-yl)methyl)-3-methoxyisoindolin-1-one (Example 55 and Example 56, step 2) (272 mg, 1.22 mmol) was added dropwise and the mixture stirred at −78° C. for 1 h then warmed to RT. The reaction was quenched with saturated aqueous NH$_4$Cl, extracted into EtOAc, washed with brine, dried over MgSO$_4$ and concentrated under vacuum. Purified by Biotage using 0-50% EtOAc in petrol gave (3R)-3-(4-chlorophenyl)-2-((5-chloropyridin-2-yl)methyl)-6-(1-hydroxy-1-(1-tosyl-1H-pyrazol-5-yl)ethyl)-3-methoxyisoindolin-1-one (76 mg). The intermediate was dissolved in MeOH (8.1 mL) and 3.0M aqueous NaOH (2.71 mL) was added and the mixture stirred at RT for 45 minutes. The reaction was diluted with water, extracted into EtOAc, washed with brine, dried over MgSO$_4$ and concentrated under vacuum. Purified by Biotage (C18)

using 50-100% MeCN (0.1% HCOOH) in water (0.1% HCOOH) gave the mixture of isomers (27 mg) which were separated by chiral HPLC.

Example 134 Fast Running Isomer

1H NMR (500 MHz, CDCl₃) 8.36 (1H, s) 8.10-8.04 (1H, m), 7.79-7.78 (1H, m), 7.61-7.59 (1H, m), 7.30-7.28 (1H, m), 7.21-7.14 (6H, m), 6.51-6.50 (1H, m), 4.71-4.61 (2H, m), 2.87-2.83 (3H, m), 2.10-2.02 (3H, m). MS: [M+H]⁺ =509.

Example 135 Slow Running Isomer

1H NMR (500 MHz, CDCl₃) 8.37 (1H, s) 8.06-8.05 (1H, m), 7.81-7.79 (1H, m), 7.65-7.64 (1H, m), 7.34-7.31 (1H, m), 7.21-7.13 (6H, m), 6.52-6.51 (1H, m), 4.72 (2H, s br), 2.86 (3H, s), 2.06 (3H, s). MS: [M–H]⁻=507

Examples 136 and 137: (3R)-3-(4-Chlorophenyl)-2-[(5-chloropyridin-2-yl)methyl]-4-fluoro-6-[2-hydroxy-1-(4-methylpiperazin-1-yl)propan-2-yl]-3-[(1-hydroxycyclopropyl)methoxy]-2,3-dihydro-1H-isoindol-1-one (*both isomers separated and isolated)

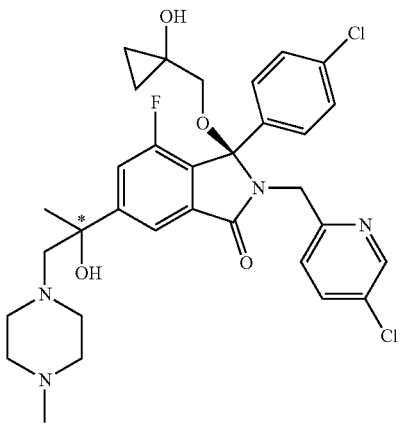

The title compounds were made using procedures similar to those described in Examples 31, 22 and 23.

Example 136 (Fast Running Diastereoisomer)

1H NMR (400 MHz, DMSO-d6): 8.33 (1H, d), 7.79 (1H, s), 7.68 (1H, dd), 7.50 (1H, d), 7.29 (2H, d), 7.26 (2H, d), 7.14 (1H, d), 5.50 (1H, s), 5.19 (1H, s), 4.69-4.25 (2H, m), 3.17 (1H, d), 2.89 (1H, d), 2.41-2.25 (5H, m), 2.16 (4H, s), 2.08 (3H, s), 1.50 (3H, s), 0.55 (2H, s), 0.40-0.22 (2H, m).
MS: [M+H]⁺=629

Example 137 (Slow Running Diastereoisomer)

1H NMR (400 MHz, DMSO-d6): 8.34 (1H, d), 7.81 (1H, s), 7.70 (1H, dd), 7.49 (1H, d), 7.33-7.23 (4H, m), 7.16 (1H, d), 5.49 (1H, s), 5.19 (1H, s), 4.49 (2H, d), 3.18 (1H, d), 2.89 (1H, d), 2.34 (4H, s), 2.17 (4H, s), 2.08 (3H, s), 1.49 (3H, s), 0.54 (2H, s), 0.37-0.20 (2H, m).
MS: [M+H]⁺=629

Examples 138 and 139: (3R)-3-(4-Chlorophenyl)-2-[(5-chloropyridin-2-yl)methyl]-6-[1-(dimethylamino)-2-hydroxypropan-2-yl]-4-fluoro-3-[(3S)-oxolan-3-yloxy]-2,3-dihydro-1H-isoindol-1-one (*both isomers separated and isolated)

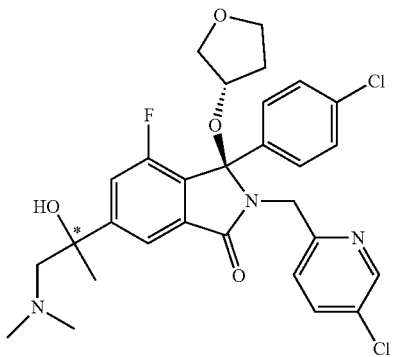

The title compounds were made using procedures similar to those described in Examples 75, 22 and 23.

Example 138 (Faster Running Diastereoisomer)

1H NMR (400 MHz, DMSO-d6): 8.39 (1H, d), 7.85 (1H, s), 7.74 (1H, dd), 7.51 (1H, d), 7.34-7.21 (5H, m), 5.21 (1H, s), 4.47 (2H, q), 4.04-3.97 (1H, m), 3.73 (1H, q), 3.58-3.50 (1H, m), 3.45-3.39 (1H, m), 3.38 (1H, d), 3.12 (1H, dd), 2.70-2.66 (1H, m), 2.11 (6H, s), 1.72-1.61 (1H, m), 1.48 (4H, s).
MS: [M+H]⁺=574

Example 139 (Slower Running Diastereoisomer)

1H NMR (400 MHz, DMSO-d6): 8.38 (1H, d), 7.80 (1H, s), 7.73 (1H, dd), 7.53 (1H, d), 7.34-7.17 (5H, m), 5.20 (1H, s), 4.48 (2H, s), 4.10-3.95 (1H, m), 3.74 (1H, q), 3.60-3.49 (1H, m), 3.13 (1H, dd), 2.59 (1H, d), 2.11 (6H, s), 1.77-1.52 (2H, m), 1.48 (3H, s).
MS: [M+H]⁺=574

Examples 140 and 141: (3R)-3-(4-Chlorophenyl)-2-[(5-chloropyridin-2-yl)methyl]-6-(1-ethoxy-2-hydroxypropan-2-yl)-4-fluoro-3-[(3S)-oxolan-3-yloxy]-2,3-dihydro-1H-isoindol-1-one (*both isomers separated and isolated)

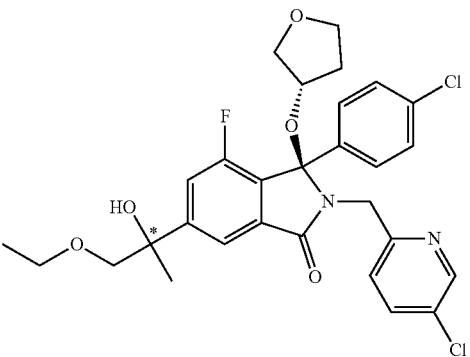

The title compounds were made using procedures similar to those described in Example 75, and Example 130, but using sodium ethoxide instead of sodium methoxide Example 140 (Faster Running Diastereoisomer)

1H NMR (400 MHz, DMSO-d6): 8.38 (1H, d), 7.85 (1H, d), 7.74 (1H, dd), 7.51 (1H, dd), 7.34-7.19 (5H, m), 5.44 (1H, s), 4.66-4.25 (2H, m), 4.05-3.97 (1H, m), 3.74 (1H, q), 3.59-3.37 (6H, m), 3.14 (1H, dd), 1.75-1.61 (1H, m), 1.60-1.49 (1H, m), 1.46 (3H, s), 1.04 (3H, t) MS: [M−H]⁻=573

Example 141 (Slower Running Diastereoisomer)

1H NMR (400 MHz, DMSO-d6): 8.38 (1H, d), 7.83 (1H, d), 7.73 (1H, dd), 7.53 (1H, d), 7.32-7.22 (5H, m), 5.43 (1H, s), 4.48 (2H, s), 4.05-3.97 (1H, m), 3.74 (1H, q), 3.63-3.35 (6H, m), 3.15 (1H, dd), 1.76-1.62 (1H, m), 1.62-1.51 (1H, m), 1.47 (3H, s), 1.04 (3H, t).
MS: [M−H]⁻=573

Examples 142 and 143: (3R)-3-(4-Chlorophenyl)-2-[(5-chloropyridin-2-yl)($^2$H$_2$)methyl]-4-fluoro-6-[2-hydroxy-1-($^2$H$_3$)methoxypropan-2-yl]-3-[(3S)-oxolan-3-yloxy]-2,3-dihydro-1H-isoindol-1-one (*both isomers separated and isolated)

The title compounds were made using procedures similar to those described in Example 75, and Example 130, but using d4-MeOH instead of MeOH.

Example 142 (Faster Running Diastereoisomer)

1H NMR (400 MHz, DMSO-d6): 8.40-8.35 (1H, m), 7.82 (1H, d), 7.74 (1H, dd), 7.52 (1H, dd), 7.34-7.19 (5H, m), 5.48 (1H, s), 4.05-3.97 (1H, m), 3.74 (1H, q), 3.60-3.35 (4H, m), 3.16 (1H, dd), 1.74-1.60 (1H, m), 1.60-1.49 (1H, m), 1.46 (3H, s); MS: [M+H]⁺=564

Example 143 (Slower Running Diastereoisomer)

1H NMR (400 MHz, DMSO-d6): 8.40-8.35 (1H, m), 7.82 (1H, d), 7.73 (1H, dd), 7.52 (1H, dd), 7.33-7.18 (5H, m), 5.48 (1H, s), 4.05-3.97 (1H, m), 3.74 (1H, q), 3.60-3.35 (4H, m), 3.16 (1H, dd), 1.75-1.62 (1H, m), 1.62-1.50 (1H, m), 1.45 (3H, s); MS: [M+H]⁺=564

Example 144: 2-{[1-({[(1R)-1-(4-Chlorophenyl)-2-[(5-chloropyridin-2-yl)methyl]-7-fluoro-5-(2-hydroxypropan-2-yl)-3-oxo-2,3-dihydro-1H-isoindol-1-yl]oxy}methyl)cyclopropyl]methoxy}acetic Acid

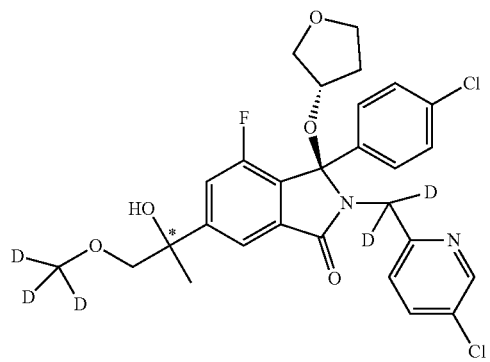

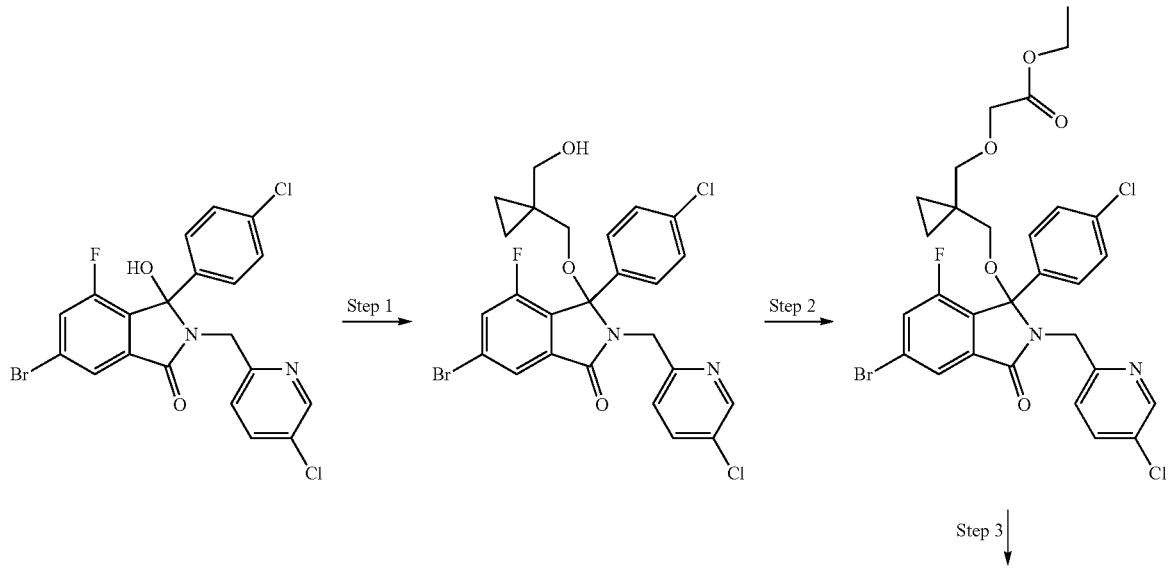

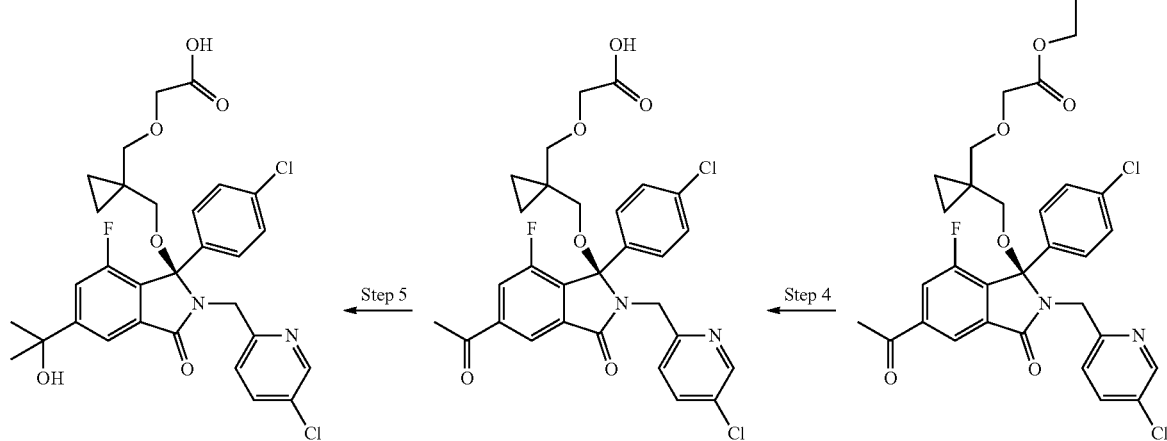

Step 1: 6-Bromo-3-(4-chlorophenyl)-2-[(5-chloro-pyridin-2-yl)methyl]-4-fluoro-3-{[1-(hydroxymethyl)cyclopropyl]methoxy}-2,3-dihydro-1H-isoindol-1-one The title compound was prepared from 6-bromo-3-(4-chloro-phenyl)-2-(5-chloro-pyridin-2-ylmethyl)-4-fluoro-3-hydroxy-2,3-dihydro-isoindol-1-one (Example 1, step 1) in a similar manner to that described in Example 3, step 2 using (1-hydroxymethyl-cyclopropyl)-methanol instead of 1-hydroxymethyl-cyclopropanol. MS: [M+H]$^+$=567

Step 2: Ethyl 2-{[1-({[5-bromo-1-(4-chlorophenyl)-2-[(5-chloropyridin-2-yl)methyl]-7-fluoro-3-oxo-2,3-dihydro-1H-isoindol-1-yl]oxy}methyl)cyclopropyl]methoxy}acetate To a solution of 6-bromo-3-(4-chlorophenyl)-2-[(5-chloropyridin-2-yl)methyl]-4-fluoro-3-{[1-(hydroxymethyl)cyclopropyl]methoxy}-2,3-dihydro-1H-isoindol-1-one (2.7 g, 4.77 mmol) in DCM (30 mL) were added ethyl-diazoacetate (15% in toluene, 3.6 mL, 4.77 mmol) and RhOAc$_2$ (20 mg) and the reaction mixture was stirred for 4 days. Further ethyl diazoacetate (15% in toluene 7.2 mL, 9.54 mmol) was added and stirred for 24 h. Water was added and the product was extracted with DCM. The organic phase was dried, the solvent evaporated. The crude product was purified on Silica, eluted with petrol—EtOAc to afford the product (1.08 g, 35%). MS: [M+H]$^+$=653

Step 3: Ethyl 2-{[1-({[(1R)-5-acetyl-1-(4-chloro-phenyl)-2-[(5-chloropyridin-2-yl)methyl]-7-fluoro-3-oxo-2,3-dihydro-1H-isoindol-1-yl]oxy}methyl)cyclopropyl]methoxy}acetate Ethyl 2-{[1-({[5-bromo-1-(4-chlorophenyl)-2-[(5-chloro-pyridin-2-yl)methyl]-7-fluoro-3-oxo-2,3-dihydro-1H-isoindol-1-yl]oxy}methyl)cyclopropyl]methoxy}acetate (1.0 g, 1.53 mmol) was converted to the title compound (0.61 g, 65%) in a similar manner to that described in Example 1, step 3. The enantiomers were separated by preparative chiral chromatography.

Fast running enantiomer: 217 mg, 23%, MS: [M+H]$^+$=615
Slow running enantiomer: 170 mg, 18%, MS: [M+H]$^+$=615
The faster running enantiomer was used in step 4

Step 4: 2-{[1-({[(1R)-5-Acetyl-1-(4-chlorophenyl)-2-[(5-chloropyridin-2-yl)methyl]-7-fluoro-3-oxo-2,3-dihydro-1H-isoindol-1-yl]oxy}methyl)cyclopropyl]methoxy}acetic Acid To a solution of ethyl 2-{[1-({[(1R)-5-acetyl-1-(4-chlorophenyl)-2-[(5-chloropyridin-2-yl)methyl]-7-fluoro-3-oxo-2,3-dihydro-1H-isoindol-1-yl]oxy}methyl)cyclopropyl]methoxy}acetate (217 mg, 0.35 mmol) in THF (6 mL) and water (2 mL) was added LiOH×H$_2$O (150 mg, 3.5 mmol) and the reaction mixture was stirred for 30 mins. Water was added, the pH was adjusted to pH=5 with 1M HCl and the product was extracted with ethyl acetate. The organic phase was dried, the solvent evaporated to afford the product (172 mg, 84%).
MS: [M+H]$^+$=587

Step 5: 2-{[1-({[(1R)-1-(4-Chlorophenyl)-2-[(5-chloropyridin-2-yl)methyl]-7-fluoro-5-(2-hydroxypropan-2-yl)-3-oxo-2,3-dihydro-1H-isoindol-1-yl]oxy}methyl)cyclopropyl]methoxy}acetic acid 2-{[1-({[(1R)-5-Acetyl-1-(4-chlorophenyl)-2-[(5-chloro-pyridin-2-yl)methyl]-7-fluoro-3-oxo-2,3-dihydro-1H-isoindol-1-yl]oxy}methyl)cyclopropyl]methoxy}acetic acid (170 mg, 0.29 mmol) was converted to the title compound (41 mg, 24%) in a similar manner as described in Example 1, step 4.
1H NMR (400 MHz, DMSO-d6): 12.89-11.96 (1H, m), 8.36 (1H, d), 7.79 (1H, d), 7.71 (1H, dd), 7.50 (1H, dd), 7.33-7.23 (4H, m), 7.20 (1H, d), 5.57-5.12 (1H, m), 4.46 (2H, s), 4.01-3.87 (2H, m), 3.47-3.41 (1H, m), 3.38-3.33 (1H, m), 3.03 (1H, d), 2.93 (1H, d), 1.48 (6H, s), 0.41 (2H, s), 0.33-0.15 (2H, m); MS: [M+H]$^+$=603

Examples 145 and 146: 2-[(1R)-1-(4-Chlorophenyl)-2-[(5-chloropyridin-2-yl)methyl]-1-methoxy-3-oxo-2,3-dihydro-1H-isoindol-5-yl]-2-hydroxy-N-methylpropanamide (*both isomers separated and isolated)

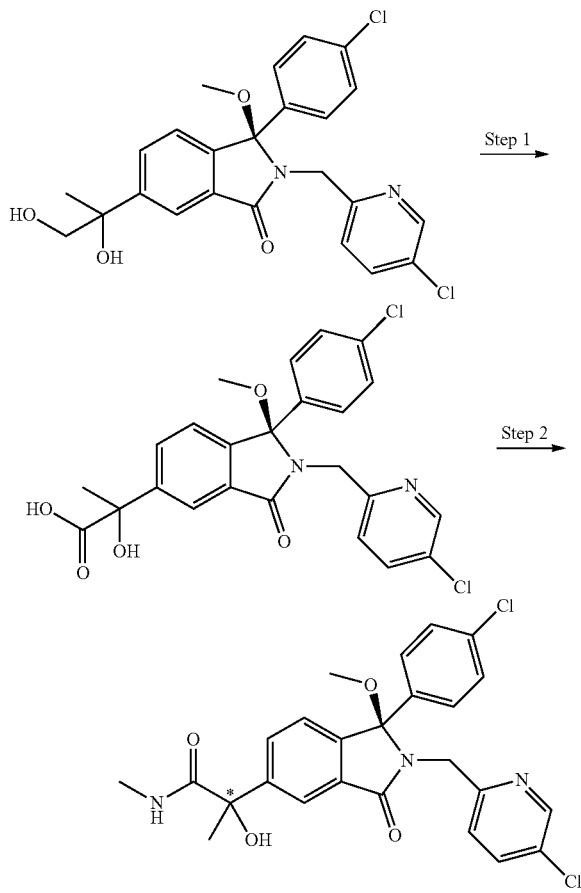

Step 1: 2-[(1R)-1-(4-Chlorophenyl)-2-[(5-chloropyridin-2-yl)methyl]-1-methoxy-3-oxo-2,3-dihydro-1H-isoindol-5-yl]-2-hydroxypropanoic acid (R)-3-(4-Chlorophenyl)-2-((5-chloropyridin-2-yl)methyl)-6-((R)-1,2-dihydroxypropan-2-yl)-3-methoxyisoindolin-1-one (made using procedures similar to those described in Examples 2 and 14)(3.28 g, 6.93 mmol) was dissolved in acetonitrile (35 mL) and sodium phosphate buffer (1M, pH 6.5, 27 mL) was added. TEMPO (270 mg, 1.73 mmol), sodium chlorite (1.25 g, 13.9 mmol) and sodium hypochlorite (10 mg, 0.139 mmol) were added sequentially at room temperature. The mixture was heated at 55° C. for 18 h, before cooling to room temperature and adding water. The pH was adjusted to pH 8 with 1M NaOH, Na$_2$SO$_3$ added and the pH adjusted to pH 2 with 2M HCl. The mixture was extracted with EtOAc, the combined organics dried over MgSO$_4$ and the solvent removed in vacuo. FCC [dichloromethane-methanol (100:0)→(93:7)] of the crude residue afforded the racemic mixture (1.95 g, 58%, 8.5:1 by NMR); MS: [M−H]$^-$=485.2.

Step 2: 2-[(1R)-1-(4-Chlorophenyl)-2-[(5-chloropyridin-2-yl)methyl]-1-methoxy-3-oxo-2,3-dihydro-1H-isoindol-5-yl]-2-hydroxy-N-methylpropanamide To 2-[(1R)-1-(4-chlorophenyl)-2-[(5-chloropyridin-2-yl)methyl]-1-methoxy-3-oxo-2,3-dihydro-1H-isoindol-5-yl]-2-hydroxypropanoic acid (220 mg, 0.451 mmol) in anhydrous THF (6.4 mL) was added CDI (146 mg, 0.903 mmol) and the mixture heated at 80° C. for 3 h. After cooling to 50° C., methylamine (2M in THF, 0.80 mL, 1.58 mmol) was added and the reaction mixture stirred at this temperature for 1.5 h. After cooling to room temperature, EtOAc (10 ml) was added, washed with saturated aqueous NaHCO$_3$ (15 ml), brine (15 mL), dried over anhydrous Na$_2$SO$_4$, filtered and the solvent removed in vacuo. FCC [petrol-ethyl acetate (100:0)→(0:100)] of the crude residue afforded the racemic mixture (94 mg, 42%, 7:1 by NMR). Purification by chiral HPLC gave the title compounds.

Example 145 Major, Fast Running Isomer (67 mg, 30%)

1H NMR (400 MHz, DMSO-d6): 8.39 (1H, d), 8.03-7.93 (2H, m), 7.81 (1H, dd), 7.74 (1H, dd), 7.34-7.16 (6H, m), 6.30 (1H, s), 4.53 (1H, d), 4.37 (1H, d), 2.77 (3H, s), 2.58 (3H, d), 1.66 (3H, s); MS: [M−H]$^-$=499

Example 146 Minor, Slow Running Isomer (6 mg, 3%)

MS: [M−H]$^-$=499
separated and isolated) The following compounds were made in a similar fashion using the appropriate amine and amide coupling reagent (CDI or EDCl/HOAt).

Examples 147 and 148: 2-[(1R)-1-(4-Chlorophenyl)-2-[(5-chloropyridin-2-yl)methyl]-1-methoxy-3-oxo-2,3-dihydro-1H-isoindol-5-yl]-N-ethyl-2-hydroxypropanamide (*both isomers separated and isolated)

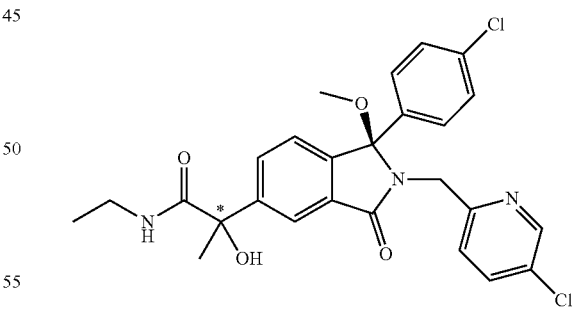

The compounds were prepared using ethylamine and CDI.

Example 147 Major, Fast Running Isomer (59 mg, 24%)

1H NMR (400 MHz, DMSO-d6): 8.39 (1H, d), 8.02-7.93 (2H, m), 7.81 (1H, dd), 7.74 (1H, dd), 7.33-7.16 (6H, m), 6.29 (1H, s), 4.53 (1H, d), 4.37 (1H, d), 3.17-2.98 (2H, m), 2.77 (3H, s), 1.66 (3H, s), 0.99 (3H, t); MS: [M−H]$^-$ 513

Example 148 Minor, Slow Running Isomer (6 mg, 3%)

MS: [M−H]⁻ 513

Examples 149 and 150: 2-[(1R)-1-(4-Chlorophenyl)-2-[(5-chloropyridin-2-yl)methyl]-1-methoxy-3-oxo-2,3-dihydro-1H-isoindol-5-yl]-N-[2-(dimethylamino)ethyl]-2-hydroxypropanamide (*both isomers separated and isolated)

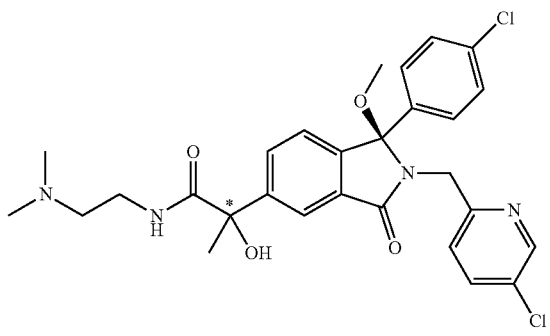

The compounds were prepared using N1,N1-dimethylethane-1,2-diamine and CDI.

Example 149 Major, Fast Running Isomer (139 mg)

1H NMR (400 MHz, DMSO-d6): 8.39 (1H, d), 7.99 (1H, d), 7.87-7.79 (2H, m), 7.74 (1H, dd), 7.33-7.21 (6H, m), 6.36 (1H, s), 4.53 (1H, d), 4.37 (1H, d), 3.21-3.06 (2H, m), 2.77 (3H, s), 2.27 (2H, t), 2.11 (6H, s), 1.66 (3H, s); MS: [M+H]⁺=557

Example 150 Minor, Slow Running Isomer (16 mg)

1H NMR (400 MHz, DMSO-d6): 8.38 (1H, d), 8.00 (1H, d), 7.89-7.70 (3H, m), 7.32-7.20 (6H, m), 6.36 (1H, s), 4.52 (1H, d), 4.38 (1H, d), 3.23-3.07 (2H, m), 2.77 (3H, s), 2.34-2.28 (2H, m), 2.13 (6H, s), 1.67 (3H, s); MS: [M+H]⁺=557

Examples 151 and 152: 2-[(1R)-1-(4-Chlorophenyl)-2-[(5-chloropyridin-2-yl)methyl]-1-methoxy-3-oxo-2,3-dihydro-1H-isoindol-5-yl]-2-hydroxy-N-(propan-2-yl)propanamide (*both isomers separated and isolated)

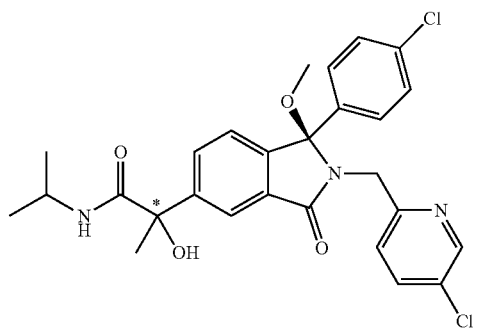

The compounds were prepared using propan-2-amine and CDI.

Example 151 Major, Fast Running Isomer (181 mg)

1H NMR (400 MHz, DMSO-d6): 8.39 (1H, d), 7.99 (1H, d), 7.84-7.71 (2H, m), 7.61 (1H, d), 7.34-7.21 (6H, m), 6.31 (1H, s), 4.53 (1H, d), 4.37 (1H, d), 3.88-3.77 (1H, m), 2.77 (3H, s), 1.66 (3H, s), 1.10 (3H, d), 0.99 (3H, d); MS: [M−H]⁻=526

Example 152 Minor, Slow Running Isomer (14.5 mg)

1H NMR (400 MHz, DMSO-d6): 8.39 (1H, d), 7.99 (1H, d), 7.84-7.71 (2H, m), 7.61 (1H, d), 7.33-7.20 (6H, m), 6.31 (1H, s), 4.56-4.48 (1H, m), 4.38 (1H, d), 3.88-3.77 (1H, m), 2.81-2.74 (3H, m), 1.66 (3H, s), 1.12-1.09 (3H, m), 1.00 (3H, d). MS: [M−H]⁻=526

Examples 153 and 154: 6-{[(1R)-1-(4-Chlorophenyl)-7-fluoro-1-{[1-(1-hydroxyethyl)cyclopropyl]methoxy}-5-(2-hydroxypropan-2-yl)-3-oxo-2,3-dihydro-1H-isoindol-2-yl]methyl}pyridine-3-carbonitrile (*both isomers separated and isolated)

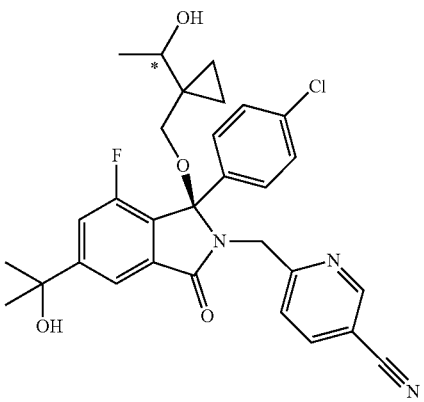 [SMILES: CC(O)C1(CO[C@]2(c3ccc(Cl)cc3)c3c(F)cc(C(C)(C)O)cc3C(=O)N2Cc2ccc(C#N)cn2)CC1]

Starting from 6-((5-bromo-1-(4-chlorophenyl)-7-fluoro-1-hydroxy-3-oxoisoindolin-2-yl)methyl)nicotinonitrile (Example 3, Step 1), the title compounds were prepared in a similar manner to Example 1, but using Preparation 15 instead of {1-[hydroxy(²H₂)methyl]cyclopropyl}(²H₂) methanol. Isomers were separated and isolated by preparative chiral HPLC.

Example 153, Fast Running Isomer (24 mg)

1H NMR (400 MHz, DMSO-d6): 8.79 (1H, d), 8.12 (1H, dd), 7.81 (1H, d), 7.54 (1H, dd), 7.39 (1H, d), 7.37-7.21 (4H, m), 5.53-5.13 (1H, m), 4.50 (2H, s), 3.48-3.36 (1H, m), 3.22 (1H, d), 2.89 (1H, d), 1.49 (6H, s), 1.08 (3H, d), 0.51-0.31 (2H, m), 0.20-0.10 (1H, m), 0.06--0.03 (1H, m). MS: [M−H]⁻=548

Example 154, Slow Running Isomer (24 mg)

1H NMR (400 MHz, DMSO-d6): 8.78 (1H, d), 8.12 (1H, dd), 7.81 (1H, d), 7.56-7.49 (1H, m), 7.39 (1H, d), 7.30 (2H, d), 7.25 (2H, d), 5.46-5.26 (1H, m), 4.45 (3H, s), 3.27 (1H, d), 2.84 (1H, d), 1.49 (6H, s), 1.03 (3H, d), 0.47-0.35 (2H, m), 0.22-0.10 (2H, m). MS: [M–H]⁻=548

Example 155: 2-({[1-({[(1R)-1-(4-chlorophenyl)-2-[(5-chloropyridin-2-yl)methyl]-7-fluoro-5-(2-hydroxypropan-2-yl)-3-oxo-2,3-dihydro-1H-isoindol-1-yl]oxy}methyl)cyclopropyl]methyl}amino)-N-methylacetamide

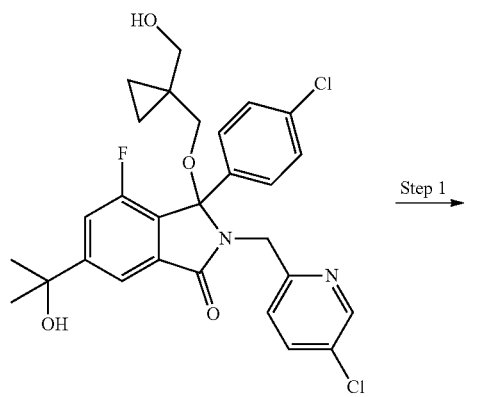

Step 1

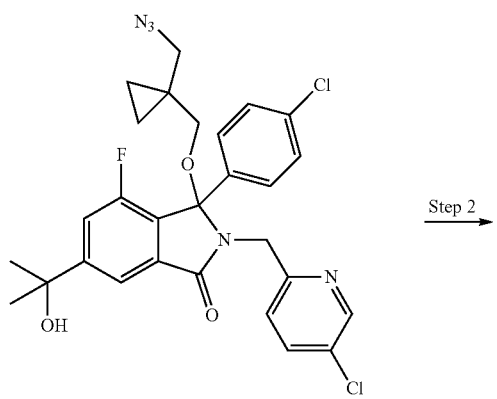

Step 2

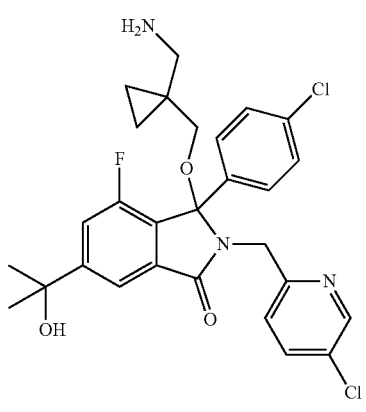

Step 3

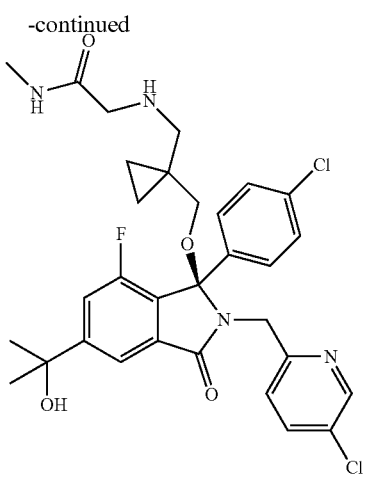

Step 1: 3-((1-(Azidomethyl)cyclopropyl)methoxy)-3-(4-chlorophenyl)-2-((5-chloropyridin-2-yl)methyl)-4-fluoro-6-(2-hydroxypropan-2-yl)isoindolin-1-one To a solution of 3-(4-chlorophenyl)-2-((5-chloropyridin-2-yl)methyl)-4-fluoro-3-((1-(hydroxymethyl)cyclopropyl)methoxy)-6-(2-hydroxypropan-2-yl)isoindolin-1-one (prepared in a similar manner as in Example 1, steps 1-4 using (1-hydroxymethyl-cyclopropyl)-methanol instead of {1-[hydroxy($^2$H$_2$)methyl]cyclopropyl}($^2$H$_2$)methanol in step 2) (1.17 g, 2.15 mmol) in THF (27 mL) was added dropwise DPPA (652 mg, 0.51 mL, 2.37 mmol) and the resulting solution cooled to 0° C. DBU (327 mg, 0.32 mL, 2.15 mmol) was added dropwise over 10 minutes and the reaction stirred at 0° C. for 1 h, upon which a white precipitate formed. The reaction was warmed to RT and heated at 45° C. for 4 days then cooled to RT. The reaction was diluted with EtOAc, washed with water), 0.5M aqueous NaOH solution, water, brine, dried over MgSO₄ and concentrated under vacuum. Purified by Biotage using 0-100% EtOAc in petrol gave the title compound as a colourless oil (521 mg). ¹H NMR (500 MHz, CDCl₃) 8.32 (1H, d), 7.81 (1H, d), 7.48 (1H, dd), 7.42 (1H, dd), 7.25-7.17 (5H, m), 4.54-4.47 (2H, m), 3.44 (1H, d), 3.14 (1H, d), 3.02 (1H, d), 2.95 (1H, d), 1.62 (3H, s), 1.61 (3H, s), 0.52-0.50 (2H, m), 0.35-0.33 (2H, m).

Step 2: 3-((1-(Aminomethyl)cyclopropyl)methoxy)-3-(4-chlorophenyl)-2-((5-chloropyridin-2-yl)methyl)-4-fluoro-6-(2-hydroxypropan-2-yl)isoindolin-1-one At 0° C., to a solution of 3-((1-(azidomethyl)cyclopropyl)methoxy)-3-(4-chlorophenyl)-2-((5-chloropyridin-2-yl)methyl)-4-fluoro-6-(2-hydroxypropan-2-yl)isoindolin-1-one (468 mg, 0.82 mmol) in THF (2.4 mL) was added portionwise PPh₃ (237 mg, 0.90 mmol) and stirred at 0° C. for 1 h. Water (0.43 mL) was added and the reaction heated at 55° C. for 2 h then at RT overnight. The reaction was concentrated onto isolute and purified by Biotage using 0-80% EtOAc in petrol (amino column) to give the title compound as a white solid (352 mg). ¹H NMR (500 MHz, CDCl₃) 8.38 (1H, d), 7.79 (1H, d), 7.51 (1H, dd), 7.40 (1H, dd), 7.29-7.26 (3H, m), 7.21-7.20 (2H, m), 4.53 (1H, d), 4.42 (1H, d), 3.06 (1H, d), 2.99 (1H, d), 2.81 (1H, d), 2.58 (1H, d), 1.61 (3H, s), 1.60 (3H, s), 0.46-0.41 (2H, m), 0.31-0.21 (2H, m).

Step 3: 2-({[1-({[(1R)-1-(4-chlorophenyl)-2-[(5-chloropyridin-2-yl)methyl]-7-fluoro-5-(2-hydroxypropan-2-yl)-3-oxo-2,3-dihydro-1H-isoindol-1-yl]oxy}methyl)cyclopropyl]methyl}amino)-N-methylacetamide To a microwave vial was added 3-((1-(aminomethyl)cyclopropyl)methoxy)-3-(4-chlorophenyl)-2-((5-chloropyridin-2-yl)methyl)-4-fluoro-6-(2-hydroxypropan-2-yl)isoindolin-1-one (267 mg, 0.49 mmol), 2-chloro-N-methylacetamide (53 mg, 0.49 mmol) and sodium iodide (7.3 mg, 0.049 mmol) followed by DMF (6.6 mL) and Et$_3$N (0.23 mL, 1.62 mmol) and heated at 80° C. for 4 h then cooled to RT. The reaction was extracted with EtOAc (3×50 mL), washed with brine, dried over MgSO$_4$ and concentrated under vacuum. Purified by Biotage (amino column) using 0-100% EtOAc in petrol gave the racemic mixture as a white solid (152 mg) which was separated by chiral HPLC.

Example 155, Slow Running Isomer (60 mg, 20%)

1H NMR (400 MHz, DMSO-d6): 8.35 (1H, d), 7.80 (1H, d), 7.72 (1H, dd), 7.61-7.47 (2H, m), 7.32-7.18 (5H, m), 5.35 (1H, s), 4.78-4.31 (2H, m), 3.10-3.01 (3H, m), 3.01-2.93 (1H, m), 2.61-2.54 (4H, m), 2.43-2.36 (1H, m), 1.48 (6H, s), 0.39-0.29 (2H, m), 0.26-0.09 (2H, m); MS: [M+H]$^+$=586

Example 156: N-{[1-({[(1R)-1-(4-Chlorophenyl)-2-[(5-chloropyridin-2-yl)methyl]-7-fluoro-5-(2-hydroxypropan-2-yl)-3-oxo-2,3-dihydro-1H-isoindol-1-yl]oxy}methyl)cyclopropyl]methyl}acetamide

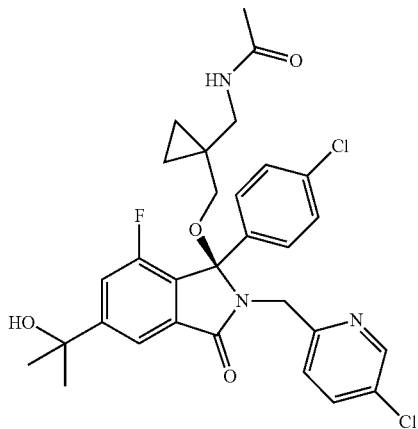 [SMILES: CC(=O)NCC1(CO[C@]2(c3ccc(Cl)cc3)c3c(F)cc(C(C)(C)O)cc3C(=O)N2Cc2ccc(Cl)cn2)CC1]

To a solution of 3-((1-(aminomethyl)cyclopropyl)methoxy)-3-(4-chlorophenyl)-2-((5-chloropyridin-2-yl)methyl)-4-fluoro-6-(2-hydroxypropan-2-yl)isoindolin-1-one (Example 155, step 2) (349 mg, 0.64 mmol) in DCM/MeOH (3.8 mL/1.3 mL) was added Et$_3$N (0.10 mL, 0.77 mmol) followed by Ac$_2$O (79 mg, 0.77 mmol) and stirred at RT for 2 h. The reaction was diluted with DCM (20 mL), washed with brine, dried over MgSO$_4$ and concentrated under vacuum. Purified by Biotage (amino column) using 40-100% EtOAc in petrol gave the racemic mixture as a white solid (352 mg), which was separated by chiral HPLC.

Example 156, Slow Running Isomer (159 mg, 42%)

1H NMR (400 MHz, DMSO-d6): 8.35 (1H, d), 7.79 (1H, d), 7.71 (1H, dd), 7.65 (1H, t), 7.50 (1H, dd), 7.32-7.22 (4H, m), 7.20 (1H, d), 5.36 (1H, s), 4.59-4.25 (2H, m), 3.21-3.06 (3H, m), 2.81 (1H, d), 1.78 (3H, s), 1.48 (6H, s), 0.43-0.33 (2H, m), 0.24-0.10 (2H, m); MS: [M+H]$^+$=586

Example 157 and 158: (3R)-3-(4-Chlorophenyl)-2-[(5-chloropyridin-2-yl)methyl]-6-[2-hydroxy-1-(2-oxoimidazolidin-1-yl)propan-2-yl]-3-methoxy-2,3-dihydro-1H-isoindol-1-one (*both isomers separated and isolated)

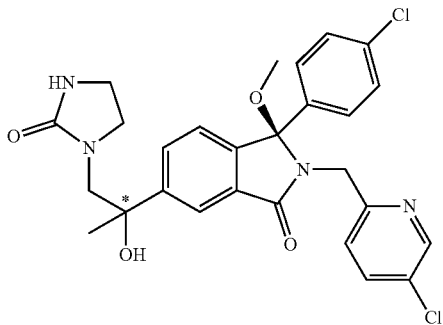 [SMILES: CO[C@]1(c2ccc(Cl)cc2)c2ccc(C(C)(O)CN3CCNC3=O)cc2C(=O)N1Cc1ccc(Cl)cn1]

NaH (60%, 53 mg, 1.32 mmol) was added to a solution of 2-imidazolidinone (380 mg, 4.4 mmol) in DMF (3 mL) under inert atmosphere. The suspension was stirred at room temperature for 10 min. and then (3R)-3-(4-chlorophenyl)-2-[(5-chloropyridin-2-yl)methyl]-3-methoxy-6-(2-methyloxiran-2-yl)-2,3-dihydro-1H-isoindol-1-one (Example 99 and Example 100, step 1)(200 mg, 0.44 mmol) was added. The reaction was stirred at 60° C. for 18 h, quenched with water (10 mL) and extracted with EtOAc (2×20 mL). The organic phase was dried over Na$_2$SO$_4$, filtered and concentrated in vacuo. The residue was purified by column chromatography (gradient 0-100% EtOAc in petrol followed by gradient 0-20% MeOH in EtOAc) and the isomers were separated by chiral HPLC to give:

Example 157 Isomer 1 as a White Solid (13 mg, 5%)

$^1$H NMR (400 MHz, DMSO-d$_6$): 8.39 (1H, d), 7.93 (1H, d), 7.79-7.68 (2H, m), 7.33-7.15 (6H, m), 6.28 (1H, s), 5.56 (1H, s), 4.50 (1H, d), 4.39 (1H, d), 3.30 (2H, d), 3.28-3.18 (2H, m), 3.18-3.05 (2H, m), 2.77 (3H, s), 1.47 (3H, s). MS: [M−H]$^-$=539.

Example 158 Isomer 2 as a White Solid (12 mg, 5%)

$^1$H NMR (400 MHz, DMSO-d$_6$): 8.40 (1H, d), 7.95 (1H, s), 7.78-7.70 (2H, m), 7.34-7.15 (6H, m), 6.28 (1H, s), 5.57 (1H, s), 4.53 (1H, d), 4.37 (1H, d), 3.32-3.28 (2H, m), 3.28-3.17 (2H, m), 3.17-3.05 (2H, m), 2.76 (3H, s), 1.46 (3H, s). MS: [M−H]$^-$=539.

Example 159 and 160: (3R)-3-(4-Chlorophenyl)-2-[(5-chloropyridin-2-yl)methyl]-6-[2-hydroxy-1-(1H-imidazol-1-yl)propan-2-yl]-3-methoxy-2,3-dihydro-1H-isoindol-1-one (*both isomers separated and isolated)

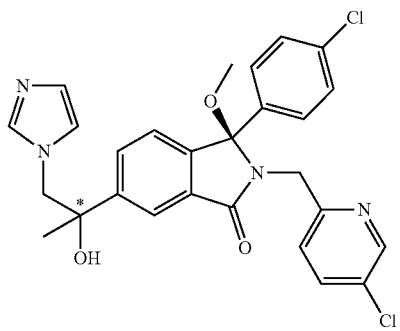 [SMILES: CO[C@]1(c2ccc(Cl)cc2)c2ccc(C(C)(O)Cn3ccnc3)cc2C(=O)N1Cc1ccc(Cl)cn1]

The title compounds were prepared following similar methods to those described in Examples 157 and 158 using imidazole instead of 2-imidazolidinone to give after chiral HPLC:

Example 159 Isomer 1 (36 mg, 16%)

$^1$H NMR (400 MHz, DMSO-d$_6$): 8.40 (1H, d), 7.94 (1H, d), 7.78-7.69 (2H, m), 7.37 (1H, s), 7.35-7.14 (6H, m), 6.92 (1H, s), 6.74 (1H, s), 5.71 (1H, s), 4.52 (1H, d), 4.37 (1H, d), 4.25 (1H, d), 4.15 (1H, d), 2.76 (3H, s), 1.43 (3H, s).
MS: [M−H]$^−$=523.

Example 160 Isomer 2 (35 mg, 16%)

$^1$H NMR (400 MHz, DMSO-d$_6$): 8.39 (1H, d), 7.95 (1H, d), 7.78-7.68 (2H, m), 7.41 (1H, s), 7.33-7.17 (6H, m), 6.92 (1H, s), 6.78 (1H, s), 5.71 (1H, s), 4.51 (1H, d), 4.39 (1H, d), 4.26 (1H, d), 4.16 (1H, d), 2.77 (3H, s), 1.45 (3H, s). MS: [M−H]$^−$=523.

Example 161 and 162: (3R)-3-(4-Chlorophenyl)-2-[(5-chloropyridin-2-yl)methyl]-6-[1-(1,2-dimethyl-1H-imidazol-4-yl)-1-hydroxyethyl]-4-fluoro-3-methoxy-2,3-dihydro-1H-isoindol-1-one (*both isomers separated and isolated)

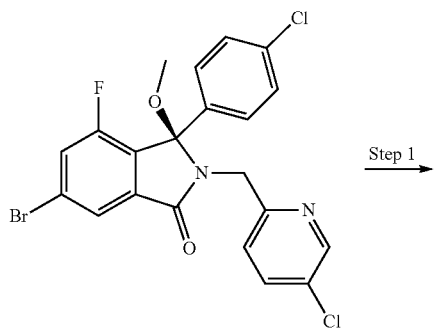

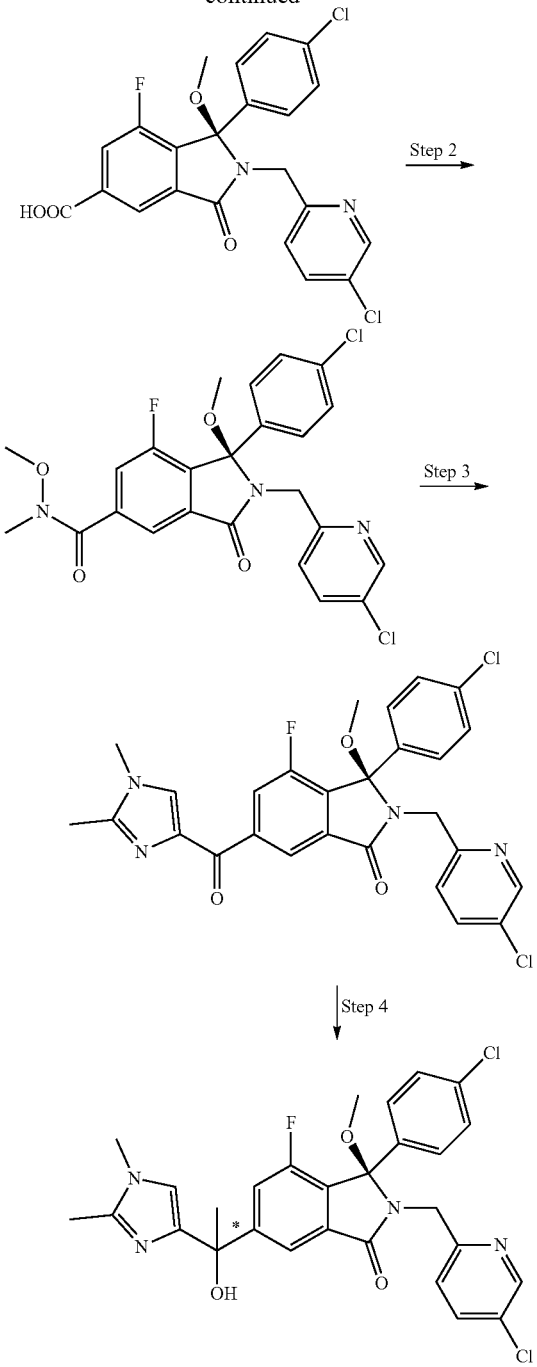

Step 1: (1R)-1-(4-Chlorophenyl)-2-[(5-chloropyridin-2-yl)methyl]-7-fluoro-1-methoxy-3-oxo-2,3-dihydro-1H-isoindole-5-carboxylic acid A mixture of 6-bromo-3-(4-chlorophenyl)-2-[(5-chloropyridin-2-yl)methyl]-4-fluoro-3-methoxy-2,3-dihydro-1H-isoindol-1-one (Example 2, step 1-3(R) isomer, isolated by preparative chiral HPLC) (6.0 g, 12.1 mmol), LiHCOO.H$_2$O (3.4 g, 48.5 mmol), Pd(OAc)$_2$ (271 mg, 1.21 mmol), Xantphos (1.39 g, 2.42 mmol) and TEA (7.0 mL, 48.5 mmol) in DMF (70 mL) was degassed for 15 min with N$_2$ and then Ac$_2$O (4.6 mL, 48.5 mmol) was slowly added (CAREFULL:

gas evolution). The resulting mixture was stirred at 80° C. under inert atmosphere for 2 h. The reaction was cooled to room temperature and most of the DMF was removed in vacuo. The residue was partitioned between 1N HCl (80 mL) and EtOAc (80 mL), the organic phase was separated and washed with brine (4×50 mL), dried over MgSO$_4$, filtered and concentrated in vacuo to give a light orange solid which was used in the next step without any further purification. MS: [M+H]$^+$=461.

Step 2: (1R)-1-(4-Chlorophenyl)-2-[(5-chloropyridin-2-yl)methyl]-7-fluoro-N,1-dimethoxy-N-methyl-3-oxo-2,3-dihydro-1H-isoindole-5-carboxamide TEA (3.3 mL, 22.6 mmol) was added to a solution of (1R)-1-(4-chlorophenyl)-2-[(5-chloropyridin-2-yl)methyl]-7-fluoro-1-methoxy-3-oxo-2,3-dihydro-1H-isoindole-5-carboxylic acid (6.9 g, 15.1 mmol), N,O-dimethylhydroxylamine hydrochloride (1.8 g, 18.1 mmol), EDC (3.5 g, 18.1 mmol) and HOBt (2.4 g, 18.1 mmol) in DMF (60 mL). The reaction was stirred at 45° C., under inert atmosphere, for 3 h. The mixture was cooled to room temperature, diluted with EtOAc (80 mL) and washed with water (80 mL) and brine (3×50 mL). The organic phase was dried over MgSO$_4$, filtered and concentrated in vacuo. The residue was columned on silica gel (gradient 0-100% EtOAC in Petrol) to give the desired product as a yellow solid (4.65 g, 76% over 2 steps). MS: [M-OMe]$^-$=472.

Step 3: (3R)-3-(4-Chlorophenyl)-2-[(5-chloropyridin-2-yl)methyl]-6-(1,2-dimethyl-1H-imidazole-4-carbonyl)-4-fluoro-3-methoxy-2,3-dihydro-1H-isoindol-1-one BuLi (2.5M in hexane, 1.65 mL, 4.13 mmol) was added to a solution of 4-bromo-1,2-dimethyl-1H-imidazole (682 mg, 3.9 mmol) in dry THF (15 mL) under inert atmosphere at −70° C. The solution was stirred for 8 min and then BuLi (2.5M in hexane, 0.5 mL, 1.2 mmol) was slowly added maintaining the internal temperature at −70° C. After 5 min a solution of (1R)-1-(4-chlorophenyl)-2-[(5-chloropyridin-2-yl)methyl]-7-fluoro-N, 1-dimethoxy-N-methyl-3-oxo-2,3-dihydro-1H-isoindole-5-carboxamide (600 mg, 3.9 mmol) in dry THF (8 mL) was slowly added. The resulting mixture was stirred at −70° C. for 15 min and then it was slowly allowed to warm up to 0° C. and stirred at the same temperature for 10 min. The reaction was quenched with sat. NH$_4$Cl and extracted with EtOAc. The organic phase was dried over MgSO$_4$, filtered and concentrated in vacuo. The residue was columned on silica gel (gradient 0-100% EtOAC in Petrol) to give 220 mg of a yellow gum (35%). MS: [M+H]$^+$=539.

Step 4: (3R)-3-(4-Chlorophenyl)-2-[(5-chloropyridin-2-yl)methyl]-6-[1-(1,2-dimethyl-1H-imidazol-4-yl)-1-hydroxyethyl]-4-fluoro-3-methoxy-2,3-dihydro-1H-isoindol-1-one The title compound was prepared following similar methods to those described in Example 1, step 4 starting from (3R)-3-(4-chlorophenyl)-2-[(5-chloropyridin-2-yl)methyl]-6-(1,2-dimethyl-1H-imidazole-4-carbonyl)-4-fluoro-3-methoxy-2,3-dihydro-1H-isoindol-1-one (200 mg, 0.37 mmol). The two diastereoisomers were separated by chiral HPLC.

Example 161 Isomer 1 (28 mg, 14%)

$^1$H NMR (400 MHz, DMSO-d$_6$): 8.39 (1H, d), 7.80 (1H, d), 7.74 (1H, dd), 7.52 (1H, dd), 7.31 (2H, d), 7.25 (3H, d), 6.87 (1H, s), 5.66 (1H, s), 4.51 (1H, d), 4.32 (1H, d), 3.49 (3H, s), 2.87 (3H, s), 2.24 (3H, s), 1.72 (3H, s); MS: [M+H]$^+$=555.

Example 162 Isomer 2 (33 mg, 16%)

$^1$H NMR (400 MHz, DMSO-d$_6$): 8.38 (1H, d), 7.79 (1H, d), 7.73 (1H, dd), 7.52 (1H, dd), 7.30 (2H, d), 7.25 (3H, dd), 6.87 (1H, s), 5.65 (1H, s), 4.49 (1H, d), 4.35 (1H, d), 3.49 (3H, s), 2.88 (3H, s), 2.24 (3H, s), 1.72 (3H, s); MS: [M+H]$^+$=555.

The following compounds were prepared in a similar fashion to Example 161 using the appropriate lithiated heterocycle.

Example 163 and 164: (3R)-3-(4-chlorophenyl)-2-[(5-chloropyridin-2-yl)methyl]-4-fluoro-6-[1-hydroxy-1-(1H-imidazol-2-yl)ethyl]-3-methoxy-2,3-dihydro-1H-isoindol-1-one (*both isomers separated and isolated)

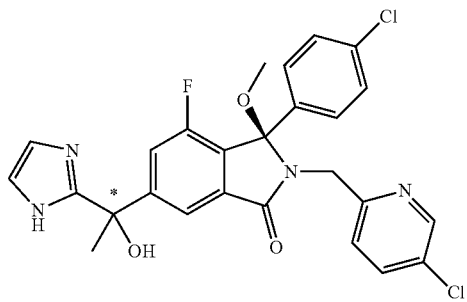 [SMILES: CO[C@]1(c2ccc(Cl)cc2)c2c(F)cc(C(C)(O)c3ncc[nH]3)cc2C(=O)N1Cc1ccc(Cl)cn1]

The compounds were prepared using SEM-protected imidazole and BuLi, followed by subsequent deprotection (TBAF).

Example 163 Fast Running Isomer

1H NMR (400 MHz, DMSO-d6): 12.21-11.31 (1H, m), 8.38 (1H, d), 7.77-7.67 (2H, m), 7.57-7.49 (1H, m), 7.30 (2H, d), 7.24 (3H, dd), 6.93 (2H, s), 6.41 (1H, s), 4.49 (1H, d), 4.35 (1H, d), 2.88 (3H, s), 1.87 (3H, s); MS: [M−H]$^-$=525

Example 164 Slow Running Isomer

1H NMR (400 MHz, DMSO-d6): 11.82 (1H, s), 8.38 (1H, d), 7.77-7.69 (2H, m), 7.52 (1H, dd), 7.31 (2H, d), 7.25 (3H, dd), 7.00 (1H, t), 6.84 (1H, s), 6.40 (1H, s), 4.50 (1H, d), 4.33 (1H, d), 2.87 (3H, s), 1.87 (3H, s).
MS: [M+H]$^+$=527

Example 165 and 166: (3R)-3-(4-Chlorophenyl)-2-[(5-chloropyridin-2-yl)methyl]-4-fluoro-6-[1-hydroxy-1-(1,3-thiazol-2-yl)ethyl]-3-methoxy-2,3-dihydro-1H-isoindol-1-one (*both isomers separated and isolated)

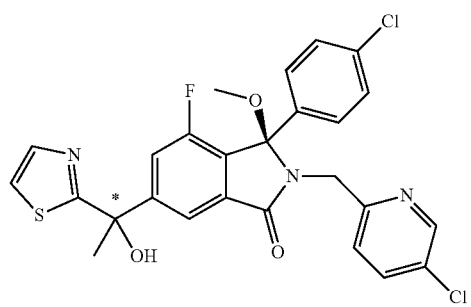 [SMILES: CO[C@]1(c2ccc(Cl)cc2)c2c(F)cc(C(C)(O)c3nccs3)cc2C(=O)N1Cc1ccc(Cl)cn1]

The compounds were prepared using thiazole.

Example 165 Fast Running Isomer

1H NMR (400 MHz, DMSO-d6): 8.38 (1H, d), 7.89 (1H, d), 7.80-7.70 (2H, m), 7.67-7.59 (2H, m), 7.33-7.22 (5H, m), 7.10 (1H, s), 4.50 (1H, d), 4.35 (1H, d), 2.87 (3H, s), 1.96 (3H, s); MS: [M-OMe]$^+$=512

Example 166 Slow Running Isomer

1H NMR (400 MHz, DMSO-d6): 8.38 (1H, d), 7.89 (1H, d), 7.79 (1H, d), 7.73 (1H, dd), 7.67-7.59 (2H, m), 7.30 (2H, d), 7.25 (3H, d), 7.10 (1H, s), 4.50 (1H, d), 4.35 (1H, d), 2.87 (3H, s), 1.95 (3H, s); MS: [M-OMe]$^+$=512

Example 167: (2S)-3-{[(1R)-1-(4-Chlorophenyl)-2-[(5-chloropyridin-2-yl)methyl]-7-fluoro-5-(2-hydroxypropan-2-yl)-3-oxo-2,3-dihydro-1H-isoindol-1-yl]oxy}-2-methylpropanamide

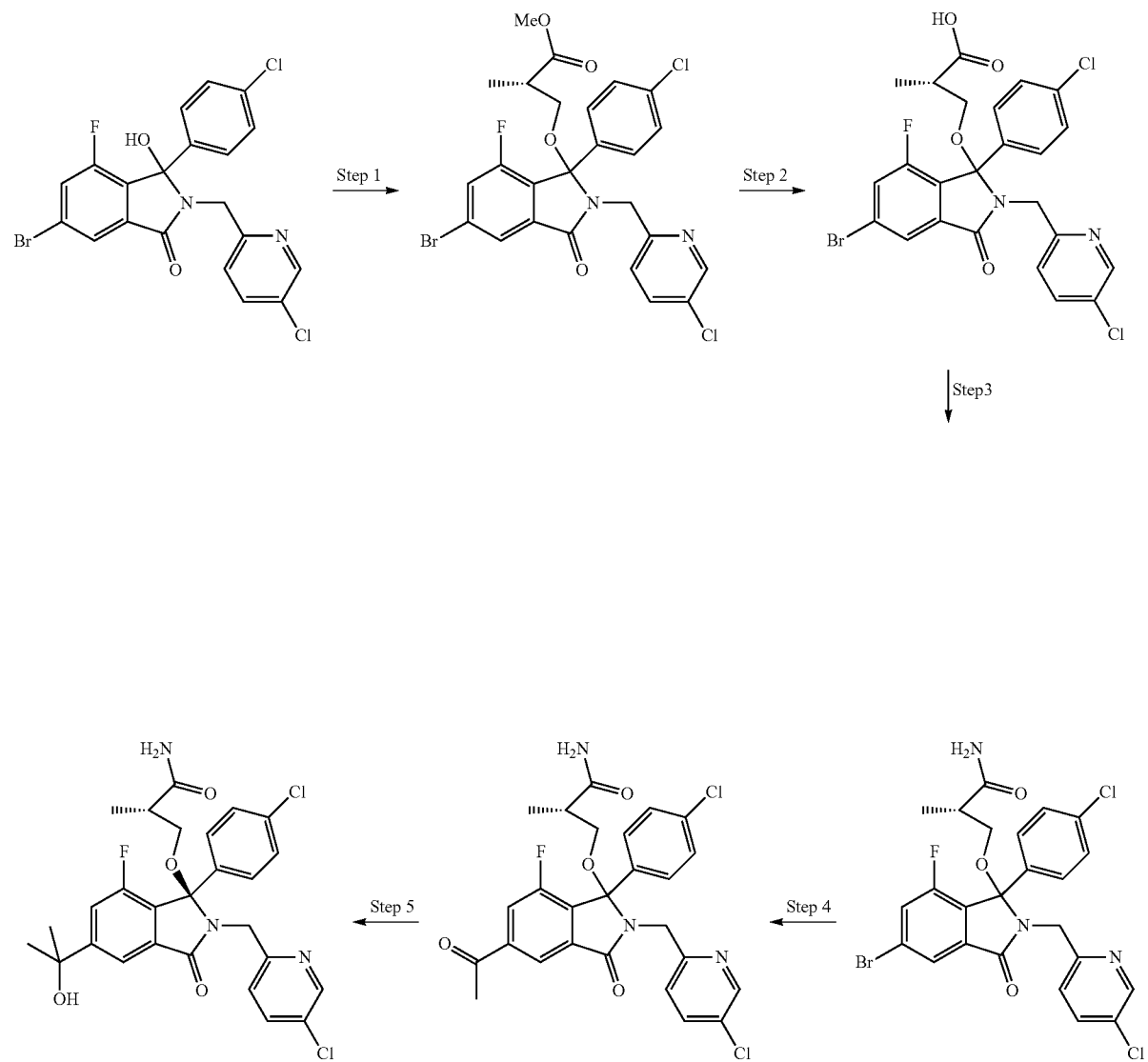

Step 1: Methyl (2S)-3-{[5-bromo-1-(4-chlorophenyl)-2-[5-chloropyridin-2-yl)methyl]-7-fluoro-3-oxo-2,3-dihydro-1H-isoindol-1-yl]oxy}-2-methylpropanoate 6-Bromo-3-(4-chloro-phenyl)-2-(5-chloro-pyridin-2-yl-methyl)-4-fluoro-3-hydroxy-2,3-dihydro-isoindol-1-one (Example 1, step 1) was reacted with (S)-methyl 3-hydroxy-2-methylpropanoate in a similar manner to that described in Example 1, step 2 to give the title compound. MS: [M+H]⁺=583

Step 2: (2S)-3-{[5-Bromo-1-(4-chlorophenyl)-2-[(5-chloropyridin-2-yl)methyl]-7-fluoro-3-oxo-2,3-dihydro-1H-isoindol-1-yl]oxy}-2-methylpropanoic acid (2R)-3-{[5-Bromo-1-(4-chlorophenyl)-2-[(5-chloropyridin-2-yl)methyl]-7-fluoro-3-oxo-2,3-dihydro-1H-isoindol-1-yl]oxy}-2-methylpropanoate (1.14 g, 1.96 mmol) and LiOH.H₂O (0.33 g, 7.84 mmol) were combined in THF/H₂O (10:1, 11 ml) at 0° C. The reaction mixture was warmed to room temperature overnight and stirred and that temperature for 18 hours. The reaction was diluted with ethyl acetate (20 ml) and washed with 2M HCl. The aqueous layer was extracted with ethyl acetate (2×20 ml) and the combined organic extracts were dried over MgSO₄ and concentrated in vacuo to give the title compound (1.03 g, 92%). MS: [M+H]⁺=569

Step 3: (2S)-3-{[5-Bromo-1-(4-chlorophenyl)-2-[(5-chloropyridin-2-yl)methyl]-7-fluoro-3-oxo-2,3-dihydro-1H-isoindol-1-yl]oxy}-2-methylpropanamide Methyl chloroformate (0.14 ml, 1.81 mmol) and triethylamine (0.25 ml, 1.81 mmol) were added to a stirring solution of (2R)-3-{[5-bromo-1-(4-chlorophenyl)-2-[(5-chloropyridin-2-yl)methyl]-7-fluoro-3-oxo-2,3-dihydro-1H-isoindol-1-yl]oxy}-2-methylpropanoic acid (1.03 g, 1.81 mmol) in THF (10 ml) at −15° C. under N₂. The reaction was allowed to warm to 15° C. over 1.5 hours. Methyl chloroformate (0.14 ml, 1.81 mmol), triethylamine (0.25 ml, 1.81 mmol) and THF (5 ml) were added and the stirring was continued for 1 hour. Ammonia (7M in MeOH, 3.87 ml) was added and the reaction was stirred for 1 hour. The reaction mixture was filtered and the solids were washed with THF (10 ml). Volatiles were removed in vacuo and the residue was purified by Biotage using 0-100% EtOAc/Petrol then 0-20% MeOH/EtOAc as the eluent to afford the title compound (0.72 g, 70%); MS: [M+H]⁺=568

Step 4: (2S)-3-{[5-Acetyl-1-(4-chlorophenyl)-2-[(5-chloropyridin-2-yl)methyl]-7-fluoro-3-oxo-2,3-dihydro-1H-isoindol-1-yl]oxy}-2-methylpropanamide The title compound was prepared from (2R)-3-{[5-bromo-1-(4-chlorophenyl)-2-[(5-chloropyridin-2-yl)methyl]-7-fluoro-3-oxo-2,3-dihydro-1H-isoindol-1-yl]oxy}-2-methylpropanamide in a similar manner to Example 1, step 3. (517 mg, 77%); MS: [M+H]⁺=574

Step 5: (2S)-3-{[(1R)-1-(4-Chlorophenyl)-2-[(5-chloropyridin-2-yl)methyl]-7-fluoro-5-(2-hydroxypropan-2-yl)-3-oxo-2,3-dihydro-1H-isoindol-1-yl]oxy}-2-methylpropanamide The title compound was prepared from (2R)-3-{[5-acetyl-1-(4-chlorophenyl)-2-[(5-chloropyridin-2-yl)methyl]-7-fluoro-3-oxo-2,3-dihydro-1H-isoindol-1-yl]oxy}-2-methylpropanamide in a similar manner to Example 66, step 3. Separation by chiral preparative LCMS gave Example 167 as a colourless solid. ¹H NMR (400 MHz, DMSO-d6): 8.38 (1H, d), 7.81 (1H, d), 7.74 (1H, dd), 7.51 (1H, d), 7.37-7.28 (3H, m), 7.28-7.22 (3H, m), 6.84 (1H, s), 5.38 (1H, s), 4.49 (1H, d), 4.42 (1H, d), 3.08-2.96 (2H, m), 2.32-2.22 (1H, m), 1.48 (6H, s), 0.85 (3H, d). MS: [M+H]⁺=546

Example 168: (2R)-3-{[(1R)-1-(4-Chlorophenyl)-2-[(5-chloropyridin-2-yl)methyl]-7-fluoro-5-(2-hydroxypropan-2-yl)-3-oxo-2,3-dihydro-1H-isoindol-1-yl]oxy}-2-methylpropanamide

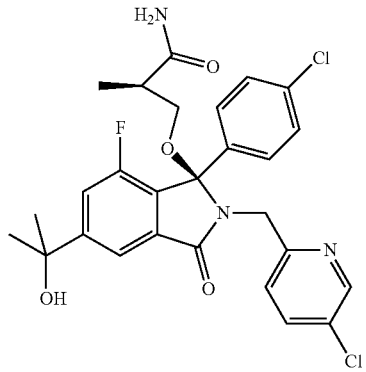 [SMILES: C[C@H](CO[C@]1(c2ccc(Cl)cc2)c2c(F)cc(C(C)(C)O)cc2C(=O)N1Cc1ccc(Cl)cn1)C(N)=O]

Example 168 was prepared in a similar manner to Example 167 using (R)-methyl 3-hydroxy-2-methylpropanoate. 1H NMR (400 MHz, DMSO-d6): 8.29 (1H, d), 7.82 (1H, s), 7.65 (1H, dd), 7.53 (1H, d), 7.39 (1H, s), 7.23 (2H, d), 7.21 (2H, d), 7.11 (1H, d), 6.92 (1H, s), 5.37 (1H, s), 4.60 (1H, d), 4.37 (1H, d), 3.26 (1H, t), 2.80 (1H, t), 1.49 (7H, s), 0.99 (3H, d). MS: [M+H]⁺=546

Example 169: 6-[(1S)-1-[(1R)-1-(4-Chlorophenyl)-7-fluoro-1-{[1-(hydroxymethyl)cyclopropyl]methoxy}-5-(2-hydroxypropan-2-yl)-3-oxo-2,3-dihydro-1H-isoindol-2-yl]ethyl]pyridine-3-carbonitrile Example 170: 6-[(1R)-1-[(1R)-1-(4-Chlorophenyl)-7-fluoro-1-{[1-(hydroxymethyl)cyclopropyl]methoxy}-5-(2-hydroxypropan-2-yl)-3-oxo-2,3-dihydro-1H-isoindol-2-yl]ethyl]pyridine-3-carbonitrile Example 169

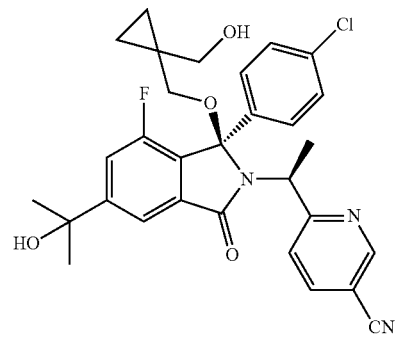

-continued

Example 170

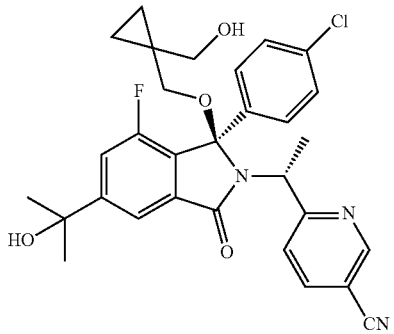

Starting from 5-bromo-2-(4-chloro-benzoyl)-3-fluoro-benzoic acid (Manchester Organics, MOL1216), the title compounds were prepared in a similar manner to Example 3; using HATU and Preparation 31 instead of SOCl$_2$ and 6-aminomethyl-nicotinonitrile respectively. LaCl$_3$.2LiCl was used instead of ZnCl$_2$ in step 4. Both iomers can be obtained by using the appropriate chiral sulfinaine in Preparation 31.

Example 169

$^1$H NMR (400 MHz, DMSO-d6): 8.66 (1H, d), 8.07 (1H, dd), 7.76 (1H, d), 7.55-7.44 (2H, m), 7.22-7.09 (4H, m), 5.38 (1H, s), 4.55 (1H, t), 3.54 (1H, dd), 3.45 (1H, d), 3.38-3.34 (1H, m), 2.90 (1H, d), 1.84 (3H, d), 1.48 (7H, s), 0.53-0.37 (4H, m). MS: [M+H]$^+$=550

Example 170

$^1$H NMR (400 MHz, DMSO-d6): 8.66 (1H, d), 8.07 (1H, dd), 7.77 (1H, d), 7.55-7.43 (2H, m), 7.23-7.09 (4H, m), 5.38 (1H, s), 4.55 (1H, t), 3.54 (1H, dd), 3.49-3.37 (2H, m), 2.90 (1H, d), 1.84 (3H, d), 1.48 (7H, s), 0.54-0.37 (4H, m); MS: [M+H]$^+$=550

Example 171 and 172: (3R)-3-(4-Chlorophenyl)-2-[(5-chloropyridin-2-yl)methyl]-4-fluoro-6-(2-hydroxypropan-2-yl)-3-[(1-methanesulfinylcyclopropyl)methoxy]-2,3-dihydro-1H-isoindol-1-one (*both isomers separated and isolated)

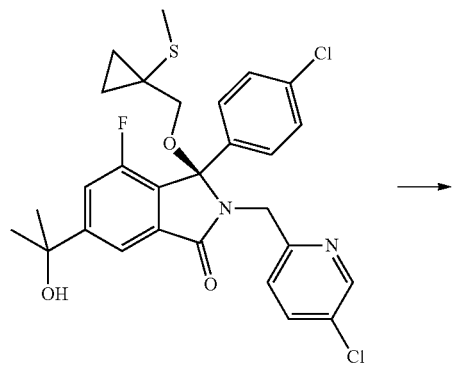

-continued

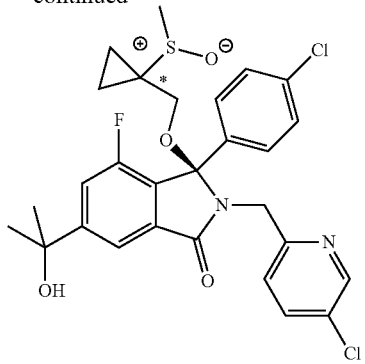

(3R)-3-(4-Chlorophenyl)-2-[(5-chloropyridin-2-yl)methyl]-4-fluoro-6-(2-hydroxypropan-2-yl)-3-{[1-(methylsulfanyl)cyclopropyl]methoxy}-2,3-dihydro-1H-isoindol-1-one (Prepared using procedures similar to those described in to Example 3, using Preparation 32) (60 mg, 0.11 mmol) was dissolved in 1M HCl (2 ml) and methanol (4 ml). Sodium periodate (69 mg, 0.32 mmol) was added and the reaction was stirred for 2 hours. The reaction mixture was diluted with water (10 ml) and extracted with DCM (3×20 ml). The combined organic extracts were dried over MgSO$_4$ and concentrated in vacuo. Separation by preparative chiral LCMS gave the title compounds.

Example 171

$^1$H NMR (400 MHz, CDCl$_3$): 8.38 (1H, d), 7.83 (1H, d), 7.55 (1H, dd), 7.51-7.35 (1H, m), 7.35-7.15 (6H, m), 4.53 (1H, d), 4.35 (1H, d), 3.58 (1H, d), 3.50 (1H, q), 3.31 (1H, d), 2.65 (3H, s), 2.01 (1H, s), 1.33-1.20 (3H, m), 1.20-1.13 (1H, m), 0.82-0.62 (2H, m). MS: [M+H]$^+$=577

Example 172

$^1$H NMR (400 MHz, CDCl$_3$): 8.40 (1H, d), 7.82 (1H, d), 7.58 (1H, dd), 7.46 (1H, dd), 7.35-7.29 (1H, m), 7.26 (2H, d), 4.59 (1H, d), 4.26 (1H, d), 3.60 (1H, d), 3.39 (1H, d), 2.68 (3H, s), 2.04 (1H, s), 1.63 (7H, d), 1.33-1.24 (1H, m), 1.12-1.00 (1H, m), 0.81-0.68 (2H, m). MS: [M+H]$^+$=577

Example 173: 6-{[(1R)-1-(4-Chlorophenyl)-7-fluoro-5-(2-hydroxypropan-2-yl)-1-methoxy-3-oxo-2,3-dihydro-1H-isoindol-2-yl]methyl}pyridine-3-carbonitrile

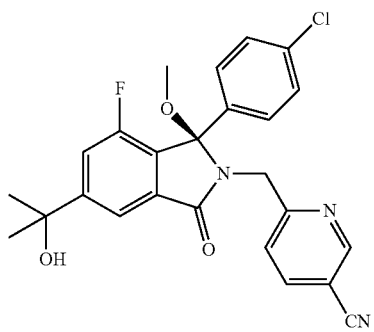 [SMILES: CO[C@]1(c2ccc(Cl)cc2)c2c(F)cc(C(C)(C)O)cc2C(=O)N1Cc1ccc(C#N)cn1]

351

The title compound was prepared in a similar manner to Example 2 using 6-[5-bromo-1-(4-chloro-phenyl)-7-fluoro-1-hydroxy-3-oxo-1,3-dihydro-isoindol-2-ylmethyl]-nicotinonitrile (Example 3, step 1).

$^1$H NMR (400 MHz, DMSO-d6): 8.80 (1H, d), 8.12 (1H, dd), 7.83 (1H, d), 7.54 (1H, dd), 7.40 (1H, d), 7.30 (2H, d), 7.29-7.22 (2H, m), 5.37 (1H, s), 4.56 (1H, d), 4.49 (1H, d), 2.93 (3H, s), 1.49 (6H, s). MS: [M-CH$_3$O]$^+$=434

Example 174: (3R)-3-(4-Chlorophenyl)-2-[(1S)-1-(5-chloropyridin-2-yl)prop-2-en-1-yl]-4-fluoro-3-[(1-hydroxycyclopropyl)methoxy]-6-(2-hydroxypropan-2-yl)-2,3-dihydro-1H-isoindol-1-one

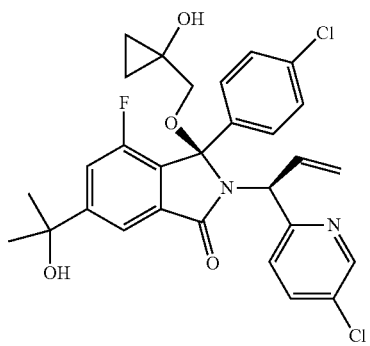 [SMILES: C=C[C@@H](c1ccc(Cl)cn1)N1C(=O)c2cc(C(C)(C)O)cc(F)c2[C@]1(OCC1(O)CC1)c1ccc(Cl)cc1]

352

Starting from 5-bromo-2-(4-chloro-benzoyl)-3-fluoro-benzoic acid (Manchester Organics, MOL1216), the title compound was prepared in a similar manner to Example 3; using HATU and Preparation 33 instead of SOCl$_2$ and 6-aminomethyl-nicotinonitrile respectively. LaCl$_3$.2LiCl was used instead of ZnCl$_2$ in step 4.

$^1$H NMR (400 MHz, DMSO-d6): 8.22 (1H, d), 7.78-7.68 (2H, m), 7.54-7.47 (1H, m), 7.38 (1H, d), 7.29 (2H, d), 7.16 (2H, d), 6.65-6.53 (1H, m), 5.62 (1H, s), 5.35 (1H, s), 5.28-5.17 (2H, m), 5.01 (1H, d), 3.48 (1H, d), 2.93 (1H, d), 1.48 (6H, d), 0.70-0.63 (2H, m), 0.58-0.45 (2H, m); MS: [M+H]$^+$=557

Example 175 and 176: 1-({[(1R)-1-(4-Chlorophenyl)-2-[(5-chloropyridin-2-yl)methyl]-7-fluoro-5-[hydroxy(1-methyl-1H-pyrazol-4-yl)methyl]-3-oxo-2,3-dihydro-1H-isoindol-1-yl]oxy}methyl)cyclopropane-1-carboxamide (*both isomers separated and isolated)

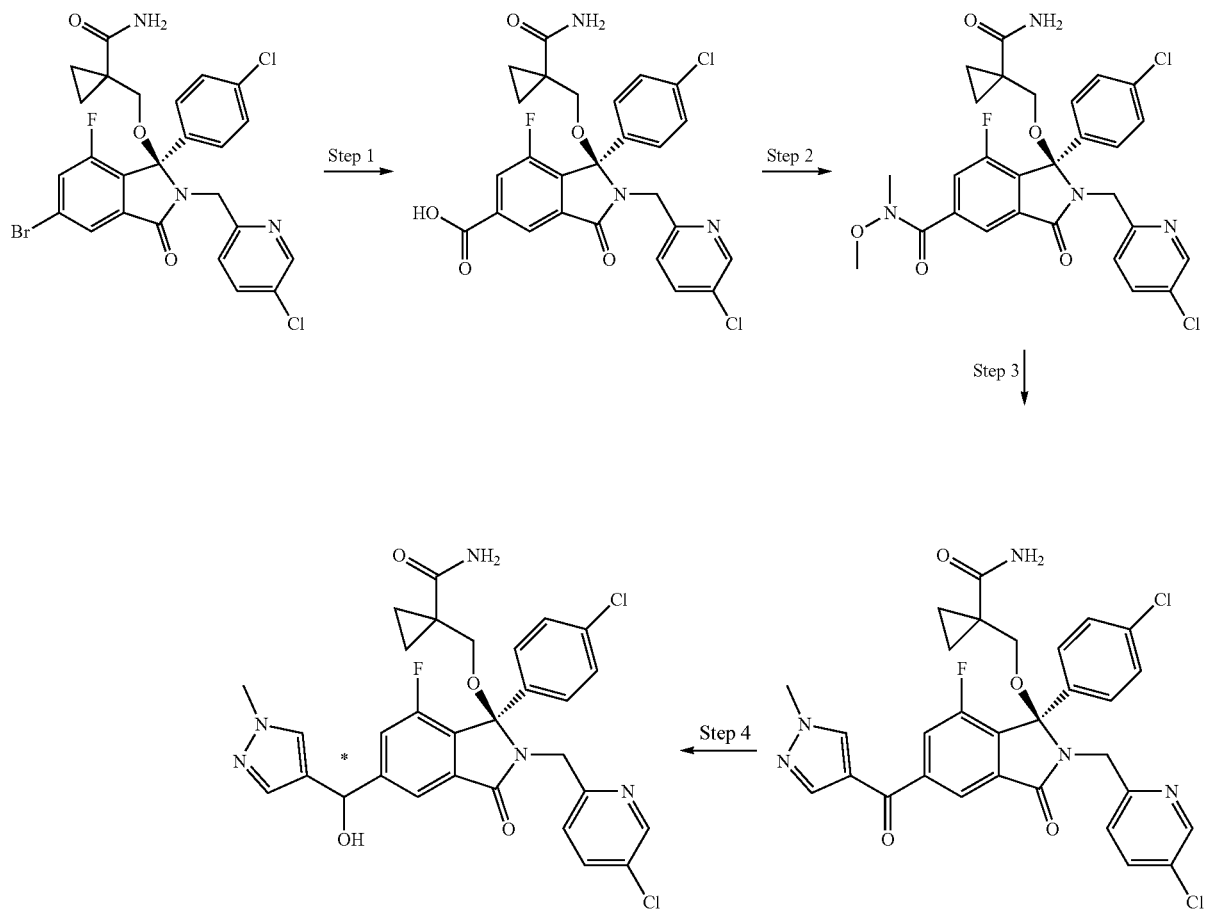

Step 1: (1R)-1-[(1-Carbamoylcyclopropyl)methoxy]-1-(4-chlorophenyl)-2-[(5-chloropyridin-2-yl)methyl]-7-fluoro-3-oxo-2,3-dihydro-1H-isoindole-5-carboxylic Acid 1-({[(1R)-5-Bromo-1-(4-chlorophenyl)-2-[(5-chloropyridin-2-yl)methyl]-7-fluoro-3-oxo-2,3-dihydro-1H-isoindol-1-yl]oxy}methyl)cyclopropane-1-carboxamide (Example 4, step 1, the R-enantiomer was separated by chiral HPLC) (5.0 g, 8.6 mmol), was converted to the title compound (3.6 g, 78%) following a similar procedure as described in Example 161 and Example 162, step 1. MS: [M+H]⁺=544.

Step 2: (1R)-1-[(1-Carbamoylcyclopropyl)methoxy]-1-(4-chlorophenyl)-2-[(5-chloropyridin-2-yl)methyl]-7-fluoro-N-methoxy-N-methyl-3-oxo-2,3-dihydro-1H-isoindole-5-carboxamide (1R)-1-[(1-Carbamoylcyclopropyl)methoxy]-1-(4-chlorophenyl)-2-[(5-chloropyridin-2-yl)methyl]-7-fluoro-3-oxo-2,3-dihydro-1H-isoindole-5-carboxylic acid (2.1 g, 3.8 mmol) was reacted with N,O-dimethylhydroxylamine hydrochloride (443 mg, 4.5 mmol), following a similar procedure as described in Example 161 and Example 162, step 2 to afford the title compound as a cream solid (963 mg, 44%). MS: [M+H]⁺=587.

Step 3: 1-({[(1R)-1-(4-Chlorophenyl)-2-[(5-chloropyridin-2-yl)methyl]-7-fluoro-5-(1-methyl-1H-pyrazole-4-carbonyl)-3-oxo-2,3-dihydro-1H-isoindol-1-yl]oxy}methyl)cyclopropane-1-carboxamide To a solution of n-BuLi (2.06M in hexanes, 500 µL, 1.19 mmol) in THF (3 mL) at −78° C. was added dropwise a solution of 4-bromo-1-methyl-1H-pyrazole (123 µL, 1.19 mmol) in THF (1 mL), keeping the temperature <−65° C. The reaction was stirred for 30 minutes before dropwise addition of (1R)-1-[(1-carbamoylcyclopropyl)methoxy]-1-(4-chlorophenyl)-2-[(5-chloropyridin-2-yl)methyl]-7-fluoro-N-methoxy-N-methyl-3-oxo-2,3-dihydro-1H-isoindole-5-carboxamide (200 mg, 0.34 mmol) in THF (1 mL) over 5 minutes. The reaction was stirred for 10 minutes at −78° C. before warming to room temperature whereupon the reaction was quenched with saturated NH₄Cl solution (2 mL). The reaction was diluted with water (2 mL) and extracted with 3×EtOAc (5 mL). The combined organics were washed with brine (5 mL), dried over MgSO₄, concentrated in vacuo and purified by Biotage using 20-100% EtOAc/in petrol as the eluent to give the title compound as a cream solid (141 mg, 68%). MS: [M+H]⁺=608.

Step 4: 1-({[(1R)-1-(4-Chlorophenyl)-2-[(5-chloropyridin-2-yl)methyl]-7-fluoro-5-[hydroxy(1-methyl-1H-pyrazol-4-yl)methyl]-3-oxo-2,3-dihydro-1H-isoindol-1-yl]oxy}methyl)cyclopropane-1-carboxamide To a solution of 1-({[(1R)-1-(4-chlorophenyl)-2-[(5-chloropyridin-2-yl)methyl]-7-fluoro-5-(1-methyl-1H-pyrazole-4-carbonyl)-3-oxo-2,3-dihydro-1H-isoindol-1-yl]oxy}methyl)cyclopropane-1-carboxamide (141 mg, 0.23 mmol) in EtOH (3 mL) at 0° C. was added NaBH₄ (35 mg, 0.92 mmol) and the reaction was allowed to warm to room temperature over 3 hours. Saturated NH₄Cl solution (1 mL) was added and the reaction diluted with water (2 mL) before extraction with 3×EtOAc (5 mL). The combined organics were washed with brine (5 mL), dried over MgSO₄ and concentrated in vacuo to give the diastereomeric mixture as a white solid (129 mg). Chiral HPLC separation of the mixture gave:

Example 175 *(Fast Running) as a White Solid (45 mg)

1H NMR (400 MHz, DMSO-d6): 8.34 (1H, dd), 7.74-7.70 (2H, m), 7.56 (1H, s), 7.45 (1H, d), 7.33-7.28 (3H, m), 7.25-7.21 (3H, m), 7.05-6.80 (2H, m), 5.94 (1H, d), 5.81 (1H, d), 4.46 (2H, s), 3.78 (3H, s), 3.48 (1H, d), 3.08 (1H, d), 0.99-0.86 (2H, m), 0.58-0.46 (2H, m). MS: [M+H]⁺=610.

Example 176 *(Slow Running) as a White Solid (37 mg)

1H NMR (400 MHz, DMSO-d6): 8.34 (1H, dd), 7.74-7.68 (2H, m), 7.56 (1H, s), 7.46 (1H, d), 7.34-7.28 (3H, m), 7.23 (3H, dd), 6.93 (2H, s), 5.94 (1H, d), 5.81 (1H, d), 4.46 (2H, s), 3.78 (3H, s), 3.48 (1H, d), 3.07 (1H, d), 1.01-0.88 (2H, m), 0.59-0.46 (2H, m). MS: [M+H]⁺=610.

Examples 177 and 178: 1-({[(1R)-1-(4-Chlorophenyl)-2-[(5-chloropyridin-2-yl)methyl]-7-fluoro-5-[1-hydroxy-1-(1-methyl-1H-pyrazol-4-yl)ethyl]-3-oxo-2,3-dihydro-1H-isoindol-1-yl]oxy}methyl)cyclopropane-1-carboxamide (*both isomers separated and isolated)

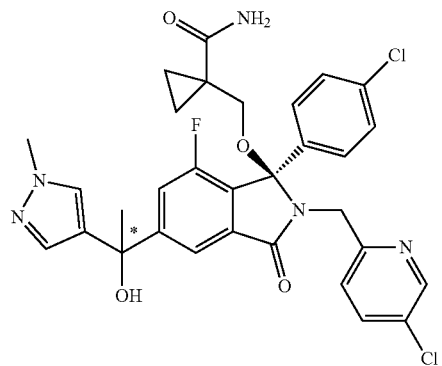 [SMILES: Cn1cc(C(C)(O)c2cc(F)c3c(c2)C(=O)N(Cc2ccc(Cl)cn2)[C@@]3(OCC2(C(N)=O)CC2)c2ccc(Cl)cc2)cn1]

The title compound was prepared from 1-({[(1R)-1-(4-chlorophenyl)-2-[(5-chloropyridin-2-yl)methyl]-7-fluoro-5-(1-methyl-1H-pyrazole-4-carbonyl)-3-oxo-2,3-dihydro-1H-isoindol-1-yl]oxy}methyl)cyclopropane-1-carboxamide (Example 175 and Example 176, step 3) following similar methods to those described in Example 1, step 4.

Chiral HPLC separation of the mixture gave:

Example 177 *(Fast Running) as a White Solid (20 mg)

1H NMR (400 MHz, DMSO-d6): 8.34 (1H, dd), 7.74-7.70 (2H, m), 7.60 (1H, d), 7.50 (1H, dd), 7.35 (1H, d), 7.30 (2H, d), 7.24-7.20 (3H, m), 7.07-6.77 (2H, m), 5.87 (1H, s), 4.45 (2H, s), 3.79 (3H, s), 3.45 (1H, d), 3.10 (1H, d), 1.79 (3H, s), 1.00-0.88 (2H, m), 0.58-0.44 (2H, m). MS: [M+H]⁺= 624.

Example 178 *(Slow Running) as a White Solid (21 mg)

1H NMR (400 MHz, DMSO-d6): 8.34 (1H, dd), 7.74-7.70 (2H, m), 7.60 (1H, d), 7.51 (1H, dd), 7.36 (1H, d), 7.30

(2H, d), 7.22 (3H, d), 6.92 (2H, s), 5.87 (1H, s), 4.45 (2H, s), 3.78 (3H, s), 3.45 (1H, d), 3.09 (1H, d), 1.79 (3H, s), 1.01-0.88 (2H, m), 0.58-0.44 (2H, m). MS: [M+H]⁺=624.

Examples 179 and 180: 1-({[(1R)-1-(4-Chlorophenyl)-2-[(5-chloropyridin-2-yl)methyl]-5-[1-(1-ethyl-1H-pyrazol-4-yl)-1-hydroxyethyl]-7-fluoro-3-oxo-2,3-dihydro-1H-isoindol-1-yl]oxy}methyl)cyclopropane-1-carboxamide (*both isomers separated and isolated)

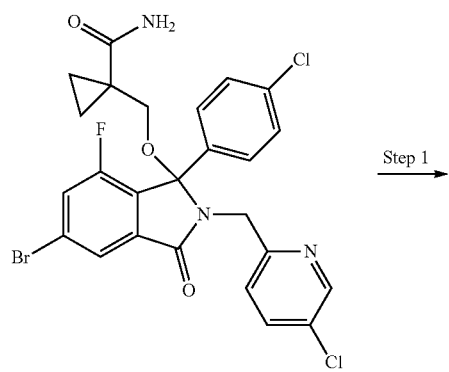

Step 1

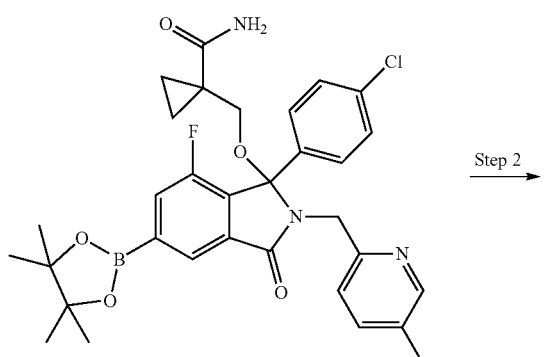

Step 2

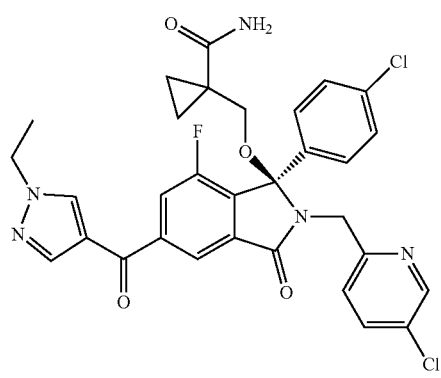

Step 3

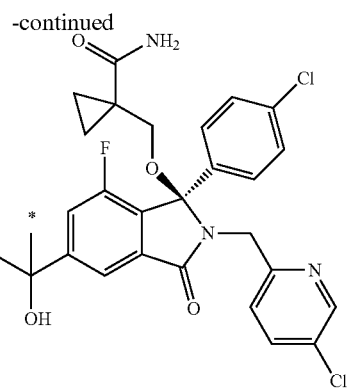

Step 1: 1-({[1-(4-Chlorophenyl)-2-[(5-chloropyridin-2-yl)methyl]-7-fluoro-3-oxo-5-(4,4,5,5-tetramethyl-1,3,2-dioxaborolan-2-yl)-2,3-dihydro-1H-isoindol-1-yl]oxy}methyl)cyclopropane-1-carboxamide 1-[5-Bromo-1-(4-chloro-phenyl)-2-(5-chloro-pyridin-2-ylmethyl)-7-fluoro-3-oxo-2,3-dihydro-1H-isoindol-1-yloxymethyl]-cyclopropanecarboxylic acid amide (Example 4, step 1) (10.0 g, 17.3 mmol), bis(pinacolato)diboron (4.6 g, 18.1 mmol) and KOAc (3.4 g, 34.6 mmol) were combined in dioxane (64 mL) and degassed with nitrogen for 15 minutes before addition of Pd(dppf)Cl₂.DCM (424 mg, 0.52 mmol) and degassing for a further 5 minutes. The reaction was heated at 90° C. for 2 hours before cooling to room temperature, diluting with water (60 mL) and extracting with 3×EtOAc (50 mL). The combined organics were washed with brine (60 mL), dried over MgSO₄ and reduced in vacuo to give the title compound as a brown solid (12.4 g, 92%). MS: [M+H]⁺=626.

Step 2: 1-({[(1R)-1-(4-Chlorophenyl)-2-[(5-chloropyridin-2-yl)methyl]-5-(1-ethyl-1H-pyrazole-4-carbonyl)-7-fluoro-3-oxo-2,3-dihydro-1H-isoindol-1-yl]oxy}methyl)cyclopropane-1-carboxamide 1-({[1-(4-Chlorophenyl)-2-[(5-chloropyridin-2-yl)methyl]-7-fluoro-3-oxo-5-(4,4,5,5-tetramethyl-1,3,2-dioxaborolan-2-yl)-2,3-dihydro-1H-isoindol-1-yl]oxy}methyl)cyclopropane-1-carboxamide (5.0 g, 8.0 mmol), 1-ethyl-4-iodo-pyrazole (1.9 g, 8.5 mmol), K₂CO₃ (3.3 g, 24.0 mmol) and Pd(dppf)Cl₂.DCM (654 mg, 0.80 mmol) were combined in a round bottomed flask and back-filled with nitrogen before the addition of anisole (80 mL). The solution was sparged with a CO balloon before a fresh CO balloon was added on top of the condenser and the reaction was heated at 100° C. for 18 hours. The reaction was allowed to cool, filtered through celite and reduced in vacuo before the residue was purified by Biotage using 0-100% EtOAc/in petrol as the eluent, followed by achiral preparative HPLC to give the racemic mixture as a yellow solid (626 mg). Chiral HPLC of the mixture gave the title compound (250 mg, 5%). MS: [M+H]$^+$=622.

Step 3: 1-({[(1R)-1-(4-Chlorophenyl)-2-[(5-chloropyridin-2-yl)methyl]-5-[1-(1-ethyl-1H-pyrazol-4-yl)-1-hydroxyethyl]-7-fluoro-3-oxo-2,3-dihydro-1H-isoindol-1-yl]oxy}methyl)cyclopropane-1-carboxamide 1-({[(1R)-1-(4-Chlorophenyl)-2-[(5-chloropyridin-2-yl)methyl]-5-(1-ethyl-1H-pyrazole-4-carbonyl)-7-fluoro-3-oxo-2,3-dihydro-1H-isoindol-1-yl]oxy}methyl)cyclopropane-1-carboxamide was converted to the title compound following similar methods to those described in Example 1, step 4.

Chiral HPLC separation of the diastereomeric mixture gave:

Example 179 *(Fast Running) as a White Solid (65 mg)

1H NMR (400 MHz, DMSO-d6): 8.34 (1H, d), 7.75-7.69 (2H, m), 7.66 (1H, s), 7.51 (1H, dd), 7.36 (1H, d), 7.30 (2H, d), 7.23 (3H, d), 7.05-6.95 (1H, m), 6.89-6.76 (1H, m), 5.87 (1H, s), 4.45 (2H, s), 4.07 (2H, q), 3.45 (1H, d), 3.09 (1H, d), 1.80 (3H, s), 1.35 (3H, t), 1.00-0.88 (2H, m), 0.57-0.45 (2H, m). MS: [M+H]$^+$=638.

Example 180 *(Slow Running) as a White Solid (82 mg)

1H NMR (400 MHz, DMSO-d6): 8.34 (1H, d), 7.75-7.69 (2H, m), 7.66 (1H, s), 7.50 (1H, dd), 7.36 (1H, d), 7.30 (2H, d), 7.22 (3H, d), 7.00 (1H, d), 6.83 (1H, s), 5.87 (1H, s), 4.46 (2H, s), 4.08 (2H, q), 3.45 (1H, d), 3.09 (1H, d), 1.80 (3H, s), 1.35 (3H, t), 1.00-0.87 (2H, m), 0.57-0.44 (2H, m). MS: [M+H]$^+$=638.

Examples 181 and 182: (3R)-6-{1-[1-(1-Acetylazetidin-3-yl)-1H-pyrazol-4-yl]-1-hydroxyethyl}-3-(4-chlorophenyl)-2-[(5-chloropyridin-2-yl)methyl]-4-fluoro-3-methoxy-2,3-dihydro-1H-isoindol-1-one (*both isomers separated and isolated)

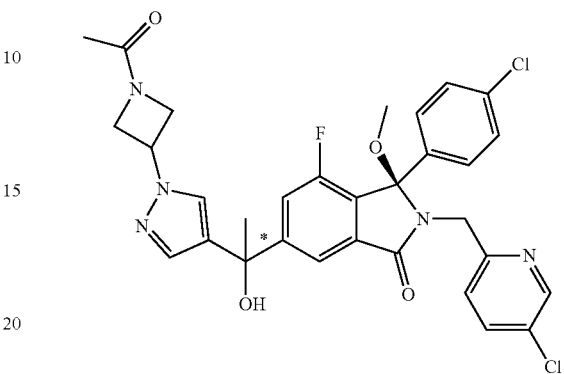

Example 181, Isomer 1 (35 mg, 6% Over 2 Steps)

$^1$H NMR (400 MHz, DMSO-d$_6$): 8.38 (1H, d), 7.83 (1H, s), 7.77-7.70 (2H, m), 7.55-7.47 (2H, m), 7.34-7.17 (5H, m), 5.94 (1H, s), 5.24-5.14 (1H, m), 4.56-4.46 (2H, m), 4.40-4.29 (2H, m), 4.29-4.20 (1H, m), 4.11-4.02 (1H, m), 2.88 (3H, s), 1.81 (6H, d); MS: [M+H]$^+$=624.

Example 182, Isomer 2 (45 mg, 7%, Over 2 Steps)

$^1$H NMR (400 MHz, DMSO-d$_6$): 8.38 (1H, d), 7.84 (1H, s), 7.77-7.70 (2H, m), 7.55-7.47 (2H, m), 7.34-7.18 (5H, m), 5.94 (1H, s), 5.25-5.15 (1H, m), 4.57-4.46 (2H, m), 4.41-4.30 (2H, m), 4.30-4.21 (1H, m), 4.11-4.03 (1H, m), 2.89 (3H, s), 1.81 (6H, s); MS: [M+H]$^+$=624.

Examples 183 and 184: (3R)-3-(4-Chlorophenyl)-2-[(5-chloropyridin-2-yl)methyl]-6-[1-(1-ethyl-1H-pyrazol-4-yl)-1-hydroxyethyl]-4-fluoro-3-[(1-hydroxycyclopropyl)methoxy]-2,3-dihydro-1H-isoindol-1-one (*both isomers separated and isolated)

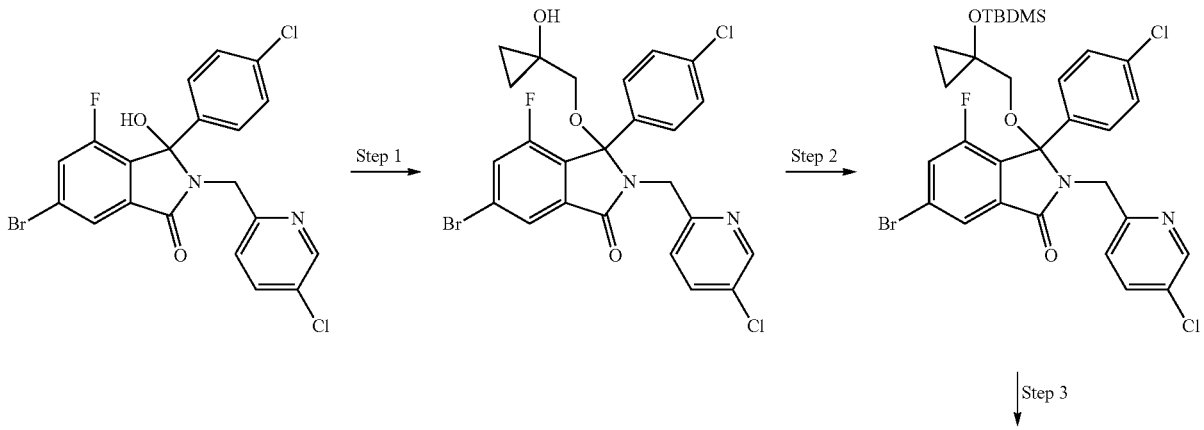

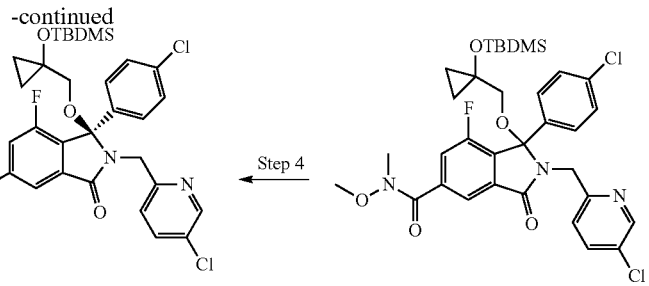
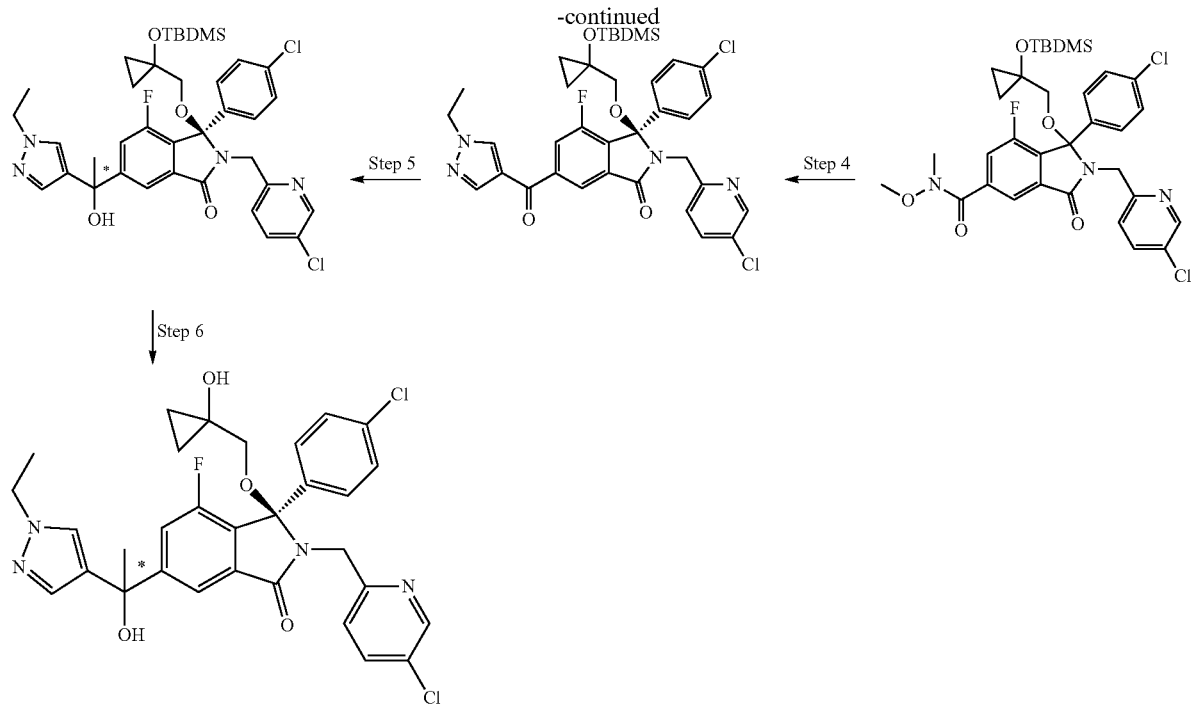

Step 1: 6-Bromo-3-(4-chlorophenyl)-2-[(5-chloropyridin-2-yl)methyl]-4-fluoro-3-[(1-hydroxycyclopropyl)methoxy]-2,3-dihydro-1H-isoindol-1-one The title compound was prepared from 6-bromo-3-(4-chloro-phenyl)-2-(5-chloro-pyridin-2-ylmethyl)-4-fluoro-3-hydroxy-2,3-dihydro-isoindol-1-one (Example 1, step 1) and 1-hydroxymethyl-cyclopropanol (Preparation 2) in a similar manner to that described in Example 3, step 2; MS: [M-$C_4H_8O_2$]$^+$=465.

Step 2: 6-Bromo-3-({1-[(tert-butyldimethylsilyl)oxy]cyclopropyl}methoxy)-3-(4-chlorophenyl)-2-[(5-chloropyridin-2-yl)methyl]-4-fluoro-2,3-dihydro-1H-isoindol-1-one 6-Bromo-3-(4-chlorophenyl)-2-[(5-chloropyridin-2-yl)methyl]-4-fluoro-3-[(1-hydroxycyclopropyl)methoxy]-2,3-dihydro-1H-isoindol-1-one (10.9 g, 19.7 mmol was reacted with tert-butyldimethylsilyl chloride (6.8 g, 45.3 mmol) in a similar manner as described in Example 22 and Example 23, step 1 to give the title compound as a colourless oil (11.9 g, 91%). MS: [M-$C_{10}H_{21}O_2Si$]$^+$=465.

Step 3: 1-({1-[(tert-Butyldimethylsilyl)oxy]cyclopropyl}methoxy)-1-(4-chlorophenyl)-2-[(5-chloropyridin-2-yl)methyl]-7-fluoro-N-methoxy-N-methyl-3-oxo-2,3-dihydro-1H-isoindole-5-carboxamide 6-Bromo-3-({1-[(tert-butyldimethylsilyl)oxy]cyclopropyl}methoxy)-3-(4-chlorophenyl)-2-[(5-chloropyridin-2-yl)methyl]-4-fluoro-2,3-dihydro-1H-isoindol-1-one (2.3 g, 3.5 mmol), N,O-Dimethylhydroxylamine hydrochloride (501 mg, 5.1 mmol), Xantphos G3 catalyst (322 mg, 0.3 mmol) and $Na_2CO_3$ (1.1 g, 10.2 mmol) were placed in a round bottomed flask and back-filled with nitrogen before addition of toluene (34 mL). The solution was sparged with CO for 15 min before a fresh balloon of CO was placed on the condenser and the reaction heated at 100° C. for over 18 hrs. The reaction was cooled, diluted with water (30 mL) and extracted with 3×EtOAc (30 mL). The combined organics were brine (50 mL), dried over $MgSO_4$, reduced in vacuo and purified by Biotage using 0-100% EtOAc/in petrol as the eluent to give the title compound as an orange amorphous solid (1.3 g, 57%). MS: [M-$C_{10}H_{21}O_2Si$]$^+$=472.

Step 4: (3R)-3-({1-[(tert-Butyldimethylsilyl)oxy]cyclopropyl}methoxy)-3-(4-chlorophenyl)-2-[(5-chloropyridin-2-yl)methyl]-6-(1-ethyl-1H-pyrazole-4-carbonyl)-4-fluoro-2,3-dihydro-1H-isoindol-1-one The title compound was prepared from 1-({1-[(tert-butyldimethylsilyl)oxy]cyclopropyl}methoxy)-1-(4-chlorophenyl)-2-[(5-chloropyridin-2-yl)methyl]-7-fluoro-N-methoxy-N-methyl-3-oxo-2,3-dihydro-1H-isoindole-5-carboxamide in a similar manner to that described in Example 175 and Example 176, step 3, using 4-bromo-1-ethyl-1H-pyrazole instead of 4-bromo-1-methyl-1H-pyrazole. The desired enantiomer was separated by chiral HPLC. MS: [M-$C_{10}H_{21}O_2Si$]$^+$=507.

Step 5: (3R)-3-({1-[(tert-Butyldimethylsilyl)oxy]cyclopropyl}methoxy)-3-(4-chlorophenyl)-2-[(5-chloropyridin-2-yl)methyl]-6-[1-(1-ethyl-1H-pyrazol-4-yl)-1-hydroxyethyl]-4-fluoro-2,3-dihydro-1H-isoindol-1-one The title compound was prepared from (3R)-3-({1-[(tert-butyldimethylsilyl)oxy]cyclopropyl}methoxy)-3-(4-chlorophenyl)-2-[(5-chloropyridin-2-yl)methyl]-6-(1-ethyl-1H-pyrazole-4-carbonyl)-4-fluoro-2,3-dihydro-1H-isoindol-1-one following similar methods to those described in Example 1, step 4; MS: [M-$C_{10}H_{21}O_2Si$]$^+$=523.

Step 6: (3R)-3-(4-Chlorophenyl)-2-[(5-chloropyridin-2-yl)methyl]-6-[1-(1-ethyl-1H-pyrazol-4-yl)-1-hydroxyethyl]-4-fluoro-3-[(1-hydroxycyclopropyl)methoxy]-2,3-dihydro-1H-isoindol-1-one The title compound was prepared from (3R)-3-({1-[(tert-butyldimethylsilyl)oxy]cyclopropyl}methoxy)-3-(4-chlorophenyl)-2-[(5-chloropyridin-2-yl)methyl]-6-[1-(1-ethyl-1H-pyrazol-4-yl)-1-hydroxyethyl]-4-fluoro-2,3-dihydro-1H-isoindol-1-one (1.9 g, 2.5 mmol) using a similar procedure as described in Example 22 and Example 23, step 4. Chiral HPLC separation of the mixture gave:

Example 183 *(Fast Running) as a White Solid
(425 mg, 28%)

1H NMR (400 MHz, DMSO-d6): 8.33 (1H, dd), 7.72 (1H, d), 7.68 (1H, dd), 7.66 (1H, d), 7.49 (1H, dd), 7.36 (1H, d), 7.31 (2H, d), 7.28 (2H, d), 7.17 (1H, d), 5.86 (1H, s), 5.48 (1H, s), 4.48 (2H, s), 4.10-4.04 (2H, m), 3.15 (1H, d), 2.97 (1H, d), 1.80 (3H, s), 1.37-1.33 (3H, m), 0.57-0.49 (2H, m), 0.38-0.32 (1H, m), 0.28-0.23 (1H, m). MS: [M−H]$^-$=609.

Example 184 *(Slow Running) as a White Solid
(437 mg, 28%)

1H NMR (400 MHz, DMSO-d6): 8.33 (1H, dd), 7.71 (1H, d), 7.70-7.66 (2H, m), 7.48 (1H, dd), 7.36 (1H, d), 7.31 (2H, d), 7.27 (2H, d), 7.17 (1H, d), 5.87 (1H, s), 5.48 (1H, s), 4.48 (2H, s), 4.08 (2H, q), 3.15 (1H, d), 2.97 (1H, d), 1.79 (3H, s), 1.35 (3H, t), 0.57-0.49 (2H, m), 0.38-0.32 (1H, m), 0.28-0.23 (1H, m). MS: [M−H]$^-$=609.

Examples 185 and 186: (3R)-3-(4-Chlorophenyl)-2-[(5-chloropyridin-2-yl)methyl]-4-fluoro-6-[1-hydroxy-1-(5-methyl-1,3,4-oxadiazol-2-yl)ethyl]-3-[(1-hydroxycyclopropyl)methoxy]-2,3-dihydro-1H-isoindol-1-one (*both isomers separated and isolated)

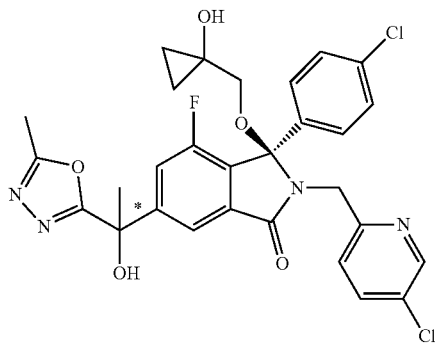 [SMILES: Cc1nnc(C(C)(O)c2cc(F)c3c(c2)C(=O)N(Cc2ccc(Cl)cn2)[C@@]3(OCC2(O)CC2)c2ccc(Cl)cc2)o1]

Prepared in a similar manner as Example 175 and Example 176, but using 1-methyloxadiazole with MgBr$_2$.Et$_2$O as an additive instead of 4-bromo-1-methyl-1H-pyrazole alone in step 4.

Example 185 *(Fast Running) as a White Solid
(237 mg)

1H NMR (400 MHz, DMSO-d6): 8.34 (1H, dd), 7.75 (1H, d), 7.70 (1H, dd), 7.51 (1H, dd), 7.34 (2H, d), 7.29 (2H, d), 7.20 (1H, d), 6.94 (1H, s), 5.50 (1H, d), 4.50 (2H, s), 3.17 (1H, d), 2.99 (1H, d), 2.49 (3H, s), 1.94 (3H, s), 0.57-0.50 (2H, m), 0.38-0.33 (1H, m), 0.26 (1H, dd). MS: [M-C$_4$H$_7$O$_2$]$^+$=511.

Example 186 *(Slow Running) as a White Solid
(251 mg)

1H NMR (400 MHz, DMSO-d6): 8.34 (1H, dd), 7.75 (1H, d), 7.70 (1H, dd), 7.51 (1H, dd), 7.33 (2H, d), 7.29 (2H, d), 7.19 (1H, d), 6.94 (1H, s), 5.50 (1H, s), 4.50 (2H, s), 3.18 (1H, d), 2.99 (1H, d), 2.49 (3H, s), 1.94 (3H, s), 0.57-0.50 (2H, m), 0.39-0.31 (1H, m), 0.31-0.24 (1H, m). MS: [M-C$_4$H$_7$O$_2$]$^+$=511.

Examples 187 and 188: (3R)-3-(4-Chlorophenyl)-2-[(5-chloropyridin-2-yl)methyl]-4-fluoro-6-[1-hydroxy-1-(1-methyl-1H-1,2,3-triazol-4-yl)ethyl]-3-methoxy-2,3-dihydro-1H-isoindol-1-one (*both isomers separated and isolated)

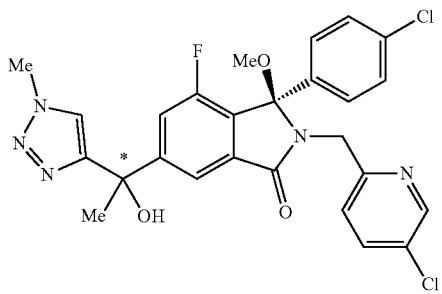 [SMILES: CO[C@]1(c2ccc(Cl)cc2)c2c(F)cc(C(C)(O)c3cn(C)nn3)cc2C(=O)N1Cc1ccc(Cl)cn1]

Starting from (3R)-6-bromo-3-(4-chlorophenyl)-2-[(5-chloropyridin-2-yl)methyl]-4-fluoro-3-methoxy-2,3-dihydro-1H-isoindol-1-one (Example 2, step 1, separated by preparatory chiral LCMS), the title compound was made using similar methods to those described in Example 183 and Example 184, steps 3, 4 and 5, but using 4-bromo-1-methyl-1H-1,2,3-triazole instead of 4-bromo-1-ethyl-1H-pyrazole in step 4.

Example 187 (Fast Diastereomer 68.6 mg, 30%)

$^1$H NMR (400 MHz, CDCl$_3$): 8.35 (1H, d), 7.73 (1H, s), 7.66 (1H, s), 7.56-7.36 (1H, m), 7.27-7.17 (6H, m), 4.61 (1H, d), 4.38 (1H, d), 3.71 (3H, s), 2.92 (3H, s), 2.01 (3H, s), 0.94-0.80 (1H, m). MS: [M+H$^+$]=543

Example 188 (Slow Diastereomer 62.8 mg, 28%)

$^1$H NMR (400 MHz, CDCl$_3$): 8.35 (1H, s), 7.67 (2H, d), 7.50 (1H, d), 7.30-7.15 (7H, m), 4.62 (1H, d), 4.40-4.31 (1H, m), 3.72 (3H, s), 2.90 (3H, s), 2.00 (3H, s). MS: [M+H$^+$]=543

Example 189 and 190: (3R)-3-(4-Chlorophenyl)-2-[(5-chloropyridin-2-yl)methyl]-4-fluoro-6-[1-hydroxy-1-(1-methyl-1H-pyrazol-3-yl)ethyl]-3-methoxy-2,3-dihydro-1H-isoindol-1-one (*both isomers separated and isolated)

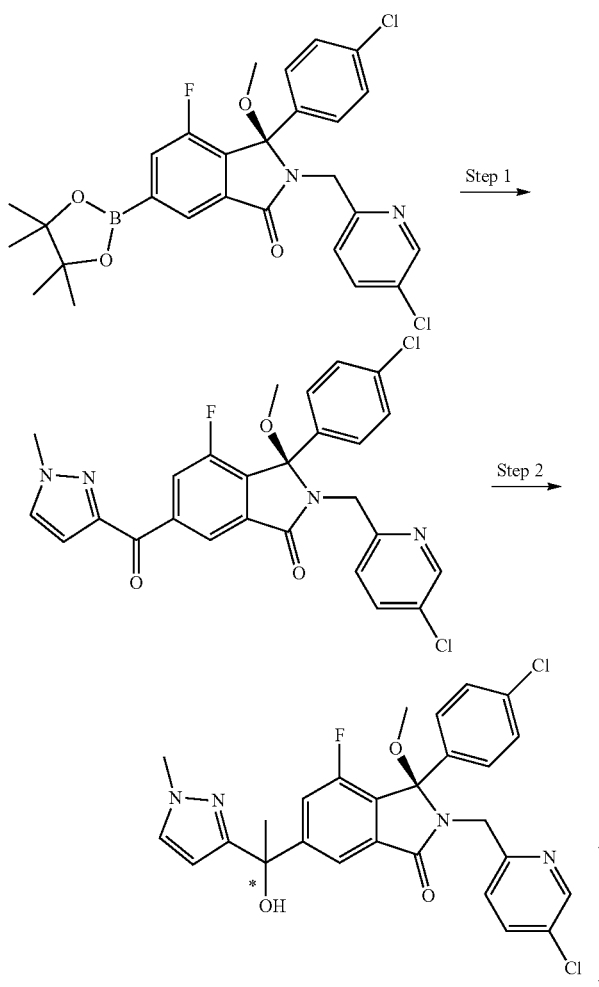

Starting with (3R)-3-(4-chlorophenyl)-2-[(5-chloropyridin-2-yl)methyl]-4-fluoro-3-methoxy-6-(4,4,5,5-tetramethyl-1,3,2-dioxaborolan-2-yl)-2,3-dihydro-1H-isoindol-1-one (prepared in a similar manner to Example 179, step 1) and 3-iodo-1-methylpyrazole, the title compound was prepared using procedures similar to those described in Example 179, but using toluene instead of anisole.

Example 189 (Slow Running Isomer, 102 mg, 24%)

$^1$H NMR (400 MHz, DMSO-d$_6$): 8.37 (1H, d), 7.76-7.68 (2H, m), 7.57 (1H, d), 7.47 (1H, d), 7.29 (2H, d), 7.24 (3H, dd), 6.16 (1H, d), 5.95 (1H, s), 4.49 (1H, d), 4.34 (1H, d), 3.81 (3H, s), 2.87 (3H, s), 1.80 (3H, s). MS: [M+H$^+$]=542.

Example 190 (Fast Running Isomer 79 mg, 18%)

$^1$H NMR (400 MHz, CDCl$_3$): 8.35 (1H, d), 7.77 (1H, d), 7.55-7.38 (2H, m), 7.31 (1H, d), 7.27-7.15 (6H, m), 6.18 (1H, d), 4.61 (1H, d), 4.38 (1H, d), 3.87 (3H, s), 2.90 (3H, s), 1.89 (3H, s). MS: [M+H$^+$]=542.

Example 191 and 192: (3R)-3-(4-Chlorophenyl)-2-[(5-chloropyridin-2-yl)methyl]-6-(1-{1-[2-(dimethylamino)ethyl]-1H-pyrazol-4-yl}-1-hydroxyethyl)-4-fluoro-3-methoxy-2,3-dihydro-1H-isoindol-1-one

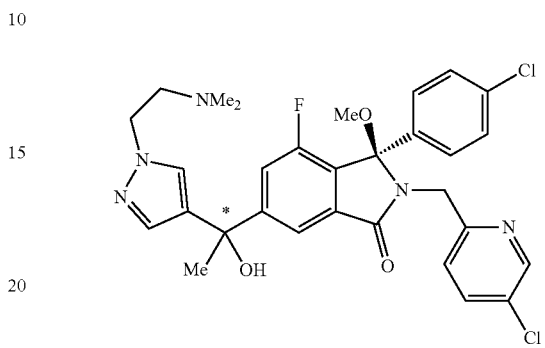

The title compound was prepared in a similar fashion to Example 189.

Example 191 (Isomer 1, 75.7 mg, 16%) g $^1$H NMR (400 MHz, CDCl$_3$): 8.35 (1H, d), 7.78 (1H, d), 7.48 (1H, dd), 7.39 (3H, d), 7.28-7.17 (5H, m), 4.62 (1H, d), 4.39 (1H, d), 4.22-4.12 (2H, m), 2.91 (3H, s), 2.73 (2H, t), 2.26-2.22 (5H, m), 1.89 (3H, s). MS: [M+H$^+$]=599

Example 192 (Isomer 2, 104 mg, 23%)

$^1$H NMR (400 MHz, CDCl$_3$): 8.35 (1H, d), 7.78 (1H, d), 7.59-7.45 (1H, m), 7.42-7.36 (3H, m), 7.30-7.06 (6H, m), 4.61 (1H, d), 4.40 (1H, d), 4.21-4.13 (2H, m), 2.92 (3H, s), 2.74 (2H, t), 2.25 (6H, s). MS: [M+H$^+$]=599.2

Examples 193 and 194: 1-({[(1R)-1-(4-chlorophenyl)-2-[(5-chloropyridin-2-yl)methyl]-7-fluoro-5-[1-hydroxy-1-(1,3-thiazol-4-yl)ethyl]-3-oxo-2,3-dihydro-1H-isoindol-1-yl]oxy}methyl)cyclopropane-1-carboxamide (*both isomers separated and isolated)

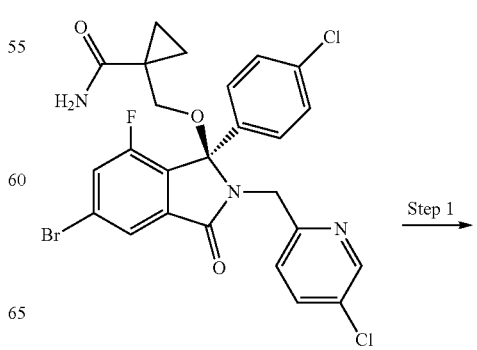

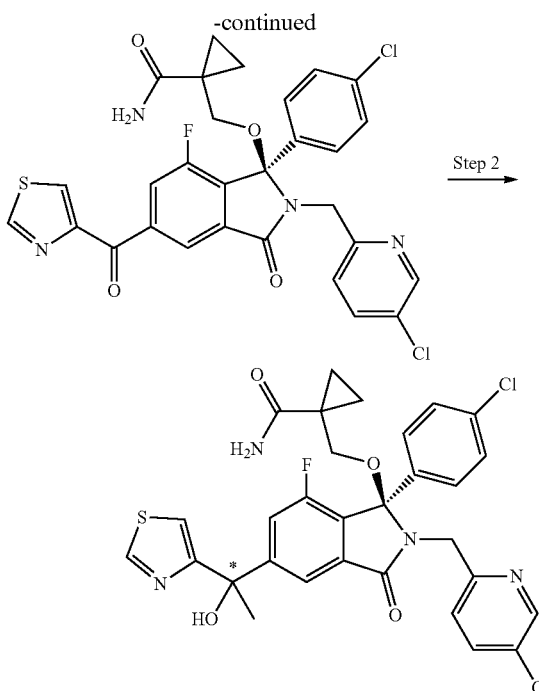

Step 1: (R)-1-(((1-(4-Chlorophenyl)-2-((5-chloropyridin-2-yl)methyl)-7-fluoro-3-oxo-5-(thiazole-4-carbonyl)isoindolin-1-yl)oxy)methyl)cyclopropanecarboxamide In a reaction tube, 1-({[(1R)-5-bromo-1-(4-chlorophenyl)-2-[(5-chloropyridin-2-yl)methyl]-7-fluoro-3-oxo-2,3-dihydro-1H-isoindol-1-yl]oxy}methyl)cyclopropane-1-carboxamide (Example 4, step 1, the R-enantiomer was separated by chiral HPLC) (1 g, 1.7 mmol), 4-(tributylstannyl)thiazole (776 mg, 2.1 mmol), lithium chloride (220 mg, 5.2 mmol) and PdCl$_2$(dppf).CH$_2$Cl$_2$ (71 mg, 0.087 mmol) were suspended in degassed (with CO) DMF (10 mL). CO gas was further bubbled through the mixture for 1 min, the reaction tube was sealed, and heated at 110° C. with a CO balloon for 18 h. The reaction was diluted with water (20 mL) and EtOAc (25 mL). The aqueous was extracted with EtOAc (2×25 mL), organic layers were combined and further washed with 4% LiCl (2×25 mL). Organics were dried over MgSO$_4$, filtered and solvent removed in vacuo. Crude material was purified by column chromatography, Biotage Isolera, 50 g KP-sil cartridge 10-100% EtOAc in isohexane to afford the title compound (930 mg, 89%). [M-(1-(hydroxymethyl)cyclopropane-carboxamide)]+=496.

Step 2: 1-({[(1R)-1-(4-chlorophenyl)-2-[(5-chloropyridin-2-yl)methyl]-7-fluoro-5-[1-hydroxy-1-(1,3-thiazol-4-yl)ethyl]-3-oxo-2,3-dihydro-1H-isoindol-1-yl]oxy}methyl)cyclopropane-1-carboxamide The title compounds were prepared from R)-1-(((1-(4-chlorophenyl)-2-((5-chloropyridin-2-yl)methyl)-7-fluoro-3-oxo-5-(thiazole-4-carbonyl)isoindolin-1-yl)oxy)methyl)cyclopropanecarboxamide in a similar manner to that described for Example 200, step 5. Purification by chiral preparative HPLC gave the title compounds.

Example 193: *Faster Running Isomer $^1$H NMR (400 MHz, CDCl$_3$) 8.78 (1H, d), 8.37 (1H, d), 7.70 (1H, d), 7.58 (1H, dd), 7.46 (1H, dd), 7.37 (1H, d), 7.32-7.27 (5H, m), 4.44 (1H, d), 4.23 (1H, d), 3.60 (1H, d), 3.48 (1H, s), 3.05 (1H, d), 1.97 (3H, s), 1.43-1.36 (1H, m), 1.23-1.17 (1H, m), 0.63-0.47 (2H, m). MS: [M+H]$^+$=627.

Example 194: *Slower Running Isomer $^1$H NMR (400 MHz, CDCl$_3$) 8.77 (1H, d), 8.37 (1H, d), 7.66 (1H, d), 7.59 (1H, dd), 7.47 (1H, dd), 7.39 (1H, d), 7.34 (1H, d), 7.30 (4H, d), 4.45 (1H, d), 4.20 (1H, d), 3.62 (1H, d), 3.46 (1H, s), 3.03 (1H, d), 1.95 (3H, s), 1.42-1.36 (1H, m), 1.26-1.16 (1H, m), 0.63-0.57 (1H, m), 0.52-0.46 (1H, m). MS: [M+H]$^+$=627.

Examples 195 and 196: (3R)-3-(4-chlorophenyl)-2-[(5-chloropyridin-2-yl)methyl]-4-fluoro-6-[1-hydroxy-1-(1-methyl-1H-imidazol-4-yl)ethyl]-3-[(1-hydroxycyclopropyl)methoxy]-2,3-dihydro-1H-isoindol-1-one (*both isomers separated and isolated)

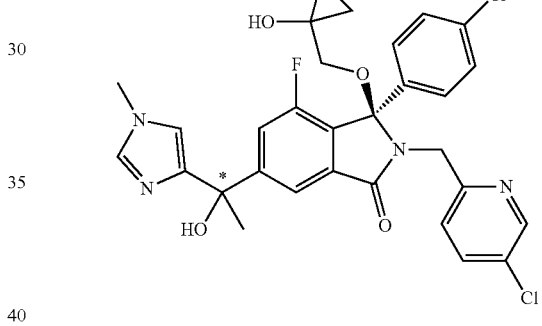

The title compounds were made in a similar manner to Example 193, using CataXium® instead of PdCl$_2$(dppf).CH$_2$Cl$_2$ and 1-methyl-4-(tributylstannyl)-1H-imidazole instead of 4-(tributylstannyl)thiazole.

Example 195: *Faster Running Isomer $^1$H NMR (400 MHz, CDCl$_3$) 8.34 (1H, d), 7.63 (1H, s), 7.54 (1H, dd), 7.47 (1H, d), 7.38-7.30 (4H, m), 7.24 (2H, d), 6.84 (1H, s), 4.52-4.38 (2H, m), 3.68 (3H, s), 3.55 (1H, s), 3.49-3.46 (1H, m), 2.97 (1H, d), 1.81 (3H, s), 1.26 (1H, s), 0.89-0.73 (2H, m), 0.59-0.51 (1H, m), 0.39-0.32 (1H, m). MS: [M+H]$^+$=597.

Example 196: *Slower Running Isomer $^1$H NMR (400 MHz, CDCl$_3$) 8.35 (1H, d), 7.66 (1H, s), 7.53 (1H, dd), 7.47 (1H, d), 7.38 (1H, s), 7.34-7.28 (3H, m), 7.24-7.19 (2H, m), 6.83 (1H, s), 4.46 (2H, d), 3.70 (3H, s), 3.56-3.45 (2H, m), 2.99 (1H, d), 1.83 (3H, s), 1.26 (1H, s), 0.89-0.75 (2H, m), 0.58-0.51 (1H, m), 0.41-0.34 (1H, m). MS: [M+H]$^+$=597.

367

Examples 197 and 198: 1-({[(1R)-1-(4-chlorophenyl)-2-[(5-chloropyridin-2-yl)methyl]-5-[1-(1,2-dimethyl-1H-imidazol-4-yl)-1-hydroxyethyl]-7-fluoro-3-oxo-2,3-dihydro-1H-isoindol-1-yl]oxy}methyl)cyclopropane-1-carboxamide

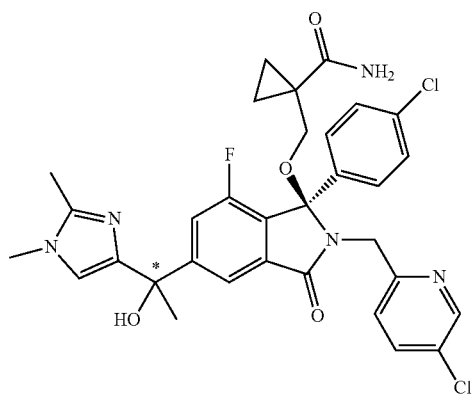 [SMILES: Cc1nc(C(C)(O)c2cc(F)c3c(c2)C(=O)N(Cc2ccc(Cl)cn2)[C@@]3(OCC2(C(N)=O)CC2)c2ccc(Cl)cc2)cn1C]

Starting with (R)-1-(((5-bromo-1-(4-chlorophenyl)-2-((5-chloropyridin-2-yl)methyl)-7-fluoro-3-oxoisoindolin-1-yl)oxy)methyl)cyclopropanecarboxamide (Example 4, Step 1, 3(R)-isomer, isolated by preparatice chiral HPLC), the title compound was prepared in a similar manner to Example 179, but with bis(dibenzylideneacetone)palladium(0), cataCXium® A and 4-bromo-1,2-dimethyl-1H-imidazole used instead of 1-ethyl-4-iodo-pyrazole and Pd(dppf)Cl₂.DCM. Also, no ZnCl₂ was used in the final addition of MeMgCl.

Example 197 *Slower Eluting Isomer

¹H NMR (400 MHz, CDCl₃) 8.36 (1H, d), 7.65 (1H, s), 7.57 (1H, dd), 7.51 (1H, d), 7.35 (1H, d), 7.25-7.20 (5H, m), 6.74 (1H, s), 5.41 (1H, d), 4.44 (1H, d), 4.23 (1H, d), 3.55-3.45 (5H, d), 3.10 (1H, d), 2.33 (3H, s), 1.78 (3H, s), 1.42-1.35 (1H, m), 1.23-1.16 (1H, m), 0.63-0.46 (2H, m); MS: [M+H]⁺=638.2.

Example 198 *Faster Eluting Isomer

¹H NMR (400 MHz, CDCl₃) 8.36 (1H, d), 7.62 (1H, s), 7.58 (1H, dd), 7.53 (1H, s), 7.52-7.49 (1H, m), 7.38 (1H, d), 7.33-7.27 (4H, m), 6.74 (1H, s), 5.41 (1H, d), 4.44 (1H, d), 4.23 (1H, d), 3.55-3.45 (5H, d), 3.10 (1H, d), 2.33 (3H, s), 1.78 (3H, s), 1.42-1.35 (1H, m), 1.23-1.16 (1H, m), 0.63-0.46 (2H, m); MS: [M+H]⁺=638.2.

368

Examples 199 and 200: (3R)-3-(4-chlorophenyl)-2-[(5-chloropyridin-2-yl)methyl]-4-fluoro-6-[1-hydroxy-1-(1-methyl-1H-pyrazol-4-yl)ethyl]-3-[(1-hydroxycyclopropyl)methoxy]-2,3-dihydro-1H-isoindol-1-one (*both isomers separated and isolated)

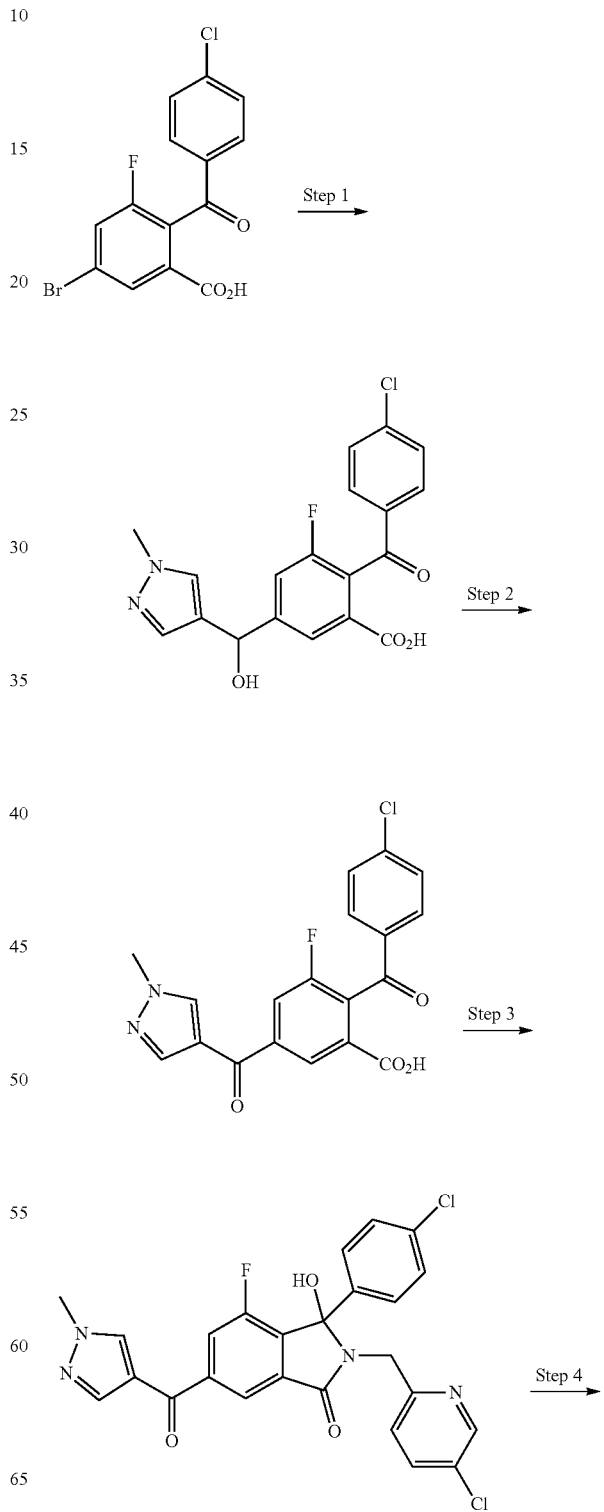

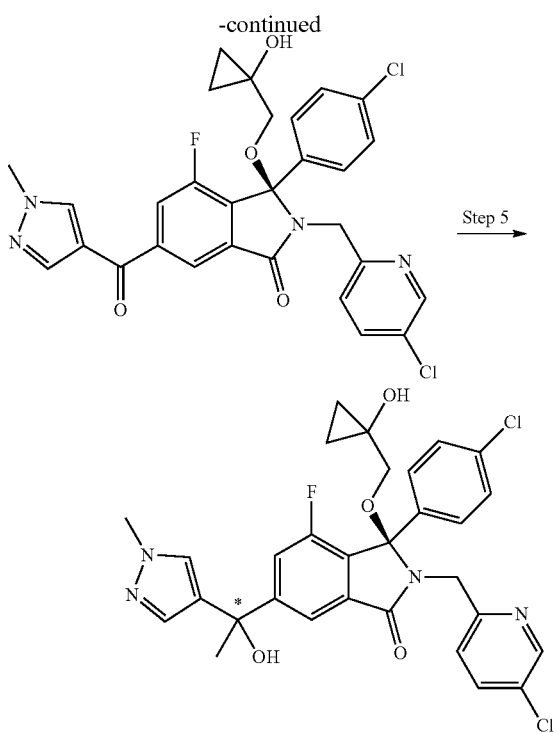

Step 1: 2-(4-Chlorobenzoyl)-3-fluoro-5-(hydroxy(1-methyl-1H-pyrazol-4-yl)methyl)benzoic Acid A 5 litre round bottom flask fitted with an overhead stirrer was charged with 5-bromo-2-(4-chlorobenzoyl)-3-fluorobenzoic acid (100 g, 0.28 mol) and anhydrous THF (1.5 L). The solution was cooled to −3° C. and a solution of methyl magnesium chloride (2.15M in THF, 130 mL, 0.279 mol) was added dropwise at such a rate that the internal temperature remained below −1° C. (25 min). On complete addition, the mixture was stirred at 0° C. for 15 min then cooled to −78° C. A solution of n-butyllithium (2.2M in hexanes, 152 m, 0.334 mol) was added dropwise over 30 min at such a rate that the internal temperature remained below −70° C. On complete addition the mixture was stirred at −78° C. for 30 min. A solution of 1-methyl-1H-pyrazole-4-carboxaldehyde (39.7 g, 0.36 mol) in anhydrous THF (500 mL) was added dropwise over 20 min at such a rate that the internal temperature remained below −70° C. On complete addition the mixture was stirred at −78° C. for 15 min, the cooling bath removed and the mixture allowed to reach rt. The mixture was quenched with 1M HCl, the pH adjusted to 1-2 and extracted with EtOAc (2×500 mL). The combined organics were dried over MgSO$_4$ and the solvent removed under reduced pressure. The residue was divided into 4 equal portions and each portion chromatographed on silica gel (300 g) eluting with a gradient of 0-20% MeOH in dichloromethane to afford the title compound as a colourless solid (48.33 g, 44%). Impure fractions were pooled, evaporated and chromatographed to afford a further quantity of title compound (11.05 g; 10%); [M+H]$^+$=389.

Step 2: 2-(4-Chlorobenzoyl)-3-fluoro-5-(1-methyl-1H-pyrazole-4-carbonyl)benzoic Acid To a stirred mixture of 2-(4-chlorobenzoyl)-3-fluoro-5-(hydroxy(1-methyl-1H-pyrazol-4-yl)methyl)benzoic acid (20 g, 51.48 mmol) in EtOAc (86 mL) at 0° C. was added 10% aqueous KBr (29.83 mL, 25 mmol) followed by TEMPO (0.816 g, 5.23 mmol). To the stirred mixture was added a solution of sodium hydrogen carbonate (5.4 g, 64.25 mmol) and sodium hypochlorite (89 mL, 5-20% aqueous solution) in water (47 mL) at such a rate that the reaction temperature remained below 5° C. Addition was stopped upon complete oxidation as indicated by LCMS (approximately half of the solution was required). The reaction was quenched by addition of dilute aqueous sodium sulfite solution and the mixture extracted with EtOAc (4×500 mL). The combined organics were dried over MgSO$_4$ and the solvent removed under reduced pressure to give the title compound as a pale orange solid (15.27 g, 76%). The aqueous layer was acidified with 2M HCl and extracted with EtOAc (500 mL). The organics were dried (MgSO$_4$) and the solvent removed under reduced pressure to give a further quantity of the title compound (3.44 g; 17%); [M+H]$^+$=387.

Step 3: 3-(4-Chlorophenyl)-2-((5-chloropyridin-2-yl)methyl)-4-fluoro-3-hydroxy-6-(1-methyl-1H-pyrazole-4-carbonyl)isoindolin-1-one 2-(4-Chlorobenzoyl)-3-fluoro-5-(1-methyl-1H-pyrazole-4-carbonyl)benzoic acid (20.15 g, 52.2 mmol), (5-chloropyridin-2-yl)methanamine dihydrochloride (12.29 g, 57.4 mmol) and diisopropylethylamine (28.3 mL, 167 mmol) were stirred in DMF (160 mL) at RT under nitrogen. HATU (29.8 g, 78.3 mmol) was added and the reaction mixture stirred at rt for 1.25 h. The reaction mixture was diluted with water, sat. aq. NaHCO$_3$ solution and EtOAc. The layers were separated and the aqueous phase was extracted with EtOAc. The combined organics were washed with 4% LiCl aq. solution, dried over MgSO$_4$, filtered and the solvent removed under reduced pressure. The residue was purified on silica (340 g SNAP cartridge) eluting with a gradient of 10-100% EtOAc in iso-hexanes to give the title compound (23.6 g, 89% yield). $^1$H NMR (400 MHz, CDCl$_3$) 8.47 (1H, s), 8.41 (1H, d), 8.03 (1H, s), 7.95 (1H, s), 7.92 (1H, s), 7.74 (1H, dd), 7.68 (1H, d), 7.51 (2H, d), 7.44-7.36 (3H, m), 5.00 (1H, d), 4.13 (1H, d), 3.98 (3H, s).

Step 4: (R)-3-(4-Chlorophenyl)-2-((5-chloropyridin-2-yl)methyl)-4-fluoro-3-((1-hydroxycyclopropyl)methoxy)-6-(1-methyl-1H-pyrazole-4-carbonyl)isoindolin-1-one 3-(4-Chlorophenyl)-2-((5-chloropyridin-2-yl)methyl)-4-fluoro-3-hydroxy-6-(1-methyl-1H-pyrazole-4-carbonyl)isoindolin-1-one (8.52 g, 16.7 mmol) and DMF (a few drops) were stirred in THF (100 mL) at 0° C. under nitrogen. Thionyl chloride (3.0 mL, 41.7 mmol) was added dropwise and the reaction mixture was stirred at RT for 40 min. The solution was concentrated under reduced pressure, re-dissolved in THF (100 mL) and a solution of 1-(hydroxymethyl)cyclopropanol (2.94 g, 33.4 mmol) in THF (20 mL) was added followed by potassium carbonate (4.62 g, 33.4 mmol). The reaction mixture was stirred at RT for 1 d. A colourless solid had precipitated which was filtered off and washed with minimal THF. The solid was dissolved in dichloromethane and water and the layers were separated. The aqueous phase was extracted with dichloromethane and the combined organics were washed with water, dried (phase separator) and concentrated under reduced pressure. Purification by chiral SFC gave the title compound (faster eluting isomer; 2.48 g, 51% yield).

$^1$H NMR (400 MHz, CDCl$_3$) 8.39 (1H, d), 8.11 (1H, d), 7.96 (2H, d), 7.66 (1H, d), 7.59 (1H, d), 7.39-7.34 (3H, m), 7.28-7.25 (2H, m), 4.55-4.42 (2H, m), 4.00 (3H, s), 3.62 (1H, dd), 3.00 (1H, d), 0.93-0.78 (2H, m), 0.63-0.56 (1H, m), 0.43-0.36 (1H, m), (OH not observed); [α]$^D$=+50.87 (MeOH).

Step 5: (3R)-3-(4-chlorophenyl)-2-[(5-chloropyridin-2-yl)methyl]-4-fluoro-6-[1-hydroxy-1-(1-methyl-1H-pyrazol-4-yl)ethyl]-3-[(1-hydroxycyclopropyl)methoxy]-2,3-dihydro-1H-isoindol-1-one 3R-3-(4-Chlorophenyl)-2-((5-chloropyridin-2-yl)methyl)-4-fluoro-3-((1-hydroxycyclopropyl)methoxy)-6-(1-methyl-1H-pyrazole-4-carbonyl)isoindolin-1-one (2.44 g, 4.2 mmol) was dissolved in THF (26 mL). LaCl$_3$.2LiCl (0.6M in THF, 7.0 mL, 4.2 mmol) was added and the solution stirred at RT under nitrogen for 30 min and then cooled in an ice bath. Methylmagnesium chloride (2.15M in THF, 5.0 mL, 10.8 mmol) was added dropwise forming a dark red solution and then a precipitate. After 10 min, the reaction was quenched with sat. aq. NH$_4$Cl solution. Dichloromethane and water were added, the phases separated, and the aqueous phase re-extracted with dichloromethane. The combined organic extracts were dried (phase separator) and concentrated under reduced pressure. The residue was purified on silica (50 g SNAP cartridge) eluting with a gradient of 20-100% EtOAc in iso-hexanes followed by chiral SFC gave two isomers of the title compound.

Example 199: *Faster Eluting Isomer $^1$H NMR (400 MHz, CDCl$_3$) 8.34 (1H, d), 7.70 (1H, d), 7.55 (1H, dd), 7.40-7.31 (5H, m), 7.26-7.23 (3H, m), 4.52-4.38 (2H, m), 4.06 (1H, s), 3.86 (3H, s), 3.50-3.48 (1H, m), 2.99 (1H, d), 2.35 (1H, s), 1.88 (3H, s), 0.89-0.75 (2H, m), 0.58-0.52 (1H, m), 0.40-0.34 (1H, m); MS: [M+H]$^+$=597.

Example 200: *Slower Eluting Isomer $^1$H NMR (400 MHz, CDCl$_3$) 8.34 (1H, d), 7.72 (1H, d), 7.55 (1H, dd), 7.41-7.30 (5H, m), 7.27-7.22 (3H, m), 4.52-4.40 (2H, m), 4.02 (1H, s), 3.87 (3H, s), 3.49 (1H, d), 2.99 (1H, d), 2.28 (1H, s), 1.89 (3H, s), 0.89-0.76 (2H, m), 0.58-0.52 (1H, m), 0.41-0.34 (1H, m); MS: [M+H]$^+$=597.

Examples 201 and 202: 1-({[(1R)-1-(4-chlorophenyl)-2-[(5-chloropyridin-2-yl)methyl]-7-fluoro-5-[1-hydroxy-1-(1-methyl-1H-pyrazol-4-yl)ethyl]-3-oxo-2,3-dihydro-1H-isoindol-1-yl]oxy}methyl)cyclopropane-1-carbonitrile (*both isomers separated and isolated)

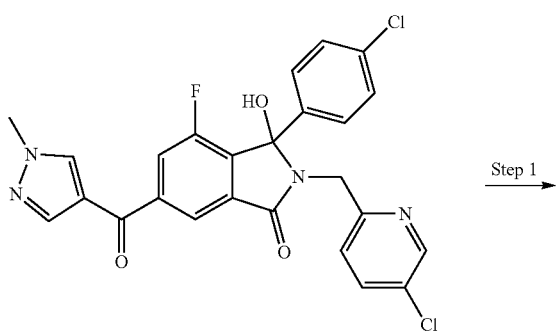

Step 1

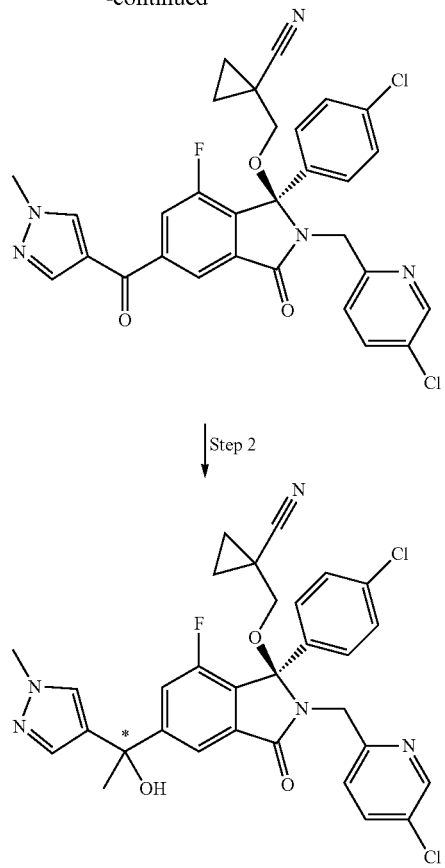

Step 1: (R)-1-(((1-(4-Chlorophenyl)-2-((5-chloropyridin-2-yl)methyl)-7-fluoro-5-(1-methyl-1H-pyrazole-4-carbonyl)-3-oxoisoindolin-1-yl)oxy)methyl)cyclopropanecarbonitrile 3-(4-Chlorophenyl)-2-((5-chloropyridin-2-yl)methyl)-4-fluoro-3-hydroxy-6-(1-methyl-1H)pyrazole-4-carbonyl)isoindolin-1-one (Examples 199 and 200, step 3, 12.0 g, 23.6 mmol), 1-(hydroxymethyl)cyclopropanecarbonitrile (4.46 g, 46 mmol) and indium(III) bromide (12.5 g, 35.2 mmol) were heated to reflux in 1,2-dichloroethane (200 mL) for 4 h. The orange suspension was cooled to RT and concentrated under reduced pressure. EtOAc and water were added and the mixture stirred at RT for 0.5 h. The layers were separated and the organic layer was dried over MgSO$_4$, filtered and concentrated under reduced pressure. The residue was purified on silica (340 g SNAP cartridge) eluting with a gradient of 25-75% EtOAc in dichloromethane followed by chiral SFC to give the title compound (1.58 g, 23% yield). $^1$H NMR (400 MHz, CDCl$_3$) 8.40 (1H, d), 8.15 (1H, s), 7.98 (2H, d), 7.68 (1H, d), 7.56 (1H, dd), 7.35 (2H, d), 7.31-7.21 (3H, m), 4.64 (1H, d), 4.41 (1H, d), 4.01 (3H, s), 3.48 (1H, d), 3.01 (1H, d), 1.31-1.25 (2H, m), 0.87-0.82 (2H, m); [α]$^D$=+44.86 (MeOH).

Step 2: 1-({[(1R)-1-(4-chlorophenyl)-2-[(5-chloropyridin-2-yl)methyl]-7-fluoro-5-[1-hydroxy-1-(1-methyl-1H-pyrazol-4-yl)ethyl]-3-oxo-2,3-dihydro-1H-isoindol-1-yl]oxy}methyl)cyclopropane-1-carbonitrile (R)-1-(((1-(4-Chlorophenyl)-2-((5-chloropyridin-2-yl)methyl)-7-fluoro-5-(1-methyl-1H-pyrazole-4-carbonyl)-3- oxoisoindolin-1-yl)oxy)methyl)cyclopropanecarbonitrile (1.48 g, 2.51 mmol) was stirred in THF (22 mL) at −15° C. under nitrogen. Methylmagnesium chloride (1.75M in THF, 3.2 mL, 5.52 mmol) was added dropwise forming an orange solution which was stirred for 10 min. The reaction was quenched with sat. aq. NH$_4$Cl solution, water was added and the reaction was warmed to RT.

The aqueous phase was separated and re-extracted with dichloromethane (2×50 mL) and the combined organics were dried (phase separator) and concentrated under reduced pressure. The residue was purified on silica (50 g SNAP cartridge) eluting with a gradient of 40-100% EtOAc in isohexanes followed by chiral SFC to give the title compounds.

Example 201 (*Faster Eluting Isomer) (213 mg)

$^1$H NMR (400 MHz, CDCl$_3$) 8.37 (1H, d), 7.74 (1H, d), 7.53 (1H, dd), 7.45-7.38 (2H, m), 7.33-7.20 (6H, m) 4.61 (1H, d), 4.36 (1H, d), 3.88 (3H, s), 3.34 (1H, d), 3.02 (1H, d), 2.20 (1H, s), 1.89 (3H, s), 1.27-1.22 (2H, m), 0.83-0.78 (2H, m). MS: [M+H]+=606.

Example 202 (*Slower Eluting Isomer) (231 mg)

$^1$H NMR (400 MHz, CDCl$_3$) 8.37 (1H, dd), 7.76 (1H, d), 7.53 (1H, dd), 7.42 (1H, dd), 7.38 (1H, s), 7.33-7.19 (6H, m), 4.60 (1H, d), 4.38 (1H, d), 3.88 (3H, s), 3.35 (1H, d), 3.01 (1H, d), 2.26 (1H, s), 1.90 (3H, s), 1.27-1.23 (2H, m), 0.83-0.78 (2H, m). MS: [M+H]$^+$=606.

TABLE 1

Penultimate ketone Intermediates

| Structure | Name | Comment | NMR Data | MS Data |
|---|---|---|---|---|
| 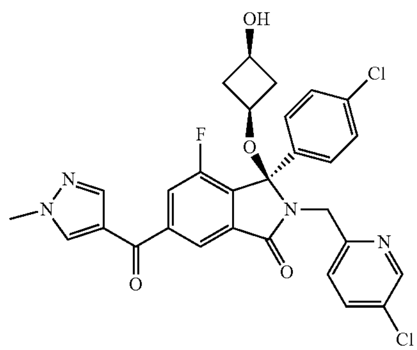 [SMILES: Cn1cc(C(=O)c2cc(F)c3c(c2)C(=O)N(Cc2ccc(Cl)cn2)[C@@]3(O[C@H]2C[C@@H](O)C2)c2ccc(Cl)cc2)cn1] | (R)-(4-chlorophenyl)-2-((5-chloropyridin-2-yl)methyl)-4-fluoro-3-((1S,3S)-3-hydroxycyclobutoxy)-6-(1-methyl-1H-pyrazole-4-carbonyl)isoindolin-1-one | Prepared in a similar manner to 200 step 4 |  | [M + H]+ = 581 |
| 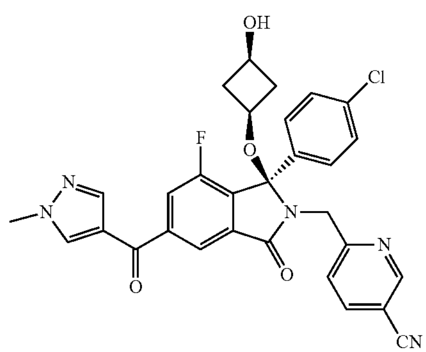 [SMILES: Cn1cc(C(=O)c2cc(F)c3c(c2)C(=O)N(Cc2ccc(C#N)cn2)[C@@]3(O[C@H]2C[C@@H](O)C2)c2ccc(Cl)cc2)cn1] | 6-{[(1R)-1-(4-chlorophenyl)-7-fluoro-1-(cis-3-hydroxycyclobutoxy)-5-(1-methyl-1H-pyrazole-4-carbonyl)-3-oxo-2,3-dihydro-1H-isoindol-2-yl]methyl}pyridine-3-carbonitrile | Prepared in a similar manner to 200 step 4 |  | [M − H]− = 570 |
| 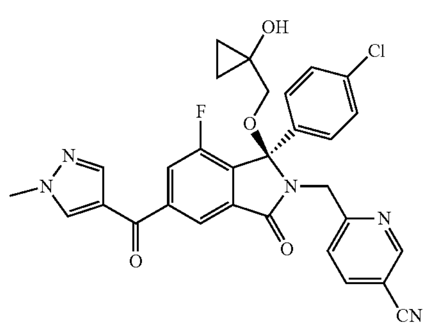 [SMILES: Cn1cc(C(=O)c2cc(F)c3c(c2)C(=O)N(Cc2ccc(C#N)cn2)[C@@]3(OCC2(O)CC2)c2ccc(Cl)cc2)cn1] | 6-{[(1R)-1-(4-chlorophenyl)-7-fluoro-1-[(1-hydroxycyclopropyl)methoxy]-5-(1-methyl-1H-pyrazole-4-carbonyl)-3-oxo-2,3-dihydro-1H-isoindol-2-yl]methyl}pyridine-3-carbonitrile | Prepared in a similar manner to 200 step 4 |  |  |

TABLE 1-continued

Penultimate ketone Intermediates

| Structure | Name | Comment | NMR Data | MS Data |
|---|---|---|---|---|
| 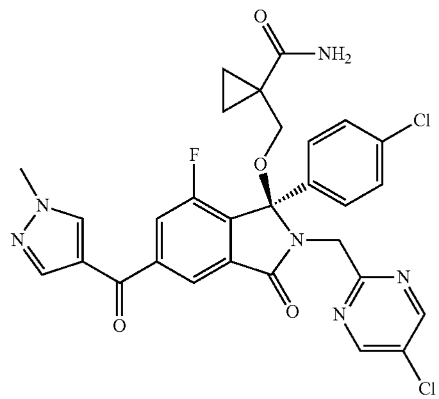 [SMILES: Cn1cc(C(=O)c2cc(F)c3c(c2)C(=O)N(Cc2ncc(Cl)cn2)[C@@]3(OCC2(C(N)=O)CC2)c2ccc(Cl)cc2)cn1] | (R)-1-(((1-(4-chloro-phenyl)-2-((5-chloropyrimidin-2-yl)methyl)-7-fluoro-5-(1-methyl-1H-pyrazole-4-carbonyl)-3-oxoisoindolin-1-yl)oxy)methyl)cyclopropane-carboxamide | Prepared in a similar manner to 200 step 4 | | [M + H]+ = 609 |
| 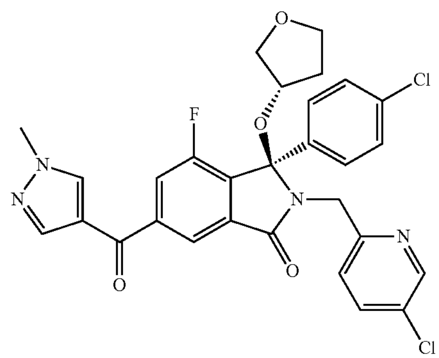 [SMILES: Cn1cc(C(=O)c2cc(F)c3c(c2)C(=O)N(Cc2ccc(Cl)cn2)[C@@]3(O[C@H]2CCOC2)c2ccc(Cl)cc2)cn1] | (R)-3-(4-chloro-phenyl)-2-((5-chloro-pyridin-2-yl)methyl)-4-fluoro-6-(1-methyl-1H-pyrazole-4-carbonyl)-3-(((S)-tetrahy-drofuran-3-yl)oxy)isoindolin-1-one | Prepared in a similar manner to 200 step 4 | | [M + H]+ = 581 |
| 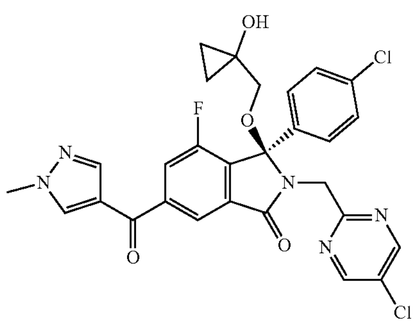 [SMILES: Cn1cc(C(=O)c2cc(F)c3c(c2)C(=O)N(Cc2ncc(Cl)cn2)[C@@]3(OCC2(O)CC2)c2ccc(Cl)cc2)cn1] | (R)-3-(4-chloro-phenyl)-2-((5-chloro-pyrimidin-2-yl)methyl)-4-fluoro-3-((1-hydroxy-cyclopropyl)methoxy)-6-(1-methyl-1H-pyrazole-4-carbonyl)isoindolin-1-one | Prepared in a similar manner to 200 step 4 | $^1$H NMR (400 MHz, CDCl$_3$) 8.54 (2H, s), 8.16 (1H, d), 7.98 (2H, d), 7.68 (1H, dd), 7.27-7.25 (4H, m), 4.67 (2H, s), 4.00 (3H, s), 3.72 (1H, d), 3.11 (1H, d), 2.98 (1H, s), 0.87-0.81 (2H, m), 0.59-0.53 (1H, m), 0.45-0.39 (1H, m) | |
| 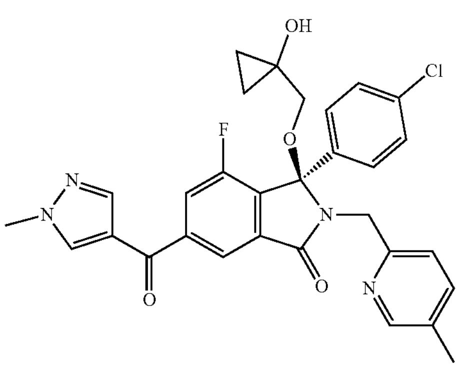 | (R)-3-(4-chloro-phenyl)-4-fluoro-3-((1-hydroxy-cyclopropyl)methoxy)-6-(1-methyl-1H-pyrazole-4-carbonyl)-2-((5-methylpyridin-2-yl)methyl)isoindolin-1-one | Prepared in a similar manner to 200 step 4 | | MS: [M − 1-(hydroxymethyl)cyclopropanol]+ = 473 |

TABLE 1-continued

Penultimate ketone Intermediates

| Structure | Name | Comment | NMR Data | MS Data |
|---|---|---|---|---|
| 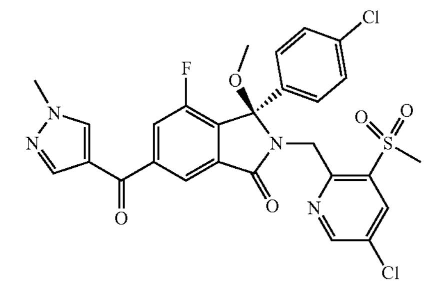 [SMILES: CO[C@]1(c2ccc(Cl)cc2)c2c(F)cc(C(=O)c3cnn(C)c3)cc2C(=O)N1Cc1ncc(Cl)cc1S(C)(=O)=O] | (R)-2-((5-chloro-3-(methylsulfonyl)pyridin-2-yl)methyl)-3-(4-chlorophenyl)-4-fluoro-3-methoxy-6-(1-methyl-1H-pyrazole-4-carbonyl)isoindolin-1-one | Prepared in a similar manner to 202 step 1 | | MS: [M − H]− = 601 |
| 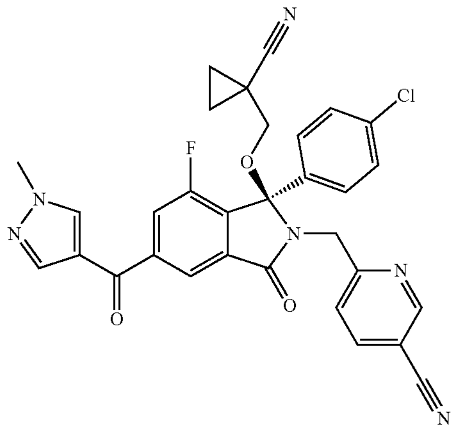 [SMILES: Cn1cc(C(=O)c2cc(F)c3c(c2)C(=O)N(Cc2ccc(C#N)cn2)[C@@]3(OCC2(C#N)CC2)c2ccc(Cl)cc2)cn1] | (R)-6-((1-(4-chlorophenyl)-1-((1-cyanocyclopropyl)methoxy)-7-fluoro-5-(1-methyl-1H-pyrazole-4-carbonyl)-3-oxoisoindolin-2-yl)methyl)nicotinonitrile | Prepared in a similar manner to 202 step 1 | | [M + H]+ = 581 |
| 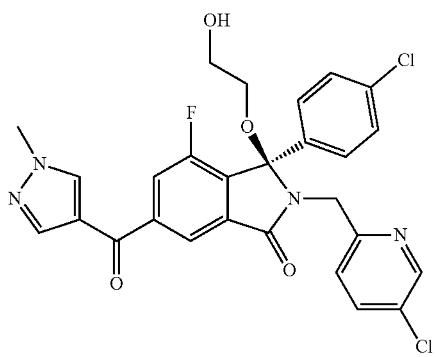 [SMILES: Cn1cc(C(=O)c2cc(F)c3c(c2)C(=O)N(Cc2ccc(Cl)cn2)[C@@]3(OCCO)c2ccc(Cl)cc2)cn1] | (R)-3-(4-chlorophenyl)-2-((5-chloropyridin-2-yl)methyl)-4-fluoro-3-(2-hydroxyethoxy)-6-(1-methyl-1H-pyrazole-4-carbonyl)isoindolin-1-one | Prepared in a similar manner to 202 step 1 | | [M + H]+ = 555 |
| 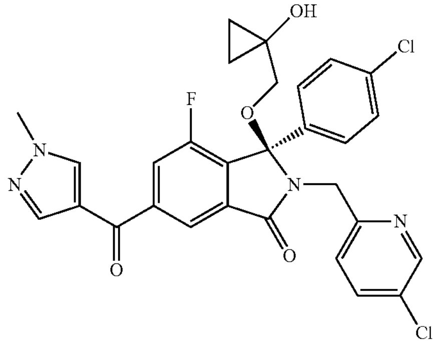 | (R)-3-(4-chlorophenyl)-2-((5-chloropyridin-2-yl)methyl)-4-fluoro-3-((1-hydroxycyclopropyl)methoxy)-6-(1-methyl-1H-pyrazole-4-carbonyl)isoindolin-1-one | Prepared in a similar manner to 200 step 4 | $^1$H NMR (400 MHz, CDCl$_3$) 8.39 (1H, d), 8.11 (1H, d), 7.96 (2H, d), 7.66 (1H, d), 7.59 (1H, dd), 7.39-7.34 (3H, m), 7.28-7.25 (2H, m), 4.55-4.42 (2H, m), 4.00 (3H, s), 3.62 (1H, dd), 3.00 (1H, d), 0.93-0.78 (2H, m), 0.63-0.56 (1H, m), 0.43-0.36 (1H, m), (OH not observed) | |

TABLE 1-continued

Penultimate ketone Intermediates

| Structure | Name | Comment | NMR Data | MS Data |
|---|---|---|---|---|
| | (R)-1-(((1-(4-chlorophenyl)-7-fluoro-2-((5-fluoropyridin-2-yl)methyl)-5-(1-methyl-1H-pyrazole-4-carbonyl)-3-oxoisoindolin-1-yl)oxy)methyl)cyclopropanecarboxamide | Prepared in a similar manner to 200 step 4 | | [M + H]+ = 592 |
| | (R)-1-(((1-(4-chlorophenyl)-7-fluoro-2-((6-methoxypyridin-3-yl)methyl)-5-(1-methyl-1H-pyrazole-4-carbonyl)-3-oxoisoindolin-1-yl)oxy)methyl)cyclopropanecarboxamide | Prepared in a similar manner to 202 step 1 | | [M + H]+ = 604 |
| 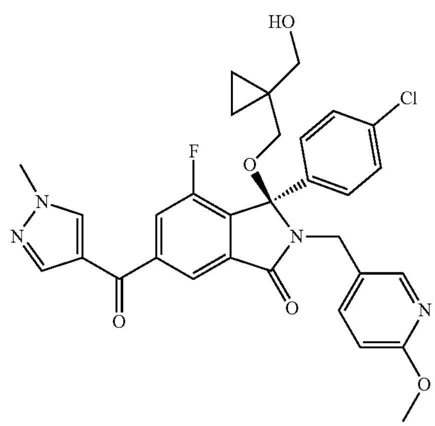 [SMILES: COc1ccc(CN2C(=O)c3cc(C(=O)c4cnn(C)c4)cc(F)c3[C@]2(OCC2(CO)CC2)c2ccc(Cl)cc2)cn1] | (R)-3-(4-chlorophenyl)-4-fluoro-3-((1-(hydroxymethyl)cyclopropyl)methoxy)-2-((6-methoxypyridin-3-yl)methyl)-6-(1-methyl-1H-pyrazole-4-carbonyl)isoindolin-1-one | Prepared in a similar manner to 200 step 4 | | [M + H]+ = 591 |
| 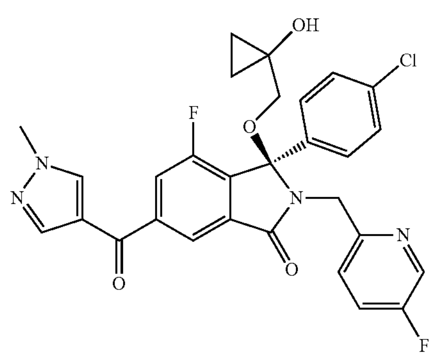 [SMILES: Cn1cc(C(=O)c2cc(F)c3c(c2)C(=O)N(Cc2ccc(F)cn2)[C@@]3(OCC2(O)CC2)c2ccc(Cl)cc2)cn1] | (R)-3-(4-chlorophenyl)-4-fluoro-2-((5-fluoropyridin-2-yl)methyl)-3-((1-hydroxy-cyclopropyl)methoxy)-6-(1-methyl-1H-pyrazole-4-carbonyl)isoindolin-1-one | Prepared in a similar manner to 200 step 4 | | [M + H]+ = 565 |

TABLE 1-continued

Penultimate ketone Intermediates

| Structure | Name | Comment | NMR Data | MS Data |
|---|---|---|---|---|
| 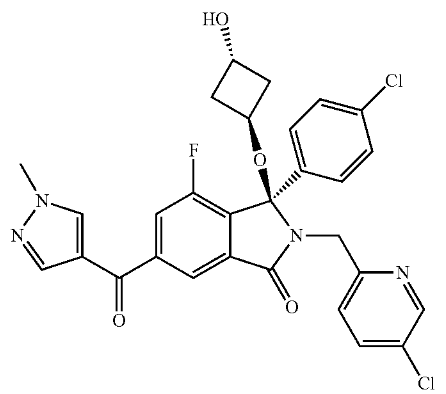 [SMILES: Cn1cc(C(=O)c2cc(F)c3c(c2)C(=O)N(Cc2ccc(Cl)cn2)[C@@]3(O[C@H]2C[C@H](O)C2)c2ccc(Cl)cc2)cn1] | (3R)-3-(4-chloro-phenyl)-2-((5-chloropyridin-2-yl)methyl)-4-fluoro-3-((1R,3R)-trans-3-hydroxycyclobutoxy)-6-(1-methyl-1H-pyrazole-4-carbonyl)isoindolin-1-one | Prepared in a similar manner to 200 step 4 | | [M + H]+ = 581 |
| 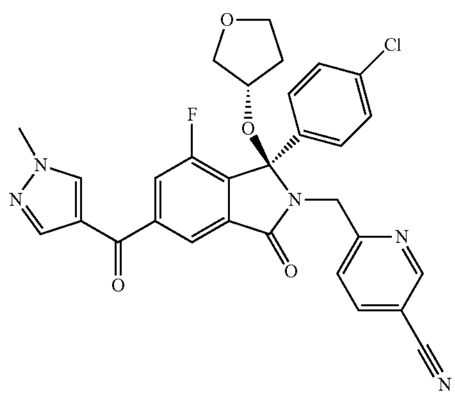 | 6-(((R)-1-(4-chloro-phenyl)-7-fluoro-5-(1-methyl-1H-pyrazole-4-carbonyl)-3-oxo-1-(((S)-tetrahydrofuran-3-yl)oxy)isoindolin-2-yl)methyl)nicotinonitrile | Prepared in a similar manner to 200 step 4 | | MS: [M − (S)-tetrahydrofuran-3-ol]+ = 484 |
| 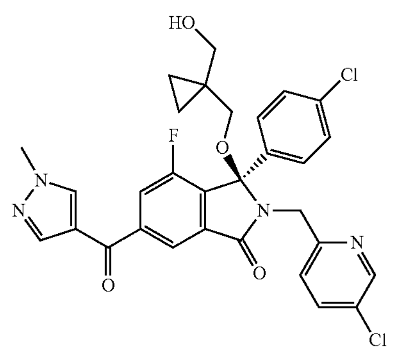 | (R)-3-(4-chloro-phenyl)-2-((5-chloro-pyridin-2-yl)methyl)-4-fluoro-3-((1-(hydroxy-methyl)cyclopropyl)methoxy)-6-(1-methyl-1H-pyrazole-4-carbonyl)isoindolin-1-one | Prepared in a similar manner to 200 step 4 | | MS: [M − cyclopropane-1,1-diyldimethanol]+ = 493 |
| 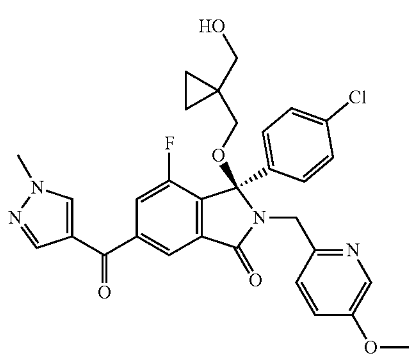 [SMILES: COc1ccc(CN2C(=O)c3cc(C(=O)c4cnn(C)c4)cc(F)c3[C@]2(OCC2(CO)CC2)c2ccc(Cl)cc2)nc1] | (R)-3-(4-chloro-phenyl)-4-fluoro-3-((1-(hydroxymethyl)cyclopropyl)methoxy)-2-((6-methoxypyridin-3-yl)methyl)-6-(1-methyl-1H-pyrazole-4-carbonyl)isoindolin-1-one | Prepared in a similar manner to 200 step 4 | | [M + H]+ = 591 |

TABLE 1-continued

Penultimate ketone Intermediates

| Structure | Name | Comment | NMR Data | MS Data |
|---|---|---|---|---|
| 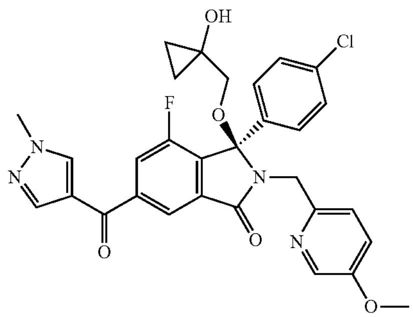 [SMILES: COc1ccc(CN2C(=O)c3cc(C(=O)c4cnn(C)c4)cc(F)c3[C@]2(OCC2(O)CC2)c2ccc(Cl)cc2)nc1] | (R)-3-(4-chloro-phenyl)-4-fluoro-3-((1-hydroxy-cyclopropyl)methoxy)-2-((5-methoxy-pyridin-2-yl)methyl)-6-(1-methyl-1H-pyrazole-4-carbonyl)isoindolin-1-one | Prepared in a similar manner to 200 step 4 | | [M + H]+ = 577 |
| 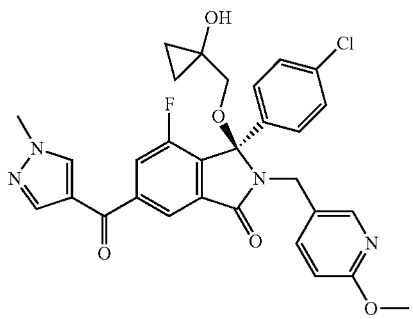 [SMILES: COc1ccc(CN2C(=O)c3cc(C(=O)c4cnn(C)c4)cc(F)c3[C@]2(OCC2(O)CC2)c2ccc(Cl)cc2)cn1] | (R)-3-(4-chloro-phenyl)-4-fluoro-3-((1-hydroxy-cyclopropyl)methoxy)-2-((6-methoxy-pyridin-3-yl)methyl)-6-(1-methyl-1H-pyrazole-4-carbonyl)isoindolin-1-one | Prepared in a similar manner to 200 step 4 | | [M + H]+ = 577 |
| 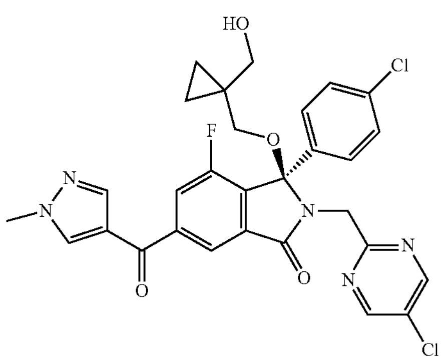 [SMILES: Cn1cc(C(=O)c2cc(F)c3c(c2)C(=O)N(Cc2ncc(Cl)cn2)[C@@]3(OCC2(CO)CC2)c2ccc(Cl)cc2)cn1] | (R)-3-(4-chloro-phenyl)-2-((5-chloro-pyrimidin-2-yl)methyl)-4-fluoro-3-((1-(hydroxymethyl)cyclopropyl)methoxy)-6-(1-methyl-1H-pyrazole-4-carbonyl)isoindolin-1-one | Prepared in a similar manner to 200 step 4 | | [M + formic acid-H]- = 640.3 |
| 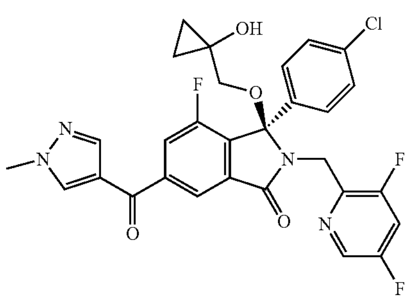 [SMILES: Cn1cc(C(=O)c2cc(F)c3c(c2)C(=O)N(Cc2ncc(F)cc2F)[C@@]3(OCC2(O)CC2)c2ccc(Cl)cc2)cn1] | (R)-3-(4-chloro-phenyl)-2-((3,5-difluoropyridin-2-yl)methyl)-4-fluoro-3-((1-hydroxy-cyclopropyl)methoxy)-6-(1-methyl-1H-pyrazole-4-carbonyl)isoindolin-1-one | Prepared in a similar manner to 200 step 4 | | [M + formic acid-H]- = 627.3 |

TABLE 1-continued

Penultimate ketone Intermediates

| Structure | Name | Comment | NMR Data | MS Data |
|---|---|---|---|---|
| | (R)-6-((1-(4-chlorophenyl)-7-fluoro-1-((1-(hydroxymethyl)cyclopropyl)methoxy)-5-(1-methyl-1H-imidazole-4-carbonyl)-3-oxoisoindolin-2-yl)methyl)nicotinonitrile | Prepared in a similar manner to 200 step 4 | | [M − H]− = 584 |
| | 6-{[(1R)-1-(4-chlorophenyl)-7-fluoro-1-({1-[hydroxy(²H₂)methyl]cyclopropyl}(²H₂)methoxy)-5-(1-methyl-1H-pyrazole-4-carbonyl)-3-oxo-2,3-dihydro-1H-isoindol-2-yl]methyl}pyridine-3-carbonitrile | Prepared in a similar manner to 200 step 4 | | [M − OCD2C(cPr)C2OH]+ 484 |
| | (R)-3-(4-chlorophenyl)-2-((5-chloropyridin-2-yl)methyl)-4-fluoro-3-((R)-2-hydroxypropoxy)-6-(1-methyl-1H-pyrazole-4-carbonyl)isoindolin-1-one | Prepared in a similar manner to 200 step 4 | | [M + H]+ = 569 |
| | 6-(((R)-1-(4-chlorophenyl)-7-fluoro-5-(1-methyl-1H-pyrazole-4-carbonyl)-3-oxo-1-(((S)-tetrahydrofuran-3-yl)oxy)isoindolin-2-yl)methyl)nicotinonitrile | Prepared in a similar manner to 200 step 4 | | [M + H]+ = 572 |

TABLE 1-continued

Penultimate ketone Intermediates

| Structure | Name | Comment | NMR Data | MS Data |
|---|---|---|---|---|
| | 6-(((R)-1-(4-chlorophenyl)-7-fluoro-1-((1S,3S)-3-hydroxycyclobutoxy)-5-(1-methyl-1H-pyrazole-4-carbonyl)-3-oxoisoindolin-2-yl)methyl)nicotinonitrile | Prepared in a similar manner to 200 step 4 | | [M + H]$^+$ = 572 |
| | 6-(((R)-1-(4-chlorophenyl)-7-fluoro-5-(1-methyl-1H-pyrazole-3-carbonyl)-3-oxo-1-(((S)-tetrahydrofuran-3-yl)oxy)isoindolin-2-yl)methyl)nicotinonitrile | Prepared in a similar manner to 202 step 1 | | [M − H]$^−$ = 572 |
| | 6-{[(1R)-1-(4-chlorophenyl)-7-fluoro-1-(2-hydroxyethoxy)-5-(1-methyl-1H-imidazole-4-carbonyl)-3-oxo-2,3-dihydro-1H-isoindol-2-yl]methyl}pyridine-3-cartbonitrile | Prepared in a similar manner to 202 step 1 | | [M + Na]+ = 568 |

TABLE 1-continued

Penultimate ketone Intermediates

| Structure | Name | Comment | NMR Data | MS Data |
|---|---|---|---|---|
| | 6-{[(1R)-1-(4-chlorophenyl)-7-fluoro-5-(1-methyl-1H-imidazole-4-carbonyl)-3-oxo-1-((3S)-oxolan-3-yloxy]-2,3-dihydro-1H-isoindol-2-yl]methyl}pyridine-3-carbonitrile | Prepared in a similar manner to 200 step 4 | | ES+ 572 |
| | 6-{[(1R)-1-(4-chlorophenyl)-7-fluoro-5-(1-methyl-1H-imidazole-4-carbonyl)-3-oxo-1-((3R)-oxolan-3-yloxy]-2,3-dihydro-1H-isoindol-2-yl]methyl}pyridine-3-carbonitrile | Prepared in a similar manner to 202 step 1 | | |
| | (3R)-3-(4-chlorophenyl)-2-[(6-chloropyridin-3-yl)methyl]-4-fluoro-3-(2-hydroxyethoxy)-6-(1-methyl-1H-imidazole-4-carbonyl)-2,3-dihydro-1H-isoindol-1-one | Prepared in a similar manner to 200 step 4 | | ES+ 555 |
| | 2-{[(1R)-1-(4-chlorophenyl)-7-fluoro-5-(1-methyl-1H-imidazole-4-carbonyl)-3-oxo-1-[(3S)-oxolan-3-yloxy]-2,3-dihydro-1H-isoindol-2-yl]methyl}pyrimidine-5-carbonitrile | Prepared in a similar manner to 202 step 1 | | [M − H]− = 571.0 |

TABLE 1-continued

Penultimate ketone Intermediates

| Structure | Name | Comment | NMR Data | MS Data |
|---|---|---|---|---|
| 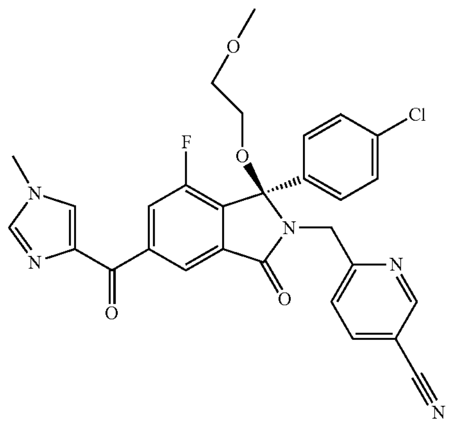 [SMILES: COCCO[C@]1(c2ccc(Cl)cc2)c2c(F)cc(C(=O)c3cn(C)cn3)cc2C(=O)N1Cc1ccc(C#N)cn1] | 6-{[1-(4-chloro-phenyl)-7-fluoro-1-(2-methoxy-ethoxy)-5-(1-methyl-1H-imidazole-4-carbonyl)-3-oxo-2,3-dihydro-1H-isoindol-2-yl]methyl}pyridine-3-carbonitrile | Prepared in a similar manner to 202 step 1 | | [M + NA]$^+$ = 582 |
| 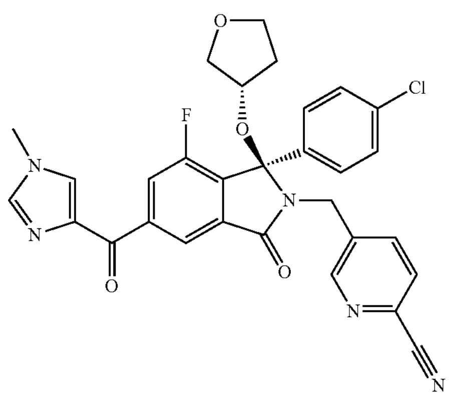 [SMILES: Cn1cnc(C(=O)c2cc(F)c3c(c2)C(=O)N(Cc2ccc(C#N)nc2)[C@@]3(O[C@H]2CCOC2)c2ccc(Cl)cc2)c1] | 5-{[1-(4-chloro-phenyl)-7-fluoro-5-(1-methyl-1H-imidazole-4-carbonyl)-3-oxo-1-[(3S)-oxolan-3-yloxy]-2,3-dihydro-1H-isoindol-2-yl]methyl}pyridine-2-carbonitrile | Prepared in a similar manner to 200 step 4 | | [M + H]$^+$ = 572 |
| | 6-{[1-(4-chloro-phenyl)-7-fluoro-1-[(3-fluorooxetan-3-yl)methoxy]-5-(1-methyl-1H-imidazole-4-carbonyl)-3-oxo-2,3-dihydro-1H-isoindol-2-yl]methyl}pyridine-3-carbonitrile | Prepared in a similar manner to 202 step 1 | | [M + H]$^+$ = 590 |

TABLE 1-continued

| Penultimate ketone Intermediates | | | | |
|---|---|---|---|---|
| Structure | Name | Comment | NMR Data | MS Data |
| | 6-{[1-(4-chloro-phenyl)-7-fluoro-1-[(2R)-2-hydroxy-propoxy]-5-(1-methyl-1H-imidazole-4-carbonyl)-3-oxo-2,3-dihydro-1H-isoindol-2-yl]methyl}pyridine-3-carbonitrile | Prepared in a similar manner to 200 step 4 | | $[M - C_3H_6O_2]^- = 484$ |
| | 6-{[1-(4-chloro-phenyl)-7-fluoro-1-({1-[hydroxy($^2$H$_2$)methyl]cyclopropyl}($^2$H$_2$)methoxy)-5-(1-methyl-1H-imidazole-4-carbonyl)-3-oxo-2,3-dihydro-1H-isoindol-2-yl]methyl}pyridine-3-carbonitrile | Prepared in a similar manner to 200 step 4 | | $[M - H]^- = 588$ |
| | (R)-2-((1-(4-chloro-phenyl)-1-((1-cyanocyclopropyl)methoxy)-7-fluoro-5-(1-methyl-1H-imidazole-4-carbonyl)-3-oxoisoindolin-2-yl)methyl)pyrimidine-5-carbonitrile | Prepared in a similar manner to Example 202 step 1 | | $[M + H]+ = 582$ |

TABLE 1-continued

Penultimate ketone Intermediates

| Structure | Name | Comment | NMR Data | MS Data |
|---|---|---|---|---|
| | (R)-3-(4-chloro-phenyl)-2-((5-chloropyrimidin-2-yl)methyl)-4-fluoro-3-((cis)-3-hydroxy-cyclobutoxy)-6-(1-methyl-1H-imidazole-4-carbonyl)isoindolin-1-one | Prepared in a similar manner to Example 202 step 1 | | [M + H]+ = 582 |
| | (R)-6-((1-(4-chloro-phenyl)-7-fluoro-1-((2-(hydroxy-methyl)allyl)oxy)-5-(1-methyl-1H-imidazole-4-carbonyl)-3-oxoisoindolin-2-yl)methyl)nicotinonitrile | Prepared in a similar manner to Example 202 step 1 | | [M − H]− = 570 |
| | (3R)-2-[(5-chloro-3-hydroxypyridin-2-yl)methyl]-3-(4-chlorophenyl)-4-fluoro-6-(1-methyl-1H-imidazole-4-carbonyl)-3-[cis-3-hydroxy-cyclobutoxy]-2,3-dihydro-1H-isoindol-1-one | Starting from Preparation 40. Prepared in a similar manner to 200 step 4, followed by TFA deprotection of PMB group | | MS [M + H]+ = 597 |

Starting from the appropriate acid intermediate (for example, Example 200 Step 2, Preparation 20, Preparation 21), the following compounds were prepared using procedures similar to those described in Example 200 and Example 202.

The appropriate amines (for example. Preparation 17, Preparation 18, Preparation 19), or commercially available amines, were introduced with (typically) HATU. Subsequent coupling of the appropriate alcohol with the isoindolinone intermediates was typically facilitated using SOCl$_2$ or InBr$_3$. In cases where alcohols were not commercially available, preparations are described herein (e.g Preparation 1). The compounds were obtained as single isomers, with the configuration shown, using chiral preparative HPLC.

Example 203 and 204: (3R)-3-(4-chlorophenyl)-2-[(5-chloropyrimidin-2-yl)methyl]-4-fluoro-6-[1-hydroxy-1-(1-methyl-1H-pyrazol-4-yl)ethyl]-3-[(1-hydroxycyclopropyl)methoxy]-2,3-dihydro-1H-isoindol-1-one (*both isomers separated and isolated)

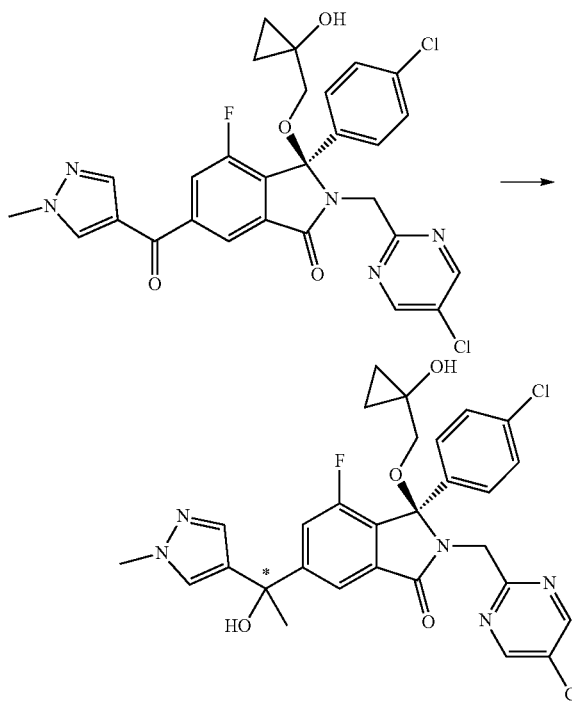

(R)-3-(4-Chlorophenyl)-2-((5-chloropyrimidin-2-yl)methyl)-4-fluoro-3-((1-hydroxycyclopropyl)methoxy)-6-(1-methyl-1H-pyrazole-4-carbonyl)isoindolin-1-one (502 mg, 0.86 mmol) was dissolved in anhydrous dichloromethane at 0° C. with stirring under an atmosphere of nitrogen. AlMe₃ (3.4 mL, 2M in hexanes, 6.9 mmol) was added dropwise at 0° C. with stirring. The reaction was stirred at 0° C. for 50 min then quenched by the addition of saturated NH₄Cl (10 mL). The reaction was diluted with dichloromethane (50 mL) and water (10 mL) and the solids were removed by filtration. The phases were separated and the aqueous phase was re-extracted with dichloromethane (20 mL). The combined organic extracts were passed through a phase separation cartridge, concentrated under reduced pressure and purified column chromatography on silica, eluting with a gradient of 0-5% methanol in ethyl acetate to afford the diastereomeric mixture as a colourless foam (385 mg) which was separated using chiral SFC.

Example 203 *Slower Eluting Isomer

¹H NMR (400 MHz, CDCl₃) 8.51 (2H, s), 7.75 (1H, d), 7.43-7.35 (4H, m), 7.27 (1H, s), 7.22 (2H, d), 4.63 (2H, d), 3.88 (3H, s), 3.63 (1H, d), 3.11 (1H, d), 3.01 (1H, s), 2.29 (1H, s), 1.90 (3H, s), 0.81 (2H, dd), 0.56-0.50 (1H, m), 0.43-0.37 (1H, m). MS: [M+H]+=598.2.

Example 204 *Faster Eluting Isomer

¹H NMR (400 MHz, CDCl₃) 8.52 (2H, s), 7.74 (1H, d), 7.40-7.35 (4H, m), 7.28 (1H, s), 7.23 (2H, d), 4.63 (2H, s), 3.88 (3H, s), 3.64 (1H, d), 3.11 (1H, d), 3.00 (1H, s), 2.26 (1H, s), 1.90 (3H, s), 0.81 (2H, dd), 0.55-0.49 (1H, m), 0.41-0.36 (1H, m). MS: [M+H]+=598.2.

Starting from the appropriate ketone intermediate (for example, the ketones shown in the Table 1 hereinabove under the heading "Penultimate Ketone Intermediates"), the following Examples were prepared by reaction with an appropriate nucleophile (for example, an alkyl organometallic reagent), using methods similar to those described in Examples 200 Step 5, Example 202 Step 2, Example 203, Example 336 or Example 337.

Purification by preparative achiral and/or chiral HPLC gave final compounds as single isomer (unless stated otherwise). In Table 2, an asterisk indicates the compound was isolated as a single isomer at the position shown.

TABLE 2

| Example | Structure | Name | Comment | NMR Data | MS Data |
|---|---|---|---|---|---|
| 205 | 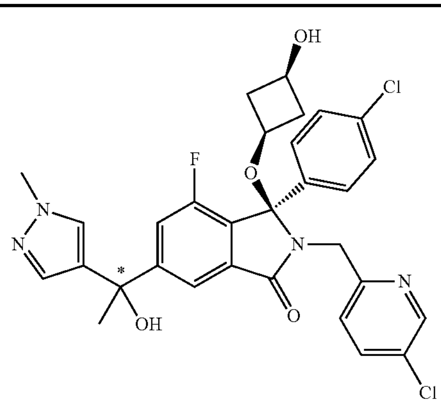 | (3R)-3-(4-chlorophenyl)-2-[(5-chloropyridin-2-yl)methyl]-4-fluoro-6-[1-hydroxy-1-(1-methyl-1H-pyrazol-4-yl)ethyl]-3-(cis-3-hydroxycyclobutoxy)-2,3-dihydro-1H-isoindol-1-one | Prepared in a similar manner to 200 step 5 | ¹H NMR (400 MHz, CDCl₃) 8.34 (1H, d), 7.74 (1H, d), 7.48 (1H, dd), 7.39-7.35 (2H, m), 7.29-7.26 (3H, m), 7.22-7.16 (3H, m), 4.63 (1H, d), 4.34 (1H, d), 3.88 (3H, s), 3.63 (1H, dd), 3.31-3.23 (1H, m), 2.25 (1H, s), 2.14-2.05 (1H, m), 1.98-1.89 (5H, m), 1.87-1.78 (1H, m), 1.68 (1H, d) | [M + H]+ = 597 |

TABLE 2-continued

| Example | Name | Comment | NMR Data | MS Data |
|---|---|---|---|---|
| 206 | (3R)-3-(4-chlorophenyl)-2-[(5-chloropyridin-2-yl)methyl]-4-fluoro-6-[1-hydroxy-1-(1-methyl-1H-pyrazol-4-yl)ethyl]-3-[trans-3-hydroxy-cyclobutoxy]-2,3-dihydro-1H-isoindol-1-one | Prepared in a similar manner to 200 step 5 | $^1$H NMR (400 MHz, CDCl$_3$) 8.33 (1H, d), 7.77 (1H, d), 7.49 (1H, dd), 7.38-7.34 (2H, m), 7.28-7.17 (6H, m, overlapping CDCl3 peak), 4.62 (1H, d) 4.39-4.33 (2H, m), 4.10-4.02 (1H, m), 3.88 (3H, s), 2.29 (1H, s), 2.25 (1H, dd), 2.19-2.10 (1H, m), 1.91 (3H, s), 1.75-1.66 (1H, m), 1.55 (1H, s, overlapping with H2O peak), 1.53-1.49 (1H, m) | [M + H]+ = 597 |
| 207 | (3R)-3-(4-chlorophenyl)-2-[(5-chloropyridin-2-yl)methyl]-4-fluoro-6-[1-hydroxy-1-(1-methyl-1H-pyrazol-4-yl)ethyl]-3-[trans-3-hydroxycyclo-butoxy]-2,3-dihydro-1H-isoindol-1-one | Prepared in a similar manner to 200 step 5 | $^1$H NMR (400 MHz, CDCl$_3$) 8.34 (1H, d), 7.76 (1H, d), 7.49 (1H, dd), 7.39-7.34 (2H, m), 7.27-7.18 (6H, m, overlapping CDCl3 peak), 4.64 (1H, d), 4.39-4.31 (2H, m), 4.09-4.01 (1H, m), 3.88 (3H, s), 2.29-2.23 (2H, m), 2.17-2.09 (1H, m), 1.90 (3H, s), 1.73-1.66 (1H, m), 1.53-1.50 (1H, m), 1.26 (1H, s) | [M + H]+ = 597 |
| 208 | (3R)-3-(4-chlorophenyl)-2-[(5-chloropyridin-2-yl)methyl]-4-fluoro-6-[1-hydroxy-1-(1-methyl-1H-pyrazol-4-yl)ethyl]-3-[cis-3-hydroxycyclo-butoxy]-2,3-dihydro-1H-isoindol-1-one | Prepared in a similar manner to 200 step 5 | $^1$H NMR (400 MHz, CDCl$_3$) 8.34 (1H, d), 7.75 (1H, d), 7.48 (1H, dd), 7.38-7.34 (2H, m), 7.29-7.25 (3H, m), 7.22-7.16 (3H, m), 4.62 (1H, d), 4.35 (1H, d), 3.89 (3H, s), 3.63 (1H, dd), 3.32-3.24 (1H, m), 2.20 (1H, s), 2.15-2.06 (1H, m), 1.97-1.80 (6H, m), 1.63 (1H, d) | [M + H]+ = 597 |
| 209 | 1-({[(1R)-1-(4-chlorophenyl)-7-fluoro-2-[(5-fluoropyridin-2-yl)methyl]-5-[1-hydroxy-1-(1-methyl-1H-pyrazol-4-yl)ethyl]-3-oxo-2,3-dihydro-1H-isoindol-1-yl]oxy}methyl)cyclopropane-1-carboxamide | Prepared in a similar manner to 202 step 2 | $^1$H NMR (400 MHz, CDCl$_3$) 8.27 (1H, d), 7.73 (1H, d), 7.48-7.43 (2H, m), 7.38-7.27 (8H, m), 5.45 (1H, s), 4.49 (1H, d), 4.24 (1H, d), 3.88 (3H, s), 3.57 (1H, d), 3.04 (1H, d), 2.30 (1H, s), 1.90 (3H, s), 1.42-1.36 (1H, m), 1.22-1.15 (1H, m), 0.63-0.56 (1H, m), 0.50-0.44 (1H, m) | [M + H]+ = 608 |

TABLE 2-continued

| Example | Name | Comment | NMR Data | MS Data |
|---|---|---|---|---|
| 210 | 1-({[(1R)-1-(4-chlorophenyl)-7-fluoro-2-[(5-fluoropyridin-2-yl)methyl]-5-[1-hydroxy-1-(1-methyl-1H-pyrazol-4-yl)ethyl]-3-oxo-2,3-dihydro-1H-isoindol-1-yl]oxy}methyl)cyclopropane-1-carboxamide | Prepared in a similar manner to 202 step 2 | $^1$H NMR (400 MHz, CDCl$_3$) 8.27 (1H, d), 7.71 (1H, d), 7.48-7.41 (2H, m), 7.39 (1H, s), 7.35-7.27 (7H, m), 5.45 (1H, s), 4.50 (1H, d), 4.22 (1H, d), 3.87 (3H, s), 3.58 (1H, d), 3.03 (1H, d), 2.31 (1H, s), 1.89 (3H, s), 1.43-1.36 (1H, m), 1.22-1.15 (1H, m), 0.62-0.56 (1H, m), 0.50-0.43 (1H, m) | [M + H]+ = 608 |
| 211 | 6-{[(1R)-1-(4-chlorophenyl)-1-[(1-cyanocyclopropyl)methoxy]-7-fluoro-5-[1-hydroxy-1-(1-methyl-1H-pyrazol-4-yl)ethyl]-3-oxo-2,3-dihydro-1H-isoindol-2-yl]methyl}pyridine-3-carbonitrile | Prepared in a similar manner to 202 step 2 | $^1$H NMR (400 MHz, CDCl$_3$) 8.68 (1H, d), 7.81 (1H, dd), 7.76 (1H, d), 7.44 (1H, dd), 7.38 (1H, s), 7.34-7.29 (4H, m), 7.23 (2H, d), 4.65-4.51 (2H, m), 3.89 (3H, s), 3.57 (1H, d), 2.88 (1H, d), 2.22 (1H, s), 1.91 (3H, s), 1.35-1.23 (2H, m), 0.94-0.79 (2H, m) | [M + H]+ = 597 |
| 212 | 6-{[(1R)-1-(4-chlorophenyl)-1-[(1-cyanocyclopropyl)methoxy]-7-fluoro-5-[1-hydroxy-1-(1-methyl-1H-pyrazol-4-yl)ethyl]-3-oxo-2,3-dihydro-1H-isoindol-2-yl]methyl}pyridine-3-carbonitrile | Prepared in a similar manner to 202 step 2 | $^1$H NMR (400 MHz, CDCl$_3$) 8.68 (1H, d), 7.81 (1H, dd), 7.74 (1H, d), 7.44 (1H, dd), 7.39 (1H, s), 7.35-7.29 (4H, m), 7.24 (2H, d), 4.63 (1H, d), 4.52 (1H, d), 3.89 (3H, s), 3.56 (1H, d), 2.89 (1H, d), 2.18 (1H, d), 1.90 (3H, s), 1.35-1.24 (2H, m), 0.93-0.79 (2H, m) | [M + H]+ = 597 |
| 213 | (3R)-3-(4-chlorophenyl)-2-[(5-chloropyridin-2-yl)methyl]-4-fluoro-6-[1-hydroxy-1-(1-methyl-1H-pyrazol-4-yl)ethyl]-3-(2-hydroxyethoxy)-2,3-dihydro-1H-isoindol-1-one | Prepared in a similar manner to 202 step 2 | $^1$H NMR (400 MHz, CDCl$_3$) 8.36 (1H, d), 7.73 (1H, d), 7.55 (1H, dd), 7.41-7.29 (6H, m), 7.24 (2H, d), 4.52 (1H, d), 4.37 (1H, d), 3.87 (3H, s), 3.84-3.76 (1H, m), 3.68-3.60 (1H, m), 3.40-3.34 (1H, m), 3.26-3.20 (2H, m), 2.37 (1H, s), 1.88 (3H, s) | [M + H]+ = 571 |

TABLE 2-continued

| Example | Structure | Name | Comment | NMR Data | MS Data |
|---|---|---|---|---|---|
| 214 | 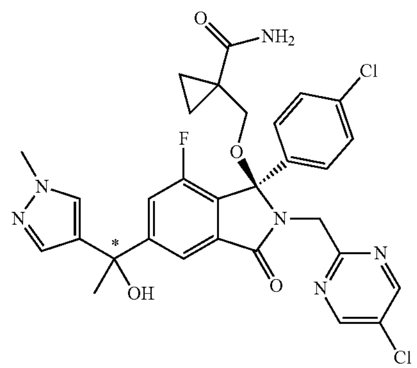 [SMILES: Cn1cc(C(C)(O)c2cc(F)c3c(c2)C(=O)N(Cc2ncc(Cl)cn2)[C@@]3(OCC2(C(N)=O)CC2)c2ccc(Cl)cc2)cn1] | 1-({[(1R)-1-(4-chlorophenyl)-2-[(5-chloro-pyrimidin-2-yl)methyl]-7-fluoro-5-[1-hydroxy-1-(1-methyl-1H-pyrazol-4-yl)ethyl]-3-oxo-2,3-dihydro-1H-isoindol-yl]oxy}methyl)cyclo-propane-1-carboxamide | Prepared in a similar manner to 203 | $^1$H NMR (400 MHz, CDCl$_3$) 8.53 (2H, s), 7.77 (1H, d), 7.48 (1H, dd), 7.40 (1H, s), 7.35-7.24 (5H, m), 6.72 (1H, s), 5.41 (1H, s), 4.53 (2H, d), 3.89 (3H, s), 3.57 (1H, d), 3.45 (1H, d), 2.30 (1H, s), 1.92 (3H, s), 1.38-1.32 (1H, m), 1.25-1.19 (1H, m), 0.62-0.45 (2H, m) | [M + H]+ = 625 |
| 215 | 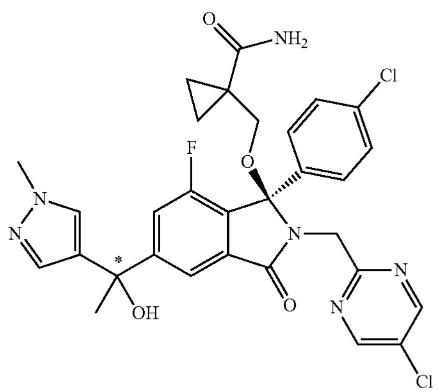 [SMILES: Cn1cc(C(C)(O)c2cc(F)c3c(c2)C(=O)N(Cc2ncc(Cl)cn2)[C@@]3(OCC2(C(N)=O)CC2)c2ccc(Cl)cc2)cn1] | 1-({[(1R)-1-(4-chlorophenyl)-2-[(5-chloro-pyrimidin-2-yl)methyl]-7-fluoro-5-[1-hydroxy-1-(1-methyl-1H-pyrazol-4-yl)ethyl]-3-oxo-2,3-dihydro-1H-isoindol-1-yl]oxy}methyl)cyclo-propane-1-carboxamide | Prepared in a similar manner to 203 | $^1$H NMR (400 MHz, CDCl$_3$) 8.53 (2H, s), 7.77 (1H, d), 7.48 (1H, dd), 7.40 (1H, s), 7.35-7.24 (5H, m), 6.72 (1H, s), 5.41 (1H, s), 4.53 (2H, d), 3.89 (3H, s), 3.57 (1H, d), 3.45 (1H, d), 2.30 (1H, s), 1.92 (3H, s), 1.38-1.32 (1H, m), 1.25-1.19 (1H, m), 0.62-0.45 (2H, m) | [M + H]+ = 625 |
| 216 | 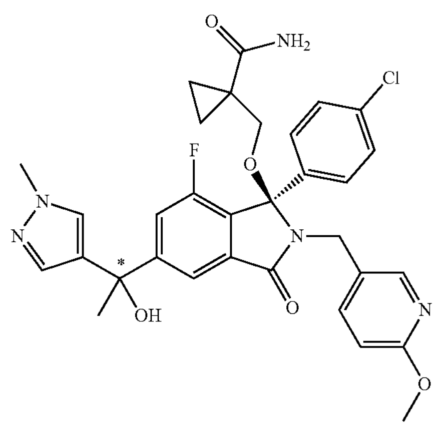 [SMILES: COc1ccc(CN2C(=O)c3cc(C(C)(O)c4cnn(C)c4)cc(F)c3[C@]2(OCC2(C(N)=O)CC2)c2ccc(Cl)cc2)cn1] | 1-({[(1R)-1-(4-chlorophenyl)-7-fluoro-5-[1-hydroxy-1-(1-methyl-1H-pyrazol-4-yl)ethyl]-2-[(6-methoxy-pyridin-3-yl)methyl]-3-oxo-2,3-dihydro-1H-isoindol-1-yl]oxy}methyl)cyclo-propane-1-carboxamide | Prepared in a similar manner to 202 step 2 | $^1$H NMR (400 MHz, CDCl$_3$) 7.79-7.77 (2H, m), 7.48-7.44 (2H, m), 7.39 (1H, s), 7.29 (1H, s), 7.27-7.24 (2H, m), 7.21 (2H, d), 6.57 (1H, d), 6.46 (1H, s), 5.37 (1H, s), 4.41 (1H, d), 4.15 (1H, d), 3.88 (6H, d), 3.40 (1H, d), 2.62 (1H, d), 2.29 (1H, s), 1.92 (3H, s), 1.28-1.12 (2H, m), 0.36-0.20 (2H, m) | [M + H]+ = 620 |
| 217 | 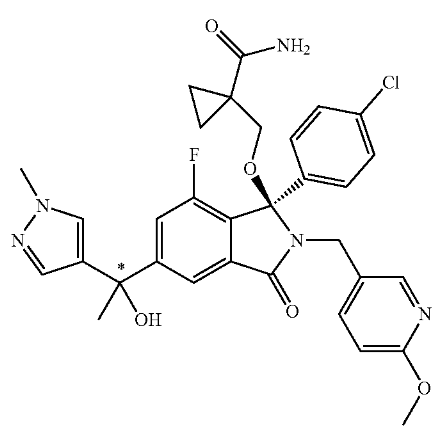 [SMILES: COc1ccc(CN2C(=O)c3cc(C(C)(O)c4cnn(C)c4)cc(F)c3[C@]2(OCC2(C(N)=O)CC2)c2ccc(Cl)cc2)cn1] | 1-({[(1R)-1-(4-chlorophenyl)-7-fluoro-5-[1-hydroxy-1-(1-methyl-1H-pyrazol-4-yl)ethyl]-2-[(6-methoxy-pyridin-3-yl)methyl]-3-oxo-2,3-dihydro-1H-isoindol-1-yl]oxy}methyl)cyclopropane-1-carboxamide | Prepared in a similar manner to 202 step 2 | $^1$H NMR (400 MHz, CDCl$_3$) 7.80-7.77 (2H, m), 7.49-7.43 (2H, m), 7.41 (1H, s), 7.30 (1H, s), 7.28-7.25 (2H, m), 7.21 (2H, d), 6.58 (1H, d), 6.46 (1H, s), 5.36 (1H, s), 4.42 (1H, d), 4.13 (1H, d), 3.88 (6H, d), 3.39 (1H, d), 2.61 (1H, d), 2.26 (1H, s), 1.91 (3H, s), 1.27-1.12 (2H, m), 0.35-0.14 (2H, m) | [M + H]+ = 620 |

TABLE 2-continued

| Example | Structure | Name | Comment | NMR Data | MS Data |
|---|---|---|---|---|---|
| 218 | 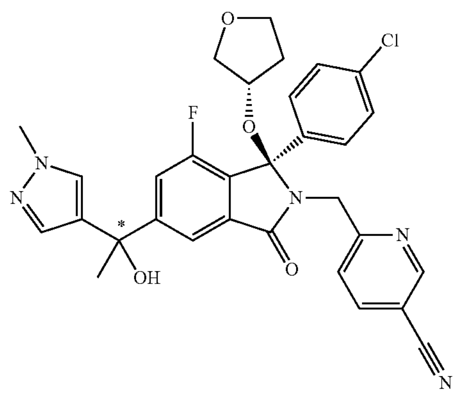 [SMILES: Cn1cc(C(C)(O)c2cc(F)c3c(c2)C(=O)N(Cc2ccc(C#N)cn2)[C@@]3(O[C@H]2CCOC2)c2ccc(Cl)cc2)cn1] | 6-{[(1R)-1-(4-chlorophenyl)-7-fluoro-5-[1-hydroxy-1-(1-methyl-1H-pyrazol-4-yl)ethyl]-3-oxo-1-[(3S)-oxolan-3-yl-oxy]-2,3-dihydro-1H-isoindol-2-yl]methyl}pyridine-3-carbonitrile | Prepared in a similar manner to 202 step 2 | $^1$H NMR (400 MHz, CDCl$_3$) 8.64 (1H, s), 7.80-7.75 (2H, m), 7.46 (1H, d), 7.39 (1H, s), 7.32 (2H, d), 7.24-7.13 (4H, m), 4.67 (1H, d), 4.56 (1H, d), 4.03 (1H, dd), 3.90 (3H, s), 3.73-3.62 (2H, m), 3.35 (1H, dd), 2.28 (1H, s), 1.92 (3H, s), 1.77-1.67 (2H, m), 0.91 (1H, dd) | [M + H]+ = 588 |
| 219 | 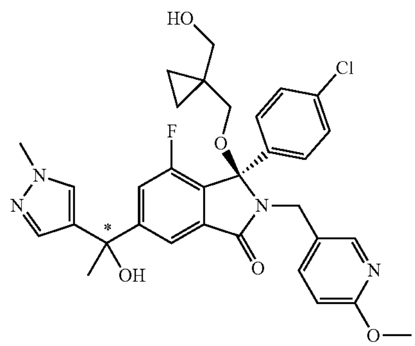 [SMILES: COc1ccc(CN2C(=O)c3cc(C(C)(O)c4cnn(C)c4)cc(F)c3[C@]2(OCC2(CO)CC2)c2ccc(Cl)cc2)cn1] | (3R)-3-(4-chlorophenyl)-4-fluoro-6-[1-hydroxy-1-(1-methyl-1H-pyrazol-4-yl)ethyl]-3-{[1-(hydroxymethyl)cyclopropyl]methoxy}-2-[(6-methoxypyridin-3-yl)methyl]-2,3-dihydro-1H-isoindol-1-one | Prepared in a similar manner to 202 step 2 | $^1$H NMR (400 MHz, CDCl$_3$) 7.85 (1H, d), 7.73 (1H, s), 7.52 (1H, dd), 7.39 (2H, d), 7.27-7.26 (1H, m), 7.23 (4H, s), 6.57 (1H, d), 4.46 (1H, d), 4.18 (1H, d), 3.88 (6H, s), 3.57 (1H, dd), 3.44 (1H, dd), 2.96 (1H, d), 2.78 (1H, d), 2.24 (1H, s), 1.90 (3H, s), 1.66 (1H, dd), 0.48-0.43 (2H, m), 0.30-0.20 (2H, m) | [M + H]+ = 607 |
| 220 | 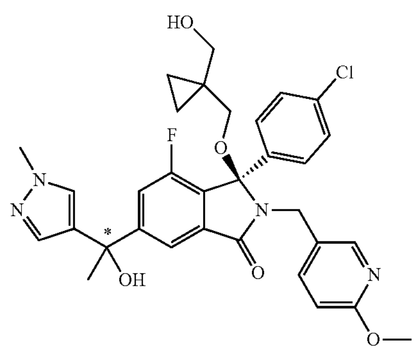 [SMILES: COc1ccc(CN2C(=O)c3cc(C(C)(O)c4cnn(C)c4)cc(F)c3[C@]2(OCC2(CO)CC2)c2ccc(Cl)cc2)cn1] | (3R)-3-(4-chlorophenyl)-4-fluoro-6-[1-hydroxy-1-(1-methyl-1H-pyrazol-4-yl)ethyl]-3-{[1-(hydroxymethyl)cyclopropyl]methoxy}-2-[(6-methoxypyridin-3-yl)methyl]-2,3-dihydro-1H-isoindol-1-one | Prepared in a similar manner to 202 step 2 | $^1$H NMR (400 MHz, CDCl$_3$) 7.86 (1H, s), 7.73 (1H, s), 7.53 (1H, dd), 7.38 (2H, d), 2.28-7.26 (1H, m), 7.23 (4H, m), 6.60-6.56 (1H, s), 4.48 (1H, d), 4.17 (1H, d), 3.88 (6H, s), 3.57 (1H, dd), 3.43 (1H, dd), 2.96 (1H, d), 2.76 (1H, d), 2.24 (1H, s), 1.89 (3H, s), 1.67 (1H, dd), 0.45 (2H, dd), 0.29-0.19 (2H, m) | [M + H]+ = 607 |
| 221 | 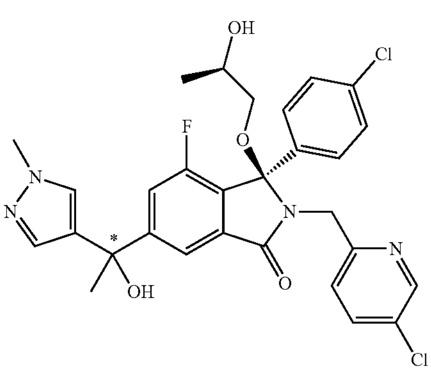 | (3R)-3-(4-chlorophenyl)-2-[(5-chloropyridin-2-yl)methyl]-4-fluoro-6-[1-hydroxy-1-(1-methyl-1H-pyrazol-4-yl)ethyl]-3-[(2R)-2-hydroxypropoxy]-2,3-dihydro-1H-isoindol-1-one | Prepared in a similar manner to 202 step 2 | $^1$H NMR (400 MHz, d$_6$-DMSO) 8.40 (1H, dd), 7.79 (1H, s), 7.75 (1H, dd), 7.67 (1H, s), 7.56 (1H, d), 7.42 (1H, s), 7.33 (4H, s), 7.21 (1H, d), 5.95 (1H, s), 4.76 (1H, d), 4.54 (2H, s), 3.84 (3H, s), 3.67-3.59 (1H, m), 3.07 (1H, dd), 2.71 (1H, dd), 1.85 (3H, s), 1.07 (3H, d) | [M + H]+ = 509 |

TABLE 2-continued

| Example | Structure | Name | Comment | NMR Data | MS Data |
|---|---|---|---|---|---|
| 222 | 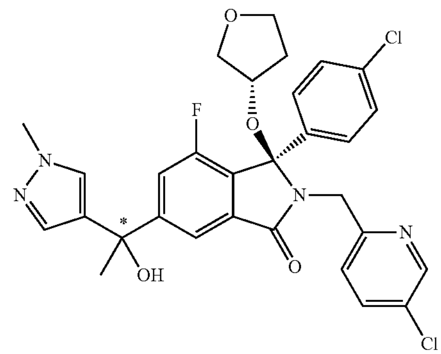 [SMILES: Cn1cc(C(C)(O)c2cc(F)c3c(c2)C(=O)N(Cc2ccc(Cl)cn2)[C@@]3(O[C@H]2CCOC2)c2ccc(Cl)cc2)cn1] | (3R)-3-(4-chlorophenyl)-2-[(5-chloropyridin-2-yl)methyl]-4-fluoro-6-[1-hydroxy-1-(1-methyl-1H-pyrazol-4-yl)ethyl]-3-[(3S)-oxolan-3-yl-oxy]-2,3-dihydro-1H-isoindol-1-one | Prepared in a similar manner to 202 step 2 | $^1$H NMR (400 MHz, CDCl$_3$) 8.32 (1H, d), 7.78 (1H, d), 7.49 (1H, dd), 7.46-7.38 (2H, m), 7.24-7.14 (6H, m), 4.55 (2H, s), 3.99 (1H, dd), 3.90 (3H, s), 3.88-3.82 (1H, m), 3.71-3.60 (2H, m), 3.32 (1H, dd), 2.26 (1H, s), 1.92 (3H, s), 1.69 -1.62 (2H, m) | [M + H]+ = 597 |
| 223 | 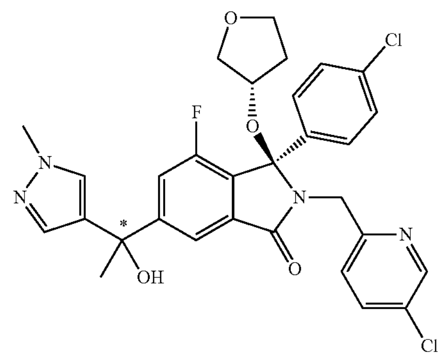 [SMILES: Cn1cc(C(C)(O)c2cc(F)c3c(c2)C(=O)N(Cc2ccc(Cl)cn2)[C@@]3(O[C@H]2CCOC2)c2ccc(Cl)cc2)cn1] | (3R)-3-(4-chlorophenyl)-2-[(5-chloropyridin-2-yl)methyl]-4-fluoro-6-[1-hydroxy-1-(1-methyl-1H-pyrazol-4-yl)ethyl]-3-[(3S)-oxolan-3-yl-oxy]-2,3-dihydro-1H-isoindol-1-one | Prepared in a similar manner to 202 step 2 | $^1$H NMR (400 MHz, CDCl$_3$) 8.33 (1H, d), 7.79 (1H, d), 7.49 (1H, dd), 7.44-7.39 (2H, m), 7.25-7.15 (6H, m), 4.54 (2H, d), 4.01-3.97 (1H, m), 3.89 (3H, s), 3.91-3.81 (1H, m), 3.70-3.60 (2H, m), 3.31 (1H, dd), 2.29 (1H, s), 1.91 (3H, s), 1.64 (2H, q); | [M + H]+ = 597 |
| 224 | 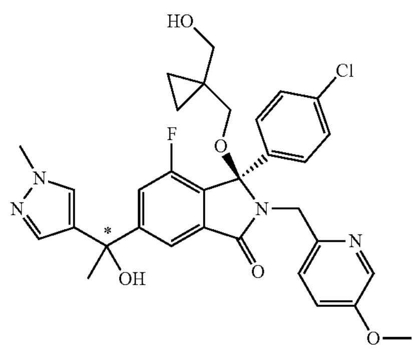 [SMILES: COc1ccc(CN2C(=O)c3cc(C(C)(O)c4cnn(C)c4)cc(F)c3[C@]2(OCC2(CO)CC2)c2ccc(Cl)cc2)nc1] | (3R)-3-(4-chlorophenyl)-4-fluoro-6-[1-hydroxy-1-(1-methyl-1H-pyrazol-4-yl)ethyl]-3-{[1-(hydroxymethyl)cyclopropyl]methoxy}-2-[(5-methoxy-pyridin-2-yl)methyl]-2,3-dihydro-1H-isoindol-1-one | Prepared in a similar manner to 202 step 2 | $^1$H NMR (400 MHz, CDCl$_3$) 8.09 (1H, d), 7.69 (1H, d), 7.37 (3H, d), 7.30 (2H, d), 7.25-7.22 (3H, m), 7.09 (1H, dd), 4.42 (1H, d), 4.31 (1H, d), 3.87 (3H, s), 3.84-3.73 (5H, m), 3.56 (1H, d), 3.32 (1H, dd), 2.69 (1H, d), 2.32 (1H, s), 1.88 (3H, s), 0.54-0.44 (3H, m), 0.30-0.25 (1H, m) | [M + H]+ = 607 |
| 225 | 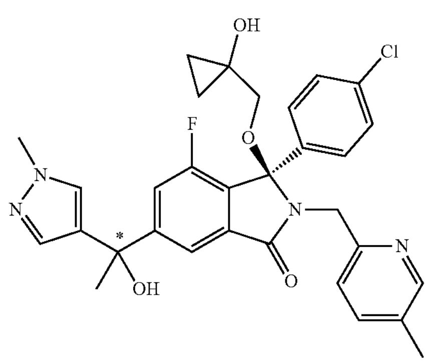 [SMILES: Cc1ccc(CN2C(=O)c3cc(C(C)(O)c4cnn(C)c4)cc(F)c3[C@]2(OCC2(O)CC2)c2ccc(Cl)cc2)nc1] | (3R)-3-(4-chlorophenyl)-4-fluoro-6-[1-hydroxy-1-(1-methyl-1H-pyrazol-4-yl)ethyl]-3-[(1-hydroxycyclopropyl)methoxy]-2-[(5-methyl-pyridin-2-yl)methyl]-2,3-dihydro-1H-isoindol-1-one | Prepared in a similar manner to 203 | $^1$H NMR (400 MHz, CDCl$_3$) 8.25-8.21 (1H, m), 7.67 (1H, s), 7.45-7.34 (6H, m), 7.29-7.26 (3H, m), 5.32 (1H, s), 4.47 (1H, d), 4.36 (1H, d), 3.86 (3H, s), 3.67 (1H, d), 2.92 (1H, d), 2.37 (1H, s), 2.28 (3H, s), 1.89 (3H, s), 0.95-0.73 (2H, m), 0.64-0.57 (1H, m), 0.37-0.30 (1H, m); | [M + H]+ = 577 |

TABLE 2-continued

| Example | Structure | Name | Comment | NMR Data | MS Data |
|---|---|---|---|---|---|
| 226 | 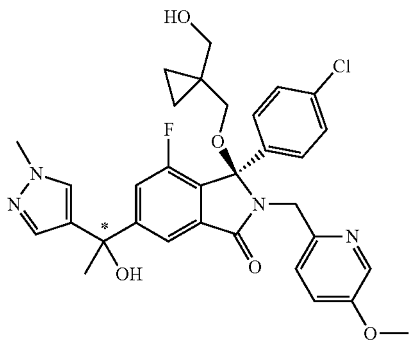 [SMILES: COc1ccc(CN2C(=O)c3cc(C(C)(O)c4cnn(C)c4)cc(F)c3[C@]2(OCC2(CO)CC2)c2ccc(Cl)cc2)nc1] | (3R)-3-(4-chlorophenyl)-4-fluoro-6-[1-hydroxy-1-(1-methyl-1H-pyrazol-4-yl)ethyl]-3-{[1-(hydroxymethyl)cyclopropyl]methoxy}-2-[(5-methoxypyridin-2-yl)methyl]-2,3-dihydro-1H-isoindol-1-one | Prepared in a similar manner to 202 step 2 | ¹H NMR (400 MHz, CDCl₃) 8.10 (1H, dd), 7.67 (1H, d), 7.41-7.35 (3H, m), 7.31 (2H, d), 7.28-7.22 (3H, m), 7.10 (1H, dd), 4.43 (1H, d), 4.29 (1H, d), 3.84 (8H, d), 3.57 (1H, d), 3.31 (1H, dd), 2.68 (1H, d), 2.31 (1H, s), 1.87 (3H, s), 0.55-0.45 (3H, m), 0.30-0.25 (1H, m) | [M + H]+ = 607 |
| 227 | 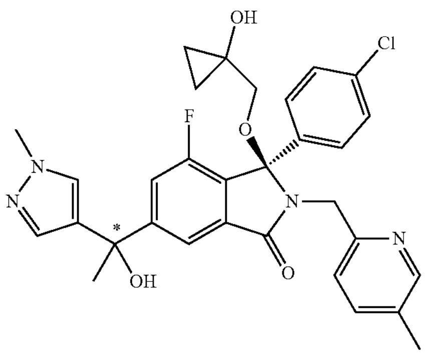 [SMILES: Cc1ccc(CN2C(=O)c3cc(C(C)(O)c4cnn(C)c4)cc(F)c3[C@]2(OCC2(O)CC2)c2ccc(Cl)cc2)nc1] | (3R)-3-(4-chlorophenyl)-4-fluoro-6-[1-hydroxy-1-(1-methyl-1H-pyrazol-4-yl)ethyl]-3-[(1-hydroxycyclopropyl)methoxy]-2-[(5-methylpyridin-2-yl)methyl]-2,3-dihydro-1H-isoindol-1-one | Prepared in a similar manner to 203 | ¹H NMR (400 MHz, CDCl₃) 8.21-8.18 (1H, m), 7.70 (1H, s), 7.43-7.31 (7H, m), 7.26-7.22 (2H, m), 5.30 (1H, s), 4.50-4.36 (2H, m), 3.87 (3H, s), 3.71-3.63 (1H, m), 2.92 (1H, d), 2.51 (1H, s), 2.28 (3H, s), 1.89 (3H, s), 0.94-0.84 (1H, m), 0.81-0.73 (1H, m), 0.65-0.56 (1H, m), 0.38-0.30 (1H, m) | [M + H]+ = 577 |
| 228 | 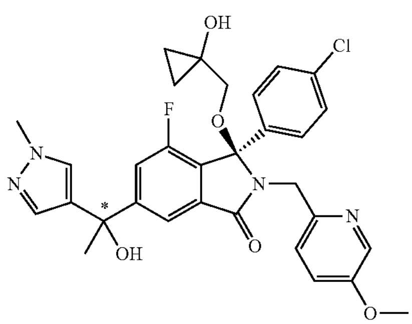 [SMILES: COc1ccc(CN2C(=O)c3cc(C(C)(O)c4cnn(C)c4)cc(F)c3[C@]2(OCC2(O)CC2)c2ccc(Cl)cc2)nc1] | (3R)-3-(4-chlorophenyl)-4-fluoro-6-[1-hydroxy-1-(1-methyl-1H-pyrazol-4-yl)ethyl]-3-[(1-hydroxycyclopropyl)methoxy]-2-[(5-methoxypyridin-2-yl)methyl]-2,3-dihydro-1H-isoindol-1-one | Prepared in a similar manner to 202 step 2 | ¹H NMR (400 MHz, CDCl₃) 8.05 (1H, d), 7.70 (1H, s), 7.38-7.31 (5H, m), 7.26-7.21 (3H, m), 7.09 (1H, dd), 5.01 (1H, s), 4.50-4.38 (2H, m), 3.87 (3H, s), 3.81 (3H, s), 3.61 (1H, d), 2.92 (1H, d), 2.33 (1H, s), 1.88 (3H, s), 0.93-0.75 (2H, m), 0.63-0.55 (1H, m), 0.40-0.32 (1H, m) | [M + H]+ = 593 |
| 229 | 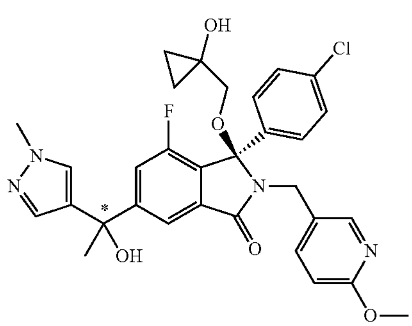 [SMILES: COc1ccc(CN2C(=O)c3cc(C(C)(O)c4cnn(C)c4)cc(F)c3[C@]2(OCC2(O)CC2)c2ccc(Cl)cc2)cn1] | (3R)-3-(4-chlorophenyl)-4-fluoro-6-[1-hydroxy-1-(1-methyl-1H-pyrazol-4-yl)ethyl]-3-[(1-hydroxycyclopropyl)methoxy]-2-[(6-methoxypyridin-3-yl)methyl]-2,3-dihydro-1H-isoindol-1-one | Prepared in a similar manner to 202 step 2 | ¹H NMR (400 MHz, CDCl₃) 7.85 (1H, d), 7.75 (1H, dd), 7.53 (1H, dd), 7.39 (2H, s), 7.29-7.23 (5H, m), 6.60-6.55 (1H, m), 4.53-4.46 (1H, m), 4.20-4.12 (1H, m), 3.88 (6H, dd), 3.49 (1H, s), 3.06 (1H, d), 2.79-2.75 (1H, m), 1.89 (3H, s), 1.47-1.43 (1H, m), 0.80-0.76 (2H, m), 0.34-0.30 (2H, m) | [M + H]+ = 593 |

TABLE 2-continued

| Example | Structure | Name | Comment | NMR Data | MS Data |
|---|---|---|---|---|---|
| 230 | 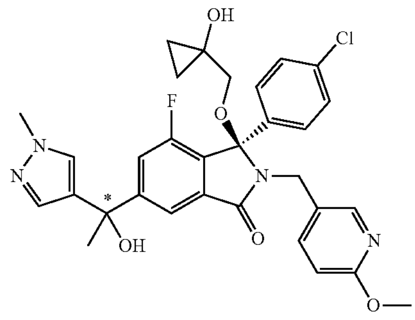 [SMILES: COc1ccc(CN2C(=O)c3cc(C(C)(O)c4cnn(C)c4)cc(F)c3[C@]2(OCC2(O)CC2)c2ccc(Cl)cc2)cn1] | (3R)-3-(4-chlorophenyl)-4-fluoro-6-[1-hydroxy-1-(1-methyl-1H-pyrazol-4-yl)ethyl]-3-[(1-hydroxycyclopropyl)methoxy]-2-[(6-methoxypyridin-3-yl)methyl]-2,3-dihydro-1H-isoindol-1-one | Prepared in a similar manner to 202 step 2 | $^1$H NMR (400 MHz, CDCl$_3$) 7.85 (1H, d), 7.75 (1H, d), 7.52 (1H, dd), 7.42-7.36 (2H, m), 7.29-7.25 (5H, m), 6.57 (1H, d), 4.48 (1H, d), 4.18 (1H, d), 3.90-3.86 (6H, m), 3.06 (1H, d), 2.80 (1H, d), 2.45 (1H, s), 2.26 (1H, s), 1.91 (3H, s), 0.77 (2H, d), 0.35-0.30 (2H, m) | [M + H]+ = 593 |
| 231 | 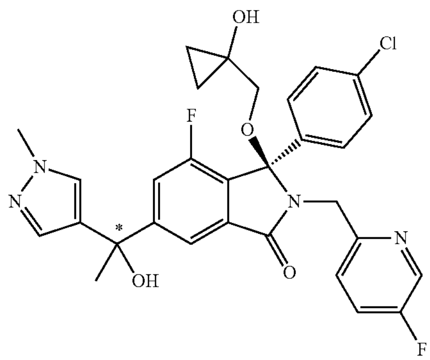 [SMILES: Cn1cc(C(C)(O)c2cc(F)c3c(c2)C(=O)N(Cc2ccc(F)cn2)[C@@]3(OCC2(O)CC2)c2ccc(Cl)cc2)cn1] | (3R)-3-(4-chlorophenyl)-4-fluoro-2-[(5-fluoropyridin-2-yl)methyl]-6-[1-hydroxy-1-(1-methyl-1H-pyrazol-4-yl)ethyl]-3-[(1-hydroxycyclopropyl)methoxy)-2,3-dihydro-1H-isoindol-1-one | Prepared in a similar manner to 202 step 2 | $^1$H NMR (400 MHz, d$_6$-DMSO) 8.33 (1H, d), 7.76 (1H, d), 7.67 (1H, s), 7.58-7.51 (2H, m), 7.41 (1H, s), 7.38-7.30 (4H, m), 7.26 (1H, dd), 5.95 (1H, s), 5.57 (1H, s), 4.54 (2H, s), 3.84 (3H, s), 3.16 (1H, d), 3.01 (1H, d), 1.83 (3H, s), 0.57 (2H, d), 0.39 (1H, dd), 0.28 (1H, dd) | [M + H]+ = 581 |
| 232 | 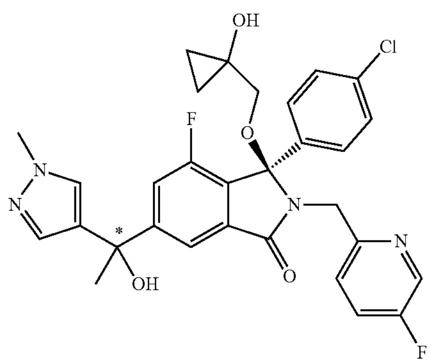 [SMILES: Cn1cc(C(C)(O)c2cc(F)c3c(c2)C(=O)N(Cc2ccc(F)cn2)[C@@]3(OCC2(O)CC2)c2ccc(Cl)cc2)cn1] | (3R)-3-(4-chlorophenyl)-4-fluoro-2-[(5-fluoropyridin-2-yl)methyl]-6-[1-hydroxy-1-(1-methyl-1H-pyrazol-4-yl)ethyl]-3-[(1-hydroxycyclopropyl)methoxy]-2,3-dihydro-1H-isoindol-1-one | Prepared in a similar manner to 202 step 2 | $^1$H NMR (400 MHz, CDCl$_3$) 8.24 (1H, d), 7.71 (1H, d), 7.45-7.37 (3H, m), 7.36-7.28 (3H, m), 7.28-7.22 (3H, m), 4.53 (1H, d), 4.42 (1H, d), 4.03 (1H, s), 3.87 (3H, s), 3.47 (1H, d), 2.99 (1H, d), 2.26 (1H, s), 1.88 (3H, s), 0.90-0.75 (2H, m), 0.58-0.51 (1H, m), 0.40-0.33 (1H, m) | [M + H]+ = 581 |

Example 233 and 234: (3R)-3-(4-chlorophenyl)-2-[(5-chloropyridin-2-yl)methyl]-6-[2-hydroxy-1-(pyridin-3-yloxy)propan-2-yl]-3-methoxy-2,3-dihydro-1H-isoindol-1-one (*both isomers separated and isolated)

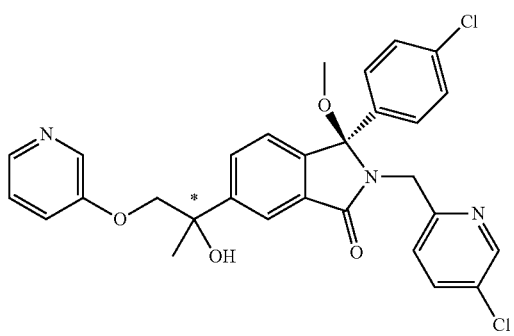 [SMILES: CO[C@]1(c2ccc(Cl)cc2)c2ccc(C(C)(O)COc3cccnc3)cc2C(=O)N1Cc1ccc(Cl)cn1]

To a stirred solution of 3-hydroxypyridine (313 mg, 3.29 mmol) in DMF (4 mL) was added sodium hydride (60% in mineral oil, 40 mg, 0.99 mmol) under N$_2$, stirred at RT for 1 h, then heated to 60° C. for 20 minutes before addition of (3R)-3-(4-chlorophenyl)-2-((5-chloropyridin-2-yl)methyl)-3-methoxy-6-(2-methyloxiran-2-yl)isoindolin-1-one (Example 99, Example 100, step 1) (150 mg, 0.33 mmol). The reaction was stirred at 60° C. for a further 5 days then partitioned between H$_2$O (50 mL) and EtOAc (50 mL). The layers were shaken and separated, the aqueous re-extracted with EtOAc (50 mL), the combined organic extracts dried (MgSO$_4$), filtered and concentrated in vacuo. Purified by HPLC and separated by chiral SFC, the title compound was isolated as two isomers (faster eluting isomer, 26.5 mg, 15% yield and slower eluting isomer, 22.4 mg, 12% yield).

Example 233 *Faster Eluting Isomer $^1$H NMR (400 MHz, CDCl$_3$); 8.34 (1H, d), 8.29 (1H, d), 8.25 (1H, dd), 8.05 (1H, d), 7.79 (1H, dd), 7.48 (1H, dd), 7.25-7.16 (8H, m), 4.61 (1H, d), 4.47 (1H, d), 4.21-4.11 (2H, m), 2.85 (1H, s), 2.82 (3H, s), 1.73 (3H, s). MS: [M+H]$^+$= 550.

Example 234 *Slower Eluting Isomer

¹H NMR (400 MHz, CDCl₃); 8.34 (1H, d), 8.29 (1H, d), 8.25 (1H, dd), 8.05 (1H, d), 7.79 (1H, dd), 7.48 (1H, dd), 7.25-7.16 (8H, m), 4.61 (1H, d), 4.48 (1H, d), 4.20-4.10 (2H, m), 2.91 (1H, s), 2.82 (3H, s), 1.73 (3H, s). MS: [M+H]⁺ =550.

Starting from of (3R)-3-(4-chlorophenyl)-2-((5-chloropyridin-2-yl)methyl)-3-methoxy-6-(2-methyloxiran-2-yl) isoindolin-1-one (Example 99, Example 100, step 1), and the appropriate amine or alcohol, the following Examples were prepared using procedures similar to those described in Example 104 or Example 233. Purification by preparative achiral and/or chiral HPLC gave final compounds as single isomer (unless stated otherwise). In the table below, an asterisk indicates the compound was isolated as a single isomer at the position shown.

| Example | Structure | Name | Comment | NMR Data | MS Data |
|---|---|---|---|---|---|
| 237 | 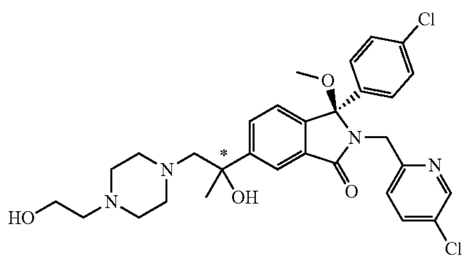 [SMILES: CO[C@]1(c2ccc(Cl)cc2)c2ccc(C(C)(O)CN3CCN(CCO)CC3)cc2C(=O)N1Cc1ccc(Cl)cn1] | (3R)-3-(4-chlorophenyl)-2-[(5-chloropyridin-2-yl)methyl]-6-{2-hydroxy-1-[4-(2-hydroxyethyl)piperazin-1-yl]propan-2-yl}-3-methoxy-2,3-dihydro-1H-isoindol-1-one | Prepared in a similar manner to Example 104 | ¹H NMR (400 MHz, CDCl3) 8.34 (1H, d), 7.99 (1H, d), 7.69 (1H, dd), 7.48 (1H, dd), 7.24-7.20 (2H, m), 7.19-7.14 (3H, m), 7.10 (1H, d), 4.59 (1H, d), 4.47 (1H, d), 3.59-3.54 (2H, m), 2.83 (1H, d), 2.79 (3H, s), 2.69 (1H, d), 2.52-2.41 (9H, m), 2.33-2.33 (3H, m), 1.50 (3H, s) | [M + H]+ = 585 |
| 238 | 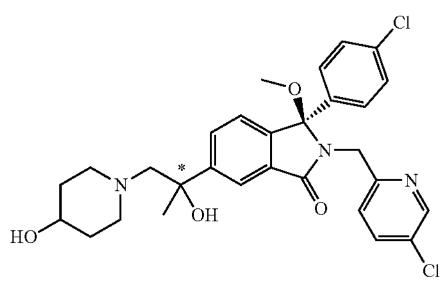 [SMILES: CO[C@]1(c2ccc(Cl)cc2)c2ccc(C(C)(O)CN3CCC(O)CC3)cc2C(=O)N1Cc1ccc(Cl)cn1] | (3R)-3-(4-chlorophenyl)-2-[(5-chloropyridin-2-yl)methyl]-6-[2-hydroxy-1-(4-hydroxypiperidin-1-yl)propan-2-yl]-3-methoxy-2,3-dihydro-1H-isoindol-1-one | Prepared in a similar manner to Example 104 | ¹H NMR (400 MHz, CDCl3) 8.34 (1H, d), 7.95 (1H, d), 7.73 (1H, dd), 7.48 (1H, dd), 7.22 (2H, d), 7.19-7.14 (3H, m), 7.10 (1H, d), 4.60 (1H, d), 4.46 (1H, d), 3.63-3.63 (1H, m), 2.81 (1H, d), 2.78 (3H, s), 2.67 (2H, d), 2.27-2.25 (2H, m), 2.21-2.18 (1H, m), 1.68-1.67 (3H, m), 1.50 (4H, s), 1.47-1.41 (2H, m) | [M + H]+ = 556 |
| 239 | 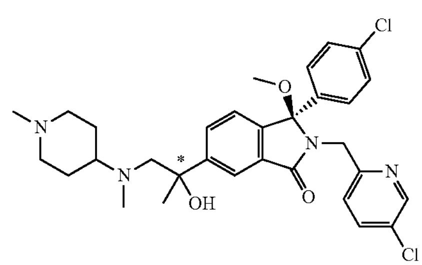 [SMILES: CO[C@]1(c2ccc(Cl)cc2)c2ccc(C(C)(O)CN(C)C3CCN(C)CC3)cc2C(=O)N1Cc1ccc(Cl)cn1] | (3R)-3-(4-chlorophenyl)-2-[(5-chloropyridin-2-yl)methyl]-6-{2-hydroxy-1-[methyl(1-methylpiperidin-4-yl)amino]propan-2-yl}-3-methoxy-2,3-dihydro-1H-isoindol-1-one | Prepared in a similar manner to Example 104 | ¹H NMR (400 MHz, DMSO) 8.40 (1H, d), 7.93 (1H, d), 7.77-7.70 (2H, m), 7.31-7.21 (5H, m), 7.15 (1H, d), 5.01 (1H, s), 4.54 (1H, d), 4.35 (1H, d), 2.76 (3H, s), 2.68-2.53 (4H, m), 2.12 (3H,s), 2.05 (3H, s), 1.96-1.88 (1H, m), 1.58 (2H, dd), 1.48 (3H, s), 1.35-1.22 (4H, m); | [M + H]+ = 583 |
| 240 | 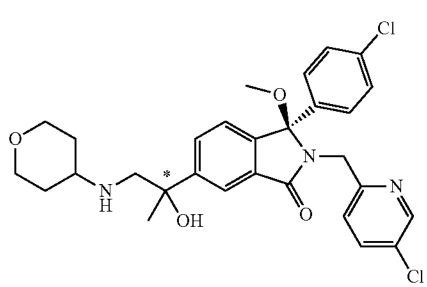 [SMILES: CO[C@]1(c2ccc(Cl)cc2)c2ccc(C(C)(O)CNC3CCOCC3)cc2C(=O)N1Cc1ccc(Cl)cn1] | (3R)-3-(4-chlorophenyl)-2-[(5-chloropyridin-2-yl)methyl]-6-{2-hydroxy-1-[(oxan-4-yl)amino]propan-2-yl}-3-methoxy-2,3-dihydro-1H-isoindol-1-one | Prepared in a similar manner to Example 104 | ¹H NMR (400 MHz, CDCl3) 8.35 (1H, d), 7.93 (1H, d), 7.74 (1H, dd), 7.48 (1H, dd), 7.25-7.21 (3H, m), 7.19-7.11 (3H, m), 4.61 (1H, d), 4.47 (1H, d), 4.31 (1H, s), 3.97-3.89 (2H, m), 3.37-3.27 (2H, m), 3.09 (1H, d), 2.81 (3H, s), 2.80 (1H, d), 2.62-2.53 (1H, m), 1.85-1.71 (2H, m), 1.50 (3H, s), 1.37-1.24 (3H, m) | [M + H]+ = 556 |

| Example | Structure | Name | Comment | NMR Data | MS Data |
|---|---|---|---|---|---|
| 241 | 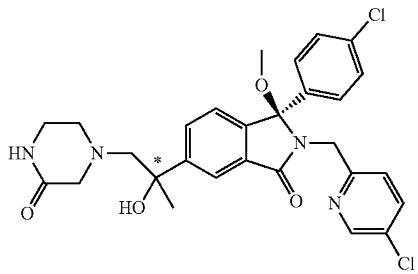 [SMILES: CO[C@]1(c2ccc(Cl)cc2)c2ccc(C(C)(O)CN3CCNC(=O)C3)cc2C(=O)N1Cc1ccc(Cl)cn1] | (3R)-3-(4-chlorophenyl)-2-[(5-chloropyridin-2-yl)methyl]-6-[2-hydroxy-1-(3-oxo-piperazin-1-yl)propan-2-yl]-3-methoxy-2,3-dihydro-1H-isoindol-1-one | Prepared in a similar manner to Example 104 | $^1$H NMR (400 MHz, CDCl3) 8.34 (1H, d), 7.99 (1H, d), 7.70 (1H, dd), 7.48 (1H, dd), 7.24-7.12 (6H, m), 5.81 (1H, s), 4.59 (1H, d), 4.48 (1H, d), 3.74 (1H, s), 3.29-3.23 (2H, m), 3.11 (1H, d), 2.98 (1H, d), 2.92 (1H, d), 2.81-2.76 (4H, m), 2.73-2.66 (1H, m), 2.63-2.58 (1H, m), 1.55 (3H, s) | [M + H]+ = 555 |
| 242 | 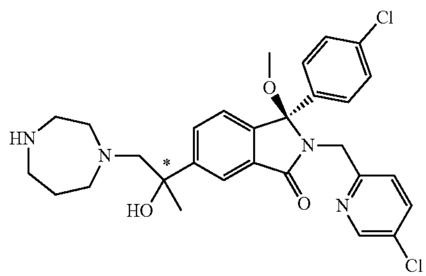 [SMILES: CO[C@]1(c2ccc(Cl)cc2)c2ccc(C(C)(O)CN3CCCNCC3)cc2C(=O)N1Cc1ccc(Cl)cn1] | (3R)-3-(4-chlorophenyl)-2-[(5-chloropyridin-2-yl)methyl]-6-[1-(1,4-diazepan-1-yl)-2-hydroxy-propan-2-yl]-3-methoxy-2,3-dihydro-1H-isoindol-1-one | Prepared in a similar manner to Example 104 | 1H NMR (400 MHz, CDCl3) 8.34 (1H, d), 7.95 (1H, d), 7.75 (1H, dd), 7.47 (1H, dd), 7.23-7.14 (5H, m), 7.10 (1H, d), 4.59 (1H, d), 4.47 (1H, d), 3.05 (1H, d), 2.89-2.85 (1H, m), 2.82-2.77 (4H, m), 2.74-2.54 (8H, m), 1.61-1.52 (2H, m), 1.51 (3H, s); OH not observed | [M + H]+ = 555 |
| 243 | 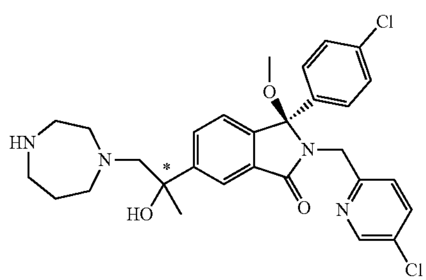 [SMILES: CO[C@]1(c2ccc(Cl)cc2)c2ccc(C(C)(O)CN3CCCNCC3)cc2C(=O)N1Cc1ccc(Cl)cn1] | (3R)-3-(4-chlorophenyl)-2-[(5-chloropyridin-2-yl)methyl]-6-[1-(1,4-diazepan-1-yl)-2-hydroxy-propan-2-yl]-3-methoxy-2,3-dihydro-1H-isoindol-1-one | Prepared in a similar manner to Example 104 | $^1$H NMR (400 MHz, CDCl3) 8.34 (1H, d), 7.98 (1H, d), 7.72 (1H, dd), 7.47 (1H, dd), 7.23 (1H, d), 7.20-7.14 (4H, m), 7.10 (1H, d), 4.59 (1H, d), 4.47 (1H, d), 3.04 (1H, d), 2.89-2.85 (1H, m), 2.82-2.78 (4H, m), 2.74-2.54 (8H, m), 1.56 (2H, dd), 1.51 (3H, s); OH not observed | [M + H]+ = 555 |
| 244 | 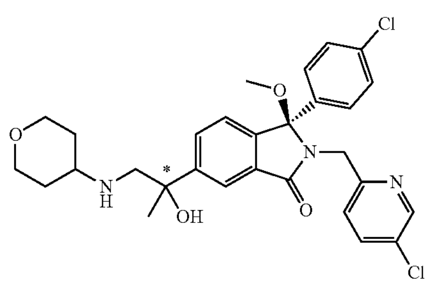 [SMILES: CO[C@]1(c2ccc(Cl)cc2)c2ccc(C(C)(O)CNC3CCOCC3)cc2C(=O)N1Cc1ccc(Cl)cn1] | (3R)-3-(4-chlorophenyl)-2-[(5-chloropyridin-2-yl)methyl]-6-{2-hydroxy-1-[(oxan-4-yl)amino]propan-2-yl}-3-methoxy-2,3-dihydro-1H-isoindol-1-one | Prepared in a similar manner to Example 104 | $^1$H NMR (400 MHz, CDCl3) 8.35 (1H, d), 7.95 (1H, d), 7.72 (1H, dd), 7.48 (1H, dd), 7.25-7.20 (3H, m), 7.19-7.11 (3H, m), 4.61 (1H, d), 4.47 (1H, d), 3.97-3.90 (2H, m), 3.37-3.28 (2H, m), 3.10 (1H, d), 2.82-2.79 (5H, m), 2.62-2.54 (1H, m), 1.85-1.72 (2H, m), 1.51 (3H, s), 1.37-1.24 (3H, m) | [M + H]+ = 556 |
| 245 | 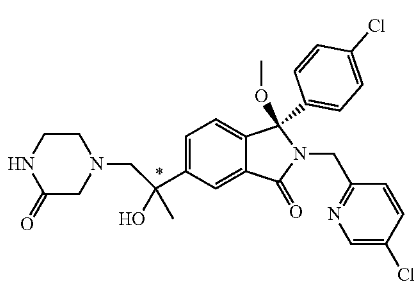 [SMILES: CO[C@]1(c2ccc(Cl)cc2)c2ccc(C(C)(O)CN3CCNC(=O)C3)cc2C(=O)N1Cc1ccc(Cl)cn1] | (3R)-3-(4-chlorophenyl)-2-[(5-chloropyridin-2-yl)methyl]-6-[2-hydroxy-1-(3-oxo-piperazin-1-yl)propan-2-yl]-3-methoxy-2,3-dihydro-1H-isoindol-1-one | Prepared in a similar manner to Example 104 | '$^1$H NMR (400 MHz, CDCl3) 8.34 (1H, d), 7.97 (1H, d), 7.72 (1H, dd), 7.48 (1H, dd), 7.24-7.12 (6H, m), 5.75 (1H, s), 4.60 (1H, d), 4.47 (1H, d), 3.74 (1H, s), 3.32-3.22 (2H, m), 3.08 (1H, d), 2.98-2.89 (2H, m), 2.79 (4H, d), 2.74-2.67 (1H, m), 2.64-2.56 (1H, m), 1.55 (3H, s) | [M + H]+ = 555 |

-continued

| Example | Structure | Name | Comment | NMR Data | MS Data |
|---|---|---|---|---|---|
| 246 | 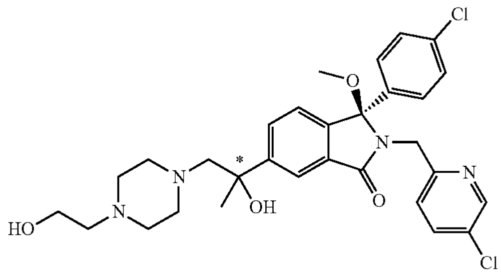 [SMILES: CO[C@]1(c2ccc(Cl)cc2)c2ccc(C(C)(O)CN3CCN(CCO)CC3)cc2C(=O)N1Cc1ccc(Cl)cn1] | (3R)-3-(4-chlorophenyl)-2-[(5-chloro-pyridin-2-yl)methyl]-6-{2-hydroxy-1-[4-(2-hydroxyethyl)piperazin-1-yl]propan-2-yl}-3-methoxy-2,3-dihydro-1H-isoindol-1-one | Prepared in a similar manner to Example 104 | $^1$H NMR (400 MHz, CDCl3) 8.35 (1H, d), 7.97 (1H, d), 7.72 (1H, dd), 7.48 (1H, dd), 7.24-7.15 (5H, m), 7.10 (1H, d), 4.60 (1H, d), 4.46 (1H, d), 3.60-3.55 (2H, m), 2.84 (1H, d), 2.78 (3H, s), 2.69 (1H, d), 2.53-2.41 (12H, m), 1.51 (3H, s) | [M + H]+ = 585 |
| 247 | 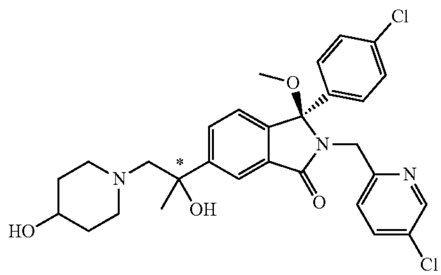 [SMILES: CO[C@]1(c2ccc(Cl)cc2)c2ccc(C(C)(O)CN3CCC(O)CC3)cc2C(=O)N1Cc1ccc(Cl)cn1] | (3R)-3-(4-chlorophenyl)-2-[(5-chloro-pyridin-2-yl)methyl]-6-[2-hydroxy-1-(4-hydroxy-piperidin-1-yl)propan-2-yl]-3-methoxy-2,3-dihydro-1H-isoindol-1-one | Prepared in a similar manner to Example 104 | $^1$H NMR (400 MHz, CDCl3) 8.34 (1H, d), 7.97 (1H, d), 7.71 (1H, dd), 7.48 (1H, dd), 7.24-7.14 (5H, m), 7.10 (1H, d), 4.59 (1H, d), 4.47 (1H, d), 3.65 (1H, s), 2.79 (4H, s), 2.71-2.64 (2H, m), 2.41-2.37 (1H, m), 2.31-2.20 (2H, m), 1.68-1.68 (3H, m), 1.50 (4H, s), 1.44-1.41 (2H, m) | [M + H]+ = 556 |
| 248 | 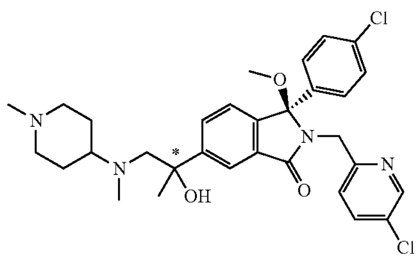 [SMILES: CO[C@]1(c2ccc(Cl)cc2)c2ccc(C(C)(O)CN(C)C3CCN(C)CC3)cc2C(=O)N1Cc1ccc(Cl)cn1] | (3R)-3-(4-chlorophenyl)-2-[(5-chloro-pyridin-2-yl)methyl]-6-{2-hydroxy-1-[methyl(1-methyl-piperidin-4-yl)amino]propan-2-yl}-3-methoxy-2,3-dihydro-1H-isoindol-1-one | Prepared in a similar manner to Example 104 | $^1$H NMR (400 MHz, DMSO) 8.39 (1H, d), 7.91 (1H, s), 7.75 (2H, dd), 7.30-7.20 (5H, m), 7.16 (1H, d), 5.01 (1H, s), 4.51 (1H, d), 4.39 (1H, d), 2.77 (3H, s), 2.69-2.53 (4H, m), 2.12 (3H, s), 2.06 (3H, s), 1.96-1.91 (1H, m), 1.66-1.65 (2H, m), 1.50 (3H, s), 1.34-1.22 (4H, m) | [M + H]+ = 583 |
| 249 | 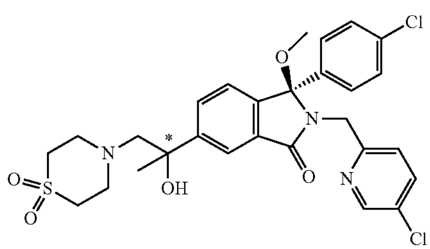 [SMILES: CO[C@]1(c2ccc(Cl)cc2)c2ccc(C(C)(O)CN3CCS(=O)(=O)CC3)cc2C(=O)N1Cc1ccc(Cl)cn1] | 4-{2-[(1R)-1-(4-chloro-phenyl)-2-[(5-chloro-pyridin-2-yl)methyl]-1-methoxy-3-oxo-2,3-dihydro-1H-isoindol-5-yl]-2-hydroxy-propyl}-1λ6-thiomorpho-line-1,1-dione | Prepared in a similar manner to Example 104 | $^1$H NMR (400 MHz, CDCl3) 8.35 (1H, d), 7.97 (1H, d), 7.67 (1H, dd), 7.49 (1H, dd), 7.23 (1H, d), 7.21-7.16 (4H, m), 7.14 (1H, d), 4.61 (1H, d), 4.46 (1H, d), 3.31 (1H, s), 3.05-2.91 (9H, m), 2.79 (4H, s), 1.57 (3H, s) | [M + H]+ = 590 |
| 250 | 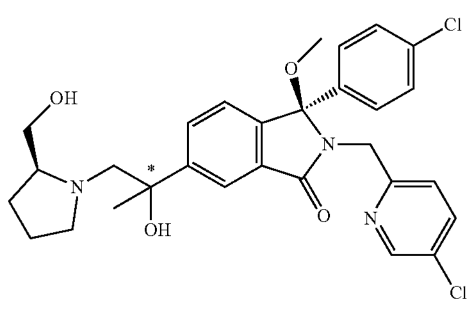 [SMILES: CO[C@]1(c2ccc(Cl)cc2)c2ccc(C(C)(O)CN3CCC[C@H]3CO)cc2C(=O)N1Cc1ccc(Cl)cn1] | (3R)-3-(4-chlorophenyl)-2-[(5-chloro-pyridin-2-yl)methyl]-6-{2-hydroxy-1-[(2S)-2-(hydroxy-methyl)pyrrolidin-1-yl]propan-2-yl}-3-methoxy-2,3-dihydro-1H-isoindol-1-one | Prepared in a similar manner to Example 104 | $^1$H NMR (400 MHz, CDCl3) 8.34 (1H, d), 7.97 (1H, d), 7.72 (1H, dd), 7.47 (1H, dd), 7.24-7.11 (6H, m), 4.60 (1H, d), 4.46 (1H, d), 3.45-3.29 (3H, m), 2.96 (1H, d), 2.84 (1H, d), 2.81 (3H, s), 2.77-2.70 (1H, m), 2.63-2.55 (1H, m), 1.88-1.73 (3H, m), 1.59-1.54 (6H, m) | [M + H]+ = 556 |

-continued

| Example | Name | Comment | NMR Data | MS Data |
|---|---|---|---|---|
| 251 | (3R)-3-(4-chlorophenyl)-2-[(5-chloropyridin-2-yl)methyl]-6-{2-hydroxy-1-[(2S)-2-(hydroxymethyl)pyrrolidin-1-yl]propan-2-yl}-3-methoxy-2,3-dihydro-1H-isoindol-1-one | Prepared in a similar manner to Example 104 | $^1$H NMR (400 MHz, CDCl3) 8.34 (1H, d), 7.98 (1H, d), 7.75 (1H, dd), 7.47 (1H, dd), 7.24-7.14 (6H, m), 4.60 (1H, d), 4.47 (1H, d), 3.61 (1H, dd), 3.50 (1H, dd), 3.05 (2H, dd), 2.79 (5H, s), 2.26-2.19 (1H, m), 1.97-1.89 (1H, m), 1.82-1.67 (1H, m), 1.57-1.51 (7H, m) | [M + H]+ = 556 |
| 252 | 4-{2-[(1R)-1-(4-chlorophenyl)-2-[(5-chloropyridin-2-yl)methyl]-1-methoxy-3-oxo-2,3-dihydro-1H-isoindol-5-yl]-2-hydroxypropyl}-1λ6-thiomorpholine-1,1-dione | Prepared in a similar manner to Example 104 | $^1$H NMR (400 MHz, CDCl3) 8.35 (1H, d), 7.95 (1H, d), 7.69 (1H, dd), 7.49 (1H, dd), 7.23 (1H, d), 7.19-7.17 (4H, m), 7.14 (1H, d), 4.61 (1H, d), 4.46 (1H, d), 3.28 (1H, s), 3.05-2.91 (9H, m), 2.79 (4H, s), 1.57 (3H, s) | [M + H]+ = 590 |
| 253 | (3R)-6-{1-[(1-acetyl-piperidin-4-yl)(methyl)amino]-2-hydroxypropan-2-yl}-3-(4-chlorophenyl)-2-[(5-chloropyridin-2-yl)methyl]-3-methoxy-2,3-dihydro-1H-isoindol-1-one | Prepared in a similar manner to Example 104 | $^1$H NMR (400 MHz, CDCl3) 8.34 (1H, d), 7.96 (1H, d), 7.75-7.69 (1H, m), 7.47 (1H, dd), 7.24-7.09 (6H, m), 4.69 (1H, d), 4.60 (1H, d), 4.47 (1H, d), 3.87-3.80 (1H, m), 2.85 (2H, dd), 2.79 (3H, s), 2.74 (1H, dd), 2.51-2.30 (2H, m), 2.08 (3H, d), 1.98 (3H, d), 1.76-1.64 (2H, m), 1.51 (3H, s), 1.46-1.29 (2H, m) | [M + H]+ = 611 |
| 253a | (3R)-6-{1-[(1-acetylpiperidin-4-yl)(methyl)amino]-2-hydroxypropan-2-yl}-3-(4-chlorophenyl)-2-[(5-chloropyridin-2-yl)methyl]-3-methoxy-2,3-dihydro-1H-isoindol-1-one | Prepared in a similar manner to Example 104 | $^1$H NMR (400 MHz, CDCl3) 8.35 (1H, d), 7.97 (1H, d), 7.70 (1H, ddd), 7.52-7.46 (1H, m), 7.26-7.10 (6H, m), 4.70-4.58 (2H, m), 4.48-4.43 (2H, m), 3.86-3.77 (1H, m), 2.96-2.70 (6H, m), 2.51-2.24 (2H, m), 2.07 (3H, d), 1.99 (3H, d), 1.78-1.62 (2H, m), 1.51 (3H, d), 1.44-1.28 (2H, m), (rotamers observed), | [M + H]+ = 611 |
| 254 | (3R)-6-[1-(4-aminopiperidin-1-yl)-2-hydroxypropan-2-yl]-3-(4-chlorophenyl)-2-[(5-chloropyridin-2-yl)methyl]-3-methoxy-2,3-dihydro-1H-isoindol-1-one | Prepared in a similar manner to Example 104 | $^1$H NMR (400 MHz, DMSO) 8.39 (1H, d), 7.92 (1H, s), 7.77-7.72 (2H, m), 7.28 (2H, d), 7.25-7.19 (3H, m), 7.16 (1H, d), 5.05 (1H, s), 4.52-4.38 (2H, m), 2.77 (3H, s), 2.56 (2H, d), 2.49-2.36 (4H, m), 2.02 (2H, dd), 1.50 (3H, s), 1.47-1.43 (3H, m), 1.16-1.05 (2H, m); | [M + H]+ = 555 |

-continued

| Example | Structure | Name | Comment | NMR Data | MS Data |
|---|---|---|---|---|---|
| 255 | 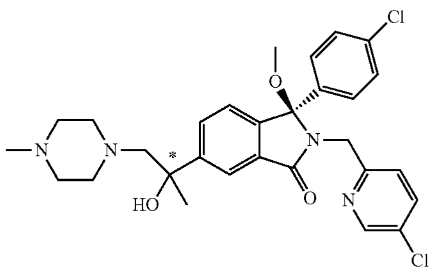 [SMILES: CO[C@]1(c2ccc(Cl)cc2)c2ccc(C(C)(O)CN3CCN(C)CC3)cc2C(=O)N1Cc1ccc(Cl)cn1] | (3R)-3-(4-chlorophenyl)-2-[(5-chloro-pyridin-2-yl)methyl]-6-[2-hydroxy-1-(4-methyl-piperazin-1-yl)propan-2-yl]-3-methoxy-2,3-dihydro-1H-isoindol-1-one | Prepared in a similar manner to Example 104 | $^1$H NMR (400 MHz, CDCl3) 8.34 (1H, d), 7.99 (1H, d), 7.69 (1H, dd), 7.48 (1H, dd), 7.25-7.14 (5H, m), 7.10 (1H, d), 4.59 (1H, d), 4.47 (1H, d), 2.83 (1H, d), 2.79 (3H, s), 2.68 (1H, d), 2.47-2.29 (8H, m), 2.22 (3H, s), 1.50 (3H, s); OH not observed | [M + H]+ = 555 |
| 256 | 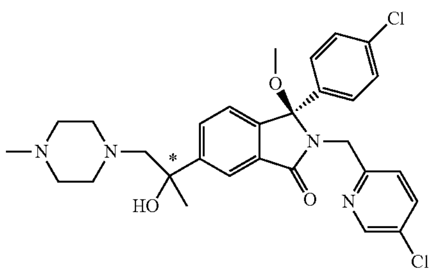 [SMILES: CO[C@]1(c2ccc(Cl)cc2)c2ccc(C(C)(O)CN3CCN(C)CC3)cc2C(=O)N1Cc1ccc(Cl)cn1] | (3R)-3-(4-chlorophenyl)-2-[(5-chloro-pyridin-2-yl)methyl]-6-[2-hydroxy-1-(4-methyl-piperazin-1-yl)propan-2-yl]-3-methoxy-2,3-dihydro-1H-isoindol-1-one | Prepared in a similar manner to Example 104 | $^1$H NMR (400 MHz, CDCl3) 8.34 (1H, d), 7.97 (1H, d), 7.72 (1H, dd), 7.48 (1H, dd), 7.24-7.14 (5H, m), 7.10 (1H, d), 4.60 (1H, d), 4.46 (1H, d), 2.83 (1H, d), 2.78 (3H, s), 2.68 (1H, d), 2.47-2.27 (8H, m), 2.23 (3H, s), 1.50 (3H, s); OH not observed | [M + H]+ = 555 |
| 257 | 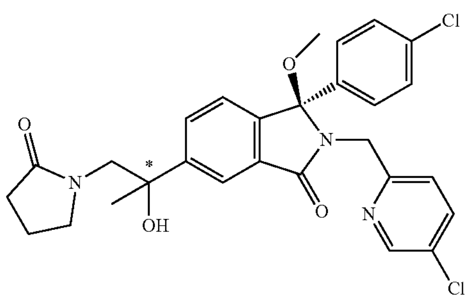 [SMILES: CO[C@]1(c2ccc(Cl)cc2)c2ccc(C(C)(O)CN3CCCC3=O)cc2C(=O)N1Cc1ccc(Cl)cn1] | (3R)-3-(4-chlorophenyl)-2-[(5-chloro-pyridin-2-yl)methyl]-6-[2-hydroxy-1-(2-oxo-pyrrolidin-1-yl)propan-2-yl]-3-methoxy-2,3-dihydro-1H-isoindol-1-one | Prepared in a similar manner to Example 233 | $^1$H NMR (400 MHz, CDCl3) 8.35 (1H, d), 7.98 (1H, d), 7.82 (1H, dd), 7.48 (1H, dd), 7.24 (1H, d), 7.20 (2H, d), 7.17 (2H, d), 7.14 (1H, d), 5.21 (1H, s), 4.61 (1H, d), 4.45 (1H, d), 3.71 (1H, d), 3 46-3.31 (2H, m), 2.96-2.89 (1H, m), 2.80 (3H, s), 2.37-2.30 (2H, m), 1.99-1.92 (1H, m), 1.81-1.70 (1H, m), 1.55 (3H, s) | [M + H]+ = 540 |
| 258 | 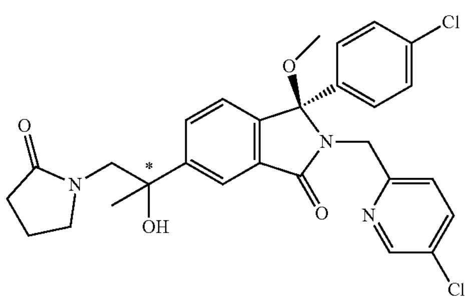 [SMILES: CO[C@]1(c2ccc(Cl)cc2)c2ccc(C(C)(O)CN3CCCC3=O)cc2C(=O)N1Cc1ccc(Cl)cn1] | (3R)-3-(4-chlorophenyl)-2-[(5-chloro-pyridin-2-yl)methyl]-6-[2-hydroxy-1-(2-oxopyrrolidin-1-yl)propan-2-yl]-3-methoxy-2,3-dihydro-1H-isoindol-1-one | Prepared in a similar manner to Example 233 | $^1$H NMR (400 MHz, CDCl3) 8.34 (1H, d), 7.97 (1H, d), 7.83 (1H, dd), 7.48 (1H, dd), 7.23-7.13 (6H, m), 5.23 (1H, s), 4.60 (1H, d), 4.48 (1H, d), 3.74 (1H, d), 3.46-3.30 (2H, m), 2.97-2.90 (1H, m), 2.80 (3H, s), 2.39-2.32 (2H, m), 2.02-1.90 (1H, m), 1.84-1.72 (1H, m), 1.62 (3H, s) | [M + H]+ = 540 |
| 259 | 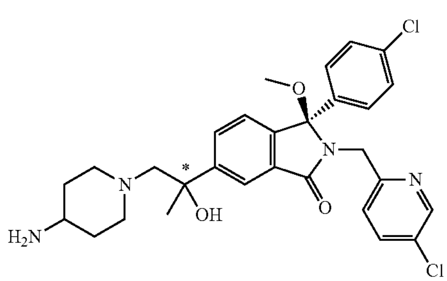 [SMILES: CO[C@]1(c2ccc(Cl)cc2)c2ccc(C(C)(O)CN3CCC(N)CC3)cc2C(=O)N1Cc1ccc(Cl)cn1] | (3R)-6-[1-(4-amino-piperidin-1-yl)-2-hydroxy-propan-2-yl)-3-(4-chloro-phenyl)-2-[(5-chloro-pyridin-2-yl)methyl]-3-methoxy-2,3-dihydro-1H-isoindol-1-one | Prepared in a similar manner to Example 104 | $^1$H NMR (400 MHz, DMSO) 8.40 (1H, d), 7.95 (1H, d), 7.77-7.71 (2H, m), 7.30 (2H, d), 7.27-7.20 (3H, m), 7.15 (1H, d), 5.06 (1H, s), 4.53 (1H, d), 4.35 (1H, d), 2.75 (3H, s), 2.58 (2H, d), 2.45-2.33 (4H, m), 2.05-1.99 (2H, m), 1.52-1.44 (6H, m), 1.12-1.05 (2H, m); | [M + H]+ = 555 |

-continued

| Example | Structure | Name | Comment | NMR Data | MS Data |
|---|---|---|---|---|---|
| 260 | 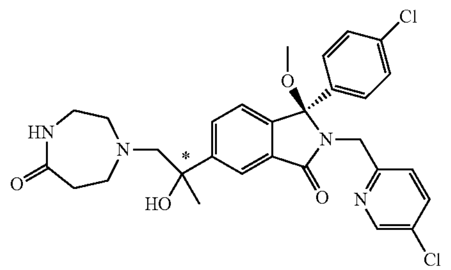 [SMILES: CO[C@]1(c2ccc(Cl)cc2)c2ccc(C(C)(O)CN3CCNC(=O)CC3)cc2C(=O)N1Cc1ccc(Cl)cn1] | (3R)-3-(4-chlorophenyl)-2-[(5-chloropyridin-2-yl)methyl]-6-[2-hydroxy-1-(5-oxo-1,4-diazepan-1-yl)propan-2-yl]-3-methoxy-2,3-dihydro-1H-isoindol-1-one | Prepared in a similar manner to Example 104 | ¹H NMR (400 MHz, CDCl3) 8.33 (1H, d), 7.98 (1H, d), 7.71 (1H, dd), 7.46 (1H, dd), 7.23-7.19 (3H, m), 7.16-7.11 (3H, m), 5.73 (1H, dd), 4.58 (1H, d), 4.49 (1H, d), 3.79 (1H, s), 3.40-3.31 (2H, m), 3.25 (2H, q), 3.00 (1H, d), 2.92-2.82 (3H, m), 2.81 (3H, s), 1.74-1.56 (2H, m), 1.55 (3H, s) | [M + H]+ = 569 |
| 261 | 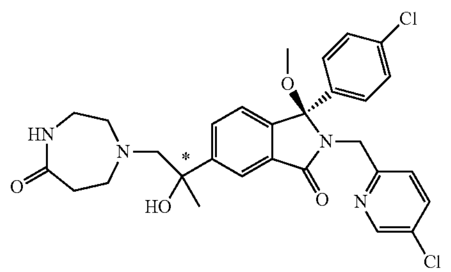 [SMILES: CO[C@]1(c2ccc(Cl)cc2)c2ccc(C(C)(O)CN3CCNC(=O)CC3)cc2C(=O)N1Cc1ccc(Cl)cn1] | (3R)-3-(4-chlorophenyl)-2-[(5-chloropyridin-2-yl)methyl]-6-[2-hydroxy-1-(5-oxo-1,4-diazepan-1-yl)propan-2-yl]-3-methoxy-2,3-dihydro-1H-isoindol-1-one | Prepared in a similar manner to Example 104 | ¹H NMR (400 MHz, CDCl3) 8.34 (1H, d), 8.01 (1H, d), 7.68 (1H, dd), 7.47 (1H, dd), 7.24-7.20 (3H, m), 7.17-7.11 (3H, m), 5.73 (1H, dd), 4.60 (1H, d), 4.46 (1H, d), 3.80 (1H, s), 3.39 (1H, d), 3.25 (3H, dd), 3.01 (1H, d), 2.94-2.81 (3H, m), 2.80 (3H, s), 1.71-1.58 (2H, m), 1.55 (3H, s) | [M + H]+ = 569 |
| 262 | 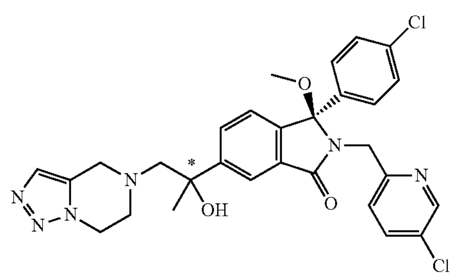 [SMILES: CO[C@]1(c2ccc(Cl)cc2)c2ccc(C(C)(O)CN3CCn4nncc4C3)cc2C(=O)N1Cc1ccc(Cl)cn1] | (3R)-3-(4-chlorophenyl)-2-[(5-chloropyridin-2-yl)methyl]-6-(2-hydroxy-1-{4H,5H,6H,7H-[1,2,3]triazolo[1,5-a]pyrazin-5-yl}propan-2-yl)-3-methoxy-2,3-dihydro-1H-isoindol-1-one | Prepared in a similar manner to Example 104 | ¹H NMR (400 MHz, DMSO) 8.40 (1H, d), 7.98 (1H, d), 7.78-7.73 (2H, m), 7.46 (1H, s), 7.31 (2H, d), 7.27-7.16 (4H, m), 5.34 (1H,s), 4.53 (1H, d), 4.36 (1H, d), 4.21 (2H, dd), 3.77 (2H), 3.01-2.87 (2H, m), 2.79 (2H, s), 2.76 (3H, s), 1.53 (3H, s); | [M + H]+ = 579 |
| 235 | 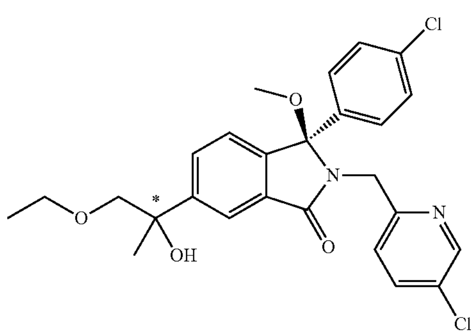 [SMILES: CCOCC(C)(O)c1ccc2c(c1)C(=O)N(Cc1ccc(Cl)cn1)[C@@]2(OC)c1ccc(Cl)cc1] | (3R)-3-(4-chlorophenyl)-2-[(5-chloropyridin-2-yl)methyl]-6-(1-ethoxy-2-hydroxypropan-2-yl)-3-methoxy-2,3-dihydro-1H-isoindol-1-one | Prepared in a similar manner to 274 | ¹H NMR (400 MHz, CDCl3) 8.34 (1H, d), 7.97 (1H, d), 7.74 (1H, dd), 7.47 (1H, dd), 7.25-7.20 (3H, m), 7.18-7.12 (3H, m), 4.60 (1H, d), 4.47 (1H, d), 3.62-3.52 (4H, m), 3.04 (1H, s), 2.81 (3H, s), 1.56 (3H, s), 1.18 (3H, dd) | [M + H]+ = 501 |
| 236 | 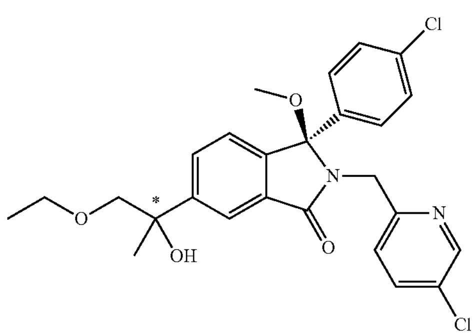 [SMILES: CCOCC(C)(O)c1ccc2c(c1)C(=O)N(Cc1ccc(Cl)cn1)[C@@]2(OC)c1ccc(Cl)cc1] | (3R)-3-(4-chlorophenyl)-2-[(5-chloropyridin-2-yl)methyl]-6-(1-ethoxy-2-hydroxypropan-2-yl)-3-methoxy-2,3-dihydro-1H-isoindol-1-one | Prepared in a similar manner to 274 | ¹H NMR (400 MHz, CDCl3) 8.34 (1H, d), 7.97 (1H, d), 7.73 (1H, dd), 7.47 (1H, dd), 7.25-7.20 (3H, m), 7.18-7.11 (3H, m), 4.60 (1H, d), 4.47 (1H, d), 3.63-3.52 (4H, m), 3.04 (1H, s), 2.81 (3H, s), 1.55 (3H, s), 1.17 (3H, dd) | [M + H]+ = 501 |

-continued

| Example | Structure | Name | Comment | NMR Data | MS Data |
|---|---|---|---|---|---|
| 263 | 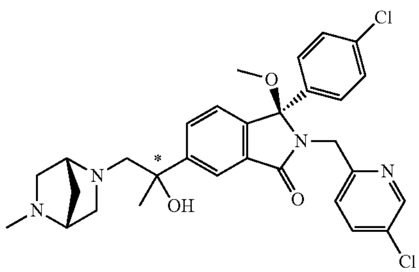 [SMILES: CO[C@]1(c2ccc(Cl)cc2)c2ccc(C(C)(O)CN3C[C@H]4C[C@@H]3CN4C)cc2C(=O)N1Cc1ccc(Cl)cn1] | (3R)-3-(4-chlorophenyl)-2-[(5-chloropyridin-2-yl)methyl]-6-{2-hydroxy-1-[(1S,4S)-5-methyl-2,5-diazabicyclo[2.2.1]heptan-2-yl]propan-2-yl}-3-methoxy-2,3-dihydro-1H-isoindol-1-one | Prepared in a similar manner to Example 104 | ¹H NMR (400 MHz, DMSO) 8.39 (1H, d), 7.90 (1H, d), 7.76-7.72 (2H, m), 7.29 (2H, d), 7.26-7.20 (3H, m), 7.16 (1H, d), 4.98 (1H, s), 4.50 (1H, d), 4.39 (1H, d), 3.00 (2H, s), 2.79-2.73 (4H, m), 2.67 (1H, d), 2.47-2.37 (4H, m), 2.18 (3H, s), 1.51-1.41 (5H, m); | [M + H]+ = 567 |
| 264 | 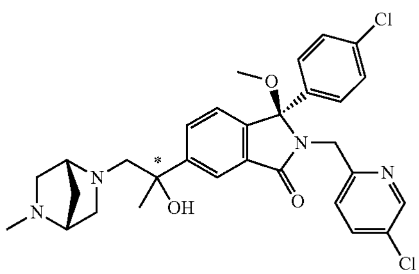 [SMILES: CO[C@]1(c2ccc(Cl)cc2)c2ccc(C(C)(O)CN3C[C@H]4C[C@@H]3CN4C)cc2C(=O)N1Cc1ccc(Cl)cn1] | (3R)-3-(4-chlorophenyl)-2-[(5-chloropyridin-2-yl) methyl]-6-{2-hydroxy-1-[(1S,4S)-5-methyl-2,5-diazabicyclo[2.2.1]heptan-2-yl]propan-2-yl}-3-methoxy-2,3-dihydro-1H-isoindol-1-one | Prepared in a similar manner to Example 104 | ¹H NMR (400 MHz, DMSO) 8.39 (1H, d), 7.95 (1H, d), 7.77-7.71 (2H, m), 7.30 (2H, d), 7.27-7.21 (3H, m), 7.15 (1H, d), 4.96 (1H, s), 4.52 (1H, d), 4.36 (1H, d), 3.01 (2H, d), 2.80 (1H, d), 2.75 (3H, s), 2.66 (1H, d), 2.49-2.39 (4H, m), 2.18 (3H, s), 1.51 (1H, d), 1.47-1.42 (4H, m); | [M + H]+ = 567 |
| 265 | 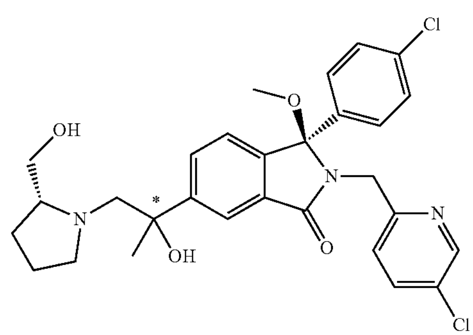 [SMILES: CO[C@]1(c2ccc(Cl)cc2)c2ccc(C(C)(O)CN3CCC[C@@H]3CO)cc2C(=O)N1Cc1ccc(Cl)cn1] | (3R)-3-(4-chlorophenyl)-2-[(5-chloropyridin-2-yl)methyl]-6-{2-hydroxy-1-[(2R)-2-(hydroxymethyl)pyrrolidin-1-yl]propan-2-yl}-3-methoxy-2,3-dihydro-1H-isoindol-1-one | Prepared in a similar manner to Example 104 | ¹H NMR (400 MHz, CDCl3) 8.34 (1H, d), 8.01 (1H, d), 7.71 (1H, dd), 7.48 (1H, dd), 7.25-7.14 (5H, m), 7.11 (1H, d), 4.60 (1H, d), 4.47 (1H, d), 3.60 (1H, dd), 3.49 (1H, dd), 3.05 (2H, q), 2.80 (4H, s), 2.26-2.20 (1H, m), 1.98-1.91 (1H, m), 1.82-1.72 (1H, m), 1.58-1.47 (8H, m) | [M + H]+ = 556 |
| 266 | 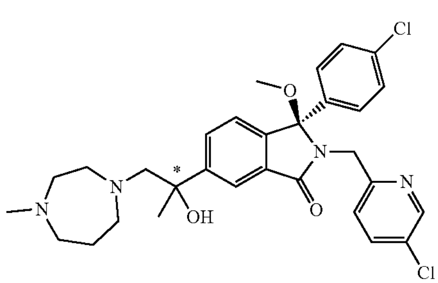 [SMILES: CO[C@]1(c2ccc(Cl)cc2)c2ccc(C(C)(O)CN3CCCN(C)CC3)cc2C(=O)N1Cc1ccc(Cl)cn1] | (3R)-3-(4-chlorophenyl)-2-[(5-chloropyridin-2-yl)methyl]-6-[2-hydroxy-1-(4-methyl-1,4-diazepan-1-yl)propan-2-yl]-3-methoxy-2,3-dihydro-1H-isoindol-1-one | Prepared in a similar manner to Example 104 | ¹H NMR (400 MHz, CDCl3) 8.34 (1H, d), 7.97 (1H, d), 7.71 (1H, dd), 7.47 (1H, dd), 7.24-7.13 (5H, m), 7.09 (1H, d), 4.59 (1H, d), 4.47 (1H, d), 3.01 (1H, d), 2.79 (4H, s), 2.71-2.53 (6H, m), 2.41 (2H, dd), 2.30 (3H, s), 1.68-1.59 (3H, m), 1.50 (3H, s) | [M + H]+ = 569 |

| Example | Structure | Name | Comment | NMR Data | MS Data |
|---|---|---|---|---|---|
| 267 | 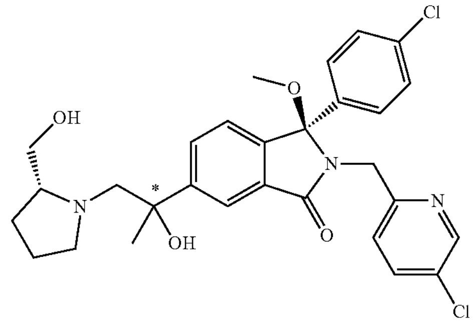 [SMILES: CO[C@]1(c2ccc(Cl)cc2)c2ccc(C(C)(O)CN3CCC[C@@H]3CO)cc2C(=O)N1Cc1ccc(Cl)cn1] | (3R)-3-(4-chlorophenyl)-2-[(5-chloro-pyridin-2-yl)methyl]-6-{2-hydroxy-1-[(2R)-2-(hydroxy-methyl)pyrrolidin-1-yl]propan-2-yl}-3-meth-oxy-2,3-dihydro-1H-isoindol-1-one | Prepared in a similar manner to Example 104 | $^1$H NMR (400 MHz, CDCl3) 8.33 (1H, d), 7.96 (1H, d), 7.73 (1H, dd), 7.46 (1H, dd), 7.22-7.19 (3H, m), 7.16-7.11 (3H, m), 4.60-4.47 (2H, m), 3.40-3.30 (3H, m), 2.97 (1H, d), 2.85 (1H, d), 2.82 (3H, s), 2.77-2.70 (1H, m), 2.63-2.56 (1H, m), 1.88-1.74 (3H, m), 1.61 (3H, s), 1.59-1.54 (3H, m) | [M + H]+ = 556 |
| 268 | 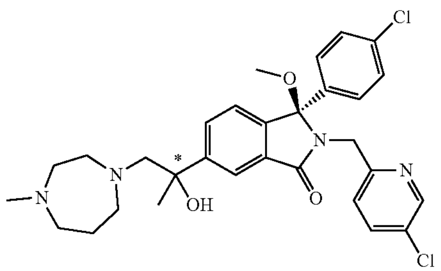 [SMILES: CO[C@]1(c2ccc(Cl)cc2)c2ccc(C(C)(O)CN3CCCN(C)CC3)cc2C(=O)N1Cc1ccc(Cl)cn1] | (3R)-3-(4-chlorophenyl)-2-[(5-chloro-pyridin-2-yl)methyl]-6-[2-hydroxy-1-(4-methyl-1,4-diazepan-1-yl)propan-2-yl]-3-meth-oxy-2,3-dihydro-1H-isoindol-1-one | Prepared in a similar manner to Example 104 | $^1$H NMR (400 MHz, CDCl3) 8.34 (1H, d), 7.94 (1H, d), 7.75 (1H, dd), 7.47 (1H, dd), 7.24-7.14 (5H, m), 7.10 (1H, d), 4.59 (1H, d), 4.46 (1H, d), 3.02 (1H, d), 2.78 (4H, s), 2.70-2.54 (6H, m), 2.42-2.38 (2H, m), 2.31 (3H, s), 1.68-1.58 (3H, m), 1.50 (3H, s) | [M + H]+ = 569 |
| 269 | 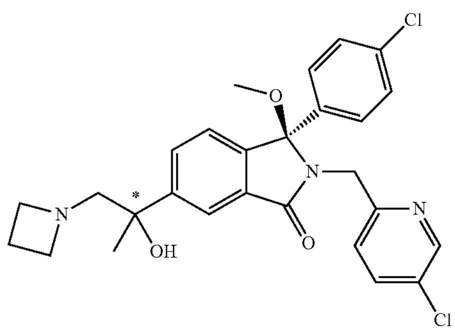 [SMILES: CO[C@]1(c2ccc(Cl)cc2)c2ccc(C(C)(O)CN3CCC3)cc2C(=O)N1Cc1ccc(Cl)cn1] | (3R)-6-[1-(azetidin-1-yl)-2-hydroxy-propan-2-yl]-3-(4-chloro-phenyl)-2-[(5-chloropyridin-2-yl)methyl]-3-methoxy-2,3-dihydro-1H-isoindol-1-one | Prepared in a similar manner to Example 104 | $^1$H NMR (400 MHz, CDCl3) 8.34 (1H, d), 7.97 (1H, d), 7.70 (1H, dd), 7.47 (1H, dd), 7.24-7.14 (5H, m), 7.09 (1H, d), 4.59 (1H, d), 4.46 (1H, d), 4.35-4.34 (1H, m), 3.10 (2H, q), 2.99 (2H, q), 2.81-2.77 (4H, m), 2.69 (1H, d), 2.00-1.91 (2H, m), 1.45 (3H, s) | [M + H]+ = 512 |
| 270 | 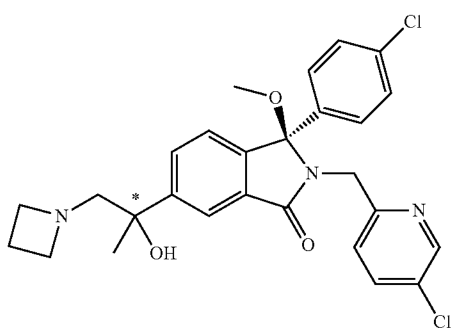 [SMILES: CO[C@]1(c2ccc(Cl)cc2)c2ccc(C(C)(O)CN3CCC3)cc2C(=O)N1Cc1ccc(Cl)cn1] | (3R)-6-[1-(azetidin-1-yl)-2-hydroxy-propan-2-yl]-3-(4-chloro-phenyl)-2-[(5-chloropyridin-2-yl)methyl]-3-methoxy-2,3-dihydro-1H-isoindol-1-one | Prepared in a similar manner to Example 104 | $^1$H NMR (400 MHz, CDCl3) 8.33 (1H, d), 7.94 (1H, d), 7.74 (1H, dd), 7.47 (1H, dd), 7.24-7.14 (5H, m), 7.09 (1H, d), 4.59 (1H, d), 4.47 (1H, d), 4.35 (1H, s), 3.13-2.96 (4H, m), 2.81 (1H, d), 2.78 (3H, s), 2.70 (1H, d), 2.00-1.91 (2H, m), 1.45 (3H, s) | [M + H]+ = 512 |
| 271 | 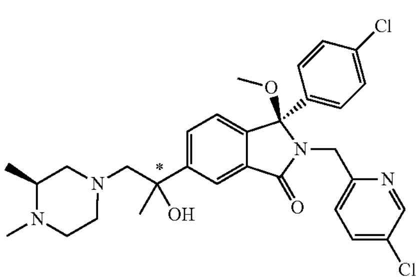 [SMILES: CO[C@]1(c2ccc(Cl)cc2)c2ccc(C(C)(O)CN3CCN(C)[C@@H](C)C3)cc2C(=O)N1Cc1ccc(Cl)cn1] | (3R)-3-(4-chlorophenyl)-2-[(5-chloro-pyridin-2-yl)methyl]-6-{1-[(3S)-3,4-dimethyl-piperazin-1-yl]-2-hydroxy-propan-2-yl}-3-methoxy-2,3-dihydro-1H-isoindol-1-one | Prepared in a similar manner to Example 104 | $^1$H NMR (400 MHz, CDCl3) 8.34 (1H, d), 7.98 (1H, d), 7.69 (1H, dd), 7.48 (1H, dd), 7.25-7.14 (5H, m), 7.10 (1H, d), 4.59 (1H, d), 4.47 (1H, d), 2.79-2.79 (4H, m), 2.68-2.62 (2H, m), 2.49-2.45 (1H, m), 2.21 (6H, s), 2.15-2.05 (3H, m), 1.49 (3H, s), 1.00 (3H, d) | [M + H]+ = 569 |

-continued

| Example | Structure | Name | Comment | NMR Data | MS Data |
|---|---|---|---|---|---|
| 272 | 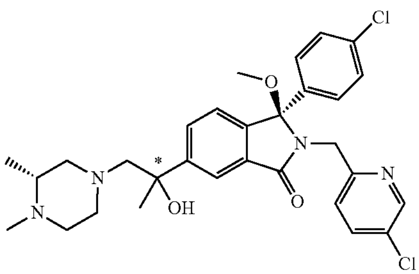 [SMILES: CO[C@]1(c2ccc(Cl)cc2)c2ccc(C(C)(O)CN3CCN(C)[C@H](C)C3)cc2C(=O)N1Cc1ccc(Cl)cn1] | (3R)-3-(4-chlorophenyl)-2-[(5-chloropyridin-2-yl)methyl]-6-{1-[(3R)-3,4-dimethylpiperazin-1-yl]-2-hydroxypropan-2-yl}-3-methoxy-2,3-dihydro-1H-isoindol-1-one | Prepared in a similar manner to Example 104 | $^1$H NMR (400 MHz, CDCl3) 8.34 (1H, d), 7.98 (1H, d), 7.70 (1H, dd), 7.47 (1H, dd), 7.24-7.17 (3H, m), 7.16-7.09 (3H, m), 4.59 (1H, d), 4.50-4.44 (2H, m), 2.81-2.80 (4H, m), 2.75-2.56 (4H, m), 2.32-2.25 (1H, m), 2.20 (3H, s), 1.91-1.79 (3H, m), 1.51 (3H, s), 0.70 (3H, d) | [M + H]+ = 569 |
| 273 | 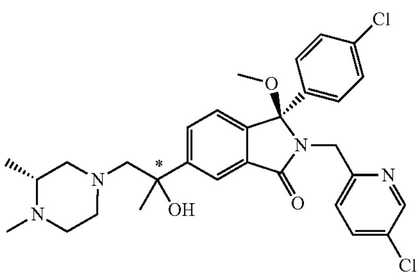 [SMILES: CO[C@]1(c2ccc(Cl)cc2)c2ccc(C(C)(O)CN3CCN(C)[C@H](C)C3)cc2C(=O)N1Cc1ccc(Cl)cn1] | (3R)-3-(4-chlorophenyl)-2-[(5-chloropyridin-2-yl)methyl]-6-{1-[(3R)-3,4-dimethylpiperazin-1-yl]-2-hydroxypropan-2-yl}-3-methoxy-2,3-dihydro-1H-isoindol-1-one | Prepared in a similar manner to Example 104 | $^1$H NMR (400 MHz, CDCl3) 8.34 (1H, d), 7.96 (1H, d), 7.72 (1H, dd), 7.47 (1H, dd), 7.25-7.14 (5H, m), 7.10 (1H, d), 4.60 (1H, d), 4.46 (2H, d), 2.81 (1H, d), 2.78 (3H, s), 2.68-2.62 (2H, m), 2.51-2.44 (1H, m), 2.22 (5H, m), 2.15-2.07 (3H, m), 1.50 (3H, s), 1.00 (3H, d) | [M + H]+ = 569 |
| 274 | 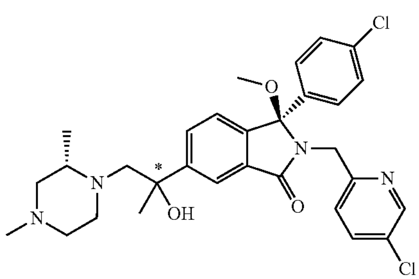 [SMILES: CO[C@]1(c2ccc(Cl)cc2)c2ccc(C(C)(O)CN3CCN(C)C[C@@H]3C)cc2C(=O)N1Cc1ccc(Cl)cn1] | (3R)-3-(4-chlorophenyl)-2-[(5-chloropyridin-2-yl)methyl]-6-{1-[(2S)-2,4-dimethylpiperazin-1-yl]-2-hydroxypropan-2-yl}-3-methoxy-2,3-dihydro-1H-isoindol-1-one | Prepared in a similar manner to Example 104 | $^1$H NMR (400 MHz, CDCl3) 8.34 (1H, d), 7.99 (1H, d), 7.69 (1H, dd), 7.48 (1H, dd), 7.25-7.14 (5H, m), 7.10 (1H, d), 4.59 (1H, d), 4.47 (1H, d), 2.99 (1H, d), 2.79 (3H, s), 2.68 (1H, d), 2.60-2.48 (2H, m), 2.32-2.20 (2H, m), 2.18-2.17 (4H, m), 2.01-1.97 (1H, m), 1.93-1.87 (1H, m), 1.50 (3H, s), 1.46-1.28 (1H, m), 1.05 (3H, d) | [M + H]+ = 569 |
| 275 | 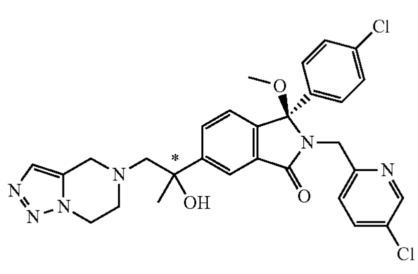 [SMILES: CO[C@]1(c2ccc(Cl)cc2)c2ccc(C(C)(O)CN3CCn4nncc4C3)cc2C(=O)N1Cc1ccc(Cl)cn1] | (3R)-3-(4-chlorophenyl)-2-[(5-chloropyridin-2-yl)methyl]-6-(2-hydroxy-1-{4H,5H,6H,7H-[1,2,3]triazolo[1,5-a]pyrazin-5-yl}propan-2-yl)-3-methoxy-2,3-dihydro-1H-isoindol-1-one | Prepared in a similar manner to Example 104 | $^1$H NMR (400 MHz, DMSO) 8.39 (1H, d), 7.97 (1H, d), 7.80-7.72 (2H, m), 7.45 (1H, s), 7.29 (2H, d), 7.25-7.16 (4H, m), 5.34 (1H, s), 4.50 (1H, d), 4.39 (1H, d), 4.21 (2H, dd), 3.77 (2H, d), 3.01-2.89 (2H, m), 2.79 (2H, s), 2.77 (3H, s), 1.55 (3H, s); | [M + H]+ = 579 |

431

Examples 276 and 277: 6-{[(1R)-1-(4-chlorophenyl)-1-[(I-cyanocyclopropyl)methoxy]-7-fluoro-5-[2-hydroxy-1-(pyrrolidin-1-yl)propan-2-yl]-3-oxo-2,3-dihydro-1H-isoindol-2-yl]methyl}pyridine-3-carbonitrile (*both isomers separated and isolated)

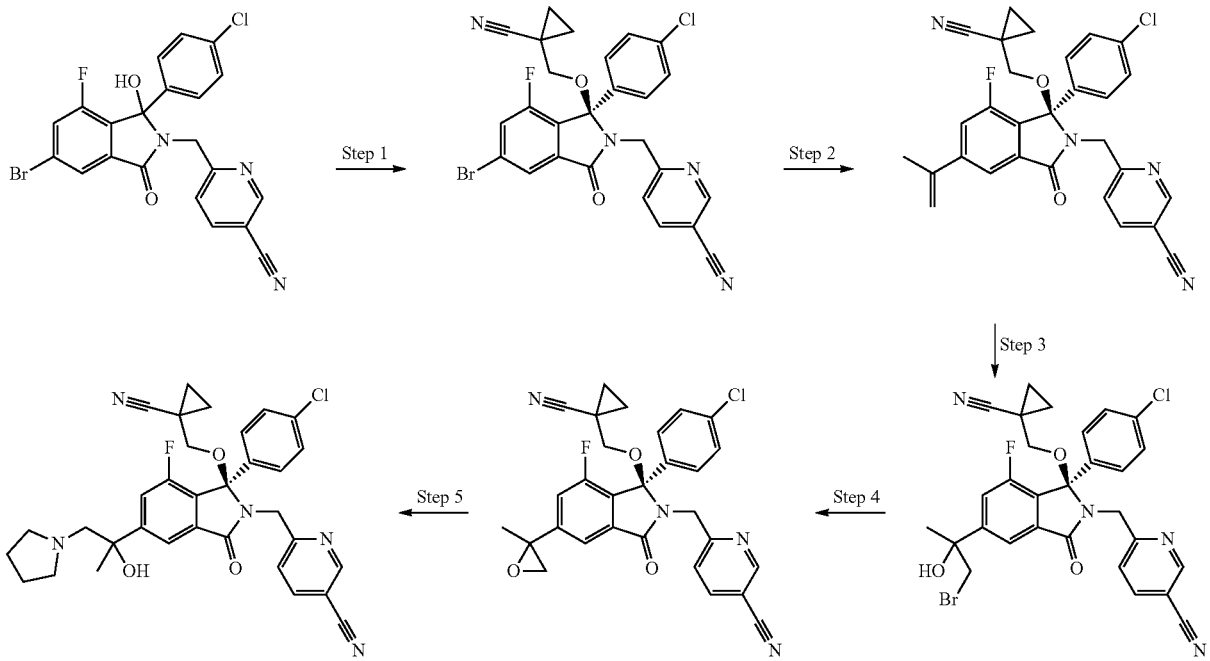

Step 1: (R)-6-((5-Bromo-1-(4-chlorophenyl)-1-((1-cyanocyclopropyl)methoxy)-7-fluoro-3-oxoisoindolin-2-yl)methyl)nicotinonitrile The title compound was prepared as the racemate from 6-((5-bromo-1-(4-chlorophenyl)-7-fluoro-1-hydroxy-3-oxoisoindolin-2-yl)methyl)nicotinonitrile (8.9 g, 18.9 mmol) using the method of Example 1, step 2 (7.9 g). Separation by chiral SFC gave: Slower running isomer (3.9 g, 37%). MS [M+H]$^+$=553

Step 2: (R)-6-((1-(4-Chlorophenyl)-1-((1-cyanocyclopropyl)methoxy)-7-fluoro-3-oxo-5-(prop-1-en-2-yl)isoindolin-2-yl)methyl)nicotinonitrile Step 2 was performed in a similar manner to Example 4, step 2 to give the title compound (2.3 g, 63% yield). MS: [M+Na]$^+$=535.

Step 3: 6-(((1R)-5-(1-Bromo-2-hydroxypropan-2-yl)-1-(4-chlorophenyl)-1-((1-cyanocyclopropyl)methoxy)-7-fluoro-3-oxoisoindolin-2-yl)methyl)nicotinonitrile N-Bromosuccinimide (2.2 g, 12.35 mmol) was added in one portion to a stirred, RT solution of (R)-6-((1-(4-chlorophenyl)-1-((1-cyanocyclopropyl)methoxy)-7-fluoro-3-oxo-5-(prop-1-en-2-yl)isoindolin-2-yl)methyl)nicotinonitrile (3.76 g, 7.34 mmol) and H$_2$O (0.22 mL, 12.33 mmol) in DMSO (50 mL). After 1 h, the mixture was poured into H$_2$O (500 mL) and extracted into EtOAc (2×300 mL). Pooled organics were washed with H$_2$O (200 mL), brine (100 mL), dried (MgSO$_4$) and the solvent evaporated. The residue was purified by chromatography using 0-100% EtOAc in isohexane as the eluent to afford 6-(((1R)-5-(1-bromo-2-hydroxypropan-2-yl)-1-(4-chlorophenyl)-1-((1-cyanocyclopropyl)methoxy)-7-fluoro-3-oxoisoindolin-2-yl)methyl)nicotinonitrile (3.4 g, 76% yield); MS: [M+H]$^+$=609.

Step 4: 6-(((1R)-1-(4-Chlorophenyl)-1-((1-cyanocyclopropyl)methoxy)-7-fluoro-5-(2-methyloxiran-2-yl)-3-oxoisoindolin-2-yl)methyl)nicotinonitrile A solution of NaOH (0.26 g, 6.5 mmol) in H$_2$O (45 mL) was added to a stirred, RT solution of 6-(((1R)-5-(1-bromo-2-hydroxypropan-2-yl)-1-(4-chlorophenyl)-1-((1-cyanocyclopropyl)methoxy)-7-fluoro-3-oxoisoindolin-2-yl)methyl)nicotinonitrile (3.43 g, 5.6 mmol) in 1,4-dioxane (56 mL). After 1 h, H$_2$O (300 mL) was added and the mixture extracted with EtOAc (2×250 mL). Pooled organics were dried (MgSO4) and evaporated to afford 6-(((1R)-1-(4-chlorophenyl)-1-((1-cyanocyclopropyl)methoxy)-7-fluoro-5-(2-methyloxiran-2-yl)-3-oxoisoindolin-2-yl)methyl)nicotinonitrile as a colourless foam (2.9 g, 98%); MS: [M+H]$^+$=529.

Step 5: 6-{[(1R)-1-(4-chlorophenyl)-1-[(1-cyanocyclopropyl)methoxy]-7-fluoro-5-[2-hydroxy-1-(pyrrolidin-1-yl)propan-2-yl]-3-oxo-2,3-dihydro-1H-isoindol-2-yl]methyl}pyridine-3-carbonitrile A solution of 6-(((1R)-1-(4-chlorophenyl)-1-((1-cyanocyclopropyl)methoxy)-7-fluoro-5-(2-methyloxiran-2-yl)-3-oxoisoindolin-2-yl)methyl)nicotinonitrile (0.96 g, 1.8 mmol) and pyrrolidine (0.17 mL, 2.03 mmol) in MeOH (10 mL) was stirred in a capped tube at RT under nitrogen for 18 h. Evaporation under reduced pressure and chromatography using 0-10% MeOH containing 7N NH$_3$ in EtOAc as the eluent afforded a pale yellow gum which was further purified using a 5 g SCX cartridge eluting with 1N NH$_3$ in MeOH to give the title compound as a racemate (400 mg). Purification by chiral SFC gave the title compounds.

Example 276: *Faster Eluting Isomer $^1$H NMR (400 MHz, D6-DMSO) 8.85 (1H, d), 8.19 (1H, dd), 7.86 (1H, s), 7.61 (1H, d), 7.47 (1H, d), 7.44-7.35 (4H, m), 5.22 (1H, s), 4.62 (2H, s), 3.47 (1H, d), 3.05 (1H, d), 2.78 (2H, d), 2.54-2.46 (4H, m), 1.64 (4H, s), 1.53 (3H, s), 1.29 (2H, d), 0.94-0.83 (2H, m). MS: [M+H]$^+$=600.

Example 277: *Slower Eluting Isomer $^1$H NMR (400 MHz, D6-DMSO) 8.86 (1H, d), 8.20 (1H, dd), 7.87 (1H, s), 7.63-7.58 (1H, m), 7.47 (1H, d), 7.42 (2H, d), 7.37 (2H, d), 5.22 (1H, s), 4.61 (2H, d), 3.47 (1H, d), 3.04 (1H, d), 2.79 (2H, s), 2.53-2.47 (4H, m), 1.64 (4H, dd), 1.53 (3H, s), 1.28 (2H, d), 0.92-0.81 (2H, m). MS: [M+H]$^+$=600.

Example 278 and 279: 6-{[(1R)-1-(4-chlorophenyl)-1-[(1-cyanocyclopropyl)methoxy]-7-fluoro-5-[2-hydroxy-1-(4-methylpiperazin-1-yl)propan-2-yl]-3-oxo-2,3-dihydro-1H-isoindol-2-yl]methyl}pyridine-3-carbonitrile (*both isomers separated and isolated)

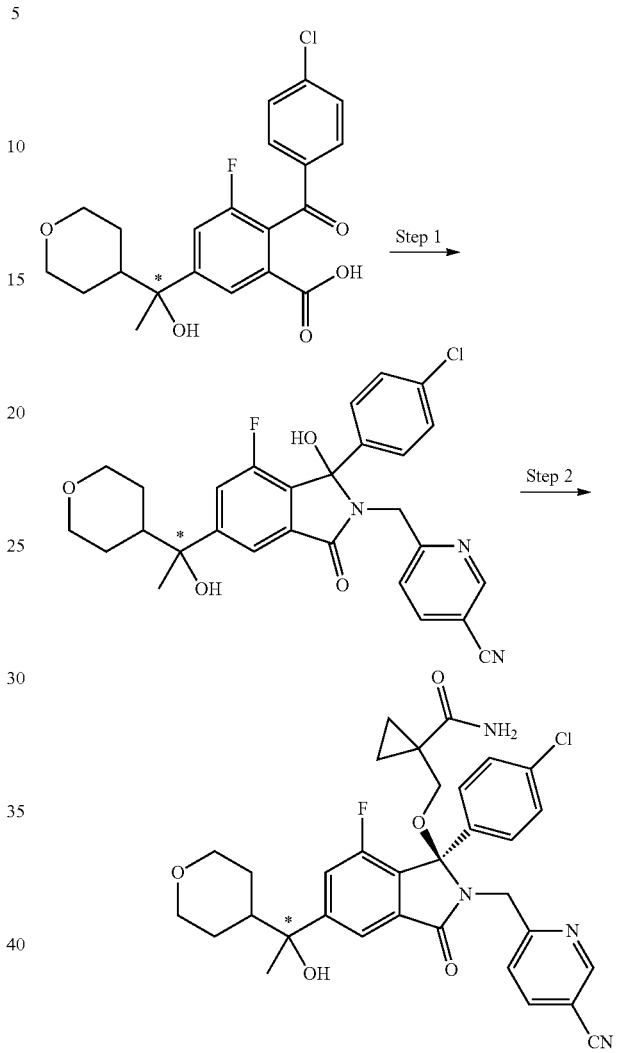

The title compounds were prepared in a similar manner to that described for Example 276

Example 278: *Fast Running Isomer $^1$H NMR (400 MHz, D6-DMSO) 8.85 (1H, s), 8.18 (1H, dd), 7.85 (1H, s), 7.60 (1H, d), 7.46-7.38 (3H, m), 7.35 (2H, d), 5.27 (1H, s), 4.62 (2H, d), 3.46 (1H, d), 3.39-3.35 (2H, m), 3.03 (1H, d), 2.41 (4H, s), 2.20 (4H, s), 2.14 (3H, s), 1.55 (3H, s), 1.30 (2H, d), 0.95-0.84 (2H, m). MS: [M+H]$^+$=629.

Example 279: *Slow Running Isomer $^1$H NMR (400 MHz, D6-DMSO) 8.86 (1H, d), 8.20 (1H, dd), 7.87 (1H, s), 7.60 (1H, d), 7.48-7.40 (3H, m), 7.35 (2H, d), 5.29 (1H, s), 4.61 (2H, d), 3.46 (1H, d), 3.02 (1H, d), 2.45-2.36 (4H, m), 2.24 (6H, s), 2.14 (3H, s), 1.54 (3H, s), 1.29 (2H, d), 0.93-0.81 (2H, m). MS: [M+H]$^+$=629.

Example 280

1-({[(1R)-1-(4-chlorophenyl)-2-[(5-cyanopyridin-2-yl)methyl]-7-fluoro-5-[1-hydroxy-1-(oxan-4-yl)ethyl]-3-oxo-2,3-dihydro-1H-isoindol-1-yl]oxy}methyl)cyclopropane-1-carboxamide
(Example isolated as a single isomer at the position shown*)

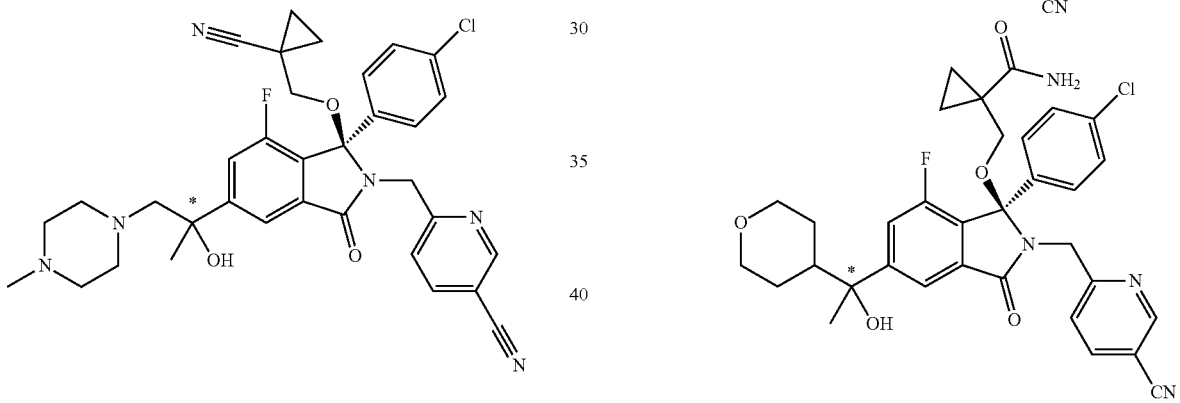

Step 1: 6-((1-(4-Chlorophenyl)-7-fluoro-1-hydroxy-5-(1-hydroxy-1-(tetrahydro-2H-pyran-4-yl)ethyl)-3-oxoisoindolin-2-yl)methyl)nicotinonitrile HATU (1.11 g, 2.91 mmol), was stirred in dimethyl formamide (8 mL) under an atmosphere of nitrogen at RT then (−)-2-(4-chlorobenzoyl)-3-fluoro-5-(1-hydroxy-1-(tetrahydro-2H-pyran-4-yl)ethyl)benzoic acid (Preparation 22; 0.79 g, 1.95 mmol) and 6-(aminomethyl)nicotinonitrile dihydrochloride (0.44 g, 2.14 mmol) were added followed by Hunig's base (1.52 g, 1.11 mL, 6.22 mmol). The reaction was allowed to stir at RT for 5 h then diluted with EtOAc (40 mL) and washed with saturated aqueous sodium hydrogen carbonate (30 mL). The layers were separated and the organic portion washed with 4% aqueous lithium chloride solution (2×10 mL). The aqueous portion was extracted with EtOAc (2×20 mL). The combined organic portions were dried (MgSO$_4$) and concentrated under reduced pressure. The crude residue was purified by Biotage using 50 g SNAP silica cartridge, eluting with EtOAc in iso-hexane (20-100% gradient elution). Fractions containing pure product were concentrated under reduced pressure to obtain the title compound (1.02 g, 100% yield). MS: [M-OH]⁺=504; [M-H]⁻=520.

Step 2: 1-({[(1R)-1-(4-chlorophenyl)-2-[(5-cyano-pyridin-2-yl)methyl]-7-fluoro-5-[1-hydroxy-1-(oxan-4-yl)ethyl]-3-oxo-2,3-dihydro-1H-isoindol-1-yl]oxy}methyl)cyclopropane-1-carboxamide 6-((1-(4-Chlorophenyl)-7-fluoro-1-hydroxy-5-(1-hydroxy-1-(tetrahydro-2H-pyran-4-yl)ethyl)-3-oxoisoindolin-2-yl)methyl)nicotinonitrile (0.65 g, 1.24 mmol), 1-(hydroxymethyl)cyclopropanecarboxamide (0.72 g, 6.23 mmol) and indium(III) bromide (1.33 g, 3.74 mmol) were heated to reflux in 1,2-dichloroethane (13 mL) for 1.5 h. Further indium(III) bromide (1.33 g, 3.74 mmol) was added and the reaction was allowed to stir for 1.5 h at reflux. The reaction mixture was allowed to cool then diluted with DCM (30 mL) and water (30 mL). The layers were separated and the aqueous portion was extracted with DCM (2×20 ml). The combined organic portions were passed through a phase separation cartridge and concentrated under reduced pressure. The crude residue was purified by Biotage using 25 g SNAP silica cartridge, eluting with EtOAc in iso-hexane (20-100% gradient elution) then methanol in EtOAc (0-10% gradient elution). Fractions containing pure product were concentrated under reduced pressure leaving 0.20 g which was separated using chiral SFC to afford the title compound (58 mg, 15%).

Example 280 *Slower Eluting Isomer

¹H NMR (400 MHz, CDCl₃) 8.68 (1H, d), 7.87 (1H, dd), 7.70 (1H, d), 7.49-7.42 (2H, m), 7.28 (4H, s), 4.52-4.40 (2H, m), 4.06-3.92 (2H, m), 3.47 (1H, d), 3.39-3.22 (3H, m), 1.59 (5H, m), 1.50-1.36 (3H, m), 1.28-1.19 (2H, m), 0.63-0.50 (2H, m); MS: [M+H]⁺=619

Example 281: 1-({[(1R)-1-(4-chlorophenyl)-2-[(5-cyanopyridin-2-yl)methyl]-7-fluoro-5-[1-hydroxy-1-(oxan-4-yl)ethyl]-3-oxo-2,3-dihydro-1H-isoindol-1-yl]oxy}methyl)cyclopropane-1-carboxamide (*single isomer separated and isolated)

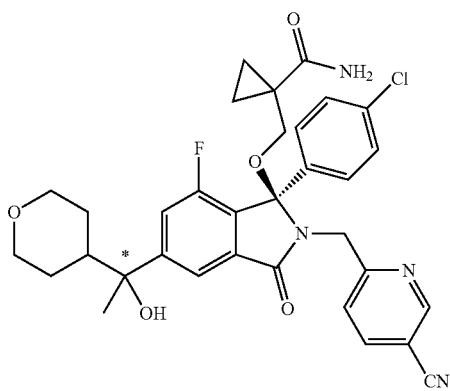 [SMILES: CC(O)(c1cc(F)c2c(c1)C(=O)N(Cc1ccc(C#N)cn1)[C@@]2(OCC1(C(N)=O)CC1)c1ccc(Cl)cc1)C1CCOCC1]

The title compound was prepared in an analogous fashion to Example 280, but using (+)-2-(4-chlorobenzoyl)-3-fluoro-5-(1-hydroxy-1-(tetrahydro-2H-pyran-4-yl)ethyl) benzoic acid instead of (−)-2-(4-chlorobenzoyl)-3-fluoro-5-(1-hydroxy-1-(tetrahydro-2H-pyran-4-yl)ethyl)benzoic acid. Purification by chiral SFC afforded the title compound.

1H NMR (400 MHz, DMSO-d6): 8.78-8.73 (1H, m), 8.10 (1H, dd), 7.77-7.71 (1H, m), 7.48 (1H, d), 7.36 (1H, d), 7.33-7.18 (4H, m), 6.99 (1H, s), 6.82 (1H, s), 5.22-5.17 (1H, m), 4.78-4.33 (2H, m), 3.93-3.85 (1H, m), 3.78 (1H, d), 3.51 (1H, d), 3.27-3.11 (2H, m), 3.08 (1H, d), 1.83 (1H, t), 1.56 (1H, d), 1.48 (3H, s), 1.44-1.24 (2H, m), 1.13-0.87 (3H, m), 0.61-0.46 (2H, m). MS: [M+H]⁻=617

Example 282 and 283: 6-{[(1R)-1-(4-chlorophenyl)-1-[(1-cyanocyclopropyl)methoxy]-7-fluoro-5-[1-hydroxy-1-(oxan-4-yl)ethyl]-3-oxo-2,3-dihydro-1H-isoindol-2-yl]methyl}pyridine-3-carbonitrile (*Examples were prepared and isolated as a single isomer)

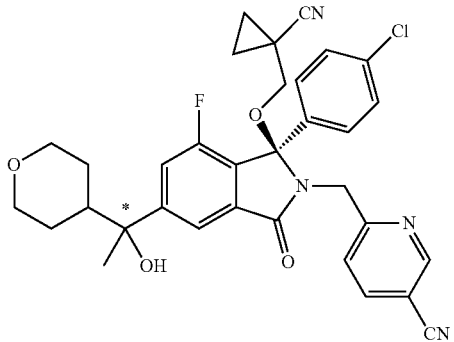 [SMILES: CC(O)(c1cc(F)c2c(c1)C(=O)N(Cc1ccc(C#N)cn1)[C@@]2(OCC1(C#N)CC1)c1ccc(Cl)cc1)C1CCOCC1]

The title compounds were prepared in an analoagous fashion to Example 280 and 281 respectively, but using hydroxymethyl)cyclopropanecarbonitrile instead of 1-(hydroxymethyl)cyclopropanecarboxamide.

Example 282

¹H NMR (400 MHz, CDCl₃) 8.70 (1H, d), 7.82 (1H, dd,), 7.71 (1H, d), 7.41-7.30 (4H, m), 7.26 (1H, s), 7.24 (1H, s), 4.64 (1H, d), 4.54 (1H, d), 4.05-3.92 (2H, m), 3.57 (1H, d), 3.39-3.26 (2H, m), 2.88 (1H, d), 1.88-1.79 (1H, m), 1.76 (1H, s), 1.59 (3H, s), 1.48-1.22 (6H, m), 0.94-0.79 (2H, m); MS: [M+H]⁺=601.2.

Example 283

¹H NMR (400 MHz, CDCl₃) 8.69 (1H, d), 7.82 (1H, dd), 7.74 (1H, d), 7.34 (3H, s), 7.27-7.22 (3H, m), 4.64 (1H, d), 4.54 (1H, d), 4.06-3.91 (2H, m), 3.57 (1H, d), 3.39-3.25 (2H, m), 2.92 (1H, d), 1.88-1.80 (2H, m), 1.60 (3H, s), 1.49-1.20 (6H, m), 0.95-0.79 (2H, m); MS: [M+H]⁺=601.4.

Example 284 and 285: 1-({[(1R)-1-(4-chlorophenyl)-2-[(5-chloropyrimidin-2-yl)methyl]-7-fluoro-5-[1-hydroxy-1-(oxan-4-yl)ethyl]-3-oxo-2,3-dihydro-1H-isoindol-1-yl]oxy}methyl)cyclopropane-1-carboxamide (*both isomer separated and isolated)

Example 286: (3R)-3-(4-chlorophenyl)-2-[(5-chloropyridin-2-yl)methyl]-4-fluoro-6-{1-hydroxy-1-[1-(pyrimidin-2-yl)piperidin-4-yl]ethyl}-3-methoxy-2,3-dihydro-1H-isoindol-1-one (Example prepared and isolated as a single isomer at the position shown*)

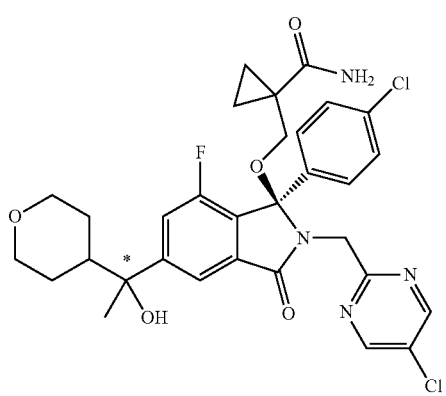 [SMILES: CC(O)(c1cc(F)c2c(c1)C(=O)N(Cc1ncc(Cl)cn1)[C@@]2(OCC1(C(N)=O)CC1)c1ccc(Cl)cc1)C1CCOCC1]

The title compounds were prepared in an analoagous fashion to Example 280 and 281 respectively, but using (5-chloropyrimidin-2-yl)methanamine hydrochloride instead of 6-(aminomethyl)nicotinonitrile dihydrochloride.

Example 284

$^1$H NMR (400 MHz, CDCl$_3$) 8.54 (2H, s), 7.74 (1H, d), 7.41 (1H, dd), 7.35-7.30 (2H, m), 7.29-7.27 (2H, m), 6.75-6.72 (1H, bs), 5.43-5.40 (1H, bs), 4.54 (2H, d), 4.07-3.93 (2H, m), 3.58 (1H, d), 3.50-3.30 (3H, m), 1.91-1.81 (1H, m), 1.79 (1H, s), 1.63-1.55 (3H, m), 1.49-1.19 (6H, m), 0.62-0.55 (1H, m), 0.51-0.44 (1H, m); MS: [M+H]$^+$=629.2.

Example 285

$^1$H NMR (400 MHz, CDCl$_3$) 8.54 (2H, s), 7.74 (1H, d), 7.41 (1H, dd), 7.35-7.30 (2H, m), 7.29-7.27 (2H, m), 6.75-6.72 (1H, bs), 5.43-5.40 (1H, bs), 4.54 (2H, d), 4.07-3.93 (2H, m), 3.58 (1H, d), 3.46 (1H, d), 3.40-3.26 (2H, m), 1.91-1.81 (1H, m), 1.79 (1H, s), 1.63-1.55 (3H, m), 1.49-1.19 (6H, m), 0.62-0.55 (1H, m), 0.51-0.44 (1H, m); MS: [M+H]$^+$=629.2.

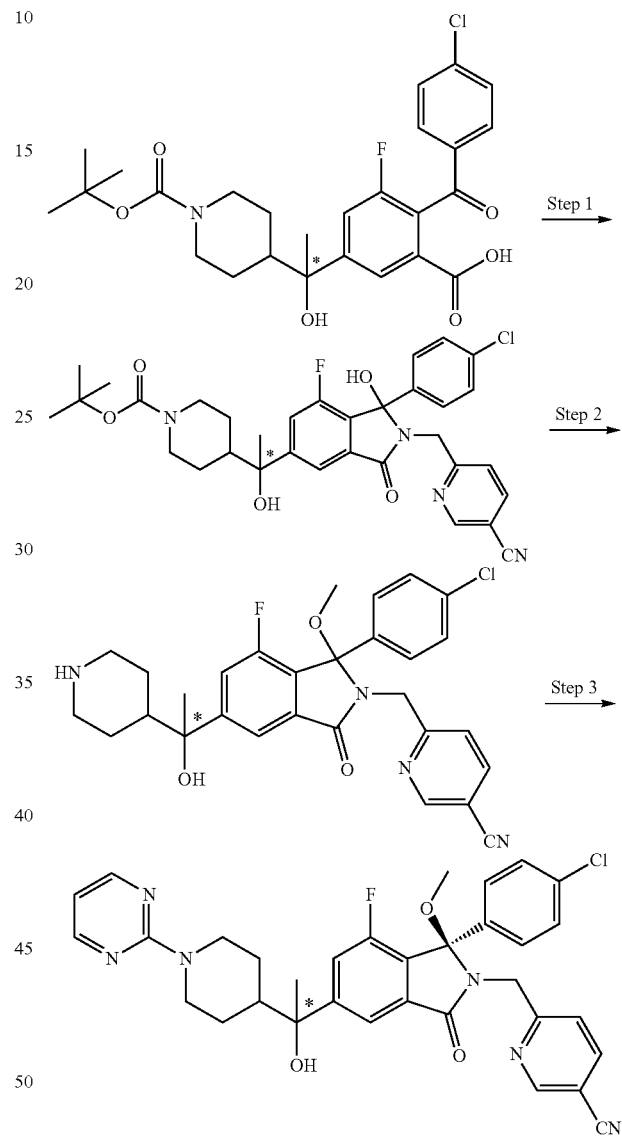

Step 1: tert-Butyl 4-[1-[1-(4-chlorophenyl)-2-[(5-chloro-2-pyridyl)methyl]-7-fluoro-1-hydroxy-3-oxo-isoindolin-5-yl]-1-hydroxy-ethyl]piperidine-1-carboxylate Using (−)-5-[1-(1-tert-butoxycarbonyl-4-piperidyl)-1-hydroxy-ethyl]-2-(4-chlorobenzoyl)-3-fluoro-benzoic acid (Preparation 24, step 3, slower-running enantiomer; 2.29 g, 4.53 mmol), step 1 was performed in a similar fashion to that described in Example 280 step 1, to give the title compound as an off-white solid (2.50 g, 87% yield). MS: [M−H$_2$O)]$^+$= 612.

Step 2: 3-(4-Chlorophenyl)-2-[(5-chloro-2-pyridyl)methyl]-4-fluoro-6-[1-hydroxy-1-(4-piperidyl)ethyl]-3-methoxy-isoindolin-1-one Using tert-butyl 4-[1-[1-(4-chlorophenyl)-2-[(5-chloro-2-pyridyl)methyl]-7-fluoro-1-hydroxy-3-oxo-isoindolin-5-yl]-1-hydroxy-ethyl]piperidine-1-carboxylate (2.50 g, 3.97 mmol), step 2 was performed in a similar fashion to that described in Example 280 step 2 to give the title compound as a yellow foam (1.11 g, 50% yield); MS: [M+HCOOH]$^-$= 588.

Step 3: (3R)-3-(4-chlorophenyl)-2-[(5-chloropyridin-2-yl)methyl]-4-fluoro-6-{1-hydroxy-1-[1-(pyrimidin-2-yl)piperidin-4-yl]ethyl}-3-methoxy-2,3-dihydro-1H-isoindol-1-one A mixture of 3-(4-chlorophenyl)-2-[(5-chloro-2-pyridyl)methyl]-4-fluoro-6-[1-hydroxy-1-(4-piperidyl)ethyl]-3-methoxy-isoindolin-1-one (350 mg, 0.65 mmol), 2-chloropyrimidine (84 mg, 0.73 mmol) and potassium carbonate (180 mg, 1.30 mmol) in DMF (7 mL) was heated under nitrogen at 70° C. for 1 h. Further 2-chloropyrimidine (10 mg, 0.087 mmol) was added and the mixture heated for a further 1 h. The mixture was cooled to RT, diluted with EtOAc then washed with saturated sodium hydrogen carbonate solution and brine. The organic phase was dried (MgSO$_4$), filtered and concentrated under reduced pressure. The crude product was purified by column chromatography on silica, eluting with a gradient of 0-3% methanol in DCM to afford a yellow foam (320 mg). The diastereomeric mixture was separated by chiral preparative HPLC to afford the title compound (130 mg, 64% yield).

Example 286 *Slower Eluting Isomer $^1$H NMR (400 MHz, CDCl$_3$) 8.38 (1H, dd), 8.30-8.26 (2H, m), 7.75 (1H, s), 7.50 (1H, dd), 7.36 (1H, m), 7.28-7.18 (5H, m), 6.47-6.42 (1H, m), 4.88-4.78 (2H, m), 4.68-4.62 (1H, m), 4.44-4.38 (1H, m), 2.92 (3H, d), 2.82-2.69 (2H, m), 1.93-1.78 (2H, m), 1.73 (1H, m), 1.57 (3H, m), 1.50-1.46 (1H, m), 1.36-1.24 (2H, m). MS: [M+H]$^+$=622.

Example 287: 6-{[(1R)-1-(4-chlorophenyl)-7-fluoro-5-[1-hydroxy-1-(1-methylpiperidin-4-yl)ethyl]-1-{[1-(hydroxymethyl)cyclopropyl]methoxy}-3-oxo-2,3-dihydro-1H-isoindol-2-yl]methyl}pyridine-3-carbonitrile (*single isomer separated and isolated)

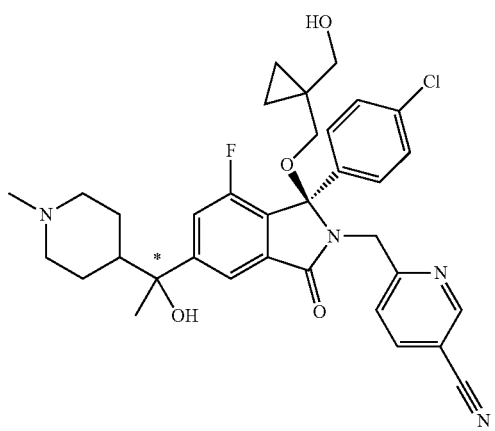 [SMILES: CN1CCC(C(C)(O)c2cc(F)c3c(c2)C(=O)N(Cc2ccc(C#N)cn2)[C@@]3(OCC2(CO)CC2)c2ccc(Cl)cc2)CC1]

The title compound was prepared from 2-(4-chlorobenzoyl)-3-fluoro-5-(1-hydroxy-1-(1-methylpiperidin-4-yl)ethyl)benzoic acid (Preparation 25) using methods similar to those described in Example 280, using cyclopropane-1,1-diyldimethanol instead of 1-(hydroxymethyl)cyclopropanecarboxamide.

Example 287 (Faster Eluting Isomer)

$^1$H NMR (400 MHz, CDCl$_3$) 8.68 (1H, d), 7.81 (1H, dd), 7.68 (1H, d), 7.44-7.36 (2H, m), 7.28 (2H, d), 7.21 (2H, d), 4.54 (2H, d), 3.62 (1H, d), 3.46 (1H, d), 3.33 (1H, d), 2.93-2.83 (3H, m), 2.23 (3H, s), 1.89-1.79 (4H, m), 1.70 (1H, d), 1.59 (3H, s), 1.43-1.25 (4H, m), 0.54-0.41 (3H, m), 0.32-0.27 (1H, m). MS: [M+H]$^+$=619.

Example 288: 6-{[(1R)-1-(4-chlorophenyl)-7-fluoro-5-[1-hydroxy-1-(1-methylpiperidin-4-yl)ethyl]-1-{[1-(hydroxymethyl)cyclopropyl]methoxy}-3-oxo-2,3-dihydro-1H-isoindol-2-yl]methyl}pyridine-3-carbonitrile (*single isomer separated and isolated)

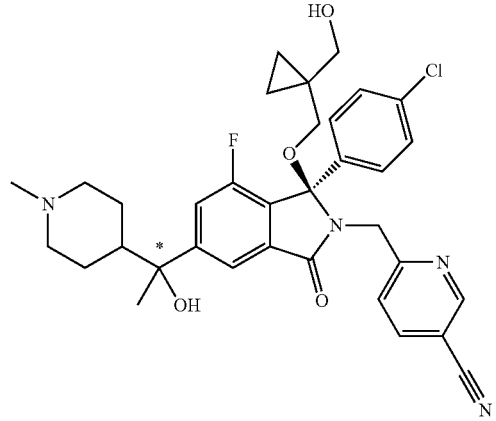 [SMILES: CN1CCC(C(C)(O)c2cc(F)c3c(c2)C(=O)N(Cc2ccc(C#N)cn2)[C@@]3(OCC2(CO)CC2)c2ccc(Cl)cc2)CC1]

The title compound was prepared from 2-(4-chlorobenzoyl)-3-fluoro-5-(1-hydroxy-1-(1-methylpiperidin-4-yl)ethyl)benzoic acid (Preparation 26, derived from (+)-5-(1-(1-(tert-butoxycarbonyl)piperidin-4-yl)-1-hydroxyethyl)-2-(4-chlorobenzoyl)-3-fluorobenzoic acid) using methods similar to those described in Example 280, using cyclopropane-1,1-diyldimethanol instead of 1-(hydroxymethyl)cyclopropanecarboxamide.

Example 288

$^1$H NMR (400 MHz, CDCl$_3$) 8.68 (1H, d), 7.81 (1H, dd), 7.71 (1H, d), 7.42 (1H, d), 7.36 (1H, dd), 7.27 (2H, d), 7.21 (2H, d), 4.54 (2H, s), 3.61 (1H, d), 3.47 (1H, d), 3.33 (1H, d), 2.95-2.83 (3H, m), 2.23 (3H, s), 1.91-1.70 (6H, m), 1.59 (3H, s), 1.43-1.33 (3H, m), 0.54-0.41 (3H, m), 0.32-0.27 (1H, m). MS: [M+H]$^+$=619.

Example 289 and 290: 6-{[(1R)-1-(4-chlorophenyl)-7-fluoro-5-[1-hydroxy-1-(piperidin-4-yl)ethyl]-1-{[1-(hydroxymethyl)cyclopropyl]methoxy}-3-oxo-2,3-dihydro-1H-isoindol-2-yl]methyl}pyridine-3-carbonitrile (*both isomers separated and isolated)

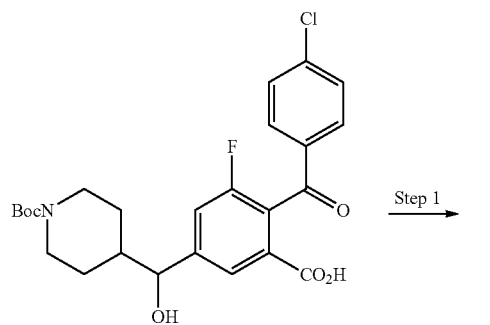

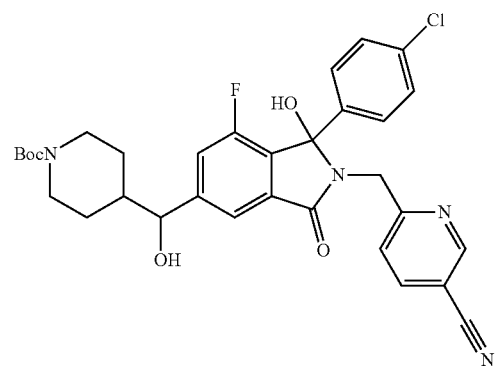

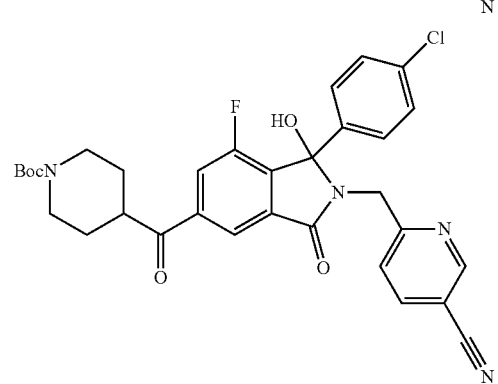

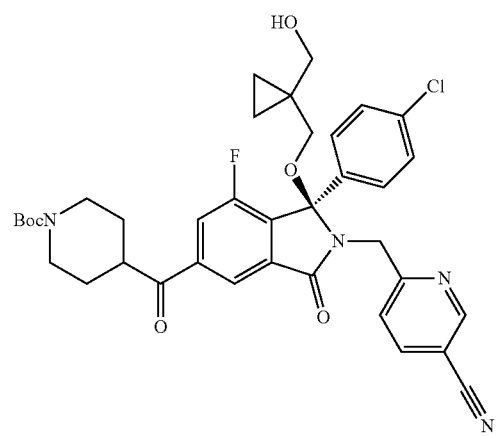

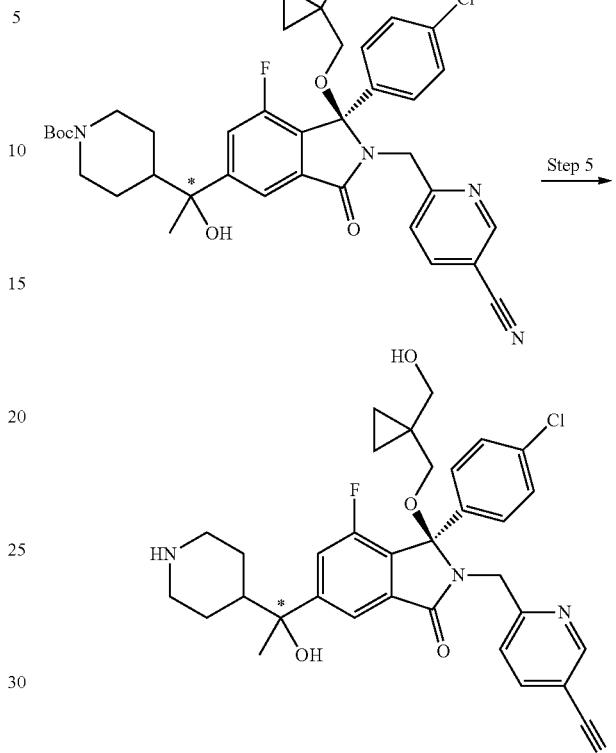

Step 1: tert-Butyl 4-((1-(4-chlorophenyl)-2-((5-cyanopyridin-2-yl)methyl)-7-fluoro-1-hydroxy-3-oxoisoindolin-5-yl)(hydroxy)methyl)piperidine-1-carboxylate The title compound was prepared from 5-((1-(tert-butoxycarbonyl)piperidin-4-yl)(hydroxy)methyl)-2-(4-chlorobenzoyl)-3-fluorobenzoic acid (Preparation 24, step 1) in a similar manner to that described in the Example 280, step 1. MS: [M−H]⁻=605.

Step 2: tert-Butyl 4-(1-(4-chlorophenyl)-2-((5-cyanopyridin-2-yl)methyl)-7-fluoro-1-((1-(hydroxymethyl)cyclopropyl)methoxy)-3-oxoisoindoline-5-carbonyl)piperidine-1-carboxylate Dess-Martin periodinate (2.89 g, 6.8 mmol) was added to a solution of tert-butyl 4-((1-(4-chlorophenyl)-2-((5-cyanopyridin-2-yl)methyl)-7-fluoro-1-hydroxy-3-oxoisoindolin-5-yl)(hydroxy)methyl)piperidine-1-carboxylate (3.4 g, 5.44 mmol) in DCM (110 mL) and the mixture was stirred at RT for 1.25 h. DCM (100 mL) was added and the reaction was quenched with 10% aqueous Na₂S₂O₃ solution (100 mL) and saturated aqueous NaHCO₃ solution (100 mL). The mixture was stirred for 15 min at RT and the layers were separated. The aqueous phase was extracted with DCM and the combined organics were dried (phase separator) and concentrated under reduced pressure to give the title compound (3.15 g) as an orange solid which was used in the next step without further purification. MS: [M−H]⁻=603.

Step 3: (R)-tert-Butyl 4-(1-(4-chlorophenyl)-2-((5-cyanopyridin-2-yl)methyl)-7-fluoro-1-((1-(hydroxymethyl)cyclopropyl)methoxy)-3-oxoisoindoline-5-carbonyl)piperidine-1-carboxylate Using tert-butyl 4-(1-(4-chlorophenyl)-2-((5-cyanopyridin-2-yl)methyl)-7-fluoro-1-((1-(hydroxymethyl)cyclopropyl)methoxy)-3-oxoisoindoline-5-carbonyl)piperidine-1-carboxylate (2.08 g, 3.44 mmol), Step 3 was performed in a similar fashion to Example 2, step 1, using cyclopropane-1,1-diyldimethanol (702 mg, 6.88 mmol) instead of MeOH. The desired iomer was isolated by chiral SCF chromatography as the faster eluting isomers (536 mg). MS: [M+H]⁺ =689.

Step 4: (R)-tert-Butyl 4-(1-(1-(4-chlorophenyl)-2-((5-cyanopyridin-2-yl)methyl)-7-fluoro-1-((1-(hydroxymethyl)cyclopropyl)methoxy)-3-oxoisoindolin-5-yl)-1-hydroxyethyl)piperidine-1-carboxylate (R)-tert-Butyl 4-(1-(4-chlorophenyl)-2-((5-cyanopyridin-2-yl)methyl)-7-fluoro-1-((1-(hydroxymethyl)cyclopropyl)methoxy)-3-oxoisoindoline-5-carbonyl)piperidine-1-carboxylate (60 mg, 0.087 mmol) was stirred in THF (2 mL) at RT under nitrogen. LaCl₃.2LiCl (0.6M in THF, 0.15 mL, 0.087 mmol) was added and the solution stirred at RT for 0.5 h then cooled in an ice bath. MeMgBr (3M in Et₂O, 0.15 mL, 0.44 mmol) was added drop-wise and the red solution was stirred at 0° C. for 40 min and then quenched with saturated aqueous NH₄Cl solution. Water and DCM were added and the layers separated (phase separator) and the organic concentrated in vacuo leaving the title compound (51 mg) which was used in the next step without further purification. MS: [M-Boc]⁻=603.

Step 5: 6-{[(1R)-1-(4-chlorophenyl)-7-fluoro-5-[1-hydroxy-1-(piperidin-4-yl)ethyl]-1-{[1-(hydroxymethyl)cyclopropyl]methoxy}-3-oxo-2,3-dihydro-1H-isoindol-2-yl]methyl}pyridine-3-carbonitrile The title compound was prepared from tert-butyl 4-(1-(1-(4-chlorophenyl)-2-((5-cyanopyridin-2-yl)methyl)-7-fluoro-1-((1-(hydroxymethyl)cyclopropyl)methoxy)-3-oxoisoindolin-5-yl)-1-hydroxyethyl)piperidine-1-carboxylate in a similar manner to that described in Preparation 25, step 1. Separation via chiral SFC gave the title compounds.

Example 289 *Slower Eluting Isomer

¹H NMR (400 MHz, CDCl₃) 8.68 (1H, d), 7.81 (1H, dd), 7.71 (1H, s), 7.42 (1H, d), 7.38-7.33 (1H, m), 7.29-7.19 (4H, m), 4.54 (2H, s), 3.60 (1H, d), 3.48 (1H, d), 3.33 (1H, d), 3.10 (2H, dd), 2.94 (1H, d), 2.60-2.47 (2H, m), 1.91-1.82 (2H, m), 1.77-1.67 (2H, m), 1.57 (3H, s), 1.38-1.20 (4H, m), 0.54-0.41 (3H, m), 0.32-0.27 (1H, m). MS: [M+H]⁺=606.

Example 290 *Faster Eluting Isomer

¹H NMR (400 MHz, CDCl₃) 8.68 (1H, d), 7.81 (1H, dd), 7.68 (1H, d), 7.43 (1H, d), 7.39-7.36 (1H, m), 7.28 (2H, d), 7.22 (2H, d), 4.54 (2H, s), 3.61 (1H, d), 3.47 (1H, d), 3.32 (1H, d), 3.10 (2H, dd), 2.91 (1H, d), 2.60-2.49 (2H, m), 1.73-1.68 (5H, m), 1.58 (3H, s), 1.38 (1H, d), 1.29-1.20 (2H, m), 0.54-0.41 (3H, m), 0.32-0.28 (1H, m). MS: =623 [M+H]⁺=606.

Example 291 and 292: 6-{[(1R)-5-[1-(1-acetylpiperidin-4-yl)-1-hydroxyethyl]-1-(4-chlorophenyl)-7-fluoro-1-{[1-(hydroxymethyl)cyclopropyl]methoxy}-3-oxo-2,3-dihydro-1H-isoindol-2-yl]methyl}pyridine-3-carbonitrile (*both isomers separated and isolated)

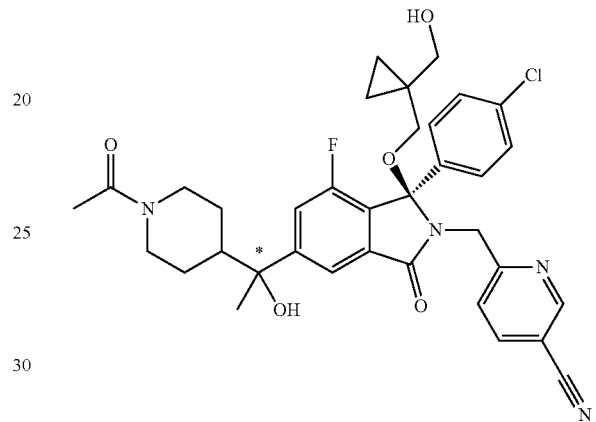

The title compound was prepared from 6-((1-(4-chlorophenyl)-7-fluoro-5-(1-hydroxy-1-(piperidin-4-yl)ethyl)-1-((1-(hydroxymethyl)cyclopropyl) methoxy)-3-oxoisoindolin-2-yl)methyl)nicotinonitrile (Example 289 and 290, step 5, before chiral SFC) in a similar manner to that described in Example 300 step 2. Chiral preparative HPLC gave the title compounds.

Example 291 *Slower Eluting Isomer

¹H NMR (400 MHz, CDCl₃) 8.70-8.68 (1H, m), 7.82 (1H, dd), 7.67 (1H, d), 7.44 (1H, d), 7.37 (1H, dd), 7.30-7.27 (2H, m), 7.23 (2H, dd), 4.76-4.62 (1H, m), 4.55 (2H, d), 3.82 (1H, dd), 3.60 (1H, dd), 3.49 (1H, dd), 3.32 (1H, dd), 2.91 (2H, d), 2.48-2.37 (1H, m), 2.22 (1H, dd), 2.051, 2.045 (3H, 2s), 1.83-1.77 (3H, m), 1.61, 1.60 (3H, 2s), 1.49-1.17 (3H, m), 0.54-0.51 (2H, m), 0.45-0.40 (1H, m), 0.33-0.26 (1H, m). MS: [M+H]⁺=646.

Example 292 *Faster Eluting Isomer

¹H NMR (400 MHz, CDCl₃) 8.69 (1H, dd), 7.84-7.80 (1H, m), 7.70 (1H, d), 7.43 (1H, dd), 7.34 (1H, dd), 7.29 (1H, s), 7.27-7.20 (3H, m), 4.76-4.61 (1H, m), 4.54 (2H, s), 3.90-3.75 (1H, m), 3.62-3.46 (2H, m), 3.34 (1H, dd), 2.99-2.91 (2H, m), 2.49-2.36 (1H, m), 2.25-2.18 (1H, m), 2.06 and 2.05 (3H, 2s), 1.82-1.74 (3H, m), 1.60 (3H, s), 1.40 (1H, dd), 1.29-1.18 (2H, m), 0.54-0.51 (2H, m), 0.42 (1H, d), 0.33-0.26 (1H, m). MS: [M+H]⁺=646.

Example 293: (3R)-6-[1-(1-acetylpiperidin-4-yl)-1-hydroxyethyl]-3-(4-chlorophenyl)-2-[(5-chloropyridin-2-yl)methyl]-4-fluoro-3-methoxy-2,3-dihydro-1H-isoindol-1-one (Example isolated as a single isomer at the position shown*)

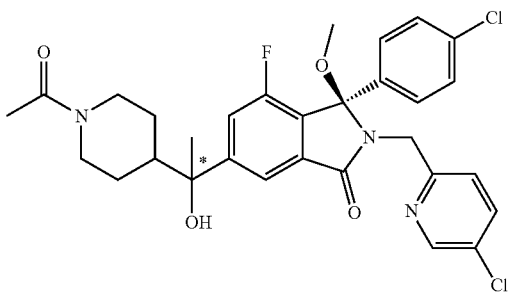 [SMILES: CO[C@]1(c2ccc(Cl)cc2)c2c(F)cc(C(C)(O)C3CCN(C(C)=O)CC3)cc2C(=O)N1Cc1ccc(Cl)cn1]

Acetyl chloride (95 µL, 1.33 mmol) was added to a mixture of 3-(4-chlorophenyl)-2-[(5-chloro-2-pyridyl)methyl]-4-fluoro-6-[1-hydroxy-1-(4-piperidyl)ethyl]-3-methoxy-isoindolin-1-one (650 mg, 1.20 mmol) (Example 286, step 2) and diisopropylethylamine (630 µL, 3.61 mmol) in DCM (15 mL). The solution was stirred at RT for 1 h, then diluted with DCM and washed with saturated sodium hydrogen carbonate solution. The organic phase was dried (MgSO$_4$), filtered and concentrated under reduced pressure. The crude product was purified by column chromatography on silica, eluting with a gradient of 0-3% methanol in DCM to afford cream foam (550 mg). The diastereomeric mixture was separated by chiral preparative HPLC to afford the title compound (190 mg, 54% yield).

Example 293 *Slower Eluting Isomer $^1$H NMR (400 MHz, CDCl$_3$) 8.37 (1H, dd), 7.71 (1H, s), 7.50 (1H, dd), 7.33 (1H, dd), 7.28-7.20 (5H, m), 4.75-4.60 (2H, m), 4.41 (1H, dd), 3.87-3.76 (1H, m), 3.02-2.88 (1H, m), 2.91 (3H, s), 2.49-2.36 (1H, m), 2.05 (3H, d), 1.83-1.74 (3H, m), 1.61 (3H, s), 1.50-1.18 (3H, m). MS: [M+H]$^+$=586.

Example 294: (3R)-3-(4-chlorophenyl)-2-[(5-chloropyridin-2-yl)methyl]-4-fluoro-6-[1-hydroxy-1-(1-methanesulfonylpiperidin-4-yl)ethyl]-3-methoxy-2,3-dihydro-1H-isoindol-1-one (Example isolated as a single isomer at the position shown*)

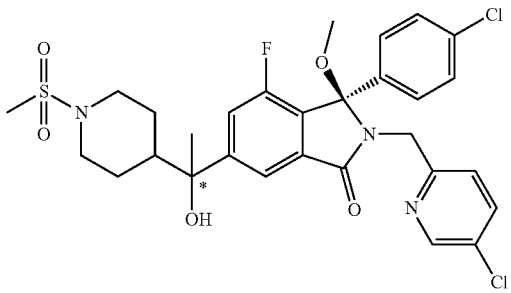 [SMILES: CO[C@]1(c2ccc(Cl)cc2)c2c(F)cc(C(C)(O)C3CCN(S(C)(=O)=O)CC3)cc2C(=O)N1Cc1ccc(Cl)cn1]

The title compound was made in a similar fashion to Example 293, using methane sulfonyl chloride instead of acetyl chloride. $^1$H NMR (400 MHz, CDCl$_3$) 8.37 (1H, d), 7.71 (1H, d), 7.51 (1H, dd), 7.34 (1H, dd), 7.28-7.20 (5H, m), 4.65 (1H, d), 4.40 (1H, d), 3.89-3.78 (2H, m), 2.91 (3H, s), 2.75 (3H, s), 2.62-2.50 (2H, m), 1.82 (1H, d), 1.75 (1H, s), 1.75-1.65 (1H, m), 1.61 (3H, s), 1.52-1.40 (3H, m). MS: [M+H]$^+$=622.

Example 295: (3R)-3-(4-chlorophenyl)-2-[(5-chloropyridin-2-yl)methyl]-4-fluoro-6-{1-hydroxy-1-[1-(1,3-oxazole-2-carbonyl)piperidin-4-yl]ethyl}-3-methoxy-2,3-dihydro-1H-isoindol-1-one (Example isolated as a single isomer at the position shown*)

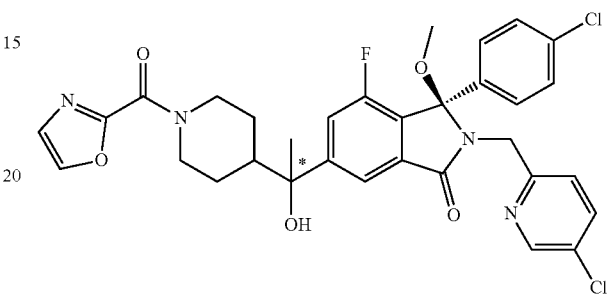

The title compound was made in a similar fashion to Example 293, using 2-oxazole carboxylic acid, HATU, DMF instead of acetyl chloride/DCM.

Example 295 *Slower Eluting Isomer $^1$H NMR (400 MHz, DMSO) 8.45 (1H, m), 8.33 (1H, d), 7.83-7.78 (2H, m), 7.53 (1H, dd), 7.47 (1H, d), 7.39-7.28 (5H, m), 5.35 (1H, s), 4.68-4.43 (4H, m), 3.17-3.01 (1H, m), 2.94 (3H, d), 2.83-2.68 (1H, m), 2.07-2.00 (1H, m), 1.91-1.80 (1H, m), 1.54 (3H, d), 1.45-1.25 (3H, m). MS: [M+H]$^+$= 639.

Example 296: (3R)-3-(4-chlorophenyl)-2-[(5-chloropyridin-2-yl)methyl]-4-fluoro-6-{1-hydroxy-1-[1-(2-hydroxyacetyl)piperidin-4-yl]ethyl}-3-methoxy-2,3-dihydro-1H-isoindol-1-one (Example isolated as a single isomer at the position shown*)

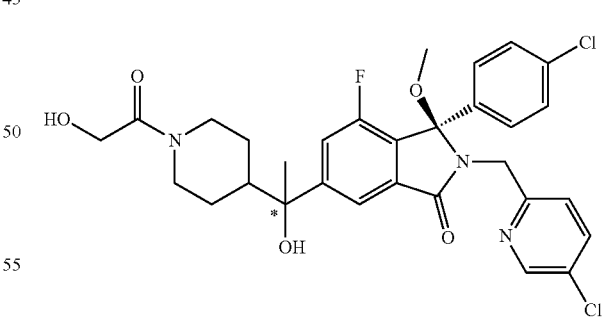

The title compound was made in a similar fashion to Example 293, using acetoxyacetic acid, HATU, DMF instead of acetyl chloride/DCM, followed by treatment with aqueous lithium hydroxide to furnish the hydroxyacetate.

Example 296 *Faster Eluting Isomer $^1$H NMR (400 MHz, DMSO) 8.46 (1H, d), 7.81 (2H, dd), 7.52 (1H, d), 7.38 (2H, d), 7.35-7.29 (3H, m), 5.31 (1H, s), 4.58 (1H, d), 4.49-4.37 (2H, m), 4.40 (1H, d), 4.13-4.03 (2H, m), 3.78-3.63 (1H, dd), 2.94 (3H, s), 2.94-2.75 (1H, m), 2.60-2.45 (1H, m), 1.97-1.89 (1H, m), 1.81-1.75 (1H, m), 1.53 (3H, s), 1.33-1.13 (3H, m). MS: [M+H]$^+$=602.

Example 297: 6-{[(1R)-5-[1-(1-acetylpiperidin-4-yl)-1-hydroxyethyl]-1-(4-chlorophenyl)-7-fluoro-1-methoxy-3-oxo-2,3-dihydro-1H-isoindol-2-yl]methyl}pyridine-3-carbonitrile (Example isolated as a single isomer at the position shown*)

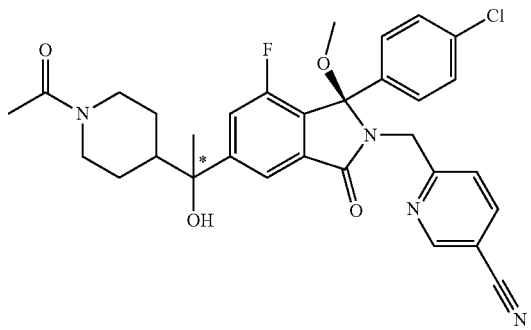 [SMILES: CO[C@]1(c2ccc(Cl)cc2)c2c(F)cc(C(C)(O)C3CCN(C(C)=O)CC3)cc2C(=O)N1Cc1ccc(C#N)cn1]

Prepared in a similar manner to that described for Example 280 and 293 from (−)-5-[1-(1-tert-butoxycarbonyl-4-piperidyl)-1-hydroxy-ethyl]-2-(4-chlorobenzoyl)-3-fluoro-benzoic acid (Preparation 24), but using MeOH instead of 1-hydroxymethyl-cyclopropanecarboxylic acid amide.

Example 297 *Faster Eluting Isomer $^1$H NMR (400 MHz, DMSO) 8.86 (1H, d), 8.19 (1H, dd), 7.82 (1H, d), 7.53 (1H, d), 7.46 (1H, d), 7.39-7.31 (4H, m), 5.30 (1H, d), 4.64 (1H, d), 4.53 (1H, d), 4.54-4.39 (1H, m), 3.90-3.81 (1H, dd), 3.00-2.88 (1H, m), 2.98 (3H, s), 2.48-2.34 (1H, m), 2.00 (3H, d), 1.95-1.87 (1H, m), 1.79-1.72 (1H, m), 1.53 (3H, s), 1.32-1.09 (3H, m). MS: [M−H]$^+$=577.

Example 298 and 299: (3R)-3-(4-chlorophenyl)-2-[(5-chloropyridin-2-yl)methyl]-6-(1-{1-[2-(dimethylamino)acetyl]piperidin-4-yl}-1-hydroxyethyl)-4-fluoro-3-methoxy-2,3-dihydro-1H-isoindol-1-one (Example isolated as a single isomer at the position shown*)

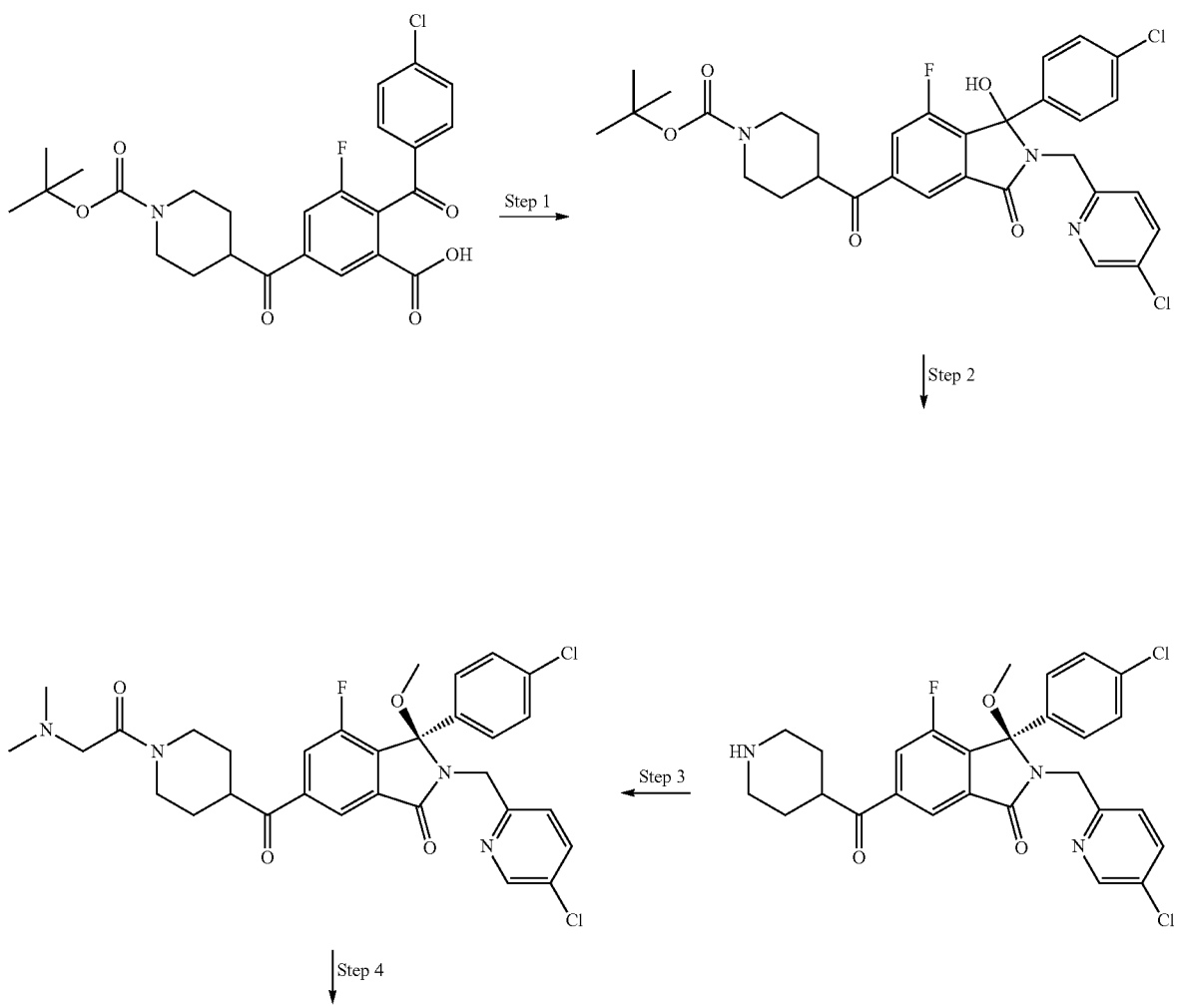

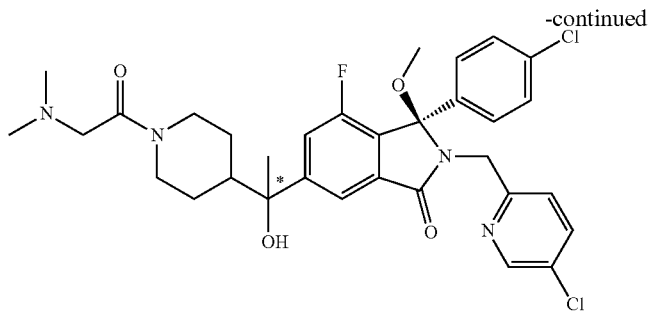

Step 1 and Step 2

Starting from (Preparation 24, Step 2), step 1 and 2 were performed using conditions similar to those described in Example 286. Chiral preparative HPLC gave the title compound (slow-running isomer). MS: [M+H]⁺=528.

Step 3: 3R-3-(4-Chlorophenyl)-2-[(5-chloro-2-pyridyl)methyl]-6-[1-[2-(dimethylamino)acetyl]piperidine-4-carbonyl]-4-fluoro-3-methoxy-isoindolin-1-one Prepared in a similar manner to that described for Example 293, using N,N-dimethylaminoacetyl chloride hydrochloride instead of acetyl chloride. MS: [M+H]⁺=613.

Step 4: (3R)-3-(4-chlorophenyl)-2-[(5-chloropyridin-2-yl)methyl]-6-(1-{1-[2-(dimethylamino)acetyl]piperidin-4-yl}-1-hydroxyethyl)-4-fluoro-3-methoxy-2,3-dihydro-1H-isoindol-1-one Prepared in a similar manner to that described for Preparation 23, step 3. Chiral preparative HPLC gave the title compounds (two isomers).

Example 298 *Fast Running Isomer $^1$H NMR (400 MHz, CDCl$_3$) 8.37 (1H, dd), 7.71 (1H, d), 7.50 (1H, dd), 7.33 (1H, d), 7.28-7.18 (5H, m), 4.72-4.60 (2H, m), 4.40 (1H, dd), 4.13 (1H, dd), 3.14-2.98 (2H, m), 2.91 (3H, s), 2.87-2.81 (1H, m), 2.49-2.35 (1H, m), 2.23 (6H, s), 1.86-1.73 (3H, m), 1.57 (3H, s), 1.60-1.47 (1H, m), 1.33-1.16 (2H, m). MS: [M+H]⁺=629.

Example 299 *Slow Running Isomer $^1$H NMR (400 MHz, CDCl$_3$) 8.38 (1H, s), 7.75-7.70 (1H, m), 7.51 (1H, dd), 7.35 (1H, d), 7.29-7.19 (5H, m), 4.72-4.60 (2H, m), 4.44-4.36 (1H, m), 4.15 (1H, dd), 3.15-2.98 (2H, m), 2.93 (3H, s), 2.88-2.83 (1H, m), 2.47-2.37 (1H, m), 2.25 (6H, d), 1.85-1.74 (3H, m), 1.60 (3H, s), 1.46-1.23 (3H, m). MS: [M+H]⁺=629.

Example 300: (3R)-6-[1-(1-acetylpiperidin-4-yl)-1-hydroxyethyl]-3-(4-chlorophenyl)-2-[(5-chloropyridin-2-yl)methyl]-4-fluoro-3-[(1-hydroxycyclopropyl)methoxy]-2,3-dihydro-1H-isoindol-1-one (Example isolated as a single isomer at the position shown*)

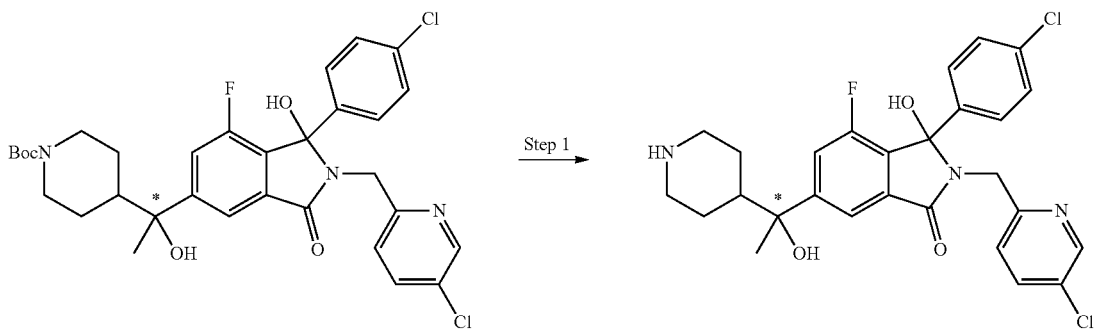

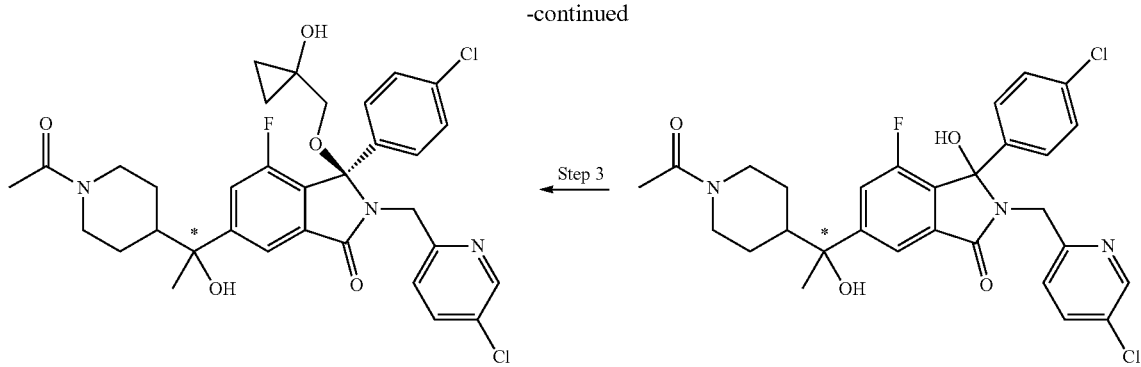

Step 1: 3-(4-Chlorophenyl)-2-((5-chloropyridin-2-yl)methyl)-4-fluoro-3-hydroxy-6-(1-hydroxy-1-(piperidin-4-yl)ethyl)isoindolin-1-one To a round bottomed flask was added tert-butyl 4-(1-(1-(4-chlorophenyl)-2-((5-chloropyridin-2-yl)methyl)-7-fluoro-1-hydroxy-3-oxoisoindolin-5-yl)-1-hydroxyethyl)piperidine-1-carboxylate (286, step 1) (500 mg, 0.80 mmol) and 4M HCl dioxane (5 mL). The reaction was stirred at RT for 1 h. A saturated solution of NaHCO₃ (10 mL) was added and the resultant mixture extracted with EtOAc (2×25 mL) dried (MgSO₄), filtered and the solvent removed in vacuo. The crude mixture was taken up in MeOH (5 mL) and loaded onto an SCXII column (10 g), the column wash flushed with MeOH (20 mL) and then 3M NH₃ MeOH (20 mL). The ammonia wash was concentrated in vacuo to give the title compound (286 mg, 56% yield) as a yellow solid. MS: [M−H]⁻=628.

Step 2: 6-(1-(1-Acetylpiperidin-4-yl)-1-hydroxyethyl)-3-(4-chlorophenyl)-2-((5-chloropyridin-2-yl)methyl)-4-fluoro-3-hydroxyisoindolin-1-one A round bottomed flask containing 3-(4-chlorophenyl)-2-((5-chloropyridin-2-yl)methyl)-4-fluoro-3-hydroxy-6-(1-hydroxy-1-(piperidin-4-yl)ethyl)isoindolin-1-one (286 mg, 0.55 mmol) was flushed with N₂. The solid was dissolved in DCM at RT and stirred. To this was added, in sequence; acetic acid (99 mg, 1.65 mmol), DIPEA (426 mg, 3.3 mmol) and T3P (1:1 DMF, 349 mg, 1.1 mmol). The reaction was stirred for a further 30 min. The reaction was then quenched with H₂O (30 mL), extracted with EtOAc (2×25 mL), dried (MgSO₄), filtered and the solvent removed in vacuo. The crude solid was taken up in DCM and loaded onto a 25 g SNAP silica cartridge and eluted with MeOH in DCM (0 to 5%). Fractions containing product were concentrated in vacuo to give a yellow solid (249 mg 81% yield). MS: [M−OH]⁺=554.

Step 3: (3R)-6-[1-(1-acetylpiperidin-4-yl)-1-hydroxyethyl]-3-(4-chlorophenyl)-2-[(5-chloropyridin-2-yl)methyl]-4-fluoro-3-[(1-hydroxycyclopropyl)methoxy]-2,3-dihydro-1H-isoindol-1-one 6-(1-(1-Acetylpiperidin-4-yl)-1-hydroxyethyl)-3-(4-chlorophenyl)-2-((5-chloropyridin-2-yl)methyl)-4-fluoro-3-hydroxyisoindolin-1-one (199 mg, 0.34 mmol) was reacted with 1-(hydroxymethyl)cyclopropanol (90 mg, 1.02 mmol) in a similar manner to that described in Example 3, step 2.

The diastereomeric mixture was separated by chiral SFC to afford the title compound as a white solid (3 mg, 1% yield).

¹H NMR (400 MHz, CDCl₃) 8.36 (1H, dd), 7.65 (1H, d), 7.56 (1H Hz), 7.38-7.31 (4H, m), 7.28-7.24 (2H, m), 4.73-4.63 (1H, m), 4.54-4.40 (2H, m), 4.00 (1H, s), 3.86-3.69 (1H, m), 3.51-3.46 (1H, m), 3.01-2.90 (2H, m), 2.47-2.36 (1H, m), 2.05 (3H), 1.84-1.72 (3H, m), 1.58 (3H, d), 1.47-1.16 (3H, m), 0.90-0.76 (2H, m), 0.58-0.52 (1H, m), 0.41-0.34 (1H, m). MS: [M+H]⁺=642.

Example 301: 1-({[(1R)-5-[1-(1-acetylpiperidin-4-yl)-1-hydroxyethyl]-1-(4-chlorophenyl)-2-[(5-chloropyridin-2-yl)methyl]-7-fluoro-3-oxo-2,3-dihydro-1H-isoindol-1-yl]oxy}methyl)cyclopropane-1-carbonitrile (Example isolated as a single isomer at the position shown*)

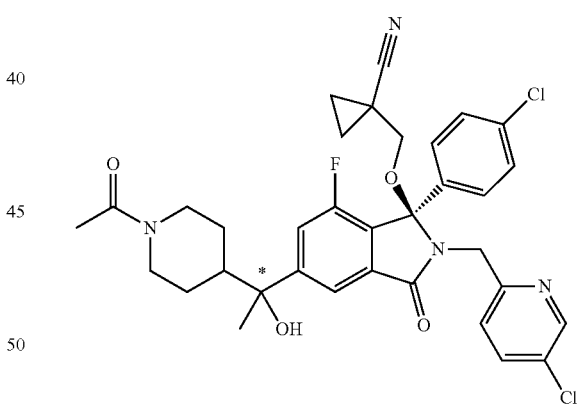

Starting from tert-butyl 4-(1-(1-(4-chlorophenyl)-2-((5-chloropyridin-2-yl)methyl)-7-fluoro-1-hydroxy-3-oxoisoindolin-5-yl)-1-hydroxyethyl)piperidine-1-carboxylate (Example 286, step 1) the title compound was prepared using methods similar to those described in Example 286 and Example 300. ¹H NMR (400 MHz, CDCl₃) 8.38 (1H, dd), 7.69 (1H, s), 7.56-7.52 (1H, m), 7.38-7.32 (3H, m), 7.28-7.21 (3H, m), 4.75-4.60 (2H, m), 3.87 (1H, s), 3.79 (1H, s), 3.33 (1H, d), 3.05-2.89 (2H, m), 2.48-2.36 (1H, m), 2.05 (3H, d), 1.84-1.77 (2H, m), 1.75 (1H, s), 1.59 (3H, s), 1.47-1.17 (5H, m), 0.84-0.79 (2H, m). MS: [M+H]⁺=651.

Example 302 and 303: 1-({[(1R)-5-[1-(1-acetylpiperidin-4-yl)-1-hydroxyethyl]-1-(4-chlorophenyl)-2-[(5-chloropyridin-2-yl)methyl]-7-fluoro-3-oxo-2,3-dihydro-1H-isoindol-1-yl]oxy}methyl)cyclopropane-1-carboxamide (Example isolated as a single isomer at the position shown*)

dryness. The residue was dissolved in DCM (20 mL) and DIPEA (0.68 mL, 3.94 mmol) added followed by dropwise addition of 1M acetyl chloride in DCM (0.68 mL) at RT under nitrogen. After 1 h, the mixture was washed with saturated aqueous NaHCO₃ (20 mL) and the organics dried (MgSO₄) and evaporated. Chromatography using 0-15% MeOH in EtOAc as the eluent gave (R)-1-(((5-(1-acetylpi-

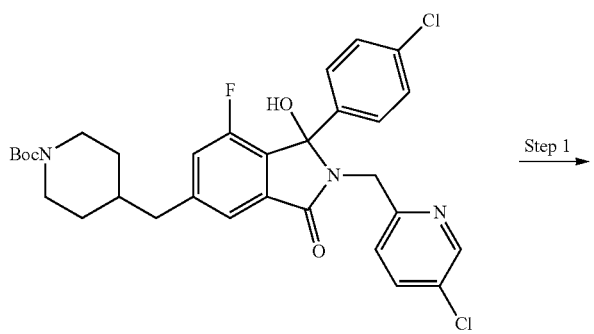

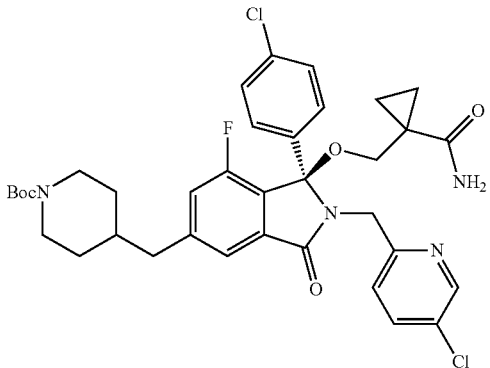

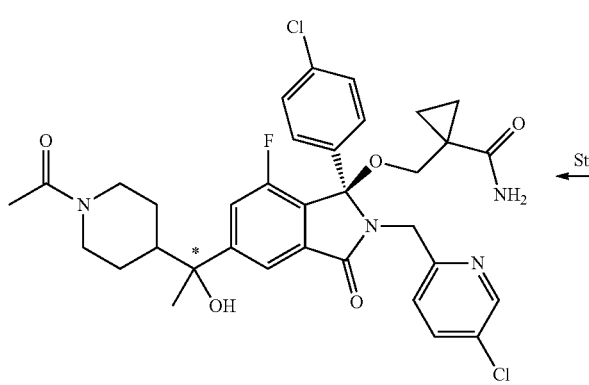

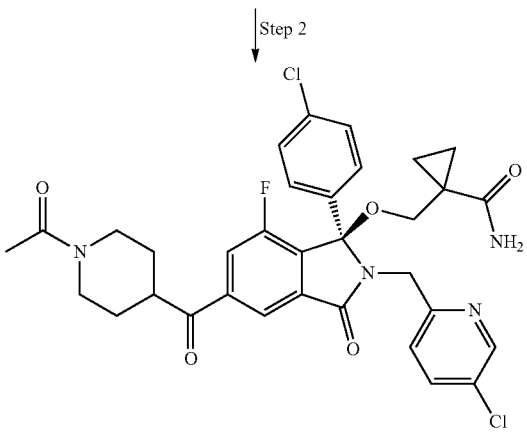

Step 1: (R)-tert-Butyl 4-(1-((1-carbamoylcyclopropyl)methoxy)-1-(4-chlorophenyl)-2-((5-chloropyridin-2-yl)methyl)-7-fluoro-3-oxoisoindoline-5-carbonyl)piperidine-1-carboxylate Starting from tert-butyl 4-(1-(4-chlorophenyl)-2-((5-chloropyridin-2-yl)methyl)-7-fluoro-1-hydroxy-3-oxoisoindoline-5-carbonyl)piperidine-1-carboxylate (prepared in Examples 298 and 299, step 1) (10 g, 16.28 mmol) Step 1 was performed in a similar fashion to Example 4 step 1, to give product (750 mg, 21%). MS [M-1-(hydroxymethyl) cyclopropanecarboxamide]⁺=596.

Step 2: (R)-1-(((5-(1-Acetylpiperidine-4-carbonyl)-1-(4-chlorophenyl)-2-((5-chloropyridin-2-yl)methyl)-7-fluoro-3-oxoisoindolin-1-yl)oxy)methyl)cyclopropanecarboxamide A solution of (R)-tert-butyl 4-(1-((1-carbamoylcyclopropyl)methoxy)-1-(4-chlorophenyl)-2-((5-chloropyridin-2-yl)methyl)-7-fluoro-3-oxoisoindoline-5-carbonyl)piperidine-1-carboxylate (750 mg, 1.05 mmol) in 4M HCl in dioxan (20 mL) was stirred at RT for 15 minutes then evaporated to peridine-4-carbonyl)-1-(4-chlorophenyl)-2-((5-chloropyridin-2-yl)methyl)-7-fluoro-3-oxoisoindolin-1-yl)oxy) methyl)cyclopropanecarboxamide (545 mg, 79%). MS [M+H]⁺=653.

Step 3: 1-({[(1R)-5-[1-(1-acetylpiperidin-4-yl)-1-hydroxyethyl]-1-(4-chlorophenyl)-2-[(5-chloropyridin-2-yl)methyl]-7-fluoro-3-oxo-2,3-dihydro-1H-isoindol-1-yl]oxy}methyl)cyclopropane-1-carboxamide The title compounds were prepared from (R)-1-(((5-(1-acetylpiperidine-4-carbonyl)-1-(4-chlorophenyl)-2-((5-chloropyridin-2-yl)methyl)-7-fluoro-3-oxoisoindolin-1-yl)oxy)methyl)cyclopropanecarboxamide (540 mg, 0.828 mmol) using the method of Examples 199 and 200, step 5 to afford the racemate (380 mg, 61%). Isomer separation by SFC gave the title compounds.

Example 302: *Fast Running Isomer

¹H NMR (400 MHz, d6-DMSO) 8.35 (1H, d), 7.73 (2H, d), 7.47 (1H, d), 7.31 (2H, d), 7.23 (3H, d), 7.05 (1H, s), 6.85-6.84 (1H, m), 5.23 (1H, s), 4.48-4.33 (3H, m), 3.87-3.72 (1H, m), 3.47 (1H, dd), 3.07 (1H, dd), 2.96-2.79 (1H, m), 2.42-2.27 (1H, m), 1.95 (3H, d), 1.89-1.81 (1H, m), 1.69 (1H, d), 1.48 (3H, s), 1.26-1.16 (3H, m), 0.99-0.90 (2H, m), 0.57-0.46 (2H, m). MS [M+H]$^+$=669.

Example 303: *Slow Running Isomer $^1$H NMR (400 MHz, d6-DMSO) 8.36 (1H, d), 7.74 (2H, dd), 7.47 (1H, d), 7.32 (2H, d), 7.24 (3H, d), 7.05 (1H, s), 6.84-6.83 (1H, m), 5.25 (1H, d), 4.49-4.41 (3H, m), 3.79 (1H, dd), 3.47 (1H, d), 3.06 (1H, d), 2.95-2.81 (1H, m), 2.42-2.29 (1H, m), 1.95 (3H, d), 1.88-1.81 (1H, m), 1.69 (1H, dd), 1.47 (3H, s), 1.25-1.14 (3H, m), 1.07-0.87 (2H, m), 0.55-0.44 (2H, m). MS [M+H]$^+$=669.

Example 304: (3R)-3-(4-chlorophenyl)-2-[(5-chloro-pyridin-2-yl)methyl]-4-fluoro-6-[1-hydroxy-1-(1-methylpiperidin-4-yl)ethyl]-3-methoxy-2,3-dihydro-1H-isoindol-1-one (Example isolated as a single isomer at the position shown*)

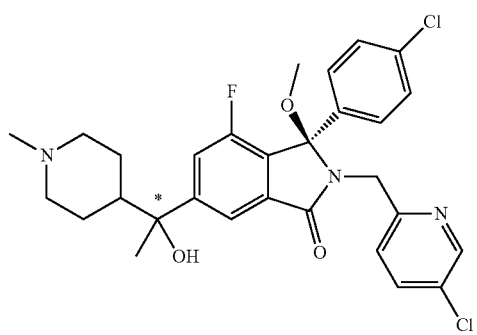 [SMILES: CO[C@]1(c2ccc(Cl)cc2)c2c(F)cc(C(C)(O)C3CCN(C)CC3)cc2C(=O)N1Cc1ccc(Cl)cn1]

Starting from from 2-(4-chlorobenzoyl)-3-fluoro-5-(1-hydroxy-1-(1-methylpiperidin-4-yl)ethyl)benzoic acid (Preparation 25), the title compound was prepared using procedures similar to those described in Example 280, but using 5-chloropyridine-2-yl)methaneamine dihydrochloride and methanol as the appropriate amine and alcohol respectively. $^1$H NMR (400 MHz, CDCl$_3$) 8.34 (1H, d), 7.94 (1H, d), 7.66 (1H, dd), 7.48 (1H, dd), 7.25-7.14 (5H, m), 7.11 (1H, d), 4.60 (1H, d), 4.47 (1H, d), 2.88 (2H, dd), 2.81 (3H, s), 2.23 (3H, s), 1.90-1.58 (7H, m), 1.45-1.35 (3H, m); OH not observed MS: [M+H]$^+$=558.

Example 305: 1-({[(1R)-1-(4-chlorophenyl)-2-[(5-chloropyridin-2-yl)methyl]-7-fluoro-5-[1-hydroxy-1-(1-methylpiperidin-4-yl)ethyl]-3-oxo-2,3-dihydro-1H-isoindol-1-yl]oxy}methyl)cyclopropane-1-carboxamide-one (Example isolated as a single isomer at the position shown*)

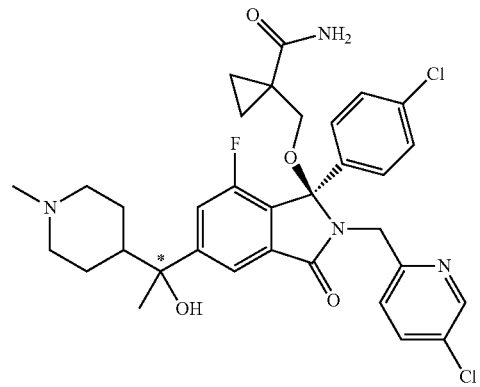 [SMILES: CN1CCC(C(C)(O)c2cc(F)c3c(c2)C(=O)N(Cc2ccc(Cl)cn2)[C@@]3(OCC2(C(N)=O)CC2)c2ccc(Cl)cc2)CC1]

The title compound was prepared from from (2-(4-chlorobenzoyl)-3-fluoro-5-(1-hydroxy-1-(1-methylpiperidin-4-yl)ethyl)benzoic acid (Preparation 25) by using procedures similar to those described in Example 280, but using 1-hydroxymethyl-cyclopropanecarboxylic acid amide instead of MeOH. The enantiomers were separated via chrial HPLC.

Example 305 (*Slower Running Isomer) (38 mg)

$^1$H NMR (400 MHz, MeOD) 8.33 (1H, d), 7.82 (1H, s), 7.69 (1H, dd), 7.51-7.49 (1H, m), 7.35-7.25 (5H, m), 4.54 (2H, d), 3.60 (1H, d), 3.15 (1H, d), 2.91 (2H, dd), 2.23 (3H, s), 2.03-1.89 (2H, m), 1.80 (1H, d), 1.71-1.62 (1H, m), 1.59 (3H, s), 1.45-1.38 (3H, m), 1.24-1.17 (1H, m), 1.13-1.06 (1H, m), 0.72-0.58 (2H, m); MS: [M+H]$^+$=641.

Example 306: 1-({[(1R)-1-(4-chlorophenyl)-2-[(5-chloropyridin-2-yl)methyl]-7-fluoro-5-[1-hydroxy-1-(1-methylpiperidin-4-yl)ethyl]-3-oxo-2,3-dihydro-1H-isoindol-1-yl]oxy}methyl)cyclopropane-1-carboxamide-one (Example isolated as a single isomer at the position shown*)

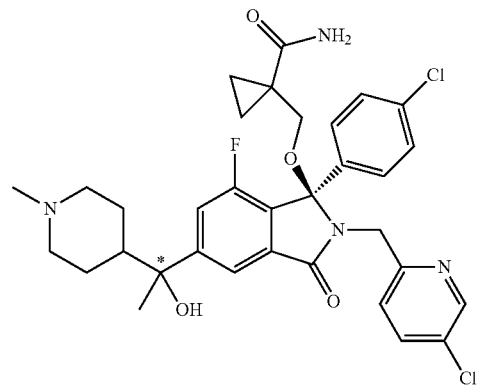 [SMILES: CN1CCC(C(C)(O)c2cc(F)c3c(c2)C(=O)N(Cc2ccc(Cl)cn2)[C@@]3(OCC2(C(N)=O)CC2)c2ccc(Cl)cc2)CC1]

Using Preparation 26 (2-(4-chlorobenzoyl)-3-fluoro-5-(1-hydroxy-1-(1-methylpiperidin-4-yl)ethyl)benzoic), the title compound was prepared by using procedures similar to those described in Example 280. The enantiomers were separated via chrial HPLC.

Example 306 (*Slower Running Isomer) (57 mg)

$^1$H NMR (400 MHz, d6-DMSO) $^1$H NMR (400 MHz, DMSO) 8.35 (1H, d), 7.75-7.72 (2H, m), 7.46 (1H, d), 7.31 (2H, d), 7.23 (3H, d), 7.05 (1H, br s), 6.84 (1H, br s), 4.47 (2H, s), 3.45 (1H, d), 3.08 (1H, d), 2.78 (1H, d), 2.72-2.67 (1H, m), 2.08 (3H, s), 1.76-1.58 (3H, m), 1.47 (4H, s), 1.39-1.16 (4H, m), 1.00-0.88 (2H, m), 0.57-0.42 (2H, m); MS: [M+H]$^+$=641.

Examples 307 and 308: (3R)-3-(4-chlorophenyl)-2-[(5-chloropyridin-2-yl)methyl]-4-fluoro-6-[1-hydroxy-1-(1-methylazetidin-3-yl)ethyl]-3-methoxy-2,3-dihydro-1H-isoindol-1-one (*both isomers separated and isolated)

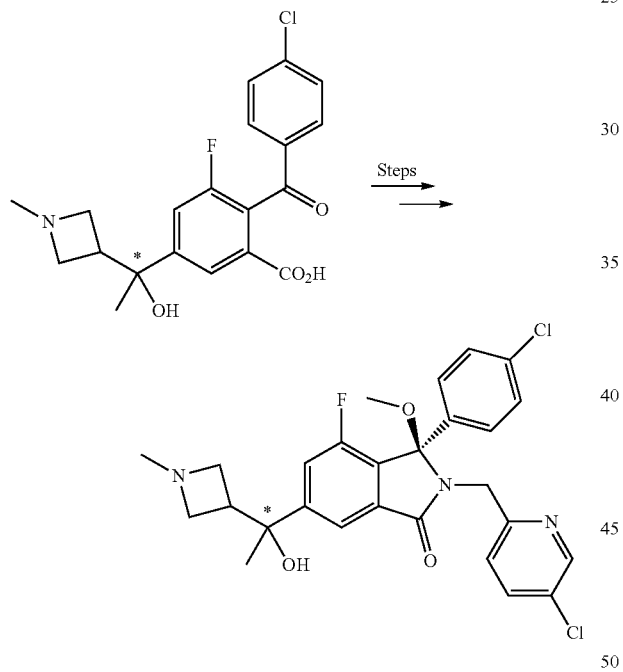

Starting from both isomers of 2-(4-chlorobenzoyl)-3-fluoro-5-[1-hydroxy-1-(1-methylazetidin-3-yl)ethyl]benzoic acid [prepared from Preparation 27 (Fast running isomer A and slow running isomer B) using methods similar to those describe in Preparation 25 and 26], the title compound was prepared using procedures similar to those described in Example Example 304. In the case of iomer (B), SOCl$_2$/MeOH was used instead of InBr$_3$/MeOH. In this way, Preparation 27 [Fast running isomer (Isomer A)] was used to make Example 307 and Preparation 27 [Slow running isomer (Isomer B)] was used to make Example 308.

Example 307

$^1$H NMR (400 MHz, CDCl$_3$) 8.36 (1H, d), 7.68 (1H, d), 7.53-7.47 (2H, m), 7.27-7.18 (5H, m), 5.30 (1H, s), 4.63 (1H, d), 4.39 (1H, d), 3.49-3.45 (1H, m), 3.21 (1H, dd), 2.91 (5H, s), 2.67-2.61 (1H, m), 2.24 (3H, s), 1.50 (3H, s). MS [M+H]$^+$=530.

Example 308

$^1$H NMR (400 MHz, CDCl$_3$) 8.36 (1H, d), 7.70 (1H, d), 7.51-7.47 (2H, m), 7.28-7.18 (5H, m), 5.36 (1H, br s), 4.63 (1H, d), 4.39 (1H, d), 3.47 (1H, dd), 3.21 (1H, dd), 2.90 (5H, s), 2.68-2.62 (1H, m), 2.25 (3H, s), 1.49 (3H, s). MS [M+H]$^+$=530.

Example 309 and 310: 6-{[(1R)-1-(4-chlorophenyl)-7-fluoro-5-[1-hydroxy-1-(pyridin-2-yl)ethyl]-1-{[1-(hydroxymethyl)cyclopropyl]methoxy}-3-oxo-2,3-dihydro-1H-isoindol-2-yl]methyl}pyridine-3-carbonitrile (*both isomers separated and isolated)

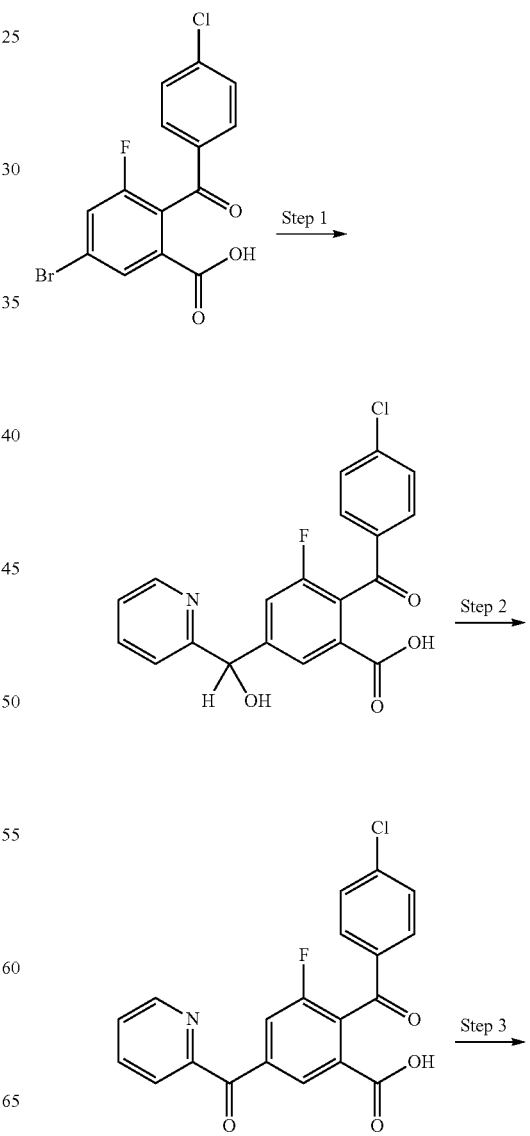

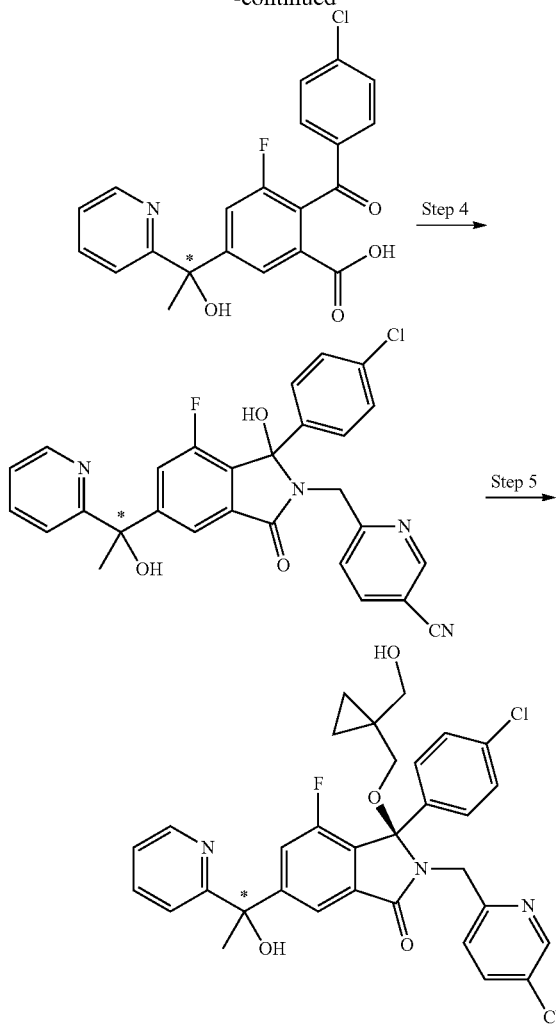

Slower eluting isomer (0.8 g, 20% yield). MS: [M+H]+= 400.1; $[\alpha]_D^{20}$=−4.42 (c 1.2, MeOH).

Step 4 and 5

Using (+)-2-(4-chlorobenzoyl)-3-fluoro-5-(1-hydroxy-1-(pyridin-2-yl)ethyl)benzoic acid and (−)-2-(4-chlorobenzoyl)-3-fluoro-5-(1-hydroxy-1-(pyridin-2-yl)ethyl)benzoic acid, Step 4 and 5 were performed in a similar manner to Example 280 (but using (1-hydroxymethyl-cyclopropyl)-methanol instead of 1-hydroxymethyl-cyclopropanecarboxylic acid amide, to give Example 309 and Example 310 respectively.

Example 309 (10 mg)

$^1$H NMR (400 MHz, DMSO) 8.59 (1H, d), 8.38 (1H, d), 7.91 (1H, dd), 7.66-7.61 (2H, m), 7.58 (1H, td), 7.40 (1H, dd), 7.19 (1H, d), 7.12-7.05 (5H, m), 6.18 (1H, s), 4.41-4.29 (2H, m), 4.26 (1H, t), 3.21-3.17 (1H, m), 3.13-3.09 (1H, m), 2.92 (1H, d), 2.71 (1H, d), 1.75 (3H, s), 0.20-0.13 (2H, m), 0.03--0.01 (1H, m), −0.05--0.09 (1H, m); MS: [M+H]+= 599

Example 310. (55 mg)

$^1$H NMR (400 MHz, CDCl$_3$) 8.67 (1H, d), 8.53 (1H, d), 7.81-7.78 (2H, m), 7.75-7.70 (1H, m), 7.44-7.40 (2H, m), 7.35 (1H, d), 7.24 (3H, d), 7.18 (2H, d), 6.07 (1H, s), 4.52 (2H, s), 3.63 (1H), 3.45-3.34 (2H, m), 2.86 (1H, d), 2.24 (1H, dd), 1.95 (3H, s), 0.55-0.27 (4H, m); MS: [M+H]+= 599.

Examples 311 and 312: 4-{1-[(1R)-1-(4-chlorophenyl)-2-[(5-chloropyridin-2-yl)methyl]-7-fluoro-1-methoxy-3-oxo-2,3-dihydro-1H-isoindol-5-yl]-1-hydroxyethyl}-1λ6-thiane-1,1-dione (*both isomers separated and isolated)

Step 1: 2-(4-Chlorobenzoyl)-3-fluoro-5-(hydroxy(pyridin-2-yl)methyl)benzoic Acid Step 1 was performed in a similar manner to Example 200, Step 1, but using 2-pyridinecarboxaldehyde instead of 1-methyl-1H-pyrazole-4-carboxaldehyde. MS: [M+H]+= 386.1

Step 2: 2-(4-Chlorobenzoyl)-3-fluoro-5-picolinoylbenzoic Acid

Step 2 was performed in a similar manner to the procedure described in Example 289, Step 2, but using acetone instead of DCM. MS: [M+H]+=384.

Step 3: 2-(4-Chlorobenzoyl)-3-fluoro-5-(1-hydroxy-1-(pyridin-2-yl)ethyl)benzoic Acid Step 3 was performed in a similar manner Example 66, Step 3 to give colourless foam which was separated using chiral SFC to give:

Faster eluting isomer (1.22 g, 32% yield). MS: [M+H]+= 400.1; $[\alpha]_D^{20}$=+4.42 (c 1.3, MeOH).

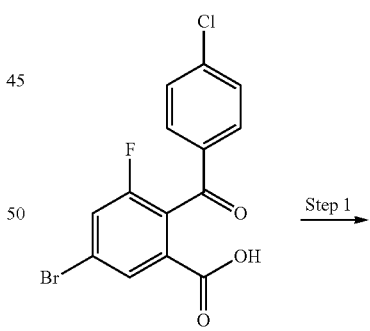

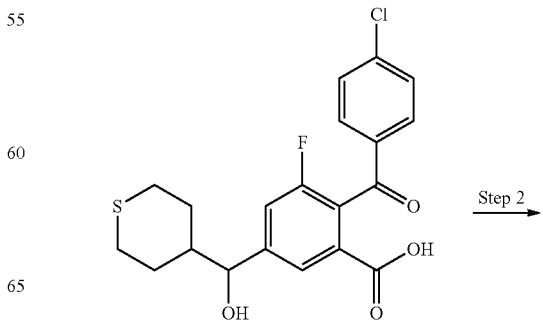

461
-continued

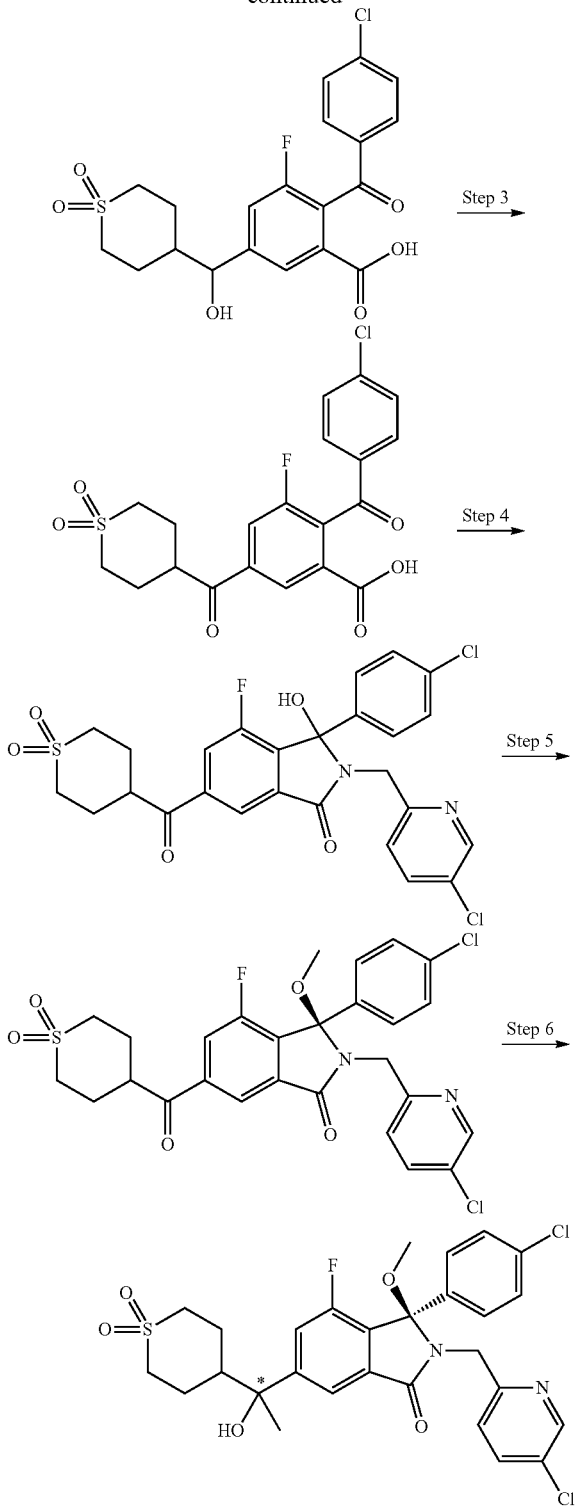

Step 1: 2-(4-Chlorobenzoyl)-3-fluoro-5-(hydroxy(tetrahydro-2H-thiopyran-4-yl)methyl)benzoic Acid The title compound was prepared from 5-bromo-2-(4-chlorobenzoyl)-3-fluorobenzoic acid and thiane-4-carbaldehyde in a similar manner to that described for 200, step 1. MS: [M+H]⁺=409.1.

462

Step 2: 2-(4-Chlorobenzoyl)-5-((1,1-dioxidotetra-hydro-2H-thiopyran-4-yl)(hydroxy)methyl)-3-fluorobenzoic Acid 2-(4-Chlorobenzoyl)-3-fluoro-5-(hydroxy(tetrahydro-2H-thiopyran-4-yl)methyl)benzoic acid (5.55 g, 13 mmol) was dissolved in dioxane (220 mL) and water (22 mL). Sodium periodate (7.28 g, 34 mmol) was added in one portion and the mixture was stirred at 60° C. overnight. More sodium periodate (2.91 g, 13 mmol) was added, and heating was continued for a further 5 h. The reaction was concentrated to approximately 50 mL under reduced pressure and then partitioned between DCM (300 mL) and 1M aqueous HCl solution (200 mL). The organic phase was collected and the aqueous phase was extracted with more DCM (200 mL). The combined organic phases were passed through a hydrophobic frit and evaporated to dryness under reduced pressure to give the title compound (6 g, quant) as a pale yellow solid. LCMS indicated the crude product was a mixture of sulfone and sulfoxide (85:15). The product was used in the subsequent step without further purification. MS: [M–H]⁻=439.

Steps 3-6

Steps 3-6 were performed in a similar manner to Example 200, steps 2-5, but using InB₃/MeOH instead of SOCl₂/1-(hydroxymethyl)cyclopropanol in step 5. In step 5, the 3R isomer was separated by chiral SCF HPLC and reacted in step 6.

Example 311 *Slower Eluting Isomer

¹H NMR (400 MHz, CDCl₃) 8.37 (1H, d), 7.75 (1H, d), 7.51 (1H, dd), 7.34 (1H, dd), 7.29-7.25 (2H, m), 7.23-7.20 (3H, m), 4.65 (1H, d), 4.39 (1H, d), 3.11-3.02 (2H, m), 2.91 (5H, s), 2.15-2.09 (1H, m), 2.05 (1H, s), 2.03-1.91 (3H, m), 1.88-1.81 (1H, m), 1.65 (3H, s); MS: [M+H]⁺=593

Example 312 *Faster Eluting Isomer

¹H NMR (400 MHz, CDCl₃) 8.37 (1H, d), 7.75 (1H, d), 7.51 (1H, dd), 7.34 (1H, dd), 7.29-7.24 (2H, m), 7.24-7.20 (3H, m), 4.66 (1H, d), 4.38 (1H, d), 3.12-3.01 (2H, m), 2.98-2.87 (5H, m), 2.13 (1H, d), 2.05-1.95 (4H, m), 1.89-1.80 (1H, m), 1.65 (3H, s); MS: [M+H]⁺=593

Examples 313 and 314: 4-{1-[(1R)-1-(4-chlorophenyl)-2-[(5-chloropyridin-2-yl)methyl]-7-fluoro-1-(2-hydroxyethoxy)-3-oxo-2,3-dihydro-1H-isoindol-5-yl]-1-hydroxyethyl}-1λ6-thiane-1,1-dione (*both isomers separated and isolated)

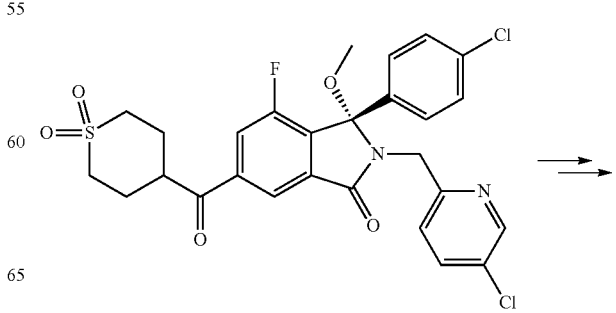

-continued

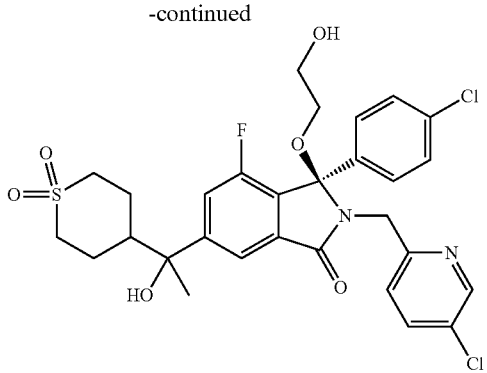

Starting from (S)-3-(4-chlorophenyl)-2-((5-chloropyridin-2-yl)methyl)-6-(1,1-dioxidotetrahydro-2H-thiopyran-4-carbonyl)-4-fluoro-3-methoxyisoindolin-1-one (isolated from Example 311, step 5), the title compound was made in a similar manner to Example 202, using ethane-1,2-diol instead of 1-(hydroxymethyl)cyclopropanecarbonitrile. The resulting isomers were separated at each stage by chiral SFC to afford the title compounds.

Example 313 *Slower Eluting Isomer $^1$H NMR (400 MHz, CDCl$_3$) 8.38 (1H, d), 7.69 (1H, d), 7.57 (1H, dd), 7.36 (1H, dd), 7.34-7.32 (1H, m), 7.32-7.30 (1H, m), 7.29-7.25 (3H, m), 4.55 (1H, d), 4.37 (1H, d), 3.81 (1H, t), 3.66 (1H, d), 3.42-3.35 (1H, m), 3.23-3.16 (2H, m), 3.10-3.01 (2H, m), 2.96-2.85 (2H, m), 2.14-2.08 (1H, m), 2.03-1.95 (4H, m), 1.86-1.78 (1H, m), 1.63 (3H, s); MS: [M+H]$^+$=623.

Example 314 *Faster Eluting Isomer $^1$H NMR (400 MHz, CDCl$_3$) 8.38 (1H, d), 7.69 (1H, d), 7.57 (1H, dd), 7.36 (1H, d), 7.31 (2H, d), 7.28-7.24 (3H, m), 4.55 (1H, d), 4.36 (1H, d), 3.84-3.77 (1H, m), 3.70-3.62 (1H, m), 3.40 (1H, ddd), 3.25-3.19 (2H, m), 3.10-2.99 (2H, m), 2.97-2.84 (2H, m), 2.12 (1H, d), 2.01-1.94 (4H, m), 1.86-1.77 (1H, m), 1.64 (3H, s); MS: [M+H]$^+$=623.

Example 315: (3R)-3-(4-chlorophenyl)-4-fluoro-6-(2-hydroxypropan-2-yl)-3-methoxy-2-[(2-methoxy-6-methylpyridin-3-yl)methyl]-2,3-dihydro-1H-isoindol-1-one

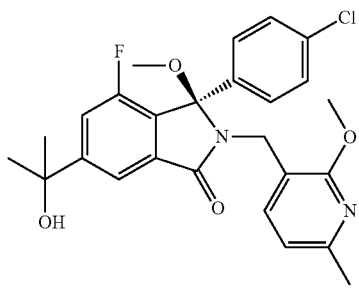 [SMILES: COc1nc(C)ccc1CN1C(=O)c2cc(C(C)(C)O)cc(F)c2[C@]1(OC)c1ccc(Cl)cc1]

Starting with Preparation 34, the title compound was prepared in a similar manner to Example 280, but using (6-methyl-2-methoxypyridin-3-yl)methanamine instead of 6-(aminomethyl)nicotinonitrile dihydrochloride and MeOH instead of 1-(hydroxymethyl)cyclopropanecarboxamide.

$^1$H NMR (400 MHz, CDCl$_3$) 7.80 (1H, s), 7.43-7.37 (2H, m), 7.21 (2H, d), 7.17 (2H, d), 6.54 (1H, d), 4.50 (1H, d), 4.32 (1H, d), 3.79 (3H, s), 2.87 (3H, s), 2.36 (3H, s), 1.80 (1H, s), 1.56 (6H, s). MS: [M+H]$^+$=485.

Example 316 and 317: 6-{[(1R)-1-(4-chlorophenyl)-7-fluoro-5-[1-hydroxy-1-(1-methyl-1H-pyrazol-4-yl)ethyl]-1-{[1-(hydroxymethyl)cyclopropyl]methoxy}-3-oxo-2,3-dihydro-1H-isoindol-2-yl]methyl}pyridine-3-carbonitrile (*both isomers separated and isolated)

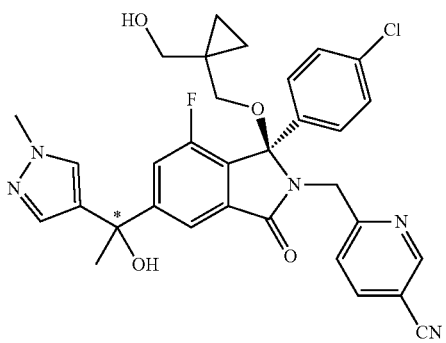 [SMILES: Cn1cc(C(C)(O)c2cc(F)c3c(c2)C(=O)N(Cc2ccc(C#N)cn2)[C@@]3(OCC2(CO)CC2)c2ccc(Cl)cc2)cn1]

The title compounds were prepared in a similar manner to Example 89, using 4-bromo-1-methyl-1H-pyrazole and n-BuLi instead of tetrahydropyran magnesium chloride.

Example 316 *Faster Running Isomer (30 mg)

$^1$H NMR (400 MHz, CDCl$_3$) 8.67 (1H, d), 7.81 (1H, dd), 7.73 (1H, d), 7.44-7.39 (3H, m), 7.27 (3H, d), 7.21 (2H, d), 4.53 (2H, s), 3.88 (3H, s), 3.62 (1H, dd), 3.46 (1H, dd), 3.34 (1H, d), 2.92 (1H, d), 2.27 (1H, dd), 2.22 (1H, s), 1.90 (3H, s), 0.54-0.41 (3H, m), 0.31-0.27 (1H, m). MS: [M+H]$^+$=602.

Example 317 *Slower Running Isomer (42 mg)

$^1$H NMR (400 MHz, CDCl$_3$) 8.67 (1H, d), 7.80 (1H, dd), 7.74 (1H, d), 7.44-7.38 (3H, m), 7.30-7.26 (3H, m), 7.20 (2H, d), 4.53 (2H, d), 3.89 (3H, s), 3.62 (1H, dd), 3.46 (1H, dd), 3.34 (1H, d), 2.92 (1H, d), 2.26 (1H, dd), 2.23 (1H, s), 1.91 (3H, s), 0.54-0.41 (3H, m), 0.32-0.27 (1H, m). MS: [M+H]$^+$=602.

Example 318 and 319: (3R)-3-(4-chlorophenyl)-2-[(5-chloropyridin-2-yl)methyl]-6-[1-hydroxy-1-(1-methylpiperidin-4-yl)ethyl]-3-methoxy-2,3-dihydro-1H-isoindol-1-one (*both isomers separated and isolated)

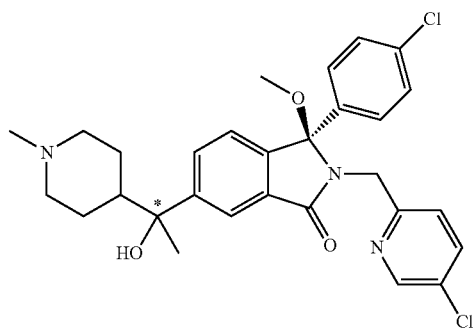 [SMILES: CO[C@]1(c2ccc(Cl)cc2)c2ccc(C(C)(O)C3CCN(C)CC3)cc2C(=O)N1Cc1ccc(Cl)cn1]

The title compounds were prepared in a similar manner to Example 55, using (1-methylpiperidin-4-yl)magnesium bromide and LaCl$_3$.2LiCl instead of 4-bromopyrazole/n-BuLi.

Example 318 *Faster Running Isomer (8 mg)

$^1$H NMR (400 MHz, CDCl$_3$) 8.34 (1H, d), 7.94 (1H, d), 7.66 (1H, dd), 7.48 (1H, dd), 7.25-7.14 (5H, m), 7.11 (1H, d), 4.60 (1H, d), 4.47 (1H, d), 2.88 (2H, dd), 2.81 (3H, s), 2.23 (3H, s), 1.90-1.58 (7H, m), 1.45-1.35 (3H, m); OH not observed. MS: [M+H]$^+$=540.

Example 319 *Slower Running Isomer (6 mg)

$^1$H NMR (400 MHz, CDCl$_3$) 8.34 (1H, d), 7.93 (1H, d), 7.67 (1H, dd), 7.48 (1H, dd), 7.25-7.20 (3H, m), 7.17 (2H, d), 7.11 (1H, d), 4.60 (1H, d), 4.48 (1H, d), 2.92-2.82 (2H, m), 2.80 (3H, s), 2.23 (3H, s), 1.88-1.57 (7H, m), 1.48-1.20 (3H, m); OH not observed. MS: [M+H]$^+$=540.

Examples 320 and 321: (3R)-3-(4-chlorophenyl)-2-[(5-chloropyridin-2-yl)methyl]-6-[1-hydroxy-1-(pyridin-2-yl)ethyl]-3-methoxy-2,3-dihydro-1H-isoindol-1-one (*both isomers separated and isolated)

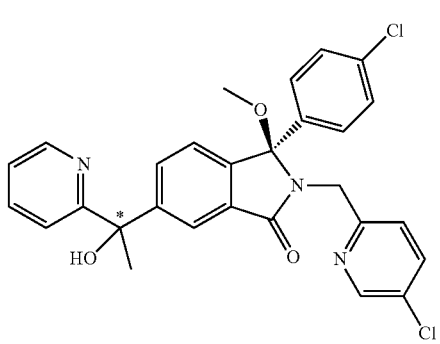 [SMILES: CO[C@]1(c2ccc(Cl)cc2)c2ccc(C(C)(O)c3ccccn3)cc2C(=O)N1Cc1ccc(Cl)cn1]

The title compounds were prepared in a similar manner to Example 55, using 2-bromopyridine and LaCl$_3$.2LiCl instead of 4-bromopyrazole.

Example 320 *Faster Running Isomer (6 mg)

$^1$H NMR (400 MHz, CDCl$_3$) 8.54 (1H, d), 8.33 (1H, d), 8.00 (1H, d), 7.75-7.67 (2H, m), 7.46 (1H, dd), 7.32 (1H, d), 7.22-7.13 (6H, m), 7.09 (1H, d), 6.01 (1H, s), 4.58 (1H, d), 4.45 (1H, d), 2.78 (3H, s), 1.97 (3H, s). MS: [M+H]$^+$=520.

Example 321 *Slower Running Isomer (5 mg)

$^1$H NMR (400 MHz, CDCl$_3$) 8.54 (1H, d), 8.33 (1H, d), 8.00 (1H, d), 7.75-7.67 (2H, m), 7.46 (1H, dd), 7.32 (1H, d), 7.22-7.13 (6H, m), 7.09 (1H, d), 6.02 (1H, s), 4.58 (1H, d), 4.45 (1H, d), 2.78 (3H, s), 1.97 (3H, s). MS: [M+H]$^+$=520.

Examples 322 and 323: (3R)-3-(4-chlorophenyl)-2-[(5-chloropyridin-2-yl)methyl]-6-[2-hydroxy-1-(pyridin-4-yl)propan-2-yl]-3-methoxy-2,3-dihydro-1H-isoindol-1-one (*both isomers separated and isolated)

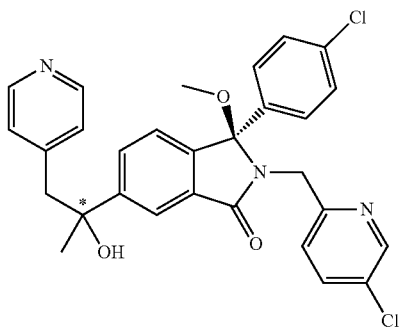 [SMILES: CO[C@]1(c2ccc(Cl)cc2)c2ccc(C(C)(O)Cc3ccncc3)cc2C(=O)N1Cc1ccc(Cl)cn1]

The title compounds were prepared in a similar manner to Example 55, using 4-methylpyridine and LaCl$_3$.2LiCl instead of 4-bromopyrazole.

Example 322: *Faster Running Isomer $^1$H NMR (400 MHz, CDCl$_3$) 8.39 (2H, d), 8.35 (1H, d), 7.97 (1H, d), 7.56 (1H, dd), 7.49 (1H, dd), 7.24-7.17 (5H, m), 7.07 (1H, d), 6.93 (2H, d), 4.60 (1H, d), 4.48 (1H, d), 3.06 (2H, s), 2.81 (3H, s), 1.97 (1H, s), 1.67 (3H, s). MS [M+H]$^+$=534

Example 323: *Slower Running Isomer $^1$H NMR (400 MHz, CDCl$_3$) 8.40 (2H, d), 8.35 (1H, d), 7.99 (1H, d), 7.57 (1H, dd), 7.49 (1H, dd), 7.24-7.21 (1H, m), 7.19 (4H, s), 7.09 (1H, d), 6.95 (2H, d), 4.61 (1H, d), 4.46 (1H, d), 3.06 (2H, d), 2.80 (3H, s), 1.99 (1H, s), 1.65 (3H, s). MS [M+H]$^+$=534

Example 324 and 325: (3R)-3-(4-chlorophenyl)-2-[(5-chloropyridin-2-yl)methyl]-6-[1-(1,2-dimethyl-1H-imidazol-4-yl)-1-hydroxyethyl]-4-fluoro-3-[(1-hydroxycyclopropyl)methoxy]-2,3-dihydro-1H-isoindol-1-one

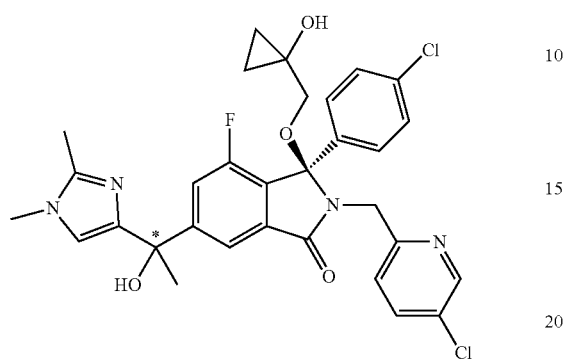

The title compound was made in a similar manner to Example 183, but using 4-bromo-1,2-dimethyl-1H-imidazole instead of 4-bromo-1-ethyl-1H-pyrazole Example 324 *Faster Eluting Isomer $^1$H NMR (400 MHz, CDCl$_3$) 8.35 (1H, d), 7.61 (1H, s), 7.54 (1H, dd), 7.47 (1H, d), 7.38-7.30 (4H, m), 7.23 (1H, d), 6.74 (1H, s), 4.51-4.36 (2H, m), 4.03 (1H, s), 3.58-3.51 (5H, m), 2.96 (1H, d), 2.32 (3H, s), 1.77 (3H, s), 0.90-0.74 (2H, m), 0.60-0.53 (1H, m), 0.40-0.33 (1H, m); MS: [M+H]$^+$=611.2.

Example 325 *Slower Eluting Isomer $^1$H NMR (400 MHz, CDCl$_3$) 8.35 (1H, d), 7.63 (1H, s), 7.56-7.51 (1H, m), 7.50-7.45 (1H, m), 7.35-7.28 (4H, m), 7.24-7.20 (1H, m), 6.73 (1H, s), 4.51-4.39 (2H, m), 3.94 (1H, s), 3.59-3.45 (5H, m), 3.02-2.98 (1H, m), 2.34 (3H, s), 1.78 (3H, s), 0.89-0.76 (2H, m), 0.58-0.51 (1H, m), 0.43-0.34 (1H, m); MS: [M+H]$^+$=611.2.

Example 326: (3R)-3-(4-chlorophenyl)-2-[(5-chloropyridin-2-yl)methyl]-4-fluoro-3-[(1-{[(2-hydroxyethyl)amino]methyl}cyclopropyl)methoxy]-6-(2-hydroxypropan-2-yl)-2,3-dihydro-1H-isoindol-1-one

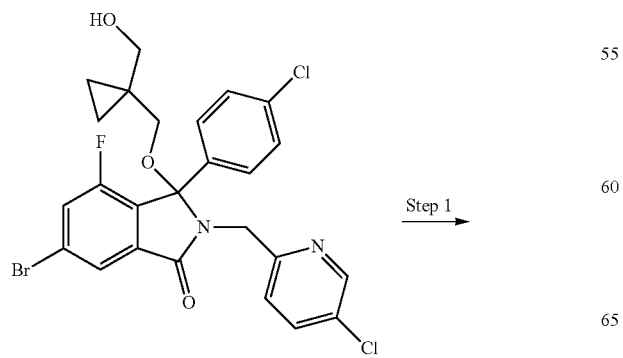

Step 1 →

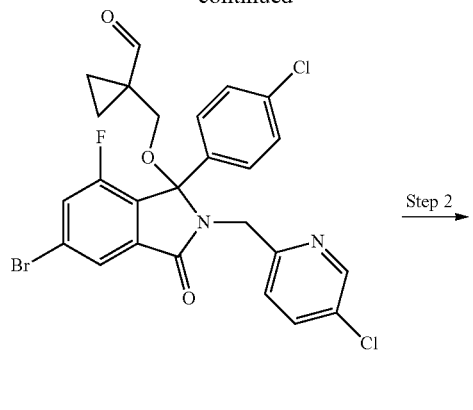

Step 2 →

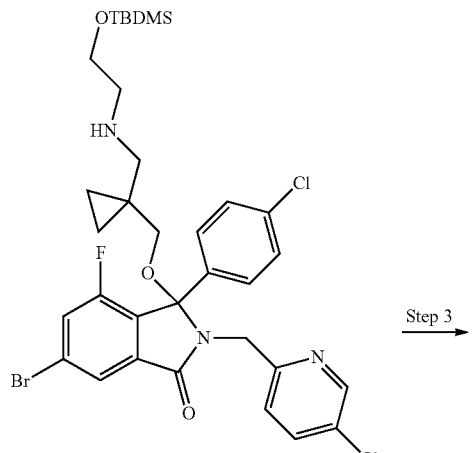

Step 3 →

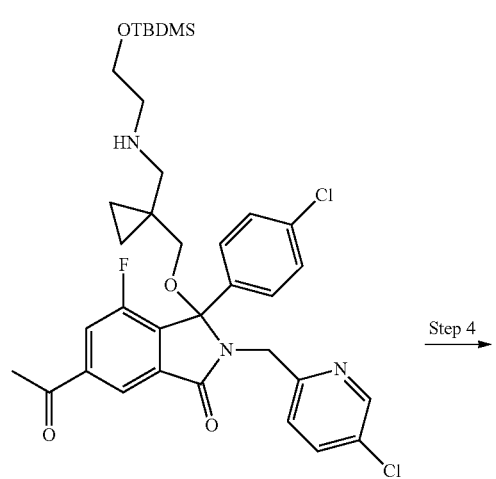

Step 4 →

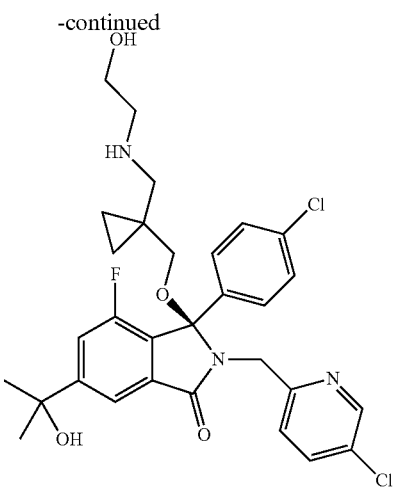

Step 1: 1-(((5-Bromo-1-(4-chlorophenyl)-2-((5-chloropyridin-2-yl)methyl)-7-fluoro-3-oxoisoindolin-1-yl)oxy)methyl)cyclopropane-1-carbaldehyde 6-Bromo-3-(4-chlorophenyl)-2-((5-chloropyridin-2-yl)methyl)-4-fluoro-3-((1-(hydroxymethyl)cyclopropyl)methoxy)isoindolin-1-one) prepared as in Example 1, steps 1 and 2 using 1,1-bis(hydroxymethyl)cyclopropane in step 2) (3.00 g, 5.30 mmol) was dissolved in anhydrous DCM (53 mL) and DMP (2.70 g, 10.6 mmol) was added portionwise at room temperature. The reaction mixture was allowed to stir at ambient temperature for 2.25 h and quenched with saturated aqueous sodium thiosulphate (50 mL). The product was extracted with DCM (2×75 mL), the combined organics washed with saturated aqueous NaHCO$_3$ (75 mL), brine (75 mL) and dried (MgSO$_4$), filtered and the solvent removed in vacuo to afford the title compound in quantitative yield; $^1$H NMR (500 MHz, CDCl$_3$) δ 8.97 (1H, s, CHO), 8.39 (1H, d, J=2.3 Hz, ArH), 7.97 (1H, d, J=1.5 Hz, ArH), 7.57 (1H, dd, J=2.5 and 8.4 Hz, ArH), 7.45 (1H, dd, J=1.4 and 8.1 Hz, ArH), 7.34 (1H, s, ArH), 7.25-7.30 (4H, m, 4×ArH), 4.66 (1H, d, J=15.4 Hz, NC—H'), 4.57 (1H, d, J=15.4 Hz, NC—H), 3.58 (1H, d, J=9.6 Hz, 2'-H), 3.15 (1H, d, J=9.6 Hz, 2'-H'), 1.08-1.19 (2H, m, Cy-Pr—H$_2$), 0.87-0.97 (2H, m, Cy-Pr—H).

Step 2: 6-Bromo-3-((1-(((2-((tert-butyldimethylsilyl)oxy)ethyl)amino)methyl)cyclopropyl) methoxy)-3-(4-chlorophenyl)-2-((5-chloropyridin-2-yl)methyl)-4-fluoroisoindolin-1-one 1-(((5-Bromo-1-(4-chlorophenyl)-2-((5-chloropyridin-2-yl)methyl)-7-fluoro-3-oxoisoindolin-1-yl)oxy)methyl)cyclopropane-1-carbaldehyde (4.16 g, 7.37 mmol) was dissolved in anhydrous DCM (37 mL) and MgSO$_4$ (2.0 g) added at room temperature. Stirred for 5 min before protected amine (Preparation 16) was added and stirring continued for 6.5 h. The solids were filtered and the filtrate concentrated before taking up in methanol (37 mL) and NaBH$_4$ (906 mg, 23.0 mmol) added portionwise. The reaction mixture was stirred for 2 h, water (20 mL) added and partitioned with EtOAc (40 mL). The organic phase was separated, dried (MgSO$_4$), filtered and the solvent removed in vacuo. FCC [amine silica, petrol-ethyl acetate (100:0)→(70:30)] of the crude residue afforded the title compound (3.12 g, 58%); $^1$H NMR (500 MHz, CDCl$_3$) δ 8.27-8.31 (1H, m, ArH), 7.85 (1H, d, J=1.5 Hz, ArH), 7.42-7.46 (1H, m, ArH), 7.30 (1H, dd, J=1.5 and 8.1 Hz, ArH), 7.10-7.22 (5H, m, 5×ArH), 4.40-4.58 (2H, m, NC—H and NC—H'), 3.57-3.70 (2H, m, CH$_2$), 2.93-3.05 (2H, m, CH$_2$), 2.58-2.76 (3H, m, CH$_2$), 2.42-2.53 (1H, m, CH$_2$), 0.84 (9H, s, (CH$_3$)$_3$), 0.22-0.41 (4H, m, Cy-Pr—H and Cy-Pr—H'), 0.00 (6H, s, (CH$_3$)$_2$).

Step 3: 6-Acetyl-3-((1-(((2-((tert-butyldimethylsilyl)oxy)ethyl)amino)methyl)cyclopropyl)methoxy)-3-(4-chlorophenyl)-2-((5-chloropyridin-2-yl)methyl)-4-fluoroisoindolin-1-one The title compound was prepared from 6-bromo-3-((1-(((2-((tert-butyldimethylsilyl)oxy)ethyl)amino)methyl)cyclopropyl) methoxy)-3-(4-chlorophenyl)-2-((5-chloropyridin-2-yl)methyl)-4-fluoroisoindolin-1-one in a similar manner to that described in Example 1, step 3; $^1$H NMR (500 MHz, CDCl$_3$) δ8.30 (1H, d, J=2.4 Hz, ArH), 8.26 (1H, d, J=1.2 Hz, ArH), 7.78 (1H, dd, J=1.2 and 9.2 Hz, ArH), 7.49 (1H, dd, J=2.5 and 8.4 Hz, ArH), 7.15-7.24 (5H, m, 5×ArH), 4.55-4.63 (2H, m, NC—H and NC—H'), 3.59-3.62 (2H, m, CH$_2$), 3.13 (1H, d, J=9.0 Hz, CH$_2$), 2.87-2.96 (2H, m, CH$_2$), 2.69-2.81 (2H, m, CH$_2$), 2.66 (3H, s, CH$_3$), 2.51 (1H, d, J=12.1 Hz, CH$_2$), 0.91 (9H, s, (CH$_3$)$_3$), 0.21-0.45 (4H, m, Cy-Pr—H and Cy-Pr—H'), 0.09 (6H, s, (CH$_3$)$_2$).

Step 4: (3R)-3-(4-chlorophenyl)-2-[(5-chloropyridin-2-yl)methyl]-4-fluoro-3-[(1-{[(2-hydroxyethyl)amino]methyl}cyclopropyl)methoxy]-6-(2-hydroxypropan-2-yl)-2,3-dihydro-1H-isoindol-1-one The title compound was prepared from 6-acetyl-3-((1-(((2-((tert-butyldimethylsilyl)oxy)ethyl) amino)methyl)cyclopropyl)methoxy)-3-(4-chlorophenyl)-2-((5-chloropyridin-2-yl)methyl)-4-fluoroisoindolin-1-one in a similar manner to that described in Example 1, step 4. Purification by semi-preparative HPLC and Chiral HPLC gave the title compound.

1H NMR (400 MHz, DMSO-d6): 8.35 (1H, d), 7.79 (1H, d), 7.71 (1H, dd), 7.53-7.45 (1H, m), 7.33-7.14 (5H, m), 5.35 (1H, s), 4.47 (2H, s), 4.38 (1H, s), 3.40 (2H, s), 3.02 (1H, d), 2.94 (1H, d), 1.48 (6H, d), 0.32 (2H, s), 0.26-0.10 (2H, m). MS: [M+H]$^+$=588.

Examples 327 and 328: (3R)-3-(4-Chlorophenyl)-2-[(5-chloropyridin-2-yl)methyl]-6-[2-hydroxy-1-(3-oxomorpholin-4-yl)propan-2-yl]-3-methoxy-2,3-dihydro-1H-isoindol-1-one (*both isomers separated and isolated)

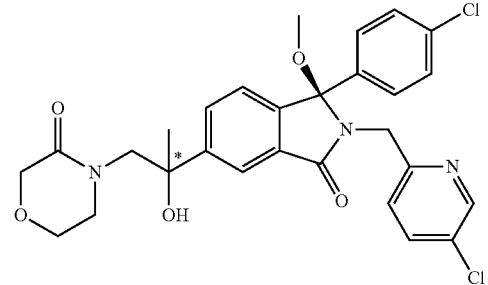 [SMILES: CO[C@]1(c2ccc(Cl)cc2)c2ccc(C(C)(O)CN3CCOCC3=O)cc2C(=O)N1Cc1ccc(Cl)cn1]

The title compounds were prepared following similar methods to those described in Examples 157 and 158 using morpholin-3-one instead of 2-imidazolidinone to give after chiral HPLC:

Example 327, Isomer 1 (52 mg, 21% Yield)

$^1$H NMR (400 MHz, DMSO-d6): 8.39 (1H, d), 7.94 (1H, s), 7.80-7.69 (2H, m), 7.33-7.07 (6H, m), 5.65 (1H, s), 4.50 (1H, d), 4.39 (1H, d), 3.99 (1H, d), 3.85 (1H, d), 3.78-3.60 (3H, m), 3.57-3.38 (3H, m), 2.76 (3H, s), 1.52 (3H, s); LCMS: [M–H]$^-$=554.

Example 328, Isomer 2 (53 mg, 21% Yield)

$^1$H NMR (400 MHz, DMSO-d6): 8.39 (1H, d), 7.96 (1H, s), 7.74 (2H, dd), 7.34-7.13 (6H, m), 5.65 (1H, s), 4.51 (1H, d), 4.38 (1H, d), 3.98 (1H, d), 3.81 (1H, d), 3.75-3.61 (3H, m), 3.53 (1H, d), 3.47-3.40 (2H, m), 2.76 (3H, s), 1.52 (3H, s); LCMS: [M–H]$^-$=554.

Examples 329 and 330: 1-{2-[(1R)-1-(4-Chlorophenyl)-2-[(5-chloropyridin-2-yl)methyl]-1-methoxy-3-oxo-2,3-dihydro-1H-isoindol-5-yl]-2-hydroxypropyl}imidazolidine-2,4-dione (*both isomers separated and isolated)

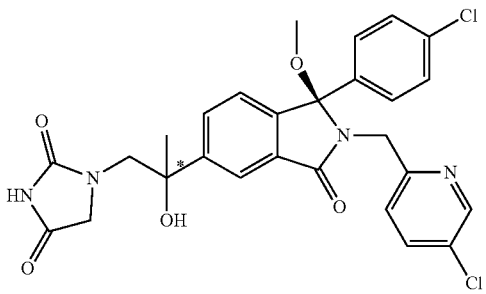 [SMILES: CO[C@]1(c2ccc(Cl)cc2)c2ccc(C(C)(O)CN3CC(=O)NC3=O)cc2C(=O)N1Cc1ccc(Cl)cn1]

The title compounds were prepared following similar methods to those described in Examples 157 and 158 using imidazolidine-2,4-dione instead of 2-imidazolidinone to give after chiral HPLC:

Example 329, Isomer 1 (32 mg, 13% Yield)

$^1$H NMR (400 MHz, DMSO-d6): 8.40 (1H, d), 8.00-7.90 (2H, m), 7.78-7.65 (2H, m), 7.30 (2H, d), 7.23 (3H, dd), 7.14 (1H, d), 5.49 (1H, s), 4.51 (1H, d), 4.37 (1H, d), 3.81 (2H, s), 3.69-3.53 (2H, m), 2.76 (3H, s), 1.52 (3H, s); LCMS: [M–H]$^-$=554.

Example 330, Isomer 2 (32 mg, 13% Yield)

$^1$H NMR (400 MHz, DMSO-d6): 8.39 (1H, d), 7.97 (1H, s), 7.89 (1H, d), 7.77-7.69 (2H, m), 7.28 (2H, d), 7.22 (3H, d), 7.16 (1H, d), 5.48 (1H, s), 4.48 (1H, d), 4.41 (1H, d), 3.81 (2H, s), 3.67-3.52 (2H, m), 2.78 (3H, s), 1.54 (3H, s); LCMS: [M–H]$^-$=554.

Example 331: (3R)-3-(4-Chlorophenyl)-2-[(1R)-1-(5-chloropyridin-2-yl)-2,3-dihydroxypropyl]-4-fluoro-3-[(1-hydroxycyclopropyl)methoxy]-6-(2-hydroxypropan-2-yl)-2,3-dihydro-1H-isoindol-1-one

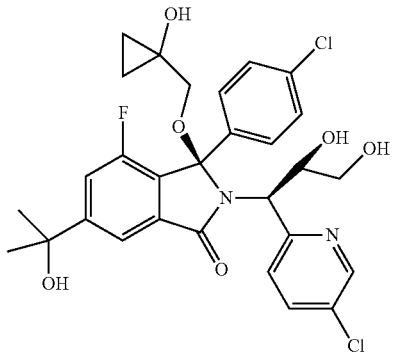

Potassium osmate (1.7 mg, 0.004 mmol) and N-methylmorpholine N-oxide (10.5 mg, 0.09 mmol) were added to a stirring solution of (3R)-3-(4-chlorophenyl)-2-[(1S)-1-(5-chloropyridin-2-yl)prop-2-en-1-yl]-4-fluoro-3-[(1-hydroxycyclopropyl) methoxy]-6-(2-hydroxypropan-2-yl)-2,3-dihydro-1H-isoindol-1-one (Example 174) (25 mg, 0.04 mmol) in THF (3 ml). After 2 hrs additional N-methylmorpholine N-oxide (10.5 mg, 0.09 mmol) was added and the reaction was stirred overnight. NaIO$_4$ (38.4 mg, 0.18 mmol) and water (3 ml) were added and stirring was continued for 24 hr. The reaction was quenched with sat. sodium metabisulfite and extracted with ethyl acetate (10 ml×3). The combined organics were dried over MgSO$_4$, concentrated in vacuo and purified by prep HPLC (Basic_04) to give the title compound as a 1:0.6 mixture of diastereomers. $^1$H NMR (400 MHz, CDCl$_3$) 8.16 (0.6H, d), 8.11 (1H, t), 7.88 (1.6H, dd), 7.49-7.36 (4H, m), 7.21-6.99 (4H, m), 6.99-6.86 (3H, m), 5.75 (0.6H, s), 5.06 (1H, s), 4.96 (0.6H, d), 4.84 (1H, d), 4.62 (1.6H, s), 4.26 (1H, s), 4.21-4.07 (1.6H, m), 3.81-3.73 (0.6H, m), 3.69 (0.6H, d), 3.63 (1H, d), 3.59-3.42 (1H, m), 3.41-3.27 (1.6H, m), 3.00 (0.6H, d), 2.84 (1H, d), 2.30 (1H, s), 2.23 (0.6H, s), 2.21-2.16 (2H, m), 1.89 (2H, s), 0.97 (1.6H, d), 0.94-0.71 (3.6H, m), 0.62-0.47 (1.6H, m). MS: [M+H]$^+$=591

Example 332: (3R)-3-(4-chlorophenyl)-2-[(5-chloropyridin-2-yl)methyl]-4-fluoro-6-[1-hydroxy-1-(4-methyl-1H-imidazol-2-yl)ethyl]-3-[(1-hydroxycyclopropyl)methoxy]-2,3-dihydro-1H-isoindol-1-one (*Example 332 was isolated as a mixture of 2 isomers)

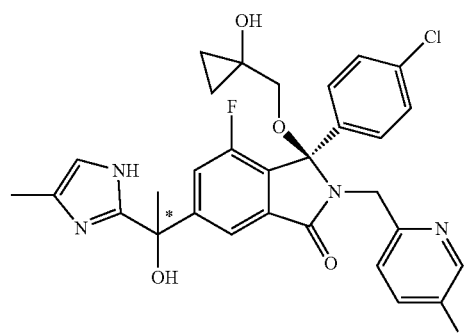

Prepared in a similar manner as Example 183 and Example 184, but using 4-methyl-1-{[2-(trimethylsilyl)ethoxy]methyl}-1H-imidazole instead of 4-bromo-1-methyl-1H-pyrazole in step 4. The title compound was isolated as a mixture of diasteroisomers. 1H NMR (400 MHz, DMSO-d6): 11.62-11.43 (1H, m), 8.33 (1H, t), 7.75-7.72 (1H, m), 7.70-7.66 (1H, m), 7.50 (1H, d), 7.34-7.24 (5H, m), 7.17 (1H, dd), 6.60 (1H, d), 6.31 (1H, s), 4.48 (2H, d), 3.14 (1H, dd), 2.96 (1H, d), 2.12-2.08 (3H, m), 1.84 (3H, s), 0.53 (2H, s), 0.38-0.32 (1H, m), 0.29-0.21 (1H, m). MS: [M–H]⁻=595.

Example 333 and 334: 6-{[(1R)-1-(4-Chlorophenyl)-7-fluoro-5-[1-hydroxy-1-(1,3-thiazol-4-yl)propyl]-1-(2-hydroxyethoxy)-3-oxo-2,3-dihydro-1H-isoindol-2-yl]methyl}pyridine-3-carbonitrile (*both isomers separated and isolated)

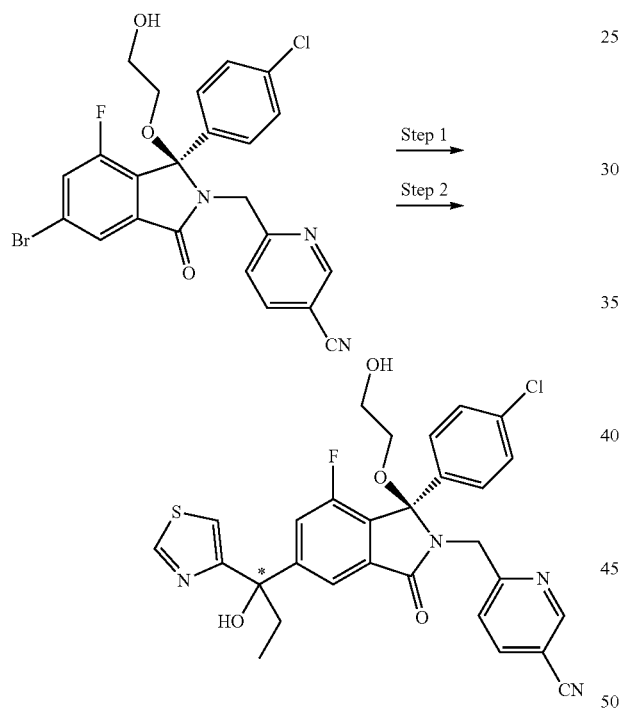

The title compounds were prepared from 6-{[(1R)-1-(4-chlorophenyl)-7-fluoro-1-(2-hydroxyethoxy)-5-methyl-3-oxo-2,3-dihydro-1H-isoindol-2-yl]methyl}pyridine-3-carbonitrile (prepared in a similar fashion to Example 3, Step 2, followed by isolation of the 3R isomer by preparative chiral HPLC) using similar precedures to those described in Example 194, step 1 and Example 336 for Steps 1 and 2 respectively.

Example 333 (Fast Running Isomer)

1H NMR (400 MHz, DMSO_cap): 9.03 (1H, d), 8.68 (1H, d), 8.00 (1H, dd), 7.82 (1H, d), 7.60-7.49 (2H, m), 7.33-7.13 (5H, m), 6.00 (1H, s), 4.61 (1H, t), 4.57-4.40 (2H, m), 3.37-3.15 (2H, m), 3.09-2.97 (1H, m), 2.91-2.79 (1H, m), 2.33-2.07 (2H, m), 0.65 (3H, t). MS: [M-CH₂CH₂OH]⁺=517.

Example 334 (Slow Running Isomer)

1H NMR (400 MHz, DMSO_cap): 9.08 (1H, d), 8.76 (1H, d), 8.08 (1H, dd), 7.90 (1H, d), 7.66-7.56 (2H, m), 7.38-7.22 (5H, m), 6.07 (1H, s), 4.67 (1H, t), 4.64-4.46 (2H, m), 3.42-3.31 (2H, m), 3.14-3.05 (1H, m), 2.97-2.87 (1H, m), 2.40-2.17 (2H, m), 0.72 (3H, t).

Examples 335 and 336: 6-{[1-(4-chlorophenyl)-7-fluoro-5-[1-hydroxy-1-(1-methyl-1H-pyrazol-3-yl)propyl]-3-oxo-1-[(3S)-oxolan-3-yloxy]-2,3-dihydro-1H-isoindol-2-yl]methyl}pyridine-3-carbonitrile (*both isomers separated and isolated)

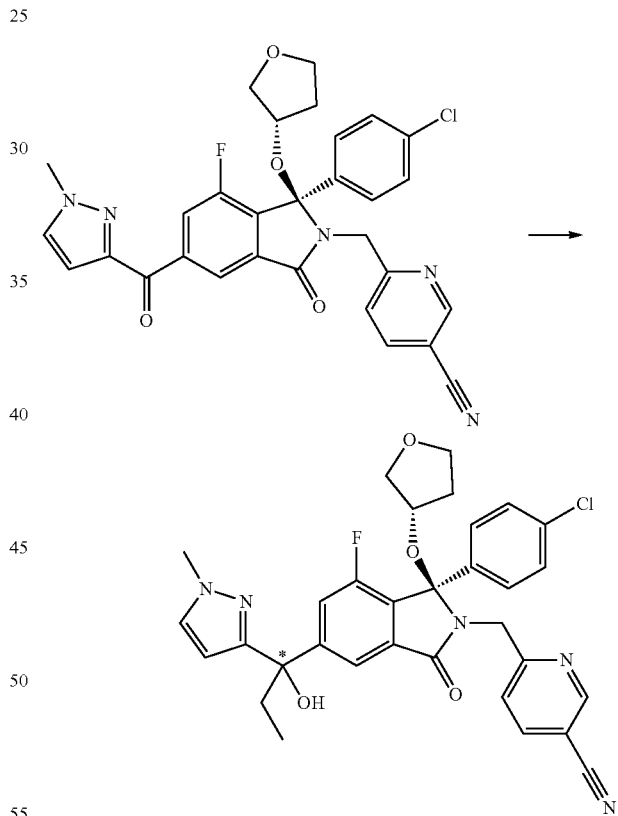

To a solution of 6-(((R)-1-(4-chlorophenyl)-7-fluoro-5-(1-methyl-1H-pyrazole-3-carbonyl)-3-oxo-1-(((S)-tetrahydrofuran-3-yl)oxy)isoindolin-2-yl)methyl)nicotinonitrile (700 mg, 1.2 mmol) in THF was added ZnCl₂ (0.5M in THF, 2.4 mL, 1.2 mmol) and stirred for 1 hr at room temperature. The solution was cooled to −30° C. and EtMgCl (2.0M in THF, 3.1 mL, 6.1 mmol) was added over 5 min, keeping the T<−20° C. (reaction went an immediate red). The reaction

475 was stirred for 15 min and then quenched with 20 mL sat. NH₄Cl, diluted with 10 mL water and extracted with 3×EtOAc (20 mL). The combined organics were washed with brine, dried over MgSO₄ and reduced in vacuo to give 790 mg of an orange solid. The crude was purified by column chromatography (Biotage) 40-100% EA in PE to give the desired product as a white solid (397 mg, 54% yield). The diastereoisomers were separated by chiral preparative HPLC.

Example 335: *Fast Running Isomer

1H NMR (400 MHz, DMSO-d6): 8.79 (1H, dd), 8.11 (1H, dd), 7.81 (1H, d), 7.57 (1H, d), 7.50 (1H, dd), 7.42 (1H, d), 7.28 (2H, d), 7.26 (2H, d), 6.20 (1H, d), 5.76 (1H, s), 4.55 (2H, s), 4.07-4.02 (1H, m), 3.82 (3H, s), 3.74 (1H, q), 3.58-3.52 (1H, m), 3.44-3.38 (1H, m), 3.17-3.12 (1H, m), 2.22-2.14 (2H, m), 1.75-1.68 (1H, m), 1.60-1.51 (1H, m), 0.72 (3H, t). [M−H]⁻=600.

Example 336: *Slow Running Isomer

1H NMR (400 MHz, DMSO-d6): 8.77 (1H, dd), 8.09 (1H, dd), 7.74 (1H, d), 7.59 (1H, d), 7.53 (1H, dd), 7.40 (1H, d), 7.29-7.26 (2H, m), 7.26-7.23 (2H, m), 6.20 (1H, d), 5.75 (1H, s), 4.58 (1H, d), 4.53 (1H, d), 4.07-4.01 (1H, m), 3.83 (3H, s), 3.74 (1H, q), 3.59-3.53 (1H, m), 3.42-3.37 (1H, m), 3.14 (1H, dd), 2.24-2.13 (2H, m), 1.79-1.70 (1H, m), 1.63-1.55 (1H, m), 0.72 (3H, t). [M−H]⁻=600.

Examples 337 and 338: 6-{[(1R)-1-(4-chlorophenyl)-7-fluoro-5-[1-hydroxy-1-(1-methyl-1H-imidazol-4-yl)propyl]-1-{[1-(hydroxymethyl)cyclopropyl]methoxy}-3-oxo-2,3-dihydro-1H-isoindol-2-yl]methyl}pyridine-3-carbonitrile (*both isomers separated and isolated)

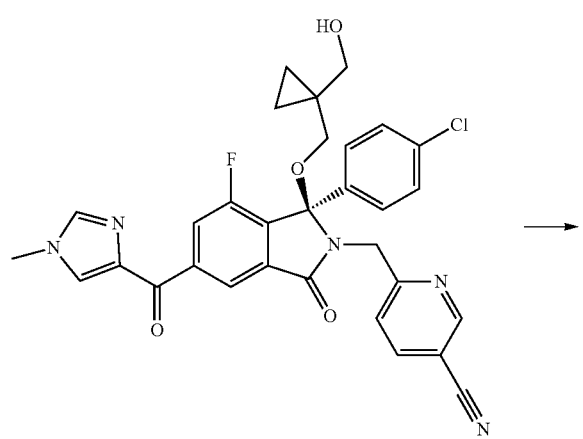

→

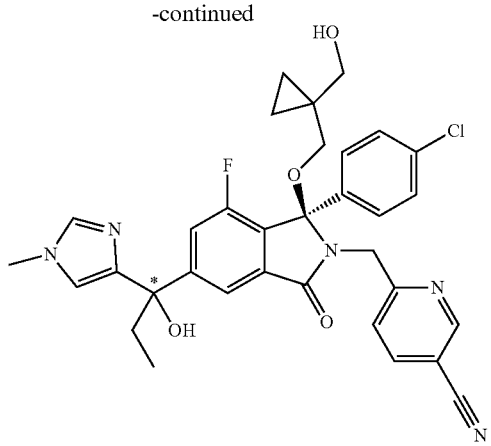

(R)-6-((1-(4-Chlorophenyl)-7-fluoro-1-((1-(hydroxymethyl)cyclopropyl)methoxy)-5-(1-methyl-1H-imidazole-4-carbonyl)-3-oxoisoindolin-2-yl)methyl)nicotinonitrile (496 mg, 0.85 mmol) was stirred in THF (10 mL) at −20° C. under nitrogen and EtMgBr (3.19M in Me-THF) was added dropwise. The red mixture was stirred at −20° C. for 5 min and quenched with NH₄Cl solution (10 mL) and DCM (10 mL) and stirred for 30 min. The layers were separated and the organic was concentrated in vacuo. The residue was loaded onto a 25 g interchim column in DCM and eluted with 0-4% MeOH in EtOAc to give the title compound (176 mg) which was purified by chiral SFC.

Example 337: *Fast Running Isomer

¹H NMR (400 MHz, CDCl₃) 8.67 (1H, d), 7.78 (1H, dd), 7.70 (1H, d), 7.54-7.50 (1H, m), 7.38 (2H, d), 7.25 (2H, d), 7.18 (2H, d), 6.84 (1H, d), 4.52 (2H, d), 3.69 (3H, s), 3.64-3.55 (2H, m), 3.45 (1H, d), 3.31 (1H, d), 2.90 (1H, d), 2.25-2.07 (3H, m), 0.86 (3H, t), 0.53-0.39 (3H, m), 0.30-0.25 (1H, m). [M+H]⁺=616.

Example 338: *Slow Running Isomer

¹H NMR (400 MHz, CDCl₃) 8.67 (1H, d), 7.80 (1H, dd), 7.68 (1H, d), 7.54-7.50 (1H, m), 7.41 (1H, d), 7.36 (1H, s), 7.28-7.25 (2H, m), 7.20 (2H, d), 6.84 (1H, s), 4.51 (2H, s), 3.69 (4H, s), 3.56 (1H, s), 3.43-3.32 (2H, m), 2.88 (1H, d), 2.33-2.06 (3H, m), 0.85 (3H, t), 0.53-0.40 (3H, m), 0.30-0.25 (1H, m). [M+H]⁺=616.

Starting from the appropriate ketone intermediate (for example, the ketones shown in Table 1: hereinabove under the heading "Penultimate Ketone Intermediates"), the following Examples were prepared by reaction with an appropriate nucleophile (for example, an alkyl organometallic reagent), using methods similar to those described in Examples 200 Step 5, Example 202 Step 2, Example 203, Example 336 or Example 337. Purification by preparative achiral and/or chiral HPLC gave final compounds as single isomer (unless stated otherwise). In the table below, an asterisk indicates the compound was isolated as a single isomer at the position shown.

| Example | Structure | Name | Comment | NMR Data | MS Data |
|---|---|---|---|---|---|
| 339 | 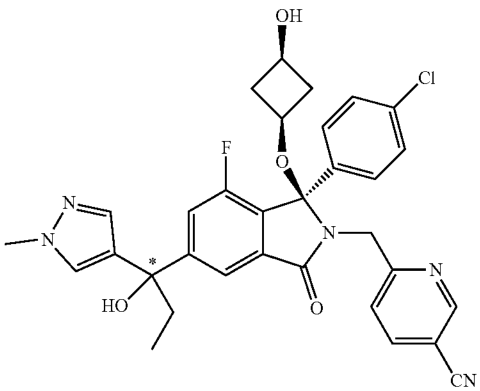 [SMILES: CCC(O)(c1cc(F)c2c(c1)C(=O)N(Cc1ccc(C#N)cn1)[C@@]2(O[C@H]1C[C@@H](O)C1)c1ccc(Cl)cc1)c1cnn(C)c1] | 6-{[(1R)-1-(4-chlorophenyl)-7-fluoro-5-[1-hydroxy-1-(1-methyl-1H-pyrazol-4-yl)propyl]-3-oxo-1-[cis-3-hydroxycyclobutoxy]-2,3-dihydro-1H-isoindol-2-yl]methyl}pyridine-3-carbonitrile | Prepared in a similar manner to Example 337 | $^1$H NMR (400 MHz, CDCl3) 8.66 (1H, d), 7.76 (1H, dd), 7.68 (1H, d), 7.42-7.37 (2H, m), 7.31-7.28 (3H, m), 7.25-7.23 (1H, m), 7.19 (2H, d), 4.62 (1H, d), 4.49 (1H, d), 3.89 (3H, s), 3.67 (1H, dd), 3.36-3.29 (1H, m), 2.25-2.14 (3H, m), 2.03 (1H, s), 2.01-1.92 (2H, m), 1.87-1.78 (1H, m), 1.63 (1H, d), 0.84 (3H, dd) | [M − H]− = 600.2 |
| 340 | 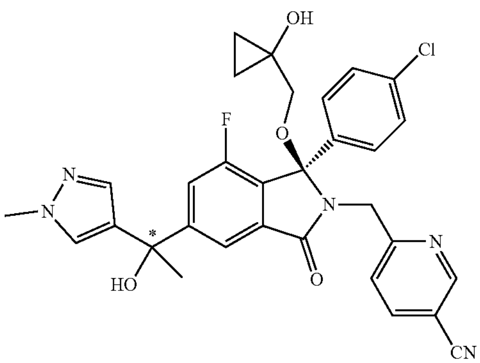 [SMILES: Cn1cc(C(C)(O)c2cc(F)c3c(c2)C(=O)N(Cc2ccc(C#N)cn2)[C@@]3(OCC2(O)CC2)c2ccc(Cl)cc2)cn1] | 6-{[(1R)-1-(4-chlorophenyl)-7-fluoro-5-[1-hydroxy-1-(1-methyl-1H-pyrazol-4-yl)ethyl]-1-[(1-hydroxycyclopropyl)methoxy]-3-oxo-2,3-dihydro-1H-isoindol-2-yl]methyl}pyridine-3-carbonitrile | Prepared in a similar manner to Example 202 step 2 | $^1$H NMR (400 MHz, CDCl3) d 8.65 (d, 1H), 7.81 (dd, 1H), 7.73 (d, 1H), 7.46-7.38 (m, 3H), 7.32-7.28 (m, 3H), 7.22 (d, 2H), 4.55 (s, 2H), 3.88 (s, 3H), 3.45-3.40 (m, 1H), 3.30 (s, 1H), 3.04 (d, 1H), 2.22 (s, 1H), 1.89 (s, 3H), 0.88-0.77 (m, 2H), 0.57-0.50 (m, 1H), 0.42-0.36 (m, 1H). | [M + H]+ = 588 |
| 341 | 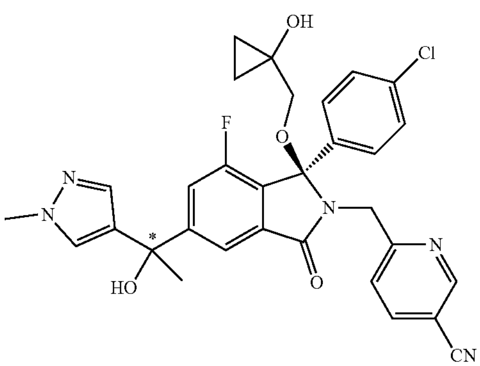 [SMILES: Cn1cc(C(C)(O)c2cc(F)c3c(c2)C(=O)N(Cc2ccc(C#N)cn2)[C@@]3(OCC2(O)CC2)c2ccc(Cl)cc2)cn1] | 6-{[(1R)-1-(4-chlorophenyl)-7-fluoro-5-[1-hydroxy-1-(1-methyl-1H-pyrazol-4-yl)ethyl]-1-[(1-hydroxycyclopropyl)methoxy]-3-oxo-2,3-dihydro-1H-isoindol-2-yl]methyl}pyridine-3-carbonitrile | Prepared in a similar manner to Example 202 step 2 | $^1$H NMR (400 MHz, CDCl3) d 8.65 (d, 1H), 7.81 (dd, 1H), 7.74 (d, 1H), 7.45-7.38 (m, 3H), 7.30 (d, 3H), 7.22 (d, 2H), 4.55 (s, 2H), 3.89 (s, 3H), 3.43 (d, 1H), 3.27 (s, 1H), 3.04 (d, 1H), 2.20 (s, 1H), 1.90 (s, 3H), 0.88-0.78 (m, 2H), 0.57-0.51 (m, 1H), 0.43-0.37 (m, 1H). | [M + H]+ = 588 |
| 342 | 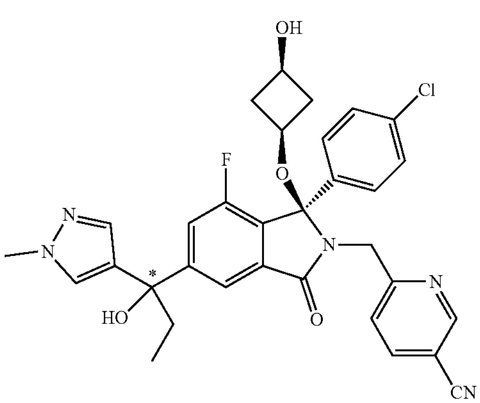 [SMILES: CCC(O)(c1cc(F)c2c(c1)C(=O)N(Cc1ccc(C#N)cn1)[C@@]2(O[C@H]1C[C@@H](O)C1)c1ccc(Cl)cc1)c1cnn(C)c1] | 6-{[(1R)-1-(4-chlorophenyl)-7-fluoro-5-[1-hydroxy-1-(1-methyl-1H-pyrazol-4-yl)propyl]-3-oxo-1-[cis-3-hydroxycyclobutoxy]-2,3-dihydro-1H-isoindol-2-yl]methyl}pyridine-3-carbonitrile | Prepared in a similar manner to Example 202, Step 2 | $^1$H NMR (400 MHz, CDCl3) 8.67 (1H, d), 7.78-7.74 (2H, m), 7.37-7.27 (5H, m), 7.25-7.24 (1H, m), 7.19 (2H, d), 4.63 (1H, d), 4.47 (1H, d), 3.88 (3H, s), 3.71-3.63 (1H, m), 3.36-3.28 (1H, m), 2.24-2.12 (3H, m), 2.05 (1H, s), 2.00-1.92 (2H, m), 1.87-1.79 (1H, m), 1.63 (1H, d), 0.85 (3H, dd) | [M − H]− = 600.2 |

| Example | Name | Comment | NMR Data | MS Data |
|---|---|---|---|---|
| 343 | (3R)-3-(4-chlorophenyl)-2-[(5-chloropyridin-2-yl)methyl]-4-fluoro-6-[1-hydroxy-1-(1-methyl-1H-pyrazol-4-yl)ethyl]-3-(2-hydroxyethoxy)-2,3-dihydro-1H-isoindol-1-one | Prepared in a similar manner to Example 202, step 2 | ¹H NMR (400 MHz, CDCl3): 8.37 (d, 1H), 7.71 (d, 1H), 7.55 (dd, 1H), 7.41-7.30 (m, 7H), 7.24 (s, 1H), 4.52 (d, 1H), 4.34 (d, 1H), 3.87 (s, 3H), 3.84-3.76 (m, 1H), 3.68-3.60 (m, 1H), 3.40-3.34 (m, 1H), 3.25-3.19 (m, 2H), 2.26 (s, 1H), 1.88 (s, 3H). | [M + H]+ = 571 |
| 344 | 6-{[(1R)-1-(4-chlorophenyl)-7-fluoro-5-[1-hydroxy-1-(1-methyl-1H-pyrazol-4-yl)ethyl]-3-oxo-1-[(3S)-oxolan-3-yloxy]-2,3-dihydro-1H-isoindol-2-yl]methyl}pyridine-3-carbonitrile | Prepared in a similar manner to Example 202 step 2 | ¹H NMR (400 MHz, CDCl3) 8.65 (1H, s), 7.81-7.75 (2H, m), 7.44 (1H, d), 7.40 (1H, s), 7.34 (1H, d), 7.30 (1H, s), 7.22 (2H, d), 7.17 (2H, d), 4.68-4.53 (2H, m), 4.05-4.01 (1H, m), 3.90 (4H, s), 3.72-3.63 (2H, m), 3.34 (1H, dd), 2.20 (1H, s), 1.92 (3H, s), 1.75-1.65 (2H, m). | [M − C4O2H7]+ = 500 |
| 345 | (3R)-3-(4-chlorophenyl)-2-[(5-chloro-pyridin-2-yl)methyl]-4-fluoro-6-[1-hydroxy-1-(1-methyl-1H-pyrazol-4-yl)ethyl]-3-{[1-(hydroxymethyl)cyclopropyl]methoxy}-2,3-dihydro-1H-isoindol-1-one | Prepared in a similar manner to Example 202 step 2 | ¹H NMR (400 MHz, CDCl3) 8.38 (1H, d, J = 2.1 Hz), 7.69 (1H, d, J = 1.4 Hz), 7.55 (1H, dd, J = 2.4, 8.3 Hz), 7.39 (2H, dt, J = 1.2, 5.1 Hz), 7.35 (1H, dd, J = 0.6, 8.3 Hz), 7.31-7.26 (3H, m), 7.24 (2H, d, J = 8.9 Hz), 4.47 (1H, d, J = 14.9 Hz), 4.34 (1H, d, J = 14.9 Hz), 3.87 (3H, s), 3.69 (1H, d, J = 11.5 Hz), 3.43-3.38 (2H, m), 2.89 (1H, s), 2.82 (1H, d, J = 9.2 Hz), 2.22-2.21 (1H, m), 1.88 (3H, s), 0.54-0.41 (3H, m), 0.30-0.25 (1H, m); | [M + H]+ = 611 |
| 346 | (3R)-3-(4-chlorophenyl)-2-[(5-chloropyridin-2-yl)methyl]-4-fluoro-6-[1-hydroxy-1-(1-methyl-1H-pyrazol-4-yl)ethyl]-3-{[1-(hydroxymethyl)cyclopropyl]methoxy}-2,3-dihydro-1H-isoindol-1-one | Prepared in a similar manner to Example 202 step 2 | ¹H NMR (400 MHz, CDCl3) 8.37 (1H, d, J = 2.3 Hz), 7.71 (1H, d, J = 1.4 Hz), 7.54 (1H, dd, J = 2.4, 8.3 Hz), 7.40 (1H, dd, J = 1.3, 10.2 Hz), 7.37 (1H, d, J = 0.7 Hz), 7.34 (1H, d, J = 8.5 Hz), 7.31-7.26 (3H, m), 7.23 (2H, d, J = 8.9 Hz), 4.47 (1H, d, J = 14.9 Hz), 4.36 (1H, d, J = 11.7 Hz), 3.41 (2H, d, J = 9.3 Hz), 2.82 (2H, d, J = 9.2 Hz), 2.26-2.19 (1H, m), 1.89 (3H, s), 0.54-0.41 (3H, m), 0.30-0.25 (1H, | [M + H]+ = 611 |

-continued

| Example | Structure | Name | Comment | NMR Data | MS Data |
|---|---|---|---|---|---|
| 347 | 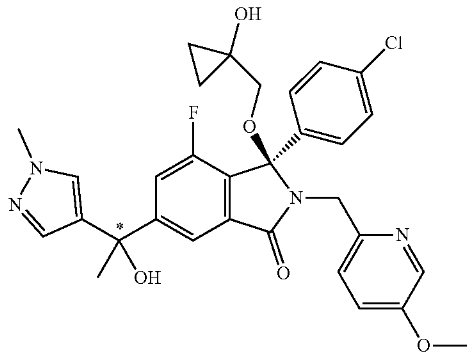 [SMILES: COc1ccc(CN2C(=O)c3cc(C(C)(O)c4cnn(C)c4)cc(F)c3[C@]2(OCC2(O)CC2)c2ccc(Cl)cc2)nc1] | (3R)-3-(4-chlorophenyl)-4-fluoro-6-[1-hydroxy-1-(1-methyl-1H-pyrazol-4-yl)ethyl]-3-[(1-hydroxycyclopropyl)methoxy]-2-[(5-methoxypyridin-2-yl)methyl]-2,3-dihydro-1H-isoindol-1-one | Prepared in a similar manner to Example 202 step 2 | ¹H NMR (400 MHz, CDCl3) 8.06 (1H, d), 7.67 (1H, d), 7.39-7.32 (6H, m), 7.26-7.22 (2H, m), 7.09 (1H, dd), 5.05 (1H, s), 4.49-4.36 (2H, m), 3.83 (6H, d), 3.61 (1H, dd), 2.92 (1H, d), 2.31 (1H, s), 1.87 (3H, s), 0.91-0.74 (2H, m), 0.63-0.55 (1H, m), 0.36 (1H, m) | [M + H]+ = 593 |
| 348 | 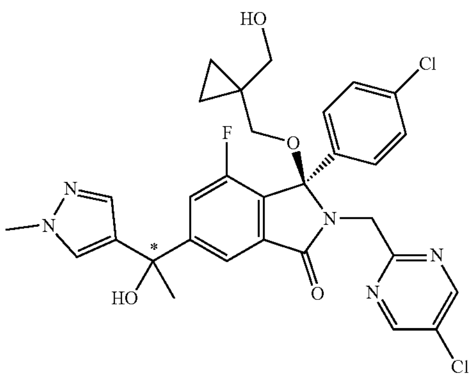 [SMILES: Cn1cc(C(C)(O)c2cc(F)c3c(c2)C(=O)N(Cc2ncc(Cl)cn2)[C@@]3(OCC2(CO)CC2)c2ccc(Cl)cc2)cn1] | (3R)-3-(4-chlorophenyl)-2-[(5-chloropyrimidin-2-yl)methyl]-4-fluoro-6-[1-hydroxy-1-(1-methyl-1H-pyrazol-4-yl)ethyl]-3-{[1-(hydroxymethyl)cyclopropyl]methoxy}-2,3-dihydro-1H-isoindol-1-one | Prepared in a similar manner to Example 203, slowest eluting isomer | ¹H NMR (400 MHz, CDCl3) 8.53 (2H, s), 7.72 (1H, d), 7.40 (1H, s), 7.35 (2H, d), 7.28 (1H, s), 7.22 (2H, s), 4.59 (2H, d), 3.88 (3H, s), 3.61-3.45 (4H, m), 3.01 (1H, d), 2.18 (1H, s), 2.11 (1H, dd), 1.89 (3H, s), 0.53-0.42 (3H, m), 0.34-0.29 (1H, m) | [M + H]+ = 612 |
| 349 | 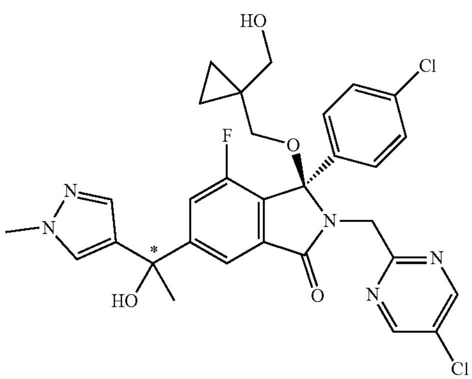 [SMILES: Cn1cc(C(C)(O)c2cc(F)c3c(c2)C(=O)N(Cc2ncc(Cl)cn2)[C@@]3(OCC2(CO)CC2)c2ccc(Cl)cc2)cn1] | (3R)-3-(4-chlorophenyl)-2-[(5-chloropyrimidin-2-yl)methyl]-4-fluoro-6-[1-hydroxy-1-(1-methyl-1H-pyrazol-4-yl)ethyl]-3-{[1-(hydroxymethyl)cyclopropyl]methoxy}-2,3-dihydro-1H-isoindol-1-one | Prepared in a similar manner to Example 203, fastest eluting isomer | ¹H NMR (400 MHz, CDCl3) 8.52 (2H, s), 7.73 (1H, d), 7.44-7.39 (2H, m), 7.35 (2H, d), 7.27 (1H, s), 7.21 (2H, d), 4.66-4.54 (2H, m), 3.88 (3H, s), 3.62-3.46 (3H, m), 3.01 (1H, d), 2.18 (1H, s), 2.09 (1H, dd), 1.91 (3H, s), 0.52-0.42 (3H, m), 0.35-0.31 (1H, m) | [M + H]+ = 612 |
| 350 | 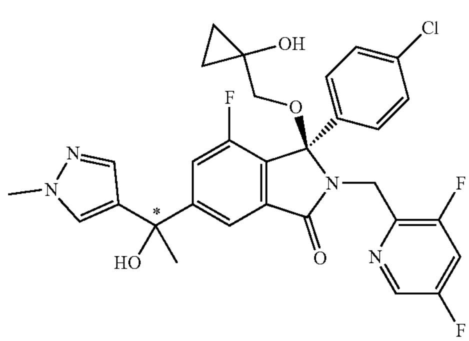 [SMILES: Cn1cc(C(C)(O)c2cc(F)c3c(c2)C(=O)N(Cc2ncc(F)cc2F)[C@@]3(OCC2(O)CC2)c2ccc(Cl)cc2)cn1] | (3R)-3-(4-chlorophenyl)-2-[(3,5-difluoropyridin-2-yl)methyl]-4-fluoro-6-[1-hydroxy-1-(1-methyl-1H-pyrazol-4-yl)ethyl]-3-[(1-hydroxycyclopropyl)methoxy]-2,3-dihydro-1H-isoindol-1-one | Prepared in a similar manner to Example 202 step 2, slowest eluting isomer | ¹H NMR (400 MHz, CDCl3) 8.16 (1H, d), 7.72 (1H, d), 7.40-7.36 (2H, m), 7.30 (2H, d), 7.28-7.20 (3H, m), 7.04-6.99 (1H, m), 4.61 (2H, d), 3.88 (4H, s), 3.61 (1H, dd), 2.99 (1H, d), 2.20 (1H, s), 1.89 (3H, s), 0.91-0.78 (2H, m), 0.61-0.54 (1H, m), 0.43-0.37 (1H, m) | [M + H]+ = 599 |

-continued

| Example | Structure | Name | Comment | ¹H NMR Data | MS Data |
|---|---|---|---|---|---|
| 351 | 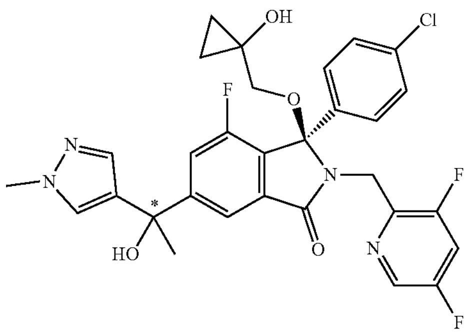 [SMILES: Cn1cc(C(C)(O)c2cc(F)c3c(c2)C(=O)N(Cc2ncc(F)cc2F)[C@@]3(OCC2(O)CC2)c2ccc(Cl)cc2)cn1] | (3R)-3-(4-chlorophenyl)-2-[(3,5-difluoropyridin-2-yl)methyl]-4-fluoro-6-[1-hydroxy-1-(1-methyl-1H-pyrazol-4-yl)ethyl]-3-[(1-hydroxycyclopropyl)methoxy]-2,3-dihydro-1H-isoindol-1-one | Prepared in a similar manner to Example 202 step 2, fastest eluting isomer | ¹H NMR (400 MHz, CDCl3) 8.17 (1H, d), 7.71 (1H, d), 7.40-7.36 (2H, m), 7.30 (2H, d), 7.28-7.21 (3H, d), 7.05-6.99 (1H, m), 4.60 (2H, s), 3.89-3.87 (4H, m), 3.60 (1H, dd), 3.00 (1H, d), 2.21 (1H, s), 1.88 (3H, s), 0.90-0.78 (2H, m), 0.61-0.54 (1H, m), 0.43-0.36 (1H, m) | [M + H]+ = 599 |
| 352 | 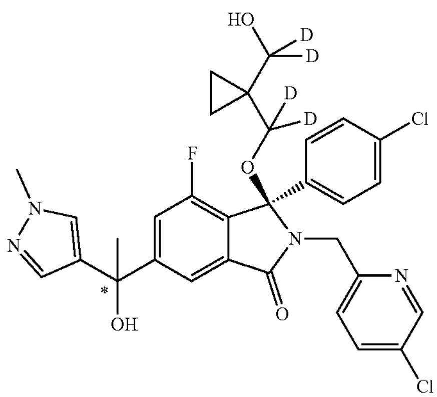 | 6-{[(1R)-1-(4-chlorophenyl)-7-fluoro-1-({1-[hydroxy(²H₂)methyl]cyclopropyl}(²H₂)methoxy)-5-[1-hydroxy-1-(1-methyl-1H-pyrazol-4-yl)ethyl]-3-oxo-2,3-dihydro-1H-isoindol-2-yl]methyl}pyridine-3-carbonitrile | Prepared in a similar manner to Example 200 step 5, fastest eluting isomer | ¹H NMR (400 MHz, DMSO) 8.76 (1H, d), 8.08 (1H, dd), 7.70 (1H, d), 7.60 (1H, s), 7.49 (1H, d), 7.34 (2H, d), 7.26 (4H, d), 5.88 (1H, s), 4.59-4.46 (2H, m), 4.39 (1H, s), 3.77 (3H, s), 1.78 (3H, s), 0.33 (2H, dd), 0.21-0.09 (2H, m); | [M + H]+ = 606 |
| 353 | 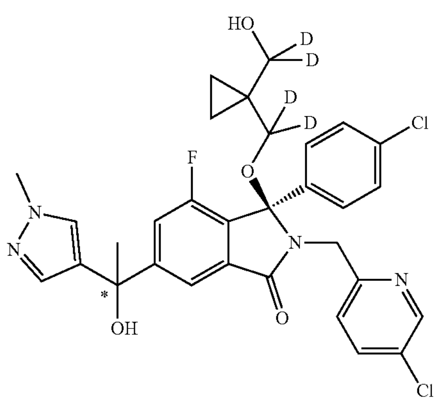 | 6-{[(1R)-1-(4-chlorophenyl)-7-fluoro-1-({1-[hydroxy(²H₂)methyl]cyclopropyl}(²H₂)methoxy)-5-[1-hydroxy-1-(1-methyl-1H-pyrazol-4-yl)ethyl]-3-oxo-2,3-dihydro-1H-isoindol-2-yl]methyl}pyridine-3-carbonitrile | Prepared in a similar manner to Example 200 step 5, slowest eluting isomer | ¹H NMR (400 MHz, DMSO) 8.75 (1H, d), 8.07 (1H, dd), 7.70 (1H, d), 7.60 (1H, s), 7.49-7.46 (1H, m), 7.34 (2H, d), 7.25 (4H, d), 5.88 (1H, s), 4.59-4.45 (2H, m), 4.38 (1H, s), 3.77 (3H, s), 1.78 (3H, s), 0.33 (2H, dd), 0.20-0.09 (2H, m); | [M + H]+ = 606 |
| 354 | 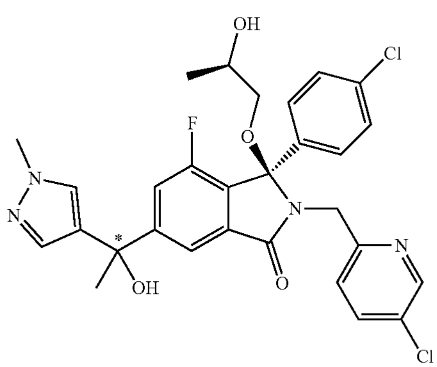 [SMILES: C[C@@H](O)CO[C@]1(c2ccc(Cl)cc2)c2c(F)cc(C(C)(O)c3cnn(C)c3)cc2C(=O)N1Cc1ccc(Cl)cn1] | (3R)-3-(4-chlorophenyl)-2-[(5-chloropyridin-2-yl)methyl]-4-fluoro-6-[1-hydroxy-1-(1-methyl-1H-pyrazol-4-yl)ethyl]-3-[(2R)-2-hydroxypropoxy]-2,3-dihydro-1H-isoindol-1-one | Prepared in a similar manner to Example 200 step 5, fastest eluting isomer | ¹H NMR (400 MHz, DMSO) 8.39 (1H, d), 7.78-7.72 (2H, m), 7.67 (1H, s), 7.54 (1H, d), 7.41 (1H, s), 7.32 (4H, s), 7.20 (1H, d), 5.94 (1H, s), 4.75 (1H, d), 4.53 (2H, s), 3.84 (3H, s), 3.66-3.58 (1H, m), 3.06 (1H, dd), 2.70 (1H, dd), 1.84 (3H, s), 1.06 (3H, d); | [M + H]+ = 585 |

| Example | Structure | Name | Comment | NMR Data | MS Data |
|---|---|---|---|---|---|
| 355 | 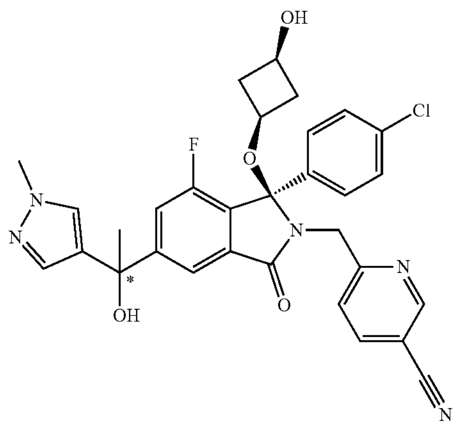 [SMILES: Cn1cc(C(C)(O)c2cc(F)c3c(c2)C(=O)N(Cc2ccc(C#N)cn2)[C@@]3(O[C@H]2C[C@@H](O)C2)c2ccc(Cl)cc2)cn1] | 6-{[1-(4-chlorophenyl)-7-fluoro-5-[1-hydroxy-1-(1-methyl-1H-pyrazol-4-yl)ethyl]-3-oxo-1-[cis-3-hydroxycyclobutoxy]-2,3-dihydro-1H-isoindol-2-yl]methyl}pyridine-3-carbonitrile | Prepared in a similar manner to Example 200 step 5, fastest eluting isomer | $^1$H NMR (400 MHz, CDCl3) 8.65 (1H, d), 7.81 (1H, dd), 7.73 (1H, d), 7.46-7.38 (3H, m), 7.32-7.28 (3H, m), 7.22 (2H, d), 4.55 (2H, s), 3.88 (3H, s), 3.43 (1H, d), 3.30 (1H, s), 3.04 (1H, d), 2.22 (1H, s), 1.89 (3H, s), 0.88-0.77 (2H, m), 0.57-0.50 (1H, m), 0.42-0.36 (1H, m); | [M + H]+ = 588 |
| 356 | 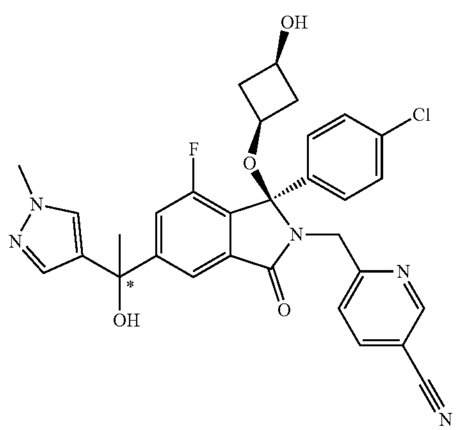 [SMILES: Cn1cc(C(C)(O)c2cc(F)c3c(c2)C(=O)N(Cc2ccc(C#N)cn2)[C@@]3(O[C@H]2C[C@@H](O)C2)c2ccc(Cl)cc2)cn1] | 6-{[1-(4-chlorophenyl)-7-fluoro-5-[1-hydroxy-1-(1-methyl-1H-pyrazol-4-yl)ethyl]-3-oxo-1-[cis-3-hydroxycyclobutoxy]-2,3-dihydro-1H-isoindol-2-yl]methyl}pyridine-3-carbonitrile | Prepared in a similar manner to Example 200 step 5, slowest eluting isomer | $^1$H NMR (400 MHz, CDCl3) 8.65 (1H, d), 7.81 (1H, dd), 7.74 (1H, d), 7.45-7.38 (3H, m), 7.34-7.28 (3H, m), 7.22 (2H, d), 4.55 (2H, s), 3.89 (3H, s), 3.43 (1H, d), 3.27 (1H, s), 3.04 (1H, d), 2.20 (1H, s), 1.90 (3H, s), 0.88-0.78 (2H, m), 0.57-0.51 (1H, m), 0.43-0.37 (1H, m); | [M + H]+ = 588 |
| 357 | 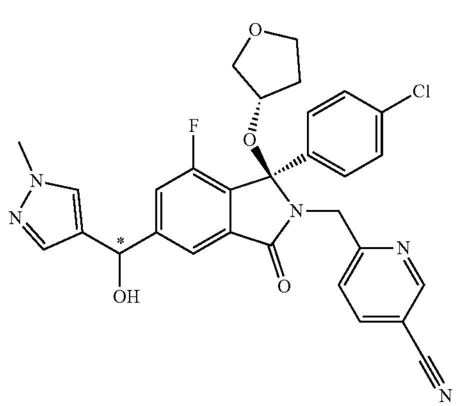 [SMILES: Cn1cc(C(O)c2cc(F)c3c(c2)C(=O)N(Cc2ccc(C#N)cn2)[C@@]3(O[C@H]2CCOC2)c2ccc(Cl)cc2)cn1] | 6-{[(1R)-1-(4-chlorophenyl)-7-fluoro-5-[hydroxy(1-methyl-1H-pyrazol-4-yl)methyl]-3-oxo-1-[(3S)-oxolan-3-yloxy]-2,3-dihydro-1H-isoindol-2-yl]methyl}pyridine-3-carbonitrile | Isolated as the reduction product during the preparation of Example 358 (slowest eluting isomer) | $^1$H NMR (400 MHz, MeOD) 8.67 (1H, d), 7.97 (1H, dd), 7.84 (1H, s), 7.56 (1H, s), 7.49 (1H, d), 7.44-7.39 (2H, m), 7.29 (2H, d), 7.22 (2H, d), 5.94 (1H, s), 4.80 (1H, d), 4.58 (1H, d), 4.20-4.14 (1H, m), 3.97-3.90 (1H, m), 3.89 (3H, s), 3.76-3.63 (2H, m), 3.38-3.36 (1H, m), 1.97-1.78 (2H, m); | [M + H]+ = 574 |

| Example | Structure | Name | Comment | NMR Data | MS Data |
|---|---|---|---|---|---|
| 358 | 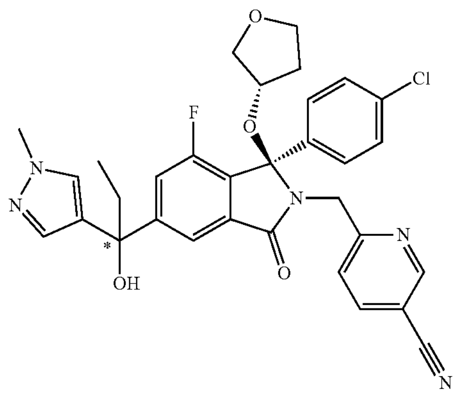 [SMILES: CCC(O)(c1cc(F)c2c(c1)C(=O)N(Cc1ccc(C#N)cn1)[C@@]2(O[C@H]1CCOC1)c1ccc(Cl)cc1)c1cnn(C)c1] | 6-{[(1R)-1-(4-chlorophenyl)-7-fluoro-5-[1-hydroxy-1-(1-methyl-1H-pyrazol-4-yl)propyl]-3-oxo-1-[(3S)-oxolan-3-yloxy]-2,3-dihydro-1H-isoindol-2-yl]methyl}pyridine-3-carbonitrile | Prepared in a similar manner to Example 203 (using AlEt₃), slowest eluting isomer | ¹H NMR (400 MHz, MeOD) 8.54 (1H, d, J = 1.8 Hz), 7.83 (1H, dd), 7.70 (1H, d), 7.48 (1H, s), 7.42 (1H, dd), 7.32 (1H, s), 7.27 (1H, d), 7.15 (2H, d), 7.08 (2H, d), 4.66 (1H, d), 4.45 (1H, d), 4.05-4.00 (1H, m), 3.83-3.77 (1H, m), 3.76 (3H, s), 3.62-3.49 (2H, m), 3.19-3.16 (1H, m), 2.21-2.08 (2H, m), 1.81-1.67 (2H, m), 1.19 (1H, s), 0.75 (3H, dd, J = 7.3, 7.3 Hz); | [M + H]+ = 602 |
| 359 | 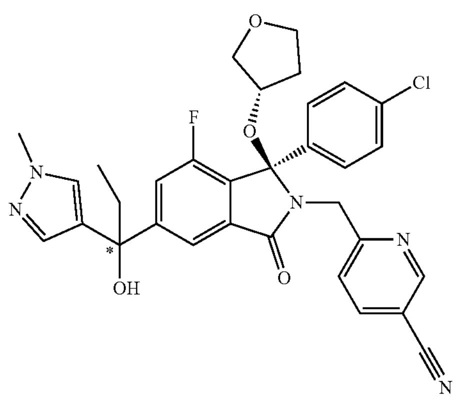 [SMILES: CCC(O)(c1cc(F)c2c(c1)C(=O)N(Cc1ccc(C#N)cn1)[C@@]2(O[C@H]1CCOC1)c1ccc(Cl)cc1)c1cnn(C)c1] | 6-{[(1R)-1-(4-chlorophenyl)-7-fluoro-5-[1-hydroxy-1-(1-methyl-1H-pyrazol-4-yl)propyl]-3-oxo-1-[(3S)-oxolan-3-yloxy]-2,3-dihydro-1H-isoindol-2-yl]methyl}pyridine-3-carbonitrile | Prepared in a similar manner to Example 203 (using AlEt₃), fastest eluting isomer | ¹H NMR (400 MHz, MeOD) 8.67 (1H, d), 7.97 (1H, dd), 7.87 (1H, d), 7.60 (1H, s), 7.52 (1H, dd), 7.45 (1H, s), 7.41 (1H, d), 7.29 (2H, d), 7.22 (2H, d), 4.78 (1H, d), 4.59 (1H, d), 4.18-4.12 (1H, m), 3.95-3.90 (1H, m), 3.89 (3H, s), 3.75-3.62 (2H, m), 3.31 (1H, d), 2.31-2.23 (2H, m), 1.95-1.76 (2H, m), 1.32 (1H, s), 0.88 (3H, dd); | [M + H]+ = 602 |
| 360 | 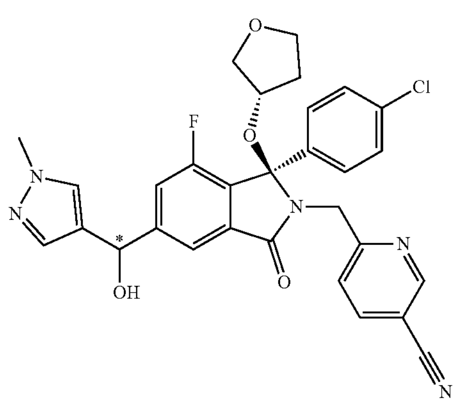 [SMILES: Cn1cc(C(O)c2cc(F)c3c(c2)C(=O)N(Cc2ccc(C#N)cn2)[C@@]3(O[C@H]2CCOC2)c2ccc(Cl)cc2)cn1] | 6-{[(1R)-1-(4-chlorophenyl)-7-fluoro-5-[hydroxy(1-methyl-1H-pyrazol-4-yl)methyl]-3-oxo-1-[(3S)-oxolan-3-yloxy]-2,3-dihydro-1H-isoindol-2-yl]methyl}pyridine-3-carbonitrile | Isolated as the reduction product during the preparation of Example 358 (fastest eluting isomer) | ¹H NMR (400 MHz, MeOD) 8.67 (1H, d), 7.97 (1H, dd), 7.86 (1H, s), 7.56 (1H, s), 7.47 (1H, d), 7.44-7.39 (2H, m), 7.29 (2H, d,), 7.22 (2H, d), 5.94 (1H, s), 4.80 (1H, d), 4.59 (1H, d), 4.20-4.14 (1H, m), 3.97-3.90 (1H, m), 3.89 (3H, s), 3.76-3.64 (2H, m), 3.37 (1H, d), 1.96-1.78 (2H, m); | [M + H]+ = 574 |

| Example | Structure | Name | Comment | NMR Data | MS Data |
|---|---|---|---|---|---|
| 361 | 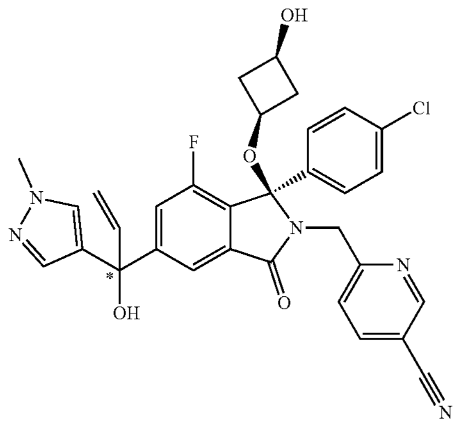 | 6-{[(1R)-1-(4-chlorophenyl)-7-fluoro-5-[1-hydroxy-1-(1-methyl-1H-pyrazol-4-yl)prop-2-en-1-yl]-3-oxo-1-[cis-3-hydroxy-cyclobutoxy]-2,3-dihydro-1H-isoindol-2-yl]methyl}pyridine-3-carbonitrile | Prepared in a similar manner to Example 200 step 5 (Using vinyl magnesium bromide, slowest eluting isomer | $^1$H NMR (400 MHz, CDCl3) 8.66 (1H, d), 7.78-7.74 (2H, m), 7.39-7.35 (1H, m), 7.33-7.27 (4H, m), 7.24 (1H, s), 7.19 (2H, d), 6.37 (1H, dd), 5.42-5.30 (2H, m), 4.62 (1H, d), 4.49 (1H, d), 3.90 (3H, s), 3.67 (1H, dd), 3.35-3.29 (1H, m), 2.29 (1H, s), 2.20-2.12 (1H, m), 2.01-1.85 (3H, m), 1.63 (1H, d); | [M + H]+ = 600 |
| 362 | 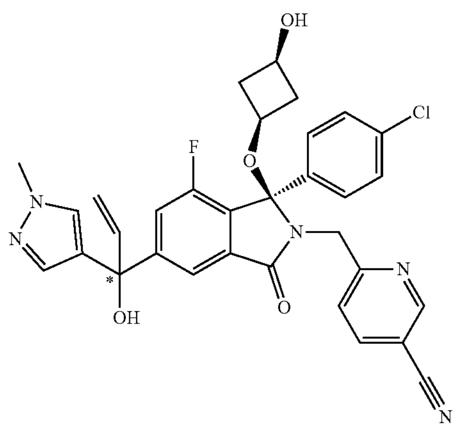 | 6-{[(1R)-1-(4-chlorophenyl)-7-fluoro-5-[1-hydroxy-1-(1-methyl-1H-pyrazol-4-yl)prop-2-en-1-yl]-3-oxo-1-[cis-3-hydroxy-cyclobutoxy]-2,3-dihydro-1H-isoindol-2-yl]methyl}pyridine-3-carbonitrile | Prepared in a similar manner to Example 200 step 5 (Using vinyl magnesium bromide, fastest eluting isomer | $^1$H NMR (400 MHz, CDCl3) 8.66 (1H, d), 7.78-7.75 (2H, m), 7.36 (1H, dd), 7.32-7.27 (4H, m), 7.24 (1H, s), 7.19 (2H, d), 6.37 (1H, dd), 5.42-5.30 (2H, m), 4.63 (1H, d), 4.48 (1H, d), 3.89 (3H, s), 3.72-3.64 (1H, m), 3.37-3.29 (1H, m), 2.33 (1H, s), 2.19-2.11 (1H, m), 2.01-1.84 (3H, m), 1.66 (1H, d, J = 6.0 Hz); | [M + H]+ = 600 |
| 363 | 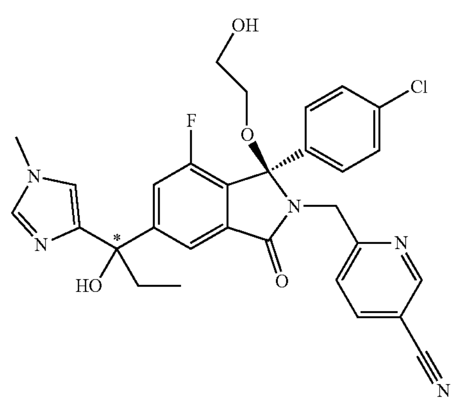 [SMILES: CCC(O)(c1cc(F)c2c(c1)C(=O)N(Cc1ccc(C#N)cn1)[C@@]2(OCCO)c1ccc(Cl)cc1)c1cn(C)cn1] | 6-{[(1R)-1-(4-chlorophenyl)-7-fluoro-5-[1-hydroxy-1-(1-methyl-1H-imidazol-4-yl)propyl]-1-(2-hydroxyethoxy)-3-oxo-2,3-dihydro-1H-isoindol-2-yl]methyl}pyridine-3-carbonitrile | Prepared in a similar manner to Example 337 | $^1$H NMR (400 MHz, CDCl3) d 8.67 (d, 1H), 7.81 (dd, 1H), 7.71 (d, 1H), 7.51 (dd, 1H), 7.44 (d, 1H), 7.35 (s, 1H), 7.28 (d, 2H), 7.22 (d, 2H), 6.84 (d, 1H), 4.57 (d, 1H), 4.47 (d, 1H), 3.82-3.72 (m, 1H), 3.68 (s, 3H), 3.65-3.59 (m, 1H), 3.53 (s, 1H), 3.35-3.29 (m, 1H), 3.24-3.18 (m, 1H), 2.54 (dd, 1H), 2.23-2.06 (m, 2H), 0.85 (dd, 3H). | [M + H] = 576 |

-continued

| Example | Structure | Name | Comment | NMR Data | MS Data |
|---|---|---|---|---|---|
| 364 | 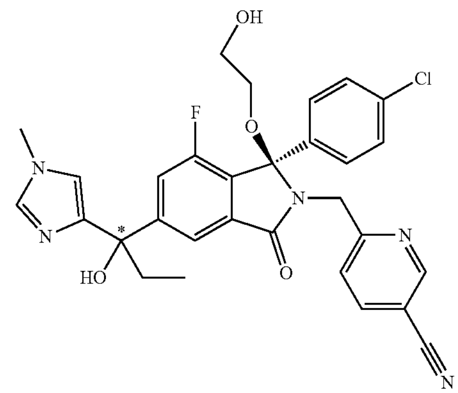 [SMILES: CCC(O)(c1cc(F)c2c(c1)C(=O)N(Cc1ccc(C#N)cn1)[C@@]2(OCCO)c1ccc(Cl)cc1)c1cn(C)cn1] | 6-{[(1R)-1-(4-chlorophenyl)-7-fluoro-5-[1-hydroxy-1-(1-methyl-1H-imidazol-4-yl)propyl]-1-(2-hydroxyethoxy)-3-oxo-2,3-dihydro-1H-isoindol-2-yl]methyl}pyridine-3-carbonitrile | Prepared in a similar manner to Example 337 | $^1$H NMR (400 MHz, CDCl3) d 8.67 (d, 1H), 7.80 (dd, 1H), 7.70 (d, 1H), 7.55-7.49 (m, 1H), 7.42 (d, 1H), 7.36 (s, 1H), 7.20 (d, 2H), 6.84 (d, 1H), 4.60-4.46 (m, 2H), 3.70-3.69 (m, 5H), 3.53 (s, 1H), 3.36-3.30 (m, 1H), 3.24-3.18 (m, 1H), 2.49 (dd, 1H), 2.23-2.07 (m, 2H), 0.86 (dd, 3H). | [M + H] = 576 |
| 365 | 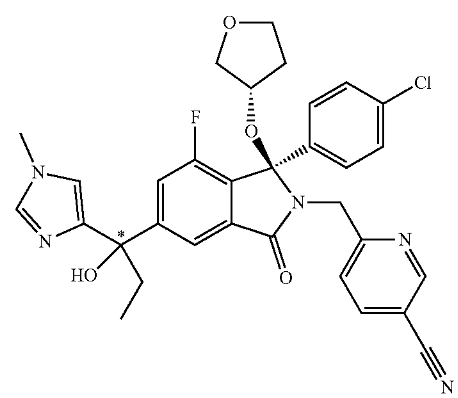 [SMILES: CCC(O)(c1cc(F)c2c(c1)C(=O)N(Cc1ccc(C#N)cn1)[C@@]2(O[C@H]1CCOC1)c1ccc(Cl)cc1)c1cn(C)cn1] | 6-{[(1R)-1-(4-chlorophenyl)-7-fluoro-5-[1-hydroxy-1-(1-methyl-1H-imidazol-4-yl)propyl]-3-oxo-1-[(3S)-oxolan-3-yloxy]-2,3-dihydro-1H-isoindol-2-yl]methyl}pyridine-3-carbonitrile | Prepared in a similar manner to Example 337 | $^1$H NMR (400 MHz, CDCl3) 8.63 (1H, d), 7.77-7.71 (2H, m), 7.56 (1H, d), 7.38 (1H, s), 7.29 (1H, d), 7.20 (2H, d), 7.13 (2H, d), 6.86 (1H, s), 4.65 (1H, d), 4.54 (1H, d), 4.04-3.97 (1H, m), 3.86 (1H, q), 3.71 (3H, s), 3.69-3.57 (3H, m), 3.30 (1H, dd), 2.25-2.02 (2H, m), 1.74-1.66 (2H, m), 0.85 (3H, t); | [M + H] = 602.5 |
| 366 | 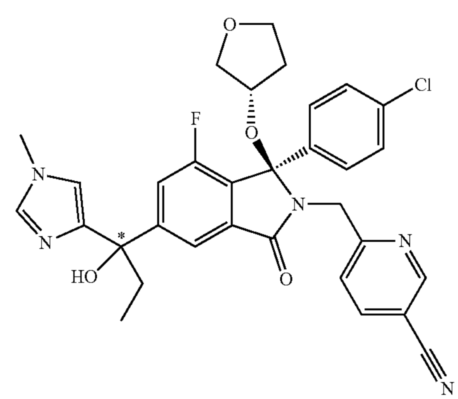 [SMILES: CCC(O)(c1cc(F)c2c(c1)C(=O)N(Cc1ccc(C#N)cn1)[C@@]2(O[C@H]1CCOC1)c1ccc(Cl)cc1)c1cn(C)cn1] | 6-{[(1R)-1-(4-chlorophenyl)-7-fluoro-5-[1-hydroxy-1-(1-methyl-1H-imidazol-4-yl)propyl]-3-oxo-1-[(3S)-oxolan-3-yloxy]-2,3-dihydro-1H-isoindol-2-yl]methyl}pyridine-3-carbonitrile | Prepared in a similar manner to Example 337 | $^1$H NMR (400 MHz, CDCl3) 8.64 (1H, d), 7.82 (1H, s), 7.76 (1H, dd), 7.48 (1H, d), 7.37 (1H, s), 7.32 (1H, d), 7.20 (2H, d), 7.14 (2H, d), 6.84 (1H, s), 4.65 (1H, d), 4.55 (1H, d), 4.03-3.97 (1H, m), 3.86 (1H, q), 3.70 (3H, s), 3.69-3.57 (3H, m), 3.32 (1H, dd), 2.25-2.00 (2H, m), 1.72-1.64 (2H, m), 0.86 (3H, t); | [M + H] = 602.5 |
| 367 | 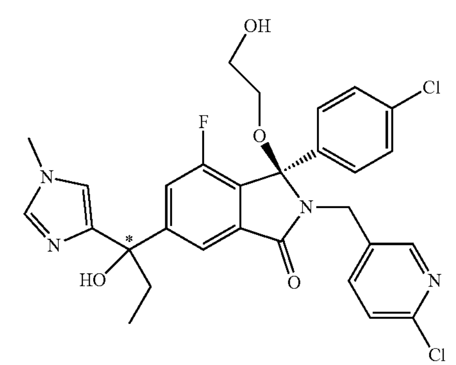 [SMILES: CCC(O)(c1cc(F)c2c(c1)C(=O)N(Cc1ccc(Cl)nc1)[C@@]2(OCCO)c1ccc(Cl)cc1)c1cn(C)cn1] | (3R)-3-(4-chlorophenyl)-2-[(6-chloropyridin-3-yl)methyl]-4-fluoro-6-[1-hydroxy-1-(1-methyl-1H-imidazol-4-yl)propyl]-3-(2-hydroxyethoxy)-2,3-dihydro-1H-isoindol-1-one | Prepared in a similar manner to Example 337 | $^1$H NMR (400 MHz, CDCl3) 8.14 (1H, d), 7.71 (1H, s), 7.54 (1H, dd), 7.49 (1H, d), 7.36 (1H, s), 7.23 (4H, s), 7.14 (1H, d), 6.84 (1H, s), 4.51 (1H, d), 4.22 (1H, d), 3.69 (3H, s), 3.61-3.57 (3H, m), 3.08-2.93 (2H, m), 2.23-2.04 (2H, m), 0.85 (3H, dd) | [M + H]+ = 585 |

| Example | Structure | Name | Comment | NMR Data | MS Data |
|---|---|---|---|---|---|
| 368 | 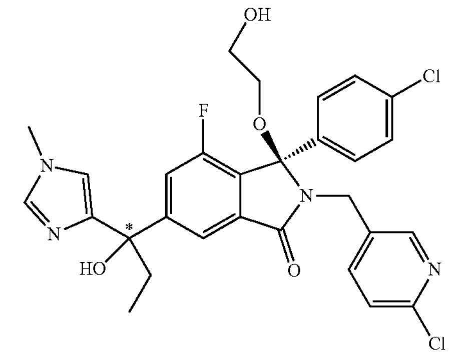 [SMILES: CCC(O)(c1cc(F)c2c(c1)C(=O)N(Cc1ccc(Cl)nc1)[C@@]2(OCCO)c1ccc(Cl)cc1)c1cn(C)cn1] | (3R)-3-(4-chlorophenyl)-2-[(6-chloropyridin-3-yl)methyl]-4-fluoro-6-[1-hydroxy-1-(1-methyl-1H-imidazol-4-yl)propyl]-3-(2-hydroxyethoxy)-2,3-dihydro-1H-isoindol-1-one | Prepared in a similar manner to Example 337 | ¹H NMR (400 MHz, CDCl3) 8.15 (1H, d), 7.71 (1H, s), 7.56 (1H, dd), 7.47 (1H, d), 7.36 (1H, s), 7.24 (4H, s), 7.14 (1H, d), 6.84 (1H, s), 4.52 (1H, d), 4.20 (1H, d), 3.69 (3H, s), 3.61-3.53 (3H, m), 3.07-3.01 (1H, m), 2.96-2.90 (1H, m), 2.23-2.06 (2H, m), 0.85 (3H, dd) | [M + H]+ = 585 |
| 369 | 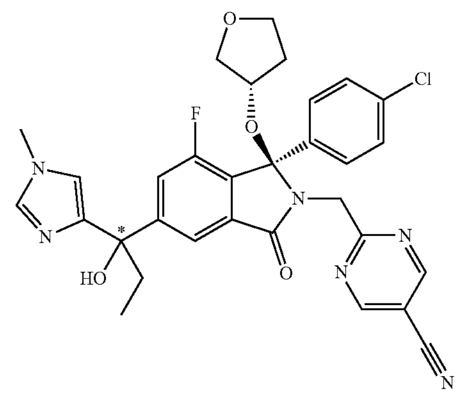 [SMILES: CCC(O)(c1cc(F)c2c(c1)C(=O)N(Cc1ncc(C#N)cn1)[C@@]2(O[C@H]1CCOC1)c1ccc(Cl)cc1)c1cn(C)cn1] | 2-{[(1R)-1-(4-chlorophenyl)-7-fluoro-5-[1-hydroxy-1-(1-methyl-1H-imidazol-4-yl)propyl]-3-oxo-1-[(3S)-oxolan-3-yloxy]-2,3-dihydro-1H-isoindol-2-yl]methyl}pyrimidine-5-carbonitrile | Prepared in a similar manner to Example 203 (using AlEt3), Slowest eluting isomer | ¹H NMR (400 MHz, CDCl3) 8.79 (2H, s), 7.69 (1H, d, J), 7.58 (1H, dd), 7.37 (1H, s), 7.31 (2H, d), 7.15 (2H, d), 6.86 (1H, d), 4.80 (1H, d), 4.60 (1H, d), 4.21 (1H, ddd), 3.90 (1H, q), 3.75-3.66 (5H, m), 3.56 (1H, s), 3.36 (1H, dd), 2.25-2.08 (2H, m), 1.94-1.73 (2H, m), 0.86 (3H, dd); | [M + H]+ = 603.3 |
| 370 | 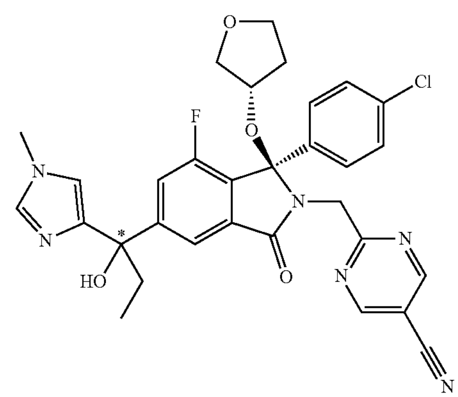 [SMILES: CCC(O)(c1cc(F)c2c(c1)C(=O)N(Cc1ncc(C#N)cn1)[C@@]2(O[C@H]1CCOC1)c1ccc(Cl)cc1)c1cn(C)cn1] | 2-{[(1R)-1-(4-chlorophenyl)-7-fluoro-5-[1-hydroxy-1-(1-methyl-1H-imidazol-4-yl)propyl]-3-oxo-1-[(3S)-oxolan-3-yloxy]-2,3-dihydro-1H-isoindol-2-yl]methyl}pyrimidine-5-carbonitrile | Prepared in a similar manner to Example 203 (using AlEt3), fastest eluting isomer | ¹H NMR (400 MHz, CDCl3) 8.80 (2H, s), 7.79 (1H, d), 7.50 (1H, dd), 7.36 (1H, s), 7.33 (2H, d), 7.17 (2H, d), 6.84 (1H, d), 4.77 (1H, d), 4.61 (1H, d), 4.21 (1H, ddd), 3.93-3.86 (1H, m), 3.74-3.66 (5H, m), 3.56 (1H, s), 3.38 (1H, dd), 2.24-2.08 (2H, m), 1.91-1.71 (2H, m), 0.86 (3H, dd); | MS+ = 603.3 |
| 371 | 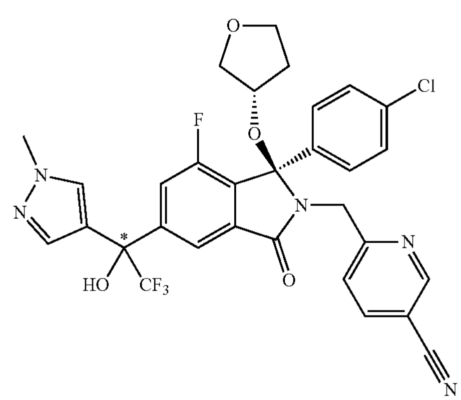 [SMILES: Cn1cc(C(O)(c2cc(F)c3c(c2)C(=O)N(Cc2ccc(C#N)cn2)[C@@]3(O[C@H]2CCOC2)c2ccc(Cl)cc2)C(F)(F)F)cn1] | 6-{[(1R)-1-(4-chlorophenyl)-7-fluoro-3-oxo-1-[(3S)-oxolan-3-yloxy]-5-[2,2,2-trifluoro-1-hydroxy-1-(1-methyl-1H-pyrazol-4-yl)ethyl]-2,3-dihydro-1H-isoindol-2-yl]methyl}pyridine-3-carbonitrile | Prepared in a similar manner to Example 202 step 2, but using TMSCF3/CsF instead of MeMgCl | 1H NMR (400 MHz, CDCl3): 8.63 (1H, d), 7.91 (1H, s), 7.78 (1H, dd), 7.57-7.43 (2H, m), 7.43-7.32 (2H, m), 7.25-7.10 (4H, m), 4.60 (2H, q), 4.06-3.96 (1H, m), 3.91 (3H, s), 3.90-3.77 (1H, m), 3.76-3.64 (1H, m), 3.61 (1H, dd), 3.29 (1H, dd), 1.78-1.63 (2H, m). | 554 [M − C4H7O2]+ |

| Example | Structure | Name | Comment | NMR Data | MS Data |
|---|---|---|---|---|---|
| 372 | 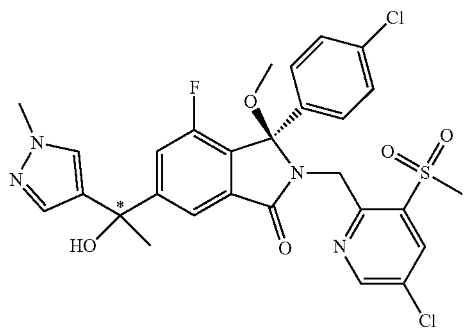 [SMILES: CO[C@]1(c2ccc(Cl)cc2)c2c(F)cc(C(C)(O)c3cnn(C)c3)cc2C(=O)N1Cc1ncc(Cl)cc1S(C)(=O)=O] | (3R)-2-[(5-chloro-3-methanesulfonyl-pyridin-2-yl)methyl]-3-(4-chlorophenyl)-4-fluoro-6-[1-hydroxy-1-(1-methyl-1H-pyrazol-4-yl)ethyl]-3-methoxy-2,3-dihydro-1H-isoindol-1-one | Prepared in a similar manner to Example 202 step 2 | ¹H NMR (400 MHz, CDCl3) 8.60 (1H, d), 8.23 (1H, dd), 7.71 (1H, s), 7.45-7.37 (5H, m), 7.28-7.25 (2H, m), 4.96 (1H, d), 4.71 (1H, d), 3.89-3.87 (3H, m), 3.19 (6H, 2s), 2.18 (1H, s), 1.90 (3H, s); | 619 (M + H)⁺ |
| 373 | 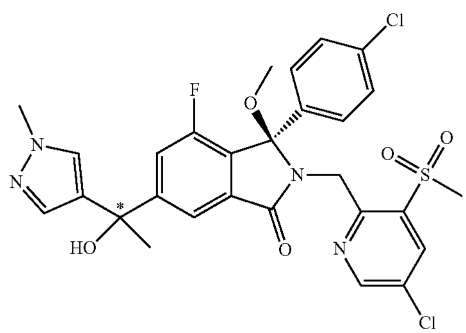 [SMILES: CO[C@]1(c2ccc(Cl)cc2)c2c(F)cc(C(C)(O)c3cnn(C)c3)cc2C(=O)N1Cc1ncc(Cl)cc1S(C)(=O)=O] | (3R)-2-[(5-chloro-3-methanesulfonyl-pyridin-2-yl)methyl]-3-(4-chlorophenyl)-4-fluoro-6-[1-hydroxy-1-(1-methyl-1H-pyrazol-4-yl)ethyl]-3-methoxy-2,3-dihydro-1H-isoindol-1-one | Prepared in a similar manner to Example 202 step 2 | ¹H NMR (400 MHz, CDCl3) 8.60 (1H, s), 8.23 (1H, dd), 7.71 (1H, s), 7.44-7.37 (5H, m), 7.28-7.26 (1H, m), 7.25-7.23 (1H, m), 4.96 (1H, d), 4.73 (1H, d), 3.88 (3H, s), 3.22-3.17 (6H, m), 2.18 (1H, s), 1.91 (3H, s) | 619 (M + H)⁺ |

Examples 374 and 375: 6-{[(1R)-1-(4-chlorophenyl)-7-fluoro-5-[1-hydroxy-1-(1-methyl-2-oxo-1,2-dihydropyridin-4-yl)propyl]-3-oxo-1-[(3S)-oxolan-3-yloxy]-2,3-dihydro-1H-isoindol-2-yl]methyl}pyridine-3-carbonitrile (*both isomers separated and isolated)

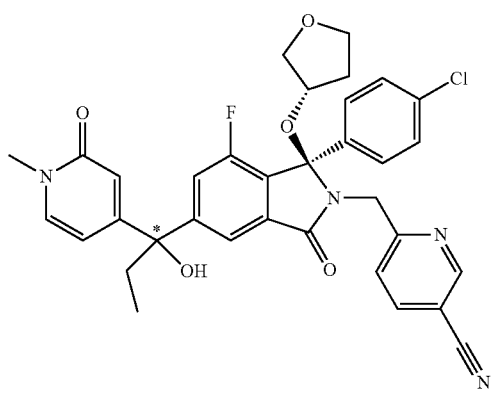 [SMILES: CCC(O)(c1cc(F)c2c(c1)C(=O)N(Cc1ccc(C#N)cn1)[C@@]2(O[C@H]1CCOC1)c1ccc(Cl)cc1)c1ccn(C)c(=O)c1]

Starting from 1-methyl-2-oxo-1,2-dihydropyridine-4-carbaldehyde, and the appropriate starting materials, the title compound was prepared by following procedures similar to those described for Example 200; but using Dess-Martin periodinane, InBr₃ and EtMgCl instead in Steps 2, 4 and 5 respectively.

Example 374

¹H NMR (400 MHz, DMSO) 8.77 (1H, d), 8.09 (1H, dd), 7.76 (1H, d), 7.56 (2H, d), 7.40 (1H, d), 7.29-7.21 (4H, m), 6.59 (1H, d), 6.24 (1H, dd), 5.95 (1H, s), 4.54 (2H, s), 4.05-3.99 (1H, m), 3.77-3.68 (1H, m), 3.56-3.49 (1H, m), 3.38 (1H, dd), 3.35 (3H, s), 3.10 (1H, dd), 2.27-2.19 (2H, m), 1.74-1.64 (1H, m), 1.57-1.48 (1H, m), 0.75 (3H, t). MS=672 (M−H⁺)⁻.

Example 375

¹H NMR (400 MHz, DMSO) 8.84 (1H, d), 8.16 (1H, dd), 7.86 (1H, d), 7.66-7.60 (2H, m), 7.47 (1H, d), 7.35-7.28 (4H, m), 6.65 (1H, d), 6.31 (1H, dd), 6.01 (1H, s), 4.61 (2H, d), 4.11-4.06 (1H, m), 3.78 (1H, q), 3.64-3.57 (1H, m), 3.44 (1H, dd), 3.41 (3H, s), 3.17 (1H, dd), 2.30 (2H, q), 1.82-1.71 (1H, m), 1.65-1.56 (1H, m), 0.82 (3H, t). MS=672 (M−H+)⁻.

Example 376: 6-[1-(1-Acetylpiperidin-4-yl)-1-hydroxyethyl]-3-(4-chlorophenyl)-2-[(5-chloropyridin-2-yl)methyl]-4-fluoro-3-hydroxy-2,3-dihydro-1H-isoindol-1-one (single configuration at position shown*. Mixture of epimers at the 3-position)

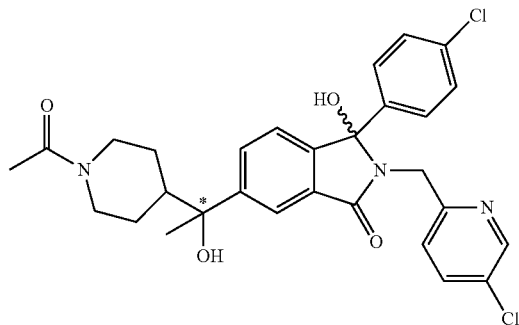 [SMILES: CC(=O)N1CCC(C(C)(O)c2ccc3c(c2)C(=O)N(Cc2ccc(Cl)cn2)C3(O)c2ccc(Cl)cc2)CC1]

4N aq. HCl (2.5 mL) was added to a solution of (3R)-6-[1-(1-acetylpiperidin-4-yl)-1-hydroxyethyl]-3-(4-chlorophenyl)-2-[(5-chloropyridin-2-yl)methyl]-4-fluoro-3-methoxy-2,3-dihydro-1H-isoindol-1-one (Example 293) (60 mg, 0.1 mmol) in dioxane (5 mL) and the reaction was stirred at 45° C. for 18 h. The reaction was quenched with NaHCO₃ and extracted with EtOAc. The organic phase was dried over Na₂SO₄, filtered and concentrated in vacuo. The residue was purified by chromatography on silica gel (gradient 0-20% MeOH in EtOAc) to give the desired product as a white solid (38 mg, 66%). $^1$H NMR (400 MHz, DMSO-$d_6$): 8.38 (2H, t), 7.81-7.70 (2H, m), 7.69 (1H, d), 7.64 (1H, d), 7.46 (2H, d), 7.40 (2H, t), 7.34-7.21 (10H, m), 5.23-5.17 (2H, m), 4.54 (2H, dd), 4.50-4.41 (1H, m), 4.36 (3H, dd), 3.86 (1H, d), 3.75 (1H, d), 2.96-2.82 (2H, m), 2.42-2.29 (4H, m), 1.95 (6H, d), 1.79 (4H, s), 1.47 (6H, d), 1.23 (4H, d); MS: [M−H]⁻=571.

Examples 377 and 378: (3R)-3-(4-chlorophenyl)-2-[(5-chloropyridin-2-yl)methyl]-6-[2-hydroxy-1-(piperidin-4-yloxy)propan-2-yl]-3-methoxy-2,3-dihydro-1H-isoindol-1-one (*both isomers separated and isolated)

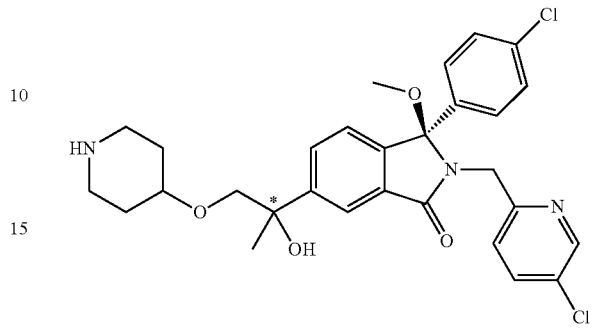

The title compounds were prepared in a similar manner as described in Example 234 but using benzyl 4-hydroxypiperidine-1-carboxylate instead of 3-hydroxypyridine followed by removal of the benzoyl protecting group with KOH in methanol and water at 70° C. and the isomers were separated via chiral SFC.

Example 377, Fast Running Isomer $^1$H NMR (400 MHz, CDCl₃) 8.34 (1H, d), 7.97 (1H, d), 7.74 (1H, dd), 7.47 (1H, dd), 7.24-7.19 (3H, m), 7.18-7.11 (3H, m), 4.60 (1H, d), 4.48 (1H, d), 3.62-3.57 (2H, m), 3.44-3.36 (1H, m), 3.06-2.94 (2H, m), 2.81 (3H, s), 2.63-2.51 (2H, m), 1.91-1.77 (2H, m), 1.56 (3H, s), 1.48-1.37 (3H, m), 0.92-0.82 (1H, m). MS: [M+H]⁺556.

Example 378, Slow Running Isomer $^1$H NMR (400 MHz, CDCl₃) 8.34 (1H, d), 7.98 (1H, d), 7.74 (1H, dd), 7.48 (1H, dd), 7.25-7.19 (3H, m), 7.18-7.11 (3H, m), 4.61 (1H, d), 4.46 (1H, d), 3.60-3.56 (2H, m), 3.44-3.36 (1H, m), 3.07-2.95 (2H, m), 2.81 (3H, s), 2.63-2.52 (2H, m), 1.90-1.78 (2H, m), 1.57 (3H, s), 1.50-1.34 (2H, m), 1.27-1.19 (1H, m), 0.90-0.82 (1H, m). MS: [M+H]⁺= 556.

Starting from of (3R)-3-(4-chlorophenyl)-2-((5-chloropyridin-2-yl)methyl)-3-methoxy-6-(2-methyloxiran-2-yl) isoindolin-1-one (Example 99, Example 100, step 1), and the appropriate amine or alcohol, the following Examples were prepared using procedures similar to those described in Example 104 or Example 233. Purification by preparative achiral and/or chiral HPLC gave final compounds as single isomer (unless stated otherwise). In the table below, an asterisk indicates the compound was isolated as a single isomer at the position shown.

| Example | Structure | Name | Comment | NMR data | MS data |
|---|---|---|---|---|---|
| 379 | ![structure] | (3R)-3-(4-chlorophenyl)-2-[(5-chloropyridin-2-yl)methyl]-6-{1-[(3S)-3,4-dimethylpiperazin-1-yl]-2-hydroxypropan-2-yl}-3-methoxy-2,3-dihydro-1H-isoindol-1-one | Prepared in a similar manner to Example 104 | $^1$H NMR (400 MHz, CDCl3) 8.34 (1H, d), 7.97 (1H, d), 7.71 (1H, dd), 7.48 (1H, dd), 7.24-7.10 (6H, m), 4.60 (1H, d), 4.46 (1H, d), 2.84-2.59 (9H, m), 2.37-2.29 (1H, m), 2.24 (3H, s), 1.99-1.91 (2H, m), 1.90-1.82 (1H, m), 1.51 (3H, s), 0.75 (3H, d) | [M + H]+ = 569 |

-continued

| Example | Structure | Name | Comment | NMR data | MS data |
|---|---|---|---|---|---|
| 380 | 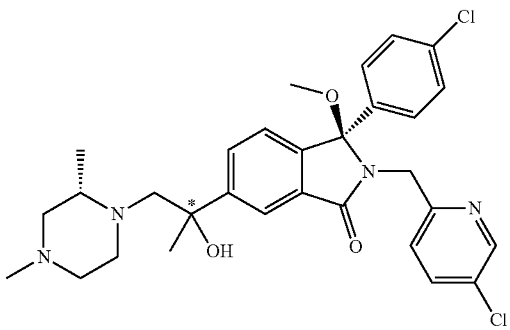 [SMILES: CO[C@]1(c2ccc(Cl)cc2)c2ccc(C(C)(O)CN3CCN(C)C[C@@H]3C)cc2C(=O)N1Cc1ccc(Cl)cn1] | (3R)-3-(4-chlorophenyl)-2-[(5-chloropyridin-2-yl)methyl]-6-{1-[(2S)-2,4-dimethyl-piperazin-1-yl]-2-hydroxypropan-2-yl}-3-methoxy-2,3-dihydro-1H-isoindol-1-one | Prepared in a similar manner to Example 104 | $^1$H NMR (400 MHz, CDCl3) 8.33 (1H, d), 7.95 (1H, d), 7.71 (1H, dd), 7.47 (1H, dd), 7.24-7.09 (6H, m), 4.59 (1H, d), 4.48 (1H, d), 2.90 (1H, d), 2.79-2.78 (4H, m), 2.65-2.49 (3H, m), 2.38-2.33 (1H, m), 2.25 (1H, d), 2.22 (3H, s), 2.07-2.04 (2H, m), 1.54 (3H, s), 0.91 (3H, d) (less OH) | [M + H]+ = 569 |
| 381 | 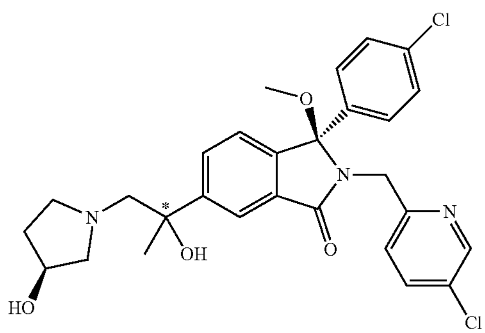 [SMILES: CO[C@]1(c2ccc(Cl)cc2)c2ccc(C(C)(O)CN3CC[C@H](O)C3)cc2C(=O)N1Cc1ccc(Cl)cn1] | (3R)-3-(4-chlorophenyl)-2-[(5-chloropyridin-2-yl)methyl]-6-{2-hydroxy-1-[(3S)-3-hydroxypyrrolidin-1-yl]propan-2-yl}-3-methoxy-2,3-dihydro-1H-isoindol-1-one | Prepared in a similar manner to Example 104 | $^1$H NMR (400 MHz, CDCl3) 8.34 (1H, d), 7.97 (1H, d), 7.76 (1H, dd), 7.48 (1H, dd), 7.24-7.14 (5H, m), 7.11 (1H, d), 4.59 (1H, d), 4.48 (1H, d), 4.27-4.23 (1H, m), 2.94 (2H, s), 2.80-2.79 (4H, m), 2.62-2.56 (1H, m), 2.39-2.32 (2H, m), 2.10-2.00 (1H, m), 1.68-1.61 (3H, m), 1.52 (3H, s) | [M + H]+ = 542 |
| 382 | 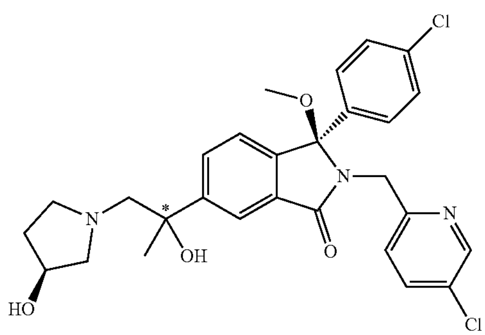 [SMILES: CO[C@]1(c2ccc(Cl)cc2)c2ccc(C(C)(O)CN3CC[C@H](O)C3)cc2C(=O)N1Cc1ccc(Cl)cn1] | (3R)-3-(4-chlorophenyl)-2-[(5-chloropyridin-2-yl)methyl]-6-{2-hydroxy-1-[(3S)-3-hydroxypyrrolidin-1-yl]propan-2-yl}-3-methoxy-2,3-dihydro-1H-isoindol-1-one | Prepared in a similar manner to Example 104 | $^1$H NMR (400 MHz, CDCl3) 8.34 (1H, d), 8.01 (1H, d), 7.72 (1H, dd), 7.48 (1H, dd), 7.26-7.14 (5H, m), 7.11 (1H, d), 4.60 (1H, d), 4.47 (1H, d), 4.26-4.23 (1H, m), 2.99-2.90 (2H, m), 2.80 (3H, s), 2.62-2.55 (2H, m), 2.48 (1H, dd), 2.37-2.31 (1H, m), 2.07-1.97 (1H, m), 1.62 (1H, d), 1.51 (3H, s), (Less OHs) | [M + H]+ = 542 |
| 383 | 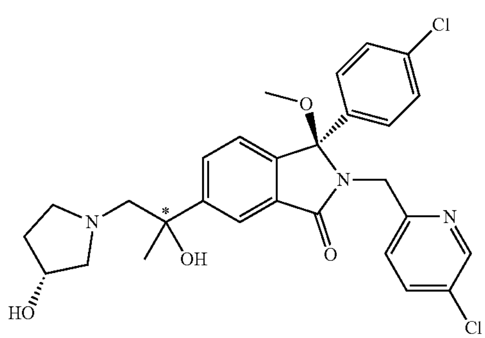 [SMILES: CO[C@]1(c2ccc(Cl)cc2)c2ccc(C(C)(O)CN3CC[C@@H](O)C3)cc2C(=O)N1Cc1ccc(Cl)cn1] | (3R)-3-(4-chlorophenyl)-2-[(5-chloropyridin-2-yl)methyl]-6-{2-hydroxy-1-[(3R)-3-hydroxypyrrolidin-1-yl]propan-2-yl}-3-methoxy-2,3-dihydroxy-1H-isoindol-1-one | Prepared in a similar manner to Example 104 | $^1$H NMR (400 MHz, CDCl3) 8.34 (1H, d), 7.98 (1H, d), 7.76 (1H, dd), 7.48 (1H, dd), 7.25-7.14 (5H, m), 7.11 (1H, d), 4.60 (1H, d), 4.47 (1H, d), 4.27-4.24 (1H, m), 2.99-2.91 (2H, m), 2.79 (3H, s), 2.61-2.49 (3H, m), 2.34-2.28 (1H, m), 2.07-1.97 (1H, m), 1.64-1.61 (1H, m), 1.51 (3H, s) (Less OHs) | [M + H]+ = 542 |

| Example | Structure | Name | Comment | NMR data | MS data |
|---|---|---|---|---|---|
| 384 | 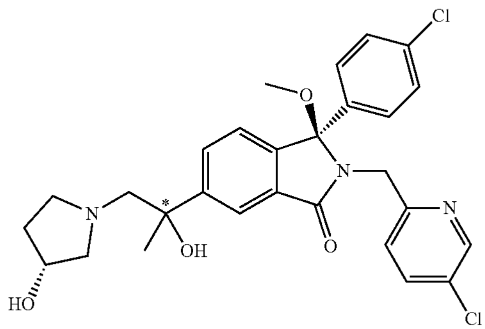 [SMILES: CO[C@]1(c2ccc(Cl)cc2)c2ccc(C(C)(O)CN3CC[C@@H](O)C3)cc2C(=O)N1Cc1ccc(Cl)cn1] | (3R)-3-(4-chlorophenyl)-2-[(5-chloropyridin-2-yl)methyl]-6-{2-hydroxy-1-[(3R)-3-hydroxypyrrolidin-1-yl]propan-2-yl}-3-methoxy-2,3-dihydro-1H-isoindol-1-one | Prepared in a similar manner to Example 104 | $^1$H NMR (400 MHz, CDCl3) 8.34 (1H, d), 7.99 (1H, d), 7.73 (1H, dd), 7.48 (1H, dd), 7.25-7.15 (5H, m), 7.11 (1H, d), 4.60 (1H, d), 4.46 (1H, d), 4.29-4.24 (1H, m), 2.94-2.93 (2H, m), 2.80-2.79 (4H, m), 2.63 (1H, dd), 2.39-2.31 (2H, m), 2.09-1.99 (1H, m), 1.67-1.59 (3H, m), 1.52 (3H, s) | [M + H]+ = 542 |

Starting from the appropriate acid (Preparation 23), amine and alcohol, the compounds in the following table 4 were prepared using methods similar to those described in Example 200 (Step 3 and 4) and/or Example 203 (using AlMe$_3$).

Preparative chiral HPLC chromatography was used to separate both chiral intermediates and final products. In the table below an asterisk (*) indicates the compound was isolated as a single isomer at the position shown.

| Example | Structure | Name | Comment | NMR Data | MS Data |
|---|---|---|---|---|---|
| 385 | 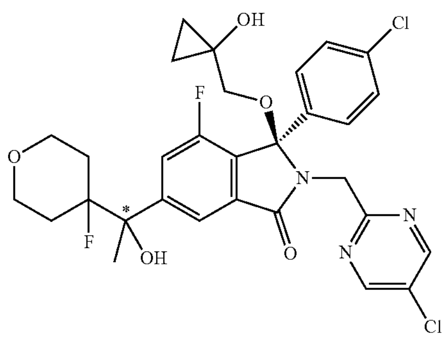 [SMILES: CC(O)(c1cc(F)c2c(c1)C(=O)N(Cc1ncc(Cl)cn1)[C@@]2(OCC1(O)CC1)c1ccc(Cl)cc1)C1(F)CCOCC1] | (3R)-3-(4-chlorophenyl)-2-[(5-chloropyrimidin-2-yl)methyl]-4-fluoro-6-[1-(4-fluorooxan-4-yl)-1-hydroxyethyl]-3-[(1-hydroxycyclopropyl)methoxy]-2,3-dihydro-1H-isoindol-1-one | Prepared in a similar manner to 200 (Steps 3 and 4) and 203 | $^1$H NMR (400 MHz, CDCl$_3$) 8.52 (2H, s), 7.84 (1H, s), 7.41 (1H, d), 7.36 (2H, d), 7.23 (2H, d), 4.65 (2H, s), 3.91-3.79 (2H, m), 3.68-3.60 (3H, m), 3.13 (1H, d), 2.98 (1H, s), 2.38 (1H, d), 2.00-1.76 (3H, m), 1.69 (3H, s), 1.50-1.44 (1H, m), 0.81 (2H, m), 0.57-0.51 (1H, m), 0.42-0.37 (1H, m). | MS: [M + H]$^+$ = 620. |
| 386 | 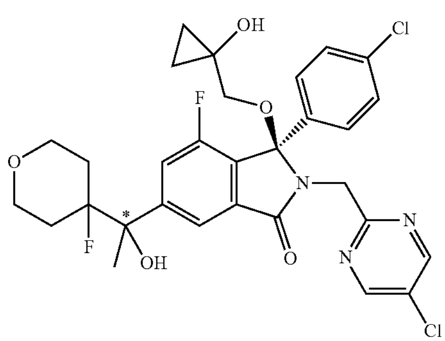 [SMILES: CC(O)(c1cc(F)c2c(c1)C(=O)N(Cc1ncc(Cl)cn1)[C@@]2(OCC1(O)CC1)c1ccc(Cl)cc1)C1(F)CCOCC1] | (3R)-3-(4-chlorophenyl)-2-[(5-chloropyrimidin-2-yl)methyl]-4-fluoro-6-[1-(4-fluorooxan-4-yl)-1-hydroxyethyl]-3-[(1-hydroxycyclopropyl)methoxy]-2,3-dihydro-1H-isoindol-1-one | Prepared in a similar manner to 200 (Steps 3 and 4) and 203 | $^1$H NMR (400 MHz, CDCl$_3$) 8.53 (2H, s), 7.81 (1H, s), 7.44 (1H, d), 7.38 (2H, d), 7.24 (2H, d), 4.65 (2H, s), 3.89-3.80 (2H, m), 3.68-3.59 (3H, m), 3.08 (1H, d), 2.98 (1H, s), 2.35 (1H, d), 1.68-1.68 (6H, m), 1.53-1.45 (1H, m), 0.84-0.80 (2H, m), 0.57-0.52 (1H, m), 0.43-0.38 (1H, m). | MS: [M − H]$^-$ = 618. |

| Example | Structure | Name | Comment | NMR Data | MS Data |
|---|---|---|---|---|---|
| 387 | 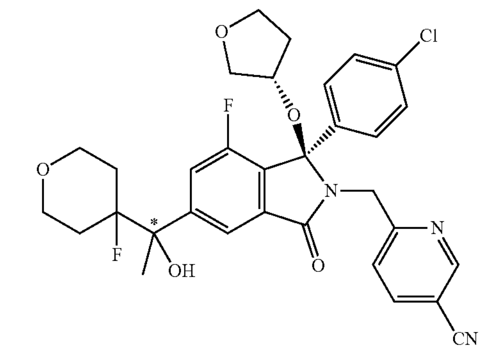 [SMILES: CC(O)(c1cc(F)c2c(c1)C(=O)N(Cc1ccc(C#N)cn1)[C@@]2(O[C@H]1CCOC1)c1ccc(Cl)cc1)C1(F)CCOCC1] | 6-{[(1R)-1-(4-chlorophenyl)-7-fluoro-5-[1-(4-fluorooxan-4-yl)-1-hydroxyethyl]-3-oxo-1-[(3S)-oxolan-3-yloxy]-2,3-dihydro-1H-isoindol-2-yl]methyl}pyridine-3-carbonitrile | Prepared in a similar manner to 200 (Steps 3 and 4) and 203 | $^1$H NMR (400 MHz, CDCl3) 8.66 (1H, d), 7.87 (1H, s), 7.79 (1H, dd), 7.46 (1H, d), 7.36 (1H, d), 7.20 (4H, q), 4.67-4.56 (2H, m), 4.07-4.01 (1H, m), 3.91-3.80 (3H, m), 3.72-3.57 (4H, m), 3.32 (1H, dd), 2.27 (1H, d), 1.99-1.73 (4H, m), 1.54 (3H, s), 1.47-1.38 (1H, m), 1.26-1.16 (1H, m). | MS: m/z = 608 [M − H$^+$]$^-$. |
| 388 | 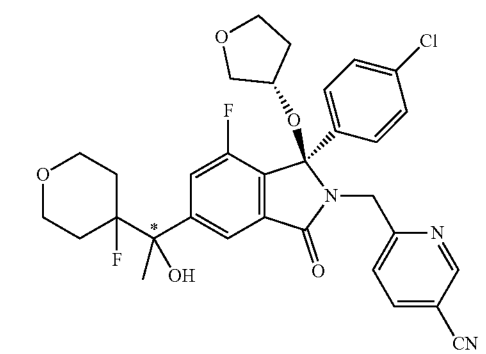 [SMILES: CC(O)(c1cc(F)c2c(c1)C(=O)N(Cc1ccc(C#N)cn1)[C@@]2(O[C@H]1CCOC1)c1ccc(Cl)cc1)C1(F)CCOCC1] | 6-{[(1R)-1-(4-chlorophenyl)-7-fluoro-5-[1-(4-fluorooxan-4-yl)-1-hydroxyethyl]-3-oxo-1-[(3S)-oxolan-3-yloxy]-2,3-dihydro-1H-isoindol-2-yl]methyl}pyridine-3-carbonitrile | Prepared in a similar manner to 200 (Steps 3 and 4) and 203 | :$^1$H NMR (400 MHz, CDCl3) 8.65 (1H, d), 7.84 (1H, s), 7.78 (1H, dd), 7.48 (1H, d), 7.35 (1H, d), 7.23 (2H, d), 7.17 (2H, d), 4.68 (1H, d), 4.57 (1H, d), 4.05-3.99 (1H, m), 3.92-3.81 (3H, m), 3.73-3.58 (4H, m), 3.92-3.81 (3H, m), 3.73-3.58 (4H, m), 3.33 (1H, dd), 2.29 (1H, s), 2.00-1.79 (4H, m), 1.72-1.69 (4H, m), 1.48 (1H, s). | MS: m/z = 608 [M − H$^+$]$^-$. |

Examples 389 and 390: (3R)-6-[1-(1-acetylazetidin-3-yl)-1-hydroxyethyl]-3-(4-chlorophenyl)-2-[(5-chloropyridin-2-yl)methyl]-4-fluoro-3-methoxy-2,3-dihydro-1H-isoindol-1-one (*The two examples were isolated as single isomers)

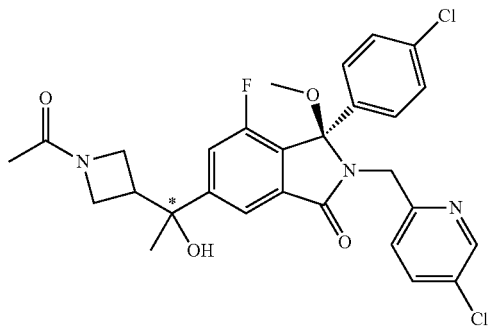 [SMILES: CO[C@]1(c2ccc(Cl)cc2)c2c(F)cc(C(C)(O)C3CN(C(C)=O)C3)cc2C(=O)N1Cc1ccc(Cl)cn1]

Starting from the separated isomers of Preparation 27. The title compounds were made using procedures similar to those described for Example 293. In this way, Preparation 27 [Slow running isomer (Isomer B)] was used to make Example 389 and Preparation 27 [Fast running isomer (Isomer A)] was used to make Example 390.

Example 389

$^1$H NMR (400 MHz, CDCl$_3$) 8.37 (1H, d), 7.78 and 7.73 (1H, 2×d, conformers A and B), 7.50 (1H, dd), 7.39 and 7.36 (1H, 2s, conformers A and B), 7.25-7.19 (5H, m), 4.64 (1H, d), 4.39 (1H, dd), 4.28-4.04 (2H, m), 3.93-3.65 (2H, m), 3.06-2.99 (1H, m), 2.97 and 2.59 (1H, 2s, conformers A and B), 2.92 and 2.90 (3H, 2s, conformers A and B), 1.88 and 1.80 (3H, 2s, conformers A and B), 1.60 (3H, s). MS: [M+H]$^+$=558

Example 390

$^1$H NMR (400 MHz, CDCl$_3$) 8.38-8.36 (1H, m), 7.75 (1H, s), 7.52-7.48 (1H, m), 7.42-7.34 (1H, m), 7.26-7.19 (5H, m), 4.67-4.60 (1H, m), 4.42-4.36 (1H, m), 4.27-4.03 (2H, m), 3.92-3.70 (2H, m), 3.05 and 2.71 (1H, 2s, conformers A and B), 3.03-2.97 (1H, m), 2.92 and 2.90 (3H, 2s, conformers A and B), 1.87 and 1.79 (3H, 2s, conformers A and B), 1.60 and 1.57 (3H, 2s, conformers A and B). MS: [M+H]$^+$=558.

Examples 391 and 392: (3R)-3-(4-chlorophenyl)-2-[(5-chloropyridin-2-yl)methyl]-4-fluoro-6-{1-hydroxy-1-[1-(2-hydroxyacetyl)azetidin-3-yl]ethyl}-3-methoxy-2,3-dihydro-1H-isoindol-1-one (*The two examples were isolated as single isomers)

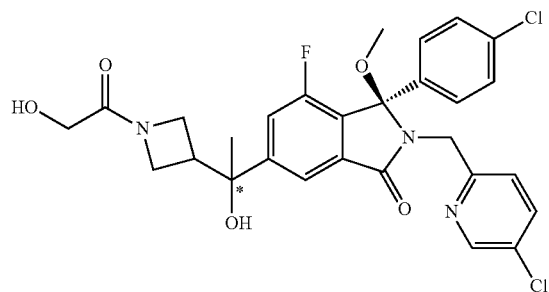 [SMILES: CO[C@]1(c2ccc(Cl)cc2)c2c(F)cc(C(C)(O)C3CN(C(=O)CO)C3)cc2C(=O)N1Cc1ccc(Cl)cn1]

Starting from Preparation 27 (fast running isomer—A), Example 391 was prepared using procedures similar to those described for Example 293; but using 2-acetoxy acetic acid and HATU instead of acetyl chloride. The acetate protecting group was removed in the final stage using LiOH in THF/H$_2$O. In the same way, Example 392 was prepared from Preparation 27 [Slow running isomer (Isomer B)].

Example 391

$^1$H NMR (400 MHz, CDCl$_3$) 8.37 (1H, dd), 7.77-7.75 (1H, m), 7.50 (1H), 7.37-7.32 (1H, m), 7.25-7.19 (5H, m), 4.68-4.61 (1H, m), 4.38 (1H, dd), 4.25-4.10 (2H, m), 4.01-3.70 (4H, m), 3.16-3.08 (1H, m), 2.91 (3H, s), 2.57 (1H, bs), 1.57 (3H, s). MS: [M+H]$^+$=574.

Example 392

$^1$H NMR (400 MHz, CDCl$_3$) 8.36 (1H, d), 7.80 (1H, d), 7.50 (1H, dd), 7.33 (1H, d), 7.26-7.18 (5H, d), 4.64 (1H, d), 4.39 (1H, d), 4.29-4.05 (2H, m), 4.03-3.87 (3H, m), 3.80-3.71 (1H, m), 3.18-3.06 (2H, m), 3.00 (1H, bs) 2.91 (3H, s), 1.55 (3H, s). MS: [M+H]$^+$=574.

Examples 393 and 394: 3-{1-[(1R)-1-(4-chlorophenyl)-2-[(5-cyanopyridin-2-yl)methyl]-7-fluoro-1-methoxy-3-oxo-2,3-dihydro-1H-isoindol-5-yl]-1-hydroxyethyl}-N,N-dimethylazetidine-1-carboxamide (*The two examples were isolated as single isomers)

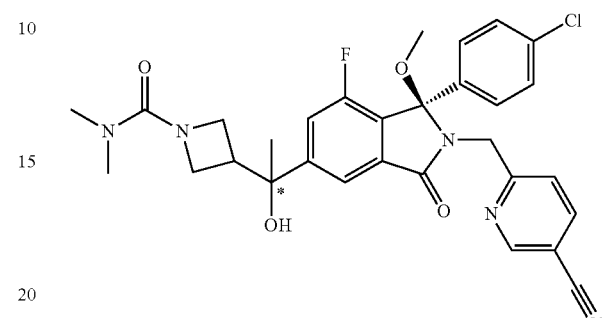

Starting from Preparation 27 (fast running isomer—A), Example 393 was prepared using procedures similar to those described for Example 293; but using dimethylcarbamoyl chloride instead of acetyl chloride. In the same way, Example 394 was prepared from Preparation 27 [Slow running isomer (Isomer B)].

Example 393

$^1$H NMR (400 MHz, CDCl$_3$) 8.69 (1H, d), 7.79 (1H, dd), 7.74 (1H, d), 7.41 (1H, dd), 7.35 (1H, d), 7.25-7.18 (4H, m), 4.67 (1H, d), 4.50 (1H, d), 4.09-4.03 (2H, m), 3.73 (2H, d), 3.03-2.97 (1H, m), 2.95 (3H, s), 2.83 (6H, s), 2.55 (1H, s), 1.53 (3H, s). MS: [M−H]$^-$=576.

Example 394

$^1$H NMR (400 MHz, CDCl$_3$) 8.68 (1H, d), 7.79 (1H, dd), 7.74 (1H, d), 7.40 (1H, dd), 7.35 (1H, d), 7.24 (2H, m), 7.20 (2H, d), 4.67 (1H, d), 4.50 (1H, d), 4.07-4.04 (2H, m), 3.73 (2H, d), 3.04-2.96 (1H, m), 2.95 (3H, s), 2.83 (6H, s), 2.38 (1H, s), 1.53 (3H, s). MS: 546.5 (M-OMe)

Examples 395 and 396: (3R)-3-(4-chlorophenyl)-2-[(5-chloropyridin-2-yl)methyl]-4-fluoro-6-[1-hydroxy-1-(pyrimidin-2-yl)ethyl]-3-[(1-hydroxycyclopropyl)methoxy]-2,3-dihydro-1H-isoindol-1-one (*both isomers separated and isolated)

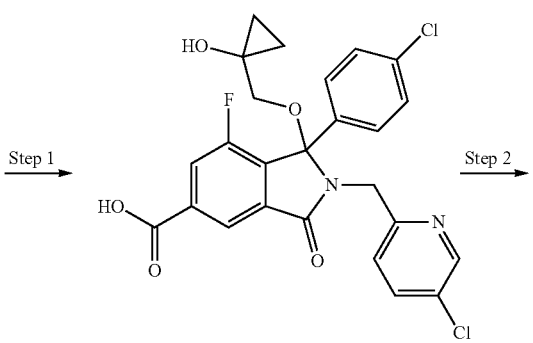

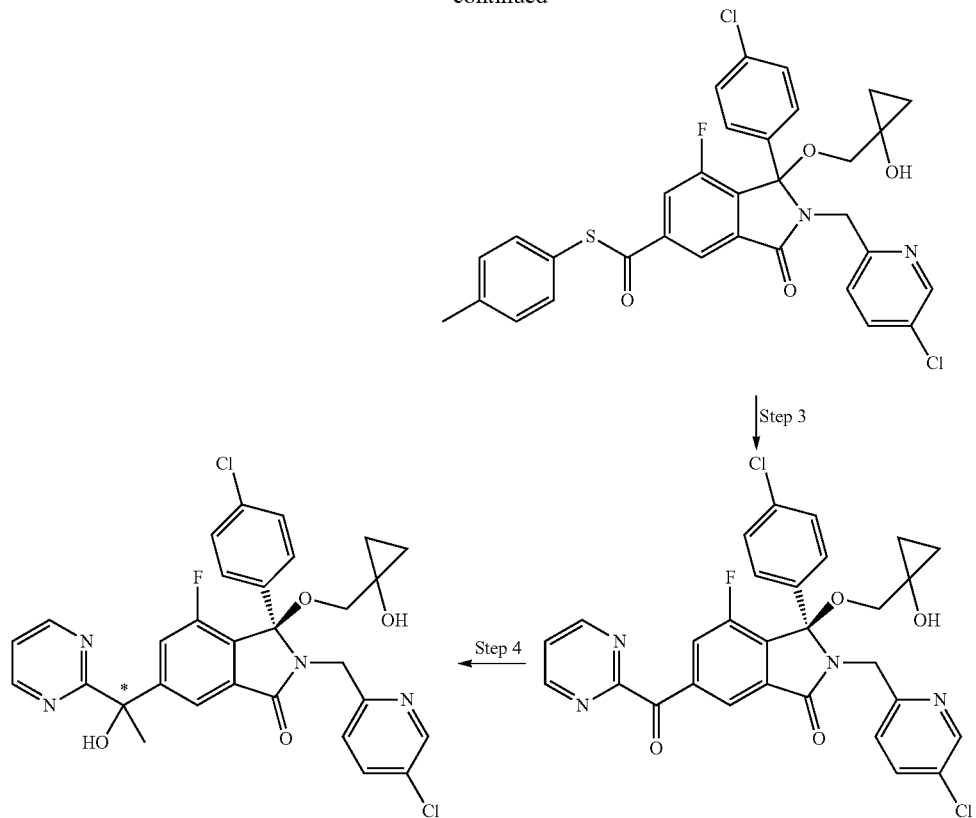

Step 1: 1-(4-Chlorophenyl)-2-((5-chloropyridin-2-yl)methyl)-7-fluoro-1-((1-hydroxycyclopropyl)methoxy)-3-oxoisoindoline-5-carboxylic Acid 6-Bromo-3-(4-chlorophenyl)-2-((5-chloropyridin-2-yl)methyl)-4-fluoro-3-((1-hydroxycyclopropyl)methoxy)isoindolin-1-one (7 g, 12.7 mmol) was converted to the title compound using a similar procedure as in Example 161, step 1. MS: [M+H]$^+$=517.

Step 2: S-p-Tolyl 1-(4-chlorophenyl)-2-((5-chloropyridin-2-yl)methyl)-7-fluoro-1-((1-hydroxycyclopropyl)methoxy)-3-oxoisoindoline-5-carbothioate 1-(4-Chlorophenyl)-2-((5-chloropyridin-2-yl)methyl)-7-fluoro-1-((1 hydroxycyclopropyl)methoxy)-3-oxoisoindoline-5-carboxylic acid (8.40 g, 16.36 mmol) in THF (226 mL) was added slowly to 4-methyl benzene thiol (4.05 g, 32.72 mmol) and DCC (3.37 g, 16.36 mmol) in THF (220 mL). The resulting mixture was stirred at RT for 18 h before a further portion of DCC (1.68 g, 8.18) and 4-methyl benzene thiol (2.02 g, 16.36 mmol) were added. The mixture was stirred a further 6 h at RT and then filtered through a pad of celite. The filtrate was concentrated in vacuo and the resulting crude material purified by column chromatography, Biotage Isolera, 300 g Interchim cartridge 10-100% EtOAc/isohexane to afford the title compound (6.13 g, 60% over two steps). MS: [M+H]$^+$=623.

Step 3: (R)-3-(4-Chlorophenyl)-2-((5-chloropyridin-2-yl)methyl)-4-fluoro-3-((1-hydroxycyclopropyl)methoxy)-6-(pyrimidine-2-carbonyl)isoindolin-1-one S-p-Tolyl-1-(4-chlorophenyl)-2-((5-chloropyridin-2-yl)methyl)-7-fluoro-1-((1-hydroxycyclopropyl)methoxy)-3-oxoisoindoline-5-carbothioate (2.19 g, 3.52 mmol), 2-(tributylstannyl)pyrimidine (1.42 g, 3.87 mmol), CuTC (1.47 g, 7.74 mmol), tri-furyl phosphine (0.16 g, 0.7 mmol) and Pd$_2$(dba)$_3$ (0.081 g, 0.088 mmol) were suspended in THF (20 mL) and iso-hexane (20 mL). The mixture was degassed with N$_2$ for 1 min and then heated at 50° C. for 1 h. The mixture was diluted with ethyl acetate (20 mL) and water (20 mL). Product was extracted into ethyl acetate (2×20 mL) and the organics washed with sat. NaHCO$_3$ (1×20 mL). The combined organics were dried (MgSO$_4$), concentrated in vacuo and the resulting crude material purified by column chromatography, Biotage Isolera, 50 g SNAP cartridge 0-3% MeOH/ethylacetate to afford the 3-(4-chlorophenyl)-2-((5-chloropyridin-2-yl)methyl)-4-fluoro-3-((1-hydroxycyclopropyl)methoxy)-6-(pyrimidine-2-carbonyl)isoindolin-1-one (0.53 g, 26%). Purification by chiral preparative LCMS gave the title compound (277 mg). MS: [M+H]$^+$=579.

Step 4: (3R)-3-(4-chlorophenyl)-2-[(5-chloropyridin-2-yl)methyl]-4-fluoro-6-[1-hydroxy-1-(pyrimidin-2-yl)ethyl]-3-[(1-hydroxycyclopropyl)methoxy]-2,3-dihydro-1H-isoindol-1-one The title compounds were prepared from (R)-3-(4-chlorophenyl)-2-((5-chloropyridin-2-yl)methyl)-4-fluoro-3-((1-hydroxycyclopropyl)methoxy)-6-(pyrimidine-2-carbonyl)isoindolin-1-one In a similar manner to that described for Example 1, step 4, followed by purification by preparative LCMS and chiral preparative LCMS.

Example 396: *Fast Running Isomer $^1$H NMR (400 MHz, CDCl$_3$) 8.75 (2H, d), 8.34 (1H, d), 8.03 (1H, d), 7.59-7.52 (2H, m), 7.35 (1H, d), 7.29 (2H, d), 7.25-7.19 (3H, m), 5.64 (1H, s), 4.50-4.39 (2H, m), 4.01 (1H, s), 3.47 (1H, dd), 2.95 (1H, d), 1.98 (3H, s), 0.88-0.74 (2H, m), 0.56-0.50 (1H, m), 0.38-0.32 (1H, m). MS: [M+H]⁺= 595.

Example 395: *Slow Running Isomer

¹H NMR (400 MHz, CDCl₃) 8.74 (2H, d), 8.33 (1H, d), 8.03 (1H, d), 7.61-7.52 (2H, m), 7.35 (1H, d), 7.30 (2H, d), 7.26-7.20 (3H, m), 5.61 (1H, s), 4.50-4.37 (2H, m), 4.00 (1H, s), 3.43 (1H, d), 2.94 (1H, d,), 1.98 (3H, s), 0.87-0.73 (2H, m), 0.55-0.48 (1H, m), 0.37-0.30 (1H, m). MS: [M+H]+=595.

Examples 397 and 398: 4-{1-[(1R)-1-(4-chlorophenyl)-2-[(5-chloropyrimidin-2-yl)methyl]-7-fluoro-1-[(1-hydroxycyclopropyl)methoxy]-3-oxo-2,3-dihydro-1H-isoindol-5-yl]-1-hydroxyethyl}-1λ6-thiane-1,1-dione (*both isomers separated and isolated)

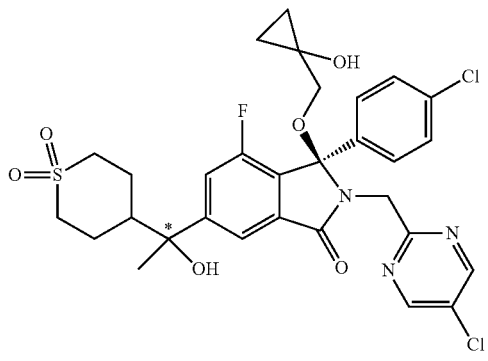 [SMILES: CC(O)(c1cc(F)c2c(c1)C(=O)N(Cc1ncc(Cl)cn1)[C@@]2(OCC1(O)CC1)c1ccc(Cl)cc1)C1CCS(=O)(=O)CC1]

Starting from 2-(4-chlorobenzoyl)-5-(1,1-dioxidotetrahydro-2H-thiopyran-4-carbonyl)-3-fluorobenzoic acid (Example 311 Step 3), the title compounds were prepared using methods similar to those described in Example 200 (Steps 3-4) and Example 203 in a subsequent fashion.

Example 398: *Faster Eluting Isomer

¹H NMR (400 MHz, DMSO) 8.74 (2H, s), 7.74 (1H, s), 7.48 (1H, d), 7.38 (2H, d), 7.32 (2H, d), 5.48 (2H, d), 4.60 (2H, s), 3.40 (1H, d), 3.08-3.05 (3H, m), 3.00-2.92 (2H, m), 2.07 (2H, m), 1.73-1.70 (3H, m), 1.50 (3H, s), 0.54 (2H, s), 0.40-0.35 (1H, m), 0.28 (1H, d); MS: [M+Na]⁺=672.3.

Example 397: *Slower Eluting Isomer

¹H NMR (400 MHz, DMSO) 8.72 (2H, s), 7.73 (1H, s), 7.47 (1H, d), 7.37 (2H, d), 7.31 (2H, d), 5.50-5.44 (2H, m), 4.58 (2H, s), 3.38 (1H, d), 3.08-2.90 (5H, m), 2.08-2.06 (2H, m), 1.79-1.68 (3H, m), 1.49 (3H, s), 0.53 (2H), 0.38-0.25 (2H, m); MS: [M–H]⁻=648.3.

Examples 399 and 400: 4-{[(1R)-1-(4-chlorophenyl)-2-[(5-chloropyrimidin-2-yl)methyl]-7-fluoro-1-[(1-hydroxycyclopropyl)methoxy]-3-oxo-2,3-dihydro-1H-isoindol-5-yl](hydroxy)methyl}-1λ6-thiane-1,1-dione (*both isomers separated and isolated)

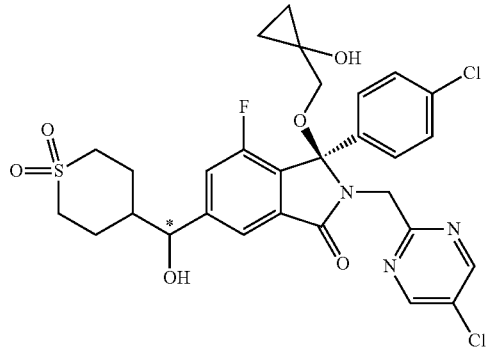 [SMILES: O=C1c2cc(C(O)C3CCS(=O)(=O)CC3)cc(F)c2[C@](OCC2(O)CC2)(c2ccc(Cl)cc2)N1Cc1ncc(Cl)cn1]

The title compounds were isolated as components from the final step in the synthesis of Example 397.

Example 399

¹H NMR (400 MHz, CDCl₃) 8.53 (2H, s), 7.68 (1H, s), 7.34 (2H, d), 7.25-7.17 (3H, m), 4.66 (1H, dd), 4.63 (2H, s), 3.64 (1H, d), 3.16-2.92 (6H, m), 2.33-2.28 (1H, m), 2.23 (1H, dd), 2.08-1.95 (2H, m), 1.90-1.85 (2H, m), 0.82 (2H, dd), 0.56-0.51 (1H, m), 0.43-0.37 (1H, m). MS (M+Na⁺)⁺= 658

Example 400

¹H NMR (400 MHz, CDCl₃) 8.53 (2H, s), 7.67 (1H, d), 7.37 (2H, d), 7.26-7.20 (3H, m), 4.67 (1H, dd), 4.64 (2H, s), 3.63 (1H, d), 3.13-3.03 (3H, m), 2.93 (3H, s), 2.33-2.27 (1H, m), 2.21 (1H, d), 2.08-1.96 (2H, m), 1.91-1.85 (2H, m), 0.82 (2H, dd), 0.55-0.50 (1H, m), 0.42-0.37 (1H, m). MS (M+Na⁺)⁺=658

Examples 401 and 402: (3R)-3-(4-chlorophenyl)-2-[(5-chloropyrimidin-2-yl)methyl]-4-fluoro-6-{1-hydroxy-1-[trans-4-hydroxycyclohexyl]ethyl}-3-{[1-(hydroxymethyl)cyclopropyl]methoxy}-2,3-dihydro-1H-isoindol-1-one (*both isomers separated and isolated)

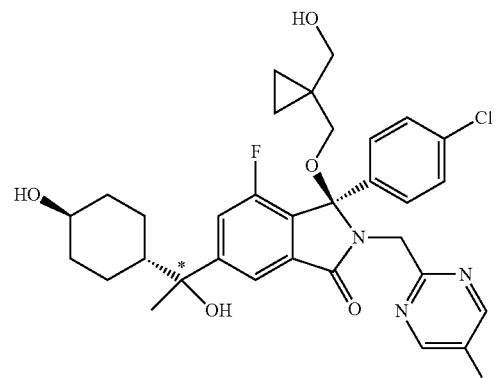

The title compounds were prepared using procedures similar to those described for Example 203, but starting from Preparation 28 (1R,4R)-4-((tert-butyldiphenylsilyl)oxy)cyclohexanecarbaldehyde) instead of 1-methyl-1H-pyrazole-4-carboxaldehyde. TBDPS protecting group was removed at the final stage using TBAF in THF.

Example 401

$^1$H NMR (400 MHz, CDCl$_3$) 8.54 (2H, s), 7.67 (1H, d), 7.38-7.34 (3H, m), 7.23 (2H, d), 4.67-4.56 (2H, m), 3.61-3.45 (4H, m), 2.99 (1H, d), 2.14-1.92 (3H, m), 1.86-1.78 (1H, m), 1.72 (1H, s), 1.63-1.58 (4H, m), 1.49-1.38 (2H, m), 1.28-1.10 (4H, m), 0.52-0.42 (3H, m), 0.34-0.29 (1H, m). MS [M-1-cyclopropane-1,1-diyldimethanol]$^+$=528

Example 402

$^1$H NMR (400 MHz, CDCl$_3$) 8.54 (2H, s), 7.71 (1H, s), 7.34 (3H, t), 7.22 (2H, d), 4.66-4.56 (2H, m), 3.62-3.46 (4H, m), 3.02 (1H, d), 2.14-1.92 (3H, m), 1.87-1.81 (1H, m), 1.69 (1H, s), 1.63-1.56 (4H, m), 1.49-1.43 (1H, m), 1.40 (1H, d), 1.28-1.11 (4H, m), 0.53-0.42 (3H, m), 0.33-0.30 (1H, m). MS=628 (M-H$^+$)$^-$=628

Examples 403 and 404: 1-({[(1R)-1-(4-chlorophenyl)-2-[(5-chloropyrimidin-2-yl)methyl]-5-(1-cyclobutyl-1-hydroxyethyl)-7-fluoro-3-oxo-2,3-dihydro-1H-isoindol-1-yl]oxy}methyl)cyclopropane-1-carboxamide (*both isomers separated and isolated)

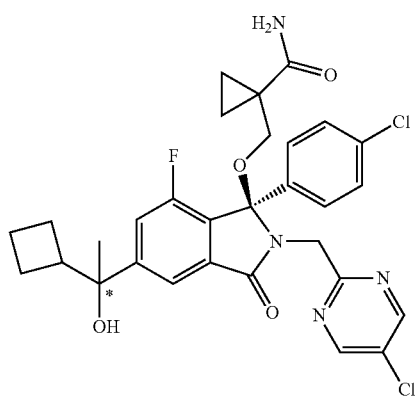 [SMILES: CC(O)(c1cc(F)c2c(c1)C(=O)N(Cc1ncc(Cl)cn1)[C@@]2(OCC1(C(N)=O)CC1)c1ccc(Cl)cc1)C1CCC1]

Starting from Preparation 29, the title compounds were prepared in a similar fashion to Example 203, but using 1-(hydroxymethyl)cyclopropanecarboxamide in place of 1-(hydroxymethyl)cyclopropanol.

Example 403: *Slower Eluting Isomer $^1$H NMR (400 MHz, CDCl$_3$) 8.54 (2H, s), 7.75 (1H, s), 7.41 (1H, dd), 7.32 (2H, d), 7.26 (2H, d), 6.74 (1H, s), 5.44-5.43 (1H, m), 4.59-4.49 (2H, m), 3.57 (1H, d), 3.42 (1H, d), 2.79-2.69 (1H, m), 2.10-1.70 (7H, m), 1.47 (3H, s), 1.38-1.31 (1H, m), 1.25-1.16 (1H, m), 0.60-0.44 (2H, m) MS: [M-H]$^-$=597

Example 404: *Faster Eluting Isomer $^1$H NMR (400 MHz, CDCl$_3$) 8.54 (2H, s), 7.74 (1H, s), 7.42 (1H, d), 7.33 (2H, d), 7.26 (2H, d), 6.74-6.74 (1H, m), 5.46-5.45 (1H, m), 4.59-4.48 (2H, m), 3.58 (1H, d), 3.41 (1H, d), 2.78-2.68 (1H, m), 2.09-1.55 (7H, m), 1.48 (3H, s), 1.38-1.31 (1H, m), 1.25-1.18 (1H, m), 0.61-0.45 (2H, m) MS: [M-H]$^-$=597

Examples 405 and 406: 6-{[(1R)-1-(4-chlorophenyl)-5-(1-cyclobutyl-1-hydroxyethyl)-7-fluoro-1-(2-hydroxyethoxy)-3-oxo-2,3-dihydro-1H-isoindol-2-yl]methyl}pyridine-3-carbonitrile (*both isomers separated and isolated)

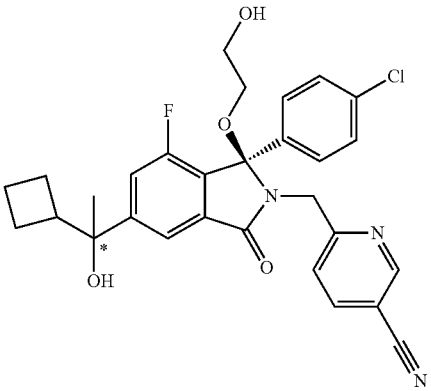 [SMILES: CC(O)(c1cc(F)c2c(c1)C(=O)N(Cc1ccc(C#N)cn1)[C@@]2(OCCO)c1ccc(Cl)cc1)C1CCC1]

Starting from 2-(4-chlorobenzoyl)-5-(cyclobutanecarbonyl)-3-fluorobenzoic acid, the title compound was prepared using procedures similar to those described in Example 200, using 6-(aminomethyl)nicotinonitrile dihydrochloride and ethylene glycol as the appropriate amine and alcohol respectively. The methyl group was added using a procedure similar to that described in Example 202, Step 2.

Example 405: *Slower Eluting Isomer $^1$H NMR (400 MHz, CDCl$_3$) 8.68 (1H, d), 7.82 (1H, dd), 7.72 (1H, d), 7.46 (1H, d), 7.37 (1H, dd), 7.29 (2H, d), 7.23 (2H, d), 4.59 (1H, d), 4.49 (1H, d), 3.82-3.74 (1H, m), 3.68-3.61 (1H, m), 3.38-3.32 (1H, m), 3.23-3.17 (1H, m), 2.77-2.67 (1H, m), 2.56 (1H, dd), 1.82-1.56 (10H, m) MS: [M+H]$^+$=536

Example 406: *Faster Eluting Isomer $^1$H NMR (400 MHz, CDCl$_3$) 8.68 (1H, d), 7.82 (1H, dd), 7.72 (1H, d), 7.46 (1H, d), 7.37 (1H, dd), 7.28 (2H, d), 7.22 (2H, d), 4.59 (1H, d), 4.49 (1H, d), 3.82-3.74 (1H, m), 3.68-3.61 (1H, m), 3.38-3.32 (1H, m), 3.23-3.18 (1H, m), 2.77-2.67 (1H, m), 2.56 (1H, dd), 1.81-1.56 (10H, m) MS: [M+H]$^+$=536

The following examples were prepared by oxidation of the corresponding pyridine analogues (described herein) using a method similar to that described in Example 10. In the Table, an asterisk (*) indicates the compound was isolated as a single isomer at the position shown.

| Example | Structure | Name | Comment | NMR Data | MS Data |
|---|---|---|---|---|---|
| 407 | 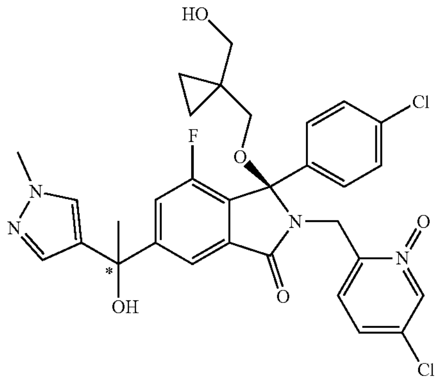 [SMILES: Cn1cc(C(C)(O)c2cc(F)c3c(c2)C(=O)N(Cc2ccc(Cl)c[n+]2[O-])[C@@]3(OCC2(CO)CC2)c2ccc(Cl)cc2)cn1] | (3R)-2-[(5-chloro-1-oxo-1λ⁵-pyridin-2-yl)methyl]-3-(4-chlorophenyl)-4-fluoro-6-[1-hydroxy-1-(1-methyl-1H-pyrazol-4-yl)ethyl]-3-{[1-(hydroxymethyl)cyclopropyl]methoxy}-2,3-dihydro-1H-isoindol-1-one | Prepared from Example 347 | $^1$H NMR (400 MHz, DMSO-d6): 8.39 (1H, d), 7.72 (1H, d), 7.61 (1H, s), 7.54-7.47 (1H, m), 7.36 (1H, d), 7.30 (4H, s), 7.22 (1H, dd), 7.13 (1H, d), 5.88 (1H, s), 4.57 (1H, d), 4.50-4.40 (2H, m), 3.79 (3H, s), 3.36 (2H, d), 3.14 (1H, d), 2.93 (1H, d), 1.80 (3H, s), 0.34 (4H, dd). | LCMS: [M − H]⁻ = 625; |
| 408 | 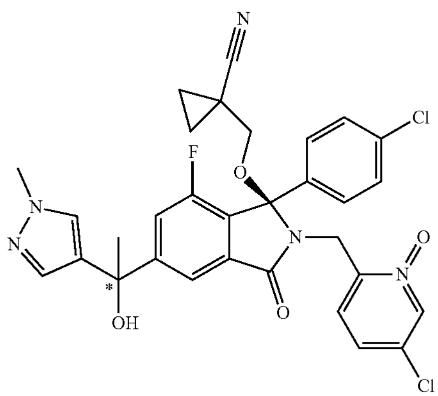 [SMILES: Cn1cc(C(C)(O)c2cc(F)c3c(c2)C(=O)N(Cc2ccc(Cl)c[n+]2[O-])[C@@]3(OCC2(C#N)CC2)c2ccc(Cl)cc2)cn1] | 1-({[(1R)-2-[(5-chloro-1-oxo-1λ⁵-pyridin-2-yl)methyl]-1-(4-chlorophenyl)-7-fluoro-5-[1-hydroxy-1-(1-methyl-1H-pyrazol-4-yl)ethyl]-3-oxo-2,3-dihydro-1H-isoindol-1-yl]oxy}methyl)cyclopropane-1-carbonitrile | Prepared from Example 202 | $^1$H NMR (400 MHz, DMSO-d6): 8.40 (1H, d), 7.74 (1H, d), 7.62 (1H, s), 7.54 (1H, dd), 7.39-7.28 (5H, m), 7.24 (1H, dd), 7.18 (1H, d), 5.89 (1H, s), 4.58 (1H, d), 4.45 (1H, d), 3.79 (3H, s), 3.34 (1H, d), 3.05 (1H, d), 1.79 (3H, s), 1.32-1.20 (2H, m), 0.99-0.84 (2H, m). | LCMS: [M − H]⁻ = 621 |
| 409 | 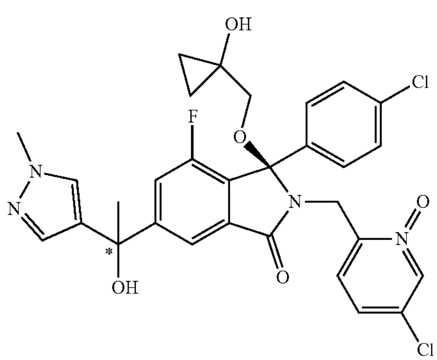 [SMILES: Cn1cc(C(C)(O)c2cc(F)c3c(c2)C(=O)N(Cc2ccc(Cl)c[n+]2[O-])[C@@]3(OCC2(O)CC2)c2ccc(Cl)cc2)cn1] | (3R)-2-[(5-chloro-1-oxo-1λ⁵-pyridin-2-yl)methyl]-3-(4-chlorophenyl)-4-fluoro-6-[1-hydroxy-1-(1-methyl-1H-pyrazol-4-yl)ethl]-3-[(1-hydroxycyclopropyl)methoxy]-2,3-dihydro-1H-isoindol-1-one | Prepared from Example 200 | $^1$H NMR (400 MHz, DMSO-d6): 8.40 (1H, d), 7.73 (1H, d), 7.62 (1H, s), 7.51 (1H, dd), 7.42-7.33 (3H, m), 7.30 (2H, d), 7.21 (1H, dd), 7.11 (1H, d), 5.89 (1H, s), 5.54 (1H, s), 4.58 (1H, d), 4.50 (1H, d), 3.79 (3H, s), 3.23 (1H, d), 2.94 (1H, d), 1.80 (3H, s), 0.58 (2H, d), 0.50-0.34 (2H, m). | LCMS: [M − H]⁻ = 612 |

The following examples were prepared in a similar manner to Example 36, by reacting the appropriate Grignard reagent, or nucleophile. With a chiral ketone intermediate. Purification by preparative chiral HPLC gave the products as single enantiomers (at the position shown*).

| Example | Structure | Name | Comment | NMR Data | MS Data |
|---|---|---|---|---|---|
| 410 | 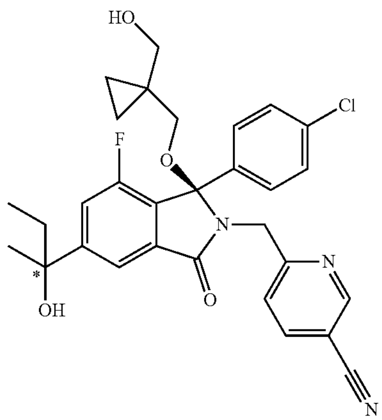 [SMILES: CCC(C)(O)c1cc(F)c2c(c1)C(=O)N(Cc1ccc(C#N)cn1)[C@@]2(OCC1(CO)CC1)c1ccc(Cl)cc1] | 6-{[(1R)-1-(4-chlorophenyl)-7-fluoro-5-(2-hydroxybutan-2-yl)-1-{[1-(hydroxymethyl)cyclopropyl]methoxy}-3-oxo-2,3-dihydro-1H-isoindol-2-yl]methyl}pyridine-3-carbonitrile | Using EtMgBr | $^1$H NMR (400 MHz, DMSO-d6): 8.77 (1H, d), 8.09 (1H, dd), 7.76 (1H, s), 7.47 (1H, d), 7.36 (1H, d), 7.33-7.16 (4H, m), 5.17 (1H, s), 4.58 (1H, d), 4.52 (1H, d), 4.41 (1H, t), 3.34 (2H, dd), 3.14 (1H, d), 2.90 (1H, d), 1.84-1.67 (2H, m), 1.46 (3H, s), 0.70 (3H, t), 0.41-0.31 (2H, m), 0.25-0.09 (2H, m). | LCMS: [M − H]$^-$ = 549 |
| 411 | 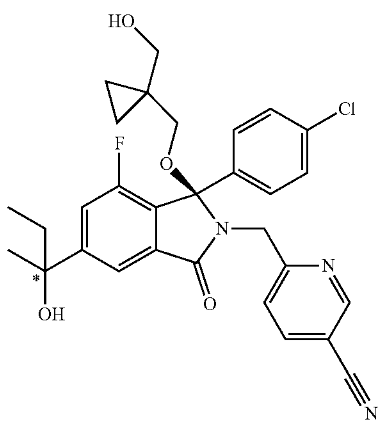 [SMILES: CCC(C)(O)c1cc(F)c2c(c1)C(=O)N(Cc1ccc(C#N)cn1)[C@@]2(OCC1(CO)CC1)c1ccc(Cl)cc1] | 6-{[(1R)-1-(4-chlorophenyl)-7-fluoro-5-(2-hydroxybutan-2-yl)-1-{[1-(hydroxymethyl)cyclopropyl]methoxy}-3-oxo-2,3-dihydro-1H-isoindol-2-yl]methyl}pyridine-3-carbonitrile | Using EtMgBr | $^1$H NMR (400 MHz, DMSO-d6): 8.77 (1H, d), 8.09 (1H, dd), 7.76 (1H, d), 7.47 (1H, d), 7.35 (1H, d), 7.32-7.19 (4H, m), 5.17 (1H, s), 4.60 (1H, d), 4.50 (1H, d), 4.42 (1H, d), 3.35 (2H, d), 3.15 (1H, d), 2.89 (1H, d), 1.83-1.66 (2H, m), 1.48 (3H, s), 0.70 (3H, t), 0.36 (2H, d), 0.26-0.10 (2H, m). | LCMS: [M − H]$^-$ = 549 |
| 412 | 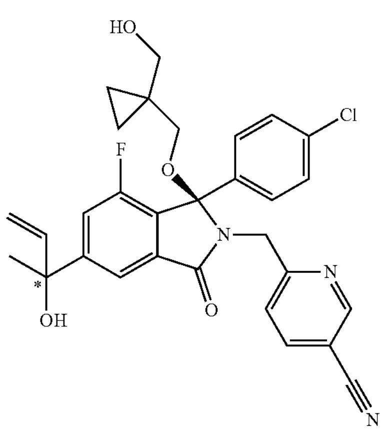 [SMILES: C=CC(C)(O)c1cc(F)c2c(c1)C(=O)N(Cc1ccc(C#N)cn1)[C@@]2(OCC1(CO)CC1)c1ccc(Cl)cc1] | 6-{[(1R)-1-(4-Chlorophenyl)-7-fluoro-5-(2-hydroxybut-3-en-2-yl)-1-{[1-(hydroxymethyl)cyclopropyl]methoxy}-3-oxo-2,3-dihydro-1H-isoindol-2-yl]methyl}pyridine-3-carbonitrile | using vinyl magnesium bromide | $^1$H NMR (400 MHz, DMSO-d6): 8.77 (1H, d), 8.09 (1H, dd), 7.77 (1H, d), 7.51-7.45 (1H, m), 7.35 (1H, d), 7.33-7.20 (4H, m), 6.16 (1H, dd), 5.69 (1H, s), 5.29 (1H, dd), 5.08 (1H, dd), 4.63-4.47 (2H, m), 4.42 (1H, s), 3.34 (2H, d), 3.14 (1H, d), 2.91 (1H, d), 1.57 (3H, s), 0.36 (2H, s), 0.25-0.11 (2H, m). | LCMS: [M − H]$^-$ = 547 |

| Example | Name | Comment | NMR Data | MS Data |
|---|---|---|---|---|
| 413 | 6-{[(1R)-1-(4-Chlorophenyl)-7-fluoro-5-(2-hydroxybut-3-en-2-yl)-1-{[1-(hydroxymethyl)cyclopropyl]methoxy}-3-oxo-2,3-dihydro-1H-isoindol-2-yl]methyl}pyridine-3-carbonitrile | using vinyl magnesium bromide | $^1$H NMR (400 MHz, DMSO-d6): 8.76 (1H, d), 8.09 (1H, dd), 7.76 (1H, s), 7.49 (1H, d), 7.35 (1H, d), 7.32-7.16 (4H, m), 6.15 (1H, dd), 5.69 (1H, s), 5.29 (1H, dd), 5.08 (1H, dd), 4.59 (1H, d), 4.51 (1H, d), 4.41 (1H, s), 3.38-3.33 (2H, m), 3.14 (1H, d), 2.91 (1H, d), 1.58 (3H, s), 0.36 (2H, s), 0.27-0.10 (2H, m). | LCMS: [M − H]$^-$ = 547 |
| 414 | 6-{[(1R)-1-(4-Chlorophenyl)-5-(1-cyclopropyl-1-hydroxyethyl)-7-fluoro-1-{[1-(hydroxymethyl)cyclopropyl]methoxy}-3-oxo-2,3-dihydro-1H-isoindol-2-yl]methyl}pyridine-3-carbonitrile | using cyclopropyl-magnesium bromide | $^1$H NMR (400 MHz, DMSO-d6): 8.77 (1H, d), 8.10 (1H, dd), 7.83 (1H, d), 7.54 (1H, d), 7.37 (1H, d), 7.34-7.23 (4H, m), 5.05 (1H, s), 4.59-4.48 (2H, m), 4.42 (1H, t), 3.34 (2H, dd), 3.14 (1H, d), 2.94 (1H, d), 1.46 (3H, s), 1.27-1.23 (1H, m), 0.59-0.50 (1H, m), 0.42-0.31 (4H, m), 0.27-0.10 (3H, m). | [M − H]$^-$ = 561 |
| 415 | 6-{[(1R)-1-(4-Chlorophenyl)-5-(1-cyclopropyl-1-hydroxyethyl)-7-fluoro-1-{[1-(hydroxymethyl)cyclopropyl]methoxy}-3-oxo-2,3-dihydro-1H-isoindol-2-yl]methyl}pyridine-3-carbonitrile | using cyclopropyl-magnesium bromide | $^1$H NMR (400 MHz, DMSO-d6): 8.77 (1H, d), 8.10 (1H, dd), 7.83 (1H, d), 7.57-7.50 (1H, m), 7.37 (1H, d), 7.34-7.22 (4H, m), 5.05 (1H, s), 4.59 (1H, d), 4.52 (1H, d), 4.43 (1H, t), 3.37-3.32 (2H, m), 3.14 (1H, d), 2.93 (1H, d), 1.46 (3H, s), 1.28-1.23 (1H, m), 0.58-0.49 (1H, m), 0.45-0.33 (4H, m), 0.33-0.05 (3H, m). | [M − H]$^-$ = 561 |

| Example | Structure | Name | Comment | NMR Data | MS Data |
|---|---|---|---|---|---|
| 416 | 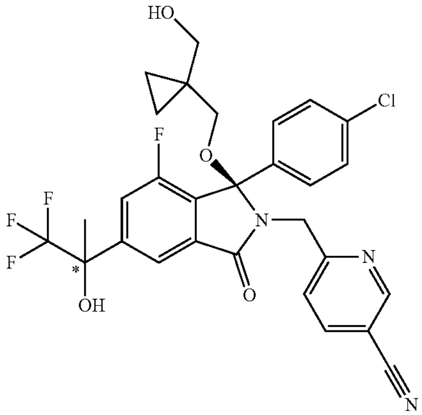 [SMILES: CC(O)(c1cc(F)c2c(c1)C(=O)N(Cc1ccc(C#N)cn1)[C@@]2(OCC1(CO)CC1)c1ccc(Cl)cc1)C(F)(F)F] | 6-{[(1R)-1-(4-chlorophenyl)-7-fluoro-1-{[1-(hydroxymethyl)cyclopropyl]methoxy}-3-oxo-5-(1,1,1-trifluoro-2-hydroxypropan-2-yl)-2,3-dihydro-1H-isoindol-2-yl]methyl}pyridine-3-carbonitrile | Using 0.1 eq CsF and 1.5 eq TMSCF₃ in DME | ¹H NMR (400 MHz, DMSO-d6): 8.77 (1H, d), 8.10 (1H, dd), 7.94-7.86 (1H, m), 7.67 (1H, d), 7.38 (1H, d), 7.33-7.29 (2H, m), 7.29-7.23 (2H, m), 7.02 (1H, s), 4.62 (1H, d), 4.52 (1H, d), 4.43 (1H, t), 3.42-3.32 (2H, m), 3.16 (1H, d), 2.92 (1H, d), 1.78 (3H, s), 0.37 (2H, s), 0.25-0.16 (2H, m). | LCMS: [M − H]⁻ = 588 |
| 417 | 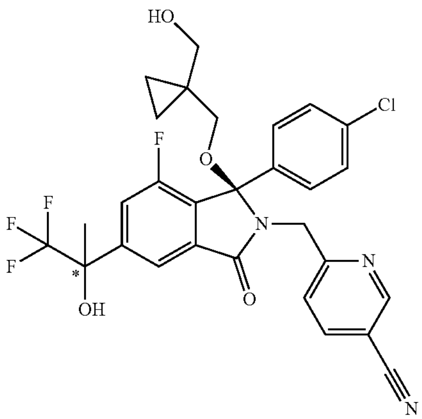 [SMILES: CC(O)(c1cc(F)c2c(c1)C(=O)N(Cc1ccc(C#N)cn1)[C@@]2(OCC1(CO)CC1)c1ccc(Cl)cc1)C(F)(F)F] | 6-{[(1R)-1-(4-chlorophenyl)-7-fluoro-1-{[1-(hydroxymethyl)cyclopropyl]methoxy}-3-oxo-5-(1,1,1-trifluoro-2-hydroxypropan-2-yl)-2,3-dihydro-1H-isoindol-2-yl]methyl}pyridine-3-carbonitrile | Using 0.1 eq CsF and 1.5 eq TMSCF₃ in DME | ¹H NMR (400 MHz, DMSO-d6): 8.80-8.75 (1H, m), 8.10 (1H, dd), 7.90 (1H, s), 7.67 (1H, d), 7.39 (1H, d), 7.31 (2H, d), 7.29-7.24 (2H, m), 7.03 (1H, s), 4.63-4.56 (1H, m), 4.56-4.49 (1H, m), 4.42 (1H, t), 3.37 (1H, dd), 3.32 (1H, d), 3.16 (1H, d), 2.93 (1H, d), 1.78 (3H, s), 0.41-0.31 (2H, m), 0.24-0.10 (2H, m). | LCMS: [M − H]⁻ = 588 |

Example 418: (3R)-3-(4-Chlorophenyl)-2-[(1R)-1-(5-chloropyridin-2-yl)-2-hydroxyethyl]-4-fluoro-3-{[1-(hydroxymethyl)cyclopropyl]methoxy}-6-(2-hydroxypropan-2-yl)-2,3-dihydro-1H-isoindol-1-one Step 1: Preparation hydroxymethylpyridine: (1R)-1-(5-Chloropyridin-2-yl)-2-(prop-2-en-1-yloxy)ethan-1-amine

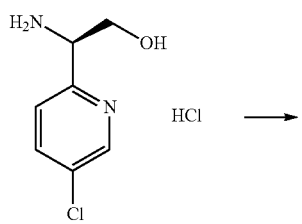

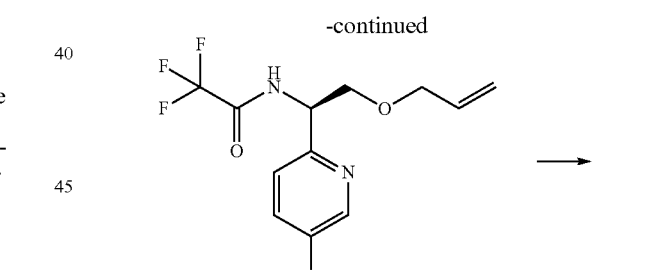

(i) N-[(1R)-1-(5-Chloropyridin-2-yl)-2-hydroxy-ethyl]-2,2,2-trifluoroacetamide

TFAA (2.1 mL, 14.8 mmoL) was slowly added to a solution of (2R)-2-amino-2-(5-chloropyridin-2-yl)ethan-1-ol (3.1 g, 14.8 mmol) and TEA (6.4 mL, 44.8 mmol) in DCM (100 mL) under inert atmosphere at room temperature and stirred at the same temperature for 10 min. The reaction was partitioned between DCM and 2N HCl. The aqueous phase was extracted with DCM (2×). The combined organic phases were dried over MgSO$_4$, filtered and concentrated in vacuo to give the desired product (4.1 g, quant. yield) as a brown oil which was used in the next step without any further purifications. LCMS: [M+H]$^+$=269.

(ii) N-[(1R)-1-(5-Chloropyridin-2-yl)-2-(prop-2-en-1-yloxy)ethyl]-2,2,2-trifluoroacetamide NaH (60% disp. in mineral oil, 774 mg, 19.4 mmol) was added in portions to a solution of N-[(1R)-1-(5-chloropyridin-2-yl)-2-hydroxyethyl]-2,2,2-trifluoroacetamide (2.6 g, 9.7 mmol) in DMF (30 mL) at 0° C. under inert atmosphere. The mixture was stirred at 0° C. for 5 min and the at room temperature for 10 min. Allyl iodide (885 μL, 9.7 mmol) was then added and the mixture was stirred for further 10 min at the room temperature. The reaction was quenched with water and extracted with EtOAc (2×). The organic phases were collected, washed with brine, dried over MgSO$_4$, filtered and concentrated in vacuo. The residue was purified by chromatography on silica gel (gradient 0-30% EtOAc in Petrol) to give the desired product as a yellow oil (1.7 g, 56% yield). LCMS: [M+H]$^+$=309.

(iii) (1R)-1-(5-Chloropyridin-2-yl)-2-(prop-2-en-1-yloxy)ethan-1-amine

2N NaOH (8 mL) was added to a solution of N-[(1R)-1-(5-chloropyridin-2-yl)-2-(prop-2-en-1-yloxy)ethyl]-2,2,2-trifluoroacetamide (2.4 g, 7.8 mmol) in NaOH (20 mL) and the mixture was stirred at room temperature for 16 h. The solvent was removed in vacuo and the residue was partitioned between water and EtOAc. The organic phase was separated, dried over MgSO$_4$, filtered and concentrated in vacuo to give the desired product as a yellow oil (1.6 g, quant. yield). LCMS: [M+H]$^+$=213.

Step 2: (3R)-3-(4-chlorophenyl)-2-[(1R)-1-(5-chloropyridin-2-yl)-2-(prop-2-en-1-yloxy)ethyl]-4-fluoro-3-{[1-(hydroxymethyl)cyclopropyl]methoxy}-6-(2-hydroxypropan-2-yl)-2,3-dihydro-1H-isoindol-1-one

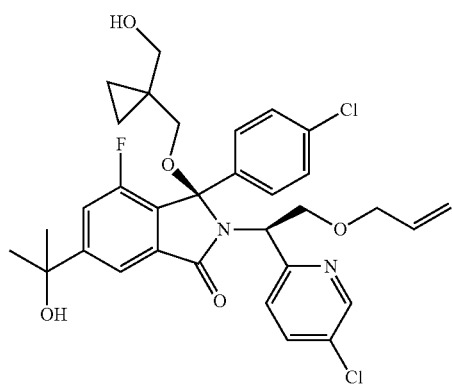 [SMILES: C=CCOC[C@@H](c1ccc(Cl)cn1)N1C(=O)c2cc(C(C)(C)O)cc(F)c2[C@]1(OCC1(CO)CC1)c1ccc(Cl)cc1]

Starting from 5-bromo-2-(4-chloro-benzoyl)-3-fluorobenzoic acid and Preparation hydroxymethylpyridine, the title compound was prepared using procedures similar to those described in Example 3; but using HATU instead of SOCl$_2$ (in Step 1), and (1-hydroxymethyl-cyclopropyl)-methanol in place of 1-hydroxymethyl-cyclopropanol (in Step 2).

Step 3: (3R)-3-(4-Chlorophenyl)-2-[(1R)-1-(5-chloropyridin-2-yl)-2-hydroxyethyl]-4-fluoro-3-{[1-(hydroxymetyl)cyclopropyl]methoxy}-6-(2-hydroxypropan-2-yl)-2,3-dihydro-1H-isoindol-1-one

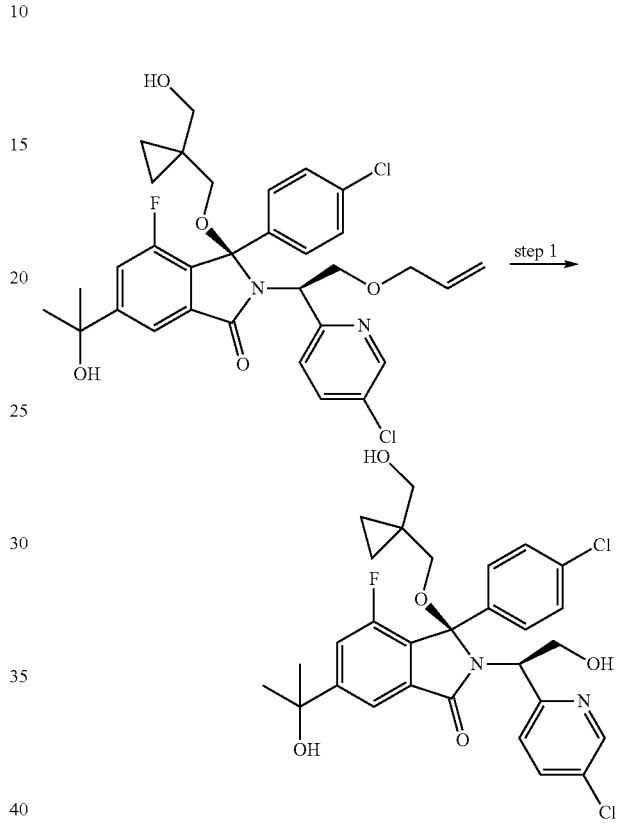

Pd(PPh$_3$)$_4$ (37 mg, 0.03 mmol) and K$_2$CO$_3$ (171 mg, 1.23 mmol) were added to a solution of (3R)-3-(4-chlorophenyl)-2-[(1R)-1-(5-chloropyridin-2-yl)-2-(prop-2-en-1-yloxy)ethyl]-4-fluoro-3-{[1-(hydroxymethyl)cyclopropyl]methoxy}-6-(2-hydroxypropan-2-yl)-2,3-dihydro-1H-isoindol-1-one (380 mg, 0.62 mmol) in MeOH (10 mL). The mixture was stirred at 80° C. for 1.5 h. The solvent was removed in vacuo and the residue was partitioned between water and EtOAc. The organic phase was separated, dried over MgSO$_4$, filtered and concentrated in vacuo. The crude material was purified by chromatography on silica gel (gradient 0-100% EtOAc in Petrol) to give the desired product as a white solid (144 mg, 40% yield).

$^1$H NMR (400 MHz, DMSO-d6): 8.17 (1H, d), 7.77 (1H, d), 7.67-7.62 (1H, m), 7.49 (1H, dd), 7.30 (1H, d), 7.10-6.97 (4H, m), 5.35 (1H, s), 5.22-5.14 (1H, m), 4.59 (1H, s), 4.55-4.42 (2H, m), 4.00-3.91 (1H, m), 3.63 (1H, d), 3.57-3.42 (2H, m), 2.92 (1H, m), 1.49 (6H, s), 0.59-0.43 (3H, m), 0.37-0.28 (1H, m). MS: [M+H]$^+$=576.

Example 419: 6-{[(1R)-1-(4-chlorophenyl)-7-fluoro-5-(2-hydroxypropan-2-yl)-3-oxo-1-{[(trans-3-hydroxycyclobutyl]methoxy}-2,3-dihydro-1H-isoindol-2-yl]methyl}pyridine-3-carbonitrile

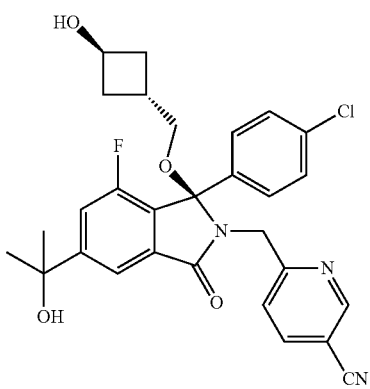 [SMILES: CC(C)(O)c1cc(F)c2c(c1)C(=O)N(Cc1ccc(C#N)cn1)[C@@]2(OC[C@H]1C[C@H](O)C1)c1ccc(Cl)cc1]

The title compound was prepared in a similar manner to Example 81 Step 1, using 3-(hydroxymethyl)cyclobutan-1-(tert-butyldimethylsilyl)-ether (trans-stereochemistry across the cyclobutane ring). $^1$H NMR (400 MHz, CDCl$_3$) 8.65 (1H, d), 7.83 (1H, s), 7.77 (1H, dd), 7.43 (1H, d), 7.33 (1H, d), 7.24 (2H, d), 7.18 (2H, d), 4.59 (2H, d), 4.34 (1H, dd), 3.17 (1H, dd), 3.01-2.95 (1H, m), 2.31-2.26 (1H, m), 2.16-2.02 (4H, m), 1.88 (1H, s), 1.71 (1H, d), 1.65-1.63 (6H, m). MS: [M-OCH$_2$cBuO]$^+$=434

Example 420: 1-({[(1R)-1-(4-chlorophenyl)-2-[(5-chloropyridin-2-yl)methyl]-7-fluoro-5-{1-hydroxy-1-[1-(2-hydroxyethyl)piperidin-4-yl]ethyl}-3-oxo-2,3-dihydro-1H-isoindol-1-yl]oxy}methyl)cyclopropane-1-carbonitrile (Example isolated as a single isomer at the position shown*)

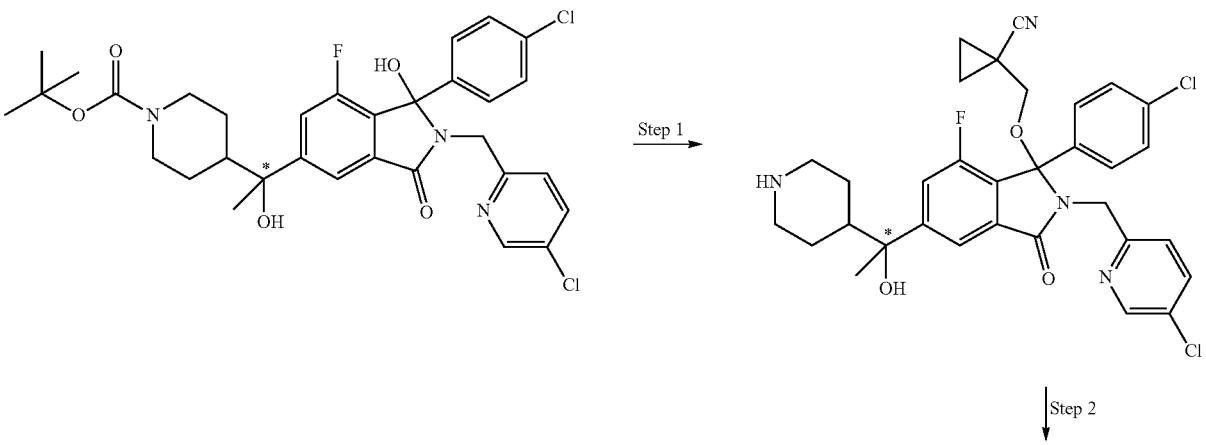

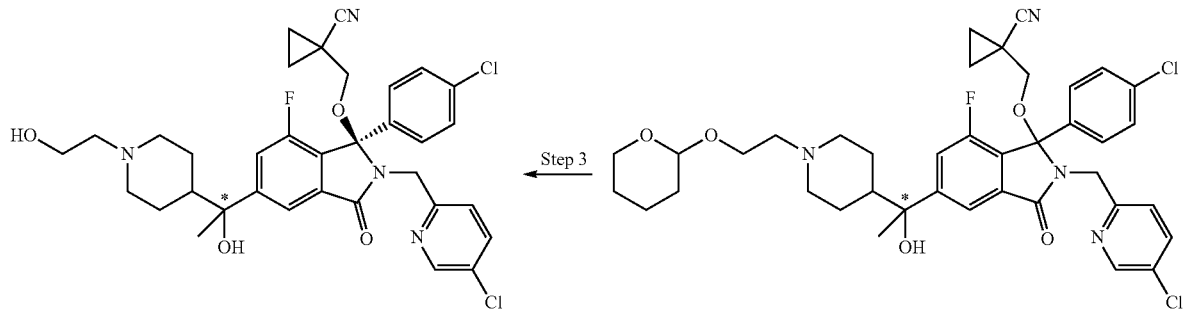

Step 1: 1-(((1-(4-Chlorophenyl)-2-((5-chloropyridin-2-yl)methyl)-7-fluoro-5-(1-hydroxy-1-(piperidin-4-yl)ethyl)-3-oxoisoindolin-1-yl)oxy)methyl)cyclopropane-1-carbonitrile The title compound was prepared from tert-butyl 4-[1-[1-(4-chlorophenyl)-2-[(5-chloro-2-pyridyl)methyl]-7-fluoro-1-hydroxy-3-oxo-isoindolin-5-yl]-1-hydroxy-ethyl]piperidine-1-carboxylate (Example 286, step 1) and 1-(hydroxymethyl)cyclopropane-1-carbonitrile in a similar manner to that of Example 286, step 2. MS: [M+H]$^+$=609.

Step 2: 1-(((1-(4-Chlorophenyl)-2-((5-chloropyridin-2-yl)methyl)-7-fluoro-5-(1-hydroxy-1-(1-(2-((tetrahydro-2H-pyran-2-yl)oxy)ethyl)piperidin-4-yl)ethyl)-3-oxoisoindolin-1-yl)oxy)methyl)cyclopropane-1-carbonitrile A mixture of 1-(((1-(4-chlorophenyl)-2-((5-chloropyridin-2-yl)methyl)-7-fluoro-5-(1-hydroxy-1-(piperidin-4-yl)ethyl)-3-oxoisoindolin-1-yl)oxy)methyl)cyclopropane-1-carbonitrile (440 mg, 0.723 mmol), 2-(2-bromoethoxy)tetrahydro-2H-pyran (0.12 mL, 0.796 mmol) and K$_2$CO$_3$ (110 mg, 0.796 mmol) in anhydrous THF (10 mL) was heated at reflux for 20 h. Further 2-(2-bromoethoxy)tetrahydro-2H-pyran (0.12 mL, 0.796 mmol) and K$_2$CO$_3$ (110 mg, 0.796 mmol) was added and heating continued for 6 h, then the mixture cooled diluted with EtOAc (50 mL) and washed with water (20 mL), brine (10 mL), dried (MgSO$_4$) and the solvent evaporated. The residue was purified by column chromatography, Biotage Isolera, 25 g KP-sil cartridge 0-20% MeOH in EtOAc to afford the title compound (310 mg, 58%). MS: [M+H]$^+$=737.

Step 3: 1-({[(1R)-1-(4-chlorophenyl)-2-[(5-chloropyridin-2-yl)methyl]-7-fluoro-5-{1-hydroxy-1-[1-(2-hydroxyethyl)piperidin-4-yl]ethyl}-3-oxo-2,3-dihydro-1H-isoindol-1-yl]oxy}methyl)cyclopropane-1-carbonitrile 2N HCl (3 mL) was added to a stirred, room temperature solution of 1-(((1-(4-chlorophenyl)-2-((5-chloropyridin-2-yl)methyl)-7-fluoro-5-(1-hydroxy-1-(1-(2-((tetrahydro-2H-pyran-2-yl)oxy)ethyl)piperidin-4-yl)ethyl)-3-oxoisoindolin-1-yl)oxy)methyl)cyclopropane-1-carbonitrile (300 mg, 0.407 mmol) in EtOH (3 mL). After 1 h, the mixture was concentrated, basified with 2M NaOH and extracted into DCM (2×20 mL). The pooled organics were dried (MgSO$_4$) and evaporated to afford the racemate (235 mg). Chiral preparative HPLC gave the title compound (faster running isomer)

Example 420

$^1$H NMR (400 MHz, MeOD): 8.32 (1H, d), 7.82 (1H, s), 7.67 (1H, dd), 7.50-7.47 (1H, m), 7.35 (2H, d), 7.28 (3H, d), 4.60-4.58 (2H, m), 3.66 (2H, dd), 3.39 (1H, d), 3.08-2.97 (3H, m), 2.50 (2H, dd), 2.09-1.91 (2H, m), 1.81 (1H, d), 1.73-1.63 (1H, m), 1.58 (3H, s), 1.46-1.40 (3H, m), 1.28-1.26 (2H, m), 0.96-0.82 (2H, m), OH protons not observed; MS: [M+H]$^+$=653.5.

Example 421: (3R)-6-[1-(1-acetylpiperidin-4-yl)-1-hydroxyethyl]-3-(4-chlorophenyl)-2-[(5-chloropyridin-2-yl)methyl]-4-fluoro-3-(2-hydroxyethoxy)-2,3-dihydro-1H-isoindol-1-one (Example isolated as a single isomer at the position shown*)

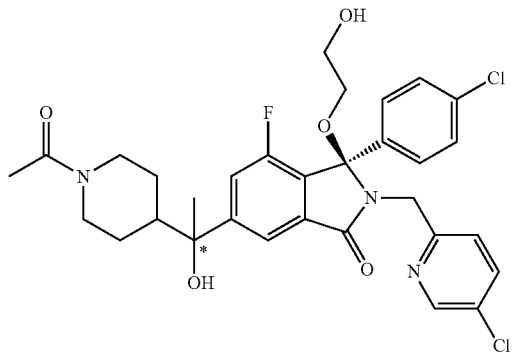 [SMILES: CC(=O)N1CCC(C(C)(O)c2cc(F)c3c(c2)C(=O)N(Cc2ccc(Cl)cn2)[C@@]3(OCCO)c2ccc(Cl)cc2)CC1]

The title compound was prepared in a similar manner to that described for Example 293, but using ethylene glycol instead of MeOH.
$^1$H NMR (400 MHz, CDCl$_3$) 8.38 (1H, dd), 7.67-7.67 (1H, m), 7.57 (1H, dd), 7.38-7.30 (4H, m), 7.27-7.25 (2H, m), 4.74-4.63 (1H, m), 4.54 (1H, dd), 4.37 (1H, dd), 3.87-3.76 (2H, m), 3.71-3.63 (1H, m), 3.42-3.35 (1H, m), 3.24-3.17 (2H, m), 3.01-2.87 (1H, m), 2.47-2.36 (1H, m), 2.04 (3H, d), 1.85-1.77 (3H, m), 1.59 (3H, d), 1.47-1.16 (3H, m). MS: [M+H]$^+$=616.

Example 422: (3R)-6-[1-(1-acetylpiperidin-4-yl)-1-hydroxyethyl]-3-(4-chlorophenyl)-2-[(5-chloropyrimidin-2-yl)methyl]-4-fluoro-3-(2-hydroxyethoxy)-2,3-dihydro-1H-isoindol-1-one (Example isolated as a single isomer at the position shown*)

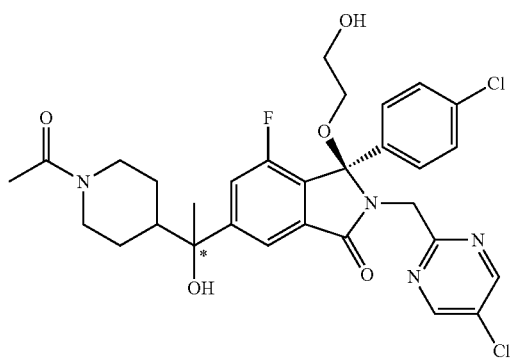 [SMILES: CC(=O)N1CCC(C(C)(O)c2cc(F)c3c(c2)C(=O)N(Cc2ncc(Cl)cn2)[C@@]3(OCCO)c2ccc(Cl)cc2)CC1]

Starting from (−)-5-[1-(1-tert-butoxycarbonyl-4-piperidyl)-1-hydroxy-ethyl]-2-(4-chlorobenzoyl)-3-fluoro-benzoic acid (Preparation 24), the title compound was prepared in a similar fashion to Example 293, but using 1-(5-chloropyrimidin-2-yl)methanamine hydrochloride and ethylene glycol as the appropriate amine and alcohol.
$^1$H NMR (400 MHz, CDCl$_3$) 8.54 (2H, s), 7.71 (1H, d, J=1.3 Hz), 7.39-7.31 (3H, m), 7.24 (2H, d, J=8.6 Hz), 4.71-4.61 (3H, m), 3.80-3.73 (2H, m), 3.68-3.58 (2H, m), 3.27-3.21 (1H, m), 3.02-2.88 (1H, m), 2.49-2.36 (1H, m), 2.31-2.26 (1H, m), 2.05 (3H, d, J=5.3 Hz), 1.88-1.77 (3H, m), 1.59 (3H, s), 1.46-1.31 (1H, m), 1.31-1.17 (2H, m). MS: [M-OCH$_2$CH$_2$OH]$^-$=555.

Example 423: (3R)-3-(4-chlorophenyl)-2-[(5-chloro-pyrimidin-2-yl)methyl]-4-fluoro-6-[1-hydroxy-1-(1-methylpiperidin-4-yl)ethyl]-3-[(3S)-oxolan-3-yloxy]-2,3-dihydro-1H-isoindol-1-one (Example isolated as a single isomer at the position shown*)

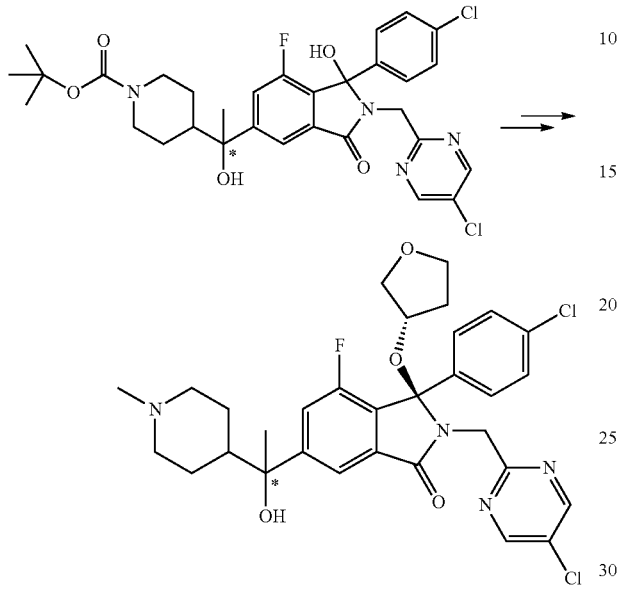

The title compound was prepared using procedures similar to those used for Example 286, but using 1-(5-chloro-pyrimidine-2-yl)methanramine hydrochloride (as the appropriate amine in Step 1) and (S)-(+)-3-hydroxy-tetrahydrofuran instead of methanol (in Step 2). N-methylation was achieved using NaCNBH₃/formaldehyde (for procedure see Preparation 25, Step 2) instead of 2-chloropyrimidine in the final step.

¹H NMR (400 MHz, CDCl₃) 8.52 (2H, s), 7.72 (1H, s), 7.37-7.32 (3H, m), 7.18 (2H, d), 4.72 (1H, d), 4.58 (1H, d), 4.24-4.19 (1H, m), 3.89 (1H, dd), 3.75-3.66 (2H, m), 3.35 (1H, dd), 2.93 (1H, s), 2.85 (1H, s), 2.25 (3H, s), 1.88-1.79 (3H, m), 1.73-1.68 (3H, m), 1.60 (3H, s), 1.45-1.35 (4H, m); MS: [M+H]+=615.

Example 424: (3R)-6-[1-(1-acetylpiperidin-4-yl)-1-hydroxyethyl]-2-{[5-chloro-3-(hydroxymethyl)pyridin-2-yl]methyl}-3-(4-chlorophenyl)-4-fluoro-3-methoxy-2,3-dihydro-1H-isoindol-1-one (Example isolated as a single isomer at the position shown*)

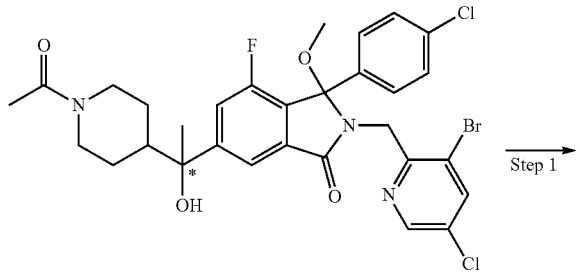

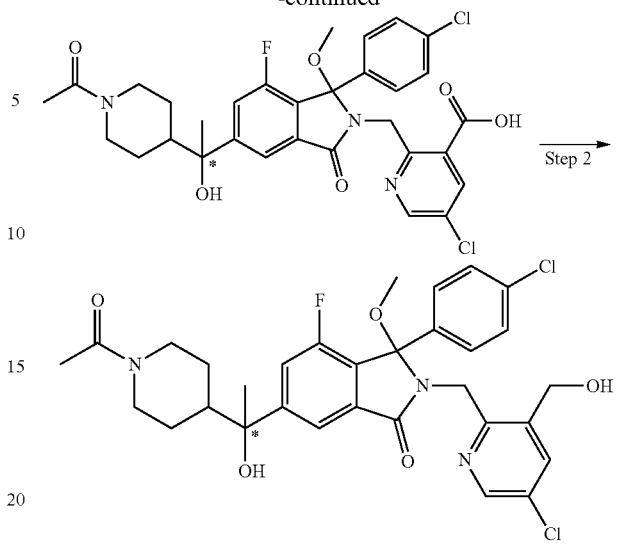

The starting material for Step 1 was prepared from (−)-5-[1-(1-tert-butoxycarbonyl-4-piperidyl)-1-hydroxy-ethyl]-2-(4-chlorobenzoyl)-3-fluoro-benzoic acid (Preparation 24) using similar condition to those described in Example 293 but using (3-bromo-5-chloropyridin-2-yl)methanamine as the appropriate amine. MS: [M+HCOOH]= 710.

Step 1 2-[[5-[1-(1-Acetyl-4-piperidyl)-1-hydroxy-ethyl]-1-(4-chlorophenyl)-7-fluoro-1-methoxy-3-oxo-isoindolin-2-yl]methyl]-5-chloro-pyridine-3-carboxylic acid The title compound was prepared using similar conditions to those described in Example 161, step 1. MS: [M−H]⁻= 628.

Step 2: (3R)-6-[1-(1-acetylpiperidin-4-yl)-1-hydroxyethyl]-2-{[5-chloro-3-(hydroxymethyl)pyridin-2-yl]methyl}-3-(4-chlorophenyl)-4-fluoro-3-methoxy-2,3-dihydro-1H-isoindol-1-one Triethylamine (186 µL, 1.33 mmol) was added to a solution of 2-[[5-[1-(1-acetyl-4-piperidyl)-1-hydroxy-ethyl]-1-(4-chlorophenyl)-7-fluoro-1-methoxy-3-oxo-isoindolin-2-yl]methyl]-5-chloro-pyridine-3-carboxylic acid (240 mg, 0.38 mmol) in dry THF (10 mL) under nitrogen followed by isobutylchloroformate (87 µL, 0.67 mmol). After stirring at RT for 45 min, water (100 µL) and sodium borohydride (50 mg, 1.33 mmol) were added. After stirring at RT for 1 h, the solution was diluted with ethyl acetate and washed with water and brine, then dried (MgSO₄) and the solvents removed under reduced pressure. The crude material was purified by column chromatography on silica, eluting with a gradient of 0-4% methanol in dichloromethane followed by chiral preparative HPLC to give the title compound (fast-running isomer; 91 mg). ¹H NMR (400 MHz, CDCl₃) 8.33 (1H, d), 7.67 (1H, d), 7.62 (1H, d), 7.33 (3H, m), 7.25-7.23 (2H, m), 4.75-4.58 (4H, m), 4.45 (1H, dd), 3.87-3.75 (1H, m), 3.38 (1H, q), 3.05 (3H, s), 3.00-2.87 (1H, m), 2.47-2.34 (1H, m), 2.04 (3H, d), 1.83-1.72 (3H, m), 1.58 (3H, s), 1.34-1.15 (3H, m). MS: [M+H]+=616

Example 425: (3R)-6-[1-(1-acetylpiperidin-4-yl)-1-hydroxyethyl]-3-(4-chlorophenyl)-2-[(5-chloropyrimidin-2-yl)methyl]-4-fluoro-3-[cis-3-hydroxycyclobutoxy]-2,3-dihydro-1H-isoindol-1-one (Example isolated as a single isomer at the position shown*)

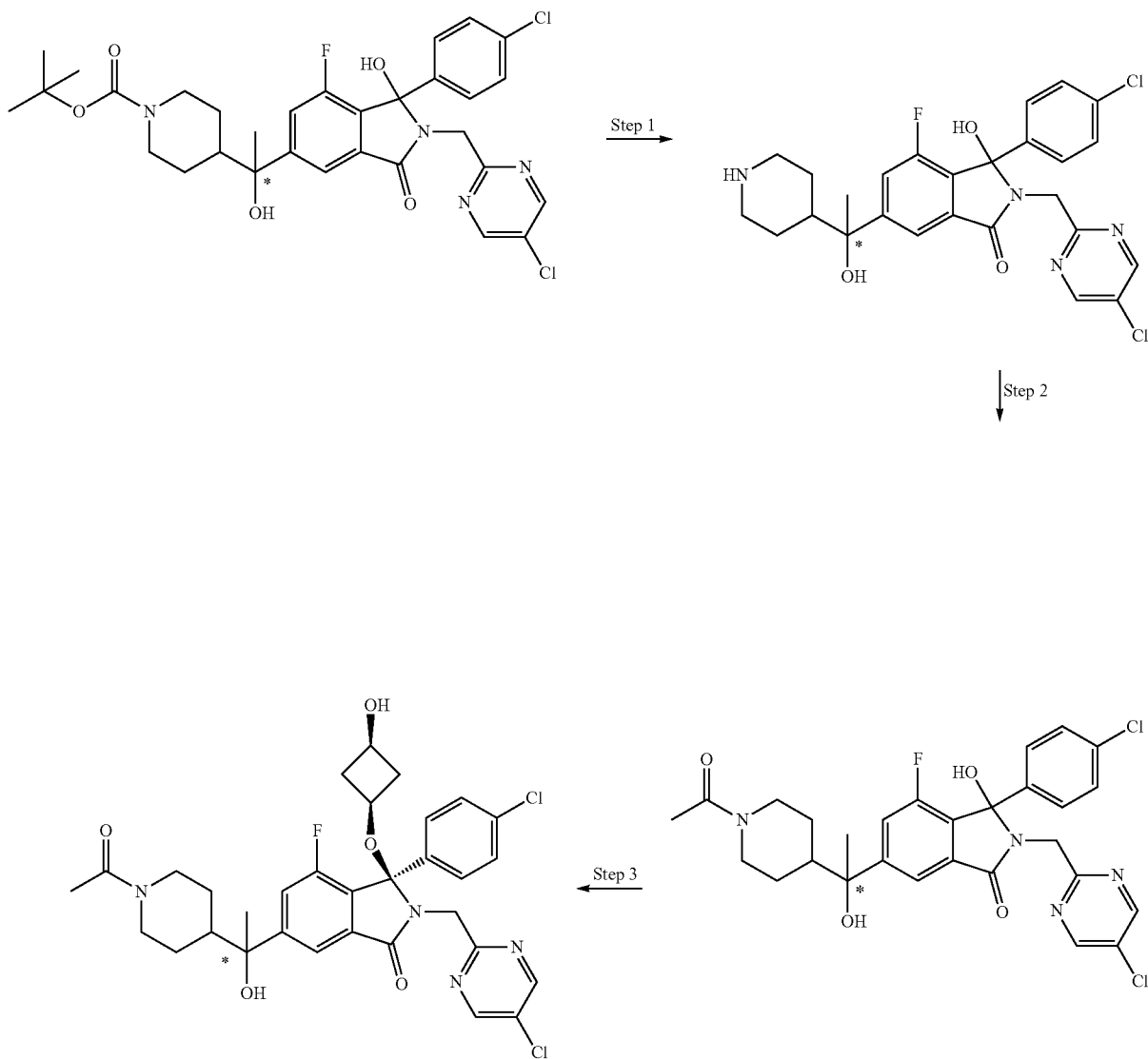

Step 1 and 2 were performed by following procedures similar to those described in Example 300, but using 1-(5-chloropyrimidin-2-yl)methanamine hydrochloride in place of (5-chloropyridin-2-yl)methanamine dihydrochloride and acetyl chloride instead of T3P/acetic acid. MS: [M+HCOOH]⁻=617.

Step 3: (3R)-6-[1-(1-acetylpiperidin-4-yl)-1-hydroxyethyl]-3-(4-chlorophenyl)-2-[(5-chloropyrimidin-2-yl)methyl]-4-fluoro-3-[cis-3-hydroxycyclobutoxy]-2,3-dihydro-1H-isoindol-1-one The title compound was prepared from 6-[1-(1-acetyl-4-piperidyl)-1-hydroxy-ethyl]-3-(4-chlorophenyl)-2-[(5-chloropyrimidin-2-yl)methyl]-4-fluoro-3-hydroxy-isoindolin-1-one and cis-3-(((1,1-dimethylethyl)dimethylsilyl)oxy) cyclobutanol in a similar manner as in Example 1, step 2 followed by TBAF deprotection as in Example 22, step 4. Chiral preparative HPLC gave the title compound (slow-running isomer; 35 mg). $^1$H NMR (400 MHz, CDCl$_3$) 8.52 (2H, s), 7.73 (1H, dd), 7.36 (2H, dd), 7.30 (1H, d), 7.22 (2H, d), 4.69-4.55 (3H, m), 3.88-3.77 (1H, m), 3.73-3.63 (1H, m), 3.63-3.56 (1H, m), 3.03-2.89 (1H, m), 2.49-2.25 (2H, m), 2.07-1.72 (10H, m), 1.61 (3H, s), 1.49-1.11 (3H, m). MS: [M+HCOOH]⁻=687

Starting from the appropriate ketone intermediate (for example, the ketones shown in the Table 1), the following Examples were prepared by reaction with an appropriate nucleophile (for example, an alkyl organometallic reagent), using methods similar to those described in Examples 200 Step 5, 202 Step 2, 203, 336 or 337.

Purification by preparative achiral and/or chiral HPLC gave final compounds as single isomer (unless stated otherwise). In the table below, an asterisk (*) indicates the compound was isolated as a single isomer at the position shown.

| Example | Structure | Name | Comment | NMR Data | MS Data |
|---|---|---|---|---|---|
| 426 | 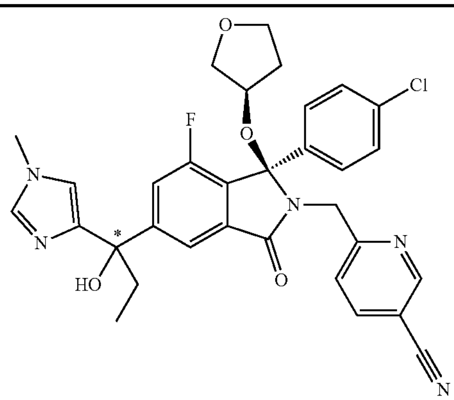 | 6-{[(1R)-1-(4-chlorophenyl)-7-fluoro-5-[1-hydroxy-1-(1-methyl-1H-imidazol-4-yl)propyl]-3-oxo-1-[(3R)-oxolan-3-yloxy]-2,3-dihydro-1H-isoindol-2-yl]methyl}pyridine-3-carbonitrile | Prepared in a similar manner to 337 | $^1$H NMR (400 MHz, CDCl3) 8.64 (1H, d), 7.76 (1H, dd), 7.69 (1H, s), 7.61-7.57 (1H, m), 7.38 (1H, s), 7.29-7.26 (1H, m), 7.21 (2H, d), 7.15 (2H, d), 6.87 (1H, s), 4.58-4.49 (2H, m), 4.07-4.01 (1H, m), 3.96-3.89 (1H, m), 3.71 (3H, s), 3.69-3.57 (2H, m), 3.45-3.42 (2H, m), 2.26-2.09 (2H, m), 1.95-1.86 (1H, m), 1.57-1.50 (1H, m), 0.73-0.55 (3H, m). | 602.2 |
| 427 | 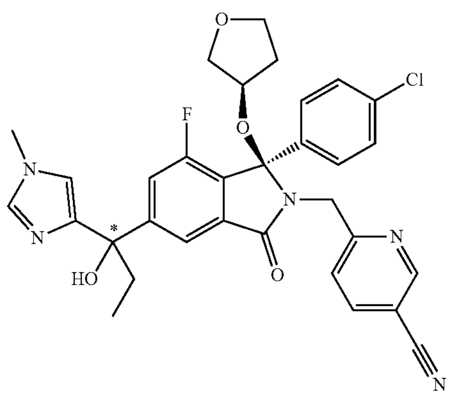 [SMILES: CCC(O)(c1cc(F)c2c(c1)C(=O)N(Cc1ccc(C#N)cn1)[C@@]2(O[C@@H]1CCOC1)c1ccc(Cl)cc1)c1cn(C)cn1] | 6-{[(1R)-1-(4-chlorophenyl)-7-fluoro-5-[1-hydroxy-1-(1-methyl-1H-imidazol-4-yl)propyl]-3-oxo-1-[(3R)-oxolan-3-yloxy]-2,3-dihydro-1H-isoindol-2-yl]methyl}pyridine-3-carbonitrile | Prepared in a similar manner to 337 | $^1$H NMR (400 MHz, CDCl3) 8.64 (1H, d), 7.78-7.75 (2H, m), 7.58-7.51 (1H, m), 7.38 (1H, s), 7.30 (1H, d), 7.22 (2H, d), 7.16 (2H, d), 6.86 (1H, d), 4.53 (2H, s), 4.06-4.00 (1H, m), 3.96-3.89 (1H, m), 3.70 (3H, s), 3.69-3.62 (1H, m), 3.57 (1H, s), 3.41 (2H, d), 2.24-2.08 (2H, m), 1.95-1.86 (1H, m), 1.62-1.51 (1H, m), 0.86 (3H, dd). | 602.2 |
| 428 | 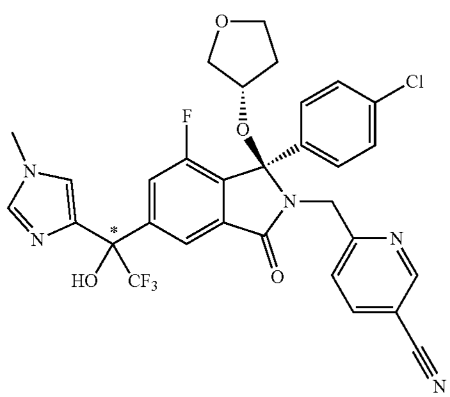 [SMILES: Cn1cnc(C(O)(c2cc(F)c3c(c2)C(=O)N(Cc2ccc(C#N)cn2)[C@@]3(O[C@H]2CCOC2)c2ccc(Cl)cc2)C(F)(F)F)c1] | 6-{[(1R)-1-(4-chlorophenyl)-7-fluoro-3-oxo-1-[(3S)-oxolan-3-yloxy]-5-[2,2,2-trifluoro-1-hydroxy-1-(1-methyl-1H-pyrazol-4-yl)ethyl]-2,3-dihydro-1H-isoindol-2-yl]methyl}pyridine-3-carbonitrile | Prepared in a similar manner to 337 step 2, but using TMSCF$_3$/CsF instead of MeMgCl | 1H NMR (400 MHz, CDCl3): 8.64 (1H, d), 7.88 (1H, s), 7.77 (1H, dd), 7.55 (1H, d), 7.47 (2H, d), 7.34 (1H, d), 7.25-7.14 (4H, m), 4.65 (1H, d), 4.57 (1H, d), 4.07-3.98 (1H, m), 3.95 (3H, s), 3.87 (1H, q), 3.73-3.58 (2H, m), 3.32 (1H, dd), 3.08 (1H, s), 1.78-1.65 (2H, m). | 554 (M − C$_4$H$_7$O$_2$)$^+$ |
| 429 | 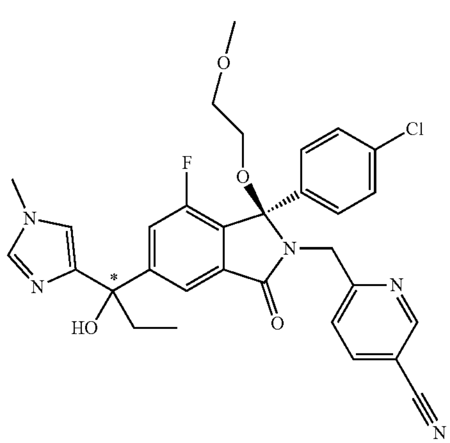 [SMILES: CCC(O)(c1cc(F)c2c(c1)C(=O)N(Cc1ccc(C#N)cn1)[C@@]2(OCCOC)c1ccc(Cl)cc1)c1cn(C)cn1] | 6-{[(1R)-1-(4-chlorophenyl)-7-fluoro-5-[1-hydroxy-1-(1-methyl-1H-imidazol-4-yl)propyl]-1-(2-methoxyethoxy)-3-oxo-2,3-dihydro-1H-isoindol-2-yl]methyl}pyridine-3-carbonitrile | Prepared in a similar manner to 203, but using AlEt$_3$ | $^1$H NMR (400 MHz, CDCl3): 8.65 (1H, Hz), 7.76-7.73 (2H, m), 7.53-7.50 (1H, m), 7.36 (1H, s), 7.30 (1H, d), 7.25 (2H, d), 7.16 (2H, d), 6.85 (1H, d), 4.66 (1H, d), 4.54 (1H, d), 3.70 (3H, s), 3.58 (1H, s), 3.43-3.31 (2H, m), 3.30 (3H, s), 3.25-3.15 (2H, m), 2.24-2.04 (2H, m), 0.86 (3H, t); | [M + H]$^+$ = 590 |

| Example | Structure | Name | Comment | NMR Data | MS Data |
|---|---|---|---|---|---|
| 430 | 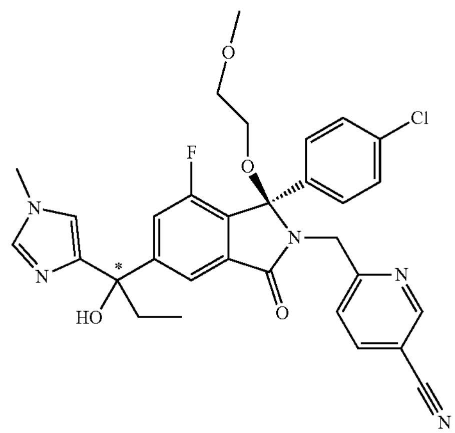 [SMILES: CCC(O)(c1cc(F)c2c(c1)C(=O)N(Cc1ccc(C#N)cn1)[C@@]2(OCCOC)c1ccc(Cl)cc1)c1cn(C)cn1] | 6-{[(1R)-1-(4-chlorophenyl)-7-fluoro-5-[1-hydroxy-1-(1-methyl-1H-imidazol-4-yl)propyl]-1-(2-methoxyethoxy)-3-oxo-2,3-dihydro-1H-isoindol-2-yl]methyl}pyridine-3-carbonitrile | Prepared in a similar manner to 203, but using AlEt$_3$ | $^1$H NMR (400 MHz, CDCl3): 8.64 (1H, d), 7.76-7.70 (2H, m), 7.54 (1H, d), 7.37 (1H, s), 7.29-7.25 (1H, m), 7.23 (2H, d), 7.14 (2H, d), 6.85 (1H, s), 4.68-4.54 (2H, m), 3.70 (3H, s), 3.58 (1H, s), 3.31-3.30 (6H, m), 2.24-2.04 (2H, m), 0.87 (3H, t) | [M + H]$^+$ = 590 |
| 431 | 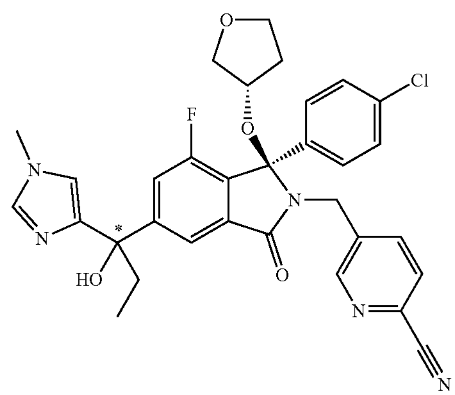 [SMILES: CCC(O)(c1cc(F)c2c(c1)C(=O)N(Cc1ccc(C#N)nc1)[C@@]2(O[C@H]1CCOC1)c1ccc(Cl)cc1)c1cn(C)cn1] | 5-{[(1R)-1-(4-chlorophenyl)-7-fluoro-5-[1-hydroxy-1-(1-methyl-1H-imidazol-4-yl)propyl]-3-oxo-1-[(3S)-oxolan-3-yloxy]-2,3-dihydro-1H-isoindol-2-yl]methyl}pyridine-2-carbonitrile | Prepared in a similar manner to 203, but using AlEt$_3$ | $^1$H NMR (400 MHz, CDCl3) 8.41 (1H, d), 7.71 (1H, d), 7.61 (1H, dd), 7.57-7.52 (1H, m), 7.48 (1H, d), 7.37 (1H, s), 7.20 (1H, s), 7.17 (3H, d), 6.85 (1H, d), 4.44 (2H, d), 3.89-3.81 (2H, m), 3.70 (3H, s), 3.67-3.59 (2H, m), 3.53 (1H, s), 3.26 (1H, dd), 2.24-2.04 (2H, m), 1.68-1.59 (2H, m), 0.85 (3H, t) | [M + H]$^+$ = 602 |
| 432 | 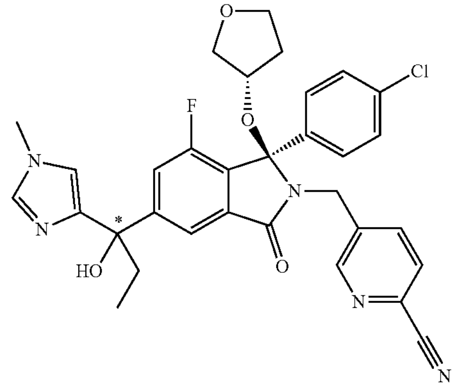 [SMILES: CCC(O)(c1cc(F)c2c(c1)C(=O)N(Cc1ccc(C#N)nc1)[C@@]2(O[C@H]1CCOC1)c1ccc(Cl)cc1)c1cn(C)cn1] | 5-{[(1R)-1-(4-chlorophenyl)-7-fluoro-5-[1-hydroxy-1-(1-methyl-1H-imidazol-4-yl)propyl]-3-oxo-1-[(3S)-oxolan-3-yloxy]-2,3-dihydro-1H-isoindol-2-yl]methyl}pyridine-2-carbonitrile | Prepared in a similar manner to 203, but using AlEt$_3$ | $^1$H NMR (400 MHz, CDCl3) 8.41 (1H, d), 7.81 (1H, d), 7.64 (1H, dd), 7.51-7.44 (2H, m), 7.36 (1H, s), 7.21-7.16 (4H, m), 6.84 (1H, d), 4.45 (2H, s), 3.88-3.80 (2H, m), 3.69 (3H, s), 3.65-3.60 (2H, m), 3.55 (1H, s), 3.28 (1H, dd), 2.23-2.07 (2H, m), 1.60 (2H, m), 0.85 (3H, t) | [M + H]$^+$ = 602 |

| Example | Structure | Name | Comment | NMR Data | MS Data |
|---|---|---|---|---|---|
| 433 | 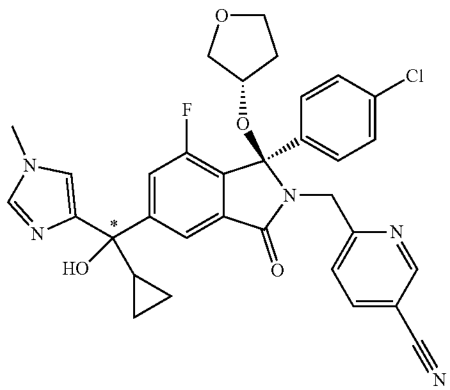 [SMILES: Cn1cnc(C(O)(c2cc(F)c3c(c2)C(=O)N(Cc2ccc(C#N)cn2)[C@@]3(O[C@H]2CCOC2)c2ccc(Cl)cc2)C2CC2)c1] | 6-{[(1R)-1-(4-chlorophenyl)-5-[cyclopropyl(hydroxy)(1-methyl-1H-imidazol-4-yl)methyl]-7-fluoro-3-oxo-1-[(3S)-oxolan-3-yloxy]-2,3-dihydro-1H-isoindol-2-yl]methyl}pyridine-3-carbonitrile | Prepared in a similar manner to 337, but using cyclopropyl-magnesium bromide | ¹H NMR (400 MHz, DMSO) 8.80 (1H, d), 8.12 (1H, dd), 7.86 (1H, s), 7.56 (1H, dd), 7.51 (1H, s), 7.43 (1H, d), 7.28 (4H, q), 7.13 (1H, d), 5.42 (1H, s), 4.56 (2H, s), 4.09-4.02 (1H, m), 3.75 (1H, q), 3.64 (3H, s), 3.60-3.53 (1H, m), 3.45 (1H, dd), 3.17 (1H, dd), 1.77-1.61 (2H, m), 1.57-1.50 (1H, m), 0.68-0.59 (1H, m), 0.46-0.29 (3H, m); | [M + H]⁺ = 614 |
| 434 | 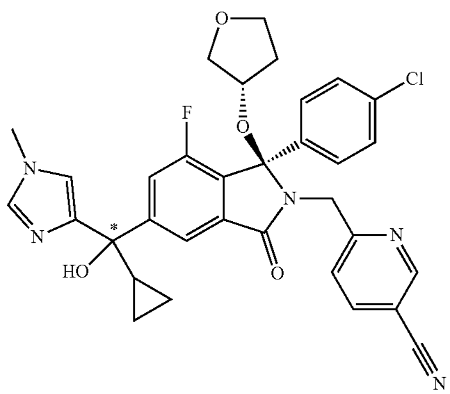 [SMILES: Cn1cnc(C(O)(c2cc(F)c3c(c2)C(=O)N(Cc2ccc(C#N)cn2)[C@@]3(O[C@H]2CCOC2)c2ccc(Cl)cc2)C2CC2)c1] | 6-{[(1R)-1-(4-chlorophenyl)-5-[cyclopropyl(hydroxy)(1-methyl-1H-imidazol-4-yl)methyl]-7-fluoro-3-oxo-1-[(3S)-oxolan-3-yloxy]-2,3-dihydro-1H-isoindol-2-yl]methyl}pyridine-3-carbonitrile | Prepared in a similar manner to 337, but using cyclopropyl-magnesium bromide | ¹H NMR (400 MHz, DMSO) 8.79 (1H, d), 8.11 (1H, dd), 7.86 (1H, s), 7.56 (1H, dd), 7.52 (1H, d), 7.42 (1H, d), 7.27 (4H, q), 7.12 (1H, d), 5.41 (1H, s), 4.57 (2H, d), 4.05 (1H, dt), 3.75 (1H, q), 3.64 (3H, s), 3.61-3.53 (1H, m), 3.44 (1H, dd), 3.17 (1H, dd), 1.79-1.53 (3H, m), 0.68-0.61 (1H, m), 0.47-0.30 (3H, m); | [M + H]⁺ = 614 |
| 435 | 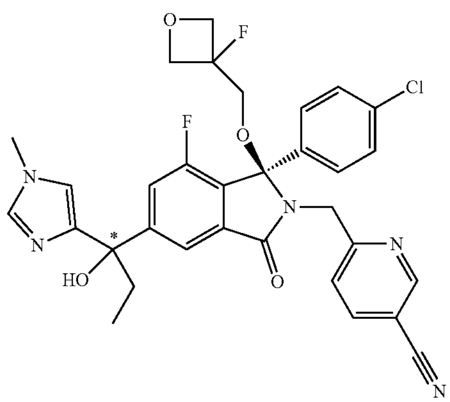 [SMILES: CCC(O)(c1cc(F)c2c(c1)C(=O)N(Cc1ccc(C#N)cn1)[C@@]2(OCC1(F)COC1)c1ccc(Cl)cc1)c1cn(C)cn1] | 6-{[(1R)-1-(4-chlorophenyl)-7-fluoro-1-[(3-fluorooxetan-3-yl)methoxy]-5-[1-hydroxy-1-(1-methyl-1H-imidazol-4-yl)propyl]-3-oxo-2,3-dihydro-1H-isoindol-2-yl]methyl}pyridine-3-carbonitrile | Prepared in a similar manner to 203, but using AlEt₃ | ¹H NMR (400 MHz, CDCl3) 8.66 (1H, d), 7.79-7.75 (2H, m), 7.55-7.51 (1H, m), 7.42 (1H, s), 7.31 (1H, d), 7.24-7.19 (4H, m), 6.87 (1H, d), 4.81-4.68 (2H, m), 4.63-4.37 (4H, m), 3.72 (3H, s), 3.69-3.60 (2H, m), 3.38 (1H, dd), 2.26-2.02 (2H, m), 0.88 (3H, t); | [M + H]⁺ = 620 |
| 436 | 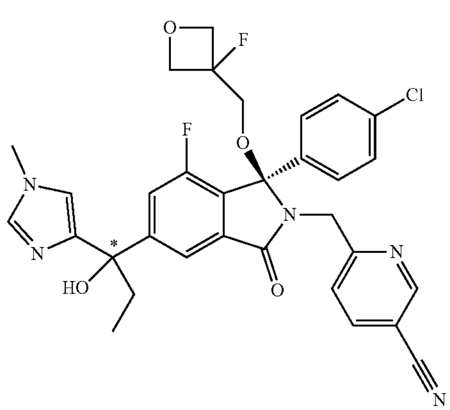 [SMILES: CCC(O)(c1cc(F)c2c(c1)C(=O)N(Cc1ccc(C#N)cn1)[C@@]2(OCC1(F)COC1)c1ccc(Cl)cc1)c1cn(C)cn1] | 6-{[(1R)-1-(4-chlorophenyl)-7-fluoro-1-[(3-fluorooxetan-3-yl)methoxy]-5-[1-hydroxy-1-(1-methyl-1H-imidazol-4-yl)propyl]-3-oxo-2,3-dihydro-1H-isoindol-2-yl]methyl}pyridine-3-carbonitrile | Prepared in a similar manner to 203, but using AlEt₃ | ¹H NMR (400 MHz, CDCl3) 8.66 (1H, d), 7.78 (1H, dd), 7.74 (1H, d), 7.58-7.51 (1H, m), 7.39 (1H, s), 7.32 (1H, d), 7.25-7.21 (4H, m), 6.88 (1H, d), 4.78-4.37 (6H, m), 3.71 (3H, s), 3.63 (2H, dd), 3.38 (1H, dd), 2.25-2.04 (2H, m), 0.87 (3H, t); | [M + H]⁺ = 620 |

-continued

| Example | Structure | Name | Comment | NMR Data | MS Data |
|---|---|---|---|---|---|
| 437 | 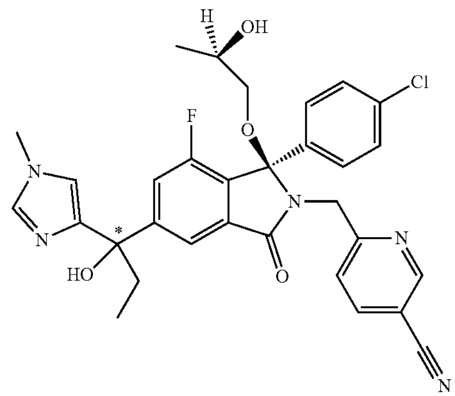 [SMILES: CCC(O)(c1cc(F)c2c(c1)C(=O)N(Cc1ccc(C#N)cn1)[C@@]2(OC[C@@H](C)O)c1ccc(Cl)cc1)c1cn(C)cn1] | 6-{[(1R)-1-(4-chlorophenyl)-7-fluoro-5-[1-hydroxy-1-(1-methyl-1H-imidazol-4-yl)propyl]-1-[(2R)-2-hydroxypropoxy]-3-oxo-2,3-dihydro-1H-isoindol-2-yl]methyl}pyridine-3-carbonitrile | Prepared in a similar manner to 337 | $^1$H NMR (400 MHz, CDCl3) 8.67 (1H, d), 7.81 (1H, dd), 7.69 (1H, d), 7.54-7.50 (1H, m), 7.44 (1H, d), 7.36 (1H, s), 7.28 (2H, m), 7.21 (2H), 6.85 (1H), 4.52 (2H, d), 4.04-3.96 (1H, m), 3.69 (3H, s), 3.55 (1H, s), 3.04 (1H, d), 2.82 (1H, d), 2.23-2.04 (2H, m), 1.06 (3H, d), 0.85 (3H, t) | 514 (M − $C_3H_7O_2$)$^+$ |
| 438 | 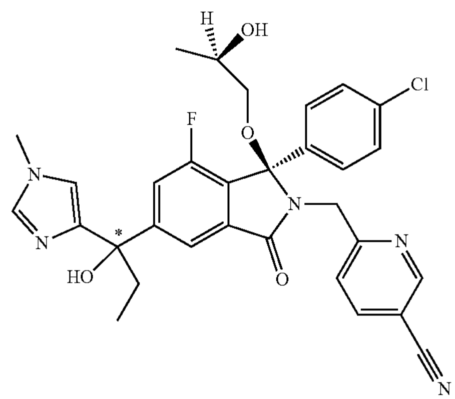 [SMILES: CCC(O)(c1cc(F)c2c(c1)C(=O)N(Cc1ccc(C#N)cn1)[C@@]2(OC[C@@H](C)O)c1ccc(Cl)cc1)c1cn(C)cn1] | 6-{[(1R)-1-(4-chlorophenyl)-7-fluoro-5-[1-hydroxy-1-(1-methyl-1H-imidazol-4-yl)propyl]-1-[(2R)-2-hydroxypropoxy]-3-oxo-2,3-dihydro-1H-isoindol-2-yl]methyl}pyridine-3-carbonitrile | Prepared in a similar manner to 337 | $^1$H NMR (400 MHz, CDCl3) 8.67 (1H, d), 7.80 (1H, dd), 7.68 (1H, d), 7.55-7.49 (2H, m), 7.41 (1H, d), 7.24 (2H, d), 7.20 (2H, d,), 6.85 (1H, s), 4.53 (2H, d), 4.02-3.96 (1H, m), 3.86-3.78 (1H, m), 3.73 (3H, s), 3.09-3.03 (2H, m), 2.27-2.04 (2H, m), 1.08 (3H, d), 0.87 (3H, t) | 514 (M − $C_3H_7O_2$)$^+$ |
| 439 | 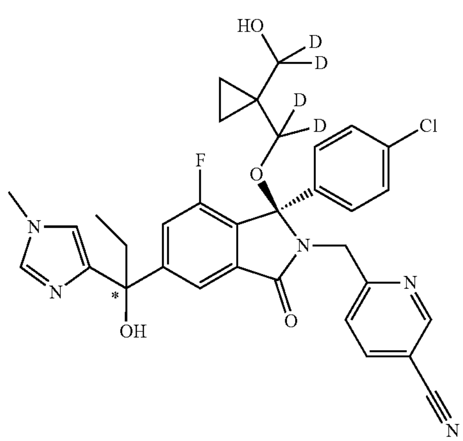 [SMILES: [2H]C([2H])(O)C1(C([2H])([2H])O[C@]2(c3ccc(Cl)cc3)c3c(F)cc(C(O)(CC)c4cn(C)cn4)cc3C(=O)N2Cc2ccc(C#N)cn2)CC1] | 6-{[(1R)-1-(4-chlorophenyl)-7-fluoro-1-({1-[hydroxy($^2$H$_2$)methyl]cyclopropyl}($^2$H$_2$)methoxy)-5-[1-hydroxy-1-(1-methyl-1H-imidazol-4-yl)propyl]-3-oxo-2,3-dihydro-1H-isoindol-2-yl]methyl}pyridine-3-carbonitrile | Prepared in a similar manner to 336 | 1H NMR (400 MHz, DMSO-d6): 8.76 (1H, dd), 8.07 (1H, dd), 7.86 (1H, d), 7.57 (1H, dd), 7.53 (1H, d), 7.34 (1H, dd), 7.26 (2H, d), 7.25-7.22 (2H, m), 7.01 (1H, d), 5.55 (1H, s), 4.58 (1H, d), 4.49 (1H, d), 4.37 (1H, s), 3.61 (3H, s), 2.19-2.03 (2H, m), 0.71 (3H, t), 0.38-0.31 (2H, m), 0.21-0.11 (2H, m) | 514 (M − $C_5D_4H_5O_2$)$^+$ |

| Example | Structure | Name | Comment | NMR Data | MS Data |
|---|---|---|---|---|---|
| 440 | 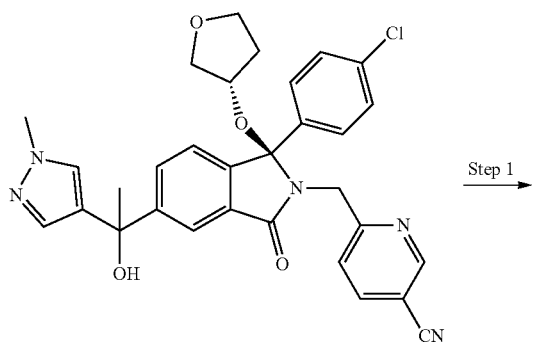 | 6-{[(1R)-1-(4-chlorophenyl)-7-fluoro-1-({1-[hydroxy($^2$H$_2$)methyl]cyclopropyl}($^2$H$_2$)methoxy)-5-[1-hydroxy-1-(1-methyl-1H-imidazol-4-yl)propyl]-3-oxo-2,3-dihydro-1H-isoindol-2-yl]methyl}pyridine-3-carbonitrile | Prepared in a similar manner to 336 | 1H NMR (400 MHz, DMSO-d6): 8.76 (1H, dd), 8.09 (1H, dd), 7.88 (1H, d), 7.56 (1H, dd), 7.51 (1H, dd), 7.36 (1H, dd), 7.28 (2H, d), 7.25 (2H, d), 7.01 (1H, d), 5.56 (1H, s), 4.54 (1H, d), 4.51 (1H, d), 4.36 (1H, s), 3.61 (3H, s), 2.19-2.04 (2H, m), 0.71 (3H, t), 0.37-0.30 (2H, m), 0.23-0.09 (2H, m). | 514 (M − C$_5$D$_4$H$_5$O$_2$)$^+$ |

Examples 441 and 442: 6-{[(1R)-1-(4-Chlorophenyl)-7-fluoro-5-[2-fluoro-1-hydroxy-1-(1-methyl-1H-pyrazol-4-yl)ethyl]-3-oxo-1-[(3S)-oxolan-3-yloxy]-2,3-dihydro-1H-isoindol-2-yl]methyl}pyridine-3-carbonitrile (*both isomers separated and isolated)

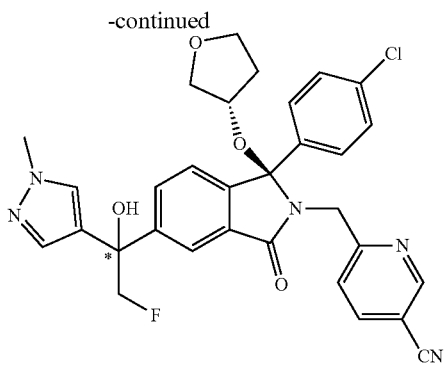

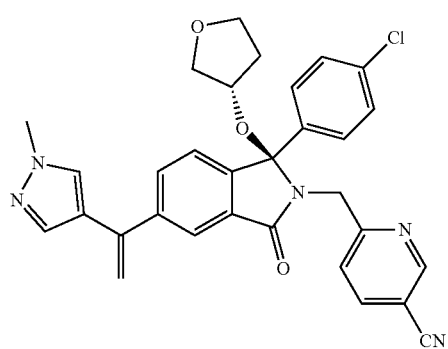

Step 1: 6-{[(1R)-1-(4-Chlorophenyl)-7-fluoro-5-[1-(1-methyl-1H-pyrazol-4-yl)ethenyl]-3-oxo-1-[(3S)-oxolan-3-yloxy]-2,3-dihydro-1H-isoindol-2-yl]methyl}pyridine-3-carbonitrile 6-{[(1R)-1-(4-Chlorophenyl)-7-fluoro-5-[1-hydroxy-1-(1-methyl-1H-pyrazol-4-yl)ethyl]-3-oxo-1-[(3S)-oxolan-3-yloxy]-2,3-dihydro-1H-isoindol-2-yl]methyl}pyridine-3-carbonitrile (chirally separated Example 218) (50 mg, 0.09 mmol) was dissolved in DCM (2 mL), PTSA (2 mg, 0.01 mmol) and anhydrous MgSO$_4$ (50 mg) were added and the reaction mixture was stirred at room temperature for 18 hours. The reaction was filtered through a pad of MgSO$_4$ and reduced in vacuo to give the title compound (35 mg, 68%) as an off white solid. MS: [M-C$_4$H$_7$O$_2$]$^+$=482.

Step 2: 6-{[(1R)-1-(4-Chlorophenyl)-7-fluoro-5-[2-fluoro-1-hydroxy-1-(1-methyl-1H-pyrazol-4-yl)ethyl]-3-oxo-1-[(3S)-oxolan-3-yloxy]-2,3-dihydro-1H-isoindol-2-yl]methyl}pyridine-3-carbonitrile 6-{[(1R)-1-(4-Chlorophenyl)-7-fluoro-5-[1-(1-methyl-1H-pyrazol-4-yl)ethenyl]-3-oxo-1-[(3S)-oxolan-3-yloxy]-2,3-dihydro-1H-isoindol-2-yl]methyl}pyridine-3-carbonitrile (139 mg, 0.24 mmol) was dissolved in MeCN (5 mL) before addition of Selectfluor® (85 mg, 0.24 mmol) and stirring for 3.5 hours at room temperature. The reaction was quenched with sat. sodium bicarbonate (6 mL) and diluted with DCM (5 mL) before the layers were separated and the aqueous layer further extracted with 3×DCM (5 mL). The combined organics were washed with brine, dried and reduced in vacuo to give 158 mg of a brown amorphous solid that was further purified by column chromatography 0-10% MeOH in EtOAc. Product fractions by LCMS were combined and reduced to give the title compound for which the two diastereoisomers were separated by chiral HPLC.

Example 441: 40 mg, White Solid

1H NMR (400 MHz, DMSO-d6): 8.78 (1H, dd), 8.11 (1H, dd), 7.81 (1H, d), 7.66 (1H, d), 7.59 (1H, dd), 7.41 (1H, dd), 7.39 (1H, d), 7.31-7.28 (2H, m), 7.28-7.25 (2H, m), 6.38-6.34 (1H, m), 4.89 (1H, dd), 4.72 (1H, dd), 4.64-4.57 (1H, m), 4.57-4.52 (1H, m), 4.10-4.05 (1H, m), 3.81 (3H, s), 3.76 (1H, q), 3.60-3.54 (1H, m), 3.47-3.42 (1H, m), 3.20 (1H, dd), 1.78-1.70 (1H, m), 1.63-1.55 (1H, m). MS: [M-C$_4$H$_7$O$_2$]$^+$=418.

Example 442: 45 mg, White Solid $^1$H NMR (400 MHz, DMSO-d6): 8.78 (1H, dd), 8.11 (1H, dd), 7.82 (1H, d), 7.67 (1H, s), 7.58 (1H, dd), 7.41 (1H, d), 7.39 (1H, d), 7.30-7.25 (4H, m), 6.36 (1H, s), 4.89 (1H, dd), 4.73 (1H, dd), 4.60 (1H, d), 4.55 (1H, d), 4.10-4.04 (1H, m), 3.81 (3H, s), 3.79-3.72 (1H, m), 3.60-3.54 (1H, m), 3.44 (1H, dd), 3.23-3.17 (1H, m), 1.78-1.70 (1H, m), 1.63-1.55 (1H, m). MS: [M-C$_4$H$_7$O$_2$]$^+$=418.

Examples 443 and 444: (3R)-2-[(5-chloro-3-hydroxypyridin-2-yl)methyl]-3-(4-chlorophenyl)-4-fluoro-6-[1-hydroxy-1-(1-methyl-1H-imidazol-4-yl)propyl]-3-(2-hydroxyethoxy)-2,3-dihydro-1H-isoindol-1-one (*both isomers separated and isolated)

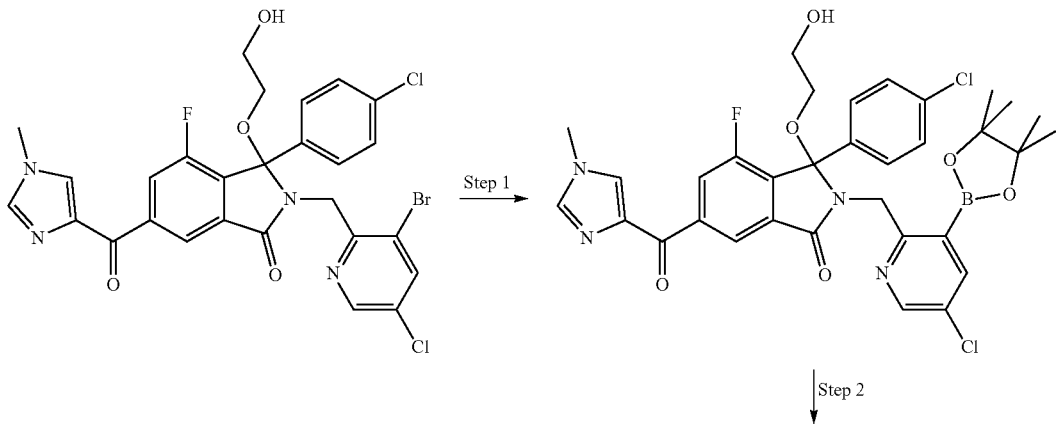

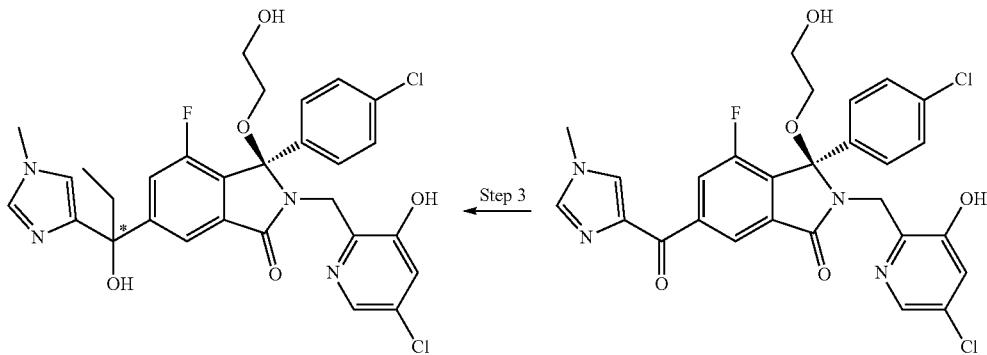

Step 1: 3-(4-Chlorophenyl)-2-[[5-chloro-3-(4,4,5,5-tetramethyl-1,3,2-dioxaborolan-2-yl)-2-pyridyl]methyl]-4-fluoro-3-(2-hydroxyethoxy)-6-(1-methylimidazole-4-carbonyl)isoindolin-1-one A mixture of 3-(4-chlorophenyl)-2-[[5-chloro-3-bromo-2-pyridyl]methyl]-4-fluoro-3-(2-hydroxyethoxy)-6-(1-methylimidazole-4-carbonyl)isoindolin-1-one (1.63 g, 2.57 mmol; prepared as in Example 200, steps 1-4, but using (3-bromo-5-chloropyridin-2-yl)methanamine) in step 3 and ethylene glycol in step 4) bis(pinacolato)diboron (0.98 g, 3.86 mmol), PdCl$_2$dppf.CH$_2$Cl$_2$ (0.21 g, 0.257 mmol) and potassium carbonate (0.76 g, 7.71 mmol) in dioxan (30 mL) was degassed with a stream of nitrogen for 10 min, then heated under nitrogen at 80° C. for 18 h. The mixture was cooled to RT, diluted with ethyl acetate and washed with water and brine. The organic phase was dried (MgSO$_4$) and the solvents removed under reduced pressure. The crude product was purified by column chromatography on silica, eluting with a gradient of 0-5% methanol in ethyl acetate to give the title compound (1.51 g, 86%) as a pale brown oil. MS: [M–H]$^-$=679.

Step 2: (3R)-2-[(5-Chloro-3-hydroxy-2-pyridyl)methyl]-3-(4-chlorophenyl)-4-fluoro-3-(2-hydroxyethoxy)-6-(1-methylimidazole-4-carbonyl)isoindolin-1-one A solution of Oxone (0.82 g, 2.67 mmol) in water (20 mL) was added dropwise to a solution of 3-(4-chlorophenyl)-2-[[5-chloro-3-(4,4,5,5-tetramethyl-1,3,2-dioxaborolan-2-yl)-2-pyridyl]methyl]-4-fluoro-3-(2-hydroxyethoxy)-6-(1-methylimidazole-4-carbonyl)isoindolin-1-one (1.45 g, 2.13 mmol) in acetone (20 mL) over 1 h. The solution was diluted with water and extracted with ethyl acetate. The organic extract was washed with brine, dried (MgSO$_4$) and the solvent removed under reduced pressure. The crude product was purified by column chromatography on silica, eluting with 4% methanolic ammonia (7M) in dichloromethane followed by preparative chiral HPLC to give the title compound (slow-running isomer; 0.32 g, 26%) as a pale yellow foam. MS: [M–H]$^-$=569.

Step 3: (3R)-2-[(5-chloro-3-hydroxypyridin-2-yl)methyl]-3-(4-chlorophenyl)-4-fluoro-6-[1-hydroxy-1-(1-methyl-1H-imidazol-4-yl)propyl]-3-(2-hydroxyethoxy)-2,3-dihydro-1H-isoindol-1-one The title compounds were prepared as in Example 203, but using AlEt$_3$ instead of AlMe$_3$. The diastereoisomers were separated by chiral SFC Example 443

$^1$H NMR (400 MHz, CDCl$_3$) 7.93 (1H, d), 7.69 (1H, d), 7.52 (1H, dd), 7.36-7.32 (3H, m), 7.30-7.27 (3H, m), 6.83 (1H, d), 4.55 (1H, d), 4.26 (1H, d), 3.90-3.83 (1H, m), 3.69 (4H, s), 3.53-3.48 (1H, m), 3.24-3.13 (2H, m), 2.22-2.04 (2H, m), 0.84 (3H, t). MS: [M–H]$^-$=599

Example 444

$^1$H NMR (400 MHz, CDCl$_3$) 7.93 (1H, d), 7.72 (1H, d), 7.50 (1H, dd), 7.36 (3H, d), 7.31-7.27 (3H, m), 6.82 (1H, d), 4.56 (1H, d), 4.24 (1H, d), 3.90-3.83 (1H, m), 3.67 (4H, s), 3.53-3.48 (1H, m), 3.23-3.10 (2H, m), 2.22-2.04 (2H, m), 0.83 (3H, t). MS: [M–H]$^-$=599

Starting from the appropriate acid (Preparation 23), amine and alcohol, the compound in the following Table were prepared using methods similar to those described in Example 200 (Step 3 and 4) and/or Example 203 (using AlMe$_3$).

Preparative chiral HPLC chromatography was used to separate both chiral intermediates and final products. In the table below an asterisk (*) indicates the compound was isolated as a single isomer at the position shown.

| Example | Structure | Name | Comment | NMR Data | MS Data |
|---|---|---|---|---|---|
| 445 | 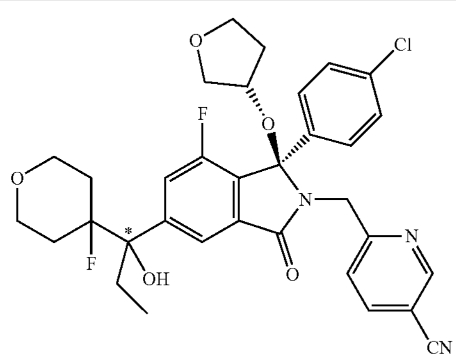 | 6-{[(1R)-1-(4-chlorophenyl)-7-fluoro-5-[1-(4-fluorooxan-4-yl)-1-hydroxypropyl]-3-oxo-1-[(3S)-oxolan-3-yloxy]-2,3-dihydro-1H-isoindol-2-yl]methyl}pyridine-3-carbonitrile | Prepared in a similar manner to Example 200, but using EtLi and Et$_2$Zn in step 5 | $^1$H NMR (400 MHz, CDCl3) 8.67 (1H, d), 7.85 (1H, s), 7.80 (1H, dd), 7.42-7.36 (2H, m), 7.25-7.17 (4H, m), 4.62 (2H, s), 3.90-3.79 (3H, m), 3.71-3.61 (4H, m), 3.34-3.24 (1H, m), 2.22-2.18 (2H, m), 2.03-1.86 (3H, m), 1.74-1.61 (3H, m), 1.47-1.39 (1H, m), 0.95-0.86 (1H, m), 0.71 (3H, t) | [M – C$_4$H$_7$O$_2$]$^+$ = 536 |

| Example | Structure | Name | Comment | NMR Data | MS Data |
|---|---|---|---|---|---|
| 446 | 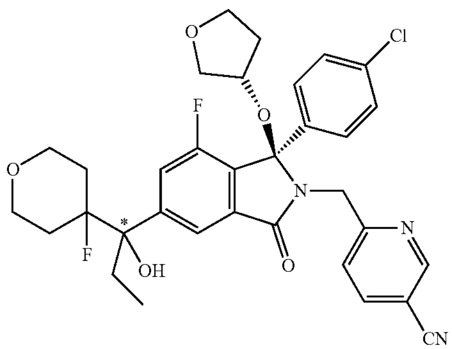 | 6-{[(1R)-1-(4-chlorophenyl)-7-fluoro-5-[1-(4-fluorooxan-4-yl)-1-hydroxypropyl]-3-oxo-1-[(3S)-oxolan-3-yloxy]-2,3-dihydro-1H-isoindol-2-yl]methyl}pyridine-3-carbonitrile | Prepared in a similar manner to Example 200, but using EtLi and Et₂Zn in step 5 | ¹H NMR (400 MHz, CDCl3) 8.65 (1H, d), 7.80-7.77 (2H, m), 7.49 (1H, d), 7.35 (1H, d), 7.23 (2H, d), 7.17 (2H, d), 4.69 (1H, d), 4.56 (1H, d), 4.05-3.99 (1H, m), 3.91-3.80 (3H, m), 3.72-3.59 (4H, m), 3.34-3.23 (1H, m), 2.23-2.19 (2H, m), 2.03-1.67 (6H, m), 1.53-1.44 (1H, m), 0.71 (3H, t) | [M − $C_4H_7O_2$]⁺ = 536 |

Example 447: (3R)-3-(4-Chlorophenyl)-2-[(5-chloropyrimidin-2-yl)methyl]-4-fluoro-6-[1-(4-fluorooxan-4-yl)-1-hydroxyethyl]-3-({1-[hydroxy($^2H_2$)methyl]cyclopropyl}($^2H_2$)methoxy)-2,3-dihydro-1H-isoindol-1-one (Example isolated as a single isomer at the position shown*)

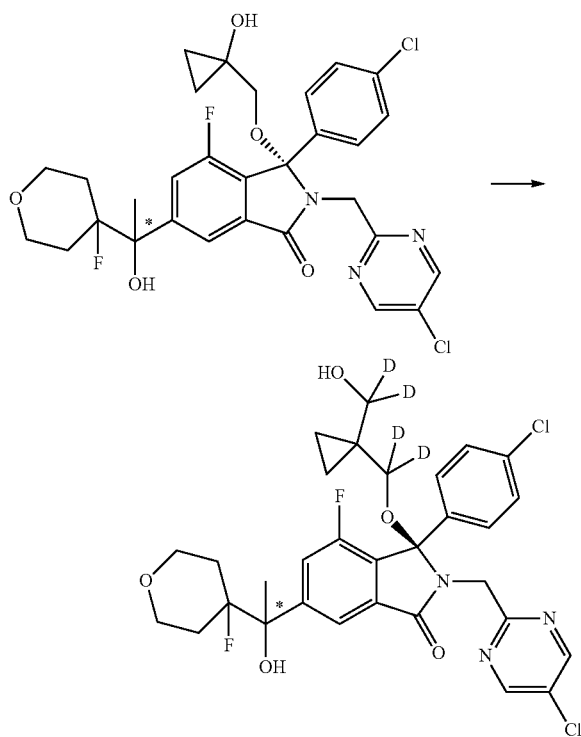

The title compound was prepared from 3S)-3-(4-chlorophenyl)-2-[(5-chloropyrimidin-2-yl)methyl]-4-fluoro-6-[1-(4-fluorooxan-4-yl)-1-hydroxyethyl]-3-[(1-hydroxycyclopropyl)methoxy]-2,3-dihydro-1H-isoindol-1-one and {1-[hydroxy($^2H_2$)methyl]cyclopropyl}($^2H_2$)methanol using the conditions described in, Example 1, step 2. The starting material was prepared in a similar manner to Example 386. Purification by chiral HPLC gave the title compound.

Example 447: (32 mg, 25% Yield)

¹H NMR (400 MHz, DMSO-d6): 8.75-8.69 (2H, m), 7.77-7.71 (1H, m), 7.51-7.44 (1H, m), 7.35-7.25 (4H, m), 5.88-5.83 (1H, m), 4.64-4.47 (2H, m), 4.37 (1H, s), 3.83 (1H, dd), 3.71 (1H, dd), 3.47 (1H, t), 3.42-3.33 (1H, m), 2.11-1.83 (2H, m), 1.83-1.68 (2H, m), 1.58 (3H, s), 0.41-0.30 (2H, m), 0.26-0.12 (2H, m); LCMS: [M−H]⁻=636.

Example 448: (3R)-3-(4-Chlorophenyl)-2-[(5-chloropyrimidin-2-yl)methyl]-4-fluoro-6-[1-hydroxy-1-(piperidin-4-yl)propyl]-3-[(3S)-oxolan-3-yloxy]-2,3-dihydro-1H-isoindol-1-one (*Single isomer at position shown)

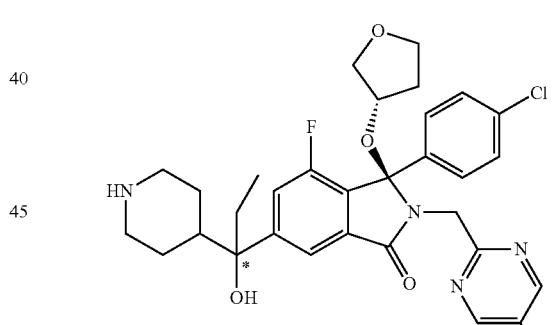

Starting from 5-(1-{1-[(tert-butoxy)carbonyl]piperidin-4-yl}-1-hydroxypropyl)-2-(4-chlorobenzoyl)-3-fluorobenzoic acid (Preparation 30, isomer A) the title compound was prepared in a similar fashion to Example 286, steps 1 and 2, but using 1-(5-chloropyrimidine-2-yl)methanramine hydrochloride in step 1 and (S)-(+)-3-hydroxy-tetrahydrofuran in step 2. ¹H NMR (400 MHz, CDCl₃) 8.52 (2H, s), 7.67 (1H, s), 7.37-7.32 (3H, m), 7.19 (2H, d), 4.72 (1H, d), 4.59 (1H, d), 4.23 (1H, ddd), 3.88 (1H, q), 3.74-3.63 (2H, m), 3.33-3.21 (2H, m), 3.12 (1H, d), 2.69-2.53 (2H, m), 2.27-2.26 (2H, m), 1.98-1.68 (5H, m), 1.43-1.33 (2H, m), 1.22 (1H, d), 0.67 (3H, t); MS: [M+H]⁺=615.

In one example of the method of Example 448 the compound synthesised is the isomer shown below ((3R)-3-(4-chlorophenyl)-2-[(5-chloropyrimidin-2-yl)methyl]-4- fluoro-6-[(1S)-1-hydroxy-1-(piperidin-4-yl)propyl]-3-[(3S)-oxolan-3-yloxy]-2,3-dihydro-1H-isoindol-1-one):

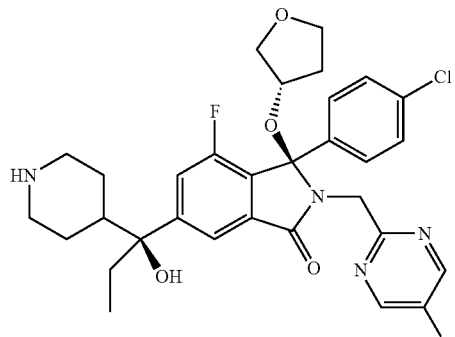

Example 449: (3R)-3-(4-chlorophenyl)-2-[(5-chloropyrimidin-2-yl)methyl]-4-fluoro-6-[1-hydroxy-1-(1-methylpiperidin-4-yl)propyl]-3-[(3S)-oxolan-3-yloxy]-2,3-dihydro-1H-isoindol-1-one (*Single isomer at position shown)

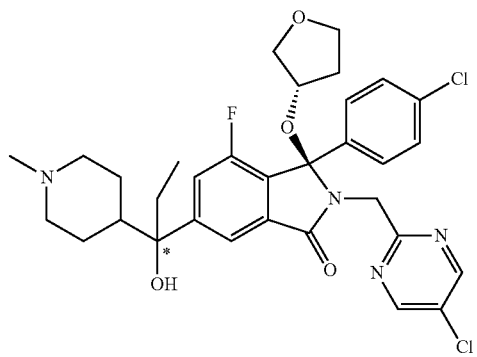 [SMILES: CCC(O)(c1cc(F)c2c(c1)C(=O)N(Cc1ncc(Cl)cn1)[C@@]2(O[C@H]1CCOC1)c1ccc(Cl)cc1)C1CCN(C)CC1]

The title compound was prepared from Example 448 using a similar procedure as in Preparation 25, step 2. $^1$H NMR (400 MHz, CDCl$_3$) 8.52 (2H, s), 7.65 (1H, d), 7.40-7.32 (3H, m), 7.18 (2H, d), 4.73 (1H, d), 4.58 (1H, d), 4.21 (1H, ddd), 3.88 (1H, q), 3.74-3.62 (2H, m), 3.29 (1H, dd), 2.94 (1H, d), 2.83 (1H, d), 2.24 (3H, s), 1.97-1.79 (6H, m), 1.78-1.69 (3H, m), 1.47-1.33 (2H, m), 1.28-1.23 (1H, m), 0.69 (3H, t). MS: [M+H]$^+$=629

In one example of the method of Example 449 the compound synthesised is the isomer shown below ((3R)-3-(4-chlorophenyl)-2-[(5-chloropyrimidin-2-yl)methyl]-4-fluoro-6-[(1S)-1-hydroxy-1-(1-methylpiperidin-4-yl)propyl]-3-[(3S)-oxolan-3-yloxy]-2,3-dihydro-1H-isoindol-1-one):

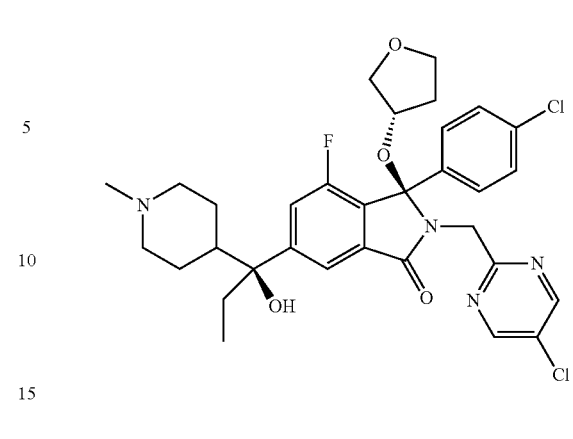

Example 450: (3R)-3-(4-chorophenyl)-2-[(5-chloropyrimidin-2-ylmethyl]-4-fluoro-6-[1-hydroxy-1-(piperidin-4-yl)propyl]-3-methoxy-2,3-dihydro-1H-isoindol-1-one (*Single isomer at position shown)

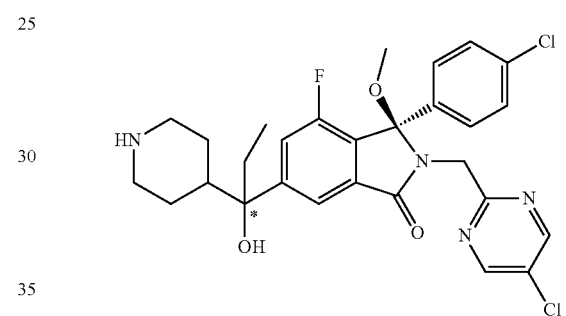

Starting from 5-(1-{1-[(tert-butoxy)carbonyl]piperidin-4-yl}-1-hydroxypropyl)-2-(4-chlorobenzoyl)-3-fluorobenzoic acid (Preparation 30, isomer A) the title compound was prepared in a similar fashion to Example 286, steps 1 and 2, but using 1-(5-chloropyrimidine-2-yl)methanramine hydrochloride in step 1. $^1$H NMR (400 MHz, CDCl$_3$) 8.53 (2H, s), 7.67 (1H, s), 7.34 (3H, d), 7.21 (2H, d), 4.69 (1H, d), 4.59 (1H, d), 3.14 (1H, m), 3.09 (3H, s), 3.03 (1H, m), 2.67-2.48 (2H, m), 1.97-1.75 (4H, m), 1.28-1.11 (3H, m), 0.70 (3H, t). MS: [M-OCH$_3$]$^+$=527.

In one example of the method of Example 450 the compound synthesised is the isomer shown below ((3R)-3-(4-chlorophenyl)-2-[(5-chloropyrimidin-2-yl)methyl]-4-fluoro-6-[(1S)-1-hydroxy-1-(piperidin-4-yl)propyl]-3-methoxy-2,3-dihydro-1H-isoindol-1-one):

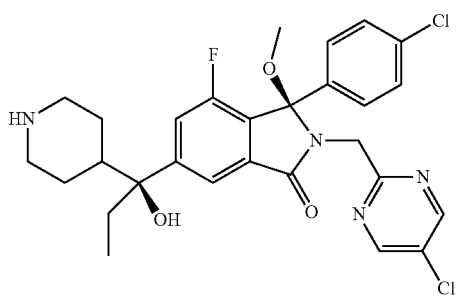 [SMILES: CC[C@@](O)(c1cc(F)c2c(c1)C(=O)N(Cc1ncc(Cl)cn1)[C@@]2(OC)c1ccc(Cl)cc1)C1CCNCC1]

Examples 451 and 452: 2-[(1R)-1-(4-chlorophenyl)-2-[(5-chloropyridin-2-yl)methyl]-1-methoxy-3-oxo-2,3-dihydro-1H-isoindol-5-yl]-2-hydroxy-N-(1-methylpiperidin-4-yl)propanamide (*both isomers separated and isolated)

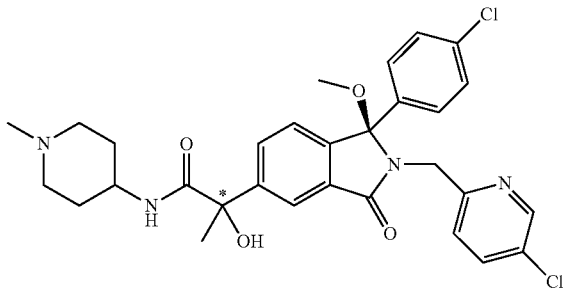 [SMILES: CO[C@]1(c2ccc(Cl)cc2)c2ccc(C(C)(O)C(=O)NC3CCN(C)CC3)cc2C(=O)N1Cc1ccc(Cl)cn1]

To a solution of 2-[(1R)-1-(4-chlorophenyl)-2-[(5-chloropyridin-2-yl)methyl]-1-methoxy-3-oxo-2,3-dihydro-1H-isoindol-5-yl]-2-hydroxypropanoic acid (Example 145 and Example 146, step 1) (75 mg, 0.154 mmol) and 1-methylpiperidin-4-amine (25 µL, 0.20 mmol) in chloroform (3.0 mL) was added HOAt (36 mg, 0.262 mmol) and EDCl (35 µL, 0.20 mmol) at room temperature and the yellow mixture stirred for 20 h. The solvent was removed in vacuo and the residue taken up in EtOAc (10 mL) and washed with saturated aqueous NaHCO$_3$ (10 mL), H$_2$O (10 mL) and brine (10 mL), dried over anhydrous MgSO$_4$, filtered and the solvent removed in vacuo. FCC [dichloromethane-methanol (100:0)→(85:15)] of the crude residue afforded the racemic mixture (57 mg, 63%, 6.1:1 by NMR). Purification by chiral HPLC gave the title compounds.

Example 451 Major, Fast Running Isomer 1

H NMR (400 MHz, DMSO-d6): 8.39 (1H, d), 7.99 (1H, d), 7.80 (1H, dd), 7.74 (1H, dd), 7.68 (1H, d), 7.33-7.15 (6H, m), 6.34 (1H, s), 4.53 (1H, d), 4.36 (1H, d), 3.53-3.37 (1H, m), 2.77 (3H, s), 2.72-2.56 (2H, m), 2.12 (3H, s), 1.98-1.79 (2H, m), 1.66 (4H, s), 1.63-1.35 (3H, m); MS: [M+H]$^+$=583.

Example 452 Minor, Slow Running Isomer

1H NMR (400 MHz, DMSO-d6): 8.38 (1H, d), 7.99 (1H, d), 7.83-7.65 (3H, m), 7.33-7.17 (6H, m), 6.33 (1H, s), 4.51 (1H, d), 4.39 (1H, d), 3.52-3.43 (1H, m), 2.77 (3H, s), 2.73-2.59 (2H, m), 2.13 (3H, s), 2.01-1.82 (2H, m), 1.66 (4H, s), 1.61-1.40 (3H, m); MS: [M+H]$^+$=583.

Examples 453 and 454: 2-[(1R)-1-(4-Chlorophenyl)-2-[(5-chloropyridin-2-yl)methyl]-1-methoxy-3-oxo-2,3-dihydro-1H-isoindol-5-yl]-2-hydroxy-N-(1-methyl-1H-pyrazol-4-yl)propanamide (*both isomers separated and isolated)

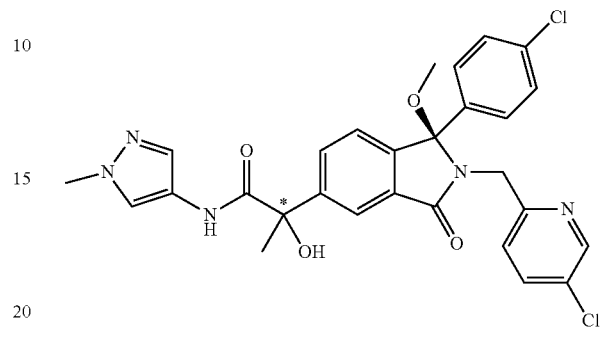

The compounds were prepared in a similar manner to Examples 451 and 452 using 1-methyl-1H-pyrazol-4-amine and CDI.

Example 453 Major, Fast Running Isomer (121 mg, 36%)

H NMR (400 MHz, DMSO-d6): 10.07 (1H, s), 8.38 (1H, d), 8.06 (1H, d), 7.93-7.83 (2H, m), 7.73 (1H, dd), 7.55 (1H, s), 7.31-7.21 (6H, m), 6.58 (1H, s), 4.56-4.48 (1H, m), 4.36 (1H, d), 3.75 (3H, s), 2.77 (3H, s), 1.74 (3H, s); MS: [M−H]$^-$ 564

Example 454 Minor, Slow Running Isomer (15 mg, 4.5%)

1H NMR (400 MHz, DMSO-d6): 10.08 (1H, s), 8.38 (1H, d), 8.07 (1H, d), 7.92-7.83 (2H, m), 7.72 (1H, dd), 7.55 (1H, s), 7.31-7.19 (6H, m), 6.58 (1H, s), 4.55-4.47 (1H, m), 4.39 (1H, d), 3.75 (3H, s), 2.77 (3H, s), 1.75 (3H, s); MS: [M−H]$^-$ 564.

Examples 455 and 456: 2-[(1R)-1-(4-Chlorophenyl)-2-[(5-chloropyridin-2-yl)methyl]-1-methoxy-3-oxo-2,3-dihydro-1H-isoindol-5-yl]-2-hydroxy-N-(1-methylazetidin-3-yl)propanamide (*both isomers separated and isolated)

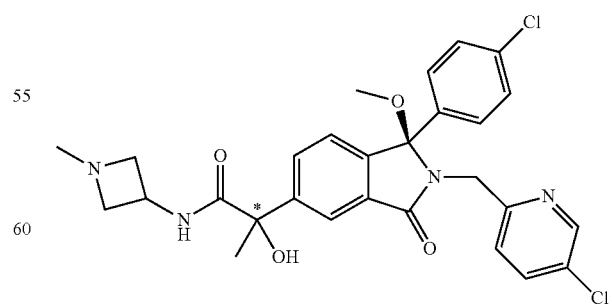

The compounds were prepared in a similar manner to Examples 451 and 452 using 3-amino-1-N-methyl-azetidine and EDCl/HOAt.

Example 455 Minor, Fast Running Isomer

1H NMR (400 MHz, DMSO-d6): 8.39 (1H, d), 8.29 (1H, d), 7.99 (1H, d), 7.80 (1H, dd), 7.74 (1H, dd), 7.33-7.16 (6H, m), 6.38 (1H, s), 4.53 (1H, d), 4.36 (1H, d), 4.24-4.15 (1H, m), 3.51 (1H, t), 3.46-3.40 (1H, m), 3.04-2.90 (2H, m), 2.77 (3H, s), 2.23 (3H, s), 1.65 (3H, s); MS: [M+H]$^+$=555

Example 456 Major, Slow Running Isomer

1H NMR (400 MHz, DMSO-d6): 8.38 (1H, d), 8.29 (1H, d), 7.99 (1H, d), 7.80 (1H, dd), 7.73 (1H, dd), 7.32-7.19 (6H, m), 6.37 (1H, s), 4.51 (1H, d), 4.38 (1H, d), 4.24-4.15 (1H, m), 3.51 (1H, t), 3.43 (1H, d), 3.02-2.89 (2H, m), 2.77 (3H, s), 2.23 (3H, s), 1.66 (3H, s); MS: [M+H]$^+$=555

Examples 457 and 458: tert-Butyl 3-(4-{1-[(1R)-1-(4-chlorophenyl)-2-[(5-chloropyridin-2-yl)methyl]-7-fluoro-1-methoxy-3-oxo-2,3-dihydro-1H-isoindol-5-yl]-1-hydroxyethyl}-1H-pyrazol-1-yl)azetidine-1-carboxylate (*both isomers separated and isolated)

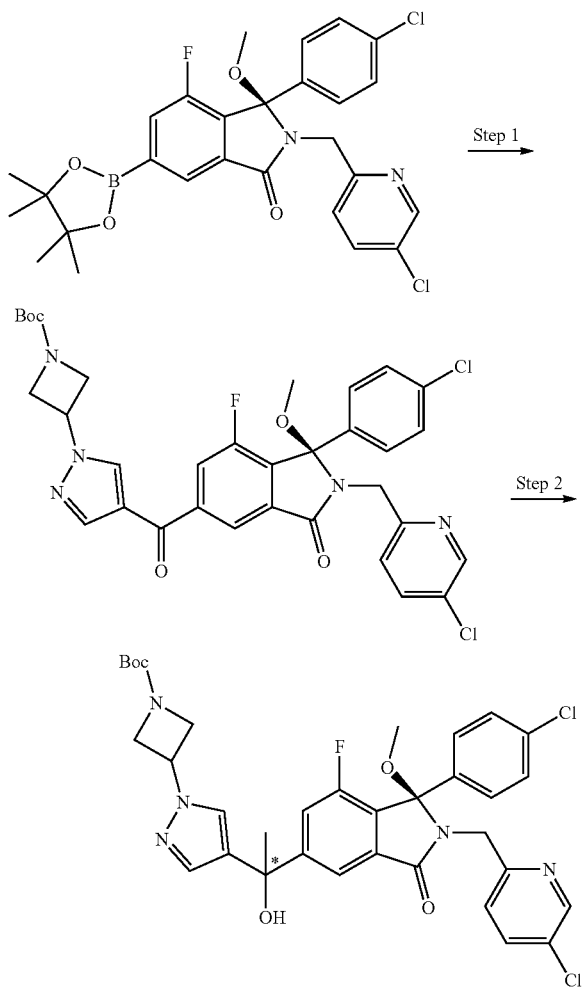 [SMILES: CO[C@]1(c2ccc(Cl)cc2)c2c(F)cc(B3OC(C)(C)C(C)(C)O3)cc2C(=O)N1Cc1ccc(Cl)cn1 ; CO[C@]1(c2ccc(Cl)cc2)c2c(F)cc(C(=O)c3cnn(C4CN(C(=O)OC(C)(C)C)C4)c3)cc2C(=O)N1Cc1ccc(Cl)cn1 ; CO[C@]1(c2ccc(Cl)cc2)c2c(F)cc(C(C)(O)c3cnn(C4CN(C(=O)OC(C)(C)C)C4)c3)cc2C(=O)N1Cc1ccc(Cl)cn1]

1: tert-Butyl 3-{4-[(1R)-1-(4-chlorophenyl)-2-[(5-chloropyridin-λ-yl)methyl]-7-fluoro-1-methoxy-3-oxo-2,3-dihydro-1H-isoindole-5-carbonyl]-1H-pyrazol-1-yl}azetidine-1-carboxylate Starting with (3R)-3-(4-chlorophenyl)-2-[(5-chloropyridin-2-yl)methyl]-4-fluoro-3-methoxy-6-(4,4,5,5-tetramethyl-1,3,2-dioxaborolan-2-yl)-2,3-dihydro-1H-isoindol-1-one (prepared in a similar manner to Example 179, step 1) and 3-(4-iodo-1H-pyrazol-1-yl)azetidine-1-carboxylate (Preparation 30), Step 1 was performed in a similar manner to Example 179, step 2, using toluene instead of anisole. MS: [M+H]$^+$=666.

Step 2: tert-Butyl 3-(4-{1-[(1R)-1-(4-chlorophenyl)-2-[(5-chloropyridin-2-yl)methyl]-7-fluoro-1-methoxy-3-oxo-2,3-dihydro-1H-isoindol-5-yl]-1-hydroxyethyl}-1H-pyrazol-1-yl)azetidine-1-carboxylate The title compound was prepared following similar methods to those described in Example 1, step 4. The two diastereoisomers were separated by chiral HPLC.

Example 457, Isomer 1 (31 mg, 15%)

$^1$H NMR (400 MHz, DMSO-d$_6$): 8.38 (1H, d), 7.80 (1H, s), 7.78-7.70 (2H, m), 7.56-7.46 (2H, m), 7.34-7.17 (5H, m), 5.92 (1H, s), 5.20-5.10 (1H, m), 4.50 (1H, d), 4.34 (1H, d), 4.25 (2H, t), 4.10 (2H, d), 2.88 (3H, s), 1.81 (3H, s), 1.40 (9H, s); MS: [M+H]$^+$=682.

Example 458, Isomer 2 (34 mg, 17%)

$^1$H NMR (400 MHz, DMSO-d$_6$): 8.38 (1H, d), 7.81 (1H, s), 7.77-7.70 (2H, m), 7.55-7.47 (2H, m), 7.34-7.19 (5H, m), 5.93 (1H, s), 5.20-5.11 (1H, m), 4.50 (1H, d), 4.39-4.31 (1H, m), 4.31-4.18 (2H, m), 4.10 (2H, d), 2.88 (3H, s), 1.81 (3H, s), 1.41 (9H, s); MS: [M+H]$^+$=682.

Example 459: 2-(4-{1-[(1R)-1-(4-chlorophenyl)-2-[(5-chloropyridin-2-yl)methyl]-7-fluoro-1-methoxy-3-oxo-2,3-dihydro-1H-isoindol-5-yl]-1-hydroxyethyl}piperidin-1-yl)acetic acid (*Single isomer at position shown)

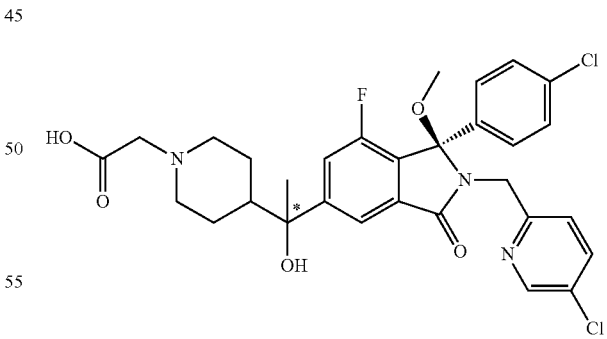

The title compound was made in a similar fashion to Example 293, using methyl bromoacetate/DMF/K$_2$CO$_3$ instead of acetyl chloride/DCM; followed by treatment with aqueous lithium hydroxide to furnish the carboxylic acid.

Example 459 *Slower Eluting Isomer $^1$H NMR (400 MHz, DMSO) 8.45 (1H, d), 7.84-7.78 (2H, m), 7.52 (1H, d), 7.38 (2H, d), 7.36-7.28 (3H, m), 5.39-5.36

(1H, br s), 4.58 (1H, d), 4.41 (1H, d), 3.25-3.15 (4H, m), 2.94 (3H, s), 2.54-2.49 (2H, m), 1.78-1.77 (2H, m), 1.54 (5H, m), 1.36-1.28 (2H, m). MS: [M+H]⁺=602.

Example 460: (3R)-3-(4-Chlorophenyl)-3-{[1-(hydroxymethyl)cyclopropyl]methoxy}-6-(2-hydroxypropan-2-yl)-2-[(5-methylpyrazin-2-yl)methyl]-2,3-dihydro-1H-isoindol-1-one

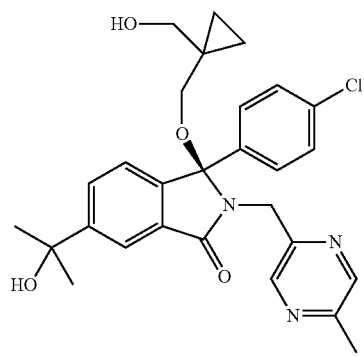 [SMILES: Cc1cnc(CN2C(=O)c3cc(C(C)(C)O)ccc3[C@]2(OCC2(CO)CC2)c2ccc(Cl)cc2)cn1]

The title compound was prepared in a similar manner to that described in Example 6, steps 1-4 using (5-methylpyrazin-2-yl)methanamine instead of (5-chloropyridine-2-yl)methaneamine dihydrochloride in step 1 and (1-hydroxymethyl-cyclopropyl)-methanol instead of ethylene glycol in step 2. MS: [M-C₅H₉O₂]⁺=406. 1H NMR (400 MHz, DMSO-d6): 8.26 (2H, d), 7.91 (1H, d), 7.74 (1H, dd), 7.28 (2H, d), 7.25-7.12 (3H, m), 5.24 (1H, s), 4.56-4.41 (3H, m), 3.48-3.37 (1H, m), 3.28 (1H, dd), 2.97-2.76 (2H, m), 2.40 (3H, s), 1.47 (6H, s), 0.34 (2H, d), 0.24-0.08 (2H, m).

Example 461: 2-{[(1R)-1-(4-chlorophenyl)-7-fluoro-5-[1-hydroxy-1-(1-methyl-1H-imidazol-4-yl)propyl]-1-[(trans-3-hydroxycyclopentyl)oxy]-3-oxo-2,3-dihydro-1H-isoindol-2-yl]methyl}pyrimidine-5-carbonitrile (Example prepared and isolated as a single isomer at the positions shown*)

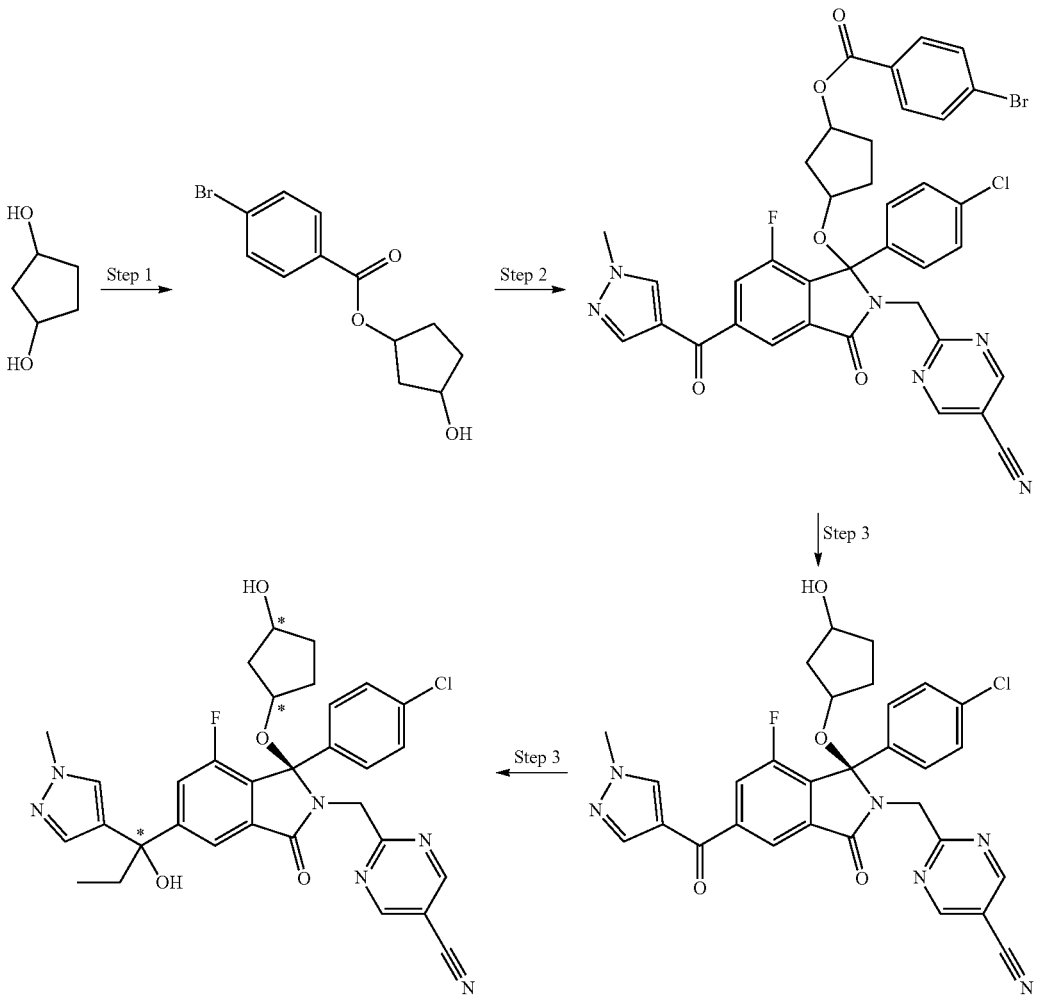 [SMILES: OC1CCC(O)C1 ; O=C(OC1CCC(O)C1)c1ccc(Br)cc1 ; Cn1cc(C(=O)c2cc(F)c3c(c2)C(=O)N(Cc2ncc(C#N)cn2)C3(OC2CCC(OC(=O)c3ccc(Br)cc3)C2)c2ccc(Cl)cc2)cn1 ; CCC(O)(c1cc(F)c2c(c1)C(=O)N(Cc1ncc(C#N)cn1)[C@@]2(OC1CCC(O)C1)c1ccc(Cl)cc1)c1cnn(C)c1 ; Cn1cc(C(=O)c2cc(F)c3c(c2)C(=O)N(Cc2ncc(C#N)cn2)[C@@]3(OC2CCC(O)C2)c2ccc(Cl)cc2)cn1]

Step 1: trans-3-Hydroxycyclopentyl 4-bromobenzoate

4-Bromobenzoyl chloride (1.72 g, 7.84 mmol) was added portion wise over 10 minutes to a stirred solution of cyclopentane-1,3-diol (cis/trans mixture ex Aldrich, 0.8 g, 7.84 mmol) in pyridine (5 mL) at 10° C. Further pyridine (2 mL) was added and the mixture stirred with warming to room temperature over 3 hours. The mixture was poured into $H_2O$ (300 mL), extracted with diethyl ether (2×200 mL) and the combined extracts dried ($MgSO_4$) and the solvent evaporated. The residual solid was purified by achiral SFC to afford the racemic trans-cyclopentane-1,3-diol (1.02 g). Chiral separation by SFC gave:

Faster eluting trans-isomer (0.45 g, 20.1%) $^1$H NMR (400 MHz, $CDCl_3$) 7.86 (2H, d), 7.57 (2H, d), 5.55-5.49 (1H, m), 4.59-4.53 (1H, m), 2.36-2.26 (1H, m), 2.14-2.10 (3H, m), 1.90-1.81 (1H, m), 1.75-1.67 (1H, m), 1.48-1.40 (1H, m).

Slow eluting trans-isomer (0.485 g, 21.7%) $^1$H NMR (400 MHz, $CDCl_3$) 7.86 (2H, d), 7.57 (2H, d), 5.55-5.49 (1H, m), 4.59-4.53 (1H, m), 2.36-2.26 (1H, m), 2.14-2.10 (3H, m), 1.90-1.81 (1H, m), 1.75-1.67 (1H, m), 1.58-1.47 (1H, m).

Step 2: trans-3-((1-(4-Chlorophenyl)-2-((5-cyanopyrimidin-2-yl)methyl)-7-fluoro-5-(1-methyl-1H-imidazole-4-carbonyl)-3-oxoisoindolin-1-yl)oxy)cyclopentyl 4-bromobenzoate A mixture of 2-((1-(4-chlorophenyl)-7-fluoro-1-hydroxy-5-(1-methyl-1H-imidazole-4-carbonyl)-3-oxoisoindolin-2-yl)methyl)pyrimidine-5-carbonitrile (1.50 g, 2.99 mmol), trans-3-hydroxycyclopentyl 4-bromobenzoate (fast eluting isomer) (2.13 g, 7.5 mmol) and indium bromide (2.13 g, 6 mmol) in 1,2-dichloroethane (30 mL) was heated at reflux for 3 h under a nitrogen atmosphere. On cooling the mixture was partitioned between DCM (30 mL) and $H_2O$ (200 mL) and the aqueous layer extracted with EtOAc (2×200 mL). Combined organics were dried ($MgSO_4$) and evaporated. The residue was chromatographed on silica gel eluting with 0-100% EtOAc in isohexane gradient to afford the title compound (1.94 g, 85%). $^1$H NMR (400 MHz, $CDCl_3$) 8.80 (1H, s), 8.75 (1H, s), 8.72 (1H, s), 8.19 (1H, dd), 7.84-7.81 (2H, m), 7.75 (1H, d), 7.59-7.50 (3H, m), 7.36 (2H, d), 7.21-7.16 (2H, m), 5.51-5.42 (1H, m), 4.84 (1H, dd,), 4.60 (1H, dd), 4.33-4.22 (1H, m), 3.83 (3H, d), 2.31-2.06 (2H, m), 1.94-1.86 (1H, m), 1.82-1.63 (3H, m).

Step 3: 2-((1-(4-Chlorophenyl)-7-fluoro-1-((trans-3-hydroxycyclopentyl)oxy)-5-(1-methyl-1H-imidazole-4-carbonyl)-3-oxoisoindolin-2-yl)methyl)pyrimidine-5-carbonitrile A mixture of trans-3-((1-(4-chlorophenyl)-2-((5-cyanopyrimidin-2-yl)methyl)-7-fluoro-5-(1-methyl-1H-imidazole-4-carbonyl)-3-oxoisoindolin-1-yl)oxy)cyclopentyl 4-bromobenzoate (1.94 g, 2.53 mmol) and lithium hydroxide (1.09 g, 45 mmol) in $H_2O$ (50 mL), THF (150 mL) and methanol (30 mL) was stirred at room temperature for 1.5 h, concentrated to approximately 100 mL, diluted with $H_2O$ and extracted with ethyl acetate (2×100 mL). Combined organics were dried ($MgSO_4$) and evaporated to afford a pale yellow solid. This was dissolved in anhydrous THF (20 mL), cooled to 0° C. under nitrogen, triethylamine (0.57 mL, 4 mmol) added followed by dropwise addition of trifluoroacetic anhydride (0.57 mL, 4 mmol). After stirring at 0° C. for 50 minutes 1:1 2M $Na_2CO_3$: saturated $NaHCO_3$ (30 mL) was added, the mixture stirred at room temperature for 3 h and then extracted with EtOAc (2×100 mL).

Combined organics were dried ($MgSO_4$) and the solvent evaporated to afford a pale yellow foam (1.33 g). Chromatography on silica gel eluting with 0-5% MeOH in EtOAc gradient afforded the title compound as a mixture of isomers (1.07 g). Chiral separation by SFC gave:

Fast eluting isomer (0.43 g, 29%) $^1$H NMR (400 MHz, $CDCl_3$) 9.06 (1H, s), 8.79 (1H, s), 8.74 (1H, s), 8.19-8.12 (1H, m), 7.82 (1H, d), 7.55 (1H, s), 7.37-7.32 (2H, m), 7.18-7.11 (2H, m), 4.85 (1H, d), 4.60 (1H, d), 4.45-4.43 (1H, m), 4.29-4.19 (1H, m), 3.95 (1H, s), 3.83 (3H, s), 2.10-2.02 (1H, m), 1.99-1.92 (1H, m), 1.69-1.62 (1H, m), 1.56-1.42 (2H, m), 1.29-1.23 (1H, m).

Slow eluting isomer B (0.34 g, 23%) $^1$H NMR (400 MHz, $CDCl_3$) 8.80 (2H, s), 8.73 (1H, s), 8.16 (1H, d,), 7.82 (1H, s), 7.55 (1H, s), 7.35 (2H, d), 7.17 (2H, d), 4.83 (1H, d), 4.59 (1H, d), 4.44-4.38 (1H, m), 4.31-4.24 (1H, m), 3.83 (3H, s), 3.49 (1H, s), 2.13-2.02 (1H, m), 1.87-1.79 (1H, m), 1.71-1.42 (4H, m).

Step 4: 2-{[(1R)-1-(4-chlorophenyl)-7-fluoro-5-[1-hydroxy-1-(1-methyl-1H-imidazol-4-yl)propyl]-1-[(trans-3-hydroxycyclopentyl)oxy]-3-oxo-2,3-dihydro-1H-isoindol-2-yl]methyl}pyrimidine-5-carbonitrile To a stirred solution of trans-2-((1-(4-chlorophenyl)-7-fluoro-1-((3-hydroxycyclopentyl)oxy)-5-(1-methyl-1H-imidazole-4-carbonyl)-3-oxoisoindolin-2-yl)methyl)pyrimidine-5-carbonitrile (fast eluting isomer) (0.43 g, 0.733 mmol) in anhydrous DCM (15 mL) at −10° C. under nitrogen was added 1M triethylaluminium in hexanes (3 mL, 3 mmol) dropwise over 5 minutes. On complete addition stirring was continued at −10° C. for 10 minutes and the reaction quenched with saturated aqueous $NH_4Cl$ (10 mL) and $H_2O$ (10 mL) and stirred at room temperature for 10 minutes. The layers were separated, the aqueous extracted with DCM (3×30 mL) and combined organics dried ($MgSO_4$) and the solvent evaporated. Chromatography on silica gel eluting with 0-100% EtOAc in isohexane gradient then 0-5% MeOH in EtOAc gradient gave the crude product (308 mg). Chiral SFC followed by purification of each isomer by preparative HPLC gave the title compound as the slow eluting isomer (52.4 mg, 11.6%) $^1$H NMR (400 MHz, $CDCl_3$) 8.77 (2H, s), 7.66 (1H, s), 7.57 (1H, dd), 7.38 (1H, s), 7.28 (2H, d), 7.12 (2H, d), 6.86 (1H, d), 4.83 (1H, d), 4.56 (1H, d), 4.45-4.38 (1H, m), 4.19-4.12 (1H, m), 3.71 (3H, s), 3.70-3.61 (1H, m), 2.26-1.84 (4H, m), 1.57-1.46 (3H, m), 1.38-1.24 (2H, m), 0.87 (3H, t). MS $[M+H]^+$=617.

Starting from the appropriate ketone intermediate (for example, the ketones shown in the Table 1), the following Examples in table 5 below were prepared by reaction with an appropriate nucleophile (for example, an alkyl organometallic reagent), using methods similar to those described in Examples 200 Step 5, 202 Step 2, 203, 336, 337 or other Examples cited in the table. Purification by preparative achiral and/or chiral HPLC gave final compounds as single isomer (unless stated otherwise). In the table below, an asterisk (*) indicates the compound was isolated as a single isomer at the position shown.

| Example | Name | Comment | NMR Data | MS Data |
|---|---|---|---|---|
| 462 | 2-{[(1R)-1-(4-chlorophenyl)-1-[(1-cyanocyclopropyl)methoxy]-7-fluoro-5-[1-hydroxy-1-(1-methyl-1H-imidazol-4-yl)propyl]-3-oxo-2,3-dihydro-1H-isoindol-2-yl]methyl} pyrimidine-5-carbonitrile | Prepared in a similar manner to 337 | $^1$H NMR (400 MHz, CDCl$_3$) 8.86 (2H, s), 7.73 (1H, s), 7.53-7.51 (1H, m), 7.36 (3H, d), 7.28-7.24 (2H, m), 6.84 (1H, s), 4.79 (1H, d), 4.60 (1H, d), 4.04 (1H, d), 3.70 (3H, s), 3.58 (1H, s), 2.74 (1H, d), 2.24-2.07 (2H, m), 1.34-1.21 (2H, m), 1.00-0.93 (m, 1H), 0.90-0.85 (4H, m). | [M + H]$^+$ = 612 |
| 463 | 2-{[(1R)-1-(4-chlorophenyl)-1-[(1-cyanocyclopropyl)methoxy]-7-fluoro-5-[1-hydroxy-1-(1-methyl-1H-imidazol-4-yl)propyl]-3-oxo-2,3-dihydro-1H-isoindol-2-yl]methyl} pyrimidine-5-carbonitrile | Prepared in a similar manner to 337 | $^1$H NMR (400 MHz, CDCl$_3$) 8.86 (2H, s), 7.65 (1H, s), 7.57 (1H, d), 7.39-7.36 (3H, m), 7.28 (2H, d), 6.89 (1H, s), 4.80 (1H, d), 4.57 (1H, d), 4.05 (1H, d), 3.70 (3H, s), 3.53 (1H, s), 2.70 (1H, d), 2.21-2.06 (2H, m), 1.35-1.20 (2H, m), 1.00-0.94 (1H, m), 0.88-0.83 (4H, m). | [M + H]$^+$ = 612 |
| 464 | (3R)-3-(4-chlorophenyl)-2-[(5-chloropyrimidin-2-yl)methyl]-4-fluoro-6-[1-hydroxy-1-(1-methyl-1H-imidazol-4-yl)propyl]-3-[cis-3-hydroxycyclobutoxy]-2,3-dihydro-1H-isoindol-1-one | Prepared in a similar manner to 337 | $^1$H NMR (400 MHz, CDCl$_3$) 8.49 (2H, s), 7.66 (1H, s), 7.36 (1H, s), 7.31 (2H, d), 7.16 (2H, d), 6.83 (1H, s), 4.65-4.53 (2H, m), 3.74 (1H, s), 3.69 (3H, s), 3.67-3.52 (2H, m), 2.36-2.05 (4H, m), 2.04-1.91 (2H, m), 1.90-1.69 (2H, m), 0.84 (3H, dd). | [M + H]$^+$ = 612 |
| 465 | (3R)-3-(4-chlorophenyl)-2-[(5-chloropyrimidin-2-yl)methyl]-4-fluoro-6-[1-hydroxy-1-(1-methyl-1H-imidazol-4-yl)propyl]-3-[cis-3-hydroxycyclobutyl]-2,3-dihydro-1H-isoindol-1-one | Prepared in a similar manner to 337 | $^1$H NMR (400 MHz, CDCl$_3$) 8.50 (2H, s), 7.73 (1H, s), 7.43 (2H, d), 7.36-7.32 (2H, m), 7.19 (2H, d), 6.83 (1H, s), 4.64 (1H, d), 4.54 (1H, d), 3.72 (1H, s), 3.69 (3H, s), 3.67-3.51 (2H, m), 2.27-1.86 (7H, m), 0.84 (3H, dd). | [M + H]$^+$ = 612 |

-continued

| Example | Structure | Name | Comment | NMR Data | MS Data |
|---|---|---|---|---|---|
| 466 | 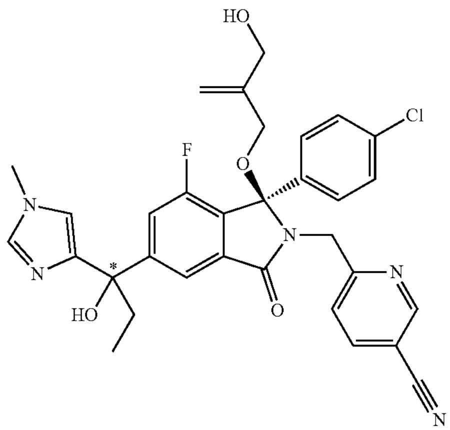 [SMILES: C=C(CO)CO[C@]1(c2ccc(Cl)cc2)c2c(F)cc(C(O)(CC)c3cn(C)cn3)cc2C(=O)N1Cc1ccc(C#N)cn1] | 6-{[(1R)-1-(4-chlorophenyl)-7-fluoro-5-[1-hydroxy-1-(1-methyl-1H-imidazol-4-yl)propyl]-1-(3-hydroxy-2-methyl-idenepropoxy)-3-oxo-2,3-dihydro-1H-isoindol-2-yl]methyl}pyridine-3-carbonitrile | Prepared in a similar manner to 337 | ¹H NMR (400 MHz, CDCl₃) 8.66 (1H, d), 7.77 (1H, dd), 7.72 (1H, d), 7.54-7.50 (1H, m), 7.37 (1H, s), 7.33 (1H, d), 7.24 (2H, d), 7.19 (2H, d), 6.86 (1H, d), 5.08 (1H, s), 4.91 (1H, s), 4.63 (1H, d), 4.49 (1H, d), 4.12 (2H, d), 3.75 (1H, d), 3.70 (3H, s), 3.63-3.54 (2H, m), 2.25-2.08 (2H, m), 0.87 (3H, dd). One exchangeable not observed | [M + H]⁺ = 602 |
| 467 | 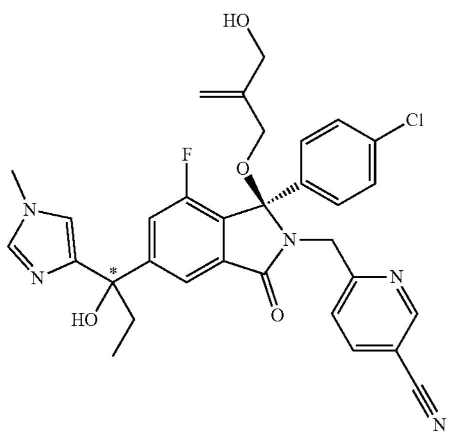 [SMILES: C=C(CO)CO[C@]1(c2ccc(Cl)cc2)c2c(F)cc(C(O)(CC)c3cn(C)cn3)cc2C(=O)N1Cc1ccc(C#N)cn1] | 6-{[(1R)-1-(4-chlorophenyl)-7-fluoro-5-[1-hydroxy-1-(1-methyl-1H-imidazol-4-yl)propyl]-1-(3-hydroxy-2-methyl-idenepropoxy)-3-oxo-2,3-dihydro-1H-isoindol-2-yl]methyl}pyridine-3-carbonitrile | Prepared in a similar manner to 337 | ¹H NMR (400 MHz, CDCl₃) 8.66 (1H, d), 7.77 (1H, dd), 7.72 (1H, d), 7.55-7.50 (1H, m), 7.38-7.33 (2H, m), 7.27-7.20 (4H, m), 6.86 (1H, d), 5.07 (1H, s), 4.92 (1H, s), 4.64 (1H, d), 4.46 (1H, d), 4.10 (2H, d), 3.74 (1H, d), 3.70 (3H, s), 3.62-3.56 (2H, m), 2.24-2.08 (2H, m), 0.86 (3H, dd). One exchangeable not observed | [M + H]⁺ = 602 |
| 468 | 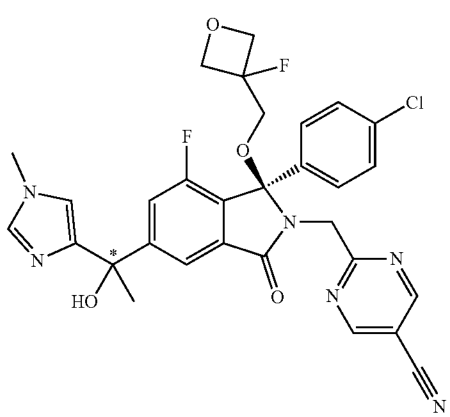 [SMILES: Cn1cnc(C(C)(O)c2cc(F)c3c(c2)C(=O)N(Cc2ncc(C#N)cn2)[C@@]3(OCC2(F)COC2)c2ccc(Cl)cc2)c1] | 2-{[(1R)-1-(4-chlorophenyl)-7-fluoro-1-[(3-fluorooxetan-3-yl)methoxy]-5-[1-hydroxy-1-(1-methyl-1H-imidazol-4-yl)ethyl]-3-oxo-2,3-dihydro-1H-isoindol-2-yl]methyl}pyrimidine-5-carbonitrile | Prepared in a similar manner to 202 step 2 | ¹H NMR (400 MHz, CDCl₃) 8.82 (2H, s), 7.75 (1H, d), 7.56-7.52 (1H, m), 7.40 (1H, s), 7.31 (2H, d), 7.23 (2H, d), 6.88 (1H, d), 4.81-4.54 (6H, m), 4.31 (1H, dd), 3.99 (1H, dd), 3.71 (3H, s), 3.55-3.43 (1H, m), 1.86 (3H, s), | [M + H]⁺ = 607 |

| Example | Structure | Name | Comment | NMR Data | MS Data |
|---|---|---|---|---|---|
| 469 | 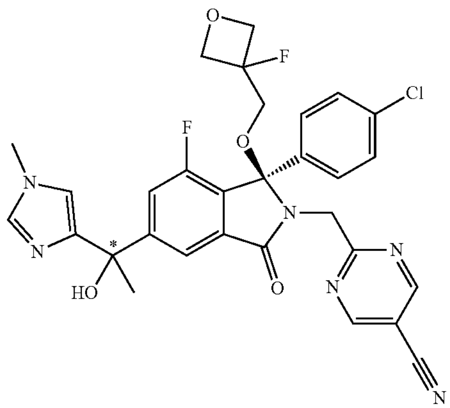 [SMILES: Cn1cnc(C(C)(O)c2cc(F)c3c(c2)C(=O)N(Cc2ncc(C#N)cn2)[C@@]3(OCC2(F)COC2)c2ccc(Cl)cc2)c1] | 2-{[(1R)-1-(4-chlorophenyl)-7-fluoro-1-[(3-fluorooxetan-3-yl)methoxy]-5-[1-hydroxy-1-(1-methyl-1H-imidazol-4-yl)ethyl]-3-oxo-2,3-dihydro-1H-isoindol-2-yl]methyl} pyrimidine-5-carbonitrile | Prepared in a similar manner to 202 step 2 | $^1$H NMR (400 MHz, CDCl$_3$) 8.82 (2H, s), 7.70 (1H, d), 7.56 (1H, d), 7.40 (1H, s), 7.32 (2H, d), 7.24-7.27 (2H, d, overlapping CHCl3), 6.90 (1H, d), 4.82-4.51 (6H, m), 4.29 (1H, dd,), 4.00 (1H, dd), 3.71 (3H, s), 3.53-3.43 (1H, m), 1.84 (3H, s). | [M + H]$^+$ = 607 |
| 470 | 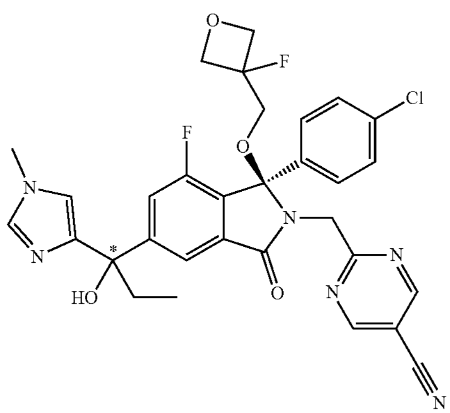 [SMILES: CCC(O)(c1cc(F)c2c(c1)C(=O)N(Cc1ncc(C#N)cn1)[C@@]2(OCC1(F)COC1)c1ccc(Cl)cc1)c1cn(C)cn1] | 2-{[(1R)-1-(4-chorophenyl)-7-fluoro-1-[(3-fluorooxetan-3-yl)methoxy]-5-[1-hydroxy-1-(1-methyl-1H-imidazol-4-yl)propyl]-3-oxo-2,3-dihydro-1H-isoindol-2-yl]methyl} pyrimidine-5-carbonitrile | Prepared in a similar manner to 337 | $^1$H NMR (400 MHz, CDCl$_3$) 8.82 (2H, s), 7.78 (1H, d), 7.57-7.51 (1H, m), 7.38 (1H, d), 7.30 (2H, d), 7.25-7.21 (2H, m), 6.87 (1H, d), 4.80-4.54 (6H, m), 4.30 (1H, dd), 4.04-3.95 (1H, m), 3.71 (3H, s), 3.46 (1H, dd), 2.26-2.09 (2H, m), 0.89 (3H, dd). | [M + H]$^+$ = 621 |
| 471 | 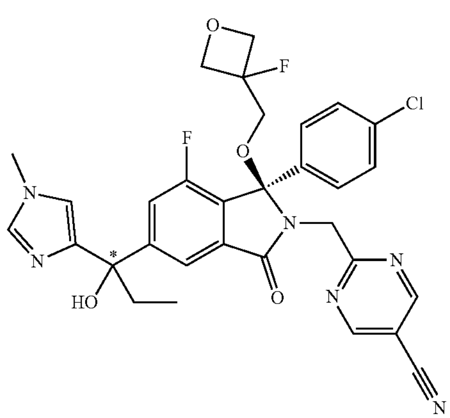 [SMILES: CCC(O)(c1cc(F)c2c(c1)C(=O)N(Cc1ncc(C#N)cn1)[C@@]2(OCC1(F)COC1)c1ccc(Cl)cc1)c1cn(C)cn1] | 2-{[(1R)-1-(4-chlorophenyl)-7-fluoro-1-[(3-fluorooxetan-3-yl)methoxy]-5-[1-hydroxy-1-(1-methyl-1H-imidazol-4-yl)propyl]-3-oxo-2,3-dihydro-1H-isoindol-2-yl]methyl} pyrimidine-5-carbonitrile | Prepared in a similar manner to 337 | $^1$H NMR (400 MHz, CDCl$_3$) 8.83 (2H, s), 7.73 (1H, d), 7.58 (1H, dd), 7.37 (1H, s), 7.32 (2H, d), 7.24 (2H, d), 6.88 (1H, d), 4.82-4.51 (6H, m), 4.29 (1H, dd), 3.97 (1H, dd), 3.70 (3H, s), 3.46 (1H, dd), 2.24-2.08 (2H, m), 0.87 (3H, dd). | [M + H]$^+$ = 621 |

| Example | Structure | Name | Comment | NMR Data | MS Data |
|---|---|---|---|---|---|
| 472 | 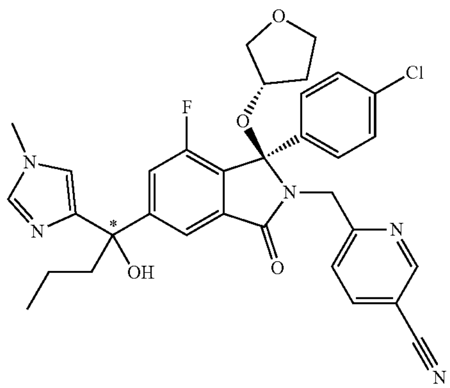 [SMILES: CCCC(O)(c1cc(F)c2c(c1)C(=O)N(Cc1ccc(C#N)cn1)[C@@]2(O[C@H]1CCOC1)c1ccc(Cl)cc1)c1cn(C)cn1] | 6-{[(1R)-1-(4-chlorophenyl)-7-fluoro-5-[1-hydroxy-1-(1-methyl-1H-imidazol-4-yl)butyl]-3-oxo-1-[(3S)-oxolan-3-yloxy]-2,3-dihydro-1H-isoindol-2-yl]methyl}pyridine-3-carbonitrile | Prepared in a similar manner to 202 step 2 using n-PrMgCl | $^1$H NMR (400 MHz, CDCl$_3$) 8.64 (1H, d), 7.77-7.72 (2H, m), 7.56 (1H, d), 7.37 (1H, s), 7.29 (1H, d), 7.19 (2H, d), 7.13 (2H, d), 6.86 (1H, s), 4.65 (1H, d), 4.54 (1H, d), 4.03-3.97 (1H, m), 3.86 (1H, q), 3.70 (3H, s), 3.70-3.61 (2H, m), 3.55 (1H, s), 3.31 (1H, dd), 2.18-2.02 (2H, m), 1.74-1.65 (2H, m), 1.48-1.38 (1H, m), 1.18-1.08 (1H, m), 0.90 (3H, t). | [M + H]$^+$ = 616 |
| 473 | 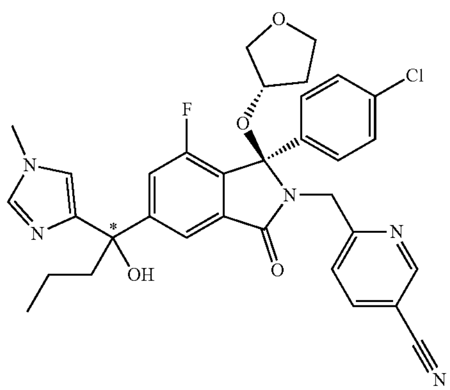 [SMILES: CCCC(O)(c1cc(F)c2c(c1)C(=O)N(Cc1ccc(C#N)cn1)[C@@]2(O[C@H]1CCOC1)c1ccc(Cl)cc1)c1cn(C)cn1] | 6-{[(1R)-1-(4-chlorophenyl)-7-fluoro-5-[1-hydroxy-1-(1-methyl-1H-imidazol-4-yl)butyl]-3-oxo-1-[(3S)-oxolan-3-yloxy]-2,3-dihydro-1H-isoindol-2-yl]methyl}pyridine-3-carbonitrile | Prepared in a similar manner to 202 step 2 using n-PrMgCl | $^1$H NMR (400 MHz, CDCl$_3$) 8.64 (1H, d), 7.82 (1H, s), 7.76 (1H, dd), 7.48 (1H, d), 7.36 (1H, s), 7.32 (1H, d), 7.20 (2H, d), 7.14 (2H, d), 6.83 (1H, s), 4.65 (1H, d), 4.55 (1H, d), 4.03-3.97 (1H, m), 3.86 (1H, q), 3.70-3.63 (5H, m), 3.56 (1H, s), 3.33 (1H, dd), 2.18-2.00 (2H, m), 1.71-1.63 (2H, m), 1.46-1.36 (1H, m), 1.26-1.11 (1H, m), 0.90 (3H, dd). | [M + H]$^+$ = 616 |
| 474 | 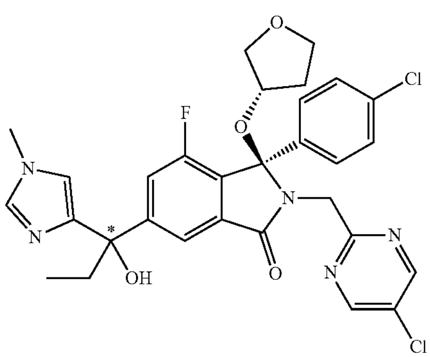 [SMILES: CCC(O)(c1cc(F)c2c(c1)C(=O)N(Cc1ncc(Cl)cn1)[C@@]2(O[C@H]1CCOC1)c1ccc(Cl)cc1)c1cn(C)cn1] | (3R)-3-(4-chlorophenyl)-2-[(5-chloropyrimidin-2-yl)methyl]-4-fluoro-6-[1-hydroxy-1-(1-methyl-1H-imidazol-4-yl)propyl]-3-[(3S)-oxolan-3-yloxy]-2,3-dihydro-1H-isoindol-1-one | Prepared in a similar manner to 337 | $^1$H NMR (400 MHz, CDCl$_3$) 8.50 (2H, s), 7.78 (1H, s), 7.50-7.46 (1H, m), 7.36 (1H, s), 7.32 (2H, d), 7.17 (2H, d), 6.83 (1H, s), 4.69 (1H, d), 4.57 (1H, d), 4.20 (1H, ddd), 3.87 (1H, q), 3.73-3.65 (5H, m), 3.57 (1H, s), 3.36 (1H, dd), 2.24-2.08 (2H, m), 1.85-1.67 (2H, m), 0.85 (3H, t). | [M + H]$^+$ = 612 |
| 475 | 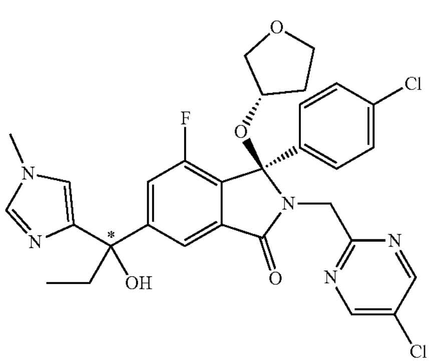 [SMILES: CCC(O)(c1cc(F)c2c(c1)C(=O)N(Cc1ncc(Cl)cn1)[C@@]2(O[C@H]1CCOC1)c1ccc(Cl)cc1)c1cn(C)cn1] | (3R)-3-(4-chlorophenyl)-2-[(5-chloropyrimidin-2-yl)methyl]-4-fluoro-6-[1-hydroxy-1-(1-methyl-1H-imidazol-4-yl)propyl]-3-[(3S)-oxolan-3-yloxy]-2,3-dihydro-1H-isoindol-1-one | Prepared in a similar manner to 337 | $^1$H NMR (400 MHz, CDCl$_3$) 8.49 (2H, s), 7.68 (1H, s), 7.57 (1H, d), 7.37 (1H, s), 7.30 (2H, d), 7.14 (2H, d), 6.85 (1H, d), 4.71 (1H, d), 4.55 (1H, d), 4.21 (1H, ddd), 3.88 (1H, q), 3.74-3.65 (5H, m), 3.56 (1H, s), 3.34 (1H, dd), 2.24-2.02 (2H, m), 1.86-1.71 (2H, m), 0.85 (3H, t). | [M + H]$^+$ = 612 |

| Example | Structure | Name | Comment | NMR Data | MS Data |
|---|---|---|---|---|---|
| 476 | 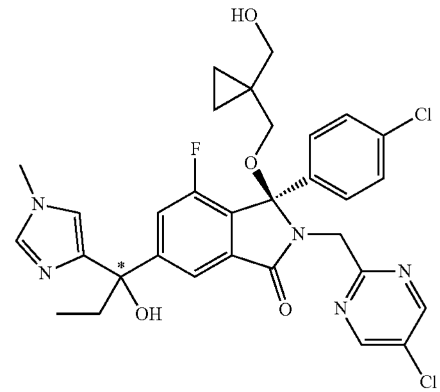 [SMILES: CCC(O)(c1cc(F)c2c(c1)C(=O)N(Cc1ncc(Cl)cn1)[C@@]2(OCC1(CO)CC1)c1ccc(Cl)cc1)c1cn(C)cn1] | (3R)-3-(4-chlorophenyl)-2-[(5-chloropyrimidin-2-yl)methyl]-4-fluoro-6-[1-hydroxy-1-(1-methyl-1H-imidazol-4-yl)propyl]-3-{[1-(hydroxymethyl)cyclopropyl]methoxy}-2,3-dihydro-1H-isoindol-1-one | Prepared in a similar manner to 337 | ¹H NMR (400 MHz, CDCl₃) 8.52 (2H, s), 7.66 (1H, s), 7.53 (1H, dd), 7.36-7.32 (3H, m), 7.21 (2H, d), 6.84 (1H, s), 4.58 (2H, d), 3.69 (3H, s), 3.63-3.53 (3H, m), 3.41 (1H, d), 2.96 (1H, d), 2.23-2.05 (3H, m), 0.85 (3H, t), 0.52-0.42 (3H, m), 0.32-0.29 (1H, m). | [M + H]⁺ = 626 |
| 477 | 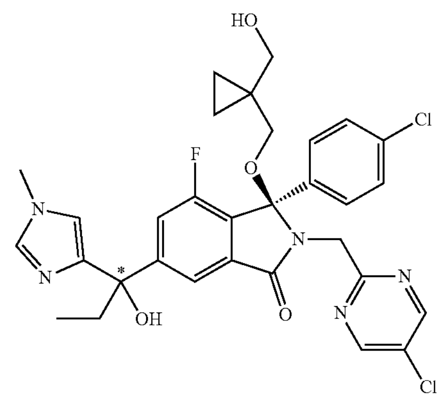 [SMILES: CCC(O)(c1cc(F)c2c(c1)C(=O)N(Cc1ncc(Cl)cn1)[C@@]2(OCC1(CO)CC1)c1ccc(Cl)cc1)c1cn(C)cn1] | (3R)-3-(4-chlorophenyl)-2-[(5-chloropyrimidin-2-yl)methyl]-4-fluoro-6-[1-hydroxy-1-(1-methyl-1H-imidazol-4-yl)propyl]-3-{[1-(hydroxymethyl)cyclopropyl]methoxy}-2,3-dihydro-1H-isoindol-1-one | Prepared in a similar manner to 337 | ¹H NMR (400 MHz, CDCl₃) 8.51 (2H, s), 7.67 (1H, s), 7.53 (1H, dd), 7.36 (1H, s), 7.32 (2H, d), 7.18 (2H, d), 6.82 (1H, d), 4.66-4.52 (2H, m), 3.69 (3H, s), 3.63-3.44 (4H, m), 2.99 (1H, d), 2.25-2.07 (3H, m), 0.86 (3H, t), 0.52-0.41 (3H, m), 0.33-0.30 (1H, m). | [M + H]⁺ = 626 |
| 478 | 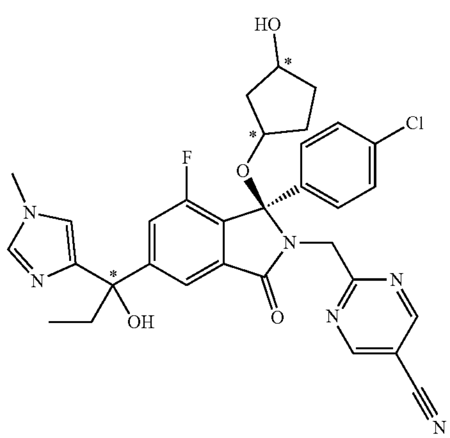 [SMILES: CCC(O)(c1cc(F)c2c(c1)C(=O)N(Cc1ncc(C#N)cn1)[C@@]2(OC1CCC(O)C1)c1ccc(Cl)cc1)c1cn(C)cn1] | 2-{[(1R)-1-(4-chlorophenyl)-7-fluoro-5-[1-hydroxy-1-(1-methyl-1H-imidazol-4-yl)propyl]-1-[(trans-3-hydroxycyclopentyl)oxy]-3-oxo-2,3-dihydro-1H-isoindol-2-yl]methyl}pyrimidine-5-carbonitrile | Prepared in a similar manner to Example 461 using step 1 slow isomer, step 3 slow isomer, step 4 fast isomer | ¹H NMR (400 MHz, CDCl₃) 8.78 (2H, s), 7.74 (1H, s), 7.53-7.49 (1H, m), 7.37 (1H, s), 7.30 (2H, d), 7.14 (2H, d), 6.84 (1H, d), 4.79 (1H, d), 4.57 (1H, d), 4.38 (1H, d), 4.23-4.16 (1H, m), 3.70 (3H, s), 3.59 (1H, s), 2.23-2.00 (3H, m), 1.83-1.75 (1H, m), 1.65-1.60 (2H, m), 1.54-1.40 (2H, m), 1.25 (1H, br s), 0.86 (3H, t). | [M + H]⁺ = 617 |

| Example | Structure | Name | Comment | NMR Data | MS Data |
|---|---|---|---|---|---|
| 479 | 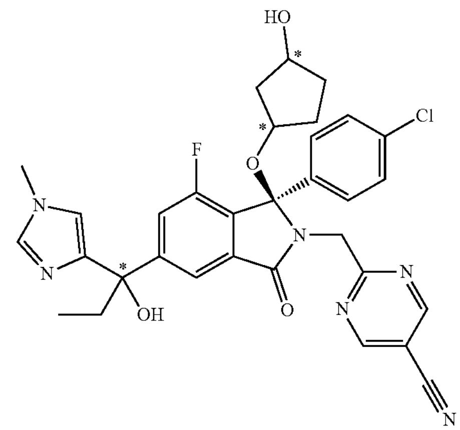 [SMILES: CCC(O)(c1cc(F)c2c(c1)C(=O)N(Cc1ncc(C#N)cn1)[C@@]2(OC1CCC(O)C1)c1ccc(Cl)cc1)c1cn(C)cn1] | 2-{[(1R)-1-(4-chlorophenyl)-7-fluoro-5-[1-hydroxy-1-(1-methyl-1H-imidazol-4-yl)propyl]-1-[(trans-3-hydroxycyclopentyl)oxy]-3-oxo-2,3-dihydro-1H-isoindol-2-yl]methyl} pyrimidine-5-carbonitrile | Prepared in a similar manner to Example 461 using step 1 slow isomer, step 3 slow isomer, step 4 slow isomer | $^1$H NMR (400 MHz, CDCl$_3$) 8.77 (2H, s), 7.64 (1H, s), 7.60 (1H, d), 7.37 (1H, s), 7.29 (2H, d), 7.12 (2H, d), 6.86 (1H, d), 4.82 (1H, d), 4.55 (1H, d), 4.42 (1H, d), 4.24-4.17 (1H, m), 3.71 (3H, s), 3.60 (1H, s), 2.26-2.00 (3H, m), 1.85-1.77 (1H, m), 1.67-1.47 (4H, m), 1.32-1.20 (1H, m), 0.86 (3H, t). | [M + H]$^+$ = 617 |
| 480 | 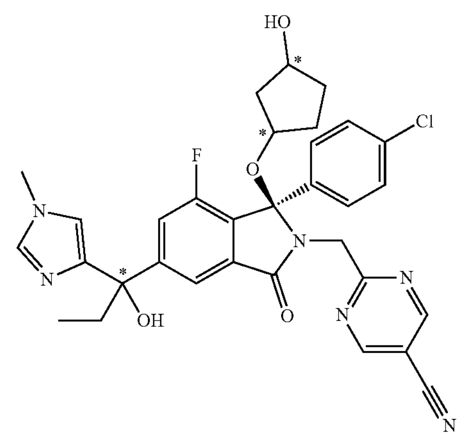 [SMILES: CCC(O)(c1cc(F)c2c(c1)C(=O)N(Cc1ncc(C#N)cn1)[C@@]2(OC1CCC(O)C1)c1ccc(Cl)cc1)c1cn(C)cn1] | 2-{[(1R)-1-(4-chlorophenyl)-7-fluoro-5-[1-hydroxy-1-(1-methyl-1H-imidazol-4-yl)propyl]-1-[(trans-3-hydroxycyclopentyl)oxy]-3-oxo-2,3-dihydro-1H-isoindol-2-yl]methyl} pyrimidine-5-carbonitrile | Prepared in a similar manner to Example 461 using step 1 fast isomer, step 3 fast isomer, step 4 fast isomer | $^1$H NMR (400 MHz, CDCl$_3$) 8.77 (2H, s), 7.66 (1H, s), 7.57 (1H, d), 7.38 (1H, s), 7.28 (2H, d), 7.12 (2H, d), 6.86 (1H, d), 4.83 (1H, d), 4.56 (1H, d), 4.45-4.38 (1H, m), 4.19-4.12 (1H, m), 3.71 (3H, s), 3.70-3.61 (1H, m), 2.26-1.84 (4H, m), 1.56-1.33 (5H, m), 0.87 (3H, t). | [M + H]$^+$ = 617 |
| 481 | 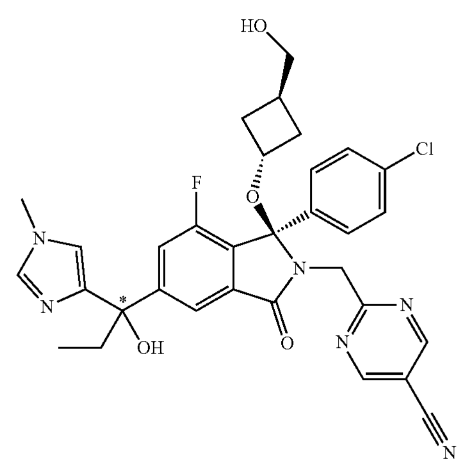 [SMILES: CCC(O)(c1cc(F)c2c(c1)C(=O)N(Cc1ncc(C#N)cn1)[C@@]2(O[C@H]1C[C@H](CO)C1)c1ccc(Cl)cc1)c1cn(C)cn1] | 2-{[(1R)-1-(4-chlorophenyl)-7-fluoro-5-[1-hydroxy-1-(1-methyl-1H-imidazol-4-yl)propyl]-3-oxo-1-[trans-3-(hydroxymethyl)cyclobutoxy]-2,3-dihydro-1H-isoindol-2-yl]methyl} pyrimidine-5-carbonitrile | Prepared in a similar manner to 337 | $^1$H NMR (400 MHz, CDCl$_3$) 8.79 (2H, s), 7.65 (1H, d), 7.51 (1H, dd), 7.38 (1H, s), 7.33 (2H, d), 7.17 (2H, d), 6.85 (1H, d), 4.66 (2H, s), 4.17-4.08 (1H, m), 3.71 (3H, s), 3.59 (1H, s), 3.47-3.41 (2H, m), 2.31-2.09 (6H, m), 1.81-1.72 (1H, m), 1.42-1.32 (2H, m), 0.85 (3H, t), one exchangeable proton not observed. | [M + H]$^+$ = 617. |

| Example | Structure | Name | Comment | NMR Data | MS Data |
|---|---|---|---|---|---|
| 482 | 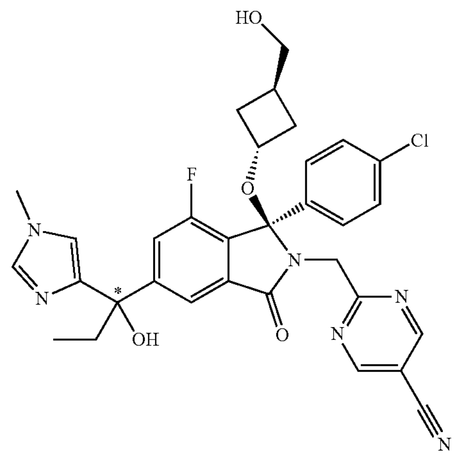 [SMILES: CCC(O)(c1cc(F)c2c(c1)C(=O)N(Cc1ncc(C#N)cn1)[C@@]2(O[C@H]1C[C@H](CO)C1)c1ccc(Cl)cc1)c1cn(C)cn1] | 2-{[(1R)-1-(4-chlorophenyl)-7-fluoro-5-[1-hydroxy-1-(1-methyl-1H-imidazol-4-yl)propyl]-3-oxo-1-[trans-3-(hydroxymethyl)cyclobutoxy]-2,3-dihydro-1H-isoindol-2-yl]methyl}pyrimidine-5-carbonitrile | Prepared in a similar manner to 337 | $^1$H NMR (400 MHz, CDCl3) 8.80 (2H, s), 7.75 (1H, d), 7.45 (1H, dd), 7.35 (3H, d), 7.19 (2H, d), 6.82 (1H, d), 4.65 (2H, d), 4.15-4.07 (1H, m), 3.69 (3H, s), 3.53 (1H, s), 3.43 (2H, dd), 2.29-2.08 (6H, m), 1.78-1.70 (1H, m), 1.29-1.25 (1H, m), 0.86 (3H) | [M + H]$^+$ = 617. |
| 483 | 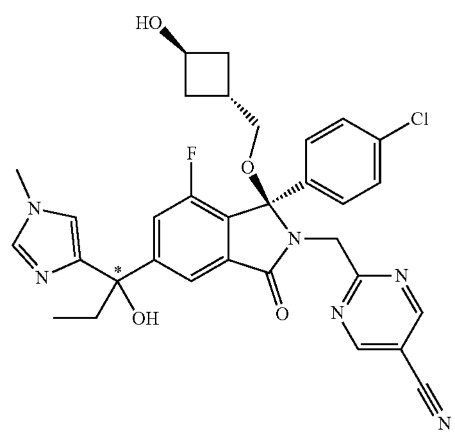 [SMILES: CCC(O)(c1cc(F)c2c(c1)C(=O)N(Cc1ncc(C#N)cn1)[C@@]2(OC[C@H]1C[C@H](O)C1)c1ccc(Cl)cc1)c1cn(C)cn1] | 2-{[(1R)-1-(4-chlorophenyl)-7-fluoro-5-[1-hydroxy-1-(1-methyl-1H-imidazol-4-yl)propyl]-3-oxo-1-{[trans-3-hydroxycyclobutyl]methoxy}-2,3-dihydro-1H-isoindol-2-yl]methyl}pyrimidine-5-carbonitrile | Prepared in a similar manner to 337 | $^1$H NMR (400 MHz, CDCl$_3$) 8.79 (2H, s), 7.71 (1H, d), 7.57-7.52 (1H, m), 7.38 (1H, s), 7.32 (2H, d), 7.17 (2H, d), 6.85 (1H, d), 4.73 (1H, d), 4.63 (1H, d), 4.40-4.32 (1H, m), 3.70 (3H, s), 3.58 (1H, s), 3.46 (1H, dd), 3.04 (1H, dd), 2.39-2.32 (1H, m), 2.25-2.01 (6H, m), 1.31-1.25 (1H, m), 0.88 (3H, t). | [M + H]$^+$ = 617. |
| 484 | 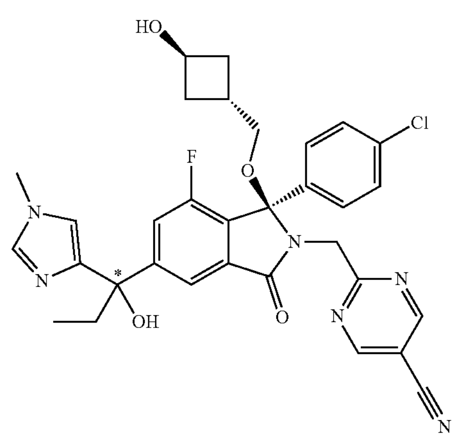 [SMILES: CCC(O)(c1cc(F)c2c(c1)C(=O)N(Cc1ncc(C#N)cn1)[C@@]2(OC[C@H]1C[C@H](O)C1)c1ccc(Cl)cc1)c1cn(C)cn1] | 2-{[(1R)-1-(4-chlorophenyl)-7-fluoro-5-[1-hydroxy-1-(1-methyl-1H-imidazol-4-yl)propyl]-3-oxo-1-{[trans-3-hydroxycyclobutyl]methoxy}-2,3-dihydro-1H-isoindol-2-yl]methyl}pyrimidine-5-carbonitrile | Prepared in a similar manner to 337 | $^1$H NMR (400 MHz, CDCl3) 8.80 (2H, s), 7.68 (1H, d), 7.58-7.51 (1H, m), 7.38-7.32 (3H, m), 7.19 (2H, d), 6.87 (1H, d), 4.67 (2H, d), 4.35 (1H, dd), 3.70 (3H, s), 3.54 (1H, s), 3.44 (1H, dd), 3.04 (1H, dd), 2.34-2.28 (1H, m), 2.23-1.99 (6H, m), 1.66 (1H, d), 0.86 (3H, dd) | [M + H]$^+$ = 617. |

-continued

| Example | Structure | Name | Comment | NMR Data | MS Data |
|---|---|---|---|---|---|
| 485 | 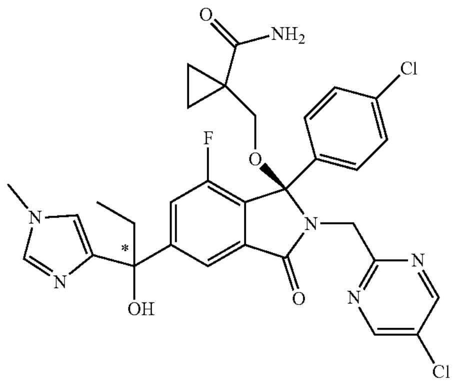 [SMILES: CCC(O)(c1cc(F)c2c(c1)C(=O)N(Cc1ncc(Cl)cn1)[C@@]2(OCC1(C(N)=O)CC1)c1ccc(Cl)cc1)c1cn(C)cn1] | 1-({[(1R)-1-(4-chlorophenyl)-2-[(5-chloropyrimidin-2-yl)methyl]-7-fluoro-5-[1-hydroxy-1-(1-methyl-1H-imidazol-4-yl)propyl]-3-oxo-2,3-dihydro-1H-isoindol-1-yl]oxy}methyl)cyclopropane-1-carboxamide | Prepared in a similar manner to Example 200, using EtMgCl | $^1$H NMR (400 MHz, DMSO-$d_6$): 8.71 (2H, s), 7.86 (1H, d), 7.57 (1H, d), 7.51 (1H, s), 7.30 (2H, d), 7.25 (2H, d), 7.01 (1H, d), 6.96 (1H, s), 6.80 (1H, s), 5.56 (1H, s), 4.63 (1H, d), 4.50 (1H, d), 3.66 (1H, d), 3.61 (3H, s), 3.07 (1H, d), 2.21-2.02 (2H, m), 1.03-0.86 (2H, m), 0.71 (3H, t), 0.61-0.47 (2H, m) | [M + H]$^+$ = 639. |
| 486 | 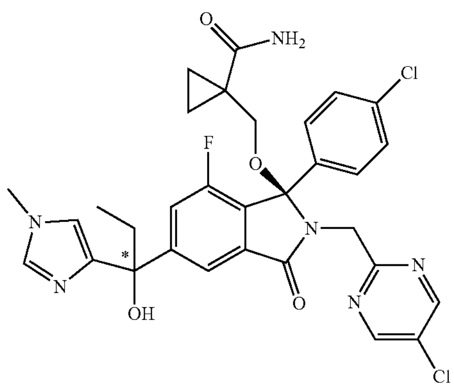 [SMILES: CCC(O)(c1cc(F)c2c(c1)C(=O)N(Cc1ncc(Cl)cn1)[C@@]2(OCC1(C(N)=O)CC1)c1ccc(Cl)cc1)c1cn(C)cn1] | 1-({[(1R)-1-(4-chlorophenyl)-2-[(5-chloropyrimidin-2-yl)methyl]-7-fluoro-5-[1-hydroxy-1-(1-methyl-1H-imidazol-4-yl)propyl]-3-oxo-2,3-dihydro-1H-isoindol-1-yl]oxy}methyl)cyclopropane-1-carboxamide | Prepared in a similar manner to Example 200, using EtMgCl | $^1$H NMR (400 MHz, DMSO-$d_6$): 8.70 (2H, s), 7.84 (1H, s), 7.59 (1H, d), 7.52 (1H, s), 7.29 (2H, d), 7.24 (2H, d), 7.01 (1H, d), 6.96 (1H, s), 6.81 (1H, s), 5.56 (1H, s), 4.66 (1H, d), 4.49 (1H, d), 3.65 (1H, d), 3.61 (3H, s), 3.06 (1H, d), 2.22-2.01 (2H, m), 1.04-0.86 (2H, m), 0.72 (3H, t), 0.55 (2H, t) | [M + H]$^+$ = 639. |
| 487 | 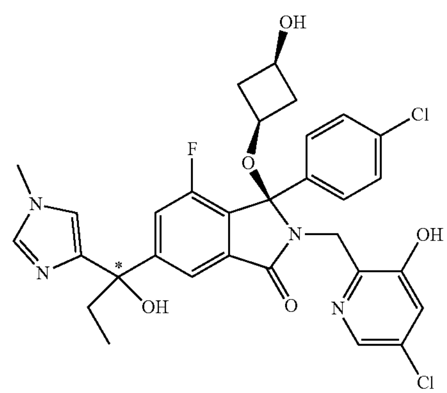 [SMILES: CCC(O)(c1cc(F)c2c(c1)C(=O)N(Cc1ncc(Cl)cc1O)[C@@]2(O[C@H]1C[C@@H](O)C1)c1ccc(Cl)cc1)c1cn(C)cn1] | (3R)-2-[(5-chloro-3-hydroxypyridin-2-yl)methyl]-3-(4-chlorophenyl)-4-fluoro-6-[1-hydroxy-1-(1-methyl-1H-imidazol-4-yl)propyl]-3-[cis-3-hydroxycyclobutoxy]-2,3-dihydro-1H-isoindol-1-one | Prepared in a similar manner to 203, but using AlEt$_3$ | $^1$H NMR (400 MHz, DMSO) 7.83 (1H, d), 7.77 (1H, s), 7.54-7.47 (2H, m), 7.33-7.26 (4H, m), 7.00 (2H, dd), 5.54 (1H, s), 4.98-4.90 (1H, bs), 4.44 (1H, d), 4.21 (1H, d), 3.62 (3H, s), 3.50-3.42 (2H, m), 2.16-2.06 (2H, m), 1.99-1.91 (1H, m), 1.76-1.65 (2H, m), 1.60-1.53 (1H, m), 0.70 (3H, dd) | [M + H]$^+$ = 627. |
| 488 | 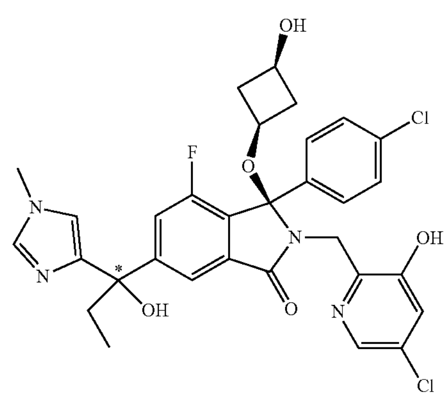 [SMILES: CCC(O)(c1cc(F)c2c(c1)C(=O)N(Cc1ncc(Cl)cc1O)[C@@]2(O[C@H]1C[C@@H](O)C1)c1ccc(Cl)cc1)c1cn(C)cn1] | (3R)-2-[(5-chloro-3-hydroxypyridin-2-yl)methyl]-3-(4-chlorophenyl)-4-fluoro-6-[1-hydroxy-1-(1-methyl-1H-imidazol-4-yl)propyl]-3-[cis-3-hydroxycyclobutoxy]-2,3-dihydro-1H-isoindol-1-one | Prepared in a similar manner to 203, but using AlEt$_3$ | $^1$H NMR (400 MHz, DMSO) 7.83 (1H, s), 7.82 (1H, s), 7.53-7.50 (2H, m), 7.34-7.31 (4H, d), 7.00 (2H, s), 5.56 (1H, s), 4.95-4.94 (1H, m), 4.46 (1H, d), 4.18 (1H, d), 3.61 (3H, s), 3.51-3.39 (2H, m), 2.14-2.05 (2H, m), 1.94-1.85 (1H, m), 1.75-1.65 (2H, m), 1.61-1.52 (1H, m), 0.70 (3H, dd) | [M + H]$^+$ = 627. |

-continued

| Example | Structure | Name | Comment | NMR Data | MS Data |
|---|---|---|---|---|---|
| 489 | 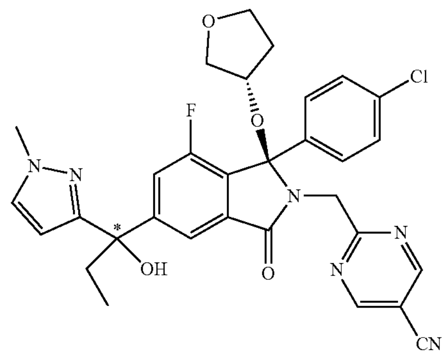 [SMILES: CCC(O)(c1cc(F)c2c(c1)C(=O)N(Cc1ncc(C#N)cn1)[C@@]2(O[C@H]1CCOC1)c1ccc(Cl)cc1)c1ccn(C)n1] | 2-{[(1R)-1-(4-chlorophenyl)-7-fluoro-5-[1-hydroxy-1-(1-methyl-1H-pyrazol-3-yl)propyl]-3-oxo-1-[(3S)-oxolan-3-yloxy]-2,3-dihydro-1H-isoindol-2-yl]methyl}pyrimidine-5-carbonitrile | Prepared in a similar manner to 203, but using AlEt$_3$ | 1H NMR (400 MHz, DMSO-d6): 9.13 (2H, s), 7.78 (1H, d), 7.57 (1H, d), 7.51 (1H, dd), 7.30 (4H, s), 6.20 (1H, d), 5.76 (1H, s), 4.70 (1H, d), 4.58 (1H, d), 4.21-4.14 (1H, m), 3.81 (3H, s), 3.76 (1H, q), 3.63-3.55 (1H, m), 3.45 (1H, dd), 3.18 (1H, dd), 2.26-2.11 (2H, m), 1.92-1.80 (1H, m), 1.70-1.60 (1H, m), 0.72 (3H, t) | [M + H]$^+$ = 601. |
| 490 | 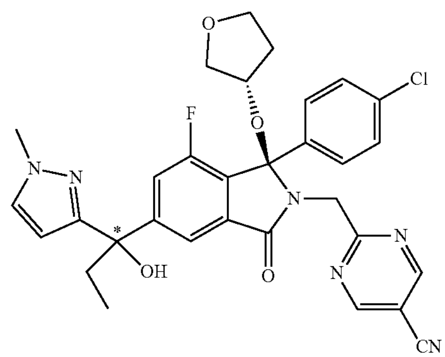 [SMILES: CCC(O)(c1cc(F)c2c(c1)C(=O)N(Cc1ncc(C#N)cn1)[C@@]2(O[C@H]1CCOC1)c1ccc(Cl)cc1)c1ccn(C)n1] | 2-{[(1R)-1-(4-chlorophenyl)-7-fluoro-5-[1-hydroxy-1-(1-methyl-1H-pyrazol-3-yl)propyl]-3-oxo-1-[(3S)-oxolan-3-yloxy]-2,3-dihydro-1H-isoindol-2-yl]methyl}pyrimidine-5-carbonitrile | Prepared in a similar manner to 203, but using AlEt$_3$ | 1H NMR (400 MHz, DMSO-d6): 9.15-8.96 (2H, m), 7.72 (1H, d), 7.58 (1H, d), 7.57-7.50 (1H, m), 7.29 (4H, s), 6.20 (1H, d), 5.75 (1H, s), 4.73 (1H, d), 4.60-4.52 (1H, m), 4.20-4.14 (1H, m), 3.83 (3H, s), 3.79-3.73 (1H, m), 3.63-3.55 (1H, m), 3.46-3.41 (1H, m), 3.21-3.14 (1H, m), 2.25-2.12 (2H, m), 1.93-1.82 (1H, m), 1.72-1.62 (1H, m), 0.72 (3H, t). | [M + H]$^+$ = 601. |
| 491 | 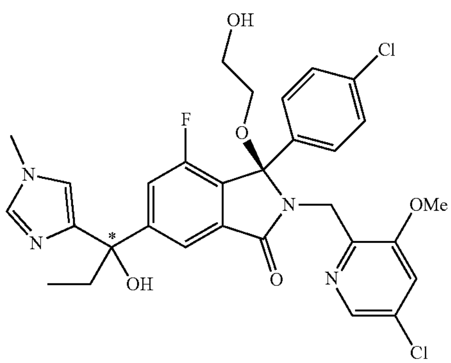 [SMILES: CCC(O)(c1cc(F)c2c(c1)C(=O)N(Cc1ncc(Cl)cc1OC)[C@@]2(OCCO)c1ccc(Cl)cc1)c1cn(C)cn1] | (3R)-2-[(5-chloro-3-methoxypyridin-2-yl)methyl]-3-(4-chlorophenyl)-4-fluoro-6-[1-hydroxy-1-(1-methyl-1H-imidazol-4-yl)propyl]-3-(2-hydroxyethoxy)-2,3-dihydro-1H-isoindol-1-one | Prepared by treatment of Example 443 with K$_2$CO$_3$/MeI | 1H NMR (400 MHz, CDCl3): 7.99 (1H, d), 7.65 (1H, s), 7.52-7.44 (1H, m), 7.35 (1H, s), 7.19 (2H, d), 7.13 (2H, d), 6.92-6.79 (2H, m), 4.65-4.52 (2H, m), 3.90-3.79 (1H, m), 3.71 (3H, s), 3.69 (3H, s), 3.68-3.59 (1H, m), 3.59-3.50 (3H, m), 3.29-3.20 (1H, m), 2.24-2.03 (2H, m), 0.85 (3H, t) | [M − H$^+$]$^-$ = 613 |
| 492 | 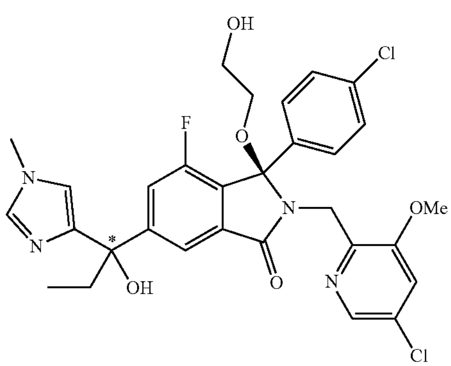 [SMILES: CCC(O)(c1cc(F)c2c(c1)C(=O)N(Cc1ncc(Cl)cc1OC)[C@@]2(OCCO)c1ccc(Cl)cc1)c1cn(C)cn1] | (3R)-2-[(5-chloro-3-methoxypyridin-2-yl)methyl]-3-(4-chlorophenyl)-4-fluoro-6-[1-hydroxy-1-(1-methyl-1H-imidazol-4-yl)propyl]-3-(2-hydroxyethoxy)-2,3-dihydro-1H-isoindol-1-one | Prepared by treatment of Example 444 with K$_2$CO$_3$/MeI | 1H NMR (400 MHz, DMSO-d6): 7.94 (1H, d), 7.84 (1H, d), 7.51 (2H, d), 7.41 (1H, d), 7.29 (4H, s), 7.01 (1H, d), 5.54 (1H, s), 4.61 (1H, s), 4.51 (1H, d), 4.32 (1H, d), 3.76 (3H, s), 3.60 (3H, s), 3.27-3.18 (2H, m), 2.94-2.86 (1H, m), 2.20-2.02 (2H, m), 0.71 (3H, t). | [M − OCH$_2$CH$_2$OH]$^+$ = 553 |

Starting from the appropriate acid (Preparation 23 or Preparation 36, Step 1), plus the appropriate amine and alcohol, the compounds in the following table 6 below were prepared using methods similar to those described in Example 200 (Step 3 and 4) and/or Example 203 (using AlMe$_3$).

Preparative chiral HPLC chromatography was used to separate both chiral intermediates and final products. In the table below an asterisk (*) indicates the compound was isolated as a single isomer at the position shown.

| Example | Structure | Name | Comment | NMR Data | MS Data |
|---|---|---|---|---|---|
| 493 | 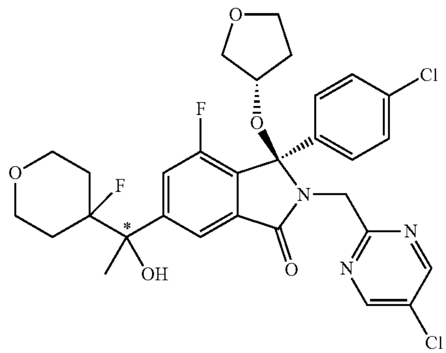 [SMILES: CC(O)(c1cc(F)c2c(c1)C(=O)N(Cc1ncc(Cl)cn1)[C@@]2(O[C@H]1CCOC1)c1ccc(Cl)cc1)C1(F)CCOCC1] | (3R)-3-(4-chlorophenyl)-2-[(5-chloropyrimidin-2-yl)methyl]-4-fluoro-6-[1-(4-fluorooxan-4-yl)-1-hydroxyethyl]-3-[(3S)-oxolan-3-yloxy]-2,3-dihydro-1H-isoindol-1-one | Prepared in a similar manner to Example 200 (Steps 3 and 4) and 203. | ¹H NMR (400 MHz, CDCl₃) 8.53 (2H, s), 7.83 (1H, s), 7.46 (1H, d), 7.35 (2H, d), 7.20 (2H, d), 4.73 (1H, d), 4.59 (1H, d), 4.25-4.19 (1H, m), 3.93-3.81 (3H, m), 3.75-3.58 (4H, m), 3.36 (1H, dd), 2.34-2.31 (1H, m), 1.96-1.60 (8H, m), 1.52-1.43 (1H, m). | [M − H]⁻ = 618 |
| 494 | 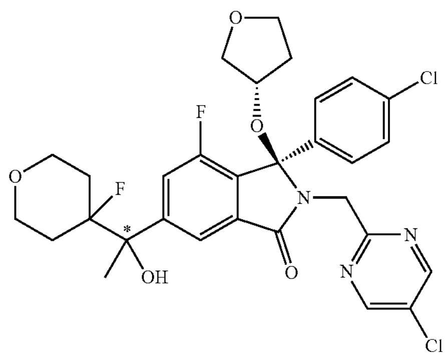 [SMILES: CC(O)(c1cc(F)c2c(c1)C(=O)N(Cc1ncc(Cl)cn1)[C@@]2(O[C@H]1CCOC1)c1ccc(Cl)cc1)C1(F)CCOCC1] | (3R)-3-(4-chlorophenyl)-2-[(5-chloropyrimidin-2-yl)methyl]-4-fluoro-6-[1-(4-fluorooxan-4-yl)-1-hydroxyethyl]-3-[(3S)-oxolan-3-yloxy]-2,3-dihydro-1H-isoindol-1-one | Prepared in a similar manner to Example 200 (Steps 3 and 4) and 203. | ¹H NMR (400 MHz, CDCl₃) 8.53 (2H, s), 7.86 (1H, s), 7.43 (1H, d), 7.33 (2H, d), 7.19 (2H, d), 4.73-4.58 (2H, m), 4.28-4.23 (1H, m), 3.93-3.81 (3H, m), 3.75-3.57 (4H, m), 3.35 (1H, dd), 2.29 (1H, d), 1.71-1.68 (8H, m), 1.48-1.45 (1H, m). | [M − H]⁻ = 618 |
| 495 | 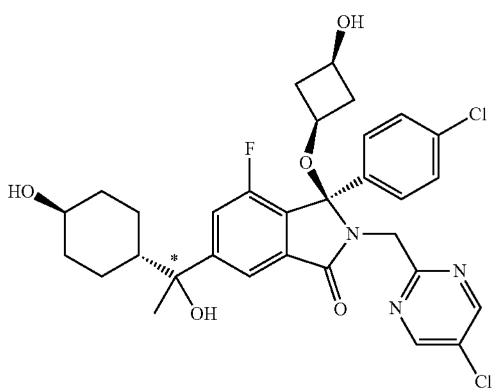 [SMILES: CC(O)(c1cc(F)c2c(c1)C(=O)N(Cc1ncc(Cl)cn1)[C@@]2(O[C@H]1C[C@@H](O)C1)c1ccc(Cl)cc1)[C@H]1CC[C@H](O)CC1] | (3R)-3-(4-chlorophenyl)-2-[(5-chloropyrimidin-2-yl)methyl]-4-fluoro-6-{1-hydroxy-1-[trans-4-hydroxycyclohexyl]}-3-[cis-3-hydroxycyclobutyl]-2,3-dihydro-1H-isoindol-1-one *slow eluting isomer | Prepared in a similar manner to Example 203. Plus final deprotection with TBAF | ¹H NMR (400 MHz, CDCl₃) 8.52 (2H, s), 7.72 (1H, d), 7.35 (2H, d), 7.30 (1H, dd), 7.21 (2H, d), 4.69-4.54 (2H, m), 3.73-3.56 (2H, m), 3.52-3.46 (1H, m), 2.34-2.25 (1H, m), 2.05-1.80 (6H, m), 1.69-1.55 (6H, m), 1.47-1.36 (2H, m), 1.28-1.09 (4H, m). | [M + H]⁺ = 616. |
| 496 | 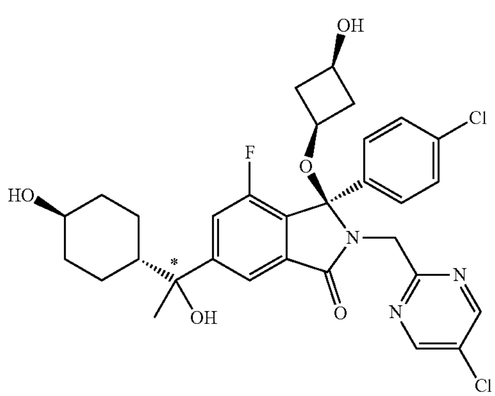 [SMILES: CC(O)(c1cc(F)c2c(c1)C(=O)N(Cc1ncc(Cl)cn1)[C@@]2(O[C@H]1C[C@@H](O)C1)c1ccc(Cl)cc1)[C@H]1CC[C@H](O)CC1] | (3R)-3-(4-chlorophenyl)-2-[(5-chloropyrimidin-2-yl)methyl]-4-fluoro-6-{1-hydroxy-1-[trans-4-hydroxycyclohexyl]}-3-[cis-3-hydroxycyclobutyl]-2,3-dihydro-1H-isoindol-1-one: *fast eluting isomer | Prepared in a similar manner to Example 203. Plus final deprotection with TBAF | ¹H NMR (400 MHz, CDCl₃) 8.52 (2H, s), 7.71 (1H, d), 7.36-7.29 (3H, m), 7.21 (2H, d), 4.67 (1H, d), 4.55 (1H, d), 3.74-3.59 (2H, m), 3.53-3.46 (1H, m), 2.34-2.25 (1H, m), 2.08-1.80 (6H, m), 1.69-1.55 (6H, m, overlapping H₂O), 1.45-1.38 (2H, m), 1.29-1.11 (4H, m). | [M + H]⁺ = 616. |

| Example | Structure | Name | Comment | NMR Data | MS Data |
|---|---|---|---|---|---|
| 497 | 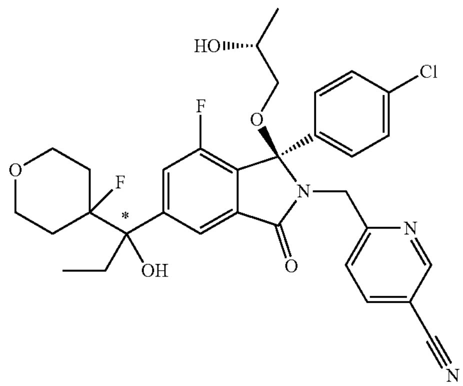 [SMILES: CCC(O)(c1cc(F)c2c(c1)C(=O)N(Cc1ccc(C#N)cn1)[C@@]2(OC[C@@H](C)O)c1ccc(Cl)cc1)C1(F)CCOCC1] | 6-{[(1R)-1-(4-chlorophenyl)-7-fluoro-5-[1-(4-fluorooxan-4-yl)-1-hydroxypropyl]-1-[(2R)-2-hydroxypropoxy]-3-oxo-2,3-dihydro-1H-isoindol-2-yl]methyl}pyridine-3-carbonitrile | Prepared in a similar manner to Example 200, but using Et₂Zn/EtLi in Step 5 (see Preparation 30) | ¹H NMR (400 MHz, CDCl₃) 8.68 (1H, d), 7.83 (1H, dd), 7.76 (1H, s), 7.48-7.42 (2H, m), 7.29 (2H, d), 7.24 (2H, d), 4.63-4.50 (2H, m), 3.87-3.79 (3H, m), 3.68-3.59 (2H, m), 3.26 (1H, dd), 2.89 (1H, dd), 2.63 (1H, dd), 2.23-2.18 (2H, m), 2.00-1.80 (4H, m), 1.55-1.45 (1H, m), 1.15 (3H, d), 0.71 (3H, t) | [M − H]⁻ 610 |
| 498 | 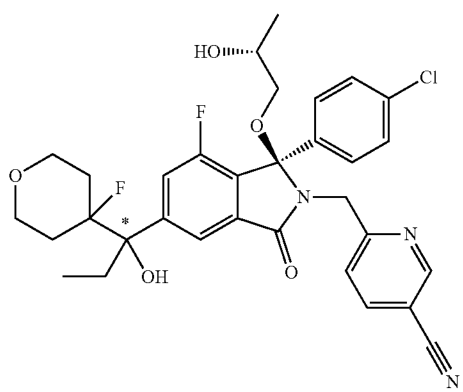 [SMILES: CCC(O)(c1cc(F)c2c(c1)C(=O)N(Cc1ccc(C#N)cn1)[C@@]2(OC[C@@H](C)O)c1ccc(Cl)cc1)C1(F)CCOCC1] | 6-{[(1R)-1-(4-chlorophenyl)-7-fluoro-5-[1-(4-fluorooxan-4-yl)-1-hydroxypropyl]-1-[(2R)-2-hydroxypropoxy]-3-oxo-2,3-dihydro-1H-isoindol-2-yl]methyl}pyridine-3-carbonitrile | Prepared in a similar manner to Example 200, but using Et₂Zn/EtLi in Step 5 (see Preparation 30) | ¹H NMR (400 MHz, CDCl₃) 8.70 (1H, d), 7.84 (1H, dd), 7.78 (1H, s), 7.48 (1H, d), 7.42 (1H, d), 7.30-7.23 (4H, m), 4.61 (1H, d), 4.51 (1H, d), 4.04-3.97 (1H, m), 3.88-3.78 (2H, m), 3.69-3.57 (2H, m), 3.15-3.01 (2H, m), 2.78 (1H, d), 2.22 (1H, dd), 2.17 (1H, d), 2.01-1.93 (4H, m), 1.51-1.44 (1H, m), 1.10 (3H, d), 0.70 (3H, t) | [M − H]⁻ 610 |
| 499 | 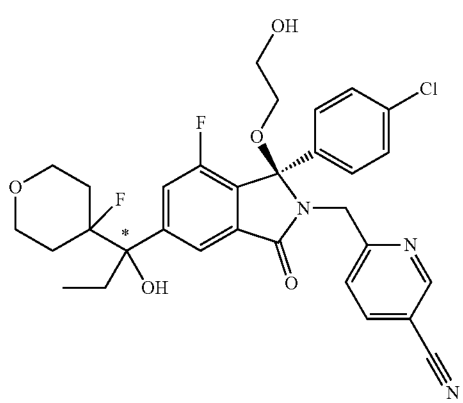 [SMILES: CCC(O)(c1cc(F)c2c(c1)C(=O)N(Cc1ccc(C#N)cn1)[C@@]2(OCCO)c1ccc(Cl)cc1)C1(F)CCOCC1] | 6-{[(1R)-1-(4-chlorophenyl)-7-fluoro-5-[1-(4-fluorooxan-4-yl)-1-hydroxypropyl]-1-(2-hydroxyethoxy)-3-oxo-2,3-dihydro-1H-isoindol-2-yl]methyl}pyridine-3-carbonitrile | Prepared in a similar manner to Example 200, but using Et2Zn/EtLi in Step 5 (see Preparation 30, Step 1) | ¹H NMR (400 MHz, CDCl₃) 8.69 (d, 1H), 7.84 (dd, 1H), 7.76 (s, 1H), 7.49-7.44 (m, 2H), 7.31 (d, 2H), 7.25-7.23 (m, 2H), 4.63-4.49 (m, 2H), 3.86-3.77 (m, 3H), 3.69-3.59 (m, 3H), 3.40-3.34 (m, 1H), 3.23-3.17 (m, 1H), 2.58-2.54 (m, 1H), 2.22-2.15 (m, 2H), 2.02-1.83 (m, 3H), 1.67-1.45 (m, 2H), 0.71 (dd, 3H). | [M + H]⁺ = 598 |

| Example | Structure | Name | Comment | NMR Data | MS Data |
|---|---|---|---|---|---|
| 500 | 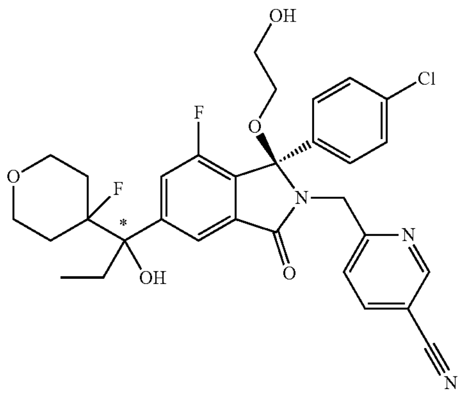 [SMILES: CCC(O)(c1cc(F)c2c(c1)C(=O)N(Cc1ccc(C#N)cn1)[C@@]2(OCCO)c1ccc(Cl)cc1)C1(F)CCOCC1] | 6-{[(1R)-1-(4-chlorophenyl)-7-fluoro-5-[1-(4-fluorooxan-4-yl)-1-hydroxypropyl]-1-(2-hydroxyethoxy)-3-oxo-2,3-dihydro-1H-isoindol-2-yl]methyl}pyridine-3-carbonitrile | Prepared in a similar manner to Example 200, but using Et2Zn/EtLi in Step 5 (see Preparation 30, Step 1) | $^1$H NMR (400 MHz, CDCl3) 8.70 (d, 1H), 7.84 (dd, 1H), 7.77 (s, 1H), 7.48 (d, 1H), 7.42 (d, 1H), 7.30 (d, 2H), 7.25-7.22 (m, 2H), 4.62 (d, 1H), 4.49 (d, 1H), 3.86-3.74 (m, 3H), 3.68-3.58 (m, 3H), 3.41-3.35 (m, 1H), 3.23-3.17 (m, 1H), 2.55-2.50 (m, 1H), 2.22 (dd, 1H), 2.15 (d, 1H), 2.02-1.80 (m, 3H), 1.68-1.43 (m, 2H), 0.71 (dd, 3H). | [M + H]+ = 598 |

Starting from the appropriate acid intermediate [e.g. (−)-(S)— or (+)-(R)-2-(4-chlorobenzoyl)-3-fluoro-5-(1-(4-fluorotetrahydro-2H-pyran-4-yl)-1-hydroxypropyl)benzoic acid (Preparation 35, Preparation 36 or Preparation 34), the following compounds in table 7 below were prepared using procedures similar to those described in Example 280, using the appropriate amine in step 1 and alcohol in step 2. Preparative chiral HPLC chromatography was used to separate both chiral intermediates and final products. In the table below an asterisk (*) indicates the compound was isolated as a single isomer at the position shown.

| Example | Structure | Name | NMR Data | MS Data |
|---|---|---|---|---|
| 501 | 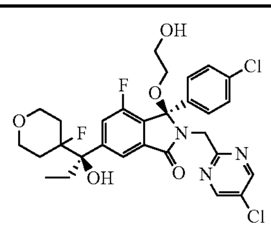 | (3R)-3-(4-chlorophenyl)-2-[(5-chloropyrimidin-2-yl)methyl]-4-fluoro-6-[(1R)-1-(4-fluorooxan-4-yl)-1-hydroxypropyl]-3-(2-hydroxyethoxy)-2,3-dihydro-1H-isoindol-1-one | $^1$H NMR (400 MHz, CDCl$_3$) 8.54 (2H, s), 7.78 (1H, s), 7.43 (1H, d), 7.38-7.35 (1H, m), 7.25-7.23 (2H, m), 4.71-4.58 (2H, m), 3.85-3.73 (3H, m), 3.68-3.57 (4H, m), 3.25-3.19 (1H, m), 2.27-2.18 (3H, m), 2.03-1.84 (3H, m), 1.69-1.59 (1H, m), 1.55-1.46 (1H, m), 0.71 (3H, t). | [M + H]$^+$ = 608 |
| 502 | 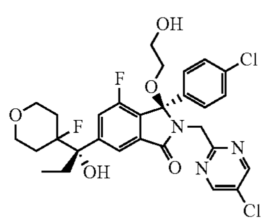 [SMILES: CC[C@](O)(c1cc(F)c2c(c1)C(=O)N(Cc1ncc(Cl)cn1)[C@@]2(OCCO)c1ccc(Cl)cc1)C1(F)CCOCC1] | (3R)-3-(4-chlorophenyl)-2-[(5-chloropyrimidin-2-yl)methyl]-4-fluoro-6-[(1S)-1-(4-fluorooxan-4-yl)-1-hydroxypropyl]-3-(2-hydroxyethoxy)-2,3-dihydro-1H-isoindol-1-one | $^1$H NMR (400 MHz, CDCl$_3$) 8.55 (2H, s), 7.79 (1H, s), 7.42 (1H, d), 7.35 (2H, d), 7.24-7.23 (2H, m), 4.70 (1H, d), 4.59 (1H, d), 3.88-3.73 (3H, m), 3.68-3.61 (4H, m), 3.26-3.20 (1H, m), 2.26-2.21 (3H, m), 2.01-1.96 (4H, m), 1.56-1.45 (1H, m), 0.71 (3H, t). | [M + H]$^+$ = 608 |
| 503 | 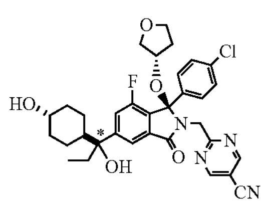 [SMILES: CCC(O)(c1cc(F)c2c(c1)C(=O)N(Cc1ncc(C#N)cn1)[C@@]2(O[C@H]1CCOC1)c1ccc(Cl)cc1)[C@H]1CC[C@H](O)CC1] | 2-{[(1R)-1-(4-chlorophenyl)-7-fluoro-5-{1-hydroxy-1-[trans-4-hydroxycyclohexyl]propyl}-3-oxo-1-[(3S)-oxolan-3-yloxy]-2,3-dihydro-1H-isoindol-2-yl]methyl}pyrimidine-5-carbonitrile | 1H NMR (400 MHz, CDCl3): 8.83 (2H, s), 7.67 (1H, s), 7.35 (3H, d), 7.20 (2H, d), 4.79 (1H, d), 4.64 (1H, d), 4.24 (1H, t), 3.94-3.85 (1H, m), 3.78-3.60 (2H, m), 3.56-3.41 (1H, m), 3.30 (1H, dd), 2.06 (1H, d), 2.01-1.84 (5H, m), 1.83-1.73 (1H, m), 1.65 (1H, d), 1.45 (1H, d), 1.35-1.22 (3H, m), 1.22-1.04 (3H, m), 0.67 (3H, t) | [M − C$_4$H$_7$O$_2^-$]$^+$ = 533 |
| 504 | 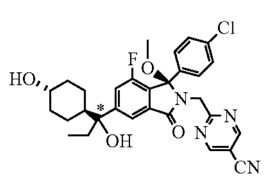 [SMILES: CCC(O)(c1cc(F)c2c(c1)C(=O)N(Cc1ncc(C#N)cn1)[C@@]2(OC)c1ccc(Cl)cc1)[C@H]1CC[C@H](O)CC1] | 2-{[(1R)-1-(4-chlorophenyl)-7-fluoro-5-{1-hydroxy-1-[trans-4-hydroxycyclohexyl]propyl}-1-methoxy-3-oxo-2,3-dihydro-1H-isoindol-2-yl]methyl}pyrimidine-5-carbonitrile | 1H NMR (400 MHz, CDCl3): 8.84 (2H, s), 7.68 (1H, d), 7.39-7.30 (3H, m), 7.22 (2H, d), 4.74 (1H, dd), 4.66 (1H, dd), 3.54-3.42 (1H, m), 3.13 (3H, d), 2.02-1.85 (4H, m), 1.70-1.56 (3H, m), 1.44 (1H, s), 1.32 (2H, d), 1.22-1.05 (3H, m), 0.68 (3H, t). | [M − C$_4$H$_7$O$_2^-$]]$^+$ = 533 |

| Example | Structure | Name | NMR Data | MS Data |
|---|---|---|---|---|
| 505 | 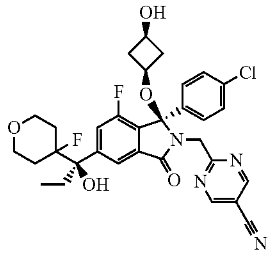 [SMILES: CC[C@@](O)(c1cc(F)c2c(c1)C(=O)N(Cc1ncc(C#N)cn1)[C@@]2(O[C@H]1C[C@@H](O)C1)c1ccc(Cl)cc1)C1(F)CCOCC1] | 2-{[(1R)-1-(4-chlorophenyl)-7-fluoro-5-[(1R)-1-(4-fluorooxan-4-yl)-1-hydroxypropyl]-3-oxo-1-[cis-3-hydroxycyclobutoxy]-2,3-dihydro-1H-isoindol-2-yl]methyl}pyrimidine-5-carbonitrile | $^1$H NMR (400 MHz, CDCl$_3$) 8.83 (2H, s), 7.75 (1H, s), 7.44 (1H, d), 7.38 (2H, d), 7.22 (2H, d), 4.69-4.68 (2H, m), 3.84 (2H, dd), 3.77-3.59 (4H, m), 2.43-2.34 (1H, m), 2.24-2.17 (2H, m), 2.11-1.79 (6H, m), 1.69 (1H, d), 1.55-1.45 (2H m), 0.71 (3H, t). | [M − H]$^−$ = 623 |
| 506 | 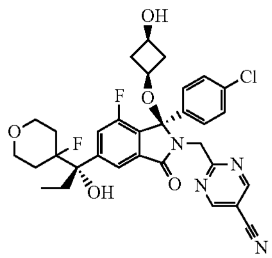 [SMILES: CC[C@](O)(c1cc(F)c2c(c1)C(=O)N(Cc1ncc(C#N)cn1)[C@@]2(O[C@H]1C[C@@H](O)C1)c1ccc(Cl)cc1)C1(F)CCOCC1] | 2-{[(1R)-1-(4-chlorophenyl)-7-fluoro-5-[(1S)-1-(4-fluorooxan-4-yl)-1-hydroxypropyl]-3-oxo-1-[cis-3-hydroxycyclobutoxy]-2,3-dihydro-1H-isoindol-2-yl]methyl}pyrimidine-5-carbonitrile | $^1$H NMR (400 MHz, CDCl$_3$) 8.83 (2H, s), 7.76 (1H, s), 7.44 (1H, d), 7.38 (2H, d), 7.22 (2H, d), 4.69 (2H, s), 3.88-3.80 (2H, m), 3.75-3.59 (4H, m), 2.42-2.33 (2H, m), 2.26-2.16 (1H, m), 2.09-1.82 (7H, m), 1.62-1.44 (2H, m), 0.71 (3H, t). | [M + H]$^+$ = 625 |
| 507 | 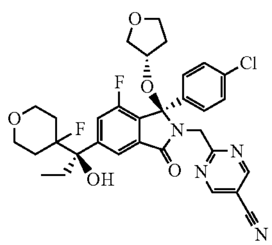 [SMILES: CC[C@@](O)(c1cc(F)c2c(c1)C(=O)N(Cc1ncc(C#N)cn1)[C@@]2(O[C@H]1CCOC1)c1ccc(Cl)cc1)C1(F)CCOCC1] | 2-{[(1R)-1-(4-chlorophenyl)-7-fluoro-5-[(1R)-1-(4-fluorooxan-4-yl)-1-hydroxypropyl]-3-oxo-1-[(3S)-oxolan-3-yloxy]-2,3-dihydro-1H-isoindol-2-yl]methyl}pyrimidine-5-carbonitrile | $^1$H NMR (400 MHz, CDCl$_3$) 8.83 (2H, s), 7.77 (1H, s), 7.50 (1H, d), 7.37 (2H, d), 7.20 (2H, d), 4.82 (1H, d), 4.63 (1H, d), 4.22 (1H, m), 3.95-3.80 (3H, m), 3.77-3.61 (4H, m), 3.32 (1H, dd), 2.25-2.18 (2H, m), 2.02-1.78 (5H, m), 1.67-1.46 (2H, m), 0.71 (3H, t). | [M + H]$^+$ = 625 |
| 508 | 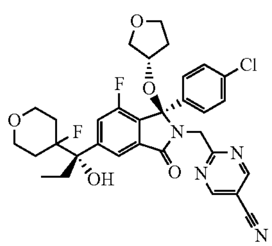 [SMILES: CC[C@](O)(c1cc(F)c2c(c1)C(=O)N(Cc1ncc(C#N)cn1)[C@@]2(O[C@H]1CCOC1)c1ccc(Cl)cc1)C1(F)CCOCC1] | 2-{[(1R)-1-(4-chlorophenyl)-7-fluoro-5-[(1S)-1-(4-fluorooxan-4-yl)-1-hydroxypropyl]-3-oxo-1-[(3S)-oxolan-3-yloxy]-2,3-dihydro-1H-isoindol-2-yl]methyl}pyrimidine-5-carbonitrile | $^1$H NMR (400 MHz, CDCl$_3$) 8.84 (2H, s), 7.83 (1H, s), 7.44 (1H, d), 7.35 (2H, d), 7.21 (2H, d), 4.77 (1H, d), 4.66 (1H, d), 4.31-4.24 (1H, m), 3.94-3.58 (7H, m), 3.33 (1H, dd), 2.24-2.19 (2H, m), 2.04-1.83 (4H, m), 1.77-1.62 (2H, m), 1.47-1.40 (1H, m), 0.71 (3H, t). | [M + H]$^+$ = 625 |
| 509 | 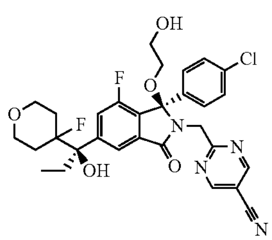 [SMILES: CC[C@@](O)(c1cc(F)c2c(c1)C(=O)N(Cc1ncc(C#N)cn1)[C@@]2(OCCO)c1ccc(Cl)cc1)C1(F)CCOCC1] | 2-{[(1R)-1-(4-chlorophenyl)-7-fluoro-5-[(1R)-1-(4-fluorooxan-4-yl)-1-hydroxypropyl]-1-(2-hydroxyethoxy)-3-oxo-2,3-dihydro-1H-isoindol-2-yl]methyl}pyrimidine-5-carbonitrile | $^1$H NMR (400 MHz, CDCl$_3$) 8.84 (2H, s), 7.78 (1H, s), 7.46 (1H, d), 7.38 (2H, d), 7.28-7.2 (2H, m), 4.79-4.66 (2H, m), 3.87-3.74 (3H, m), 3.71-3.60 (4H, m), 3.25-3.19 (1H, m), 2.22-2.19 (2H, m), 2.02-1.89 (4H, m), 1.67-1.62 (1H, m), 1.50-1.45 (1H, m), 0.72 (3H, t). | [M − H]$^−$ = 597 |
| 510 | 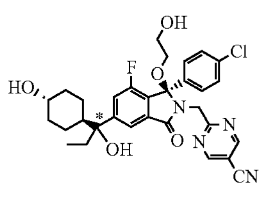 [SMILES: CCC(O)(c1cc(F)c2c(c1)C(=O)N(Cc1ncc(C#N)cn1)[C@@]2(OCCO)c1ccc(Cl)cc1)[C@H]1CC[C@H](O)CC1] | 2-{[(1R)-1-(4-chlorophenyl)-7-fluoro-5-{1-hydroxy-1-[trans-4-hydroxycyclohexyl]propyl}-1-(2-hydroxyethoxy)-3-oxo-2,3-dihydro-1H-isoindol-2-yl]methyl}pyrimidine-5-carbonitrile | $^1$H NMR (400 MHz, CDCl$_3$) 8.84 (2H, s), 7.67 (1H, d), 7.37 (3H, d), 7.24-7.27 (2H, m, overlapping CHCl$_3$), 4.72 (2H, q), 3.80-3.59 (3H, m), 3.52-3.45 (1H, m), 3.25-3.19 (1H, m), 2.02-1.89 (6H, m), 1.69-1.64 (1H, m), 1.63 (1H, s), 1.41-1.07 (6H, m), 0.68 (3H, t) | [M − H]- = 593. |

| Example | Structure | Name | NMR Data | MS Data |
|---|---|---|---|---|
| 511 | 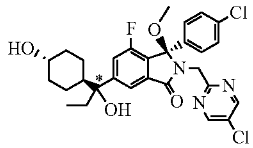 [SMILES: CCC(O)(c1cc(F)c2c(c1)C(=O)N(Cc1ncc(Cl)cn1)[C@@]2(OC)c1ccc(Cl)cc1)[C@H]1CC[C@H](O)CC1] | (3R)-3-(4-chlorophenyl)-2-[(5-chloropyrimidin-2-yl)methyl]-4-fluoro-6-{1-hydroxy-1-[trans-4-hydroxycyclohexyl]propyl}-3-methoxy-2,3-dihydro-1H-isoindol-1-one | ¹H NMR (400 MHz, CDCl₃) 8.53 (2H, s), 7.67 (1H, d), 7.36-7.30 (3H, m), 7.21 (2H, d), 4.69 (1H, d), 4.60 (1H, d), 3.52-3.45 (1H, m), 3.09 (3H, s), 2.08-1.89 (5H, m), 1.69-1.64 (1H, m), 1.63 (2H, s), 1.40-1.07 (5H, m), 0.68 (3H, t). | [M − H]⁻ = 572 |
| 512 | 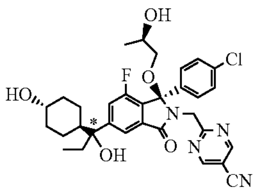 [SMILES: CCC(O)(c1cc(F)c2c(c1)C(=O)N(Cc1ncc(C#N)cn1)[C@@]2(OC[C@@H](C)O)c1ccc(Cl)cc1)[C@H]1CC[C@H](O)CC1] | 2-{[(1R)-1-(4-chlorophenyl)-7-fluoro-5-{1-hydroxy-1-[trans-4-hydroxycyclohexyl]propyl}-1-[(2R)-2-hydroxypropoxy]-3-oxo-2,3-dihydro-1H-isoindol-2-yl]methyl}pyrimidine-5-carbonitrile | ¹H NMR (400 MHz, CDCl₃) 8.84 (2H, s), 7.67 (1H, s), 7.38-7.33 (3H, m), 7.24 (1H, s), 4.78 (1H, d), 4.67 (1H, d), 3.98-3.93 (1H, m), 3.48-3.47 (1H, m), 3.36-3.31 (1H, m), 3.03 (1H, dd), 2.11-1.89 (6H, m), 1.43 (1H, s), 1.36-1.10 (6H, m), 1.08 (3H, d), 0.69 (3H, dd). 2 exchangeable protons not observed | [M − H]⁻ = 607 |
| 513 | 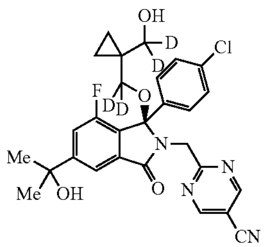 [SMILES: [2H]C([2H])(O)C1(C([2H])([2H])O[C@]2(c3ccc(Cl)cc3)c3c(F)cc(C(C)(C)O)cc3C(=O)N2Cc2ncc(C#N)cn2)CC1] | 2-{[(1R)-1-(4-chlorophenyl)-7-fluoro-1-({1-[hydroxydideuteromethyl]cyclopropyl}dideuteromethoxy)-5-(2-hydroxypropan-2-yl)-3-oxo-2,3-dihydro-1H-isoindol-2-yl]methyl}pyrimidine-5-carbonitrile | 1H NMR (400 MHz, CDCl3): 8.83 (2H, s), 7.79 (1H, d), 7.44 (1H, dd), 7.36 (2H, d), 7.22 (2H, d), 4.72 (1H, d), 4.70-4.62 (1H, m), 1.83 (1H, s), 1.74 (1H, s), 1.62 (6H, d), 0.55-0.43 (3H, m), 0.36-0.31 (1H, m) | [M − C3]⁺ = 435. |

Example 514: 5-chloro-2-{[(1R)-1-(4-chlorophenyl)-7-fluoro-5-[(1R)-1-(4-fluorooxan-4-yl)-1-hydroxypropyl]-1-methoxy-3-oxo-2,3-dihydro-1H-isoindol-2-yl]methyl}pyridine-3-carboxylic acid (tris(hydroxymethyl)aminomethane salt)

Step 1-2

Starting from (+)-(R)-2-(4-chlorobenzoyl)-3-fluoro-5-(1-(4-fluorotetrahydro-2H-pyran-4-yl)-1-hydroxypropyl)benzoic acid (Preparation 35), (3-bromo-5-chloropyridin-2-yl)

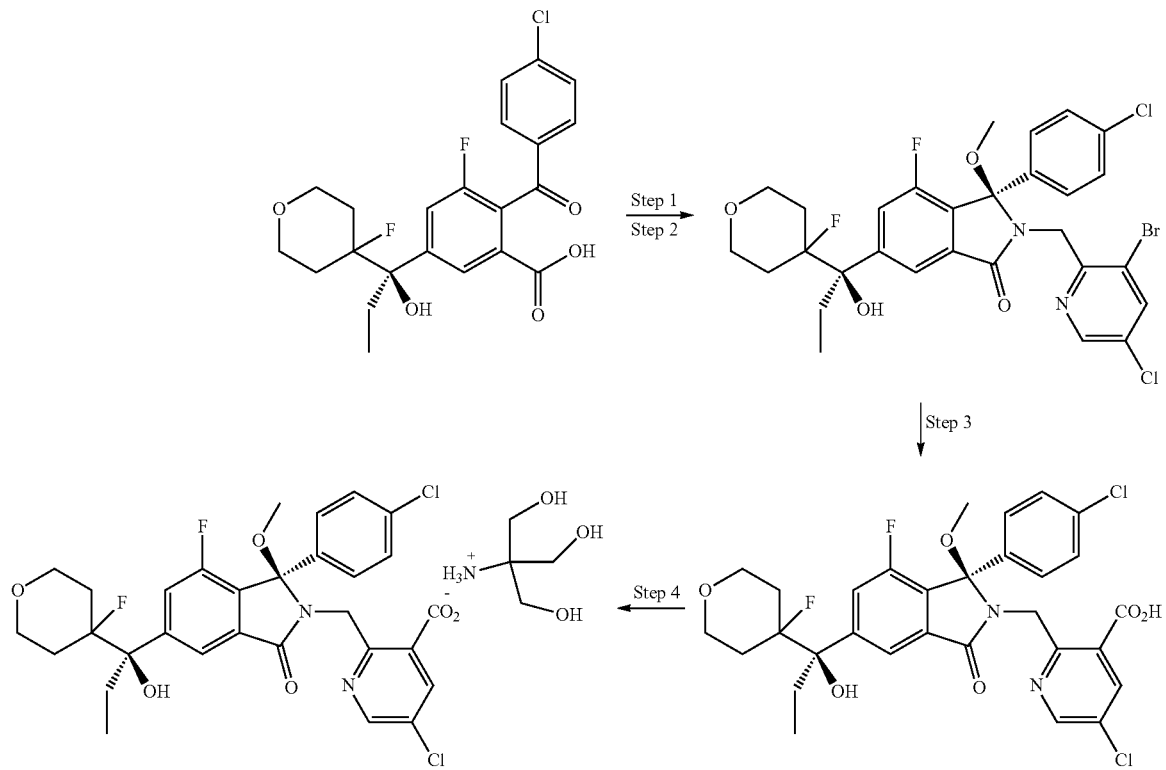

methanamine and MeOH, Steps 1-2 were performed using procedures similar to those described in Example 280, Steps 1-2, to give (R)-2-((3-bromo-5-chloropyridin-2-yl)methyl)-3-(4-chlorophenyl)-4-fluoro-6-((R)-1-(4-fluorotetrahydro-2H-pyran-4-yl)-1-hydroxypropyl)-3-methoxyisoindolin-1-one. [M+H]$^+$=655.

Step 3: 5-chloro-2-(((R)-1-(4-chlorophenyl)-7-fluoro-5-((R)-1-(4-fluorotetrahydro-2H-pyran-4-yl)-1-hydroxypropyl)-1-methoxy-3-oxoisoindolin-2-yl)methyl)nicotinic acid A mixture of (R)-2-((3-bromo-5-chloropyridin-2-yl)methyl)-3-(4-chlorophenyl)-4-fluoro-6-((R)-1-(4-fluorotetrahydro-2H-pyran-4-yl)-1-hydroxypropyl)-3-methoxyisoindolin-1-one (0.23 g, 0.35 mmol), LiHCOO.H$_2$O (0.10 g, 1.41 mmol), Pd(OAc)$_2$ (15.9 mg, 0.2 mmol), Xantphos (0.81 g, 0.14 mmol) and TEA (0.2 mL, 1.41 mmol) in DMF (5 mL) was degassed for 15 min with N$_2$ and then Ac$_2$O (0.13 mL, 1.41 mmol) was slowly added. The resulting mixture was stirred at 80° C. under inert atmosphere for 18 hours. The reaction was cooled to room temperature and the DMF was removed under reduced pressure. The residue was partitioned between water (10 mL) and EtOAc (10 mL), the organic phase was separated and washed with brine (4×50 mL), dried over MgSO$_4$, filtered and concentrated under reduced pressure to give a light orange solid which was purified by reverse phase HPLC. MS: [M+H]$^+$=621.

Step 4

5-chloro-2-(((R)-1-(4-chlorophenyl)-7-fluoro-5-((R)-1-(4-fluorotetrahydro-2H-pyran-4-yl)-1-hydroxypropyl)-1-methoxy-3-oxoisoindolin-2-yl)methyl)nicotinic acid (140 mg, 0.22 mmol) was stirred in methanol (1 mL) at room temperature then tris(hydroxymethyl)aminomethane (27 mg, 0.22 mmol) was added. The reaction was allowed to stir for 30 minutes during which time all the solids dissolved.

The volatiles were removed under reduced pressure to afford the title compound as colourless solid (128 mg, 93%). $^1$H NMR (400 MHz, CDCl$_3$) 8.25 (1H, d), 7.91 (1H, s), 7.78 (1H, s), 7.35 (2H, d), 7.29-7.19 (1H, m, overlapping CDCl$_3$), 7.20 (2H, d), 5.09-5.00 (1H, m), 4.72-4.67 (1H, m), 4.18-3.27 (12H, m), 3.09 (3H, s), 2.14-2.08 (1H, m), 1.93-1.62 (3H, m), 1.30-1.16 (1H, m), 0.60 (3H, dd) NH3+ missing MS: [M+H]$^+$=621

Example 515: 3-{[(1R)-1-(4-chlorophenyl)-7-fluoro-5-[(1R)-1-(4-fluorooxan-4-yl)-1-hydroxypropyl]-1-methoxy-3-oxo-2,3-dihydro-1H-isoindol-2-yl]methyl}-6-methylpyridine-2-carboxylic Acid

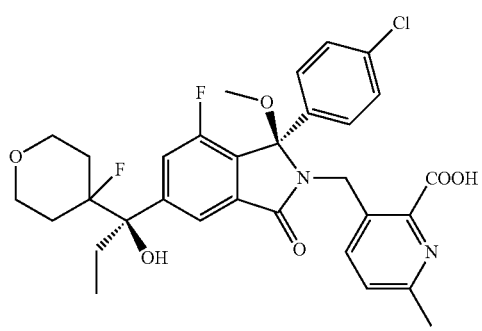 [SMILES: CC[C@@](O)(c1cc(F)c2c(c1)C(=O)N(Cc1ccc(C)nc1C(=O)O)[C@@]2(OC)c1ccc(Cl)cc1)C1(F)CCOCC1]

Starting from Preparation 41, the title compound was prepared using procedures similar to those described in Example 514. 1H NMR (400 MHz, DMSO-d6): 7.73 (1H, s), 7.46 (1H, d), 7.33-7.22 (4H, m), 7.05 (1H, d), 6.78 (1H, d), 4.52 (2H, s), 3.81 (1H, dd), 3.49 (1H, d), 3.37 (11H, s), 2.87 (3H, s), 2.28 (3H, s), 2.21-2.08 (1H, m), 2.05-1.70 (5H, m), 0.60 (3H, t). MS: [M–H$^-$]$^-$=599

Example 516: (3R)-3-(4-chlorophenyl)-2-[(5-chloropyrimidin-2-yl)dideuteromethyl]-4-fluoro-6-[1-(4-fluorooxan-4-yl)-1-hydroxyethyl]-3-[(3S)-oxolan-3-yloxy]-2,3-dihydro-1H-isoindol-1-one (Example isolated as a single isomer at the position shown*)

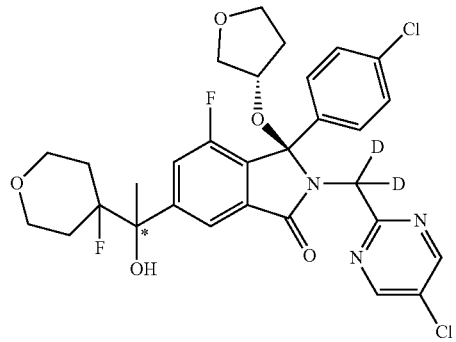 [SMILES: [2H]C([2H])(c1ncc(Cl)cn1)N1C(=O)c2cc(C(C)(O)C3(F)CCOCC3)cc(F)c2[C@]1(O[C@H]1CCOC1)c1ccc(Cl)cc1]

To a solution of (3R)-3-(4-chlorophenyl)-2-[(5-chloropyrimidin-2-yl)methyl]-4-fluoro-6-[1-(4-fluorooxan-4-yl)-1-hydroxyethyl]-3-[(3S)-oxolan-3-yloxy]-2,3-dihydro-1H-isoindol-1-one (Example 493) (25 mg 0.04 mmol) in CD$_3$OD (2.4 mL) was added K$_2$CO$_3$ and the mixture was stirred for 3 hr. D$_2$O was added and the compound was extracted with CHCl$_3$. The organic phase was dried and the solvent was evaporated to afford the title compound (24.6 mg, 98%). $^1$H NMR (400 MHz, DMSO-d$_6$): 8.75 (2H, s), 7.77 (1H, s), 7.50 (1H, d), 7.31 (4H, s), 5.89 (1H, s), 4.21-4.14 (1H, m), 3.87-3.67 (3H, m), 3.63-3.55 (1H, m), 3.52-3.41 (2H, m), 3.19 (1H, dd), 2.09-1.97 (1H, m), 1.97-1.61 (5H, m), 1.58 (3H, s), 1.05 (1H, d). MS: [M+H]$^+$=534 (M-C-3 sidechain).

Example 517: (3R)-3-(4-chlorophenyl)-2-[(5-chloropyrimidin-2-yl)methyl]-4-fluoro-6-{1-hydroxy-1-[trans-4-hydroxycyclohexyl]propyl}-3-(2-hydroxyethoxy)-2,3-dihydro-1H-isoindol-1-one (Example isolated as a single isomer at the position shown*)

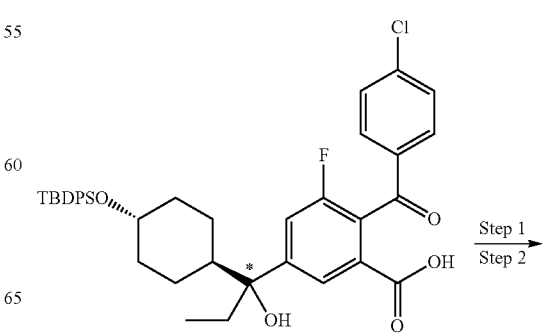

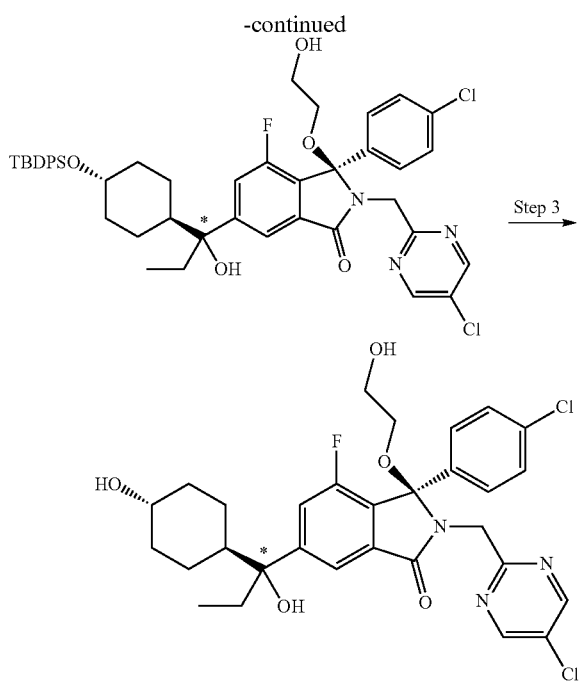

Step 1-2

Starting from (−)-5-(1-trans-4-((tert-butyldiphenylsilyl)oxy)cyclohexyl)-1-hydroxypropyl)-2-(4-chlorobenzoyl)-3-fluorobenzoic acid (Preparation 36, step 2) and (5-chloropyrimidin-2-yl)methanamine, Step 1-2 were performed using procedures similar to those described in Example 280 to give (3R)-6-(1-trans-4-((tert-butyldiphenylsilyl)oxy)cyclohexyl)-1-hydroxypropyl)-3-(4-chlorophenyl)-2-((5-chloropyrimidin-2-yl)methyl)-4-fluoro-3-(2-hydroxyethoxy)isoindolin-1-one. MS: [M-OH(CH$_2$)$_2$O]$^+$=782.

Step 3

Tetrabutylammonium fluoride (TBAF) (0.76 mL, 1M in THF, 0.76 mmol) was added drop-wise (3R)-6-(1-trans-4-((tert-butyldiphenylsilyl)oxy)cyclohexyl)-1-hydroxypropyl)-3-(4-chlorophenyl)-2-((5-chloropyrimidin-2-yl)methyl)-4-fluoro-3-(2-hydroxyethoxy)isoindolin-1-one (160 mg, 0.19 mmol) in THF (5 mL) and the mixture was stirred at room temperature for 11 days. The reaction was diluted with water (40 mL) and extracted with ethyl acetate (2×40 mL). The combined organic layers were dried (MgSO$_4$), filtered and evaporated to dryness under reduced pressure to give crude product. The residue was purified by column chromatography (gradient elution, 30% to 100% ethyl acetate in iso-hexane) to give the title compound (0.88 g, 80%) as mixture of diastereoisomers. Purification by chiral preparative HPLC gave the title compound as a white solid (27 mg). $^1$H NMR (400 MHz, CDCl$_3$) 8.54 (2H, s), 7.65 (1H, s), 7.37-7.30 (3H, m), 7.24-7.23 (2H, m), 4.64 (2H, q), 3.80-3.72 (1H, m), 3.68-3.58 (2H, m), 3.51-3.44 (1H, m), 3.25-3.20 (1H, m), 2.24-2.20 (1H, m), 2.08-1.88 (6H, m), 1.68-1.61 (1H, m), 1.38-1.10 (6H, m), 0.67 (3H, t). MS: [M+H]$^+$=604

Starting from the appropriate acid intermediate, (−)-5-(1-trans-4-((tert-butyldiphenylsilyl)oxy)cyclohexyl)-1-hydroxypropyl)-2-(4-chlorobenzoyl)-3-fluorobenzoic acid or (+)-5-(1-trans-4-((tert-butyldiphenylsilyl)oxy)cyclohexyl)-1-hydroxypropyl)-2-(4-chlorobenzoyl)-3-fluorobenzoic acid (Preparation 36: step 2) the following compounds in table 8 below were prepared using procedures similar to those described in Example 280, using the appropriate amine in step 1 and alcohol in step 2. The compounds were obtained as single isomers, with the configuration shown (*), using chiral preparative HPLC.

| Example | Structure | Name | NMR Data | MS Data |
|---|---|---|---|---|
| 518 | 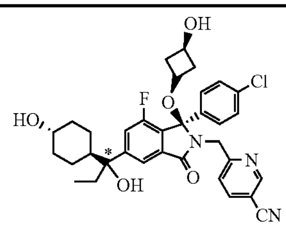 | 6-{[(1R)-1-(4-chlorophenyl)-7-fluoro-5-{1-hydroxy-1-[trans-4-hydroxycyclohexyl]propyl}-3-oxo-1-[cis-3-hydroxycyclobutoxy]-2,3-dihydro-1H-isoindol-2-yl]methyl}pyridine-3-carbonitrile | $^1$H NMR (400 MHz, CDCl$_3$) 8.68 (1H, d), 7.78 (1H, dd), 7.65 (1H, s), 7.33-7.28 (4H, m), 7.21 (2H, d), 4.64 (d, 1H), 4.49 (1H, d), 3.71-3.61 (1H, m), 3.52-3.44 (1H, m), 3.38-3.29 (1H, m), 2.22-2.13 (1H, m), 2.09-1.87 (6H, m), 1.79-1.63 (3H, m), 1.62 (1H, s), 1.40 (1H, d), 1.31-1.07 (6H, m), 0.66 (3H, dd). | [M + H]$^+$ = 620 |
| 519 | 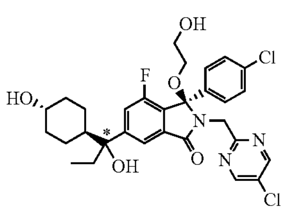 [SMILES: CCC(O)(c1cc(F)c2c(c1)C(=O)N(Cc1ncc(Cl)cn1)[C@@]2(OCCO)c1ccc(Cl)cc1)[C@H]1CC[C@H](O)CC1] | (3R)-3-(4-chlorophenyl)-2-[(5-chloropyrimidin-2-yl)methyl]-4-fluoro-6-{1-hydroxy-1-[trans-4-hydroxycyclohexyl]propyl}-3-(2-hydroxyethoxy)-2,3-dihydro-1H-isoindol-1-one | $^1$H NMR (400 MHz, CDCl$_3$) 8.54 (2H, s), 7.65 (1H, s), 7.37-7.33 (3H, m), 7.24 (2H, d), 4.64 (2H, q), 3.80-3.72 (1H, m), 3.68-3.58 (2H, m), 3.52-3.45 (1H, m), 3.25-3.19 (1H, m), 2.23 (1H, dd), 2.07-1.88 (6H, m), 1.68-1.61 (1H, m), 1.39-1.06 (6H, m), 0.67 (3H, t). | [M + H]$^+$ = 604 |
| 520 | 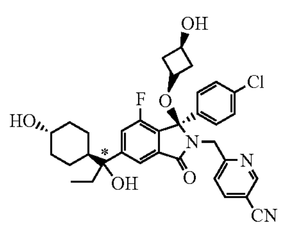 | 6-{[(1R)-1-(4-chlorophenyl)-7-fluoro-5-{1-hydroxy-1-[trans-4-hydroxycyclohexyl]propyl}-3-oxo-1-[cis-3-hydroxycyclobutoxy]-2,3-dihydro-1H-isoindol-2-yl]methyl}pyridine-3-carbonitrile | $^1$H NMR (400 MHz, CDCl$_3$) 8.68 (1H, d), 7.78 (1H, dd), 7.69 (1H, s), 7.32 (1H, d), 7.28 (2H, s), 7.26 (2H, s), 7.25-7.19 (3H, m), 4.65 (1H, d), 4.47 (1H, d), 3.67 (1H, dd), 3.50-3.46 (1H, m), 3.39-3.31 (1H, m), 2.21-2.12 (1H, m), 2.08-1.88 (6H, m), 1.79-1.66 (2H, m), 1.63 (1H, s), 1.42 (1H, d), 1.30-1.25 (2H, m), 1.25-1.07 (3H, m), 0.67 (3H, dd). | [M + H]$^+$ = 620 |

| Example | Structure | Name | NMR Data | MS Data |
|---|---|---|---|---|
| 521 | 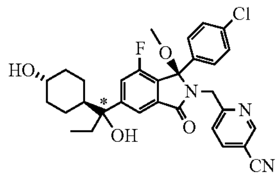 [SMILES: CCC(O)(c1cc(F)c2c(c1)C(=O)N(Cc1ccc(C#N)cn1)[C@@]2(OC)c1ccc(Cl)cc1)[C@H]1CC[C@H](O)CC1] | 6-{[(1R)-1-(4-chlorophenyl)-7-fluoro-5-{1-hydroxy-1-[trans-4-hydroxycyclohexyl]propyl}-1-methoxy-3-oxo-2,3-dihydro-1H-isoindol-2-yl]methyl}pyridine-3-carbonitrile | 1H NMR (400 MHz, CDCl3): 8.71 (1H, d), 7.80 (1H, dd), 7.70 (1H, s), 7.44-7.32 (2H, m), 7.32-7.26 (2H, m), 7.23 (2H, d), 4.68 (1H, d), 4.54 (1H, d), 3.50 (1H, s), 2.97 (3H, s), 2.13-1.84 (5H, m), 1.73-1.58 (3H, m), 1.34 (1H, d), 1.31-1.24 (2H, m), 1.24-1.07 (2H, m), 0.70 (3H, t). | [M − OMe⁻]+ = 532. |

Examples 522 and 523: (3R)-3-(4-chlorophenyl)-2-[(5-chloropyrimidin-2-yl)methyl]-4-fluoro-6-[2-hydroxy-1-(4-methylpiperazin-1-yl)butan-2-yl]-3-[(3S)-oxolan-3-yloxy]-2,3-dihydro-1H-isoindol-1-one (*both isomers separated and isolated)

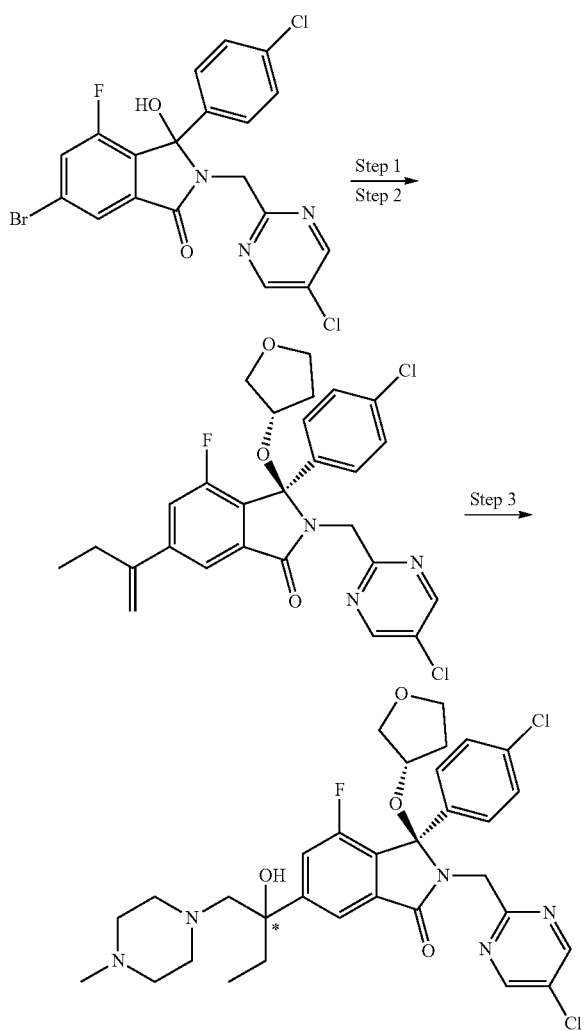

Step 1-2

Using (S)-tetrahydrofuran-3-ol and 2-(but-1-en-2-yl)-4,4,5,5-tetramethyl-1,3,2-dioxaborolane (Preparation 37), Steps 1 and 2 were performed using procedures similar to those described in Example 14 (steps 1-2) respectively; to give (R)-6-(but-1-en-2-yl)-3-(4-chlorophenyl)-2-((5-chloropyrimidin-2-yl)methyl)-4-fluoro-3-(((S)-tetrahydrofuran-3-yl)oxy)isoindolin-1-one. MS [M+Na]⁺=550.

Step 3

N-Bromosuccinimide (168 mg, 0.95 mmol) was added in one portion to a stirred solution of (R)-6-(but-1-en-2-yl)-3-(4-chlorophenyl)-2-((5-chloropyrimidin-2-yl)methyl)-4-fluoro-3-(((S)-tetrahydrofuran-3-yl)oxy)isoindolin-1-one (250 mg, 0.47 mmol) and H₂O (0.5 mL, 12.33 mmol) in DMSO (5 mL) at room temperature. The reaction was stirred for 2 hours. After this time 1-methylpiperazine (235 mg, 2.35 mmol) was added and the reaction heated at 70° C. for 18 hours. The reaction was cooled to room temperature and the crude mix was purified via reverse phase preparative HPLC to give the title compound (140 mg) as a mix of diastereoisomers, which were separated by chiral SFC to give the title compounds.

Example 522: *Fast Eluting Isomer

¹H NMR (400 MHz, CDCl₃) 8.52 (2H, s), 7.74 (1H, d), 7.40 (1H, dd), 7.32 (2H, d), 7.18 (2H, d), 4.70 (1H, d), 4.59 (1H, d), 4.22 (1H, ddd), 3.88 (1H, q), 3.73-3.62 (2H, m), 3.25 (1H, dd), 2.84 (1H, d), 2.73 (1H, d), 2.50-2.46 (1H, m), 2.34-2.31 (8H, m), 2.23 (3H, s), 1.85-1.69 (4H, m), 0.69 (3H, Hz, dd). MS [M+H]⁺=644.

Example 523: *Slow Eluting Isomer

¹H NMR (400 MHz, CDCl₃) 8.52 (2H, s), 7.71 (1H, d), 7.43 (1H, dd), 7.32 (2H, d), 7.18 (2H, d), 4.70 (1H, d), 4.58 (1H, d), 4.53-4.53 (1H, m), 4.25-4.19 (1H, m), 3.88 (1H, q), 3.73-3.60 (2H, m), 3.19 (1H, dd), 2.84 (1H, d), 2.72 (1H, d), 2.45-2.39 (2H, m), 2.30 (6H, d), 2.22 (3H, s), 1.86-1.68 (4H, m), 0.71 (3H, dd). MS [M+H]⁺=644.

The following compounds in table 9 below were prepared using procedures similar to those described in Example 522 with the appropriate alcohol and amine being used in steps 1 and 3 respectively. Preparative chiral SFC was used to isolate products as single isomers. In the table below, an asterisk indicates the compound was isolated as a single isomer at the position shown.

| Example | Structure | Name | NMR Data | MS Data |
|---|---|---|---|---|
| 524 | 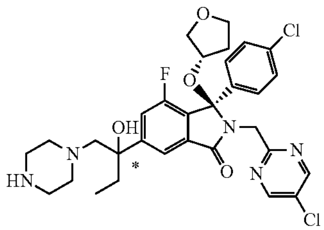 [SMILES: CCC(O)(CN1CCNCC1)c1cc(F)c2c(c1)C(=O)N(Cc1ncc(Cl)cn1)[C@@]2(O[C@H]1CCOC1)c1ccc(Cl)cc1] | (3R)-3-(4-chlorophenyl)-2-[(5-chloropyrimidin-2-yl)methyl]-4-fluoro-6-[2-hydroxy-1-(piperazin-1-yl)butan-2-yl]-3-[(3S)-oxolan-3-yloxy]-2,3-dihydro-1H-isoindol-1-one (*fast eluting isomer) | $^1$H NMR (400 MHz, CDCl$_3$) 8.52 (2H, s), 7.75 (1H, d), 7.40 (1H, dd), 7.32 (2H, d), 7.18 (2H, d), 4.70 (1H, d), 4.59 (1H, d), 4.25-4.19 (1H, m), 3.91-3.84 (1H, m), 3.73-3.62 (2H, m), 3.25 (1H, dd), 2.85-2.67 (6H, m), 2.38 (2H, s), 2.30-2.24 (2H, m), 1.85-1.72 (4H, m), 0.69 (3H, dd) | [M + H]$^+$ = 630 |
| 525 | 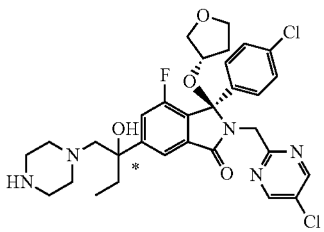 [SMILES: CCC(O)(CN1CCNCC1)c1cc(F)c2c(c1)C(=O)N(Cc1ncc(Cl)cn1)[C@@]2(O[C@H]1CCOC1)c1ccc(Cl)cc1] | (3R)-3-(4-chlorophenyl)-2-[(5-chloropyrimidin-2-yl)methyl]-4-fluoro-6-[2-hydroxy-1-(piperazin-1-yl)butan-2-yl]-3-[(3S)-oxolan-3-yloxy]-2,3-dihydro-1H-isoindol-1-one (*slow eluting isomer) | $^1$H NMR (400 MHz, CDCl$_3$) 8.52 (2H, s), 7.72 (1H, d), 7.43 (1H, dd), 7.32 (2H, d), 7.18 (2H, d), 4.70 (1H, d), 4.58 (1H, d), 4.21 (1H, ddd), 3.87 (1H, q), 3.72-3.59 (2H, m), 3.19 (1H, dd), 2.85-2.66 (6H, m), 2.38 (2H, d), 2.27-2.23 (2H, m), 1.86-1.69 (4H, m), 0.71 (3H, dd) | [M + H]$^+$ = 630. |
| 526 | 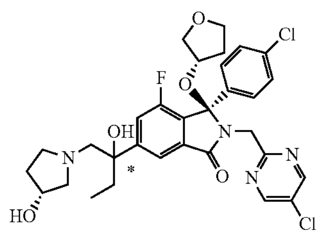 [SMILES: CCC(O)(CN1CC[C@@H](O)C1)c1cc(F)c2c(c1)C(=O)N(Cc1ncc(Cl)cn1)[C@@]2(O[C@H]1CCOC1)c1ccc(Cl)cc1] | (3R)-3-(4-chlorophenyl)-2-[(5-chloropyrimidin-2-yl)methyl]-4-fluoro-6-{2-hydroxy-1-[(3R)-3-hydroxypyrrolidin-1-yl]butan-2-yl}-3-[(3S)-oxolan-3-yloxy]-2,3-dihydro-1H-isoindol-1-one (*fast eluting isomer) | $^1$H NMR (400 MHz, CDCl$_3$) 8.53 (2H, s), 7.78 (1H, s), 7.40 (1H, d), 7.33 (2H, d), 7.19 (2H, d), 4.70 (1H, d), 4.59 (1H, d), 4.30-4.19 (2H, m), 3.88 (1H, q), 3.73-3.62 (2H, m), 3.26 (1H, dd), 3.00 (1H, d), 2.91 (1H, d), 2.75 (1H, dd), 2.61 (1H, dd), 2.38-2.31 (2H, m), 2.09-2.00 (1H, m), 1.84-1.61 (7H, m), 0.71 (3H, dd) | [M + H]$^+$ = 631 |
| 527 | 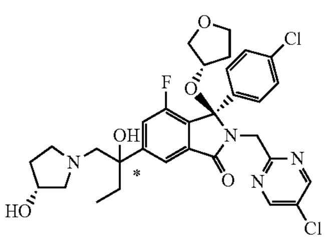 [SMILES: CCC(O)(CN1CC[C@@H](O)C1)c1cc(F)c2c(c1)C(=O)N(Cc1ncc(Cl)cn1)[C@@]2(O[C@H]1CCOC1)c1ccc(Cl)cc1] | (3R)-3-(4-chlorophenyl)-2-[(5-chloropyrimidin-2-yl)methyl]-4-fluoro-6-{2-hydroxy-1-[(3R)-3-hydroxypyrrolidin-1-yl]butan-2-yl}-3-[(3S)-oxolan-3-yloxy]-2,3-dihydro-1H-isoindol-1-one (*slow eluting isomer) | $^1$H NMR (400 MHz, CDCl$_3$) 8.52 (2H, s), 7.73 (1H, s), 7.47 (1H, d), 7.33 (2H, d), 7.19 (2H, d), 4.71 (1H, d), 4.58 (1H, d), 4.27-4.18 (2H, m), 3.88 (1H, q), 3.74-3.59 (2H, m), 3.23 (1H, dd), 3.02 (1H, d), 2.89 (1H, d), 2.62-2.52 (2H, m), 2.39-2.33 (2H, m), 2.08-1.97 (1H, m), 1.92-1.50 (7H, m), 0.72 (3H, dd) | [M + H]$^+$ = 631 |
| 528 | 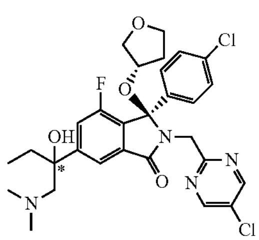 [SMILES: CCC(O)(CN(C)C)c1cc(F)c2c(c1)C(=O)N(Cc1ncc(Cl)cn1)[C@@]2(O[C@H]1CCOC1)c1ccc(Cl)cc1] | (3R)-3-(4-chlorophenyl)-2-[(5-chloropyrimidin-2-yl)methyl]-6-[1-(dimethylamino)-2-hydroxybutan-2-yl]-4-fluoro-3-[(3S)-oxolan-3-yloxy]-2,3-dihydro-1H-isoindol-1-one | $^1$H NMR (400 MHz, CDCl$_3$) 8.52 (2H, s), 7.75 (1H, d), 7.41 (1H, dd), 7.32 (2H, d), 7.18 (2H, d), 4.70 (1H, d), 4.59 (1H, d), 4.25-4.20 (1H, m), 3.88 (1H, q), 3.73-3.63 (2H, m), 3.30-3.24 (1H, m), 2.78-2.72 (2H, m), 2.61 (1H, s), 2.11 (6H, s), 1.81-1.70 (4H, m), 0.69 (3H, dd) | [M + H]$^+$ = 589 |
| 529 | 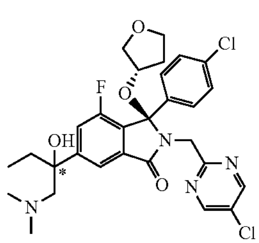 [SMILES: CCC(O)(CN(C)C)c1cc(F)c2c(c1)C(=O)N(Cc1ncc(Cl)cn1)[C@@]2(O[C@H]1CCOC1)c1ccc(Cl)cc1] | (3R)-3-(4-chlorophenyl)-2-[(5-chloropyrimidin-2-yl)methyl]-6-[1-(dimethylamino)-2-hydroxybutan-2-yl]-4-fluoro-3-[(3S)-oxolan-3-yloxy]-2,3-dihydro-1H-isoindol-1-one | $^1$H NMR (400 MHz, CDCl3) 8.52 (2H, s), 7.72 (1H, d), 7.48-7.44 (1H, m), 7.32 (2H, d), 7.18 (2H, d), 4.71 (1H, d), 4.58 (1H, d), 4.24-4.18 (1H, m), 3.95-3.84 (1H, m), 3.73-3.62 (2H, m), 3.24 (1H, dd), 2.73 (2H, d), 2.10 (6H, s), 1.86-1.71 (4H, m), 0.70 (3H, dd) | [M + H]$^+$ = 589 |

| Example | Structure | Name | NMR Data | MS Data |
|---|---|---|---|---|
| 530 | 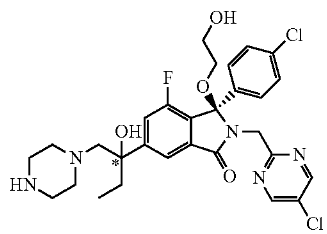 [SMILES: CCC(O)(CN1CCNCC1)c1cc(F)c2c(c1)C(=O)N(Cc1ncc(Cl)cn1)[C@@]2(OCCO)c1ccc(Cl)cc1] | (3R)-3-(4-chlorophenyl)-2-[(5-chloropyrimidin-2-yl)methyl]-4-fluoro-6-[2-hydroxy-1-(piperazin-1-yl)butan-2-yl]-3-(2-hydroxyethoxy)-2,3-dihydro-1H-isoindol-1-one (*fast eluting isomer) | $^1$H NMR (400 MHz, CDCl$_3$) 8.54 (2H, s), 7.70 (1H, s), 7.41 (1H, d), 7.33 (2H, d), 7.23 (2H, d), 4.70-4.56 (2H, m), 3.80-3.72 (m, 1H), 3.66-3.56 (2H, m), 3.24-3.18 (1H, m), 2.83-2.66 (6H, m), 2.42-2.38 (2H, m), 2.29-2.23 (2H, m), 1.78-1.69 (2H, m), 0.70 (3H, dd) | [M + H]$^+$ = 604 |
| 531 | 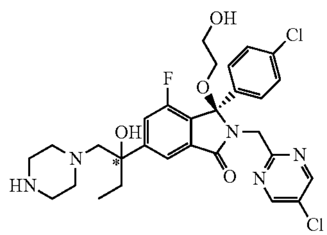 [SMILES: CCC(O)(CN1CCNCC1)c1cc(F)c2c(c1)C(=O)N(Cc1ncc(Cl)cn1)[C@@]2(OCCO)c1ccc(Cl)cc1] | (3R)-3-(4-chlorophenyl)-2-[(5-chloropyrimidin-2-yl)methyl]-4-fluoro-6-[2-hydroxy-1-(piperazin-1-yl)butan-2-yl]-3-(2-hydroxyethoxy)-2,3-dihydro-1H-isoindol-1-one (*slow eluting isomer) | $^1$H NMR (400 MHz, CDCl$_3$) 8.54 (2H, s), 7.72 (1H, s), 7.40 (1H, d), 7.33 (2H, d), 7.23 (2H, d), 4.70-4.56 (2H, m), 3.78-3.71 (1H, m), 3.66-3.56 (2H, m), 3.21-3.16 (1H, m), 2.83-2.77 (5H, m), 2.68 (1H, d), 2.39 (2H, s), 2.31-2.26 (2H, m), 1.79-1.69 (2H, m), 0.70 (3H, dd) | [M + H]$^+$ = 604 |
| 532 | 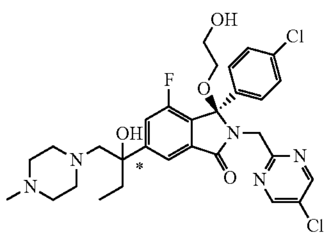 [SMILES: CCC(O)(CN1CCN(C)CC1)c1cc(F)c2c(c1)C(=O)N(Cc1ncc(Cl)cn1)[C@@]2(OCCO)c1ccc(Cl)cc1] | (3R)-3-(4-chlorophenyl)-2-[(5-chloropyrimidin-2-yl)methyl]-4-fluoro-6-[2-hydroxy-1-(4-methylpiperazin-1-yl)butan-2-yl]-3-(2-hydroxyethoxy)-2,3-dihydro-1H-isoindol-1-one (*fast eluting isomer) | $^1$H NMR (400 MHz, CDCl$_3$) 8.54 (2H, s), 7.70 (1H, s), 7.41 (1H, d), 7.33 (2H, d), 7.23 (2H, d), 4.68 (1H, d), 4.59 (1H, d), 4.52 (1H, s), 3.80-3.72 (1H, m), 3.66-3.56 (2H, m), 3.24-3.18 (1H, m), 2.82 (1H, d), 2.72 (1H, d), 2.46-2.26 (8H, m), 2.22 (3H, s), 1.78-1.70 (2H, m), 0.70 (3H, dd) | [M + H]$^+$ = 618 |
| 533 | 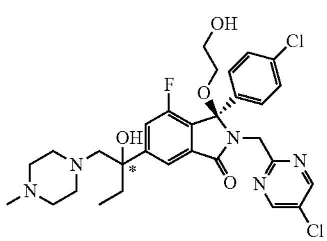 [SMILES: CCC(O)(CN1CCN(C)CC1)c1cc(F)c2c(c1)C(=O)N(Cc1ncc(Cl)cn1)[C@@]2(OCCO)c1ccc(Cl)cc1] | (3R)-3-(4-chlorophenyl)-2-[(5-chloropyrimidin-2-yl)methyl]-4-fluoro-6-[2-hydroxy-1-(4-methylpiperazin-1-yl)butan-2-yl]-3-(2-hydroxyethoxy)-2,3-dihydro-1H-isoindol-1-one (*slow eluting isomer) | $^1$H NMR (400 MHz, CDCl$_3$) 8.54 (2H, s), 7.71 (1H, s), 7.39 (1H, d), 7.33 (2H, d), 7.23 (2H, d), 4.69-4.56 (2H, m), 4.50 (1H, s), 3.73 (1H, s), 3.65-3.56 (2H, m), 3.22-3.16 (1H, m), 2.82 (1H, d), 2.72 (1H, d), 2.52-2.25 (7H, m), 2.26 (1H, s), 2.23 (3H, s), 1.75 (2H, ddd), 0.70 (3H, dd) | [M + H]$^+$ = 618 |
| 534 | 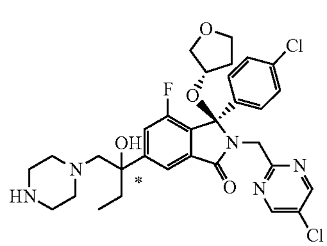 | 1-({[(1R)-1-(4-chlorophenyl)-2-[(5-chloropyrimidin-2-yl)methyl]-7-fluoro-5-[2-hydroxy-1-(4-methylpiperazin-1-yl)butan-2-yl]-3-oxo-2,3-dihydro-1H-isoindol-1-yl]oxy}methyl)cyclopropane-1-carbonitrile (*fast eluting isomer) | $^1$H NMR (400 MHz, CDCl$_3$) 8.57 (2H, s), 7.73 (1H, d), 7.40-7.34 (3H, m), 7.28 (2H, s), 4.72 (1H, d), 4.54-4.48 (2H, m), 3.87 (1H, d), 2.88 (1H, d), 2.76 (2H, dd), 2.49-2.33 (8H, m), 2.25 (3H, s), 1.78-1.71 (2H, m), 1.26 (2H, dd), 0.90-0.74 (2H, m), 0.69 (3H, dd) | [M + H]$^+$ = 653 |
| 535 | 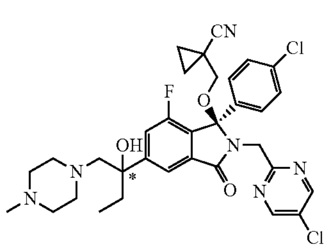 [SMILES: CCC(O)(CN1CCN(C)CC1)c1cc(F)c2c(c1)C(=O)N(Cc1ncc(Cl)cn1)[C@@]2(OCC1(C#N)CC1)c1ccc(Cl)cc1] | 1-({[(1R)-1-(4-chlorophenyl)-2-[(5-chloropyrimidin-2-yl)methyl]-7-fluoro-5-[2-hydroxy-1-(4-methylpiperazin-1-yl)butan-2-yl]-3-oxo-2,3-dihydro-1H-isoindol-1-yl]oxy}methyl)cyclopropane-1-carbonitrile (*slow eluting isomer) | $^1$H NMR (400 MHz, CDCl$_3$) 8.57 (2H, s), 7.68 (1H, d), 7.43 (1H, dd), 7.37 (2H, d), 7.28 (2H, d), 4.73 (1H, d), 4.51 (2H, d), 3.92 (1H, d), 2.87-2.79 (2H, m), 2.72 (1H, d), 2.47-2.25 (8H, br m), 2.23 (3H, s), 1.78-1.71 (2H, m), 1.29-1.23 (2H, m), 0.92-0.86 (1H, m), 0.81-0.75 (1H, m), 0.71 (3H, dd) | [M + H]$^+$ = 653 |

| Example | Structure | Name | NMR Data | MS Data |
|---|---|---|---|---|
| 536 | 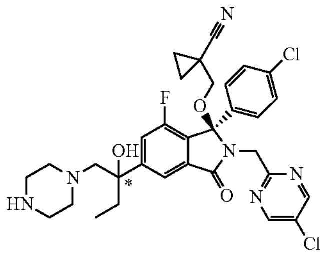 [SMILES: CCC(O)(CN1CCNCC1)c1cc(F)c2c(c1)C(=O)N(Cc1ncc(Cl)cn1)[C@@]2(OCC1(C#N)CC1)c1ccc(Cl)cc1] | 1-({[(1R)-1-(4-chlorophenyl)-2-[(5-chloropyrimidin-2-yl)methyl]-7-fluoro-5-[2-hydroxy-1-(piperazin-1-yl)butan-2-yl]-3-oxo-2,3-dihydro-1H-isoindol-1-yl]oxy}methyl)cyclopropane-1-carbonitrile (*fast eluting isomer) | $^1$H NMR (400 MHz, CDCl$_3$) 8.57 (2H, s), 7.68 (1H, s), 7.44 (1H, dd), 7.36 (2H, d), 7.29-7.26 (2H, m), 4.73 (1H, d), 4.51 (1H, d), 3.91 (1H, d), 2.87-2.66 (7H, m), 2.44-2.37 (2H, m), 2.29-2.23 (2H, m), 1.78-1.71 (2H, m), 1.28-1.23 (2H, m), 0.92-0.87 (1H, m), 0.80-0.75 (1H, m), 0.71 (3H, dd) | [M + H]$^+$ = 639 |
| 537 | 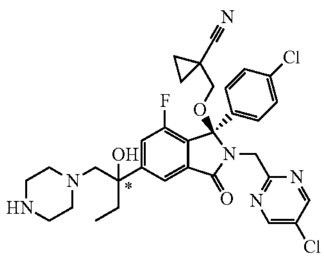 [SMILES: CCC(O)(CN1CCNCC1)c1cc(F)c2c(c1)C(=O)N(Cc1ncc(Cl)cn1)[C@@]2(OCC1(C#N)CC1)c1ccc(Cl)cc1] | 1-({[(1R)-1-(4-chlorophenyl)-2-[(5-chloropyrimidin-2-yl)methyl]-7-fluoro-5-[2-hydroxy-1-(piperazin-1-yl)butan-2-yl]-3-oxo-2,3-dihydro-1H-isoindol-1-yl]oxy}methyl)cyclopropane-1-carbonitrile (*slow eluting isomer) | $^1$H NMR (400 MHz, CDCl$_3$) 8.57 (2H, s), 7.72 (1H, s), 7.41-7.35 (3H, m), 7.28-7.26 (2H, m), 4.72 (1H, d), 4.51 (1H, d), 3.87 (1H, d), 2.87 (1H, d), 2.81-2.67 (6H, m), 2.44-2.38 (2H, m), 2.30 (2H, dd), 1.75 (2H, q), 1.26 (2H, dd), 0.89-0.86 (1H, m), 0.79-0.75 (1H, m), 0.70 (3H, dd) | [M + H]$^+$ = 639 |
| 538 | 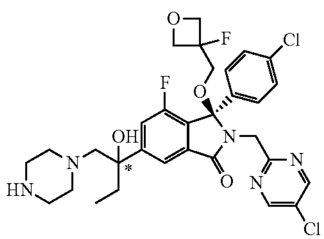 [SMILES: CCC(O)(CN1CCNCC1)c1cc(F)c2c(c1)C(=O)N(Cc1ncc(Cl)cn1)[C@@]2(OCC1(F)COC1)c1ccc(Cl)cc1] | (3R)-3-(4-chlorophenyl)-2-[(5-chloropyrimidin-2-yl)methyl]-4-fluoro-3-[(3-fluorooxetan-3-yl)methoxy]-6-[2-hydroxy-1-(piperazin-1-yl)butan-2-yl]-2,3-dihydro-1H-isoindol-1-one (*fast eluting isomer) | $^1$H NMR (400 MHz, CDCl$_3$) 8.55 (2H, s), 7.76 (1H, s), 7.42 (1H, d), 7.31 (2H, d), 7.25-7.23 (2H, m), 4.77-4.67 (3H, m), 4.56-4.48 (3H, m), 4.32 (1H, dd), 4.03 (1H, dd), 3.33 (1H, dd), 2.83-2.68 (6H, m), 2.41 (2H, s), 2.31-2.28 (2H, m), 1.80-1.73 (2H, m), 1.26-1.20 (1H, m), 0.71 (3H, dd) | [M + H]$^+$ = 648 |
| 539 | 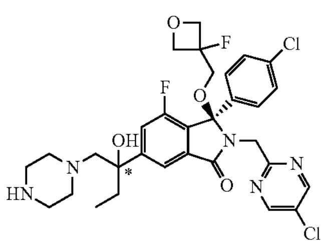 [SMILES: CCC(O)(CN1CCNCC1)c1cc(F)c2c(c1)C(=O)N(Cc1ncc(Cl)cn1)[C@@]2(OCC1(F)COC1)c1ccc(Cl)cc1] | (3R)-3-(4-chlorophenyl)-2-[(5-chloropyrimidin-2-yl)methyl]-4-fluoro-3-[(3-fluorooxetan-3-yl)methoxy]-6-[2-hydroxy-1-(piperazin-1-yl)butan-2-yl]-2,3-dihydro-1H-isoindol-1-one (*slow eluting isomer) | 1H NMR (400 MHz, CDCl$_3$) 8.55 (2H, s), 7.73 (1H, s), 7.45 (2H, d), 7.31 (2H, d), 7.24-7.21 (2H, m), 4.77-4.67 (3H, m), 4.57-4.47 (3H, m), 4.32 (1H, dd), 4.04 (1H, dd), 3.36 (1H, dd), 2.84-2.68 (6H, m), 2.40 (2H, d), 2.31-2.26 (2H, m), 1.79-1.72 (2H, m), 0.72 (3H, dd). | [M + H]$^+$ = 648 |

Starting from the appropriate acid intermediate [e.g. (−)-5-(1-(1-(tert-butoxycarbonyl)-4-fluoropiperidin-4-yl)-1-hydroxypropyl)-2-(4-chlorobenzoyl)-3-fluorobenzoic acid—slow eluting isomer (Preparation 38)], the following compounds in table 10 below were prepared in a similar fashion to Example 286, steps 1 and 2, using the appropriate amine in step 1 and alcohol in step 2. The appropriate amines were obtained commercially or prepared as described (e.g. Preparation 19). The appropriate alcohols, where not commercially available, were prepared as described herein (for example Preparation 1). The compounds were obtained as single isomers (*), with the configuration shown, using chiral preparative HPLC.

| Example | Structure | Name | NMR Data and comments | MS Data |
|---|---|---|---|---|
| 540 | 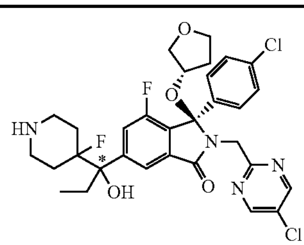 | (3R)-3-(4-chlorophenyl)-2-[(5-chloropyrimidin-2-yl)methyl]-4-fluoro-6-[1-(4-fluoropiperidin-4-yl)-1-hydroxypropyl]-3-[(3S)-oxolan-3-yloxy]-2,3-dihydro-1H-isoindol-1-one | Prepared from (+)-5-(1-(1-(tert-butoxycarbonyl)-4-fluoropiperidin-4-yl)-1-hydroxypropyl)-2-(4-chlorobenzoyl)-3-fluorobenzoic acid - fast eluting isomer<br>$^1$H NMR (400 MHz, CDCl$_3$) 8.53 (2H, s), 7.75 (1H, s), 7.52-7.47 (1H, m), 7.36 (2H, d), 7.22 (2H, d), 4.59 (2H, s), 4.29-4.23 (1H, m), 3.99-3.92 (1H, m), 3.71-3.65 (1H, m), 3.57 (1H, dd), 3.48 (1H, dd), 2.95-2.82 (4H, m), 2.25-2.16 (2H, m), 2.06-1.86 (3H, m), 1.82-1.77 (1H, m), 1.68 (2H, dd), 1.44-1.38 (1H, m), 1.30-1.25 (1H, m), 0.70 (3H, t). | [M + H]$^+$ = 633 |

| Example | Structure | Name | NMR Data and comments | MS Data |
|---|---|---|---|---|
| 541 | 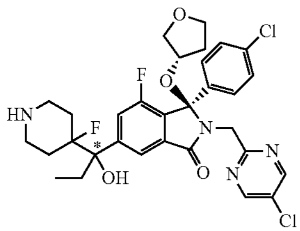 [SMILES: CCC(O)(c1cc(F)c2c(c1)C(=O)N(Cc1ncc(Cl)cn1)[C@@]2(O[C@H]1CCOC1)c1ccc(Cl)cc1)C1(F)CCNCC1] | (3R)-3-(4-chlorophenyl)-2-[(5-chloropyrimidin-2-yl)methyl]-4-fluoro-6-[1-(4-fluoropiperidin-4-yl)-1-hydroxypropyl]-3-[(3S)-oxolan-3-yloxy]-2,3-dihydro-1H-isoindol-1-one | Prepared from (−)-5-(1-(1-(tert-butoxycarbonyl)-4-fluoropiperidin-4-yl)-1-hydroxypropyl)-2-(4-chlorobenzoyl)-3-fluorobenzoic acid - slow eluting isomer. ¹H NMR (400 MHz, CDCl₃) 8.53 (2H, s), 7.76 (1H, s), 7.48 (1H, d), 7.37 (2H, d), 7.19 (2H, d), 4.74 (1H, d), 4.58 (1H, d), 4.21 (1H, ddd), 3.88 (1H, q), 3.74-3.62 (2H, m), 3.29 (1H, dd), 2.96-2.82 (4H, m), 2.26-2.16 (2H, m), 2.06-1.95 (2H, m), 1.88-1.60 (4H, m), 1.45-1.20 (2H, m), 0.69 (3H, dd). | [M + H]⁺ = 633 |
| 542 | 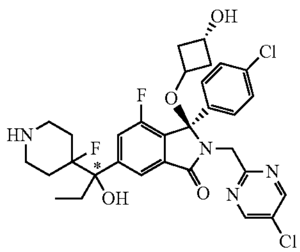 | (3R)-3-(4-chlorophenyl)-2-[(5-chloropyrimidin-2-yl)methyl]-4-fluoro-6-[1-(4-fluoropiperidin-4-yl)-1-hydroxypropyl]-3-[cis-3-hydroxycyclobutoxy]-2,3-dihydro-1H-isoindol-1-one | ¹H NMR (400 MHz, CDCl₃) 8.53 (2H, s), 7.83 (1H, s), 7.37-7.31 (3H, m), 7.22 (2H, d), 4.68 (1H, d), 4.53 (1H, d), 3.74-3.61 (2H, m), 2.95-2.81 (4H, m), 2.33-2.14 (2H, m), 2.07-1.93 (4H, m), 1.88-1.57 (6H, m), 1.49-1.25 (1H, m), 0.68 (3H, t). | [M + H]⁺ = 633 |
| 543 | 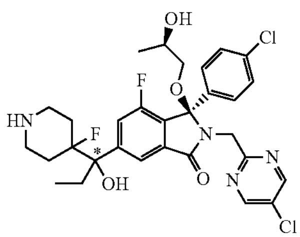 [SMILES: CCC(O)(c1cc(F)c2c(c1)C(=O)N(Cc1ncc(Cl)cn1)[C@@]2(OC[C@@H](C)O)c1ccc(Cl)cc1)C1(F)CCNCC1] | (3R)-3-(4-chlorophenyl)-2-[(5-chloropyrimidin-2-yl)methyl]-4-fluoro-6-[1-(4-fluoropiperidin-4-yl)-1-hydroxypropyl]-3-[(2R)-2-hydroxypropoxy]-2,3-dihydro-1H-isoindol-1-one | ¹H NMR (400 MHz, CDCl₃) 8.54 (2H, s), 7.76 (1H, s), 7.44 (1H, d), 7.36 (2H, d), 7.24 (2H, d), 4.65 (2H, d), 4.02-3.95 (1H, m), 3.33 (1H, dd), 3.04 (1H, dd), 2.94-2.82 (4H, m), 2.61 (1H, s), 2.25-2.15 (2H, m), 2.06-1.95 (2H, m), 1.83-1.74 (1H, m), 1.44-1.24 (2H, m), 1.09 (3H, d), 0.70 (3H, t), 0.07 (2H, s). | [M + H]⁺ = 621 |
| 544 | 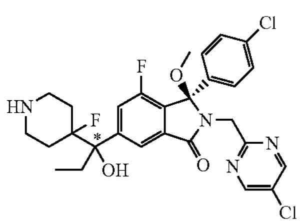 [SMILES: CCC(O)(c1cc(F)c2c(c1)C(=O)N(Cc1ncc(Cl)cn1)[C@@]2(OC)c1ccc(Cl)cc1)C1(F)CCNCC1] | (3R)-3-(4-chlorophenyl)-2-[(5-chloropyrimidin-2-yl)methyl]-4-fluoro-6-[1-(4-fluoropiperidin-4-yl)-1-hydroxypropyl]-3-methoxy-2,3-dihydro-1H-isoindol-1-one | ¹H NMR (400 MHz, CDCl₃) 8.53 (2H, s), 7.79 (1H, s), 7.44 (1H, d), 7.36 (2H, d), 7.22 (2H, d), 4.69 (1H, d), 4.60 (1H, d), 3.09 (3H, s), 2.96-2.82 (4H, m), 2.27-2.16 (2H, m), 2.07-1.95 (2H, m), 1.84-1.56 (2H, m), 1.44-1.25 (1H, m), 0.70 (3H, t), OH and NH missing. | [M + H]⁺ = 577 |
| 545 | 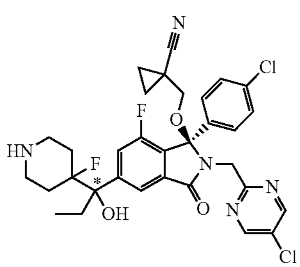 [SMILES: CCC(O)(c1cc(F)c2c(c1)C(=O)N(Cc1ncc(Cl)cn1)[C@@]2(OCC1(C#N)CC1)c1ccc(Cl)cc1)C1(F)CCNCC1] | 1-({[(1R)-1-(4-chlorophenyl)-2-[(5-chloropyrimidin-2-yl)methyl]-7-fluoro-5-[1-(4-fluoropiperidin-4-yl)-1-hydroxypropyl]-3-oxo-2,3-dihydro-1H-isoindol-1-yl]oxy}methyl)cyclopropane-1-carbonitrile | ¹H NMR (400 MHz, CDCl₃) 8.57 (2H, s), 7.77 (1H, s), 7.46-7.39 (3H, m), 7.29 (2H, d), 4.73 (1H, d), 4.53 (1H, d), 3.91 (1H, d), 2.94-2.85 (5H, m), 2.24-2.14 (2H, m), 2.06-1.95 (2H, m), 1.82-1.74 (1H, m), 1.70-1.64 (2H, m), 1.43-1.24 (3H, m), 0.95-0.79 (2H, m), 0.70 (3H, t). | [M + H]⁺ = 642 |
| 546 | 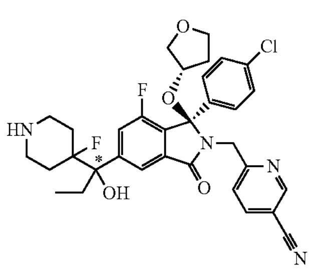 [SMILES: CCC(O)(c1cc(F)c2c(c1)C(=O)N(Cc1ccc(C#N)cn1)[C@@]2(O[C@H]1CCOC1)c1ccc(Cl)cc1)C1(F)CCNCC1] | 6-{[(1R)-1-(4-chlorophenyl)-7-fluoro-5-[1-(4-fluoropiperidin-4-yl)-1-hydroxypropyl]-3-oxo-1-[(3S)-oxolan-3-yloxy]-2,3-dihydro-1H-isoindol-2-yl]methyl}pyridine-3-carbonitrile | ¹H NMR (400 MHz, CDCl₃) 8.65 (1H, d), 7.80-7.77 (2H, m), 7.50 (1H, d), 7.34 (1H, d), 7.24 (2H, d), 7.16 (2H, d), 4.70 (1H, d), 4.55 (1H, d), 4.05-3.98 (1H, m), 3.87 (1H, q), 3.72-3.59 (2H, m), 3.27 (1H, m), 3.00-2.85 (4H, m), 2.26-2.16 (2H, m), 2.08-1.63 (7H, m), 1.53-1.34 (1H, m), 0.69 (3H, t). | [M + H]⁺ = 623 |

| Example | Structure | Name | NMR Data and comments | MS Data |
|---|---|---|---|---|
| 547 | 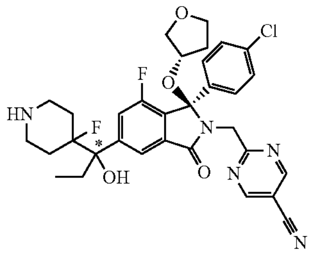 [SMILES: CCC(O)(c1cc(F)c2c(c1)C(=O)N(Cc1ncc(C#N)cn1)[C@@]2(O[C@H]1CCOC1)c1ccc(Cl)cc1)C1(F)CCNCC1] | 2-{[(1R)-1-(4-chlorophenyl)-7-fluoro-5-[1-(4-fluoropiperidin-4-yl)-1-hydroxypropyl]-3-oxo-1-[(3S)-oxolan-3-yloxy]-2,3-dihydro-1H-isoindol-2-yl]methyl}pyrimidine-5-carbonitrile | $^1$H NMR (400 MHz, CDCl$_3$) 8.83 (2H, s), 7.76 (1H, s), 7.50 (1H, d), 7.38 (2H, d), 7.19 (2H, d), 4.83 (1H, d), 4.62 (1H, d), 4.25-4.19 (1H, m), 3.90 (1H, q), 3.76-3.64 (2H, m), 3.32 (1H, dd), 2.97-2.85 (4H, m), 2.26-2.17 (2H, m), 2.09-1.73 (6H, m), 1.47-1.32 (3H, m), 0.69 (3H, dd). | [M + H]$^+$ = 624 |
| 548 | 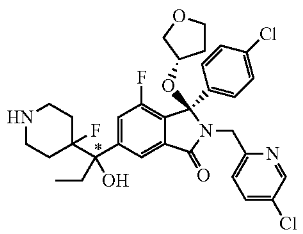 [SMILES: CCC(O)(c1cc(F)c2c(c1)C(=O)N(Cc1ccc(Cl)cn1)[C@@]2(O[C@H]1CCOC1)c1ccc(Cl)cc1)C1(F)CCNCC1] | (3R)-3-(4-chlorophenyl)-2-[(5-chloropyridin-2-yl)methyl]-4-fluoro-6-[1-(4-fluoropiperidin-4-yl)-1-hydroxypropyl]-3-[(3S)-oxolan-3-yloxy]-2,3-dihydro-1H-isoindol-1-one | $^1$H NMR (400 MHz, CDCl$_3$) 8.33 (1H, d), 7.76 (1H, s), 7.52-7.46 (2H, m), 7.24-7.16 (5H, m), 4.56 (2H, dd), 4.01-3.95 (1H, m), 3.84 (1H, q), 3.69-3.57 (2H, m), 3.23 (1H, dd), 2.95-2.83 (4H, m), 2.26-1.77 (5H, m), 1.46-1.25 (3H, m), 0.68 (3H, dd), Exchangeables not observed. | [M + H]$^+$ = 632 |
| 549 | 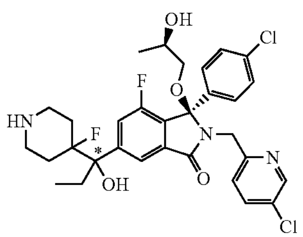 [SMILES: CCC(O)(c1cc(F)c2c(c1)C(=O)N(Cc1ccc(Cl)cn1)[C@@]2(OC[C@@H](C)O)c1ccc(Cl)cc1)C1(F)CCNCC1] | (3R)-3-(4-chlorophenyl)-2-[(5-chloropyridin-2-yl)methyl]-4-fluoro-6-[1-(4-fluoropiperidin-4-yl)-1-hydroxypropyl]-3-[(2R)-2-hydroxypropoxy]-2,3-dihydro-1H-isoindol-1-one | $^1$H NMR (400 MHz, CDCl$_3$) 8.38 (1H, d), 7.72 (1H, s), 7.56 (1H, dd), 7.42 (1H, d), 7.36 (1H, d), 7.32 (2H, d), 7.25 (2H, d), 4.52-4.39 (2H, m), 4.08-4.00 (1H, m), 3.15-3.01 (2H, m), 2.93-2.81 (4H, m), 2.27-2.13 (2H, m), 2.04-1.94 (2H, m), 1.81-1.53 (4H, m), 1.42-1.22 (1H, m), 1.09 (3H, d), 0.68 (3H, dd). | [M + H]+ = 620 |

Example 550: (3R)-3-(4-chlorophenyl)-2-[(5-chloropyrimidin-2-yl)methyl]-4-fluoro-6-[(1S)-1-hydroxy-1-[1-(2-hydroxyethyl)piperidin-4-yl]propyl]-3-methoxy-2,3-dihydro-1H-isoindol-1-one

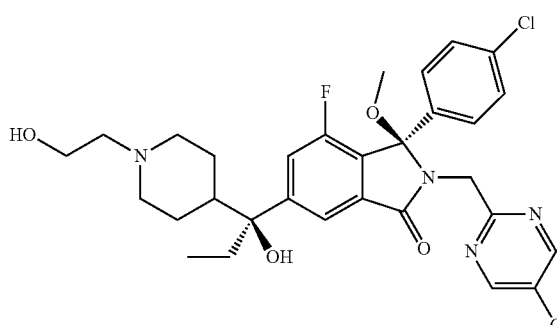

To a stirred mixture of (R)-3-(4-chlorophenyl)-2-((5-chloropyrimidin-2-yl)methyl)-4-fluoro-6-((S)-1-hydroxy-1-(piperidin-4-yl)propyl)-3-methoxyisoindolin-1-one (Example 450, 400 mg, 0.72 mmol) and K$_2$CO$_3$ (300 mg, 2.17 mmol) in DMF (5 mL) was added 2-bromoethanol (0.077 mL, 1.09 mmol). The mixture was stirred at room temperature for 18 h, then at 60° C. for 2.5 h. After this time, further 2-bromoethanol (0.05 mL, 0.71 mmol) was added and heating continued for 66 h. Further 2-bromoethanol (0.03 mL, 0.42 mmol) and K$_2$CO$_3$ (300 mg, 2.17 mmol) were added and the mixture stirred at 60° C. for a further 18 h. The mixture was diluted with EtOAc and washed twice with water, once with brine, dried (MgSO$_4$) and evaporated. The residual oil (340 mg) was purified by achiral preparative HPLC to afford the title compound (200 mg). Chiral preparative SFC afforded the faster eluting isomer (72 mg, 16%). $^1$H NMR (400 MHz, CDCl$_3$) 8.53 (2H, s), 7.67 (1H, d), 7.36-7.32 (3H, m), 7.21 (2H, d), 4.72-4.57 (2H, m), 3.57 (2H, dd), 3.09 (3H, s), 2.99 (1H, d), 2.87 (1H, d), 2.69 (1H, s), 2.48 (2H, dd), 2.08-1.82 (5H, m), 1.73-1.66 (2H, m), 1.43-1.30 (2H, m), 1.26-1.19 (1H, m), 0.69 (3H, t). [M+H]$^+$=603.

Example 551: (3R)-3-(4-chlorophenyl)-2-[(5-chloropyrimidin-2-yl)methyl]-4-fluoro-6-[(1S)-1-hydroxy-1-[1-(oxetan-3-yl)piperidin-4-yl]propyl]-3-methoxy-2,3-dihydro-1H-isoindol-1-one

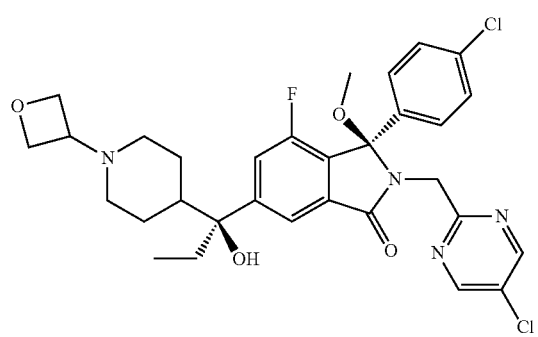 [SMILES: CC[C@@](O)(c1cc(F)c2c(c1)C(=O)N(Cc1ncc(Cl)cn1)[C@@]2(OC)c1ccc(Cl)cc1)C1CCN(C2COC2)CC1]

A carousel tube was charged with (R)-3-(4-chlorophenyl)-2-((5-chloropyrimidin-2-yl)methyl)-4-fluoro-6-((S)-1-hydroxy-1-(piperidin-4-yl)propyl)-3-methoxyisoindolin-1-one (Example 450, 326 mg, 0.58 mmol), oxetan-3-one (84 mg, 1.16 mmol), DCM (7.5 mL) and acetic acid (70 µL, 1.16 mmol). The mixture was stirred at room temperature for 1 h and then sodium triacetoxyborohydride (0.24 mg, 1.16 mmol) was added. The reaction was stirred overnight and then quenched with saturated aqueous NaHCO$_3$ solution (20 mL) and extracted with ethyl acetate (2×25 mL). The combined organic layers were dried (MgSO$_4$), filtered and evaporated under reduced pressure to give a crude yellow foam. The title compound (50 mg) was isolated by chiral SFC purification as an off white foam. $^1$H NMR (400 MHz, CDCl$_3$) 8.53 (2H, s), 7.66 (1H, d), 7.37-7.33 (3H, m), 7.21 (2H, d), 4.72-4.54 (6H, m), 3.45-3.37 (1H, m), 3.09 (3H, s), 2.83 (1H, d), 2.73 (1H, d), 1.98-1.66 (6H, m), 1.47-1.25 (3H, m), 0.70 (3H, dd), OH not observed. MS: [M+H]$^+$=615.

Example 552: (3R)-3-(4-chlorophenyl)-2-[(5-chloropyrimidin-2-yl)methyl]-4-fluoro-6-[1-[4-fluoro-1-(oxetan-3-yl)piperidin-4-yl]-1-hydroxypropyl]-3-methoxy-2,3-dihydro-1H-isoindol-1-one (*prepared and isolated as a single isomer)

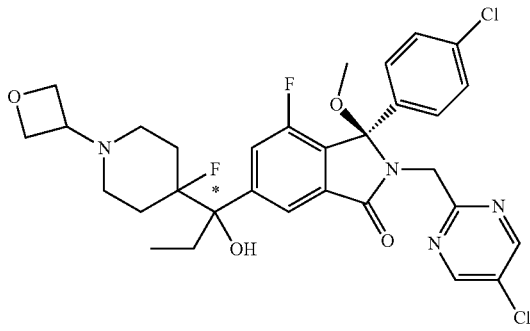 [SMILES: CCC(O)(c1cc(F)c2c(c1)C(=O)N(Cc1ncc(Cl)cn1)[C@@]2(OC)c1ccc(Cl)cc1)C1(F)CCN(C2COC2)CC1]

Starting from Example 544, the title compound was prepared by following procedures similar to those described in Example 551. $^1$H NMR (400 MHz, CDCl$_3$) 8.54 (2H, s), 7.77 (1H, s), 7.45 (1H, d), 7.38 (2H, d), 7.23 (2H, d), 4.72-4.51 (6H, m), 3.49-3.42 (1H, m), 3.09 (3H, s), 2.63-2.56 (2H, m), 2.26-2.17 (2H, m), 2.12-1.43 (6H, m), 0.70 (3H, dd), OH not observed. MS: [M+H]$^+$=633.

Starting from the appropriate acid intermediate [e.g. (−)-5-[1-(1-tert-butoxycarbonyl-4-piperidyl)-1-hydroxy-ethyl]-2-(4-chlorobenzoyl)-3-fluoro-benzoic acid (Preparation 24), 5-[(1S)-1-{1-[(tert-butoxy)carbonyl]piperidin-4-yl}-1-hydroxypropyl]-2-(4-chlorobenzoyl)-3-fluorobenzoic acid (Preparation 30B) or (−)-5-(1-(1-(tert-butoxycarbonyl)-4-fluoropiperidin-4-yl)-1-hydroxypropyl)-2-(4-chlorobenzoyl)-3-fluorobenzoic acid—slow eluting isomer (Preparation 38), the following compounds were prepared in three steps in a similar fashion to Example 286, steps 1 and 2 (using the appropriate amine in step 1 and alcohol in step 2) followed by reductive methylation (NaBH$_3$CN) using procedures similar to that described in Preparation 25, step 2. The appropriate amines were obtained commercially or prepared as described (e.g. Preparation 19). The appropriate alcohols, where not commercially available, were prepared as described herein (for example Preparation 1). The compounds were obtained as single isomers using chiral preparative HPLC. Examples 566 and 567 were prepared using (+)-5-[(1R)-1-{1-[(tert-butoxy)carbonyl]piperidin-4-yl}-1-hydroxypropyl]-2-(4-chlorobenzoyl)-3-fluorobenzoic acid (prepared in an analogous fashion to Preparation 30B)

| Example | Structure | Name | NMR Data | MS Data |
|---|---|---|---|---|
| 553 | 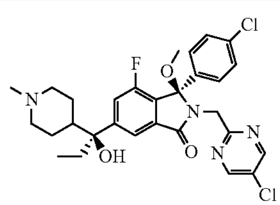 [SMILES: CC[C@@](O)(c1cc(F)c2c(c1)C(=O)N(Cc1ncc(Cl)cn1)[C@@]2(OC)c1ccc(Cl)cc1)C1CCN(C)CC1] | (3R)-3-(4-chlorophenyl)-2-[(5-chloropyrimidin-2-yl)methyl]-4-fluoro-6-[(1S)-1-hydroxy-1-(1-methylpiperidin-4-yl)propyl]-3-methoxy-2,3-dihydro-1H-isoindol-1-one | $^1$H NMR (400 MHz, CDCl$_3$) 8.53 (2H, s), 7.67 (1H, d), 7.37-7.32 (3H, m), 7.21 (2H, d), 4.71-4.57 (2H, m), 3.09 (3H, s), 2.92 (1H, d), 2.84 (1H, d), 2.24 (3H, s), 1.97-1.81 (6H, m), 1.45-1.25 (3H, m), 0.71 (3H, t), 1 exchangeable proton not observed. | [M + H]$^+$ = 573 |
| 554 | 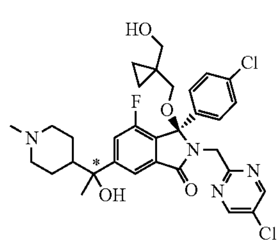 [SMILES: CN1CCC(C(C)(O)c2cc(F)c3c(c2)C(=O)N(Cc2ncc(Cl)cn2)[C@@]3(OCC2(CO)CC2)c2ccc(Cl)cc2)CC1] | (3R)-3-(4-chlorophenyl)-2-[(5-chloropyrimidin-2-yl)methyl]-4-fluoro-6-[1-hydroxy-1-(1-methylpiperidin-4-yl)ethyl]-3-{[1-(hydroxymethyl)cyclopropyl]methoxy}-2,3-dihydro-1H-isoindol-1-one | $^1$H NMR (400 MHz, CDCl$_3$) 8.54 (2H, s), 7.67 (1H, d), 7.40-7.34 (3H, m), 7.22 (2H, d), 4.67-4.55 (2H, m), 3.62-3.45 (3H, m), 2.99 (1H, d), 2.93-2.81 (2H, m), 2.23 (3H, s), 2.16 (1H, s), 1.89-1.77 (3H, m), 1.73-1.67 (1H, m), 1.43-1.31 (3H, m), 0.52-0.42 (3H, m), 0.34-0.30 (1H, m), 4 aliphatic protons hidden under water peak. | [M + H]$^+$ = 629 |

-continued

| Example | Structure | Name | NMR Data | MS Data |
|---|---|---|---|---|
| 555 | 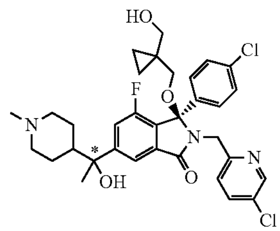 [SMILES: CN1CCC(C(C)(O)c2cc(F)c3c(c2)C(=O)N(Cc2ccc(Cl)cn2)[C@@]3(OCC2(CO)CC2)c2ccc(Cl)cc2)CC1] | (3R)-3-(4-chlorophenyl)-2-[(5-chloropyridin-2-yl)methyl]-4-fluoro-6-[1-hydroxy-1-(1-methylpiperidin-4-yl)ethyl]-3-{[1-(hydroxymethyl)cyclopropyl]methoxy}-2,3-dihydro-1H-isoindol-1-one | $^1$H NMR (400 MHz, CDCl$_3$) 8.38 (1H, d), 7.65 (1H, d), 7.55 (1 H, dd), 7.35 (2H, d), 7.30 (2H, d), 7.24 (2H, d), 4.48 (1H, d), 4.38 (1H, d), 3.69 (1H, d), 3.43-3.37 (2H, m), 2.96-2.78 (3H, m), 2.25 (3H, s), 1.98-1.85 (3H, m, overlapping H2O), 1.73-1.68 (1H, m), 1.58 (4H, s), 1.45-1.35 (3H, m), 1.28-1.21 (1H, m), 0.53-0.41 (3H, m), 0.30-0.25 (1H, m). | [M + H]$^+$ = 628 |
| 556 | 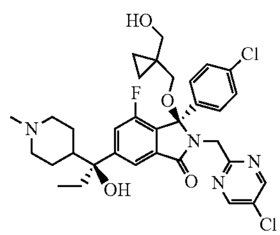 [SMILES: CC[C@@](O)(c1cc(F)c2c(c1)C(=O)N(Cc1ncc(Cl)cn1)[C@@]2(OCC1(CO)CC1)c1ccc(Cl)cc1)C1CCN(C)CC1] | (3R)-3-(4-chlorophenyl)-2-[(5-chloropyrimidin-2-yl)methyl]-4-fluoro-6-[(1S)-1-hydroxy-1-(1-methylpiperidin-4-yl)propyl]-3-{[1-(hydroxymethyl)cyclopropyl]methoxy}-2,3-dihydro-1H-isoindol-1-one | $^1$H NMR (400 MHz, CDCl$_3$) 8.54 (2H, s), 7.63 (1H, d), 7.37-7.32 (3H, m), 7.22 (2H, d), 4.68-4.54 (2H, m), 3.61-3.46 (3H, m), 3.00-2.90 (2H, m), 2.84-2.81 (1H, m), 2.23 (3H, s), 1.96-1.79 (5H, m), 1.66 (2H, m), 1.41-1.20 (5H, m), 0.71 (3H, t), 0.51 (1H, dd), 0.49-0.41 (1H, m), 0.34-0.30 (1H, m). | [M + H]$^+$ = 643 |
| 557 | 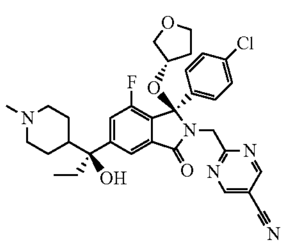 [SMILES: CC[C@@](O)(c1cc(F)c2c(c1)C(=O)N(Cc1ncc(C#N)cn1)[C@@]2(O[C@H]1CCOC1)c1ccc(Cl)cc1)C1CCN(C)CC1] | 2-{[(1R)-1-(4-chlorophenyl)-7-fluoro-5-[(1S)-1-hydroxy-1-(1-methylpiperidin-4-yl)propyl]-3-oxo-1-[(3S)-oxolan-3-yloxy]-2,3-dihydro-1H-isoindol-2-yl]methyl}pyrimidine-5-carbonitrile | $^1$H NMR (400 MHz, CDCl$_3$) 8.83 (2H, s), 7.66 (1H, d), 7.40 (1H, d), 7.36 (2H, d), 7.19 (2H, d), 4.82 (1H, d), 4.63 (1H, d), 4.25-4.19 (1H, m), 3.90 (1H, q), 3.76-3.64 (2H, m), 3.32 (1H, dd), 2.95 (1H, d), 2.84 (1H, d), 2.25 (3H, s), 1.98-1.83 (6H, m), 1.49-1.31 (3H, m), 1.30-1.23 (2H, m), 0.90-0.82 (1H, m), 0.70 (3H, t). | [M + H]$^+$ = 620 |
| 558 | 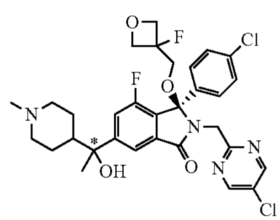 [SMILES: CN1CCC(C(C)(O)c2cc(F)c3c(c2)C(=O)N(Cc2ncc(Cl)cn2)[C@@]3(OCC2(F)COC2)c2ccc(Cl)cc2)CC1] | (3R)-3-(4-chlorophenyl)-2-[(5-chloropyrimidin-2-yl)methyl]-4-fluoro-3-[(3-fluorooxetan-3-yl)methoxy]-6-[1-hydroxy-1-(1-methylpiperidin-4-yl)ethyl]-2,3-dihydro-1H-isoindol-1-one | $^1$H NMR (400 MHz, CDCl$_3$) 8.55 (2H, s), 7.74 (1H, d), 7.41 (1H, dd), 7.33 (2H, d), 7.24 (2H, s), 4.79-4.67 (3H, m), 4.59-4.49 (2H, m), 4.34 (1H, dd), 4.13-3.99 (1H, m), 3.40 (1H, ddd), 2.94-2.84 (2H, m), 2.24 (3H, s), 1.91-1.79 (2H, m), 1.74-1.70 (1H, m), 1.60 (3H, s), 1.44-1.24 (4H, m), 0.90-0.82 (1H, m). | [M + H]$^+$ = 633 |
| 559 | 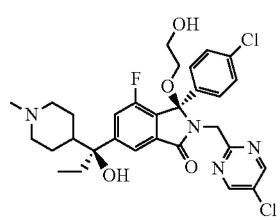 [SMILES: CC[C@@](O)(c1cc(F)c2c(c1)C(=O)N(Cc1ncc(Cl)cn1)[C@@]2(OCCO)c1ccc(Cl)cc1)C1CCN(C)CC1] | (3R)-3-(4-chlorophenyl)-2-[(5-chloropyrimidin-2-yl)methyl]-4-fluoro-6-[(1S)-1-hydroxy-1-(1-methylpiperidin-4-yl)propyl]-3-(2-hydroxyethoxy)-2,3-dihydro-1H-isoindol-1-one | $^1$H NMR (400 MHz, CDCl$_3$) 8.54 (2H, s), 7.66 (1H, d), 7.37-7.31 (3H, m), 7.24 (2H, d), 4.70-4.58 (2H, m), 3.76 (1H, ddd), 3.67-3.56 (2H, m), 3.25-3.19 (2H, m), 2.94 (1H, d), 2.87-2.82 (1H, m), 2.24 (3H, s), 1.97-1.81 (5H, m), 1.69-1.61 (2H, m), 1.43-1.20 (4H, m), 0.70 (3H, t). | [M + H]$^+$ = 603 |
| 560 | 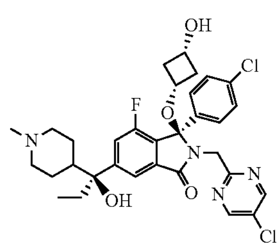 [SMILES: CC[C@@](O)(c1cc(F)c2c(c1)C(=O)N(Cc1ncc(Cl)cn1)[C@@]2(O[C@H]1C[C@@H](O)C1)c1ccc(Cl)cc1)C1CCN(C)CC1] | (3R)-3-(4-chlorophenyl)-2-[(5-chloropyrimidin-2-yl)methyl]-4-fluoro-6-[(1S)-1-hydroxy-1-(1-methylpiperidin-4-yl)propyl]-3-[cis-3-hydroxycyclobutoxy]-2,3-dihydro-1H-isoindol-1-one | $^1$H NMR (400 MHz, CDCl$_3$) 8.52 (2H, s), 7.63 (1H, s), 7.37-7.31 (3H, m), 7.20 (2H, d), 4.68-4.55 (2H, m), 3.72-3.57 (2H, m), 2.93 (1H, d), 2.82 (1H, d), 2.35-2.27 (1H, m), 2.23 (3H, s), 2.05-1.79 (9H, m), 1.69-1.62 (2H, m), 1.44-1.31 (2H, m), 1.24 (1H, d), 0.68 (3H, t). | [M + H]$^+$ = 629 |

| Example | Name | NMR Data | MS Data |
|---|---|---|---|
| 561 | 2-{[(1R)-1-(4-chlorophenyl)-7-fluoro-5-[1-(4-fluoro-1-methylpiperidin-4-yl)-1-hydroxypropyl]-3-oxo-1-[(3S)-oxolan-3-yloxy]-2,3-dihydro-1H-isoindol-2-yl]methyl}pyrimidine-5-carbonitrile | $^1$H NMR (400 MHz, CDCl$_3$) 8.83 (2H, s), 7.72 (1H, s), 7.54 (1H, d), 7.38 (2H, d), 7.19 (2H, d), 4.84 (1H, d), 4.61 (1H, d), 4.19 (1H, ddd), 3.94-3.87 (1H, m), 3.76-3.63 (2H, m), 3.32 (1H, dd), 2.73-2.65 (2H, m), 2.26 (3H, s), 2.25-2.15 (4H, m), 2.09-1.70 (6H, m), 1.54-1.36 (1H, m), 0.69 (3H, dd). | [M + H]$^+$ = 638 |
| 562 | (3R)-3-(4-chlorophenyl)-2-[(5-chloropyrimidin-2-yl)methyl]-4-fluoro-6-[(1S)-1-hydroxy-1-(1-methylpiperidin-4-yl)propyl]-3-[(2R)-2-hydroxypropoxy]-2,3-dihydro-1H-isoindol-1-one | $^1$H NMR (400 MHz, CDCl$_3$) 8.53 (2H, s), 7.66 (1H, d), 7.36-7.31 (3H, m), 7.23 (2H, d), 4.64 (2H, s), 3.99-3.92 (1H, m), 3.33 (1H, dd), 3.04 (2H, dd), 2.95-2.91 (1H, m), 2.32 (3H, s), 2.08-1.84 (8H, m), 1.34-1.25 (3H, m), 1.09 (3H, d), 0.74-0.68 (3H, m). | [M + H]$^+$ = 617 |
| 563 | (3R)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-methoxy-2,3-dihydro-1H-isoindol-1-one | $^1$H NMR (500 MHz, DMSO-d6) δ 8.75 (s, 2H), 7.72 (s, 1H), 7.45 (d, J = 10.9 Hz, 1H), 7.35-7.27 (m, 4H), 5.56 (s, 1H), 4.55 (d, J = 16.7 Hz, 1H), 4.51 (d, J = 16.6 Hz, 1H), 2.99 (s, 3H), 2.83-1.57 (m, 12H), 1.12 (m, 1H), 0.57 (t, J = 7.2 Hz, 3H). | [M + H]$^+$ = 591 |
| 564 | 1-({[(1R)-1-(4-chlorophenyl)-2-[(5-chloropyrimidin-2-yl)methyl]-7-fluoro-5-[1-(4-fluoro-1-methylpiperidin-4-yl)-1-hydroxypropyl]-3-oxo-2,3-dihydro-1H-isoindol-1-yl]oxy}methyl)cyclopropane-1-carbonitrile | 1H NMR (500 MHz, DMSO-d6) δ 8.76 (s, 2H), 7.69 (s, 1H), 7.46 (d, J = 10.8 Hz, 1H), 7.42-7.31 (m, 4H), 5.54 (s, 1H), 4.56 (s, 2H), 3.64 (d, J = 9.9 Hz, 1H), 3.02 (d, J = 9.9 Hz, 1H), 2.77-2.65 (m, 1H), 2.60-2.51 (m, 1H), 2.24-1.67 (m, 10H), 1.31-1.18 (m, 2H), 1.11 (t, J = 11.9 Hz, 1H), 0.96-0.82 (m, 2H), 0.56 (t, J = 7.2 Hz, 3H). | [M + H]$^+$ = 656 |
| 565 | (3R)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-(2-hydroxyethoxy)-2,3-dihydro-1H-isoindol-1-one | $^1$H NMR (400 MHz, CDCl$_3$) 8.54 (2H, s), 7.78 (1H, s), 7.43 (1H, d), 7.37 (2H, d), 7.24 (2H, d), 4.69-4.62 (2H, m), 3.79-3.74 (1H, m), 3.68-3.55 (2H, m), 3.25-3.18 (1H, m), 2.76-2.72 (2H, m), 2.42 (1H, s), 2.29 (3H, s), 2.27-2.14 (3H, m), 2.10-1.49 (6H, m), 0.70 (3H, t). | [M + H]$^+$ = 621 |
| 566 | (3R)-3-(4-chlorophenyl)-2-[(5-chloropyrimidin-2-yl)methyl]-4-fluoro-6-[(1R)-1-hydroxy-1-(1-methylpiperidin-4-yl)propyl]-3-methoxy-2,3-dihydro-1H-isoindol-1-one | $^1$H NMR (400 MHz, CDCl$_3$) 8.53 (2H, s), 7.69 (1H, s), 7.36-7.31 (3H, m), 7.21 (2H, d), 4.70 (1H, d), 4.57 (1H, d), 3.63-3.45 (1H, bs), 3.10 (3H, s), 2.97-2.93 (1H, m), 2.85-2.80 (1H, m), 2.24 (3H, s), 1.97-1.84 (5H, m), 1.44-1.35 (2H, m), 1.28-1.24 (2H, m), 0.70 (3H, t). | [M + H]$^+$ = 573 |
| 567 | (3R)-3-(4-chlorophenyl)-2-[(5-chloropyrimidin-2-yl)methyl]-4-fluoro-6-[(1R)-1-hydroxy-1-(1-methylpiperidin-4-yl)propyl]-3-[(3S)-oxolan-3-yloxy]-2,3-dihydro-1H-isoindol-1-one | $^1$H NMR (400 MHz, CDCl$_3$) 8.53 (2H, s), 7.71 (1H, d), 7.35-7.31 (3H, m), 7.19 (2H, d), 4.72-4.57 (2H, m), 4.25 (1H, ddd), 3.88 (1H, q), 3.74-3.65 (2H, m), 3.31 (1H, dd), 2.93 (1H, d), 2.82 (1H, d), 2.23 (3H, s), 2.01 (9H, s), 1.48-1.19 (3H, m), 0.69 (3H, t). | [M + H]$^+$ = 629 |

-continued

| Example | Structure | Name | NMR Data | MS Data |
|---|---|---|---|---|
| 568 | 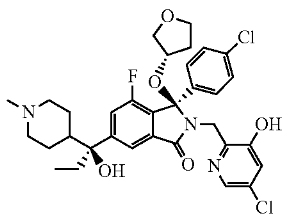 [SMILES: CC[C@@](O)(c1cc(F)c2c(c1)C(=O)N(Cc1ncc(Cl)cc1O)[C@@]2(O[C@H]1CCOC1)c1ccc(Cl)cc1)C1CCN(C)CC1] | 2-[(5-chloro-3-hydroxypyridin-2-yl)methyl]-3-(4-chlorophenyl)-4-fluoro-6-[(1S)-1-hydroxy-1-(1-methylpiperidin-4-yl)propyl]-3-[(3S)-oxolan-3-yloxy]-2,3-dihydro-1H-isoindol-1-one | $^1$H NMR (400 MHz, CDCl$_3$) 7.80 (1H, d), 7.66 (1H, d), 7.40-7.35 (1H, m), 7.25-7.22 (5H, m), 4.53 (2H, dd), 3.90-3.80 (2H, m), 3.69-3.57 (2H, m), 3.22 (1H, dd), 2.96 (1H, s), 2.89-2.87 (1H, m), 2.29 (3H, s), 1.96-1.83 (6H, m), 1.70-1.63 (4H, m), 0.67 (3H, t), 0.07 (2H, s), OH not observed. | [M + H]$^+$ = 644 |
| 570 | 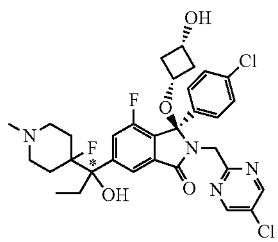 | (3R)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-[cis-3-hydroxycyclobutoxy]-2,3-dihydro-1H-isoindol-1-one | $^1$H NMR (400 MHz, CDCl$_3$) 8.52 (2H, s), 7.72 (1H, s), 7.46 (1H, d), 7.37 (2H, d), 7.21 (2H, d), 4.62 (2H, dd), 3.71-3.55 (2H, m), 2.71-2.62 (3H, m), 2.39-2.28 (2H, m), 2.25 (3H, s), 2.23-2.13 (3H, m), 2.08-1.70 (7H, m), 1.58-1.39 (1H, m), 0.69 (3H, t). | [M + H]$^+$ = 642 |
| 571 | 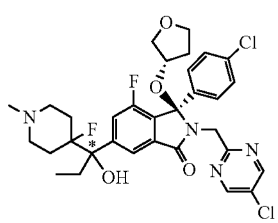 [SMILES: CCC(O)(c1cc(F)c2c(c1)C(=O)N(Cc1ncc(Cl)cn1)[C@@]2(O[C@H]1CCOC1)c1ccc(Cl)cc1)C1(F)CCN(C)CC1] | (3R)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-[(3S)-oxolan-3-yloxy]-2,3-dihydro-1H-isoindol-1-one | $^1$H NMR (400 MHz, CDCl$_3$) 8.52 (2H, s), 7.73 (1H, s), 7.51 (1H, d), 7.37 (2H, d), 7.19 (2H, d), 4.74 (1H, d), 4.56 (1H, d), 4.20 (1H, m), 3.88 (1H, q), 3.74-3.62 (2H, m), 3.29 (1H, dd), 2.74-2.66 (2H, m), 2.26 (3H, s), 2.25-2.14 (5H, m), 2.04-1.67 (6H, m), 0.69 (3H, dd). | [M + H]$^+$ = 647 |
| 572 | 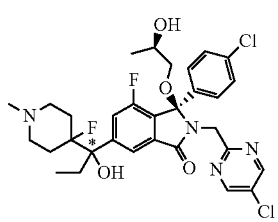 [SMILES: CCC(O)(c1cc(F)c2c(c1)C(=O)N(Cc1ncc(Cl)cn1)[C@@]2(OC[C@@H](C)O)c1ccc(Cl)cc1)C1(F)CCN(C)CC1] | (3R)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-[(2R)-2-hydroxypropoxy]-2,3-dihydro-1H-isoindol-1-one | $^1$H NMR (400 MHz, CDCl$_3$) 8.54 (2H, s), 7.75 (1H, s), 7.45 (1H, d), 7.36 (2H, d), 7.24 (2H, d), 4.69-4.59 (2H, m), 4.01-3.94 (1H, m), 3.34-3.29 (1H, m), 3.03 (1H, dd), 2.72-2.65 (2H, m), 2.45 (1H, dd), 2.25 (3H, s), 2.23-2.15 (4H, m), 2.08-1.72 (5H, m), 1.09 (3H, d), 0.70 (3H, dd). | [M + H]$^+$ = 635 |
| 574 | 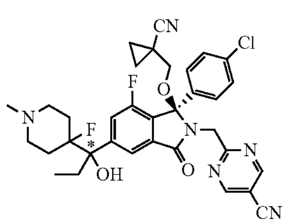 [SMILES: CCC(O)(c1cc(F)c2c(c1)C(=O)N(Cc1ncc(C#N)cn1)[C@@]2(OCC1(C#N)CC1)c1ccc(Cl)cc1)C1(F)CCN(C)CC1] | 2-{[(1R)-1-(4-chlorophenyl)-1-[(1-cyanocyclopropyl)methoxy]-7-fluoro-5-[1-(4-fluoro-1-methylpiperidin-4-yl)-1-hydroxypropyl]-3-oxo-2,3-dihydro-1H-isoindol-2-yl]methyl}pyrimidine-5-carbonitrile | $^1$H NMR (400 MHz, CDCl$_3$) 8.88 (2H, s), 7.77 (1H, s), 7.46 (1H, d), 7.41 (2H, d), 7.30 (2H, d), 4.81 (1H, d), 4.63 (1H, d), 4.04 (1H, d), 2.76-2.64 (3H, m), 2.30 (1H, d), 2.26 (3H, s), 2.24-2.13 (3H, m), 2.09-1.70 (4H, m), 1.51-1.25 (3H, m), 0.98 (1H, ddd), 0.85 (1H, ddd), 0.70 (3H, dd) | [M + H]+ = 647. |
| 575 | 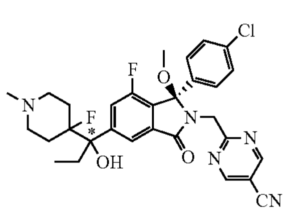 [SMILES: CCC(O)(c1cc(F)c2c(c1)C(=O)N(Cc1ncc(C#N)cn1)[C@@]2(OC)c1ccc(Cl)cc1)C1(F)CCN(C)CC1] | 2-{[(1R)-1-(4-chlorophenyl)-7-fluoro-5-[1-(4-fluoro-1-methylpiperidin-4-yl)-1-hydroxypropyl]-1-methoxy-3-oxo-2,3-dihydro-1H-isoindol-2-yl]methyl}pyrimidine-5-carbonitrile | $^1$H NMR (400 MHz, CDCl$_3$) 8.84 (2H, s), 7.77 (1H, s), 7.48 (1H, d), 7.37 (2H, d), 7.22 (2H, d), 4.70 (2H, dd), 3.12 (3H, s), 2.73-2.64 (2H, m), 2.30-2.30 (1H, m), 2.26 (3H, s), 2.24-2.13 (3H, m), 2.10-1.70 (4H, m), 1.55-1.35 (1H, m), 0.71 (3H, dd) | [M + H]+ = 582. |

Example 563a: (3R)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-methoxy-2,3-dihydro-1H-isoindol-1-one-L-(+)-lactic acid salt (Example isolated as a single isomer at the position shown*)

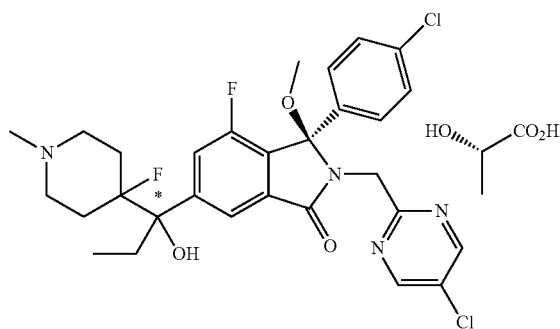

(3R)-3-(4-Chlorophenyl)-2-[(5-chloropyrimidin-2-yl)methyl]-4-fluoro-6-[1-(4-fluoro-1-methylpiperidin-4-yl)-1-hydroxypropyl]-3-methoxy-2,3-dihydro-1H-isoindol-1-one (Example 563) (130 mg) was dissolved in EtOH (2 mL), to which was added L(+)-lactic acid (1 mol. eq. as a solution in EtOH). The solution was evaporated to dryness and triturated with diethylether to give a colourless solid (147 mg). 1H NMR (500 MHz, DMSO-d6) δ 8.75 (s, 2H), 7.71 (s, 1H), 7.45 (d, J=10.9 Hz, 1H), 7.36-7.26 (m, 4H), 5.56 (s, 1H), 4.55 (d, J=16.7 Hz, 1H), 4.51 (d, J=16.6 Hz, 1H), 3.99 (q, J=6.9 Hz, 1H), 2.99 (s, 3H), 2.72 (d, J=11.2 Hz, 1H), 2.63-2.55 (m, 1H), 2.21-2.10 (m, 4H), 2.13-2.03 (m, 1H), 2.03-1.69 (m, 5H), 1.22 (d, J=6.9 Hz, 3H), 1.17-1.05 (m, 1H), 0.56 (t, J=7.2 Hz, 3H). LCMS: m/z=559 [M-OMe$^-$]$^+$.

Example 563b: (3R)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-methoxy-2,3-dihydro-1H-isoindol-1-one—hydrochloride salt (Example isolated as a single isomer at the position shown*)

(3R)-3-(4-Chlorophenyl)-2-[(5-chloropyrimidin-2-yl)methyl]-4-fluoro-6-[1-(4-fluoro-1-methylpiperidin-4-yl)-1-hydroxypropyl]-3-methoxy-2,3-dihydro-1H-isoindol-1-one (Example 563) (131 mg) was dissolved in EtOAc (1.5 mL), to which was added hydrochloric acid (166 µL; 2N in diethylether). The resulting precipitate was collected by filtration and washed successively with diethylether and hexane to give the product as a colourless solid (117 mg).

1H NMR (500 MHz, DMSO-d6) δ 10.02 (broad s, 1H), 8.75 (s, 2H), 7.74 (s, 1H), 7.49 (d, J=10.7 Hz, 1H), 7.31 (m, 4H), 5.84 (s, 1H), 4.55 (d, J=16.6 Hz, 1H), 4.52 (d, J=16.6 Hz, 1H), 3.44-3.34 (m, 1H), 3.29-3.21 (m, 1H), 3.04 (d, J=12.1 Hz, 1H), 3.01 (s, 3H), 2.99-2.89 (m, 1H), 2.73 (d, J=4.3 Hz, 3H), 2.26-1.98 (m, 4H), 1.99-1.88 (m, 1H), 1.56-1.40 (m, 1H), 0.59 (t, J=7.2 Hz, 3H). LCMS: m/z=559 [M-OMe$^-$]$^+$ Example 564a: 1-({[(1R)-1-(4-chlorophenyl)-2-[(5-chloropyrimidin-2-yl)methyl]-7-fluoro-5-[1-(4-fluoro-1-methylpiperidin-4-yl)-1-hydroxypropyl]-3-oxo-2,3-dihydro-1H-isoindol-1-yl]oxy}methyl)cyclopropane-1-carbonitrile-L-(+)-lactic acid salt (Example isolated as a single isomer at the position shown*)

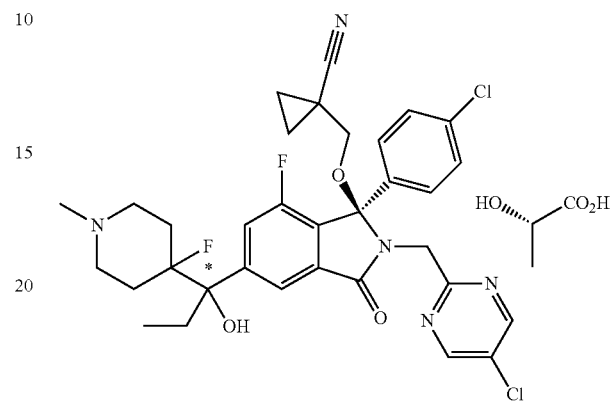

Starting from 1-({[(1R)-1-(4-chlorophenyl)-2-[(5-chloropyrimidin-2-yl)methyl]-7-fluoro-6-[1-(4-fluoro-1-methylpiperidin-4-yl)-1-hydroxypropyl]-3-oxo-2,3-dihydro-1H-isoindol-1-yl]oxy}methyl)cyclopropane-1-carbonitrile (Example 564), the title compound was prepared using procedures similar to those described in Example 563a. $^1$H NMR (500 MHz, DMSO-d6) δ 8.76 (s, 2H), 7.69 (s, 1H), 7.46 (d, J=10.8 Hz, 1H), 7.42-7.32 (m, 4H), 5.55 (s, 1H), 4.56 (s, 2H), 3.99 (q, J=6.9 Hz, 1H), 3.63 (d, J=9.9 Hz, 1H), 3.02 (d, J=9.9 Hz, 1H), 2.71 (d, J=11.1 Hz, 1H), 2.61-2.55 (m, 1H), 2.20-2.10 (m, 4H), 2.10-2.01 (m, 1H), 2.01-1.68 (m, 5H), 1.25-1.19 (m, 5H), 1.12 (t, J=12.2 Hz, 1H), 0.96-0.82 (m, 2H), 0.56 (t, J=7.2 Hz, 3H). LCMS: m/z=656 [M+H*].

Example 564b: 1-({[(1R)-1-(4-chlorophenyl)-2-[(5-chloropyrimidin-2-yl)methyl]-7-fluoro-5-[1-(4-fluoro-1-methylpiperidin-4-yl)-1-hydroxypropyl]-3-oxo-2,3-dihydro-1H-isoindol-1-yl]oxy}methyl)cyclopropane-1-carbonitrile—hydrochloride salt (Example isolated as a single isomer at the position shown*)

Starting from 1-({[(1R)-1-(4-chlorophenyl)-2-[(5-chloropyrimidin-2-yl)methyl]-7-fluoro-5-[1-(4-fluoro-1-methylpiperidin-4-yl)-1-hydroxypropyl]-3-oxo-2,3-dihydro-1H-isoindol-1-yl]oxy}methyl)cyclopropane-1-carbonitrile (Example 564), the title compound was prepared using procedures similar to those described in Example 563b. 1H NMR (500 MHz, DMSO-d6) δ 10.13 (broad s, 1H), 8.76 (s, 2H), 7.73 (s, 1H), 7.49 (d, J=10.7 Hz, 1H), 7.44-7.32 (m, 4H), 5.80 (s, 1H), 4.56 (d, J=17.0 Hz, 1H), 4.55 (d, J=16.9 Hz, 1H), 3.65 (d, J=9.9 Hz, 1H), 3.45-3.32 (m, 1H), 3.27-3.19 (m, 1H), 3.05 (d, J=9.9 Hz, 1H), 3.03-2.87 (m, 2H), 2.71 (s, 3H), 2.27-1.87 (m, 5H), 1.60-1.47 (m, 1H), 1.30-1.18 (m, 2H), 1.00-0.87 (m, 2H), 0.60 (t, J=7.2 Hz, 3H). LCMS: m/z=656 [M+H$^+$]$^+$.

Example 541a: (3R)-3-(4-chlorophenyl)-2-[(5-chloropyrimidin-2-yl)methyl]-4-fluoro-6-[1-(4-fluoropiperidin-4-yl)-1-hydroxypropyl]-3-[(3S)-oxolan-3-yloxy]-2,3-dihydro-1H-isoindol-1-one-L-(+)-lactic acid salt (Example isolated as a single isomer at the position shown*)

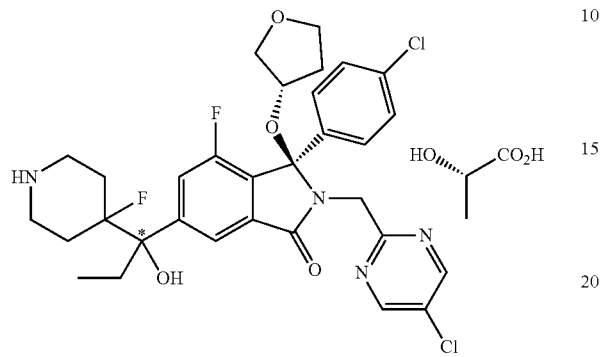

Starting from (3R)-3-(4-chlorophenyl)-2-[(5-chloropyrimidin-2-yl)methyl]-4-fluoro-6-[1-(4-fluoropiperidin-4-yl)-1-hydroxypropyl]-3-[(3S)-oxolan-3-yloxy]-2,3-dihydro-1H-isoindol-1-one (Example 541), the title compound was prepared by using procedures similar to those described in Example 563a. LCMS: m/z=633 [M+H$^{+-}$]$^+$.

Example 576: 2-{[(1R)-1-(4-chlorophenyl)-7-fluoro-1-({1-[hydroxydideuteromethyl]cyclopropyl}dideuteromethoxy)-5-(2-hydroxybutan-2-yl)-3-oxo-2,3-dihydro-1H-isoindol-2-yl]methyl}pyrimidine-5-carbonitrile (*single isomer separated and isolated)

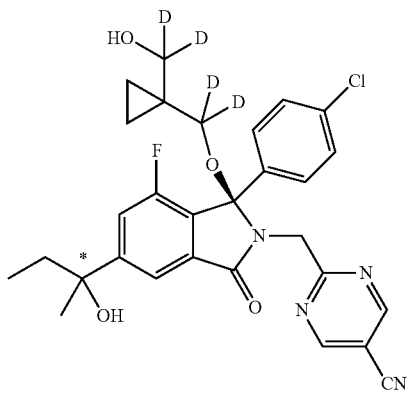 [SMILES: [2H]C([2H])(O)C1(C([2H])([2H])O[C@]2(c3ccc(Cl)cc3)c3c(F)cc(C(C)(O)CC)cc3C(=O)N2Cc2ncc(C#N)cn2)CC1]

Starting from (−)-2-(4-chlorobenzoyl)-3-fluoro-5-(2-hydroxybutan-2-yl)benzoic acid (Preparation 39), and the appropriate amine and alcohol, the title compound was prepared using procedures similar to those described in Example 280. The product was isolated as the faster-eluting diastereoisomer. 1H NMR (400 MHz, DMSO): 9.11 (2H, s), 7.74 (1H, d), 7.48 (1H, d), 7.36-7.31 (2H, m), 7.30 (2H, d), 5.17 (1H, s), 4.68 (1H, d), 4.59 (1H, d), 4.37 (1H, s), 1.82-1.68 (2H, m), 1.47 (3H, s), 0.70 (3H, t), 0.41-0.30 (2H, m), 0.27-0.16 (2H, m). MS [M-C3]+=449.

Example 577: 2-{[(1R)-1-(4-chlorophenyl)-7-fluoro-1-({1-[hydroxydideuteromethyl]cyclopropyl}dideuteromethoxy)-5-(2-hydroxybutan-2-yl)-3-oxo-2,3-dihydro-1H-isoindol-2-yl]methyl}pyrimidine-5-carbonitrile (*single isomer separated and isolated)

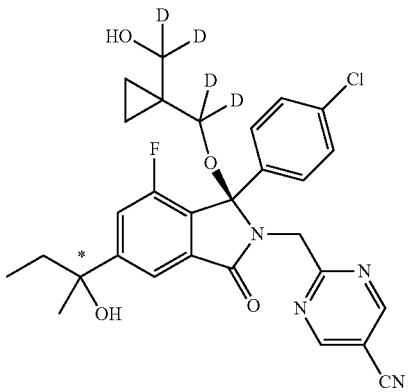 [SMILES: [2H]C([2H])(O)C1(C([2H])([2H])O[C@]2(c3ccc(Cl)cc3)c3c(F)cc(C(C)(O)CC)cc3C(=O)N2Cc2ncc(C#N)cn2)CC1]

Starting from (+)-2-(4-chlorobenzoyl)-3-fluoro-5-(2-hydroxybutan-2-yl)benzoic acid (preparation 39) and the appropriate amine and alcohol, the title compound was prepared using procedures similar to those described in Example 280. The product was isolated as the faster-eluting diastereoisomer. 1H NMR (400 MHz, DMSO): 9.11 (2H, s), 7.74 (1H, s), 7.47 (1H, d), 7.35-7.25 (4H, m), 5.18 (1H, d), 4.70 (1H, d), 4.58 (1H, d), 4.38 (1H, d), 1.81-1.68 (2H, m), 1.47 (3H, s), 0.70 (3H, t), 0.42-0.31 (2H, m), 0.27-0.17 (2H, m). MS [M-C3]+=449.

Example 578: (3R)-3-(4-chlorophenyl)-2-[(5-chloropyrimidin-2-yl)methyl]-4-fluoro-6-[1-(4-fluorooxan-4-yl)-1-hydroxyethyl]-3-(2-hydroxyethoxy)-2,3-dihydro-1H-isoindol-1-one (Example isolated as a single isomer at the position shown*)

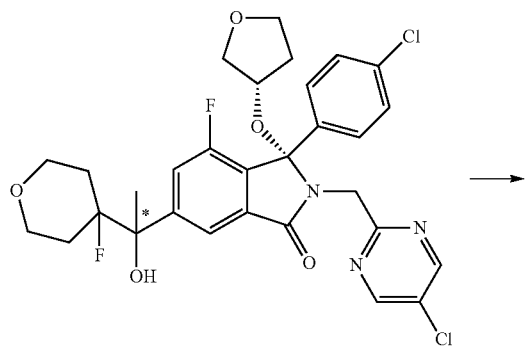

-continued

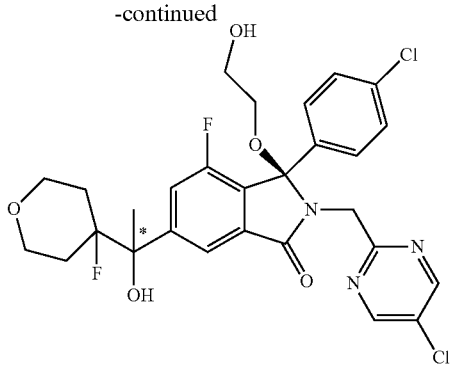

The title compound was prepared from (3S)-3-(4-chlorophenyl)-2-[(5-chloropyrimidin-2-yl)methyl]-4-fluoro-6-[1-(4-fluorooxan-4-yl)-1-hydroxyethyl]-3-[(3S)-oxolan-3-yloxy]-2,3-dihydro-1H-isoindol-1-one and ethane-1,2-diol using the conditions described in, Example 1, step 2. The starting material is the (3S epimer) of Example 493 and was prepared using similar procedures to those described therein. Purification of the product by chiral HPLC gave the title compound (18 mg, 33% yield). ¹H NMR (400 MHz, DMSO-d₆): 8.72 (2H, s), 7.77 (1H, s), 7.48 (1H, d), 7.39-7.26 (4H, m), 5.87 (1H, s), 4.71-4.59 (2H, m), 4.55 (1H, d), 3.83 (1H, dd), 3.71 (1H, dd), 3.55-3.32 (5H, m), 3.02-2.93 (1H, m), 2.10-1.66 (4H, m), 1.57 (3H, s); LCMS: [M−H]⁻= 592.

Example 579: 6-{[(1R)-1-(4-chlorophenyl)-7-fluoro-1-[(2S)-3-fluoro-2-hydroxypropoxy]-5-[1-(4-fluorooxan-4-yl)-1-hydroxyethyl]-3-oxo-2,3-dihydro-1H-isoindol-2-yl]methyl}pyridine-3-carbonitrile (Example isolated as a single isomer at the position shown*)

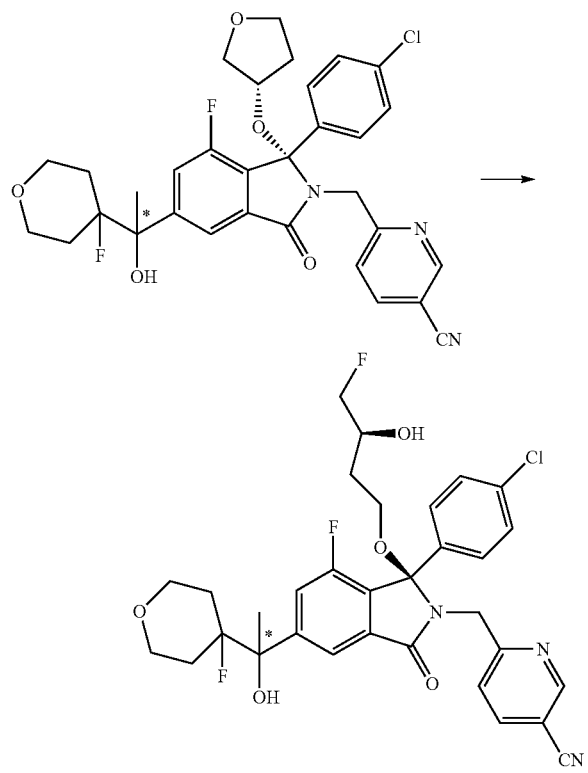

The title compound was prepared from 6-{[(1S)-1-(4-chlorophenyl)-7-fluoro-5-[1-(4-fluorooxan-4-yl)-1-hydroxyethyl]-3-oxo-1-[(3S)-oxolan-3-yloxy]-2,3-dihydro-1H-isoindol-2-yl]methyl}pyridine-3-carbonitrile and (2S)-3-fluoropropane-1,2-diol using the conditions described in, Example 1, step 2. The starting material is the (3S epimer) of Example 388 and was prepared using similar procedures to those described therein. Purification of the product by chiral HPLC gave the title compound. 1H NMR (400 MHz, DMSO-d6): 8.77 (1H, d), 8.09 (1H, dd), 7.80 (1H, s), 7.50 (1H, d), 7.38-7.24 (5H, m), 5.88 (1H, s), 5.27 (1H, d), 4.63-4.56 (1H, m), 4.54 (1H, d), 4.48-4.36 (1H, m), 4.36-4.24 (1H, m), 3.83 (1H, dd), 3.76-3.63 (2H, m), 3.47 (1H, t), 3.36 (1H, d), 3.18 (1H, dd), 2.93 (1H, dd), 2.10-1.70 (4H, m), 1.59 (3H, s); LCMS: [M−H]⁻=614.

Example 580: (3R)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-[2-hydroxy(1,1,2,2-tetradeutero)ethoxy]-2,3-dihydro-1H-isoindol-1-one

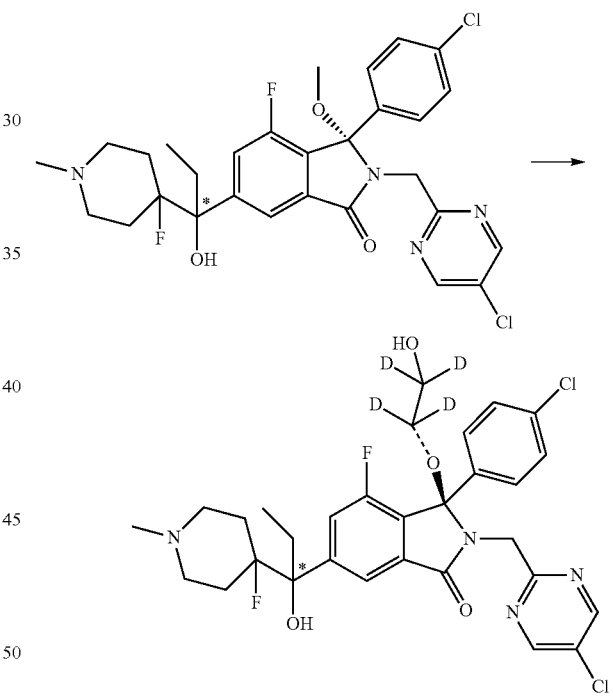

The title compound was prepared from (3S)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-methoxy-2,3-dihydro-1H-isoindol-1-one and tetradeuteroethane-1,2-diol using the conditions described in, Example 1, step 2. The starting material is the (3S epimer) of Example 563 and was prepared using similar procedures to those described therein. Purification of the product by chiral HPLC gave the title compound. 1H NMR (400 MHz, Me-d3-OD): 8.61 (2H, s), 7.88 (1H, s), 7.53 (1H, d), 7.42 (2H, d), 7.26 (2H, d), 4.74-4.62 (2H, m), 2.87-2.79 (1H, m), 2.76-2.68 (1H, m), 2.37-2.17 (6H, m), 2.16-1.95 (3H, m), 1.95-1.84 (1H, m), 1.38-1.28 (1H, m), 0.70 (3H, t). [M+H⁺]⁺=647.

Biological Assays

MDM2-p53 Interaction Using a 96-Well Plate Binding Assay (ELISA)

The ELISA assay was performed in streptavidin coated plates which were preincubated with 200 µl per well of 1 µg ml$^{-1}$ biotinylated IP3 peptide. The plates were ready to use for MDM2 binding after washing the plate with PBS.

Compounds and control solutions in DMSO aliquoted in 96-well plates were pre-incubated in a final 2.5-5% (v/v) DMSO concentration at room temperature (for example 20° C.) for 20 min with 190 µl aliquots of optimized concentrations of in vitro translated MDM2, before transfer of the MDM2-compound mixture to the b-IP3 streptavidin plates, and incubation at 4° C. for 90 min. After washing three times with PBS to remove unbound MDM2, each well was incubated at 20° C. for 1 hour with a TBS-Tween (50 mM Tris pH7.5; 150 mM NaCl; 0.05% Tween 20 nonionic detergent) buffered solution of primary mouse monoclonal anti-MDM2 antibody (Ab-5, Calbiochem, used at a 1/10000 or 1/200 dilution depending on the antibody stock solution used), then washed three times with TBS-Tween before incubation for 45 mins at 20° C. with a TBS-Tween buffered solution of a goat-anti-mouse horseradish peroxidase (HRP) conjugated secondary antibody (used at 1/20000 or 1/2000 depending on the antibody stock solution). The unbound secondary antibody was removed by washing three times with TBS-Tween. The bound HRP activity was measured by enhanced chemiluminesence (ECL™, Amersham Biosciences) using the oxidation of the diacylhydrazide substrate, luminol, to generate a quantifiable light signal. The percentage of MDM2 inhibition at a given concentration is calculated as the [1−(RLU detected in the compound treated sample−RLU negative DMSO control)÷(RLU of DMSO positive and negative controls)]×100 or as the (RLU detected in the compound treated sample÷RLU of DMSO controls)×100. The IC$_{50}$ was calculated using a plot of % MDM2 inhibition vs concentration and is the average of two or three independent experiments.

Western Blot Analysis

SJSA cells were treated for 6 hours with 5, 10 and 20 µM of compounds in 0.5% DMSO. The cells together with 0.5% DMSO only controls were washed with ice-cold phosphate buffered saline (PBS) and protein extracts prepared by lysing the cells in SDS buffer (62.5 mM Tris pH 6.8; 2% sodium dodecyl sulphate(SDS); 10% glycerol) with sonication for 2×5 seconds (Soniprep 150ME) to break down high molecular weight DNA and reduce the viscosity of the samples. The protein concentration of the samples was estimated using the Pierce BCA assay system (Pierce, Rockford, Ill.) and 50 µg aliquots of protein analysed using standard SDS-polyacrylamide gel electrophoresis (SDS-PAGE) and Western immunoblotting procedures. β-mercaptoethanol (5%) and bromophenol blue (0.05%) were added and the samples, which were then boiled for 5 minutes, followed by brief centrifugation, before loading onto a pre-cast 4-20% gradient Tris-Glycine buffered SDS-polyacrylamide gel (Invitrogen). Molecular weight standards (SeeBlue™, Invitrogen) were included on every gel and electrophoresis was carried out in a Novex XL tank (Invitrogen) at 180 volts for 90 minutes.

The separated proteins were transferred electrophoretically overnight from the gel onto a Hybond C nitrocellulose membrane (Amersham) using a BioRad electrophoresis tank and 25 mM Tris, 190 mM glycine and 20% methanol transfer buffer at 30 volts for two hours or at 70 volts. Primary antibodies used for immunodetection of the transferred proteins were: mouse monoclonal NCL-p53DO-7 (Novocastra) at 1:1000; MDM2(Ab-1, clone IF2) (Oncogene) at 1:500; WAF1 (Ab-1, clone 4D10) (Oncogene) at 1:100; Actin (AC40) (Sigma) at 1:1000. The secondary antibody used was peroxidase conjugated, affinity purified, goat anti-mouse (Dako) at 1:1000. Protein detection and visualisation was performed by enhanced chemiluminescence (ECL™, Amersham) with light detection by exposure to blue-sensitive autoradiography film (Super RX, Fuji).

Protocol A: SJSA-1 and SN40R2 Assays

The MDM2 amplified cell lines tested were an isogenic matched pair of p53 wild-type and mutated osteosarcoma (SJSA-1 and SN40R2, respectively) All cell cultures were grown in RPMI 1640 medium (Gibco, Paisley, UK) supplemented with 10% fetal calf serum and routinely tested and confirmed negative for *mycoplasma* infection. The growth of cells and its inhibition was measured using the sulphorhodamine B (SRB) method as previously outlined. 100 µl of 3×10$^4$/ml and 2×10$^4$/ml SJSA-1 and SN40R2 cells, respectively, were seeded into 96-well tissue culture plates and incubated at 37° C. in a 5% CO$_2$ humidified incubator for 24 hrs, after which the medium was replaced with 100 µl of test medium containing a range of MDM2-p53 antagonist concentrations and incubated for a further 72 hrs to allow cell growth before adding 25 µL of 50% trichloroacetic acid (TCA) to fix the cells for 1 h at 4° C. The TCA was washed off with distilled water and 100 µL of SRB dye (0.4% w/v in 1% acetic acid) (Sigma-Aldrich, Poole, Dorset) added to each well of the plate. Following incubation with the SRB dye at room temperature for 30 min, the plates were washed with 1% acetic acid and left to dry. The SRB stained protein, which is a measure of the number of cells in a well, was then resuspended in 100 µL of 10 mM Tris-HCl (pH 10.5) and the absorbance at λ=570 nm measured in each well using a FluoStar Omega Plate reader. The GI$_{50}$ was calculated by non-linear regression analysis of the data using Prism v4.0 statistical software.

Protocol B: SJSA-1 and SN40R2 Assays

The CellTiter-Glo® Luminescent Cell Viability Assay is a homogeneous method to determine the number of viable cells in culture based on quantitation of the ATP present, which signals the presence of metabolically active cells. Both SJSA-1 and SN40R2 were grown in RPMI 1640 (Life Technologies #61870) supplemented with 10% FBS (PAA #A15-204) and 10 U/ml penicillin/streptomycin. 2000 cells in 75 µl were seeded in each well of a 96 well plate and left at 37° C. in a 5% CO$_2$ humidified incubator for 24 hrs. A range of MDM2-p53 antagonist concentrations in DMSO was then added to the cells to a final DMSO concentration of 0.3%, and incubated for a further 72 hrs to allow cell growth. 100 µl of CTG reagent (Promega #G7573) was added to all wells and luminescence was measured on the topcount. The EC$_{50}$ values were determined from a sigmoidal 4 parameter curve fit using XLfit in conjunction with Activity Base (IDBS; Guildford, Surrey, UK).

Anti-Proliferative Activity

Inhibition of cell growth is measured using the Alamar Blue assay (Nociari, M. M, Shalev, A., Benias, P., Russo, C. *Journal of Immunological Methods* 1998, 213, 157-167). The method is based on the ability of viable cells to reduce resazurin to its fluorescent product resorufin. For each proliferation assay cells are plated onto 96 well plates and allowed to recover for 16 hours prior to the addition of inhibitor compounds (in 0.1% DMSO v/v) for a further 72 hours. At the end of the incubation period 10% (v/v) Alamar Blue is added and incubated for a further 6 hours prior to determination of fluorescent product at 535 nM ex/590 nM em. The anti-proliferative activities of compounds of the invention can be determined by measuring the ability of the compounds to inhibit growth in cancer cell lines for example as available from DSMZ, ECACC or ATCC.

Results

TABLE 1 biological data obtained from assays as described herein

| E.g. | MDM2 IC50 (μM) | SJSA-1 IC50 (μM) (Protocol A) | SJSA1 IC50 (μM) (Protocol B) | SN40R2 IC50 (μM) (Protocol A) | SN40R2 IC50 (μM) (Protocol B) |
|---|---|---|---|---|---|
| 7 | 0.0036 | 0.11 | 0.34 | 26 | 8% at 10 |
| 8 | 0.053 | 2.0 | 3.8 | 34% at 30 | 11% at 10 |
| 6 | 0.023 | 1.7 | 2.5 | 13% at 30 | 4% at 10 |
| 9 | 0.015 | 0.82 | | 32% at 30 | |
| 93 | 0.030 | 1.0 | | 40% at 30 | |
| 31 | 0.017 | 0.55 | 0.76 | 20% at 30 | 0% at 10 |
| 1 | 0.0020 | 0.088 | 0.2 | 24 | 14% at 10 |
| 94 | 0.10 | 2.4 | | 15% at 30 | |
| 2 | 0.026 | 1.7 | 3.4 | 38% at 30 | 10% at 10 |
| 47 | 0.12 | 1.6 | | 24 | |
| 46 | 0.016 | 0.59 | 0.76 | 42% at 30 | 13% at 10 |
| 10 | 0.016 | 0.32 | | 6% at 30 | |
| 44 | 0.015 | 0.28 | | 24 | |
| 61 | 0.11 | 0.86 | | 26% at 30 | |
| 62 | 0.041 | 0.75 | | 29% at 30 | |
| 5 | 0.0038 | 0.20 | 0.28 | 20% at 30 | 7% at 10 |
| 38 | 0.0094 | 0.64 | | 15% at 30 | |
| 39 | 0.0044 | 0.17 | | 3% at 30 | |
| 45 | 0.0084 | 0.23 | | 27 | |
| 63 | 0.032 | 0.57 | | 27 | |
| 11 | 0.0087 | 0.23 | 0.46 | 15% at 30 | |
| 32 | 0.0012 | 0.089 | 0.14 | 27 | 9% at 10 |
| 12 | 0.046 | 1.5 | | 0% at 30 | |
| 33 | 0.010 | 0.61 | | 31% at 30 | |
| 13 | 0.0077 | 0.52 | 0.73 | 24 | 21% at 10 |
| 48 | 0.018 | 0.60 | 0.56 | 4% at 30 | −3% at 10 |
| 64 | 0.040 | 0.75 | | 3% at 30 | |
| 95 | 0.060 | 2.0 | | 19 | |
| 34 | 0.085 | 0.97 | 2.2 | 14% at 30 | 20% at 30 |
| 16 | 0.030 | 0.27 | | 24% at 30 | |
| 17 | 0.0038 | 0.10 | 0.21 | 29% at 30 | |
| 3 | 0.12 | 0.96 | | 7% at 30 | 9% at 30 |
| 14 | 0.029 | 0.55 | | 13% at 30 | |
| 15 | 0.0068 | 0.21 | | 22% at 30 | |
| 54 | 0.10 | 2.2 | | 25 | |
| 59 | 0.034 | 0.70 | | 34% at 30 | |
| 4 | 0.010 | 0.23 | 0.24 | 24% at 30 | 9% at 10 |
| 49 | 0.040 | 0.38 | | 18% at 30 | |
| 60 | 0.020 | 0.55 | | 27 | |
| 18 | 0.020 | 0.51 | | 20% at 30 | |
| 19 | 0.0027 | 0.069 | | 20% at 30 | |
| 65 | 0.021 | 0.41 | | 24 | |
| 35 | 0.010 | 0.45 | 0.8 | 8% at 30 | 6% at 10 |
| 42 | 0.010 | 0.45 | 0.60 | 29% at 30 | 14% at 10 |
| 43 | 0.026 | 0.49 | 0.48 | 16% at 30 | 13% at 10 |
| 40 | 0.046 | 0.81 | 1.0 | 2% at 30 | 9% at 10 |
| 41 | 0.013 | 0.32 | 0.47 | 15% at 30 | 8% at 10 |
| 37 | 0.035 | 0.26 | | 25 | 12 |
| 50 | 0.0088 | 0.23 | | 24 | |
| 96 | 0.14 | | | | |
| 51 | 0.69 | | | | |
| 22 | 0.0018 | 0.16 | 0.059 | 19 | 13 |
| 23 | 0.0074 | 0.55 | | 17 | |
| 36 | 0.0051 | 0.21 | 0.18 | 13% at 30 | |
| 74 | 0.015 | 0.31 | | 24 | |
| 28 | 0.014 | 0.19 | | 44% at 30 | |
| 55 | 0.49 | | | | |
| 56 | 0.021 | 0.33 | | 24 | |
| 30 | 0.017 | 0.30 | | 0% at 30 | |
| 24 | 0.0077 | 0.24 | | 42% at 30 | |
| 25 | 0.0018 | 0.054 | 0.090 | 26 | 13% at 10 |
| 26 | 0.027 | 0.58 | | 28 | |
| 27 | 42% @ 0.0030 | 0.24 | 0.71 | 23 | 11% at 10 |
| 52 | 0.031 | 0.25 | | 15% at 30 | |
| 87 | 0.031 | 0.71 | | 19 | |
| 77 | 0.076 | 2.2 | | 48% at 30 | |
| 78 | 0.026 | 0.77 | | 26 | |
| 53 | 0.12 | | | | |

TABLE 1-continued biological data obtained from assays as described herein

| E.g. | MDM2 IC50 (μM) | SJSA-1 IC50 (μM) (Protocol A) | SJSA1 IC50 (μM) (Protocol B) | SN40R2 IC50 (μM) (Protocol A) | SN40R2 IC50 (μM) (Protocol B) |
|---|---|---|---|---|---|
| 29 | 0.012 | 0.39 | 0.52 | 16% at 30 | 25% at 30 |
| 20 | 0.026 | 1.6 | | 4% at 30 | |
| 21 | 0.0052 | 0.27 | | 10% at 30 | |
| 119 | 0.018 | 0.53 | | 47% at 30 | |
| 118 | 0.034 | 0.67 | | 39% at 30 | |
| 79 | 0.0046 | 0.12 | 0.38 | 25 | 2% at 10 |
| 97 | 0.013 | 0.37 | | 24 | |
| 98 | 0.018 | 0.43 | | 23 | |
| 73 | 0.082 | 1.8 | | 0% at 30 | |
| 75 | 0.0045 | 0.14 | 0.47 | 29 | 15% at 10 |
| 70 | 0.0032 | 0.21 | | 48% at 30 | |
| 76 | 0.0065 | 0.54 | | 20 | |
| 71 | 0.082 | 5.3 | | 33% at 30 | |
| 124 | 0.093 | 1.9 | | 2% at 30 | |
| 122 | 0.033 | 0.68 | | 9.9 | |
| 123 | 0.0098 | 0.23 | | 21 | |
| 120 | 0.085 | 1.9 | | 39% at 30 | |
| 121 | 0.023 | 0.55 | | 28% at 30 | |
| 104 | 52% @ 1.0 | | | | |
| 105 | 0.015 | 0.40 | | 9.8 | |
| 67 | 0.029 | 0.71 | | 36% at 30 | |
| 85 | 0.0017 | 0.10 | | 34% at 30 | |
| 86 | 0.15 | | | | |
| 110 | 55% @ 1.0 | | | | |
| 111 | 0.059 | 2.0 | | 29 | |
| 106 | 0.52 | 5.2 | | 24 | |
| 107 | 0.016 | 0.38 | | 29 | |
| 108 | 0.79 | 8.2 | | 16 | |
| 109 | 0.11 | 1.7 | 3.5 | 18 | 24% at 10 |
| 114 | 0.12 | 2.0 | | 10% at 30 | |
| 115 | 81% @ 0.10 | 5.2 | | 13% at 30 | |
| 82 | 0.027 | 0.62 | | 32% at 30 | |
| 83 | 41% @ 0.0010 | 0.038 | | 36% at 30 | |
| 66 | 0.0099 | 0.51 | 0.73 | 18 | 13 |
| 89 | 0.011 | 0.45 | | 23% at 30 | |
| 90 | 0.00064 | 0.046 | | 24% at 30 | |
| 112 | 0.18 | 5.4 | | 15% at 30 | |
| 113 | 0.0069 | 0.50 | | 13% at 30 | |
| 84 | 0.022 | 1.3 | | 23% at 30 | |
| 99 | 35% @ 1.0 | | | | |
| 100 | 0.016 | 0.47 | | 38% at 20 | |
| 101 | 0.013 | 0.28 | | 25% at 30 | |
| 72 | 0.0086 | 0.36 | | 35% at 30 | |
| 81 | 0.11 | | | | |
| 91 | 41% @ 0.15 | | | | |
| 92 | 0.0059 | 0.24 | | 21 | |
| 102 | 37% @ 0.30 | | | | |
| 103 | 0.022 | 0.43 | | 9.5 | |
| 68 | 0.0016 | 3.2 | | 19% at 30 | |
| 69 | 0.0081 | 7.6 | | 32% at 30 | |
| 57 | 44% @ 0.30 | | | | |
| 58 | 0.0053 | 0.23 | | 24 | |
| 88 | 0.028 | 1.5 | | 12% at 30 | |
| 125 | 0.10 | | | | |
| 126 | 0.015 | | | | |
| 116 | 48% @ 0.10 | | | | |
| 117 | 0.0078 | 0.26 | | 26 | |
| 419 | 0.018 | 0.70 | | 21% at 30 | |
| 318 | 11% @ 0.025 | | | | |
| 319 | 0.0076 | 0.16 | | 14 | |
| 327 | 42% @ 0.30 | 9.3 | | 9% at 30 | |
| 328 | 42% @ 0.10 | 2.3 | | 25 | |
| 329 | 61% @ 0.30 | 3.0 | | 8% at 30 | |
| 330 | 36% @ 0.30 | 7.1 | | 18% at 30 | |
| 381 | 33% @ 0.30 | 46% at 10 | | 17 | |
| 382 | 0.036 | 0.82 | | 18 | |
| 383 | 31% @ 0.30 | 6.6 | | 18 | |
| 384 | 39% @ 0.030 | 0.36 | | 16 | |
| 157 | 39% @ 0.30 | 6.4 | | 30% at 30 | |
| 158 | 57% @ 0.10 | 1.2 | | 30% at 30 | |
| 242 | 35% @ 0.30 | 6.3 | | 6.2 | |
| 243 | 0.018 | 0.63 | | 5.8 | |
| 245 | 51% @ 0.30 | 7.4 | | 16 | |
| 241 | 0.012 | 0.58 | | 8.9 | |

TABLE 1-continued

| | | biological data obtained from assays as described herein | | | |
|---|---|---|---|---|---|
| E.g. | MDM2 IC50 (μM) | SJSA-1 IC50 (μM) (Protocol A) | SJSA1 IC50 (μM) (Protocol B) | SN40R2 IC50 (μM) (Protocol A) | SN40R2 IC50 (μM) (Protocol B) |
| 239 | 0.015 | | | | |
| 248 | 37% @ 0.30 | | | | |
| 247 | 0.022 | 0.76 | | 18 | |
| 238 | 41% @ 0.30 | 52% at 10 | | 19 | |
| 246 | 37% @ 0.30 | 7.6 | | 18 | |
| 237 | 0.013 | 0.55 | | 16 | |
| 244 | 36% @ 0.30 | 40% at 10 | | 18 | |
| 240 | 0.032 | 0.91 | | 17 | |
| 159 | 0.031 | 1.2 | | 24 | |
| 160 | 43% @ 0.30 | | | | |
| 167 | 0.011 | 0.64 | | 19% at 30 | |
| 253 | 53% @ 1.0 | | | | |
| 253a | 0.035 | 0.85 | | 29 | |
| 252 | 41% @ 0.30 | | | | |
| 249 | 0.013 | 0.51 | | 34% at 30 | |
| 251 | 61% @ 1.0 | | | | |
| 250 | 0.0072 | 1.6 | | 18 | |
| 320 | 0.0060 | 2.7 | | 24 | |
| 321 | 0.0027 | 1.4 | | 22 | |
| 258 | 50% @ 1.0 | | | | |
| 257 | 0.12 | 1.9 | | 29% at 30 | |
| 256 | 59% @ 1.0 | | | | |
| 255 | 0.0032 | 0.51 | | 16 | 7.1 |
| 254 | 45% @ 0.30 | | | | |
| 259 | 0.0097 | 0.96 | | 5.5 | |
| 127 | 45% @ 0.0033 | 0.38 | | 20% at 30 | |
| 134 | 47% @ 0.30 | | | | |
| 135 | 0.049 | 1.6 | | 38% at 30 | |
| 323 | 46% @ 0.64 | | | | |
| 324 | 0.028 | 0.57 | | 23 | |
| 260 | 39% @ 1.0 | | | | |
| 261 | 0.048 | 0.65 | | 19 | |
| 169 | 0.0046 | 0.26 | | 43 | |
| 170 | 4% @ 0.10 | | | | |
| 275 | 43% @ 0.30 | | | | |
| 262 | 0.033 | 0.47 | | 22 | |
| 233 | 37% @ 1.0 | | | | |
| 234 | 0.015 | 0.38 | | 21 | |
| 128 | 0.11 | 2.4 | | 23 | |
| 129 | 0.0047 | 0.24 | | 21 | |
| 263 | 45% @ 1.0 | | | | |
| 264 | 0.043 | 0.67 | | 8.0 | |
| 235 | 40% @ 1.0 | | | | |
| 236 | 0.041 | 0.72 | | 28 | |
| 316 | 0.0072 | 0.86 | | 17% at 30 | |
| 317 | 0.0016 | 0.19 | | 36% at 50 | |
| 377 | 0.11 | | | | |
| 378 | 52% @ 0.30 | | | | |
| 376 | 0.0040 | | 0.32 | | 18% at 10 |
| 302 | 63% @ 0.10 | 5.3 | | 9% at 30 | |
| 303 | 0.0016 | 0.55 | | 13% at 30 | |
| 268 | 45% @ 1.0 | | | | |
| 266 | 0.015 | | | | |
| 267 | 42% @ 1.0 | | | | |
| 265 | 0.044 | | | | |
| 289 | 0.012 | | | | |
| 291 | 45% @ 0.0010 | | | | |
| 292 | 0.021 | | | | |
| 172 | 0.13 | | | | |
| 171 | 0.14 | | | | |
| 270 | 33% @ 1.0 | | | | |
| 269 | 0.16 | | | | |
| 290 | 0.0025 | | | | |
| 168 | 0.039 | | | | |
| 175 | 0.0061 | | | | |
| 176 | 0.0010 | | | | |
| 379 | 52% @ 1.0 | | | | |
| 271 | 0.014 | | | | |
| 380 | 59% @ 1.0 | | | | |
| 274 | 0.0097 | | | | |
| 309 | 0.0023 | | | | |
| 273 | 47% @ 1.0 | | | | |
| 272 | 0.0088 | | | | |
| 177 | 47% @ 0.030 | | | | |

TABLE 1-continued biological data obtained from assays as described herein

| E.g. | MDM2 IC50 (µM) | SJSA-1 IC50 (µM) (Protocol A) | SJSA1 IC50 (µM) (Protocol B) | SN40R2 IC50 (µM) (Protocol A) | SN40R2 IC50 (µM) (Protocol B) |
|---|---|---|---|---|---|
| 178 | 0.00079 | 0.16 | 0.10 | 43% at 50 | 18% at 30 |
| 145 | 0.21 | | | | |
| 147 | 44% @ 0.10 | | | | |
| 310 | 53% @ 0.0010 | | | | |
| 173 | 0.025 | | | | |
| 146 | 0.081 | | | | |
| 148 | 0.035 | | | | |
| 153 | 0.015 | | | | |
| 154 | 0.014 | | | | |
| 287 | 0.0031 | | | | |
| 151 | 32% @ 0.30 | | | | |
| 152 | 0.30 | | | | |
| 149 | 53% @ 1.0 | | | | |
| 150 | 49% @ 0.10 | | | | |
| 345 | 0.0037 | | | | |
| 346 | 46% @ 0.00030 | 0.031 | 0.012 | 20 | 12 |
| 288 | 0.046 | | | | |
| 281 | 58% @ 0.10 | | | | |
| 280 | 0.0063 | | | | |
| 131 | 0.092 | | | | |
| 130 | 0.0057 | | 0.17 | | 8% at 10 |
| 285 | 41% @ 0.10 | | | | |
| 284 | 0.0025 | | 0.017 | | 12% at 30 |
| 132 | 51% @ 0.30 | | | | |
| 133 | 33% @ 1.0 | | | | |
| 305 | 0.0015 | | 1.9 | | 32% at 30 |
| 282 | 0.0021 | | 0.061 | | 5% at 30 |
| 283 | 57% @ 0.10 | | | | |
| 304 | 0.0022 | | 0.36 | | 9.0 |
| 161 | 0.016 | | 4.3 | | 28% at 30 |
| 162 | 0.0022 | | 0.22 | | 13 |
| 308 | 0.044 | | | | |
| 136 | 0.037 | | 1.4 | | 13 |
| 137 | 0.0016 | 0.20 | 0.27 | 21 | 11 |
| 306 | 55% @ 0.030 | | 6.6 | | 13 |
| 199 | 49% @ 0.030 | | 0.83 | | 16% at 30 |
| 200 | 0.00071 | 0.066 | 0.099 | 40 | 21% at 30 |
| 189 | 0.013 | | 1.0 | | 47% at 30 |
| 190 | 0.037 | | 5.0 | | 19% at 30 |
| 205 | 0.0012 | 0.18 | 0.22 | 34 | 12 |
| 206 | 0.0015 | | 0.45 | | 13 |
| 207 | 56% @ 0.10 | | 2.2 | | 13 |
| 307 | 62% @ 0.030 | | 1.9 | | 11 |
| 315 | 0.46 | | 12 | | 13 |
| 163 | 0.042 | | 3.1 | | 13 |
| 164 | 0.034 | | 2.2 | | 28% at 30 |
| 165 | 0.017 | | 1.4 | | 13 |
| 166 | 48% @ 0.010 | | 3.8 | | 33% at 30 |
| 208 | 0.027 | | 2.3 | | 24% at 30 |
| 298 | 0.00066 | 0.22 | 0.55 | 7.6 | 8.9 |
| 299 | 0.0096 | | 2.0 | | 8.0 |
| 191 | 0.048 | | 2.5 | | 11 |
| 192 | 0.0021 | | 1.4 | | 11 |
| 420 | 68% @ 0.0010 | 0.49 | 0.87 | 17 | 4.4 |
| 301 | 75% @ 0.0010 | 0.070 | 0.036 | 28 | 12 |
| 286 | 0.0041 | | 0.68 | | 12 |
| 293 | 0.0011 | 0.11 | 0.37 | 35 | 45% at 30 |
| 209 | 0.0041 | 0.59 | 0.45 | 22% at 50 | 17% at 30 |
| 210 | 46% @ 0.030 | | | | 17% at 30 |
| 187 | 0.0055 | | 0.89 | | 5% at 10 |
| 188 | 49% @ 0.10 | | | | |
| 294 | 0.00093 | | 0.077 | | 23% at 10 |
| 197 | 0.00062 | | 0.21 | | 2% at 10 |
| 198 | 0.0050 | | | | |
| 211 | 0.0010 | 0.28 | 0.36 | 41% at 50 | 5% at 10 |
| 212 | 54% @ 0.030 | | | | |
| 202 | 72% @ 0.0010 | 0.064 | 0.11 | 24 | 13% at 10 |
| 201 | 0.0029 | | 0.76 | | 9% at 10 |
| 194 | 0.0033 | | | | |
| 193 | 0.00077 | 0.13 | 0.14 | 34 | 11% at 10 |
| 144 | 0.0021 | | 2.9 | | 3% at 10 |
| 300 | 60% @ 0.0010 | | | | |
| 179 | 48% @ 0.030 | | | | |
| 180 | 0.00095 | | 0.16 | | 14% at 10 |

TABLE 1-continued biological data obtained from assays as described herein

| E.g. | MDM2 IC50 (μM) | SJSA-1 IC50 (μM) (Protocol A) | SJSA1 IC50 (μM) (Protocol B) | SN40R2 IC50 (μM) (Protocol A) | SN40R2 IC50 (μM) (Protocol B) |
|---|---|---|---|---|---|
| 295 | 0.00093 | | | | |
| 138 | 0.0044 | | 0.56 | | 18% at 10 |
| 139 | 42% @ 0.030 | | | | |
| 156 | 0.0011 | | 0.25 | | 9% at 10 |
| 213 | 0.0021 | 0.26 | 0.25 | 42% at 50 | 3% at 10 |
| 343 | 49% @ 0.10 | | | | |
| 203 | 0.0012 | 0.10 | 0.080 | 19% at 50 | 7% at 10 |
| 204 | 0.012 | | 0.94 | | −1% at 10 |
| 214 | 0.0014 | 0.26 | 0.22 | 12% at 50 | 0% at 10 |
| 215 | 51% @ 0.030 | | | | |
| 311 | 0.0026 | | 0.25 | | 11% at 10 |
| 312 | 57% @ 0.030 | | | | |
| 216 | 0.0032 | | 0.28 | | 1% at 10 |
| 217 | 52% @ 0.10 | | | | |
| 181 | 42% @ 0.010 | | | | |
| 182 | 0.0013 | | 0.88 | | 6% at 10 |
| 140 | 0.00070 | | 0.23 | | |
| 141 | 0.017 | | 1.8 | | |
| 142 | 0.00073 | | 0.23 | | |
| 143 | 0.0043 | | 0.86 | | |
| 277 | 0.0012 | | 1.2 | | 5% at 10 |
| 276 | 0.0036 | | 2.5 | | 33% at 10 |
| 279 | 0.00097 | | 0.57 | | 17% at 10 |
| 278 | 0.0034 | | 2.6 | | 18% at 10 |
| 196 | 0.0013 | 0.11 | 0.15 | 27% at 50 | 7% at 10 |
| 218 | 0.00086 | 0.22 | 0.43 | 31% at 50 | 4% at 10 |
| 219 | 0.00095 | 0.087 | 0.11 | 33 | 8% at 10 |
| 220 | 0.0081 | | 0.60 | | 14% at 10 |
| 296 | 62% @ 0.0010 | 0.11 | 0.16 | 32 | 12% at 10 |
| 195 | 0.0055 | | 0.61 | | 4% at 10 |
| 221 | 0.033 | | 2.2 | | 3% at 10 |
| 222 | 80% @ 0.0010 | 0.064 | 0.099 | 36 | 14% at 10 |
| 223 | 0.0026 | | 0.52 | | 8% at 10 |
| 324 | 0.0048 | | 2.2 | | 2% at 10 |
| 224 | 0.00070 | 0.078 | 0.12 | 47 | 6% at 10 |
| 226 | 0.0095 | | 0.57 | | 3% at 10 |
| 225 | 48% @ 0.030 | | 1.8 | | 9% at 10 |
| 347 | 63% @ 0.10 | | 1.7 | | |
| 325 | 0.0013 | | 0.24 | | |
| 227 | 0.0048 | | 0.29 | | 8% at 10 |
| 228 | 61% @ 0.010 | | 0.21 | | |
| 174 | 0.0038 | | | | |
| 183 | 0.0042 | | 0.43 | | 4% at 10 |
| 184 | 0.00092 | | 0.14 | | 8% at 10 |
| 372 | 52% @ 0.10 | | 2.6 | | |
| 373 | 0.0023 | | 0.26 | | 12% at 10 |
| 297 | 0.0026 | | 0.76 | | 5% at 10 |
| 229 | 51% @ 0.10 | | 1.4 | | |
| 230 | 0.0055 | | 0.22 | | 0% at 10 |
| 344 | 0.010 | | 1.9 | | 0% at 10 |
| 231 | 0.0028 | | 0.33 | | 5% at 10 |
| 232 | 50% @ 0.10 | | 2.3 | | 5% at 10 |
| 185 | 47% @ 0.010 | | 2.2 | | 8% at 10 |
| 186 | 0.0089 | | 0.42 | | 2% at 10 |
| 313 | 0.0028 | | 0.95 | | 2% at 10 |
| 314 | 52% @ 0.010 | | 66% at 10 | | 9% at 10 |
| 155 | 0.0094 | | 0.31 | | |
| 353 | 69% @ 0.0010 | 0.19 | 0.27 | 44% at 50 | 6% at 10 |
| 352 | 0.0055 | | 1.1 | | 13% at 10 |
| 385 | 0.0061 | | 0.45 | | 5% at 10 |
| 354 | 0.0013 | 0.16 | 0.34 | 36 | 8% at 10 |
| 421 | 0.00084 | | 0.59 | | 5% at 10 |
| 357 | 0.0015 | | 0.30 | | 10% at 10 |
| 360 | 0.0032 | | 0.74 | | 9% at 10 |
| 358 | 74% @ 0.0010 | | 0.039 | | 9% at 10 |
| 359 | 50% @ 0.10 | | 3.9 | | 6% at 10 |
| 389 | 41% @ 0.10 | | 4.2 | | 9% at 10 |
| 390 | 0.0035 | | 0.63 | | 11% at 10 |
| 391 | 0.0066 | | 0.66 | | 2% at 10 |
| 350 | 54% @ 0.030 | | 0.51 | | 2% at 10 |
| 351 | 25% @ 0.10 | | 4.3 | | 5% at 10 |
| 405 | 0.010 | | 0.63 | | 6% at 10 |
| 406 | 54% @ 0.10 | | 3.9 | | 11% at 10 |
| 418 | 0.00081 | 0.12 | 0.28 | 25 | 8% at 10 |

TABLE 1-continued biological data obtained from assays as described herein

| E.g. | MDM2 IC50 (μM) | SJSA-1 IC50 (μM) (Protocol A) | SJSA1 IC50 (μM) (Protocol B) | SN40R2 IC50 (μM) (Protocol A) | SN40R2 IC50 (μM) (Protocol B) |
|---|---|---|---|---|---|
| 326 | 50% @ 0.030 | | 2.0 | | 16% at 10 |
| 407 | 62% @ 0.0010 | | 0.58 | | −9% at 10 |
| 408 | 0.0011 | | 0.75 | | 5% at 10 |
| 409 | 0.0019 | 0.28 | 0.41 | 12% at 50 | 5% at 10 |
| 395 | 44% @ 0.030 | | | | |
| 396 | 0.0044 | | 0.28 | | 9% at 10 |
| 392 | 45% @ 0.10 | | | | |
| 340 | 56% @ 0.10 | | 2.0 | | |
| 348 | 0.0026 | | 0.27 | | 5% at 10 |
| 349 | 79% @ 0.0010 | 0.042 | 0.028 | 44 | 6% at 10 |
| 341 | 0.0023 | 0.53 | 0.50 | 15% at 30 | −0% at 10 |
| 386 | 0.00065 | 0.034 | 0.019 | 45 | 6% at 10 |
| 331 | 49% @ 0.030 | | | | |
| 403 | 52% @ 0.030 | | 1.2 | | 2% at 10 |
| 397 | 49% @ 0.030 | | 2.5 | | 7% at 10 |
| 422 | 0.0032 | | 1.1 | | |
| 404 | 0.0018 | 0.16 | 0.095 | 25 | 12% at 10 |
| 355 | 16% @ 0.10 | | 4.7 | | |
| 356 | 0.0059 | 1.1 | 0.96 | 17% at 50 | 5% at 10 |
| 410 | 0.0022 | | 0.19 | | 4% at 10 |
| 411 | 0.00093 | 0.11 | 0.077 | 40 | 6% at 10 |
| 412 | 0.0023 | | 0.27 | | 8% at 10 |
| 413 | 0.0020 | 0.22 | 0.24 | 41 | 12% at 10 |
| 398 | 0.0023 | 0.58 | 0.58 | 16% at 50 | 4% at 10 |
| 423 | 0.0020 | 0.24 | 0.25 | 34 | |
| 416 | 0.0011 | 0.17 | 0.15 | 19 | 25% at 10 |
| 417 | 0.0052 | | 0.41 | | 16% at 10 |
| 332 | 60% @ 0.030 | | 2.6 | | 5% at 10 |
| 414 | 60% @ 0.0030 | | 0.11 | | |
| 415 | 0.00084 | | 0.24 | | |
| 393 | 0.0065 | | 0.79 | | |
| 394 | 18% @ 0.10 | | | | |
| 424 | 45% @ 0.0030 | | 0.69 | | |
| 338 | 50% @ 0.030 | | 1.5 | | 6% at 10 |
| 337 | 48% @ 0.00010 | 0.051 | 0.058 | 46 | 7% at 10 |
| 361 | 0.0039 | | 0.78 | | 8% at 10 |
| 362 | 52% @ 0.10 | | | | |
| 425 | 0.0019 | | 0.74 | | 7% at 10 |
| 399 | 50% @ 0.00030 | | 11% at 10 | | 2% at 10 |
| 400 | 0.0031 | | 1.1 | | 4% at 10 |
| 363 | 48% @ 0.10 | | | | |
| 364 | 0.0055 | | 0.47 | | 9% at 10 |
| 333 | 0.0044 | | 0.22 | | 5% at 10 |
| 334 | 42% @ 0.10 | | 73% at 10 | | 4% at 10 |
| 365 | 0.0011 | 0.067 | 0.10 | 33% at 50 | −0% at 10 |
| 366 | 0.19 | | 2.7 | | 2% at 10 |
| 335 | 51% @ 0.10 | | 2.8 | | 7% at 10 |
| 336 | 56% @ 0.0010 | 0.10 | 0.16 | 42 | 4% at 10 |
| 401 | 37% @ 0.00030 | 0.0089 | 0.0098 | 36 | 6% at 10 |
| 402 | 0.0043 | | 0.21 | | 5% at 10 |
| 367 | 0.0026 | 0.22 | 0.11 | 46 | 1% at 10 |
| 368 | 27% @ 0.10 | | 52% at 10 | | 6% at 10 |
| 371 | 43% @ 0.030 | | 2.3 | | 3% at 10 |
| 374 | 0.00090 | 0.64 | 0.85 | 26% at 50 | 2% at 10 |
| 375 | 37% @ 0.10 | | | | |
| 387 | 42% @ 0.10 | | | | |
| 388 | 0.0021 | 0.066 | 0.23 | 39 | 4% at 10 |
| 369 | 0.00061 | 0.058 | 0.062 | 18% at 50 | 5% at 10 |
| 370 | 51% @ 0.10 | | 3.5 | | 0% at 10 |
| 339 | 0.00051 | | 0.21 | | 3% at 10 |
| 342 | 25% @ 0.10 | | 21% at 10 | | 4% at 10 |
| 428 | 65% @ 0.0010 | 0.11 | 0.19 | 22 | 12% at 10 |
| 429 | 65% @ 0.10 | | | | |
| 430 | 59% @ 0.0010 | 0.11 | 0.18 | 33% at 50 | 4% at 10 |
| 431 | 48% @ 0.0010 | 0.11 | 0.16 | 39% at 50 | 5% at 10 |
| 432 | 45% @ 0.030 | | 6.2 | | 8% at 10 |
| 443 | 58% @ 0.0010 | 0.11 | 0.093 | 38 | 3% at 10 |
| 444 | 63% @ 0.10 | | | | |
| 433 | 0.011 | | 1.5 | | 20% at 30 |
| 434 | 0.0013 | | 0.47 | | 7% at 10 |
| 448 | 84% @ 0.0010 | | 0.86 | | 48% at 30 |
| 445 | 43% @ 0.0010 | | 3.3 | | 16% at 10 |
| | 56% @ 0.10 | | | | |
| 446 | 76% @ 0.0010 | 0.018 | 0.023 | 29 | 13% at 10 |

TABLE 1-continued biological data obtained from assays as described herein

| E.g. | MDM2 IC50 (μM) | SJSA-1 IC50 (μM) (Protocol A) | SJSA1 IC50 (μM) (Protocol B) | SN40R2 IC50 (μM) (Protocol A) | SN40R2 IC50 (μM) (Protocol B) |
|---|---|---|---|---|---|
| 447 | 74% @ 0.0010 | | 0.011 | | 10% at 10 |
| 435 | 66% @ 0.0010 | | 0.015 | | 0% at 10 |
| 436 | 53% @ 0.10 | | | | |
| 426 | 0.00072 | 0.22 | 0.32 | 29% at 50 | 4% at 10 |
| 427 | 41% @ 0.10 | | | | |
| 437 | 51% @ 0.030 | | 2.5 | | −4% at 10 |
| 438 | 0.0016 | | 0.34 | | 2% at 10 |
| 439 | 85% @ 0.0010 | 0.045 | 0.030 | 46% at 50 | 3% at 10 |
| 440 | 0.012 | | 1.9 | | 7% at 10 |
| 449 | 78% @ 0.0010 | 0.041 | 0.012 | 18 | 19% at 10 |
| 450 | 76% @ 0.0010 | | 0.38 | | 15% at 10 |
| 441 | 0.012 | | 1.5 | | 1% at 10 |
| 442 | 0.0034 | 0.42 | 0.50 | 26% at 50 | 6% at 10 |
| 451 | 0.078 | | | | |
| 452 | 0.15 | | | | |
| 453 | 0.094 | | | | |
| 454 | 0.035 | | | | |
| 455 | 58% @ 1.0 | | | | |
| 456 | 0.21 | | | | |
| 457 | 53% @ 0.30 | | | | |
| 458 | 44% @ 0.010 | | | | 12 |
| 459 | 0.0020 | | 6.4 | | 7% at 10 |
| 460 | 0.48 | | | | |
| 461 | 0.00053 | 0.075 | 0.091 | 19% at 50 | 6% at 10 |
| 462 | 80% @ 0.0010 | 0.073 | 0.047 | 37% at 50 | 4% at 10 |
| 463 | 73% @ 0.10 | | | | |
| 464 | 0.0019 | | 0.18 | | 46% at 10 |
| 465 | 29% @ 0.10 | | | | |
| 466 | 0.00086 | 0.21 | 0.14 | 41% at 50 | 4% at 10 |
| 467 | 36% @ 0.10 | | | | |
| 468 | 0.0035 | | 0.48 | | 2% at 10 |
| 469 | 52% @ 0.030 | | | | |
| 470 | 0.001 | | 0.1 | | 3% at 10 |
| 471 | 38% @ 0.10 | | 3.5 | | 2% at 10 |
| 472 | 48% @ 0.0030 | | 0.39 | | 10% at 10 |
| 473 | 44% @ 0.10 | | 104% at 10 | | 11% at 10 |
| 474 | 38% @ 0.030 | | 1.3 | | 12% at 10 |
| 475 | 71% @ 0.0010 | 0.028 | 0.022 | 46% at 50 | 7% at 10 |
| 476 | 51% @ 0.030 | | 0.6 | | 4% at 10 |
| 477 | 86% @ 0.0010 | 0.013 | 0.0091 | | 5% at 10 |
| 478 | 58% @ 0.10 | | 81% at 10 | | −0% at 10 |
| 479 | 0.0006 | | 0.079 | | 2% at 10 |
| 480 | 67% @ 0.10 | | 3.7 | | 2% at 10 |
| 481 | 0.0014 | | 0.33 | | 8% at 10 |
| 483 | 58% @ 0.0010 | | 0.2 | | 9% at 10 |
| 485 | 58% @ 0.10 | | 4.2 | | 3% at 10 |
| 486 | 59% @ 0.0010 | 0.075 | 0.051 | 10% at 50 | 7% at 10 |
| 493 | 0.00054 | 0.038 | 0.02 | 25 | 11% at 10 |
| 494 | 0.013 | | | | |
| 495 | 0.0011 | 0.068 | 0.054 | 34% at 50 | 7% at 10 |
| 496 | 56% @ 0.10 | | 1.8 | | −0% at 10 |
| 500 | 21% @ 0.10 | | 16% at 10 | | 6% at 10 |
| 501 | 0.0031 | 0.015 | 0.022 | 6.4 | 8% at 3.0 |
| 502 | 18% @ 0.10 | | 4.9 | | 11% at 10 |
| 503 | 87% @ 0.0010 | | 0.011 | | 13% at 10 |
| 505 | 60% @ 0.0010 | | 0.027 | | 5% at 10 |
| 506 | 36% @ 0.030 | | 3.4 | | 2% at 10 |
| 507 | 65% @ 0.0030 | | 0.02 | | 5% at 3 |
| 508 | 17% @ 0.10 | | 11% at 10 | | 9% at 10 |
| 509 | 0.00094 | | 0.042 | | 6% at 10 |
| 510 | 79% @ 0.0010 | 0.084 | 0.073 | 5% at 50 | 9% at 10 |
| 511 | 72% @ 0.0010 | | 0.018 | | 10% at 10 |
| 512 | 0.00048 | 0.053 | 0.025 | 27% at 50 | 5% at 10 |
| 514 | | | 0.64 | | 3% at 10 |
| 516 | 0.0012 | | 0.038 | | 4% at 10 |
| 517 | 82% @ 0.0010 | 0.019 | 0.01 | 26% at 50 | 5% at 10 |
| 518 | 79% @ 0.0010 | 0.058 | 0.065 | 46% at 50 | 10% at 10 |
| 519 | 35% @ 0.030 | | 1.9 | | 12% at 10 |
| 520 | 32% @ 0.030 | | 3.9 | | 5% at 10 |
| 521 | 77% @ 0.0010 | 0.035 | 0.033 | 37 | 11% at 10 |
| 524 | 0.021 | | 1.1 | | 35% at 10 |
| 525 | 50% @ 0.0010 | 0.17 | 0.078 | 17 | 40% at 10 |
| 526 | 0.0013 | 0.11 | 0.11 | | 9% at 10 |
| 527 | 0.017 | | 1.4 | | 14% at 10 |

TABLE 1-continued

| | | biological data obtained from assays as described herein | | | |
|---|---|---|---|---|---|
| E.g. | MDM2 IC50 (µM) | SJSA-1 IC50 (µM) (Protocol A) | SJSA1 IC50 (µM) (Protocol B) | SN40R2 IC50 (µM) (Protocol A) | SN40R2 IC50 (µM) (Protocol B) |
| 528 | 0.0029 | | 0.32 | | 10% at 10 |
| 530 | 0.0031 | | 0.39 | | 2% at 10 |
| 531 | 42% @ 0.10 | | 4.3 | | 8% at 10 |
| 532 | 0.0031 | | 0.14 | | 7% at 10 |
| 533 | 44% @ 0.10 | | 4 | | 20% at 10 |
| 534 | 0.0088 | | 0.7 | | 44% at 10 |
| 535 | 65% @ 0.0010 | 0.05 | 0.058 | 18 | 45% at 10 |
| 536 | 64% @ 0.0010 | | 0.13 | | 46% at 10 |
| 522 | 0.0007 | 0.053 | 0.048 | 19 | 24% at 10 |
| 523 | 50% @ 0.030 | | 1.5 | | 29% at 10 |
| 537 | | | 0.76 | | 45% at 10 |
| 538 | 44% @ 0.030 | | 2.2 | | 43% at 10 |
| 539 | 41% @ 0.0010 | | 0.092 | | 38% at 10 |
| 540 | 33% @ 0.030 | | 1.8 | | 62% at 10 |
| 541 | 64% @ 0.00030 | 0.19 | 0.014 | 13 | 10 |
| 542 | 57% @ 0.010 | | 3.1 | | −1% at 10 |
| 543 | 68% @ 0.0010 | | 0.69 | | −6% at 10 |
| 544 | 86% @ 0.0010 | 0.032 | 0.041 | 7.4 | 109% at 10 |
| 545 | 94% @ 0.0010 | | 0.094 | | 4% at 3 |
| 546 | 86% @ 0.0010 | | 0.7 | | 17% at 10 |
| 547 | 82% @ 0.0010 | | 0.96 | | 4% at 10 |
| 548 | 82% @ 0.0010 | 0.14 | 0.17 | 6.3 | 111% at 10 |
| 549 | 85% @ 0.0010 | | 0.27 | | 33% at 10 |
| 553 | 0.0006 | | 0.065 | | 24% at 10 |
| 554 | 74% @ 0.0010 | 0.21 | 0.07 | 46% at 50 | 11% at 10 |
| 555 | 55% @ 0.0010 | | 0.079 | | 58% at 10 |
| 556 | 91% @ 0.0010 | 0.056 | 0.0064 | 27 | 14% at 10 |
| 557 | 81% @ 0.0010 | 0.25 | 0.037 | 37% at 10 | 6% at 10 |
| 558 | 53% @ 0.0030 | 0.22 | 0.082 | 35 | 6% at 10 |
| 559 | 0.00062 | 0.46 | 0.052 | 22% at 50 | 1% at 10 |
| 560 | 30% @ 0.0010 | | 0.13 | | 3% at 10 |
| 561 | 47% @ 0.0010 | 0.021 | 0.065 | 26 | 12% at 10 |
| 562 | 0.0013 | | 0.25 | | 1% at 10 |
| 563 | 76% @ 0.0010 | 0.025 | 0.027 | 15 | 72% at 10 |
| 564 | 86% @ 0.0010 | 0.018 | 0.00038 | 16 | 10% at 3 |
| 565 | 65% @ 0.0010 | 0.045 | 0.035 | 33 | 11% at 10 |
| 566 | 47% @ 0.030 | | 1.9 | | 46% at 10 |
| 567 | 57% @ 0.10 | | | | |
| 568 | 76% @ 0.0010 | | 0.094 | | 36% at 10 |
| 570 | 83% @ 0.0010 | 0.034 | 0.046 | | 26% at 10 |
| 571 | 77% @ 0.0010 | 0.023 | 0.0085 | 17 | 38% at 10 |
| 572 | 53% @ 0.00075 | 0.019 | 0.022 | 18 | 23% at 10 |
| 550 | 0.00098 | 0.077 | 0.056 | 17 | 33% at 10 |
| 551 | 70% @ 0.0010 | 0.031 | 0.026 | 36 | 13% at 10 |
| 552 | 79% @ 0.0010 | 0.028 | 0.02 | 21 | 7% at 10 |
| 513 | 0.0031 | 0.26 | 0.38 | 19% at 50 | 4% at 10 |
| 576 | 42% @ 0.0030 | | 0.14 | | 5% at 10 |
| 577 | 0.00093 | | 0.079 | | 7% at 10 |
| 491 | 0.0089 | | 0.81 | | 5% at 10 |
| 578 | 0.002 | | 0.12 | | 4% at 10 |
| 499 | 68% @ 0.0010 | | 0.053 | | 2% at 10 |
| 498 | 32% @ 0.10 | | 96% at 10 | | 4% at 10 |
| 497 | 83% @ 0.0010 | 0.039 | 0.046 | 45 | 10% at 10 |
| 487 | 59% @ 0.0010 | 0.12 | 0.025 | 27 | 12% at 10 |
| 488 | 56% @ 0.10 | | | | |
| 529 | 0.028 | | 2.2 | | 17% at 10 |
| 482 | 58% @ 0.10 | | 5 | | 3% at 10 |
| 484 | | | 4.9 | | 2% at 10 |
| 574 | 45% @ 0.0010 | 0.021 | 0.016 | 17 | 27% at 10 |
| 575 | 38% @ 0.0010 | 0.028 | 0.066 | 21 | 14% at 10 |
| 504 | 71% @ 0.0010 | 0.039 | 0.034 | 48 | 0% at 10 |
| 492 | 31% @ 0.10 | | 25% at 10 | | 19% at 10 |
| 579 | 41% @ 0.030 | | 19% at 10 | | 4% at 10 |
| 515 | 0.0014 | | 1.0 | | 8% at 10 |
| 489 | | | 3.3 | | −9% at 10 |
| 490 | 0.0023 | | 0.27 | | −0% at 10 |
| 580 | | | 0.014 | | 13% at 10 |

Where more than one data point has been obtained, the table above shows an average (e.g. geometric or arithmetic mean) of these data points.

It is of course to be understood that the invention is not intended to be restricted to the details of the above embodiments which are described by way of example only.

Combination Protocol for Cell Proliferation

The effect of a compound of formula (I) (Compound 1) in combination with an anticancer agent (Compound II) can be assessed using the following technique. Cells from human cells lines (e.g. SJSA-1) were seeded onto 96-well tissue culture plates at a concentration of $2.5 \times 10^3$, $6.0 \times 10^3$, or $4.0 \times 10^3$ cells/well respectively. Cells were allowed to recover for 24-48 hours prior to addition of compound(s) or vehicle control (0.35-0.5% DMSO) as follows:

Compounds were added concurrent for 72-96 hours. Following a total of 72-96 hours compound incubation, cells were fixed with ice-cold 10% (w/v) trichloroacetic acid for 1 hour on ice and then washed four times with dH$_2$O using a plate washer (Labsystems Wellwash Ascent) and air-dried. Cells were then stained with 0.4% (w/v) Sulforhodamine B (Sigma) in 1% acetic acid for 20 min at room temperature and then washed four times with 1% (v/v) acetic acid and air-dried before the addition of 10 mM Tris buffer to solubilise the dye. Colourmetric product was quantified by reading at Abs490 nm or Abs570 nm on a Wallac Victor$^2$ plate reader (1420 multilabel counter, Perkin Elmer Life Sciences). The IC$_{50}$ for Compound II in the presence of varying doses of Compound I was determined. Synergy was determined when the IC$_{50}$ shifted down in the presence of sub-effective doses of Compound I. Additivity was determined when the response to Compound II and Compound I together resulted in an effect equivalent to the sum of the two compounds individually. Antagonistic effects were defined as those causing the IC$_{50}$ to shift upwards, i.e. those where the response to the two compounds was less than the sum of the effect of the two compounds individually.

PHARMACEUTICAL FORMULATIONS EXAMPLES (i) Tablet Formulation

A tablet composition containing a compound of the formula (I) is prepared by mixing an appropriate amount of the compound (for example 50-250 mg) with an appropriate diluent, disintegrant, compression agent and/or glidant. One possible tablet comprises 50 mg of the compound with 197 mg of lactose (BP) as diluent, and 3 mg magnesium stearate as a lubricant and compressing to form a tablet in known manner. The compressed tablet may be optionally film coated.

(ii) Capsule Formulation

A capsule formulation is prepared by mixing 100-250 mg of a compound of the formula (I) with an equivalent amount of lactose and filling the resulting mixture into standard hard gelatin capsules. An appropriate disintegrant and/or glidant can be included in appropriate amounts as required.

(iii) Injectable Formulation I

A parenteral composition for administration by injection can be prepared by dissolving a compound of the formula (I) (e.g. in a salt form) in water containing 10% propylene glycol to give a concentration of active compound of 1.5% by weight. The solution is then made isotonic, sterilised by filtration or by terminal sterilisation, filled into an ampoule or vial or pre-filled syringe, and sealed.

(iv) Injectable Formulation II

A parenteral composition for injection is prepared by dissolving in water a compound of the formula (I) (e.g. in salt form) (2 mg/ml) and mannitol (50 mg/ml), sterile filtering the solution or by terminal sterilisation, and filling into sealable 1 ml vials or ampoules or pre-filled syringe.

(v) Injectable Formulation III

A formulation for i.v. delivery by injection or infusion can be prepared by dissolving the compound of formula (I) (e.g. in a salt form) in water at 20 mg/ml and then adjusted for isotonicity. The vial is then sealed and sterilised by autoclaving or filled into an ampoule or vial or pre-filled syringe, sterilised by filtration and sealed.

(vi) Injectable Formulation IV

A formulation for i.v. delivery by injection or infusion can be prepared by dissolving the compound of formula (I) (e.g. in a salt form) in water containing a buffer (e.g. 0.2M acetate pH 4.6) at 20 mg/ml. The vial, ampoule or pre-filled syringe is then sealed and sterilised by autoclaving or sterilized by filtration and sealed.

(vii) Subcutaneous or Intramuscular Injection Formulation

A composition for sub-cutaneous or intramuscular administration is prepared by mixing a compound of the formula (I) with pharmaceutical grade corn oil to give a concentration of 5-50 mg/ml. The composition is sterilised and filled into a suitable container.

(viii) Lyophilised Formulation I

Aliquots of formulated compound of formula (I) are put into 50 ml vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

(ix) Lyophilised Formulation II

Aliquots of formulated compound of formula (I) or a salt thereof as defined herein are put into 50 mL vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

(x) Lyophilised Formulation for Use in i.v. Administration III

An aqueous buffered solution is prepared by dissolving a compound of formula I in a buffer. The buffered solution is filled, with filtration to remove particulate matter, into a container (such as a Type 1 glass vial) which is then partially sealed (e.g. by means of a Fluorotec stopper). If the compound and formulation are sufficiently stable, the formulation is sterilised by autoclaving at 121° C. for a suitable period of time. If the formulation is not stable to autoclaving, it can be sterilised using a suitable filter and filled under sterile conditions into sterile vials. The solution is freeze dried using a suitable cycle. On completion of the freeze drying cycle the vials are back filled with nitrogen to atmospheric pressure, stoppered and secured (e.g. with an aluminium crimp). For intravenous administration, the freeze dried solid can be reconstituted with a pharmaceutically acceptable diluent, such as 0.9% saline or 5% dextrose. The solution can be dosed as is, or can be diluted further into an infusion bag (containing a pharmaceutically acceptable diluent, such as 0.9% saline or 5% dextrose), before administration.

(xii) Powder in a Bottle

A composition for oral administration is prepared by filling a bottle or vial with a compound of the formula (I). The composition is then reconstituted with a suitable diluent for example water, fruit juice, or commercially available vehicle such as OraSweet or Syrspend. The reconstituted solution may be dispensed into dosing cups or oral syringes for administration.

The invention claimed is:

1. A compound of formula (I):

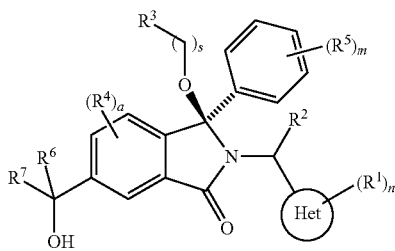

(I)

or a tautomer or a solvate or a pharmaceutically acceptable salt thereof, wherein:

Het is pyridinyl, pyrimidinyl, pyrazinyl or pyridazinyl, or an N-oxide thereof;

$R^1$ is attached to a carbon atom and is independently selected from hydroxy, halogen, nitro, nitrile, $C_{1-4}$alkyl, halo$C_{1-4}$alkyl, hydroxy$C_{1-4}$alkyl, $C_{2-6}$alkenyl, $C_{1-4}$alkoxy, halo$C_{1-4}$alkoxy, $C_{2-4}$alkynyl, $-O_{0,1}-(CR^xR^y)_v-CO_2H$, $-(CR^xR^y)v-CO_2C_{1-4}$alkyl, $-(CR^xR^y)_v-CON(C_{1-4}$alkyl$)_2$, $-P(=O)(R^x)_2$, $-S(O)_d-R^x$, $-S(O)_d$-heterocyclic group with 3 to 6 ring members and $-S(O)_d-N(R)_2$;

$R^2$ is selected from hydrogen, $C_{1-4}$ alkyl, $C_{2-6}$alkenyl, hydroxy$C_{1-4}$alkyl, $-(CR^xR^y)_u-CO_2H$, $-(CR^xR^y)_u-CO_2C_{1-4}$alkyl, and $-(CR^xR^y)_u-CONR^xR^y$;

s is selected from 0 and 1;

$R^3$ is hydrogen or $-(A)_t-(CR^xR^y)_q-X$;

t is selected from 0 and 1;

q is selected from 0, 1 and 2;

wherein when $R^3$ is $-(A)_t-(CR^xR^y)_q-X$ then (i) at least one of s, t and q is other than 0 and (ii) when t is 0 then s is 1 and q is other than 0;

A is a $C_{3-6}$cycloalkyl group or a heterocyclic group with 3 to 6 ring members, wherein the heterocyclic group comprises one or more heteroatoms selected from N, O, S and oxidised forms thereof;

X is selected from hydrogen, halogen, $-CN$, $-OR^9$, $-(CH_2)_v-CO_2H$, $-(CH_2)_v-CO_2C_{1-4}$alkyl, $-S(O)_d-R^x$, $-C(=O)-C_{1-4}$alkyl, $-S(O)_d-N(H)_e(C_{1-4}$alkyl$)_{2-e}$, $-NR^xR^y$, $-NHSO_2R^x$, $-NR^xCOR^y$, and $-C(=O)NR^xR^y$;

$R^4$ and $R^5$ are independently selected from halogen, nitrile, $C_{1-4}$ alkyl, halo$C_{1-4}$alkyl, $C_{1-4}$alkoxy and halo$C_{1-4}$alkoxy;

$R^6$ and $R^7$ are independently selected from hydrogen, $C_{1-6}$alkyl, halo$C_{1-6}$alkyl, $C_{2-6}$alkenyl, $C_{2-6}$alkynyl, hydroxy, hydroxy$C_{1-6}$alkyl, $-COOC_{1-6}$alkyl, $-(CH_2)_j-O-C_{1-6}$alkyl, $-(CH_2)_j-O$-(hydroxy $C_{1-6}$alkyl), $-C_{1-6}$alkyl-NR$^x$R$^y$, $-(CR^xR^y)_p-CONR^xR^y$, $-(CR^xR^y)_p-NRXCORy$, $-(CR^xR^y)_p-O-$ $CH_2-CONR^xR^y$, heterocyclic group with 3 to 7 ring members, $-CH_2$-heterocyclic group with 3 to 7 ring members, $-CH_2-O$-heterocyclic group with 3 to 7 ring members, $-CH_2-NH$-heterocyclic group with 3 to 7 ring members, $-CH_2-N(C_{1-6}$alkyl$)$-heterocyclic group with 3 to 7 ring members, $-C(=O)NH$-heterocyclic group with 3 to 7 ring members, $C_{3-8}$cycloalkyl, $-CH_2-C_{3-8}$cycloalkyl, $-CH_2-O-C_{3-8}$cycloalkyl, and $C_{3-8}$cycloalkenyl, wherein said cycloalkyl, cycloalkenyl or heterocyclic groups may be optionally substituted by one or more $R^z$ groups, and wherein in each instance the heterocyclic group comprises one or more heteroatoms selected from N, O, S and oxidised forms thereof;

or the $R^6$ and $R^7$ groups, together with the carbon atom to which they are attached, can join to form a $C_{3-6}$cycloalkyl or heterocyclyl group with 3 to 6 ring members, wherein the heterocyclic group comprises one or more heteroatoms selected from N, O, S and oxidised forms thereof, and wherein said $C_{3-6}$cycloalkyl and heterocyclyl groups may be optionally substituted by one or more $R^z$ groups;

$R^8$ and $R^9$ are independently selected from hydrogen, $C_{1-6}$alkyl, halo$C_{1-6}$alkyl, hydroxy$C_{1-6}$alkyl, $-(CH_2)_k-O-C_{1-6}$alkyl, $-(CH_2)_k-O$-(hydroxy $C_{1-6}$alkyl), hydroxy$C_{1-6}$alkoxy, $-(CH_2)_k-CO_2C_{1-6}$alkyl, $-(CH_2)_k-CO_2H$, $-C_{1-6}$ alkyl-N(H)$_e(C_{1-4}$alkyl$)_{2-e}$, $-(CH_2)_j-C_{3-8}$cycloalkyl and $-(CH_2)_j-C_{3-8}$cycloalkenyl;

$R^x$ and $R^y$ are independently selected from hydrogen, halogen, nitro, nitrile, $C_{1-6}$alkyl, halo$C_{1-6}$alkyl, $C_{2-6}$alkenyl, $C_{2-6}$alkynyl, hydroxy, hydroxy$C_{1-6}$alkyl, $C_{1-6}$alkoxy, $-(CH_2)_k-O-C_{1-6}$alkyl, hydroxy $C_{1-6}$alkoxy, $-COOC_{1-6}$alkyl, $-N(H)_e(C_{1-4}$alkyl$)_{2-e}$, $-C_{1-6}$alkyl-N(H)$_e(C_{1-4}$alkyl$)_{2-e}$, $-(CH_2)_k-C(=O)N(H)_e(C_{1-4}$alkyl$)_{2-e}$, $C_{3-8}$cycloalkyl and $C_{3-8}$cycloalkenyl;

or the $R^x$ and $R^y$ groups, together with the carbon or nitrogen atom to which they are attached, can join to form a $C_{3-6}$cycloalkyl or saturated heterocyclyl group with 3 to 6 ring members which may be optionally fused to an aromatic heterocyclyl group of 3 to 5 ring members;

or when on a carbon atom the $R^x$ and $R^y$ groups can join together to form a=CH$_2$ group;

$R^z$ is independently selected from halogen, nitro, nitrile, $C_{1-6}$alkyl, halo$C_{1-6}$alkyl, $C_{2-6}$alkenyl, $C_{2-6}$alkynyl, =O, hydroxy, hydroxy$C_{1-6}$alkyl, $C_{1-6}$alkoxy, $-(CH_2)_k-O-C_{1-6}$alkyl, hydroxy$C_{1-6}$alkoxy, $-C(=O)C_{1-6}$alkyl, $-C(=O)C_{1-6}$alkyl-OH, $-C(=O)C_{1-6}$alkyl-N(H)$_e(C_{1-4}$alkyl$)_{2-e}$, $-C(=O)N(H)_e(C_{1-4}$alkyl$)_{2-e}$, $-(CH_2)r-CO_2C_{1-6}$alkyl, $-(CH_2)r-CO_2H$, $-N(H)_e(C_1$-4alkyl$)_{2-e}$, $-C_{1-6}$alkyl-N(H)$_e(C_{1-4}$alkyl$)_{2-e}$, heterocyclyl group with 3 to 6 ring members, heterocyclyl group with 3 to 6 ring members substituted by $-C(=O)C_{1-4}$alkyl, heterocyclyl group with 3 to 6 ring members substituted by $-C(=O)OC_{1-4}$alkyl, heterocyclyl group with 3 to 6 ring members substituted by $-C(=O)N(H)_e(C_{1-4}$alkyl$)_{2-e}$, $-C(=O)$heterocyclyl group with 3 to 6 ring members, $C_{3-8}$cycloalkyl and $C_{3-8}$cycloalkenyl, wherein if $R^7$ is pyridine then $R^z$ is other than $-NH_2$;

a, j, d, e, n, r and p are independently selected from 0, 1 and 2;

k and m are independently selected from 1 and 2;

u is selected from 0, 1, 2 and 3; and v and w are independently is selected from 0 and 1.

2. A compound according to claim 1, wherein $R^1$ is halogen, hydroxy, nitrile, $C_{1-4}$alkyl, $C_{2-4}$alkynyl, or $C_{1-4}$alkoxy.

3. A compound according to claim 1, wherein $R^2$ is selected from hydrogen, $C_{1-4}$ alkyl, hydroxy$C_{1-4}$alkyl and $-(CR^xR^y)_u-CO_2H$.

4. A compound according to claim 1, wherein $R^3$ is:
(i) $-(A)_r-(CR^xR^y)_q-X$ and A is a $C_{3-6}$cycloalkyl group; or
(ii) H and s is 1.

5. A compound according to claim 1, wherein s is 1.

6. A compound according to claim 1, wherein X is hydrogen, halogen, —CN, —$OR^9$, or —C(=O)$NR^xR^y$.

7. A compound according to claim 1, wherein the compound is a compound of the formula

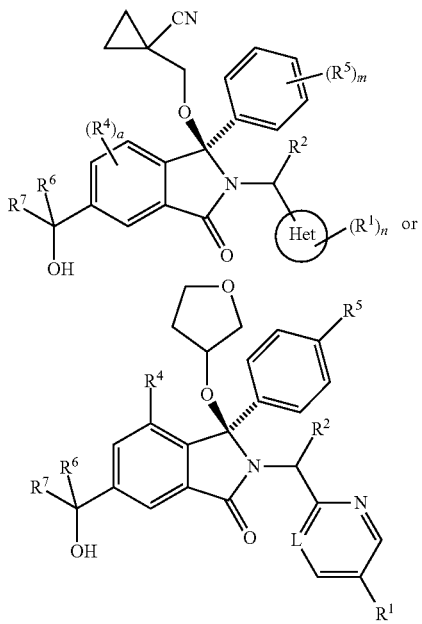

or a tautomer or a solvate or a pharmaceutically acceptable salt thereof, wherein L is $CR^1$, CH or N.

8. A compound according to claim 1, wherein a is 1 and $R^4$ is F and at the 4-position of the isoindolinone ring.

9. A compound according to claim 1, wherein $R^5$ is chloro and m is 1 and the substituent $R^5$ is at the para-position of the phenyl group.

10. A compound according to claim 1, wherein:
(i) $R^7$ is selected from a heterocyclic group with 3 to 7 ring members and a —$CH_2$-heterocyclic group with 3 to 7 ring members, wherein said heterocyclic groups may be optionally substituted by one or more $R^z$ groups, and wherein in each instance the heterocyclic group comprises one or more heteroatoms selected from N, O, S and oxidised forms thereof; or
(ii) $R^6$ is methyl or ethyl.

11. A compound according to claim 1, wherein Het is pyridinyl or pyrimidinyl.

12. A compound according to claim 1, or a tautomer or a solvate or a pharmaceutically acceptable salt thereof, wherein the compound is selected from:
(3R)-3-(4-chlorophenyl)-2-[(5-chloropyridin-2-yl)methyl]-4-fluoro-3-({1-[hydroxy($^2H_2$)methyl]cyclopropyl}($^2H_2$)methoxy)-6-(2-hydroxypropan-2-yl)-2,3-dihydro-1H-isoindol-1-one;

(3R)-3-(4-chlorophenyl)-2-[(5-chloropyridin-2-yl)methyl]-4-fluoro-6-(2-hydroxypropan-2-yl)-3-methoxy-2,3-dihydro-1H-isoindol-1-one;

6-{[(1R)-1-(4-chlorophenyl)-7-fluoro-1-[(1-hydroxycyclopropyl)methoxy]-5-(2-hydroxypropan-2-yl)-3-oxo-2,3-dihydro-1H-isoindol-2-yl]methyl}pyridine-3-carbonitrile;

1-({[(1R)-1-(4-chlorophenyl)-2-[(5-chloropyridin-2-yl)methyl]-7-fluoro-5-(2-hydroxypropan-2-yl)-3-oxo-2,3-dihydro-1H-isoindol-1-yl]oxy}methyl)cyclopropane-1-carboxamide;

6-{[(1R)-1-(4-chlorophenyl)-7-fluoro-1-({1-[hydroxy($^2H_2$)methyl]cyclopropyl}($^2H_2$)methoxy)-5-(2-hydroxypropan-2-yl)-3-oxo-2,3-dihydro-1H-isoindol-2-yl]methyl}pyridine-3-carbonitrile;

(3R)-3-(4-chlorophenyl)-2-[(5-chloropyridin-2-yl)methyl]-3-(2-hydroxyethoxy)-6-(2-hydroxypropan-2-yl)-2,3-dihydro-1H-isoindol-1-one;

(3R)-3-(4-chlorophenyl)-2-[(5-chloropyridin-2-yl)methyl]-3-{[1-(hydroxymethyl)cyclopropyl]methoxy}-6-(2-hydroxypropan-2-yl)-2,3-dihydro-1H-isoindol-1-one;

(3R)-3-(4-chlorophenyl)-2-[(5-chloropyridin-2-yl)methyl]-6-(2-hydroxypropan-2-yl)-3-methoxy-2,3-dihydro-1H-isoindol-1-one;

(3R)-3-(4-chlorophenyl)-2-[(5-chloropyridin-2-yl)methyl]-6-(2-hydroxypropan-2-yl)-3-(3-hydroxypropoxy)-2,3-dihydro-1H-isoindol-1-one;

(3R)-2-[(5-chloro-1-oxo-1λ5-pyridin-2-yl)methyl]-3-(4-chlorophenyl)-3-{[1-(hydroxymethyl)cyclopropyl]methoxy}-6-(2-hydroxypropan-2-yl)-2,3-dihydro-1H-isoindol-1-one;

(3R)-3-(4-chlorophenyl)-2-[(5-chloropyridin-2-yl)methyl]-4-fluoro-3-[(1-hydroxycyclopropyl)methoxy]-6-(2-hydroxypropan-2-yl)-2,3-dihydro-1H-isoindol-1-one;

(3R)-3-(4-chlorophenyl)-4-fluoro-3-({1-[hydroxy($^2H_2$)methyl]cyclopropyl}($^2H_2$)methoxy)-6-(2-hydroxypropan-2-yl)-2-[(6-methylpyridazin-3-yl)methyl]-2,3-dihydro-1H-isoindol-1-one;

(3R)-3-(4-chlorophenyl)-2-[(5-chloropyridin-2-yl)methyl]-4-fluoro-6-(2-hydroxypropan-2-yl)-3-[(1-methoxycyclopropyl)methoxy]-2,3-dihydro-1H-isoindol-1-one;

(3R)-3-(4-chlorophenyl)-2-[(5-chloropyridin-2-yl)methyl]-6-(1,2-dihydroxypropan-2-yl)-3-{[1-(hydroxymethyl)cyclopropyl]methoxy}-2,3-dihydro-1H-isoindol-1-one;

(3R)-3-(4-chlorophenyl)-2-[(5-chloropyridin-2-yl)methyl]-6-(1,2-dihydroxypropan-2-yl)-4-fluoro-3-({1-[hydroxy($^2H_2$)methyl]cyclopropyl}($^2H_2$)methoxy)-2,3-dihydro-1H-isoindol-1-one;

(3R)-3-(4-chlorophenyl)-2-[(5-chloropyridin-2-yl)methyl]-6-(2,4-dihydroxybutan-2-yl)-3-{[1-(hydroxymethyl)cyclopropyl]methoxy}-2,3-dihydro-1H-isoindol-1-one;

6-{[(1R)-1-(4-chlorophenyl)-5-(2,4-dihydroxybutan-2-yl)-7-fluoro-1-({1-[hydroxy($^2H_2$)methyl]cyclopropyl}($^2H_2$)methoxy)-3-oxo-2,3-dihydro-1H-isoindol-2-yl]methyl}pyridine-3-carbonitrile;

(3R)-3-(4-chlorophenyl)-2-[(5-chloropyridin-2-yl)methyl]-6-[1-(dimethylamino)-2-hydroxypropan-2-yl]-4-fluoro-3-({1-[hydroxy($^2H_2$)methyl]cyclopropyl}($^2H_2$)methoxy)-2,3-dihydro-1H-isoindol-1-one;

(3R)-3-(4-chlorophenyl)-2-[(5-chloropyridin-2-yl)methyl]-4-fluoro-3-({1-[hydroxy($^2H_2$)methyl]cyclopropyl}($^2$H$_2$)methoxy)-6-(2-hydroxy-1-methoxypropan-2-yl)-2,3-dihydro-1H-isoindol-1-one;

(3R)-3-(4-chlorophenyl)-2-[(5-chloropyridin-2-yl)methyl]-4-fluoro-3-[3-hydroxy-2-(hydroxymethyl)-2-methylpropoxy]-6-(2-hydroxypropan-2-yl)-2,3-dihydro-1H-isoindol-1-one;

1-({[(1R)-1-(4-chlorophenyl)-2-[(5-chloropyridin-2-yl)methyl]-7-fluoro-5-(2-hydroxypropan-2-yl)-3-oxo-2,3-dihydro-1H-isoindol-1-yl]oxy}methyl)cyclopropane-1-carbonitrile;

(3R)-3-(4-chlorophenyl)-4-fluoro-3-{[1-(hydroxymethyl)cyclopropyl]methoxy}-6-(2-hydroxypropan-2-yl)-2-[(5-methylpyridin-2-yl)methyl]-2,3-dihydro-1H-isoindol-1-one;

(3R)-3-(4-chlorophenyl)-4-fluoro-3-{[1-(hydroxymethyl)cyclopropyl]methoxy}-6-(2-hydroxypropan-2-yl)-2-[(5-methoxypyridin-2-yl)methyl]-2,3-dihydro-1H-isoindol-1-one;

3-(4-chlorophenyl)-2-[(5-chloropyrimidin-2-yl)methyl]-4-fluoro-3-{[1-(hydroxymethyl)cyclopropyl]methoxy}-6-(2-hydroxypropan-2-yl)-2,3-dihydro-1H-isoindol-1-one;

(3R)-3-(4-chlorophenyl)-2-[(5-chloropyridin-2-yl)methyl]-3-[(1-hydroxycyclopropyl)methoxy]-6-(2-hydroxypropan-2-yl)-2,3-dihydro-1H-isoindol-1-one;

(3R)-3-(4-chlorophenyl)-2-[(5-chloropyridin-2-yl)methyl]-3-({1-[hydroxy($^2$H$_2$)methyl]cyclopropyl}($^2$H$_2$)methoxy)-6-(2-hydroxypropan-2-yl)-2,3-dihydro-1H-isoindol-1-one;

(3R)-3-(4-chlorophenyl)-2-[(5-chloropyridin-2-yl)methyl]-4-fluoro-6-(2-hydroxypropan-2-yl)-3-[(1-methanesulfonylcyclopropyl)methoxy]-2,3-dihydro-1H-isoindol-1-one;

N-[1-({[(1R)-1-(4-chlorophenyl)-2-[(5-chloropyridin-2-yl)methyl]-7-fluoro-5-(2-hydroxypropan-2-yl)-3-oxo-2,3-dihydro-1H-isoindol-1-yl]oxy}methyl)cyclopropyl]acetamide;

6-{[(1R)-1-(4-chlorophenyl)-1-({1-[hydroxy($^2$H$_2$)methyl]cyclopropyl}($^2$H$_2$)methoxy)-5-(2-hydroxypropan-2-yl)-3-oxo-2,3-dihydro-1H-isoindol-2-yl]methyl}pyridine-3-carbonitrile;

6-{[(1R)-1-(4-chlorophenyl)-7-fluoro-1-{[1-(hydroxymethyl)cyclopropyl]methoxy}-5-(2-hydroxypropan-2-yl)-3-oxo-2,3-dihydro-1H-isoindol-2-yl]methyl}pyridine-3-carbonitrile;

(3R)-3-(4-chlorophenyl)-4-fluoro-3-({1-[hydroxy($^2$H$_2$)methyl]cyclopropyl}($^2$H$_2$)methoxy)-6-(2-hydroxypropan-2-yl)-2-[(6-methoxypyridin-3-yl)methyl]-2,3-dihydro-1H-isoindol-1-one;

(3R)-3-(4-chlorophenyl)-2-[(5-chloropyridin-2-yl)methyl]-3-[(3-hydroxycyclopentyl)oxy]-6-(2-hydroxypropan-2-yl)-2,3-dihydro-1H-isoindol-1-one;

6-{[(1R)-1-(4-chlorophenyl)-7-fluoro-1-[(3-hydroxycyclopentyl)oxy]-5-(2-hydroxypropan-2-yl)-3-oxo-2,3-dihydro-1H-isoindol-2-yl]methyl}pyridine-3-carbonitrile;

(3R)-3-(4-chlorophenyl)-2-[(5-chloropyridin-2-yl)methyl]-3-{[(1R, 3R)-3-hydroxycyclopentyl]oxy}-6-(2-hydroxypropan-2-yl)-2,3-dihydro-1H-isoindol-1-one;

(3R)-3-(4-chlorophenyl)-2-[(5-chloropyridin-2-yl)methyl]-3-{[(1 S,3S)-3-hydroxycyclopentyl]oxy}-6-(2-hydroxypropan-2-yl)-2,3-dihydro-1H-isoindol-1-one;

(3S)-3-(4-chloro-2-fluorophenyl)-2-[(5-chloropyridin-2-yl)methyl]-3-{[1-(hydroxymethyl)cyclopropyl]methoxy}-6-(2-hydroxypropan-2-yl)-2,3-dihydro-1H-isoindol-1-one;

(3R)-2-[(5-chloropyridin-2-yl)methyl]-3-(4-ethylphenyl)-3-{[1-(hydroxymethyl)cyclopropyl]methoxy}-6-(2-hydroxypropan-2-yl)-2,3-dihydro-1H-isoindol-1-one;

4-[(1R)-2-[(5-chloropyridin-2-yl)methyl]-1-({1-[hydroxy($^2$H$_2$)methyl]cyclopropyl}($^2$H$_2$)methoxy)-5-(2-hydroxypropan-2-yl)-3-oxo-2,3-dihydro-1H-isoindol-1-yl]benzonitrile;

(3R)-2-[(5-chloropyridin-2-yl)methyl]-3-(4-fluorophenyl)-3-({1-[hydroxy($^2$H$_2$)methyl]cyclopropyl}($^2$H$_2$)methoxy)-6-(2-hydroxypropan-2-yl)-2,3-dihydro-1H-isoindol-1-one;

(3R)-2-[(5-chloropyridin-2-yl)methyl]-3-({1-[hydroxy($^2$H$_2$)methyl]cyclopropyl}($^2$H$_2$)methoxy)-6-(2-hydroxypropan-2-yl)-3-[4-(trifluoromethyl)phenyl]-2,3-dihydro-1H-isoindol-1-one;

(3R)-2-[(5-chloropyridin-2-yl)methyl]-3-[4-(1,1-difluoroethyl)phenyl]-3-{[1-(hydroxymethyl)cyclopropyl]methoxy}-6-(2-hydroxypropan-2-yl)-2,3-dihydro-1H-isoindol-1-one;

(3R)-2-[(5-chloropyridin-2-yl)methyl]-3-(3,4-difluorophenyl)-3-({1-[hydroxy($^2$H$_2$)methyl]cyclopropyl}($^2$H$_2$)methoxy)-6-(2-hydroxypropan-2-yl)-2,3-dihydro-1H-isoindol-1-one;

(3R)-2-[(5-chloropyridin-2-yl)methyl]-3-({1-[hydroxy($^2$H$_2$)methyl]cyclopropyl}($^2$H$_2$)methoxy)-6-(2-hydroxypropan-2-yl)-3-[4-(trifluoromethoxy)phenyl]-2,3-dihydro-1H-isoindol-1-one;

(3R)-4-chloro-3-(4-chlorophenyl)-2-[(5-chloropyridin-2-yl)methyl]-6-(2-hydroxypropan-2-yl)-3-methoxy-2,3-dihydro-1H-isoindol-1-one;

(3R)-3-(4-chlorophenyl)-2-[(5-chloropyridin-2-yl)methyl]-6-[1-hydroxy-1-(1H-pyrazol-4-yl)ethyl]-3-methoxy-2,3-dihydro-1H-isoindol-1-one;

(3R)-3-(4-chlorophenyl)-2-[(5-chloropyridin-2-yl)methyl]-6-[1-hydroxy-1-(1-methyl-1H-pyrazol-4-yl)ethyl]-3-methoxy-2,3-dihydro-1H-isoindol-1-one;

(3R)-3-(4-chlorophenyl)-2-[(5-chloropyridin-2-yl)methyl]-3-[(2S)-3-hydroxy-2-methyl(3,3-$^2$H$_2$)propoxy]-6-(2-hydroxypropan-2-yl)-2,3-dihydro-1H-isoindol-1-one;

(3R)-3-(4-chlorophenyl)-2-[(5-chloropyridin-2-yl)methyl]-3-[(2R)-3-hydroxy-2-methyl(3,3-$^2$H$_2$)propoxy]-6-(2-hydroxypropan-2-yl)-2,3-dihydro-1H-isoindol-1-one;

3-{[(1R)-1-(4-chlorophenyl)-2-[(5-chloropyridin-2-yl)methyl]-5-(2-hydroxypropan-2-yl)-3-oxo-2,3-dihydro-1H-isoindol-1-yl]oxy}-1λ6-thiolane-1,1-dione;

2-[1-({[(1R)-1-(4-chlorophenyl)-2-[(5-chloropyridin-2-yl)methyl]-5-(2-hydroxypropan-2-yl)-3-oxo-2,3-dihydro-1H-isoindol-1-yl]oxy}methyl)cyclopropyl]acetonitrile;

(3R)-3-[(1-acetylazetidin-3-yl)methoxy]-3-(4-chlorophenyl)-2-[(5-chloropyridin-2-yl)methyl]-6-(2-hydroxypropan-2-yl)-2,3-dihydro-1H-isoindol-1-one;

(3R)-3-(4-chlorophenyl)-2-[(5-chloropyridin-2-yl)methyl]-3-[3-(hydroxymethyl)cyclobutoxy]-6-(2-hydroxypropan-2-yl)-2,3-dihydro-1H-isoindol-1-one;

(3R)-3-[(1-aminocyclopropyl)methoxy]-3-(4-chlorophenyl)-2-[(5-chloropyridin-2-yl)methyl]-4-fluoro-6-(2-hydroxypropan-2-yl)-2,3-dihydro-1H-isoindol-1-one;

1-({[(1R)-1-(4-chlorophenyl)-2-[(5-chloropyridin-2-yl)methyl]-7-fluoro-5-(2-hydroxypropan-2-yl)-3-oxo-2, 3-dihydro-1H-isoindol-1-yl]oxy}methyl)-N-methylcyclopropane-1-carboxamide;
1-({[(1R)-1-(4-chlorophenyl)-2-[(5-chloropyridin-2-yl)methyl]-7-fluoro-5-[2-hydroxy-1-(piperazin-1-yl)propan-2-yl]-3-oxo-2,3-dihydro-1H-isoindol-1-yl]oxy}methyl)cyclopropane-1-carboxamide;
1-({[(1R)-1-(4-chlorophenyl)-2-[(1S)-1-(5-chloropyridin-2-yl)ethyl]-7-fluoro-5-(2-hydroxypropan-2-yl)-3-oxo-2,3-dihydro-1H-isoindol-1-yl]oxy}methyl)cyclopropane-1-carboxamide;
1-({[(1R)-1-(4-chlorophenyl)-2-[(1R)-1-(5-chloropyridin-2-yl)ethyl]-7-fluoro-5-(2-hydroxypropan-2-yl)-3-oxo-2,3-dihydro-1H-isoindol-1-yl]oxy}methyl)cyclopropane-1-carboxamide;
(3R)-3-(4-chlorophenyl)-2-[(1S)-1-(5-chloropyridin-2-yl)ethyl]-3-[(1-hydroxycyclopropyl)methoxy]-6-(2-hydroxypropan-2-yl)-2,3-dihydro-1H-isoindol-1-one;
6-{[(1R)-1-(4-chlorophenyl)-7-fluoro-1-{[2-(hydroxymethyl)cyclopentyl]oxy}-5-(2-hydroxypropan-2-yl)-3-oxo-2,3-dihydro-1H-isoindol-2-yl]methyl}pyridine-3-carbonitrile;
(3R)-3-(4-chlorophenyl)-2-[(5-chloropyridin-2-yl)methyl]-6-(2-hydroxypropan-2-yl)-3-[(3-methyloxetan-3-yl)methoxy]-2,3-dihydro-1H-isoindol-1-one;
(3R)-3-(4-chlorophenyl)-2-[(5-chloropyridin-2-yl)methyl]-4-fluoro-6-(2-hydroxypropan-2-yl)-3-[(3S)-oxolan-3-yloxy]-2,3-dihydro-1H-isoindol-1-one;
(3R)-3-(4-chlorophenyl)-2-[(5-chloropyridin-2-yl)methyl]-4-fluoro-6-(2-hydroxypropan-2-yl)-3-[(3R)-oxolan-3-yloxy]-2,3-dihydro-1H-isoindol-1-one;
(3R)-3-(4-chlorophenyl)-2-[(5-chloropyridin-2-yl)methyl]-6-[1-hydroxy-1-(pyridin-3-yl)ethyl]-3-methoxy-2,3-dihydro-1H-isoindol-1-one;
(3R)-3-(4-chlorophenyl)-2-[(5-chloropyridin-2-yl)methyl]-6-[1-hydroxy-1-(oxan-4-yl)ethyl]-3-methoxy-2,3-dihydro-1H-isoindol-1-one;
6-{[(1R)-1-(4-chlorophenyl)-7-fluoro-1-[(3-hydroxycyclobutyl)methoxy]-5-(2-hydroxypropan-2-yl)-3-oxo-2,3-dihydro-1H-isoindol-2-yl]methyl}pyridine-3-carbonitrile;
1-({[(1R)-1-(4-chlorophenyl)-2-[(5-chloropyridin-2-yl)methyl]-7-fluoro-5-[1-hydroxy-1-(oxan-4-yl)ethyl]-3-oxo-2,3-dihydro-1H-isoindol-1-yl]oxy}methyl)cyclopropane-1-carboxamide;
6-{[(1R)-1-(4-chlorophenyl)-7-fluoro-1-(3-hydroxycyclobutoxy)-5-(2-hydroxypropan-2-yl)-3-oxo-2,3-dihydro-1H-isoindol-2-yl]methyl}pyridine-3-carbonitrile;
(3R)-6-[1-(1-acetylpiperidin-4-yl)-1-hydroxyethyl]-3-(4-chlorophenyl)-2-[(5-chloropyridin-2-yl)methyl]-3-methoxy-2,3-dihydro-1H-isoindol-1-one;
6-{[(1R)-1-(4-chlorophenyl)-1-(cyclopropylmethoxy)-5-(2-hydroxypropan-2-yl)-3-oxo-2,3-dihydro-1H-isoindol-2-yl]methyl}pyridine-3-carbonitrile;
(3R)-3-(4-chlorophenyl)-2-[(5-chloropyridin-2-yl)methyl]-6-[1-hydroxy-1-(1-oxo-1A$^5$-pyridin-3-yl)ethyl]-3-methoxy-2,3-dihydro-1H-isoindol-1-one;
6-{[(1R)-1-(4-chlorophenyl)-7-fluoro-5-[1-hydroxy-1-(oxan-4-yl)ethyl]-1-{[1-(hydroxymethyl)cyclopropyl]methoxy}-3-oxo-2,3-dihydro-1H-isoindol-2-yl]methyl}pyridine-3-carbonitrile;
(3R)-3-(4-chlorophenyl)-2-[(5-chloropyridin-2-yl)methyl]-6-[2-hydroxy-1-(oxan-4-yl)propan-2-yl]-3-methoxy-2,3-dihydro-1H-isoindol-1-one;
(3R)-3-(4-chlorophenyl)-2-[(5-chloropyridin-2-yl)methyl]-3-(3-hydroxy-3-methylbutoxy)-6-(2-hydroxypropan-2-yl)-2,3-dihydro-1H-isoindol-1-one;
(3R)-3-(4-chlorophenyl)-2-[(5-chloropyridin-2-yl)methyl]-6-(2-hydroxypropan-2-yl)-3-(2-methanesulfonylethoxy)-2,3-dihydro-1H-isoindol-1-one;
(3R)-3-(4-chlorophenyl)-2-[(5-chloropyridin-2-yl)methyl]-3-(cyclobutylmethoxy)-6-(2-hydroxypropan-2-yl)-2,3-dihydro-1H-isoindol-1-one;
(3R)-3-(4-chlorophenyl)-2-[(5-chloropyridin-2-yl)methyl]-3-(2-hydroxy-2-methylpropoxy)-6-(2-hydroxypropan-2-yl)-2,3-dihydro-1H-isoindol-1-one;
(3R)-3-(4-chlorophenyl)-2-[(5-chloropyridin-2-yl)methyl]-4-fluoro-3-(2-hydroxybutoxy)-6-(2-hydroxypropan-2-yl)-2,3-dihydro-1H-isoindol-1-one;
2-{2-[(1R)-1-(4-chlorophenyl)-2-[(5-chloropyridin-2-yl)methyl]-1-methoxy-3-oxo-2,3-dihydro-1H-isoindol-5-yl]-2-hydroxypropoxy}-N,N-dimethylacetamide;
(3R)-3-(4-chlorophenyl)-2-[(5-chloropyridin-2-yl)methyl]-4-fluoro-3-{[1-(2-hydroxyethoxy)cyclopropyl]methoxy}-6-(2-hydroxypropan-2-yl)-2,3-dihydro-1H-isoindol-1-one;
(3R)-3-(4-chlorophenyl)-2-[(5-chloropyridin-2-yl)methyl]-6-[2-hydroxy-1-(2-hydroxyethoxy)propan-2-yl]-3-methoxy-2,3-dihydro-1H-isoindol-1-one;
(3R)-3-(4-chlorophenyl)-2-[(5-chloropyridin-2-yl)methyl]-6-[2-hydroxy-1-(piperazin-1-yl)propan-2-yl]-3-methoxy-2,3-dihydro-1H-isoindol-1-one;
(3R)-3-(4-chlorophenyl)-2-[(5-chloropyridin-2-yl)methyl]-6-[2-hydroxy-1-(morpholin-4-yl)propan-2-yl]-3-methoxy-2,3-dihydro-1H-isoindol-1-one;
(3R)-3-(4-chlorophenyl)-2-[(5-chloropyridin-2-yl)methyl]-6-[2-hydroxy-1-(methylamino)propan-2-yl]-3-methoxy-2,3-dihydro-1H-isoindol-1-one;
(3R)-3-(4-chlorophenyl)-2-[(5-chloropyridin-2-yl)methyl]-6-[1-(cyclopropylamino)-2-hydroxypropan-2-yl]-3-methoxy-2,3-dihydro-1H-isoindol-1-one;
(3R)-3-(4-chlorophenyl)-2-[(5-chloropyridin-2-yl)methyl]-6-[2-hydroxy-1-(4-methyl-3-oxopiperazin-1-yl)propan-2-yl]-3-methoxy-2,3-dihydro-1H-isoindol-1-one;
N-{2-[(1R)-1-(4-chlorophenyl)-2-[(5-chloropyridin-2-yl)methyl]-1-methoxy-3-oxo-2,3-dihydro-1H-isoindol-5-yl]-2-hydroxypropyl}acetamide;
(3R)-6-[1-(4-acetylpiperazin-1-yl)-2-hydroxypropan-2-yl]-3-(4-chlorophenyl)-2-[(5-chloropyridin-2-yl)methyl]-3-methoxy-2,3-dihydro-1H-isoindol-1-one;
6-{[(1R)-1-(4-chlorophenyl)-7-fluoro-1-[(2-hydroxycyclopentyl)oxy]-5-(2-hydroxypropan-2-yl)-3-oxo-2,3-dihydro-1H-isoindol-2-yl]methyl}pyridine-3-carbonitrile;
(3R)-3-(4-chlorophenyl)-2-[(5-chloropyridin-2-yl)methyl]-6-[1-hydroxy-1-(pyrimidin-5-yl)ethyl]-3-methoxy-2,3-dihydro-1H-isoindol-1-one;
(3R)-3-(4-chlorophenyl)-2-[(5-chloropyridin-2-yl)methyl]-6-[1-hydroxy-1-(pyridin-4-yl)ethyl]-3-methoxy-2,3-dihydro-1H-isoindol-1-one;
(3R)-3-(4-chlorophenyl)-2-[(5-chloropyridin-2-yl)methyl]-6-[1-hydroxy-1-(2-methoxypyridin-4-yl)ethyl]-3-methoxy-2,3-dihydro-1H-isoindol-1-one;
1-({[(1R)-5-[1-(4-acetylpiperazin-1-yl)-2-hydroxypropan-2-yl]-1-(4-chlorophenyl)-2-[(5-chloropyridin-2-yl)methyl]-7-fluoro-3-oxo-2,3-dihydro-1H-isoindol-1-yl]oxy}methyl)cyclopropane-1-carboxamide;
1-({[(1R)-1-(4-chlorophenyl)-2-[(5-chloropyridin-2-yl)methyl]-7-fluoro-5-[2-hydroxy-1-(4-m ethylpiperazin-1-yl)propan-2-yl]-3-oxo-2,3-dihydro-1H-isoindol-1-yl]oxy}methyl)cyclopropane-1-carboxamide;
1-({[(1R)-1-(4-chlorophenyl)-2-[(5-chloropyridin-2-yl)methyl]-7-fluoro-5-(2-hydroxy-1-methoxypropan-2- yl)-3-oxo-2,3-dihydro-1H-isoindol-1-yl]oxy}methyl)cyclopropane-1-carboxamide;

(3R)-3-(4-chlorophenyl)-2-[(5-chloropyridin-2-yl)methyl]-6-[1-hydroxy-1-(1-methyl-1H-imidazol-5-yl)ethyl]-3-methoxy-2,3-dihydro-1H-isoindol-1-one;

(3R)-3-(4-chlorophenyl)-2-[(5-chloropyridin-2-yl)methyl]-6-[1-hydroxy-1-(1H-pyrazol-5-yl)ethyl]-3-methoxy-2,3-dihydro-1H-isoindol-1-one;

(3R)-3-(4-chlorophenyl)-2-[(5-chloropyridin-2-yl)methyl]-4-fluoro-6-[2-hydroxy-1-(4-methylpiperazin-1-yl)propan-2-yl]-3-[(1-hydroxycyclopropyl)methoxy]-2,3-dihydro-1H-isoindol-1-one;

(3R)-3-(4-chlorophenyl)-2-[(5-chloropyridin-2-yl)methyl]-6-[1-(dimethylamino)-2-hydroxypropan-2-yl]-4-fluoro-3-[(3S)-oxolan-3-yloxy]-2,3-dihydro-1H-isoindol-1-one;

(3R)-3-(4-chlorophenyl)-2-[(5-chloropyridin-2-yl)methyl]-6-(1-ethoxy-2-hydroxypropan-2-yl)-4-fluoro-3-[(3S)-oxolan-3-yloxy]-2,3-dihydro-1H-isoindol-1-one;

(3R)-3-(4-chlorophenyl)-2-[(5-chloropyridin-2-yl)($^2$H$_2$)methyl]-4-fluoro-6-[2-hydroxy-1-($^2$H$_3$)methoxypropan-2-yl]-3-[(3S)-oxolan-3-yloxy]-2,3-dihydro-1H-isoindol-1-one;

2-{[1-({[(1R)-1-(4-chlorophenyl)-2-[(5-chloropyridin-2-yl)methyl]-7-fluoro-5-(2-hydroxypropan-2-yl)-3-oxo-2,3-dihydro-1H-isoindol-1-yl]oxy}methyl)cyclopropyl]methoxy}acetic acid;

2-[(1R)-1-(4-chlorophenyl)-2-[(5-chloropyridin-2-yl)methyl]-1-methoxy-3-oxo-2,3-dihydro-1H-isoindol-5-yl]-2-hydroxy-N-methylpropanamide;

2-[(1R)-1-(4-chlorophenyl)-2-[(5-chloropyridin-2-yl)methyl]-1-methoxy-3-oxo-2,3-dihydro-1H-isoindol-5-yl]-N-ethyl-2-hydroxypropanamide;

2-[(1R)-1-(4-chlorophenyl)-2-[(5-chloropyridin-2-yl)methyl]-1-methoxy-3-oxo-2,3-dihydro-1H-isoindol-5-yl]-N-[2-(dimethylamino)ethyl]-2-hydroxypropanamide;

2-[(1R)-1-(4-chlorophenyl)-2-[(5-chloropyridin-2-yl)methyl]-1-methoxy-3-oxo-2,3-dihydro-1H-isoindol-5-yl]-2-hydroxy-N-(propan-2-yl)propanamide;

6-{[(1R)-1-(4-chlorophenyl)-7-fluoro-1-{[1-(1-hydroxyethyl)cyclopropyl]methoxy}-5-(2-hydroxypropan-2-yl)-3-oxo-2,3-dihydro-1H-isoindol-2-yl]methyl}pyridine-3-carbonitrile;

2-({[1-({[(1R)-1-(4-chlorophenyl)-2-[(5-chloropyridin-2-yl)methyl]-7-fluoro-5-(2-hydroxypropan-2-yl)-3-oxo-2,3-dihydro-1H-isoindol-1-yl]oxy}methyl)cyclopropyl]methyl}amino)-N-methylacetamide;

N-{[1-({[(1R)-1-(4-chlorophenyl)-2-[(5-chloropyridin-2-yl)methyl]-7-fluoro-5-(2-hydroxypropan-2-yl)-3-oxo-2,3-dihydro-1H-isoindol-1-yl]oxy}methyl)cyclopropyl]methyl}acetamide;

(3R)-3-(4-chlorophenyl)-2-[(5-chloropyridin-2-yl)methyl]-6-[2-hydroxy-1-(2-oxoimidazolidin-1-yl)propan-2-yl]-3-methoxy-2,3-dihydro-1H-isoindol-1-one;

(3R)-3-(4-chlorophenyl)-2-[(5-chloropyridin-2-yl)methyl]-6-[2-hydroxy-1-(1H-imidazol-1-yl)propan-2-yl]-3-methoxy-2,3-dihydro-1H-isoindol-1-one;

(3R)-3-(4-chlorophenyl)-2-[(5-chloropyridin-2-yl)methyl]-6-[1-(1,2-dimethyl-1H-imidazol-4-yl)-1-hydroxyethyl]-4-fluoro-3-methoxy-2,3-dihydro-1H-isoindol-1-one;

(3R)-3-(4-chlorophenyl)-2-[(5-chloropyridin-2-yl)methyl]-4-fluoro-6-[1-hydroxy-1-(1H-imidazol-2-yl)ethyl]-3-methoxy-2,3-dihydro-1H-isoindol-1-one;

(3R)-3-(4-chlorophenyl)-2-[(5-chloropyridin-2-yl)methyl]-4-fluoro-6-[1-hydroxy-1-(1,3-thiazol-2-yl)ethyl]-3-methoxy-2,3-dihydro-1H-isoindol-1-one;

(2S)-3-{[(1R)-1-(4-chlorophenyl)-2-[(5-chloropyridin-2-yl)methyl]-7-fluoro-5-(2-hydroxypropan-2-yl)-3-oxo-2,3-dihydro-1H-isoindol-1-yl]oxy}-2-methylpropanamide;

(2R)-3-{[(1R)-1-(4-chlorophenyl)-2-[(5-chloropyridin-2-yl)methyl]-7-fluoro-5-(2-hydroxypropan-2-yl)-3-oxo-2,3-dihydro-1H-isoindol-1-yl]oxy}-2-methylpropanamide;

6-[(1S)-1-[(1R)-1-(4-chlorophenyl)-7-fluoro-1-{[1-(hydroxymethyl)cyclopropyl]methoxy}-5-(2-hydroxypropan-2-yl)-3-oxo-2,3-dihydro-1H-isoindol-2-yl]ethyl]pyridine-3-carbonitrile;

6-[(1R)-1-[(1R)-1-(4-chlorophenyl)-7-fluoro-1-{[1-(hydroxymethyl)cyclopropyl]methoxy}-5-(2-hydroxypropan-2-yl)-3-oxo-2,3-dihydro-1H-isoindol-2-yl]ethyl]pyridine-3-carbonitrile;

(3R)-3-(4-chlorophenyl)-2-[(5-chloropyridin-2-yl)methyl]-4-fluoro-6-(2-hydroxypropan-2-yl)-3-[(1-methanesulfinylcyclopropyl)methoxy]-2,3-dihydro-1H-isoindol-1-one;

6-{[(1R)-1-(4-chlorophenyl)-7-fluoro-5-(2-hydroxypropan-2-yl)-1-methoxy-3-oxo-2,3-dihydro-1H-isoindol-2-yl]methyl}pyridine-3-carbonitrile;

(3R)-3-(4-chlorophenyl)-2-[(1S)-1-(5-chloropyridin-2-yl)prop-2-en-1-yl]-4-fluoro-3-[(1-hydroxycyclopropyl)methoxy]-6-(2-hydroxypropan-2-yl)-2,3-dihydro-1H-isoindol-1-one;

1-({[(1R)-1-(4-chlorophenyl)-2-[(5-chloropyridin-2-yl)methyl]-7-fluoro-5-[hydroxy(1-methyl-1H-pyrazol-4-yl)methyl]-3-oxo-2,3-dihydro-1H-isoindol-1-yl]oxy}methyl)cyclopropane-1-carboxamide;

1-({[(1R)-1-(4-chlorophenyl)-2-[(5-chloropyridin-2-yl)methyl]-7-fluoro-5-[1-hydroxy-1-(1-methyl-1H-pyrazol-4-yl)ethyl]-3-oxo-2,3-dihydro-1H-isoindol-1-yl]oxy}methyl)cyclopropane-1-carboxamide;

1-({[(1R)-1-(4-chlorophenyl)-2-[(5-chloropyridin-2-yl)methyl]-5-[1-(1-ethyl-1H-pyrazol-4-yl)-1-hydroxyethyl]-7-fluoro-3-oxo-2,3-dihydro-1H-isoindol-1-yl]oxy}methyl)cyclopropane-1-carboxamide;

(3R)-6-{1-[1-(1-acetylazetidin-3-yl)-1H-pyrazol-4-yl]-1-hydroxyethyl}-3-(4-chlorophenyl)-2-[(5-chloropyridin-2-yl)methyl]-4-fluoro-3-methoxy-2,3-dihydro-1H-isoindol-1-one;

(3R)-3-(4-chlorophenyl)-2-[(5-chloropyridin-2-yl)methyl]-6-[1-(1-ethyl-1H-pyrazol-4-yl)-1-hydroxyethyl]-4-fluoro-3-[(1-hydroxycyclopropyl)methoxy]-2,3-dihydro-1H-isoindol-1-one;

(3R)-3-(4-chlorophenyl)-2-[(5-chloropyridin-2-yl)methyl]-4-fluoro-6-[-hydroxy-1-(5-methyl-1,3,4-oxadiazol-2-yl)ethyl]-3-[(1-hydroxycyclopropyl)methoxy]-2,3-dihydro-1H-isoindol-1-one;

(3R)-3-(4-chlorophenyl)-2-[(5-chloropyridin-2-yl)methyl]-4-fluoro-6-[-hydroxy-1-(1-methyl-1H-1,2,3-triazol-4-yl)ethyl]-3-methoxy-2,3-dihydro-1H-isoindol-1-one;

(3R)-3-(4-chlorophenyl)-2-[(5-chloropyridin-2-yl)methyl]-4-fluoro-6-[-hydroxy-1-(1-methyl-1H-pyrazol-3-yl)ethyl]-3-methoxy-2,3-dihydro-1H-isoindol-1-one;

(3R)-3-(4-chlorophenyl)-2-[(5-chloropyridin-2-yl)methyl]-6-(1-{1-[2-(dimethylamino)ethyl]-1H-pyrazol-4-yl}-1-hydroxyethyl)-4-fluoro-3-methoxy-2,3-dihydro-1H-isoindol-1-one;

1-({[(1R)-1-(4-chlorophenyl)-2-[(5-chloropyridin-2-yl) methyl]-7-fluoro-5-[-hydroxy-1-(1,3-thiazol-4-yl) ethyl]-3-oxo-2,3-dihydro-1H-isoindol-1-yl] oxy}methyl)cyclopropane-1-carboxamide;

(3R)-3-(4-chlorophenyl)-2-[(5-chloropyridin-2-yl) methyl]-4-fluoro-6-[-hydroxy-1-(1-methyl-1H-imidazol-4-yl)ethyl]-3-[(1-hydroxycyclopropyl)methoxy]-2,3-dihydro-1H-isoindol-1-one;

1-({[(1R)-1-(4-chlorophenyl)-2-[(5-chloropyridin-2-yl) methyl]-5-[-(1,2-dimethyl-1H-imidazol-4-yl)-1-hydroxyethyl]-7-fluoro-3-oxo-2,3-dihydro-1H-isoindol-1-yl]oxy}methyl)cyclopropane-1-carboxamide;

(3R)-3-(4-chlorophenyl)-2-[(5-chloropyridin-2-yl) methyl]-4-fluoro-6-[-hydroxy-1-(1-methyl-1H-pyrazol-4-yl)ethyl]-3-[(1-hydroxycyclopropyl)methoxy]-2,3-dihydro-1H-isoindol-1-one;

1-({[(1R)-1-(4-chlorophenyl)-2-[(5-chloropyridin-2-yl) methyl]-7-fluoro-5-[1-hydroxy-1-(1-methyl-1H-pyrazol-4-yl)ethyl]-3-oxo-2,3-dihydro-1H-isoindol-1-yl] oxy}methyl)cyclopropane-1-carbonitrile;

(3R)-3-(4-chlorophenyl)-2-[(5-chloropyrimidin-2-yl) methyl]-4-fluoro-6-[1-hydroxy-1-(1-methyl-1H-pyrazol-4-yl)ethyl]-3-[(1-hydroxycyclopropyl)methoxy]-2,3-dihydro-1H-isoindol-1-one;

(3R)-3-(4-chlorophenyl)-2-[(5-chloropyridin-2-yl) methyl]-4-fluoro-6-[-hydroxy-1-(1-methyl-1H-pyrazol-4-yl)ethyl]-3-[cis-3-hydroxycyclobutoxy]-2,3-dihydro-1H-isoindol-1-one;

(3R)-3-(4-chlorophenyl)-2-[(5-chloropyridin-2-yl) methyl]-4-fluoro-6-[-hydroxy-1-(1-methyl-1H-pyrazol-4-yl)ethyl]-3-[trans-3-hydroxycyclobutoxy]-2,3-dihydro-1H-isoindol-1-one;

1-({[(1R)-1-(4-chlorophenyl)-7-fluoro-2-[(5-fluoropyridin-2-yl)methyl]-5-[1-hydroxy-1-(1-methyl-1H-pyrazol-4-yl)ethyl]-3-oxo-2,3-dihydro-1H-isoindol-1-yl] oxy}methyl)cyclopropane-1-carboxamide;

6-{[(1R)-1-(4-chlorophenyl)-1-[(1-cyanocyclopropyl) methoxy]-7-fluoro-5-[1-hydroxy-1-(1-methyl-1H-pyrazol-4-yl)ethyl]-3-oxo-2,3-dihydro-1H-isoindol-2-yl]methyl}pyridine-3-carbonitrile;

(3R)-3-(4-chlorophenyl)-2-[(5-chloropyridin-2-yl) methyl]-4-fluoro-6-[-hydroxy-1-(1-methyl-1H-pyrazol-4-yl)ethyl]-3-(2-hydroxyethoxy)-2,3-dihydro-1H-isoindol-1-one;

1-({[(1R)-1-(4-chlorophenyl)-2-[(5-chloropyrimidin-2-yl)methyl]-7-fluoro-5-[1-hydroxy-1-(1-methyl-1H-pyrazol-4-yl)ethyl]-3-oxo-2,3-dihydro-1H-isoindol-1-yl]oxy}methyl)cyclopropane-1-carboxamide;

1-({[(1R)-1-(4-chlorophenyl)-7-fluoro-5-[1-hydroxy-1-(1-methyl-1H-pyrazol-4-yl)ethyl]-2-[(6-methoxypyridin-3-yl)methyl]-3-oxo-2,3-dihydro-1H-isoindol-1-yl] oxy}methyl)cyclopropane-1-carboxamide;

6-{[(1R)-1-(4-chlorophenyl)-7-fluoro-5-[1-hydroxy-1-(1-methyl-1H-pyrazol-4-yl)ethyl]-3-oxo-1-[(3S)-oxolan-3-yloxy]-2,3-dihydro-1H-isoindol-2-yl] methyl}pyridine-3-carbonitrile;

(3R)-3-(4-chlorophenyl)-4-fluoro-6-[1-hydroxy-1-(1-methyl-1H-pyrazol-4-yl)ethyl]-3-{[1-(hydroxymethyl) cyclopropyl]methoxy}-2-[(6-m ethoxypyridin-3-yl) methyl]-2,3-dihydro-1H-isoindol-1-one;

(3R)-3-(4-chlorophenyl)-2-[(5-chloropyridin-2-yl) methyl]-4-fluoro-6-[1-hydroxy-1-(1-methyl-1H-pyrazol-4-yl)ethyl]-3-[(2R)-2-hydroxypropoxy]-2,3-dihydro-1H-isoindol-1-one;

(3R)-3-(4-chlorophenyl)-2-[(5-chloropyridin-2-yl) methyl]-4-fluoro-6-[-hydroxy-1-(1-methyl-1H-pyrazol-4-yl)ethyl]-3-[(3S)-oxolan-3-yloxy]-2,3-dihydro-1H-isoindol-1-one;

(3R)-3-(4-chlorophenyl)-4-fluoro-6-[1-hydroxy-1-(1-methyl-1H-pyrazol-4-yl)ethyl]-3-{[1-(hydroxymethyl) cyclopropyl]methoxy}-2-[(5-methoxypyridin-2-yl) methyl]-2,3-dihydro-1H-isoindol-1-one;

(3R)-3-(4-chlorophenyl)-4-fluoro-6-[1-hydroxy-1-(1-methyl-1H-pyrazol-4-yl)ethyl]-3-[(1-hydroxycyclopropyl)methoxy]-2-[(5-methylpyridin-2-yl)methyl]-2,3-dihydro-1H-isoindol-1-one;

(3R)-3-(4-chlorophenyl)-4-fluoro-6-[1-hydroxy-1-(1-methyl-1H-pyrazol-4-yl)ethyl]-3-[(1-hydroxycyclopropyl)methoxy]-2-[(5-methoxypyridin-2-yl)methyl]-2,3-dihydro-1H-isoindol-1-one;

(3R)-3-(4-chlorophenyl)-4-fluoro-6-[1-hydroxy-1-(1-methyl-1H-pyrazol-4-yl)ethyl]-3-[(1-hydroxycyclopropyl)methoxy]-2-[(6-methoxypyridin-3-yl)methyl]-2,3-dihydro-1H-isoindol-1-one;

(3R)-3-(4-chlorophenyl)-4-fluoro-2-[(5-fluoropyridin-2-yl)methyl]-6-[1-hydroxy-1-(1-methyl-1H-pyrazol-4-yl)ethyl]-3-[(1-hydroxycyclopropyl)methoxy]-2,3-dihydro-1H-isoindol-1-one;

(3R)-3-(4-chlorophenyl)-2-[(5-chloropyridin-2-yl) methyl]-6-[2-hydroxy-1-(pyridin-3-yloxy)propan-2-yl]-3-methoxy-2,3-dihydro-1H-isoindol-1-one;

(3R)-3-(4-chlorophenyl)-2-[(5-chloropyridin-2-yl) methyl]-6-(1-ethoxy-2-hydroxypropan-2-yl)-3-methoxy-2,3-dihydro-1H-isoindol-1-one;

(3R)-3-(4-chlorophenyl)-2-[(5-chloropyridin-2-yl) methyl]-6-{2-hydroxy-1-[4-(2-hydroxyethyl)piperazin-1-yl]propan-2-yl}-3-methoxy-2,3-dihydro-1H-isoindol-1-one;

(3R)-3-(4-chlorophenyl)-2-[(5-chloropyridin-2-yl) methyl]-6-[2-hydroxy-1-(4-hydroxypiperidin-1-yl)propan-2-yl]-3-methoxy-2,3-dihydro-1H-isoindol-1-one;

(3R)-3-(4-chlorophenyl)-2-[(5-chloropyridin-2-yl) methyl]-6-{2-hydroxy-1-[methyl(1-methylpiperidin-4-yl)amino]propan-2-yl}-3-methoxy-2,3-dihydro-1H-isoindol-1-one;

(3R)-3-(4-chlorophenyl)-2-[(5-chloropyridin-2-yl) methyl]-6-{2-hydroxy-1-[(oxan-4-yl)amino]propan-2-yl}-3-methoxy-2,3-dihydro-1H-isoindol-1-one;

(3R)-3-(4-chlorophenyl)-2-[(5-chloropyridin-2-yl) methyl]-6-[2-hydroxy-1-(3-oxopiperazin-1-yl)propan-2-yl]-3-methoxy-2,3-dihydro-1H-isoindol-1-one;

(3R)-3-(4-chlorophenyl)-2-[(5-chloropyridin-2-yl) methyl]-6-[1-(1,4-diazepan-1-yl)-2-hydroxypropan-2-yl]-3-methoxy-2,3-dihydro-1H-isoindol-1-one;

4-{2-[(1R)-1-(4-chlorophenyl)-2-[(5-chloropyridin-2-yl) methyl]-1-methoxy-3-oxo-2,3-dihydro-1H-isoindol-5-yl]-2-hydroxypropyl}-1λ6-thiomorpholine-1,1-dione;

(3R)-3-(4-chlorophenyl)-2-[(5-chloropyridin-2-yl) methyl]-6-{2-hydroxy-1-[(2S)-2-(hydroxymethyl)pyrrolidin-1-yl]propan-2-yl}-3-methoxy-2,3-dihydro-1H-isoindol-1-one;

(3R)-6-{1-[(1-acetylpiperidin-4-yl)(methyl)amino]-2-hydroxypropan-2-yl}-3-(4-chlorophenyl)-2-[(5-chloropyridin-2-yl)methyl]-3-methoxy-2,3-dihydro-1H-isoindol-1-one;

(3R)-6-[1-(4-aminopiperidin-1-yl)-2-hydroxypropan-2-yl]-3-(4-chlorophenyl)-2-[(5-chloropyridin-2-yl) methyl]-3-methoxy-2,3-dihydro-1H-isoindol-1-one;

(3R)-3-(4-chlorophenyl)-2-[(5-chloropyridin-2-yl) methyl]-6-[2-hydroxy-1-(4-methylpiperazin-1-yl)propan-2-yl]-3-methoxy-2,3-dihydro-1H-isoindol-1-one;

(3R)-3-(4-chlorophenyl)-2-[(5-chloropyridin-2-yl)methyl]-6-[2-hydroxy-1-(2-oxopyrrolidin-1-yl)propan-2-yl]-3-methoxy-2,3-dihydro-1H-isoindol-1-one;

(3R)-3-(4-chlorophenyl)-2-[(5-chloropyridin-2-yl)methyl]-6-[2-hydroxy-1-(5-oxo-1,4-diazepan-1-yl)propan-2-yl]-3-methoxy-2,3-dihydro-1H-isoindol-1-one;

(3R)-3-(4-chlorophenyl)-2-[(5-chloropyridin-2-yl)methyl]-6-(2-hydroxy-1-{4H,5H,6H,7H-[1,2,3]triazolo[1,5-a]pyrazin-5-yl}propan-2-yl)-3-methoxy-2,3-dihydro-1H-isoindol-1-one;

(3R)-3-(4-chlorophenyl)-2-[(5-chloropyridin-2-yl)methyl]-6-{2-hydroxy-1-[(1 S,4S)-5-methyl-2,5-diazabicyclo[2.2.1]heptan-2-yl]propan-2-yl}-3-methoxy-2,3-dihydro-1H-isoindol-1-one;

(3R)-3-(4-chlorophenyl)-2-[(5-chloropyridin-2-yl)methyl]-6-{2-hydroxy-1-[(2R)-2-(hydroxymethyl)pyrrolidin-1-yl]propan-2-yl}-3-methoxy-2,3-dihydro-1H-isoindol-1-one;

(3R)-3-(4-chlorophenyl)-2-[(5-chloropyridin-2-yl)methyl]-6-[2-hydroxy-1-(4-methyl-1,4-diazepan-1-yl)propan-2-yl]-3-methoxy-2,3-dihydro-1H-isoindol-1-one;

(3R)-6-[1-(azetidin-1-yl)-2-hydroxypropan-2-yl]-3-(4-chlorophenyl)-2-[(5-chloropyridin-2-yl)methyl]-3-methoxy-2,3-dihydro-1H-isoindol-1-one;

(3R)-3-(4-chlorophenyl)-2-[(5-chloropyridin-2-yl)methyl]-6-{1-[(3S)-3,4-dimethylpiperazin-1-yl]-2-hydroxypropan-2-yl}-3-methoxy-2,3-dihydro-1H-isoindol-1-one;

(3R)-3-(4-chlorophenyl)-2-[(5-chloropyridin-2-yl)methyl]-6-{1-[(3R)-3,4-dimethylpiperazin-1-yl]-2-hydroxypropan-2-yl}-3-methoxy-2,3-dihydro-1H-isoindol-1-one;

(3R)-3-(4-chlorophenyl)-2-[(5-chloropyridin-2-yl)methyl]-6-{1-[(2S)-2,4-dimethylpiperazin-1-yl]-2-hydroxypropan-2-yl}-3-methoxy-2,3-dihydro-1H-isoindol-1-one;

6-{[(1R)-1-(4-chlorophenyl)-1-[(1-cyanocyclopropyl)methoxy]-7-fluoro-5-[2-hydroxy-1-(pyrrolidin-1-yl)propan-2-yl]-3-oxo-2,3-dihydro-1H-isoindol-2-yl]methyl}pyridine-3-carbonitrile;

6-{[(1R)-1-(4-chlorophenyl)-1-[(1-cyanocyclopropyl)methoxy]-7-fluoro-5-[2-hydroxy-1-(4-methylpiperazin-1-yl)propan-2-yl]-3-oxo-2,3-dihydro-1H-isoindol-2-yl]methyl}pyridine-3-carbonitrile;

1-({[(1R)-1-(4-chlorophenyl)-2-[(5-cyanopyridin-2-yl)methyl]-7-fluoro-5-[1-hydroxy-1-(oxan-4-yl)ethyl]-3-oxo-2,3-dihydro-1H-isoindol-1-yl]oxy}methyl)cyclopropane-1-carboxamide;

6-{[(1R)-1-(4-chlorophenyl)-1-[(1-cyanocyclopropyl)methoxy]-7-fluoro-5-[1-hydroxy-1-(oxan-4-yl)ethyl]-3-oxo-2,3-dihydro-1H-isoindol-2-yl]methyl}pyridine-3-carbonitrile;

1-({[(1R)-1-(4-chlorophenyl)-2-[(5-chloropyrimidin-2-yl)methyl]-7-fluoro-5-[1-hydroxy-1-(oxan-4-yl)ethyl]-3-oxo-2,3-dihydro-1H-isoindol-1-yl]oxy}methyl)cyclopropane-1-carboxamide;

(3R)-3-(4-chlorophenyl)-2-[(5-chloropyridin-2-yl)methyl]-4-fluoro-6-{1-hydroxy-1-[1-(pyrimidin-2-yl)piperidin-4-yl]ethyl}-3-methoxy-2,3-dihydro-1H-isoindol-1-one;

6-{[(1R)-1-(4-chlorophenyl)-7-fluoro-5-[1-hydroxy-1-(1-methylpiperidin-4-yl)ethyl]-1-{[1-(hydroxymethyl)cyclopropyl]methoxy}-3-oxo-2,3-dihydro-1H-isoindol-2-yl]methyl}pyridine-3-carbonitrile;

6-{[(1R)-1-(4-chlorophenyl)-7-fluoro-5-[1-hydroxy-1-(piperidin-4-yl)ethyl]-1-{[1-(hydroxymethyl)cyclopropyl]methoxy}-3-oxo-2,3-dihydro-1H-isoindol-2-yl]methyl}pyridine-3-carbonitrile;

6-{[(1R)-5-[1-(1-acetylpiperidin-4-yl)-1-hydroxyethyl]-1-(4-chlorophenyl)-7-fluoro-1-{[1-(hydroxymethyl)cyclopropyl]methoxy}-3-oxo-2,3-dihydro-1H-isoindol-2-yl]methyl}pyridine-3-carbonitrile;

(3R)-6-[1-(1-acetylpiperidin-4-yl)-1-hydroxyethyl]-3-(4-chlorophenyl)-2-[(5-chloropyridin-2-yl)methyl]-4-fluoro-3-methoxy-2,3-dihydro-1H-isoindol-1-one;

(3R)-3-(4-chlorophenyl)-2-[(5-chloropyridin-2-yl)methyl]-4-fluoro-6-[1-hydroxy-1-(1-methanesulfonylpiperidin-4-yl)ethyl]-3-methoxy-2,3-dihydro-1H-isoindol-1-one;

(3R)-3-(4-chlorophenyl)-2-[(5-chloropyridin-2-yl)methyl]-4-fluoro-6-{1-hydroxy-1-[1-(1,3-oxazole-2-carbonyl)piperidin-4-yl]ethyl}-3-methoxy-2,3-dihydro-1H-isoindol-1-one;

(3R)-3-(4-chlorophenyl)-2-[(5-chloropyridin-2-yl)methyl]-4-fluoro-6-{1-hydroxy-1-[1-(2-hydroxyacetyl)piperidin-4-yl]ethyl}-3-methoxy-2,3-dihydro-1H-isoindol-1-one;

6-{[(1R)-5-[1-(1-acetylpiperidin-4-yl)-1-hydroxyethyl]-1-(4-chlorophenyl)-7-fluoro-1-methoxy-3-oxo-2,3-dihydro-1H-isoindol-2-yl]methyl}pyridine-3-carbonitrile;

(3R)-3-(4-chlorophenyl)-2-[(5-chloropyridin-2-yl)methyl]-6-(1-{1-[2-(dimethylamino)acetyl]piperidin-4-yl}-1-hydroxyethyl)-4-fluoro-3-methoxy-2,3-dihydro-1H-isoindol-1-one;

(3R)-6-[1-(1-acetylpiperidin-4-yl)-1-hydroxyethyl]-3-(4-chlorophenyl)-2-[(5-chloropyridin-2-yl)methyl]-4-fluoro-3-[(1-hydroxycyclopropyl)methoxy]-2,3-dihydro-1H-isoindol-1-one;

1-({[(1R)-5-[1-(1-acetylpiperidin-4-yl)-1-hydroxyethyl]-1-(4-chlorophenyl)-2-[(5-chloropyridin-2-yl)methyl]-7-fluoro-3-oxo-2,3-dihydro-1H-isoindol-1-yl]oxy}methyl)cyclopropane-1-carbonitrile;

1-({[(1R)-5-[1-(1-acetylpiperidin-4-yl)-1-hydroxyethyl]-1-(4-chlorophenyl)-2-[(5-chloropyridin-2-yl)methyl]-7-fluoro-3-oxo-2,3-dihydro-1H-isoindol-1-yl]oxy}methyl)cyclopropane-1-carboxamide;

(3R)-3-(4-chlorophenyl)-2-[(5-chloropyridin-2-yl)methyl]-4-fluoro-6-[1-hydroxy-1-(1-methylpiperidin-4-yl)ethyl]-3-methoxy-2,3-dihydro-1H-isoindol-1-one;

1-({[(1R)-1-(4-chlorophenyl)-2-[(5-chloropyridin-2-yl)methyl]-7-fluoro-5-[1-hydroxy-1-(1-methylpiperidin-4-yl)ethyl]-3-oxo-2,3-dihydro-1H-isoindol-1-yl]oxy}methyl)cyclopropane-1-carboxamide;

(3R)-3-(4-chlorophenyl)-2-[(5-chloropyridin-2-yl)methyl]-4-fluoro-6-[1-hydroxy-1-(1-methylazetidin-3-yl)ethyl]-3-methoxy-2,3-dihydro-1H-isoindol-1-one;

6-{[(1R)-1-(4-chlorophenyl)-7-fluoro-5-[1-hydroxy-1-(pyridin-2-yl)ethyl]-1-{[1-(hydroxymethyl)cyclopropyl]methoxy}-3-oxo-2,3-dihydro-1H-isoindol-2-yl]methyl}pyridine-3-carbonitrile;

4-{1-[(1R)-1-(4-chlorophenyl)-2-[(5-chloropyridin-2-yl)methyl]-7-fluoro-1-methoxy-3-oxo-2,3-dihydro-1H-isoindol-5-yl]-1-hydroxyethyl}-1λ6-thiane-1,1-dione;

4-{1-[(1R)-1-(4-chlorophenyl)-2-[(5-chloropyridin-2-yl)methyl]-7-fluoro-1-(2-hydroxyethoxy)-3-oxo-2,3-dihydro-1H-isoindol-5-yl]-1-hydroxyethyl}-1λ6-thiane-1,1-dione;

(3R)-3-(4-chlorophenyl)-4-fluoro-6-(2-hydroxypropan-2-yl)-3-m ethoxy-2-[(2-methoxy-6-methylpyridin-3-yl)methyl]-2,3-dihydro-1H-isoindol-1-one;

6-{[(1R)-1-(4-chlorophenyl)-7-fluoro-5-[1-hydroxy-1-(1-methyl-1H-pyrazol-4-yl)ethyl]-1-{[1-(hydroxymethyl)cyclopropyl]methoxy}-3-oxo-2,3-dihydro-1H-isoindol-2-yl]methyl}pyridine-3-carbonitrile;

(3R)-3-(4-chlorophenyl)-2-[(5-chloropyridin-2-yl)methyl]-6-[1-hydroxy-1-(1-methylpiperidin-4-yl)ethyl]-3-methoxy-2,3-dihydro-1H-isoindol-1-one;

(3R)-3-(4-chlorophenyl)-2-[(5-chloropyridin-2-yl)methyl]-6-[1-hydroxy-1-(pyridin-2-yl)ethyl]-3-methoxy-2,3-dihydro-1H-isoindol-1-one;

(3R)-3-(4-chlorophenyl)-2-[(5-chloropyridin-2-yl)methyl]-6-[2-hydroxy-1-(pyridin-4-yl)propan-2-yl]-3-methoxy-2,3-dihydro-1H-isoindol-1-one;

(3R)-3-(4-chlorophenyl)-2-[(5-chloropyridin-2-yl)methyl]-6-[-(1,2-dimethyl-1H-imidazol-4-yl)-1-hydroxyethyl]-4-fluoro-3-[(1-hydroxycyclopropyl)methoxy]-2,3-dihydro-1H-isoindol-1-one;

(3R)-3-(4-chlorophenyl)-2-[(5-chloropyridin-2-yl)methyl]-4-fluoro-3-[(1-{[(2-hydroxyethyl)amino]methyl}cyclopropyl)methoxy]-6-(2-hydroxypropan-2-yl)-2,3-dihydro-1H-isoindol-1-one;

(3R)-3-(4-chlorophenyl)-2-[(5-chloropyridin-2-yl)methyl]-6-[2-hydroxy-1-(3-oxomorpholin-4-yl)propan-2-yl]-3-methoxy-2,3-dihydro-1H-isoindol-1-one;

1-{2-[(1R)-1-(4-chlorophenyl)-2-[(5-chloropyridin-2-yl)methyl]-1-methoxy-3-oxo-2,3-dihydro-1H-isoindol-5-yl]-2-hydroxypropyl}imidazolidine-2,4-dione;

(3R)-3-(4-chlorophenyl)-2-[(1R)-1-(5-chloropyridin-2-yl)-2,3-dihydroxypropyl]-4-fluoro-3-[(1-hydroxycyclopropyl)m ethoxy]-6-(2-hydroxypropan-2-yl)-2,3-dihydro-1H-isoindol-1-one;

(3R)-3-(4-chlorophenyl)-2-[(5-chloropyridin-2-yl)methyl]-4-fluoro-6-[-hydroxy-1-(4-methyl-1H-imidazol-2-yl)ethyl]-3-[(1-hydroxycyclopropyl)methoxy]-2,3-dihydro-1H-isoindol-1-one;

6-{[(1R)-1-(4-chlorophenyl)-7-fluoro-5-[1-hydroxy-1-(1,3-thiazol-4-yl)propyl]-1-(2-hydroxyethoxy)-3-oxo-2,3-dihydro-1H-isoindol-2-yl]methyl}pyridine-3-carbonitrile;

6-{[(1R)-1-(4-chlorophenyl)-7-fluoro-5-[1-hydroxy-1-(1-methyl-1H-pyrazol-3-yl)propyl]-3-oxo-1-[(3S)-oxolan-3-yloxy]-2,3-dihydro-1H-isoindol-2-yl]methyl}pyridine-3-carbonitrile;

6-{[(1R)-1-(4-chlorophenyl)-7-fluoro-5-[1-hydroxy-1-(1-methyl-1H-imidazol-4-yl)propyl]-1-{[1-(hydroxymethyl)cyclopropyl]methoxy}-3-oxo-2,3-dihydro-1H-isoindol-2-yl]methyl}pyridine-3-carbonitrile;

6-{[(1R)-1-(4-chlorophenyl)-7-fluoro-5-[1-hydroxy-1-(1-methyl-1H-pyrazol-4-yl)propyl]-3-oxo-1-[cis-3-hydroxycyclobutoxy]-2,3-dihydro-1H-isoindol-2-yl]methyl}pyridine-3-carbonitrile;

6-{[(1R)-1-(4-chlorophenyl)-7-fluoro-5-[1-hydroxy-1-(1-methyl-1H-pyrazol-4-yl)ethyl]-1-[(1-hydroxycyclopropyl)methoxy]-3-oxo-2,3-dihydro-1H-isoindol-2-yl]methyl}pyridine-3-carbonitrile;

(3R)-3-(4-chlorophenyl)-2-[(5-chloropyridin-2-yl)methyl]-4-fluoro-6-[1-hydroxy-1-(1-methyl-1H-pyrazol-4-yl)ethyl]-3-{[1-(hydroxymethyl)cyclopropyl]methoxy}-2,3-dihydro-1H-isoindol-1-one;

(3R)-3-(4-chlorophenyl)-2-[(5-chloropyrimidin-2-yl)methyl]-4-fluoro-6-[1-hydroxy-1-(1-methyl-1H-pyrazol-4-yl)ethyl]-3-{[1-(hydroxymethyl)cyclopropyl]methoxy}-2,3-dihydro-1H-isoindol-1-one;

(3R)-3-(4-chlorophenyl)-2-[(3,5-difluoropyridin-2-yl)methyl]-4-fluoro-6-[-hydroxy-1-(1-methyl-1H-pyrazol-4-yl)ethyl]-3-[(1-hydroxycyclopropyl)methoxy]-2,3-dihydro-1H-isoindol-1-one;

6-{[(1R)-1-(4-chlorophenyl)-7-fluoro-1-({1-[hydroxy($^2H_2$)methyl]cyclopropyl}($^2H_2$)methoxy)-5-[1-hydroxy-1-(1-methyl-1H-pyrazol-4-yl)ethyl]-3-oxo-2,3-dihydro-1H-isoindol-2-yl]methyl}pyridine-3-carbonitrile;

6-{[1-(4-chlorophenyl)-7-fluoro-5-[1-hydroxy-1-(1-methyl-1H-pyrazol-4-yl)ethyl]-3-oxo-1-[cis-3-hydroxycyclobutoxy]-2,3-dihydro-1H-isoindol-2-yl]methyl}pyridine-3-carbonitrile;

6-{[(1R)-1-(4-chlorophenyl)-7-fluoro-5-[hydroxy(1-methyl-1H-pyrazol-4-yl)methyl]-3-oxo-1i -[(3S)-oxolan-3-yloxy]-2,3-dihydro-1H-isoindol-2-yl]methyl}pyridine-3-carbonitrile;

6-{[(1R)-1-(4-chlorophenyl)-7-fluoro-5-[1-hydroxy-1-(1-methyl-1H-pyrazol-4-yl)propyl]-3-oxo-1-[(3S)-oxolan-3-yloxy]-2,3-dihydro-1H-isoindol-2-yl]methyl}pyridine-3-carbonitrile;

6-{[(1R)-1-(4-chlorophenyl)-7-fluoro-5-[1-hydroxy-1-(1-methyl-1H-pyrazol-4-yl)prop-2-en-1-yl]-3-oxo-1-[cis-3-hydroxycyclobutoxy]-2,3-dihydro-1H-isoindol-2-yl]methyl}pyridine-3-carbonitrile;

6-{[(1R)-1-(4-chlorophenyl)-7-fluoro-5-[1-hydroxy-1-(1-methyl-1H-imidazol-4-yl)propyl]-1-(2-hydroxyethoxy)-3-oxo-2,3-dihydro-1H-isoindol-2-yl]methyl}pyridine-3-carbonitrile;

6-{[(1R)-1-(4-chlorophenyl)-7-fluoro-5-[1-hydroxy-1-(1-methyl-1H-imidazol-4-yl)propyl]-3-oxo-1-[(3S)-oxolan-3-yloxy]-2,3-dihydro-1H-isoindol-2-yl]methyl}pyridine-3-carbonitrile;

(3R)-3-(4-chlorophenyl)-2-[(6-chloropyridin-3-yl)methyl]-4-fluoro-6-[1-hydroxy-1-(1-methyl-1H-imidazol-4-yl)propyl]-3-(2-hydroxyethoxy)-2,3-dihydro-1H-isoindol-1-one;

2-{[(1R)-1-(4-chlorophenyl)-7-fluoro-5-[1-hydroxy-1-(1-methyl-1H-imidazol-4-yl)propyl]-3-oxo-1-[(3S)-oxolan-3-yloxy]-2,3-dihydro-1H-isoindol-2-yl]methyl}pyrimidine-5-carbonitrile;

6-{[(1R)-1-(4-chlorophenyl)-7-fluoro-3-oxo-1-[(3S)-oxolan-3-yloxy]-5-[2,2,2-trifluoro-1-hydroxy-1-(1-methyl-1H-pyrazol-4-yl)ethyl]-2,3-dihydro-1H-isoindol-2-yl]methyl}pyridine-3-carbonitrile;

(3R)-2-[(5-chloro-3-methanesulfonylpyridin-2-yl)methyl]-3-(4-chlorophenyl)-4-fluoro-6-[1-hydroxy-1-(1-methyl-1H-pyrazol-4-yl)ethyl]-3-methoxy-2,3-dihydro-1H-isoindol-1-one;

6-{[(1R)-1-(4-chlorophenyl)-7-fluoro-5-[1-hydroxy-1-(1-methyl-2-oxo-1,2-dihydropyridin-4-yl)propyl]-3-oxo-1-[(3S)-oxolan-3-yloxy]-2,3-dihydro-1H-isoindol-2-yl]methyl}pyridine-3-carbonitrile;

6-[1-(1-acetylpiperidin-4-yl)-1-hydroxyethyl]-3-(4-chlorophenyl)-2-[(5-chloropyridin-2-yl)methyl]-4-fluoro-3-hydroxy-2,3-dihydro-1H-isoindol-1-one;

(3R)-3-(4-chlorophenyl)-2-[(5-chloropyridin-2-yl)methyl]-6-[2-hydroxy-1-(piperidin-4-yloxy)propan-2-yl]-3-methoxy-2,3-dihydro-1H-isoindol-1-one;

(3R)-3-(4-chlorophenyl)-2-[(5-chloropyridin-2-yl)methyl]-6-{2-hydroxy-1-[(3S)-3-hydroxypyrrolidin-1-yl]propan-2-yl}-3-methoxy-2,3-dihydro-1H-isoindol-1-one;

(3R)-3-(4-chlorophenyl)-2-[(5-chloropyridin-2-yl)methyl]-6-{2-hydroxy-1-[(3R)-3-hydroxypyrrolidin-1-yl]propan-2-yl}-3-methoxy-2,3-dihydro-1H-isoindol-1-one;

(3R)-3-(4-chlorophenyl)-2-[(5-chloropyrimidin-2-yl)methyl]-4-fluoro-6-[1-(4-fluorooxan-4-yl)-1-hydroxyethyl]-3-[(1-hydroxycyclopropyl)methoxy]-2,3-dihydro-1H-isoindol-1-one;

6-{[(1R)-1-(4-chlorophenyl)-7-fluoro-5-[1-(4-fluorooxan-4-yl)-1-hydroxyethyl]-3-oxo-1-[(3S)-oxolan-3-yloxy]-2,3-dihydro-1H-isoindol-2-yl]methyl}pyridine-3-carbonitrile;

(3R)-6-[1-(1-acetylazetidin-3-yl)-1-hydroxyethyl]-3-(4-chlorophenyl)-2-[(5-chloropyridin-2-yl)methyl]-4-fluoro-3-methoxy-2,3-dihydro-1H-isoindol-1-one;

(3R)-3-(4-chlorophenyl)-2-[(5-chloropyridin-2-yl)methyl]-4-fluoro-6-{-hydroxy-1-[1-(2-hydroxyacetyl)azetidin-3-yl]ethyl}-3-methoxy-2,3-dihydro-1H-isoindol-1-one;

3-{1-[(1R)-1-(4-chlorophenyl)-2-[(5-cyanopyridin-2-yl)methyl]-7-fluoro-1-methoxy-3-oxo-2,3-dihydro-1H-isoindol-5-yl]-1-hydroxyethyl}-N,N-dimethylazetidine-1-carboxamide;

(3R)-3-(4-chlorophenyl)-2-[(5-chloropyridin-2-yl)methyl]-4-fluoro-6-[-hydroxy-1-(pyrimidin-2-yl)ethyl]-3-[(1-hydroxycyclopropyl)methoxy]-2,3-dihydro-1H-isoindol-1-one;

4-{1-[(1R)-1-(4-chlorophenyl)-2-[(5-chloropyrimidin-2-yl)methyl]-7-fluoro-1-[(1-hydroxycyclopropyl)methoxy]-3-oxo-2,3-dihydro-1H-isoindol-5-yl]-1-hydroxyethyl}-1λ6-thiane-1,1-dione;

4-{[(1R)-1-(4-chlorophenyl)-2-[(5-chloropyrimidin-2-yl)methyl]-7-fluoro-1-[(1-hydroxycyclopropyl)methoxy]-3-oxo-2,3-dihydro-1H-isoindol-5-yl](hydroxy)methyl}-1λ6-thiane-1,1-dione;

(3R)-3-(4-chlorophenyl)-2-[(5-chloropyrimidin-2-yl)methyl]-4-fluoro-6-{1-hydroxy-1-[trans-4-hydroxycyclohexyl]ethyl}-3-{[1-(hydroxymethyl)cyclopropyl]methoxy}-2,3-dihydro-1H-isoindol-1-one;

1-({[(1R)-1-(4-chlorophenyl)-2-[(5-chloropyrimidin-2-yl)methyl]-5-(1-cyclobutyl-1-hydroxyethyl)-7-fluoro-3-oxo-2,3-dihydro-1H-isoindol-1-yl]oxy}methyl)cyclopropane-1-carboxamide;

6-{[(1R)-1-(4-chlorophenyl)-5-(1-cyclobutyl-1-hydroxyethyl)-7-fluoro-1-(2-hydroxyethoxy)-3-oxo-2,3-dihydro-1H-isoindol-2-yl]methyl}pyridine-3-carbonitrile;

(3R)-2-[(5-chloro-1-oxo-1λ5-pyridin-2-yl)methyl]-3-(4-chlorophenyl)-4-fluoro-6-[1-hydroxy-1-(1-methyl-1H-pyrazol-4-yl)ethyl]-3-{[1-(hydroxymethyl)cyclopropyl]methoxy}-2,3-dihydro-1H-isoindol-1-one;

1-({[(1R)-2-[(5-chloro-1-oxo-1λ5-pyridin-2-yl)methyl]-1-(4-chlorophenyl)-7-fluoro-5-[1-hydroxy-1-(1-methyl-1H-pyrazol-4-yl)ethyl]-3-oxo-2,3-dihydro-1H-isoindol-1-yl]oxy}methyl)cyclopropane-1-carbonitrile;

(3R)-2-[(5-chloro-1-oxo-1λ5-pyridin-2-yl)methyl]-3-(4-chlorophenyl)-4-fluoro-6-[1-hydroxy-1-(1-methyl-1H-pyrazol-4-yl)ethyl]-3-[(1-hydroxycyclopropyl)methoxy]-2,3-dihydro-1H-isoindol-1-one;

6-{[(1R)-1-(4-chlorophenyl)-7-fluoro-5-(2-hydroxybutan-2-yl)-1-{[1-(hydroxymethyl)cyclopropyl]methoxy}-3-oxo-2,3-dihydro-1H-isoindol-2-yl]methyl}pyridine-3-carbonitrile;

6-{[(1R)-1-(4-chlorophenyl)-7-fluoro-5-(2-hydroxybut-3-en-2-yl)-1-{[1-(hydroxymethyl)cyclopropyl]methoxy}-3-oxo-2,3-dihydro-1H-isoindol-2-yl]methyl}pyridine-3-carbonitrile;

6-{[(1R)-1-(4-chlorophenyl)-5-(1-cyclopropyl-1-hydroxyethyl)-7-fluoro-1-{[1-(hydroxymethyl)cyclopropyl]methoxy}-3-oxo-2,3-dihydro-1H-isoindol-2-yl]methyl}pyridine-3-carbonitrile;

6-{[(1R)-1-(4-chlorophenyl)-7-fluoro-1-{[1-(hydroxymethyl)cyclopropyl]methoxy}-3-oxo-5-(1,1,1-trifluoro-2-hydroxypropan-2-yl)-2,3-dihydro-1H-isoindol-2-yl]methyl}pyridine-3-carbonitrile;

(3R)-3-(4-chlorophenyl)-2-[(1R)-1-(5-chloropyridin-2-yl)-2-hydroxyethyl]-4-fluoro-3-{[1-(hydroxymethyl)cyclopropyl]methoxy}-6-(2-hydroxypropan-2-yl)-2,3-dihydro-1H-isoindol-1-one;

6-{[(1R)-1-(4-chlorophenyl)-7-fluoro-5-(2-hydroxypropan-2-yl)-3-oxo-1-{[(trans-3-hydroxycyclobutyl]methoxy}-2,3-dihydro-1H-isoindol-2-yl]methyl}pyridine-3-carbonitrile;

1-({[(1R)-1-(4-chlorophenyl)-2-[(5-chloropyridin-2-yl)methyl]-7-fluoro-5-{1-hydroxy-1-[1-(2-hydroxyethyl)piperidin-4-yl]ethyl}-3-oxo-2,3-dihydro-1H-isoindol-1-yl]oxy}methyl)cyclopropane-1-carbonitrile;

(3R)-6-[1-(1-acetylpiperidin-4-yl)-1-hydroxyethyl]-3-(4-chlorophenyl)-2-[(5-chloropyridin-2-yl)methyl]-4-fluoro-3-(2-hydroxyethoxy)-2,3-dihydro-1H-isoindol-1-one;

(3R)-6-[1-(1-acetylpiperidin-4-yl)-1-hydroxyethyl]-3-(4-chlorophenyl)-2-[(5-chloropyrimidin-2-yl)methyl]-4-fluoro-3-(2-hydroxyethoxy)-2,3-dihydro-1H-isoindol-1-one;

(3R)-3-(4-chlorophenyl)-2-[(5-chloropyrimidin-2-yl)methyl]-4-fluoro-6-[1-hydroxy-1-(1-methylpiperidin-4-yl)ethyl]-3-[(3S)-oxolan-3-yloxy]-2,3-dihydro-1H-isoindol-1-one;

(3R)-6-[1-(1-acetylpiperidin-4-yl)-1-hydroxyethyl]-2-{[5-chloro-3-(hydroxymethyl)pyridin-2-yl]methyl}-3-(4-chlorophenyl)-4-fluoro-3-m ethoxy-2,3-dihydro-1H-isoindol-1-one;

(3R)-6-[1-(1-acetylpiperidin-4-yl)-1-hydroxyethyl]-3-(4-chlorophenyl)-2-[(5-chloropyrimidin-2-yl)methyl]-4-fluoro-3-[cis-3-hydroxycyclobutoxy]-2,3-dihydro-1H-isoindol-1-one;

6-{[(1R)-1-(4-chlorophenyl)-7-fluoro-5-[1-hydroxy-1-(1-methyl-1H-imidazol-4-yl)propyl]-3-oxo-1-[(3R)-oxolan-3-yloxy]-2,3-dihydro-1H-isoindol-2-yl]methyl}pyridine-3-carbonitrile;

6-{[(1R)-1-(4-chlorophenyl)-7-fluoro-5-[1-hydroxy-1-(1-methyl-1H-imidazol-4-yl)propyl]-1-(2-methoxyethoxy)-3-oxo-2,3-dihydro-1H-isoindol-2-yl]methyl}pyridine-3-carbonitrile;

5-{[(1R)-1-(4-chlorophenyl)-7-fluoro-5-[1-hydroxy-1-(1-methyl-1H-imidazol-4-yl)propyl]-3-oxo-1-[(3S)-oxolan-3-yloxy]-2,3-dihydro-1H-isoindol-2-yl]methyl}pyridine-2-carbonitrile;

6-{[(1R)-1-(4-chlorophenyl)-5-[cyclopropyl(hydroxy)(1-methyl-1H-imidazol-4-yl)methyl]-7-fluoro-3-oxo-1-[(3S)-oxolan-3-yloxy]-2,3-dihydro-1H-isoindol-2-yl]methyl}pyridine-3-carbonitrile;

6-{[(1R)-1-(4-chlorophenyl)-7-fluoro-1-[(3-fluorooxetan-3-yl)methoxy]-5-[1-hydroxy-1-(1-methyl-1H-imidazol-4-yl)propyl]-3-oxo-2,3-dihydro-1H-isoindol-2-yl]methyl}pyridine-3-carbonitrile;

6-{[(1R)-1-(4-chlorophenyl)-7-fluoro-5-[1-hydroxy-1-(1-methyl-1H-imidazol-4-yl)propyl]-1-[(2R)-2-hydroxypropoxy]-3-oxo-2,3-dihydro-1H-isoindol-2-yl]methyl}pyridine-3-carbonitrile;

6-{[(1R)-1-(4-chlorophenyl)-7-fluoro-1-({1-[hydroxy($^{2}H_2$)methyl]cyclopropyl}($^{2}H_2$)methoxy)-5-[1-hydroxy-1-(1-methyl-1H-imidazol-4-yl)propyl]-3-oxo-2,3-dihydro-1H-isoindol-2-yl]methyl}pyridine-3-carbonitrile;

6-{[(1R)-1-(4-chlorophenyl)-7-fluoro-5-[2-fluoro-1-hydroxy-1-(1-methyl-1H-pyrazol-4-yl)ethyl]-3-oxo-1-[(3S)-oxolan-3-yloxy]-2,3-dihydro-1H-isoindol-2-yl]methyl}pyridine-3-carbonitrile;

(3R)-2-[(5-chloro-3-hydroxypyridin-2-yl)methyl]-3-(4-chlorophenyl)-4-fluoro-6-[1-hydroxy-1-(1-methyl-1H-imidazol-4-yl)propyl]-3-(2-hydroxyethoxy)-2,3-dihydro-1H-isoindol-1-one;

6-{[(1R)-1-(4-chlorophenyl)-7-fluoro-5-[1-(4-fluorooxan-4-yl)-1-hydroxypropyl]-3-oxo-1-[(3S)-oxolan-3-yloxy]-2,3-dihydro-1H-isoindol-2-yl]methyl}pyridine-3-carbonitrile;

(3R)-3-(4-chlorophenyl)-2-[(5-chloropyrimidin-2-yl)methyl]-4-fluoro-6-[1-(4-fluorooxan-4-yl)-1-hydroxyethyl]-3-({1-[hydroxy($^2$H$_2$)methyl]cyclopropyl}($^2$H$_2$)methoxy)-2,3-dihydro-1H-isoindol-1-one;

(3R)-3-(4-chlorophenyl)-2-[(5-chloropyrimidin-2-yl)methyl]-4-fluoro-6-[1-hydroxy-1-(piperidin-4-yl)propyl]-3-[(3S)-oxolan-3-yloxy]-2,3-dihydro-1H-isoindol-1-one;

(3R)-3-(4-chlorophenyl)-2-[(5-chloropyrimidin-2-yl)methyl]-4-fluoro-6-[1-hydroxy-1-(1-methylpiperidin-4-yl)propyl]-3-[(3S)-oxolan-3-yloxy]-2,3-dihydro-1H-isoindol-1-one;

(3R)-3-(4-chlorophenyl)-2-[(5-chloropyrimidin-2-yl)methyl]-4-fluoro-6-[1-hydroxy-1-(piperidin-4-yl)propyl]-3-methoxy-2,3-dihydro-1H-isoindol-1-one;

2-[(1R)-1-(4-chlorophenyl)-2-[(5-chloropyridin-2-yl)methyl]-1-methoxy-3-oxo-2,3-dihydro-1H-isoindol-5-yl]-2-hydroxy-N-(1-methylpiperidin-4-yl)propanamide;

2-[(1R)-1-(4-chlorophenyl)-2-[(5-chloropyridin-2-yl)methyl]-1-methoxy-3-oxo-2,3-dihydro-1H-isoindol-5-yl]-2-hydroxy-N-(1-methyl-1H-pyrazol-4-yl)propanamide;

2-[(1R)-1-(4-chlorophenyl)-2-[(5-chloropyridin-2-yl)methyl]-1-methoxy-3-oxo-2,3-dihydro-1H-isoindol-5-yl]-2-hydroxy-N-(1-methylazetidin-3-yl)propanamide;

tert-butyl 3-(4-{1-[(1R)-1-(4-chlorophenyl)-2-[(5-chloropyridin-2-yl)methyl]-7-fluoro-1-methoxy-3-oxo-2,3-dihydro-1H-isoindol-5-yl]-1-hydroxyethyl}-1H-pyrazol-1-yl)azetidine-1-carboxylate;

2-(4-{1-[(1R)-1-(4-chlorophenyl)-2-[(5-chloropyridin-2-yl)methyl]-7-fluoro-1-methoxy-3-oxo-2,3-dihydro-1H-isoindol-5-yl]-1-hydroxyethyl}piperidin-1-yl)acetic acid;

(3R)-3-(4-chlorophenyl)-3-{[1-(hydroxymethyl)cyclopropyl]methoxy}-6-(2-hydroxypropan-2-yl)-2-[(5-methylpyrazin-2-yl)methyl]-2,3-dihydro-1H-isoindol-1-one;

2-{[(1R)-1-(4-chlorophenyl)-7-fluoro-5-[1-hydroxy-1-(1-methyl-1H-imidazol-4-yl)propyl]-1-[(trans-3-hydroxycyclopentyl)oxy]-3-oxo-2,3-dihydro-1H-isoindol-2-yl]methyl}pyrimidine-5-carbonitrile;

2-{[(1R)-1-(4-chlorophenyl)-1-[(1-cyanocyclopropyl)methoxy]-7-fluoro-5-[1-hydroxy-1-(1-methyl-1H-imidazol-4-yl)propyl]-3-oxo-2,3-dihydro-1H-isoindol-2-yl]methyl}pyrimidine-5-carbonitrile;

(3R)-3-(4-chlorophenyl)-2-[(5-chloropyrimidin-2-yl)methyl]-4-fluoro-6-[1-hydroxy-1-(1-methyl-1H-imidazol-4-yl)propyl]-3-[cis-3-hydroxycyclobutoxy]-2,3-dihydro-1H-isoindol-1-one;

6-{[(1R)-1-(4-chlorophenyl)-7-fluoro-5-[1-hydroxy-1-(1-methyl-1H-imidazol-4-yl)propyl]-1-(3-hydroxy-2-methylidenepropoxy)-3-oxo-2,3-dihydro-1H-isoindol-2-yl]methyl}pyridine-3-carbonitrile;

2-{[(1R)-1-(4-chlorophenyl)-7-fluoro-1-[(3-fluorooxetan-3-yl)methoxy]-5-[1-hydroxy-1-(1-methyl-1H-imidazol-4-yl)ethyl]-3-oxo-2,3-dihydro-1H-isoindol-2-yl]methyl}pyrimidine-5-carbonitrile;

2-{[(1R)-1-(4-chlorophenyl)-7-fluoro-1-[(3-fluorooxetan-3-yl)methoxy]-5-[1-hydroxy-1-(1-methyl-1H-imidazol-4-yl)propyl]-3-oxo-2,3-dihydro-1H-isoindol-2-yl]methyl}pyrimidine-5-carbonitrile;

6-{[(1R)-1-(4-chlorophenyl)-7-fluoro-5-[1-hydroxy-1-(1-methyl-1H-imidazol-4-yl)butyl]-3-oxo-1-[(3S)-oxolan-3-yloxy]-2,3-dihydro-1H-isoindol-2-yl]methyl}pyridine-3-carbonitrile;

(3R)-3-(4-chlorophenyl)-2-[(5-chloropyrimidin-2-yl)methyl]-4-fluoro-6-[1-hydroxy-1-(1-methyl-1H-imidazol-4-yl)propyl]-3-[(3S)-oxolan-3-yloxy]-2,3-dihydro-1H-isoindol-1-one;

(3R)-3-(4-chlorophenyl)-2-[(5-chloropyrimidin-2-yl)methyl]-4-fluoro-6-[1-hydroxy-1-(1-methyl-1H-imidazol-4-yl)propyl]-3-{[1-(hydroxymethyl)cyclopropyl]methoxy}-2,3-dihydro-1H-isoindol-1-one;

2-{[(1R)-1-(4-chlorophenyl)-7-fluoro-5-[1-hydroxy-1-(1-methyl-1H-imidazol-4-yl)propyl]-3-oxo-1-[trans-3-(hydroxymethyl)cyclobutoxy]-2,3-dihydro-1H-isoindol-2-yl]methyl}pyrimidine-5-carbonitrile;

2-{[(1R)-1-(4-chlorophenyl)-7-fluoro-5-[1-hydroxy-1-(1-methyl-1H-imidazol-4-yl)propyl]-3-oxo-1-{[trans-3-hydroxycyclobutyl]methoxy}-2,3-dihydro-1H-isoindol-2-yl]methyl}pyrimidine-5-carbonitrile;

1-({[(1R)-1-(4-chlorophenyl)-2-[(5-chloropyrimidin-2-yl)methyl]-7-fluoro-5-[1-hydroxy-1-(1-methyl-1H-imidazol-4-yl)propyl]-3-oxo-2,3-dihydro-1H-isoindol-1-yl]oxy}methyl)cyclopropane-1-carboxamide;

(3R)-2-[(5-chloro-3-hydroxypyridin-2-yl)methyl]-3-(4-chlorophenyl)-4-fluoro-6-[1-hydroxy-1-(1-methyl-1H-imidazol-4-yl)propyl]-3-[cis-3-hydroxycyclobutoxy]-2,3-dihydro-1H-isoindol-1-one;

2-{[(1R)-1-(4-chlorophenyl)-7-fluoro-5-[1-hydroxy-1-(1-methyl-1H-pyrazol-3-yl)propyl]-3-oxo-1-[(3S)-oxolan-3-yloxy]-2,3-dihydro-1H-isoindol-2-yl]methyl}pyrimidine-5-carbonitrile;

(3R)-2-[(5-chloro-3-methoxypyridin-2-yl)methyl]-3-(4-chlorophenyl)-4-fluoro-6-[1-hydroxy-1-(1-methyl-1H-imidazol-4-yl)propyl]-3-(2-hydroxyethoxy)-2,3-dihydro-1H-isoindol-1-one;

(3R)-3-(4-chlorophenyl)-2-[(5-chloropyrimidin-2-yl)methyl]-4-fluoro-6-[1-(4-fluorooxan-4-yl)-1-hydroxyethyl]-3-[(3S)-oxolan-3-yloxy]-2,3-dihydro-1H-isoindol-1-one;

(3R)-3-(4-chlorophenyl)-2-[(5-chloropyrimidin-2-yl)methyl]-4-fluoro-6-{1-hydroxy-1-[trans-4-hydroxycyclohexyl]}-3-[cis-3-hydroxycyclobutoxy]-2,3-dihydro-1H-isoindol-1-one;

6-{[(1R)-1-(4-chlorophenyl)-7-fluoro-5-[1-(4-fluorooxan-4-yl)-1-hydroxypropyl]-1-[(2R)-2-hydroxypropoxy]-3-oxo-2,3-dihydro-1H-isoindol-2-yl]methyl}pyridine-3-carbonitrile;

6-{[(1R)-1-(4-chlorophenyl)-7-fluoro-5-[1-(4-fluorooxan-4-yl)-1-hydroxypropyl]-1-(2-hydroxyethoxy)-3-oxo-2,3-dihydro-1H-isoindol-2-yl]methyl}pyridine-3-carbonitrile;

(3R)-3-(4-chlorophenyl)-2-[(5-chloropyrimidin-2-yl)methyl]-4-fluoro-6-[(1R)-1-(4-fluorooxan-4-yl)-1-hydroxypropyl]-3-(2-hydroxyethoxy)-2,3-dihydro-1H-isoindol-1-one;

(3R)-3-(4-chlorophenyl)-2-[(5-chloropyrimidin-2-yl)
methyl]-4-fluoro-6-[(1S)-1-(4-fluorooxan-4-yl)-1-hy-
droxypropyl]-3-(2-hydroxyethoxy)-2,3-dihydro-1H-
isoindol-1-one;

2-{[(1R)-1-(4-chlorophenyl)-7-fluoro-5-{1-hydroxy-1-
[trans-4-hydroxycyclohexyl]propyl}-3-oxo-1-[(3S)-
oxolan-3-yloxy]-2,3-dihydro-1H-isoindol-2-yl]
methyl}pyrimidine-5-carbonitrile;

2-{[(1R)-1-(4-chlorophenyl)-7-fluoro-5-{1-hydroxy-1-
[trans-4-hydroxycyclohexyl]propyl}-1-methoxy-3-
oxo-2,3-dihydro-1H-isoindol-2-yl]methyl}pyrimidine-
5-carbonitrile;

2-{[(1R)-1-(4-chlorophenyl)-7-fluoro-5-[(1R)-1-(4-fluo-
rooxan-4-yl)-1-hydroxypropyl]-3-oxo-1-[cis-3-hy-
droxycyclobutoxy]-2,3-dihydro-1H-isoindol-2-yl]
methyl}pyrimidine-5-carbonitrile;

2-{[(1R)-1-(4-chlorophenyl)-7-fluoro-5-[(1S)-1-(4-fluo-
rooxan-4-yl)-1-hydroxypropyl]-3-oxo-1-[cis-3-hy-
droxycyclobutoxy]-2,3-dihydro-1H-isoindol-2-yl]
methyl}pyrimidine-5-carbonitrile;

2-{[(1R)-1-(4-chlorophenyl)-7-fluoro-5-[(1R)-1-(4-fluo-
rooxan-4-yl)-1-hydroxypropyl]-3-oxo-1-[(3S)-oxolan-
3-yloxy]-2,3-dihydro-1H-isoindol-2-yl]
methyl}pyrimidine-5-carbonitrile;

2-{[(1R)-1-(4-chlorophenyl)-7-fluoro-5-[(1S)-1-(4-fluo-
rooxan-4-yl)-1-hydroxypropyl]-3-oxo-1-[(3S)-oxolan-
3-yloxy]-2,3-dihydro-1H-isoindol-2-yl]
methyl}pyrimidine-5-carbonitrile;

2-{[(1R)-1-(4-chlorophenyl)-7-fluoro-5-[(1R)-1-(4-fluo-
rooxan-4-yl)-1-hydroxypropyl]-1-(2-hydroxyethoxy)-
3-oxo-2,3-dihydro-1H-isoindol-2-yl]
methyl}pyrimidine-5-carbonitrile;

2-{[(1R)-1-(4-chlorophenyl)-7-fluoro-5-{1-hydroxy-1-
[trans-4-hydroxycyclohexyl]propyl}-1-(2-hydroxy-
ethoxy)-3-oxo-2,3-dihydro-1H-isoindol-2-yl]
methyl}pyrimidine-5-carbonitrile;

(3R)-3-(4-chlorophenyl)-2-[(5-chloropyrimidin-2-yl)
methyl]-4-fluoro-6-{1-hydroxy-1-[trans-4-hydroxycy-
clohexyl]propyl}-3-methoxy-2,3-dihydro-1H-isoindol-
1-one;

2-{[(1R)-1-(4-chlorophenyl)-7-fluoro-5-{1-hydroxy-1-
[trans-4-hydroxycyclohexyl]propyl}-1-[(2R)-2-hy-
droxypropoxy]-3-oxo-2,3-dihydro-1H-isoindol-2-yl]
methyl}pyrimidine-5-carbonitrile;

2-{[(1R)-1-(4-chlorophenyl)-7-fluoro-1-({1-[hydroxydi-
deuterom ethyl]cyclopropyl}dideuteromethoxy)-5-(2-
hydroxypropan-2-yl)-3-oxo-2,3-dihydro-1H-isoindol-
2-yl]methyl}pyrimidine-5-carbonitrile;

5-chloro-2-{[(1R)-1-(4-chlorophenyl)-7-fluoro-5-[(1R)-
1-(4-fluorooxan-4-yl)-1-hydroxypropyl]-1-methoxy-3-
oxo-2,3-dihydro-1H-isoindol-2-yl]methyl}pyridine-3-
carboxylic acid;

3-{[(1R)-1-(4-chlorophenyl)-7-fluoro-5-[(1R)-1-(4-fluo-
rooxan-4-yl)-1-hydroxypropyl]-1-methoxy-3-oxo-2,3-
dihydro-1H-isoindol-2-yl]methyl}-6-methylpyridine-
2-carboxylic acid;

(3R)-3-(4-chlorophenyl)-2-[(5-chloropyrimidin-2-yl)di-
deuteromethyl]-4-fluoro-6-[1-(4-fluorooxan-4-yl)-1-
hydroxyethyl]-3-[(3S)-oxolan-3-yloxy]-2,3-dihydro-
1H-isoindol-1-one;

(3R)-3-(4-chlorophenyl)-2-[(5-chloropyrimidin-2-yl)
methyl]-4-fluoro-6-{1-hydroxy-1-[trans-4-hydroxycy-
clohexyl]propyl}-3-(2-hydroxyethoxy)-2,3-dihydro-
1H-isoindol-1-one;

6-{[(1R)-1-(4-chlorophenyl)-7-fluoro-5-{1-hydroxy-1-
[trans-4-hydroxycyclohexyl]propyl}-3-oxo-1-[cis-3-
hydroxycyclobutoxy]-2,3-dihydro-1H-isoindol-2-yl]
methyl}pyridine-3-carbonitrile;

6-{[(1R)-1-(4-chlorophenyl)-7-fluoro-5-{1-hydroxy-1-
[trans-4-hydroxycyclohexyl]propyl}-1-methoxy-3-
oxo-2,3-dihydro-1H-isoindol-2-yl]methyl}pyridine-3-
carbonitrile;

(3R)-3-(4-chlorophenyl)-2-[(5-chloropyrimidin-2-yl)
methyl]-4-fluoro-6-[2-hydroxy-1-(4-methylpiperazin-
1-yl)butan-2-yl]-3-[(3S)-oxolan-3-yloxy]-2,3-dihydro-
1H-isoindol-1-one;

(3R)-3-(4-chlorophenyl)-2-[(5-chloropyrimidin-2-yl)
methyl]-4-fluoro-6-[2-hydroxy-1-(piperazin-1-yl)bu-
tan-2-yl]-3-[(3S)-oxolan-3-yloxy]-2,3-dihydro-1H-
isoindol-1-one;

(3R)-3-(4-chlorophenyl)-2-[(5-chloropyrimidin-2-yl)
methyl]-4-fluoro-6-{2-hydroxy-1-[(3R)-3-hydroxy-
pyrrolidin-1-yl]butan-2-yl}-3-[(3S)-oxolan-3-yloxy]-
2,3-dihydro-1H-isoindol-1-one;

(3R)-3-(4-chlorophenyl)-2-[(5-chloropyrimidin-2-yl)
methyl]-6-[1-(dimethylamino)-2-hydroxybutan-2-yl]-
4-fluoro-3-[(3S)-oxolan-3-yloxy]-2,3-dihydro-1H-
isoindol-1-one;

(3R)-3-(4-chlorophenyl)-2-[(5-chloropyrimidin-2-yl)
methyl]-4-fluoro-6-[2-hydroxy-1-(piperazin-1-yl)bu-
tan-2-yl]-3-(2-hydroxyethoxy)-2,3-dihydro-1H-isoin-
dol-1-one;

(3R)-3-(4-chlorophenyl)-2-[(5-chloropyrimidin-2-yl)
methyl]-4-fluoro-6-[2-hydroxy-1-(4-methylpiperazin-
1-yl)butan-2-yl]-3-(2-hydroxyethoxy)-2,3-dihydro-
1H-isoindol-1-one;

1-({[(1R)-1-(4-chlorophenyl)-2-[(5-chloropyrimidin-2-
yl)methyl]-7-fluoro-5-[2-hydroxy-1-(4-methylpiper-
azin-1-yl)butan-2-yl]-3-oxo-2,3-dihydro-1H-isoindol-
1-yl]oxy}methyl)cyclopropane-1-carbonitrile;

1-({[(1R)-1-(4-chlorophenyl)-2-[(5-chloropyrimidin-2-
yl)methyl]-7-fluoro-5-[2-hydroxy-1-(piperazin-1-yl)
butan-2-yl]-3-oxo-2,3-dihydro-1H-isoindol-1-yl]
oxy}methyl)cyclopropane-1-carbonitrile;

(3R)-3-(4-chlorophenyl)-2-[(5-chloropyrimidin-2-yl)
methyl]-4-fluoro-3-[(3-fluorooxetan-3-yl)methoxy]-6-
[2-hydroxy-1-(piperazin-1-yl)butan-2-yl]-2,3-dihydro-
1H-isoindol-1-one;

(3R)-3-(4-chlorophenyl)-2-[(5-chloropyrimidin-2-yl)
methyl]-4-fluoro-6-[1-(4-fluoropiperidin-4-yl)-1-hy-
droxypropyl]-3-[(3S)-oxolan-3-yloxy]-2,3-dihydro-
1H-isoindol-1-one;

(3R)-3-(4-chlorophenyl)-2-[(5-chloropyrimidin-2-yl)
methyl]-4-fluoro-6-[1-(4-fluoropiperidin-4-yl)-1-hy-
droxypropyl]-3-[cis-3-hydroxycyclobutoxy]-2,3-di-
hydro-1H-isoindol-1-one;

(3R)-3-(4-chlorophenyl)-2-[(5-chloropyrimidin-2-yl)
methyl]-4-fluoro-6-[1-(4-fluoropiperidin-4-yl)-1-hy-
droxypropyl]-3-[(2R)-2-hydroxypropoxy]-2,3-di-
hydro-1H-isoindol-1-one;

(3R)-3-(4-chlorophenyl)-2-[(5-chloropyrimidin-2-yl)
methyl]-4-fluoro-6-[1-(4-fluoropiperidin-4-yl)-1-hy-
droxypropyl]-3-methoxy-2,3-dihydro-1H-isoindol-1-
one;

1-({[(1R)-1-(4-chlorophenyl)-2-[(5-chloropyrimidin-2-
yl)methyl]-7-fluoro-5-[1-(4-fluoropiperidin-4-yl)-1-
hydroxypropyl]-3-oxo-2,3-dihydro-1H-isoindol-1-yl]
oxy}methyl)cyclopropane-1-carbonitrile;

6-{[(1R)-1-(4-chlorophenyl)-7-fluoro-5-[1-(4-fluoropip-
eridin-4-yl)-1-hydroxypropyl]-3-oxo-1-[(3S)-oxolan-
3-yloxy]-2,3-dihydro-1H-isoindol-2-yl]
methyl}pyridine-3-carbonitrile;

2-{[(1R)-1-(4-chlorophenyl)-7-fluoro-5-[1-(4-fluoropiperidin-4-yl)-1-hydroxypropyl]-3-oxo-1-[(3S)-oxolan-3-yloxy]-2,3-dihydro-1H-isoindol-2-yl]methyl}pyrimidine-5-carbonitrile;

(3R)-3-(4-chlorophenyl)-2-[(5-chloropyridin-2-yl)methyl]-4-fluoro-6-[1-(4-fluoropiperidin-4-yl)-1-hydroxypropyl]-3-[(3S)-oxolan-3-yloxy]-2,3-dihydro-1H-isoindol-1-one;

(3R)-3-(4-chlorophenyl)-2-[(5-chloropyridin-2-yl)methyl]-4-fluoro-6-[1-(4-fluoropiperidin-4-yl)-1-hydroxypropyl]-3-[(2R)-2-hydroxypropoxy]-2,3-dihydro-1H-isoindol-1-one;

(3R)-3-(4-chlorophenyl)-2-[(5-chloropyrimidin-2-yl)methyl]-4-fluoro-6-[(1S)-1-hydroxy-1-[1-(2-hydroxyethyl)piperidin-4-yl]propyl]-3-m ethoxy-2,3-dihydro-1H-isoindol-1-one;

(3R)-3-(4-chlorophenyl)-2-[(5-chloropyrimidin-2-yl)methyl]-4-fluoro-6-[(1S)-1-hydroxy-1-[1-(oxetan-3-yl)piperidin-4-yl]propyl]-3-methoxy-2,3-dihydro-1H-isoindol-1-one;

(3R)-3-(4-chlorophenyl)-2-[(5-chloropyrimidin-2-yl)methyl]-4-fluoro-6-[1-[4-fluoro-1-(oxetan-3-yl)piperidin-4-yl]-1-hydroxypropyl]-3-methoxy-2,3-dihydro-1H-isoindol-1-one;

(3R)-3-(4-chlorophenyl)-2-[(5-chloropyrimidin-2-yl)methyl]-4-fluoro-6-[(1S)-1-hydroxy-1-(1-methylpiperidin-4-yl)propyl]-3-methoxy-2,3-dihydro-1H-isoindol-1-one;

(3R)-3-(4-chlorophenyl)-2-[(5-chloropyrimidin-2-yl)methyl]-4-fluoro-6-[1-hydroxy-1-(1-methylpiperidin-4-yl)ethyl]-3-{[1-(hydroxymethyl)cyclopropyl]methoxy}-2,3-dihydro-1H-isoindol-1-one;

(3R)-3-(4-chlorophenyl)-2-[(5-chloropyridin-2-yl)methyl]-4-fluoro-6-[1-hydroxy-1-(1-methylpiperidin-4-yl)ethyl]-3-{[1-(hydroxymethyl)cyclopropyl]methoxy}-2,3-dihydro-1H-isoindol-1-one;

(3R)-3-(4-chlorophenyl)-2-[(5-chloropyrimidin-2-yl)methyl]-4-fluoro-6-[(1S)-1-hydroxy-1-(1-methylpiperidin-4-yl)propyl]-3-{[1-(hydroxymethyl)cyclopropyl]methoxy}-2,3-dihydro-1H-isoindol-1-one;

2-{[(1R)-1-(4-chlorophenyl)-7-fluoro-5-[(1S)-1-hydroxy-1-(1-methylpiperidin-4-yl)propyl]-3-oxo-1-[(3S)-oxolan-3-yloxy]-2,3-dihydro-1H-isoindol-2-yl]methyl}pyrimidine-5-carbonitrile;

(3R)-3-(4-chlorophenyl)-2-[(5-chloropyrimidin-2-yl)methyl]-4-fluoro-3-[(3-fluorooxetan-3-yl)methoxy]-6-[1-hydroxy-1-(1-methylpiperidin-4-yl)ethyl]-2,3-dihydro-1H-isoindol-1-one;

(3R)-3-(4-chlorophenyl)-2-[(5-chloropyrimidin-2-yl)methyl]-4-fluoro-6-[(1S)-1-hydroxy-1-(1-methylpiperidin-4-yl)propyl]-3-(2-hydroxyethoxy)-2,3-dihydro-1H-isoindol-1-one;

(3R)-3-(4-chlorophenyl)-2-[(5-chloropyrimidin-2-yl)methyl]-4-fluoro-6-[(1S)-1-hydroxy-1-(1-methyl piperidin-4-yl)propyl]-3-[cis-3-hydroxycyclobutoxy]-2,3-dihydro-1H-isoindol-1-one;

2-{[(1R)-1-(4-chlorophenyl)-7-fluoro-5-[1-(4-fluoro-1-methylpiperidin-4-yl)-1-hydroxypropyl]-3-oxo-1-[(3S)-oxolan-3-yloxy]-2,3-dihydro-1H-isoindol-2-yl]methyl}pyrimidine-5-carbonitrile;

(3R)-3-(4-chlorophenyl)-2-[(5-chloropyrimidin-2-yl)methyl]-4-fluoro-6-[(1S)-1-hydroxy-1-(1-methylpiperidin-4-yl)propyl]-3-[(2R)-2-hydroxypropoxy]-2,3-dihydro-1H-isoindol-1-one;

(3R)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-methoxy-2,3-dihydro-1H-isoindol-1-one;

1-({[(1R)-1-(4-chlorophenyl)-2-[(5-chloropyrimidin-2-yl)methyl]-7-fluoro-5-[1-(4-fluoro-1-methylpiperidin-4-yl)-1-hydroxypropyl]-3-oxo-2,3-dihydro-1H-isoindol-1-yl]oxy}methyl)cyclopropane-1-carbonitrile;

(3R)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-(2-hydroxyethoxy)-2,3-dihydro-1H-isoindol-1-one;

(3R)-3-(4-chlorophenyl)-2-[(5-chloropyrimidin-2-yl)methyl]-4-fluoro-6-[(1R)-1-hydroxy-1-(1-methylpiperidin-4-yl)propyl]-3-methoxy-2,3-dihydro-1H-isoindol-1-one;

(3R)-3-(4-chlorophenyl)-2-[(5-chloropyrimidin-2-yl)methyl]-4-fluoro-6-[(1R)-1-hydroxy-1-(1-methylpiperidin-4-yl)propyl]-3-[(3S)-oxolan-3-yloxy]-2,3-dihydro-1H-isoindol-1-one;

2-[(5-chloro-3-hydroxypyridin-2-yl)methyl]-3-(4-chlorophenyl)-4-fluoro-6-[(1S)-1-hydroxy-1-(1-methylpiperidin-4-yl)propyl]-3-[(3S)-oxolan-3-yloxy]-2,3-dihydro-1H-isoindol-1-one;

(3R)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-[cis-3-hydroxycyclobutoxy]-2,3-dihydro-1H-isoindol-1-one;

(3R)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-[(3S)-oxolan-3-yloxy]-2,3-dihydro-1H-isoindol-1-one;

(3R)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-[(2R)-2-hydroxypropoxy]-2,3-dihydro-1H-isoindol-1-one;

2-{[(1R)-1-(4-chlorophenyl)-1-[(1-cyanocyclopropyl)methoxy]-7-fluoro-5-[1-(4-fluoro-1-methylpiperidin-4-yl)-1-hydroxypropyl]-3-oxo-2,3-dihydro-1H-isoindol-2-yl]methyl}pyrimidine-5-carbonitrile;

2-{[(1R)-1-(4-chlorophenyl)-7-fluoro-5-[1-(4-fluoro-1-methylpiperidin-4-yl)-1-hydroxypropyl]-1-methoxy-3-oxo-2,3-dihydro-1H-isoindol-2-yl]methyl}pyrimidine-5-carbonitrile;

2-{[(1R)-1-(4-chlorophenyl)-7-fluoro-1-({1-[hydroxydideuteromethyl]cyclopropyl}dideuteromethoxy)-5-(2-hydroxybutan-2-yl)-3-oxo-2,3-dihydro-1H-isoindol-2-yl]methyl}pyrimidine-5-carbonitrile;

(3R)-3-(4-chlorophenyl)-2-[(5-chloropyrimidin-2-yl)methyl]-4-fluoro-6-[1-(4-fluorooxan-4-yl)-1-hydroxyethyl]-3-(2-hydroxyethoxy)-2,3-dihydro-1H-isoindol-1-one;

6-{[(1R)-1-(4-chlorophenyl)-7-fluoro-1-[(2S)-3-fluoro-2-hydroxypropoxy]-5-[1-(4-fluorooxan-4-yl)-1-hydroxyethyl]-3-oxo-2,3-dihydro-1H-isoindol-2-yl]methyl}pyridine-3-carbonitrile; and (3R)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-[2-hydroxy(1,1,2,2-tetradeutero)ethoxy]-2,3-dihydro-1H-isoindol-1-one.

13. A compound according to claim 1, or a tautomer, N-oxide, pharmaceutically acceptable salt or solvate thereof, wherein the compound is selected from:

(3R)-3-(4-chlorophenyl)-2-[(5-chloropyrimidin-2-yl)methyl]-4-fluoro-6-[2-hydroxy-1-(4-methylpiperazin-1-yl)butan-2-yl]-3-[(3S)-oxolan-3-yloxy]-2,3-dihydro-1H-isoindol-1-one;

(3R)-3-(4-chlorophenyl)-2-[(5-chloropyrimidin-2-yl)
methyl]-4-fluoro-6-[1-(4-fluoro-1-methylpiperidin-4-
yl)-1-hydroxypropyl]-3-methoxy-2,3-dihydro-1H-
isoindol-1-one;
1-({[(1R)-1-(4-chlorophenyl)-2-[(5-chloropyrimidin-2-
yl)methyl]-7-fluoro-5-[1-(4-fluoro-1-methylpiperidin-
4-yl)-1-hydroxypropyl]-3-oxo-2,3-dihydro-1H-isoin-
dol-1-yl]oxy}methyl)cyclopropane-1-carbonitrile;
(3R)-3-(4-chlorophenyl)-2-[(5-chloropyrimidin-2-yl)
methyl]-4-fluoro-6-[1-(4-fluoro-1-methylpiperidin-4-
yl)-1-hydroxypropyl]-3-[cis-3-hydroxycyclobutoxy]-
2,3-dihydro-1H-isoindol-1-one; and
(3R)-3-(4-chlorophenyl)-2-[(5-chloropyrimidin-2-yl)
methyl]-4-fluoro-6-[1-(4-fluoro-1-methylpiperidin-4-
yl)-1-hydroxypropyl]-3-[(2R)-2-hydroxypropoxy]-2,3-
dihydro-1H-isoindol-1-one.

14. A pharmaceutical composition comprising a compound of formula (I) as defined in claim 1, or a tautomer or a solvate or a pharmaceutically acceptable salt thereof.

15. A method of inhibiting the interaction of p53 with MDM2 in a subject, the method comprising administering to the subject a compound as defined in claim 1, or a tautomer or a solvate or a pharmaceutically acceptable salt thereof.

16. A process for the preparation of a compound of formula (I) as defined in claim 1, or a tautomer, N-oxide, pharmaceutically acceptable salt, or solvate thereof which comprises:
(a) reacting a compound of the following formula with an organometallic reagent:

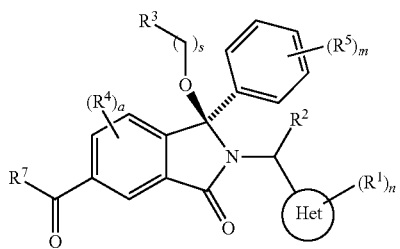

wherein Het, $R^1$, $R^2$, $R^3$, $R^4$, $R^5$, $R^7$, a, s m and n are as defined in claim 1; and/or
(b) interconversion of a compound of formula (I) or protected derivative thereof to a further compound of formula (I) or protected derivative thereof; and/or
(c) deprotection of a protected derivative of a compound of formula (I); and/or
(d) providing a compound of formula (I) and forming a pharmaceutically acceptable salt of the compound.

17. A compound according to claim 2, wherein n is 1 and $R^1$ is chloro or nitrile.

18. A compound according to claim 17, wherein $R^1$ is chloro.

19. A compound according to claim 3, wherein $R^2$ is hydrogen.

20. A compound according to claim 4, wherein $R^3$ is -(A)$_r$-(CR$^x$R$^y$)$_q$-X and A is a cyclopropyl group.

21. A compound according to claim 1, wherein the compound is (3R)-3-(4-chlorophenyl)-2-[(5-chloropyrimidin-2-yl)methyl]-4-fluoro-6-[2-hydroxy-1-(4-methylpiperazin-1-yl)butan-2-yl]-3-[(3S)-oxolan-3-yloxy]-2,3-dihydro-1H-isoindol-1-one or a tautomer, N-oxide, pharmaceutically acceptable salt or solvate thereof.

22. A compound according to claim 1, wherein the compound is (3R)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-methoxy-2,3-dihydro-1H-isoindol-1-one or a tautomer, N-oxide, pharmaceutically acceptable salt or solvate thereof.

23. A compound according to claim 1, wherein the compound is 1-({[(1R)-1-(4-chlorophenyl)-2-[(5-chloropyrimidin-2-yl)methyl]-7-fluoro-5-[1-(4-fluoro-1-methylpiperidin-4-yl)-1-hydroxypropyl]-3-oxo-2,3-dihydro-1H-isoindol-1-yl]oxy}methyl)cyclopropane-1-carbonitrile or a tautomer, N-oxide, pharmaceutically acceptable salt or solvate thereof.

24. A compound according to claim 1, wherein the compound is (3R)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-[cis-3-hydroxycyclobutoxy]-2, 3-dihydro-1H-isoindol-1-one or a tautomer, N-oxide, pharmaceutically acceptable salt or solvate thereof.

25. A compound according to claim 1, wherein the compound is (3R)-3-(4-chlorophenyl)-2-[(5-chloropyrimidin-2-yl)methyl]-4-fluoro-6-[1-(4-fluoro-1-methylpiperidin-4-yl)-1-hydroxypropyl]-3-[(2R)-2-hydroxypropoxy]-2, 3-dihydro-1H-isoindol-1-one or a tautomer, N-oxide, pharmaceutically acceptable salt or solvate thereof.

* * * * *

UNITED STATES PATENT AND TRADEMARK OFFICE
CERTIFICATE OF CORRECTION

PATENT NO. : 10,526,311 B2
APPLICATION NO. : 15/763724
DATED : January 7, 2020
INVENTOR(S) : Chessari et al.

Page 1 of 3

It is certified that error appears in the above-identified patent and that said Letters Patent is hereby corrected as shown below:

In the Claims

Column 635, Lines 36-37: Claim 1, Delete "-(CR$^x$R$^y$)v-CO$_2$C$_{1-4}$alkyl," and insert -- -(CR$^x$R$^y$)$_v$-CO$_2$C$_{1-4}$alkyl, --

Column 635, Line 67: Claim 1, Delete "-NRXCOR$_y$," and insert -- -NR$^x$COR$^y$, --

Column 636, Line 45: Claim 1, Delete "a=CH$_2$" and insert -- a =CH$_2$ --

Column 636, Line 52: Claim 1, Delete "-(CH$_2$)r-CO$_2$C$_{1-6}$alkyl," and insert -- -(CH$_2$)$_r$-CO$_2$C$_{1-6}$alkyl, --

Column 636, Line 53: Claim 1, Delete "-(CH$_2$)r-CO$_2$H," and insert -- -(CH$_2$)$_r$-CO$_2$H, --

Column 636, Line 53: Claim 1, Delete "-N(H)$_e$(C$_1$ -4alkyl)$_{2-e}$," and insert -- -N(H)$_e$(C$_{1-4}$alkyl)$_{2-e}$, --

Column 636, Line 67: Claim 1, Delete "v and w are independently is selected from 0 and 1." and insert -- v is selected from 0 and 1. --

Column 637, Line 5: Claim 3, Delete "C$_{1-4}$     alkyl" and insert -- C$_{1-4}$ alkyl --

Column 639, Line 61: Claim 12, Delete "(1R, 3R)" and insert -- (1R,3R) --

Column 639, Line 65: Claim 12, Delete "(1 S,3S)" and insert -- (1S,3S) --

Column 641, Line 56: Claim 12, Delete "1A$^5$" and insert -- 1$\lambda^5$ --

Column 642, Line 63: Claim 12, Delete "1-(4-m ethylpiperazin-" and insert -- 1-(4-methylpiperazin- --

Column 644, Line 53: Claim 12, Delete "-6-[-hydroxy-" and insert -- -6-[1-hydroxy- --

Signed and Sealed this
Twenty-first Day of July, 2020

Andrei Iancu
*Director of the United States Patent and Trademark Office*

CERTIFICATE OF CORRECTION (continued)
U.S. Pat. No. 10,526,311 B2

Column 644, Line 57: Claim 12, Delete "-6-[-hydroxy-" and insert -- -6-[1-hydroxy- --

Column 644, Line 61: Claim 12, Delete "-6-[-hydroxy-" and insert -- 6-[1-hydroxy- --

Column 644, Line 65: Claim 12, Delete "-I H-pyra-" and insert -- -1H-pyra- --

Column 645, Line 2: Claim 12, Delete "-5-[-hydroxy-" and insert -- -5-[1-hydroxy- --

Column 645, Line 6: Claim 12, Delete "-6-[-hydroxy-" and insert -- 6-[1-hydroxy- --

Column 645, Line 10: Claim 12, Delete "5-[-(1,2-dimethyl-" and insert -- 5-[1-(1,2-dimethyl- --

Column 645, Line 15: Claim 12, Delete "-6-[-hydroxy-" and insert -- -6-[1-hydroxy- --

Column 645, Line 27: Claim 12, Delete "-6-[-hydroxy-" and insert -- -6-[1-hydroxy- --

Column 645, Line 31: Claim 12, Delete "-6-[-hydroxy-" and insert -- -6-[1-hydroxy- --

Column 645, Line 44: Claim 12, Delete "-6-[-hydroxy-" and insert -- -6-[1-hydroxy- --

Column 645, Line 62: Claim 12, Delete "-[(6-m ethoxypyridin-3-yl)" and insert -- -[(6-methoxypyridin-3-yl) --

Column 646, Line 2: Claim 12, Delete "-6-[-hydroxy-" and insert -- -6-[1-hydroxy- --

Column 647, Line 14: Claim 12, Delete "1-[(1 S,4S)-" and insert -- 1-[(1S,4S)- --

Column 648, Line 66: Claim 12, Delete "yl)-3-m ethoxy-2-" and insert -- yl)-3-methoxy-2- --

Column 649, Line 31: Claim 12, Delete "m ethoxy]-6-" and insert -- methoxy]-6- --

Column 649, Line 34: Claim 12, Delete "-6-[-hydroxy-" and insert -- -6-[1-hydroxy- --

Column 649, Line 67: Claim 12, Delete "-6-[-hydroxy-" and insert -- -6-[1-hydroxy- --

Column 650, Line 13: Claim 12, Delete "3-oxo-1i -[(3S)-" and insert -- 3-oxo-1-[(3S)- --

Column 651, Line 13: Claim 12, Delete "6-{-hydroxy-" and insert -- 6-{1-hydroxy- --

Column 651, Line 22: Claim 12, Delete "-6-[-hydroxy-" and insert -- -6-[1-hydroxy- --

Column 652, Line 33: Claim 12, Delete "3-m ethoxy" and insert -- 3-methoxy --

Column 653, Line 42: Claim 12, Delete "5-yl]-1-hydroxyethyl}-I H-pyrazol-" and insert -- 5-yl]-1-hydroxyethyl}-1H-pyrazol- --

CERTIFICATE OF CORRECTION (continued)
U.S. Pat. No. 10,526,311 B2

Column 655, Line 47: Claim 12, Delete "deuterom ethyl]" and insert -- deuteromethyl] --

Column 657, Line 16: Claim 12, Delete "-3-m ethoxy-" and insert -- -3-methoxy- --

Column 657, Line 56: Claim 12, Delete "1-methyl pip-" and insert -- 1-methylpip- --